United States Patent
Kobayashi et al.

(10) Patent No.: US 9,237,745 B2
(45) Date of Patent: *Jan. 19, 2016

(54) AMIDE DERIVATIVE, PEST CONTROL AGENT CONTAINING THE AMIDE DERIVATIVE, AND USE OF THE AMIDE DERIVATIVE

(71) Applicant: Mitsui Chemicals Agro, Inc., Tokyo (JP)

(72) Inventors: Yumi Kobayashi, Mobara (JP); Hidenori Daido, Otsu (JP); Hiroyuki Katsuta, Chiba (JP); Michikazu Nomura, Mobara (JP); Hidetaka Tsukada, Omuta (JP); Atsushi Hirabayashi, Omuta (JP); Yusuke Takahashi, Omuta (JP); Yoji Aoki, Chiba (JP); Atsuko Kawahara, Mobara (JP); Yasuaki Fukazawa, Mobara (JP); Mai Hirose, Chiba (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 204 days.

This patent is subject to a terminal disclaimer.

(21) Appl. No.: 13/845,664

(22) Filed: Mar. 18, 2013

(65) Prior Publication Data

US 2013/0231392 A1 Sep. 5, 2013

Related U.S. Application Data

(60) Division of application No. 13/016,604, filed on Jan. 28, 2011, now Pat. No. 8,686,044, which is a continuation-in-part of application No. PCT/JP2009/061914, filed on Jun. 30, 2009.

(60) Provisional application No. 61/329,695, filed on Apr. 30, 2010.

(30) Foreign Application Priority Data

Aug. 13, 2008 (JP) ................................. 2008-208714
Jan. 29, 2010 (JP) ................................. 2010-019747

(51) Int. Cl.
*A61K 31/16* (2006.01)
*A61K 31/165* (2006.01)
(Continued)

(52) U.S. Cl.
CPC ............... *A01N 37/22* (2013.01); *A01N 37/46* (2013.01); *A01N 43/40* (2013.01); *A01N 43/78* (2013.01); *A61K 31/167* (2013.01);
(Continued)

(58) Field of Classification Search
CPC ............................ A61K 31/16; A61K 31/165
See application file for complete search history.

(56) References Cited

U.S. PATENT DOCUMENTS

2007/0027154 A1 2/2007 Yoshida et al.
2007/0275980 A1 11/2007 Yoshida et al.
2009/0099204 A1 4/2009 Yoshida et al.

FOREIGN PATENT DOCUMENTS

CA 2554437 8/2005
CN 1871209 11/2006
(Continued)

OTHER PUBLICATIONS

Chinese Office Action dated Jan. 15, 2014 filed in corresponding Chinese patent application for No. 200980131076.5 and English translation thereof.

(Continued)

*Primary Examiner* — Yong Chong
(74) *Attorney, Agent, or Firm* — Rankin, Hill & Clark LLP

(57) ABSTRACT

An amide derivative represented by the following Formula (1) is provided as an amide derivative showing a significantly excellent effect for a pest control action. In the following Formula (1), A represents a carbon atom, a nitrogen atom, or the like, and K represents a non-metal atomic group necessary for forming a cyclic linking group derived from benzene or a heterocyclic. X represents a halogen atom or the like; n represents an integer of from 0 to 4. $R_1$ and $R_2$ represent hydrogen atoms, alkyl groups, or the like. T represents $-C(=G_1)-Q_1$ or $-C(=G_1)-G_2Q_2$, and $G_1$ to $G_3$ each represent oxygen atoms or the like. $Q_1$ and $Q_2$ each represent a hydrogen atom, an alkyl group, an aryl group, or the like. $Y_1$ and $Y_5$ each represent a halogen atom or the like, $Y_2$ and $Y_4$ each represent a hydrogen atom or the like, and $Y_3$ represents a C2-C5 haloalkyl group.

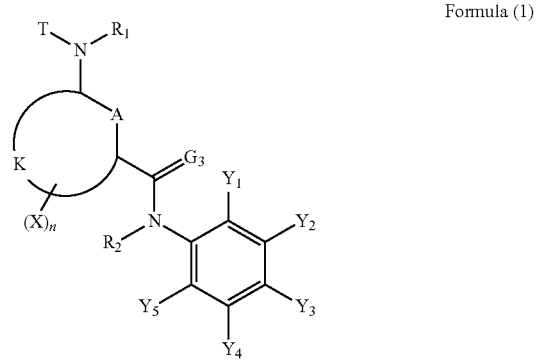

Formula (1)

14 Claims, No Drawings

(51) Int. Cl.

| | | |
|---|---|---|
| *A01N 37/22* | (2006.01) | |
| *A01N 37/46* | (2006.01) | |
| *A01N 43/40* | (2006.01) | |
| *A01N 43/78* | (2006.01) | |
| *A61K 31/167* | (2006.01) | |
| *C07C 237/42* | (2006.01) | |
| *C07C 255/57* | (2006.01) | |
| *C07C 255/60* | (2006.01) | |
| *C07D 213/82* | (2006.01) | |
| *C07C 233/88* | (2006.01) | |

(52) U.S. Cl.
CPC ............ *C07C 233/88* (2013.01); *C07C 237/42* (2013.01); *C07C 255/57* (2013.01); *C07C 255/60* (2013.01); *C07D 213/82* (2013.01)

(56) References Cited

FOREIGN PATENT DOCUMENTS

| | | |
|---|---|---|
| CN | 1926094 | 3/2007 |
| EP | 1661886 | 5/2006 |
| EP | 1714958 | 10/2006 |
| EP | 1911751 | 4/2008 |
| EP | 1916236 | 4/2008 |
| EP | 2072501 | 6/2009 |
| EP | 2319830 | 5/2011 |
| JP | 2007-31395 | 2/2007 |
| JP | 2010037311 | 2/2010 |
| JP | 2011506504 | 3/2011 |
| JP | 2011530490 | 12/2011 |
| WO | 2005/021488 | 3/2005 |
| WO | 2005/073165 | 8/2005 |
| WO | 2006/137376 | 12/2006 |
| WO | 2006/137395 | 12/2006 |
| WO | 2007013332 | 2/2007 |
| WO | 2007/051560 | 5/2007 |
| WO | 2007/083394 | 7/2007 |
| WO | 2007083411 | 7/2007 |
| WO | 2008/074427 | 6/2008 |
| WO | 2008/075453 | 6/2008 |
| WO | 2008/075459 | 6/2008 |
| WO | 2008/107091 | 9/2008 |
| WO | 2009/049845 | 4/2009 |
| WO | 2009/080203 | 7/2009 |
| WO | 2010-018714 | 2/2010 |
| WO | 2010-018857 | 2/2010 |
| WO | 2010013567 | 2/2010 |

OTHER PUBLICATIONS

International Search Report Dated Mar. 8, 2011 issued in PCT/JP2009/061914.

Office Action dated Dec. 4, 2012 issued in the corresponding Canadian Patent Application No. 2733557.

Corresponding Japanese Office Action dated Feb. 26, 2013, and the English Translation thereof.

Chinese Office Action dated Mar. 1, 2013 filed in corresponding Chinese Application No. 200980131076.5; English translation thereof.

Canadian Office Action dated Aug. 21, 2013 filed in the corresponding Canadian patent application No. 2733557.

European Office Action dated Jun. 17, 2013 filed in the corresponding European patent application No. 09806610.3.

US Office Action dated Mar. 14, 2013 filed in related U.S. Appl. No. 13/016,604.

Australia Examination 1st Report dated May 23, 2014 issued in the corresponding Australian patent application No. 2011211197.

Extended European Search Report dated Sep. 15, 2015 issued in the corresponding European patent application No. 11737126.0.

US Office Action dated Sep. 10, 2015 issued in US corresponding U.S. Appl. No. 13/949,866.

AMIDE DERIVATIVE, PEST CONTROL AGENT CONTAINING THE AMIDE DERIVATIVE, AND USE OF THE AMIDE DERIVATIVE

CROSS-REFERENCE TO RELATED APPLICATIONS

This application is a continuation-in-part application of PCT Application PCT/JP2009/061914, filed Jun. 30, 2009, and claims the benefit of U.S. provisional Application No. 61/329,695, filed Apr. 30, 2010, the disclosures of which are incorporated by reference herein. This application also claims priority under 35 USC 119 from Japanese patent Application No. 2008-208714, filed on Aug. 13, 2008 and Japanese patent Application No. 2010-019747, filed on Jan. 29, 2010, the disclosures of which are incorporated by reference herein.

BACKGROUND OF THE INVENTION

1. Field of the Invention

The present invention relates to a pest control agent, an amide derivative contained in the pest control agent, and a method for using the amide derivative.

2. Description of the Related Art

Various amide derivatives are described in the pamphlets of International Publication WO 2005/21488, International Publication WO 2005/73165, International Publication WO 2006/137376, and International Publication WO 2006/137395.

SUMMARY OF THE INVENTION

In the production of, for example, agricultural and horticultural crops, due to causes such as currently-occurring large scale damage due to pests or the like and the propagation of pests having resistance to existing chemicals, there is a demand for a novel agricultural/horticultural pest control agent.

It is an object of the present invention to provide an amide derivative showing a pesticidal effect against a wide range of agricultural/horticultural pests, a pest control agent containing the amide derivative as an active ingredient, and a pest controlling method.

The present inventors have conducted intensive studies to develop a novle pest control agent, and as a result, they have found that the aromatic carboxamide derivative represented by Formula (1) of the present invention is a novel compound unknown in the literature, and it is also a pest control agent, particularly an agricultural/horticultural pest control agent, showing a particularly high efficiency, thereby completing the present invention.

Further, they have also discovered a novel preparation method and a useful intermediate for the preparation of the compound of the present invention. As a result, they have completed the present invention.

That is, the present invention is as follows.

<1> An amide derivative represented by the following Formula (1):

1. An amide derivative represented by the following Formula (1):

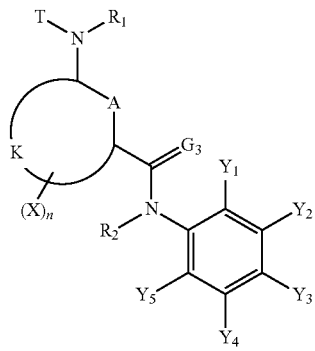

Formula (1)

Wherein, in Formula (1), A represents a carbon atom, an oxygen atom, a nitrogen atom, an oxidized nitrogen atom, or a sulfur atom. K represents a non-metal atom group necessary for forming a cyclic linking group derived from benzene, pyridine, pyridine-N-oxide, pyrimidine, pyrazine, pyridazine, triazine, pyrrole, pyrazole, imidazole, oxazole, isoxazole, thiazole, isothiazole, furan, thiophene, oxadiazole, thiodiazole, or triazole, in combination with A and two carbon atoms to which A bonds.

X represents a hydrogen atom, a halogen atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylsulfonyloxy group, a C1-C6 haloalkylsulfonyloxy group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkylcarbonyloxy group, a C2-C7 haloalkylcarbonyloxy group, arylcarbonyloxy group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a C4-C10 cycloalkyloxycarbonyl group, a C4-C10 halocycloalkyloxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C2-C7 alkoxycarbonyloxy group, a C2-C7 haloalkoxycarbonyloxy group, an arylcarbonylamino group, an amino group, a carbamoyl group, a cyano group, a hydroxy group, pentafluorosulfanyl group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkenylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, a phenyl group, or a heterocyclic group, and when there are plural X's, each X may be the same as or different from an other.

n represents an integer of from 0 to 4.

T represents —C(=$G_1$)-$Q_1$ or —C(=G1)-$G_2Q_2$.

$G_1$ and $G_2$ each independently represent an oxygen atom or a sulfur atom, $Q_1$ and $Q_2$ each represent a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a benzyl group, a phenyl group which may have a substituent, a naphthyl group, or a heterocyclic group which may have a substituent.

$Y_1$ and $Y_5$ each independently represent a halogen atom, a C1-C6 haloalkoxy group, or a C1-C3 haloalkyl group, $Y_2$ and $Y_4$ each independently represent a hydrogen atom, a halogen atom, or a C1-C4 alkyl group, $Y_3$ represents a C2-C5 haloalkyl group.

Wherein in $Q_1$ and $Q_2$, the substituent of a phenyl group which may have a substituent and a heterocyclic group which may have a substituent represents one or more substituent selected from a group consisting of a halogen atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkylcarbonyloxy group, a C2-C7 haloalkylcarbonyloxy group, a C1-C6 alkylsulfonyloxy group, a C1-C6 haloalkylsulfonyloxy group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a C4-C10 cycloalkyloxycarbonyl group, a C4-C10 halocycloalkyloxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkenylaminocarbonyl group, a C3-C7 haloallcenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, an amino group, a carbamoyl group, a cyano group, a nitro group, a hydroxy group, pentafluorosulfanyl group, a phenyl group which may have a substituent, and a heterocyclic group which may have a substituent, and when there are two or more substituents, the substituents may be the same as or different from each other.

Wherein the heterocyclic group in X, $Q_1$, and $Q_2$ represent a pyridyl group, a pyridine-N-oxide group, a pyrimidinyl group, a pyrazinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrolyl group, an imidazolyl group, a triazolyl group, a pyrazolyl group, or a tetrazolyl group.

$G_3$ represents an oxygen atom or a sulfur atom.

$R_1$ and $R_2$ each independently represent a hydrogen atom, an oxygen atom, a halogen atom, a hydroxy group, a nitro group, a nitroso group, a trimethylsilyl group, a t-butyldimethylsilyl group, a cyano group, an amino group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)$R_7$, wherein $R_7$ represents a C1-C6 alkyl group, a C1-C6 haloalkyl group, a C1-C6 alkoxy group, or a C1-C6 haloalkoxy group.

However the amide derivative represented by Formula (1) is not one of (A) to (I).

(A) A case where, in Formula (1), K represents a non-metal atom group necessary for forming a cyclic linking group derived from pyridine in combination with A and two carbon atoms to which A bonds, $Y_1$ represents a halogen atom, and $Y_5$ represents a C1-C6 haloalkoxy group, and T is —C(=$G_1$)-$Q_1$.

(B) A case where, in Formula (1), K represents a non-metal atom group necessary for forming a cyclic linking group derived from pyrrole, pyrazole, imidazole, oxazole, isoxazole, thiazole, isothiazole, furan, thiophene, oxadiazole, thiodiazole, or triazole, in combination with A and two carbon atoms to which A bonds, $Y_1$ and $Y_5$ represent each independently a halogen atom, and T is —C(=$G_1$)-$G_2Q_2$.

(C) A case where, in Formula (1), K represents a non-metal atom group necessary for forming a cyclic linking group derived from pyrrole, pyrazole, imidazole, oxazole, isoxazole, thiazole, isothiazole, furan, thiophene, oxadiazole, thiodiazole, or triazole, in combination with A and two carbon atoms to which A bonds, T represents —C(=G$_1$)-Q$_1$, Y$_1$ is a halogen atom, and Y$_5$ represents a halogen atom or a haloalkoxy group.

(D) A case where, the amide derivative is an amide compound represented by the following Formula (2):

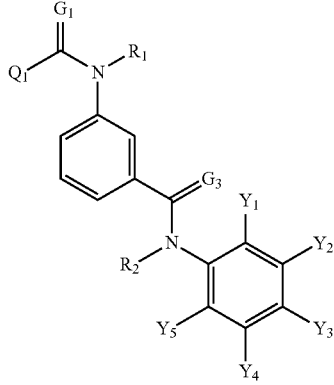

Formula (2)

Wherein in Formula (2), Y$_2$ to Y$_4$, Q$_1$, G$_1$, G$_3$, R$_1$, and R$_2$ have the same definitions as Y$_2$ to Y$_4$, Q$_1$, G$_1$, G$_3$, R$_1$, and R$_2$, respectively, in Formula (1), Y$_1$ represents a halogen atom, and Y$_5$ represents a C1-C2 haloalkoxy group.

(E) A case where, in Formula (2), Y$_1$ and Y$_5$ each independently represent a halogen atom, all X's represent hydrogen atoms, and Y$_3$ represents a C2-C3 haloalkyl group.

(F) A case where, the amide derivative is an amide derivative represented by the following Formula (3)

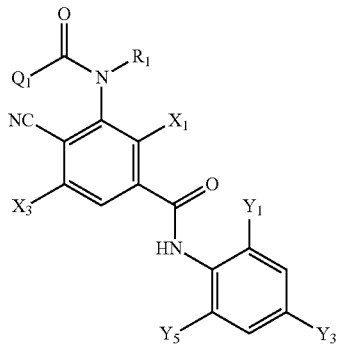

Formula (3)

Wherein in Formula (3), Y$_1$ and Y$_5$ each independently represent a halogen atom, X$_1$ and X$_3$ each independently represent a hydrogen atom or a fluorine atom, Q$_1$ has the same definition as Q$_1$ in Formula (1), R$_1$ represents a hydrogen atom or a methyl group, and Y$_3$ represents a C3-C4 perfluoroalkyl group.

(G) A case where the amide derivative is an amide derivative represented by the following Formula (4):

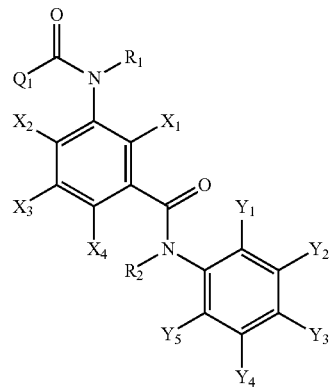

Formula (4)

Wherein in Formula (4), X$_1$ represents a fluorine atom, X$_2$, X$_3$, and X$_4$ represent hydrogen atoms, Y$_1$ and Y$_5$ are different from each other and represent a bromine atom or a trifluoromethoxy group, Y$_2$ and Y$_4$ represent hydrogen atoms, Y$_3$ represents a heptafluoroisopropyl group, Q$_1$ represents a phenyl group or a 2-chloropyridin-3-yl group, and R$_1$ and R$_2$ are different from each other, and each represent a hydrogen atom or a methyl group.

Alternatively, X$_1$ represents a fluorine atom, X$_2$, X$_3$, and X$_4$ represent hydrogen atoms, Y$_1$ and Y$_5$ represent bromine atoms, Y$_2$ and Y$_4$ represent hydrogen atoms, Y$_3$ represents a pentafluoroethyl group, Q$_1$ represents a 2-fluorophenyl group, and R$_1$ and R$_2$ each independently represent a hydrogen atom or a methyl group}.

(H) A case where, the amide derivative is an amide derivative represented by the following Formula (5):

Formula (5)

Wherein, in Formula (5), Y$_1$ and Y$_5$ each independently represent a halogen atom, X$_1$ represents a hydrogen atom or a fluorine atom, Q$_2$ represents a 2,2,2-trichloroethyl group or a 3,3,3-trifluoro-n-propyl group, and Y$_3$ represents a C2-C4 haloalkyl group.

(I) A case where the amide derivative is an amide derivative represented by the following Formula (6):

Formula (6)

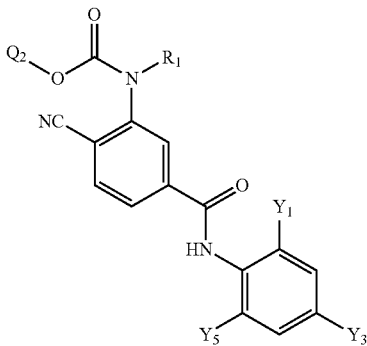

Wherein, in Formula (6), Y₁ and Y₅ each independently represent a halogen atom, Q₂ has the same definition as Q₂ in Formula (1), R₁ represents a hydrogen atom or a methyl group, and Y₃ represents a C3-C4 haloalkyl group.

<2> The amide compound according to <1>, which is represented by the following Formula (7):

Formula (7)

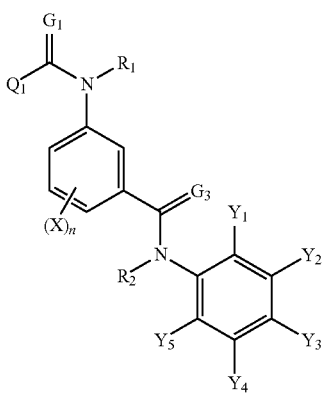

Wherein, in Formula (7), n represents 4, and X, Y₁ to Y₅, Q₁, G₁, G₃, R₁, and R₂ have the same definitions as X, Y₁ to Y₅, Q₁, G₁, G₃, R₁, and R₂, respectively, in Formula (1).

<3> The amide derivative according to <2>, which is represented by the following Formula (8):

Formula (8)

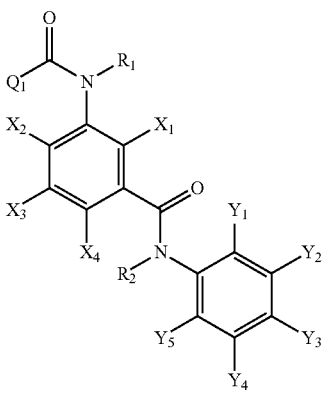

Wherein, in Formula (8), Q₁ represents a phenyl group which may have a substituent or a pyridyl group which may have a substituent.

X₁, X₂, X₃, and X₄ each independently represent a hydrogen atom or a fluorine atom.

R₁ and R₂ each independently represent a hydrogen atom or a C1-C3 alkyl group.

Y₁ and Y₅ each independently represent a halogen atom, a C1-C3 haloalkoxy group, or a C1-C3 haloalkyl group, Y₂ and Y₄ each independently represent a hydrogen atom, a halogen atom, or a C1-C4 alkyl group, and Y₃ represents a C3-C4 haloalkyl group.

In a case where Y₁ and Y₅ represent halogen atoms simultaneously, at least one of X₁ and X₂ represents a fluorine atom. Further, in a case where Y₁ or Y₅ represents a C1-C3 haloalkoxy group, X₂ represents a fluorine atom.

<4> The amide derivative according to <3>, wherein in Formula (8), Y₃ represents a C3-C4 perfluoroalkyl group.

<5> The amide derivative according to <4>, wherein in Formula (8), Y₁ and Y₅ each independently represent a chlorine atom, a bromine atom, an iodine atom, a trifluoromethoxy group, a trifluoromethyl group, or a pentafluoroethyl group, and Y₂ and Y₄ represent hydrogen atoms.

<6> The amide derivative according to <5>, wherein in Formula (8), X₁ and X₂ each independently represent a hydrogen atom or a fluorine atom, and X₃ and X₄ represent hydrogen atoms.

<7> The amide derivative according to <6>, wherein in Formula (8), R₁ and R₂ each independently represent a hydrogen atom or a methyl group.

<8> The amide derivative according to claim 7, wherein in Formula (8), Q₁ represents a phenyl group or a pyridyl group which may have a substituent selected from a group consisting of a halogen atom, a C1 haloalkyl group, a nitro group, and a cyano group.

<9> The amide derivative according to claim 8, wherein in Formula (8), the number of the substituents in Q₁ is 1 or 2.

<10> The amide derivative according to <9>, wherein in Formula (8), Q₁ represents a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a (2-triofluoromethyl)phenyl group, a (3-triofluoromethyl)phenyl group, a (4-triofluoromethyl)phenyl group, a 2-nitrophenyl group, a 3-nitrophenyl group, a 4-nitrophenyl group, a 2-cyanophenyl group, a 3-cyanophenyl group, a 4-cyanophenyl group, a 2,6-difluorophenyl group, a 3,4-dichlorophenyl group, a 2,4-dichlorophenyl group, a 2-chloro-4-fluorophenyl group, a 2-chloro-4,5-difluorophenyl group, a 4-bromo-2-chlorophenyl group, a 2-bromo-4-chlorophenyl group, a 2-bromo-4-fluorophenyl group, a 2-chloro-4-nitrophenyl group, a 3,5-dicyanophenyl group, a 4-cyano-2-fluorophenyl group, a 2-chloro-4-cyanophenyl group, a pyridin-3-yl group, a 2-fluoropyridin-3-yl group, a 2-chloropyridin-3-yl group, a 2-bromopyridin-3-yl group, a 2-iodopyridin-3-yl group, a 2-(trifluoromethyl)pyridin-3-yl group, a 2-nitoropyridin-3-yl group, a 2-cyanopyridin-3-yl group, a 6-fluoropyridin-3-yl group, a 6-chloropyridin-3-yl group, a 6-bromopyridin-3-yl group, a 6-iodopyridin-3-yl group, a 6-(trifluoromethyl)pyridin-3-yl group, a 6-nitoropyridin-3-yl group, a 6-cyanopyridin-3-yl group, a 5-fluoropyridin-3-yl group, a 5-chloropyridin-3-yl group, a 5-bromopyridin-3-yl group, a 5-iodopyridin-3-yl group, a 5-(trifluoromethyl)pyridin-3-yl group, a 5-nitropyridin-3-yl group, a 5-cyanopyridin-3-yl group, a 4-fluoropyridin-3-yl group, a 4-chloropyridin-3-yl group, a 4-bromopyridin-3-yl group, a 4-iodopyridin-3-yl group, a 4-(trifluoromethyl)pyridin-3-yl group, a 4-nitropyridin-3-yl group, a 4-cyanopyridin-3-yl group, a 2,6-dichloropyridin-3-yl group, a pyridin-3-yl N-oxide group, a pyridin-4-yl group, a 2-chloropyridin-4-yl group, a 3-bromopyridin-4-yl group, a 3,5-dichloropyridin-4-yl group, a 3-(trifluoromethyl)pyridine-4-yl group, a 2,6-dicyanopyridin-4-yl group, a pyridin-4-yl N-oxide group, a pyridin-2-yl group, a 3-chloropyridin-2-yl group, a 4-bromopyridin-2-yl group, a 5-iodopyridin-2-yl group, a 6-chloropyridin-2-yl group, or a 4-cyanopyridin-2-yl group, <11> The amide derivative according to <10>, wherein the compound represented by Formula (8) is 3-benzamido-N-(2-bromo-6-chloro-4-(perfluoropropan-2-yl)phenyl)-2-fluorobenzamide, 2-chloro-N-(3-(2,6-dibromo-4-(perfluoropropan-2-yl)phenylcarbamoyl)-2-fluorophenyl)nicotinamide, 3-(4-cyano-N-methylbenzamido)-N-(2,6-dibromo-4-(perfluoropropan-2-yl)phenyl)-2-fluorobenzamide, 2-chloro-N-(3-(2,6-dibromo-4-(perfluoropropan-2-yl)phenylcarbamoyl)-2-fluorophenyl)-N-methylnicotinamide, 3-benzamido-N-(2,6-diiodo-4-(perfluoropropan-2-yl)phenyl)-2-fluorobenzamide, 3-benzamido-N-(2,6-dibromo-4-(perfluoropropan-2-yl)phenyl)-2-fluorobenzamide, N-(2,6-dibromo-4-(perfluoropropan-2-yl)phenyl)-2-fluoro-3-(N-methylbenzamido)benzamide, 6-chloro-N-(3-(2,6-dibromo-4-(perfluoropropan-2-yl)phenylcarbamoyl)-2-fluorophenyl)-N-methylnicotinamide, 3-(3-cyano-N-methylbenzamido)-N-(2,6-dibromo-4-(perfluoropropan-2-yl)phenyl)-2-fluorobenzamide, N-(2,6-dichloro-4-(perfluoropropan-2-yl)phenyl)-2-fluoro-3-(N-methylbenzamido)benzamide, 3-(4-cyano-N-methylbenzamido)-N-(2,6-dichloro-4-(perfluoropropan-2-yl)phenyl)-2-fluorobenzamide, 2-chloro-N-(3-(2,6-dichloro-4-(perfluoropropan-2-yl)phenylcarbamoyl)-2-fluorophenyl)-N-methylnicotinamide, N-(2,6-diiodo-4-(perfluoropropan-2-yl)phenyl)-2-fluoro-3-(N-methylbenzamido)benzamide, 3-(4-cyano-N-methylbenzamido)-N-(2,6-diiodo-4-(perfluoropropan-2-yl)phenyl)-2-fluorobenzamide, 3-benzamido-N-(2,6-dibromo-4-(perfluorobutan-2-yl)phenyl)-2-fluorobenzamide, N-(2,6-diiodo-4-(perfluoropropan-2-yl)phenyl)-2-fluoro-3-(2-fluorobenzamido)benzamide, N-(2,6-diiodo-4-(perfluoropropan-2-yl)phenyl)-2-fluoro-3-(4-fluorobenzamido)benzamide, 3-(2,6-difluorobenzamido)-N-(2,6-diiodo-4-(perfluoropropan-2-yl)phenyl)-2-fluorobenzamide, N-(2-bromo-6-iodo-4-(perfluoropropan-2-yl)phenyl)-2-fluoro-3-(N-methylbenzamido)benzamide, N-(3-(2-bromo-6-iodo-4-(perfluoropropan-2-yl)phenylcarbamoyl)-2-fluorophenyl)-2-chloro-N-methylnicotinamide, 3-(4-cyanobenzamido)-N-(2,6-dibromo-4-(perfluorobutan-2-yl)phenyl)-2-fluorobenzamide, 3-(3-cyanobenzamido)-N-(2,6-dibromo-4-(perfluorobutan-2-yl)phenyl)-2-fluorobenzamide, N-(2,6-dibromo-4-(perfluorobutan-2-yl)phenyl)-2-fluoro-3-(N-methylbenzamido)benzamide, 3-(4-cyano-N-methylbenzamido)-N-(2,6-dibromo-4-(perfluorobutan-2-yl)phenyl)-2-fluorobenzamide, 3-(3-cyano-N-methylbenzamido)-N-(2,6-dibromo-4-(perfluorobutan-2-yl)phenyl)-2-fluorobenzamide, 6-chloro-N-(3-(2,6-dibromo-4-(perfluorobutan-2-yl)phenylcarbamoyl)-2-fluorophenyl)-N-methylnicotinamide, 3-benzamido-N-(2,6-diiodo-4-(perfluorobutan-2-yl)phenyl)-2-fluorobenzamide, 3-(3-cyanobenzamido)-N-(2,6-diiodo-4-(perfluorobutan-2-yl)phenyl)-2-fluorobenzamide, 3-(4-cyanobenzamido)-N-(2,6-diiodo-4-(perfluorobutan-2-yl)phenyl)-2-fluorobenzamide, N-(2,6-diiodo-4-(perfluorobutan-2-yl)phenyl)-2-fluoro-3-(N-methylbenzamido)benzamide, 3-(3-cyano-N-methylbenzamido)-N-(2,6-diiodo-4-(perfluorobutan-2-yl)phenyl)-2-fluorobenzamide, 3-(4-cyano-N-methylbenzamido)-N-(2,6-diiodo-4-(perfluorobutan-2-yl)phenyl)-2-fluorobenzamide, 3-benzamido-N-(2,6-diiodo-4-(perfluorobutan-2-yl)phenyl)benzamide, 2-chloro-N-(3-(2,6-diiodo-4-(perfluorobutan-2-yl)phenylcarbamoyl)phenyl)nicotinamide, 6-chloro-N-(3-(2,6-diiodo-4-(perfluorobutan-2-yl)phenylcarbamoyl)phenyl)nicotinamide, 3-cyano-N-(3-(2,6-diiodo-4-(perfluorobutan-2-yl)phenylcarbamoyl)phenyl)benzamide, 3-(4-cyanobenzamido)-N-(2,6-diiodo-4-(perfluorobutan-2-yl)phenyl)benzamide, N-(3-(2,6-diiodo-4-(perfluorobutan-2-yl)phenylcarbamoyl)phenyl)-2-fluorobenzamide, N-(2,6-diiodo-4-(perfluorobutan-2-yl)phenyl)-3-(3-fluorobenzamido)benzamide, N-(2,6-diiodo-4-(perfluorobutan-2-yl)phenyl)-3-(4-fluorobenzamido)benzamide, N-(3-(2,6-diiodo-4-(perfluorobutan-2-yl)phenylcarbamoyl)phenyl)-2,6-difluorobenzamide, N-(3-(2,6-diiodo-4-(perfluorobutan-2-yl)phenylcarbamoyl)phenyl)-N-methylbenzamide, 2-chloro-N-(3-(2,6-diiodo-4-(perfluorobutan-2-yl)phenylcarbamoyl)phenyl)-N-methylnicotinamide, 6-chloro-N-(3-(2,6-diiodo-4-(perfluorobutan-2-yl)phenylcarbamoyl)phenyl)-N-methylnicotinamide, 3-cyano-N-(3-(2,6-diiodo-4-(perfluorobutan-2-yl)phenylcarbamoyl)phenyl)-N-methylbenzamide, 4-cyano-N-(3-(2,6-diiodo-4-(perfluorobutan-2-yl)phenylcarbamoyl)phenyl)-N-methylbenzamide, N-(3-(2,6-diiodo-4-(perfluorobutan-2-yl)phenylcarbamoyl)phenyl)-2-fluoro-N-methylbenzamide, N-(3-(2,6-diiodo-4-(perfluorobutan-2-yl)phenylcarbamoyl)phenyl)-3-fluoro-N-methylbenzamide, N-(3-(2,6-diiodo-4-(perfluorobutan-2-yl)phenylcarbamoyl)phenyl)-4-fluoro-N-methylbenzamide, N-(3-(2,6-diiodo-4-(perfluorobutan-2-yl)phenylcarbamoyl)phenyl)-2,6-difluoro-N-methylbenzamide, 2-chloro-N-(3-(2,6-diiodo-4-(perfluorobutan-2-yl)phenylcarbamoyl)-2-fluorophenyl)nicotinamide, 6-chloro-N-(3-(2,6-diiodo-4-(perfluorobutan-2-yl)phenylcarbamoyl)-2-fluorophenyl)nicotinamide, N-(2,6-diiodo-4-(perfluorobutan-2-yl)phenyl)-2-fluoro-3-(2-fluorobenzamido)benzamide, N-(2,6-diiodo-4-(perfluorobutan-2-yl)phenyl)-2-fluoro-3-(3-fluorobenzamido)benzamide, N-(2,6-diiodo-4-(perfluorobutan-2-yl)phenyl)-2-fluoro-3-(4-fluorobenzamido)benzamide, difluorobenzamido)-N-(2,6-diiodo-4-(perfluorobutan-2-yl)phenyl)-2-fluorobenzamide, 3-benzamido-N-(2,6-dibromo-4-(perfluorobutan-2-yl)phenyl)benzamide, 6-chloro-N-(3-(2,6-dibromo-4-(perfluorobutan-2-yl)phenylcarbamoyl)phenyl)nicotinamide, N-(3-(2,6-dibromo-4-(perfluorobutan-2-yl)phenylcarbamoyl)phenyl)-2-fluorobenzamide, 2-chloro-N-(3-(2,6-dibromo-4-(perfluorobutan-2-yl)phenylcarbamoyl)phenyl)nicotinamide, N-(2,6-dibromo-4-(perfluorobutan-2-yl)phenyl)-3-(3-fluorobenzamido)benzamide, N-(2,6-dibromo-4-(perfluorobutan-2-yl)phenyl)-3-(4-fluorobenzamido)benzamide, N-(3-(2,6-dibromo-4-(perfluorobutan-2-yl)phenylcarbamoyl)phenyl)-2,6-difluorobenzamide, 3-cyano-N-(3-(2,6-dibromo-4-(perfluorobutan-2-yl)phenylcarbamoyl)phenyl)benzamide, 3-(4-cyanobenzamido)-N-(2,6-dibromo-4-(perfluorobutan-2-yl)phenyl)benzamide, 2-chloro-N-(3-(2,6-diiodo-4-(perfluorobutan-2-yl)phenylcarbamoyl)-2-fluorophenyl)-N-methylnicotinamide, 6-chloro-N-(3-(2,6-diiodo-4-(perfluorobutan-2-yl)phenylcarbamoyl)-2-fluorophenyl)-N-methylnicotinamide, N-(3-(2,6-diiodo-4-(perfluorobutan-2-yl)phenylcarbamoyl)-2-fluorophenyl)-2-fluoro-N-methylbenzamide, N-(2,6-diiodo-4-(perfluorobutan-2-yl)phenyl)-2-fluoro-3-(3-fluoro-N-methylbenzamido)benzamide, N-(2,6-diiodo-4-

(perfluorobutan-2-yl)phenyl)-2-fluoro-3-(4-fluoro-N-methylbenzamido)benzamide, N-(3-(2,6-diiodo-4-(perfluorobutan-2-yl)phenylcarbamoyl)-2-fluorophenyl)-2,6-difluoro-N-methylbenzamide, N-(3-(2,6-dibromo-4-(perfluorobutan-2-yl)phenylcarbamoyl)phenyl)-N-methylbenzamide, 2-chloro-N-(3-(2,6-dibromo-4-(perfluorobutan-2-yl)phenylcarbamoyl)phenyl)-N-methylnicotinamide, 6-chloro-N-(3-(2,6-dibromo-4-(perfluorobutan-2-yl)phenylcarbamoyl)phenyl)-N-methylnicotinamide, 3-cyano-N-(3-(2,6-dibromo-4-(perfluorobutan-2-yl)phenylcarbamoyl)phenyl)-N-methylbenzamide, 4-cyano-N-(3-(2,6-dibromo-4-(perfluorobutan-2-yl)phenylcarbamoyl)phenyl)-N-methylbenzamide, N-(3-(2,6-dibromo-4-(perfluorobutan-2-yl)phenylcarbamoyl)phenyl)-2-fluoro-N-methylbenzamide, N-(3-(2,6-dibromo-4-(perfluorobutan-2-yl)phenylcarbamoyl)phenyl)-3-fluoro-N-methylbenzamide, N-(3-(2,6-dibromo-4-(perfluorobutan-2-yl)phenylcarbamoyl)phenyl)-4-fluoro-N-methylbenzamide, N-(3-(2,6-dibromo-4-(perfluorobutan-2-yl)phenylcarbamoyl)phenyl)-2,6-difluoro-N-methylbenzamide, 2-chloro-N-(3-(2,6-dibromo-4-(perfluorobutan-2-yl)phenylcarbamoyl)-2-fluorophenyl)nicotinamide, 6-chloro-N-(3-(2,6-dibromo-4-(perfluorobutan-2-yl)phenylcarbamoyl)-2-fluorophenyl)nicotinamide, N-(2,6-dibromo-4-(perfluorobutan-2-yl)phenyl)-2-fluoro-3-(2-fluorobenzamido)benzamide, N-(2,6-dibromo-4-(perfluorobutan-2-yl)phenyl)-2-fluoro-3-(3-fluorobenzamido)benzamide, N-(2,6-dibromo-4-(perfluorobutan-2-yl)phenyl)-2-fluoro-3-(4-fluorobenzamido)benzamide, N-(2,6-dibromo-4-(perfluorobutan-2-yl)phenyl)-3-(2,6-difluorobenzamido)-2-fluorobenzamide, 2-chloro-N-(3-(2,6-diiodo-4-(perfluoropropan-2-yl)phenylcarbamoyl)-2-fluorophenyl)nicotinamide, 6-chloro-N-(3-(2,6-diiodo-4-(perfluoropropan-2-yl)phenylcarbamoyl)-2-fluorophenyl)nicotinamide, 3-(3-cyanobenzamido)-N-(2,6-diiodo-4-(perfluoropropan-2-yl)phenyl)-2-fluorobenzamide, 3-(4-cyanobenzamido)-N-(2,6-diiodo-4-(perfluoropropan-2-yl)phenyl)-2-fluorobenzamide, N-(2,6-diiodo-4-(perfluoropropan-2-yl)phenyl)-2-fluoro-3-(3-fluorobenzamido)benzamide, 2-chloro-N-(3-(2,6-dibromo-4-(perfluorobutan-2-yl)phenylcarbamoyl)-2-fluorophenyl)-N-methylnicotinamide, N-(3-(2,6-dibromo-4-(perfluorobutan-2-yl)phenylcarbamoyl)-2-fluorophenyl)-2-fluoro-N-methylbenzamide, N-(3-(2,6-dibromo-4-(perfluorobutan-2-yl)phenylcarbamoyl)-2-fluoro-3-(3-fluoro-N-methylbenzamido)benzamide, N-(2,6-dibromo-4-(perfluorobutan-2-yl)phenyl)-2-fluoro-3-(4-fluoro-N-methylbenzamido)benzamide, N-(3-(2,6-dibromo-4-(perfluorobutan-2-yl)phenylcarbamoyl)-2-fluorophenyl)-2,6-difluoro-N-methylbenzamide, 3-(3-cyano-N-methylbenzamido)-N-(2,6-diiodo-4-(perfluoropropan-2-yl)phenyl)-2-fluorobenzamide, N-(3-(2,6-diiodo-4-(perfluoropropan-2-yl)phenylcarbamoyl)-2-fluorophenyl)-2-fluoro-N-methylbenzamide, N-(2,6-diiodo-4-(perfluoropropan-2-yl)phenyl)-2-fluoro-3-(3-fluoro-N-methylbenzamido)benzamide, 6-chloro-N-(3-(2,6-diiodo-4-(perfluoropropan-2-yl)phenylcarbamoyl)-2-fluorophenyl)-N-methylnicotinamide, N-(2,6-diiodo-4-(perfluoropropan-2-yl)phenyl)-2-fluoro-3-(4-fluoro-N-methylbenzamido)benzamide, N-(3-(2,6-diiodo-4-(perfluoropropan-2-yl)phenylcarbamoyl)-2-fluorophenyl)-2,6-difluoro-N-methylbenzamide, N-(2,6-dibromo-4-(perfluoropropan-2-yl)phenyl)-2-fluoro-3-(2-fluorobenzamido)benzamide, N-(2,6-dibromo-4-(perfluoropropan-2-yl)phenyl)-2-fluoro-3-(3-fluorobenzamido)benzamide, N-(2,6-dibromo-4-(perfluoropropan-2-yl)phenyl)-2-fluoro-3-(4-fluorobenzamido)benzamide, N-(2,6-dibromo-4-(perfluoropropan-2-yl)phenyl)-3-(2,6-difluorobenzamido)-2-fluorobenzamide, 6-chloro-N-(3-(2,6-dibromo-4-(perfluoropropan-2-yl)phenylcarbamoyl)-2-fluorophenyl)nicotinamide, 3-(3-cyanobenzamido)-N-(2,6-dibromo-4-(perfluoropropan-2-yl)phenyl)-2-fluorobenzamide, 3-(4-cyanobenzamido)-N-(2,6-dibromo-4-(perfluoropropan-2-yl)phenyl)-2-fluorobenzamide, 2-chloro-N-(3-(2,6-diiodo-4-(perfluoropropan-2-yl)phenylcarbamoyl)-2-fluorophenyl)-N-methylnicotinamide, N-(3-(2,6-dibromo-4-(perfluoropropan-2-yl)phenylcarbamoyl)-2-fluorophenyl)-2-fluoro-N-methylbenzamide, N-(2,6-dibromo-4-(perfluoropropan-2-yl)phenyl)-2-fluoro-3-(3-fluoro-N-methylbenzamido)benzamide, N-(2,6-dibromo-4-(perfluoropropan-2-yl)phenyl)-2-fluoro-3-(4-fluoro-N-methylbenzamido)benzamide, N-(3-(2,6-dibromo-4-(perfluoropropan-2-yl)phenylcarbamoyl)-2-fluorophenyl)-2,6-difluoro-N-methylbenzamide, 3-benzamido-N-(2-bromo-4-(perfluoropropan-2-yl)-6-(trifluoromethoxy)phenyl)-2-fluorobenzamide, N-(3-(2-bromo-4-(perfluoropropan-2-yl)-6-(trifluoromethoxy)phenylcarbamoyl)-2-fluorophenyl)-2-chloronicotinamide, N-(2-bromo-4-(perfluoropropan-2-yl)-6-(trifluoromethoxy)phenyl)-3-(4-cyanobenzamido)-2-fluorobenzamide, 3-benzamido-N-(2-bromo-4-(perfluoropropan-2-yl)-6-(trifluoromethyl)phenyl)benzamide, N-(3-(2-bromo-4-(perfluoropropan-2-yl)-6-(trifluoromethyl)phenylcarbamoyl)phenyl)-2-chloronicotinamide, N-(3-(2-bromo-4-(perfluoropropan-2-yl)-6-(trifluoromethyl)phenylcarbamoyl)phenyl)-N-methylbenzamide, N-(3-(2-bromo-4-(perfluoropropan-2-yl)-6-(trifluoromethyl)phenylcarbamoyl)phenyl)-2-chloro-N-methylnicotinamide, 3-benzamido-N-(2-chloro-4-(perfluoropropan-2-yl)-6-(trifluoromethyl)phenyl)benzamide, 2-chloro-N-(3-(2-chloro-4-(perfluoropropan-2-yl)-6-(trifluoromethyl)phenylcarbamoyl)phenyl)nicotinamide, N-(2-bromo-4-(perfluoropropan-2-yl)-6-(trifluoromethyl)phenyl)-3-(3-cyanobenzamido)benzamide, N-(2-bromo-4-(perfluoropropan-2-yl)-6-(trifluoromethyl)phenyl)-3-(4-cyanobenzamido)benzamide, N-(3-(2-bromo-4-(perfluoropropan-2-yl)-6-(trifluoromethyl)phenylcarbamoyl)phenyl)-3-cyano-N-methylbenzamide, N-(3-(2-bromo-4-(perfluoropropan-2-yl)-6-(trifluoromethyl)phenylcarbamoyl)phenyl)-4-cyano-N-methylbenzamide, N-(3-(2-bromo-4-(perfluoropropan-2-yl)-6-(trifluoromethyl)phenylcarbamoyl)phenyl)-2-fluoro-N-methylnicotinamide, N-(3-(2-bromo-4-(perfluoropropan-2-yl)-6-(trifluoromethyl)phenylcarbamoyl)phenyl)-N-methyl-4-nitrobenzamide, N-(3-(2-bromo-4-(perfluoropropan-2-yl)-6-(trifluoromethyl)phenylcarbamoyl)phenyl)-6-chloro-N-methylnicotinamide, N-(3-(2-bromo-4-(perfluoropropan-2-yl)-6-(trifluoromethyl)phenylcarbamoyl)phenyl)-6-cyano-N-methylnicotinamide, N-(3-(2-bromo-4-(perfluoropropan-2-yl)-6-(trifluoromethyl)phenylcarbamoyl)phenyl)-N-methyl-3-nitrobenzamide, N-(2-bromo-4-(perfluoropropan-2-yl)-6-(trifluoromethyl)phenyl)-N-methyl-3-(N-methylbenzamido)benzamide, N-(3-(2-bromo-4-(perfluoropropan-2-yl)-6-(trifluoromethyl)phenyl)(methyl)carbamoyl)phenyl)-2-chloro-N-methylnicotinamide, 2-bromo-N-(3-(2-bromo-4-(perfluoropropan-2-yl)-6-(trifluoromethyl)phenylcarbamoyl)phenyl)nicotinamide, 2-chloro-N-(3-(2-chloro-4-(perfluoropropan-2-yl)-6-(trifluoromethyl)phenylcarbamoyl)phenyl)-N-methylnicotinamide, N-(3-(2-chloro-4-(perfluoropropan-2-yl)-6-(trifluoromethyl)phenylcarbamoyl)phenyl)-4-cyano-N- methylbenzamide, 3-benzamido-N-(2-bromo-4-(perfluoropropan-2-yl)-6-(trifluoromethyl)phenyl)-4-fluorobenzamide, N-(5-(2-bromo-4-(perfluoropropan-2-yl)-6-(trifluoromethyl)phenylcarbamoyl)-2-fluorophenyl)-2-chloronicotinamide, N-(3-((2-bromo-4-(perfluoropropan-2-yl)-6-(trifluoromethyl)phenyl)(methyl)carbamoyl)phenyl)-2-chloronicotinamide, N-(2-bromo-4-(perfluoropropan-2-yl)-6-(trifluoromethyl)phenyl)-4-fluoro-3-(N-methylbenzamido)benzamide, N-(2-bromo-4-(perfluoropropan-2-yl)-6-(trifluoromethyl)phenyl)-3-(4-cyano-N-methylbenzamido)-4-fluorobenzamide, N-(5-(2-bromo-4-(perfluoropropan-2-yl)-6-(trifluoromethyl)phenylcarbamoyl)-2-fluorophenyl)-2-chloro-N-methylnicotinamide, 3-benzamido-N-(4-(perfluoropropan-2-yl)-2,6-bis(trifluoromethyl)phenyl)benzamide, 2-chloro-N-(3-(4-(perfluoropropan-2-yl)-2,6-bis(trifluoromethyl)phenylcarbamoyl)phenyl)nicotinamide, N-methyl-N-(3-(4-(perfluoropropan-2-yl)-2,6-bis(trifluoromethyl)phenylcarbamoyl)phenyl)benzamide, 2-chloro-N-methyl-N-(3-(4-(perfluoropropan-2-yl)-2,6-bis(trifluoromethyl)phenylcarbamoyl)phenyl)nicotinamide, 3-benzamido-N-(2-bromo-4-(perfluoropropan-2-yl)-6-(trifluoromethyl)phenyl)-N-methylbenzamide, N-(2-bromo-4-(perfluoropropan-2-yl)-6-(trifluoromethyl)phenyl)-3-(3-cyanobenzamido)-N-methylbenzamide, N-(2-bromo-4-(perfluoropropan-2-yl)-6-(trifluoromethyl)phenyl)-3-(4-cyanobenzamido)-N-methylbenzamide, N-(2-bromo-4-(perfluoropropan-2-yl)-6-(trifluoromethyl)phenyl)-3-(3-cyano-N-methylbenzamido)-N-methylbenzamide, N-(2-bromo-4-(perfluoropropan-2-yl)-6-(trifluoromethyl)phenyl)-3-(4-cyano-N-methylbenzamido)-N-methylbenzamide, 2-bromo-N-(3-(2-bromo-4-(perfluoropropan-2-yl)-6-(trifluoromethyl)phenylcarbamoyl)phenyl)-N-methylnicotinamide, 3-benzamido-N-(2-bromo-4-(perfluoropropan-2-yl)-6-(trifluoromethyl)phenyl)-2-fluorobenzamide, 2-bromo-N-(3-((2-bromo-4-(perfluoropropan-2-yl)-6-(trifluoromethyl)phenyl)(methyl)carbamoyl)phenyl)nicotinamide, N-(3-(2-bromo-4-(perfluoropropan-2-yl)-6-(trifluoromethyl)phenylcarbamoyl)-2-fluorophenyl)-2-chloronicotinamide, 3-benzamido-N-(2-iodo-4-(perfluoropropan-2-yl)-6-(trifluoromethyl)phenyl)benzamide, 2-chloro-N-(3-(2-iodo-4-(perfluoropropan-2-yl)-6-(trifluoromethyl)phenylcarbamoyl)phenyl)nicotinamide, N-(3-(2-bromo-4-(perfluoropropan-2-yl)-6-(trifluoromethyl)phenylcarbamoyl)phenyl)-4-cyano-2-fluoro-N-methylbenzamide, N-(3-(2-bromo-4-(perfluoropropan-2-yl)-6-(trifluoromethyl)phenylcarbamoyl)phenyl)-4-cyano-2-fluorobenzamide, 3-cyano-N-(3-(4-(perfluoropropan-2-yl)-2,6-bis(trifluoromethyl)phenylcarbamoyl)phenyl)benzamide, 3-(4-cyanobenzamido)-N-(4-(perfluoropropan-2-yl)-2,6-bis(trifluoromethyl)phenyl)benzamide, 3-cyano-N-methyl-N-(3-(4-(perfluoropropan-2-yl)-2,6-bis(trifluoromethyl)phenylcarbamoyl)phenyl)benzamide, 4-cyano-N-methyl-N-(3-(4-(perfluoropropan-2-yl)-2,6-bis(trifluoromethyl)phenylcarbamoyl)phenyl)benzamide, N-(2-bromo-4-(perfluoropropan-2-yl)-6-(trifluoromethyl)phenyl)-3-(4-cyanobenzamido)-2-fluorobenzamide, N-(3-(2-bromo-4-(perfluoropropan-2-yl)-6-(trifluoromethyl)phenylcarbamoyl)-2-fluorophenyl)-2-chloro-N-methylnicotinamide, N-(2-bromo-4-(perfluoropropan-2-yl)-6-(trifluoromethyl)phenyl)-3-(4-cyano-N-methylbenzamido)-2-fluorobenzamide, N-(2-bromo-4-(perfluoropropan-2-yl)-6-(trifluoromethyl)phenyl)-2-fluoro-3-(N-methylbenzamido)benzamide, N-(2-bromo-4-(perfluoropropan-2-yl)-6-(trifluoromethyl)phenyl)-3-(3-cyano-N-methylbenzamido)-2-fluorobenzamide, N-(3-(2-bromo-4-(perfluoropropan-2-yl)-6-(trifluoromethyl)phenylcarbamoyl)phenyl)-2-chloro-4-cyano-N-methylbenzamide, 3-benzamido-N-methyl-N-(4-(perfluoropropan-2-yl)-2,6-bis(trifluoromethyl)phenyl)benzamide, 2-chloro-N-(3-(methyl(4-(perfluoropropan-2-yl)-2,6-bis(trifluoromethyl)phenyl)carbamoyl)phenyl)nicotinamide, 3-(3-cyanobenzamido)-N-methyl-N-(4-(perfluoropropan-2-yl)-2,6-bis(trifluoromethyl)phenyl)benzamide, 2-bromo-N-(3-(methyl(4-(perfluoropropan-2-yl)-2,6-bis(trifluoromethyl)phenyl)carbamoyl)phenyl)nicotinamide, 2-bromo-N-(3-(4-(perfluoropropan-2-yl)-2,6-bis(trifluoromethyl)phenylcarbamoyl)phenyl)nicotinamide, 2-bromo-N-methyl-N-(3-(4-(perfluoropropan-2-yl)-2,6-bis(trifluoromethyl)phenylcarbamoyl)phenyl)nicotinamide, 3-(4-cyanobenzamido)-N-(2-iodo-4-(perfluoropropan-2-yl)-6-(trifluoromethyl)phenyl)benzamide, 3-cyano-N-(3-(2-iodo-4-(perfluoropropan-2-yl)-6-(trifluoromethyl)phenylcarbamoyl)phenyl)benzamide, 2-bromo-N-(3-(2-iodo-4-(perfluoropropan-2-yl)-6-(trifluoromethyl)phenylcarbamoyl)phenyl)nicotinamide, 4-cyano-N-(3-(2-iodo-4-(perfluoropropan-2-yl)-6-(trifluoromethyl)phenylcarbamoyl)phenyl)-N-methylbenzamide, 2-chloro-N-(3-(2-iodo-4-(perfluoropropan-2-yl)-6-(trifluoromethyl)phenylcarbamoyl)phenyl)-N-methylnicotinamide, N-(3-(2-bromo-4-(perfluoropropan-2-yl)-6-(trifluoromethyl)phenylcarbamoyl)phenyl)-2-iodonicotinamide, N-(2-bromo-4-(perfluoropropan-2-yl)-6-(trifluoromethyl)phenylcarbamoyl)-2-fluorophenyl)-N-methylnicotinamide, N-(3-(2-bromo-4-(perfluoropropan-2-yl)-6-(trifluoromethyl)phenylcarbamoyl)-2-fluorophenyl)-6-fluoro-N-methylnicotinamide, N-(3-(2-bromo-4-(perfluoropropan-2-yl)-6-(trifluoromethyl)phenylcarbamoyl)-2-fluorophenyl)-4-cyano-2-fluoro-N-methylbenzamide, N-(3-(2-bromo-4-(perfluoropropan-2-yl)-6-(trifluoromethyl)phenylcarbamoyl)-2-fluorophenyl)-6-chloro-N-methylnicotinamide, N-(3-(2-bromo-4-(perfluoropropan-2-yl)-6-(trifluoromethyl)phenylcarbamoyl)-2-fluorophenyl)-3,5-dicyano-N-methylbenzamide, 3-benzamido-2-fluoro-N-(4-(perfluoropropan-2-yl)-2,6-bis(trifluoromethyl)phenyl)benzamide, N-(3-(2-bromo-4-(perfluoropropan-2-yl)-6-(trifluoromethyl)phenylcarbamoyl)phenyl)-3,5-dicyano-N-methylbenzamide, 3-benzamido-2-fluoro-N-(2-iodo-4-(perfluoropropan-2-yl)-6-(trifluoromethyl)phenyl)benzamide, 2-chloro-N-(2-fluoro-3-(2-iodo-4-(perfluoropropan-2-yl)-6-(trifluoromethyl)phenylcarbamoyl)phenyl)nicotinamide, 3-benzamido-N-(2-bromo-6-(perfluoroethyl)-4-(perfluoropropan-2-yl)phenyl)-2-fluorobenzamide, 3-benzamido-N-(2-bromo-4-(perfluorobutan-2-yl)-6-(trifluoromethyl)phenyl)-2-fluorobenzamide, N-(3-(2-bromo-4-(perfluorobutan-2-yl)-6-(trifluoromethyl)phenylcarbamoyl)-2-fluorophenyl)-2-chloronicotinamide, N-(2-bromo-6-(perfluoroethyl)-4-(perfluoropropan-2-yl)phenyl)-3-(4-cyanobenzamido)-2-fluorobenzamide, N-(2-bromo-4-(perfluorobutan-2-yl)-6-(trifluoromethyl)phenyl)-2-fluoro-3-(N-methylbenzamido)benzamide, N-(2-bromo-4-(perfluorobutan-2-yl)-6-(trifluoromethyl)phenyl)-3-(3-cyano-N-methylbenzamido)-2-fluorobenzamide, N-(2-bromo-4-(perfluorobutan-2-yl)-6-(trifluoromethyl)phenyl)-3-(4-cyano-N-methylbenzamido)-2-fluorobenzamide, 2-fluoro-N-(2-iodo-4-(perfluoropropan-2-yl)-6-(trifluoromethyl)phenyl)-3-(N-methylbenzamido)benzamide, 3-(4-cyano-N-methylbenzamido)-2-fluoro-N-(2-iodo-4-(perfluoropropan-2-yl)-6-(trifluoromethyl)phenyl)benzamide, N-(3-(2-bromo-4-(perfluorobutan-2-yl)-6-(trifluoromethyl)phenylcarbamoyl)phenyl)-N-methylbenzamide, 3-benzamido-N-(2-bromo-4-(perfluorobutan-2-yl)-6-(trifluoromethyl)phenyl)benzamide, 3-benzamido-2-fluoro-N-(2-iodo-4-(perfluorobutan-2-yl)-6-(trifluoromethyl)phenyl)benzamide, 2-fluoro-N-(2-iodo-4-(perfluorobutan-2-yl)-6-(trifluoromethyl)phenyl)-3-(N-methylbenzamido)benzamide, 3-(4-cyano-N-methylbenzamido)-2-fluoro-N-(2-iodo-4-(perfluorobutan-2-yl)-6-(trifluoromethyl)phenyl)benzamide, 3-(3-cyano-N-methylbenzamido)-2-fluoro-N-(2-iodo-4-(perfluoropropan-2-yl)-6-(trifluoromethyl)phenyl)benzamide, 2-fluoro-N-(2-fluoro-3-(2-iodo-4-(perfluoropropan-2-yl)-6-(trifluoromethyl)phenylcarbamoyl)phenyl)-N-methylbenzamide, 2-fluoro-3-(3-fluoro-N-methylbenzamido)-N-(2-iodo-4-(perfluoropropan-2-yl)-6-(trifluoromethyl)phenyl)benzamide, 2-fluoro-3-(4-fluoro-N-methylbenzamido)-N-(2-iodo-4-(perfluoropropan-2-yl)-6-(trifluoromethyl)phenyl)benzamide, 2,6-difluoro-N-(2-fluoro-3-(2-iodo-4-(perfluoropropan-2-yl)-6-(trifluoromethyl)phenylcarbamoyl)phenyl)-N-methylbenzamide, 6-chloro-N-(2-fluoro-3-(2-iodo-4-(perfluoropropan-2-yl)-6-(trifluoromethyl)phenylcarbamoyl)phenyl)nicotinamide, 3-(3-cyanobenzamido)-2-fluoro-N-(2-iodo-4-(perfluoropropan-2-yl)-6-(trifluoromethyl)phenyl)benzamide, 3-(4-cyanobenzamido)-2-fluoro-N-(2-iodo-4-(perfluoropropan-2-yl)-6-(trifluoromethyl)phenyl)benzamide, 2-fluoro-3-(2-fluorobenzamido)-N-(2-iodo-4-(perfluoropropan-2-yl)-6-(trifluoromethyl)phenyl)benzamide, 2-fluoro-3-(3-fluorobenzamido)-N-(2-iodo-4-(perfluoropropan-2-yl)-6-(trifluoromethyl)phenyl)benzamide, N-(3-(2-bromo-4-(perfluoropropan-2-yl)-6-(trifluoromethyl)phenylcarbamoyl)-2-fluorophenyl)-2-fluoro-N-methylbenzamide, N-(3-(2-bromo-4-(perfluoropropan-2-yl)-6-(trifluoromethyl)phenylcarbamoyl)-2-fluorophenyl)-2,6-difluoro-N-methylbenzamide, N-(2-bromo-4-(perfluoropropan-2-yl)-6-(trifluoromethyl)phenyl)-2-fluoro-3-(3-fluoro-N-methylbenzamido)benzamide, N-(2-bromo-4-(perfluoropropan-2-yl)-6-(trifluoromethyl)phenyl)-2-fluoro-3-(4-fluoro-N-methylbenzamido)benzamide, N-(3-(2-bromo-4-(perfluoropropan-2-yl)-6-(trifluoromethyl)phenylcarbamoyl)-2-fluorophenyl)-2-chloronicotinamide, N-(3-(2-bromo-4-(perfluoropropan-2-yl)-6-(trifluoromethyl)phenylcarbamoyl)-2-fluorophenyl)-6-chloronicotinamide, N-(2-bromo-4-(perfluoropropan-2-yl)-6-(trifluoromethyl)phenyl)-3-(3-cyanobenzamido)-2-fluorobenzamide, N-(2-bromo-4-(perfluoropropan-2-yl)-6-(trifluoromethyl)phenyl)-2-fluoro-3-(2-fluorobenzamido)benzamide, N-(2-bromo-4-(perfluoropropan-2-yl)-6-(trifluoromethyl)phenyl)-2-fluoro-3-(3-fluorobenzamido)benzamide, N-(2-bromo-4-(perfluoropropan-2-yl)-6-(trifluoromethyl)phenyl)-2-fluoro-3-(4-fluorobenzamido)benzamide, N-(3-(2-bromo-4-(perfluoropropan-2-yl)-6-(trifluoromethyl)phenylcarbamoyl)-2-fluorophenyl)-N-methylnicotinamide, 2-chloro-N-(2-fluoro-3-(2-iodo-4-(perfluoropropan-2-yl)-6-(trifluoromethyl)phenylcarbamoyl)phenyl)-N-methylnicotinamide, 2-fluoro-3-(4-fluorobenzamido)-N-(2-iodo-4-(perfluoropropan-2-yl)-6-(trifluoromethyl)phenyl)benzamide, 3-(2,6-difluorobenzamido)-2-fluoro-N-(2-iodo-4-(perfluoropropan-2-yl)-6-(trifluoromethyl)phenyl)benzamide, 6-chloro-N-(2-fluoro-3-(2-iodo-4-(perfluoropropan-2-yl)-6-(trifluoromethyl)phenylcarbamoyl)phenyl)-N-methylnicotinamide, N-(3-(2-bromo-4-(perfluoropropan-2-yl)-6-(trifluoromethyl)phenylcarbamoyl)phenyl)-6-chloronicotinamide, N-(3-(2-bromo-4-(perfluoropropan-2-yl)-6-(trifluoromethyl)phenylcarbamoyl)phenyl)-2-fluorobenzamide, N-(2-bromo-4-(perfluoropropan-2-yl)-6-(trifluoromethyl)phenyl)-3-(3-fluorobenzamido)benzamide, N-(2-bromo-4-(perfluoropropan-2-yl)-6-(trifluoromethyl)phenyl)-3-(4-fluorobenzamido)benzamide, N-(3-(2-bromo-4-(perfluoropropan-2-yl)-6-(trifluoromethyl)phenylcarbamoyl)phenyl)-2,6-difluorobenzamide, N-(2-bromo-4-(perfluoropropan-2-yl)-6-(trifluoromethyl)phenyl)-3-(2,6-difluorobenzamido)-2-fluorobenzamide, 3-fluoro-N-(3-(2-iodo-4-(perfluoropropan-2-yl)-6-(trifluoromethyl)phenylcarbamoyl)phenyl)benzamide, 3-(4-fluorobenzamido)-N-(2-iodo-4-(perfluoropropan-2-yl)-6-(trifluoromethyl)phenyl)benzamide, 2-fluoro-N-(3-(2-iodo-4-(perfluoropropan-2-yl)-6-(trifluoromethyl)phenylcarbamoyl)phenyl)benzamide, 2,6-difluoro-N-(3-(2-iodo-4-(perfluoropropan-2-yl)-6-(trifluoromethyl)phenylcarbamoyl)phenyl)benzamide, 6-chloro-N-(3-(2-iodo-4-(perfluoropropan-2-yl)-6-(trifluoromethyl)phenylcarbamoyl)phenyl)nicotinamide, 6-chloro-N-(3-(2-iodo-4-(perfluoropropan-2-yl)-6-(trifluoromethyl)phenylcarbamoyl)phenyl)-N-methylnicotinamide, 3-cyano-N-(3-(2-iodo-4-(perfluoropropan-2-yl)-6-(trifluoromethyl)phenylcarbamoyl)phenyl)-N-methylbenzamide, 2-fluoro-N-(3-(2-iodo-4-(perfluoropropan-2-yl)-6-(trifluoromethyl)phenylcarbamoyl)phenyl)-N-methylbenzamide, 3-fluoro-N-(3-(2-iodo-4-(perfluoropropan-2-yl)-6-(trifluoromethyl)phenylcarbamoyl)phenyl)-N-methylbenzamide, 4-fluoro-N-(3-(2-iodo-4-(perfluoropropan-2-yl)-6-(trifluoromethyl)phenylcarbamoyl)phenyl)-N-methylbenzamide, N-(3-(2-bromo-4-(perfluoropropan-2-yl)-6-(trifluoromethyl)phenylcarbamoyl)phenyl)-2-fluoro-N-methylbenzamide, N-(3-(2-bromo-4-(perfluoropropan-2-yl)-6-(trifluoromethyl)phenylcarbamoyl)phenyl)-3-fluoro-N-methylbenzamide, N-(3-(2-bromo-4-(perfluoropropan-2-yl)-6-(trifluoromethyl)phenylcarbamoyl)phenyl)-4-fluoro-N-methylbenzamide, N-(3-(2-bromo-4-(perfluoropropan-2-yl)-6-(trifluoromethyl)phenylcarbamoyl)phenyl)-2,6-difluoro-N-methylbenzamide, 2,4-dichloro-N-(3-(2-iodo-4-(perfluoropropan-2-yl)-6-(trifluoromethyl)phenylcarbamoyl)phenyl)benzamide, 3-(2,4-dichlorobenzamido)-2-fluoro-N-(2-iodo-4-(perfluoropropan-2-yl)-6-(trifluoromethyl)phenyl)benzamide, 2,6-difluoro-N-(3-(2-iodo-4-(perfluoropropan-2-yl)-6-(trifluoromethyl)phenylcarbamoyl)phenyl)-N-methylbenzamide, 3-(2-chloro-4-fluorobenzamido)-2-fluoro-N-(2-iodo-4-(perfluoropropan-2-yl)-6-(trifluoromethyl)phenyl)benzamide, N-(3-(2-iodo-4-(perfluoropropan-2-yl)-6-(trifluoromethyl)phenylcarbamoyl)phenyl)-N-methylbenzamide, 3-benzamido-N-(2-iodo-4-(perfluorobutan-2-yl)-6-(trifluoromethyl)phenyl)benzamide, 2-chloro-N-(3-(2-iodo-4-(perfluorobutan-2-yl)-6-(trifluoromethyl)phenylcarbamoyl)phenyl)nicotinamide, 6-chloro-N-(3-(2-iodo-4-(perfluorobutan-2-yl)-6-(trifluoromethyl)phenylcarbamoyl)phenyl)nicotinamide, 3-cyano-N-(3-(2-iodo-4-(perfluorobutan-2-yl)-6-(trifluoromethyl)phenylcarbamoyl)phenyl)benzamide, 3-(4-cyanobenzamido)-N-(2-iodo-4-(perfluorobutan-2-yl)-6-(trifluoromethyl)phenyl)benzamide, 2-fluoro-N-(3-(2-iodo-4-(perfluorobutan-2-yl)-6-(trifluoromethyl)phenylcarbamoyl)phenyl)benzamide, 3-fluoro-N-(3-(2-iodo-4-(perfluorobutan-2-yl)-6-(trifluoromethyl)phenylcarbamoyl)phenyl)benzamide, 3-(4-fluorobenzamido)-N-(2-iodo-4-(perfluorobutan-2-yl)-6-(trifluoromethyl)phenyl)benzamide, 2,6-difluoro-N-(3-(2-iodo-4-(perfluorobutan-2-yl)-6-(trifluoromethyl)phenylcarbamoyl)phenyl)benzamide, N-(3-(2-iodo-4-(perfluorobutan-2-yl)-6-(trifluoromethyl)phenylcarbamoyl)phenyl)-N-methylbenzamide, 2-chloro-N-(3-(2-iodo-4-(perfluorobutan-2-yl)-6-(trifluoromethyl)phenylcarbamoyl)phenyl)-N-methylnicotinamide, 3-cyano-N-(3-(2-iodo-4-(perfluorobutan-2-yl)-6-(trifluoromethyl)phenylcarbamoyl)phenyl)-N-methylbenzamide, 4-cyano-N-

(3-(2-iodo-4-(perfluorobutan-2-yl)-6-(trifluoromethyl)phenylcarbamoyl)phenyl)-N-methylbenzamide,
3-fluoro-N-(3-(2-iodo-4-(perfluorobutan-2-yl)-6-(trifluoromethyl)phenylcarbamoyl)phenyl)-N-methylbenzamide, 4-fluoro-N-(3-(2-iodo-4-(perfluorobutan-2-yl)-6-(trifluoromethyl)phenylcarbamoyl)phenyl)-N-methylbenzamide, N-(3-(2-bromo-4-(perfluoropropan-2-yl)-6-(trifluoromethyl)phenylcarbamoyl)-2-fluorophenyl)-N-methylisonicotinamide, 3-((3-(2-bromo-4-(perfluoropropan-2-yl)-6-(trifluoromethyl)phenylcarbamoyl)-2-fluorophenyl)(methyl)carbamoyl)pyridine 1-oxide, 4-((3-(2-bromo-4-(perfluoropropan-2-yl)-6-(trifluoromethyl)phenylcarbamoyl)-2-fluorophenyl)(methyl)carbamoyl)pyridine 1-oxide, 2-chloro-4-fluoro-N-(3-(2-iodo-4-(perfluoropropan-2-yl)-6-(trifluoromethyl)phenylcarbamoyl)phenyl)benzamide, N-(3-(2-bromo-4-(perfluorobutan-2-yl)-6-(trifluoromethyl)phenylcarbamoyl)phenyl)-2-chloronicotinamide, N-(2-bromo-4-(perfluorobutan-2-yl)-6-(trifluoromethyl)phenyl)-3-(3-cyanobenzamido)benzamide, N-(3-(2-bromo-4-(perfluorobutan-2-yl)-6-(trifluoromethyl)phenylcarbamoyl)phenyl)-2-fluorobenzamide, N-(2-bromo-4-(perfluorobutan-2-yl)-6-(trifluoromethyl)phenyl)-3-(3-fluorobenzamido)benzamide, N-(3-(2-bromo-4-(perfluorobutan-2-yl)-6-(trifluoromethyl)phenylcarbamoyl)phenyl)-6-chloronicotinamide, N-(2-bromo-4-(perfluorobutan-2-yl)-6-(trifluoromethyl)phenyl)-3-(4-cyanobenzamido)benzamide, N-(2-bromo-4-(perfluorobutan-2-yl)-6-(trifluoromethyl)phenyl)-3-(4-fluorobenzamido)benzamide, N-(3-(2-bromo-4-(perfluorobutan-2-yl)-6-(trifluoromethyl)phenylcarbamoyl)phenyl)-2,6-difluorobenzamide, N-(3-(2-bromo-4-(perfluorobutan-2-yl)-6-(trifluoromethyl)phenylcarbamoyl)phenyl)-2-chloro-N-methylnicotinamide, N-(3-(2-bromo-4-(perfluorobutan-2-yl)-6-(trifluoromethyl)phenylcarbamoyl)phenyl)-3-cyano-N-methylbenzamide, N-(3-(2-bromo-4-(perfluorobutan-2-yl)-6-(trifluoromethyl)phenylcarbamoyl)phenyl)-2-fluoro-N-methylbenzamide, N-(3-(2-bromo-4-(perfluorobutan-2-yl)-6-(trifluoromethyl)phenylcarbamoyl)phenyl)-3-fluoro-N-methylbenzamide, N-(3-(2-bromo-4-(perfluorobutan-2-yl)-6-(trifluoromethyl)phenylcarbamoyl)phenyl)-6-chloro-N-methylnicotinamide, N-(3-(2-bromo-4-(perfluorobutan-2-yl)-6-(trifluoromethyl)phenylcarbamoyl)phenyl)-4-cyano-N-methylbenzamide,
N-(3-(2-bromo-4-(perfluorobutan-2-yl)-6-(trifluoromethyl)phenylcarbamoyl)phenyl)-4-fluoro-N-methylbenzamide, N-(3-(2-bromo-4-(perfluorobutan-2-yl)-6-(trifluoromethyl)phenylcarbamoyl)phenyl)-2,6-difluoro-N-methylbenzamide, 6-chloro-N-(2-fluoro-3-(2-iodo-4-(perfluorobutan-2-yl)-6-(trifluoromethyl)phenylcarbamoyl)phenyl)nicotinamide, 3-(3-cyanobenzamido)-2-fluoro-N-(2-iodo-4-(perfluorobutan-2-yl)-6-(trifluoromethyl)phenyl)benzamide, 3-(4-cyanobenzamido)-2-fluoro-N-(2-iodo-4-(perfluorobutan-2-yl)-6-(trifluoromethyl)phenyl)benzamide, 2-fluoro-3-(2-fluorobenzamido)-N-(2-iodo-4-(perfluorobutan-2-yl)-6-(trifluoromethyl)phenyl)benzamide, 2-fluoro-3-(3-fluorobenzamido)-N-(2-iodo-4-(perfluorobutan-2-yl)-6-(trifluoromethyl)phenyl)benzamide, 2-fluoro-3-(4-fluorobenzamido)-N-(2-iodo-4-(perfluorobutan-2-yl)-6-(trifluoromethyl)phenyl)benzamide, 3-(2,6-difluorobenzamido)-2-fluoro-N-(2-iodo-4-(perfluorobutan-2-yl)-6-(trifluoromethyl)phenyl)benzamide, N-(3-(2-bromo-4-(perfluorobutan-2-yl)-6-(trifluoromethyl)phenylcarbamoyl)-2-fluorophenyl)-6-chloronicotinamide, N-(2-bromo-4-(perfluorobutan-2-yl)-6-(trifluoromethyl)phenyl)-3-(3-cyanobenzamido)-2-fluorobenzamide, N-(2-bromo-4-(perfluorobutan-2-yl)-6-(trifluoromethyl)phenyl)-3-(4-cyanobenzamido)-2-fluorobenzamide, N-(2-bromo-4-(perfluorobutan-2-yl)-6-(trifluoromethyl)phenyl)-2-fluoro-3-(2-fluorobenzamido)benzamide, N-(2-bromo-4-(perfluorobutan-2-yl)-6-(trifluoromethyl)phenyl)-2-fluoro-3-(3-fluorobenzamido)benzamide, N-(2-bromo-4-(perfluorobutan-2-yl)-6-(trifluoromethyl)phenyl)-2-fluoro-3-(4-fluorobenzamido)benzamide, N-(2-bromo-4-(perfluorobutan-2-yl)-6-(trifluoromethyl)phenyl)-3-(2,6-difluorobenzamido)-2-fluorobenzamide, 2-chloro-N-(2-fluoro-3-(2-iodo-4-(perfluorobutan-2-yl)-6-(trifluoromethyl)phenylcarbamoyl)phenyl)-N-methylnicotinamide, 6-chloro-N-(2-fluoro-3-(2-iodo-4-(perfluorobutan-2-yl)-6-(trifluoromethyl)phenylcarbamoyl)phenyl)-N-methylnicotinamide, 3-(3-cyano-N-methylbenzamido)-2-fluoro-N-(2-iodo-4-(perfluorobutan-2-yl)-6-(trifluoromethyl)phenyl)benzamide, 2-fluoro-N-(2-fluoro-3-(2-iodo-4-(perfluorobutan-2-yl)-6-(trifluoromethyl)phenylcarbamoyl)phenyl)-N-methylbenzamide,
2-fluoro-3-(3-fluoro-N-methylbenzamido)-N-(2-iodo-4-(perfluorobutan-2-yl)-6-(trifluoromethyl)phenyl)benzamide, 2-fluoro-3-(4-fluoro-N-methylbenzamido)-N-(2-iodo-4-(perfluorobutan-2-yl)-6-(trifluoromethyl)phenyl)benzamide, 2-chloro-4,5-difluoro-N-(3-(2-iodo-4-(perfluoropropan-2-yl)-6-(trifluoromethyl)phenylcarbamoyl)phenyl)benzamide, 2-chloro-4-fluoro-N-(3-(2-iodo-4-(perfluoropropan-2-yl)-6-(trifluoromethyl)phenylcarbamoyl)phenyl)-N-methylbenzamide, N-(3-(2-bromo-4-(perfluoropropan-2-yl)-6-(trifluoromethyl)phenylcarbamoyl)phenyl)-2-chloro-4-fluorobenzamide, 2-chloro-N-(3-(2-iodo-4-(perfluoropropan-2-yl)-6-(trifluoromethyl)phenylcarbamoyl)phenyl)benzamide, 3-(2-chlorobenzamido)-2-fluoro-N-(2-iodo-4-(perfluoropropan-2-yl)-6-(trifluoromethyl)phenyl)benzamide, 2-chloro-N-(3-(2-iodo-4-(perfluoropropan-2-yl)-6-(trifluoromethyl)phenylcarbamoyl)phenyl)-N-methylbenzamide, N-(3-(2-bromo-4-(perfluoropropan-2-yl)-6-(trifluoromethyl)phenylcarbamoyl)phenyl)-2-chlorobenzamide, 2-chloro-N-(3-(2-iodo-4-(perfluoropropan-2-yl)-6-(trifluoromethyl)phenylcarbamoyl)phenyl)-4-nitrobenzamide, N-(2-fluoro-3-(2-iodo-4-(perfluoropropan-2-yl)-6-(trifluoromethyl)phenylcarbamoyl)phenyl)-N-methylnicotinamide, 3-((2-fluoro-3-(2-iodo-4-(perfluoropropan-2-yl)-6-(trifluoromethyl)phenylcarbamoyl)phenyl)(methyl)carbamoyl)pyridine 1-oxide, 4-bromo-2-chloro-N-(3-(2-iodo-4-(perfluoropropan-2-yl)-6-(trifluoromethyl)phenylcarbamoyl)phenyl)benzamide, 2-bromo-4-chloro-N-(3-(2-iodo-4-(perfluoropropan-2-yl)-6-(trifluoromethyl)phenylcarbamoyl)phenyl)benzamide, 2-bromo-4-fluoro-N-(3-(2-iodo-4-(perfluoropropan-2-yl)-6-(trifluoromethyl)phenylcarbamoyl)phenyl)benzamide, 2-fluoro-3-(3-fluoro-N-methylbenzamido)-N-(2-iodo-4-(perfluoropropan-2-yl)-6-(trifluoromethyl)phenyl)-N-methylbenzamide, N-(2-bromo-4-(perfluoropropan-2-yl)-6-(trifluoromethyl)phenyl)-2-fluoro-N-methyl-3-(N-methylbenzamido)benzamide, or N-(2-chloro-4-(perfluoropropan-2-yl)-6-(trifluoromethyl)phenyl)-2-fluoro-3-(N-methylbenzamido)benzamide.

<12> The amide derivative according to <2>, wherein in Formula (7), at least one of X represents a chlorine atom, a bromine atom, an iodine atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylsulfonyloxy group, a C1-C6 haloalkylsulfonyloxy group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkylcarbonyloxy group, a C2-C7 haloalkylcarbonyloxy group, arylcarbonyloxy group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 halo alkynyloxycarbonyl group, a C4-C10 cycloalkyloxycarbonyl group, a C4-C10 halocycloalkyloxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C2-C7 alkoxycarbonyloxy group, a C2-C7 haloalkoxycarbonyloxy group, an arylcarbonylamino group, an amino group, a carbamoyl group, a cyano group, a hydroxy group, pentafluorosulfanyl group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkenylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, a phenyl group, or a heterocyclic group, and when there are plural X's, each X may be the same as or different from an other. $Y_1$ represents a halogen atom, a C1-C6 haloalkoxy group, or a C1-C3 haloalkyl group. $Y_5$ represents a C1-C6 haloalkoxy group, or C1-C3 haloalkyl group.

<13> The amide derivative according to <12>, wherein in Formula (7), $Y_3$ represents a C2-C4 perfluoroalkyl group.

<14> The amide derivative according to <13>, wherein in Formula (7), $Y_1$ represents a halogen atom or a C1-C3 haloalkyl group, and $Y_5$ represents a C1-C3 haloalkyl group.

<15> The amide derivative according to <14>, wherein in Formula (7), $Y_2$ and $Y_4$ represent a hydrogen atom.

<16> The amide derivative according to <15>, wherein in Formula (7), $X_1$ to $X_4$ each independently represents a hydrogen atom, a halogen atom, or a cyano group.

<17> The amide derivative according to <1>, which is represented by the following Formula (9):

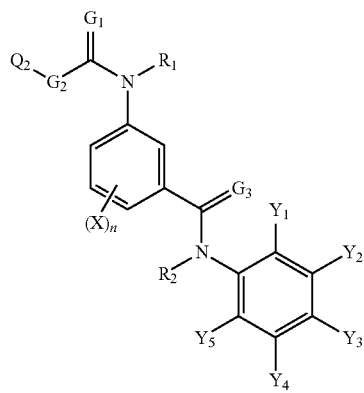

Formula (9)

Wherein, in Formula (9), n represents 4, and X, $Y_1$ to $Y_5$, $Q_2$, $G_1$ to $G_3$, $R_1$, and $R_2$ have the same definitions as X, $Y_1$ to $Y_5$, $Q_2$, $G_1$ to $G_3$, $R_1$, and $R_2$, respectively, in Formula (1).

<18> The amide derivative according to <17>, wherein in Formula (9), $Y_1$ represents a halogen atom, a C1-C6 haloalkoxy group, or a C1-C3 haloalkyl group, and $Y_5$ is a C1-C6 haloalkoxy group or a C1-C3 haloalkyl group.

<19> The amide derivative according to <18>, wherein in Formula (9), $Y_3$ represents a C2-C4 perfluoroalkyl group.

<20> The amide derivative according to <19>, wherein in Formula (9), $Y_1$ and $Y_5$ represent halogen atoms or C1-C3 haloalkyl groups, and either $Y_1$ or $Y_5$ represent a C1-C3 haloalkyl group.

<21> The amide derivative according to <20>, wherein in Formula (9), $Y_2$ and $Y_4$ represent hydrogen atoms.

<22> The amide derivative according to <21>, wherein in Formula (9), $X_1$ to $X_4$ each independently represents a hydrogen atom, a halogen atom, or a cyano group.

<23> The amide derivative according to <1>, wherein in Formula (1), K represents a non-metal atom group necessary for forming a cyclic linking group derived from pyridine, pyridine-N-oxide, pyrimidine, pyrazine, pyridazine, triazine, pyrrole, pyrazole, imidazole, oxazole, isoxazole, thiazole, isothiazole, furan, thiophene, oxadiazole, thiodiazole, or triazole, in combination with A and two carbon atoms to which A bonds.

<24> The amide derivative according to <23>, wherein in Formula (1), K represents a non-metal atom group necessary for forming a cyclic linking group derived from pyridine, in combination with A and two carbon atoms to which A bonds, and when T is —C(=$G_1$)-$Q_1$, $Y_1$ and $Y_5$ each independently represents a halogen atom or a C1-C3 haloalkyl group.

<25> The amide derivative according to <23>, wherein in Formula (1), K represents a non-metal atom group necessary for forming a cyclic linking group derived from pyrrole, pyrazole, imidazole, oxazole, isoxazole, thiazole, isothiazole, furan, thiophene, oxadiazole, thiodiazole, or trizole, in combination with A and two carbon atoms to which A bonds, and in a case where T represents —C(=$G_1$)-$Q_1$, $R_1$ represents an oxygen atom, a halogen atom, a hydroxy group, a nitro group, a nitroso group, a trimethylsilyl group, a t-butyldimethylsilyl group, a cyano group, an amino group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)$R_7$ (wherein $R_7$ represents a C1-C6 alkyl group, a C1-C6 haloalkyl group, a C1-C6 alkoxy group, or a C1-C6 haloalkoxy group).

<26> The amide derivative according to <23>, wherein in Formula (1), K represents a non-metal atom group necessary for forming a cyclic linking group derived from pyrrole, pyrazole, imidazole, oxazole, isoxazole, thiazole, isothiazole, furan, thiophene, oxadiazole, thiodiazole, or trizole, in combination with A and two carbon atoms to which A bonds, and in a case where T represents —C(=$G_1$)-$Q_1$, $R_2$ represents an oxygen atom, a halogen atom, a hydroxy group, a nitro group, a nitroso group, a trimethylsilyl group, a t-butyldimethylsilyl group, a cyano group, an amino group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)$R_7$ (wherein $R_7$ represents a C1-C6 alkyl group, a C1-C6 haloalkyl group, a C1-C6 alkoxy group, or a C1-C6 haloalkoxy group).

<27> The amide derivative according to any one of <23> to <26>, wherein in Formula (1), $Y_3$ represents a C2-C4 perfluoroalkyl group.

<28> The amide derivative according to <27>, wherein in Formula (1), $Y_1$ and $Y_5$ each independently represent a halogen atom or a C1-C3 haloalkyl group, and either $Y_1$ or $Y_5$ represent a C1-C3 haloalkyl group.

<29> The amide derivative according to <28>, wherein in Formula (1), $Y_2$ and $Y_4$ represent hydrogen atoms.

<30> The amide derivative according to <29>, wherein in Formula (1), K represents a non-metal atom group necessary for forming a cyclic linking group derived from pyridine, pyridine-N-oxide, pyrrole, thiazole, furan, or thiophene, in combination with A and two carbon atoms to which A bonds.

<31> The amide derivative according to <29>, wherein in Formula (1), K represents a non-metal atom group necessary for forming a cyclic linking group derived from pyridine, pyridine-N-oxide, or thiazole, in combination with A and two carbon atoms to which A bonds.

<32> The amide derivative according to <16>, wherein in Formula (7), $G_1$ and $G_3$ represent oxygen atoms.

<33> The amide derivative according to <22>, wherein in Formula (9), $G_1$, $G_2$, and $G_3$ represent oxygen atoms.

<34> The amide derivative according to <31>, wherein in Formula (1), $G_1$, $G_2$, and $G_3$ represent oxygen atoms.

<35> A pest control agent comprising at least one amide derivative according to any one of <1> to <34> as an active ingredient.

<36> An agricultural chemical comprising at least one amide derivative according to any one of <1> to <34> as an active ingredient.

<37> A pesticide comprising at least one amide derivative according to any one of <1> to <34> as an active ingredient.

<38> A pest controlling method, comprising applying a chemical agent according to any one of <35> to <37>.

<39> A compound represented by the following Formula (56):

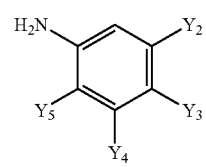

Formula (56)

Wherein, wherein $Y_5$ represents a C1-C3 haloalkyl group, and $Y_2$, $Y_3$, and $Y_4$ represent the same definitions as $Y_2$, $Y_3$, and $Y_4$, respectively, in <1>.

<40> A compound represented by the following Formula (57):

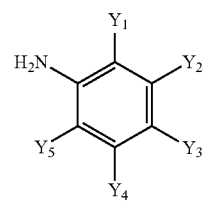

Formula (57)

Wherein $Y_5$ represents a C1-C3 haloalkyl group, and $Y_1$, $Y_2$, $Y_3$, and $Y_4$ represent the same definitions as $Y_1$, $Y_2$, $Y_3$, and $Y_4$, respectively, in <1>.

<41> The compound according to <40>, wherein in Formula (57), $Y_1$ represents a halogen atom.

<42> A method for producing a compound represented by the following Formula (57a) according to <41>, including reacting a compound represented by Formula (56) according to <39> with a halogenating agent:

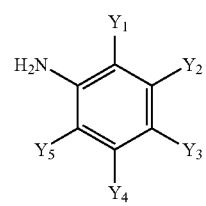

Formula (57a)

Wherein $Y_5$ represents a C1-C3 haloalkyl group, $Y_2$, $Y_3$, and $Y_4$ represent the same definitions as $Y_2$, $Y_3$, and $Y_4$, respectively, in <1>, and $Y_1$ represents a halogen atom.

<43> A compound represented by the following Formula (60a):

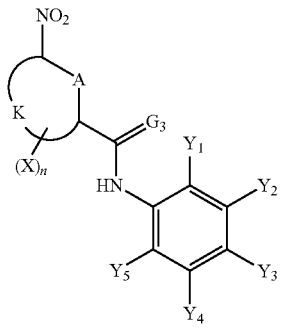

Formula (60a)

Wherein A, K, X, n, $G_3$, $Y_1$, $Y_2$, $Y_3$, $Y_4$, and $Y_5$ have the same definitions as A, K, X, n, $G_3$, $Y_1$, $Y_2$, $Y_3$, $Y_4$, and $Y_5$, respectively, in <1>. In a case where K forms a benzene ring together with A and two carbon atoms to which A bonds and all X's represent hydrogen atoms, $Y_5$ represents a C1-C3 haloalkyl group. Further, when K forms a benzene ring together with A and two carbon atoms to which A bonds and X's are cyano groups, $Y_5$ represents a C1-C6 haloalkoxy group or a C1-C3 haloalkyl group.

<44> A method for producing a compound represented by the following Formula (60a) according to <43>, comprising reacting a compound represented by the following Formula (59) with a compound represented by the following Formula (57b):

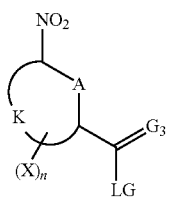

Formula (59)

Wherein LG represents a functional group having a leaving ability, such as a halogen atom, a hydroxy group, or the like, and A, K, X, n, and $G_3$ have the same definitions as A, K, X, n, and $G_3$, respectively, in <1>.

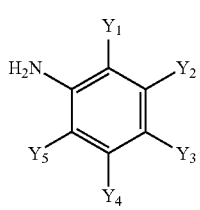

Formula (57b)

Wherein $Y_1$, $Y_2$, $Y_3$, $Y_4$, and $Y_5$ have the same definitions as $Y_1$, $Y_2$, $Y_3$, $Y_4$, and $Y_5$, respectively, in <1>.

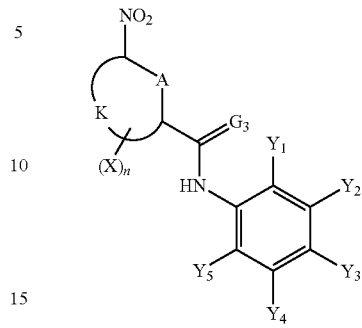

Formula (60a)

Wherein A, K, X, n, $G_3$, $Y_1$, $Y_2$, $Y_3$, $Y_4$, and $Y_5$ have the same definitions as A, K, X, n, $G_3$, $Y_1$, $Y_2$, $Y_3$, $Y_4$, and $Y_5$, respectively, in <1>. In a case where K forms a benzene ring together with A and two carbon atoms to which A bonds and X's represent all hydrogen atoms, $Y_5$ represents a C1-C3 haloalkyl group. Further, in a case where K forms a benzene ring together with A and two carbon atoms to which A bonds and X represents a cyano group, $Y_5$ represents a C1-C6 haloalkoxy group or a C1-C3 haloalkyl group.

<45> A compound represented by the following Formula (61a):

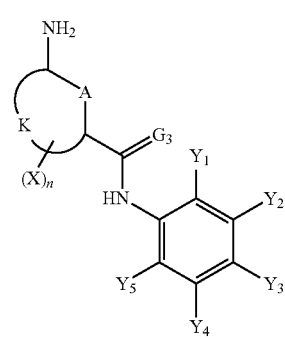

Formula (61a)

Wherein A, K, X, n, $G_3$, $Y_1$, $Y_2$, $Y_3$, $Y_4$, and $Y_5$ represent the same definitions as A, K, X, n, $G_3$, $Y_1$, $Y_2$, $Y_3$, $Y_4$, and $Y_5$, respectively, in <1>. In a case where K forms a benzene ring together with A and two carbon atoms to which A bonds and all X's represent hydrogen atoms, $Y_5$ represents a C1-C3 haloalkyl group. Further, when K forms a benzene ring together with A and two carbon atoms to which A bonds and X represents a cyano group, $Y_5$ represents a C1-C6 haloalkoxy group or a C1-C3 haloalkyl group.

<46> A method for producing a compound represented by the following Formula (61a) according to <45>, including reacting a compound represented by Formula (60a) according to <43> with a reducing agent:

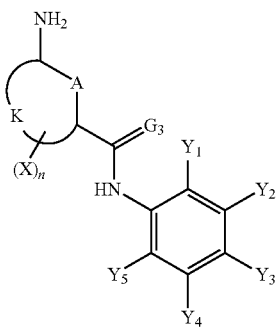

Formula (61a)

Wherein A, K, X, n, $G_3$, $Y_1$, $Y_2$, $Y_3$, $Y_4$, and $Y_5$ have the same definitions as A, K, X, n, $G_3$, $Y_1$, $Y_2$, $Y_3$, $Y_4$, and $Y_5$, respectively, in <1>. In a case where K forms a benzene ring together with A and two carbon atoms to which A bonds and all X's represent hydrogen atoms, $Y_5$ represents a C1-C3 haloalkyl group. Further, when K forms a benzene ring together with A and two carbon atoms to which A bonds and X represents a cyano group, $Y_5$ represents a C1-C6 haloalkoxy group or a C1-C3 haloalkyl group.

<47> A compound represented by the following Formula (69):

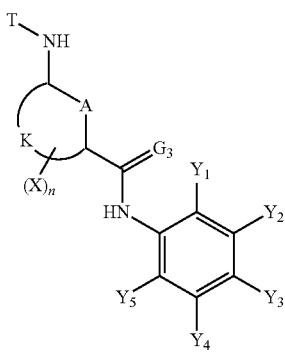

Formula (69)

Wherein T, A, K, X, n, $G_3$, $Y_1$, $Y_2$, $Y_3$, $Y_4$, and $Y_5$ have the same definitions as T, A, K, X, n, $G_3$, $Y_1$, $Y_2$, $Y_3$, $Y_4$, and $Y_5$, respectively, in <1>.

<48> A method for producing a compound represented by the following Formula (69) according to <47>, including reacting a compound represented by the following Formula (61b) with a compound represented by the following Formula (62):

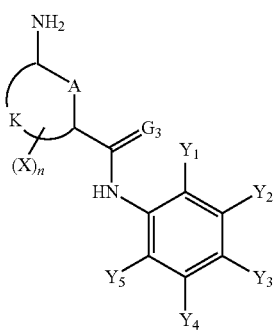

Formula (61b)

Wherein A, K, X, n, $G_3$, $Y_1$, $Y_2$, $Y_3$, $Y_4$, and $Y_5$ have the same definitions as A, K, X, n, $G_3$, $Y_1$, $Y_2$, $Y_3$, $Y_4$, and $Y_5$, respectively, in <1>.

T-LG           Formula (62)

Wherein LG represents a functional group having a leaving ability, such as a halogen atom, a hydroxy group, and the like, and T represents the same definition as T in <1>.

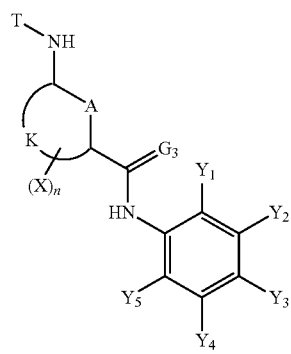

Formula (69)

Wherein T, A, K, X, $G_3$, $Y_1$, $Y_2$, $Y_3$, $Y_4$, and $Y_5$ represent the same definitions as T, A, K, X, n, $G_3$, $Y_1$, $Y_2$, $Y_3$, $Y_4$, and $Y_5$, respectively, in <1>.

<49> A compound represented by the following Formula (51a):

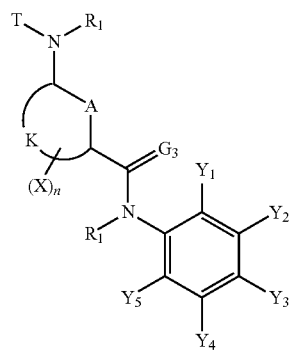

Formula (51a)

Wherein T, $R_1$, A, K, X, n, $G_3$, $Y_1$, $Y_2$, $Y_3$, $Y_4$, and $Y_5$ have the same definitions as T, $R_1$, A, K, X, n, $G_3$, $Y_1$, $Y_2$, $Y_3$, $Y_4$, and $Y_5$, respectively, in <1>.

<50> A method for producing a compound represented by the following Formula (51b), including reacting a compound represented by the following Formula (69) according to <47> with a compound represented by the following Formula (64):

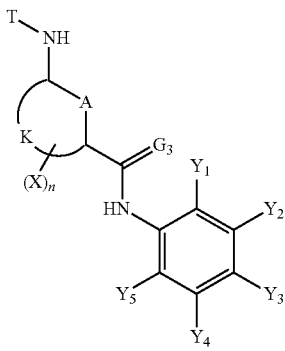

Formula (69)

Wherein T, A, K, X, n, G₃, Y₁, Y₂, Y₃, Y₄, and Y₅ have the same definitions as T, A, K, X, n, G₃, Y₁, Y₂, Y₃, Y₄, and Y₅, respectively, in <1>.

R₁-LG                                    Formula (64)

Wherein LG represents a functional group having a leaving ability, such as a halogen atom, a hydroxy group, or the like, R₁ represents a trimethylsilyl group, a t-butyldimethylsilyl group, a cyano group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloallcenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)R₇ (wherein R₇ represents a C1-C6 alkyl group, a C1-C6 haloalkyl group, a C1-C6 alkoxy group, or a C1-C6 haloalkoxy group.

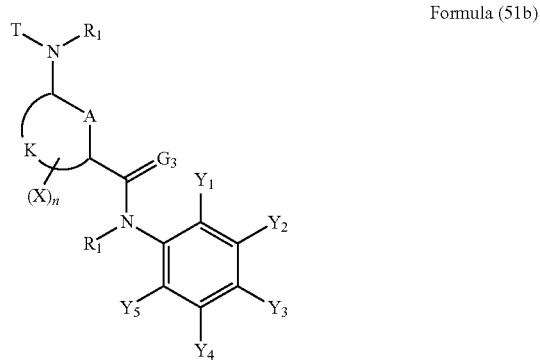

Formula (51b)

Wherein R₁ represents the same definition as R₁ in Formula (64), and T, A, K, X, n, G₃, Y₁, Y₂, Y₃, Y₄, and Y₅ have the same definitions as T, A, K, X, n, G₃, Y₁, Y₂, Y₃, Y₄, and Y₅, respectively, in <1>.

<51> A compound represented by the following Formula (57c):

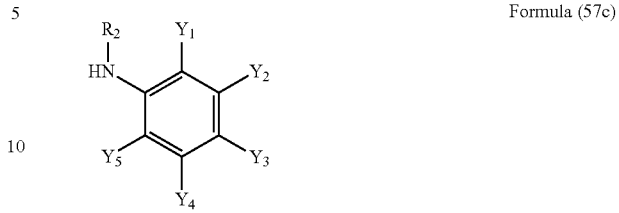

Formula (57c)

Wherein Y₅ represents a C1-C6 haloalkoxy group or a C1-C3 haloalkyl group, R₂ represents an oxygen atom, a halogen atom, a hydroxy group, a nitro group, a nitroso group, a trimethylsilyl group, a t-butyldimethylsilyl group, a cyano group, an amino group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)R₇ (wherein R₇ represents a C1-C6 alkyl group, a C1-C6 haloalkyl group, a C1-C6 alkoxy group, or a C1-C6 haloalkoxy group), and Y₁, Y₂, Y₃, and Y₄ have the same definitions as Y₁, Y₂, Y₃, and Y₄, respectively, in <1>.

<52> A method for producing a compound represented by the following Formula (57m), including reacting a compound represented by the following Formula (57k) with a compound represented by the following Formula (66):

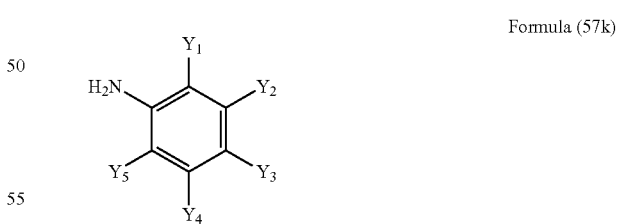

Formula (57k)

Wherein Y₅ represents a C1-C6 haloalkoxy group or a C1-C3 haloalkyl group, and Y₁, Y₂, Y₃, and Y₄ have the same definitions as Y₁, Y₂, Y₃, and Y₄, respectively, in <1>.

R₂-LG                                    Formula (66)

Wherein, LG represents a functional group having a leaving ability, such as a halogen atom, a hydroxy group, or the like, R₂ represents a trimethylsilyl group, a t-butyldimethylsilyl group, a cyano group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)$R_7$, wherein $R_7$ represents a C1-C6 alkyl group, a C1-C6 haloalkyl group, a C1-C6 alkoxy group, or a C1-C6 haloalkoxy group.

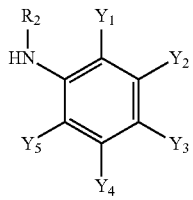

Formula (57m)

Wherein $Y_5$ represents a C1-C6 haloalkoxy group or a C1-C3 haloalkyl group, $R_2$ represents the same definition as $R_2$ in Formula (66), and $Y_1$, $Y_2$, $Y_3$, and $Y_4$ have the same definitions as $Y_1$, $Y_2$, $Y_3$, and $Y_4$, respectively, in <1>.

<53> A method for producing a compound represented by the following Formula (57n), including reacting a compound represented by the following Formula (57k) according to <52> with an aldehyde:

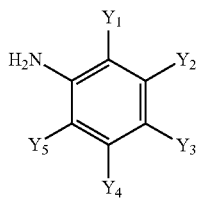

Formula (57k)

Wherein $Y_5$ represents a C1-C6 haloalkoxy group or a C1-C3 haloalkyl group, and $Y_1$, $Y_2$, $Y_3$, and $Y_4$ have the same definitions as $Y_1$, $Y_2$, $Y_3$, and $Y_4$, respectively, in <1>.

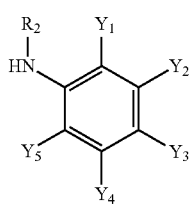

Formula (57n)

Wherein $Y_5$ represents a C1-C6 haloalkoxy group or a C1-C3 haloalkyl group, $R_2$ represents a C1-C6 alkyl group which may have a substituent, a C1-C6 haloalkyl group which may have a substituent, or a benzyl group, and $Y_1$, $Y_2$, $Y_3$, and $Y_4$ have the same definitions as $Y_1$, $Y_2$, $Y_3$, and $Y_4$, respectively, in <1>.

<54> A compound represented by the following Formula (60):

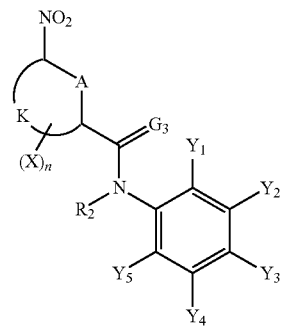

Formula (60)

Wherein $R_2$ represents the same definition as $R_2$ in <51>, and A, K, X, n, $G_3$, $Y_1$, $Y_2$, $Y_3$, $Y_4$, and $Y_5$ have the same definitions as A, K, X, n, $G_3$, $Y_1$, $Y_2$, $Y_3$, $Y_4$, and $Y_5$, respectively, in <1>.

<55> A method for producing a compound represented by the following Formula (60e), including reacting a compound represented by the following Formula (60f) with a compound represented by the following Formula (66) according to <52>:

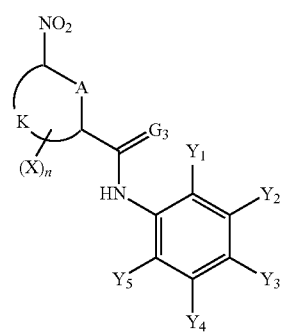

Formula (60f)

Wherein A, K, X, n, $G_3$, $Y_1$, $Y_2$, $Y_3$, $Y_4$, and $Y_5$ have the same definitions as A, K, X, n, $G_3$, $Y_1$, $Y_2$, $Y_3$, $Y_4$, and $Y_5$, respectively, in <1>.

$R_2$-LG                Formula (66)

Wherein LG represents a functional group having a leaving ability, such as a halogen atom, a hydroxy group, or the like, $R_2$ represents a trimethylsilyl group, a t-butyldimethylsilyl group, a cyano group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)R$_7$ (wherein R$_7$ represents a C1-C6 alkyl group, a C1-C6 haloalkyl group, a C1-C6 alkoxy group, or a C1-C6 haloalkoxy group.

Formula (60e)

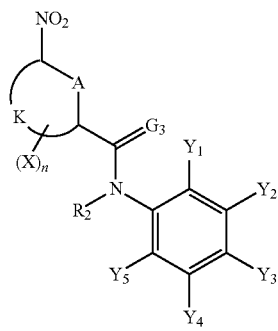

Wherein R$_2$ has the same definition as R$_2$ in Formula (66), and A, K, X, n, G$_3$, Y$_1$, Y$_2$, Y$_3$, Y$_4$, and Y$_5$ have the same definitions as A, K, X, n, G$_3$, Y$_1$, Y$_2$, Y$_3$, Y$_4$, and Y$_5$, respectively, in <1>.

<56> A method for producing a compound represented by the following Formula (60) according to <54>; including reacting a compound represented by the following Formula (57d) with a compound represented by the following Formula (59) according to <44>:

Formula (57d)

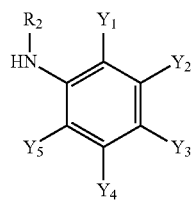

Wherein R$_2$ has the same definition as R$_2$ in <51>, and Y$_1$, Y$_2$, Y$_3$, Y$_4$, and Y$_5$ have the same definitions as Y$_1$, Y$_2$, Y$_3$, Y$_4$, and Y$_5$, respectively, in <1>.

Formula (59)

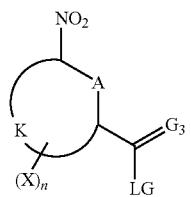

Wherein LG represents a functional group having a leaving ability, such as a halogen atom, a hydroxy group, or the like, and A, K, X, n, and G$_3$ have the same definitions as A, K, X, n, and G$_3$, respectively, in <1>.

Formula (60)

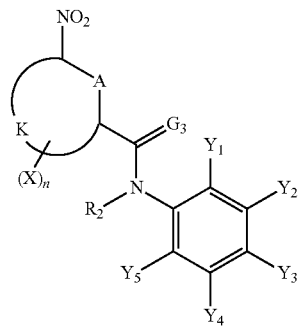

Wherein R$_2$ has the same definition as R$_2$ in <51>, and A, K, X, n, G$_3$, Y$_1$, Y$_2$, Y$_3$, Y$_4$, and Y$_5$ have the same definitions as A, K, X, n, G$_3$, Y$_1$, Y$_2$, Y$_3$, Y$_4$, and Y$_5$, respectively, in <1>.

<57> A compound represented by the following Formula (61):

Formula (61)

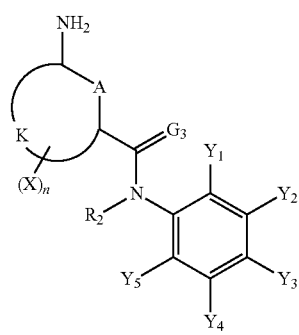

Wherein R$_2$ has the same definition as R$_2$ in <51>, and A, K, X, n, G$_3$, Y$_1$, Y$_2$, Y$_3$, Y$_4$, and Y$_5$ have the same definitions as A, K, X, n, G$_3$, Y$_1$, Y$_2$, Y$_3$, Y$_4$, and Y$_5$, respectively, in <1>.

<58> A method for producing a compound represented by the following Formula (61) according to <57>, including the compound represented by Formula (60) according to <54> in the presence of a reducing agent:

Formula (61)

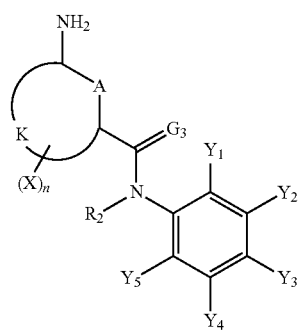

Wherein $R_2$ has the same definition as $R_2$ in <51>, and A, K, X, n, $G_3$, $Y_1$, $Y_2$, $Y_3$, $Y_4$, and $Y_5$ have the same definitions as A, K, X, n, $G_3$, $Y_1$, $Y_2$, $Y_3$, $Y_4$, and $Y_5$, respectively, in <1>.

<59> A compound represented by the following Formula (63):

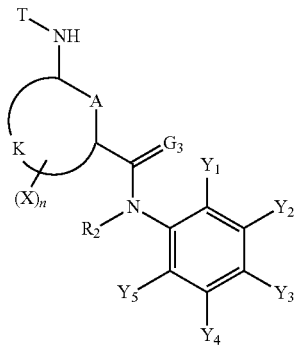

Formula (63)

Wherein T, $R_2$, A, K, X, n, $G_3$, $Y_1$, $Y_2$, $Y_3$, $Y_4$, and $Y_5$ have the same definitions as T, $R_2$, A, K, X, n, $G_3$, $Y_1$, $Y_2$, $Y_3$, $Y_4$, and $Y_5$, respectively, in <1>.

<60> A method for producing a compound represented by the following Formula (63) according to <59>, including reacting a compound represented by the following Formula (61e) with a compound represented by the following Formula (62) according to <48>:

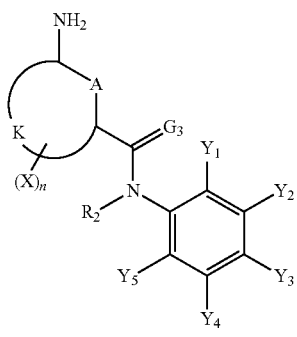

Formula (61e)

Wherein $R_2$, A, K, X, n, $G_3$, $Y_1$, $Y_2$, $Y_3$, $Y_4$, and $Y_5$ have the same definitions as $R_2$, A, K, X, n, $G_3$, $Y_1$, $Y_2$, $Y_3$, $Y_4$, and $Y_5$, respectively, in <1>.

T-LG          Formula (62)

(wherein LG represents a functional group having a leaving ability, such as a halogen atom, a hydroxy group, or the like, and T has the same definition as T in <1>.

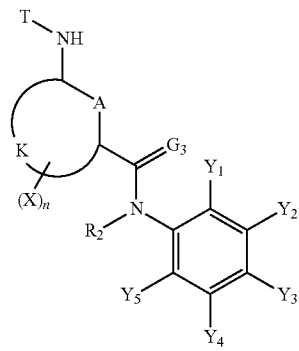

Formula (63)

Wherein T, $R_2$, A, K, X, n, $G_3$, $Y_1$, $Y_2$, $Y_3$, $Y_4$, and $Y_5$ represent the same definitions as T, $R_2$, A, K, X, n, $G_3$, $Y_1$, $Y_2$, $Y_3$, $Y_4$, and $Y_5$, respectively, in <1>.

<61> A method for producing a compound represented by the following Formula (1b), including reacting a compound represented by the following Formula (63) according to <59> with a compound represented by the following Formula (64) according to <50>:

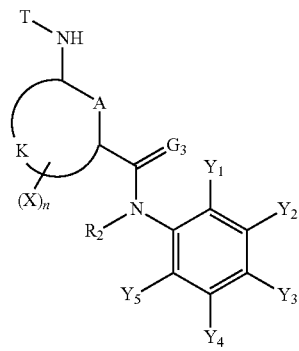

Formula (63)

Wherein T, $R_2$, A, K, X, n, $G_3$, $Y_1$, $Y_2$, $Y_3$, $Y_4$, and $Y_5$ have the same definitions as T, $R_2$, A, K, X, n, $G_3$, $Y_1$, $Y_2$, $Y_3$, $Y_4$, and $Y_5$, respectively, in <1>.

$R_1$-LG          Formula ((64)

Wherein, LG represents a functional group having a leaving ability, such as a halogen atom, a hydroxy group, or the like, $R_1$ represents a trimethylsilyl group, a t-butyldimethylsilyl group, a cyano group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)R$_7$, wherein R$_7$ represents a C1-C6 alkyl group, a C1-C6 haloalkyl group, a C1-C6 alkoxy group, or a C1-C6 haloalkoxy group.

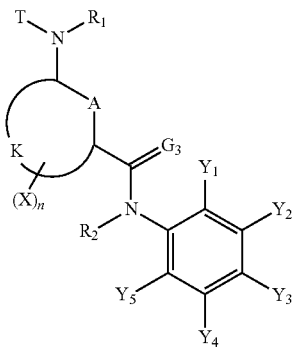

Formula (1b)

Wherein R$_1$ has the same definition as R$_1$ in Formula (64), and R$_2$, A, K, X, n, G$_3$, Y$_2$, Y$_3$, Y$_4$, and Y$_5$ have the same definitions as R$_2$, A, K, X, n, G$_3$, Y$_1$, Y$_2$, Y$_3$, Y$_4$, and Y$_5$, respectively, in <1>.

<62> A compound represented by the following Formula (65a):

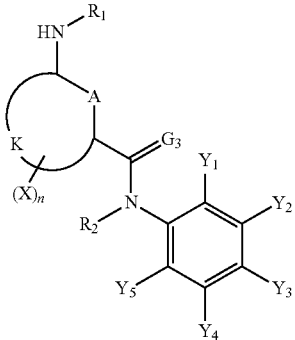

Formula (65a)

Wherein R$_1$, R$_2$, A, K, X, n, G$_3$, Y$_1$, Y$_2$, Y$_3$, Y$_4$, and Y$_5$ have the same definitions as R$_1$, R$_2$, A, K, X, n, G$_3$, Y$_1$, Y$_2$, Y$_3$, Y$_4$, and Y$_5$, respectively, in <1>. In a case where K forms a benzene ring together with A and two carbon atoms to which A bonds, all X's represent hydrogen atoms, and R$_2$ represents a hydrogen atom, Y$_5$ is a C1-C3 haloalkyl group. Further, in a case where K forms a benzene ring together with A and two carbon atoms to which A bonds, X represents a cyano group, and R$_1$ and R$_2$ represent hydrogen atoms, and Y$_5$ represents a C1-C6 haloalkoxy group or a C1-C3 haloalkyl group.

<63> A method for producing a compound represented by the following Formula (65c), including reacting a compound represented by the following Formula (61e) according to <60> with an aldehyde:

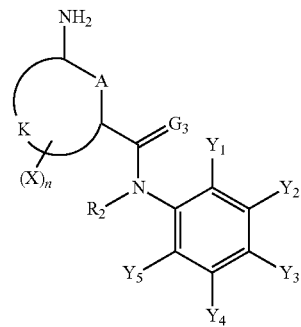

Formula (61e)

Wherein R$_2$, A, K, X, n, G$_3$, Y$_1$, Y$_2$, Y$_3$, Y$_4$, and Y$_5$ have the same definitions as R$_2$, A, K, X, n, G$_3$, Y$_1$, Y$_2$, Y$_3$, Y$_4$, and Y$_5$, respectively, in <1>.

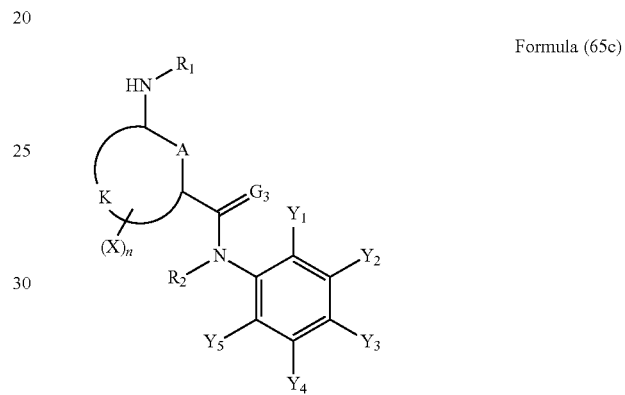

Formula (65c)

Wherein R$_1$ represents a C1-C6 alkyl group which may have a substituent, a C1-C6 haloalkyl group which may have a substituent, or a benzyl group, and R$_2$, A, K, X, n, G$_3$, Y$_1$, Y$_2$, Y$_3$, Y$_4$, and Y$_5$ represent the same definitions as R$_2$, A, K, X, n, G$_3$, Y$_1$, Y$_2$, Y$_3$, Y$_4$, and Y$_5$, respectively, in <1>. In a case where K forms a benzene ring together with A and two carbon atoms to which A bonds, all X's represent hydrogen atoms, and R$_2$ represents a hydrogen atom, Y$_5$ represents a C1-C3 haloalkyl group.

<64> A method for producing a compound represented by the following Formula (1), including reacting a compound represented by the following Formula (65b) with a compound represented by the following Formula (62) according to <48>:

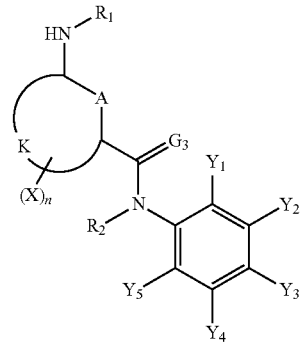

Formula (65b)

Wherein $R_1$, $R_2$, A, K, X, n, $G_3$, $Y_1$, $Y_2$, $Y_3$, $Y_4$, and $Y_5$ have the same definitions as $R_1$, $R_2$, A, K, X, n, $G_3$, $Y_1$, $Y_2$, $Y_3$, $Y_4$, and $Y_5$, respectively, in <1>.

T-LG  Formula (62)

Wherein LG represents a functional group having a leaving ability, such as a halogen atom, a hydroxy group, or the like, and T has the same definition as T in <1>.

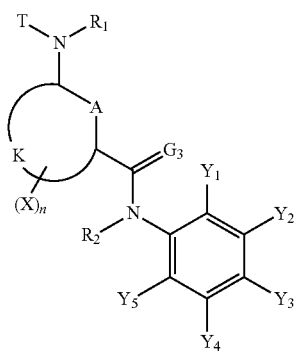

Formula (1)

<65> A compound represented by the following Formula (68):

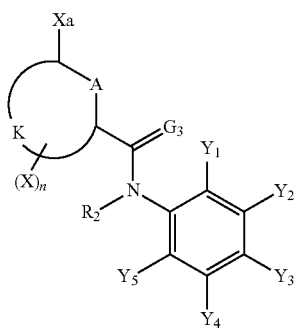

Formula (68)

Wherein Xa represents a chlorine atom, a bromine atom, or an iodine atom, and $R_2$, A, K, X, n, $G_3$, $Y_1$, $Y_2$, $Y_3$, $Y_4$, and $Y_5$ have the same definitions as $R_2$, A, K, X, n, $G_3$, $Y_1$, $Y_2$, $Y_3$, $Y_4$, and $Y_5$, respectively, in <23>.

<66> A method for producing a compound represented by the following Formula (68) according to <65>, including reacting a compound represented by the following Formula (57j) with a compound represented by the following Formula (67):

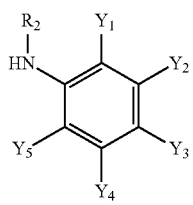

Formula (57j)

Wherein $R_2$, $Y_1$, $Y_2$, $Y_3$, $Y_4$, and $Y_5$ have the same definitions as $R_2$, $Y_1$, $Y_2$, $Y_3$, $Y_4$, and $Y_5$, respectively, in <1>.

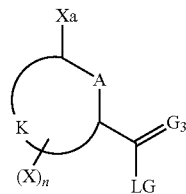

Formula (67)

Wherein LG represents a functional group having a leaving ability, such as a halogen atom, a hydroxy group, or the like, Xa represents a chlorine atom, a bromine atom, or an iodine atom, and A, K, X, n, and $G_3$ have the same definitions as A, K, X, n, and $G_3$, respectively, in <23>.

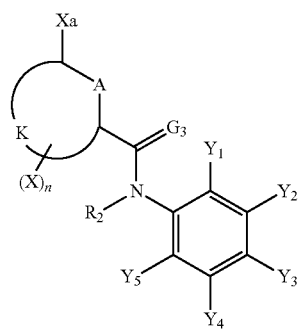

Formula (68)

Wherein Xa represents a chlorine atom, a bromine atom, or an iodine atom, and $R_2$, A, K, X, n, $G_3$, $Y_1$, $Y_2$, $Y_3$, $Y_4$, and $Y_5$ have the same definitions as $R_2$, A, K, X, n, $G_3$, $Y_1$, $Y_2$, $Y_3$, $Y_4$, and $Y_5$, respectively, in <23>.

<67> A method for producing a compound represented by the following Formula (65d), including reacting a compound represented by the following Formula (68) according to <65> with an aminating agent:

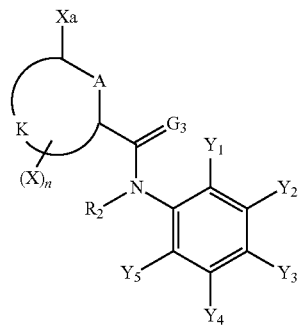

Formula (68)

Wherein Xa represents a chlorine atom, a bromine atom, or an iodine atom, and $R_2$, A, K, X, n, $G_3$, $Y_1$, $Y_2$, $Y_3$, $Y_4$, and $Y_5$ have the same definitions as $R_2$, A, K, X, n, $G_3$, $Y_1$, $Y_2$, $Y_3$, $Y_4$, and $Y_5$, respectively, in <23>.

Formula (65d)

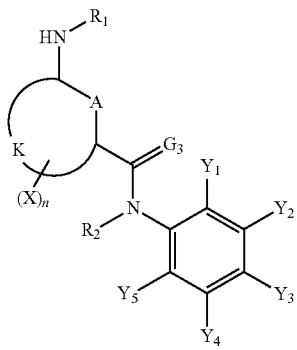

Wherein $R_1, R_2, A, K, X, n, G_3, Y_1, Y_2, Y_3, Y_4$, and $Y_5$ have the same definitions as $R_1, R_2, A, K, X, n, G_3, Y_1, Y_2, Y_3, Y_4$, and $Y_5$, respectively, in <23>.

<68> A compound represented by the following Formula (70):

Formula (70)

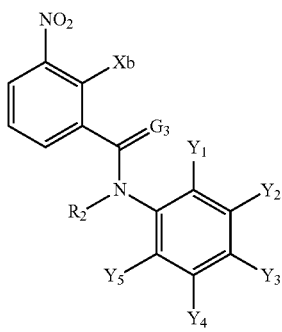

Wherein Xb represents a chlorine atom, a bromine atom, or an iodine atom, and $R_2, G_3, Y_1, Y_2, Y_3, Y_4$, and $Y_5$ have the same definition as, respectively, in <1>.

<69> A compound represented by the following Formula (72):

Formula (72)

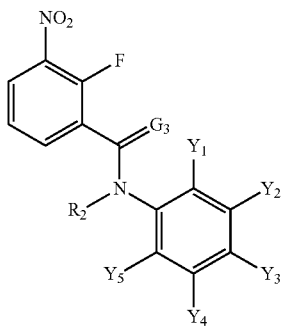

Wherein $R_2, G_3, Y_1, Y_2, Y_3, Y_4$, and $Y_5$ have the same definitions as $R_2, G_3, Y_1, Y_2, Y_3, Y_4$, and $Y_5$, respectively, in <1>.

<70> A method for producing a compound represented by the following Formula (72) according to <69>, including reacting a compound represented by Formula (70) according to <68> with a fluorinating agent:

Formula (72)

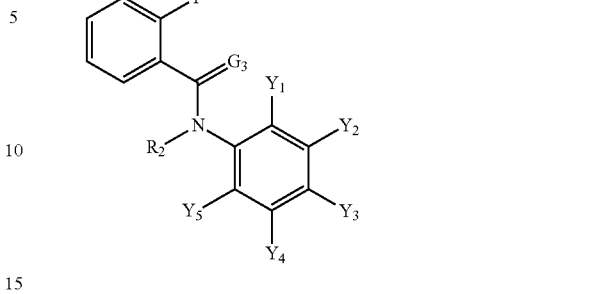

Wherein $R_2, G_3, Y_1, Y_2, Y_3, Y_4$, and $Y_5$ have the same definitions as $R_2, G_3, Y_1, Y_2, Y_3, Y_4$, and $Y_5$, respectively, in <1>.

<71> A compound represented by the following Formula (73):

Formula (73)

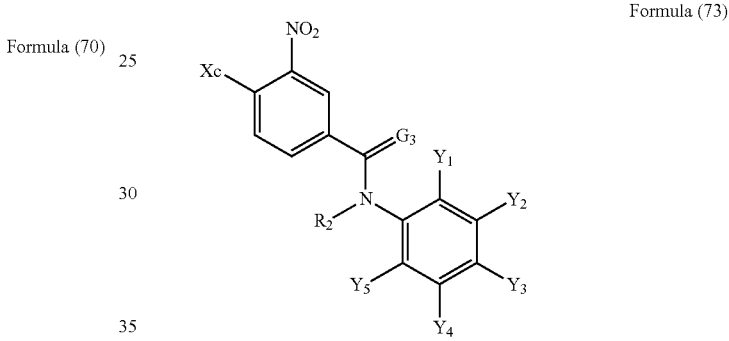

Wherein Xc represents a halogen atom, and $R_2, G_3, Y_1, Y_2, Y_3, Y_4$, and $Y_5$ have the same definitions as $R_2, G_3, Y_1, Y_2, Y_3, Y_4$, and $Y_5$, respectively, in <1>.

<72> A compound represented by the following Formula (75):

Formula (75)

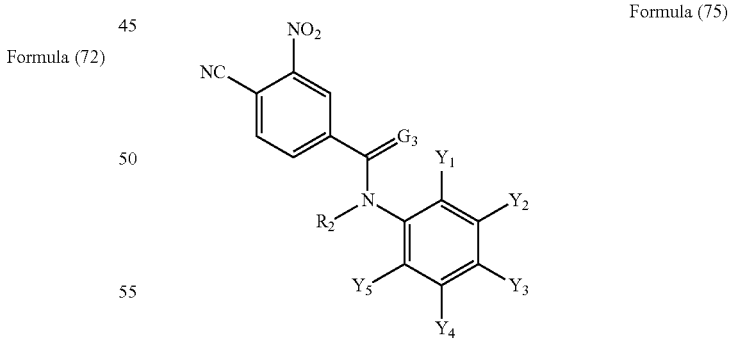

Wherein $Y_5$ represents a C1-C6 haloalkoxy group or a C1-C3 haloalkyl group, and $R_2, G_3, Y_1, Y_2, Y_3$, and $Y_4$ have the same definitions as $R_2, G_3, Y_1, Y_2, Y_3$, and $Y_4$, respectively, in <1>.

<73> A method for producing a compound represented by the following Formula (75) according to <72>, including reacting a compound represented by Formula (73) according to <71>, in which $Y_5$ is a C1-C6 haloalkoxy group or a C1-C3 haloalkyl group, with a cyanating agent:

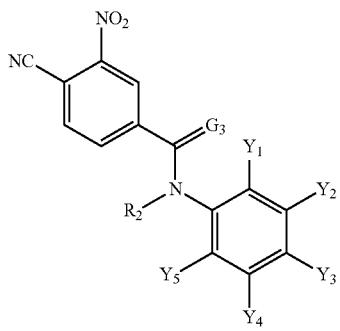

Formula (75)

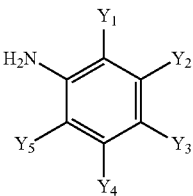

Formula (57f)

Wherein $Y_5$ represents a C1-C3 haloalkyl group, $Y_2$, $Y_3$, and $Y_4$ represent the same definitions as $Y_2$, $Y_3$, and $Y_4$, respectively, in <3>, and $Y_1$ represents a halogen atom.

<78> A compound represented by the following Formula (60b):

Wherein $Y_5$ represents a C1-C6 haloalkoxy group or a C1-C3 haloalkyl group, $R_2$, $G_3$, $Y_1$, $Y_2$, $Y_3$, and $Y_4$ have the same definitions as $R_2$, $G_3$, $Y_1$, $Y_2$, $Y_3$, and $Y_4$, respectively, in <1>.

<74> A compound represented by the following Formula (56a):

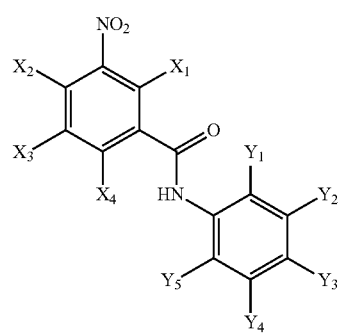

Formula (60b)

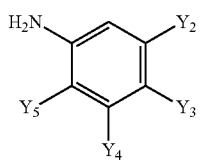

Formula (56a)

Wherein $Y_5$ represents a C1-C3 haloalkyl group, and $Y_2$, $Y_3$, and $Y_4$ have the same definitions as $Y_2$, $Y_3$, and $Y_4$, respectively, in <3>.

<75> A compound represented by the following Formula (57e):

Wherein $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>. In a case where $X_1$, $X_2$, $X_3$, and $X_4$ represent all hydrogen atoms, $Y_5$ represents a C1-C3 haloalkyl group, and in a case where $X_2$ represents a cyano group, and $X_1$, $X_3$, and $X_4$ represent hydrogen atoms, $Y_5$ represents a C1-C3 haloalkoxy group or a C1-C3 haloalkyl group.

<79> A method for producing a compound represented by the following Formula (60b) according to <78>, including reacting a compound represented by the following Formula (59a) with a compound represented by the following Formula (57g):

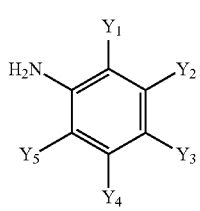

Formula (57e)

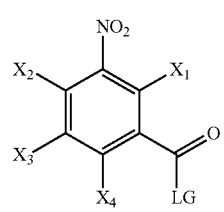

Formula (59a)

Wherein $Y_5$ represents a C1-C3 haloalkyl group, and $Y_1$, $Y_2$, $Y_3$, and $Y_4$ have the same definitions as $Y_1$, $Y_2$, $Y_3$, and $Y_4$ according to <3>.

<76> The compound according to <75>, wherein in Formula (57e), $Y_1$ is a halogen atom.

<77> A method for producing a compound represented by the following Formula (57f) according to <76>, including reacting a compound represented by Formula (56a) according to <74> with a halogenating agent:

Wherein LG represents a functional group having a leaving ability, such as a halogen atom, a hydroxy group, or the like, and $X_1$, $X_2$, $X_3$, and $X_4$ have the same definitions as $X_1$, $X_2$, $X_3$, and $X_4$ in <3>.

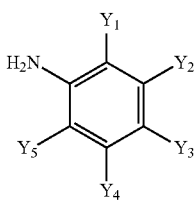

Formula (57g)

Wherein $Y_1$, $Y_2$, $Y_3$, $Y_4$, and $Y_5$ have the same definitions as $Y_1$, $Y_2$, $Y_3$, $Y_4$, and $Y_5$, respectively, in <3>.

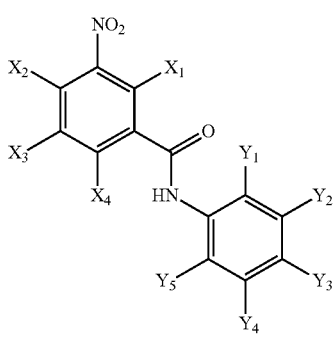

Formula (60b)

Wherein $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>. In a case where $X_1$, $X_2$, $X_3$, and $X_4$ represent all hydrogen atoms, $Y_5$ represents a C1-C3 haloalkyl group, and in a case where $X_2$ represents a cyano group, and $X_1$, $X_3$, and $X_1$ represent hydrogen atoms, $Y_5$ represents a C1-C3 haloalkoxy group or a C1-C3 haloalkyl group.

<80> A compound represented by the following Formula (61f):

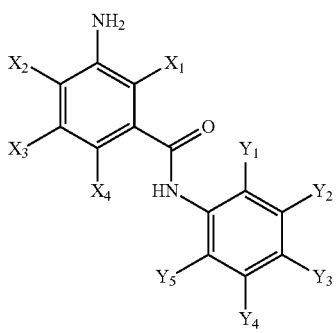

Formula (61f)

Wherein $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>. In a case where $X_1$, $X_2$, $X_3$, and $X_4$ represent all hydrogen atoms, $Y_5$ represents a C1-C3 haloalkyl group, and in a case where $X_2$ represents a cyano group, and $X_1$, $X_3$, and $X_4$ represent hydrogen atoms, $Y_5$ represents a C1-C3 haloalkoxy group or a C1-C3 haloalkyl group.

<81> A method for producing a compound represented by the following Formula (61f) according to <80>, including reacting a compound represented by a compound represented by Formula (60b) according to <78> in the presence of a reducing agent:

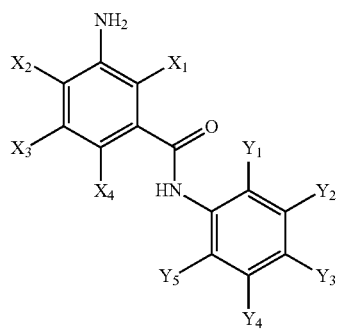

Formula (61f)

Wherein $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>. In a case where $X_1$, $X_2$, $X_3$, and $X_4$ represent all hydrogen atoms, $Y_5$ represents a C1-C3 haloalkyl group, and in a case where $X_2$ represents a cyano group, and $X_1$, $X_3$, and $X_4$ represent hydrogen atoms, $Y_5$ represents a C1-C3 haloalkoxy group or a C1-C3 haloalkyl group.

<82> A compound represented by the following Formula (69a):

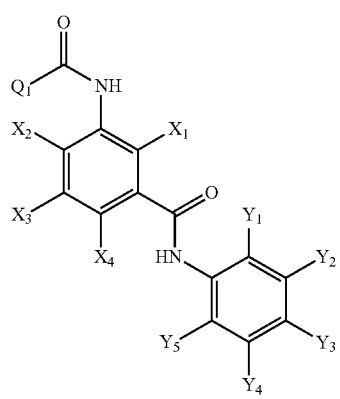

Formula (69a)

Wherein $Q_1$, $X_1$, $X_2$, $X_3$, $X_4$, $Y_1$, $Y_2$, $Y_3$, $Y_4$, and $Y_5$ have the same definitions as $Q_1$, $X_1$, $X_2$, $X_3$, $X_4$, $Y_1$, $Y_2$, $Y_3$, $Y_4$, and $Y_5$, respectively, in <3>.

<83> A method for producing a compound represented by the following Formula (69a) according to <82>, including reacting a compound represented by the following Formula (61c) with a compound represented by the following Formula (62a):

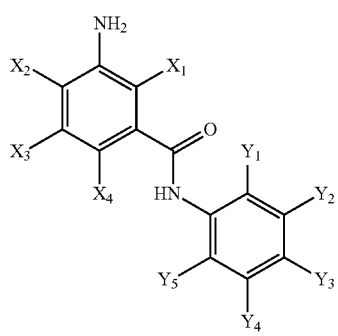

Formula (61c)

Wherein $X_1$, $X_2$, $X_3$, $X_4$, $Y_1$, $Y_2$, $Y_3$, $Y_4$, and $Y_5$ represent the same definitions as $X_1$, $X_2$, $X_3$, $X_4$, $Y_1$, $Y_2$, $Y_3$, $Y_4$, and $Y_5$, respectively, in <3>.

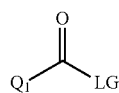

Formula (62a)

Wherein LG represents a functional group having a leaving ability, such as a halogen atom, a hydroxy group, or the like, and $Q_1$ represents the same definition as $Q_1$ in <3>.

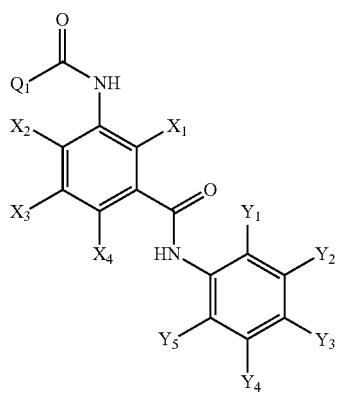

Formula (69a)

Wherein $Q_1$, $X_1$, $X_2$, $X_3$, $X_4$, $Y_1$, $Y_2$, $Y_3$, $Y_4$, and $Y_5$ represent the same definitions as $Q_1$, $X_1$, $X_2$, $X_3$, $X_4$, $Y_1$, $Y_2$, $Y_3$, $Y_4$, and $Y_5$, respectively, in <3>.

<84> A compound represented by the following Formula (53a):

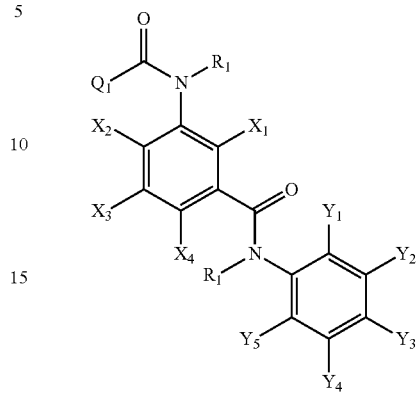

Formula (53a)

Wherein $Q_1$, $R_1$, $X_1$, $X_2$, $X_3$, $X_4$, $Y_1$, $Y_2$, $Y_3$, $Y_4$, and $Y_5$ have the same definitions as $Q_1$, $R_1$, $X_1$, $X_2$, $X_3$, $X_4$, $Y_1$, $Y_2$, $Y_3$, $Y_4$, and $Y_5$, respectively, in <3>.

<85> A method for producing a compound represented by the following Formula (53b), including reacting a compound represented by the following Formula (69a) according to <82> with a compound represented by the following Formula (64a):

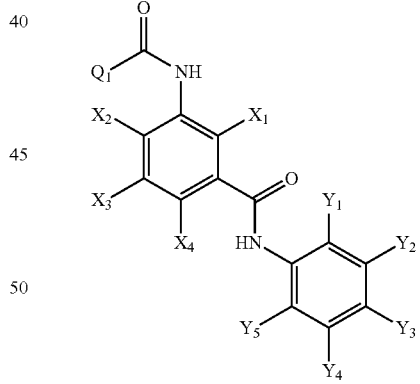

Formula (69a)

Wherein $Q_1$, $X_1$, $X_2$, $X_3$, $X_4$, $Y_1$, $Y_2$, $Y_3$, $Y_4$, and $Y_5$ have the same definitions as $Q_1$, $X_1$, $X_2$, $X_3$, $X_4$, $Y_1$, $Y_2$, $Y_3$, $Y_4$, and $Y_5$, respectively, in <3>.

Formula (64a)

Wherein LG represents a functional group having a leaving ability, such as a halogen atom, a hydroxy group, or the like, and $R_1$ represents a C1-C3 alkyl group.

Formula (53b)

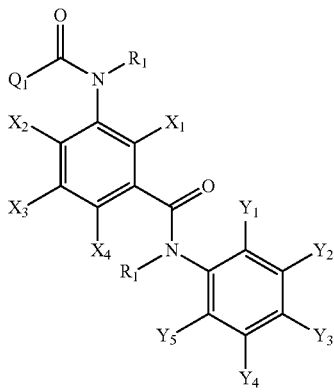

Wherein $R_1$ has the same definition as $R_1$ in Formula (64a), and $Q_1, X_1, X_2, X_3, X_4, Y_1, Y_2, Y_3, Y_4,$ and $Y_5$ have the same definitions as $Q_1, X_1, X_2, X_3, X_4, Y_1, Y_2, Y_3, Y_4,$ and $Y_5$, respectively, in <3>.

<86> A compound represented by the following Formula (57h):

Formula (57h)

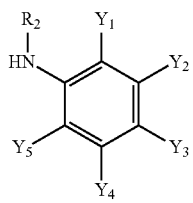

Wherein $Y_5$ represents a C1-C3 haloalkoxy group or a C1-C3 haloalkyl group, $R_2$ represents a C1-C3 alkyl group, and $Y_1, Y_2, Y_3,$ and $Y_4$ have the same definitions as $Y_1, Y_2, Y_3,$ and $Y_4$, respectively, in <3>.

<87> A method for producing a compound represented by the following Formula (57h) according to <86>, including reacting a compound represented by the following Formula (57l) with a compound represented by the following Formula (66a):

Formula (57l)

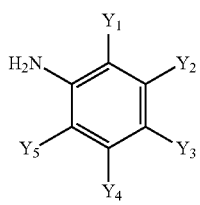

Wherein $Y_5$ represents a C1-C3 haloalkoxy group or a C1-C3 haloalkyl group, and $Y_2, Y_3,$ and $Y_4$ have the same definitions as $Y_1, Y_2, Y_3,$ and $Y_4$, respectively, in <3>.

$R_2$-LG  Formula (66a)

Wherein LG represents a functional group having a leaving ability, such as a halogen atom, a hydroxy group, or the like, and $R_2$ represents a C1-C3 alkyl group.

Formula (57h)

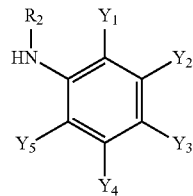

Wherein $Y_5$ represents a C1-C3 haloalkoxy group or a C1-C3 haloalkyl group, $R_2$ represents a C1-C3 alkyl group, and $Y_1, Y_2, Y_3,$ and $Y_4$ have the same definitions as $Y_1, Y_2, Y_3,$ and $Y_4$, respectively, in <3>.

<88> A method for producing a compound represented by the following Formula (57h) according to <86>, including reacting a compound represented by the following Formula (57l) according to <87> with an aldehyde:

Formula (57l)

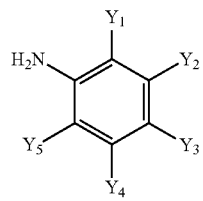

Wherein $Y_5$ represents a C1-C3 haloalkoxy group or a C1-C3 haloalkyl group, and $Y_1, Y_2, Y_3,$ and $Y_4$ have the same definitions as $Y_1, Y_2, Y_3,$ and $Y_4$, respectively, in <3>.

Formula (57h)

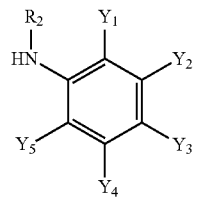

Wherein $Y_5$ represents a C1-C3 haloalkoxy group or a C1-C3 haloalkyl group, $R_2$ represents a C1-C3 alkyl group, and $Y_1, Y_2, Y_3,$ and $Y_4$ have the same definitions as $Y_1, Y_2, Y_3,$ and $Y_4$, respectively, in <3>.

<89> A compound represented by the following Formula (60c):

Formula (60c)

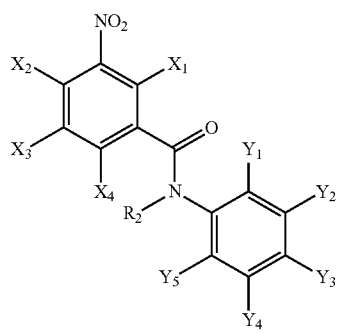

Wherein $R_2$ represents a C1-C3 alkyl group, and $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>.

<90> A method for producing a compound represented by the following Formula (60c) according to <89>, including reacting a compound represented by the following Formula (60d) with a compound represented by the following Formula (66a) according to <87>:

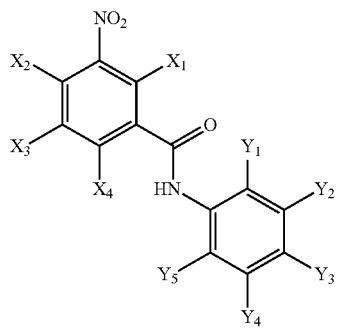

Formula (60d)

Wherein. $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>.

$R_2$-LG    Formula (66a)

Wherein LG represents a functional group having a leaving ability, such as a halogen atom, a hydroxy group, or the like, and $R_2$ represents a C1-C3 alkyl group.

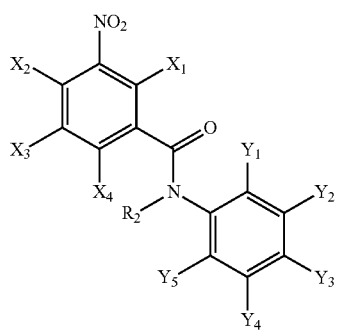

Formula (60c)

(Wherein $R_2$ represents a C1-C3 alkyl group, and $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>.

<91> A method for producing a compound represented by the following Formula (60c) according to <89>, including reacting a compound represented by the following Formula (57i) with a compound represented by the following Formula (59a) according to <79>:

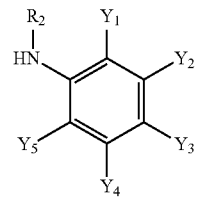

Formula (57i)

Wherein $R_2$ represents a C1-C3 alkyl group, and $Y_1$, $Y_2$, $Y_3$, $Y_4$, and $Y_5$ have the same definitions as $Y_1$, $Y_2$, $Y_3$, $Y_4$, and $Y_5$, respectively, in <3>.

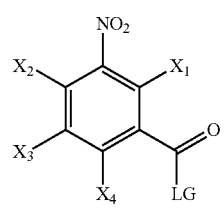

Formula (59a)

Wherein LG represents a functional group having a leaving ability, such as a halogen atom, a hydroxy group, or the like, $X_1$, $X_2$, $X_3$, and $X_4$ have the same definitions as $X_1$, $X_2$, $X_3$, and $X_4$ in <3>.

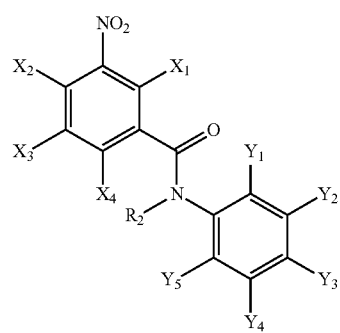

Formula (60c)

Wherein $R_2$ represents a C1-C3 alkyl group, and $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>.

<92> A compound represented by the following Formula (61g):

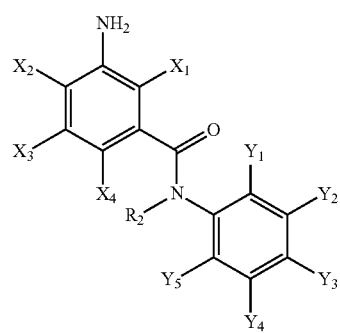

Formula (61g)

Wherein $R_2$ represents a C1-C3 alkyl group, and $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>.

<93> A method for producing a compound represented by the following Formula (61g) according to <92>, including reacting a compound represented by Formula (60c) according to <89> in the presence of a reducing agent:

Formula (61g)

Wherein $R_2$ represents a C1-C3 alkyl group, and $X_1$, $X_2$, $X_3$, $X_4$, $Y_1$, $Y_2$, $Y_3$, $Y_4$, and $Y_5$ have the same definitions as $X_1$, $X_2$, $X_3$, $X_4$, $Y_1$, $Y_2$, $Y_3$, $Y_4$, and $Y_5$, respectively, in <3>.

<94> A compound represented by the following Formula (63c):

Formula (63c)

Wherein $Q_1$, $R_2$, $X_1$, $X_2$, $X_3$, $X_4$, $Y_1$, $Y_2$, $Y_3$, $Y_4$, and $Y_5$ have the same definitions as $Q_1$, $R_2$, $X_1$, $X_2$, $X_3$, $X_4$, $Y_1$, $Y_2$, $Y_3$, $Y_4$, and $Y_5$, respectively, in <3>.

<95> A method for producing a compound represented by the following Formula (63c) according to <94>, including reacting a compound represented by the following Formula (61d) with a compound represented by the following Formula (62a) according to <83>:

Formula (61d)

Wherein $R_2$, $X_1$, $X_2$, $X_3$, $X_4$, $Y_1$, $Y_2$, $Y_3$, $Y_4$, and $Y_5$ have the same definitions as $R_2$, $X_1$, $X_2$, $X_3$, $X_4$, $Y_1$, $Y_2$, $Y_3$, $Y_4$, and $Y_5$, respectively, in <3>.

Formula (62a)

Wherein LG represents a functional group having a leaving ability, such as a halogen atom, a hydroxy group, or the like, and $Q_1$ has the same definition as Q1 in <3>.

Formula (63c)

Wherein $Q_1$, $R_2$, $X_1$, $X_2$, $X_3$, $X_4$, $Y_1$, $Y_2$, $Y_3$, $Y_4$, and $Y_5$ have the same definitions as $Q_1$, $R_2$, $X_1$, $X_2$, $X_3$, $X_4$, $Y_1$, $Y_2$, $Y_3$, $Y_4$, and $Y_5$, respectively, in <3>.

<96> A method for producing a compound represented by the following Formula (3a), including reacting a compound represented by the following Formula (63c) according to <94> with a compound represented by the following Formula (64a) according to <85>:

Formula (63c)

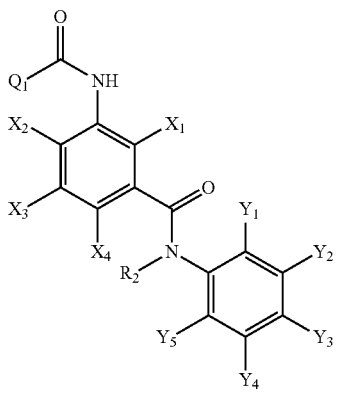

Wherein $Q_1, R_2, X_1, X_2, X_3, X_4, Y_1, Y_2, Y_3, Y_4$, and $Y_5$ have the same definitions as $Q_1, R_2, X_1, X_2, X_3, X_4, Y_1, Y_2, Y_3, Y_4$, and $Y_5$, respectively, in <3>.

$R_1$-LG  Formula (64a)

Wherein LG represents a functional group having a leaving ability, such as a halogen atom, a hydroxy group, or the like, and $R_1$ represents a C1-C3 alkyl group.

Formula (3a)

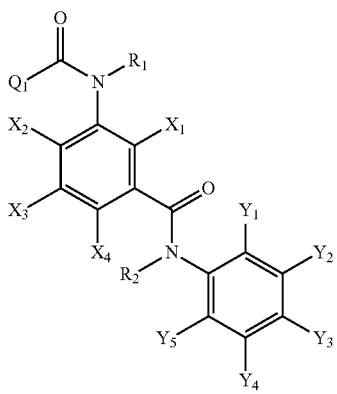

Wherein $R_1$ has the same definition as $R_1$ in Formula (64a), and $Q_1, R_2, X_1, X_2, X_3, X_4, Y_1, Y_2, Y_3, Y_4$, and $Y_5$ have the same definitions as $Q_1, R_2, X_1, X_2, X_3, X_4, Y_1, Y_2, Y_3, Y_4$, and $Y_5$, respectively, in <3>.

<97> A compound represented by the following Formula (65e):

Formula (65e)

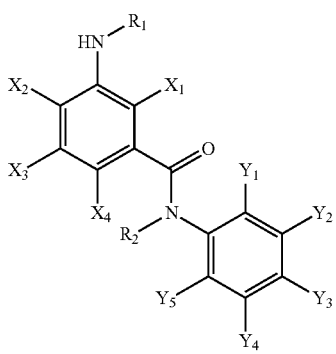

Wherein $R_1, R_2, X_1, X_2, X_3, X_4, Y_1, Y_2, Y_3, Y_4$, and $Y_5$ have the same definitions as $R_1, R_2, X_1, X_2, X_3, X_4, Y_1, Y_2, Y_3, Y_4$, and $Y_5$, respectively, in <3>. In a case where $X_1, X_2, X_3$, and $X_4$, represent all hydrogen atoms, and $R_2$ represents a hydrogen atom, $Y_5$ represents a C1-C3 haloalkyl group, and in a case where $X_2$ represents a cyano group, $X_1, X_3$, and $X_4$ represent hydrogen atoms, and $R_1$ and $R_2$ represent hydrogen atoms, $Y_5$ represents a C1-C3 haloalkoxy group or a C1-C3 haloalkyl group.

<98> A method for producing a compound represented by the following Formula (65f), including reacting a compound represented by the following Formula (61d) with an aldehyde:

Formula (61d)

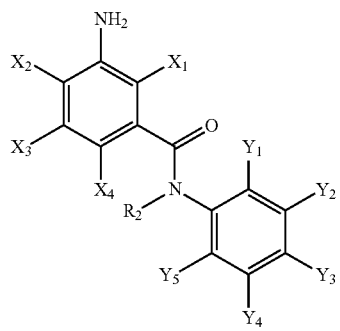

Wherein $R_2, X_1, X_2, X_3, X_4, Y_1, Y_2, Y_3, Y_4$, and $Y_5$ have the same definitions as $R_2, X_1, X_2, X_3, X_4, Y_1, Y_2, Y_3, Y_4$, and $Y_5$, respectively, in <3>.

Formula (65f)

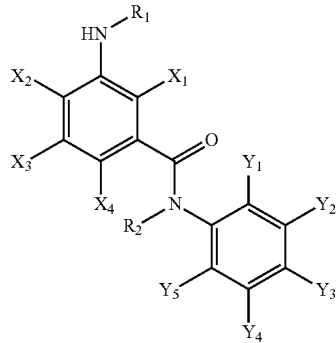

Wherein $R_1$ represents a C1-C3 alkyl group, and $R_2, X_1, X_2, X_3, X_4, Y_1, Y_2, Y_3, Y_4$, and $Y_5$ have the same definitions as $R_2, X_1, X_2, X_3, X_4, Y_1, Y_2, Y_3, Y_4$, and $Y_5$, respectively, in <3>. In a case where $X_1, X_2, X_3$, and $X_4$ represent all hydrogen atoms, and $R_2$ represents a hydrogen atom, $Y_5$ represents a C1-C3 haloalkyl group.

<99> A method for producing a compound represented by the following Formula (3) according to <3>, including reacting a compound represented by the following Formula (65g) with a compound represented by the following Formula (62a) according to <83>:

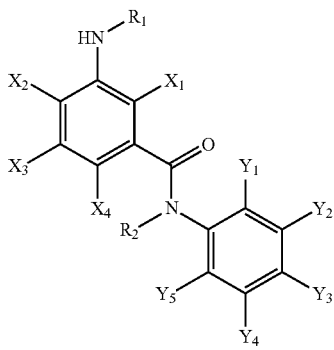

Formula (65g)

Wherein $R_1, R_2, X_1, X_2, X_3, X_4, Y_1, Y_2, Y_3, Y_4,$ and $Y_5$ have the same definitions as $R_1, R_2, X_1, X_2, X_3, X_4, Y_1, Y_2, Y_3, Y_4,$ and $Y_5$, respectively, in <3>.

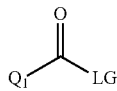

Formula (62a)

Wherein LG represents a functional group having a leaving ability, such as a halogen atom, a hydroxy group, or the like, and $Q_1$ has the same definition as $Q_1$ in <3>.

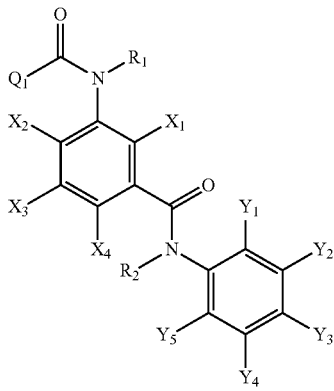

Formula (3)

<100> A compound represented by the following Formula (70a):

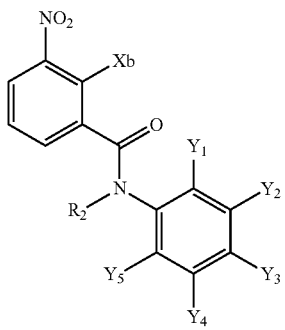

Formula (70a)

Wherein Xb represents a chlorine atom, a bromine atom, or an iodine atom, and $R_2, Y_1, Y_2, Y_3, Y_4,$ and $Y_5$ have the same definitions as $R_2, Y_1, Y_2, Y_3, Y_4,$ and $Y_5$, respectively, in <3>.

<101> A compound represented by the following Formula (72a):

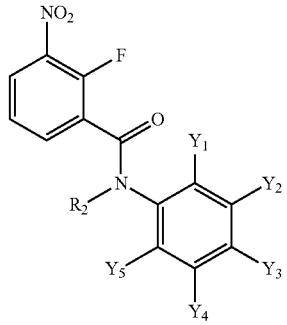

Formula (72a)

Wherein $R_2, Y_1, Y_2, Y_3, Y_4,$ and $Y_5$ have the same definitions as $R_2, Y_1, Y_2, Y_3, Y_4,$ and $Y_5$, respectively, in <3>.

<102> A method for producing a compound represented by the following Formula (72a) according to <101>, including reacting a compound represented by Formula (70a) according to <100> with a fluorinating agent:

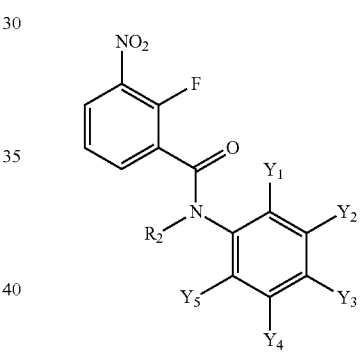

Formula (72a)

Wherein $R_2, Y_1, Y_2, Y_3, Y_4,$ and $Y_5$ have the same definitions as $R_2, Y_1, Y_2, Y_3, Y_4,$ and $Y_5$, respectively, in <3>.

<103> A composition for controlling a pest comprising as an active ingredient at least one amide derivative represented by the following Formula (A1):

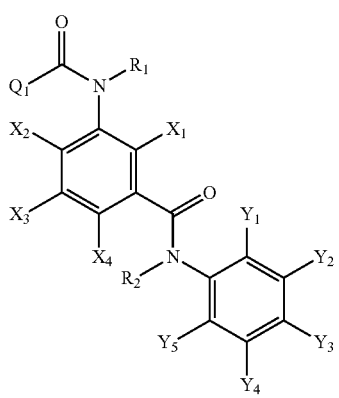

Formula (A1)

Wherein, in Formula (A1), $Q_1$ represents a phenyl group or a phenyl group substituted with a halogen atom; $X_1$ represents a fluorine atom; $X_2$, $X_3$, and $X_4$ are each a hydrogen atom; $R_1$ represents a hydrogen atom or a C1-C3 alkyl group; $R_2$ is a hydrogen atom; $Y_1$ and $Y_5$ each independently represent a halogen atom or a C1-C3 haloalkyl group; $Y_2$ and $Y_4$ each represent a hydrogen atom; and $Y_3$ represents a heptafluoroisopropyl group.

<104> The composition according to <103>, wherein the pest is an animal parasite.

<105> The composition according to <104>, wherein in Formula (A1), $Q_1$ represents a phenyl group or a phenyl group substituted with a single fluorine atom; $R_1$ represents a hydrogen atom or a methyl group; and $Y_1$ and $Y_5$ each independently represent a bromine or iodine atom or a trifluoromethyl group.

<106> The composition according to <105>, wherein the amide derivative represented by Formula (A1) is 2-fluoro-3-(N-methylbenzamide)-N-(2-bromo-6-trifluoromethyl-4-(heptafluoropropan-2-yl)phenyl)benzamide, 2-fluoro-3-(4-fluoro-N-methylbenzamide)-N-(2-iodo-6-trifluoromethyl-4-(heptafluoropropan-2-yl)phenyl)benzamide, 2-fluoro-3-(3-fluoro-N-methylbenzamide)-N-(2-iodo-6-trifluoromethyl-4-(heptafluoropropan-2-yl)phenyl) benzamide, 2-fluoro-3-(4-fluorobenzamide)-N-(2-iodo-6-trifluoromethyl-4-(heptafluoropropan-2-yl)phenyl) benzamide, or 2-fluoro-3-(N-methylbenzamide)-N-(2,6-dibromo-4-(heptafluoropropan-2-yl)phenyl)benzamide.

<107> A method for exterminating animal parasites, comprising administering to an animal the composition according to <104> to <106>.

<108> The method according to <107>, wherein the animal parasite is an ectoparasite.

<109> The method according to <108>, wherein the ectoparasite is Siphonaptera pests.

<110> The method according to <108>, wherein the ectoparasite is Acarina pests.

According to the present invention, an amide derivative showing a pesticidal effect against a wide range of agricultural/horticultural pests, a pest control agent containing the amide derivative as an active ingredient, and a pest controlling method are provided.

DETAILED DESCRIPTION OF THE INVENTION

An amide compound according to the present invention is represented by the following Formula (1).

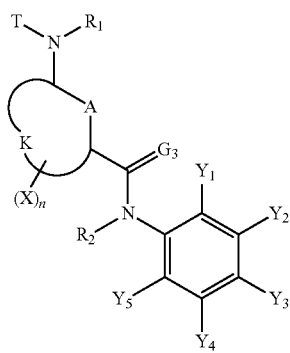

Formula (1)

In Formula (1), A represents a carbon atom, an oxygen atom, a nitrogen atom, an oxidized nitrogen atom, or a sulfur atom. K represents a non-metal atom group necessary for forming a cyclic linking group derived from benzene, pyridine, pyridine-N-oxide, pyrimidine, pyrazine, pyridazine, triazine, pyrrole, pyrazole, imidazole, oxazole, isoxazole, thiazole, isothiazole, furan, thiophene, oxadiazole, thiodiazole, or triazole, in combination with A and two carbon atoms to which A bonds.

X represents a hydrogen atom, a halogen atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C1-C6 alkylsulfonyloxy group, a C1-C6 haloalkylsulfonyloxy group, a C2-C7 alkylcarbonyl group, a C2-C7 haloalkylcarbonyl group, a C2-C7 alkylcarbonyloxy group, a C2-C7 haloalkylcarbonyloxy group, arylcarbonyloxy group, a C2-C7 alkoxycarbonyl group, a C2-C7 haloalkoxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C2-C7 alkoxycarbonyloxy group, a C2-C7 haloalkoxycarbonyloxy group, an arylcarbonylamino group, an amino group, a carbamoyl group, a cyano group, a hydroxy group, pentafluorosulfanyl group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkenylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, a phenyl group, or a heterocyclic group, and when there are plural X's, each X may be the same as or different from an other.

n represents an integer of from 0 to 4. T represents —C(=$G_1$)-$Q_1$ or —C(=$G_1$)-$G_2Q_2$. $G_1$ and $G_2$ each independently represent an oxygen atom or a sulfur atom, and $Q_1$ and $Q_2$ represent a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a benzyl group, a phenyl group which may have a substituent, a naphthyl group, or a heterocyclic group which may have a substituent.

$Y_1$ and $Y_5$ each independently represent a halogen atom, a C1-C6 haloalkoxy group, or a C1-C3 haloalkyl group, $Y_2$ and $Y_4$ each independently represent a hydrogen atom, a halogen atom, or a C1-C4 alkyl group, $Y_3$ represents a C2-C5 haloalkyl group.

Further, in $Q_1$ and $Q_2$, the substituent of a phenyl group which may have a substituent and a heterocyclic group which may have a substituent represents one or more substituent selected from a group consisting of a halogen atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C2-C7 alkylcarbonyl group, a C2-C7 haloalkylcarbonyl group, a C2-C7 alkylcarbonyloxy group, a C2-C7 haloalkylcarbonyloxy group, a C1-C6 alkylsulfonyloxy group, a C1-C6 haloalkylsulfonyloxy group, a C2-C7 alkoxycarbonyl group, a C2-C7 haloalkoxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkenylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, an amino group, a carbamoyl group, a cyano group, a nitro group, a hydroxy group, pentafluorosulfanyl group, a phenyl group which may have a substituent, and a heterocyclic group which may have a substituent, and when there are two or more substituents, each substituent may be the same as or different from each other.

Moreover, the heterocyclic group in X, $Q_1$, and $Q_2$ represent a pyridyl group, a pyridine-N-oxide group, a pyrimidinyl group, a pyrazinyl group, a pyridazyl group, furyl group, thienyl group, an oxazolyl group, an isoxazolyl group, an oxadiazolyl group, a thiazolyl group, an isothiazolyl group, a thiadiazolyl group, a pyrrolyl group, an imidazolyl group, a triazolyl group, a pyrazolyl group, or a tetrazolyl group.

$G_3$ represents an oxygen atom or a sulfur atom.

$R_1$ and $R_2$ each independently represent a hydrogen atom, an oxygen atom, a halogen atom, a hydroxy group, a nitro group, a nitroso group, a trimethylsilyl group, a t-butyldimethylsilyl group, a cyano group, an amino group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)$R_7$ (wherein $R_7$ represents a C1-C6 alkyl group, a C1-C6 haloalkyl group, a C1-C6 alkoxy group, or a C1-C6 haloalkoxy group).

However the amide derivative represented by Formula (1) is not one of (A) to (I):

(A) A case where in Formula (1), K represents a non-metal atom group necessary for forming a cyclic linking group derived from pyridine in combination with A and two carbon atoms to which A bonds, $Y_1$ represents a halogen atom, and $Y_5$ represents a C1-C6 haloalkoxy group, and T is —C(=$G_1$)-$Q_1$.

(B) A case where in Formula (1), K represents a non-metal atom group necessary for forming a cyclic linking group derived from pyrrole, pyrazole, imidazole, oxazole, isoxazole, thiazole, isothiazole, furan, thiophene, oxadiazole, thiodiazole, or triazole, in combination with A and two carbon atoms to which A bonds, $Y_1$ and $Y_5$ represent each independently a halogen atom, and T is —C(=$G_1$)-$G_2Q_2$.

(C) A case where in Formula (1), K represents a non-metal atom group necessary for forming a cyclic linking group derived from pyrrole, pyrazole, imidazole, oxazole, isoxazole, thiazole, isothiazole, furan, thiophene, oxadiazole, thiodiazole, or triazole, in combination with A and two carbon atoms to which A bonds, T represents —C(=$G_1$)-$Q_1$, $Y_1$ is a halogen atom, and $Y_5$ represents a halogen atom or a haloalkoxy group.

(D) A case where the amide derivative is an amide compound represented by the following Formula (2):

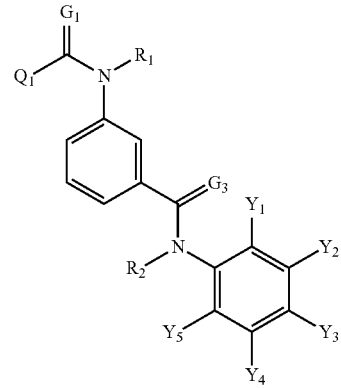

Formula (2)

In Formula (2), $Y_2$ to $Y_4$, $Q_1$, $G_1$, $G_3$, $R_1$, and $R_2$ have the same definitions as $Y_2$ to $Y_4$, $Q_1$, $G_1$, $G_3$, $R_1$, and $R_2$, respectively, in Formula (1), $Y_1$ represents a halogen atom, and $Y_5$ represents a C1-C2 haloalkoxy group.

(E) A case where in Formula (2), $Y_1$ and $Y_5$ represent halogen atoms, all X's represent hydrogen atoms, and $Y_3$ represents a C2-C3 haloalkyl group.

(F) A case where the amide derivative is an amide derivative represented by the following Formula (3)

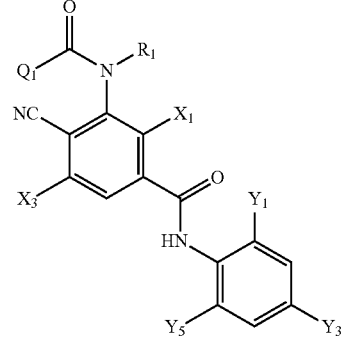

Formula (3)

In Formula (3), $Y_1$ and $Y_5$ each independently represent a halogen atom, $X_1$ and $X_3$ each independently represent a hydrogen atom or a fluorine atom, $Q_1$ has the same definition as $Q_1$ in Formula (1), $R_1$ represents a hydrogen atom or a methyl group, and $Y_3$ represents a C3-C4 perfluoroalkyl group.

(G) A case where the amide derivative is an amide derivative represented by the following Formula (4):

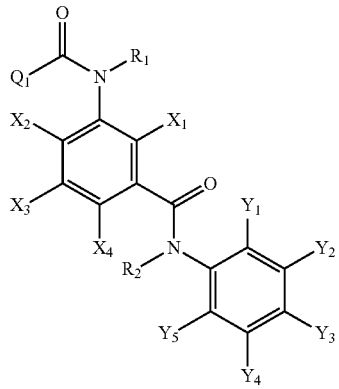

Formula (4)

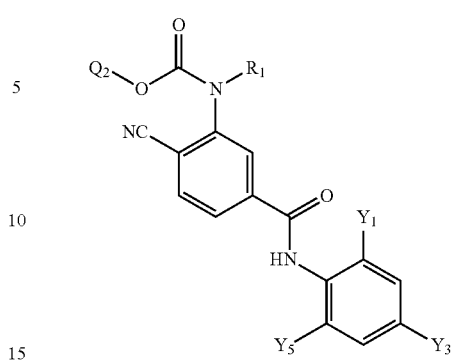

Formula (6)

In Formula (4), $X_1$ represents a fluorine atom, $X_2$, $X_3$, and $X_4$ represent hydrogen atoms, $Y_1$ and $Y_5$ are different from each other and represent a bromine atom or a trifluoromethoxy group, $Y_2$ and $Y_4$ represent hydrogen atoms, $Y_3$ represents a heptafluoroisopropyl group, $Q_1$ represents a phenyl group or a 2-chloropyridin-3-yl group, and $R_1$ and $R_2$ are different from each other, and represent a hydrogen atom or a methyl group.

Alternatively, $X_1$ represents a fluorine atom, $X_2$, $X_3$, and $X_4$ represent hydrogen atoms, $Y_1$ and $Y_5$ represent bromine atoms, $Y_2$ and $Y_4$ represent hydrogen atoms, $Y_3$ represents a pentafluoroethyl group, $Q_1$ represents a 2-fluorophenyl group, and $R_1$ and $R_2$ each independently represent a hydrogen atom or a methyl group.

(H) A case where the amide derivative is an amide derivative represented by the following Formula (5):

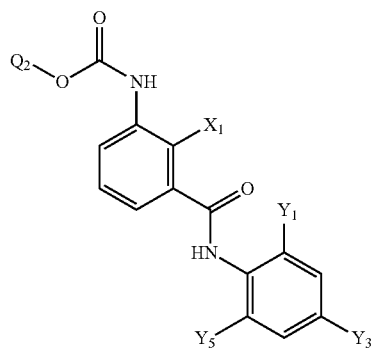

Formula (5)

In Formula (5), $Y_1$ and $Y_5$ each independently represent a halogen atom, $X_1$ represents a hydrogen atom or a fluorine atom, $Q_2$ represents a 2,2,2-trichloroethyl group or a 3,3,3-trifluoro-n-propyl group, and $Y_3$ represents a C2-C4 haloalkyl group.

(I) A case where the amide derivative is an amide derivative represented by the following Formula (6)

In Formula (6), $Y_1$ and $Y_5$ each independently represent a halogen atom, $Q_2$ has the same definition as $Q_2$ in Formula (1), $R_1$ represents a hydrogen atom or a methyl group, and $Y_3$ represents a C3-C4 haloalkyl group In the aspect of a pest control activity, the amide derivative preferably represented by the following Formula (7), and more preferably represented by the following Formula (8).

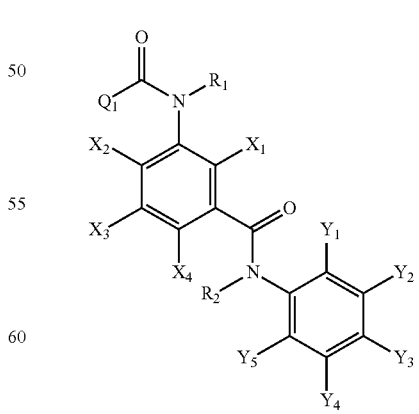

Formula (7)

In Formula (7), X, n is 4, $Y_1$ to $Y_5$, $Q_1$, $G_1$, $G_3$, $R_1$, and $R_2$ have the same definitions as X, $Y_1$ to $Y_5$, $Q_1$, $G_1$, $G_3$, $R_1$, and $R_2$, respectively, in Formula (1).

Formula (8)

In Formula (8), $Q_1$ represents a phenyl group which may have a substituent or a pyridyl group which may have a substituent. $X_1$, $X_2$, $X_3$ and $X_4$ each independently represent hydrogen atoms or fluorine atoms. $R_1$ and $R_2$ each independently represent hydrogen atoms or C1-C3 alkyl groups.

$Y_1$ and $Y_5$ each independently represent halogen atoms, C1-C3 haloalkoxyl groups, or C1-C3 haloalkyl groups, $Y_2$ and $Y_4$ each independently represent hydrogen atoms, halogen atoms, C1-C4 alkyl groups, and $Y_3$ represents a C3-C4 haloalkyl group.

In a case where $Y_1$ and $Y_5$ represent halogen atoms simultaneously, at least one of $X_1$ and $X_2$ represents a fluorine atom. Further, in a case where $Y_1$ or $Y_5$ represents a C1-C3 haloalkoxy group, $X_2$ represents a fluorine atom.

The terms used in the formulae including the Formula (1) and the like according to the present invention, have the same meanings as described below in the definitions.

The "halogen atom" represents a fluorine atom, a chlorine atom, a bromine atom, or an iodine atom.

The expression "Ca—Cb (wherein a and b represent an integer of 1 or more)", for example, "C1-C3" means the number of carbon atoms of from 1 to 3, the "C2-C6" means the number of carbon atoms of from 2 to 6, and the "C1-C4" means the number of carbon atoms of from 1 to 4.

"n-" means normal, "i-" means iso, "s-" means secondary, and "t-" means tertiary.

The "C1-C3 alkyl group" in the present invention represents, for example, a linear or branched alkyl group having from 1 to 3 carbon atoms such as methyl, ethyl, n-propyl, propyl, and the like.

The "C1-C3 haloalkyl group" represents, for example, a linear or branched alkyl group having from 1 to 3 carbon atoms, that is substituted with one or more halogen atoms which may be the same as or different from each other, such as trifluoromethyl, pentafluoroethyl, heptafluoro-n-propyl, heptafluoro-i-propyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 2,3,3,3-trifluoro-n-propyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, and the like.

The "C1-C4 alkyl group" represents, for example, a linear or branched alkyl group having from 1 to 4 carbon atoms such as methyl, ethyl, n-propyl, i-propyl, n-butyl, s-butyl, t-butyl, and the like.

The "C1-C3 haloalkoxy group" represents, for example, a linear or branched alkoxy group having from 1 to 3 carbon atoms, that is substituted with one or more halogen atoms which may be the same as or different from each other, such as trifluoromethoxy, pentafluoroethoxy, heptafluoro-n-propyloxy, heptafluoro-i-propyloxy, 2,2-difluoroethoxy, 2,2-dichloroethoxy, 2,2,2-trifluoroethoxy, 2-fluoroethoxy, 2-chloroethoxy, 2-bromoethoxy, 2-iodoethoxy, 2,2,2-trichloroethoxy, 2,2,2-tribromoethoxy, 1,3-difluoro-2-propyloxy, 1,3-dichloro-2-propyloxy, 1-chloro-3-fluoro-2-propyloxy, 1,1,1-trifluoro-2-propyloxy, 2,3,3,3-trifluoro-n-propyloxy, 1,1,1,3,3,3-hexafluoro-2-propyloxy, 1,1,1,3,3,3-hexafluoro-2-chloro-2-propyloxy, 1,1,1,3,3,3-hexafluoro-2-bromo-2-propyloxy, 1,1,2,3,3,3-hexafluoro-2-chloro-n-propyloxy, 1,1,2,3,3,3-hexafluoro-2-bromo-n-propyloxy, 1,1,2,3,3,3-hexafluoro-1-bromo-2-propyloxy, 2,2,3,3,3-pentafluoro-n-propyloxy, 3-fluoro-n-propyloxy, 3-chloro-n-propyloxy, 3-bromo-n-propyloxy, and the like.

The "C3-C4 perfluoroalkyl group" represents, for example, a linear or branched alkyl group having from 3 to 4 carbon atoms, that all hydrogen atoms is substituted with fluorine atoms such as perfluoro-n-propyl, perfluoro-1-propyl, perfluoro-n-butyl, perfluoro-1-butyl, perfluoro-s-butyl, perfluoro-t-butyl, and the like.

The "C1 haloalkyl group" represents, for example, a methyl group that is substituted with one or more halogen atoms which may be the same as or different from each other, such as trifluoromethyl, 1,1-difluoro-1-bromomethyl, and the like.

The "C1-C6 alkyl group" in the present invention represents, for example, a linear or branched alkyl group having from 1 to 6 carbon atoms such as methyl, ethyl, n-propyl, propyl, n-butyl, s-butyl, t-butyl, n-pentyl, 2-pentyl, neopentyl, 4-methyl-2-pentyl, n-hexyl, 3-methyl-n-pentyl, and the like.

The "C1-C6 haloalkyl group" represents, for example, a linear or branched alkyl group having from 1 to 6 carbon atoms, that is substituted with one or more halogen atoms which may be the same as or different from each other, such as trifluoromethyl, pentafluoroethyl, heptafluoro-n-propyl, heptafluoro-i-propyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 2,3,3,3-trifluoro-n-propyl, 4,4,4-trifluoro-n-butyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, 3,3,4,4,4-pentafluoro-2-butyl, nonafluoro-n-butyl, nonafluoro-2-butyl, 5,5,5-trifluoro-n-pentyl, 4,4,5,5,5-pentafluoro-2-pentyl, 3-chloro-n-pentyl, 4-bromo-2-pentyl, and the like.

The "C3-C9 cycloalkyl group" represents, for example, a cycloalkyl group having from 3 to 9 carbon atoms, that has a cyclic structure, such as cyclopropyl, cyclobutyl, cyclopentyl, 2-methylcyclopentyl, 3-methylcyclopentyl, cyclohexyl, 2-methylcyclohexyl, 3-methylcyclohexyl, 4-methylcyclohexyl, and the like.

The "C3-C9 halocycloalkyl group" represents, for example, a cycloalkyl group having 3 to 9 carbon atoms, that is substituted with one or more halogen atoms which may be the same as or different from each other and has a cyclic structure, such as, 2,2,3,3-tetrafluorocyclobutyl, 2-chlorocyclohexyl, 4-chlorocyclohexyl, and the like.

The "C2-C6 alkenyl group" represents, for example, an alkenyl group having from 2 to 6 carbon atoms, that has a double bond in the carbon chain, such as vinyl, allyl, 2-butenyl, 3-butenyl, and the like.

The "C2-C6 haloalkenyl group" represents, for example, a linear or branched alkenyl group having from 2 to 6 carbon atoms, that is substituted with one or more halogen atoms which may be the same as or different from each other and has a double bond in the carbon chain, such as 3,3-difluoro-2-propenyl, 3,3-dichloro-2-propenyl, 3,3-dibromo-2-propenyl, 2,3-dibromo-2-propenyl, 4,4-difluoro-3-butenyl, 3,4,4-tribromo-3-butenyl, and the like.

The "C2-C6 alkynyl group" represents, for example, an alkynyl group having from 2 to 6 carbon atoms, that has a triple bond in the carbon chain, such as propargyl, 1-butyn-3-yl, 1-butyn-3-methyl-3-yl, and the like.

The "C2-C6 haloalkynyl group" represents, for example, a linear or branched alkynyl group having from 2 to 6 carbon atoms, that is substituted with one or more halogen atoms which may be the same as or different from each other and has a triple bond in the carbon chain, such as fluoroethynyl, chloroethynyl, bromoethynyl, 3,3,3-trifluoro-1-propynyl, 3,3,3-trichloro-1-propynyl, 3,3,3-tribromo-1-propynyl, 4,4,4-trifluoro-1-butynyl, 4,4,4-trichloro-1-butynyl, 4,4,4-tribromo-1-butynyl, and the like.

The "C1-C6 alkoxy group" represents, for example, a linear, branched, or cyclic alkoxy group having from 1 to 6 carbon atoms, such as methoxy, ethoxy, n-propyloxy, i-propyloxy, cyclopropoxy, n-butoxy, s-butoxy, i-butoxy, t-butoxy, n-pentyloxy, i-pentyloxy, n-hexyloxy, cyclohexyloxy, and the like.

The "C1-C6 haloalkoxy group" represents, for example, a linear, branched, or cyclic alkoxy group having from 1 to 6 carbon atoms, that is substituted with one or more halogen atoms which may be the same as or different from each other, such as trifluoromethoxy, pentafluoroethoxy, 2-chloroethoxy, 2,2,2-trifluoroethoxy, heptafluoro-n-propoxy, heptafluoro-i-propoxy, 1,1,1,3,3,3-hexafluoro-2-propoxy, 3-fluoro-n-propoxy, 1-chlorocyclopropoxy, 2-bromocyclopropoxy, 3,3,4,4,4-pentafluoro-2-butoxy, nonafluoro-n-butoxy, nonafluoro-2-butoxy, 5,5,5-trifluoro-n-pentyloxy, 4,4,5,5,5-pentafluoro-2-pentyloxy, 3-chloro-n-pentyloxy, 4-bromo-2-pentyloxy, 4-chlorobutyloxy, 2-iodo-n-propyloxy, and the like.

The "C1-C6 alkylthio group" represents, for example, a linear, branched, or cyclic alkylthio group having from 1 to 6 carbon atoms, such as methylthio, ethylthio, n-propylthio, i-propylthio, cyclopropylthio, n-butylthio, s-butylthio, i-butylthio, t-butylthio, n-pentylthio, pentylthio, n-hexylthio, cyclohexylthio, and the like.

The "C1-C6 haloalkylthio group" represents, for example, a linear, branched, or cyclic alkylthio group having from 1 to 6 carbon atoms, that is substituted with one or more halogen atoms which may be the same as or different from each other, such as trifluoromethylthio, pentafluoroethylthio, 2-chloroethylthio, 2,2,2-trifluoroethylthio, heptafluoro-n-propylthio, heptafluoro-i-propylthio, 1,1,1,3,3,3-hexafluoro-2-propylthio, 3-fluoro-n-propylthio, 1-chlorocyclopropylthio, 2-bromocyclopropylthio, 3,3,4,4,4-pentafluoro-2-butylthio, nonafluoro-n-butylthio, nonafluoro-2-butylthio, 5,5,5-trifluoro-n-pentylthio, 4,4,5,5,5-pentafluoro-2-pentylthio, 3-chloro-n-pentylthio, 4-bromo-2-pentylthio, 4-chlorobutylthio, 2-iodo-n-propylthio, and the like.

The "C1-C6 alkylsulfinyl group" represents, for example, a linear, branched, or cyclic alkylsulfinyl group having from 1 to 6 carbon atoms, such as methylsulfinyl, ethylsulfinyl, n-propylsulfinyl, i-propylsulfinyl, cyclopropylsulfinyl, n-butylsulfinyl, s-butylsulfinyl, i-butylsulfinyl, t-butylsulfinyl, n-pentylsulfinyl, i-pentylsulfinyl, n-hexylsulfinyl, cyclohexylsulfinyl, and the like.

The "C1-C6 haloalkylsulfinyl group" represents, for example, a linear, branched, or cyclic alkylsulfinyl group having from 1 to 6 carbon atoms, that is substituted with one or more halogen atoms which may be the same as or different from each other, such as trifluoromethylsulfinyl, pentafluoroethylsulfinyl, 2-chloroethylsulfinyl, 2,2,2-trifluoroethylsulfinyl, heptafluoro-n-propylsulfinyl, heptafluoro-i-propylsulfinyl, 1,1,1,3,3,3-hexafluoro-2-propylsulfinyl, 3-fluoro-n-propylsulfinyl, 1-chlorocyclopropylsulfinyl, 2-bromocyclopropylsulfinyl, 3,3,4,4,4-pentafluoro-2-butylsulfinyl, nonafluoro-n-butylsulfinyl, nonafluoro-2-butylsulfinyl, 5,5,5-trifluoro-n-pentylsulfinyl, 4,4,5,5,5-pentafluoro-2-pentylsulfinyl, 3-chloro-n-pentylsulfinyl, 4-bromo-2-pentylsulfinyl, 4-chlorobutylsulfinyl, 2-iodo-n-propylsulfinyl, and the like.

The "C1-C6 alkylsulfonyl group" represents, for example, a linear, branched, or cyclic alkylsulfonyl group having from 1 to 6 carbon atoms, such as methylsulfonyl, ethylsulfonyl, n-propylsulfonyl, i-propylsulfonyl, cyclopropylsulfonyl, n-butylsulfonyl, s-butylsulfonyl, i-butylsulfonyl, t-butylsulfonyl, n-pentylsulfonyl, i-pentylsulfonyl, n-hexylsulfonyl, cyclohexylsulfonyl, and the like.

The "C1-C6 haloalkylsulfonyl group" represents, for example, a linear, branched, or cyclic alkylsulfonyl group having from 1 to 6 carbon atoms, that is substituted with one or more halogen atoms which may be the same as or different from each other, such as trifluoromethylsulfonyl, pentafluoroethylsulfonyl, 2-chloroethylsulfonyl, 2,2,2-trifluoroethylsulfonyl, heptafluoro-n-propylsulfonyl, heptafluoro-i-propylsulfonyl, 1,1,1,3,3,3-hexafluoro-2-propylsulfonyl, 3-fluoro-n-propylsulfonyl, 1-chlorocyclopropylsulfonyl, 2-bromocyclopropylsulfonyl, 3,3,4,4,4-pentafluoro-2-butylsulfonyl, nonafluoro-n-butylsulfonyl, nonafluoro-2-butylsulfonyl, 5,5,5-trifluoro-n-pentylsulfonyl, 4,4,5,5,5-pentafluoro-2-pentylsulfonyl, 3-chloro-n-pentylsulfonyl, 4-bromo-2-pentylsulfonyl, 4-chlorobutylsulfonyl, 2-iodo-n-propylsulfonyl, and the like.

The "C1-C6 alkylsulfonyloxy group" represents, for example, a linear, branched, or cyclic alkylsulfonyloxy group having from 1 to 6 carbon atoms, such as methanesulfonyloxy, ethanesulfonyloxy, n-propanesulfonyloxy, i-propanesulfonyloxy, cyclopropanesulfonyloxy, n-butanesulfonyloxy, s-butanesulfonyloxy, i-butanesulfonyloxy, t-butanesulfonyloxy, n-pentanesulfonyloxy, i-pentanesulfonyloxy, n-hexanesulfonyloxy, cyclohexanesulfonyloxy, and the like.

The "C1-C6 haloalkylsulfonyloxy group" represents, for example, a linear, branched, or cyclic alkylsulfonyloxy group having from 1 to 6 carbon atoms, that is substituted with one or more halogen atoms which may be the same as or different from each other, such as trifluoromethanesulfonyloxy, pentafluoropropanesulfonyloxy, 2-chloropropanesulfonyloxy, 2,2,2-trifluoropropanesulfonyloxy, heptafluoro-n-propanesulfonyloxy, heptafluoro-i-propanesulfonyloxy, 1,1,1,3,3,3-hexafluoro-2-propanesulfonyloxy, 3-fluoro-n-propanesulfonyloxy, 1-chlorocyclopropanesulfonyloxy, 2-bromocyclopropanesulfonyloxy, 3,3,4,4,4-pentafluoro-2-butanesulfonyloxy, nonafluoro-n-butanesulfonyloxy, nonafluoro-2-butanesulfonyloxy, 5,5,5-trifluoro-n-pentanesulfonyloxy, 4,4,5,5,5-pentafluoro-2-pentanesulfonyloxy, 3-chloro-n-pentanesulfonyloxy, 4-bromo-2-pentanesulfonyloxy, 4-chlorobutanesulfonyloxy, 2-iodo-n-propanesulfonyloxy, and the like.

The "C2-C7 alkylcarbonyl group" represents, for example, a linear, branched, or cyclic alkylcarbonyl group having from 2 to 7 carbon atoms, such as acetyl, propionyl, propylcarbonyl, cyclopropylcarbonyl, n-butylcarbonyl, s-butylcarbonyl, t-butylcarbonyl, n-pentylcarbonyl, 2-pentylcarbonyl, neopentylcarbonyl, cyclopentylcarbonyl, and the like.

The "C2-C7 haloalkylcarbonyl group" represents, for example, a linear, branched, or cyclic alkylcarbonyl group having from 2 to 7 carbon atoms, that is substituted with one or more halogen atoms which may be the same as or different from each other, such as trifluoroacetyl, pentafluoropropionyl, 2-chloropropionyl, 2,2,2-trifluoropropionyl, heptafluoro-n-propylcarbonyl, heptafluoro-i-propylcarbonyl, 1,1,1,3,3,3-hexafluoro-2-propylcarbonyl, 3-fluoro-n-propylcarbonyl, 1-chlorocyclopropylcarbonyl, 2-bromocyclopropylcarbonyl, 3,3,4,4,4-pentafluoro-2-butylcarbonyl, nonafluoro-n-butylcarbonyl, nonafluoro-2-butylcarbonyl, 5,5,5-trifluoro-n-pentylcarbonyl, 4,4,5,5,5-pentafluoro-2- pentylcarbonyl, 3-chloro-n-pentylcarbonyl, 4-bromo-2-pentylcarbonyl, 4-chlorobutylcarbonyl, 2-iodo-n-propyl carbonyl, and the like.

The "C2-C7 alkylcarbonyloxy group" represents, for example, a linear, branched, or cyclic alkylcarbonyloxy group having from 2 to 7 carbon atoms, such as acetyloxy, propionyloxy, i-propylcarbonyloxy, cyclopropylcarbonyloxy, n-butylcarbonyloxy, s-butylcarbonyloxy, t-butylcarbonyloxy, n-pentylcarbonyloxy, 2-pentylcarbonyloxy, neopentylcarbonyloxy, cyclopentylcarbonyloxy, and the like.

The "C2-C7 haloalkylcarbonyloxy group" represents, for example, a linear, branched, or cyclic alkylcarbonyloxy group having from 2 to 7 carbon atoms, that is substituted with one or more halogen atoms which may be the same as or different from each other, such as trifluoroacetyloxy, pentafluoropropionyloxy, 2-chloropropionyloxy, 2,2,2-trifluoropropionyloxy, heptafluoro-n-propylcarbonyloxy, heptafluoro-i-propylcarbonyloxy, 1,1,1,3,3,3-hexafluoro-2-propylcarbonyloxy, 3-fluoro-n-propylcarbonyloxy, 1-chlorocyclopropylcarbonyloxy, 2-bromocyclopropylcarbonyloxy, 3,3,4,4,4-pentafluoro-2-butylcarbonyloxy, nonafluoro-n-butylcarbonyloxy, nonafluoro-2-butylcarbonyloxy, 5,5,5-trifluoro-n-pentylcarbonyloxy, 4,4,5,5,5-pentafluoro-2-pentylcarbonyloxy, 3-chloro-n-pentylcarbonyloxy, 4-bromo-2-pentylcarbonyloxy, 4-chlorobutylcarbonyloxy, 2-iodo-n-propylcarbonyloxy, and the like.

The "C2-C7 alkoxycarbonyl group" represents, for example, a linear, branched, or cyclic alkoxycarbonyl group having from 2 to 7 carbon atoms, such as methoxycarbonyl, ethoxycarbonyl, isopropoxycarbonyl, cyclopropoxycarbonyl, n-butoxycarbonyl, s-butoxycarbonyl, t-butoxycarbonyl, n-pentyloxycarbonyl, 2-pentyloxycarbonyl, neopentyloxycarbonyl, cyclopentyloxycarbonyl, and the like.

The "C2-C7 haloalkoxycarbonyl group" represents, for example, a linear, branched, or cyclic alkoxycarbonyl group having from 2 to 7 carbon atoms, that is substituted with one or more halogen atoms which may be the same as or different from each other, such as trifluoromethoxycarbonyl, pentafluoroethoxycarbonyl, 2-chloroethoxycarbonyl, 2,2,2-trifluoroethoxycarbonyl, heptafluoro-n-propoxycarbonyl, heptafluoro-i-propoxycarbonyl, 1,1,1,3,3,3-hexafluoro-2-propoxycarbonyl, 3-fluoro-n-propoxycarbonyl, 1-chlorocyclopropoxycarbonyl, 2-bromocyclopropoxycarbonyl, 3,3,4,4,4-pentafluoro-2-butoxycarbonyl, nonafluoro-n-butoxycarbonyl, nonafluoro-2-butoxycarbonyl, 5,5,5-trifluoro-n-pentyloxycarbonyl, 4,4,5,5,5-pentafluoro-2-pentyloxycarbonyl, 3-chloro-n-pentyloxycarbonyl, 4-bromo-2-pentyloxycarbonyl, 4-cWorobutyloxycarbonyl, 2-iodo-n-propyloxycarbonyl, and the like.

The "C2-C7 alkylcarbonylamino group" represents, for example, a linear, branched, or cyclic alkylcarbonylamino group having from 2 to 7 carbon atoms, such as acetylamino, propionylamino, n-propylcarbonylamino, i-propylcarbonylamino, cyclopropylcarbonylamino, n-butylcarbonylamino, s-butylcarbonylamino, i-butylcarbonylamino, t-butylcarbonylamino, n-pentylcarbonylamino, i-pentylcarbonylamino, n-hexylcarbonylamino, cyclohexylcarbonylamino, and the like.

The "C2-C7 haloalkylcarbonylamino group" represents, for example, a linear, branched, or cyclic alkylcarbonylamino group having from 2 to 7 carbon atoms, that is substituted with one or more halogen atoms which may be the same as or different from each other, such as trifluoroacetylamino, pentafluoropropionylamino, 2-chloropropionylamino, 2,2,2-trifluoropropionylamino, heptafluoro-n-propylcarbonylamino, heptafluoro-i-propylcarbonylamino, 1,1,1,3,3,3-hexafluoro-2-propylcarbonylamino, 3-fluoro-n-propylcarbonylamino, 1-chlorocyclopropylcarbonylamino, 2-bromocyclopropylcarbonylamino, 3,3,4,4,4-pentafluoro-2-butylcarbonylamino, nonafluoro-n-butylcarbonylamino, nonafluoro-2-butylcarbonylamino, 5,5,5-trifluoro-n-pentylcarbonylamino, 4,4,5,5,5-pentafluoro-2-pentylcarbonylamino, 3-chloro-n-pentylcarbonylamino, 4-bromo-2-pentylcarbonylamino, 4-chlorobutylcarbonylamino, 2-iodo-n-propylcarbonylamino, and the like.

The "C2-C7 alkoxycarbonylamino group" represents, for example, a linear, branched, or cyclic alkoxycarbonylamino group having from 2 to 7 carbon atoms, such as methoxycarbonylamino, ethoxycarbonylamino, n-propyloxycarbonylamino, propyloxycarbonylamino, cyclopropoxycarbonylamino, n-butoxycarbonylamino, s-butoxycarbonylamino, i-butoxycarbonylamino, t-butoxycarbonylamino, n-pentyloxycarbonylamino, i-pentyloxycarbonylamino, n-hexyloxycarbonylamino, cyclohexyloxycarbonylamino, and the like.

The "C2-C7 haloalkoxycarbonylamino group" represents, for example, a linear, branched, or cyclic alkoxycarbonylamino group having from 2 to 7 carbon atoms, that is substituted with one or more halogen atoms which may be the same as or different from each other, such as trifluoromethoxycarbonylamino, pentafluoroethoxycarbonylamino, 2-chloroethoxycarbonylamino, 2,2,2-trifluoroethoxycarbonylamino, heptafluoro-n-propoxycarbonylamino, heptafluoro-i-propoxycarbonylamino, 1,1,1,3,3,3-hexafluoro-2-propoxycarbonylamino, 3-fluoro-n-propoxycarbonylamino, 1-chlorocyclopropoxycarbonylamino, 2-bromocyclopropoxycarbonylamino, 3,3,4,4,4-pentafluoro-2-butoxycarbonylamino, nonafluoro-n-butoxycarbonylamino, nonafluoro-2-butoxycarbonylamino, 5,5,5-trifluoro-n-pentyloxycarbonylamino, 4,4,5,5,5-pentafluoro-2-pentyloxycarbonylamino, 3-chloro-n-pentyloxycarbonylamino, 4-bromo-2-pentyloxycarbonylamino, 4-chlorobutyloxycarbonylamino, 2-iodo-n-propyloxycarbonylamino, and the like.

The "C2-C7 alkoxycarbonyloxy group" represents, for example, a linear, branched, or cyclic alkoxycarbonyloxy group having from 2 to 7 carbon atoms, such as methoxycarbonyloxy, ethoxycarbonyloxy, n-propyloxycarbonyloxy, i-propyloxycarbonyloxy, cyclopropoxycarbonyloxy, n-butoxycarbonyloxy, s-butoxycarbonyloxy, i-butoxycarbonyloxy, t-butoxycarbonyloxy, n-pentyloxycarbonyloxy, i-pentyloxycarbonyloxy, n-hexyloxycarbonyloxy, cyclohexyloxycarbonyloxy, and the like.

The "C2-C7 haloalkoxycarbonyloxy group" represents, for example, a linear, branched, or cyclic alkoxycarbonyloxy group having from 2 to 7 carbon atoms, that is substituted with one or more halogen atoms which may be the same as or different from each other, such as trifluoromethoxycarbonyloxy, pentafluoroethoxycarbonyloxy, 2-chloroethoxycarbonyloxy, 2,2,2-trifluoroethoxycarbonyloxy, heptafluoro-n-propoxycarbonyloxy, heptafluoro-i-propoxycarbonyloxy, 1,1,1,3,3,3-hexafluoro-2-propoxycarbonyloxy, 3-fluoro-n-propoxycarbonyloxy, 1-chlorocyclopropoxycarbonyloxy, 2-bromocyclopropoxycarbonyloxy, 3,3,4,4,4-pentafluoro-2-butoxycarbonyloxy, nonafluoro-n-butoxycarbonyloxy, nonafluoro-2-butoxycarbonyloxy, 5,5,5-trifluoro-n-pentyloxycarbonyloxy, 4,4,5,5,5-pentafluoro-2-pentyloxycarbonyloxy, 3-chloro-n-pentyloxycarbonyloxy, 4-bromo-2-pentyloxycarbonyloxy, 4-chlorobutyloxycarbonyloxy, 2-iodo-n-propyloxycarbonyloxy, and the like.

The "C1-C6 alkylamino group" represents, for example, a linear, branched, or cyclic alkylamino group having from 1 to 6 carbon atoms, such as methylamino, dimethylamino, ethylamino, diethylamino, n-propylamino, i-propylamino, cyclopropylamino, n-butylamino, s-butylamino, i-butylamino, t-butylamino, n-pentylamino, i-pentylamino, n-hexylamino, cyclohexylamino, and the like.

The "C1-C6 haloalkylamino group" represents, for example, a linear, branched, or cyclic alkylamino group having from 1 to 6 carbon atoms substituted with one or more halogen atoms which may be the same as or different from each other, such as trifluoromethylamino, ditrifluoromethylamino, pentafluoroethylamino, dipentafluoroethylamino, 2-chloroethylamino, 2,2,2-trifluoroethylamino, heptafluoro-n-propylamino, heptafluoro-i-propylamino, 1,1,1,3,3,3-hexafluoro-2-propylamino, 3-fluoro-n-propylamino, 1-chlorocyclopropylamino, 2-bromocyclopropylamino, 3,3,4,4,4-pentafluoro-2-butylamino, nonafluoro-n-butylamino, nonafluoro-2-butylamino, 5,5,5-trifluoro-n-pentylamino, 4,4,5,5,5-pentafluoro-2-pentylamino, 3-chloro-n-pentylamino, 4-bromo-2-pentylamino, 4-chlorobutylamino, 2-iodo-n-propylamino, and the like.

The "C2-C6 alkenyloxy group" represents, for example, an alkenyloxy group having from 2 to 6 carbon atoms, that has a double bond in the carbon chain, such as vinyloxy, allyloxy, 2-butenyloxy, 3-butenyloxy, and the like.

The "C2-C6 haloalkenyloxy group" represents, for example, a linear or branched alkenyloxy group having from 2 to 6 carbon atoms, that is substituted with one or more halogen atoms which may be the same as or different from each other and has a double bond in the carbon chain, such as 3,3-difluoro-2-propenyloxy, 3,3-dichloro-2-propenyloxy, 3,3-dibromo-2-propenyloxy, 2,3-dibromo-2-propenyloxy, 4,4-difluoro-3-butenyloxy, 3,4,4-tribromo-3-butenyloxy, and the like.

The "C2-C6 alkynyloxy group" represents, for example, an alkynyloxy group having from 2 to 6 carbon atoms, that has a triple bond in the carbon chain, such as propargyloxy, 1-butyn-3-yloxy, 1-butyn-3-methyl-3-yloxy, and the like.

The "C2-C6 haloalkynyloxy group" represents, for example, a linear or branched alkynyloxy group having from 2 to 6 carbon atoms, that is substituted with one or more halogen atoms which may be the same as or different from each other and has a triple bond in the carbon chain, such as fluoroethynyloxy, chloroethynyloxy, bromoethynyloxy, 3,3,3-trifluoro-1-propynyloxy, 3,3,3-trichloro-1-propynyloxy, 3,3,3-tribromo-1-propynyloxy, 4,4,4-trifluoro-1-butynyloxy, 4,4,4-trichloro-1-butynyloxy, 4,4,4-tribromo-1-butynyloxy, and the like.

The "C3-C9 cycloalkoxy group" represents, for example, a cycloalkyloxy group having from 3 to 9 carbon atoms, that has a cyclic structure, such as cyclopropyloxy, cyclobutyloxy, cyclopentyloxy, 2-methylcyclopentyloxy, 3-methylcyclopentyloxy, cyclohexyloxy, 2-methylcyclohexyloxy, 3-methylcyclohexyloxy, 4-methylcyclohexyloxy, and the like.

The "C3-C9 halocycloalkoxy group" represents, for example, a cycloalkyloxy group having from 3 to 9 carbon atoms, that is substituted with one or more halogen atoms which may be the same as or different from each other and has a cyclic structure, such as 2,2,3,3-tetrafluorocyclobutyloxy, 2-chlorocyclohexyloxy, 4-chlorocyclohexyloxy, and the like.

The "C3-C7 alkenylcarbonyl group" represents, for example, an alkenylcarbonyl group having from 3 to 7 carbon atoms, that has a double bond in the carbon chain, such as vinylcarbonyl, allylcarbonyl, 2-butenylcarbonyl, 3-butenylcarbonyl, and the like.

The "C3-C7 haloalkenylcarbonyl group" represents an alkenylcarbonyl group having from 3 to 7 carbon atoms, that is substituted with one or more halogen atoms which may be the same as or different from each other and has a double bond in the carbon chain, such as 3,3-difluoro-2-propenylcarbonyl, 3,3-dichloro-2-propenylcarbonyl, 3,3-dibromo-2-propenylcarbonyl, 2,3-dibromo-2-propenylcarbonyl, 4,4-difluoro-3-butenylcarbonyl, 3,4,4-tribromo-3-butenylcarbonyl, and the like.

The "C3-C7 alkynylcarbonyl group" represents an alkynylcarbonyl group having from 3 to 7 carbon atoms and has a triple bond in the carbon chain, such as propargylcarbonyl, 1-butyn-3-ylcarbonyl, 1-butyn-3-methyl-3-ylcarbonyl, and the like.

The "C3-C7 haloalkynylcarbonyl group" represents, for example, a linear or branched alkynylcarbonyl group having from 3 to 7 carbon atoms, that is substituted with one or more halogen atoms which may be the same as or different from each other and has a triple bond in the carbon chain, such as fluoroethynylcarbonyl, chloroethynylcarbonyl, bromoethynylcarbonyl, 3,3,3-trifluoro-1-propynylcarbonyl, 3,3,3-trichloro-1-propynylcarbonyl, 3,3,3-tribromo-1-propynylcarbonyl, 4,4,4-trifluoro-1-butynylcarbonyl, 4,4,4-trichloro-1-butynylcarbonyl, 4,4,4-tribromo-1-butynylcarbonyl, and the like.

The "C4-C10 cycloalkylcarbonyl group" represents, for example, a cycloalkylcarbonyl group having from 4 to 10 carbon atoms, that has a cyclic structure, such as cyclopropylcarbonyl, cyclobutylcarbonyl, cyclopentylcarbonyl, 2-methylcyclopentylcarbonyl, 3-methylcyclopentylcarbonyl, cyclohexylcarbonyl, 2-methylcyclohexylcarbonyl, 3-methylcyclohexylcarbonyl, 4-methylcyclohexylcarbonyl, and the like.

The "C4-C10 halocycloalkylcarbonyl group" represents, for example, a cycloalkylcarbonyl group having from 4 to 10 carbon atoms, that is substituted with one or more halogen atoms which may be the same as or different from each other and has a cyclic structure, such as 2,2,3,3-tetrafluorocyclobutylcarbonyl, 2-chlorocyclohexylcarbonyl, 4-chlorocyclohexylcarbonyl, and the like.

The "C3-C7 alkenyloxycarbonyl group" represents an alkenyloxycarbonyl group having 3 to 7 carbon atoms, that has a double bond in the carbon chain, such as vinyloxycarbonyl, allyloxycarbonyl, 2-butenyloxycarbonyl, 3-butenyloxycarbonyl, and the like.

The "C3-C7 haloalkenyloxycarbonyl group" represents, for example, a linear or branched alkenyloxycarbonyl group having from 3 to 7 carbon atoms, that is substituted with one or more halogen atoms which may be the same as or different from each other and has a double bond in the carbon chain, such as 3,3-difluoro-2-propenyloxycarbonyl, 3,3-dichloro-2-propenyloxycarbonyl, 3,3-dibromo-2-propenyloxycarbonyl, 2,3-dibromo-2-propenyloxycarbonyl, 4,4-difluoro-3-butenyloxycarbonyl, 3,4,4-tribromo-3-butenyloxycarbonyl, and the like.

The "C3-C7 alkynyloxycarbonyl group" represents, for example, an alkynyloxycarbonyl group having from 3 to 7 carbon atoms, that has a triple bond in the carbon chain, such as propargyloxycarbonyl, 1-butyn-3-yloxycarbonyl, 1-butyn-3-methyl-3-yloxycarbonyl, and the like.

The "C3-C7 haloalkynyloxycarbonyl group" represents, for example, a linear or branched alkynyloxycarbonyl group having from 3 to 7 carbon atoms, that is substituted with one or more halogen atoms which may be the same as or different from each other and has a triple bond in the carbon chain, such as fluoroethynyloxycarbonyl, chloroethynyloxycarbonyl, bromoethynyloxycarbonyl, 3,3,3-trifluoro-1-propynyloxycarbonyl, 3,3,3-trichloro-1-propynyloxycarbonyl, 3,3,3-tribromo-1-propynyloxycarbonyl, 4,4,4-trifluoro-1-butynyloxycarbonyl, 4,4,4-trichloro-1-butynyloxycarbonyl, 4,4,4-tribromo-1-butynyloxycarbonyl, and the like.

The "C4-C10 cycloalkyloxycarbonyl group" represents, for example, a cycloalkyloxycarbonyl group having from 4 to 10 carbon atoms, that has a cyclic structure, such as cyclopropyloxycarbonyl, cyclobutyloxycarbonyl, cyclopentyloxycarbonyl, 2-methylcyclopentyloxycarbonyl, 3-methylcyclopentyloxycarbonyl, cyclohexyloxycarbonyl, 2-methylcyclohexyloxycarbonyl, 3-methylcyclohexyloxycarbonyl, 4-methylcyclohexyloxycarbonyl, and the like.

The "C4-C10 halocycloalkyloxycarbonyl group" represents, for example, a cycloalkyloxycarbonyl group having from 4 to 10 carbon atoms, that is substituted with one or more halogen atoms which may be the same as or different from each other and has a cyclic structure, such as 2,2,3,3-tetrafluorocyclobutyloxycarbonyl, 2-chlorocyclohexyloxycarbonyl, 4-chlorocyclohexyloxycarbonyl, and the like.

The "C2-C6 alkenylamino group" represents, for example, an alkenylamino group having 2 to 6 carbon atoms, that has a double bond in the carbon chain, such as vinylamino, allylamino, 2-butenylamino, 3-butenylamino, and the like.

The "C2-C6 haloalkenylamino group" represents a linear or branched alkenylamino group having from 2 to 6 carbon atoms, that is substituted with one or more halogen atoms which may be the same as or different from each other and has a double bond in the carbon chain, such as 3,3-difluoro-2-propenylamino, 3,3-dichloro-2-propenylamino, 3,3-dibromo-2-propenylamino, 2,3-dibromo-2-propenylamino, 4,4-difluoro-3-butenylamino, 3,4,4-tribromo-3-butenylamino, and the like.

The "C2-C6 alkynylamino group" represents, for example, an alkynylamino group having from 2 to 6 carbon atoms, that has a triple bond in the carbon chain, such as propargylamino, 1-butyn-3-ylamino, 1-butyn-3-methyl-3-ylamino, and the like.

The "C2-C6 haloalkynylamino group" represents, for example, a linear or branched alkynylamino group having from 2 to 6 carbon atoms, that is substituted with one or more halogen atoms which may be the same as or different from each other and has a triple bond in the carbon chain, such as fluoroethynylamino, chloroethynylamino, bromoethynylamino, 3,3,3-trifluoro-1-propynylamino, 3,3,3-trichloro-1-propynylamino, 3,3,3-tribromo-1-propynylamino, 4,4,4-trifluoro-1-butynylamino, 4,4,4-trichloro-1-butynylamino, 4,4,4-tribromo-1-butynylamino, and the like.

The "C3-C9 cycloalkylamino group" represents, for example, a cycloalkyl group amino having from 3 to 9 carbon atoms, that has a cyclic structure, such as cyclopropylamino, cyclobutylamino, cyclopentylamino, 2-methylcyclopentylamino, 3-methylcyclopentylamino, cyclohexylamino, 2-methylcyclohexylamino, 3-methylcyclohexylamino, 4-methylcyclohexylamino, and the like.

The "C3-C9 halocycloalkylamino group" represents, for example, a cycloalkylamino group having from 3 to 9 carbon atoms, that is substituted with one or more halogen atoms which may be the same as or different from each other and has a cyclic structure, such as 2,2,3,3-tetrafluorocyclobutylamino, 2-chlorocyclohexylamino, 4-chlorocyclohexylamino, and the like.

The "C2-C7 alkylaminocarbonyl group" represents, for example, a linear or branched alkylaminocarbonyl group having from 2 to 7 carbon atoms, such as methylaminocarbonyl, ethylaminocarbonyl, n-propylaminocarbonyl, i-propylaminocarbonyl, n-butylaminocarbonyl, s-butylaminocarbonyl, t-butylaminocarbonyl, n-pentylaminocarbonyl, 2-pentylaminocarbonyl, neopentylaminocarbonyl, 4-methyl-2-pentylaminocarbonyl, n-hexylaminocarbonyl, 3-methyl-n-pentylaminocarbonyl, and the like.

The "C2-C7 haloalkylaminocarbonyl group" represents, for example, a linear or branched alkylaminocarbonyl group having from 2 to 7 carbon atoms, that is substituted with one or more halogen atoms which may be the same as or different from each other, such as trifluoromethylaminocarbonyl, pentafluoroethylaminocarbonyl, heptafluoro-n-propylaminocarbonyl, heptafluoro-i-propylaminocarbonyl, 2,2-difluoroethylaminocarbonyl, 2,2-dichloroethylaminocarbonyl, 2,2,2-trifluoroethylaminocarbonyl, 2-fluoroethylaminocarbonyl, 2-chloroethylaminocarbonyl, 2-bromoethylaminocarbonyl, 2-iodoethylaminocarbonyl, 2,2,2-trichloroethylaminocarbonyl, 2,2,2-tribromoethylaminocarbonyl, 1,3-difluoro-2-propylaminocarbonyl, 1,3-dichloro-2-propylaminocarbonyl, 1-chloro-3-fluoro-2-propylaminocarbonyl, 1,1,1-trifluoro-2-propylaminocarbonyl, 2,3,3,3-trifluoro-n-propylaminocarbonyl, 4,4,4-trifluoro-n-butylaminocarbonyl, 1,1,1,3,3,3-hexafluoro-2-propylaminocarbonyl, 1,1,1,3,3,3-hexafluoro-2-chloro-2-propylaminocarbonyl, 1,1,1,3,3,3-hexafluoro-2-bromo-2-propylaminocarbonyl, 1,1,2,3,3,3-hexafluoro-2-chloro-n-propylaminocarbonyl, 1,1,2,3,3,3-hexafluoro-2-bromo-n-propylaminocarbonyl, 1,1,2,3,3,3-hexafluoro-1-bromo-2-propylaminocarbonyl, 2,2,3,3,3-pentafluoro-n-propylaminocarbonyl, 3-fluoro-n-propylaminocarbonyl, 3-chloro-n-propylaminocarbonyl, 3-bromo-n-propylaminocarbonyl, 3,3,4,4,4-pentafluoro-2-butylaminocarbonyl, nonafluoro-n-butylaminocarbonyl, nonafluoro-2-butylaminocarbonyl, 5,5,5-trifluoro-n-pentylaminocarbonyl, 4,4,5,5,5-pentafluoro-2-pentylaminocarbonyl, 3-chloro-n-pentylaminocarbonyl, 4-bromo-2-pentylaminocarbonyl, and the like.

The "C3-C7 alkenylaminocarbonyl group" represents, for example, an alkenylaminocarbonyl group having from 3 to 7 carbon atoms, that has a double bond in the carbon chain, such as vinylaminocarbonyl, allylaminocarbonyl, 2-butenylaminocarbonyl, 3-butenylaminocarbonyl, and the like.

The "C3-C7 haloalkenylaminocarbonyl group" represents, for example, a linear or branched alkenylaminocarbonyl group having from 3 to 7 carbon atoms, that is substituted with one or more halogen atoms which may be the same as or different from each other and has a double bond in the carbon chain, such as 3,3-difluoro-2-propenylaminocarbonyl, 3,3-dichloro-2-propenylaminocarbonyl, 3,3-dibromo-2-propenylaminocarbonyl, 2,3-dibromo-2-propenylaminocarbonyl, 4,4-difluoro-3-butenylaminocarbonyl, 3,4,4-tribromo-3-butenylaminocarbonyl, and the like.

The "C3-C7 alkynylaminocarbonyl group" represents, for example, an alkynylaminocarbonyl group having from 3 to 7 carbon atoms, that has a triple bond in the carbon chain, such as propargylaminocarbonyl, 1-butyn-3-ylaminocarbonyl, 1-butyn-3-methyl-3-ylaminocarbonyl, and the like.

The "C3-C7 haloalkynylaminocarbonyl group" represents, for example, a linear or branched alkynylaminocarbonyl group having from 3 to 7 carbon atoms, that is substituted with one or more halogen atoms which may be the same as or different from each other and has a triple bond in the carbon chain, such as fluoroethynylaminocarbonyl, chloroethynylaminocarbonyl, bromoethynylaminocarbonyl, 3,3,3-trifluoro-1-propynylaminocarbonyl, 3,3,3-trichloro-1-propynylaminocarbonyl, 3,3,3-tribromo-1-propynylaminocarbonyl, 4,4,4-trifluoro-1-butynylaminocarbonyl, 4,4,4-trichloro-1-butynylaminocarbonyl, 4,4,4-tribromo-1-butynylaminocarbonyl, and the like.

The "C4-C10 cycloalkylaminocarbonyl group" represents, for example, a cycloalkylaminocarbonyl group having from 4 to 10 carbon atoms, that has a cyclic structure, such as cyclopropylaminocarbonyl, cyclobutylaminocarbonyl, cyclopentylaminocarbonyl, 2-methylcyclopentylaminocarbonyl, 3-methylcyclopentylaminocarbonyl, cyclohexylaminocarbonyl, 2-methylcyclohexylaminocarbonyl, 3-methylcyclohexylaminocarbonyl, 4-methylcyclohexylaminocarbonyl, and the like.

The "C4-C10 halocycloalkylaminocarbonyl group" represents, for example, a cycloalkylaminocarbonyl group having from 4 to 10 carbon atoms that is substituted with one or more halogen atoms which may be the same as or different from each other and has a cyclic structure, such as 2,3,3-tetrafluorocyclobutylaminocarbonyl, 2-chlorocyclohexylaminocarbonyl, 4-chlorocyclohexylaminocarbonyl, and the like.

The "aryl group" represents, for example, a monocyclic and polycyclic aromatic hydrocarbon, such as phenyl group, naphtyl group, and the like.

The "arylcarbonyloxy group" represents, for example, a arylcarbonyloxy group, such as phenylcarbonyloxy group, naphtylcarbonyloxy group, and the like.

The "arylcarbonylamino group" represents, for example, a arylcarbonylamino group, such as phenylcarbonylamino group, naphtylcarbonylamino group, and the like.

The "C1-C6 alkyl group which may have a substituent" in $R_1$ and $R_2$ represents an unsubstituted linear, branched, or cyclic alkyl group having 1 to 6 carbon atoms, or a linear, branched, or cyclic alkyl group having from 1 to 6 carbon atoms, which is substituted only with at least one of a nitro group, a phenyl group which may have a substituent, and an unsaturated heterocyclic group which may have a substituent. Further, when there are two or more substituents, these substituents may be the same as or different from each other.

The "C1-C6 haloalkyl group which may have a substituent" in $R_1$ and $R_2$ represents a linear, branched, or cyclic alkyl group having from 1 to 6 carbon atoms, which is substituted with one or more halogen atoms, or a linear, branched, or cyclic alkyl group having 1 to 6 carbon atoms, which is substituted with at least one of a nitro group, a phenyl group which may have a substituent, and an unsaturated heterocyclic group which may have a substituent, in addition to one or more halogen atoms.

The "C2-C6 alkenyl group which may have a substituent" in $R_1$ and $R_2$ represents an unsubstituted linear, branched, or cyclic alkenyl group having from 2 to 6 carbon atoms, or a linear, branched, or cyclic alkenyl group having 2 to 6 carbon atoms, which is substituted with at least one of a nitro group, a phenyl group which may have a substituent, and an unsaturated heterocyclic group which may have a substituent. Further, when there are two or more substituents, these substituents may be the same as or different from each other.

The "C2-C6 haloalkenyl group which may have a substituent" in $R_1$ and $R_2$ represents a linear, branched, or cyclic alkenyl group having from 2 to 6 carbon atoms, which is substituted only with one or more halogen atoms, or a linear, branched, or cyclic alkenyl group having 2 to 6 carbon atoms, which is substituted with at least one of a nitro group, a phenyl group which may have a substituent, and an unsaturated heterocyclic group which may have a substituent, in addition to one or more halogen atoms.

The "C2-C6 alkynyl group which may have a substituent" in $R_1$ and $R_2$ represents an unsubstituted linear, branched, or cyclic alkynyl group having from 2 to 6 carbon atoms, or a linear, branched, or cyclic alkynyl group having 2 to 6 carbon atoms, which is substituted with at least one of a nitro group, a phenyl group which may have a substituent, and an unsaturated heterocyclic group which may have a substituent. Further, when there are two or more substituents, these substituents may be the same as or different from each other.

The "C2-C6 haloalkynyl group which may have a substituent" in $R_1$ and $R_2$ represents a linear, branched, or cyclic alkynyl group having from 2 to 6 carbon atoms, which is substituted only with one or more halogen atoms, or a linear, branched, or cyclic alkynyl group having 2 to 6 carbon atoms, which is substituted with at least one of a nitro group, a phenyl group which may have a substituent, and an unsaturated heterocyclic group which may have a substituent, in addition to one or more halogen atoms.

Further, each of the substituents in the present invention may further have a substituent, and examples of the substituent include the following:

one or more substituents selected from a group consisting of a halogen atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C2-C7 alkylcarbonyl group, a C2-C7 haloalkylcarbonyl group, a C2-C7 alkylcarbonyloxy group, a C2-C7 haloalkylcarbonyloxy group, a C1-C6 alkylsulfonyloxy group, a C1-C6 haloalkylsulfonyloxy group, a C2-C7 alkoxycarbonyl group, a C2-C7 haloalkoxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C2-C7 alkylaminocarbonyl group, a C2-C7 haloalkylaminocarbonyl group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C3-C7 alkenylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, an amino group, a carbamoyl group, a sulfamoyl group, a cyano group, a nitro group, a hydroxyl group, a carboxylic group, a pentafluorosulfanyl group, a phenyl group which may have a substituent, a heterocyclic group which may have a substituent, a benzyl group which may have a substituent, a phenylcarbonyl group which may have a substituent, and a phenylamino group which may have a substituent, and when there are two or more substituents, each substituent may be the same as or different from each other.

The compounds represented by Formula (1), Formula (7), Formula (8), and the like of the present invention may include one or plural chiral carbon atoms or chiral centers in their structural Formulae, and thus two or more optical isomers may exist. However, the present invention includes each of the optical isomers and a mixture thereof at any proportions. Further, the compounds represented by Formula (1), Formula (7), Formula (8), and the like of the present invention may include two or more kinds of geometrical isomers derived from carbon-carbon double bonds in the structural Formulae. However, the present invention includes each of the geometrical isomers and a mixture thereof at any proportions.

The combinations of the substituents or atoms preferred as the substituents or the like for the amide derivative represented by Formula (1) of the present invention are as follows.

T is preferably —C(=$G_1$)-$Q_1$, $G_1$ is preferably an oxygen atom, $Q_1$ is preferably a phenyl group which may have a substituent, or a pyridyl group which may have a substituent, and $Q_1$ is more preferably a phenyl group or a pyridyl group which has one or more substituents selected from a group consisting of a halogen atom, a C1 haloalkyl group, a nitro group, and a cyano group, and when there are two or more substituents, each substituent may be the same as or different from each other.

$G_3$ is preferably an oxygen atom.

$R_1$ is preferably a hydrogen atom or a C1-C3 alkyl group.

$R_2$ is preferably a hydrogen atom.

A is preferably a carbon atom, and K is preferably a non-metal atom group which is combined with A and two carbon atoms to which A bonds to form a benzene ring.

X is preferably a hydrogen atom, a halogen atom, or a cyano group, and more preferably a hydrogen atom, a fluorine atom, or a cyano group.

When X is a substituent other than a hydrogen atom, n is preferably 0, 1, or 2.

$Y_1$ is preferably a halogen atom or a C1-C3 haloalkyl group.

$Y_5$ is preferably a C1-C3 haloalkyl group.

$Y_2$ and $Y_4$ are preferably hydrogen atoms, halogen atoms, or C1-C4 alkyl groups, and more preferably hydrogen atoms.

$Y_3$ is preferably a C2-C5 haloalkyl group, and more preferably a C2-C4 perfluoroalkyl group.

Furthermore, the combinations of the substituent or atom preferred as the substituent and the like for the amide derivative represented by Formula (8) are as follows.

$Q_1$ is preferably a phenyl group or a pyridyl group which has one or more substituents selected from a group consisting of a halogen atom, a C1 haloalkyl group, a nitro group, and a cyano group, and when there are two or more substituents, each substituent may be the same as or different from each other.

$R_1$ is preferably a hydrogen atom or a C1-C3 alkyl group.

$R_2$ is preferably a hydrogen atom.

$X_1$ and $X_2$ are preferably hydrogen atoms or fluorine atoms, and X3 and X4 are preferably hydrogen atoms.

$Y_1$ and $Y_5$ are preferably halogen atoms or C1-C3 haloalkyl groups. $Y_2$ and $Y_4$ are preferably hydrogen atoms. $Y_3$ is preferably a C3-C4 perfluoroalkyl group.

The representative methods for producing the compound of the present invention are shown below, and the method for producing the amide derivative of the present invention is not limited to the preparation methods below.

In Formula shown in the following preparation method, A, K, X, n, $R_1$, $R_2$, T, $G_3$, $Y_1$, $Y_2$, $Y_3$, $Y_4$, and $Y_5$ represent the same definitions as A, K, X, n, $R_1$, $R_2$, T, $G_3$, $Y_1$, $Y_2$, $Y_3$, $Y_4$, and $Y_5$, respectively, in Formula (1). LG represents a functional group having a leaving ability, such as a halogen atom, a hydroxy group, or the like, Hal represents a chlorine atom or a bromine atom, and Xa, Xb, and Xc represent chlorine atoms, bromine atoms, or iodine atoms.

<Preparation Method 1>

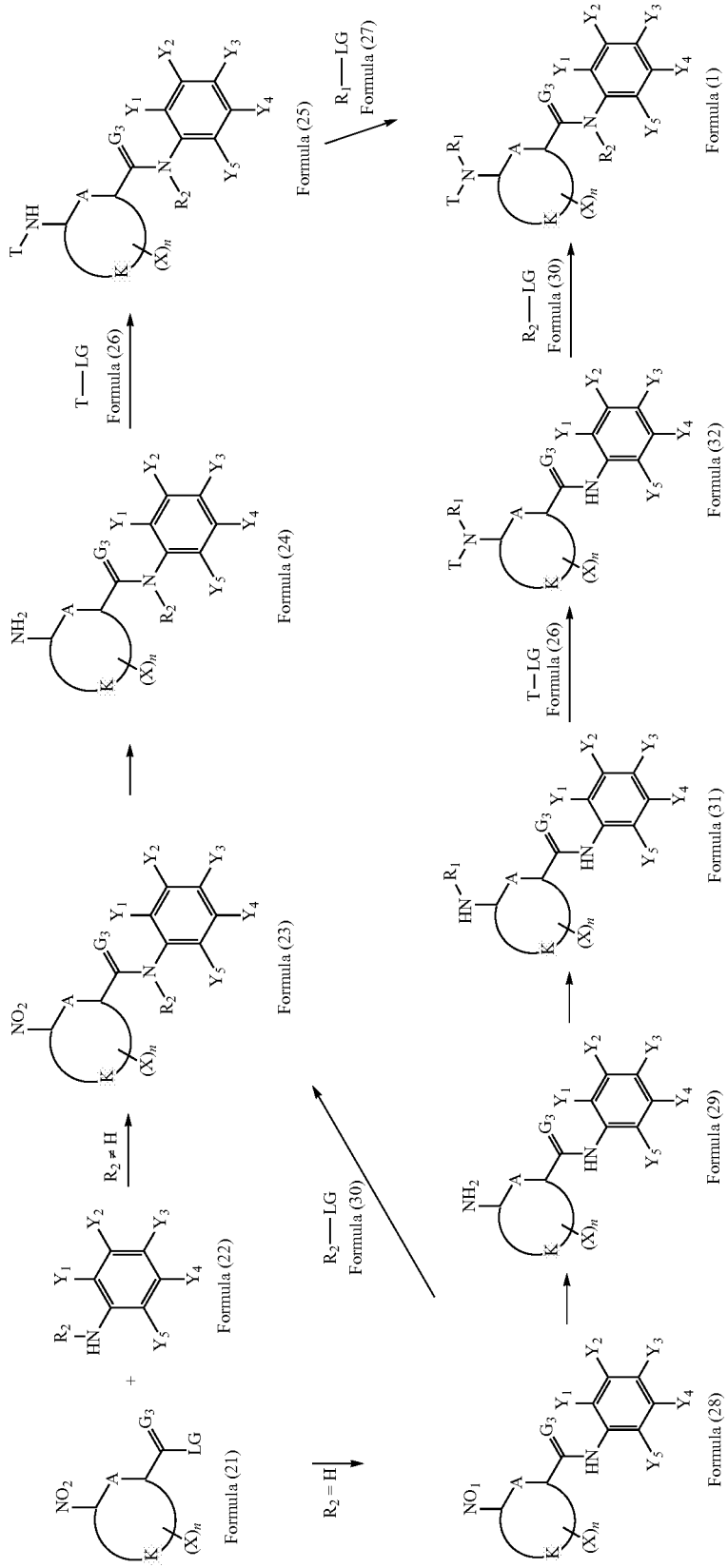

Formula(21)+Formula(22)→Formula(23)

Formula(21)+Formula(22)→Formula(28)        1-(i):

A nitro aromatic carboxamide derivative represented by Formula (23) or Formula (28) can be prepared by reacting a nitro aromatic carboxylic acid derivative having a leaving group represented by Formula (21) with an aromatic amine derivative represented by Formula (22) in a suitable solvent or without a solvent. In the present step, a suitable base can be used.

The solvent may be any of those which do not inhibit the present reaction significantly. Examples thereof may include water and aromatic hydrocarbons such as benzene, toluene, xylene, and the like, halogenated hydrocarbons such as dichloromethane, chloroform, carbon tetrachloride, and the like, chained or cyclic ethers such as diethyl ether, dioxane, tetrahydrofuran, 1,2-dimethoxy ethane, and the like, esters such as ethyl acetate, butyl acetate, and the like, alcohols such as methanol, ethanol, and the like, ketones such as acetone, methyl isobutyl ketone, cyclohexanone, and the like, amides such as dimethyl formamide, dimethylacetamide, and the like, nitriles such as acetonitrile and the like, and inert solvents such as 1,3-dimethyl-2-imidazolidinone and the like. These solvents may be used alone or as a mixture of two or more kinds thereof.

Furthermore, examples of the base may include organic bases such as triethylamine, tri-n-butyl amine, pyridine, 4-dimethylamino pyridine, and the like, alkali metal hydroxides such as sodium hydroxide, potassium hydroxide, and the like, carbonates such as sodium hydrogen carbonate, potassium carbonate, and the like, phosphates such as dipotassium monohydrogen phosphate, trisodium phosphate, and the like, alkali metal hydride salts such as sodium hydride and the like, alkali metal alkoxides such as sodium methoxide, sodium ethoxide, and the like, and lithium amides such as lithium diisopropyl amide, and the like.

These bases may be appropriately used in an amount in the range from 0.01-fold molar equivalent to 5-fold molar equivalents with respect to the compound represented by Formula (21).

The reaction temperature may be appropriately selected from −20° to the reflux temperature of the solvent used. Further, the reaction time may be appropriately selected within the range from several minutes to 96 hours.

Among the compounds represented by Formula (21), the aromatic carbonyl halide derivative can be prepared easily by a general method using a halogenating agent from an aromatic carboxylic acid. Examples of the halogenating agent include thionyl chloride, thionyl bromide, phosphorus oxychloride, oxalyl chloride, phosphorus trichloride, and the like.

Meanwhile, it is possible to prepare the compound represented by Formula (23) or Formula (28) from the nitro aromatic carboxylic acid derivative and the compound represented by Formula (22) without using a halogenating agent. Examples of the method may include a method described in, for example, Chem. Ber. p. 788 (1970), in which a condensing agent such as N,N'-dicyclohexylcarbodiimide and the like is appropriately used, suitably with the use of an additive such as 1-hydroxybenzotriazole and the like. Other condensing agents that can be used in this case may include 1-ethyl-3-(3-dimethylaminopropyl)carbodiimide, 1,1'-carbonylbis-1H-imidazole, and the like.

Furthermore, examples of other methods for producing the compound represented by Formula (23) or Formula (28) may include a mixed anhydride method using chloroformic acid esters, and examples thereof include a method described in J. Am. Chem. Soc., p. 5012 (1967), whereby the compound represented by Formula (23) or Formula (28) can be prepared. Examples of the chloroformic acid esters used in this case may include isobutyl chloroformate, isopropyl chloroformate and the like. In addition to chloroformic acid esters, diethylacetyl chloride, trimethylacetyl chloride and the like may also be included.

Both the method using a condensing agent and the mixed anhydride method are not limited by the solvent, the reaction temperature, and the reaction time according to the literature above. An inert solvent may be used which does not inhibit the progress of the appropriate reaction significantly, and the reaction temperature and the reaction time may also be selected appropriately according to the progress of the reaction.

Formula(23)→Formula(24)

Formula(28)→Formula(29)        1-(ii):

An aromatic carboxamide derivative having an amino group represented by Formula (24) or Formula (29) can be derived from the aromatic carboxamide derivative having a nitro group represented by Formula (23) or Formula (28) by means of a reduction reaction. Examples of such reduction include a method using a hydrogenation reaction and a method using a metal compound (for example, stannous chloride (anhydride), iron powder, zinc powder, and the like).

The reaction of the former method can be carried out in a suitable solvent in the presence of a catalyst at normal pressure or a higher pressure under a hydrogen atmosphere. Examples of the catalyst may include palladium catalysts such as palladium-carbon and the like, nickel catalysts such as Raney-nickel and the like, cobalt catalysts, ruthenium catalysts, rhodium catalysts, platinum catalysts, and the like, and examples of the solvent may include water; alcohols such as methanol, ethanol, and the like; aromatic hydrocarbons such as benzene, toluene, and the like; chained or cyclic ethers such as ether, dioxane, tetrahydrofuran, and the like; and esters such as ethyl acetate and the like. The pressure may be appropriately selected within a range of 0.1 MPa to 10 MPa, the reaction temperature may be appropriately selected within a range of −20° C. to the reflux temperature of the solvent used, and the reaction time may be appropriately selected within a range of several minutes to 96 hours, whereby the compound of Formula (24) or Formula (29) can be efficiently prepared.

Examples of the latter method include a method using stannous chloride (anhydride) as a metal compound under the conditions described in "Organic Syntheses" Coll. Vol. III, P. 453.

Formula(24)+Formula(26)→Formula(25)        1-(iii):

An aromatic carboxamide or carbamate derivative represented by Formula (25) can be prepared by reacting the aromatic amine derivative represented by Formula (24) with the carboxylic acid derivative or the carbonate ester derivative having a leaving group represented by Formula (26) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In Formula (26), the carbonyl chloride derivative can be prepared easily from a carboxylic acid derivative by a general method using a halogenating agent. The halogenating agent may include those exemplified in 1-(i).

There may be a method for producing a compound represented by Formula (25) from the carboxylic acid derivative (26) and the compound represented by Formula (24) without the use of a halogenating agent, and the preparation can be conducted according to the method exemplified in 1-(i).

Formula(25)+Formula(27)→Formula(1)  1-(iv):

The compound represented by Formula (1) of the present invention can be prepared by reacting the amide compound represented by Formula (25) with the compound having a leaving group such as halogen and the like, represented by Formula (27) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

Formula(28)+Formula(30)→Formula(23)  1-(v):

A compound represented by Formula (23) can be prepared by reacting the amide compound represented by Formula (28) with the compound having a leaving group such as halogen and the like, represented by Formula (30) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

Formula(29)→Formula(31)  1-(vi):

(Method A)

A compound represented by Formula (31) can be prepared by reacting the compound represented by Formula (29) with an aldehyde or a ketone in a solvent, and reacting them under a hydrogen atmosphere with the addition of a catalyst.

The solvent may be any of those which do not inhibit the progress of the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, ketones such as acetone, methyl isobutyl ketone, cyclohexanone, methyl ethyl ketone, and the like, esters such as ethyl acetate, butyl acetate, and the like, alcohols such as 1,3-dimethyl-2-imidazolidinone, sulfolane, dimethylsulfoxide, methanol, ethanol, and the like, and water. These solvents may be used alone or as a mixture of two or more kinds thereof.

Examples of the catalyst may include palladium catalysts such as palladium-carbon, palladium hydroxide-carbon, and the like, nickel catalysts such as Raney-nickel and the like, cobalt catalysts, platinum catalysts, ruthenium catalysts, rhodium catalysts, and the like.

Examples of the aldehydes may include formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, bromoacetaldehyde, and the like.

Examples of the ketones may include acetone, perfluoroacetone, methyl ethyl ketone, and the like.

The reaction pressure may be appropriately selected within the range of 1 atm to 100 atm. The reaction temperature may be appropriately selected within the range from −20° C. to the reflux temperature of the solvent used. Further, the reaction time may be appropriately selected within the range from several minutes to 96 hours.

(Method B)

A compound represented by Formula (31) can be prepared by reacting the compound represented by Formula (29) with an aldehyde or a ketone in a solvent, and treating the product with a reducing agent.

The solvent may be any of those which do not inhibit the progress of the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, ketones such as acetone, methyl isobutyl ketone, cyclohexanone, methyl ethyl ketone, and the like, esters such as ethyl acetate, butyl acetate, and the like, alcohols such as 1,3-dimethyl-2-imidazolidinone, sulfolane, dimethylsulfoxide, methanol, ethanol, and the like, water, and the like. These solvents may be used alone or as a mixture of two or more kinds thereof.

Examples of the reducing agent may include, for example, borohydrides such as sodium borohydride, sodium cyanoborohydride, sodium triacetate borohydride, and the like.

Examples of the aldehydes may include formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, bromoacetaldehyde, and the like.

Examples of the ketones may include acetone, perfluoroacetone, methyl ethyl ketone, and the like.

The reaction temperature may be appropriately selected within the range from −20° C. to the reflux temperature of the solvent used. Further, the reaction time may be appropriately selected within the range from several minutes to 96 hours.

(Method C)

A compound of Formula (31) can be prepared by reacting the compound represented by Formula (29) with an aldehyde in a solvent or without a solvent.

The solvent may be any of those which do not inhibit the progress of the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, ketones such as acetone, methyl isobutyl ketone, cyclohexanone, methyl ethyl ketone, and the like, esters such as ethyl acetate, butyl acetate, and the like, alcohols such as 1,3-dimethyl-2-imidazolidinone, sulfolane, dimethylsulfoxide, methanol, ethanol, and the like, inorganic acids such as sulfuric acid, hydrochloric acid, and the like, organic acids such as formic acid, acetic acid, and the like, water, and the like. These solvents may be used alone or as a mixture of two or more kinds thereof.

Examples of the aldehydes may include formaldehyde, acetaldehyde, propionaldehyde, and the like.

The reaction temperature may be appropriately selected within the range from −20° C. to the reflux temperature of the solvent used, and the reaction time may be appropriately selected within the range from several minutes to 96 hours.

Formula(31)+Formula(26)→General Formula(32)　　1-(vii):

An aromatic carboxamide or carbamate derivative represented by Formula (32) can be prepared by reacting the aromatic amine derivative represented by Formula (31) with the carboxylic acid derivative or the carbonate ester derivative having a leaving group represented by Formula (26) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In Formula (26), the carbonyl chloride derivative can be prepared easily from a carboxylic acid derivative by a general method using a halogenating agent. The halogenating agent may include those exemplified in 1-(i).

There may be exemplified a method for producing a compound represented by Formula (32) from the carboxylic acid derivative (26) and the compound represented by Formula (31) without the use of a halogenating agent, and the preparation can be conducted according to the method exemplified in 1-(i).

Formula(32)+Formula(30)→Formula(1)　　1-(viii):

The compound represented by Formula (1) of the present invention can be prepared by reacting the amide compound represented by Formula (32) with the compound having a leaving group such as a halogen and the like, represented by Formula (30) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

<Preparation Method 2>

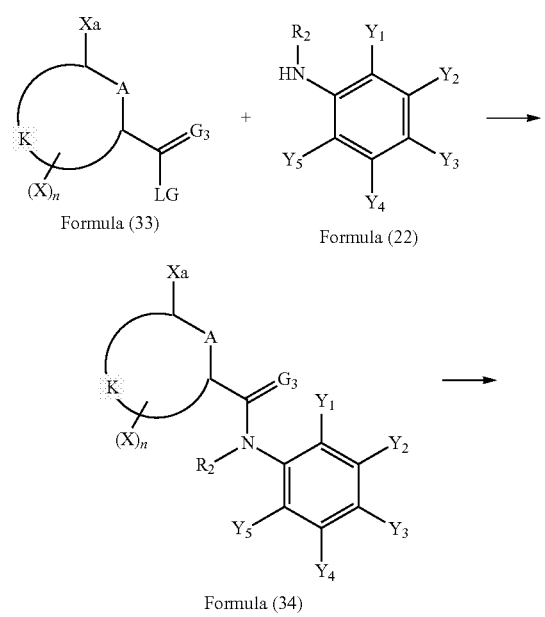

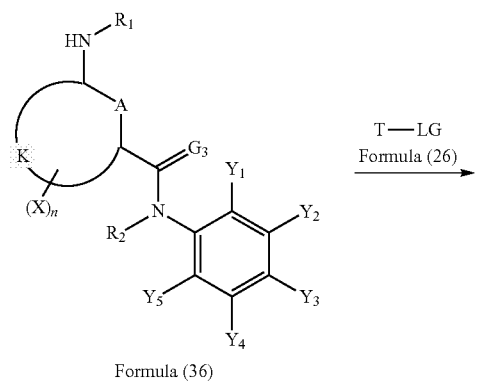

Formula (36)

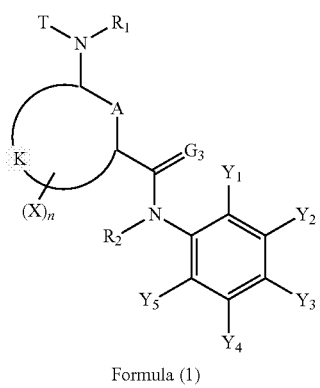

Formula (1)

Formula(33)+Formula(22)→Formula(34)　　2-(i):

A compound represented by Formula (34) can be prepared by reacting the compound represented by Formula (33) with a compound represented by Formula (22) under the condition described in 1-(i).

Formula(34)→Formula(36)　　2-(ii):

A compound represented by Formula (36) can be prepared by carrying out an amination reaction using an amination agent such as ammonia and the like according to the conditions described, for example, in J. Org. Chem. p. 280 (1958). However, the conditions such as a reaction solvent and the like are not restricted to those described in the literature, and an inert solvent which does not inhibit the proper progress of the reaction significantly may be used. The reaction temperature and reaction time may be suitably selected as the reaction proceeds. Further, examples of the amination agent include methylamine, ethylamine or the like, in addition to ammonia.

Formula(36)+Formula(26)→Formula(1)　　2-(iii):

The compound represented by Formula (1) can be prepared by reacting the compound represented by Formula (36) with a compound represented by Formula (26) according to the conditions described in 1-(i).

<Preparation Method 3>

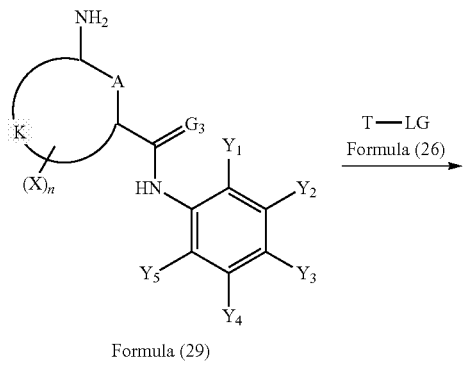

Formula (29)

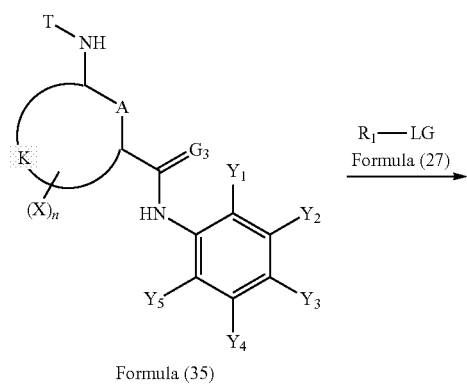

Formula (35)

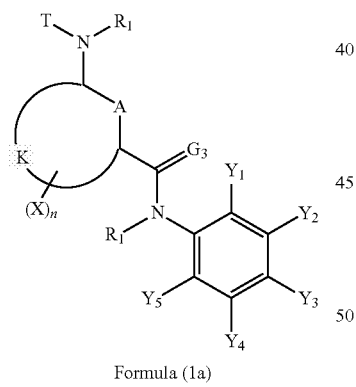

Formula (1a)

Formula(29)+Formula(26)→Formula(35)  3-(i):

An aromatic carboxamide or carbamate derivative represented by Formula (35) can be prepared by reacting the aromatic amine derivative represented by Formula (29) with the carboxylic acid derivative or the carbonate ester derivative having a leaving group represented by Formula (26) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In Formula (26), the carbonyl chloride derivative can be prepared easily from a carboxylic acid derivative by a general method using a halogenating agent. The halogenating agent may include those exemplified in 1-(i).

There may be exemplified a method for producing a compound represented by Formula (35) from the carboxylic acid derivative (26) and the compound represented by Formula (29) without the use of a halogenating agent, and the preparation can be conducted according to the method exemplified in 1-(i).

Formula(35)+Formula(27)→Formula(1a)  3-(ii):

The compound represented by Formula (1a) of the present invention can be prepared by reacting the amide compound represented by Formula (35) with the compound having a leaving group such as halogen and the like, represented by Formula (27) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

<Preparation Method 4>

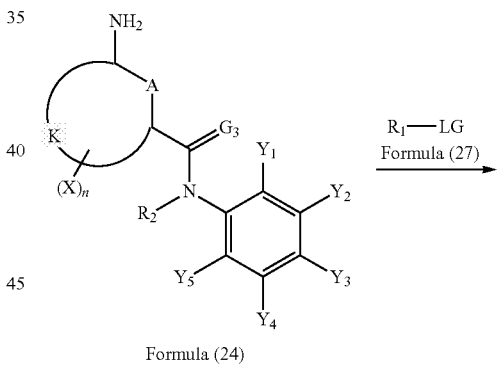

Formula (24)

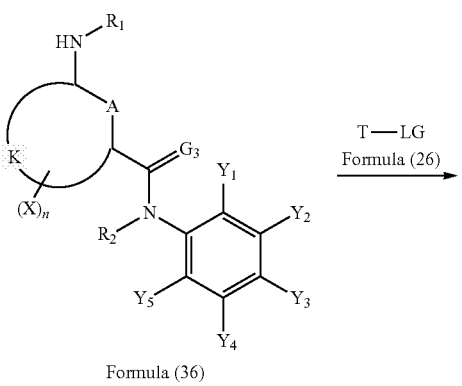

Formula (36)

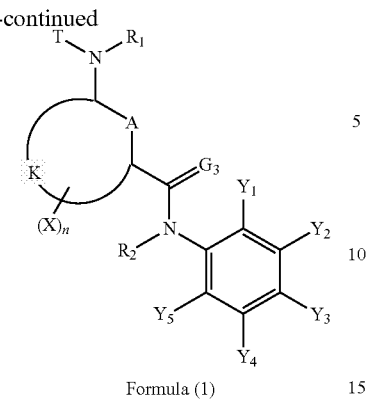

Formula (1)

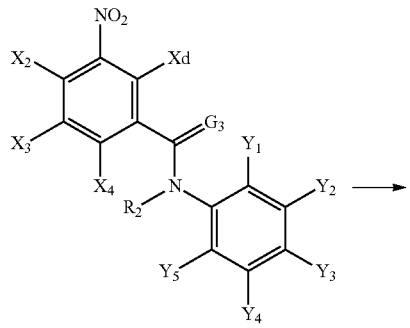

Formula (38)

Formula(24)→Formula(36)　　　　　　　　　　4-(i):

A compound represented by Formula (36) can be prepared by reacting the compound represented by Formula (24) as a starting material according to the conditions of (Method A), (Method B), or (Method C) described in 1-(vi).

Formula(24)+Formula(27)→Formula(36)　　　　4-(i'):

An aromatic carboxamide represented by Formula (36) can be prepared by reacting the aromatic amine derivative represented by Formula (24) with the carboxylic acid derivative or the carbonate ester derivative having a leaving group represented by Formula (27) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In Formula (27), the carbonyl chloride derivative can be prepared easily from a carboxylic acid derivative by a general method using a halogenating agent. The halogenating agent may include those exemplified in 1-(i).

There may be exemplified a method for producing a compound represented by Formula (36) from the carboxylic acid derivative (27) and the compound represented by Formula (24) without the use of a halogenating agent, and the preparation can be conducted according to the method exemplified in 1-(i).

Formula(36)+Formula(26)→Formula(1)　　　　4-(ii):

A compound represented by Formula (1) can be prepared by reacting the compound represented by Formula (36) and the compound represented by Formula (26) as starting materials according to the conditions described in 1-(i).

<Preparation Method 5>

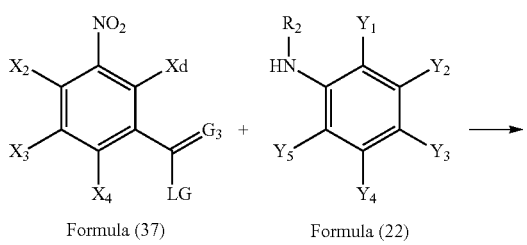

Formula (37)　　　　Formula (22)

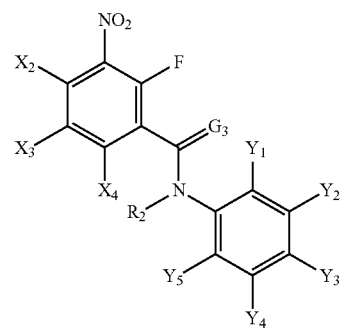

Formula (39)

Formula(37)+Formula(22)→Formula(38)　　　　5-(i):

A compound represented by Formula (38) can be prepared by reacting the compound represented by Formula (37) and the compound represented by Formula (22) according to the conditions described in 1-(i).

Formula(38)→Formula(39)　　　　　　　　　　5-(ii):

A compound represented by Formula (39) can be prepared by reacting the nitro aromatic carboxamide derivative represented by Formula (38) with a suitable fluorinating agent in a suitable solvent or without a solvent.

The solvent may be any of those which do not inhibit the progress of the reaction significantly, and examples thereof may include aliphatic hydrocarbons such as hexane, cyclohexane, methylcyclohexane, and the like, aromatic hydrocarbons such as benzene, toluene, xylene, and the like, halogenated hydrocarbons such as dichloromethane, chloroform, carbon tetrachloride, 1,2-dichloroethane, and the like, chained or cyclic ethers such as diethyl ether, dioxane, tetrahydrofuran, 1,2-dimethoxy ethane, and the like, esters such as ethyl acetate, butyl acetate, and the like, ketones such as acetone, methyl isobutyl ketone, cyclohexanone, methyl ethyl ketone, and the like, nitriles such as acetonitrile, propionitrile, and the like, and aprotic polar solvents such as 1,3-dimethyl-2-imidazolidinone, sulfolane, dimethylsulfoxide, N,N-dimethyl formamide, N-methylpyrrolidone, N,N-dimethylacetamide, and the like. These solvents may be used alone or as a mixture of two or more kinds thereof.

Examples of the fluorinating agent may include 1,1,2,2-tetrafluoroethyl diethylamine, 2-chloro-1,1,2-trifluoroethyl diethylamine, trifluorodiphenylphospholane, difluorotriphenylphospholane, fluoroformic acid esters, sulfur tetrafluoride, potassium fluoride, potassium hydrogen fluoride, cesium fluoride, rubidium fluoride, sodium fluoride, lithium fluoride, antimony (III) fluoride, antimony (V) fluoride, zinc fluoride, cobalt fluoride, lead fluoride, copper fluoride, mercury (II) fluoride, silver fluoride, silver fluoroborate, thallium (I) fluoride, molybdenum (VI) fluoride, arsenic (III) fluoride, bromine fluoride, selenium tetrafluoride, tris(dimethylamino)sulfonium difluorotrimethylsilicate, sodium hexafluorosilicate, quaternary ammonium fluorides, (2-chloroethyl)diethylamine, diethylaminosulfur trifluoride, morpholinosulfur trifluoride, silicon tetrafluoride, hydrogen fluoride, hydrofluoric acid, hydrogen fluoride-pyridine complex, hydrogen fluoride-triethylamine complex, hydrogen fluoride salts, bis(2-methoxyethyl)amino sulfurtrifluoride, 2,2-difluoro-1,3-dimethyl-2-imidazolidinone, iodine pentafluoride, tris(diethylamino)phosphonium 2,2,3,3,4,4-hexafluorocyclobutanilide, triethylammonium hexafluorocylcobutanilide, hexafluoropropene, and the like. These fluorinating agents may be used alone or as a mixture of two or more kinds thereof.

The fluorinating agent may be appropriately selected and used as a solvent, in the range of 1-fold molar equivalent to 10-fold molar equivalents with respect to the nitro aromatic carboxamide derivative represented by Formula (38).

Additives may be used, and examples thereof may include crown ethers such as 18-crown-6 and the like, phase transfer catalysts such as a tetraphenylphosphonium salt and the like, inorganic salts such as calcium fluoride, calcium chloride, and the like, metal oxides such as mercury oxide and the like, ion exchange resins, and the like. These additives may not only be added to the reaction system but also used as a pretreating agent for the fluorinating agent.

The reaction temperature may be appropriately selected within the range from −80° C. to the reflux temperature of the solvent used, and the reaction time may be appropriately selected within the range from several minutes to 96 hours.

<Preparation Method 6>

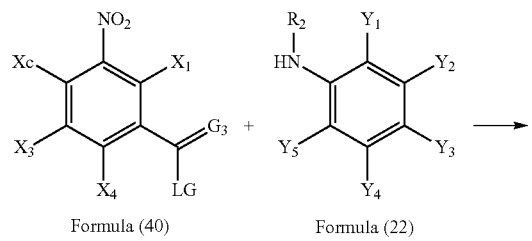

Formula (40)    Formula (22)

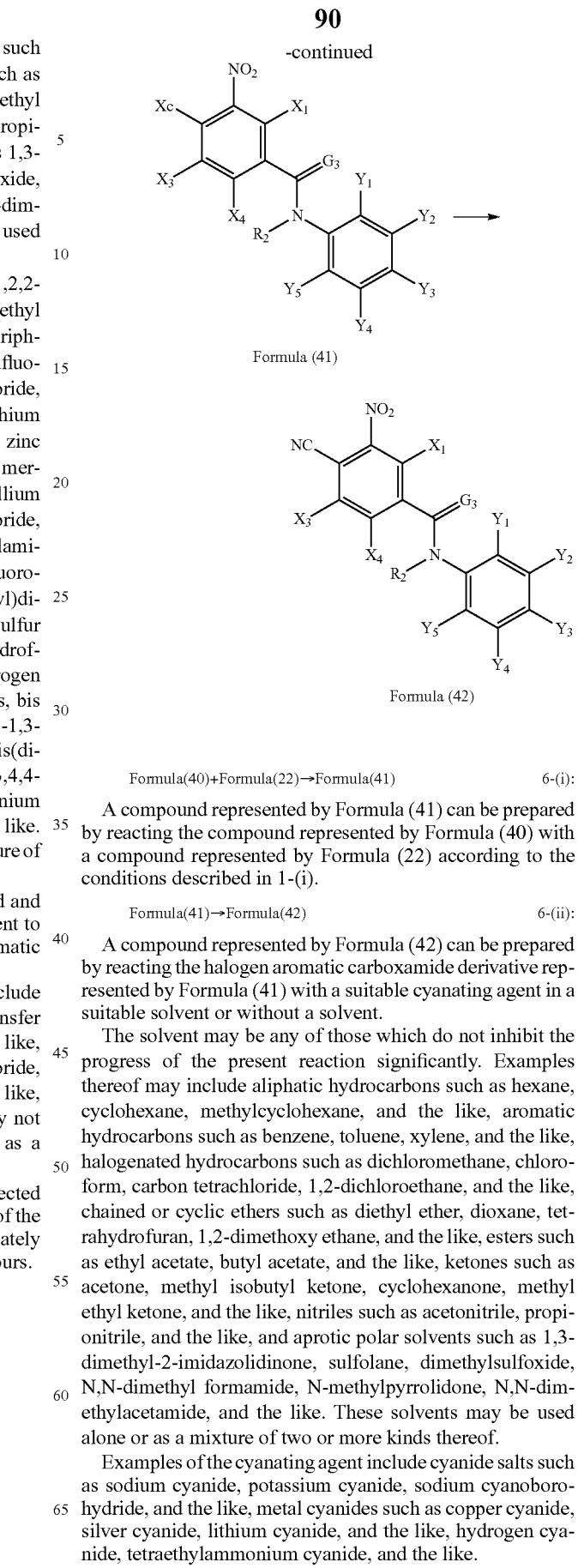

Formula (41)

Formula (42)

Formula(40)+Formula(22)→Formula(41)   6-(i):

A compound represented by Formula (41) can be prepared by reacting the compound represented by Formula (40) with a compound represented by Formula (22) according to the conditions described in 1-(i).

Formula(41)→Formula(42)   6-(ii):

A compound represented by Formula (42) can be prepared by reacting the halogen aromatic carboxamide derivative represented by Formula (41) with a suitable cyanating agent in a suitable solvent or without a solvent.

The solvent may be any of those which do not inhibit the progress of the present reaction significantly. Examples thereof may include aliphatic hydrocarbons such as hexane, cyclohexane, methylcyclohexane, and the like, aromatic hydrocarbons such as benzene, toluene, xylene, and the like, halogenated hydrocarbons such as dichloromethane, chloroform, carbon tetrachloride, 1,2-dichloroethane, and the like, chained or cyclic ethers such as diethyl ether, dioxane, tetrahydrofuran, 1,2-dimethoxy ethane, and the like, esters such as ethyl acetate, butyl acetate, and the like, ketones such as acetone, methyl isobutyl ketone, cyclohexanone, methyl ethyl ketone, and the like, nitriles such as acetonitrile, propionitrile, and the like, and aprotic polar solvents such as 1,3-dimethyl-2-imidazolidinone, sulfolane, dimethylsulfoxide, N,N-dimethyl formamide, N-methylpyrrolidone, N,N-dimethylacetamide, and the like. These solvents may be used alone or as a mixture of two or more kinds thereof.

Examples of the cyanating agent include cyanide salts such as sodium cyanide, potassium cyanide, sodium cyanoborohydride, and the like, metal cyanides such as copper cyanide, silver cyanide, lithium cyanide, and the like, hydrogen cyanide, tetraethylammonium cyanide, and the like.

These cyanating agents may be appropriately selected and used in the range of 1-fold molar equivalent to 10-fold molar equivalents with respect to the halogen aromatic carboxamide derivative represented by Formula (41).

Additives may be used, and examples thereof may include crown ethers such as 18-crown-6 and the like, phase transfer catalysts such as a tetraphenylphosphonium salt and the like, inorganic salts such as sodium iodide and the like.

The reaction temperature may be appropriately selected within the range from −20° C. to the reflux temperature of the solvent used. Further, the reaction time may be appropriately selected within the range from several minutes to 96 hours.

<Preparation Method 7>

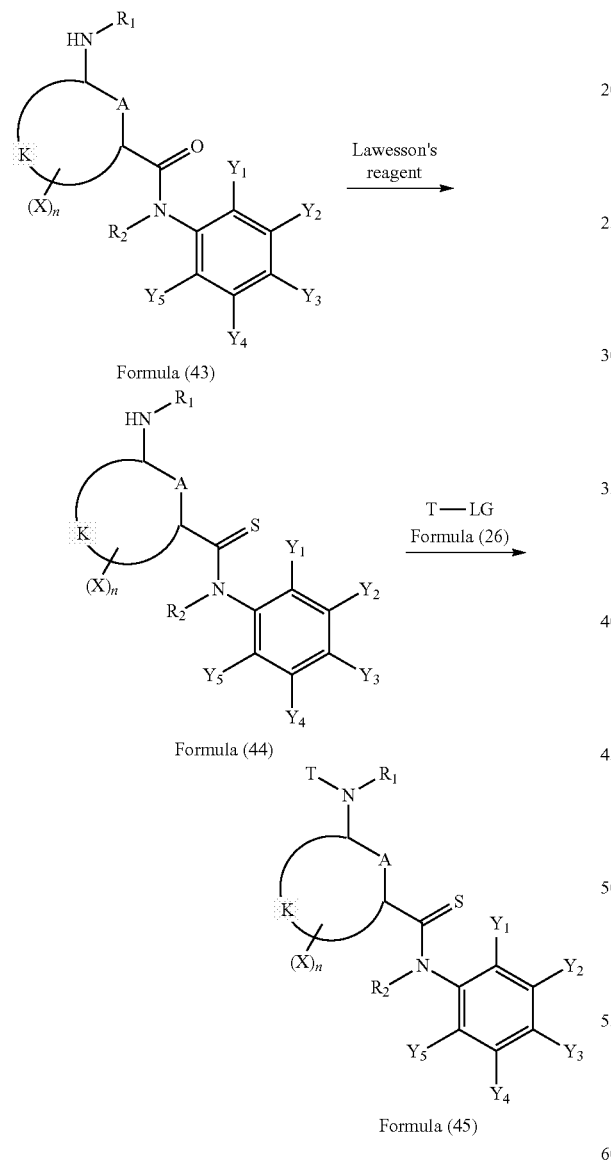

Formula(43)→Formula(44)  7-(i):

A compound represented by Formula (44) can be prepared by reacting the compound represented by Formula (43) with a Lawesson's reagent according to the known conditions described in Synthesis p. 463 (1993), Synthesis p. 829 (1984) and the like. The conditions such as a solvent, reaction temperature and the like are not restricted to those described in the literature.

Formula(44)+Formula(26)→Formula(45)  2-(ii):

A compound represented by Formula (45) can be prepared by reacting the compound represented by Formula (44) with a compound represented by Formula (26) according to the conditions described in 1-(i).

<Preparation Method 8>

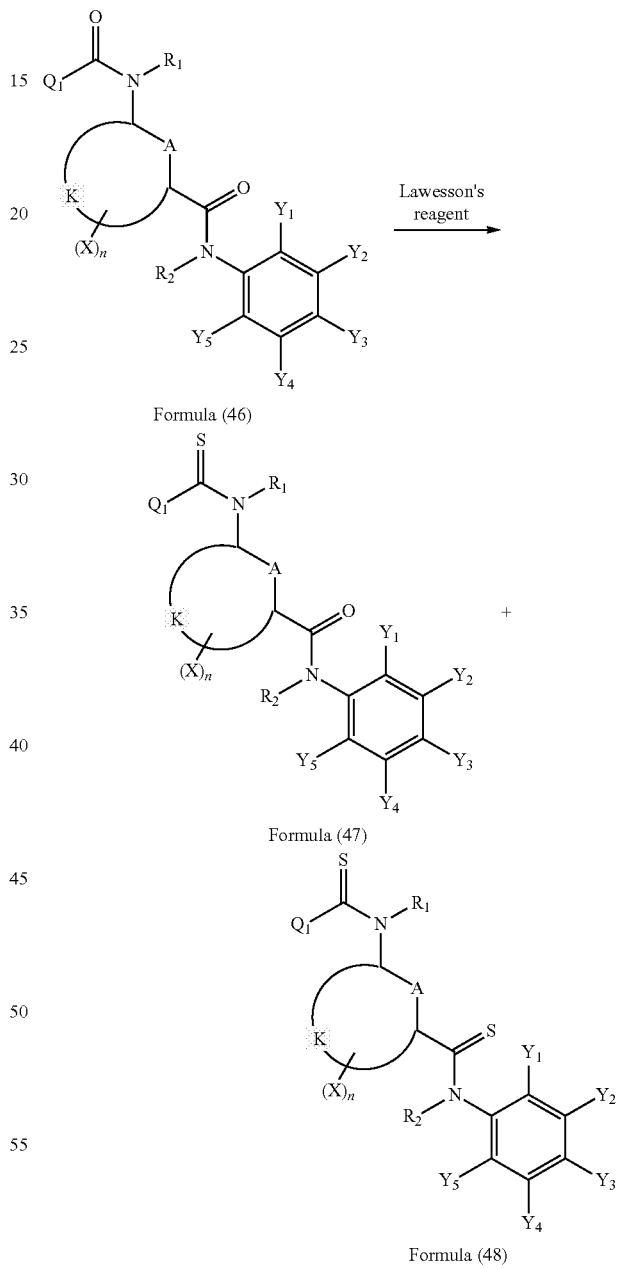

Formula(46)→Formula(47)+Formula(48)  8:

The compounds represented by Formula (47) and Formula (48) can be prepared from a compound represented by Formula (46) according to the conditions described in 7-(i). The conditions such as a solvent, a reaction temperature, and the like are not restricted to those described in the literature. These two compounds can be easily separated and purified by a known separation and purification technique such as silica gel column chromatography and the like.

<Preparation Method 9>

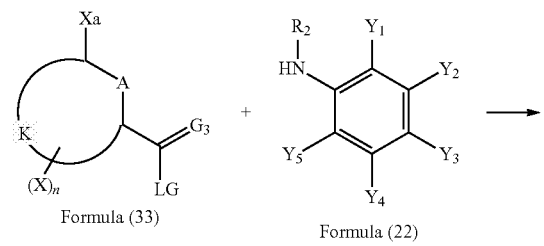

Formula (33)

Formula (22)

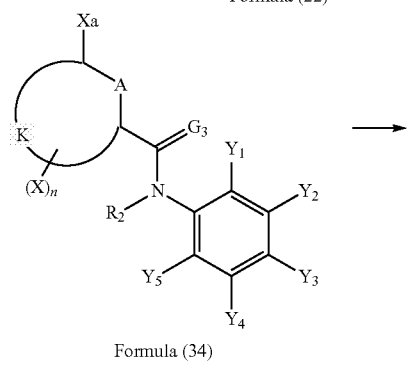

Formula (34)

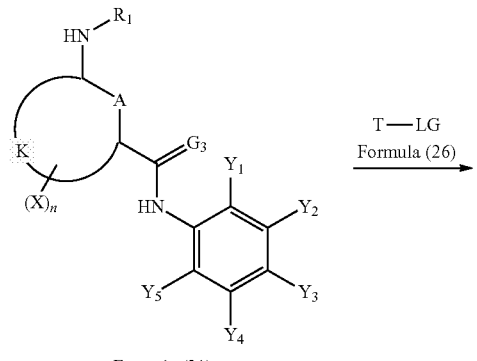

Formula (31)

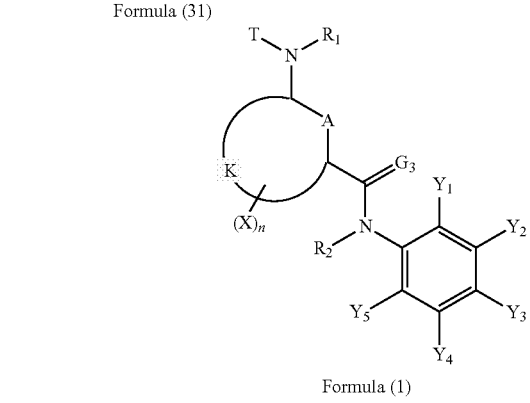

Formula (1)

Formula(49)+Formula(26)→Formula(50)　　　9-(i):

Carboxylic acids having an acylamino group represented by Formula (50) can be prepared by reacting a carboxylic acid having an amino group represented by Formula (49) as a starting material with a compound represented by Formula (26) according to the conditions described in 1-(i).

Formula(50)→Formula(51)　　　9-(ii):

A compound represented by Formula (51) can be prepared by a known general method including reacting the compound represented by Formula (50) with thionyl chloride, oxalyl chloride, phosgene, phosphorus oxychloride, phosphorus pentachloride, phosphorus trichloride, thionyl bromide, phosphorus tribromide, diethylaminosulfur trifluoride, or the like.

Formula(51)+Formula(22)→Formula(1)　　　9-(iii):

The compound represented by Formula (1) can be prepared by reacting a compound represented by Formula (51) with a compound represented by Formula (22) according to the conditions described in 1-(i).

Formula(50)+Formula(22)→Formula(1)　　　9-(iv):

The compound represented by Formula (1) can be prepared by reacting the compound represented by Formula (50) with a compound represented by Formula (22) according to the condition using a condensing agent or the condition using a mixed anhydride method according to 1-(i).

In all of the preparation methods as described above, a desired product may be isolated from the reaction system after the reaction is completed according to a general method, but if required, purification can be carried out by operations such as recrystallization, column chromatography, distillation, and the like. In addition, the desired product can be also provided to the subsequent reaction process without being separated from the reaction system.

Hereinbelow, examples of the representative compounds of the amide derivative represented by Formula (1), Formula (7), or Formula (8) as an active ingredient for the pest control agent of the present invention will be given in Table 1 to Table 51 below, but the present invention is not limited thereto.

In addition, in the tables, "n-" represents normal, "i-" represents iso, "s-" represents secondary, "t-" represents tertiary, "Me" represents a methyl group, "Et" represents an ethyl group, "n-Pr" represents a normal propyl group, "i-Pr" represents an isopropyl group, "n-Bu" represents a normal butyl group, "i-Bu" represents an isobutyl group, "s-Bu" represents a secondary butyl group, "t-Bu" represents a tertiary butyl group, "CF3" represents a trifluoromethyl group, "C2F5" represents a pentafluoroethyl group, "n-C3F7" represents a heptafluoronormal propyl group, "i-C3F7" represents a heptafluoroisopropyl group, "OCF3" represents a trifluoromethoxy group, "OC2F5" represents a pentafluoroethoxy group, "H" represents a hydrogen atom, "F" represents a fluorine atom, "Cl" represents a chlorine atom, "Br" represents a bromine atom, "I" represents an iodine atom, "O" represents an oxygen atom, "C(O)" represents a carbonyl group, "CN" represents a cyano group, "Py" represents a pyridyl group, "Ph" represents a phenyl group, and "S(O)2" represents a sulfonyl group, respectively.

TABLE 1

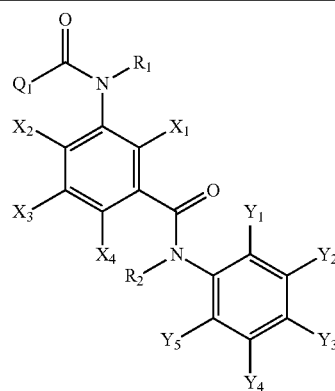

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-1 | phenyl | H | H | H | CN | H | H | Cl | H | heptafluoroisopropyl | H | OCF3 |
| 1-13 | 4-iodophenyl | H | H | H | CN | H | H | Cl | H | pentafluoroethyl | H | OCF3 |
| 1-16 | (4-trifluoromethyl)phenyl | H | H | H | CN | H | H | Cl | H | heptafluoroisopropyl | H | OC2F5 |
| 1-17 | 2-nitrophenyl | H | H | H | CN | H | H | F | H | heptafluoroisopropyl | H | OCF3 |
| 1-20 | 2-cyanophenyl | H | H | H | CN | H | H | Cl | H | pentafluoroethyl | H | OC2F5 |
| 1-21 | 3-cyanophenyl | H | H | H | CN | H | H | Cl | H | heptafluoroisopropyl | H | OCF3 |
| 1-22 | 4-cyanophenyl | H | H | H | CN | H | H | Cl | H | heptafluoroisopropyl | H | OCF3 |
| 1-28 | 4-bromo-2-chlorophenyl | H | H | H | CN | H | H | Cl | H | heptafluoroisopropyl | H | OC2F5 |
| 1-36 | 2-fluoropyridin-3-yl | H | H | H | CN | H | H | Cl | H | pentafluoroethyl | H | OCF3 |
| 1-37 | 2-chloropyridin-3-yl | H | H | H | CN | H | H | Cl | H | heptafluoroisopropyl | H | OCF3 |
| 1-44 | 6-chloropyridin-3-yl | H | H | H | CN | H | H | Cl | H | heptafluoroisopropyl | H | OC2F5 |
| 1-50 | 5-fluoropyridin-3-yl | H | H | H | CN | H | H | Cl | H | heptafluoroisopropyl | H | OC2F5 |
| 1-55 | 5-nitropyridin-3-yl | H | H | H | CN | H | H | Cl | H | pentafluoroethyl | H | OCF3 |
| 1-57 | 4-fluoropyridin-3-yl | H | H | H | CN | H | H | Cl | H | pentafluoroethyl | H | OCF3 |
| 1-59 | 4-bromopyridin-3-yl | H | H | H | CN | H | H | Cl | H | heptafluoroisopropyl | H | OC2F5 |
| 1-60 | 4-iodopyridin-3-yl | H | H | H | CN | H | H | Cl | H | heptafluoroisopropyl | H | OC2F5 |
| 1-79 | phenyl | H | H | H | CN | H | H | Cl | H | nonafluoro-2-butyl | H | OCF3 |
| 1-95 | 2-nitrophenyl | H | H | H | CN | H | H | F | H | nonafluoro-2-butyl | H | OCF3 |
| 1-99 | 3-cyanophenyl | H | H | H | CN | H | H | Cl | H | nonafluoro-2-butyl | H | OCF3 |
| 1-100 | 4-cyanophenyl | H | H | H | CN | H | H | Cl | H | nonafluoro-2-butyl | H | OCF3 |
| 1-105 | 2-chloro-4,5-difluorophenyl | H | H | H | CN | H | H | Cl | H | nonafluoro-2-butyl | H | OC2F5 |
| 1-115 | 2-chloropyridin-3-yl | H | H | H | CN | H | H | Cl | H | nonafluoro-2-butyl | H | OCF3 |
| 1-121 | 6-fluoropyridin-3-yl | H | H | H | CN | H | H | Cl | H | nonafluoro-2-butyl | H | OC2F5 |
| 1-130 | 5-bromopyridin-3-yl | H | H | H | CN | H | H | Cl | H | nonafluoro-2-butyl | H | OC2F5 |
| 1-131 | 5-iodopyridin-3-yl | H | H | H | CN | H | H | Cl | H | nonafluoro-2-butyl | H | OC2F5 |
| 1-139 | 4-(trifluoromethyl)pyridin-3-yl | H | H | H | CN | H | H | Cl | H | nonafluoro-2-butyl | H | OC2F5 |
| 1-140 | 4-nitropyridin-3-yl | H | H | H | CN | H | H | Cl | H | nonafluoro-2-butyl | H | OC2F5 |
| 1-157 | phenyl | H | H | H | CN | H | H | Br | H | heptafluoroisopropyl | H | OCF3 |
| 1-177 | 3-cyanophenyl | H | H | H | CN | H | H | Br | H | heptafluoroisopropyl | H | OCF3 |
| 1-178 | 4-cyanophenyl | H | H | H | CN | H | H | Br | H | heptafluoroisopropyl | H | OCF3 |
| 1-193 | 2-chloropyridin-3-yl | H | H | H | CN | H | H | Br | H | heptafluoroisopropyl | H | OCF3 |
| 1-200 | 6-chloropyridin-3-yl | H | H | H | CN | H | H | Br | H | heptafluoroisopropyl | H | OCF3 |
| 1-222 | pyridin-4-yl | H | H | H | CN | H | H | Br | H | heptafluoroisopropyl | H | OCF3 |
| 1-235 | phenyl | H | H | H | CN | H | H | Br | H | nonafluoro-2-butyl | H | OCF3 |
| 1-255 | 3-cyanophenyl | H | H | H | CN | H | H | Br | H | nonafluoro-2-butyl | H | OCF3 |
| 1-256 | 4-cyanophenyl | H | H | H | CN | H | H | Br | H | nonafluoro-2-butyl | H | OCF3 |
| 1-271 | 2-chloropyridin-3-yl | H | H | H | CN | H | H | Br | H | nonafluoro-2-butyl | H | OCF3 |
| 1-313 | phenyl | H | H | H | CN | H | H | I | H | heptafluoroisopropyl | H | OCF3 |
| 1-314 | 2-fluorophenyl | H | H | H | CN | H | H | I | H | heptafluoroisopropyl | H | OCF3 |
| 1-333 | 3-cyanophenyl | H | H | H | CN | H | H | I | H | heptafluoroisopropyl | H | OCF3 |
| 1-334 | 4-cyanophenyl | H | H | H | CN | H | H | I | H | heptafluoroisopropyl | H | OCF3 |
| 1-349 | 2-chloropyridin-3-yl | H | H | H | CN | H | H | I | H | heptafluoroisopropyl | H | OCF3 |
| 1-356 | 6-chloropyridin-3-yl | H | H | H | CN | H | H | I | H | heptafluoroisopropyl | H | OCF3 |
| 1-391 | phenyl | H | H | H | CN | H | H | I | H | nonafluoro-2-butyl | H | OCF3 |
| 1-411 | 3-cyanophenyl | H | H | H | CN | H | H | I | H | nonafluoro-2-butyl | H | OCF3 |
| 1-412 | 4-cyanophenyl | H | H | H | CN | H | H | I | H | nonafluoro-2-butyl | H | OCF3 |
| 1-427 | 2-chloropyridin-3-yl | H | H | H | CN | H | H | I | H | nonafluoro-2-butyl | H | OCF3 |
| 1-434 | 6-chloropyridin-3-yl | H | H | H | CN | H | H | I | H | nonafluoro-2-butyl | H | OCF3 |
| 1-469 | phenyl | H | H | H | CN | H | H | F | H | heptafluoroisopropyl | H | CF3 |
| 1-470 | phenyl | H | H | H | CN | H | H | Cl | H | heptafluoroisopropyl | H | CF3 |
| 1-471 | 2-fluorophenyl | H | H | H | CN | H | H | Cl | H | heptafluoroisopropyl | H | CF3 |
| 1-472 | 3-fluorophenyl | H | H | H | CN | H | H | Cl | H | heptafluoroisopropyl | H | CF3 |
| 1-473 | 4-fluorophenyl | H | H | H | CN | H | H | Cl | H | heptafluoroisopropyl | H | CF3 |
| 1-474 | 2-chlorophenyl | H | H | H | CN | H | H | Cl | H | heptafluoroisopropyl | H | CF3 |
| 1-475 | 3-chlorophenyl | H | H | H | CN | H | H | Cl | H | heptafluoroisopropyl | H | CF3 |
| 1-476 | 4-chlorophenyl | H | H | H | CN | H | H | Cl | H | heptafluoroisopropyl | H | CF3 |
| 1-477 | 2-bromophenyl | H | H | H | CN | H | H | Cl | H | heptafluoroisopropyl | H | CF3 |

TABLE 1-continued

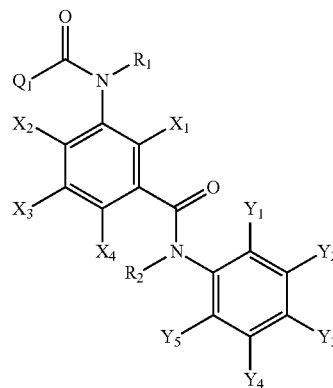

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-478 | 3-bromophenyl | H | H | H | CN | H | H | Cl | H | heptafluoroisopropyl | H | CF3 |
| 1-479 | 4-bromophenyl | H | H | H | CN | H | H | Cl | H | heptafluoroisopropyl | H | CF3 |
| 1-480 | 2-iodophenyl | H | H | H | CN | H | H | Cl | H | heptafluoroisopropyl | H | CF3 |
| 1-481 | 3-iodophenyl | H | H | H | CN | H | H | Cl | H | pentafluoroethyl | H | CF3 |
| 1-482 | 4-iodophenyl | H | H | H | CN | H | H | Cl | H | pentafluoroethyl | H | CF3 |
| 1-483 | (2-trifluoromethyl)phenyl | H | H | H | CN | H | H | Cl | H | heptafluoroisopropyl | H | CF3 |
| 1-484 | (3-trifluoromethyl)phenyl | H | H | H | CN | H | H | Cl | H | heptafluoroisopropyl | H | CF3 |
| 1-485 | (4-trifluoromethyl)phenyl | H | H | H | CN | H | H | Cl | H | heptafluoroisopropyl | H | CF3 |
| 1-486 | 2-nitrophenyl | H | H | H | CN | H | H | Cl | H | heptafluoroisopropyl | H | CF3 |
| 1-487 | 3-nitrophenyl | H | H | H | CN | H | H | Cl | H | heptafluoroisopropyl | H | CF3 |
| 1-488 | 4-nitrophenyl | H | H | H | CN | H | H | Cl | H | heptafluoroisopropyl | H | CF3 |
| 1-489 | 2-cyanophenyl | H | H | H | CN | H | H | Cl | H | pentafluoroethyl | H | C2F5 |
| 1-490 | 3-cyanophenyl | H | H | H | CN | H | H | Cl | H | heptafluoroisopropyl | H | CF3 |
| 1-491 | 4-cyanophenyl | H | H | H | CN | H | H | Cl | H | heptafluoroisopropyl | H | CF3 |
| 1-492 | 2,6-difluorophenyl | H | H | H | CN | H | H | Cl | H | heptafluoroisopropyl | H | CF3 |
| 1-493 | 3,4-dichlorophenyl | H | H | H | CN | H | H | Cl | H | heptafluoroisopropyl | H | CF3 |
| 1-494 | 2,4-dichlorophenyl | H | H | H | CN | H | H | Cl | H | heptafluoroisopropyl | H | C2F5 |
| 1-495 | 2-chloro-4-fluorophenyl | H | H | H | CN | H | H | Cl | H | heptafluoroisopropyl | H | CF3 |
| 1-496 | 2-chloro-4,5-difluorophenyl | H | H | H | CN | H | H | Cl | H | heptafluoroisopropyl | H | CF3 |
| 1-497 | 4-bromo-2-chlorophenyl | H | H | H | CN | H | H | Cl | H | heptafluoroisopropyl | H | CF3 |
| 1-498 | 2-bromo-4-chlorophenyl | H | H | H | CN | H | H | Cl | H | heptafluoroisopropyl | H | n-C3F7 |
| 1-499 | 2-bromo-4-fluorophenyl | H | H | H | CN | H | H | Cl | H | heptafluoroisopropyl | H | CF3 |
| 1-500 | 2-chloro-4-nitrophenyl | H | H | H | CN | H | H | Cl | H | heptafluoroisopropyl | H | CF3 |
| 1-501 | 3,5-dicyanophenyl | H | H | H | CN | H | H | Cl | H | heptafluoroisopropyl | H | CF3 |
| 1-502 | 4-cyano-2-fluorophenyl | H | H | H | CN | H | H | Cl | H | heptafluoroisopropyl | H | CF3 |
| 1-503 | 2-chloro-4-cyanophenyl | H | H | H | CN | H | H | Cl | H | heptafluoroisopropyl | H | CF3 |
| 1-504 | pyrdin-3-yl | H | H | H | CN | H | H | Cl | H | heptafluoroisopropyl | H | CF3 |
| 1-505 | 2-fluoropyridin-3-yl | H | H | H | CN | H | H | Cl | H | pentafluoroethyl | H | CF3 |
| 1-506 | 2-chloropyridin-3-yl | H | H | H | CN | H | H | Cl | H | heptafluoroisopropyl | H | CF3 |
| 1-507 | 2-bromopyridin-3-yl | H | H | H | CN | H | H | Cl | H | heptafluoroisopropyl | H | CF3 |
| 1-508 | 2-iodopyridin-3-yl | H | H | H | CN | H | H | Cl | H | heptafluoroisopropyl | H | CF3 |
| 1-509 | 2-(trifluoromethyl)pyridin-3-yl | H | H | H | CN | H | H | Cl | H | heptafluoroisopropyl | H | CF3 |
| 1-510 | 2-nitropyridin-3-yl | H | H | H | CN | H | H | Cl | H | heptafluoroisopropyl | H | CF3 |
| 1-511 | 2-cyanopyridin-3-yl | H | H | H | CN | H | H | Cl | H | heptafluoroisopropyl | H | CF3 |
| 1-512 | 6-fluoropyridin-3-yl | H | H | H | CN | H | H | Cl | H | heptafluoroisopropyl | H | CF3 |
| 1-513 | 6-chloropyridin-3-yl | H | H | H | CN | H | H | Cl | H | heptafluoroisopropyl | H | CF3 |
| 1-514 | 6-bromopyridin-3-yl | H | H | H | CN | H | H | Cl | H | heptafluoroisopropyl | H | CF3 |
| 1-515 | 6-iodopyridin-3-yl | H | H | H | CN | H | H | Cl | H | heptafluoroisopropyl | H | CF3 |
| 1-516 | 6-(trifluoromethyl)pyridin-3-yl | H | H | H | CN | H | H | Cl | H | heptafluoroisopropyl | H | CF3 |
| 1-517 | 6-nitropyridin-3-yl | H | H | H | CN | H | H | Cl | H | heptafluoroisopropyl | H | CF3 |
| 1-518 | 6-cyanopyridin-3-yl | H | H | H | CN | H | H | Cl | H | heptafluoroisopropyl | H | CF3 |
| 1-519 | 5-fluoropyridin-3-yl | H | H | H | CN | H | H | Cl | H | heptafluoroisopropyl | H | C2F5 |
| 1-520 | 5-chloropyridin-3-yl | H | H | H | CN | H | H | Cl | H | heptafluoroisopropyl | H | CF3 |
| 1-521 | 5-bromopyridin-3-yl | H | H | H | CN | H | H | Cl | H | heptafluoroisopropyl | H | n-C3F7 |
| 1-522 | 5-iodopyridin-3-yl | H | H | H | CN | H | H | Cl | H | heptafluoroisopropyl | H | i-C3F7 |
| 1-523 | 5-(trifluoromethyl)pyridin-3-yl | H | H | H | CN | H | H | Cl | H | heptafluoroisopropyl | H | CF3 |
| 1-524 | 5-nitropyridin-3-yl | H | H | H | CN | H | H | Cl | H | pentafluoroethyl | H | CF3 |
| 1-525 | 5-cyanopyridin-3-yl | H | H | H | CN | H | H | Cl | H | heptafluoroisopropyl | H | CF3 |
| 1-526 | 4-fluoropyridin-3-yl | H | H | H | CN | H | H | Cl | H | pentafluoroethyl | H | CF3 |
| 1-527 | 4-chloropyridin-3-yl | H | H | H | CN | H | H | Cl | H | heptafluoroisopropyl | H | CF3 |
| 1-528 | 4-bromopyridin-3-yl | H | H | H | CN | H | H | Cl | H | heptafluoroisopropyl | H | n-C3F7 |
| 1-529 | 4-iodopyridin-3-yl | H | H | H | CN | H | H | Cl | H | heptafluoroisopropyl | H | i-C3F7 |
| 1-530 | 4-(trifluoromethyl)pyridin-3-yl | H | H | H | CN | H | H | Cl | H | heptafluoroisopropyl | H | CF3 |
| 1-531 | 4-nitropyridin-3-yl | H | H | H | CN | H | H | Cl | H | heptafluoroisopropyl | H | CF3 |
| 1-532 | 4-cyanopyridin-3-yl | H | H | H | CN | H | H | Cl | H | heptafluoroisopropyl | H | CF3 |
| 1-533 | 2,6-dichloropyridin-3-yl | H | H | H | CN | H | H | Cl | H | heptafluoroisopropyl | H | CF3 |
| 1-534 | pyridin-3-yl N-oxide | H | H | H | CN | H | H | Cl | H | heptafluoroisopropyl | H | CF3 |

TABLE 1-continued

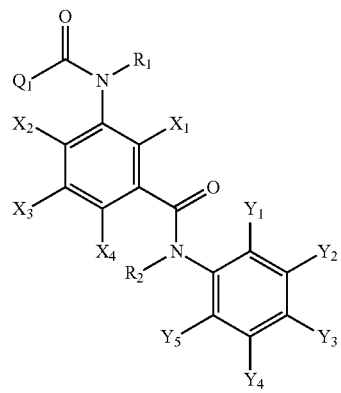

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-535 | pyridin-4-yl | H | H | H | CN | H | H | Cl | H | heptafluoroisopropyl | H | CF3 |
| 1-536 | 2-chloropyridin-4-yl | H | H | H | CN | H | H | Cl | H | heptafluoroisopropyl | H | CF3 |
| 1-537 | 3-bromopyridin-4-yl | H | H | H | CN | H | H | Cl | H | heptafluoroisopropyl | H | CF3 |
| 1-538 | 3,5-dichloropyridin-4-yl | H | H | H | CN | H | H | Cl | H | heptafluoroisopropyl | H | CF3 |
| 1-539 | 3-(trifluoromethyl)pyridin-4-yl | H | H | H | CN | H | H | Cl | H | heptafluoroisopropyl | H | CF3 |
| 1-540 | 2,6-dicyanopyridin-4-yl | H | H | H | CN | H | H | Cl | H | heptafluoroisopropyl | H | CF3 |
| 1-541 | pyridin-4-yl N-oxide | H | H | H | CN | H | H | Cl | H | heptafluoroisopropyl | H | CF3 |
| 1-542 | pyridin-2-yl | H | H | H | CN | H | H | Cl | H | heptafluoroisopropyl | H | CF3 |
| 1-543 | 3-chloropyridin-2-yl | H | H | H | CN | H | H | Cl | H | heptafluoroisopropyl | H | CF3 |
| 1-544 | 4-bromopyridin-2-yl | H | H | H | CN | H | H | Cl | H | heptafluoroisopropyl | H | CF3 |
| 1-545 | 5-iodopyridin-2-yl | H | H | H | CN | H | H | Cl | H | heptafluoroisopropyl | H | CF3 |
| 1-546 | 6-chloropyridin-2-yl | H | H | H | CN | H | H | Cl | H | heptafluoroisopropyl | H | CF3 |
| 1-547 | 4-cyanopyridin-2-yl | H | H | H | CN | H | H | Cl | H | pentafluoroethyl | H | CF3 |
| 1-548 | phenyl | H | H | H | CN | H | H | F | H | nonafluoro-2-butyl | H | CF3 |
| 1-549 | phenyl | H | H | H | CN | H | H | Cl | H | nonafluoro-2-butyl | H | CF3 |
| 1-550 | 2-fluorophenyl | H | H | H | CN | H | H | Cl | H | nonafluoro-2-butyl | H | CF3 |
| 1-551 | 3-fluorophenyl | H | H | H | CN | H | H | Cl | H | nonafluoro-2-butyl | H | CF3 |
| 1-552 | 4-fluorophenyl | H | H | H | CN | H | H | Cl | H | nonafluoro-2-butyl | H | CF3 |
| 1-553 | 2-chlorophenyl | H | H | H | CN | H | H | Cl | H | nonafluoro-2-butyl | H | CF3 |
| 1-554 | 3-chlorophenyl | H | H | H | CN | H | H | Cl | H | nonafluoro-2-butyl | H | CF3 |
| 1-555 | 4-chlorophenyl | H | H | H | CN | H | H | Cl | H | nonafluoro-2-butyl | H | CF3 |
| 1-556 | 2-bromophenyl | H | H | H | CN | H | H | Cl | H | nonafluoro-2-butyl | H | CF3 |
| 1-557 | 3-bromophenyl | H | H | H | CN | H | H | Cl | H | nonafluoro-2-butyl | H | CF3 |
| 1-558 | 4-bromophenyl | H | H | H | CN | H | H | Cl | H | nonafluoro-2-butyl | H | CF3 |
| 1-559 | 2-iodophenyl | H | H | H | CN | H | H | Cl | H | nonafluoro-2-butyl | H | CF3 |
| 1-560 | 3-iodophenyl | H | H | H | CN | H | H | Cl | H | nonafluoro-2-butyl | H | CF3 |
| 1-561 | 4-iodophenyl | H | H | H | CN | H | H | Cl | H | nonafluoro-2-butyl | H | CF3 |
| 1-562 | (2-trifluoromethyl)phenyl | H | H | H | CN | H | H | Cl | H | nonafluoro-2-butyl | H | C2F5 |
| 1-563 | (3-trifluoromethyl)phenyl | H | H | H | CN | H | H | Cl | H | nonafluoro-2-butyl | H | CF3 |
| 1-564 | (4-trifluoromethyl)phenyl | H | H | H | CN | H | H | Cl | H | nonafluoro-2-butyl | H | CF3 |
| 1-565 | 2-nitrophenyl | H | H | H | CN | H | H | Cl | H | nonafluoro-2-butyl | H | CF3 |
| 1-566 | 3-nitrophenyl | H | H | H | CN | H | H | Cl | H | nonafluoro-2-butyl | H | CF3 |
| 1-567 | 4-nitrophenyl | H | H | H | CN | H | H | Cl | H | nonafluoro-2-butyl | H | CF3 |
| 1-568 | 2-cyanophenyl | H | H | H | CN | H | H | Cl | H | nonafluoro-2-butyl | H | CF3 |
| 1-569 | 3-cyanophenyl | H | H | H | CN | H | H | Cl | H | nonafluoro-2-butyl | H | CF3 |
| 1-570 | 4-cyanophenyl | H | H | H | CN | H | H | Cl | H | nonafluoro-2-butyl | H | CF3 |
| 1-571 | 2,6-difluorophenyl | H | H | H | CN | H | H | Cl | H | nonafluoro-2-butyl | H | CF3 |
| 1-572 | 3,4-dichlorophenyl | H | H | H | CN | H | H | Cl | H | nonafluoro-2-butyl | H | CF3 |
| 1-573 | 2,4-dichlorophenyl | H | H | H | CN | H | H | Cl | H | nonafluoro-2-butyl | H | CF3 |
| 1-574 | 2-chloro-4-fluorophenyl | H | H | H | CN | H | H | Cl | H | nonafluoro-2-butyl | H | CF3 |
| 1-575 | 2-chloro-4,5-difluorophenyl | H | H | H | CN | H | H | Cl | H | nonafluoro-2-butyl | H | CF3 |
| 1-576 | 4-bromo-2-chlorophenyl | H | H | H | CN | H | H | Cl | H | nonafluoro-2-butyl | H | CF3 |
| 1-577 | 2-bromo-4-chlorophenyl | H | H | H | CN | H | H | Cl | H | nonafluoro-2-butyl | H | CF3 |
| 1-578 | 2-bromo-4-fluorophenyl | H | H | H | CN | H | H | Cl | H | nonafluoro-2-butyl | H | CF3 |
| 1-579 | 2-chloro-4-nitrophenyl | H | H | H | CN | H | H | Cl | H | nonafluoro-2-butyl | H | i-C3F7 |
| 1-580 | 3,5-dicyanophenyl | H | H | H | CN | H | H | Cl | H | nonafluoro-2-butyl | H | CF3 |
| 1-581 | 4-cyano-2-fluorophenyl | H | H | H | CN | H | H | Cl | H | nonafluoro-2-butyl | H | CF3 |
| 1-582 | 2-chloro-4-cyanophenyl | H | H | H | CN | H | H | Cl | H | nonafluoro-2-butyl | H | CF3 |
| 1-583 | pyridin-3-yl | H | H | H | CN | H | H | Cl | H | nonafluoro-2-butyl | H | CF3 |
| 1-584 | 2-fluoropyridin-3-yl | H | H | H | CN | H | H | Cl | H | nonafluoro-2-butyl | H | CF3 |
| 1-585 | 2-chloropyridin-3-yl | H | H | H | CN | H | H | Cl | H | nonafluoro-2-butyl | H | CF3 |
| 1-586 | 2-bromopyridin-3-yl | H | H | H | CN | H | H | Cl | H | nonafluoro-2-butyl | H | CF3 |
| 1-587 | 2-iodopyridin-3-yl | H | H | H | CN | H | H | Cl | H | nonafluoro-2-butyl | H | CF3 |
| 1-588 | 2-(trifluoromethyl)pyridin-3-yl | H | H | H | CN | H | H | Cl | H | nonafluoro-2-butyl | H | CF3 |
| 1-589 | 2-nitropyridin-3-yl | H | H | H | CN | H | H | Cl | H | nonafluoro-2-butyl | H | CF3 |
| 1-590 | 2-cyanopyridin-3-yl | H | H | H | CN | H | H | Cl | H | nonafluoro-2-butyl | H | CF3 |
| 1-591 | 6-fluoropyridin-3-yl | H | H | H | CN | H | H | Cl | H | nonafluoro-2-butyl | H | CF3 |

TABLE 1-continued

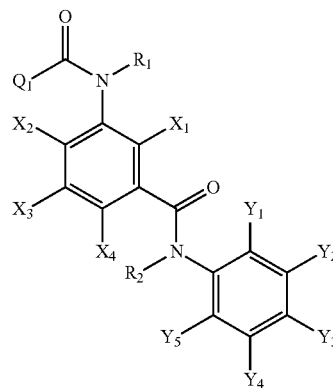

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-592 | 6-chloropyridin-3-yl | H | H | H | CN | H | H | Cl | H | nonafluoro-2-butyl | H | CF3 |
| 1-593 | 6-bromopyridin-3-yl | H | H | H | CN | H | H | Cl | H | nonafluoro-2-butyl | H | CF3 |
| 1-594 | 6-iodopyridin-3-yl | H | H | H | CN | H | H | Cl | H | nonafluoro-2-butyl | H | CF3 |
| 1-595 | 6-(trifluoromethyl)pyridin-3-yl | H | H | H | CN | H | H | Cl | H | nonafluoro-2-butyl | H | CF3 |
| 1-596 | 6-nitropyridin-3-yl | H | H | H | CN | H | H | Cl | H | nonafluoro-2-butyl | H | CF3 |
| 1-597 | 6-cyanopyridin-3-yl | H | H | H | CN | H | H | Cl | H | nonafluoro-2-butyl | H | CF3 |
| 1-598 | 5-fluoropyridin-3-yl | H | H | H | CN | H | H | Cl | H | nonafluoro-2-butyl | H | C2F5 |
| 1-599 | 5-chloropyridin-3-yl | H | H | H | CN | H | H | Cl | H | nonafluoro-2-butyl | H | CF3 |
| 1-600 | 5-bromopyridin-3-yl | H | H | H | CN | H | H | Cl | H | nonafluoro-2-butyl | H | n-C3F7 |
| 1-601 | 5-iodopyridin-3-yl | H | H | H | CN | H | H | Cl | H | nonafluoro-2-butyl | H | i-C3F7 |
| 1-602 | 5-(trifluoromethyl)pyridin-3-yl | H | H | H | CN | H | H | Cl | H | nonafluoro-2-butyl | H | CF3 |
| 1-603 | 5-nitropyridin-3-yl | H | H | H | CN | H | H | Cl | H | nonafluoro-2-butyl | H | CF3 |
| 1-604 | 5-cyanopyridin-3-yl | H | H | H | CN | H | H | Cl | H | nonafluoro-2-butyl | H | CF3 |
| 1-605 | 4-fluoropyridin-3-yl | H | H | H | CN | H | H | Cl | H | nonafluoro-2-butyl | H | C2F5 |
| 1-606 | 4-chloropyridin-3-yl | H | H | H | CN | H | H | Cl | H | nonafluoro-2-butyl | H | CF3 |
| 1-607 | 4-bromopyridin-3-yl | H | H | H | CN | H | H | Cl | H | nonafluoro-2-butyl | H | CF3 |
| 1-608 | 4-iodopyridin-3-yl | H | H | H | CN | H | H | Cl | H | nonafluoro-2-butyl | H | CF3 |
| 1-609 | 4-(trifluoromethyl)pyridin-3-yl | H | H | H | CN | H | H | Cl | H | nonafluoro-2-butyl | H | n-C3F7 |
| 1-610 | 4-nitropyridin-3-yl | H | H | H | CN | H | H | Cl | H | nonafluoro-2-butyl | H | i-C3F7 |
| 1-611 | 4-cyanopyridin-3-yl | H | H | H | CN | H | H | Cl | H | nonafluoro-2-butyl | H | CF3 |
| 1-612 | 2,6-dichloropyridin-3-yl | H | H | H | CN | H | H | Cl | H | nonafluoro-2-butyl | H | CF3 |
| 1-613 | pyridin-3-yl N-oxide | H | H | H | CN | H | H | Cl | H | nonafluoro-2-butyl | H | CF3 |
| 1-614 | pyridin-4-yl | H | H | H | CN | H | H | Cl | H | nonafluoro-2-butyl | H | CF3 |
| 1-615 | 2-chloropyridin-4-yl | H | H | H | CN | H | H | Cl | H | nonafluoro-2-butyl | H | CF3 |
| 1-616 | 3-bromopyridin-4-yl | H | H | H | CN | H | H | Cl | H | nonafluoro-2-butyl | H | CF3 |
| 1-617 | 3,5-dichloropyridin-4-yl | H | H | H | CN | H | H | Cl | H | nonafluoro-2-butyl | H | CF3 |
| 1-618 | 3-(trifluoromethyl)pyridin-4-yl | H | H | H | CN | H | H | Cl | H | nonafluoro-2-butyl | H | CF3 |
| 1-619 | 2,6-dicyanopyridin-4-yl | H | H | H | CN | H | H | Cl | H | nonafluoro-2-butyl | H | CF3 |
| 1-620 | pyridin-4-yl N-oxide | H | H | H | CN | H | H | Cl | H | nonafluoro-2-butyl | H | CF3 |
| 1-621 | pyridin-2-yl | H | H | H | CN | H | H | Cl | H | nonafluoro-2-butyl | H | CF3 |
| 1-622 | 3-chloropyridin-2-yl | H | H | H | CN | H | H | Cl | H | nonafluoro-2-butyl | H | CF3 |
| 1-623 | 4-bromopyridin-2-yl | H | H | H | CN | H | H | Cl | H | nonafluoro-2-butyl | H | CF3 |
| 1-624 | 5-iodopyridin-2-yl | H | H | H | CN | H | H | Cl | H | nonafluoro-2-butyl | H | CF3 |
| 1-625 | 6-chloropyridin-2-yl | H | H | H | CN | H | H | Cl | H | nonafluoro-2-butyl | H | CF3 |
| 1-626 | 4-cyanopyridin-2-yl | H | H | H | CN | H | H | Cl | H | nonafluoro-2-butyl | H | C2F5 |
| 1-627 | phenyl | H | H | H | CN | H | H | Br | H | heptafluoroisopropyl | H | CF3 |
| 1-628 | 2-fluorophenyl | H | H | H | CN | H | H | Br | H | heptafluoroisopropyl | H | CF3 |
| 1-629 | 3-fluorophenyl | H | H | H | CN | H | H | Br | H | heptafluoroisopropyl | H | CF3 |
| 1-630 | 4-fluorophenyl | H | H | H | CN | H | H | Br | H | heptafluoroisopropyl | H | CF3 |
| 1-631 | 2-chlorophenyl | H | H | H | CN | H | H | Br | H | heptafluoroisopropyl | H | CF3 |
| 1-632 | 3-chlorophenyl | H | H | H | CN | H | H | Br | H | heptafluoroisopropyl | H | CF3 |
| 1-633 | 4-chlorophenyl | H | H | H | CN | H | H | Br | H | heptafluoroisopropyl | H | CF3 |
| 1-634 | 2-bromophenyl | H | H | H | CN | H | H | Br | H | heptafluoroisopropyl | H | CF3 |
| 1-635 | 3-bromophenyl | H | H | H | CN | H | H | Br | H | heptafluoroisopropyl | H | CF3 |
| 1-636 | 4-bromophenyl | H | H | H | CN | H | H | Br | H | heptafluoroisopropyl | H | CF3 |
| 1-637 | 2-iodophenyl | H | H | H | CN | H | H | Br | H | heptafluoroisopropyl | H | CF3 |
| 1-638 | 3-iodophenyl | H | H | H | CN | H | H | Br | H | heptafluoroisopropyl | H | CF3 |
| 1-639 | 4-iodophenyl | H | H | H | CN | H | H | Br | H | heptafluoroisopropyl | H | CF3 |
| 1-640 | (2-trifluoromethyl)phenyl | H | H | H | CN | H | H | Br | H | heptafluoroisopropyl | H | CF3 |
| 1-641 | (3-trifluoromethyl)phenyl | H | H | H | CN | H | H | Br | H | heptafluoroisopropyl | H | CF3 |
| 1-642 | (4-trifluoromethyl)phenyl | H | H | H | CN | H | H | Br | H | heptafluoroisopropyl | H | CF3 |
| 1-643 | 2-nitrophenyl | H | H | H | CN | H | H | Br | H | heptafluoroisopropyl | H | CF3 |
| 1-644 | 3-nitrophenyl | H | H | H | CN | H | H | Br | H | heptafluoroisopropyl | H | CF3 |
| 1-645 | 4-nitrophenyl | H | H | H | CN | H | H | Br | H | heptafluoroisopropyl | H | CF3 |
| 1-646 | 2-cyanophenyl | H | H | H | CN | H | H | Br | H | heptafluoroisopropyl | H | CF3 |
| 1-647 | 3-cyanophenyl | H | H | H | CN | H | H | Br | H | heptafluoroisopropyl | H | CF3 |
| 1-648 | 4-cyanophenyl | H | H | H | CN | H | H | Br | H | heptafluoroisopropyl | H | CF3 |

TABLE 1-continued

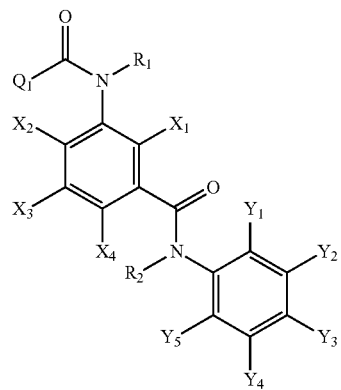

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-649 | 2,6-difluorophenyl | H | H | H | CN | H | H | Br | H | heptafluoroisopropyl | H | CF3 |
| 1-650 | 3,4-dichlorophenyl | H | H | H | CN | H | H | Br | H | heptafluoroisopropyl | H | CF3 |
| 1-651 | 2,4-dichlorophenyl | H | H | H | CN | H | H | Br | H | heptafluoroisopropyl | H | CF3 |
| 1-652 | 2-chloro-4-fluorophenyl | H | H | H | CN | H | H | Br | H | heptafluoroisopropyl | H | CF3 |
| 1-653 | 2-chloro-4,5-difluorophenyl | H | H | H | CN | H | H | Br | H | heptafluoroisopropyl | H | CF3 |
| 1-654 | 4-bromo-2-chlorophenyl | H | H | H | CN | H | H | Br | H | heptafluoroisopropyl | H | CF3 |
| 1-655 | 2-bromo-4-chlorophenyl | H | H | H | CN | H | H | Br | H | heptafluoroisopropyl | H | CF3 |
| 1-656 | 2-bromo-4-fluorophenyl | H | H | H | CN | H | H | Br | H | heptafluoroisopropyl | H | CF3 |
| 1-657 | 2-chloro-4-nitrophenyl | H | H | H | CN | H | H | Br | H | heptafluoroisopropyl | H | CF3 |
| 1-658 | 3,5-dicyanophenyl | H | H | H | CN | H | H | Br | H | heptafluoroisopropyl | H | CF3 |
| 1-659 | 4-cyano-2-fluorophenyl | H | H | H | CN | H | H | Br | H | heptafluoroisopropyl | H | CF3 |
| 1-660 | 2-chloro-4-cyanophenyl | H | H | H | CN | H | H | Br | H | heptafluoroisopropyl | H | CF3 |
| 1-661 | pyridin-3-yl | H | H | H | CN | H | H | Br | H | heptafluoroisopropyl | H | CF3 |
| 1-662 | 2-fluoropyridin-3-yl | H | H | H | CN | H | H | Br | H | heptafluoroisopropyl | H | CF3 |
| 1-663 | 2-chloropyridin-3-yl | H | H | H | CN | H | H | Br | H | heptafluoroisopropyl | H | CF3 |
| 1-664 | 2-bromopyridin-3-yl | H | H | H | CN | H | H | Br | H | heptafluoroisopropyl | H | CF3 |
| 1-665 | 2-iodopyridin-3-yl | H | H | H | CN | H | H | Br | H | heptafluoroisopropyl | H | CF3 |
| 1-666 | 2-(trifluoromethyl)pyridin-3-yl | H | H | H | CN | H | H | Br | H | heptafluoroisopropyl | H | CF3 |
| 1-667 | 2-nitropyridin-3-yl | H | H | H | CN | H | H | Br | H | heptafluoroisopropyl | H | CF3 |
| 1-668 | 2-cyanopyridin-3-yl | H | H | H | CN | H | H | Br | H | heptafluoroisopropyl | H | CF3 |
| 1-669 | 6-fluoropyridin-3-yl | H | H | H | CN | H | H | Br | H | heptafluoroisopropyl | H | CF3 |
| 1-670 | 6-chloropyridin-3-yl | H | H | H | CN | H | H | Br | H | heptafluoroisopropyl | H | CF3 |
| 1-671 | 6-bromopyridin-3-yl | H | H | H | CN | H | H | Br | H | heptafluoroisopropyl | H | CF3 |
| 1-672 | 6-iodopyridin-3-yl | H | H | H | CN | H | H | Br | H | heptafluoroisopropyl | H | CF3 |
| 1-673 | 6-(trifluoromethyl)pyridin-3-yl | H | H | H | CN | H | H | Br | H | heptafluoroisopropyl | H | CF3 |
| 1-674 | 6-nitropyridin-3-yl | H | H | H | CN | H | H | Br | H | heptafluoroisopropyl | H | CF3 |
| 1-675 | 6-cyanopyridin-3-yl | H | H | H | CN | H | H | Br | H | heptafluoroisopropyl | H | CF3 |
| 1-676 | 5-fluoropyridin-3-yl | H | H | H | CN | H | H | Br | H | heptafluoroisopropyl | H | CF3 |
| 1-677 | 5-chloropyridin-3-yl | H | H | H | CN | H | H | Br | H | heptafluoroisopropyl | H | CF3 |
| 1-678 | 5-bromopyridin-3-yl | H | H | H | CN | H | H | Br | H | heptafluoroisopropyl | H | CF3 |
| 1-679 | 5-iodopyridin-3-yl | H | H | H | CN | H | H | Br | H | heptafluoroisopropyl | H | CF3 |
| 1-680 | 5-(trifluoromethyl)pyridin-3-yl | H | H | H | CN | H | H | Br | H | heptafluoroisopropyl | H | CF3 |
| 1-681 | 5-nitropyridin-3-yl | H | H | H | CN | H | H | Br | H | heptafluoroisopropyl | H | CF3 |
| 1-682 | 5-cyanopyridin-3-yl | H | H | H | CN | H | H | Br | H | heptafluoroisopropyl | H | CF3 |
| 1-683 | 4-fluoropyridin-3-yl | H | H | H | CN | H | H | Br | H | heptafluoroisopropyl | H | CF3 |
| 1-684 | 4-chloropyridin-3-yl | H | H | H | CN | H | H | Br | H | heptafluoroisopropyl | H | CF3 |
| 1-685 | 4-bromopyridin-3-yl | H | H | H | CN | H | H | Br | H | heptafluoroisopropyl | H | CF3 |
| 1-686 | 4-iodopyridin-3-yl | H | H | H | CN | H | H | Br | H | heptafluoroisopropyl | H | CF3 |
| 1-687 | 4-(trifluoromethyl)pyridin-3-yl | H | H | H | CN | H | H | Br | H | heptafluoroisopropyl | H | CF3 |
| 1-688 | 4-nitropyridin-3-yl | H | H | H | CN | H | H | Br | H | heptafluoroisopropyl | H | CF3 |
| 1-689 | 4-cyanopyridin-3-yl | H | H | H | CN | H | H | Br | H | heptafluoroisopropyl | H | CF3 |
| 1-690 | 2,6-dichloropyridin-3-yl | H | H | H | CN | H | H | Br | H | heptafluoroisopropyl | H | CF3 |
| 1-691 | pyridin-3-yl N-oxide | H | H | H | CN | H | H | Br | H | heptafluoroisopropyl | H | CF3 |
| 1-692 | pyridin-4-yl | H | H | H | CN | H | H | Br | H | heptafluoroisopropyl | H | CF3 |
| 1-693 | 2-chloropyridin-4-yl | H | H | H | CN | H | H | Br | H | heptafluoroisopropyl | H | CF3 |
| 1-694 | 3-bromopyridin-4-yl | H | H | H | CN | H | H | Br | H | heptafluoroisopropyl | H | CF3 |
| 1-695 | 3,5-dichloropyridin-4-yl | H | H | H | CN | H | H | Br | H | heptafluoroisopropyl | H | CF3 |
| 1-696 | 3-(trifluoromethyl)pyridin-4-yl | H | H | H | CN | H | H | Br | H | heptafluoroisopropyl | H | CF3 |
| 1-697 | 2,6-dicyanopyridin-4-yl | H | H | H | CN | H | H | Br | H | heptafluoroisopropyl | H | CF3 |
| 1-698 | pyridin-4-yl N-oxide | H | H | H | CN | H | H | Br | H | heptafluoroisopropyl | H | CF3 |
| 1-699 | pyridin-2-yl | H | H | H | CN | H | H | Br | H | heptafluoroisopropyl | H | CF3 |
| 1-700 | 3-chloropyridin-2-yl | H | H | H | CN | H | H | Br | H | heptafluoroisopropyl | H | CF3 |
| 1-701 | 4-bromopyridin-2-yl | H | H | H | CN | H | H | Br | H | heptafluoroisopropyl | H | CF3 |
| 1-702 | 5-iodopyridin-2-yl | H | H | H | CN | H | H | Br | H | heptafluoroisopropyl | H | CF3 |
| 1-703 | 6-chloropyridin-2-yl | H | H | H | CN | H | H | Br | H | heptafluoroisopropyl | H | CF3 |
| 1-704 | 4-cyanopyridin-2-yl | H | H | H | CN | H | H | Br | H | heptafluoroisopropyl | H | CF3 |
| 1-705 | phenyl | H | H | H | CN | H | H | Br | H | nonafluoro-2-butyl | H | CF3 |

TABLE 1-continued

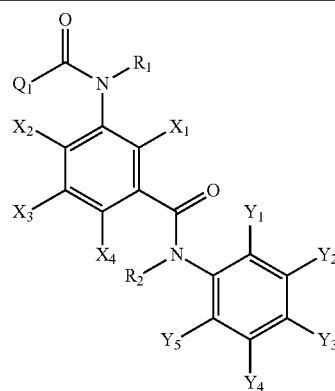

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-706 | 2-fluorophenyl | H | H | H | CN | H | H | Br | H | nonafluoro-2-butyl | H | CF3 |
| 1-707 | 3-fluorophenyl | H | H | H | CN | H | H | Br | H | nonafluoro-2-butyl | H | CF3 |
| 1-708 | 4-fluorophenyl | H | H | H | CN | H | H | Br | H | nonafluoro-2-butyl | H | CF3 |
| 1-709 | 2-chlorophenyl | H | H | H | CN | H | H | Br | H | nonatluoro-2-butyl | H | CF3 |
| 1-710 | 3-chlorophenyl | H | H | H | CN | H | H | Br | H | nonafluoro-2-butyl | H | CF3 |
| 1-711 | 4-chlorophenyl | H | H | H | CN | H | H | Br | H | nonafluoro-2-butyl | H | CF3 |
| 1-712 | 2-bromophenyl | H | H | H | CN | H | H | Br | H | nonafluoro-2-butyl | H | CF3 |
| 1-713 | 3-bromophenyl | H | H | H | CN | H | H | Br | H | nonafluoro-2-butyl | H | CF3 |
| 1-714 | 4-bromophenyl | H | H | H | CN | H | H | Br | H | nonafluoro-2-butyl | H | CF3 |
| 1-715 | 2-iodophenyl | H | H | H | CN | H | H | Br | H | nonafluoro-2-butyl | H | CF3 |
| 1-716 | 3-iodophenyl | H | H | H | CN | H | H | Br | H | nonafluoro-2-butyl | H | CF3 |
| 1-717 | 4-iodophenyl | H | H | H | CN | H | H | Br | H | nonafluoro-2-butyl | H | CF3 |
| 1-718 | (2-trifluoromethyl)phenyl | H | H | H | CN | H | H | Br | H | nonafluoro-2-butyl | H | CF3 |
| 1-719 | (3-trifluoromethyl)phenyl | H | H | H | CN | H | H | Br | H | nonafluoro-2-butyl | H | CF3 |
| 1-720 | (4-trifluoromethyl)phenyl | H | H | H | CN | H | H | Br | H | nonafluoro-2-butyl | H | CF3 |
| 1-721 | 2-nitrophenyl | H | H | H | CN | H | H | Br | H | nonafluoro-2-butyl | H | CF3 |
| 1-722 | 3-nitrophenyl | H | H | H | CN | H | H | Br | H | nonafluoro-2-butyl | H | CF3 |
| 1-723 | 4-nitrophenyl | H | H | H | CN | H | H | Br | H | nonafluoro-2-butyl | H | CF3 |
| 1-724 | 2-cyanophenyl | H | H | H | CN | H | H | Br | H | nonafluoro-2-butyl | H | CF3 |
| 1-725 | 3-cyanophenyl | H | H | H | CN | H | H | Br | H | nonafluoro-2-butyl | H | CF3 |
| 1-726 | 4-cyanophenyl | H | H | H | CN | H | H | Br | H | nonafluoro-2-butyl | H | CF3 |
| 1-727 | 2,6-difluorophenyl | H | H | H | CN | H | H | Br | H | nonafluoro-2-butyl | H | CF3 |
| 1-728 | 3,4-dichlorophenyl | H | H | H | CN | H | H | Br | H | nonafluoro-2-butyl | H | CF3 |
| 1-729 | 2,4-dichlorophenyl | H | H | H | CN | H | H | Br | H | nonafluoro-2-butyl | H | CF3 |
| 1-730 | 2-chloro-4-fluorophenyl | H | H | H | CN | H | H | Br | H | nonafluoro-2-butyl | H | CF3 |
| 1-731 | 2-chloro-4,5-difluorophenyl | H | H | H | CN | H | H | Br | H | nonafluoro-2-butyl | H | CF3 |
| 1-732 | 4-bromo-2-chlorophenyl | H | H | H | CN | H | H | Br | H | nonafluoro-2-butyl | H | CF3 |
| 1-733 | 2-bromo-4-chlorophenyl | H | H | H | CN | H | H | Br | H | nonafluoro-2-butyl | H | CF3 |
| 1-734 | 2-bromo-4-fluorophenyl | H | H | H | CN | H | H | Br | H | nonafluoro-2-butyl | H | CF3 |
| 1-735 | 2-chloro-4-nitrophenyl | H | H | H | CN | H | H | Br | H | nonafluoro-2-butyl | H | CF3 |
| 1-736 | 3,5-dicyanophenyl | H | H | H | CN | H | H | Br | H | nonafluoro-2-butyl | H | CF3 |
| 1-737 | 4-cyano-2-fluorophenyl | H | H | H | CN | H | H | Br | H | nonafluoro-2-butyl | H | CF3 |
| 1-738 | 2-chloro-4-cyanophenyl | H | H | H | CN | H | H | Br | H | nonafluoro-2-butyl | H | CF3 |
| 1-739 | pyridin-3-yl | H | H | H | CN | H | H | Br | H | nonafluoro-2-butyl | H | CF3 |
| 1-740 | 2-fluoropyridin-3-yl | H | H | H | CN | H | H | Br | H | nonafluoro-2-butyl | H | CF3 |
| 1-741 | 2-chloropyridin-3-yl | H | H | H | CN | H | H | Br | H | nonafluoro-2-butyl | H | CF3 |
| 1-742 | 2-bromopyridin-3-yl | H | H | H | CN | H | H | Br | H | nonafluoro-2-butyl | H | CF3 |
| 1-743 | 2-iodopyridin-3-yl | H | H | H | CN | H | H | Br | H | nonafluoro-2-butyl | H | CF3 |
| 1-744 | 2-(trifluoromethyl)pyridin-3-yl | H | H | H | CN | H | H | Br | H | nonafluoro-2-butyl | H | CF3 |
| 1-745 | 2-nitropyridin-3-yl | H | H | H | CN | H | H | Br | H | nonafluoro-2-butyl | H | CF3 |
| 1-746 | 2-cyanopyridin-3-yl | H | H | H | CN | H | H | Br | H | nonafluoro-2-butyl | H | CF3 |
| 1-747 | 6-fluoropyridin-3-yl | H | H | H | CN | H | H | Br | H | nonafluoro-2-butyl | H | CF3 |
| 1-748 | 6-chloropyridin-3-yl | H | H | H | CN | H | H | Br | H | nonafluoro-2-butyl | H | CF3 |
| 1-749 | 6-bromopyridin-3-yl | H | H | H | CN | H | H | Br | H | nonafluoro-2-butyl | H | CF3 |
| 1-750 | 6-iodopyridin-3-yl | H | H | H | CN | H | H | Br | H | nonafluoro-2-butyl | H | CF3 |
| 1-751 | 6-(trifluoromethyl)pyridin-3-yl | H | H | H | CN | H | H | Br | H | nonafluoro-2-butyl | H | CF3 |
| 1-752 | 6-nitropyridin-3-yl | H | H | H | CN | H | H | Br | H | nonafluoro-2-butyl | H | CF3 |
| 1-753 | 6-cyanopyridin-3-yl | H | H | H | CN | H | H | Br | H | nonafluoro-2-butyl | H | CF3 |
| 1-754 | 5-fluoropyridin-3-yl | H | H | H | CN | H | H | Br | H | nonafluoro-2-butyl | H | CF3 |
| 1-755 | 5-chloropyridin-3-yl | H | H | H | CN | H | H | Br | H | nonafluoro-2-butyl | H | CF3 |
| 1-756 | 5-bromopyridin-3-yl | H | H | H | CN | H | H | Br | H | nonafluoro-2-butyl | H | CF3 |
| 1-757 | 5-iodopyridin-3-yl | H | H | H | CN | H | H | Br | H | nonafluoro-2-butyl | H | CF3 |
| 1-758 | 5-(trifluoromethyl)pyridin-3-yl | H | H | H | CN | H | H | Br | H | nonafluoro-2-butyl | H | CF3 |
| 1-759 | 5-nitropyridin-3-yl | H | H | H | CN | H | H | Br | H | nonafluoro-2-butyl | H | CF3 |
| 1-760 | 5-cyanopyridin-3-yl | H | H | H | CN | H | H | Br | H | nonafluoro-2-butyl | H | CF3 |
| 1-761 | 4-fluoropyridin-3-yl | H | H | H | CN | H | H | Br | H | nonafluoro-2-butyl | H | CF3 |
| 1-762 | 4-chloropyridin-3-yl | H | H | H | CN | H | H | Br | H | nonafluoro-2-butyl | H | CF3 |

TABLE 1-continued

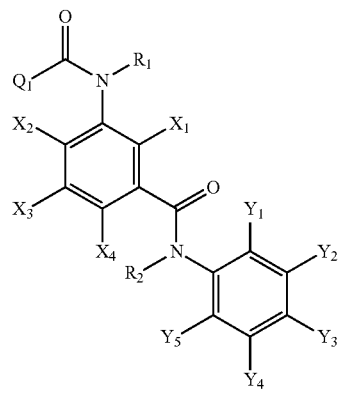

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-763 | 4-bromopyridin-3-yl | H | H | H | CN | H | H | Br | H | nonafluoro-2-butyl | H | CF3 |
| 1-764 | 4-iodopyridin-3-yl | H | H | H | CN | H | H | Br | H | nonafluoro-2-butyl | H | CF3 |
| 1-765 | 4-(trifluoromethyl)pyridin-3-yl | H | H | H | CN | H | H | Br | H | nonafluoro-2-butyl | H | CF3 |
| 1-766 | 4-nitropyridin-3-yl | H | H | H | CN | H | H | Br | H | nonafluoro-2-butyl | H | CF3 |
| 1-767 | 4-cyanopyridin-3-yl | H | H | H | CN | H | H | Br | H | nonafluoro-2-butyl | H | CF3 |
| 1-768 | 2,6-dichloropyridin-3-yl | H | H | H | CN | H | H | Br | H | nonafluoro-2-butyl | H | CF3 |
| 1-769 | pyridin-3-yl N-oxide | H | H | H | CN | H | H | Br | H | nonafluoro-2-butyl | H | CF3 |
| 1-770 | pyridin-4-yl | H | H | H | CN | H | H | Br | H | nonafluoro-2-butyl | H | CF3 |
| 1-771 | 2-chloropyridin-4-yl | H | H | H | CN | H | H | Br | H | nonafluoro-2-butyl | H | CF3 |
| 1-772 | 3-bromopyridin-4-yl | H | H | H | CN | H | H | Br | H | nonafluoro-2-butyl | H | CF3 |
| 1-773 | 3,5-dichloropyridin-4-yl | H | H | H | CN | H | H | Br | H | nonafluoro-2-butyl | H | CF3 |
| 1-774 | 3-(trifluoromethyl)pyridin-4-yl | H | H | H | CN | H | H | Br | H | nonafluoro-2-butyl | H | CF3 |
| 1-775 | 2,6-dicyanopyridin-4-yl | H | H | H | CN | H | H | Br | H | nonafluoro-2-butyl | H | CF3 |
| 1-776 | pyridin-4-yl N-oxide | H | H | H | CN | H | H | Br | H | nonafluoro-2-butyl | H | CF3 |
| 1-777 | pyridin-2-yl | H | H | H | CN | H | H | Br | H | nonafluoro-2-butyl | H | CF3 |
| 1-778 | 3-chloropyridin-2-yl | H | H | H | CN | H | H | Br | H | nonafluoro-2-butyl | H | CF3 |
| 1-779 | 4-bromopyridin-2-yl | H | H | H | CN | H | H | Br | H | nonafluoro-2-butyl | H | CF3 |
| 1-780 | 5-iodopyridin-2-yl | H | H | H | CN | H | H | Br | H | nonafluoro-2-butyl | H | CF3 |
| 1-781 | 6-chloropyridin-2-yl | H | H | H | CN | H | H | Br | H | nonafluoro-2-butyl | H | CF3 |
| 1-782 | 4-cyanopyridin-2-yl | H | H | H | CN | H | H | Br | H | nonafluoro-2-butyl | H | CF3 |
| 1-783 | phenyl | H | H | H | CN | H | H | I | H | heptafluoroisopropyl | H | CF3 |
| 1-784 | 2-fluorophenyl | H | H | H | CN | H | H | I | H | heptafluoroisopropyl | H | CF3 |
| 1-785 | 3-fluorophenyl | H | H | H | CN | H | H | I | H | heptafluoroisopropyl | H | CF3 |
| 1-786 | 4-fluorophenyl | H | H | H | CN | H | H | I | H | heptafluoroisopropyl | H | CF3 |
| 1-787 | 2-chlorophenyl | H | H | H | CN | H | H | I | H | heptafluoroisopropyl | H | CF3 |
| 1-788 | 3-chlorophenyl | H | H | H | CN | H | H | I | H | heptafluoroisopropyl | H | CF3 |
| 1-789 | 4-chlorophenyl | H | H | H | CN | H | H | I | H | heptafluoroisopropyl | H | CF3 |
| 1-790 | 2-bromophenyl | H | H | H | CN | H | H | I | H | heptafluoroisopropyl | H | CF3 |
| 1-791 | 3-bromophenyl | H | H | H | CN | H | H | I | H | heptafluoroisopropyl | H | CF3 |
| 1-792 | 4-bromophenyl | H | H | H | CN | H | H | I | H | heptafluoroisopropyl | H | CF3 |
| 1-793 | 2-iodophenyl | H | H | H | CN | H | H | I | H | heptafluoroisopropyl | H | CF3 |
| 1-794 | 3-iodophenyl | H | H | H | CN | H | H | I | H | heptafluoroisopropyl | H | CF3 |
| 1-795 | 4-iodophenyl | H | H | H | CN | H | H | I | H | heptafluoroisopropyl | H | CF3 |
| 1-796 | (2-trifluoromethyl)phenyl | H | H | H | CN | H | H | I | H | heptafluoroisopropyl | H | CF3 |
| 1-797 | (3-trifluoromethyl)phenyl | H | H | H | CN | H | H | I | H | heptafluoroisopropyl | H | CF3 |
| 1-798 | (4-trifluoromethyl)phenyl | H | H | H | CN | H | H | I | H | heptafluoroisopropyl | H | CF3 |
| 1-799 | 2-nitrophenyl | H | H | H | CN | H | H | I | H | heptafluoroisopropyl | H | CF3 |
| 1-800 | 3-nitrophenyl | H | H | H | CN | H | H | I | H | heptafluoroisopropyl | H | CF3 |
| 1-801 | 4-nitrophenyl | H | H | H | CN | H | H | I | H | heptafluoroisopropyl | H | CF3 |
| 1-802 | 2-cyanophenyl | H | H | H | CN | H | H | I | H | heptafluoroisopropyl | H | CF3 |
| 1-803 | 3-cyanophenyl | H | H | H | CN | H | H | I | H | heptafluoroisopropyl | H | CF3 |
| 1-804 | 4-cyanophenyl | H | H | H | CN | H | H | I | H | heptafluoroisopropyl | H | CF3 |
| 1-805 | 2,6-difluorophenyl | H | H | H | CN | H | H | I | H | heptafluoroisopropyl | H | CF3 |
| 1-806 | 3,4-dichlorophenyl | H | H | H | CN | H | H | I | H | heptafluoroisopropyl | H | CF3 |
| 1-807 | 2,4-dichlorophenyl | H | H | H | CN | H | H | I | H | heptafluoroisopropyl | H | CF3 |
| 1-808 | 2-chloro-4-fluorophenyl | H | H | H | CN | H | H | I | H | heptafluoroisopropyl | H | CF3 |
| 1-809 | 2-chloro-4,5-difluorophenyl | H | H | H | CN | H | H | I | H | heptafluoroisopropyl | H | CF3 |
| 1-810 | 4-bromo-2-chlorophenyl | H | H | H | CN | H | H | I | H | heptafluoroisopropyl | H | CF3 |
| 1-811 | 2-bromo-4-chlorophenyl | H | H | H | CN | H | H | I | H | heptafluoroisopropyl | H | CF3 |
| 1-812 | 2-bromo-4-fluorophenyl | H | H | H | CN | H | H | I | H | heptafluoroisopropyl | H | CF3 |
| 1-813 | 2-chloro-4-nitrophenyl | H | H | H | CN | H | H | I | H | heptafluoroisopropyl | H | CF3 |
| 1-814 | 3,5-dicyanophenyl | H | H | H | CN | H | H | I | H | heptafluoroisopropyl | H | CF3 |
| 1-815 | 4-cyano-2-fluorophenyl | H | H | H | CN | H | H | I | H | heptafluoroisopropyl | H | CF3 |
| 1-816 | 2-chloro-4-cyanophenyl | H | H | H | CN | H | H | I | H | heptafluoroisopropyl | H | CF3 |
| 1-817 | pyridin-3-yl | H | H | H | CN | H | H | I | H | heptafluoroisopropyl | H | CF3 |
| 1-818 | 2-fluoropyridin-3-yl | H | H | H | CN | H | H | I | H | heptafluoroisopropyl | H | CF3 |
| 1-819 | 2-chloropyridin-3-yl | H | H | H | CN | H | H | I | H | heptafluoroisopropyl | H | CF3 |

TABLE 1-continued

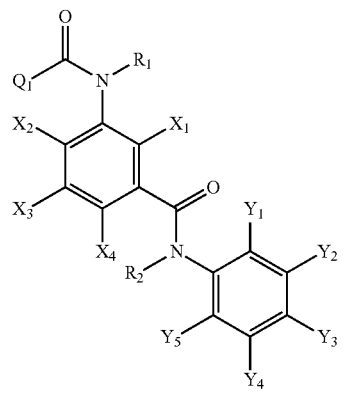

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 1-820 | 2-bromopyridin-3-yl | H | H | H | CN | H | H | I | H | heptafluoroisopropyl | H | CF3 |
| 1-821 | 2-iodopyridin-3-yl | H | H | H | CN | H | H | I | H | heptafluoroisopropyl | H | CF3 |
| 1-822 | 2-(trifluoromethyl)pyridin-3-yl | H | H | H | CN | H | H | I | H | heptafluoroisopropyl | H | CF3 |
| 1-823 | 2-nitropyridin-3-yl | H | H | H | CN | H | H | I | H | heptafluoroisopropyl | H | CF3 |
| 1-824 | 2-cyanopyridin-3-yl | H | H | H | CN | H | H | I | H | heptafluoroisopropyl | H | CF3 |
| 1-825 | 6-fluoropyridin-3-yl | H | H | H | CN | H | H | I | H | heptafluoroisopropyl | H | CF3 |
| 1-826 | 6-chloropyridin-3-yl | H | H | H | CN | H | H | I | H | heptafluoroisopropyl | H | CF3 |
| 1-827 | 6-bromopyridin-3-yl | H | H | H | CN | H | H | I | H | heptafluoroisopropyl | H | CF3 |
| 1-828 | 6-iodopyridin-3-yl | H | H | H | CN | H | H | I | H | heptafluoroisopropyl | H | CF3 |
| 1-829 | 6-(trifluoromethyl)pyridin-3-yl | H | H | H | CN | H | H | I | H | heptafluoroisopropyl | H | CF3 |
| 1-830 | 6-nitropyridin-3-yl | H | H | H | CN | H | H | I | H | heptafluoroisopropyl | H | CF3 |
| 1-831 | 6-cyanopyridin-3-yl | H | H | H | CN | H | H | I | H | heptafluoroisopropyl | H | CF3 |
| 1-832 | 5-fluoropyridin-3-yl | H | H | H | CN | H | H | I | H | heptafluoroisopropyl | H | CF3 |
| 1-833 | 5-chloropyridin-3-yl | H | H | H | CN | H | H | I | H | heptafluoroisopropyl | H | CF3 |
| 1-834 | 5-bromopyridin-3-yl | H | H | H | CN | H | H | I | H | heptafluoroisopropyl | H | CF3 |
| 1-835 | 5-iodopyridin-3-yl | H | H | H | CN | H | H | I | H | heptafluoroisopropyl | H | CF3 |
| 1-836 | 5-(trifluoromethyl)pyridin-3-yl | H | H | H | CN | H | H | I | H | heptafluoroisopropyl | H | CF3 |
| 1-837 | 5-nitropyridin-3-yl | H | H | H | CN | H | H | I | H | heptafluoroisopropyl | H | CF3 |
| 1-838 | 5-cyanopyridin-3-yl | H | H | H | CN | H | H | I | H | heptafluoroisopropyl | H | CF3 |
| 1-839 | 4-fluoropyridin-3-yl | H | H | H | CN | H | H | I | H | heptafluoroisopropyl | H | CF3 |
| 1-840 | 4-chloropyridin-3-yl | H | H | H | CN | H | H | I | H | heptafluoroisopropyl | H | CF3 |
| 1-841 | 4-bromopyridin-3-yl | H | H | H | CN | H | H | I | H | heptafluoroisopropyl | H | CF3 |
| 1-842 | 4-iodopyridin-3-yl | H | H | H | CN | H | H | I | H | heptafluoroisopropyl | H | CF3 |
| 1-843 | 4-(trifluoromethyl)pyridin-3-yl | H | H | H | CN | H | H | I | H | heptafluoroisopropyl | H | CF3 |
| 1-844 | 4-nitropyridin-3-yl | H | H | H | CN | H | H | I | H | heptafluoroisopropyl | H | CF3 |
| 1-845 | 4-cyanopyridin-3-yl | H | H | H | CN | H | H | I | H | heptafluoroisopropyl | H | CF3 |
| 1-846 | 2,6-dichloropyridin-3-yl | H | H | H | CN | H | H | I | H | heptafluoroisopropyl | H | CF3 |
| 1-847 | pyridin-3-yl N-oxide | H | H | H | CN | H | H | I | H | heptafluoroisopropyl | H | CF3 |
| 1-848 | pyridin-4-yl | H | H | H | CN | H | H | I | H | heptafluoroisopropyl | H | CF3 |
| 1-849 | 2-chloropyridin-4-yl | H | H | H | CN | H | H | I | H | heptafluoroisopropyl | H | CF3 |
| 1-850 | 3-bromopyridin-4-yl | H | H | H | CN | H | H | I | H | heptafluoroisopropyl | H | CF3 |
| 1-851 | 3,5-dichloropyridin-4-yl | H | H | H | CN | H | H | I | H | heptafluoroisopropyl | H | CF3 |
| 1-852 | 3-(trifluoromethyl)pyridin-4-yl | H | H | H | CN | H | H | I | H | heptafluoroisopropyl | H | CF3 |
| 1-853 | 2,6-dicyanopyridin-4-yl | H | H | H | CN | H | H | I | H | heptafluoroisopropyl | H | CF3 |
| 1-854 | pyridin-4-yl N-oxide | H | H | H | CN | H | H | I | H | heptafluoroisopropyl | H | CF3 |
| 1-855 | pyridin-2-yl | H | H | H | CN | H | H | I | H | heptafluoroisopropyl | H | CF3 |
| 1-856 | 3-chloropyridin-2-yl | H | H | H | CN | H | H | I | H | heptafluoroisopropyl | H | CF3 |
| 1-857 | 4-bromopyridin-2-yl | H | H | H | CN | H | H | I | H | heptafluoroisopropyl | H | CF3 |
| 1-858 | 5-iodopyridin-2-yl | H | H | H | CN | H | H | I | H | heptafluoroisopropyl | H | CF3 |
| 1-859 | 6-chloropyridin-2-yl | H | H | H | CN | H | H | I | H | heptafluoroisopropyl | H | CF3 |
| 1-860 | 4-cyanopyridin-2-yl | H | H | H | CN | H | H | I | H | heptafluoroisopropyl | H | CF3 |
| 1-861 | phenyl | H | H | H | CN | H | H | I | H | nonafluoro-2-butyl | H | CF3 |
| 1-862 | 2-fluorophenyl | H | H | H | CN | H | H | I | H | nonafluoro-2-butyl | H | CF3 |
| 1-863 | 3-fluorophenyl | H | H | H | CN | H | H | I | H | nonafluoro-2-butyl | H | CF3 |
| 1-864 | 4-fluorophenyl | H | H | H | CN | H | H | I | H | nonafluoro-2-butyl | H | CF3 |
| 1-865 | 2-chlorophenyl | H | H | H | CN | H | H | I | H | nonafluoro-2-butyl | H | CF3 |
| 1-866 | 3-chlorophenyl | H | H | H | CN | H | H | I | H | nonafluoro-2-butyl | H | CF3 |
| 1-867 | 4-chlorophenyl | H | H | H | CN | H | H | I | H | nonafluoro-2-butyl | H | CF3 |
| 1-868 | 2-bromophenyl | H | H | H | CN | H | H | I | H | nonafluoro-2-butyl | H | CF3 |
| 1-869 | 3-bromophenyl | H | H | H | CN | H | H | I | H | nonafluoro-2-butyl | H | CF3 |
| 1-870 | 4-bromophenyl | H | H | H | CN | H | H | I | H | nonafluoro-2-butyl | H | CF3 |
| 1-871 | 2-iodophenyl | H | H | H | CN | H | H | I | H | nonafluoro-2-butyl | H | CF3 |
| 1-872 | 3-iodophenyl | H | H | H | CN | H | H | I | H | nonafluoro-2-butyl | H | CF3 |
| 1-873 | 4-iodophenyl | H | H | H | CN | H | H | I | H | nonafluoro-2-butyl | H | CF3 |
| 1-874 | (2-trifluoromethyl)phenyl | H | H | H | CN | H | H | I | H | nonafluoro-2-butyl | H | CF3 |
| 1-875 | (3-trifluoromethyl)phenyl | H | H | H | CN | H | H | I | H | nonafluoro-2-butyl | H | CF3 |
| 1-876 | (4-trifluoromethyl)phenyl | H | H | H | CN | H | H | I | H | nonafluoro-2-butyl | H | CF3 |

TABLE 1-continued

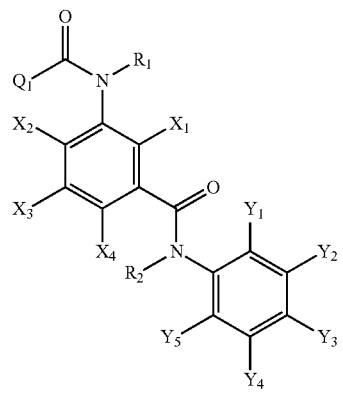

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-877 | 2-nitrophenyl | H | H | H | CN | H | H | I | H | nonafluoro-2-butyl | H | CF3 |
| 1-878 | 3-nitrophenyl | H | H | H | CN | H | H | I | H | nonafluoro-2-butyl | H | CF3 |
| 1-879 | 4-nitrophenyl | H | H | H | CN | H | H | I | H | nonafluoro-2-butyl | H | CF3 |
| 1-880 | 2-cyanophenyl | H | H | H | CN | H | H | I | H | nonafluoro-2-butyl | H | CF3 |
| 1-881 | 3-cyanophenyl | H | H | H | CN | H | H | I | H | nonafluoro-2-butyl | H | CF3 |
| 1-882 | 4-cyanophenyl | H | H | H | CN | H | H | I | H | nonafluoro-2-butyl | H | CF3 |
| 1-883 | 2,6-difluorophenyl | H | H | H | CN | H | H | I | H | nonafluoro-2-butyl | H | CF3 |
| 1-884 | 3,4-dichlorophenyl | H | H | H | CN | H | H | I | H | nonafluoro-2-butyl | H | CF3 |
| 1-885 | 2,4-dichlorophenyl | H | H | H | CN | H | H | I | H | nonafluoro-2-butyl | H | CF3 |
| 1-886 | 2-chloro-4-fluorophenyl | H | H | H | CN | H | H | I | H | nonafluoro-2-butyl | H | CF3 |
| 1-887 | 2-chloro-4,5-difluorophenyl | H | H | H | CN | H | H | I | H | nonafluoro-2-butyl | H | CF3 |
| 1-888 | 4-bromo-2-chlorophenyl | H | H | H | CN | H | H | I | H | nonafluoro-2-butyl | H | CF3 |
| 1-889 | 2-bromo-4-chlorophenyl | H | H | H | CN | H | H | I | H | nonafluoro-2-butyl | H | CF3 |
| 1-890 | 2-bromo-4-fluorophenyl | H | H | H | CN | H | H | I | H | nonafluoro-2-butyl | H | CF3 |
| 1-891 | 2-chloro-4-nitrophenyl | H | H | H | CN | H | H | I | H | nonafluoro-2-butyl | H | CF3 |
| 1-892 | 3,5-dicyanophenyl | H | H | H | CN | H | H | I | H | nonafluoro-2-butyl | H | CF3 |
| 1-893 | 4-cyano-2-fluorophenyl | H | H | H | CN | H | H | I | H | nonafluoro-2-butyl | H | CF3 |
| 1-894 | 2-chloro-4-cyanophenyl | H | H | H | CN | H | H | I | H | nonafluoro-2-butyl | H | CF3 |
| 1-895 | pyridin-3-yl | H | H | H | CN | H | H | I | H | nonafluoro-2-butyl | H | CF3 |
| 1-896 | 2-fluoropyridin-3-yl | H | H | H | CN | H | H | I | H | nonafluoro-2-butyl | H | CF3 |
| 1-897 | 2-chloropyridin-3-yl | H | H | H | CN | H | H | I | H | nonafluoro-2-butyl | H | CF3 |
| 1-898 | 2-bromopyridin-3-yl | H | H | H | CN | H | H | I | H | nonafluoro-2-butyl | H | CF3 |
| 1-899 | 2-iodopyridin-3-yl | H | H | H | CN | H | H | I | H | nonafluoro-2-butyl | H | CF3 |
| 1-900 | 2-(trifluoromethyl)pyridin-3-yl | H | H | H | CN | H | H | I | H | nonafluoro-2-butyl | H | CF3 |
| 1-901 | 2-nitropyridin-3-yl | H | H | H | CN | H | H | I | H | nonafluoro-2-butyl | H | CF3 |
| 1-902 | 2-cyanopyridin-3-yl | H | H | H | CN | H | H | I | H | nonafluoro-2-butyl | H | CF3 |
| 1-903 | 6-fluoropyridin-3-yl | H | H | H | CN | H | H | I | H | nonafluoro-2-butyl | H | CF3 |
| 1-904 | 6-chloropyridin-3-yl | H | H | H | CN | H | H | I | H | nonafluoro-2-butyl | H | CF3 |
| 1-905 | 6-bromopyridin-3-yl | H | H | H | CN | H | H | I | H | nonafluoro-2-butyl | H | CF3 |
| 1-906 | 6-iodopyridin-3-yl | H | H | H | CN | H | H | I | H | nonafluoro-2-butyl | H | CF3 |
| 1-907 | 6-(trifluoromethyl)pyridin-3-yl | H | H | H | CN | H | H | I | H | nonafluoro-2-butyl | H | CF3 |
| 1-908 | 6-nitropyridin-3-yl | H | H | H | CN | H | H | I | H | nonafluoro-2-butyl | H | CF3 |
| 1-909 | 6-cyanopyridin-3-yl | H | H | H | CN | H | H | I | H | nonafluoro-2-butyl | H | CF3 |
| 1-910 | 5-fluoropyridin-3-yl | H | H | H | CN | H | H | I | H | nonafluoro-2-butyl | H | CF3 |
| 1-911 | 5-chloropyridin-3-yl | H | H | H | CN | H | H | I | H | nonafluoro-2-butyl | H | CF3 |
| 1-912 | 5-bromopyridin-3-yl | H | H | H | CN | H | H | I | H | nonafluoro-2-butyl | H | CF3 |
| 1-913 | 5-iodopyridin-3-yl | H | H | H | CN | H | H | I | H | nonafluoro-2-butyl | H | CF3 |
| 1-914 | 5-(trifluoromethyl)pyridin-3-yl | H | H | H | CN | H | H | I | H | nonafluoro-2-butyl | H | CF3 |
| 1-915 | 5-nitropyridin-3-yl | H | H | H | CN | H | H | I | H | nonafluoro-2-butyl | H | CF3 |
| 1-916 | 5-cyanopyridin-3-yl | H | H | H | CN | H | H | I | H | nonafluoro-2-butyl | H | CF3 |
| 1-917 | 4-fluoropyridin-3-yl | H | H | H | CN | H | H | I | H | nonafluoro-2-butyl | H | CF3 |
| 1-918 | 4-chloropyridin-3-yl | H | H | H | CN | H | H | I | H | nonafluoro-2-butyl | H | CF3 |
| 1-919 | 4-bromopyridin-3-yl | H | H | H | CN | H | H | I | H | nonafluoro-2-butyl | H | CF3 |
| 1-920 | 4-iodopyridin-3-yl | H | H | H | CN | H | H | I | H | nonafluoro-2-butyl | H | CF3 |
| 1-921 | 4-(trifluoromethyl)pyridin-3-yl | H | H | H | CN | H | H | I | H | nonafluoro-2-butyl | H | CF3 |
| 1-922 | 4-nitropyridin-3-yl | H | H | H | CN | H | H | I | H | nonafluoro-2-butyl | H | CF3 |
| 1-923 | 4-cyanopyridin-3-yl | H | H | H | CN | H | H | I | H | nonafluoro-2-butyl | H | CF3 |
| 1-924 | 2,6-dichloropyridin-3-yl | H | H | H | CN | H | H | I | H | nonafluoro-2-butyl | H | CF3 |
| 1-925 | pyridin-3-yl N-oxide | H | H | H | CN | H | H | I | H | nonafluoro-2-butyl | H | CF3 |
| 1-926 | pyridin-4-yl | H | H | H | CN | H | H | I | H | nonafluoro-2-butyl | H | CF3 |
| 1-927 | 2-chloropyridin-4-yl | H | H | H | CN | H | H | I | H | nonafluoro-2-butyl | H | CF3 |
| 1-928 | 3-bromopyridin-4-yl | H | H | H | CN | H | H | I | H | nonafluoro-2-butyl | H | CF3 |
| 1-929 | 3,5-dichloropyridin-4-yl | H | H | H | CN | H | H | I | H | nonafluoro-2-butyl | H | CF3 |
| 1-930 | 3-(trifluoromethyl)pyridin-4-yl | H | H | H | CN | H | H | I | H | nonafluoro-2-butyl | H | CF3 |
| 1-931 | 2,6-dicyanopyridin-4-yl | H | H | H | CN | H | H | I | H | nonafluoro-2-butyl | H | CF3 |
| 1-932 | pyridin-4-yl N-oxide | H | H | H | CN | H | H | I | H | nonafluoro-2-butyl | H | CF3 |
| 1-933 | pyridin-2-yl | H | H | H | CN | H | H | I | H | nonafluoro-2-butyl | H | CF3 |

TABLE 1-continued

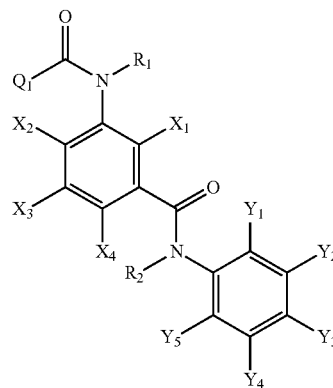

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 1-934 | 3-chloropyridin-2-yl | H | H | H | CN | H | H | I | H | nonafluoro-2-butyl | H | CF3 |
| 1-935 | 4-bromopyridin-2-yl | H | H | H | CN | H | H | I | H | nonafluoro-2-butyl | H | CF3 |
| 1-936 | 5-iodopyridin-2-yl | H | H | H | CN | H | H | I | H | nonafluoro-2-butyl | H | CF3 |
| 1-937 | 6-chloropyridin-2-yl | H | H | H | CN | H | H | I | H | nonafluoro-2-butyl | H | CF3 |
| 1-938 | 4-cyanopyridin-2-yl | H | H | H | CN | H | H | I | H | nonafluoro-2-butyl | H | CF3 |
| 1-939 | phenyl | H | H | H | CN | H | H | OCF3 | H | heptafluoroisopropyl | H | OCF3 |
| 1-954 | 3-cyanophenyl | H | H | H | CN | H | H | OCF3 | H | heptafluoroisopropyl | H | OCF3 |
| 1-955 | 4-cyanophenyl | H | H | H | CN | H | H | OCF3 | H | heptafluoroisopropyl | H | OCF3 |
| 1-970 | 2-chloropyridin-3-yl | H | H | H | CN | H | H | OCF3 | H | heptafluoroisopropyl | H | OCF3 |
| 1-995 | phenyl | H | H | H | CN | H | H | OCF3 | H | nonafluoro-2-butyl | H | OCF3 |
| 1-1010 | 3-cyanophenyl | H | H | H | CN | H | H | OCF3 | H | nonafluoro-2-butyl | H | OCF3 |
| 1-1011 | 4-cyanophenyl | H | H | H | CN | H | H | OCF3 | H | nonafluoro-2-butyl | H | OCF3 |
| 1-1026 | 2-chloropyridin-3-yl | H | H | H | CN | H | H | OCF3 | H | nonafluoro-2-butyl | H | OCF3 |
| 1-1051 | phenyl | H | H | H | CN | H | H | CF3 | H | heptafluoroisopropyl | H | OCF3 |
| 1-1066 | 3-cyanophenyl | H | H | H | CN | H | H | CF3 | H | heptafluoroisopropyl | H | OCF3 |
| 1-1067 | 4-cyanophenyl | H | H | H | CN | H | H | CF3 | H | heptafluoroisopropyl | H | OCF3 |
| 1-1082 | 2-chloropyridin-3-yl | H | H | H | CN | H | H | CF3 | H | heptafluoroisopropyl | H | OCF3 |
| 1-1107 | phenyl | H | H | H | CN | H | H | CF3 | H | nonafluoro-2-butyl | H | OCF3 |
| 1-1122 | 3-cyanophenyl | H | H | H | CN | H | H | CF3 | H | nonafluoro-2-butyl | H | OCF3 |
| 1-1123 | 4-cyanophenyl | H | H | H | CN | H | H | CF3 | H | nonafluoro-2-butyl | H | OCF3 |
| 1-1138 | 2-chloropyridin-3-yl | H | H | H | CN | H | H | CF3 | H | nonafluoro-2-butyl | H | OCF3 |
| 1-1163 | phenyl | H | H | H | CN | H | H | CF3 | H | heptafluoroisopropyl | H | CF3 |
| 1-1175 | 4-iodophenyl | H | H | H | CN | H | H | CF3 | H | pentafluoroethyl | H | CF3 |
| 1-1177 | (3-trifluoromethyl)phenyl | H | H | H | CN | H | H | C2F5 | H | heptafluoroisopropyl | H | CF3 |
| 1-1183 | 3-cyanophenyl | H | H | H | CN | H | H | CF3 | H | heptafluoroisopropyl | H | CF3 |
| 1-1184 | 4-cyanophenyl | H | H | H | CN | H | H | CF3 | H | heptafluoroisopropyl | H | CF3 |
| 1-1190 | 4-bromo-2-chlorophenyl | H | H | H | CN | H | H | n-C3F7 | H | heptafluoroisopropyl | H | CF3 |
| 1-1195 | 4-cyano-2-fluorophenyl | H | H | H | CN | H | H | i-C3F7 | H | heptafluoroisopropyl | H | CF3 |
| 1-1199 | 2-chloropyridin-3-yl | H | H | H | CN | H | H | CF3 | H | heptafluoroisopropyl | H | CF3 |
| 1-1200 | 2-bromopyridin-3-yl | H | H | H | CN | H | H | C2F5 | H | heptafluoroisopropyl | H | C2F5 |
| 1-1211 | 6-cyanopyridin-3-yl | H | H | H | CN | H | H | C2F5 | H | heptafluoroisopropyl | H | n-C3F7 |
| 1-1215 | 4-cyanopyridin-3-yl | H | H | H | CN | H | H | C2F5 | H | heptafluoroisopropyl | H | i-C3F7 |
| 1-1231 | phenyl | H | H | H | CN | H | H | CF3 | H | nonafluoro-2-butyl | H | CF3 |
| 1-1243 | 4-iodophenyl | H | H | H | CN | H | H | C2F5 | H | nonafluoro-2-butyl | H | CF3 |
| 1-1251 | 3-cyanophenyl | H | H | H | CN | H | H | CF3 | H | nonafluoro-2-butyl | H | CF3 |
| 1-1252 | 4-cyanophenyl | H | H | H | CN | H | H | CF3 | H | nonafluoro-2-butyl | H | CF3 |
| 1-1258 | 4-bromo-2-chlorophenyl | H | H | H | CN | H | H | n-C3F7 | H | nonafluoro-2-butyl | H | CF3 |
| 1-1263 | 4-cyano-2-fluorophenyl | H | H | H | CN | H | H | i-C3F7 | H | nonafluoro-2-butyl | H | CF3 |
| 1-1267 | 2-chloropyridin-3-yl | H | H | H | CN | H | H | CF3 | H | nonafluoro-2-butyl | H | CF3 |
| 1-1268 | 2-bromopyridin-3-yl | H | H | H | CN | H | H | C2F5 | H | nonafluoro-2-butyl | H | C2F5 |
| 1-1279 | 6-cyanopyridin-3-yl | H | H | H | CN | H | H | C2F5 | H | nonafluoro-2-butyl | H | n-C3F7 |
| 1-1283 | 4-cyanopyridin-3-yl | H | H | H | CN | H | H | C2F5 | H | nonafluoro-2-butyl | H | i-C3F7 |
| 1-1299 | phenyl | H | H | F | CN | H | H | Cl | H | heptafluoroisopropyl | H | OCF3 |
| 1-1319 | 3-cyanophenyl | H | H | F | CN | H | H | Cl | H | heptafluoroisopropyl | H | OCF3 |
| 1-1320 | 4-cyanophenyl | H | H | F | CN | H | H | Cl | H | heptafluoroisopropyl | H | OCF3 |
| 1-1335 | 2-chloropyridin-3-yl | H | H | F | CN | H | H | Cl | H | heptafluoroisopropyl | H | OCF3 |
| 1-1377 | phenyl | H | H | F | CN | H | H | Cl | H | nonafluoro-2-butyl | H | OCF3 |
| 1-1384 | 2-bromophenyl | H | H | F | CN | H | H | F | H | nonafluoro-2-butyl | H | OCF3 |
| 1-1397 | 3-cyanophenyl | H | H | F | CN | H | H | Cl | H | nonafluoro-2-butyl | H | OCF3 |
| 1-1398 | 4-cyanophenyl | H | H | F | CN | H | H | Cl | H | nonafluoro-2-butyl | H | OCF3 |
| 1-1413 | 2-chloropyridin-3-yl | H | H | F | CN | H | H | Cl | H | nonafluoro-2-butyl | H | OCF3 |
| 1-1455 | phenyl | H | H | F | CN | H | H | Br | H | heptafluoroisopropyl | H | OCF3 |
| 1-1475 | 3-cyanophenyl | H | H | F | CN | H | H | Br | H | heptafluoroisopropyl | H | OCF3 |
| 1-1476 | 4-cyanophenyl | H | H | F | CN | H | H | Br | H | heptafluoroisopropyl | H | OCF3 |
| 1-1491 | 2-chloropyridin-3-yl | H | H | F | CN | H | H | Br | H | heptafluoroisopropyl | H | OCF3 |
| 1-1533 | phenyl | H | H | F | CN | H | H | Br | H | nonafluoro-2-butyl | H | OCF3 |
| 1-1553 | 3-cyanophenyl | H | H | F | CN | H | H | Br | H | nonafluoro-2-butyl | H | OCF3 |

TABLE 1-continued

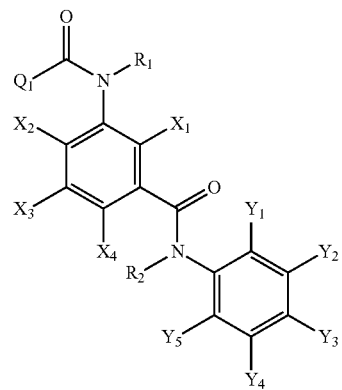

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 1-1554 | 4-cyanophenyl | H | H | F | CN | H | H | Br | H | nonafluoro-2-butyl | H | OCF3 |
| 1-1569 | 2-chloropyridin-3-yl | H | H | F | CN | H | H | Br | H | nonafluoro-2-butyl | H | OCF3 |
| 1-1611 | phenyl | H | H | F | CN | H | H | I | H | heptafluoroisopropyl | H | OCF3 |
| 1-1631 | 3-cyanophenyl | H | H | F | CN | H | H | I | H | heptafluoroisopropyl | H | OCF3 |
| 1-1632 | 4-cyanophenyl | H | H | F | CN | H | H | I | H | heptafluoroisopropyl | H | OCF3 |
| 1-1647 | 2-chloropyridin-3-yl | H | H | F | CN | H | H | I | H | heptafluoroisopropyl | H | OCF3 |
| 1-1689 | phenyl | H | H | F | CN | H | H | I | H | nonafluoro-2-butyl | H | OCF3 |
| 1-1709 | 3-cyanophenyl | H | H | F | CN | H | H | I | H | nonafluoro-2-butyl | H | OCF3 |
| 1-1710 | 4-cyanophenyl | H | H | F | CN | H | H | I | H | nonafluoro-2-butyl | H | OCF3 |
| 1-1725 | 2-chloropyridin-3-yl | H | H | F | CN | H | H | I | H | nonafluoro-2-butyl | H | OCF3 |
| 1-1767 | phenyl | H | H | F | CN | H | H | F | H | heptafluoroisopropyl | H | CF3 |
| 1-1768 | phenyl | H | H | F | CN | H | H | Cl | H | heptafluoroisopropyl | H | CF3 |
| 1-1788 | 3-cyanophenyl | H | H | F | CN | H | H | Cl | H | heptafluoroisopropyl | H | CF3 |
| 1-1789 | 4-cyanophenyl | H | H | F | CN | H | H | Cl | H | heptafluoroisopropyl | H | CF3 |
| 1-1804 | 2-chloropyridin-3-yl | H | H | F | CN | H | H | Cl | H | heptafluoroisopropyl | H | CF3 |
| 1-1846 | phenyl | H | H | F | CN | H | H | F | H | nonafluoro-2-butyl | H | CF3 |
| 1-1847 | phenyl | H | H | F | CN | H | H | Cl | H | nonafluoro-2-butyl | H | CF3 |
| 1-1867 | 3-cyanophenyl | H | H | F | CN | H | H | Cl | H | nonafluoro-2-butyl | H | CF3 |
| 1-1868 | 4-cyanophenyl | H | H | F | CN | H | H | Cl | H | nonafluoro-2-butyl | H | CF3 |
| 1-1883 | 2-chloropyridin-3-yl | H | H | F | CN | H | H | Cl | H | nonafluoro-2-butyl | H | CF3 |
| 1-1925 | phenyl | H | H | F | CN | H | H | Br | H | heptafluoroisopropyl | H | CF3 |
| 1-1945 | 3-cyanophenyl | H | H | F | CN | H | H | Br | H | heptafluoroisopropyl | H | CF3 |
| 1-1946 | 4-cyanophenyl | H | H | F | CN | H | H | Br | H | heptafluoroisopropyl | H | CF3 |
| 1-1961 | 2-chloropyridin-3-yl | H | H | F | CN | H | H | Br | H | heptafluoroisopropyl | H | CF3 |
| 1-1968 | 6-chloropyridin-3-yl | H | H | F | CN | H | H | Br | H | heptafluoroisopropyl | H | CF3 |
| 1-2003 | phenyl | H | H | F | CN | H | H | Br | H | nonafluoro-2-butyl | H | CF3 |
| 1-2023 | 3-cyanophenyl | H | H | F | CN | H | H | Br | H | nonafluoro-2-butyl | H | CF3 |
| 1-2024 | 4-cyanophenyl | H | H | F | CN | H | H | Br | H | nonafluoro-2-butyl | H | CF3 |
| 1-2039 | 2-chloropyridin-3-yl | H | H | F | CN | H | H | Br | H | nonafluoro-2-butyl | H | CF3 |
| 1-2081 | phenyl | H | H | F | CN | H | H | I | H | heptafluoroisopropyl | H | CF3 |
| 1-2101 | 3-cyanophenyl | H | H | F | CN | H | H | I | H | heptafluoroisopropyl | H | CF3 |
| 1-2102 | 4-cyanophenyl | H | H | F | CN | H | H | I | H | heptafluoroisopropyl | H | CF3 |
| 1-2117 | 2-chloropyridin-3-yl | H | H | F | CN | H | H | I | H | heptafluoroisopropyl | H | CF3 |
| 1-2159 | phenyl | H | H | F | CN | H | H | I | H | nonafluoro-2-butyl | H | CF3 |
| 1-2179 | 3-cyanophenyl | H | H | F | CN | H | H | I | H | nonafluoro-2-butyl | H | CF3 |
| 1-2180 | 4-cyanophenyl | H | H | F | CN | H | H | I | H | nonafluoro-2-butyl | H | CF3 |
| 1-2195 | 2-chloropyridin-3-yl | H | H | F | CN | H | H | I | H | nonafluoro-2-butyl | H | CF3 |
| 1-2237 | phenyl | H | H | F | CN | H | H | OCF3 | H | heptafluoroisopropyl | H | OCF3 |
| 1-2252 | 3-cyanophenyl | H | H | F | CN | H | H | OCF3 | H | heptafluoroisopropyl | H | OCF3 |
| 1-2253 | 4-cyanophenyl | H | H | F | CN | H | H | OCF3 | H | heptafluoroisopropyl | H | OCF3 |
| 1-2268 | 2-chloropyridin-3-yl | H | H | F | CN | H | H | OCF3 | H | heptafluoroisopropyl | H | OCF3 |
| 1-2293 | phenyl | H | H | F | CN | H | H | OCF3 | H | nonafluoro-2-butyl | H | OCF3 |
| 1-2308 | 3-cyanophenyl | H | H | F | CN | H | H | OCF3 | H | nonafluoro-2-butyl | H | OCF3 |
| 1-2309 | 4-cyanophenyl | H | H | F | CN | H | H | OCF3 | H | nonafluoro-2-butyl | H | OCF3 |
| 1-2324 | 2-chloropyridin-3-yl | H | H | F | CN | H | H | OCF3 | H | nonafluoro-2-butyl | H | OCF3 |
| 1-2325 | 2-bromopyridin-3-yl | H | H | F | CN | H | H | OCF3 | H | nonafluoro-2-butyl | H | OCF3 |
| 1-2349 | phenyl | H | H | F | CN | H | H | CF3 | H | heptafluoroisopropyl | H | OCF3 |
| 1-2364 | 3-cyanophenyl | H | H | F | CN | H | H | CF3 | H | heptafluoroisopropyl | H | OCF3 |
| 1-2365 | 4-cyanophenyl | H | H | F | CN | H | H | CF3 | H | heptafluoroisopropyl | H | OCF3 |
| 1-2380 | 2-chloropyridin-3-yl | H | H | F | CN | H | H | CF3 | H | heptafluoroisopropyl | H | OCF3 |
| 1-2405 | phenyl | H | H | F | CN | H | H | CF3 | H | nonafluoro-2-butyl | H | OCF3 |
| 1-2420 | 3-cyanophenyl | H | H | F | CN | H | H | CF3 | H | nonafluoro-2-butyl | H | OCF3 |
| 1-2421 | 4-cyanophenyl | H | H | F | CN | H | H | CF3 | H | nonafluoro-2-butyl | H | OCF3 |
| 1-2436 | 2-chloropyridin-3-yl | H | H | F | CN | H | H | CF3 | H | nonafluoro-2-butyl | H | OCF3 |
| 1-2461 | phenyl | H | H | F | CN | H | H | CF3 | H | heptafluoroisopropyl | H | CF3 |
| 1-2481 | 3-cyanophenyl | H | H | F | CN | H | H | CF3 | H | heptafluoroisopropyl | H | CF3 |
| 1-2482 | 4-cyanophenyl | H | H | F | CN | H | H | CF3 | H | heptafluoroisopropyl | H | CF3 |

TABLE 1-continued

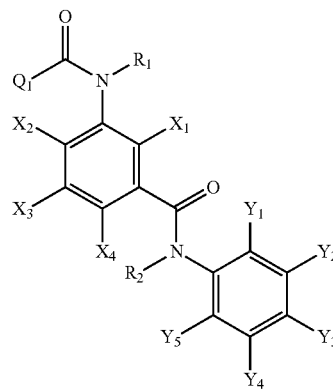

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 1-2497 | 2-chloropyridin-3-yl | H | H | F | CN | H | H | CF3 | H | heptafluoroisopropyl | H | CF3 |
| 1-2529 | phenyl | H | H | F | CN | H | H | CF3 | H | nonafluoro-2-butyl | H | CF3 |
| 1-2549 | 3-cyanophenyl | H | H | F | CN | H | H | CF3 | H | nonafluoro-2-butyl | H | CF3 |
| 1-2550 | 4-cyanophenyl | H | H | F | CN | H | H | CF3 | H | nonafluoro-2-butyl | H | CF3 |
| 1-2565 | 2-chloropyridin-3-yl | H | H | F | CN | H | H | CF3 | H | nonafluoro-2-butyl | H | CF3 |
| 1-2597 | phenyl | H | H | F | CN | F | H | Cl | H | heptafluoroisopropyl | H | OCF3 |
| 1-2617 | 3-cyanophenyl | H | H | F | CN | F | H | Cl | H | heptafluoroisopropyl | H | OCF3 |
| 1-2618 | 4-cyanophenyl | H | H | F | CN | F | H | Cl | H | heptafluoroisopropyl | H | OCF3 |
| 1-2633 | 2-chloropyridin-3-yl | H | H | F | CN | F | H | Cl | H | heptafluoroisopropyl | H | OCF3 |
| 1-2675 | phenyl | H | H | F | CN | F | H | Cl | H | nonafluoro-2-butyl | H | OCF3 |
| 1-2695 | 3-cyanophenyl | H | H | F | CN | F | H | Cl | H | nonafluoro-2-butyl | H | OCF3 |
| 1-2696 | 4-cyanophenyl | H | H | F | CN | F | H | Cl | H | nonafluoro-2-butyl | H | OCF3 |
| 1-2711 | 2-chloropyridin-3-yl | H | H | F | CN | F | H | Cl | H | nonafluoro-2-butyl | H | OCF3 |
| 1-2753 | phenyl | H | H | F | CN | F | H | Br | H | heptafluoroisopropyl | H | OCF3 |
| 1-2773 | 3-cyanophenyl | H | H | F | CN | F | H | Br | H | heptafluoroisopropyl | H | OCF3 |
| 1-2774 | 4-cyanophenyl | H | H | F | CN | F | H | Br | H | heptafluoroisopropyl | H | OCF3 |
| 1-2789 | 2-chloropyridin-3-yl | H | H | F | CN | F | H | Br | H | heptafluoroisopropyl | H | OCF3 |
| 1-2831 | phenyl | H | H | F | CN | F | H | Br | H | nonafluoro-2-butyl | H | OCF3 |
| 1-2851 | 3-cyanophenyl | H | H | F | CN | F | H | Br | H | nonafluoro-2-butyl | H | OCF3 |
| 1-2852 | 4-cyanophenyl | H | H | F | CN | F | H | Br | H | nonafluoro-2-butyl | H | OCF3 |
| 1-2867 | 2-chloropyridin-3-yl | H | H | F | CN | F | H | Br | H | nonafluoro-2-butyl | H | OCF3 |
| 1-2909 | phenyl | H | H | F | CN | F | H | I | H | heptafluoroisopropyl | H | OCF3 |
| 1-2929 | 3-cyanophenyl | H | H | F | CN | F | H | I | H | heptafluoroisopropyl | H | OCF3 |
| 1-2930 | 4-cyanophenyl | H | H | F | CN | F | H | I | H | heptafluoroisopropyl | H | OCF3 |
| 1-2945 | 2-chloropyridin-3-yl | H | H | F | CN | F | H | I | H | heptafluoroisopropyl | H | OCF3 |
| 1-2987 | phenyl | H | H | F | CN | F | H | I | H | nonafluoro-2-butyl | H | OCF3 |
| 1-3007 | 3-cyanophenyl | H | H | F | CN | F | H | I | H | nonafluoro-2-butyl | H | OCF3 |
| 1-3008 | 4-cyanophenyl | H | H | F | CN | F | H | I | H | nonafluoro-2-butyl | H | OCF3 |
| 1-3023 | 2-chloropyridin-3-yl | H | H | F | CN | F | H | I | H | nonafluoro-2-butyl | H | OCF3 |
| 1-3065 | phenyl | H | H | F | CN | F | H | F | H | heptafluoroisopropyl | H | CF3 |
| 1-3066 | phenyl | H | H | F | CN | F | H | Cl | H | heptafluoroisopropyl | H | CF3 |
| 1-3086 | 3-cyanophenyl | H | H | F | CN | F | H | Cl | H | heptafluoroisopropyl | H | CF3 |
| 1-3087 | 4-cyanophenyl | H | H | F | CN | F | H | Cl | H | heptafluoroisopropyl | H | CF3 |
| 1-3102 | 2-chloropyridin-3-yl | H | H | F | CN | F | H | Cl | H | heptafluoroisopropyl | H | CF3 |
| 1-3144 | phenyl | H | H | F | CN | F | H | F | H | nonafluoro-2-butyl | H | CF3 |
| 1-3145 | phenyl | H | H | F | CN | F | H | Cl | H | nonafluoro-2-butyl | H | CF3 |
| 1-3165 | 3-cyanophenyl | H | H | F | CN | F | H | Cl | H | nonafluoro-2-butyl | H | CF3 |
| 1-3166 | 4-cyanophenyl | H | H | F | CN | F | H | Cl | H | nonafluoro-2-butyl | H | CF3 |
| 1-3181 | 2-chloropyridin-3-yl | H | H | F | CN | F | H | Cl | H | nonafluoro-2-butyl | H | CF3 |
| 1-3223 | phenyl | H | H | F | CN | F | H | Br | H | heptafluoroisopropyl | H | CF3 |
| 1-3243 | 3-cyanophenyl | H | H | F | CN | F | H | Br | H | heptafluoroisopropyl | H | CF3 |
| 1-3244 | 4-cyanophenyl | H | H | F | CN | F | H | Br | H | heptafluoroisopropyl | H | CF3 |
| 1-3259 | 2-chloropyridin-3-yl | H | H | F | CN | F | H | Br | H | heptafluoroisopropyl | H | CF3 |
| 1-3301 | phenyl | H | H | F | CN | F | H | Br | H | nonafluoro-2-butyl | H | CF3 |
| 1-3321 | 3-cyanophenyl | H | H | F | CN | F | H | Br | H | nonafluoro-2-butyl | H | CF3 |
| 1-3322 | 4-cyanophenyl | H | H | F | CN | F | H | Br | H | nonafluoro-2-butyl | H | CF3 |
| 1-3337 | 2-chloropyridin-3-yl | H | H | F | CN | F | H | Br | H | nonafluoro-2-butyl | H | CF3 |
| 1-3379 | phenyl | H | H | F | CN | F | H | I | H | heptafluoroisopropyl | H | CF3 |
| 1-3399 | 3-cyanophenyl | H | H | F | CN | F | H | I | H | heptafluoroisopropyl | H | CF3 |
| 1-3400 | 4-cyanophenyl | H | H | F | CN | F | H | I | H | heptafluoroisopropyl | H | CF3 |
| 1-3415 | 2-chloropyridin-3-yl | H | H | F | CN | F | H | I | H | heptafluoroisopropyl | H | CF3 |
| 1-3457 | phenyl | H | H | F | CN | F | H | I | H | nonafluoro-2-butyl | H | CF3 |
| 1-3477 | 3-cyanophenyl | H | H | F | CN | F | H | I | H | nonafluoro-2-butyl | H | CF3 |
| 1-3478 | 4-cyanophenyl | H | H | F | CN | F | H | I | H | nonafluoro-2-butyl | H | CF3 |
| 1-3493 | 2-chloropyridin-3-yl | H | H | F | CN | F | H | I | H | nonafluoro-2-butyl | H | CF3 |
| 1-3535 | phenyl | H | H | F | CN | F | H | OCF3 | H | heptafluoroisopropyl | H | OCF3 |
| 1-3550 | 3-cyanophenyl | H | H | F | CN | F | H | OCF3 | H | heptafluoroisopropyl | H | OCF3 |

TABLE 1-continued

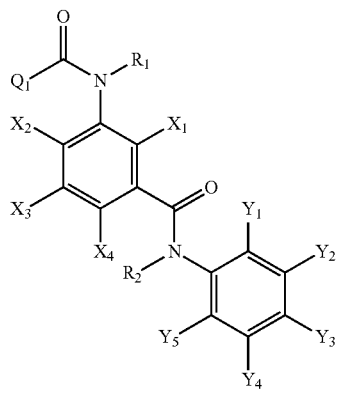

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 1-3551 | 4-cyanophenyl | H | H | F | CN | F | H | OCF3 | H | heptafluoroisopropyl | H | OCF3 |
| 1-3566 | 2-chloropyridin-3-yl | H | H | F | CN | F | H | OCF3 | H | heptafluoroisopropyl | H | OCF3 |
| 1-3591 | phenyl | H | H | F | CN | F | H | OCF3 | H | nonafluoro-2-butyl | H | OCF3 |
| 1-3606 | 3-cyanophenyl | H | H | F | CN | F | H | OCF3 | H | nonafluoro-2-butyl | H | OCF3 |
| 1-3607 | 4-cyanophenyl | H | H | F | CN | F | H | OCF3 | H | nonafluoro-2-butyl | H | OCF3 |
| 1-3622 | 2-chloropyridin-3-yl | H | H | F | CN | F | H | OCF3 | H | nonafluoro-2-butyl | H | OCF3 |
| 1-3647 | phenyl | H | H | F | CN | F | H | CF3 | H | heptafluoroisopropyl | H | OCF3 |
| 1-3662 | 3-cyanophenyl | H | H | F | CN | F | H | CF3 | H | heptafluoroisopropyl | H | OCF3 |
| 1-3663 | 4-cyanophenyl | H | H | F | CN | F | H | CF3 | H | heptafluoroisopropyl | H | OCF3 |
| 1-3678 | 2-chloropyridin-3-yl | H | H | F | CN | F | H | CF3 | H | heptafluoroisopropyl | H | OCF3 |
| 1-3703 | phenyl | H | H | F | CN | F | H | CF3 | H | nonafluoro-2-butyl | H | OCF3 |
| 1-3718 | 3-cyanophenyl | H | H | F | CN | F | H | CF3 | H | nonafluoro-2-butyl | H | OCF3 |
| 1-3719 | 4-cyanophenyl | H | H | F | CN | F | H | CF3 | H | nonafluoro-2-butyl | H | OCF3 |
| 1-3734 | 2-chloropyridin-3-yl | H | H | F | CN | F | H | CF3 | H | nonafluoro-2-butyl | H | OCF3 |
| 1-3759 | phenyl | H | H | F | CN | F | H | CF3 | H | heptafluoroisopropyl | H | CF3 |
| 1-3779 | 3-cyanophenyl | H | H | F | CN | F | H | CF3 | H | heptafluoroisopropyl | H | CF3 |
| 1-3780 | 4-cyanophenyl | H | H | F | CN | F | H | CF3 | H | heptafluoroisopropyl | H | CF3 |
| 1-3795 | 2-chloropyridin-3-yl | H | H | F | CN | F | H | CF3 | H | heptafluoroisopropyl | H | CF3 |
| 1-3827 | phenyl | H | H | F | CN | F | H | CF3 | H | nonafluoro-2-butyl | H | CF3 |
| 1-3847 | 3-cyanophenyl | H | H | F | CN | F | H | CF3 | H | nonafluoro-2-butyl | H | CF3 |
| 1-3848 | 4-cyanophenyl | H | H | F | CN | F | H | CF3 | H | nonafluoro-2-butyl | H | CF3 |
| 1-3863 | 2-chloropyridin-3-yl | H | H | F | CN | F | H | CF3 | H | nonafluoro-2-butyl | H | CF3 |

TABLE 2

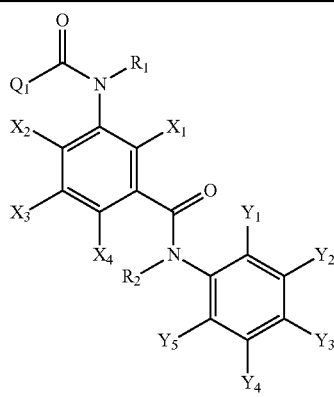

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 2-1 | phenyl | Me | H | H | CN | H | H | Cl | H | heptafluoroisopropyl | H | OCF3 |
| 2-21 | 3-cyanophenyl | Me | H | H | CN | H | H | Cl | H | heptafluoroisopropyl | H | OCF3 |
| 2-22 | 4-cyanophenyl | Me | H | H | CN | H | H | Cl | H | heptafluoroisopropyl | H | OCF3 |
| 2-37 | 2-chloropyridin-3-yl | Me | H | H | CN | H | H | Cl | H | heptafluoroisopropyl | H | OCF3 |
| 2-79 | phenyl | Me | H | H | CN | H | H | Cl | H | nonafluoro-2-butyl | H | OCF3 |
| 2-99 | 3-cyanophenyl | Me | H | H | CN | H | H | Cl | H | nonafluoro-2-butyl | H | OCF3 |
| 2-100 | 4-cyanophenyl | Me | H | H | CN | H | H | Cl | H | nonafluoro-2-butyl | H | OCF3 |
| 2-115 | 2-chloropyridin-3-yl | Me | H | H | CN | H | H | Cl | H | nonafluoro-2-butyl | H | OCF3 |

TABLE 2-continued

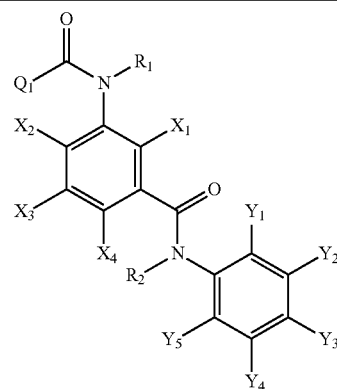

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 2-157 | phenyl | Me | H | H | CN | H | H | Br | H | heptafluoroisopropyl | H | OCF3 |
| 2-177 | 3-cyanophenyl | Me | H | H | CN | H | H | Br | H | heptafluoroisopropyl | H | OCF3 |
| 2-178 | 4-cyanophenyl | Me | H | H | CN | H | H | Br | H | heptafluoroisopropyl | H | OCF3 |
| 2-193 | 2-chloropyridin-3-yl | Me | H | H | CN | H | H | Br | H | heptafluoroisopropyl | H | OCF3 |
| 2-235 | phenyl | Me | H | H | CN | H | H | Br | H | nonafluoro-2-butyl | H | OCF3 |
| 2-255 | 3-cyanophenyl | Me | H | H | CN | H | H | Br | H | nonafluoro-2-butyl | H | OCF3 |
| 2-256 | 4-cyanophenyl | Me | H | H | CN | H | H | Br | H | nonafluoro-2-butyl | H | OCF3 |
| 2-271 | 2-chloropyridin-3-yl | Me | H | H | CN | H | H | Br | H | nonafluoro-2-butyl | H | OCF3 |
| 2-313 | phenyl | Me | H | H | CN | H | H | I | H | heptafluoroisopropyl | H | OCF3 |
| 2-333 | 3-cyanophenyl | Me | H | H | CN | H | H | I | H | heptafluoroisopropyl | H | OCF3 |
| 2-334 | 4-cyanophenyl | Me | H | H | CN | H | H | I | H | heptafluoroisopropyl | H | OCF3 |
| 2-349 | 2-chloropyridin-3-yl | Me | H | H | CN | H | H | I | H | heptafluoroisopropyl | H | OCF3 |
| 2-391 | phenyl | Me | H | H | CN | H | H | I | H | nonafluoro-2-butyl | H | OCF3 |
| 2-411 | 3-cyanophenyl | Me | H | H | CN | H | H | I | H | nonafluoro-2-butyl | H | OCF3 |
| 2-412 | 4-cyanophenyl | Me | H | H | CN | H | H | I | H | nonafluoro-2-butyl | H | OCF3 |
| 2-427 | 2-chloropyridin-3-yl | Me | H | H | CN | H | H | I | H | nonafluoro-2-butyl | H | OCF3 |
| 2-469 | phenyl | Me | H | H | CN | H | H | F | H | heptafluoroisopropyl | H | CF3 |
| 2-470 | phenyl | Me | H | H | CN | H | H | Cl | H | heptafluoroisopropyl | H | CF3 |
| 2-481 | 3-iodophenyl | Me | H | H | CN | H | H | Cl | H | pentafluoroethyl | H | CF3 |
| 2-482 | 4-iodophenyl | Me | H | H | CN | H | H | Cl | H | pentafluoroethyl | H | CF3 |
| 2-484 | (3-trifluoromethyl)phenyl | Et | H | H | CN | H | H | Cl | H | heptafluoroisopropyl | H | CF3 |
| 2-489 | 2-cyanophenyl | Me | H | H | CN | H | H | Cl | H | pentafluoroethyl | H | C2F5 |
| 2-490 | 3-cyanophenyl | Me | H | H | CN | H | H | Cl | H | heptafluoroisopropyl | H | CF3 |
| 2-491 | 4-cyanophenyl | Me | H | H | CN | H | H | Cl | H | heptafluoroisopropyl | H | CF3 |
| 2-494 | 2,4-dichlorophenyl | Me | H | H | CN | H | H | Cl | H | heptafluoroisopropyl | H | C2F5 |
| 2-495 | 2-chloro-4-fluorophenyl | n-Pr | H | H | CN | H | H | Cl | H | heptafluoroisopropyl | H | CF3 |
| 2-498 | 2-bromo-4-chlorophenyl | Me | H | H | CN | H | H | Cl | H | heptafluoroisopropyl | H | n-C3F7 |
| 2-505 | 2-fluoropyridin-3-yl | Me | H | H | CN | H | H | Cl | H | pentafluoroethyl | H | CF3 |
| 2-506 | 2-chloropyridin-3-yl | Me | H | H | CN | H | H | Cl | H | heptafluoroisopropyl | H | CF3 |
| 2-512 | 6-fluoropyridin-3-yl | i-Pr | H | H | CN | H | H | Cl | H | heptafluoroisopropyl | H | CF3 |
| 2-513 | 6-chloropyridin-3-yl | Me | H | H | CN | H | H | Cl | H | heptafluoroisopropyl | H | CF3 |
| 2-518 | 6-cyanopyridin-3-yl | Me | H | H | CN | H | H | Cl | H | heptafluoroisopropyl | H | CF3 |
| 2-519 | 5-fluoropyridin-3-yl | Me | H | H | CN | H | H | Cl | H | heptafluoroisopropyl | H | C2F5 |
| 2-521 | 5-bromopyridin-3-yl | Me | H | H | CN | H | H | Cl | H | heptafluoroisopropyl | H | n-C3F7 |
| 2-522 | 5-iodopyridin-3-yl | Me | H | H | CN | H | H | Cl | H | heptafluoroisopropyl | H | i-C3F7 |
| 2-524 | 5-nitropyridin-3-yl | Me | H | H | CN | H | H | Cl | H | pentafluoroethyl | H | CF3 |
| 2-526 | 4-fluoropyridin-3-yl | Me | H | H | CN | H | H | Cl | H | pentafluoroethyl | H | CF3 |
| 2-528 | 4-bromopyridin-3-yl | CH2CH=CH2 | H | H | CN | H | H | Cl | H | heptafluoroisopropyl | H | n-C3F7 |
| 2-529 | 4-iodopyridin-3-yl | Me | H | H | CN | H | H | Cl | H | heptafluoroisopropyl | H | i-C3F7 |
| 2-535 | pyridin-4-yl | CN | H | H | CN | H | H | Cl | H | heptafluoroisopropyl | H | CF3 |
| 2-547 | 4-cyanopyridin-2-yl | Me | H | H | CN | H | H | Cl | H | pentafluoroethyl | H | CF3 |
| 2-548 | phenyl | Me | H | H | CN | H | H | F | H | nonafluoro-2-butyl | H | CF3 |
| 2-549 | phenyl | Me | H | H | CN | H | H | Cl | H | nonafluoro-2-butyl | H | CF3 |
| 2-556 | 2-bromophenyl | CH2C≡CH | H | H | CN | H | H | Cl | H | nonafluoro-2-butyl | H | CF3 |
| 2-562 | (2-trifluoromethyl)phenyl | Me | H | H | CN | H | H | Cl | H | nonafluoro-2-butyl | H | C2F5 |
| 2-563 | (3-trifluoromethyl)phenyl | NH2 | H | H | CN | H | H | Cl | H | nonafluoro-2-butyl | H | CF3 |
| 2-569 | 3-cyanophenyl | Me | H | H | CN | H | H | Cl | H | nonafluoro-2-butyl | H | CF3 |
| 2-570 | 4-cyanophenyl | Me | H | H | CN | H | H | Cl | H | nonafluoro-2-butyl | H | CF3 |
| 2-576 | 4-bromo-2-chlorophenyl | C(O)OMe | H | H | CN | H | H | Cl | H | nonafluoro-2-butyl | H | CF3 |
| 2-579 | 2-chloro-4-nitrophenyl | Me | H | H | CN | H | H | Cl | H | nonafluoro-2-butyl | H | i-C3F7 |
| 2-585 | 2-chloropyridin-3-yl | Me | H | H | CN | H | H | Cl | H | nonafluoro-2-butyl | H | CF3 |
| 2-596 | 6-nitropyridin-3-yl | C(O)OEt | H | H | CN | H | H | Cl | H | nonafluoro-2-butyl | H | CF3 |
| 2-598 | 5-fluoropyridin-3-yl | Me | H | H | CN | H | H | Cl | H | nonafluoro-2-butyl | H | C2F5 |
| 2-600 | 5-bromopyridin-3-yl | Me | H | H | CN | H | H | Cl | H | nonafluoro-2-butyl | H | n-C3F7 |
| 2-601 | 5-iodopyridin-3-yl | Me | H | H | CN | H | H | Cl | H | nonafluoro-2-butyl | H | i-C3F7 |
| 2-605 | 4-fluoropyridin-3-yl | Me | H | H | CN | H | H | Cl | H | nonafluoro-2-butyl | H | C2F5 |
| 2-607 | 4-bromopyridin-3-yl | C(O)C(O)Me | H | H | CN | H | H | Cl | H | nonafluoro-2-butyl | H | CF3 |
| 2-609 | 4-(trifluoromethyl)pyridin-3-yl | Me | H | H | CN | H | H | Cl | H | nonafluoro-2-butyl | H | n-C3F7 |

TABLE 2-continued

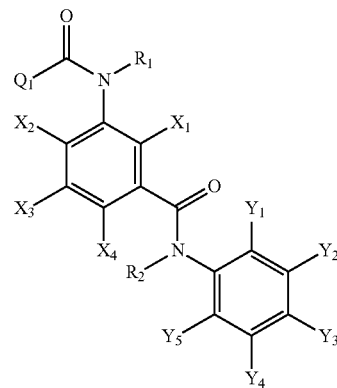

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 2-610 | 4-nitropyridin-3-yl | C(O)C(O)Et | H | H | CN | H | H | Cl | H | nonafluoro-2-butyl | H | i-C3F7 |
| 2-623 | 4-bromopyridin-2-yl | C(O)Me | H | H | CN | H | H | Cl | H | nonafluoro-2-butyl | H | CF3 |
| 2-625 | 6-chloropyridin-2-yl | C(O)Et | H | H | CN | H | H | Cl | H | nonafluoro-2-butyl | H | CF3 |
| 2-626 | 4-cyanopyridin-2-yl | Me | H | H | CN | H | H | Cl | H | nonafluoro-2-butyl | H | C2F5 |
| 2-627 | phenyl | Me | H | H | CN | H | H | Br | H | heptafluoroisopropyl | H | CF3 |
| 2-628 | 2-fluorophenyl | Me | H | H | CN | H | H | Br | H | heptafluoroisopropyl | H | CF3 |
| 2-629 | 3-fluorophenyl | Me | H | H | CN | H | H | Br | H | heptafluoroisopropyl | H | CF3 |
| 2-630 | 4-fluorophenyl | Me | H | H | CN | H | H | Br | H | heptafluoroisopropyl | H | CF3 |
| 2-631 | 2-chlorophenyl | Me | H | H | CN | H | H | Br | H | heptafluoroisopropyl | H | CF3 |
| 2-632 | 3-chlorophenyl | Me | H | H | CN | H | H | Br | H | heptafluoroisopropyl | H | CF3 |
| 2-633 | 4-chlorophenyl | Me | H | H | CN | H | H | Br | H | heptafluoroisopropyl | H | CF3 |
| 2-634 | 2-bromophenyl | Me | H | H | CN | H | H | Br | H | heptafluoroisopropyl | H | CF3 |
| 2-635 | 3-bromophenyl | Me | H | H | CN | H | H | Br | H | heptafluoroisopropyl | H | CF3 |
| 2-636 | 4-bromophenyl | Me | H | H | CN | H | H | Br | H | heptafluoroisopropyl | H | CF3 |
| 2-637 | 2-iodophenyl | Me | H | H | CN | H | H | Br | H | heptafluoroisopropyl | H | CF3 |
| 2-638 | 3-iodophenyl | Me | H | H | CN | H | H | Br | H | heptafluoroisopropyl | H | CF3 |
| 2-639 | 4-iodophenyl | Me | H | H | CN | H | H | Br | H | heptafluoroisopropyl | H | CF3 |
| 2-640 | (2-trifluoromethyl)phenyl | Me | H | H | CN | H | H | Br | H | heptafluoroisopropyl | H | CF3 |
| 2-641 | (3-trifluoromethyl)phenyl | S(O)2Me | H | H | CN | H | H | Br | H | heptafluoroisopropyl | H | CF3 |
| 2-642 | (4-trifluoromethyl)phenyl | Me | H | H | CN | H | H | Br | H | heptafluoroisopropyl | H | CF3 |
| 2-643 | 2-nitrophenyl | Me | H | H | CN | H | H | Br | H | heptafluoroisopropyl | H | CF3 |
| 2-644 | 3-nitrophenyl | Me | H | H | CN | H | H | Br | H | heptafluoroisopropyl | H | CF3 |
| 2-645 | 4-nitrophenyl | Me | H | H | CN | H | H | Br | H | heptafluoroisopropyl | H | CF3 |
| 2-646 | 2-cyanophenyl | Me | H | H | CN | H | H | Br | H | heptafluoroisopropyl | H | CF3 |
| 2-647 | 3-cyanophenyl | Me | H | H | CN | H | H | Br | H | heptafluoroisopropyl | H | CF3 |
| 2-648 | 4-cyanophenyl | Me | H | H | CN | H | H | Br | H | heptafluoroisopropyl | H | CF3 |
| 2-649 | 2,6-difluorophenyl | Me | H | H | CN | H | H | Br | H | heptafluoroisopropyl | H | CF3 |
| 2-650 | 3,4-dichlorophenyl | Me | H | H | CN | H | H | Br | H | heptafluoroisopropyl | H | CF3 |
| 2-651 | 2,4-dichlorophenyl | Me | H | H | CN | H | H | Br | H | heptafluoroisopropyl | H | CF3 |
| 2-652 | 2-chloro-4-fluorophenyl | Me | H | H | CN | H | H | Br | H | heptafluoroisopropyl | H | CF3 |
| 2-653 | 2-chloro-4,5-difluorophenyl | Me | H | H | CN | H | H | Br | H | heptafluoroisopropyl | H | CF3 |
| 2-654 | 4-bromo-2-chlorophenyl | Me | H | H | CN | H | H | Br | H | heptafluoroisopropyl | H | CF3 |
| 2-655 | 2-bromo-4-chlorophenyl | Me | H | H | CN | H | H | Br | H | heptafluoroisopropyl | H | CF3 |
| 2-656 | 2-bromo-4-fluorophenyl | Me | H | H | CN | H | H | Br | H | heptafluoroisopropyl | H | CF3 |
| 2-657 | 2-chloro-4-nitrophenyl | Me | H | H | CN | H | H | Br | H | heptafluoroisopropyl | H | CF3 |
| 2-658 | 3,5-dicyanophenyl | Me | H | H | CN | H | H | Br | H | heptafluoroisopropyl | H | CF3 |
| 2-659 | 4-cyano-2-fluorophenyl | S(O)2Et | H | H | CN | H | H | Br | H | heptafluoroisopropyl | H | CF3 |
| 2-660 | 2-chloro-4-cyanophenyl | Me | H | H | CN | H | H | Br | H | heptafluoroisopropyl | H | CF3 |
| 2-661 | pyridin-3-yl | Me | H | H | CN | H | H | Br | H | heptafluoroisopropyl | H | CF3 |
| 2-662 | 2-fluoropyridin-3-yl | Me | H | H | CN | H | H | Br | H | heptafluoroisopropyl | H | CF3 |
| 2-663 | 2-chloropyridin-3-yl | Me | H | H | CN | H | H | Br | H | heptafluoroisopropyl | H | CF3 |
| 2-664 | 2-bromopyridin-3-yl | Me | H | H | CN | H | H | Br | H | heptafluoroisopropyl | H | CF3 |
| 2-665 | 2-iodopyridin-3-yl | Me | H | H | CN | H | H | Br | H | heptafluoroisopropyl | H | CF3 |
| 2-666 | 2-(trifluoromethyl)pyridin-3-yl | Me | H | H | CN | H | H | Br | H | heptafluoroisopropyl | H | CF3 |
| 2-667 | 2-nitropyridin-3-yl | Me | H | H | CN | H | H | Br | H | heptafluoroisopropyl | H | CF3 |
| 2-668 | 2-cyanopyridin-3-yl | Me | H | H | CN | H | H | Br | H | heptafluoroisopropyl | H | CF3 |
| 2-669 | 6-fluoropyridin-3-yl | Me | H | H | CN | H | H | Br | H | heptafluoroisopropyl | H | CF3 |
| 2-670 | 6-chloropyridin-3-yl | Me | H | H | CN | H | H | Br | H | heptafluoroisopropyl | H | CF3 |
| 2-671 | 6-bromopyridin-3-yl | Me | H | H | CN | H | H | Br | H | heptafluoroisopropyl | H | CF3 |
| 2-672 | 6-iodopyridin-3-yl | Me | H | H | CN | H | H | Br | H | heptafluoroisopropyl | H | CF3 |
| 2-673 | 6-(trifluoromethyl)pyridin-3-yl | Me | H | H | CN | H | H | Br | H | heptafluoroisopropyl | H | CF3 |
| 2-674 | 6-nitropyridin-3-yl | CH2Ph | H | H | CN | H | H | Br | H | heptafluoroisopropyl | H | CF3 |
| 2-675 | 6-cyanopyridin-3-yl | Me | H | H | CN | H | H | Br | H | heptafluoroisopropyl | H | CF3 |
| 2-676 | 5-fluoropyridin-3-yl | Me | H | H | CN | H | H | Br | H | heptafluoroisopropyl | H | CF3 |
| 2-677 | 5-chloropyridin-3-yl | Me | H | H | CN | H | H | Br | H | heptafluoroisopropyl | H | CF3 |
| 2-678 | 5-bromopyridin-3-yl | Me | H | H | CN | H | H | Br | H | heptafluoroisopropyl | H | CF3 |
| 2-679 | 5-iodopyridin-3-yl | Me | H | H | CN | H | H | Br | H | heptafluoroisopropyl | H | CF3 |
| 2-680 | 5-(trifluoromethyl)pyridin-3-yl | Me | H | H | CN | H | H | Br | H | heptafluoroisopropyl | H | CF3 |

TABLE 2-continued

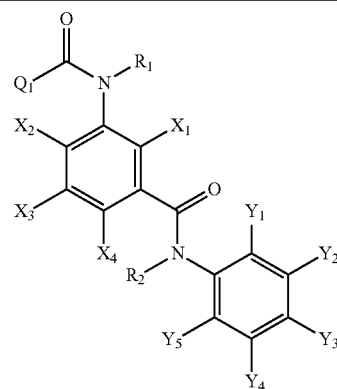

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 2-681 | 5-nitropyridin-3-yl | Me | H | H | CN | H | H | Br | H | heptafluoroisopropyl | H | CF3 |
| 2-682 | 5-cyanopyridin-3-yl | Me | H | H | CN | H | H | Br | H | heptafluoroisopropyl | H | CF3 |
| 2-683 | 4-fluoropyridin-3-yl | Me | H | H | CN | H | H | Br | H | heptafluoroisopropyl | H | CF3 |
| 2-684 | 4-chloropyridin-3-yl | Me | H | H | CN | H | H | Br | H | heptafluoroisopropyl | H | CF3 |
| 2-685 | 4-bromopyridin-3-yl | Me | H | H | CN | H | H | Br | H | heptafluoroisopropyl | H | CF3 |
| 2-686 | 4-iodopyridin-3-yl | Me | H | H | CN | H | H | Br | H | heptafluoroisopropyl | H | CF3 |
| 2-687 | 4-(trifluoromethyl)pyridin-3-yl | Me | H | H | CN | H | H | Br | H | heptafluoroisopropyl | H | CF3 |
| 2-688 | 4-nitropyridin-3-yl | CH2(3-Py) | H | H | CN | H | H | Br | H | heptafluoroisopropyl | H | CF3 |
| 2-689 | 4-cyanopyridin-3-yl | Me | H | H | CN | H | H | Br | H | heptafluoroisopropyl | H | CF3 |
| 2-690 | 2,6-dichloropyridin-3-yl | Me | H | H | CN | H | H | Br | H | heptafluoroisopropyl | H | CF3 |
| 2-691 | pyridin-3-yl N-oxide | Me | H | H | CN | H | H | Br | H | heptafluoroisopropyl | H | CF3 |
| 2-692 | pyridin-4-yl | Me | H | H | CN | H | H | Br | H | heptafluoroisopropyl | H | CF3 |
| 2-693 | 2-chloropyridin-4-yl | Me | H | H | CN | H | H | Br | H | heptafluoroisopropyl | H | CF3 |
| 2-694 | 3-bromopyridin-4-yl | Me | H | H | CN | H | H | Br | H | heptafluoroisopropyl | H | CF3 |
| 2-695 | 3,5-dichloropyridin-4-yl | Me | H | H | CN | H | H | Br | H | heptafluoroisopropyl | H | CF3 |
| 2-696 | 3-(trifluoromethyl)pyridin-4-yl | Me | H | H | CN | H | H | Br | H | heptafluoroisopropyl | H | CF3 |
| 2-697 | 2,6-dicyanopyridin-4-yl | Me | H | H | CN | H | H | Br | H | heptafluoroisopropyl | H | CF3 |
| 2-698 | pyridin-4-yl N-oxide | Me | H | H | CN | H | H | Br | H | heptafluoroisopropyl | H | CF3 |
| 2-699 | pyridin-2-yl | Me | H | H | CN | H | H | Br | H | heptafluoroisopropyl | H | CF3 |
| 2-700 | 3-chloropyridin-2-yl | Me | H | H | CN | H | H | Br | H | heptafluoroisopropyl | H | CF3 |
| 2-701 | 4-bromopyridin-2-yl | Me | H | H | CN | H | H | Br | H | heptafluoroisopropyl | H | CF3 |
| 2-702 | 5-iodopyridin-2-yl | CH2(3-Py-N-oxide) | H | H | CN | H | H | Br | H | heptafluoroisopropyl | H | CF3 |
| 2-703 | 6-chloropyridin-2-yl | Me | H | H | CN | H | H | Br | H | heptafluoroisopropyl | H | CF3 |
| 2-704 | 4-cyanopyridin-2-yl | Me | H | H | CN | H | H | Br | H | heptafluoroisopropyl | H | CF3 |
| 2-705 | phenyl | Me | H | H | CN | H | H | Br | H | nonafluoro-2-butyl | H | CF3 |
| 2-706 | 2-fluorophenyl | Me | H | H | CN | H | H | Br | H | nonafluoro-2-butyl | H | CF3 |
| 2-707 | 3-fluorophenyl | Me | H | H | CN | H | H | Br | H | nonafluoro-2-butyl | H | CF3 |
| 2-708 | 4-fluorophenyl | Me | H | H | CN | H | H | Br | H | nonafluoro-2-butyl | H | CF3 |
| 2-709 | 2-chlorophenyl | Me | H | H | CN | H | H | Br | H | nonafluoro-2-butyl | H | CF3 |
| 2-710 | 3-chlorophenyl | Me | H | H | CN | H | H | Br | H | nonafluoro-2-butyl | H | CF3 |
| 2-711 | 4-chlorophenyl | Me | H | H | CN | H | H | Br | H | nonafluoro-2-butyl | H | CF3 |
| 2-712 | 2-bromophenyl | Me | H | H | CN | H | H | Br | H | nonafluoro-2-butyl | H | CF3 |
| 2-713 | 3-bromophenyl | Me | H | H | CN | H | H | Br | H | nonafluoro-2-butyl | H | CF3 |
| 2-714 | 4-bromophenyl | Me | H | H | CN | H | H | Br | H | nonafluoro-2-butyl | H | CF3 |
| 2-715 | 2-iodophenyl | Me | H | H | CN | H | H | Br | H | nonafluoro-2-butyl | H | CF3 |
| 2-716 | 3-iodophenyl | Me | H | H | CN | H | H | Br | H | nonafluoro-2-butyl | H | CF3 |
| 2-717 | 4-iodophenyl | Me | H | H | CN | H | H | Br | H | nonafluoro-2-butyl | H | CF3 |
| 2-718 | (2-trifluoromethyl)phenyl | Me | H | H | CN | H | H | Br | H | nonafluoro-2-butyl | H | CF3 |
| 2-719 | (3-trifluoromethyl)phenyl | Me | H | H | CN | H | H | Br | H | nonafluoro-2-butyl | H | CF3 |
| 2-720 | (4-trifluoromethyl)phenyl | Me | H | H | CN | H | H | Br | H | nonafluoro-2-butyl | H | CF3 |
| 2-721 | 2-nitrophenyl | Me | H | H | CN | H | H | Br | H | nonafluoro-2-butyl | H | CF3 |
| 2-722 | 3-nitrophenyl | Me | H | H | CN | H | H | Br | H | nonafluoro-2-butyl | H | CF3 |
| 2-723 | 4-nitrophenyl | Me | H | H | CN | H | H | Br | H | nonafluoro-2-butyl | H | CF3 |
| 2-724 | 2-cyanophenyl | Me | H | H | CN | H | H | Br | H | nonafluoro-2-butyl | H | CF3 |
| 2-725 | 3-cyanophenyl | Me | H | H | CN | H | H | Br | H | nonafluoro-2-butyl | H | CF3 |
| 2-726 | 4-cyanophenyl | Me | H | H | CN | H | H | Br | H | nonafluoro-2-butyl | H | CF3 |
| 2-727 | 2,6-difluorophenyl | Me | H | H | CN | H | H | Br | H | nonafluoro-2-butyl | H | CF3 |
| 2-728 | 3,4-dichlorophenyl | Me | H | H | CN | H | H | Br | H | nonafluoro-2-butyl | H | CF3 |
| 2-729 | 2,4-dichlorophenyl | Me | H | H | CN | H | H | Br | H | nonafluoro-2-butyl | H | CF3 |
| 2-730 | 2-chloro-4-fluorophenyl | Me | H | H | CN | H | H | Br | H | nonafluoro-2-butyl | H | CF3 |
| 2-731 | 2-chloro-4,5-difluorophenyl | Me | H | H | CN | H | H | Br | H | nonafluoro-2-butyl | H | CF3 |
| 2-732 | 4-bromo-2-chlorophenyl | Et | H | H | CN | H | H | Br | H | nonafluoro-2-butyl | H | CF3 |
| 2-733 | 2-bromo-4-chlorophenyl | Me | H | H | CN | H | H | Br | H | nonafluoro-2-butyl | H | CF3 |
| 2-734 | 2-bromo-4-fluorophenyl | Me | H | H | CN | H | H | Br | H | nonafluoro-2-butyl | H | CF3 |
| 2-735 | 2-chloro-4-nitrophenyl | Me | H | H | CN | H | H | Br | H | nonafluoro-2-butyl | H | CF3 |
| 2-736 | 3,5-dicyanophenyl | Me | H | H | CN | H | H | Br | H | nonafluoro-2-butyl | H | CF3 |
| 2-737 | 4-cyano-2-fluorophenyl | Me | H | H | CN | H | H | Br | H | nonafluoro-2-butyl | H | CF3 |

TABLE 2-continued

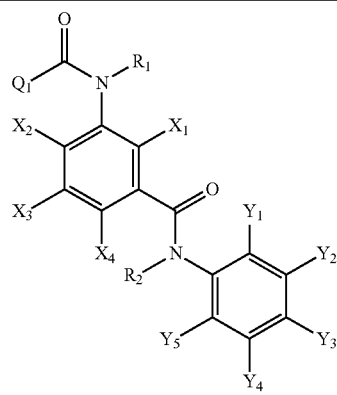

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 2-738 | 2-chloro-4-cyanophenyl | Me | H | H | CN | H | H | Br | H | nonafluoro-2-butyl | H | CF3 |
| 2-739 | pyridin-3-yl | Me | H | H | CN | H | H | Br | H | nonafluoro-2-butyl | H | CF3 |
| 2-740 | 2-fluoropyridin-3-yl | Me | H | H | CN | H | H | Br | H | nonafluoro-2-butyl | H | CF3 |
| 2-741 | 2-chloropyridin-3-yl | Me | H | H | CN | H | H | Br | H | nonafluoro-2-butyl | H | CF3 |
| 2-742 | 2-bromopyridin-3-yl | Me | H | H | CN | H | H | Br | H | nonafluoro-2-butyl | H | CF3 |
| 2-743 | 2-iodopyridin-3-yl | Me | H | H | CN | H | H | Br | H | nonafluoro-2-butyl | H | CF3 |
| 2-744 | 2-(trifluoromethyl)pyridin-3-yl | Me | H | H | CN | H | H | Br | H | nonafluoro-2-butyl | H | CF3 |
| 2-745 | 2-nitropyridin-3-yl | Me | H | H | CN | H | H | Br | H | nonafluoro-2-butyl | H | CF3 |
| 2-746 | 2-cyanopyridin-3-yl | Me | H | H | CN | H | H | Br | H | nonafluoro-2-butyl | H | CF3 |
| 2-747 | 6-fluoropyridin-3-yl | Me | H | H | CN | H | H | Br | H | nonafluoro-2-butyl | H | CF3 |
| 2-748 | 6-chloropyridin-3-yl | Me | H | H | CN | H | H | Br | H | nonafluoro-2-butyl | H | CF3 |
| 2-749 | 6-bromopyridin-3-yl | Me | H | H | CN | H | H | Br | H | nonafluoro-2-butyl | H | CF3 |
| 2-750 | 6-iodopyridin-3-yl | Me | H | H | CN | H | H | Br | H | nonafluoro-2-butyl | H | CF3 |
| 2-751 | 6-(trifluoromethyl)pyridin-3-yl | Me | H | H | CN | H | H | Br | H | nonafluoro-2-butyl | H | CF3 |
| 2-752 | 6-nitropyridin-3-yl | Me | H | H | CN | H | H | Br | H | nonafluoro-2-butyl | H | CF3 |
| 2-753 | 6-cyanopyridin-3-yl | Me | H | H | CN | H | H | Br | H | nonafluoro-2-butyl | H | CF3 |
| 2-754 | 5-fluoropyridin-3-yl | Me | H | H | CN | H | H | Br | H | nonafluoro-2-butyl | H | CF3 |
| 2-755 | 5-chloropyridin-3-yl | Me | H | H | CN | H | H | Br | H | nonafluoro-2-butyl | H | CF3 |
| 2-756 | 5-bromopyridin-3-yl | Me | H | H | CN | H | H | Br | H | nonafluoro-2-butyl | H | CF3 |
| 2-757 | 5-iodopyridin-3-yl | Me | H | H | CN | H | H | Br | H | nonafluoro-2-butyl | H | CF3 |
| 2-758 | 5-(trifluoromethyl)pyridin-3-yl | CN | H | H | CN | H | H | Br | H | nonafluoro-2-butyl | H | CF3 |
| 2-759 | 5-nitropyridin-3-yl | Me | H | H | CN | H | H | Br | H | nonafluoro-2-butyl | H | CF3 |
| 2-760 | 5-cyanopyridin-3-yl | Me | H | H | CN | H | H | Br | H | nonafluoro-2-butyl | H | CF3 |
| 2-761 | 4-fluoropyridin-3-yl | Me | H | H | CN | H | H | Br | H | nonafluoro-2-butyl | H | CF3 |
| 2-762 | 4-chloropyridin-3-yl | Me | H | H | CN | H | H | Br | H | nonafluoro-2-butyl | H | CF3 |
| 2-763 | 4-bromopyridin-3-yl | Me | H | H | CN | H | H | Br | H | nonafluoro-2-butyl | H | CF3 |
| 2-764 | 4-iodopyridin-3-yl | Me | H | H | CN | H | H | Br | H | nonafluoro-2-butyl | H | CF3 |
| 2-765 | 4-(trifluoromethyl)pyridin-3-yl | Me | H | H | CN | H | H | Br | H | nonafluoro-2-butyl | H | CF3 |
| 2-766 | 4-nitropyridin-3-yl | Me | H | H | CN | H | H | Br | H | nonafluoro-2-butyl | H | CF3 |
| 2-767 | 4-cyanopyridin-3-yl | Me | H | H | CN | H | H | Br | H | nonafluoro-2-butyl | H | CF3 |
| 2-768 | 2,6-dichloropyridin-3-yl | Me | H | H | CN | H | H | Br | H | nonafluoro-2-butyl | H | CF3 |
| 2-769 | pyridin-3-yl N-oxide | Me | H | H | CN | H | H | Br | H | nonafluoro-2-butyl | H | CF3 |
| 2-770 | pyridin-4-yl | Me | H | H | CN | H | H | Br | H | nonafluoro-2-butyl | H | CF3 |
| 2-771 | 2-chloropyridin-4-yl | Me | H | H | CN | H | H | Br | H | nonafluoro-2-butyl | H | CF3 |
| 2-772 | 3-bromopyridin-4-yl | Me | H | H | CN | H | H | Br | H | nonafluoro-2-butyl | H | CF3 |
| 2-773 | 3,5-dichloropyridin-4-yl | Me | H | H | CN | H | H | Br | H | nonafluoro-2-butyl | H | CF3 |
| 2-774 | 3-(trifluoromethyl)pyridin-4-yl | Me | H | H | CN | H | H | Br | H | nonafluoro-2-butyl | H | CF3 |
| 2-775 | 2,6-dicyanopyridin-4-yl | Me | H | H | CN | H | H | Br | H | nonafluoro-2-butyl | H | CF3 |
| 2-776 | pyridin-4-yl N-oxide | Me | H | H | CN | H | H | Br | H | nonafluoro-2-butyl | H | CF3 |
| 2-777 | pyridin-2-yl | Me | H | H | CN | H | H | Br | H | nonafluoro-2-butyl | H | CF3 |
| 2-778 | 3-chloropyridin-2-yl | Me | H | H | CN | H | H | Br | H | nonafluoro-2-butyl | H | CF3 |
| 2-779 | 4-bromopyridin-2-yl | Me | H | H | CN | H | H | Br | H | nonafluoro-2-butyl | H | CF3 |
| 2-780 | 5-iodopyridin-2-yl | Me | H | H | CN | H | H | Br | H | nonafluoro-2-butyl | H | CF3 |
| 2-781 | 6-chloropyridin-2-yl | Me | H | H | CN | H | H | Br | H | nonafluoro-2-butyl | H | CF3 |
| 2-782 | 4-cyanopyridin-2-yl | Me | H | H | CN | H | H | Br | H | nonafluoro-2-butyl | H | CF3 |
| 2-783 | phenyl | Me | H | H | CN | H | H | I | H | heptafluoroisopropyl | H | CF3 |
| 2-784 | 2-fluorophenyl | Me | H | H | CN | H | H | I | H | heptafluoroisopropyl | H | CF3 |
| 2-785 | 3-fluorophenyl | Me | H | H | CN | H | H | I | H | heptafluoroisopropyl | H | CF3 |
| 2-786 | 4-fluorophenyl | Me | H | H | CN | H | H | I | H | heptafluoroisopropyl | H | CF3 |
| 2-787 | 2-chlorophenyl | Me | H | H | CN | H | H | I | H | heptafluoroisopropyl | H | CF3 |
| 2-788 | 3-chlorophenyl | Me | H | H | CN | H | H | I | H | heptafluoroisopropyl | H | CF3 |
| 2-789 | 4-chlorophenyl | Me | H | H | CN | H | H | I | H | heptafluoroisopropyl | H | CF3 |
| 2-790 | 2-bromophenyl | Me | H | H | CN | H | H | I | H | heptafluoroisopropyl | H | CF3 |
| 2-791 | 3-bromophenyl | Me | H | H | CN | H | H | I | H | heptafluoroisopropyl | H | CF3 |
| 2-792 | 4-bromophenyl | Me | H | H | CN | H | H | I | H | heptafluoroisopropyl | H | CF3 |
| 2-793 | 2-iodophenyl | Me | H | H | CN | H | H | I | H | heptafluoroisopropyl | H | CF3 |
| 2-794 | 3-iodophenyl | Me | H | H | CN | H | H | I | H | heptafluoroisopropyl | H | CF3 |
| 2-795 | 4-iodophenyl | Me | H | H | CN | H | H | I | H | heptafluoroisopropyl | H | CF3 |

TABLE 2-continued

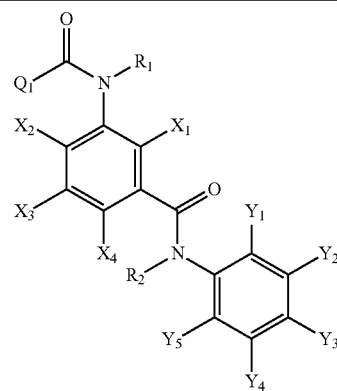

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 2-796 | (2-trifluoromethyl)phenyl | Me | H | H | CN | H | H | I | H | heptafluoroisopropyl | H | CF3 |
| 2-797 | (3-trifluoromethyl)phenyl | Me | H | H | CN | H | H | I | H | heptafluoroisopropyl | H | CF3 |
| 2-798 | (4-trifluoromethyl)phenyl | Me | H | H | CN | H | H | I | H | heptafluoroisopropyl | H | CF3 |
| 2-799 | 2-nitrophenyl | Me | H | H | CN | H | H | I | H | heptafluoroisopropyl | H | CF3 |
| 2-800 | 3-nitrophenyl | Me | H | H | CN | H | H | I | H | heptafluoroisopropyl | H | CF3 |
| 2-801 | 4-nitrophenyl | Me | H | H | CN | H | H | I | H | heptafluoroisopropyl | H | CF3 |
| 2-802 | 2-cyanophenyl | Me | H | H | CN | H | H | I | H | heptafluoroisopropyl | H | CF3 |
| 2-803 | 3-cyanophenyl | Me | H | H | CN | H | H | I | H | heptafluoroisopropyl | H | CF3 |
| 2-804 | 4-cyanophenyl | Me | H | H | CN | H | H | I | H | heptafluoroisopropyl | H | CF3 |
| 2-805 | 2,6-difluorophenyl | Me | H | H | CN | H | H | I | H | heptafluoroisopropyl | H | CF3 |
| 2-806 | 3,4-dichlorophenyl | Me | H | H | CN | H | H | I | H | heptafluoroisopropyl | H | CF3 |
| 2-807 | 2,4-dichlorophenyl | Me | H | H | CN | H | H | I | H | heptafluoroisopropyl | H | CF3 |
| 2-808 | 2-chloro-4-fluorophenyl | Me | H | H | CN | H | H | I | H | heptafluoroisopropyl | H | CF3 |
| 2-809 | 2-chloro-4,5-difluorophonyl | Me | H | H | CN | H | H | I | H | heptafluoroisopropyl | H | CF3 |
| 2-810 | 4-bromo-2-chlorophenyl | Me | H | H | CN | H | H | I | H | heptafluoroisopropyl | H | CF3 |
| 2-811 | 2-bromo-4-chlorophenyl | Me | H | H | CN | H | H | I | H | heptafluoroisopropyl | H | CF3 |
| 2-812 | 2-bromo-4-fluorophenyl | Me | H | H | CN | H | H | I | H | heptafluoroisopropyl | H | CF3 |
| 2-813 | 2-chloro-4-nitrophenyl | Me | H | H | CN | H | H | I | H | heptafluoroisopropyl | H | CF3 |
| 2-814 | 3,5-dicyanophenyl | Me | H | H | CN | H | H | I | H | heptafluoroisopropyl | H | CF3 |
| 2-815 | 4-cyano-2-fluorophenyl | Me | H | H | CN | H | H | I | H | heptafluoroisopropyl | H | CF3 |
| 2-816 | 2-chloro-4-cyanophenyl | Me | H | H | CN | H | H | I | H | heptafluoroisopropyl | H | CF3 |
| 2-817 | pyridin-3-yl | Me | H | H | CN | H | H | I | H | heptafluoroisopropyl | H | CF3 |
| 2-818 | 2-fluoropyridin-3-yl | Me | H | H | CN | H | H | I | H | heptafluoroisopropyl | H | CF3 |
| 2-819 | 2-chloropyridin-3-yl | Me | H | H | CN | H | H | I | H | heptafluoroisopropyl | H | CF3 |
| 2-820 | 2-bromopyridin-3-yl | Me | H | H | CN | H | H | I | H | heptafluoroisopropyl | H | CF3 |
| 2-821 | 2-iodopyridin-3-yl | Me | H | H | CN | H | H | I | H | heptafluoroisopropyl | H | CF3 |
| 2-822 | 2-(trifluoromethyl)pyridin-3-yl | Me | H | H | CN | H | H | I | H | heptafluoroisopropyl | H | CF3 |
| 2-823 | 2-nitropyridin-3-yl | Me | H | H | CN | H | H | I | H | heptafluoroisopropyl | H | CF3 |
| 2-824 | 2-cyanopyridin-3-yl | Me | H | H | CN | H | H | I | H | heptafluoroisopropyl | H | CF3 |
| 2-825 | 6-fluoropyridin-3-yl | Me | H | H | CN | H | H | I | H | heptafluoroisopropyl | H | CF3 |
| 2-826 | 6-chloropyridin-3-yl | Me | H | H | CN | H | H | I | H | heptafluoroisopropyl | H | CF3 |
| 2-827 | 6-bromopyridin-3-yl | Me | H | H | CN | H | H | I | H | heptafluoroisopropyl | H | CF3 |
| 2-828 | 6-iodopyridin-3 | Me | H | H | CN | H | H | I | H | heptafluoroisopropyl | H | CF3 |
| 2-829 | 6-(trifluoromethyl)pyridin-3-yl | Me | H | H | CN | H | H | I | H | heptafluoroisopropyl | H | CF3 |
| 2-830 | 6-nitropyridin-3-yl | Me | H | H | CN | H | H | I | H | heptafluoroisopropyl | H | CF3 |
| 2-831 | 6-cyanopyridin-3-yl | Me | H | H | CN | H | H | I | H | heptafluoroisopropyl | H | CF3 |
| 2-832 | 5-fluoropyridin-3-yl | Me | H | H | CN | H | H | I | H | heptafluoroisopropyl | H | CF3 |
| 2-833 | 5-chloropyridin-3-yl | Me | H | H | CN | H | H | I | H | heptafluoroisopropyl | H | CF3 |
| 2-834 | 5-bromopyridin-3-yl | Me | H | H | CN | H | H | I | H | heptafluoroisopropyl | H | CF3 |
| 2-835 | 5-iodopyridin-3-yl | Me | H | H | CN | H | H | I | H | heptafluoroisopropyl | H | CF3 |
| 2-836 | 5-(trifluoromethyl)pyridin-3-yl | Me | H | H | CN | H | H | I | H | heptafluoroisopropyl | H | CF3 |
| 2-837 | 5-nitropyridin-3-yl | Me | H | H | CN | H | H | I | H | heptafluoroisopropyl | H | CF3 |
| 2-838 | 5-cyanopyridin-3-yl | Me | H | H | CN | H | H | I | H | heptafluoroisopropyl | H | CF3 |
| 2-839 | 4-fluoropyridin-3-yl | Me | H | H | CN | H | H | I | H | heptafluoroisopropyl | H | CF3 |
| 2-840 | 4-chloropyridin-3-yl | Me | H | H | CN | H | H | I | H | heptafluoroisopropyl | H | CF3 |
| 2-841 | 4-bromopyridin-3-yl | C(O)Me | H | H | CN | H | H | I | H | heptafluoroisopropyl | H | CF3 |
| 2-842 | 4-iodopyridin-3-yl | Me | H | H | CN | H | H | I | H | heptafluoroisopropyl | H | CF3 |
| 2-843 | 4-(trifluoromethyl)pyridin-3-yl | Me | H | H | CN | H | H | I | H | heptafluoroisopropyl | H | CF3 |
| 2-844 | 4-nitropyridin-3-yl | Me | H | H | CN | H | H | I | H | heptafluoroisopropyl | H | CF3 |
| 2-845 | 4-cyanopyridin-3-yl | Me | H | H | CN | H | H | I | H | heptafluoroisopropyl | H | CF3 |
| 2-846 | 2,6-dichloropyridin-3-yl | Me | H | H | CN | H | H | I | H | heptafluoroisopropyl | H | CF3 |
| 2-847 | pyridin-3-yl N-oxide | Me | H | H | CN | H | H | I | H | heptafluoroisopropyl | H | CF3 |
| 2-848 | pyridin-4-yl | Me | H | H | CN | H | H | I | H | heptafluoroisopropyl | H | CF3 |
| 2-849 | 2-chloropyridin-4-yl | Me | H | H | CN | H | H | I | H | heptafluoroisopropyl | H | CF3 |
| 2-850 | 3-bromopyridin-4-yl | Me | H | H | CN | H | H | I | H | heptafluoroisopropyl | H | CF3 |
| 2-851 | 3,5-dichloropyridin-4-yl | Me | H | H | CN | H | H | I | H | heptafluoroisopropyl | H | CF3 |
| 2-852 | 3-(trifluoromethyl)pyridin-4-yl | Me | H | H | CN | H | H | I | H | heptafluoroisopropyl | H | CF3 |
| 2-853 | 2,6-dicyanopyridin-4-yl | Me | H | H | CN | H | H | I | H | heptafluoroisopropyl | H | CF3 |

TABLE 2-continued

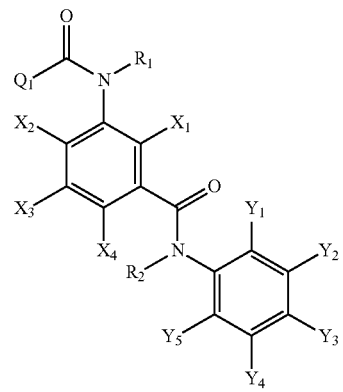

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 2-854 | pyridin-4-yl N-oxide | Me | H | H | CN | H | H | I | H | heptafluoroisopropyl | H | CF3 |
| 2-855 | pyridin-2-yl | Me | H | H | CN | H | H | I | H | heptafluoroisopropyl | H | CF3 |
| 2-856 | 3-chloropyridin-2-yl | Me | H | H | CN | H | H | I | H | heptafluoroisopropyl | H | CF3 |
| 2-857 | 4-bromopyridin-2-yl | Me | H | H | CN | H | H | I | H | heptafluoroisopropyl | H | CF3 |
| 2-858 | 5-iodopyridin-2-yl | Me | H | H | CN | H | H | I | H | heptafluoroisopropyl | H | CF3 |
| 2-859 | 6-chloropyridin-2-yl | Me | H | H | CN | H | H | I | H | heptafluoroisopropyl | H | CF3 |
| 2-860 | 4-cyanopyridin-2-yl | Me | H | H | CN | H | H | I | H | heptafluoroisopropyl | H | CF3 |
| 2-861 | phenyl | Me | H | H | CN | H | H | I | H | nonafluoro-2-butyl | H | CF3 |
| 2-862 | 2-fluorophenyl | Me | H | H | CN | H | H | I | H | nonafluoro-2-butyl | H | CF3 |
| 2-863 | 3-fluorophenyl | Me | H | H | CN | H | H | I | H | nonafluoro-2-butyl | H | CF3 |
| 2-864 | 4-fluorophenyl | Me | H | H | CN | H | H | I | H | nonafluoro-2-butyl | H | CF3 |
| 2-865 | 2-chlorophenyl | Me | H | H | CN | H | H | I | H | nonafluoro-2-butyl | H | CF3 |
| 2-866 | 3-chlorophenyl | Me | H | H | CN | H | H | I | H | nonafluoro-2-butyl | H | CF3 |
| 2-867 | 4-chlorophenyl | Me | H | H | CN | H | H | I | H | nonafluoro-2-butyl | H | CF3 |
| 2-868 | 2-bromophenyl | Me | H | H | CN | H | H | I | H | nonafluoro-2-butyl | H | CF3 |
| 2-869 | 3-bromophenyl | Me | H | H | CN | H | H | I | H | nonafluoro-2-butyl | H | CF3 |
| 2-870 | 4-bromophenyl | Me | H | H | CN | H | H | I | H | nonafluoro-2-butyl | H | CF3 |
| 2-871 | 2-iodophenyl | Me | H | H | CN | H | H | I | H | nonafluoro-2-butyl | H | CF3 |
| 2-872 | 3-iodophenyl | Me | H | H | CN | H | H | I | H | nonafluoro-2-butyl | H | CF3 |
| 2-873 | 4-iodophenyl | Me | H | H | CN | H | H | I | H | nonafluoro-2-butyl | H | CF3 |
| 2-874 | (2-trifluoromethyl)phenyl | Me | H | H | CN | H | H | I | H | nonafluoro-2-butyl | H | CF3 |
| 2-875 | (3-trifluoromethyl)phenyl | Me | H | H | CN | H | H | I | H | nonafluoro-2-butyl | H | CF3 |
| 2-876 | (4-trifluoromethyl)phenyl | Me | H | H | CN | H | H | I | H | nonafluoro-2-butyl | H | CF3 |
| 2-877 | 2-nitrophenyl | Me | H | H | CN | H | H | I | H | nonafluoro-2-butyl | H | CF3 |
| 2-878 | 3-nitrophenyl | Me | H | H | CN | H | H | I | H | nonafluoro-2-butyl | H | CF3 |
| 2-879 | 4-nitrophenyl | Me | H | H | CN | H | H | I | H | nonafluoro-2-butyl | H | CF3 |
| 2-880 | 2-cyanophenyl | Me | H | H | CN | H | H | I | H | nonafluoro-2-butyl | H | CF3 |
| 2-881 | 3-cyanophenyl | Me | H | H | CN | H | H | I | H | nonafluoro-2-butyl | H | CF3 |
| 2-882 | 4-cyanophenyl | Me | H | H | CN | H | H | I | H | nonafluoro-2-butyl | H | CF3 |
| 2-883 | 2,6-difluorophenyl | Me | H | H | CN | H | H | I | H | nonafluoro-2-butyl | H | CF3 |
| 2-884 | 3,4-dichlorophenyl | Me | H | H | CN | H | H | I | H | nonafluoro-2-butyl | H | CF3 |
| 2-885 | 2,4-dichlorophenyl | Me | H | H | CN | H | H | I | H | nonafluoro-2-butyl | H | CF3 |
| 2-886 | 2-chloro-4-fluorophenyl | Me | H | H | CN | H | H | I | H | nonafluoro-2-butyl | H | CF3 |
| 2-887 | 2-chloro-4,5-difluorophenyl | Me | H | H | CN | H | H | I | H | nonafluoro-2-butyl | H | CF3 |
| 2-888 | 4-bromo-2-chlorophenyl | Me | H | H | CN | H | H | I | H | nonafluoro-2-butyl | H | CF3 |
| 2-889 | 2-bromo-4-chlorophenyl | Me | H | H | CN | H | H | I | H | nonafluoro-2-butyl | H | CF3 |
| 2-890 | 2-bromo-4-fluorophenyl | Me | H | H | CN | H | H | I | H | nonafluoro-2-butyl | H | CF3 |
| 2-891 | 2-chloro-4-nitrophenyl | Me | H | H | CN | H | H | I | H | nonafluoro-2-butyl | H | CF3 |
| 2-892 | 3,5-dicyanophenyl | Me | H | H | CN | H | H | I | H | nonafluoro-2-butyl | H | CF3 |
| 2-893 | 4-cyano-2-fluorophenyl | Me | H | H | CN | H | H | I | H | nonafluoro-2-butyl | H | CF3 |
| 2-894 | 2-chloro-4-cyanophenyl | Me | H | H | CN | H | H | I | H | nonafluoro-2-butyl | H | CF3 |
| 2-895 | pyridin-3-yl | Me | H | H | CN | H | H | I | H | nonafluoro-2-butyl | H | CF3 |
| 2-896 | 2-fluoropyridin-3-yl | Me | H | H | CN | H | H | I | H | nonafluoro-2-butyl | H | CF3 |
| 2-897 | 2-chloropyridin-3-yl | Me | H | H | CN | H | H | I | H | nonafluoro-2-butyl | H | CF3 |
| 2-898 | 2-bromopyridin-3-yl | Me | H | H | CN | H | H | I | H | nonafluoro-2-butyl | H | CF3 |
| 2-899 | 2-iodopyridin-3-yl | Me | H | H | CN | H | H | I | H | nonafluoro-2-butyl | H | CF3 |
| 2-900 | 2-(trifluoromethyl)pyridin-3-yl | Me | H | H | CN | H | H | I | H | nonafluoro-2-butyl | H | CF3 |
| 2-901 | 2-nitropyridin-3-yl | Me | H | H | CN | H | H | I | H | nonafluoro-2-butyl | H | CF3 |
| 2-902 | 2-cyanopyridin-3-yl | Me | H | H | CN | H | H | I | H | nonafluoro-2-butyl | H | CF3 |
| 2-903 | 6-fluoropyridin-3-yl | Me | H | H | CN | H | H | I | H | nonafluoro-2-butyl | H | CF3 |
| 2-904 | 6-chloropyridin-3-yl | Me | H | H | CN | H | H | I | H | nonafluoro-2-butyl | H | CF3 |
| 2-905 | 6-bromopyridin-3-yl | Me | H | H | CN | H | H | I | H | nonafluoro-2-butyl | H | CF3 |
| 2-906 | 6-iodopyridin-3-yl | Me | H | H | CN | H | H | I | H | nonafluoro-2-butyl | H | CF3 |
| 2-907 | 6-(trifluoromethyl)pyridin-3-yl | Me | H | H | CN | H | H | I | H | nonafluoro-2-butyl | H | CF3 |
| 2-908 | 6-nitropyridin-3-yl | Me | H | H | CN | H | H | I | H | nonafluoro-2-butyl | H | CF3 |
| 2-909 | 6-cyanopyridin-3-yl | Me | H | H | CN | H | H | I | H | nonafluoro-2-butyl | H | CF3 |
| 2-910 | 5-fluoropyridin-3-yl | Me | H | H | CN | H | H | I | H | nonafluoro-2-butyl | H | CF3 |
| 2-911 | 5-chloropyridin-3-yl | Me | H | H | CN | H | H | I | H | nonafluoro-2-butyl | H | CF3 |

TABLE 2-continued

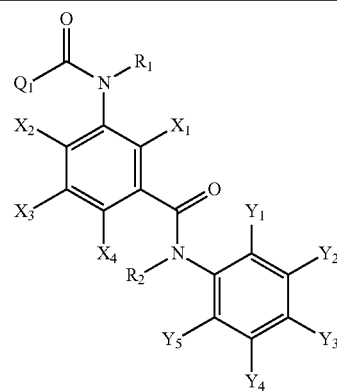

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 2-912 | 5-bromopyridin-3-yl | Me | H | H | CN | H | H | I | H | nonafluoro-2-butyl | H | CF3 |
| 2-913 | 5-iodopyridin-3-yl | Me | H | H | CN | H | H | I | H | nonafluoro-2-butyl | H | CF3 |
| 2-914 | 5-(trifluoromethyl)pyridin-3-yl | Me | H | H | CN | H | H | I | H | nonafluoro-2-butyl | H | CF3 |
| 2-915 | 5-nitropyridin-3-yl | Me | H | H | CN | H | H | I | H | nonafluoro-2-butyl | H | CF3 |
| 2-916 | 5-cyanopyridin-3-yl | Me | H | H | CN | H | H | I | H | nonafluoro-2-butyl | H | CF3 |
| 2-917 | 4-fluoropyridin-3-yl | Me | H | H | CN | H | H | I | H | nonafluoro-2-butyl | H | CF3 |
| 2-918 | 4-chloropyridin-3-yl | Me | H | H | CN | H | H | I | H | nonafluoro-2-butyl | H | CF3 |
| 2-919 | 4-bromopyridin-3-yl | Me | H | H | CN | H | H | I | H | nonafluoro-2-butyl | H | CF3 |
| 2-920 | 4-iodopyridin-3-yl | Me | H | H | CN | H | H | I | H | nonafluoro-2-butyl | H | CF3 |
| 2-921 | 4-(trifluoromethyl)pyridin-3-yl | Me | H | H | CN | H | H | I | H | nonafluoro-2-butyl | H | CF3 |
| 2-922 | 4-nitropyridin-3-yl | Me | H | H | CN | H | H | I | H | nonafluoro-2-butyl | H | CF3 |
| 2-923 | 4-cyanopyridin-3-yl | Me | H | H | CN | H | H | I | H | nonafluoro-2-butyl | H | CF3 |
| 2-924 | 2,6-dichloropyridin-3-yl | Me | H | H | CN | H | H | I | H | nonafluoro-2-butyl | H | CF3 |
| 2-925 | pyridin-3-yl N-oxide | Me | H | H | CN | H | H | I | H | nonafluoro-2-butyl | H | CF3 |
| 2-926 | pyridin-4-yl | Me | H | H | CN | H | H | I | H | nonafluoro-2-butyl | H | CF3 |
| 2-927 | 2-chloropyridin-4-yl | Me | H | H | CN | H | H | I | H | nonafluoro-2-butyl | H | CF3 |
| 2-928 | 3-bromopyridin-4-yl | Me | H | H | CN | H | H | I | H | nonafluoro-2-butyl | H | CF3 |
| 2-929 | 3,5-dichloropyridin-4-yl | Me | H | H | CN | H | H | I | H | nonafluoro-2-butyl | H | CF3 |
| 2-930 | 3-(trifluoromethyl)pyridin-4-yl | Me | H | H | CN | H | H | I | H | nonafluoro-2-butyl | H | CF3 |
| 2-931 | 2,6-dicyanopyridin-4-yl | Me | H | H | CN | H | H | I | H | nonafluoro-2-butyl | H | CF3 |
| 2-932 | pyridin-4-yl N-oxide | Me | H | H | CN | H | H | I | H | nonafluoro-2-butyl | H | CF3 |
| 2-933 | pyridin-2-yl | Me | H | H | CN | H | H | I | H | nonafluoro-2-butyl | H | CF3 |
| 2-934 | 3-chloropyridin-2-yl | Me | H | H | CN | H | H | I | H | nonafluoro-2-butyl | H | CF3 |
| 2-935 | 4-bromopyridin-2-yl | Me | H | H | CN | H | H | I | H | nonafluoro-2-butyl | H | CF3 |
| 2-936 | 5-iodopyridin-2-yl | Me | H | H | CN | H | H | I | H | nonafluoro-2-butyl | H | CF3 |
| 2-937 | 6-chloropyridin-2-yl | Me | H | H | CN | H | H | I | H | nonafluoro-2-butyl | H | CF3 |
| 2-938 | 4-cyanopyridin-2-yl | Me | H | H | CN | H | H | I | H | nonafluoro-2-butyl | H | CF3 |
| 2-939 | phenyl | Me | H | H | CN | H | H | OCF3 | H | heptafluoroisopropyl | H | OCF3 |
| 2-970 | 2-chloropyridin-3-yl | Me | H | H | CN | H | H | OCF3 | H | heptafluoroisopropyl | H | OCF3 |
| 2-995 | phenyl | Me | H | H | CN | H | H | OCF3 | H | nonafluoro-2-butyl | H | OCF3 |
| 2-1026 | 2-chloropyridin-3-yl | Me | H | H | CN | H | H | OCF3 | H | nonafluoro-2-butyl | H | OCF3 |
| 2-1051 | phenyl | Me | H | H | CN | H | H | CF3 | H | heptafluoroisopropyl | H | OCF3 |
| 2-1082 | 2-chloropyridin-3-yl | Me | H | H | CN | H | H | CF3 | H | heptafluoroisopropyl | H | OCF3 |
| 2-1107 | phenyl | Me | H | H | CN | H | H | CF3 | H | nonafluoro-2-butyl | H | OCF3 |
| 2-1138 | 2-chloropyridin-3-yl | Me | H | H | CN | H | H | CF3 | H | nonafluoro-2-butyl | H | OCF3 |
| 2-1163 | phenyl | Me | H | H | CN | H | H | CF3 | H | heptafluoroisopropyl | H | CF3 |
| 2-1183 | 3-cyanophenyl | Me | H | H | CN | H | H | CF3 | H | heptafluoroisopropyl | H | CF3 |
| 2-1184 | 4-cyanophenyl | Me | H | H | CN | H | H | CF3 | H | heptafluoroisopropyl | H | CF3 |
| 2-1199 | 2-chloropyridin-3-yl | Me | H | H | CN | H | H | CF3 | H | heptafluoroisopropyl | H | CF3 |
| 2-1231 | phenyl | Me | H | H | CN | H | H | CF3 | H | nonafluoro-2-butyl | H | CF3 |
| 2-1251 | 3-cyanophenyl | Me | H | H | CN | H | H | CF3 | H | nonafluoro-2-butyl | H | CF3 |
| 2-1252 | 4-cyanophenyl | Me | H | H | CN | H | H | CF3 | H | nonafluoro-2-butyl | H | CF3 |
| 2-1267 | 2-chloropyridin-3-yl | Me | H | H | CN | H | H | CF3 | H | nonafluoro-2-butyl | H | CF3 |
| 2-1299 | phenyl | Me | H | F | CN | H | H | Cl | H | heptafluoroisopropyl | H | OCF3 |
| 2-1319 | 3-cyanophenyl | Me | H | F | CN | H | H | Cl | H | heptafluoroisopropyl | H | OCF3 |
| 2-1320 | 4-cyanophenyl | Me | H | F | CN | H | H | Cl | H | heptafluoroisopropyl | H | OCF3 |
| 2-1335 | 2-chloropyridin-3-yl | Me | H | F | CN | H | H | Cl | H | heptafluoroisopropyl | H | OCF3 |
| 2-1377 | phenyl | Me | H | F | CN | H | H | Cl | H | nonafluoro-2-butyl | H | OCF3 |
| 2-1397 | 3-cyanophenyl | Me | H | F | CN | H | H | Cl | H | nonafluoro-2-butyl | H | OCF3 |
| 2-1398 | 4-cyanophenyl | Me | H | F | CN | H | H | Cl | H | nonafluoro-2-butyl | H | OCF3 |
| 2-1413 | 2-chloropyridin-3-yl | Me | H | F | CN | H | H | Cl | H | nonafluoro-2-butyl | H | OCF3 |
| 2-1455 | phenyl | Me | H | F | CN | H | H | Br | H | heptafluoroisopropyl | H | OCF3 |
| 2-1475 | 3-cyanophenyl | Me | H | F | CN | H | H | Br | H | heptafluoroisopropyl | H | OCF3 |
| 2-1476 | 4-cyanophenyl | Me | H | F | CN | H | H | Br | H | heptafluoroisopropyl | H | OCF3 |
| 2-1491 | 2-chloropyridin-3-yl | Me | H | F | CN | H | H | Br | H | heptafluoroisopropyl | H | OCF3 |
| 2-1533 | phenyl | Me | H | F | CN | H | H | Br | H | nonafluoro-2-butyl | H | OCF3 |
| 2-1553 | 3-cyanophenyl | Me | H | F | CN | H | H | Br | H | nonafluoro-2-butyl | H | OCF3 |
| 2-1554 | 4-cyanophenyl | Me | H | F | CN | H | H | Br | H | nonafluoro-2-butyl | H | OCF3 |

TABLE 2-continued

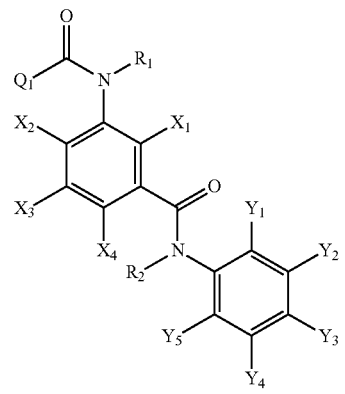

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 2-1569 | 2-chloropyridin-3-yl | Me | H | F | CN | H | H | Br | H | nonafluoro-2-butyl | H | OCF3 |
| 2-1611 | phenyl | Me | H | F | CN | H | H | I | H | heptafluoroisopropyl | H | OCF3 |
| 2-1631 | 3-cyanophenyl | Me | H | F | CN | H | H | I | H | heptafluoroisopropyl | H | OCF3 |
| 2-1632 | 4-cyanophenyl | Me | H | F | CN | H | H | I | H | heptafluoroisopropyl | H | OCF3 |
| 2-1647 | 2-chloropyridin-3-yl | Me | H | F | CN | H | H | I | H | heptafluoroisopropyl | H | OCF3 |
| 2-1689 | phenyl | Me | H | F | CN | H | H | I | H | nonafluoro-2-butyl | H | OCF3 |
| 2-1709 | 3-cyanophenyl | Me | H | F | CN | H | H | I | H | nonafluoro-2-butyl | H | OCF3 |
| 2-1710 | 4-cyanophenyl | Me | H | F | CN | H | H | I | H | nonafluoro-2-butyl | H | OCF3 |
| 2-1725 | 2-chloropyridin-3-yl | Me | H | F | CN | H | H | I | H | nonafluoro-2-butyl | H | OCF3 |
| 2-1767 | phenyl | Me | H | F | CN | H | H | F | H | heptafluoroisopropyl | H | CF3 |
| 2-1768 | phenyl | Me | H | F | CN | H | H | Cl | H | heptafluoroisopropyl | H | CF3 |
| 2-1788 | 3-cyanophenyl | Me | H | F | CN | H | H | Cl | H | heptafluoroisopropyl | H | CF3 |
| 2-1789 | 4-cyanophenyl | Me | H | F | CN | H | H | Cl | H | heptafluoroisopropyl | H | CF3 |
| 2-1804 | 2-chloropyridin-3-yl | Me | H | F | CN | H | H | Cl | H | heptafluoroisopropyl | H | CF3 |
| 2-1846 | phenyl | Me | H | F | CN | H | H | F | H | nonafluoro-2-butyl | H | CF3 |
| 2-1847 | phenyl | Me | H | F | CN | H | H | Cl | H | nonafluoro-2-butyl | H | CF3 |
| 2-1867 | 3-cyanophenyl | Me | H | F | CN | H | H | Cl | H | nonafluoro-2-butyl | H | CF3 |
| 2-1868 | 4-cyanophenyl | Me | H | F | CN | H | H | Cl | H | nonafluoro-2-butyl | H | CF3 |
| 2-1883 | 2-chloropyridin-3-yl | Me | H | F | CN | H | H | Cl | H | nonafluoro-2-butyl | H | CF3 |
| 2-1925 | phenyl | Me | H | F | CN | H | H | Br | H | heptafluoroisopropyl | H | CF3 |
| 2-1945 | 3-cyanophenyl | Me | H | F | CN | H | H | Br | H | heptafluoroisopropyl | H | CF3 |
| 2-1946 | 4-cyanophenyl | Me | H | F | CN | H | H | Br | H | heptafluoroisopropyl | H | CF3 |
| 2-1961 | 2-chloropyridin-3-yl | Me | H | F | CN | H | H | Br | H | heptafluoroisopropyl | H | CF3 |
| 2-2003 | phenyl | Me | H | F | CN | H | H | Br | H | nonafluoro-2-butyl | H | CF3 |
| 2-2023 | 3-cyanophenyl | Me | H | F | CN | H | H | Br | H | nonafluoro-2-butyl | H | CF3 |
| 2-2024 | 4-cyanophenyl | Me | H | F | CN | H | H | Br | H | nonafluoro-2-butyl | H | CF3 |
| 2-2039 | 2-chloropyridin-3-yl | Me | H | F | CN | H | H | Br | H | nonafluoro-2-butyl | H | CF3 |
| 2-2081 | phenyl | Me | H | F | CN | H | H | I | H | heptafluoroisopropyl | H | CF3 |
| 2-2101 | 3-cyanophenyl | Me | H | F | CN | H | H | I | H | heptafluoroisopropyl | H | CF3 |
| 2-2102 | 4-cyanophenyl | Me | H | F | CN | H | H | I | H | heptafluoroisopropyl | H | CF3 |
| 2-2117 | 2-chloropyridin-3-yl | Me | H | F | CN | H | H | I | H | heptafluoroisopropyl | H | CF3 |
| 2-2159 | phenyl | Me | H | F | CN | H | H | I | H | nonafluoro-2-butyl | H | CF3 |
| 2-2179 | 3-cyanophenyl | Me | H | F | CN | H | H | I | H | nonafluoro-2-butyl | H | CF3 |
| 2-2180 | 4-cyanophenyl | Me | H | F | CN | H | H | I | H | nonafluoro-2-butyl | H | CF3 |
| 2-2195 | 2-chloropyridin-3-yl | Me | H | F | CN | H | H | I | H | nonafluoro-2-butyl | H | CF3 |
| 2-2237 | phenyl | Me | H | F | CN | H | H | OCF3 | H | heptafluoroisopropyl | H | OCF3 |
| 2-2268 | 2-chloropyridin-3-yl | Me | H | F | CN | H | H | OCF3 | H | heptafluoroisopropyl | H | OCF3 |
| 2-2293 | phenyl | Me | H | F | CN | H | H | OCF3 | H | nonafluoro-2-butyl | H | OCF3 |
| 2-2324 | 2-chloropyridin-3-yl | Me | H | F | CN | H | H | OCF3 | H | nonafluoro-2-butyl | H | OCF3 |
| 2-2349 | phenyl | Me | H | F | CN | H | H | CF3 | H | heptafluoroisopropyl | H | OCF3 |
| 2-2380 | 2-chloropyridin-3-yl | Me | H | F | CN | H | H | CF3 | H | heptafluoroisopropyl | H | OCF3 |
| 2-2405 | phenyl | Me | H | F | CN | H | H | CF3 | H | nonafluoro-2-butyl | H | OCF3 |
| 2-2436 | 2-chloropyridin-3-yl | Me | H | F | CN | H | H | CF3 | H | nonafluoro-2-butyl | H | OCF3 |
| 2-2461 | phenyl | Me | H | F | CN | H | H | CF3 | H | heptafluoroisopropyl | H | CF3 |
| 2-2481 | 3-cyanophenyl | Me | H | F | CN | H | H | CF3 | H | heptafluoroisopropyl | H | CF3 |
| 2-2482 | 4-cyanophenyl | Me | H | F | CN | H | H | CF3 | H | heptafluoroisopropyl | H | CF3 |
| 2-2497 | 2-chloropyridin-3-yl | Me | H | F | CN | H | H | CF3 | H | heptafluoroisopropyl | H | CF3 |
| 2-2529 | phenyl | Me | H | F | CN | H | H | CF3 | H | nonafluoro-2-butyl | H | CF3 |
| 2-2549 | 3-cyanophenyl | Me | H | F | CN | H | H | CF3 | H | nonafluoro-2-butyl | H | CF3 |
| 2-2550 | 4-cyanophenyl | Me | H | F | CN | H | H | CF3 | H | nonafluoro-2-butyl | H | CF3 |
| 2-2565 | 2-chloropyridin-3-yl | Me | H | F | CN | H | H | CF3 | H | nonafluoro-2-butyl | H | CF3 |
| 2-2597 | phenyl | Me | H | F | CN | F | H | Cl | H | heptafluoroisopropyl | H | OCF3 |
| 2-2617 | 3-cyanophenyl | Me | H | F | CN | F | H | Cl | H | heptafluoroisopropyl | H | OCF3 |
| 2-2618 | 4-cyanophenyl | Me | H | F | CN | F | H | Cl | H | heptafluoroisopropyl | H | OCF3 |
| 2-2633 | 2-chloropyridin-3-yl | Me | H | F | CN | F | H | Cl | H | heptafluoroisopropyl | H | OCF3 |
| 2-2675 | phenyl | Me | H | F | CN | F | H | Cl | H | nonafluoro-2-butyl | H | OCF3 |
| 2-2695 | 3-cyanophenyl | Me | H | F | CN | F | H | Cl | H | nonafluoro-2-butyl | H | OCF3 |
| 2-2696 | 4-cyanophenyl | Me | H | F | CN | F | H | Cl | H | nonafluoro-2-butyl | H | OCF3 |

TABLE 2-continued

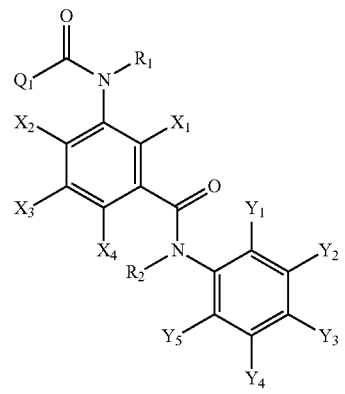

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 2-2711 | 2-chloropyridin-3-yl | Me | H | F | CN | F | H | Cl | H | nonafluoro-2-butyl | H | OCF3 |
| 2-2753 | phenyl | Me | H | F | CN | F | H | Br | H | heptafluoroisopropyl | H | OCF3 |
| 2-2773 | 3-cyanophenyl | Me | H | F | CN | F | H | Br | H | heptafluoroisopropyl | H | OCF3 |
| 2-2774 | 4-cyanophenyl | Me | H | F | CN | F | H | Br | H | heptafluoroisopropyl | H | OCF3 |
| 2-2789 | 2-chloropyridin-3-yl | Me | H | F | CN | F | H | Br | H | heptafluoroisopropyl | H | OCF3 |
| 2-2831 | phenyl | Me | H | F | CN | F | H | Br | H | nonafluoro-2-butyl | H | OCF3 |
| 2-2851 | 3-cyanophenyl | Me | H | F | CN | F | H | Br | H | nonafluoro-2-butyl | H | OCF3 |
| 2-2852 | 4-cyanophenyl | Me | H | F | CN | F | H | Br | H | nonafluoro-2-butyl | H | OCF3 |
| 2-2867 | 2-chloropyridin-3-yl | Me | H | F | CN | F | H | Br | H | nonafluoro-2-butyl | H | OCF3 |
| 2-2909 | phenyl | Me | H | F | CN | F | H | I | H | heptafluoroisopropyl | H | OCF3 |
| 2-2929 | 3-cyanophenyl | Me | H | F | CN | F | H | I | H | heptafluoroisopropyl | H | OCF3 |
| 2-2930 | 4-cyanophenyl | Me | H | F | CN | F | H | I | H | heptafluoroisopropyl | H | OCF3 |
| 2-2945 | 2-chloropyridin-3-yl | Me | H | F | CN | F | H | I | H | heptafluoroisopropyl | H | OCF3 |
| 2-2987 | phenyl | Me | H | F | CN | F | H | I | H | nonafluoro-2-butyl | H | OCF3 |
| 2-3007 | 3-cyanophenyl | Me | H | F | CN | F | H | I | H | nonafluoro-2-butyl | H | OCF3 |
| 2-3008 | 4-cyanophenyl | Me | H | F | CN | F | H | I | H | nonafluoro-2-butyl | H | OCF3 |
| 2-3023 | 2-chloropyridin-3-yl | Me | H | F | CN | F | H | I | H | nonafluoro-2-butyl | H | OCF3 |
| 2-3065 | phenyl | Me | H | F | CN | F | H | F | H | heptafluoroisopropyl | H | CF3 |
| 2-3066 | phenyl | Me | H | F | CN | F | H | Cl | H | heptafluoroisopropyl | H | CF3 |
| 2-3086 | 3-cyanophenyl | Me | H | F | CN | F | H | Cl | H | heptafluoroisopropyl | H | CF3 |
| 2-3087 | 4-cyanophenyl | Me | H | F | CN | F | H | Cl | H | heptafluoroisopropyl | H | CF3 |
| 2-3102 | 2-chloropyridin-3-yl | Me | H | F | CN | F | H | Cl | H | heptafluoroisopropyl | H | CF3 |
| 2-3144 | phenyl | Me | H | F | CN | F | H | F | H | nonafluoro-2-butyl | H | CF3 |
| 2-3165 | 3-cyanophenyl | Me | H | F | CN | F | H | Cl | H | nonafluoro-2-butyl | H | CF3 |
| 2-3166 | 4-cyanophenyl | Me | H | F | CN | F | H | Cl | H | nonafluoro-2-butyl | H | CF3 |
| 2-3181 | 2-chloropyridin-3-yl | Me | H | F | CN | F | H | Cl | H | nonafluoro-2-butyl | H | CF3 |
| 2-3223 | phenyl | Me | H | F | CN | F | H | Br | H | heptafluoroisopropyl | H | CF3 |
| 2-3243 | 3-cyanophenyl | Me | H | F | CN | F | H | Br | H | heptafluoroisopropyl | H | CF3 |
| 2-3244 | 4-cyanophenyl | Me | H | F | CN | F | H | Br | H | heptafluoroisopropyl | H | CF3 |
| 2-3259 | 2-chloropyridin-3-yl | Me | H | F | CN | F | H | Br | H | heptafluoroisopropyl | H | CF3 |
| 2-3301 | phenyl | Me | H | F | CN | F | H | Br | H | nonafluoro-2-butyl | H | CF3 |
| 2-3321 | 3-cyanophenyl | Me | H | F | CN | F | H | Br | H | nonafluoro-2-butyl | H | CF3 |
| 2-3322 | 4-cyanophenyl | Me | H | F | CN | F | H | Br | H | nonafluoro-2-butyl | H | CF3 |
| 2-3337 | 2-chloropyridin-3-yl | Me | H | F | CN | F | H | Br | H | nonafluoro-2-butyl | H | CF3 |
| 2-3379 | phenyl | Me | H | F | CN | F | H | I | H | heptafluoroisopropyl | H | CF3 |
| 2-3399 | 3-cyanophenyl | Me | H | F | CN | F | H | I | H | heptafluoroisopropyl | H | CF3 |
| 2-3400 | 4-cyanophenyl | Me | H | F | CN | F | H | I | H | heptafluoroisopropyl | H | CF3 |
| 2-3415 | 2-chloropyridin-3-yl | Me | H | F | CN | F | H | I | H | heptafluoroisopropyl | H | CF3 |
| 2-3457 | phenyl | Me | H | F | CN | F | H | I | H | nonafluoro-2-butyl | H | CF3 |
| 2-3477 | 3-cyanophenyl | Me | H | F | CN | F | H | I | H | nonafluoro-2-butyl | H | CF3 |
| 2-3478 | 4-cyanophenyl | Me | H | F | CN | F | H | I | H | nonafluoro-2-butyl | H | CF3 |
| 2-3493 | 2-chloropyridin-3-yl | Me | H | F | CN | F | H | I | H | nonafluoro-2-butyl | H | CF3 |
| 2-3494 | 2-bromopyridin-3-yl | Me | H | F | CN | F | H | I | H | nonafluoro-2-butyl | H | CF3 |
| 2-3535 | phenyl | Me | H | F | CN | F | H | OCF3 | H | heptafluoroisopropyl | H | OCF3 |
| 2-3566 | 2-chloropyridin-3-yl | Me | H | F | CN | F | H | OCF3 | H | heptafluoroisopropyl | H | OCF3 |
| 2-3591 | phenyl | Me | H | F | CN | F | H | OCF3 | H | nonafluoro-2-butyl | H | OCF3 |
| 2-3622 | 2-chloropyridin-3-yl | Me | H | F | CN | F | H | OCF3 | H | nonafluoro-2-butyl | H | OCF3 |
| 2-3647 | phenyl | Me | H | F | CN | F | H | CF3 | H | heptafluoroisopropyl | H | OCF3 |
| 2-3678 | 2-chloropyridin-3-yl | Me | H | F | CN | F | H | CF3 | H | heptafluoroisopropyl | H | OCF3 |
| 2-3703 | phenyl | Me | H | F | CN | F | H | CF3 | H | nonafluoro-2-butyl | H | OCF3 |
| 2-3734 | 2-chloropyridin-3-yl | Me | H | F | CN | F | H | CF3 | H | nonafluoro-2-butyl | H | OCF3 |
| 2-3759 | phenyl | Me | H | F | CN | F | H | CF3 | H | heptafluoroisopropyl | H | CF3 |
| 2-3779 | 3-cyanophenyl | Me | H | F | CN | F | H | CF3 | H | heptafluoroisopropyl | H | CF3 |
| 2-3780 | 4-cyanophenyl | Me | H | F | CN | F | H | CF3 | H | heptafluoroisopropyl | H | CF3 |
| 2-3795 | 2-chloropyridin-3-yl | Me | H | F | CN | F | H | CF3 | H | heptafluoroisopropyl | H | CF3 |
| 2-3827 | phenyl | Me | H | F | CN | F | H | CF3 | H | nonafluoro-2-butyl | H | CF3 |
| 2-3847 | 3-cyanophenyl | Me | H | F | CN | F | H | CF3 | H | nonafluoro-2-butyl | H | CF3 |

TABLE 2-continued

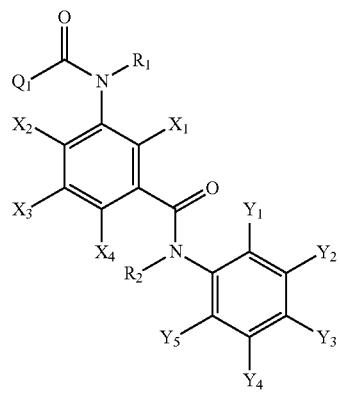

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 2-3848 | 4-cyanophenyl | Me | H | F | CN | F | H | CF3 | H | nonafluoro-2-butyl | H | CF3 |
| 2-3863 | 2-chloropyridin-3-yl | Me | H | F | CN | F | H | CF3 | H | nonafluoro-2-butyl | H | CF3 |

TABLE 3

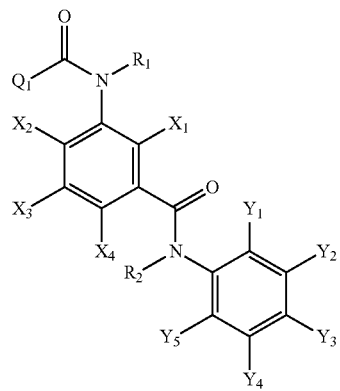

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 3-1 | phenyl | H | Me | H | CN | H | H | Cl | H | heptafluoroisopropyl | H | OCF3 |
| 3-21 | 3-cyanophenyl | H | Me | H | CN | H | H | Cl | H | heptafluoroisopropyl | H | OCF3 |
| 3-22 | 4-cyanophenyl | H | Me | H | CN | H | H | Cl | H | heptafluoroisopropyl | H | OCF3 |
| 3-37 | 2-chloropyridin-3-yl | H | Me | H | CN | H | H | Cl | H | heptafluoroisopropyl | H | OCF3 |
| 3-79 | phenyl | H | Me | H | CN | H | H | Cl | H | nonafluoro-2-butyl | H | OCF3 |
| 3-99 | 3-cyanophenyl | H | Me | H | CN | H | H | Cl | H | nonafluoro-2-butyl | H | OCF3 |
| 3-100 | 4-cyanophenyl | H | Me | H | CN | H | H | Cl | H | nonafluoro-2-butyl | H | OCF3 |
| 3-115 | 2-chloropyridin-3-yl | H | Me | H | CN | H | H | Cl | H | nonafluoro-2-butyl | H | OCF3 |
| 3-157 | phenyl | H | Me | H | CN | H | H | Br | H | heptafluoroisopropyl | H | OCF3 |
| 3-177 | 3-cyanophenyl | H | Me | H | CN | H | H | Br | H | heptafluoroisopropyl | H | OCF3 |
| 3-178 | 4-cyanophenyl | H | Me | H | CN | H | H | Br | H | heptafluoroisopropyl | H | OCF3 |
| 3-193 | 2-chloropyridin-3-yl | H | Me | H | CN | H | H | Br | H | heptafluoroisopropyl | H | OCF3 |
| 3-235 | phenyl | H | Me | H | CN | H | H | Br | H | nonafluoro-2-butyl | H | OCF3 |
| 3-255 | 3-cyanophenyl | H | Me | H | CN | H | H | Br | H | nonafluoro-2-butyl | H | OCF3 |
| 3-256 | 4-cyanophenyl | H | Me | H | CN | H | H | Br | H | nonafluoro-2-butyl | H | OCF3 |
| 3-271 | 2-chloropyridin-3-yl | H | Me | H | CN | H | H | Br | H | nonafluoro-2-butyl | H | OCF3 |
| 3-313 | phenyl | H | Me | H | CN | H | H | I | H | heptafluoroisopropyl | H | OCF3 |
| 3-333 | 3-cyanophenyl | H | Me | H | CN | H | H | I | H | heptafluoroisopropyl | H | OCF3 |
| 3-334 | 4-cyanophenyl | H | Me | H | CN | H | H | I | H | heptafluoroisopropyl | H | OC2F5 |
| 3-349 | 2-chloropyridin-3-yl | H | Me | H | CN | H | H | I | H | heptafluoroisopropyl | H | OCF3 |
| 3-391 | phenyl | H | Me | H | CN | H | H | I | H | nonafluoro-2-butyl | H | OCF3 |
| 3-411 | 3-cyanophenyl | H | Me | H | CN | H | H | I | H | nonafluoro-2-butyl | H | OCF3 |
| 3-412 | 4-cyanophenyl | H | Me | H | CN | H | H | I | H | nonafluoro-2-butyl | H | OCF3 |
| 3-427 | 2-chloropyridin-3-yl | H | Me | H | CN | H | H | I | H | nonafluoro-2-butyl | H | OCF3 |
| 3-469 | phenyl | H | Me | H | CN | H | H | F | H | heptafluoroisopropyl | H | CF3 |
| 3-470 | phenyl | H | Me | H | CN | H | H | Cl | H | heptafluoroisopropyl | H | CF3 |
| 3-484 | (3-trifluoromethyl)phenyl | H | Et | H | CN | H | H | Cl | H | pentafluoroethyl | H | CF3 |
| 3-490 | 3-cyanophenyl | H | Me | H | CN | H | H | Cl | H | heptafluoroisopropyl | H | CF3 |

TABLE 3-continued

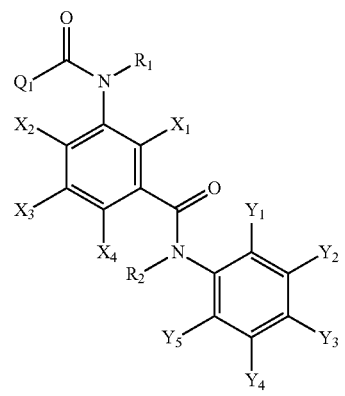

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 3-491 | 4-cyanophenyl | H | Me | H | CN | H | H | Cl | H | heptafluoroisopropyl | H | CF3 |
| 3-495 | 2-chloro-4-fluorophenyl | H | n-Pr | H | CN | H | H | Cl | H | heptafluoroisopropyl | H | C2F5 |
| 3-506 | 2-chloropyridin-3-yl | H | Me | H | CN | H | H | Cl | H | heptafluoroisopropyl | H | CF3 |
| 3-512 | 6-fluoropyridin-3-yl | H | i-Pr | H | CN | H | H | Cl | H | heptafluoroisopropyl | H | CF3 |
| 3-528 | 4-bromopyridin-3-yl | H | CH2CH=CH2 | H | CN | H | H | Cl | H | heptafluoroisopropyl | H | n-C3F7 |
| 3-535 | pyridin-4-yl | H | CN | H | CN | H | H | Cl | H | heptafluoroisopropyl | H | CF3 |
| 3-548 | phenyl | H | Me | H | CN | H | H | F | H | nonafluoro-2-butyl | H | CF3 |
| 3-549 | phenyl | H | Me | H | CN | H | H | Cl | H | nonafluoro-2-butyl | H | CF3 |
| 3-556 | 2-bromophenyl | H | CH2C≡CH | H | CN | H | H | Cl | H | nonafluoro-2-butyl | H | CF3 |
| 3-563 | (3-trifluoromethyl)phenyl | H | NH2 | H | CN | H | H | Cl | H | nonafluoro-2-butyl | H | CF3 |
| 3-569 | 3-cyanophenyl | H | Me | H | CN | H | H | Cl | H | nonafluoro-2-butyl | H | CF3 |
| 3-570 | 4-cyanophenyl | H | Me | H | CN | H | H | Cl | H | nonaftuoro-2-butyl | H | CF3 |
| 3-576 | 4-bromo-2-chlorophenyl | H | C(O)OMe | H | CN | H | H | Cl | H | nonafluoro-2-butyl | H | CF3 |
| 3-585 | 2-chloropyridin-3-yl | H | Me | H | CN | H | H | Cl | H | nonafluoro-2-butyl | H | CF3 |
| 3-596 | 6-nitropyridin-3-yl | H | C(O)OEt | H | CN | H | H | Cl | H | nonafluoro-2-butyl | H | CF3 |
| 3-607 | 4-bromopyridin-3-yl | H | C(O)C(O)Me | H | CN | H | H | Cl | H | nonafluoro-2-butyl | H | CF3 |
| 3-610 | 4-nitropyridin-3-yl | H | C(O)C(O)Et | H | CN | H | H | Cl | H | nonafluoro-2-butyl | H | i-C3F7 |
| 3-623 | 4-bromopyridin-2-yl | H | C(O)Me | H | CN | H | H | Cl | H | nonafluoro-2-butyl | H | CF3 |
| 3-625 | 6-chloropyridin-2-yl | H | C(O)Et | H | CN | H | H | Cl | H | nonafluoro-2-butyl | H | CF3 |
| 3-627 | phenyl | H | Me | H | CN | H | H | Br | H | heptafluoroisopropyl | H | CF3 |
| 3-641 | (3-trifluoromethyl)phenyl | H | S(O)2Me | H | CN | H | H | Br | H | heptafluoroisopropyl | H | CF3 |
| 3-647 | 3-cyanophenyl | H | Me | H | CN | H | H | Br | H | heptafluoroisopropyl | H | CF3 |
| 3-648 | 4-cyanophenyl | H | Me | H | CN | H | H | Br | H | heptafluoroisopropyl | H | CF3 |
| 3-659 | 4-cyano-2-fluorophenyl | H | S(O)2Et | H | CN | H | H | Br | H | heptafluoroisopropyl | H | CF3 |
| 3-663 | 2-chloropyridin-3-yl | H | Me | H | CN | H | H | Br | H | heptafluoroisopropyl | H | CF3 |
| 3-674 | 6-nitropyridin-3-yl | H | CH2Ph | H | CN | H | H | Br | H | heptafluoroisopropyl | H | CF3 |
| 3-688 | 4-nitropyridin-3-yl | H | CH2(3-Py) | H | CN | H | H | Br | H | heptafluoroisopropyl | H | CF3 |
| 3-702 | 5-iodopyridin-2-yl | H | CH2(3-Py-N-oxide) | H | CH | H | H | Br | H | heptafluoroisopropyl | H | CF3 |
| 3-705 | phenyl | H | Me | H | CN | H | H | Br | H | nonafluoro-2-butyl | H | CF3 |
| 3-725 | 3-cyanophenyl | H | Me | H | CN | H | H | Br | H | nonafluoro-2-butyl | H | CF3 |
| 3-726 | 4-cyanophenyl | H | Me | H | CN | H | H | Br | H | nonafluoro-2-butyl | H | CF3 |
| 3-732 | 4-bromo-2-chlorophenyl | H | Et | H | CN | H | H | Br | H | nonafluoro-2-butyl | H | CF3 |
| 3-741 | 2-chloropyridin-3-yl | H | Me | H | CN | H | H | Br | H | nonafluoro-2-butyl | H | CF3 |
| 3-758 | 5-(trifluoromethyl)pyridin-3-yl | H | CN | H | CN | H | H | Br | H | nonafluoro-2-butyl | H | CF3 |
| 3-783 | phenyl | H | Me | H | CN | H | H | I | H | heptafluoroisopropyl | H | CF3 |
| 3-803 | 3-cyanophenyl | H | Me | H | CN | H | H | I | H | heptafluoroisopropyl | H | CF3 |
| 3-804 | 4-cyanophenyl | H | Me | H | CN | H | H | I | H | heptafluoroisopropyl | H | CF3 |
| 3-819 | 2-chloropyridin-3-yl | H | Me | H | CN | H | H | I | H | heptafluoroisopropyl | H | CF3 |
| 3-841 | 4-bromopyridin-3-yl | H | C(O)Me | H | CN | H | H | I | H | heptafluoroisopropyl | H | CF3 |
| 3-861 | phenyl | H | Me | H | CN | H | H | I | H | nonafluoro-2-butyl | H | CF3 |
| 3-881 | 3-cyanophenyl | H | Me | H | CN | H | H | I | H | nonafluoro-2-butyl | H | CF3 |
| 3-882 | 4-cyanophenyl | H | Me | H | CN | H | H | I | H | nonafluoro-2-butyl | H | CF3 |
| 3-897 | 2-chloropyridin-3-yl | H | Me | H | CN | H | H | I | H | nonafluoro-2-butyl | H | CF3 |
| 3-939 | phenyl | H | Me | H | CN | H | H | OCF3 | H | heptafluoroisopropyl | H | OCF3 |
| 3-970 | 2-chloropyridin-3-yl | H | Me | H | CN | H | H | OCF3 | H | heptafluoroisopropyl | H | OCF3 |
| 3-995 | phenyl | H | Me | H | CN | H | H | OCF3 | H | nonafluoro-2-butyl | H | OCF3 |
| 3-1026 | 2-chloropyridin-3-yl | H | Me | H | CN | H | H | OCF3 | H | nonafluoro-2-butyl | H | OCF3 |
| 3-1051 | phenyl | H | Me | H | CN | H | H | CF3 | H | heptafluoroisopropyl | H | OCF3 |
| 3-1082 | 2-chloropyridin-3-yl | H | Me | H | CN | H | H | CF3 | H | heptafluoroisopropyl | H | OCF3 |
| 3-1107 | phenyl | H | Me | H | CN | H | H | CF3 | H | nonafluoro-2-butyl | H | OCF3 |
| 3-1138 | 2-chloropyridin-3-yl | H | Me | H | CN | H | H | CF3 | H | nonafluoro-2-butyl | H | OCF3 |
| 3-1163 | phenyl | H | Me | H | CN | H | H | CF3 | H | heptafluoroisopropyl | H | CF3 |
| 3-1183 | 3-cyanophenyl | H | Me | H | CN | H | H | CF3 | H | heptafluoroisopropyl | H | CF3 |
| 3-1184 | 4-cyanophenyl | H | Me | H | CN | H | H | CF3 | H | heptafluoroisopropyl | H | CF3 |
| 3-1199 | 2-chloropyridin-3-yl | H | Me | H | CN | H | H | CF3 | H | heptafluoroisopropyl | H | CF3 |
| 3-1231 | phenyl | H | Me | H | CN | H | H | CF3 | H | nonafluoro-2-butyl | H | CF3 |

TABLE 3-continued

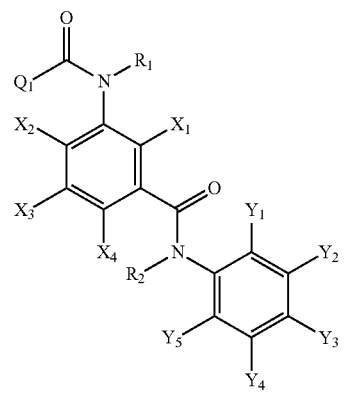

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 3-1251 | 3-cyanophenyl | H | Me | H | CN | H | H | CF3 | H | nonafluoro-2-butyl | H | C2F5 |
| 3-1252 | 4-cyanophenyl | H | Me | H | CN | H | H | CF3 | H | nonafluoro-2-butyl | H | CF3 |
| 3-1267 | 2-chloropyridin-3-yl | H | Me | H | CN | H | H | CF3 | H | nonafluoro-2-butyl | H | CF3 |
| 3-1299 | phenyl | H | Me | F | CN | H | H | Cl | H | heptafluoroisopropyl | H | OCF3 |
| 3-1319 | 3-cyanophenyl | H | Me | F | CN | H | H | Cl | H | heptafluoroisopropyl | H | OCF3 |
| 3-1320 | 4-cyanophenyl | H | Me | F | CN | H | H | Cl | H | heptafluoroisopropyl | H | OCF3 |
| 3-1335 | 2-chloropyridin-3-yl | H | Me | F | CN | H | H | Cl | H | heptafluoroisopropyl | H | OCF3 |
| 3-1377 | phenyl | H | Me | F | CN | H | H | Cl | H | nonafluoro-2-butyl | H | OCF3 |
| 3-1397 | 3-cyanophenyl | H | Me | F | CN | H | H | Cl | H | nonafluoro-2-butyl | H | OCF3 |
| 3-1398 | 4-cyanophenyl | H | Me | F | CN | H | H | Cl | H | nonafluoro-2-butyl | H | OCF3 |
| 3-1413 | 2-chloropyridin-3-yl | H | Me | F | CN | H | H | Cl | H | nonafluoro-2-butyl | H | OCF3 |
| 3-1455 | phenyl | H | Me | F | CN | H | H | Br | H | heptafluoroisopropyl | H | OCF3 |
| 3-1491 | 2-chloropyridin-3-yl | H | Me | F | CN | H | H | Br | H | heptafluoroisopropyl | H | OCF3 |
| 3-1533 | phenyl | H | Me | F | CN | H | H | Br | H | nonafluoro-2-butyl | H | OCF3 |
| 3-1553 | 3-cyanophenyl | H | Me | F | CN | H | H | Br | H | nonafluoro-2-butyl | H | OCF3 |
| 3-1554 | 4-cyanophenyl | H | Me | F | CN | H | H | Br | H | nonafluoro-2-butyl | H | OCF3 |
| 3-1569 | 2-chloropyridin-3-yl | H | Me | F | CN | H | H | Br | H | nonafluoro-2-butyl | H | OCF3 |
| 3-1611 | phenyl | H | Me | F | CN | H | H | I | H | heptafluoroisopropyl | H | OCF3 |
| 3-1631 | 3-cyanophenyl | H | Me | F | CN | H | H | I | H | heptafluoroisopropyl | H | OCF3 |
| 3-1632 | 4-cyanophenyl | H | Me | F | CN | H | H | I | H | heptafluoroisopropyl | H | OCF3 |
| 3-1647 | 2-chloropyridin-3-yl | H | Me | F | CN | H | H | I | H | heptafluoroisopropyl | H | OCF3 |
| 3-1689 | phenyl | H | Me | F | CN | H | H | I | H | nonafluoro-2-butyl | H | OCF3 |
| 3-1709 | 3-cyanophenyl | H | Me | F | CN | H | H | I | H | nonafluoro-2-butyl | H | OCF3 |
| 3-1710 | 4-cyanophenyl | H | Me | F | CN | H | H | I | H | nonafluoro-2-butyl | H | OCF3 |
| 3-1725 | 2-chloropyridin-3-yl | H | Me | F | CN | H | H | I | H | nonafluoro-2-butyl | H | OCF3 |
| 3-1767 | phenyl | H | Me | F | CN | H | H | F | H | heptafluoroisopropyl | H | CF3 |
| 3-1768 | phenyl | H | Me | F | CN | H | H | Cl | H | heptafluoroisopropyl | H | CF3 |
| 3-1788 | 3-cyanophenyl | H | Me | F | CN | H | H | Cl | H | heptafluoroisopropyl | H | CF3 |
| 3-1789 | 4-cyanophenyl | H | Me | F | CN | H | H | Cl | H | heptafluoroisopropyl | H | CF3 |
| 3-1804 | 2-chloropyridin-3-yl | H | Me | F | CN | H | H | Cl | H | heptafluoroisopropyl | H | CF3 |
| 3-1846 | phenyl | H | Me | F | CN | H | H | F | H | nonafluoro-2-butyl | H | CF3 |
| 3-1847 | phenyl | H | Me | F | CN | H | H | Cl | H | nonafluoro-2-butyl | H | CF3 |
| 3-1867 | 3-cyanophenyl | H | Me | F | CN | H | H | Cl | H | nonafluoro-2-butyl | H | CF3 |
| 3-1868 | 4-cyanophenyl | H | Me | F | CN | H | H | Cl | H | nonafluoro-2-butyl | H | CF3 |
| 3-1883 | 2-chloropyridin-3-yl | H | Me | F | CN | H | H | Cl | H | nonafluoro-2-butyl | H | CF3 |
| 3-1925 | phenyl | H | Me | F | CN | H | H | Br | H | heptafluoroisopropyl | H | CF3 |
| 3-1945 | 3-cyanophenyl | H | Me | F | CN | H | H | Br | H | heptafluoroisopropyl | H | CF3 |
| 3-1946 | 4-cyanophenyl | H | Me | F | CN | H | H | Br | H | heptafluoroisopropyl | H | CF3 |
| 3-1961 | 2-chloropyridin-3-yl | H | Me | F | CN | H | H | Br | H | heptafluoroisopropyl | H | CF3 |
| 3-2003 | phenyl | H | Me | F | CN | H | H | Br | H | nonafluoro-2-butyl | H | CF3 |
| 3-2023 | 3-cyanophenyl | H | Me | F | CN | H | H | Br | H | nonafluoro-2-butyl | H | CF3 |
| 3-2024 | 4-cyanophenyl | H | Me | F | CN | H | H | Br | H | nonafluoro-2-butyl | H | CF3 |
| 3-2039 | 2-chloropyridin-3-yl | H | Me | F | CN | H | H | Br | H | nonafluoro-2-butyl | H | CF3 |
| 3-2081 | phenyl | H | Me | F | CN | H | H | I | H | heptafluoroisopropyl | H | CF3 |
| 3-2101 | 3-cyanophenyl | H | Me | F | CN | H | H | I | H | heptafluoroisopropyl | H | CF3 |
| 3-2102 | 4-cyanophenyl | H | Me | F | CN | H | H | I | H | heptafluoroisopropyl | H | CF3 |
| 3-2117 | 2-chloropyridin-3-yl | H | Me | F | CN | H | H | I | H | heptafluoroisopropyl | H | CF3 |
| 3-2159 | phenyl | H | Me | F | CN | H | H | I | H | nonafluoro-2-butyl | H | CF3 |
| 3-2179 | 3-cyanophenyl | H | Me | F | CN | H | H | I | H | nonafluoro-2-butyl | H | CF3 |
| 3-2180 | 4-cyanophenyl | H | Me | F | CN | H | H | I | H | nonafluoro-2-butyl | H | CF3 |
| 3-2195 | 2-chloropyridin-3-yl | H | Me | F | CN | H | H | I | H | nonafluoro-2-butyl | H | CF3 |
| 3-2237 | phenyl | H | Me | F | CN | H | H | OCF3 | H | heptafluoroisopropyl | H | OCF3 |
| 3-2268 | 2-chloropyridin-3-yl | H | Me | F | CN | H | H | OCF3 | H | heptafluoroisopropyl | H | OCF3 |
| 3-2293 | phenyl | H | Me | F | CN | H | H | OCF3 | H | nonafluoro-2-butyl | H | OCF3 |
| 3-2324 | 2-chloropyridin-3-yl | H | Me | F | CN | H | H | OCF3 | H | nonafluoro-2-butyl | H | OCF3 |
| 3-2349 | phenyl | H | Me | F | CN | H | H | CF3 | H | heptafluoroisopropyl | H | OCF3 |
| 3-2380 | 2-chloropyridin-3-yl | H | Me | F | CN | H | H | CF3 | H | heptafluoroisopropyl | H | OCF3 |

TABLE 3-continued

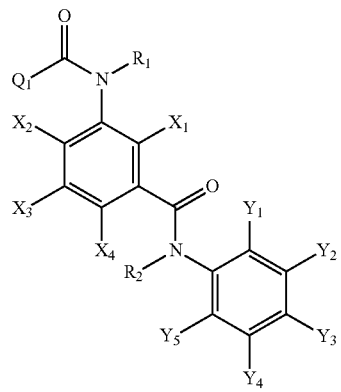

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 3-2405 | phenyl | H | Me | F | CN | H | H | CF3 | H | nonafluoro-2-butyl | H | OCF3 |
| 3-2436 | 2-chloropyridin-3-yl | H | Me | F | CN | H | H | CF3 | H | nonafluoro-2-butyl | H | OCF3 |
| 3-2461 | phenyl | H | Me | F | CN | H | H | CF3 | H | heptafluoroisopropyl | H | CF3 |
| 3-2481 | 3-cyanophenyl | H | Me | F | CN | H | H | CF3 | H | heptafluoroisopropyl | H | CF3 |
| 3-2482 | 4-cyanophenyl | H | Me | F | CN | H | H | CF3 | H | heptafluoroisopropyl | H | CF3 |
| 3-2497 | 2-chloropyridin-3-yl | H | Me | F | CN | H | H | CF3 | H | heptafluoroisopropyl | H | CF3 |
| 3-2529 | phenyl | H | Me | F | CN | H | H | CF3 | H | nonafluoro-2-butyl | H | CF3 |
| 3-2549 | 3-cyanophenyl | H | Me | F | CN | H | H | CF3 | H | nonafluoro-2-butyl | H | CF3 |
| 3-2550 | 4-cyanophenyl | H | Me | F | CN | H | H | CF3 | H | nonafluoro-2-butyl | H | CF3 |
| 3-2565 | 2-chloropyridin-3-yl | H | Me | F | CN | H | H | CF3 | H | nonafluoro-2-butyl | H | CF3 |
| 3-2597 | phenyl | H | Me | F | CN | F | H | Cl | H | heptafluoroisopropyl | H | OCF3 |
| 3-2617 | 3-cyanophenyl | H | Me | F | CN | F | H | Cl | H | heptafluoroisopropyl | H | OCF3 |
| 3-2618 | 4-cyanophenyl | H | Me | F | CN | F | H | Cl | H | heptafluoroisopropyl | H | OCF3 |
| 3-2633 | 2-chloropyridin-3-yl | H | Me | F | CN | F | H | Cl | H | heptafluoroisopropyl | H | OCF3 |
| 3-2675 | phenyl | H | Me | F | CN | F | H | Cl | H | nonafluoro-2-butyl | H | OCF3 |
| 3-2695 | 3-cyanophenyl | H | Me | F | CN | F | H | Cl | H | nonafluoro-2-butyl | H | OCF3 |
| 3-2696 | 4-cyanophenyl | H | Me | F | CN | F | H | Cl | H | nonafluoro-2-butyl | H | OCF3 |
| 3-2711 | 2-chloropyridin-3-yl | H | Me | F | CN | F | H | Cl | H | nonafluoro-2-butyl | H | OCF3 |
| 3-2753 | phenyl | H | Me | F | CN | F | H | Br | H | heptafluoroisopropyl | H | OCF3 |
| 3-2773 | 3-cyanophenyl | H | Me | F | CN | F | H | Br | H | heptafluoroisopropyl | H | OCF3 |
| 3-2774 | 4-cyanophenyl | H | Me | F | CN | F | H | Br | H | heptafluoroisopropyl | H | OCF3 |
| 3-2789 | 2-chloropyridin-3-yl | H | Me | F | CN | F | H | Br | H | heptafluoroisopropyl | H | OCF3 |
| 3-2831 | phenyl | H | Me | F | CN | F | H | Br | H | nonafluoro-2-butyl | H | OCF3 |
| 3-2851 | 3-cyanophenyl | H | Me | F | CN | F | H | Br | H | nonafluoro-2-butyl | H | OCF3 |
| 3-2852 | 4-cyanophenyl | H | Me | F | CN | F | H | Br | H | nonafluoro-2-butyl | H | OCF3 |
| 3-2867 | 2-chloropyridin-3-yl | H | Me | F | CN | F | H | Br | H | nonafluoro-2-butyl | H | OCF3 |
| 3-2909 | phenyl | H | Me | F | CN | F | H | I | H | heptafluoroisopropyl | H | OCF3 |
| 3-2929 | 3-cyanophenyl | H | Me | F | CN | F | H | I | H | heptafluoroisopropyl | H | OCF3 |
| 3-2930 | 4-cyanophenyl | H | Me | F | CN | F | H | I | H | heptafluoroisopropyl | H | OCF3 |
| 3-2945 | 2-chloropyridin-3-yl | H | Me | F | CN | F | H | I | H | heptafluoroisopropyl | H | OCF3 |
| 3-2987 | phenyl | H | Me | F | CN | F | H | I | H | nonafluoro-2-butyl | H | OCF3 |
| 3-2988 | 2-fluorophenyl | H | Me | F | CN | F | H | I | H | nonafluoro-2-butyl | H | OCF3 |
| 3-3007 | 3-cyanophenyl | H | Me | F | CN | F | H | I | H | nonafluoro-2-butyl | H | OCF3 |
| 3-3008 | 4-cyanophenyl | H | Me | F | CN | F | H | I | H | nonafluoro-2-butyl | H | OCF3 |
| 3-3023 | 2-chloropyridin-3-yl | H | Me | F | CN | F | H | I | H | nonafluoro-2-butyl | H | OCF3 |
| 3-3065 | phenyl | H | Me | F | CN | F | H | F | H | heptafluoroisopropyl | H | CF3 |
| 3-3066 | phenyl | H | Me | F | CN | F | H | Cl | H | heptafluoroisopropyl | H | CF3 |
| 3-3086 | 3-cyanophenyl | H | Me | F | CN | F | H | Cl | H | heptafluoroisopropyl | H | CF3 |
| 3-3087 | 4-cyanophenyl | H | Me | F | CN | F | H | Cl | H | heptafluoroisopropyl | H | CF3 |
| 3-3102 | 2-chloropyridin-3-yl | H | Me | F | CN | F | H | Cl | H | heptafluoroisopropyl | H | CF3 |
| 3-3144 | phenyl | H | Me | F | CN | F | H | F | H | nonafluoro-2-butyl | H | CF3 |
| 3-3145 | phenyl | H | Me | F | CN | F | H | Cl | H | nonafluoro-2-butyl | H | CF3 |
| 3-3165 | 3-cyanophenyl | H | Me | F | CN | F | H | Cl | H | nonafluoro-2-butyl | H | CF3 |
| 3-3166 | 4-cyanophenyl | H | Me | F | CN | F | H | Cl | H | nonafluoro-2-butyl | H | CF3 |
| 3-3181 | 2-chloropyridin-3-yl | H | Me | F | CN | F | H | Cl | H | nonafluoro-2-butyl | H | CF3 |
| 3-3223 | phenyl | H | Me | F | CN | F | H | Br | H | heptafluoroisopropyl | H | CF3 |
| 3-3243 | 3-cyanophenyl | H | Me | F | CN | F | H | Br | H | heptafluoroisopropyl | H | CF3 |
| 3-3244 | 4-cyanophenyl | H | Me | F | CN | F | H | Br | H | heptafluoroisopropyl | H | CF3 |
| 3-3259 | 2-chloropyridin-3-yl | H | Me | F | CN | F | H | Br | H | heptafluoroisopropyl | H | CF3 |
| 3-3301 | phenyl | H | Me | F | CN | F | H | Br | H | nonafluoro-2-butyl | H | CF3 |
| 3-3321 | 3-cyanophenyl | H | Me | F | CN | F | H | Br | H | nonafluoro-2-butyl | H | CF3 |
| 3-3322 | 4-cyanophenyl | H | Me | F | CN | F | H | Br | H | nonafluoro-2-butyl | H | CF3 |
| 3-3337 | 2-chloropyridin-3-yl | H | Me | F | CN | F | H | Br | H | nonafluoro-2-butyl | H | CF3 |
| 3-3379 | phenyl | H | Me | F | CN | F | H | I | H | heptafluoroisopropyl | H | CF3 |
| 3-3399 | 3-cyanophenyl | H | Me | F | CN | F | H | I | H | heptafluoroisopropyl | H | CF3 |
| 3-3400 | 4-cyanophenyl | H | Me | F | CN | F | H | I | H | heptafluoroisopropyl | H | CF3 |
| 3-3415 | 2-chloropyridin-3-yl | H | Me | F | CN | F | H | I | H | heptafluoroisopropyl | H | CF3 |

TABLE 3-continued

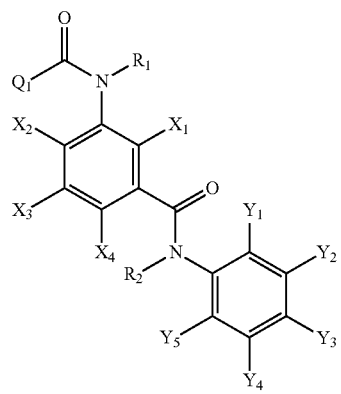

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 3-3457 | phenyl | H | Me | F | CN | F | H | I | H | nonafluoro-2-butyl | H | CF3 |
| 3-3477 | 3-cyanophenyl | H | Me | F | CN | F | H | I | H | nonafluoro-2-butyl | H | CF3 |
| 3-3478 | 4-cyanophenyl | H | Me | F | CN | F | H | I | H | nonafluoro-2-butyl | H | CF3 |
| 3-3493 | 2-chloropyridin-3-yl | H | Me | F | CN | F | H | I | H | nonafluoro-2-butyl | H | CF3 |
| 3-3535 | phenyl | H | Me | F | CN | F | H | OCF3 | H | heptafluoroisopropyl | H | OCF3 |
| 3-3566 | 2-chloropyridin-3-yl | H | Me | F | CN | F | H | OCF3 | H | heptafluoroisopropyl | H | OCF3 |
| 3-3591 | phenyl | H | Me | F | CN | F | H | OCF3 | H | nonafluoro-2-butyl | H | OCF3 |
| 3-3622 | 2-chloropyridin-3-yl | H | Me | F | CN | F | H | OCF3 | H | nonafluoro-2-butyl | H | OCF3 |
| 3-3647 | phenyl | H | Me | F | CN | F | H | CF3 | H | heptafluoroisopropyl | H | OCF3 |
| 3-3678 | 2-chloropyridin-3-yl | H | Me | F | CN | F | H | CF3 | H | heptafluoroisopropyl | H | OCF3 |
| 3-3703 | phenyl | H | Me | F | CN | F | H | CF3 | H | nonafluoro-2-butyl | H | OCF3 |
| 3-3734 | 2-chloropyridin-3-yl | H | Me | F | CN | F | H | CF3 | H | nonafluoro-2-butyl | H | OCF3 |
| 3-3759 | phenyl | H | Me | F | CN | F | H | CF3 | H | heptafluoroisopropyl | H | CF3 |
| 3-3779 | 3-cyanophenyl | H | Me | F | CN | F | H | CF3 | H | heptafluoroisopropyl | H | CF3 |
| 3-3780 | 4-cyanophenyl | H | Me | F | CN | F | H | CF3 | H | heptafluoroisopropyl | H | CF3 |
| 3-3795 | 2-chloropyridin-3-yl | H | Me | F | CN | F | H | CF3 | H | heptafluoroisopropyl | H | CF3 |

TABLE 4

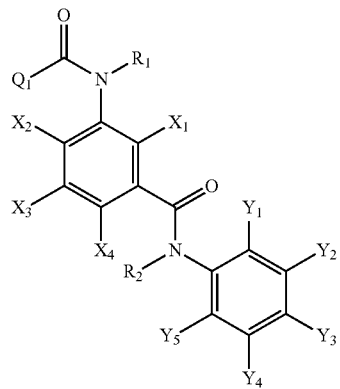

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 4-1 | phenyl | Me | Me | H | CN | H | H | Cl | H | heptafluoroisopropyl | H | OCF3 |
| 4-21 | 3-cyanophenyl | Me | Me | H | CN | H | H | Cl | H | heptafluoroisopropyl | H | OCF3 |
| 4-22 | 4-cyanophenyl | Me | Me | H | CN | H | H | Cl | H | heptafluoroisopropyl | H | OCF3 |
| 4-37 | 2-chloropyridin-3-yl | Me | Me | H | CN | H | H | Cl | H | heptafluoroisopropyl | H | OCF3 |
| 4-79 | phenyl | Me | Me | H | CN | H | H | Cl | H | nonafluoro-2-butyl | H | OCF3 |
| 4-99 | 3-cyanophenyl | Me | Me | H | CN | H | H | Cl | H | nonafluoro-2-butyl | H | OCF3 |
| 4-100 | 4-cyanophenyl | Me | Me | H | CN | H | H | Cl | H | nonafluoro-2-butyl | H | OCF3 |
| 4-115 | 2-chloropyridin-3-yl | Me | Me | H | CN | H | H | Cl | H | nonafluoro-2-butyl | H | OCF3 |
| 4-157 | phenyl | Me | Me | H | CN | H | H | Br | H | heptafluoroisopropyl | H | OCF3 |
| 4-177 | 3-cyanophenyl | Me | Me | H | CN | H | H | Br | H | heptafluoroisopropyl | H | OCF3 |
| 4-178 | 4-cyanophenyl | Me | Me | H | CN | H | H | Br | H | heptafluoroisopropyl | H | OCF3 |
| 4-193 | 2-chloropyridin-3-yl | Me | Me | H | CN | H | H | Br | H | heptafluoroisopropyl | H | OCF3 |
| 4-235 | phenyl | Me | Me | H | CN | H | H | Br | H | nonafluoro-2-butyl | H | OCF3 |
| 4-255 | 3-cyanophenyl | Me | Me | H | CN | H | H | Br | H | nonafluoro-2-butyl | H | OCF3 |

TABLE 4-continued

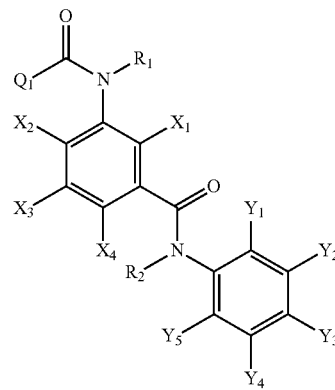

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 4-256 | 4-cyanophenyl | Me | Me | H | CN | H | H | Br | H | nonafluoro-2-butyl | H | OCF3 |
| 4-271 | 2-chloropyridin-3-yl | Me | Me | H | CN | H | H | Br | H | nonafluoro-2-butyl | H | OCF3 |
| 4-313 | phenyl | Me | Me | H | CN | H | H | I | H | heptafluoroisopropyl | H | OCF3 |
| 4-314 | 2-fluorophenyl | Me | Me | H | CN | H | H | I | H | heptafluoroisopropyl | H | OCF3 |
| 4-333 | 3-cyanophenyl | Me | Me | H | CN | H | H | I | H | heptafluoroisopropyl | H | OCF3 |
| 4-334 | 4-cyanophenyl | Me | Me | H | CN | H | H | I | H | heptafluoroisopropyl | H | OCF3 |
| 4-349 | 2-chloropyridin-3-yl | Me | Me | H | CN | H | H | I | H | heptafluoroisopropyl | H | OCF3 |
| 4-391 | phenyl | Me | Me | H | CN | H | H | I | H | nonafluoro-2-butyl | H | OCF3 |
| 4-392 | 2-fluorophenyl | Me | Me | H | CN | H | H | I | H | nonafluoro-2-butyl | H | OCF3 |
| 4-411 | 3-cyanophenyl | Me | Me | H | CN | H | H | I | H | nonafluoro-2-butyl | H | OCF3 |
| 4-412 | 4-cyanophenyl | Me | Me | H | CN | H | H | I | H | nonafluoro-2-butyl | H | OCF3 |
| 4-427 | 2-chloropyridin-3-yl | Me | Me | H | CN | H | H | I | H | nonafluoro-2-butyl | H | OCF3 |
| 4-665 | phenyl | Me | Me | H | CN | H | H | Cl | H | heptafluoroisopropyl | H | CF3 |
| 4-666 | (3-trifluoromethyl)phenyl | Et | Me | H | CN | H | H | Cl | H | heptafluoroisopropyl | H | CF3 |
| 4-667 | (4-trifluoromethyl)phenyl | Me | Et | H | CN | H | H | Cl | H | heptafluoroisopropyl | H | CF3 |
| 4-671 | 2-cyanophenyl | Me | Me | H | CN | H | H | Cl | H | pentafluoroethyl | H | C2F5 |
| 4-672 | 3-cyanophenyl | Me | Me | H | CN | H | H | Cl | H | heptafluoroisopropyl | H | CF3 |
| 4-673 | 4-cyanophenyl | Me | Me | H | CN | H | H | Cl | H | heptafluoroisopropyl | H | CF3 |
| 4-676 | 2,4-dichlorophenyl | Me | Me | H | CN | H | H | Cl | H | heptafluoroisopropyl | H | C2F5 |
| 4-677 | 2-chloro-4-fluorophenyl | n-Pr | Me | H | CN | H | H | Cl | H | heptafluoroisopropyl | H | CF3 |
| 4-680 | 2-bromo-4-chlorophenyl | Me | Me | H | CN | H | H | Cl | H | heptafluoroisopropyl | H | n-C3F7 |
| 4-681 | 2-bromo-4-fluorophenyl | Me | n-Pr | H | CN | H | H | Cl | H | heptafluoroisopropyl | H | CF3 |
| 4-687 | 2-fluoropyridin-3-yl | Me | Me | H | CN | H | H | Cl | H | pentafluoroethyl | H | CF3 |
| 4-688 | 2-chloropyridin-3-yl | Me | Me | H | CN | H | H | Cl | H | heptafluoroisopropyl | H | CF3 |
| 4-692 | 2-nitropyridin-3-yl | Me | i-Pr | H | CN | H | H | Cl | H | heptafluoroisopropyl | H | CF3 |
| 4-694 | 6-fluoropyridin-3-yl | i-Pr | Me | H | CN | H | H | Cl | H | heptafluoroisopropyl | H | CF3 |
| 4-701 | 5-fluoropyridin-3-yl | Me | Me | H | CN | H | H | Cl | H | heptafluoroisopropyl | H | C2F5 |
| 4-703 | 5-bromopyridin-3-yl | Me | Me | H | CN | H | H | Cl | H | heptafluoroisopropyl | H | n-C3F7 |
| 4-704 | 5-iodopyridin-3-yl | Me | Me | H | CN | H | H | Cl | H | heptafluoroisopropyl | H | i-C3F7 |
| 4-706 | 5-nitropyridin-3-yl | Me | CH2CH=CH2 | H | CN | H | H | Cl | H | pentafluoroethyl | H | CF3 |
| 4-708 | 4-fluoropyridin-3-yl | Me | Me | H | CN | H | H | Cl | H | pentafluoroethyl | H | CF3 |
| 4-710 | 4-bromopyridin-3-yl | CH2CH=CH2 | Me | H | CN | H | H | Cl | H | heptafluoroisopropyl | H | n-C3F7 |
| 4-711 | 4-iodopyridin-3-yl | Me | Me | H | CN | H | H | Cl | H | heptafluoroisopropyl | H | i-C3F7 |
| 4-717 | pyridin-4-yl | CN | Me | H | CN | H | H | Cl | H | heptafluoroisopropyl | H | CF3 |
| 4-724 | pyridin-2-yl | Me | CN | H | CN | H | H | Cl | H | heptafluoroisopropyl | H | CF3 |
| 4-729 | 4-cyanopyridin-2-yl | Me | Me | H | CN | H | H | Cl | H | pentafluoroethyl | H | CF3 |
| 4-730 | phenyl | Me | Me | H | CN | H | H | Fl | H | nonafluoro-2-butyl | H | CF3 |
| 4-731 | phenyl | Me | Me | H | CN | H | H | Cl | H | nonafluoro-2-butyl | H | CF3 |
| 4-732 | 2-fluorophenyl | Me | Me | H | CN | H | H | Cl | H | nonafluoro-2-butyl | H | CF3 |
| 4-739 | 3-bromophenyl | CH2C≡CH | Me | H | CN | H | H | Cl | H | nonafluoro-2-butyl | H | CF3 |
| 4-744 | (2-trifluoromethyl)phenyl | Me | Me | H | CN | H | H | Cl | H | nonafluoro-2-butyl | H | C2F5 |
| 4-745 | (3-trifluoromethyl)phenyl | Me | CH2C≡CH | H | CN | H | H | Cl | H | nonafluoro-2-butyl | H | CF3 |
| 4-746 | (4-trifluoromethyl)phenyl | NH2 | Me | H | CN | H | H | Cl | H | nonafluoro-2-butyl | H | CF3 |
| 4-750 | 2-cyanophenyl | Me | NH2 | H | CN | H | H | Cl | H | nonafluoro-2-butyl | H | CF3 |
| 4-751 | 3-cyanophenyl | Me | Me | H | CN | H | H | Cl | H | nonafluoro-2-butyl | H | CF3 |
| 4-752 | 4-cyanophenyl | Me | Me | H | CN | H | H | Cl | H | nonafluoro-2-butyl | H | CF3 |
| 4-759 | 2-bromo-4-chlorophenyl | C(O)OMe | Me | H | CN | H | H | Cl | H | nonafluoro-2-butyl | H | CF3 |
| 4-761 | 2-chloro-4-nitrophenyl | Me | C(O)OMe | H | CN | H | H | Cl | H | nonafluoro-2-butyl | H | i-C3F7 |
| 4-767 | 2-chloropyridin-3-yl | Me | Me | H | CN | H | H | Cl | H | nonafluoro-2-butyl | H | CF3 |
| 4-773 | 6-fluoropyridin-3-yl | Me | C(O)OEt | H | CN | H | H | Cl | H | nonafluoro-2-butyl | H | CF3 |
| 4-780 | 5-fluoropyridin-3-yl | C(O)OEt | Me | H | CN | H | H | Cl | H | nonafluoro-2-butyl | H | C2F5 |
| 4-781 | 5-chloropyridin-3-yl | Me | Me | H | CN | H | H | Cl | H | nonafluoro-2-butyl | H | CF3 |
| 4-782 | 5-bromopyridin-3-yl | Me | Me | H | CN | H | H | Cl | H | nonafluoro-2-butyl | H | n-C3F7 |
| 4-783 | 5-iodopyridin-3-yl | Me | Me | H | CN | H | H | Cl | H | nonafluoro-2-butyl | H | i-C3F7 |
| 4-785 | 5-nitropyridin-3-yl | Me | C(O)C(O)Me | H | CN | H | H | Cl | H | nonafluoro-2-butyl | H | CF3 |
| 4-787 | 4-fluoropyridin-3-yl | Me | Me | H | CN | H | H | Cl | H | nonafluoro-2-butyl | H | C2F5 |
| 4-789 | 4-bromopyridin-3-yl | C(O)C(O)Me | Me | H | CN | H | H | Cl | H | nonafluoro-2-butyl | H | CF3 |
| 4-790 | 4-iodopyridin-3-yl | Me | C(O)C(O)Et | H | CN | H | H | Cl | H | nonafluoro-2-butyl | H | CF3 |

TABLE 4-continued

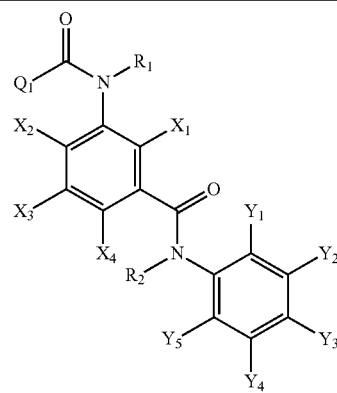

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 4-791 | 4-(trifluoromethyl)pyridin-3-yl | Me | Me | H | CN | H | H | Cl | H | nonafluoro-2-butyl | H | n-C3F7 |
| 4-792 | 4-nitropyridin-3-yl | C(O)C(O)Et | Me | H | CN | H | H | Cl | H | nonafluoro-2-butyl | H | i-C3F7 |
| 4-803 | pyridin-2-yl | Me | C(O)Me | H | CN | H | H | Cl | H | nonafluoro-2-butyl | H | CF3 |
| 4-805 | 4-bromopyridin-2-yl | Me | C(O)Et | H | CN | H | H | Cl | H | nonafluoro-2-butyl | H | CF3 |
| 4-806 | 5-iodopyridin-2-yl | C(O)Me | Me | H | CN | H | H | Cl | H | nonafluoro-2-butyl | H | CF3 |
| 4-808 | 4-cyanopyridin-2-yl | C(O)Et | Me | H | CN | H | H | Cl | H | nonafluoro-2-butyl | H | C2F5 |
| 4-809 | phenyl | Me | Me | H | CN | H | H | Br | H | heptafluoroisopropyl | H | CF3 |
| 4-823 | (3-trifluoromethyl)phenyl | S(O)2Me | Me | H | CN | H | H | Br | H | heptafluoroisopropyl | H | CF3 |
| 4-828 | 2-cyanophenyl | Me | S(O)2Me | H | CN | H | H | Br | H | heptafluoroisopropyl | H | CF3 |
| 4-829 | 3-cyanophenyl | Me | Me | H | CN | H | H | Br | H | heptafluoroisopropyl | H | CF3 |
| 4-830 | 4-cyanophenyl | Me | Me | H | CN | H | H | Br | H | heptafluoroisopropyl | H | CF3 |
| 4-839 | 2-chloro-4-nitrophenyl | Me | S(O)2Et | H | CN | H | H | Br | H | heptafluoroisopropyl | H | CF3 |
| 4-841 | 4-cyano-2-fluorophenyl | S(O)2Et | Me | H | CN | H | H | Br | H | heptafluoroisopropyl | H | CF3 |
| 4-845 | 2-chloropyridin-3-yl | Me | Me | H | CN | H | H | Br | H | heptafluoroisopropyl | H | CF3 |
| 4-853 | 6-bromopyridin-3-yl | Me | CH2Ph | H | CN | H | H | Br | H | heptafluoroisopropyl | H | CF3 |
| 4-855 | 6-(trifluoromethyl)pyridin-3-yl | Me | Me | H | CN | H | H | Br | H | heptafluoroisopropyl | H | CF3 |
| 4-856 | 6-nitropyridin-3-yl | CH2Ph | Me | H | CN | H | H | Br | H | heptafluoroisopropyl | H | CF3 |
| 4-863 | 5-nitropyridin-3-yl | Me | CH2(3-Py) | H | CN | H | H | Br | H | heptafluoroisopropyl | H | CF3 |
| 4-865 | 4-fluoropyridin-3-yl | CH2(3-Py) | Me | H | CN | H | H | Br | H | heptafluoroisopropyl | H | CF3 |
| 4-883 | 4-bromopyridin-2-yl | Me | CH2(3-Py-N-oxide) | H | CN | H | H | Br | H | heptafluoroisopropyl | H | CF3 |
| 4-886 | 4-cyanopyridin-2-yl | CH2(3-Py-N-oxide) | Me | H | CN | H | H | Br | H | heptafluoroisopropyl | H | CF3 |
| 4-887 | phenyl | Me | Me | H | CN | H | H | Br | H | nonafluoro-2-butyl | H | CF3 |
| 4-907 | 3-cyanophenyl | Me | Me | H | CN | H | H | Br | H | nonafluoro-2-butyl | H | CF3 |
| 4-908 | 4-cyanophenyl | Me | Me | H | CN | H | H | Br | H | nonafluoro-2-butyl | H | CF3 |
| 4-923 | 2-chloropyridin-3-yl | Me | Me | H | CN | H | H | Br | H | nonafluoro-2-butyl | H | CF3 |
| 4-965 | phenyl | Me | Me | H | CN | H | H | I | H | heptafluoroisopropyl | H | CF3 |
| 4-985 | 3-cyanophenyl | Me | Me | H | CN | H | H | I | H | heptafluoroisopropyl | H | CF3 |
| 4-986 | 4-cyanophenyl | Me | Me | H | CN | H | H | I | H | heptafluoroisopropyl | H | CF3 |
| 4-1001 | 2-chloropyridin-3-yl | Me | Me | H | CN | H | H | I | H | heptafluoroisopropyl | H | CF3 |
| 4-1043 | phenyl | Me | Me | H | CN | H | H | I | H | nonafluoro-2-butyl | H | CF3 |
| 4-1063 | 3-cyanophenyl | Me | Me | H | CN | H | H | I | H | nonafluoro-2-butyl | H | CF3 |
| 4-1064 | 4-cyanophenyl | Me | Me | H | CN | H | H | I | H | nonafluoro-2-butyl | H | CF3 |
| 4-1079 | 2-chloropyridin-3-yl | Me | Me | H | CN | H | H | I | H | nonafluoro-2-butyl | H | CF3 |
| 4-1121 | phenyl | Et | Et | H | CN | H | H | I | H | nonafluoro-2-butyl | H | CF3 |
| 4-1122 | phenyl | Et | n-Pr | H | CN | H | H | I | H | nonafluoro-2-butyl | H | CF3 |
| 4-1123 | phenyl | Et | i-Pr | H | CN | H | H | I | H | nonafluoro-2-butyl | H | CF3 |
| 4-1124 | phenyl | Et | CH2CH=CH2 | H | CN | H | H | I | H | nonafluoro-2-butyl | H | CF3 |
| 4-1125 | phenyl | Et | CN | H | CN | H | H | I | H | nonafluoro-2-butyl | H | CF3 |
| 4-1126 | phenyl | Et | CH2C≡CH | H | CN | H | H | I | H | nonafluoro-2-butyl | H | CF3 |
| 4-1127 | phenyl | Et | NH2 | H | CN | H | H | I | H | nonafluoro-2-butyl | H | CF3 |
| 4-1128 | phenyl | Et | C(O)OMe | H | CN | H | H | I | H | nonafluoro-2-butyl | H | CF3 |
| 4-1129 | phenyl | Et | C(O)C(O)OMe | H | CN | H | H | I | H | nonafluoro-2-butyl | H | CF3 |
| 4-1130 | phenyl | Et | C(O)Me | H | CN | H | H | I | H | nonafluoro-2-butyl | H | CF3 |
| 4-1131 | phenyl | Et | S(O)2Me | H | CN | H | H | I | H | nonafluoro-2-butyl | H | CF3 |
| 4-1132 | phenyl | Et | CH2Ph | H | CN | H | H | I | H | nonafluoro-2-butyl | H | CF3 |
| 4-1133 | phenyl | Et | CH2(3-Py) | H | CN | H | H | I | H | nonafluoro-2-butyl | H | CF3 |
| 4-1134 | phenyl | Et | CH2(3-Py-N-oxide) | H | CN | H | H | I | H | nonafluoro-2-butyl | H | CF3 |
| 4-1135 | phenyl | n-Pr | Et | H | CN | H | H | I | H | nonafluoro-2-butyl | H | CF3 |
| 4-1136 | phenyl | n-Pr | n-Pr | H | CN | H | H | I | H | nonafluoro-2-butyl | H | CF3 |
| 4-1137 | phenyl | n-Pr | i-Pr | H | CN | H | H | I | H | nonafluoro-2-butyl | H | CF3 |
| 4-1138 | phenyl | n-Pr | CH2CH=CH2 | H | CN | H | H | I | H | nonafluoro-2-butyl | H | CF3 |
| 4-1139 | phenyl | n-Pr | CN | H | CN | H | H | I | H | nonafluoro-2-butyl | H | CF3 |
| 4-1140 | phenyl | n-Pr | CH2C≡CH | H | CN | H | H | I | H | nonafluoro-2-butyl | H | CF3 |
| 4-1141 | phenyl | n-Pr | NH2 | H | CN | H | H | I | H | nonafluoro-2-butyl | H | CF3 |
| 4-1142 | phenyl | n-Pr | C(O)OMe | H | CN | H | H | I | H | nonafluoro-2-butyl | H | CF3 |

TABLE 4-continued

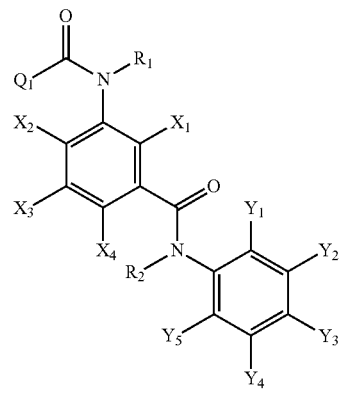

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 4-1143 | phenyl | n-Pr | C(O)C(O)OMe | H | CN | H | H | I | H | nonafluoro-2-butyl | H | CF3 |
| 4-1144 | phenyl | n-Pr | C(O)Me | H | CN | H | H | I | H | nonafluoro-2-butyl | H | CF3 |
| 4-1145 | phenyl | n-Pr | S(O)2Me | H | CN | H | H | I | H | nonafluoro-2-butyl | H | CF3 |
| 4-1146 | phenyl | n-Pr | CH2Ph | H | CN | H | H | I | H | nonafluoro-2-butyl | H | CF3 |
| 4-1147 | phenyl | n-Pr | CH2(3-Py) | H | CN | H | H | I | H | nonafluoro-2-butyl | H | CF3 |
| 4-1148 | phenyl | n-Pr | CH2(3-Py-N-oxide) | H | CN | H | H | I | H | nonafluoro-2-butyl | H | CF3 |
| 4-1149 | phenyl | i-Pr | Et | H | CN | H | H | I | H | nonafluoro-2-butyl | H | CF3 |
| 4-1150 | phenyl | i-Pr | n-Pr | H | CN | H | H | I | H | nonafluoro-2-butyl | H | CF3 |
| 4-1151 | phenyl | i-Pr | i-Pr | H | CN | H | H | I | H | nonafluoro-2-butyl | H | CF3 |
| 4-1152 | phenyl | i-Pr | CH2CH=CH2 | H | CN | H | H | I | H | nonafluoro-2-butyl | H | CF3 |
| 4-1153 | phenyl | i-Pr | CN | H | CN | H | H | I | H | nonafluoro-2-butyl | H | CF3 |
| 4-1154 | phenyl | i-Pr | CH2C≡CH | H | CN | H | H | I | H | nonafluoro-2-butyl | H | CF3 |
| 4-1155 | phenyl | i-Pr | NH2 | H | CN | H | H | I | H | nonafluoro-2-butyl | H | CF3 |
| 4-1156 | phenyl | i-Pr | C(O)OMe | H | CN | H | H | I | H | nonafluoro-2-butyl | H | CF3 |
| 4-1157 | phenyl | i-Pr | C(O)C(O)OMe | H | CN | H | H | I | H | nonafluoro-2-butyl | H | CF3 |
| 4-1158 | phenyl | i-Pr | C(O)Me | H | CN | H | H | I | H | nonafluoro-2-butyl | H | CF3 |
| 4-1159 | phenyl | i-Pr | S(O)2Me | H | CN | H | H | I | H | nonafluoro-2-butyl | H | CF3 |
| 4-1160 | phenyl | i-Pr | CH2Ph | H | CN | H | H | I | H | nonafluoro-2-butyl | H | CF3 |
| 4-1161 | phenyl | i-Pr | CH2(3-Py) | H | CN | H | H | I | H | nonafluoro-2-butyl | H | CF3 |
| 4-1162 | phenyl | i-Pr | CH2(3-Py-N-oxide) | H | CN | H | H | I | H | nonafluoro-2-butyl | H | CF3 |
| 4-1163 | phenyl | CH2CH=CH2 | Et | H | CN | H | H | I | H | nonafluoro-2-butyl | H | CF3 |
| 4-1164 | phenyl | CH2CH=CH2 | n-Pr | H | CN | H | H | I | H | nonafluoro-2-butyl | H | CF3 |
| 4-1165 | phenyl | CH2CH=CH2 | i-Pr | H | CN | H | H | I | H | nonafluoro-2-butyl | H | CF3 |
| 4-1166 | phenyl | CH2CH=CH2 | CH2CH=CH2 | H | CN | H | H | I | H | nonafluoro-2-butyl | H | CF3 |
| 4-1167 | phenyl | CH2CH=CH2 | CN | H | CN | H | H | I | H | nonafluoro-2-butyl | H | CF3 |
| 4-1168 | phenyl | CH2CH=CH2 | CH2C≡CH | H | CN | H | H | I | H | nonafluoro-2-butyl | H | CF3 |
| 4-1169 | phenyl | CH2CH=CH2 | NH2 | H | CN | H | H | I | H | nonafluoro-2-butyl | H | CF3 |
| 4-1170 | phenyl | CH2CH=CH2 | C(O)OMe | H | CN | H | H | I | H | nonafluoro-2-butyl | H | CF3 |
| 4-1171 | phenyl | CH2CH=CH2 | C(O)C(O)OMe | H | CN | I | H | I | H | nonafluoro-2-butyl | H | CF3 |
| 4-1172 | phenyl | CH2CH=CH2 | C(O)Me | H | CN | H | H | I | H | nonafluoro-2-butyl | H | CF3 |
| 4-1173 | phenyl | CH2CH=CH2 | S(O)2Me | H | CN | H | H | I | H | nonafluoro-2-butyl | H | CF3 |
| 4-1174 | phenyl | CH2CH=CH2 | CH2Ph | H | CN | H | H | I | H | nonafluoro-2-butyl | H | CF3 |
| 4-1175 | phenyl | CH2CH=CH2 | CH2(3-Py) | H | CN | H | H | I | H | nonafluoro-2-butyl | H | CF3 |
| 4-1176 | phenyl | CH2CH=CH2 | CH2(3-Py-N-oxide) | H | CN | H | H | I | H | nonafluoro-2-butyl | H | CF3 |
| 4-1177 | phenyl | CN | Et | H | CN | H | H | I | H | nonafluoro-2-butyl | H | CF3 |
| 4-1178 | phenyl | CN | n-Pr | H | CN | H | H | I | H | nonafluoro-2-butyl | H | CF3 |
| 4-1179 | phenyl | CN | i-Pr | H | CN | H | H | I | H | nonafluoro-2-butyl | H | CF3 |
| 4-1180 | phenyl | CN | CH2CH=CH2 | H | CN | H | H | I | H | nonafluoro-2-butyl | H | CF3 |
| 4-1181 | phenyl | CN | CN | H | CN | H | H | I | H | nonafluoro-2-butyl | H | CF3 |
| 4-1182 | phenyl | CN | CH2C≡CH | H | CN | H | H | I | H | nonafluoro-2-butyl | H | CF3 |
| 4-1183 | phenyl | CN | NH2 | H | CN | H | H | I | H | nonafluoro-2-butyl | H | CF3 |
| 4-1184 | phenyl | CN | C(O)OMe | H | CN | H | H | I | H | nonafluoro-2-butyl | H | CF3 |
| 4-1185 | phenyl | CN | C(O)C(O)OMe | H | CN | H | H | I | H | nonafluoro-2-butyl | H | CF3 |
| 4-1186 | phenyl | CH | C(O)Me | H | CN | H | H | I | H | nonafluoro-2-butyl | H | CF3 |
| 4-1187 | phenyl | CN | S(O)2Me | H | CN | H | H | I | H | nonafluoro-2-butyl | H | CF3 |
| 4-1188 | phenyl | CN | CH2Ph | H | CN | H | H | I | H | nonafluoro-2-butyl | H | CF3 |
| 4-1189 | phenyl | CN | CH2(3-Py) | H | CN | H | H | I | H | nonafluoro-2-butyl | H | CF3 |
| 4-1190 | phenyl | CN | CH2(3-Py-N-oxide) | H | CN | H | H | I | H | nonafluoro-2-butyl | H | CF3 |
| 4-1191 | phenyl | CH2C≡CH | Et | H | CN | H | H | I | H | nonafluoro-2-butyl | H | CF3 |
| 4-1192 | phenyl | CH2C≡CH | n-Pr | H | CN | H | H | I | H | nonafluoro-2-butyl | H | CF3 |
| 4-1193 | phenyl | CH2C≡CH | i-Pr | H | CN | H | H | I | H | nonafluoro-2-butyl | H | CF3 |
| 4-1194 | phenyl | CH2C≡CH | CH2CH=CH2 | H | CN | H | H | I | H | nonafluoro-2-butyl | H | CF3 |
| 4-1195 | phenyl | CH2C≡CH | CN | H | CN | H | H | I | H | nonafluoro-2-butyl | H | CF3 |
| 4-1196 | phenyl | CH2C≡CH | CH2C≡CH | H | CN | H | H | I | H | nonafluoro-2-butyl | H | CF3 |

TABLE 4-continued

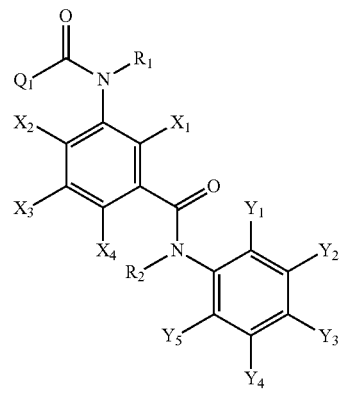

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 4-1197 | phenyl | CH2C≡CH | NH2 | H | CN | H | H | I | H | nonafluoro-2-butyl | H | CF3 |
| 4-1198 | phenyl | CH2C≡CH | C(O)OMe | H | CN | H | H | I | H | nonafluoro-2-butyl | H | CF3 |
| 4-1199 | phenyl | CH2C≡CH | C(O)C(O)OMe | H | CN | H | H | I | H | nonafluoro-2-butyl | H | CF3 |
| 4-1200 | phenyl | CH2C≡CH | C(O)Me | H | CN | H | H | I | H | nonafluoro-2-butyl | H | CF3 |
| 4-1201 | phenyl | CH2C≡CH | S(O)2Me | H | CN | H | H | I | H | nonafluoro-2-butyl | H | CF3 |
| 4-1202 | phenyl | CH2C≡CH | CH2Ph | H | CN | H | H | I | H | nonafluoro-2-butyl | H | CF3 |
| 4-1203 | phenyl | CH2C≡CH | CH2(3-Py) | H | CN | H | H | I | H | nonafluoro-2-butyl | H | CF3 |
| 4-1204 | phenyl | CH2C≡CH | CH2(3-Py-N-oxide) | H | CN | H | H | I | H | nonafluoro-2-butyl | H | CF3 |
| 4-1205 | phenyl | NH2 | Et | H | CN | H | H | I | H | nonafluoro-2-butyl | H | CF3 |
| 4-1206 | phenyl | NH2 | n-Pr | H | CN | H | H | I | H | nonafluoro-2-butyl | H | CF3 |
| 4-1207 | phenyl | NH2 | i-Pr | H | CN | H | H | I | H | nonafluoro-2-butyl | H | CF3 |
| 4-1208 | phenyl | NH2 | CH2CH═CH2 | H | CN | H | H | I | H | nonafluoro-2-butyl | H | CF3 |
| 4-1209 | phenyl | NH2 | CN | H | CN | H | H | I | H | nonafluoro-2-butyl | H | CF3 |
| 4-1210 | phenyl | NH2 | CH2C≡CH | H | CN | H | H | I | H | nonafluoro-2-butyl | H | CF3 |
| 4-1211 | phenyl | NH2 | NH2 | H | CN | H | H | I | H | nonafluoro-2-butyl | H | CF3 |
| 4-1212 | phenyl | NH2 | C(O)OMe | H | CN | H | H | I | H | nonafluoro-2-butyl | H | CF3 |
| 4-1213 | phenyl | NH2 | C(O)C(O)OMe | H | CN | H | H | I | H | nonafluoro-2-butyl | H | CF3 |
| 4-1214 | phenyl | NH2 | C(O)Me | H | CN | H | H | I | H | nonaffuoro-2-butyl | H | CF3 |
| 4-1215 | phenyl | NH2 | S(O)2Me | H | CN | H | H | I | H | nonafluoro-2-butyl | H | CF3 |
| 4-1216 | phenyl | NH2 | CH2Ph | H | CN | H | H | I | H | nonafluoro-2-butyl | H | CF3 |
| 4-1217 | phenyl | NH2 | CH2(3-Py) | H | CN | H | H | I | H | nonafluoro-2-butyl | H | CF3 |
| 4-1218 | phenyl | NH2 | CH2(3-Py-N-oxide) | H | CN | H | H | I | H | nonafluoro-2-butyl | H | CF3 |
| 4-1219 | phenyl | C(O)OMe | Et | H | CN | H | H | I | H | nonafluoro-2-butyl | H | CF3 |
| 4-1220 | phenyl | C(O)OMe | n-Pr | H | CN | H | H | I | H | nonafluoro-2-butyl | H | CF3 |
| 4-1221 | phenyl | C(O)OMe | i-Pr | H | CN | H | H | I | H | nonafluoro-2-butyl | H | CF3 |
| 4-1222 | phenyl | C(O)OMe | CH2CH═CH2 | H | CN | H | H | I | H | nonafluoro-2-butyl | H | CF3 |
| 4-1223 | phenyl | C(O)OMe | CN | H | CN | H | H | I | H | nonafluoro-2-butyl | H | CF3 |
| 4-1224 | phenyl | C(O)OMe | CH2C≡CH | H | CN | H | H | I | H | nonafluoro-2-butyl | H | CF3 |
| 4-1225 | phenyl | C(O)OMe | NH2 | H | CN | H | H | I | H | nonafluoro-2-butyl | H | CF3 |
| 4-1226 | phenyl | C(O)OMe | C(O)OMe | H | CN | H | H | I | H | nonafluoro-2-butyl | H | CF3 |
| 4-1227 | phenyl | C(O)OMe | C(O)C(O)OMe | H | CN | H | H | I | H | nonafluoro-2-butyl | H | CF3 |
| 4-1228 | phenyl | C(O)OMe | C(O)Me | H | CN | H | H | I | H | nonafluoro-2-butyl | H | CF3 |
| 4-1229 | phenyl | C(O)OMe | S(O)2Me | H | CN | H | H | I | H | nonafluoro-2-butyl | H | CF3 |
| 4-1230 | phenyl | C(O)OMe | CH2Ph | H | CN | H | H | I | H | nonafluoro-2-butyl | H | CF3 |
| 4-1231 | phenyl | C(O)OMe | CH2(3-Py) | H | CN | H | H | I | H | nonafluoro-2-butyl | H | CF3 |
| 4-1232 | phenyl | C(O)OMe | CH2(3-Py-N-oxide) | H | CN | H | H | I | H | nonafluoro-2-butyl | H | CF3 |
| 4-1233 | phenyl | C(O)C(O)OMe | Et | H | CN | H | H | I | H | nonafluoro-2-butyl | H | CF3 |
| 4-1234 | phenyl | C(O)C(O)OMe | n-Pr | H | CN | H | H | I | H | nonafluoro-2-butyl | H | CF3 |
| 4-1235 | phenyl | C(O)C(O)OMe | i-Pr | H | CN | H | H | I | H | nonafluoro-2-butyl | H | CF3 |
| 4-1236 | phenyl | C(O)C(O)OMe | CH2CH═CH2 | H | CN | H | H | I | H | nonafluoro-2-butyl | H | CF3 |
| 4-1237 | phenyl | C(O)C(O)OMe | CN | H | CN | H | H | I | H | nonafluoro-2-butyl | H | CF3 |
| 4-1238 | phenyl | C(O)C(O)OMe | CH2C≡CH | H | CN | H | H | I | H | nonafluoro-2-butyl | H | CF3 |
| 4-1239 | phenyl | C(O)C(O)OMe | NH2 | H | CN | H | H | I | H | nonafluoro-2-butyl | H | CF3 |
| 4-1240 | phenyl | C(O)C(O)OMe | C(O)OMe | H | CN | H | H | I | H | nonafluoro-2-butyl | H | CF3 |
| 4-1241 | phenyl | C(O)C(O)OMe | C(O)C(O)OMe | H | CN | H | H | I | H | nonafluoro-2-butyl | H | CF3 |
| 4-1242 | phenyl | C(O)C(O)OMe | C(O)Me | H | CN | H | H | I | H | nonafluoro-2-butyl | H | CF3 |
| 4-1243 | phenyl | C(O)C(O)OMe | S(O)2Me | H | CN | H | H | I | H | nonafluoro-2-butyl | H | CF3 |
| 4-1244 | phenyl | C(O)C(O)OMe | CH2Ph | H | CN | H | H | I | H | nonafluoro-2-butyl | H | CF3 |
| 4-1245 | phenyl | C(O)C(O)OMe | CH2(3-Py) | H | CN | H | H | I | H | nonafluoro-2-butyl | H | CF3 |
| 4-1246 | phenyl | C(O)C(O)OMe | CH2(3-Py-N-oxide) | H | CN | H | H | I | H | nonafluoro-2-butyl | H | CF3 |
| 4-1247 | phenyl | C(O)Me | Et | H | CN | H | H | I | H | nonafluoro-2-butyl | H | CF3 |
| 4-1248 | phenyl | C(O)Me | n-Pr | H | CN | H | H | I | H | nonafluoro-2-butyl | H | CF3 |
| 4-1249 | phenyl | C(O)Me | i-Pr | H | CN | H | H | I | H | nonafluoro-2-butyl | H | CF3 |
| 4-1250 | phenyl | O(O)Me | CH2CH═CH2 | H | CN | H | H | I | H | nonafluoro-2-butyl | H | CF3 |

TABLE 4-continued

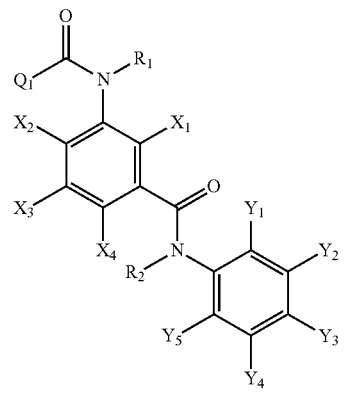

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 4-1251 | phenyl | C(O)Me | CN | H | CN | H | H | I | H | nonafluoro-2-butyl | H | CF3 |
| 4-1252 | phenyl | C(O)Me | CH2C≡CH | H | CN | H | H | I | H | nonafluoro-2-butyl | H | CF3 |
| 4-1253 | phenyl | C(O)Me | NH2 | H | CN | H | H | I | H | nonafluoro-2-butyl | H | CF3 |
| 4-1254 | phenyl | C(O)Me | C(O)OMe | H | CN | H | H | I | H | nonafluoro-2-butyl | H | CF3 |
| 4-1255 | phenyl | C(O)Me | C(O)C(O)OMe | H | CN | H | H | I | H | nonafluoro-2-butyl | H | CF3 |
| 4-1256 | phenyl | C(O)Me | C(O)Me | H | CN | H | H | I | H | nonafluoro-2-butyl | H | CF3 |
| 4-1257 | phenyl | C(O)Me | S(O)2Me | H | CN | H | H | I | H | nonafluoro-2-butyl | H | CF3 |
| 4-1258 | phenyl | C(O)Me | CH2Ph | H | CN | H | H | I | H | nonafluoro-2-butyl | H | CF3 |
| 4-1259 | phenyl | C(O)Me | CH2(3-Py) | H | CN | H | H | I | H | nonafluoro-2-butyl | H | CF3 |
| 4-1260 | phenyl | C(O)Me | CH2(3-Py-N-oxide) | H | CN | H | H | I | H | nonafluoro-2-butyl | H | CF3 |
| 4-1261 | phenyl | S(O)2Me | Et | H | CN | H | H | I | H | nonafluoro-2-butyl | H | CF3 |
| 4-1262 | phenyl | S(O)2Me | n-Pr | H | CN | H | H | I | H | nonafluoro-2-butyl | H | CF3 |
| 4-1263 | phenyl | S(O)2Me | i-Pr | H | CN | H | H | I | H | nonafluoro-2-butyl | H | CF3 |
| 4-1264 | phenyl | S(O)2Me | CH2CH=CH2 | H | CN | H | H | I | H | nonafluoro-2-butyl | H | CF3 |
| 4-1265 | phenyl | S(O)2Me | CN | H | CN | H | H | I | H | nonafluoro-2-butyl | H | CF3 |
| 4-1266 | phenyl | S(O)2Me | CH2C≡CH | H | CN | H | H | I | H | nonafluoro-2-butyl | H | CF3 |
| 4-1267 | phenyl | S(O)2Me | NH2 | H | CN | H | H | I | H | nonafluoro-2-butyl | H | CF3 |
| 4-1268 | phenyl | S(O)2Me | C(O)OMe | H | CN | H | H | I | H | nonafluoro-2-butyl | H | CF3 |
| 4-1269 | phenyl | S(O)2Me | C(O)C(O)OMe | H | CN | H | H | I | H | nonafluoro-2-butyl | H | CF3 |
| 4-1270 | phenyl | S(O)2Me | C(O)Me | H | CN | H | H | I | H | nonafluoro-2-butyl | H | CF3 |
| 4-1271 | phenyl | S(O)2Me | S(O)2Me | H | CN | H | H | I | H | nonafluoro-2-butyl | H | CF3 |
| 4-1272 | phenyl | S(O)2Me | CH2Ph | H | CN | H | H | I | H | nonafluoro-2-butyl | H | CF3 |
| 4-1273 | phenyl | S(O)2Me | CH2(3-Py) | H | CN | H | H | I | H | nonafluoro-2-butyl | H | CF3 |
| 4-1274 | phenyl | S(O)2Me | CH2(3-Py-N-oxide) | H | CN | H | H | I | H | nonafluoro-2-butyl | H | CF3 |
| 4-1275 | phenyl | CH2Ph | Et | H | CN | H | H | I | H | nonafluoro-2-butyl | H | CF3 |
| 4-1276 | phenyl | CH2Ph | n-Pr | H | CN | H | H | I | H | nonafluoro-2-butyl | H | CF3 |
| 4-1277 | phenyl | CH2Ph | i-Pr | H | CN | H | H | I | H | nonafluoro-2-butyl | H | CF3 |
| 4-1278 | phenyl | CH2Ph | CH2CH=CH2 | H | CN | H | H | I | H | nonafluoro-2-butyl | H | CF3 |
| 4-1279 | phenyl | CH2Ph | CN | H | CN | H | H | I | H | nonafluoro-2-butyl | H | CF3 |
| 4-1280 | phenyl | CH2Ph | CH2C≡CH | H | CN | H | H | I | H | nonafluoro-2-butyl | H | CF3 |
| 4-1281 | phenyl | CH2Ph | NH2 | H | CN | H | H | I | H | nonafluoro-2-butyl | H | CF3 |
| 4-1282 | phenyl | CH2Ph | C(O)OMe | H | CN | H | H | I | H | nonafluoro-2-butyl | H | CF3 |
| 4-1283 | phenyl | CH2Ph | C(O)C(O)OMe | H | CN | H | H | I | H | nonafluoro-2-butyl | H | CF3 |
| 4-1284 | phenyl | CH2Ph | C(O)Me | H | CN | H | H | I | H | nonafluoro-2-butyl | H | CF3 |
| 4-1285 | phenyl | CH2Ph | S(O)2Me | H | CN | H | H | I | H | nonafluoro-2-butyl | H | CF3 |
| 4-1286 | phenyl | CH2Ph | CH2Ph | H | CN | H | H | I | H | nonafluoro-2-butyl | H | CF3 |
| 4-1287 | phenyl | CH2Ph | CH2(3-Py) | H | CN | H | H | I | H | nonafluoro-2-butyl | H | CF3 |
| 4-1288 | phenyl | CH2Ph | CH2(3-Py-N-oxide) | H | CN | H | H | I | H | nonafluoro-2-butyl | H | CF3 |
| 4-1289 | phenyl | CH2(3-Py) | Et | H | CN | H | H | I | H | nonafluoro-2-butyl | H | CF3 |
| 4-1290 | phenyl | CH2(3-Py) | n-Pr | H | CN | H | H | I | H | nonafluoro-2-butyl | H | CF3 |
| 4-1291 | phenyl | CH2(3-Py) | i-Pr | H | CN | H | H | I | H | nonafluoro-2-butyl | H | CF3 |
| 4-1292 | phenyl | CH2(3-Py) | CH2CH=CH2 | H | CN | H | H | I | H | nonafluoro-2-butyl | H | CF3 |
| 4-1293 | phenyl | CH2(3-Py) | CN | H | CN | H | H | I | H | nonafluoro-2-butyl | H | CF3 |
| 4-1294 | phenyl | CH2(3-Py) | CH2C≡CH | H | CN | H | H | I | H | nonafluoro-2-butyl | H | CF3 |
| 4-1295 | phenyl | CH2(3-Py) | NH2 | H | CN | H | H | I | H | nonafluoro-2-butyl | H | CF3 |
| 4-1296 | phenyl | CH2(3-Py) | C(O)OMe | H | CN | H | H | I | H | nonafluoro-2-butyl | H | CF3 |
| 4-1297 | phenyl | CH2(3-Py) | C(O)C(O)OMe | H | CN | H | H | I | H | nonafluoro-2-butyl | H | CF3 |
| 4-1298 | phenyl | CH2(3-Py) | C(O)Me | H | CN | H | H | I | H | nonafluoro-2-butyl | H | CF3 |
| 4-1299 | phenyl | CH2(3-Py) | S(O)2Me | H | CN | H | H | I | H | nonafluoro-2-butyl | H | CF3 |
| 4-1300 | phenyl | CH2(3-Py) | CH2Ph | H | CN | H | H | I | H | nonafluoro-2-butyl | H | CF3 |
| 4-1301 | phenyl | CH2(3-Py) | CH2(3-Py) | H | CN | H | H | I | H | nonafluoro-2-butyl | H | CF3 |
| 4-1302 | phenyl | CH2(3-Py) | CH2(3-Py-N-oxide) | H | CN | H | H | I | H | nonafluoro-2-butyl | H | CF3 |
| 4-1303 | phenyl | CH2(3-Py-N-oxide) | Et | H | CN | H | H | I | H | nonafluoro-2-butyl | H | CF3 |

TABLE 4-continued

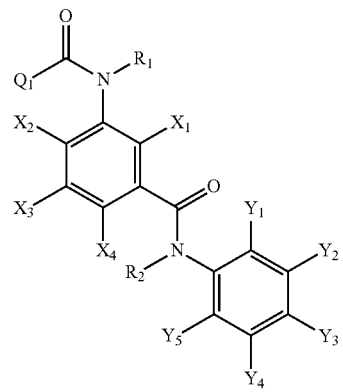

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 4-1304 | phenyl | CH2(3-Py-N-oxide) | n-Pr | H | CN | H | H | I | H | nonafluoro-2-butyl | H | CF3 |
| 4-1305 | phenyl | CH2(3-Py-N-oxide) | i-Pr | H | CN | H | H | I | H | nonafluoro-2-butyl | H | CF3 |
| 4-1306 | phenyl | CH2(3-Py-N-oxide) | CH2CH=CH2 | H | CN | H | H | I | H | nonafluoro-2-butyl | H | CF3 |
| 4-1307 | phenyl | CH2(3-Py-N-oxide) | CN | H | CN | H | H | I | H | nonafluoro-2-butyl | H | CF3 |
| 4-1308 | phenyl | CH2(3-Py-N-oxide) | CH2C≡CH | H | CN | H | H | I | H | nonafluoro-2-butyl | H | CF3 |
| 4-1309 | phenyl | CH2(3-Py-N-oxide) | NH2 | H | CN | H | H | I | H | nonafluoro-2-butyl | H | CF3 |
| 4-1310 | phenyl | CH2(3-Py-N-oxide) | C(O)OMe | H | CN | H | H | I | H | nonafluoro-2-butyl | H | CF3 |
| 4-1311 | phenyl | CH2(3-Py-N-oxide) | C(O)C(O)OMe | H | CN | H | H | I | H | nonafluoro-2-butyl | H | CF3 |
| 4-1312 | phenyl | CH2(3-Py-N-oxide) | C(O)Me | H | CN | H | H | I | H | nonafluoro-2-butyl | H | CF3 |
| 4-1313 | phenyl | CH2(3-Py-N-oxide) | S(O)2Me | H | CN | H | H | I | H | nonafluoro-2-butyl | H | CF3 |
| 4-1314 | phenyl | CH2(3-Py-N-oxide) | CH2Ph | H | CN | H | H | I | H | nonafluoro-2-butyl | H | CF3 |
| 4-1315 | phenyl | CH2(3-Py-N-oxide) | CH2(3-Py) | H | CN | H | H | I | H | nonafluoro-2-butyl | H | CF3 |
| 4-1316 | phenyl | CH2(3-Py-N-oxide) | CH2(3-Py-N-oxide) | H | CN | H | H | I | H | nonafluoro-2-butyl | H | CF3 |
| 4-1317 | phenyl | Me | Me | H | CN | H | H | OCF3 | H | heptafluoroisopropyl | H | OCF3 |
| 4-1348 | 2-chloropyridin-3-yl | Me | Me | H | CN | H | H | OCF3 | H | heptafluoroisopropyl | H | OCF3 |
| 4-1373 | phenyl | Me | Me | H | CN | H | H | OCF3 | H | nonafluoro-2-butyl | H | OCF3 |
| 4-1404 | 2-chloropyridin-3-yl | Me | Me | H | CN | H | H | OCF3 | H | nonafluoro-2-butyl | H | OCF3 |
| 4-1429 | phenyl | Me | Me | H | CN | H | H | CF3 | H | heptafluoroisopropyl | H | OCF3 |
| 4-1460 | 2-chloropyridin-3-yl | Me | Me | H | CN | H | H | CF3 | H | heptafluoroisopropyl | H | OCF3 |
| 4-1485 | phenyl | Me | Me | H | CN | H | H | CF3 | H | nonafluoro-2-butyl | H | OCF3 |
| 4-1516 | 2-chloropyridin-3-yl | Me | Me | H | CN | H | H | CF3 | H | nonafluoro-2-butyl | H | OCF3 |
| 4-1541 | phenyl | Me | Me | H | CN | H | H | CF3 | H | heptafluoroisopropyl | H | CF3 |
| 4-1561 | 3-cyanophenyl | Me | Me | H | CN | H | H | CF3 | H | heptafluoroisopropyl | H | CF3 |
| 4-1562 | 4-cyanophenyl | Me | Me | H | CN | H | H | CF3 | H | heptafluoroisopropyl | H | CF3 |
| 4-1577 | 2-chloropyridin-3-yl | Me | Me | H | CN | H | H | CF3 | H | heptafluoroisopropyl | H | CF3 |
| 4-1609 | phenyl | Me | Me | H | CN | H | H | CF3 | H | nonafluoro-2-butyl | H | CF3 |
| 4-1629 | 3-cyanophenyl | Me | Me | H | CN | H | H | CF3 | H | nonafluoro-2-butyl | H | CF3 |
| 4-1630 | 4-cyanophenyl | Me | Me | H | CN | H | H | CF3 | H | nonafluoro-2-butyl | H | CF3 |
| 4-1645 | 2-chloropyridin-3-yl | Me | Me | H | CN | H | H | CF3 | H | nonafluoro-2-butyl | H | CF3 |
| 4-1873 | phenyl | Me | Me | F | CN | H | H | Cl | H | heptafluoroisopropyl | H | OCF3 |
| 4-1893 | 3-cyanophenyl | Me | Me | F | CN | H | H | Cl | H | heptafluoroisopropyl | H | OCF3 |
| 4-1909 | 2-chloropyridin-3-yl | Me | Me | F | CN | H | H | Cl | H | heptafluoroisopropyl | H | OCF3 |
| 4-1951 | phenyl | Me | Me | F | CN | H | H | Cl | H | nonafluoro-2-butyl | H | OCF3 |
| 4-1971 | 3-cyanophenyl | Me | Me | F | CN | H | H | Cl | H | nonafluoro-2-butyl | H | OCF3 |
| 4-1972 | 4-cyanophenyl | Me | Me | F | CN | H | H | Cl | H | nonafluoro-2-butyl | H | OCF3 |
| 4-1987 | 2-chloropyridin-3-yl | Me | Me | F | CN | H | H | Cl | H | nonafluoro-2-butyl | H | OCF3 |
| 4-2029 | phenyl | Me | Me | F | CN | H | H | Br | H | heptafluoroisopropyl | H | OCF3 |
| 4-2049 | 3-cyanophenyl | Me | Me | F | CN | H | H | Br | H | heptafluoroisopropyl | H | OCF3 |
| 4-2050 | 4-cyanophenyl | Me | Me | F | CN | H | H | Br | H | heptafluoroisopropyl | H | OCF3 |
| 4-2065 | 2-chloropyridin-3-yl | Me | Me | F | CN | H | H | Br | H | heptafluoroisopropyl | H | OCF3 |
| 4-2107 | phenyl | Me | Me | F | CN | H | H | Br | H | nonafluoro-2-butyl | H | OCF3 |
| 4-2127 | 3-cyanophenyl | Me | Me | F | CN | H | H | Br | H | nonafluoro-2-butyl | H | OCF3 |
| 4-2128 | 4-cyanophenyl | Me | Me | F | CN | H | H | Br | H | nonafluoro-2-butyl | H | OCF3 |
| 4-2143 | 2-chloropyridin-3-yl | Me | Me | F | CN | H | H | Br | H | nonafluoro-2-butyl | H | OCF3 |
| 4-2185 | phenyl | Me | Me | F | CN | H | H | I | H | heptafluoroisopropyl | H | OCF3 |

TABLE 4-continued

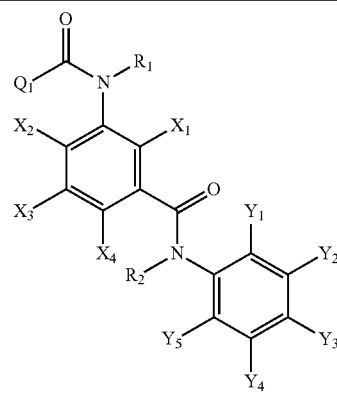

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 4-2205 | 3-cyanophenyl | Me | Me | F | CN | H | H | I | H | heptafluoroisopropyl | H | OCF3 |
| 4-2206 | 4-cyanophenyl | Me | Me | F | CN | H | H | I | H | heptafluoroisopropyl | H | OCF3 |
| 4-2221 | 2-chloropyridin-3-yl | Me | Me | F | CN | H | H | I | H | heptafluoroisopropyl | H | OCF3 |
| 4-2263 | phenyl | Me | Me | F | CN | H | H | I | H | nonafluoro-2-butyl | H | OCF3 |
| 4-2283 | 3-cyanophenyl | Me | Me | F | CN | H | H | I | H | nonafluoro-2-butyl | H | OCF3 |
| 4-2284 | 4-cyanophenyl | Me | Me | F | CN | H | H | I | H | nonafluoro-2-butyl | H | OCF3 |
| 4-2299 | 2-chloropyridin-3-yl | Me | Me | F | CN | H | H | I | H | nonafluoro-2-butyl | H | OCF3 |
| 4-2537 | phenyl | Me | Me | F | CN | H | H | Cl | H | heptafluoroisopropyl | H | CF3 |
| 4-2538 | phenyl | Et | Me | F | CN | H | H | F | H | heptafluoroisopropyl | H | CF3 |
| 4-2544 | 3-cyanophenyl | Me | Me | F | CN | H | H | Cl | H | heptafluoroisopropyl | H | CF3 |
| 4-2545 | 4-cyanophenyl | Me | Me | F | CN | H | H | Cl | H | heptafluoroisopropyl | H | CF3 |
| 4-2560 | 2-chloropyridin-3-yl | Me | Me | F | CN | H | H | Cl | H | heptafluoroisopropyl | H | CF3 |
| 4-2602 | phenyl | Me | Me | F | CN | H | H | F | H | nonafluoro-2-butyl | H | CF3 |
| 4-2603 | phenyl | Me | Me | F | CN | H | H | Cl | H | nonafluoro-2-butyl | H | CF3 |
| 4-2623 | 3-cyanophenyl | Me | Me | F | CN | H | H | Cl | H | nonafluoro-2-butyl | H | CF3 |
| 4-2624 | 4-cyanophenyl | Me | Me | F | CN | H | H | Cl | H | nonafluoro-2-butyl | H | CF3 |
| 4-2639 | 2-chloropyridin-3-yl | Me | Me | F | CN | H | H | Cl | H | nonafluoro-2-butyl | H | CF3 |
| 4-2681 | phenyl | Me | Me | F | CN | H | H | Br | H | heptafluoroisopropyl | H | CF3 |
| 4-2701 | 3-cyanophenyl | Me | Me | F | CN | H | H | Br | H | heptafluoroisopropyl | H | CF3 |
| 4-2702 | 4-cyanophenyl | Me | Me | F | CN | H | H | Br | H | heptafluoroisopropyl | H | CF3 |
| 4-2717 | 2-chloropyridin-3-yl | Me | Me | F | CN | H | H | Br | H | heptafluoroisopropyl | H | CF3 |
| 4-2759 | phenyl | Me | Me | F | CN | H | H | Br | H | nonafluoro-2-butyl | H | CF3 |
| 4-2779 | 3-cyanophenyl | Me | Me | F | CN | H | H | Br | H | nonafluoro-2-butyl | H | CF3 |
| 4-2780 | 4-cyanophenyl | Me | Me | F | CN | H | H | Br | H | nonafluoro-2-butyl | H | CF3 |
| 4-2795 | 2-chloropyridin-3-yl | Me | Me | F | CN | H | H | Br | H | nonafluoro-2-butyl | H | CF3 |
| 4-2837 | phenyl | Me | Me | F | CN | H | H | I | H | heptafluoroisopropyl | H | CF3 |
| 4-2857 | 3-cyanophenyl | Me | Me | F | CN | H | H | I | H | heptafluoroisopropyl | H | CF3 |
| 4-2858 | 4-cyanophenyl | Me | Me | F | CN | H | H | I | H | heptafluoroisopropyl | H | CF3 |
| 4-2873 | 2-chloropyridin-3-yl | Me | Me | F | CN | H | H | I | H | heptafluoroisopropyl | H | CF3 |
| 4-2915 | phenyl | Me | Me | F | CN | H | H | I | H | nonafluoro-2-butyl | H | CF3 |
| 4-2935 | 3-cyanophenyl | Me | Me | F | CN | H | H | I | H | nonafluoro-2-butyl | H | CF3 |
| 4-2936 | 4-cyanophenyl | Me | Me | F | CN | H | H | I | H | nonafluoro-2-butyl | H | CF3 |
| 4-2951 | 2-chloropyridin-3-yl | Me | Me | F | CN | H | H | I | H | nonafluoro-2-butyl | H | CF3 |
| 4-3189 | phenyl | Me | Me | F | CN | H | H | OCF3 | H | heptafluoroisopropyl | H | OCF3 |
| 4-3220 | 2-chloropyridin-3-yl | Me | Me | F | CN | H | H | OCF3 | H | heptafluoroisopropyl | H | OCF3 |
| 4-3245 | phenyl | Me | Me | F | CN | H | H | OCF3 | H | nonafluoro-2-butyl | H | OCF3 |
| 4-3276 | 2-chloropyridin-3-yl | Me | Me | F | CN | H | H | OCF3 | H | nonafluoro-2-butyl | H | OCF3 |
| 4-3301 | phenyl | Me | Me | F | CN | H | H | CF3 | H | heptafluoroisopropyl | H | OCF3 |
| 4-3332 | 2-chloropyridin-3-yl | Me | Me | F | CN | H | H | CF3 | H | heptafluoroisopropyl | H | OCF3 |
| 4-3357 | phenyl | Me | Me | F | CN | H | H | CF3 | H | nonafluoro-2-butyl | H | OCF3 |
| 4-3388 | 2-chloropyridin-3-yl | Me | Me | F | CN | H | H | CF3 | H | nonafluoro-2-butyl | H | OCF3 |
| 4-3413 | phenyl | Me | Me | F | CN | H | H | CF3 | H | heptafluoroisopropyl | H | CF3 |
| 4-3433 | 3-cyanophenyl | Me | Me | F | CN | H | H | CF3 | H | heptafluoroisopropyl | H | CF3 |
| 4-3434 | 4-cyanophenyl | Me | Me | F | CN | H | H | CF3 | H | heptafluoroisopropyl | H | CF3 |
| 4-3449 | 2-chloropyridin-3-yl | Me | Me | F | CN | H | H | CF3 | H | heptafluoroisopropyl | H | CF3 |
| 4-3481 | phenyl | Me | Me | F | CN | H | H | CF3 | H | nonafluoro-2-butyl | H | CF3 |
| 4-3493 | 4-iodophenyl | Me | Me | F | CN | H | H | C2F5 | H | nonafluoro-2-butyl | H | CF3 |
| 4-3501 | 3-cyanophenyl | Me | Me | F | CN | H | H | CF3 | H | nonafluoro-2-butyl | H | CF3 |
| 4-3502 | 4-cyanophenyl | Me | Me | F | CN | H | H | CF3 | H | nonafluoro-2-butyl | H | CF3 |
| 4-3517 | 2-chloropyridin-3-yl | Me | Me | F | CN | H | H | CF3 | H | nonafluoro-2-butyl | H | CF3 |
| 4-3745 | phenyl | Me | Me | F | CN | F | H | Cl | H | heptafluoroisopropyl | H | OCF3 |
| 4-3765 | 3-cyanophenyl | Me | Me | F | CN | F | H | Cl | H | heptafluoroisopropyl | H | OCF3 |
| 4-3766 | 4-cyanophenyl | Me | Me | F | CN | F | H | Cl | H | heptafluoroisopropyl | H | OCF3 |
| 4-3781 | 2-chloropyridin-3-yl | Me | Me | F | CN | F | H | Cl | H | heptafluoroisopropyl | H | OCF3 |
| 4-3823 | phenyl | Me | Me | F | CN | F | H | Cl | H | nonafluoro-2-butyl | H | OCF3 |
| 4-3843 | 3-cyanophenyl | Me | Me | F | CN | F | H | Cl | H | nonafluoro-2-butyl | H | OCF3 |
| 4-3844 | 4-cyanophenyl | Me | Me | F | CN | F | H | Cl | H | nonafluoro-2-butyl | H | OCF3 |
| 4-3859 | 2-chloropyridin-3-yl | Me | Me | F | CN | F | H | Cl | H | nonafluoro-2-butyl | H | OCF3 |

TABLE 4-continued

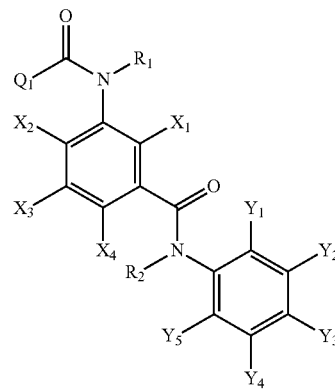

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 4-3901 | phenyl | Me | Me | F | CN | F | H | Br | H | heptafluoroisopropyl | H | OCF3 |
| 4-3921 | 3-cyanophenyl | Me | Me | F | CN | F | H | Br | H | heptafluoroisopropyl | H | OCF3 |
| 4-3922 | 4-cyanophenyl | Me | Me | F | CN | F | H | Br | H | heptafluoroisopropyl | H | OCF3 |
| 4-3937 | 2-chloropyridin-3-yl | Me | Me | F | CN | F | H | Br | H | heptafluoroisopropyl | H | OCF3 |
| 4-3979 | phenyl | Me | Me | F | CN | F | H | Br | H | nonafluoro-2-butyl | H | OCF3 |
| 4-3999 | 3-cyanophenyl | Me | Me | F | CN | F | H | Br | H | nonafluoro-2-butyl | H | OCF3 |
| 4-4000 | 4-cyanophenyl | Me | Me | F | CN | F | H | Br | H | nonafluoro-2-butyl | H | OCF3 |
| 4-4015 | 2-chloropyridin-3-yl | Me | Me | F | CN | F | H | Br | H | nonafluoro-2-butyl | H | OCF3 |
| 4-4057 | phenyl | Me | Me | F | CN | F | H | I | H | heptafluoroisopropyl | H | OCF3 |
| 4-4077 | 3-cyanophenyl | Me | Me | F | CN | F | H | I | H | heptafluoroisopropyl | H | OCF3 |
| 4-4078 | 4-cyanophenyl | Me | Me | F | CN | F | H | I | H | heptafluoroisopropyl | H | OCF3 |
| 4-4093 | 2-chloropyridin-3-yl | Me | Me | F | CN | F | H | I | H | heptafluoroisopropyl | H | OCF3 |
| 4-4135 | phenyl | Me | Me | F | CN | F | H | I | H | nonafluoro-2-butyl | H | OCF3 |
| 4-4155 | 3-cyanophenyl | Me | Me | F | CN | F | H | I | H | nonafluoro-2-butyl | H | OCF3 |
| 4-4156 | 4-cyanophenyl | Me | Me | F | CN | F | H | I | H | nonafluoro-2-butyl | H | OCF3 |
| 4-4171 | 2-chloropyridin-3-yl | Me | Me | F | CN | F | H | I | H | nonafluoro-2-butyl | H | OCF3 |
| 4-4409 | phenyl | Me | Me | F | CN | F | H | Cl | H | heptafluoroisopropyl | H | CF3 |
| 4-4410 | phenyl | Et | Me | F | CH | F | H | F | H | heptafluoroisopropyl | H | CF3 |
| 4-4416 | 3-cyanophenyl | Me | Me | F | CN | F | H | Cl | H | heptafluoroisopropyl | H | CF3 |
| 4-4417 | 4-cyanophenyl | Me | Me | F | CN | F | H | Cl | H | heptafluoroisopropyl | H | CF3 |
| 4-4432 | 2-chloropyridin-3-yl | Me | Me | F | CN | F | H | Cl | H | heptafluoroisopropyl | H | CF3 |
| 4-4474 | phenyl | Me | Me | F | CN | F | H | F | H | nonafluoro-2-butyl | H | CF3 |
| 4-4475 | phenyl | Me | Me | F | CN | F | H | Cl | H | nonafluoro-2-butyl | H | CF3 |
| 4-4495 | 3-cyanophenyl | Me | Me | F | CN | F | H | Cl | H | nonafluoro-2-butyl | H | CF3 |
| 4-4496 | 4-cyanophenyl | Me | Me | F | CN | F | H | Cl | H | nonafluoro-2-butyl | H | CF3 |
| 4-4511 | 2-chloropyridin-3-yl | Me | Me | F | CN | F | H | Cl | H | nonafluoro-2-butyl | H | CF3 |
| 4-4553 | phenyl | Me | Me | F | CN | F | H | Br | H | heptafluoroisopropyl | H | CF3 |
| 4-4573 | 3-cyanophenyl | Me | Me | F | CN | F | H | Br | H | heptafluoroisopropyl | H | CF3 |
| 4-4574 | 4-cyanophenyl | Me | Me | F | CN | F | H | Br | H | heptafluoroisopropyl | H | CF3 |
| 4-4589 | 2-chloropyridin-3-yl | Me | Me | F | CN | F | H | Br | H | heptafluoroisopropyl | H | CF3 |
| 4-4631 | phenyl | Me | Me | F | CN | F | H | Br | H | nonafluoro-2-butyl | H | CF3 |
| 4-4651 | 3-cyanophenyl | Me | Me | F | CN | F | H | Br | H | nonafluoro-2-butyl | H | CF3 |
| 4-4652 | 4-cyanophenyl | Me | Me | F | CN | F | H | Br | H | nonafluoro-2-butyl | H | CF3 |
| 4-4667 | 2-chloropyridin-3-yl | Me | Me | F | CN | F | H | Br | H | nonafluoro-2-butyl | H | CF3 |
| 4-4709 | phenyl | Me | Me | F | CN | F | H | I | H | heptafluoroisopropyl | H | CF3 |
| 4-4729 | 3-cyanophenyl | Me | Me | F | CN | F | H | I | H | heptafluoroisopropyl | H | CF3 |
| 4-4730 | 4-cyanophenyl | Me | Me | F | CN | F | H | I | H | heptafluoroisopropyl | H | CF3 |
| 4-4745 | 2-chloropyridin-3-yl | Me | Me | F | CN | F | H | I | H | heptafluoroisopropyl | H | CF3 |
| 4-4787 | phenyl | Me | Me | F | CN | F | H | I | H | nonafluoro-2-butyl | H | CF3 |
| 4-4807 | 3-cyanophenyl | Me | Me | F | CN | F | H | I | H | nonafluoro-2-butyl | H | CF3 |
| 4-4808 | 4-cyanophenyl | Me | Me | F | CN | F | H | I | H | nonafluoro-2-butyl | H | CF3 |
| 4-4823 | 2-chloropyridin-3-yl | Me | Me | F | CN | F | H | I | H | nonafluoro-2-butyl | H | CF3 |
| 4-5061 | phenyl | Me | Me | F | CN | F | H | OCF3 | H | heptafluoroisopropyl | H | OCF3 |
| 4-5092 | 2-chloropyridin-3-yl | Me | Me | F | CN | F | H | OCF3 | H | heptafluoroisopropyl | H | OCF3 |
| 4-5117 | phenyl | Me | Me | F | CN | F | H | OCF3 | H | nonafluoro-2-butyl | H | OCF3 |
| 4-5148 | 2-chloropyridin-3-yl | Me | Me | F | CN | F | H | OCF3 | H | nonafluoro-2-butyl | H | OCF3 |
| 4-5173 | phenyl | Me | Me | F | CN | F | H | CF3 | H | heptafluoroisopropyl | H | OCF3 |
| 4-5204 | 2-chloropyridin-3-yl | Me | Me | F | CN | F | H | CF3 | H | heptafluoroisopropyl | H | OCF3 |
| 4-5229 | phenyl | Me | Me | F | CN | F | H | CF3 | H | nonafluoro-2-butyl | H | OCF3 |
| 4-5260 | 2-chloropyridin-3-yl | Me | Me | F | CN | F | H | CF3 | H | nonafluoro-2-butyl | H | OCF3 |
| 4-5285 | phenyl | Me | Me | F | CN | F | H | CF3 | H | heptafluoroisopropyl | H | CF3 |
| 4-5305 | 3-cyanophenyl | Me | Me | F | CN | F | H | CF3 | H | heptafluoroisopropyl | H | CF3 |
| 4-5306 | 4-cyanophenyl | Me | Me | F | CN | F | H | CF3 | H | heptafluoroisopropyl | H | CF3 |
| 4-5321 | 2-chloropyridin-3-yl | Me | Me | F | CN | F | H | CF3 | H | heptafluoroisopropyl | H | CF3 |
| 4-5353 | phenyl | Me | Me | F | CN | F | H | CF3 | H | nonafluoro-2-butyl | H | CF3 |
| 4-5373 | 3-cyanophenyl | Me | Me | F | CN | F | H | CF3 | H | nonafluoro-2-butyl | H | CF3 |

TABLE 4-continued

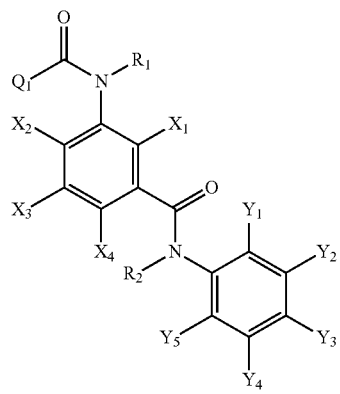

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 4-5374 | 4-cyanophenyl | Me | Me | F | CN | F | H | CF3 | H | nonafluoro-2-butyl | H | CF3 |
| 4-5389 | 2-chloropyridin-3-yl | Me | Me | F | CN | F | H | CF3 | H | nonafluoro-2-butyl | H | CF3 |

TABLE 5

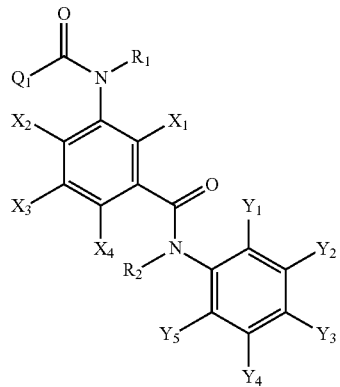

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 5-9 | 3-bromophenyl | H | Et | H | CN | H | H | Cl | F | heptafluoroisopropyl | F | OCF3 |
| 5-39 | 2-iodopyridin-3-yl | H | H | H | CN | H | H | Cl | Me | nonafluoro-2-butyl | Me | OCF3 |
| 5-144 | phenyl | H | H | H | CN | H | H | Cl | F | heptafluoroisopropyl | H | CF3 |
| 5-145 | 2-fluorophenyl | Me | H | H | CN | H | H | Cl | H | heptafluoroisopropyl | F | CF3 |
| 5-146 | 3-fluorophenyl | H | Me | H | CN | H | H | Cl | Cl | heptafluoroisopropyl | H | CF3 |
| 5-147 | 4-fluorophenyl | Me | Me | H | CN | H | H | Cl | H | heptafluoroisopropyl | Cl | CF3 |
| 5-148 | 2-chlorophenyl | H | H | H | CN | H | H | F | Br | heptafluoroisopropyl | H | CF3 |
| 5-149 | 3-chlorophenyl | H | H | H | CN | H | H | Cl | H | heptafluoroisopropyl | Br | CF3 |
| 5-150 | 4-chlorophenyl | Et | H | H | CN | H | H | Cl | I | heptafluoroisopropyl | H | C2F5 |
| 5-151 | 2-bromophenyl | H | H | H | CN | H | H | Cl | H | heptafluoroisopropyl | I | CF3 |
| 5-152 | 3-bromophenyl | H | Et | H | CN | H | H | Cl | F | heptafluoroisopropyl | F | CF3 |
| 5-153 | 4-bromophenyl | H | H | H | CN | H | H | Cl | F | heptafluoroisopropyl | Cl | CF3 |
| 5-154 | 2-iodophenyl | H | H | H | CN | H | H | Cl | F | heptafluoroisopropyl | Br | CF3 |
| 5-155 | 3-iodophenyl | Et | Et | H | CN | H | H | Cl | F | pentafluoroethyl | I | C2F5 |
| 5-156 | 4-iodophenyl | H | H | H | CN | H | H | Cl | Cl | pentafluoroethyl | F | CF3 |
| 5-157 | (2-trifluoromethyl)phenyl | H | H | H | CN | H | H | Cl | Cl | heptafluoroisopropyl | Cl | CF3 |
| 5-158 | (3-trifluoromethyl)phenyl | n-Pr | H | H | CN | H | H | Cl | Cl | heptafluoroisopropyl | Br | CF3 |
| 5-159 | (4-trifluoromethyl)phenyl | H | H | H | CN | H | H | Cl | Cl | heptafluoroisopropyl | I | n-C3F7 |
| 5-160 | 2-nitrophenyl | H | n-Pr | H | CN | H | H | Cl | Br | heptafluoroisopropyl | F | CF3 |
| 5-161 | 3-nitrophenyl | H | H | H | CN | H | H | Cl | Br | heptafluoroisopropyl | Cl | CF3 |
| 5-162 | 4-nitrophenyl | H | H | H | CN | H | H | Cl | Br | heptafluoroisopropyl | Br | CF3 |
| 5-163 | 2-cyanophenyl | n-Pr | n-Pr | H | CN | H | H | Cl | Br | pentafluoroethyl | I | CF3 |
| 5-164 | 3-cyanophenyl | H | H | H | CN | H | H | F | I | nonafluoro-2-butyl | F | CF3 |
| 5-165 | 4-cyanophenyl | H | H | H | CN | H | H | Cl | I | nonafluoro-2-butyl | Cl | CF3 |
| 5-166 | 2,6-difluorophenyl | H | H | H | CN | H | H | Cl | I | nonafluoro-2-butyl | Br | CF3 |
| 5-167 | 3,4-dichlorophenyl | H | H | H | CN | H | H | Cl | I | nonafluoro-2-butyl | I | CF3 |
| 5-168 | 2,4-dichlorophenyl | H | H | H | CN | H | H | Cl | Me | nonafluoro-2-butyl | H | CF3 |
| 5-169 | 2-chloro-4-fluorophenyl | H | H | H | CN | H | H | Cl | H | nonafluoro-2-butyl | Me | CF3 |

TABLE 5-continued

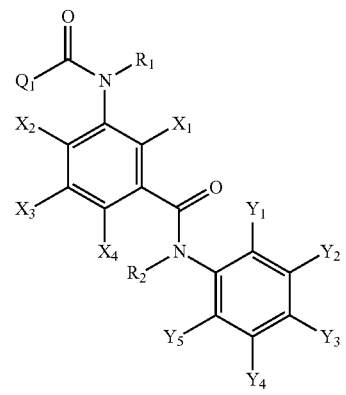

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 5-170 | 2-chloro-4,5-difluorophenyl | i-Pr | H | H | CN | H | H | Cl | Et | nonafluoro-2-butyl | H | CF3 |
| 5-171 | 4-bromo-2-chlorophenyl | H | H | H | CN | H | H | Cl | H | nonafluoro-2-butyl | Et | CF3 |
| 5-172 | 2-bromo-4-chlorophenyl | H | H | H | CN | H | H | Cl | n-Pr | nonafluoro-2-butyl | H | CF3 |
| 5-173 | 2-bromo-4-fluorophenyl | H | i-Pr | H | CN | H | H | Cl | H | nonafluoro-2-butyl | n-Pr | CF3 |
| 5-174 | 2-chloro-4-nitrophenyl | i-Pr | i-Pr | H | CN | H | H | Cl | i-Pr | nonafluoro-2-butyl | H | CF3 |
| 5-175 | 3,5-dicyanophenyl | H | H | H | CN | H | H | Cl | H | nonafluoro-2-butyl | i-Pr | CF3 |
| 5-176 | 4-cyano-2-fluorophenyl | H | H | H | CN | H | H | Cl | n-Bu | nonafluoro-2-butyl | H | CF3 |
| 5-177 | 2-chloro-4-cyanophenyl | H | H | H | CN | H | H | Cl | H | nonafluoro-2-butyl | n-Bu | CF3 |
| 5-178 | pyridin-3-yl | H | H | H | CN | H | H | Cl | i-Bu | nonafluoro-2-butyl | H | CF3 |
| 5-179 | 2-fluoropyridin-3-yl | H | H | H | CN | H | H | Cl | H | nonafluoro-2-butyl | i-Bu | CF3 |
| 5-180 | 2-chloropyridin-3-yl | H | H | H | CN | H | H | Cl | s-Bu | nonafluoro-2-butyl | H | C2F5 |
| 5-181 | 2-bromopyridin-3-yl | H | H | H | CN | H | H | Cl | H | nonafluoro-2-butyl | s-Bu | CF3 |
| 5-182 | 2-iodopyridin-3-yl | H | H | H | CN | H | H | Cl | Me | nonafluoro-2-butyl | Me | n-C3F7 |
| 5-183 | 2-(trifluoromethyl)pyridin-3-yl | H | H | H | CN | H | H | Cl | Me | nonafluoro-2-butyl | Et | i-C3F7 |
| 5-184 | 2-nitropyridin-3-yl | C(O)Me | H | H | CN | H | H | Cl | Me | nonafluoro-2-butyl | n-Pr | CF3 |
| 5-185 | 2-cyanopyridin-3-yl | H | H | H | CN | H | H | Cl | Me | nonafluoro-2-butyl | i-Pr | CF3 |
| 5-186 | 6-fluoropyridin-3-yl | H | H | H | CN | H | H | Cl | Me | nonafluoro-2-butyl | n-Bu | CF3 |
| 5-187 | 6-chloropyridin-3-yl | H | H | H | CN | H | H | Cl | Me | nonafluoro-2-butyl | i-Bu | CF3 |
| 5-188 | 6-bromopyridin-3-yl | H | C(O)Me | H | CN | H | H | Cl | Me | nonafluoro-2-butyl | s-Bu | CF3 |
| 5-189 | 6-iodopyridin-3-yl | H | H | H | CN | H | H | Cl | Et | nonafluoro-2-butyl | Me | n-C3F7 |
| 5-190 | 6-(trifluoromethyl)pyridin-3-yl | H | H | H | CN | H | H | Cl | Et | nonafluoro-2-butyl | Et | i-C3F7 |
| 5-191 | 6-nitropyridin-3-yl | C(O)Me | C(O)Me | H | CN | H | H | Cl | Et | nonafluoro-2-butyl | n-Pr | CF3 |
| 5-192 | 6-cyanopyridin-3-yl | H | H | H | CN | H | H | Cl | Et | nonafluoro-2-butyl | i-Pr | CF3 |
| 5-193 | phenyl | H | H | H | CN | H | H | Br | Et | heptafluoroisopropyl | n-Bu | CF3 |
| 5-194 | 5-fluoropyridin-3-yl | H | H | H | CN | H | H | Br | Et | heptafluoroisopropyl | i-Bu | CF3 |
| 5-195 | 5-chloropyridin-3-yl | H | H | H | CN | H | H | Br | Et | heptafluoroisopropyl | s-Bu | CF3 |
| 5-196 | 5-bromopyridin-3-yl | H | H | H | CN | H | H | Br | n-Pr | heptafluoroisopropyl | Me | CF3 |
| 5-197 | 5-iodopyridin-3-yl | H | H | H | CN | H | H | Br | n-Pr | heptafluoroisopropyl | Et | CF3 |
| 5-198 | 5-(trifluoromethyl)pyridin-3-yl | Me | Et | H | CN | H | H | Br | n-Pr | pentafluoroethyl | n-Pr | CF3 |
| 5-199 | 5-nitropyridin-3-yl | H | H | H | CN | H | H | Br | n-Pr | heptafluoroisopropyl | i-Pr | CF3 |
| 5-200 | 5-cyanopyridin-3-yl | H | H | H | CN | H | H | Br | n-Pr | pentafluoroethyl | n-Bu | CF3 |
| 5-201 | 4-fluoropyridin-3-yl | H | H | H | CN | H | H | Br | n-Pr | heptafluoroisopropyl | i-Bu | CF3 |
| 5-202 | 4-chloropyridin-3-yl | H | H | H | CN | H | H | Br | n-Pr | heptafluoroisopropyl | s-Bu | CF3 |
| 5-203 | 4-bromopyridin-3-yl | Me | n-Pr | H | CN | H | H | Br | i-Pr | heptafluoroisopropyl | Me | CF3 |
| 5-204 | 4-iodopyridin-3-yl | H | H | H | CN | H | H | Br | i-Pr | heptafluoroisopropyl | Et | CF3 |
| 5-205 | 4-(trifluoromethyl)pyridin-3-yl | H | H | H | CN | H | H | Br | i-Pr | heptafluoroisopropyl | n-Pr | CF3 |
| 5-206 | 4-nitropyridin-3-yl | H | H | H | CN | H | H | Br | i-Pr | heptafluoroisopropyl | i-Pr | CF3 |
| 5-207 | 4-cyanopyridin-3-yl | H | H | H | CN | H | H | Br | i-Pr | heptafluoroisopropyl | n-Bu | CF3 |
| 5-208 | 2,6-dichloropyridin-3-yl | H | H | H | CN | H | H | Br | i-Pr | heptafluoroisopropyl | i-Bu | CF3 |
| 5-209 | pyridin-3-yl N-oxide | Me | i-Pr | H | CN | H | H | Br | i-Pr | heptafluoroisopropyl | s-Bu | CF3 |
| 5-210 | pyridin-4-yl | H | H | H | CN | H | H | Br | n-Bu | heptafluoroisopropyl | Me | CF3 |
| 5-211 | 2-chloropyridin-4-yl | H | H | H | CN | H | H | Br | n-Bu | heptafluoroisopropyl | Et | CF3 |
| 5-212 | 3-bromopyridin-4-yl | H | H | H | CN | H | H | Br | n-Bu | heptafluoroisopropyl | n-Pr | CF3 |
| 5-213 | 3,5-dichloropyridin-4-yl | H | H | H | CN | H | H | Br | n-Bu | nonafluoro-2-butyl | i-Pr | CF3 |
| 5-214 | 3-(trifluoromethyl)pyridin-4-yl | H | H | H | CN | H | H | Br | n-Bu | nonafluoro-2-butyl | n-Bu | CF3 |
| 5-215 | 2,6-dicyanopyridin-4-yl | H | H | H | CN | H | H | Br | n-Bu | nonafluoro-2-butyl | i-Bu | CF3 |
| 5-216 | pyridin-4-yl N-oxide | Me | C(O)Me | H | CN | H | H | Br | n-Bu | nonafluoro-2-butyl | s-Bu | CF3 |
| 5-217 | pyridin-2-yl | H | H | H | CN | H | H | Br | i-Bu | nonafluoro-2-butyl | Me | CF3 |
| 5-218 | 3-chloropyridin-2-yl | H | H | H | CN | H | H | Br | i-Bu | nonafluoro-2-butyl | Et | CF3 |
| 5-219 | 4-bromopyridin-2-yl | H | H | H | CN | H | H | Br | i-Bu | nonafluoro-2-butyl | n-Pr | CF3 |
| 5-220 | 5-iodopyridin-2-yl | H | H | H | CN | H | H | Br | i-Bu | nonafluoro-2-butyl | i-Pr | CF3 |
| 5-221 | 6-chloropyridin-2-yl | H | H | H | CN | H | H | Br | i-Bu | nonafluoro-2-butyl | n-Bu | CF3 |
| 5-222 | 4-cyanopyridin-2-yl | H | H | H | CN | H | H | Br | i-Bu | nonafluoro-2-butyl | i-Bu | CF3 |
| 5-223 | phenyl | H | H | H | CN | H | H | Br | i-Bu | nonafluoro-2-butyl | s-Bu | C2F5 |
| 5-224 | 2-fluorophenyl | H | H | H | CN | H | H | Br | s-Bu | nonafluoro-2-butyl | Me | CF3 |
| 5-225 | 3-fluorophenyl | H | H | H | CN | H | H | Br | s-Bu | nonafluoro-2-butyl | Et | CF3 |
| 5-226 | 4-fluorophenyl | H | H | H | CN | H | H | Br | s-Bu | nonafluoro-2-butyl | n-Pr | CF3 |

TABLE 5-continued

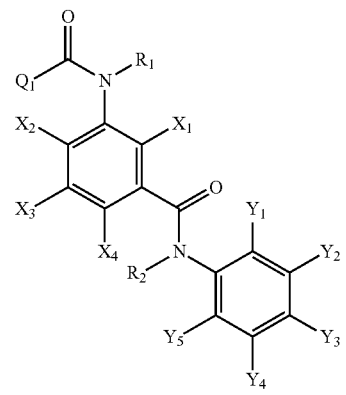

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 5-227 | 2-chlorophenyl | H | H | H | CN | H | H | Br | s-Bu | nonafluoro-2-butyl | i-Pr | CF3 |
| 5-228 | 3-chlorophenyl | H | H | H | CN | H | H | Br | s-Bu | nonafluoro-2-butyl | n-Bu | CF3 |
| 5-229 | 4-chlorophenyl | H | H | H | CN | H | H | Br | s-Bu | nonafluoro-2-butyl | i-Bu | CF3 |
| 5-230 | 2-bromophenyl | Et | Me | H | CN | H | H | Br | s-Bu | nonafluoro-2-butyl | s-Bu | CF3 |
| 5-231 | 3-bromophenyl | H | H | H | CN | H | H | Br | F | nonafluoro-2-butyl | Me | CF3 |
| 5-232 | 4-bromophenyl | H | H | H | CN | H | H | Br | F | nonafluoro-2-butyl | Et | CF3 |
| 5-233 | 2-iodophenyl | H | H | H | CN | H | H | Br | F | nonafluoro-2-butyl | n-Pr | CF3 |
| 5-234 | 3-iodophenyl | H | H | H | CN | H | H | Br | F | nonafluoro-2-butyl | i-Pr | CF3 |
| 5-235 | 4-iodophenyl | H | H | H | CN | H | H | Br | F | nonafluoro-2-butyl | n-Bu | CF3 |
| 5-236 | (2-trifluoromethyl)phenyl | H | H | H | CN | H | H | Br | F | nonafluoro-2-butyl | i-Bu | CF3 |
| 5-237 | (3-trifluoromethyl)phenyl | Et | n-Pr | H | CN | H | H | Br | F | nonafluoro-2-butyl | s-Bu | CF3 |
| 5-238 | (4-trifluoromethyl)phenyl | Et | i-Pr | H | CN | H | H | Br | Cl | nonafluoro-2-butyl | Me | CF3 |
| 5-239 | 2-nitrophenyl | H | H | H | CN | H | H | Br | Cl | nonafluoro-2-butyl | Et | CF3 |
| 5-240 | phenyl | H | H | H | CN | H | H | I | Cl | pentafluoroethyl | n-Pr | i-C3F7 |
| 5-241 | 3-nitrophenyl | H | H | H | CN | H | H | I | Cl | heptafluoroisopropyl | i-Pr | CF3 |
| 5-242 | 4-nitrophenyl | H | H | H | CN | H | H | I | Cl | heptafluoroisopropyl | n-Bu | CF3 |
| 5-243 | 2-cyenophenyl | Et | C(O)Me | H | CN | H | H | I | Cl | heptafluoroisopropyl | i-Bu | CF3 |
| 5-244 | 3-cyanophenyl | H | H | H | CN | H | H | I | Cl | heptafluoroisopropyl | s-Bu | CF3 |
| 5-245 | 4-cyanophenyl | H | H | H | CN | H | H | I | Br | heptafluoroisopropyl | Me | CF3 |
| 5-246 | 2,6-difluorophenyl | H | H | H | CN | H | H | I | Br | heptafluoroisopropyl | Et | CF3 |
| 5-247 | 3,4-dichlorophenyl | H | H | H | CN | H | H | I | Br | pentafluoroethyl | n-Pr | CF3 |
| 5-248 | 2,4-dichlorophenyl | H | H | H | CN | H | H | I | Br | heptafluoroisopropyl | i-Pr | CF3 |
| 5-249 | 2-chloro-4-fluorophenyl | H | H | H | CN | H | H | I | Br | heptafluoroisopropyl | n-Bu | CF3 |
| 5-250 | 2-chloro-4,5-difluorophenyl | H | H | H | CN | H | H | I | Br | heptafluoroisopropyl | i-Bu | CF3 |
| 5-251 | 4-bromo-2-chlorophenyl | H | H | H | CN | H | H | I | Br | heptafluoroisopropyl | s-Bu | CF3 |
| 5-252 | 2-bromo-4-chlorophenyl | n-Pr | Me | H | CN | H | H | I | I | heptafluoroisopropyl | Me | CF3 |
| 5-253 | 2-bromo-4-fluorophenyl | H | H | H | CN | H | H | I | I | heptafluoroisopropyl | Et | CF3 |
| 5-254 | 2-chloro-4-nitrophenyl | n-Pr | Et | H | CN | H | H | I | I | heptafluoroisopropyl | n-Pr | CF3 |
| 5-255 | 3,5-dicyanophenyl | H | H | H | CN | H | H | I | I | heptafluoroisopropyl | i-Pr | CF3 |
| 5-256 | 4-cyano-2-fluorophenyl | H | H | H | CN | H | H | I | I | heptafluoroisopropyl | n-Bu | CF3 |
| 5-257 | 2-chloro-4-cyanophenyl | H | H | H | CN | H | H | I | I | heptafluoroisopropyl | i-Bu | CF3 |
| 5-258 | pyridin-3-yl | H | H | H | CN | H | H | I | I | heptafluoroisopropyl | s-Bu | CF3 |
| 5-259 | 2-fluoropyridin-3-yl | H | H | H | CN | H | H | I | Me | heptafluoroisopropyl | F | C2F5 |
| 5-260 | 2-chloropyridin-3-yl | H | H | H | CN | H | H | I | Me | nonafluoro-2-butyl | Cl | CF3 |
| 5-261 | 2-bromopyridin-3-yl | H | H | H | CN | H | H | I | Me | nonafluoro-2-butyl | Br | n-C3F7 |
| 5-262 | 2-iodopyridin-3-yl | H | H | H | CN | H | H | I | Me | nonafluoro-2-butyl | I | i-C3F7 |
| 5-263 | 2-(trifluoromethyl)pyridin-3-yl | H | H | H | CN | H | H | I | Et | nonafluoro-2-butyl | F | CF3 |
| 5-264 | 2-nitropyridin-3-yl | H | H | H | CN | H | H | I | Et | nonafluoro-2-butyl | Cl | CF3 |
| 5-265 | 2-cyanopyridin-3-yl | H | H | H | CN | H | H | I | Et | nonafluoro-2-butyl | Br | CF3 |
| 5-266 | 6-fluoropyridin--yl | n-Pr | i-Pr | H | CN | H | H | I | Et | nonafluoro-2-butyl | I | C2F5 |
| 5-267 | 6-chloropyridin-3-yl | H | H | H | CN | H | H | I | n-Pr | nonafluoro-2-butyl | F | CF3 |
| 5-268 | 6-bromopyridin-3-yl | H | H | H | CN | H | H | I | n-Pr | nonafluoro-2-butyl | Cl | CF3 |
| 5-269 | 6-iodopyridin-3-yl | H | H | H | CN | H | H | I | n-Pr | nonafluoro-2-butyl | Br | CF3 |
| 5-270 | 6-(trifluoromethyl)pyridin-3-yl | H | H | H | CN | H | H | I | n-Pr | nonafluoro-2-butyl | I | n-C3F7 |
| 5-271 | 6-nitropyridin-3-yl | H | H | H | CN | H | H | I | i-Pr | nonafluoro-2-butyl | F | i-C3F7 |
| 5-272 | 6-cyanopyridin-3-yl | H | H | H | CN | H | H | I | i-Pr | nonafluoro-2-butyl | Cl | CF3 |
| 5-273 | 5-fluoropyridin-3-yl | n-Pr | C(O)Me | H | CN | H | H | I | i-Pr | nonafluoro-2-butyl | Br | CF3 |
| 5-274 | 5-chloropyridin-3-yl | H | H | H | CN | H | H | I | i-Pr | nonafluoro-2-butyl | I | CF3 |
| 5-275 | 5-bromopyridin-3-yl | H | H | H | CN | H | H | I | n-Bu | nonafluoro-2-butyl | F | CF3 |
| 5-276 | 5-iodopyridin-3-yl | H | H | H | CN | H | H | I | n-Bu | nonafluoro-2-butyl | Cl | CF3 |
| 5-277 | 5-(trifluoromethyl)pyridin-3-yl | H | H | H | CN | H | H | I | n-Bu | nonafluoro-2-butyl | Br | CF3 |
| 5-278 | 5-nitropyridin-3-yl | i-Pr | Me | H | CN | H | H | I | n-Bu | nonafluoro-2-butyl | I | CF3 |
| 5-279 | 5-cyanopyridin-3-yl | H | H | H | CN | H | H | I | i-Bu | nonafluoro-2-butyl | F | CF3 |
| 5-280 | 4-fluoropyridin-3-yl | H | H | H | CN | H | H | I | i-Bu | nonafluoro-2-butyl | Cl | CF3 |
| 5-281 | 4-chloropyridin-3-yl | H | H | H | CN | H | H | I | i-Bu | nonafluoro-2-butyl | Br | CF3 |
| 5-282 | 4-bromopyridin-3-yl | i-Pr | Et | H | CN | H | H | I | i-Bu | nonafluoro-2-butyl | I | CF3 |
| 5-283 | 4-iodopyridin-3-yl | i-Pr | n-Pr | H | CN | H | H | I | s-Bu | nonafluoro-2-butyl | F | CF3 |

TABLE 5-continued

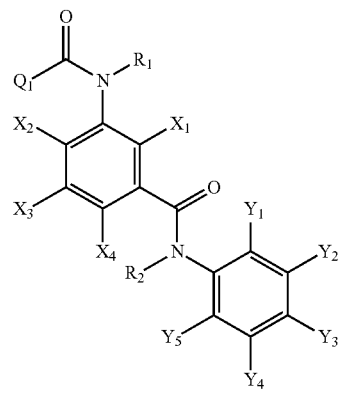

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 5-284 | 4-(trifluoromethyl)pyridin-3-yl | H | H | H | CN | H | H | I | s-Bu | nonafluoro-2-butyl | Cl | CF3 |
| 5-285 | 4-nitropyridin-3-yl | i-Pr | C(O)Me | H | CN | H | H | I | s-Bu | nonafluoro-2-butyl | Br | CF3 |
| 5-286 | 4-cyanopyridin-3-yl | H | H | H | CN | H | H | I | s-Bu | nonafluoro-2-butyl | I | CF3 |
| 5-295 | 3-bromophenyl | H | Et | H | CN | H | H | OCF3 | F | heptafluoroisopropyl | F | OCF3 |
| 5-325 | 2-iodopyridin-3-yl | H | H | H | CN | H | H | OCF3 | Me | nonafluoro-2-butyl | Me | OCF3 |
| 5-438 | 3-bromophenyl | H | Et | H | CN | H | H | OCF3 | F | heptafluoroisopropyl | F | CF3 |
| 5-468 | 2-iodopyridin-3-yl | H | H | H | CN | H | H | OCF3 | Me | nonafluoro-2-butyl | Me | CF3 |
| 5-581 | 3-bromophenyl | H | Et | H | CN | H | H | CF3 | F | heptafluoroisopropyl | F | CF3 |
| 5-611 | 2-iodopyridin-3-yl | H | H | H | CN | H | H | CF3 | Me | nonafluoro-2-butyl | Me | CF3 |
| 5-724 | 3-bromophenyl | H | Et | F | CN | H | H | Cl | F | heptafluoroisopropyl | F | OCF3 |
| 5-754 | 2-iodopyridin-3-yl | H | H | F | CN | H | H | Cl | Me | nonafluoro-2-butyl | Me | OCF3 |
| 5-863 | 2-chlorophenyl | H | H | F | CN | H | H | F | Br | heptafluoroisopropyl | H | CF3 |
| 5-869 | 2-iodophenyl | H | H | F | CN | H | H | Cl | F | heptafluoroisopropyl | Br | CF3 |
| 5-876 | 3-nitrophenyl | H | H | F | CN | H | H | Cl | Br | heptafluoroisopropyl | Cl | CF3 |
| 5-883 | 2,4-dichlorophenyl | H | H | F | CN | H | H | Cl | Me | nonafluoro-2-butyl | H | CF3 |
| 5-884 | 2-chloro-4-fluorophenyl | H | H | F | CN | H | H | Cl | H | nonafluoro-2-butyl | Me | CF3 |
| 5-885 | 2-chloro-4,5-difluorophenyl | i-Pr | H | F | CN | H | H | Cl | Et | nonafluoro-2-butyl | H | CF3 |
| 5-886 | 4-bromo-2-chlorophenyl | H | H | F | CN | H | H | Cl | H | nonafluoro-2-butyl | Et | CF3 |
| 5-897 | 2-iodopyridin-3-yl | H | H | F | CN | H | H | Cl | Me | nonafluoro-2-butyl | Me | n-C3F7 |
| 5-898 | 2-(trifluoromethyl)pyridin-3-yl | H | H | F | CN | H | H | Cl | Me | nonafluoro-2-butyl | Et | i-C3F7 |
| 5-904 | 6-iodopyridin-3-yl | H | H | F | CN | H | H | Cl | Et | nonafluoro-2-butyl | Me | n-C3F7 |
| 5-905 | 6-(trifluoromethyl)pyridin-3-yl | H | H | F | CN | H | H | Cl | Et | nonafluoro-2-butyl | Et | i-C3F7 |
| 5-911 | 5-bromopyridin-3-yl | H | H | F | CN | H | H | Br | n-Pr | heptafluoroisopropyl | Me | CF3 |
| 5-912 | 5-iodopyridin-3-yl | H | H | F | CN | H | H | Br | n-Pr | heptafluoroisopropyl | Et | CF3 |
| 5-918 | 4-bromopyridin-3-yl | Me | n-Pr | F | CN | H | H | Br | i-Pr | heptafluoroisopropyl | Me | CF3 |
| 5-919 | 4-iodopyridin-3-yl | H | H | F | CN | H | H | Br | i-Pr | heptafluoroisopropyl | Et | CF3 |
| 5-925 | pyridin-4-yl | H | H | F | CN | H | H | Br | n-Bu | heptafluoroisdpropyl | Me | CF3 |
| 5-926 | 2-chloropyridin-4-yl | H | H | F | CN | H | H | Br | n-Bu | heptafluoroisopropyl | Et | CF3 |
| 5-932 | pyridin-2-yl | H | H | F | CN | H | H | Br | i-Bu | nonafluoro-2-butyl | Me | CF3 |
| 5-933 | 3-chloropyridin-2-yl | H | H | F | CN | H | H | Br | i-Bu | nonafluoro-2-butyl | Et | CF3 |
| 5-939 | 2-fluorophenyl | H | H | F | CN | H | H | Br | s-Bu | nonafluoro-2-butyl | Me | CF3 |
| 5-940 | 3-fluorophenyl | H | H | F | CN | H | H | Br | s-Bu | nonafluoro-2-butyl | Et | CF3 |
| 5-946 | 3-bromophenyl | H | H | F | CN | H | H | Br | F | nonafluoro-2-butyl | Me | CF3 |
| 5-947 | 4-bromophenyl | H | H | F | CN | H | H | Br | F | nonafluoro-2-butyl | Et | CF3 |
| 5-953 | (4-trifluoromethyl)phenyl | Et | i-Pr | F | CN | H | H | Br | Cl | nonafluoro-2-butyl | Me | CF3 |
| 5-954 | 2-nitrophenyl | H | H | F | CN | H | H | Br | Cl | nonafluoro-2-butyl | Et | CF3 |
| 5-960 | 4-cyanophenyl | H | H | F | CN | H | H | I | Br | heptafluoroisopropyl | Me | CF3 |
| 5-961 | 2,6-difluorophenyl | H | H | F | CN | H | H | I | Br | heptafluoroisopropyl | Et | CF3 |
| 5-967 | 2-bromo-4-chlorophenyl | n-Pr | Me | F | CN | H | H | I | I | heptafluoroisopropyl | Me | CF3 |
| 5-968 | 2-bromo-4-fluorophenyl | H | H | F | CN | H | H | I | I | heptafluoroisopropyl | Et | CF3 |
| 5-974 | 2-fluoropyridin-3-yl | H | H | F | CN | H | H | I | Me | heptafluoroisopropyl | F | C2F5 |
| 5-975 | 2-chloropyridin-3-yl | H | H | F | CN | H | H | I | Me | nonafluoro-2-butyl | Cl | CF3 |
| 5-978 | 2-(trifluoromethyl)pyridin-3-yl | H | H | F | CN | H | H | I | Et | nonafluoro-2-butyl | F | CF3 |
| 5-979 | 2-nitropyridin-3-yl | H | H | F | CN | H | H | I | Et | nonafluoro-2-butyl | Cl | CF3 |
| 5-982 | 6-chloropyridin-3-yl | H | H | F | CN | H | H | I | n-Pr | nonafluoro-2-butyl | F | CF3 |
| 5-983 | 6-bromopyridin-3-yl | H | H | F | CN | H | H | I | n-Pr | nonafluoro-2-butyl | Cl | CF3 |
| 5-986 | 6-nitropyridin-3-yl | H | H | F | CN | H | H | I | i-Pr | nonafluoro-2-butyl | F | i-C3F7 |
| 5-987 | 6-cyanopyridin-3-yl | H | H | F | CN | H | H | I | i-Pr | nonafluoro-2-butyl | Cl | CF3 |
| 5-990 | 5-bromopyridin-3-yl | H | H | F | CN | H | H | I | n-Bu | nonafluoro-2-butyl | F | CF3 |
| 5-991 | 5-iodopyridin-3-yl | H | H | F | CN | H | H | I | n-Bu | nonafluoro-2-butyl | Cl | CF3 |
| 5-994 | 5-cyanopyridin-3-yl | H | H | F | CN | H | H | I | i-Bu | nonafluoro-2-butyl | F | CF3 |
| 5-995 | 4-fluoropyridin-3-yl | H | H | F | CN | H | H | I | i-Bu | nonafluoro-2-butyl | Cl | CF3 |
| 5-998 | 4-iodopyridin-3-yl | i-Pr | n-Pr | F | CN | H | H | I | s-Bu | nonafluoro-2-butyl | F | CF3 |
| 5-999 | 4-(trifluoromethyl)pyridin-3-yl | H | H | F | CN | H | H | I | s-Bu | nonafluoro-2-butyl | Cl | CF3 |
| 5-1010 | 3-bromophenyl | H | Et | F | CN | H | H | OCF3 | F | heptafluoroisopropyl | F | OCF3 |
| 5-1040 | 2-iodopyridin-3-yl | H | H | F | CN | H | H | OCF3 | Me | nonafluoro-2-butyl | Me | OCF3 |
| 5-1153 | 3-bromophenyl | H | Et | F | CN | H | H | OCF3 | F | heptafluoroisopropyl | F | CF3 |

TABLE 5-continued

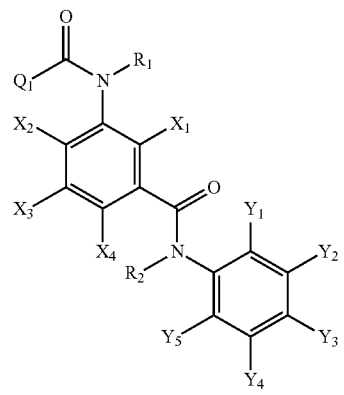

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 5-1183 | 2-iodopyridin-3-yl | H | H | F | CN | H | H | OCF3 | Me | nonafluoro-2-butyl | Me | CF3 |
| 5-1296 | 3-bromophenyl | H | Et | F | CN | H | H | CF3 | F | heptafluoroisopropyl | F | CF3 |
| 5-1326 | 2-iodopyridin-3-yl | H | H | F | CN | H | H | CF3 | Me | nonafluoro-2-butyl | Me | CF3 |
| 5-1439 | 3-bromophenyl | H | Et | F | CN | F | H | Cl | F | heptafluoroisopropyl | F | OCF3 |
| 5-1469 | 2-iodopyridin-3-yl | H | H | F | CN | F | H | Cl | Me | nonafluoro-2-butyl | Me | OCF3 |
| 5-1576 | 3-fluorophenyl | H | Me | F | CN | F | H | Cl | Cl | heptafluoroisopropyl | H | CF3 |
| 5-1583 | 4-bromophenyl | H | H | F | CN | F | H | Cl | F | heptafluoroisopropyl | Cl | CF3 |
| 5-1591 | 3-nitrophenyl | H | H | F | CN | F | H | Cl | Br | heptafluoroisopropyl | Cl | CF3 |
| 5-1598 | 2,4-dichlorophenyl | H | H | F | CN | F | H | Cl | Me | nonafluoro-2-butyl | H | CF3 |
| 5-1599 | 2-chloro-4-fluorophenyl | H | H | F | CN | F | H | Cl | H | nonafluoro-2-butyl | Me | CF3 |
| 5-1600 | 2-chloro-4,5-difluorophenyl | i-Pr | H | F | CN | F | H | Cl | Et | nonafluoro-2-butyl | H | CF3 |
| 5-1601 | 4-bromo-2-chlorophenyl | H | H | F | CN | F | H | Cl | H | nonafluoro-2-butyl | Et | CF3 |
| 5-1612 | 2-iodopyridin-3-yl | H | H | F | CN | F | H | Cl | Me | nonafluoro-2-butyl | Me | n-C3F7 |
| 5-1613 | 2-(trifluoromethyl)pyridin-3-yl | H | H | F | CN | F | H | Cl | Me | nonafluoro-2-butyl | Et | i-C3F7 |
| 5-1619 | 6-iodopyridin-3-yl | H | H | F | CN | F | H | Cl | Et | nonafluoro-2-butyl | Me | n-C3F7 |
| 5-1620 | 6-(trifluoromethyl)pyridin-3-yl | H | H | F | CN | F | H | Cl | Et | nonafluoro-2-butyl | Et | i-C3F7 |
| 5-1626 | 5-bromopyridin-3-yl | H | H | F | CN | F | H | Br | n-Pr | heptafluoroisopropyl | Me | CF3 |
| 5-1627 | 5-iodopyridin-3-yl | H | H | F | CN | F | H | Br | n-Pr | heptafluordisopropyl | Et | CF3 |
| 5-1633 | 4-bromopyridin-3-yl | Me | n-Pr | F | CN | F | H | Br | i-Pr | heptafluoroisopropyl | Me | CF3 |
| 5-1634 | 4-iodopyridin-3-yl | H | H | F | CN | F | H | Br | i-Pr | heptafluoroisopropyl | Et | CF3 |
| 5-1640 | pyridin-4-yl | H | H | F | CN | F | H | Br | n-Bu | heptafluoroisopropyl | Me | CF3 |
| 5-1641 | 2-chloropyridin-4-yl | H | H | F | CN | F | H | Br | n-Bu | heptafluoroisopropyl | Et | CF3 |
| 5-1647 | pyridin-2-yl | H | H | F | CN | F | H | Br | i-Bu | nonafluoro-2-butyl | Me | CF3 |
| 5-1648 | 3-chloropyridin-2-yl | H | H | F | CN | F | H | Br | i-Bu | nonafluoro-2-butyl | Et | CF3 |
| 5-1654 | 2-fluorophenyl | H | H | F | CN | F | H | Br | s-Bu | nonafluoro-2-butyl | Me | CF3 |
| 5-1655 | 3-fluorophenyl | H | H | F | CN | F | H | Br | s-Bu | nonafluoro-2-butyl | Et | CF3 |
| 5-1661 | 3-bromophenyl | H | H | F | CN | F | H | Br | F | nonafluoro-2-butyl | Me | CF3 |
| 5-1662 | 4-bromophenyl | H | H | F | CN | F | H | Br | F | nonafluoro-2-butyl | Et | CF3 |
| 5-1668 | (4-trifluoromethyl)phenyl | Et | i-Pr | F | CN | F | H | Br | Cl | nonafluoro-2-butyl | Me | CF3 |
| 5-1669 | 2-nitrophenyl | H | H | F | CN | F | H | Br | Cl | nonafluoro-2-butyl | Et | CF3 |
| 5-1675 | 4-cyanophenyl | H | H | F | CN | F | H | I | Br | heptafluoroisopropyl | Me | CF3 |
| 5-1676 | 2,6-difluorophenyl | H | H | F | CN | F | H | I | Br | heptafluoroisopropyl | Et | CF3 |
| 5-1682 | 2-bromo-4-chlorophenyl | n-Pr | Me | F | CN | F | H | I | I | heptafluoroisopropyl | Me | CF3 |
| 5-1683 | 2-bromo-4-fluorophenyl | H | H | F | CN | F | H | I | I | heptafluoroisopropyl | Et | CF3 |
| 5-1689 | 2-fluoropyridin-3-yl | H | H | F | CN | F | H | I | Me | heptafluoroisopropyl | F | C2F5 |
| 5-1690 | 2-chloropyridin-3-yl | H | H | F | CN | F | H | I | Me | nonafluoro-2-butyl | Cl | CF3 |
| 5-1693 | 2-(trifluoromethyl)pyridin-3-yl | H | H | F | CN | F | H | I | Et | nonafluoro-2-butyl | F | CF3 |
| 5-1694 | 2-nitropyridin-3-yl | H | H | F | CN | F | H | I | Et | nonafluoro-2-butyl | Cl | CF3 |
| 5-1697 | 6-chloropyridin-3-yl | H | H | F | CN | F | H | I | n-Pr | nonafluoro-2-butyl | F | CF3 |
| 5-1698 | 6-bromopyridin-3-yl | H | H | F | CN | F | H | I | n-Pr | nonafluoro-2-butyl | Cl | CF3 |
| 5-1701 | 6-nitropyridin-3-yl | H | H | F | CN | F | H | I | i-Pr | nonafluoro-2-butyl | F | i-C3F7 |
| 5-1702 | 6-cyanopyridin-3-yl | H | H | F | CN | F | H | I | i-Pr | nonafluoro-2-butyl | Cl | CF3 |
| 5-1705 | 5-bromopyridin-3-yl | H | H | F | CN | F | H | I | n-Bu | nonafluoro-2-butyl | F | CF3 |
| 5-1706 | 5-iodopyridin-3-yl | H | H | F | CN | F | H | I | n-Bu | nonafluoro-2-butyl | Cl | CF3 |
| 5-1709 | 5-cyanopyridin-3-yl | H | H | F | CN | F | H | I | i-Bu | nonafluoro-2-butyl | F | CF3 |
| 5-1710 | 4-fluoropyridin-3-yl | H | H | F | CN | F | H | I | i-Bu | nonafluoro-2-butyl | Cl | CF3 |
| 5-1713 | 4-iodopyridin-3-yl | i-Pr | n-Pr | F | CN | F | H | I | s-Bu | nonafluoro-2-butyl | F | CF3 |
| 5-1714 | 4-(trifluoromethyl)pyridin-3-yl | H | H | F | CN | F | H | I | s-Bu | nonafluoro-2-butyl | Cl | CF3 |
| 5-1725 | 3-bromophenyl | H | Et | F | CN | F | H | OCF3 | F | heptafluoroisopropyl | F | OCF3 |
| 5-1755 | 2-iodopyridin-3-yl | H | H | F | CN | F | H | OCF3 | Me | nonafluoro-2-butyl | Me | OCF3 |
| 5-1868 | 3-bromophenyl | H | Et | F | CN | F | H | OCF3 | F | heptafluoroisopropyl | F | CF3 |
| 5-1898 | 2-iodopyridin-3-yl | H | H | F | CN | F | H | OCF3 | Me | nonafluoro-2-butyl | Me | CF3 |
| 5-2011 | 3-bromophenyl | H | Et | F | CN | F | H | CF3 | F | heptafluoroisopropyl | F | CF3 |
| 5-2041 | 2-iodopyridin-3-yl | H | H | F | CN | F | H | CF3 | Me | nonafluoro-2-butyl | Me | CF3 |

TABLE 6

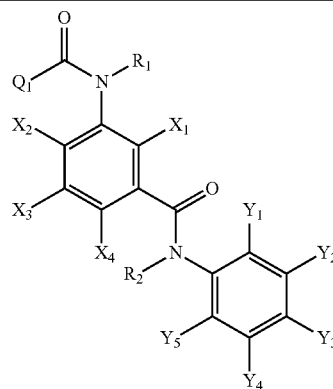

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-1 | phenyl | H | H | H | H | H | H | F | H | nonafluoro-2-butyl | H | F |
| 6-2 | 3-cyanophenyl | H | H | H | H | H | H | F | H | nonafluoro-2-butyl | H | F |
| 6-3 | 4-cyanophenyl | H | H | H | H | H | H | F | H | nonafluoro-2-butyl | H | F |
| 6-4 | 2-chloropyridin-3-yl | H | H | H | H | H | H | F | H | nonafluoro-2-butyl | H | F |
| 6-5 | phenyl | H | H | H | H | H | H | Cl | H | nonafluoro-2-butyl | H | Cl |
| 6-12 | 3-cyanophenyl | H | H | H | H | H | H | Cl | H | nonafluoro-2-butyl | H | Cl |
| 6-13 | 4-cyanophenyl | H | H | H | H | H | H | Cl | H | nonafluoro-2-butyl | H | Cl |
| 6-24 | 2-chloropyridin-3-yl | H | H | H | H | H | H | Cl | H | nonafluoro-2-butyl | H | Cl |
| 6-38 | phenyl | H | H | H | H | H | H | Br | H | nonafluoro-2-butyl | H | Br |
| 6-39 | 2-fluorophenyl | H | H | H | H | H | H | Br | H | nonafluoro-2-butyl | H | Br |
| 6-45 | 3-cyanophenyl | H | H | H | H | H | H | Br | H | nonafluoro-2-butyl | H | Br |
| 6-46 | 4-cyanophenyl | H | H | H | H | H | H | Br | H | nonafluoro-2-butyl | H | Br |
| 6-47 | 2,6-difluorophenyl | H | H | H | H | H | H | Br | H | nonafluoro-2-butyl | H | Br |
| 6-57 | 2-chloropyridin-3-yl | H | H | H | H | H | H | Br | H | nonafluoro-2-butyl | H | Br |
| 6-60 | 6-chloropyridin-3-yl | H | H | H | H | H | H | Br | H | nonafluoro-2-butyl | H | Br |
| 6-71 | phenyl | H | H | H | H | H | H | I | H | nonafluoro-2-butyl | H | I |
| 6-72 | 2-fluorophenyl | H | H | H | H | H | H | I | H | nonafluoro-2-butyl | H | I |
| 6-78 | 3-cyanophenyl | H | H | H | H | H | H | I | H | nonafluoro-2-butyl | H | I |
| 6-79 | 4-cyanophenyl | H | H | H | H | H | H | I | H | nonafluoro-2-butyl | H | I |
| 6-80 | 2,6-difluorophenyl | H | H | H | H | H | H | I | H | nonafluoro-2-butyl | H | I |
| 6-90 | 2-chloropyridin-3-yl | H | H | H | H | H | H | I | H | nonafluoro-2-butyl | H | I |
| 6-93 | 6-chloropyridin-3-yl | H | H | H | H | H | H | I | H | nonafluoro-2-butyl | H | I |
| 6-104 | phenyl | H | H | H | H | H | H | F | H | nonafluoro-2-butyl | H | Cl |
| 6-105 | phenyl | H | H | H | H | H | H | F | H | nonafluoro-2-butyl | H | Br |
| 6-106 | phenyl | H | H | H | H | H | H | F | H | nonafluoro-2-butyl | H | I |
| 6-107 | phenyl | H | H | H | H | H | H | Cl | H | nonafluoro-2-butyl | H | Br |
| 6-108 | phenyl | H | H | H | H | H | H | Cl | H | nonafluoro-2-butyl | H | I |
| 6-109 | phenyl | H | H | H | H | H | H | Br | H | nonafluoro-2-butyl | H | I |
| 6-110 | phenyl | H | H | H | H | H | H | F | H | heptafluoroisopropyl | H | CF3 |
| 6-111 | phenyl | H | H | H | H | H | H | Cl | H | heptafluoroisopropyl | H | CF3 |
| 6-131 | 3-cyanophenyl | H | H | H | H | H | H | Cl | H | heptafluoroisopropyl | H | CF3 |
| 6-132 | 4-cyanophenyl | H | H | H | H | H | H | Cl | H | heptafluoroisopropyl | H | CF3 |
| 6-147 | 2-chloropyridin-3-yl | H | H | H | H | H | H | Cl | H | heptafluoroisopropyl | H | CF3 |
| 6-189 | phenyl | H | H | H | H | H | H | F | H | nonafluoro-2-butyl | H | CF3 |
| 6-190 | phenyl | H | H | H | H | H | H | Cl | H | nonafluoro-2-butyl | H | CF3 |
| 6-210 | 3-cyanophenyl | H | H | H | H | H | H | Cl | H | nonafluoro-2-butyl | H | CF3 |
| 6-211 | 4-cyanophenyl | H | H | H | H | H | H | Cl | H | nonafluoro-2-butyl | H | CF3 |
| 6-226 | 2-chloropyridin-3-yl | H | H | H | H | H | H | Cl | H | nonafluoro-2-butyl | H | CF3 |
| 6-268 | phenyl | H | H | H | H | H | H | Br | H | heptafluoroisopropyl | H | CF3 |
| 6-269 | 2-fluorophenyl | H | H | H | H | H | H | Br | H | heptafluoroisopropyl | H | CF3 |
| 6-270 | 3-fluorophenyl | H | H | H | H | H | H | Br | H | heptafluoroisopropyl | H | CF3 |
| 6-271 | 4-fluorophenyl | H | H | H | H | H | H | Br | H | heptafluoroisopropyl | H | CF3 |
| 6-272 | 2-chlorophenyl | H | H | H | H | H | H | Br | H | heptafluoroisopropyl | H | CF3 |
| 6-288 | 3-cyanophenyl | H | H | H | H | H | H | Br | H | heptafluoroisopropyl | H | CF3 |
| 6-289 | 4-cyanophenyl | H | H | H | H | H | H | Br | H | heptafluoroisopropyl | H | CF3 |
| 6-290 | 2,6-difluorophenyl | H | H | H | H | H | H | Br | H | heptafluoroisopropyl | H | CF3 |
| 6-293 | 2-chloro-4-fluorophenyl | H | H | H | H | H | H | Br | H | heptafluoroisopropyl | H | CF3 |
| 6-300 | 4-cyano-2-fluorophenyl | H | H | H | H | H | H | Br | H | heptafluoroisopropyl | H | CF3 |
| 6-304 | 2-chloropyridin-3-yl | H | H | H | H | H | H | Br | H | heptafluoroisopropyl | H | CF3 |
| 6-305 | 2-bromopyridin-3-yl | H | H | H | H | H | H | Br | H | heptafluoroisopropyl | H | CF3 |
| 6-306 | 2-iodopyridin-3-yl | H | H | H | H | H | H | Br | H | heptafluoroisopropyl | H | CF3 |
| 6-311 | 6-chloropyridin-3-yl | H | H | H | H | H | H | Br | H | heptafluoroisopropyl | H | CF3 |
| 6-346 | phenyl | H | H | H | H | H | H | Br | H | nonafluoro-2-butyl | H | CF3 |
| 6-347 | 2-fluorophenyl | H | H | H | H | H | H | Br | H | nonafluoro-2-butyl | H | CF3 |
| 6-348 | 3-fluorophenyl | H | H | H | H | H | H | Br | H | nonafluoro-2-butyl | H | CF3 |
| 6-349 | 4-fluorophenyl | H | H | H | H | H | H | Br | H | nonafluoro-2-butyl | H | CF3 |
| 6-366 | 3-cyanophenyl | H | H | H | H | H | H | Br | H | nonafluoro-2-butyl | H | CF3 |
| 6-367 | 4-cyanophenyl | H | H | H | H | H | H | Br | H | nonafluoro-2-butyl | H | CF3 |

TABLE 6-continued

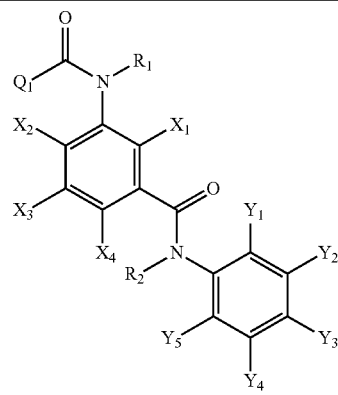

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-368 | 2,6-difluorophenyl | H | H | H | H | H | H | Br | H | nonafluoro-2-butyl | H | CF3 |
| 6-382 | 2-chloropyridin-3-yl | H | H | H | H | H | H | Br | H | nonafluoro-2-butyl | H | CF3 |
| 6-389 | 6-chloropyridin-3-yl | H | H | H | H | H | H | Br | H | nonafluoro-2-butyl | H | CF3 |
| 6-424 | phenyl | H | H | H | H | H | H | I | H | heptafluoroisopropyl | H | CF3 |
| 6-425 | 2-fluorophenyl | H | H | H | H | H | H | I | H | heptafluoroisopropyl | H | CF3 |
| 6-426 | 3-fluorophenyl | H | H | H | H | H | H | I | H | heptafluoroisopropyl | H | CF3 |
| 6-427 | 4-fluorophenyl | H | H | H | H | H | H | I | H | heptafluoroisopropyl | H | CF3 |
| 6-428 | 2-chlorophenyl | H | H | H | H | H | H | I | H | heptafluoroisopropyl | H | CF3 |
| 6-444 | 3-cyanophenyl | H | H | H | H | H | H | I | H | heptafluoroisopropyl | H | CF3 |
| 6-445 | 4-cyanophenyl | H | H | H | H | H | H | I | H | heptafluoroisopropyl | H | CF3 |
| 6-446 | 2,6-difluorophenyl | H | H | H | H | H | H | I | H | heptafluoroisopropyl | H | CF3 |
| 6-448 | 2,4-dichlorophenyl | H | H | H | H | H | H | I | H | heptafluoroisopropyl | H | CF3 |
| 6-449 | 2-chloro-4-fluorophenyl | H | H | H | H | H | H | I | H | heptafluoroisopropyl | H | CF3 |
| 6-450 | 2-chloro-4,5-difluorophenyl | H | H | H | H | H | H | I | H | heptafluoroisopropyl | H | CF3 |
| 6-451 | 4-bromo-2-chlorophenyl | H | H | H | H | H | H | I | H | heptafluoroisopropyl | H | CF3 |
| 6-452 | 2-bromo-4-chlorophenyl | H | H | H | H | H | H | I | H | heptafluoroisopropyl | H | CF3 |
| 6-453 | 2-bromo-4-fluorophenyl | H | H | H | H | H | H | I | H | heptafluoroisopropyl | H | CF3 |
| 6-454 | 2-chloro-4-nitrophenyl | H | H | H | H | H | H | I | H | heptafluoroisopropyl | H | CF3 |
| 6-460 | 2-chloropyridin-3-yl | H | H | H | H | H | H | I | H | heptafluoroisopropyl | H | CF3 |
| 6-461 | 2-bromopyridin-3-yl | H | H | H | H | H | H | I | H | heptafluoroisopropyl | H | CF3 |
| 6-467 | 6-chloropyridin-3-yl | H | H | H | H | H | H | I | H | heptafluoroisopropyl | H | CF3 |
| 6-502 | phenyl | H | H | H | H | H | H | I | H | nonafluoro-2-butyl | H | CF3 |
| 6-503 | 2-fluorophenyl | H | H | H | H | H | H | I | H | nonafluoro-2-butyl | H | CF3 |
| 6-504 | 3-fluorophenyl | H | H | H | H | H | H | I | H | nonafluoro-2-butyl | H | CF3 |
| 6-505 | 4-fluorophenyl | H | H | H | H | H | H | I | H | nonafluoro-2-butyl | H | CF3 |
| 6-522 | 3-cyanophenyl | H | H | H | H | H | H | I | H | nonafluoro-2-butyl | H | CF3 |
| 6-523 | 4-cyanophenyl | H | H | H | H | H | H | I | H | nonafluoro-2-butyl | H | CF3 |
| 6-524 | 2,6-difluorophenyl | H | H | H | H | H | H | I | H | nonafluoro-2-butyl | H | CF3 |
| 6-538 | 2-chloropyridin-3-yl | H | H | H | H | H | H | I | H | nonafluoro-2-butyl | H | CF3 |
| 6-545 | 6-chloropyridin-3-yl | H | H | H | H | H | H | I | H | nonafluoro-2-butyl | H | CF3 |
| 6-580 | phenyl | H | H | H | H | H | H | OCF3 | H | heptafluoroisopropyl | H | OCF3 |
| 6-595 | 3-cyanophenyl | H | H | H | H | H | H | OCF3 | H | heptafluoroisopropyl | H | OCF3 |
| 6-596 | 4-cyanophenyl | H | H | H | H | H | H | OCF3 | H | heptafluoroisopropyl | H | OCF3 |
| 6-611 | 2-chloropyridin-3-yl | H | H | H | H | H | H | OCF3 | H | heptafluoroisopropyl | H | OCF3 |
| 6-636 | phenyl | H | H | H | H | H | H | OCF3 | H | nonafluoro-2-butyl | H | OCF3 |
| 6-651 | 3-cyanophenyl | H | H | H | H | H | H | OCF3 | H | nonafluoro-2-butyl | H | OCF3 |
| 6-652 | 4-cyanophenyl | H | H | H | H | H | H | OCF3 | H | nonafluoro-2-butyl | H | OCF3 |
| 6-667 | 2-chloropyridin-3-yl | H | H | H | H | H | H | OCF3 | H | nonafluoro-2-butyl | H | OCF3 |
| 6-692 | phenyl | H | H | H | H | H | H | CF3 | H | heptafluoroisopropyl | H | OCF3 |
| 6-707 | 3-cyanophenyl | H | H | H | H | H | H | CF3 | H | heptafluoroisopropyl | H | OCF3 |
| 6-708 | 4-cyanophenyl | H | H | H | H | H | H | CF3 | H | heptafluoroisopropyl | H | OCF3 |
| 6-723 | 2-chloropyridin-3-yl | H | H | H | H | H | H | CF3 | H | heptafluoroisopropyl | H | OCF3 |
| 6-748 | phenyl | H | H | H | H | H | H | CF3 | H | nonafluoro-2-butyl | H | OCF3 |
| 6-763 | 3-cyanophenyl | H | H | H | H | H | H | CF3 | H | nonafluoro-2-butyl | H | OCF3 |
| 6-764 | 4-cyanophenyl | H | H | H | H | H | H | CF3 | H | nonafluoro-2-butyl | H | OCF3 |
| 6-779 | 2-chloropyridin-3-yl | H | H | H | H | H | H | CF3 | H | nonafluoro-2-butyl | H | OCF3 |
| 6-804 | phenyl | H | H | H | H | H | H | CF3 | H | heptafluoroisopropyl | H | CF3 |
| 6-824 | 3-cyanophenyl | H | H | H | H | H | H | CF3 | H | heptafluoroisopropyl | H | CF3 |
| 6-825 | 4-cyanophenyl | H | H | H | H | H | H | CF3 | H | heptafluoroisopropyl | H | CF3 |
| 6-840 | 2-chloropyridin-3-yl | H | H | H | H | H | H | CF3 | H | heptafluoroisopropyl | H | CF3 |
| 6-841 | 2-bromopyridin-3-yl | H | H | H | H | H | H | CF3 | H | heptafluoroisopropyl | H | CF3 |
| 6-872 | phenyl | H | H | H | H | H | H | CF3 | H | nonafluoro-2-butyl | H | CF3 |
| 6-892 | 3-cyanophenyl | H | H | H | H | H | H | CF3 | H | nonafluoro-2-butyl | H | CF3 |
| 6-893 | 4-cyanophenyl | H | H | H | H | H | H | CF3 | H | nonafluoro-2-butyl | H | CF3 |
| 6-908 | 2-chloropyridin-3-yl | H | H | H | H | H | H | CF3 | H | nonafluoro-2-butyl | H | CF3 |
| 6-940 | phenyl | H | H | F | H | H | H | F | H | heptafluoroisopropyl | H | F |
| 6-941 | 3-cyanophenyl | H | H | F | H | H | H | F | H | heptafluoroisopropyl | H | F |
| 6-942 | 4-cyanophenyl | H | H | F | H | H | H | F | H | heptafluoroisopropyl | H | F |

TABLE 6-continued

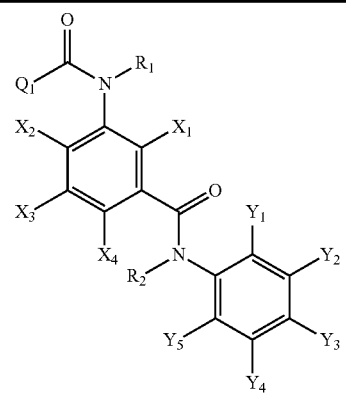

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-943 | 2-chloropyridin-3-yl | H | H | F | H | H | H | F | H | heptafluoroisopropyl | H | F |
| 6-944 | phenyl | H | H | F | H | H | H | F | H | nonafluoro-2-butyl | H | F |
| 6-945 | 3-cyanophenyl | H | H | F | H | H | H | F | H | nonafluoro-2-butyl | H | F |
| 6-946 | 4-cyanophenyl | H | H | F | H | H | H | F | H | nonafluoro-2-butyl | H | F |
| 6-947 | 2-chloropyridin-3-yl | H | H | F | H | H | H | F | H | nonafluoro-2-butyl | H | F |
| 6-948 | phenyl | H | H | F | H | H | H | Cl | H | heptafluoroisopropyl | H | Cl |
| 6-952 | 2-chlorophenyl | H | H | F | H | H | H | F | H | heptafluoroisopropyl | H | Cl |
| 6-956 | 3-bromophenyl | H | H | F | H | H | H | F | H | heptafluoroisopropyl | H | Br |
| 6-961 | (2-trifluoromethyl)phenyl | H | H | F | H | H | H | F | H | heptafluoroisopropyl | H | I |
| 6-964 | 2-nitrophenyl | H | H | F | H | H | H | Cl | H | heptafluoroisopropyl | H | Br |
| 6-968 | 3-cyanophenyl | H | H | F | H | H | H | Cl | H | heptafluoroisopropyl | H | Cl |
| 6-969 | 4-cyanophenyl | H | H | F | H | H | H | Cl | H | heptafluoroisopropyl | H | Cl |
| 6-970 | 2,6-difluorophenyl | H | H | F | H | H | H | Cl | H | heptafluoroisopropyl | H | I |
| 6-982 | pyridin-3-yl | H | H | F | H | H | H | Br | H | heptafluoroisopropyl | H | I |
| 6-984 | 2-chloropyridin-3-yl | H | H | F | H | H | H | Cl | H | heptafluoroisopropyl | H | Cl |
| 6-1026 | phenyl | H | H | F | H | H | H | Cl | H | nonafluoro-2-butyl | H | Cl |
| 6-1046 | 3-cyanophenyl | H | H | F | H | H | H | Cl | H | nonafluoro-2-butyl | H | Cl |
| 6-1047 | 4-cyanophenyl | H | H | F | H | H | H | Cl | H | nonafluoro-2-butyl | H | Cl |
| 6-1062 | 2-chloropyridin-3-yl | H | H | F | H | H | H | Cl | H | nonafluoro-2-butyl | H | Cl |
| 6-1104 | phenyl | H | H | F | H | H | H | Br | H | heptafluoroisopropyl | H | Br |
| 6-1105 | 2-fluorophenyl | H | H | F | H | H | H | Br | H | heptafluoroisopropyl | H | Br |
| 6-1106 | 3-fluorophenyl | H | H | F | H | H | H | Br | H | heptafluoroisopropyl | H | Br |
| 6-1107 | 4-fluorophenyl | H | H | F | H | H | H | Br | H | heptafluoroisopropyl | H | Br |
| 6-1124 | 3-cyanophenyl | H | H | F | H | H | H | Br | H | heptafluoroisopropyl | H | Br |
| 6-1125 | 4-cyanophenyl | H | H | F | H | H | H | Br | H | heptafluoroisopropyl | H | Br |
| 6-1126 | 2,6-difluorophenyl | H | H | F | H | H | H | Br | H | heptafluoroisopropyl | H | Br |
| 6-1140 | 2-chloropyridin-3-yl | H | H | F | H | H | H | Br | H | heptafluoroisopropyl | H | Br |
| 6-1147 | 6-chloropyridin-3-yl | H | H | F | H | H | H | Br | H | heptafluoroisopropyl | H | Br |
| 6-1182 | phenyl | H | H | F | H | H | H | Br | H | nonafluoro-2-butyl | H | Br |
| 6-1183 | 2-fluorophenyl | H | H | F | H | H | H | Br | H | nonafluoro-2-butyl | H | Br |
| 6-1184 | 3-fluorophenyl | H | H | F | H | H | H | Br | H | nonafluoro-2-butyl | H | Br |
| 6-1185 | 4-fluorophenyl | H | H | F | H | H | H | Br | H | nonafluoro-2-butyl | H | Br |
| 6-1202 | 3-cyanophenyl | H | H | F | H | H | H | Br | H | nonafluoro-2-butyl | H | Br |
| 6-1203 | 4-cyanophenyl | H | H | F | H | H | H | Br | H | nonafluoro-2-butyl | H | Br |
| 6-1204 | 2,6-difluorophenyl | H | H | F | H | H | H | Br | H | nonafluoro-2-butyl | H | Br |
| 6-1218 | 2-chloropyridin-3-yl | H | H | F | H | H | H | Br | H | nonafluoro-2-butyl | H | Br |
| 6-1225 | 6-chloropyridin-3-yl | H | H | F | H | H | H | Br | H | nonafluoro-2-butyl | H | Br |
| 6-1260 | phenyl | H | H | F | H | H | H | I | H | heptafluoroisopropyl | H | I |
| 6-1261 | 2-fluorophenyl | H | H | F | H | H | H | I | H | heptafluoroisopropyl | H | I |
| 6-1262 | 3-fluorophenyl | H | H | F | H | H | H | I | H | heptafluoroisopropyl | H | I |
| 6-1263 | 4-fluorophenyl | H | H | F | H | H | H | I | H | heptafluoroisopropyl | H | I |
| 6-1280 | 3-cyanophenyl | H | H | F | H | H | H | I | H | heptafluoroisopropyl | H | I |
| 6-1281 | 4-cyanophenyl | H | H | F | H | H | H | I | H | heptafluoroisopropyl | H | I |
| 6-1282 | 2,6-difluorophenyl | H | H | F | H | H | H | I | H | heptafluoroisopropyl | H | I |
| 6-1296 | 2-chloropyridin-3-yl | H | H | F | H | H | H | I | H | heptafluoroisopropyl | H | I |
| 6-1303 | 6-chloropyridin-3-yl | H | H | F | H | H | H | I | H | heptafluoroisopropyl | H | I |
| 6-1338 | phenyl | H | H | F | H | H | H | I | H | nonafluoro-2-butyl | H | I |
| 6-1339 | 2-fluorophenyl | H | H | F | H | H | H | I | H | nonafluoro-2-butyl | H | I |
| 6-1340 | 3-fluorophenyl | H | H | F | H | H | H | I | H | nonafluoro-2-butyl | H | I |
| 6-1341 | 4-fluorophenyl | H | H | F | H | H | H | I | H | nonafluoro-2-butyl | H | I |
| 6-1358 | 3-cyanophenyl | H | H | F | H | H | H | I | H | nonafluoro-2-butyl | H | I |
| 6-1359 | 4-cyanophenyl | H | H | F | H | H | H | I | H | nonafluoro-2-butyl | H | I |
| 6-1360 | 2,6-difluorophenyl | H | H | F | H | H | H | I | H | nonafluoro-2-butyl | H | I |
| 6-1374 | 2-chloropyridin-3-yl | H | H | F | H | H | H | I | H | nonafluoro-2-butyl | H | I |
| 6-1381 | 6-chloropyridin-3-yl | H | H | F | H | H | H | I | H | nonafluoro-2-butyl | H | I |
| 6-1416 | phenyl | H | H | F | H | H | H | F | H | heptafluoroisopropyl | H | CF3 |
| 6-1417 | phenyl | H | H | F | H | H | H | Cl | H | heptafluoroisopropyl | H | CF3 |
| 6-1418 | 2-fluorophenyl | H | H | F | H | H | H | Cl | H | heptafluoroisopropyl | H | CF3 |

TABLE 6-continued

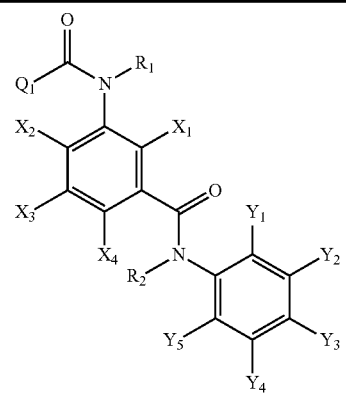

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-1422 | 3-chlorophenyl | H | H | F | H | H | H | Cl | H | heptafluoroisopropyl | H | CF3 |
| 6-1426 | 4-bromophenyl | H | H | F | H | H | H | Cl | H | heptafluoroisopropyl | H | CF3 |
| 6-1427 | 2-iodophenyl | H | H | F | H | H | H | Cl | H | pentafluoroethyl | H | CF3 |
| 6-1431 | (3-trifluoromethyl)phenyl | H | H | F | H | H | H | Cl | H | heptafluoroisopropyl | H | CF3 |
| 6-1435 | 4-nitrophenyl | H | H | F | H | H | H | Cl | H | heptafluoroisopropyl | H | CF3 |
| 6-1436 | 2-cyanophenyl | H | H | F | H | H | H | Cl | H | pentafluoroethyl | H | C2F5 |
| 6-1437 | 3-cyanophenyl | H | H | F | H | H | H | Cl | H | heptafluoroisopropyl | H | CF3 |
| 6-1438 | 4-cyanophenyl | H | H | F | H | H | H | Cl | H | heptafluoroisopropyl | H | CF3 |
| 6-1439 | 2,6-difluorophenyl | H | H | F | H | H | H | Cl | H | heptafluoroisopropyl | H | CF3 |
| 6-1440 | 3,4-dichlorophenyl | H | H | F | H | H | H | Cl | H | heptafluoroisopropyl | H | CF3 |
| 6-1441 | 2,4-dichlorophenyl | H | H | F | H | H | H | Cl | H | heptafluoroisopropyl | H | C2F5 |
| 6-1442 | 2-chloro-4-fluorophenyl | H | H | F | H | H | H | Cl | H | heptafluoroisopropyl | H | CF3 |
| 6-1445 | 2-bromo-4-chlorophenyl | H | H | F | H | H | H | Cl | H | heptafluoroisopropyl | H | n-C3F7 |
| 6-1446 | 2-bromo-4-fluorophenyl | H | H | F | H | H | H | Cl | H | heptafluoroisopropyl | H | CF3 |
| 6-1447 | 2-chloro-4-nitrophenyl | H | H | F | H | H | H | Cl | H | heptafluoroisopropyl | H | CF3 |
| 6-1448 | 3,5-dicyanophenyl | H | H | F | H | H | H | Cl | H | heptafluoroisopropyl | H | CF3 |
| 6-1449 | 4-cyano-2-fluorophenyl | H | H | F | H | H | H | Cl | H | heptafluoroisopropyl | H | CF3 |
| 6-1451 | pyridin-3-yl | H | H | F | H | H | H | Cl | H | heptafluoroisopropyl | H | CF3 |
| 6-1452 | 2-fluoropyridin-3-yl | H | H | F | H | H | H | Cl | H | pentafluoroethyl | H | CF3 |
| 6-1453 | 2-chloropyridin-3-yl | H | H | F | H | H | H | Cl | H | heptafluoroisopropyl | H | CF3 |
| 6-1456 | 2-(fluoromethyl)pyridin-3-yl | H | H | F | H | H | H | Cl | H | heptafluoroisopropyl | H | CF3 |
| 6-1457 | 2-nitropyridin-3-yl | H | H | F | H | H | H | Cl | H | heptafluoroisopropyl | H | n-C3F7 |
| 6-1460 | 6-chloropyridin-3-yl | H | H | F | H | H | H | Cl | H | heptafluoroisopropyl | H | i-C3F7 |
| 6-1467 | 5-chloropyridin-3-yl | H | H | F | H | H | H | Cl | H | heptafluoroisopropyl | H | CF3 |
| 6-1474 | 4-chloropyridin-3-yl | H | H | F | H | H | H | Cl | H | heptafluoroisopropyl | H | CF3 |
| 6-1480 | 2,6-dichloropyridin-3-yl | H | H | F | H | H | H | Cl | H | heptafluoroisopropyl | H | CF3 |
| 6-1481 | pyridin-3-yl N-oxide | H | H | F | H | H | H | Cl | H | heptafluoroisopropyl | H | CF3 |
| 6-1482 | pyridin-4-yl | H | H | F | H | H | H | Cl | H | heptafluoroisopropyl | H | CF3 |
| 6-1483 | 2-chloropyridin-4-yl | H | H | F | H | H | H | Cl | H | heptafluoroisopropyl | H | CF3 |
| 6-1485 | 3,5-dichloropyridin-4-yl | H | H | F | H | H | H | Cl | H | heptafluoroisopropyl | H | CF3 |
| 6-1488 | pyridin-4-yl N-oxide | H | H | F | H | H | H | Cl | H | heptafluoroisopropyl | H | CF3 |
| 6-1489 | pyridin-2-yl | H | H | F | H | H | H | Cl | H | heptafluoroisopropyl | H | CF3 |
| 6-1490 | 3-chloropyridin-2-yl | H | H | F | H | H | H | Cl | H | heptafluoroisopropyl | H | CF3 |
| 6-1493 | 6-chloropyridin-2-yl | H | H | F | H | H | H | Cl | H | heptafluoroisopropyl | H | CF3 |
| 6-1495 | phenyl | H | H | F | H | H | H | F | H | nonafluoro-2-butyl | H | CF3 |
| 6-1496 | phenyl | H | H | F | H | H | H | Cl | H | nonafluoro-2-butyl | H | CF3 |
| 6-1498 | 3-fluorophenyl | H | H | F | H | H | H | Cl | H | nonafluoro-2-butyl | H | CF3 |
| 6-1502 | 4-chlorophenyl | H | H | F | H | H | H | Cl | H | nonafluoro-2-butyl | H | CF3 |
| 6-1503 | 2-bromophenyl | H | H | F | H | H | H | Cl | H | nonafluoro-2-butyl | H | CF3 |
| 6-1507 | 3-iodophenyl | H | H | F | H | H | H | Cl | H | nonafluoro-2-butyl | H | CF3 |
| 6-1511 | (4-trifluoromethyl)phenyl | H | H | F | H | H | H | Cl | H | nonafluoro-2-butyl | H | CF3 |
| 6-1512 | 2-nitrophenyl | H | H | F | H | H | H | Cl | H | nonafluoro-2-butyl | H | CF3 |
| 6-1516 | 3-cyanophenyl | H | H | F | H | H | H | Cl | H | nonafluoro-2-butyl | H | CF3 |
| 6-1517 | 4-cyanophenyl | H | H | F | H | H | H | Cl | H | nonafluoro-2-butyl | H | CF3 |
| 6-1518 | 2,6-difluorophenyl | H | H | F | H | H | H | Cl | H | nonafluoro-2-butyl | H | CF3 |
| 6-1520 | 2,4-dichlorophenyl | H | H | F | H | H | H | Cl | H | nonafluoro-2-butyl | H | CF3 |
| 6-1521 | 2-chloro-4-fluorophenyl | H | H | F | H | H | H | Cl | H | nonafluoro-2-butyl | H | CF3 |
| 6-1524 | 2-bromo-4-chlorophenyl | H | H | F | H | H | H | Cl | H | nonafluoro-2-butyl | H | CF3 |
| 6-1525 | 2-bromo-4-fluorophenyl | H | H | F | H | H | H | Cl | H | nonafluoro-2-butyl | H | CF3 |
| 6-1526 | 2-chloro-4-nitrophenyl | H | H | F | H | H | H | Cl | H | nonafluoro-2-butyl | H | i-C3F7 |
| 6-1528 | 4-cyano-2-fluorophenyl | H | H | F | H | H | H | Cl | H | nonafluoro-2-butyl | H | CF3 |
| 6-1529 | 2-chloro-4-cyanophenyl | H | H | F | H | H | H | Cl | H | nonafluoro-2-butyl | H | CF3 |
| 6-1530 | pyridin-3-yl | H | H | F | H | H | H | Cl | H | nonafluoro-2-butyl | H | CF3 |
| 6-1532 | 2-chloropyridin-3-yl | H | H | F | H | H | H | Cl | H | nonafluoro-2-butyl | H | CF3 |
| 6-1539 | 6-chloropyridin-3-yl | H | H | F | H | H | H | Cl | H | nonafluoro-2-butyl | H | CF3 |
| 6-1545 | 5-fluoropyridin-3-yl | H | H | F | H | H | H | Cl | H | nonafluoro-2-butyl | H | C2F5 |
| 6-1552 | 4-fluoropyridin-3-yl | H | H | F | H | H | H | Cl | H | nonafluoro-2-butyl | H | C2F5 |
| 6-1559 | 2,6-dichloropyridin-3-yl | H | H | F | H | H | H | Cl | H | nonafluoro-2-butyl | H | CF3 |

TABLE 6-continued

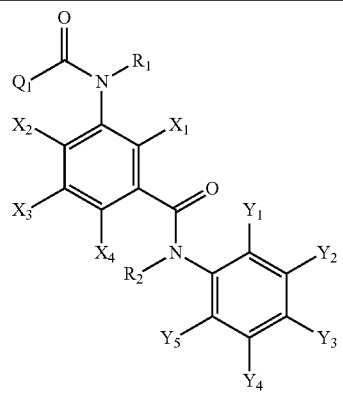

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-1560 | pyridin-3-yl N-oxide | H | H | F | H | H | H | Cl | H | nonafluoro-2-butyl | H | CF3 |
| 6-1561 | pyridin-4-yl | H | H | F | H | H | H | Cl | H | nonafluoro-2-butyl | H | CF3 |
| 6-1562 | 2-chloropyridin-4-yl | H | H | F | H | H | H | Cl | H | nonafluoro-2-butyl | H | CF3 |
| 6-1567 | pyridin-4-yl N-oxide | H | H | F | H | H | H | Cl | H | nonafluoro-2-butyl | H | CF3 |
| 6-1568 | pyridin-2-yl | H | H | F | H | H | H | Cl | H | nonafluoro-2-butyl | H | CF3 |
| 6-1569 | 3-chloropyridin-2-yl | H | H | F | H | H | H | Cl | H | nonafluoro-2-butyl | H | CF3 |
| 6-1572 | 6-chloropyridin-2-yl | H | H | F | H | H | H | Cl | H | nonafluoro-2-butyl | H | CF3 |
| 6-1574 | phenyl | H | H | F | H | H | H | Br | H | heptafluoroisopropyl | H | CF3 |
| 6-1575 | 2-fluorophenyl | H | H | F | H | H | H | Br | H | heptafluoroisopropyl | H | CF3 |
| 6-1576 | 3-fluorophenyl | H | H | F | H | H | H | Br | H | heptafluoroisopropyl | H | CF3 |
| 6-1577 | 4-fluorophenyl | H | H | F | H | H | H | Br | H | heptafluoroisopropyl | H | CF3 |
| 6-1578 | 2-chlorophenyl | H | H | F | H | H | H | Br | H | heptafluoroisopropyl | H | CF3 |
| 6-1579 | 3-chlorophenyl | H | H | F | H | H | H | Br | H | heptafluoroisopropyl | H | CF3 |
| 6-1580 | 4-chlorophenyl | H | H | F | H | H | H | Br | H | heptafluoroisopropyl | H | CF3 |
| 6-1581 | 2-bromophenyl | H | H | F | H | H | H | Br | H | heptafluoroisopropyl | H | CF3 |
| 6-1582 | 3-bromophenyl | H | H | F | H | H | H | Br | H | heptafluoroisopropyl | H | CF3 |
| 6-1583 | 4-bromophenyl | H | H | F | H | H | H | Br | H | heptafluoroisopropyl | H | CF3 |
| 6-1584 | 2-iodophenyl | H | H | F | H | H | H | Br | H | heptafluoroisopropyl | H | CF3 |
| 6-1585 | 3-iodophenyl | H | H | F | H | H | H | Br | H | heptafluoroisopropyl | H | CF3 |
| 6-1586 | 4-iodophenyl | H | H | F | H | H | H | Br | H | heptafluoroisopropyl | H | CF3 |
| 6-1587 | (2-trifluoromethyl)phenyl | H | H | F | H | H | H | Br | H | heptafluoroisopropyl | H | CF3 |
| 6-1588 | (3-trifluoromethyl)phenyl | H | H | F | H | H | H | Br | H | heptafluoroisopropyl | H | CF3 |
| 6-1589 | (4-trifluoromethyl)phenyl | H | H | F | H | H | H | Br | H | heptafluoroisopropyl | H | CF3 |
| 6-1590 | 2-nitrophenyl | H | H | F | H | H | H | Br | H | heptafluoroisopropyl | H | CF3 |
| 6-1591 | 3-nitrophenyl | H | H | F | H | H | H | Br | H | heptafluoroisopropyl | H | CF3 |
| 6-1592 | 4-nitrophenyl | H | H | F | H | H | H | Br | H | heptafluoroisopropyl | H | CF3 |
| 6-1593 | 2-cyanophenyl | H | H | F | H | H | H | Br | H | heptafluoroisopropyl | H | CF3 |
| 6-1594 | 3-cyanophenyl | H | H | F | H | H | H | Br | H | heptafluoroisopropyl | H | CF3 |
| 6-1595 | 4-cyanophenyl | H | H | F | H | H | H | Br | H | heptafluoroisopropyl | H | CF3 |
| 6-1596 | 2,6-difluorophenyl | H | H | F | H | H | H | Br | H | heptafluoroisopropyl | H | CF3 |
| 6-1597 | 3,4-dichlorophenyl | H | H | F | H | H | H | Br | H | heptafluoroisopropyl | H | CF3 |
| 6-1598 | 2,4-dichlorophenyl | H | H | F | H | H | H | Br | H | heptafluoroisopropyl | H | CF3 |
| 6-1599 | 2-chloro-4-fluorophenyl | H | H | F | H | H | H | Br | H | heptafluoroisopropyl | H | CF3 |
| 6-1600 | 2-chloro-4,5-difluorophenyl | H | H | F | H | H | H | Br | H | heptafluoroisopropyl | H | CF3 |
| 6-1601 | 4-bromo-2-chlorophenyl | H | H | F | H | H | H | Br | H | heptafluoroisopropyl | H | CF3 |
| 6-1602 | 2-bromo-4-chlorophenyl | H | H | F | H | H | H | Br | H | heptafluoroisopropyl | H | CF3 |
| 6-1603 | 2-bromo-4-fluorophenyl | H | H | F | H | H | H | Br | H | heptafluoroisopropyl | H | CF3 |
| 6-1604 | 2-chloro-4-nitrophenyl | H | H | F | H | H | H | Br | H | heptafluoroisopropyl | H | CF3 |
| 6-1605 | 3,5-dicyanophenyl | H | H | F | H | H | H | Br | H | heptafluoroisopropyl | H | CF3 |
| 6-1606 | 4-cyano-2-fluorophenyl | H | H | F | H | H | H | Br | H | heptafluoroisopropyl | H | CF3 |
| 6-1607 | 2-chloro-4-cyanophenyl | H | H | F | H | H | H | Br | H | heptafluoroisopropyl | H | CF3 |
| 6-1608 | pyridin-3-yl | H | H | F | H | H | H | Br | H | heptafluoroisopropyl | H | CF3 |
| 6-1609 | 2-fluoropyridin-3-yl | H | H | F | H | H | H | Br | H | heptafluoroisopropyl | H | CF3 |
| 6-1610 | 2-chloropyridin-3-yl | H | H | F | H | H | H | Br | H | heptafluoroisopropyl | H | CF3 |
| 6-1611 | 2-bromopyridin-3-yl | H | H | F | H | H | H | Br | H | heptafluoroisopropyl | H | CF3 |
| 6-1612 | 2-iodopyridin-3-yl | H | H | F | H | H | H | Br | H | heptafluoroisopropyl | H | CF3 |
| 6-1613 | 2-(trifluoromethyl)pyridin-3-yl | H | H | F | H | H | H | Br | H | heptafluoroisopropyl | H | CF3 |
| 6-1614 | 2-nitropyridin-3-yl | H | H | F | H | H | H | Br | H | heptafluoroisopropyl | H | CF3 |
| 6-1615 | 2-cyanopyridin-3-yl | H | H | F | H | H | H | Br | H | heptafluoroisopropyl | H | CF3 |
| 6-1616 | 6-fluoropyridin-3-yl | H | H | F | H | H | H | Br | H | heptafluoroisopropyl | H | CF3 |
| 6-1617 | 6-chloropyridin-3-yl | H | H | F | H | H | H | Br | H | heptafluoroisopropyl | H | CF3 |
| 6-1618 | 6-bromopyridin-3-yl | H | H | F | H | H | H | Br | H | heptafluoroisopropyl | H | CF3 |
| 6-1619 | 6-iodopyridin-3-yl | H | H | F | H | H | H | Br | H | heptafluoroisopropyl | H | CF3 |
| 6-1620 | 6-(trifluoromethyl)pyridin-3-yl | H | H | F | H | H | H | Br | H | heptafluoroisopropyl | H | CF3 |
| 6-1621 | 6-nitropyridin-3-yl | H | H | F | H | H | H | Br | H | heptafluoroisopropyl | H | CF3 |
| 6-1622 | 6-cyanopyridin-3-yl | H | H | F | H | H | H | Br | H | heptafluoroisopropyl | H | CF3 |
| 6-1623 | 5-fluoropyridin-3-yl | H | H | F | H | H | H | Br | H | heptafluoroisopropyl | H | CF3 |
| 6-1624 | 5-chloropyridin-3-yl | H | H | F | H | H | H | Br | H | heptafluoroisopropyl | H | CF3 |

TABLE 6-continued

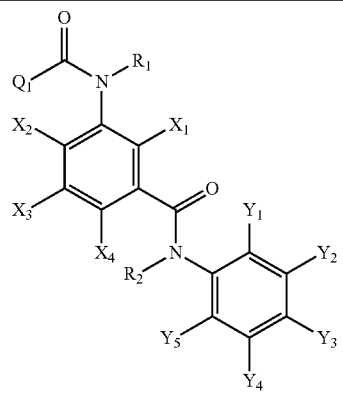

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-1625 | 5-bromopyridin-3-yl | H | H | F | H | H | H | Br | H | heptafluoroisopropyl | H | CF3 |
| 6-1626 | 5-iodopyridin-3-yl | H | H | F | H | H | H | Br | H | heptafluoroisopropyl | H | CF3 |
| 6-1627 | 5-(trifluoromethyl)pyridin-3-yl | H | H | F | H | H | H | Br | H | heptafluoroisopropyl | H | CF3 |
| 6-1628 | 5-nitropyridin-3-yl | H | H | F | H | H | H | Br | H | heptafluoroisopropyl | H | CF3 |
| 6-1629 | 5-cyanopyridin-3-yl | H | H | F | H | H | H | Br | H | heptafluoroisopropyl | H | CF3 |
| 6-1630 | 4-fluoropyridin-3-yl | H | H | F | H | H | H | Br | H | heptafluoroisopropyl | H | CF3 |
| 6-1631 | 4-chloropyridin-3-yl | H | H | F | H | H | H | Br | H | heptafluoroisopropyl | H | CF3 |
| 6-1632 | 4-bromopyridin-3-yl | H | H | F | H | H | H | Br | H | heptafluoroisopropyl | H | CF3 |
| 6-1633 | 4-iodopyridin-3-yl | H | H | F | H | H | H | Br | H | heptafluoroisopropyl | H | CF3 |
| 6-1634 | 4-(trifluoromethyl)pyridin-3-yl | H | H | F | H | H | H | Br | H | heptafluoroisopropyl | H | CF3 |
| 6-1635 | 4-nitropyridin-3-yl | H | H | F | H | H | H | Br | H | heptafluoroisopropyl | H | CF3 |
| 6-1636 | 4-cyanopyridin-3-yl | H | H | F | H | H | H | Br | H | heptafluoroisopropyl | H | CF3 |
| 6-1637 | 2,6-dichloropyridin-3-yl | H | H | F | H | H | H | Br | H | heptafluoroisopropyl | H | CF3 |
| 6-1638 | pyridin-3-yl N-oxide | H | H | F | H | H | H | Br | H | heptafluoroisopropyl | H | CF3 |
| 6-1639 | pyridin-4-yl | H | H | F | H | H | H | Br | H | heptafluoroisopropyl | H | CF3 |
| 6-1640 | 2-chloropyridin-4-yl | H | H | F | H | H | H | Br | H | heptafluoroisopropyl | H | CF3 |
| 6-1641 | 3-bromopyridin-4-yl | H | H | F | H | H | H | Br | H | heptafluoroisopropyl | H | CF3 |
| 6-1642 | 3,5-dichloropyridin-4-yl | H | H | F | H | H | H | Br | H | heptafluoroisopropyl | H | CF3 |
| 6-1643 | 3-(trifluoromethyl)pyridin-4-yl | H | H | F | H | H | H | Br | H | heptafluoroisopropyl | H | CF3 |
| 6-1644 | 2,6-dicyanopyridin-4-yl | H | H | F | H | H | H | Br | H | heptafluoroisopropyl | H | CF3 |
| 6-1645 | pyridin-4-yl N-oxide | H | H | F | H | H | H | Br | H | heptafluoroisopropyl | H | CF3 |
| 6-1646 | pyridin-2-yl | H | H | F | H | H | H | Br | H | heptafluoroisopropyl | H | CF3 |
| 6-1647 | 3-chloropyridin-2-yl | H | H | F | H | H | H | Br | H | heptafluoroisopropyl | H | CF3 |
| 6-1648 | 4-bromopyridin-2-yl | H | H | F | H | H | H | Br | H | heptafluoroisopropyl | H | CF3 |
| 6-1649 | 5-iodopyridin-2-yl | H | H | F | H | H | H | Br | H | heptafluoroisopropyl | H | CF3 |
| 6-1650 | 6-chloropyridin-2-yl | H | H | F | H | H | H | Br | H | heptafluoroisopropyl | H | CF3 |
| 6-1651 | 4-cyanopyridin-2-yl | H | H | F | H | H | H | Br | H | heptafluoroisopropyl | H | CF3 |
| 6-1652 | phenyl | H | H | F | H | H | H | Br | H | nonafluoro-2-butyl | H | CF3 |
| 6-1653 | 2-fluorophenyl | H | H | F | H | H | H | Br | H | nonafluoro-2-butyl | H | CF3 |
| 6-1654 | 3-fluorophenyl | H | H | F | H | H | H | Br | H | nonafluoro-2-butyl | H | CF3 |
| 6-1655 | 4-fluorophenyl | H | H | F | H | H | H | Br | H | nonafluoro-2-butyl | H | CF3 |
| 6-1656 | 2-chlorophenyl | H | H | F | H | H | H | Br | H | nonafluoro-2-butyl | H | CF3 |
| 6-1657 | 3-chlorophenyl | H | H | F | H | H | H | Br | H | nonafluoro-2-butyl | H | CF3 |
| 6-1658 | 4-chlorophenyl | H | H | F | H | H | H | Br | H | nonafluoro-2-butyl | H | CF3 |
| 6-1659 | 2-bromophenyl | H | H | F | H | H | H | Br | H | nonafluoro-2-butyl | H | CF3 |
| 6-1660 | 3-bromophenyl | H | H | F | H | H | H | Br | H | nonafluoro-2-butyl | H | CF3 |
| 6-1661 | 4-bromophenyl | H | H | F | H | H | H | Br | H | nonafluoro-2-butyl | H | CF3 |
| 6-1662 | 2-iodophenyl | H | H | F | H | H | H | Br | H | nonafluoro-2-butyl | H | CF3 |
| 6-1663 | 3-iodophenyl | H | H | F | H | H | H | Br | H | nonafluoro-2-butyl | H | CF3 |
| 6-1664 | 4-iodophenyl | H | H | F | H | H | H | Br | H | nonafluoro-2-butyl | H | CF3 |
| 6-1665 | (2-trifluoromethyl)phenyl | H | H | F | H | H | H | Br | H | nonafluoro-2-butyl | H | CF3 |
| 6-1666 | (3-trifluoromethyl)phenyl | H | H | F | H | H | H | Br | H | nonafluoro-2-butyl | H | CF3 |
| 6-1667 | (4-trifluoromethyl)phenyl | H | H | F | H | H | H | Br | H | nonafluoro-2-butyl | H | CF3 |
| 6-1668 | 2-nitrophenyl | H | H | F | H | H | H | Br | H | nonafluoro-2-butyl | H | CF3 |
| 6-1669 | 3-nitrophenyl | H | H | F | H | H | H | Br | H | nonafluoro-2-butyl | H | CF3 |
| 6-1670 | 4-nitrophenyl | H | H | F | H | H | H | Br | H | nonafluoro-2-butyl | H | CF3 |
| 6-1671 | 2-cyanophenyl | H | H | F | H | H | H | Br | H | nonafluoro-2-butyl | H | CF3 |
| 6-1672 | 3-cyanophenyl | H | H | F | H | H | H | Br | H | nonafluoro-2-butyl | H | CF3 |
| 6-1673 | 4-cyanophenyl | H | H | F | H | H | H | Br | H | nonafluoro-2-butyl | H | CF3 |
| 6-1674 | 2,6-difluorophenyl | H | H | F | H | H | H | Br | H | nonafluoro-2-butyl | H | CF3 |
| 6-1675 | 3,4-dichlorophenyl | H | H | F | H | H | H | Br | H | nonafluoro-2-butyl | H | CF3 |
| 6-1676 | 2,4-dichlorophenyl | H | H | F | H | H | H | Br | H | nonafluoro-2-butyl | H | CF3 |
| 6-1677 | 2-chloro-4-fluorophenyl | H | H | F | H | H | H | Br | H | nonafluoro-2-butyl | H | CF3 |
| 6-1678 | 2-chloro-4,5-difluorophenyl | H | H | F | H | H | H | Br | H | nonafluoro-2-butyl | H | CF3 |
| 6-1679 | 4-bromo-2-chlorophenyl | H | H | F | H | H | H | Br | H | nonafluoro-2-butyl | H | CF3 |
| 6-1680 | 2-bromo-4-chlorophenyl | H | H | F | H | H | H | Br | H | nonafluoro-2-butyl | H | CF3 |
| 6-1681 | 2-bromo-4-fluorophenyl | H | H | F | H | H | H | Br | H | nonafluoro-2-butyl | H | CF3 |
| 6-1682 | 2-chloro-4-nitrophenyl | H | H | F | H | H | H | Br | H | nonafluoro-2-butyl | H | CF3 |

TABLE 6-continued

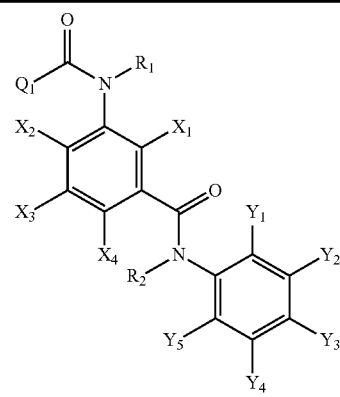

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-1683 | 3,5-dicyanophenyl | H | H | F | H | H | H | Br | H | nonafluoro-2-butyl | H | CF3 |
| 6-1684 | 4-cyano-2-fluorophenyl | H | H | F | H | H | H | Br | H | nonafluoro-2-butyl | H | CF3 |
| 6-1685 | 2-chloro-4-cyanophenyl | H | H | F | H | H | H | Br | H | nonafluoro-2-butyl | H | CF3 |
| 6-1686 | pyridin-3-yl | H | H | F | H | H | H | Br | H | nonafluoro-2-butyl | H | CF3 |
| 6-1687 | 2-fluoropyridin-3-yl | H | H | F | H | H | H | Br | H | nonafluoro-2-butyl | H | CF3 |
| 6-1688 | 2-chloropyridin-3-yl | H | H | F | H | H | H | Br | H | nonafluoro-2-butyl | H | CF3 |
| 6-1689 | 2-bromopyridin-3-yl | H | H | F | H | H | H | Br | H | nonafluoro-2-butyl | H | CF3 |
| 6-1690 | 2-iodopyridin-3-yl | H | H | F | H | H | H | Br | H | nonafluoro-2-butyl | H | CF3 |
| 6-1691 | 2-(trifluoromethyl)pyridin-3-yl | H | H | F | H | H | H | Br | H | nonafluoro-2-butyl | H | CF3 |
| 6-1692 | 2-nitropyridin-3-yl | H | H | F | H | H | H | Br | H | nonafluoro-2-butyl | H | CF3 |
| 6-1693 | 2-cyanopyridin-3-yl | H | H | F | H | H | H | Br | H | nonafluoro-2-butyl | H | CF3 |
| 6-1694 | 6-fluoropyridin-3-yl | H | H | F | H | H | H | Br | H | nonafluoro-2-butyl | H | CF3 |
| 6-1695 | 6-chloropyridin-3-yl | H | H | F | H | H | H | Br | H | nonafluoro-2-butyl | H | CF3 |
| 6-1696 | 6-bromopyridin-3-yl | H | H | F | H | H | H | Br | H | nonafluoro-2-butyl | H | CF3 |
| 6-1697 | 6-iodopyridin-3-yl | H | H | F | H | H | H | Br | H | nonafluoro-2-butyl | H | CF3 |
| 6-1698 | 6-(trifluoromethyl)pyridin-3-yl | H | H | F | H | H | H | Br | H | nonafluoro-2-butyl | H | CF3 |
| 6-1699 | 6-nitropyridin-3-yl | H | H | F | H | H | H | Br | H | nonafluoro-2-butyl | H | CF3 |
| 6-1700 | 6-cyanopyridin-3-yl | H | H | F | H | H | H | Br | H | nonafluoro-2-butyl | H | CF3 |
| 6-1701 | 5-fluoropyridin-3-yl | H | H | F | H | H | H | Br | H | nonafluoro-2-butyl | H | CF3 |
| 6-1702 | 5-chloropyridin-3-yl | H | H | F | H | H | H | Br | H | nonafluoro-2-butyl | H | CF3 |
| 6-1703 | 5-bromopyridin-3-yl | H | H | F | H | H | H | Br | H | nonafluoro-2-butyl | H | CF3 |
| 6-1704 | 5-iodopyridin-3-yl | H | H | F | H | H | H | Br | H | nonafluoro-2-butyl | H | CF3 |
| 6-1705 | 5-(trifluoromethyl)pyridin-3-yl | H | H | F | H | H | H | Br | H | nonafluoro-2-butyl | H | CF3 |
| 6-1706 | 5-nitropyridin-3-yl | H | H | F | H | H | H | Br | H | nonafluoro-2-butyl | H | CF3 |
| 6-1707 | 5-cyanopyridin-3-yl | H | H | F | H | H | H | Br | H | nonafluoro-2-butyl | H | CF3 |
| 6-1708 | 4-fluoropyridin-3-yl | H | H | F | H | H | H | Br | H | nonafluoro-2-butyl | H | CF3 |
| 6-1709 | 4-chloropyridin-3-yl | H | H | F | H | H | H | Br | H | nonafluoro-2-butyl | H | CF3 |
| 6-1710 | 4-bromopyridin-3-yl | H | H | F | H | H | H | Br | H | nonafluoro-2-butyl | H | CF3 |
| 6-1711 | 4-iodopyridin-3-yl | H | H | F | H | H | H | Br | H | nonafluoro-2-butyl | H | CF3 |
| 6-1712 | 4-(trifluoromethyl)pyridin-3-yl | H | H | F | H | H | H | Br | H | nonafluoro-2-butyl | H | CF3 |
| 6-1713 | 4-nitropyridin-3-yl | H | H | F | H | H | H | Br | H | nonafluoro-2-butyl | H | CF3 |
| 6-1714 | 4-cyanopyridin-3-yl | H | H | F | H | H | H | Br | H | nonafluoro-2-butyl | H | CF3 |
| 6-1715 | 2,6-dichloropyridin-3-yl | H | H | F | H | H | H | Br | H | nonafluoro-2-butyl | H | CF3 |
| 6-1716 | pyridin-3-yl N-oxide | H | H | F | H | H | H | Br | H | nonafluoro-2-butyl | H | CF3 |
| 6-1717 | pyridin-4-yl | H | H | F | H | H | H | Br | H | nonafluoro-2-butyl | H | CF3 |
| 6-1718 | 2-chloropyridin-4-yl | H | H | F | H | H | H | Br | H | nonafluoro-2-butyl | H | CF3 |
| 6-1719 | 3-bromopyridin-4-yl | H | H | F | H | H | H | Br | H | nonafluoro-2-butyl | H | CF3 |
| 6-1720 | 3,5-dichloropyridin-4-yl | H | H | F | H | H | H | Br | H | nonafluoro-2-butyl | H | CF3 |
| 6-1721 | 3-(trifluoromethyl)pyridin-4-yl | H | H | F | H | H | H | Br | H | nonafluoro-2-butyl | H | CF3 |
| 6-1722 | 2,6-dicyanopyridin-4-yl | H | H | F | H | H | H | Br | H | nonafluoro-2-butyl | H | CF3 |
| 6-1723 | pyridin-4-yl N-oxide | H | H | F | H | H | H | Br | H | nonafluoro-2-butyl | H | CF3 |
| 6-1724 | pyridin-2-yl | H | H | F | H | H | H | Br | H | nonafluoro-2-butyl | H | CF3 |
| 6-1725 | 3-chloropyridin-2-yl | H | H | F | H | H | H | Br | H | nonafluoro-2-butyl | H | CF3 |
| 6-1726 | 4-bromopyridin-2-yl | H | H | F | H | H | H | Br | H | nonafluoro-2-butyl | H | CF3 |
| 6-1727 | 5-iodopyridin-2-yl | H | H | F | H | H | H | Br | H | nonafluoro-2-butyl | H | CF3 |
| 6-1728 | 6-chloropyridin-2-yl | H | H | F | H | H | H | Br | H | nonafluoro-2-butyl | H | CF3 |
| 6-1729 | 4-cyanopyridin-2-yl | H | H | F | H | H | H | Br | H | nonafluoro-2-butyl | H | CF3 |
| 6-1730 | phenyl | H | H | F | H | H | H | I | H | heptafluoroisopropyl | H | CF3 |
| 6-1731 | 2-fluorophenyl | H | H | F | H | H | H | I | H | heptafluoroisopropyl | H | CF3 |
| 6-1732 | 3-fluorophenyl | H | H | F | H | H | H | I | H | heptafluoroisopropyl | H | CF3 |
| 6-1733 | 4-fluorophenyl | H | H | F | H | H | H | I | H | heptafluoroisopropyl | H | CF3 |
| 6-1734 | 2-chlorophenyl | H | H | F | H | H | H | I | H | heptafluoroisopropyl | H | CF3 |
| 6-1735 | 3-chlorophenyl | H | H | F | H | H | H | I | H | heptafluoroisopropyl | H | CF3 |
| 6-1736 | 4-chlorophenyl | H | H | F | H | H | H | I | H | heptafluoroisopropyl | H | CF3 |
| 6-1737 | 2-bromophenyl | H | H | F | H | H | H | I | H | heptafluoroisopropyl | H | CF3 |
| 6-1738 | 3-bromophenyl | H | H | F | H | H | H | I | H | heptafluoroisopropyl | H | CF3 |
| 6-1739 | 4-bromophenyl | H | H | F | H | H | H | I | H | heptafluoroisopropyl | H | CF3 |
| 6-1740 | 2-iodophenyl | H | H | F | H | H | H | I | H | heptafluoroisopropyl | H | CF3 |

TABLE 6-continued

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-1741 | 3-iodophenyl | H | H | F | H | H | H | I | H | heptafluoroisopropyl | H | CF3 |
| 6-1742 | 4-iodophenyl | H | H | F | H | H | H | I | H | heptafluoroisopropyl | H | CF3 |
| 6-1743 | (2-trifluoromethyl)phenyl | H | H | F | H | H | H | I | H | heptafluoroisopropyl | H | CF3 |
| 6-1744 | (3-trifluoromethyl)phenyl | H | H | F | H | H | H | I | H | heptafluoroisopropyl | H | CF3 |
| 6-1745 | (4-trifluoromethyl)phenyl | H | H | F | H | H | H | I | H | heptafluoroisopropyl | H | CF3 |
| 6-1746 | 2-nitrophenyl | H | H | F | H | H | H | I | H | heptafluoroisopropyl | H | CF3 |
| 6-1747 | 3-nitrophenyl | H | H | F | H | H | H | I | H | heptafluoroisopropyl | H | CF3 |
| 6-1748 | 4-nitrophenyl | H | H | F | H | H | H | I | H | heptafluoroisopropyl | H | CF3 |
| 6-1749 | 2-cyanophenyl | H | H | F | H | H | H | I | H | heptafluoroisopropyl | H | CF3 |
| 6-1750 | 3-cyanophenyl | H | H | F | H | H | H | I | H | heptafluoroisopropyl | H | CF3 |
| 6-1751 | 4-cyanophenyl | H | H | F | H | H | H | I | H | heptafluoroisopropyl | H | CF3 |
| 6-1752 | 2,6-difluorophenyl | H | H | F | H | H | H | I | H | heptafluoroisopropyl | H | CF3 |
| 6-1753 | 3,4-dichlorophenyl | H | H | F | H | H | H | I | H | heptafluoroisopropyl | H | CF3 |
| 6-1754 | 2,4-dichlorophenyl | H | H | F | H | H | H | I | H | heptafluoroisopropyl | H | CF3 |
| 6-1755 | 2-chloro-4-fluorophenyl | H | H | F | H | H | H | I | H | heptafluoroisopropyl | H | CF3 |
| 6-1756 | 2-chloro-4,5-difluorophenyl | H | H | F | H | H | H | I | H | heptafluoroisopropyl | H | CF3 |
| 6-1757 | 4-bromo-2-chlorophenyl | H | H | F | H | H | H | I | H | heptafluoroisopropyl | H | CF3 |
| 6-1758 | 2-bromo-4-chlorophenyl | H | H | F | H | H | H | I | H | heptafluoroisopropyl | H | CF3 |
| 6-1759 | 2-bromo-4-fluorophenyl | H | H | F | H | H | H | I | H | heptafluoroisopropyl | H | CF3 |
| 6-1760 | 2-chloro-4-nitrophenyl | H | H | F | H | H | H | I | H | heptafluoroisopropyl | H | CF3 |
| 6-1761 | 3,5-dicyanophenyl | H | H | F | H | H | H | I | H | heptafluoroisopropyl | H | CF3 |
| 6-1762 | 4-cyano-2-fluorophenyl | H | H | F | H | H | H | I | H | heptafluoroisopropyl | H | CF3 |
| 6-1763 | 2-chloro-4-cyanophenyl | H | H | F | H | H | H | I | H | heptafluoroisopropyl | H | CF3 |
| 6-1764 | pyridin-3-yl | H | H | F | H | H | H | I | H | heptafluoroisopropyl | H | CF3 |
| 6-1765 | 2-fluoropyridin-3-yl | H | H | F | H | H | H | I | H | heptafluoroisopropyl | H | CF3 |
| 6-1766 | 2-chloropyridin-3-yl | H | H | F | H | H | H | I | H | heptafluoroisopropyl | H | CF3 |
| 6-1767 | 2-bromopyridin-3-yl | H | H | F | H | H | H | I | H | heptafluoroisopropyl | H | CF3 |
| 6-1768 | 2-iodopyridin-3-yl | H | H | F | H | H | H | I | H | heptafluoroisopropyl | H | CF3 |
| 6-1769 | 2-(trifluoromethyl)pyridin-3-yl | H | H | F | H | H | H | I | H | heptafluoroisopropyl | H | CF3 |
| 6-1770 | 2-nitropyridin-3-yl | H | H | F | H | H | H | I | H | heptafluoroisopropyl | H | CF3 |
| 6-1771 | 2-cyanopyridin-3-yl | H | H | F | H | H | H | I | H | heptafluoroisopropyl | H | CF3 |
| 6-1772 | 6-fluoropyridin-3-yl | H | H | F | H | H | H | I | H | heptafluoroisopropyl | H | CF3 |
| 6-1773 | 6-chloropyridin-3-yl | H | H | F | H | H | H | I | H | heptafluoroisopropyl | H | CF3 |
| 6-1774 | 6-bromopyridin-3-yl | H | H | F | H | H | H | I | H | heptafluoroisopropyl | H | CF3 |
| 6-1775 | 6-iodopyridin-3-yl | H | H | F | H | H | H | I | H | heptafluoroisopropyl | H | CF3 |
| 6-1776 | 6-(trifluoromethyl)pyridin-3-yl | H | H | F | H | H | H | I | H | heptafluoroisopropyl | H | CF3 |
| 6-1777 | 6-nitropyridin-3-yl | H | H | F | H | H | H | I | H | heptafluoroisopropyl | H | CF3 |
| 6-1778 | 6-cyanopyridin-3-yl | H | H | F | H | H | H | I | H | heptafluoroisopropyl | H | CF3 |
| 6-1779 | 5-fluoropyridin-3-yl | H | H | F | H | H | H | I | H | heptafluoroisopropyl | H | CF3 |
| 6-1780 | 5-chloropyridin-3-yl | H | H | F | H | H | H | I | H | heptafluoroisopropyl | H | CF3 |
| 6-1781 | 5-bromopyridin-3-yl | H | H | F | H | H | H | I | H | heptafluoroisopropyl | H | CF3 |
| 6-1782 | 5-iodopyridin-3-yl | H | H | F | H | H | H | I | H | heptafluoroisopropyl | H | CF3 |
| 6-1783 | 5-(trifluoromethyl)pyridin-3-yl | H | H | F | H | H | H | I | H | heptafluoroisopropyl | H | CF3 |
| 6-1784 | 5-nitropyridin-3-yl | H | H | F | H | H | H | I | H | heptafluoroisopropyl | H | CF3 |
| 6-1785 | 5-cyanopyridin-3-yl | H | H | F | H | H | H | I | H | heptafluoroisopropyl | H | CF3 |
| 6-1786 | 4-fluoropyridin-3-yl | H | H | F | H | H | H | I | H | heptafluoroisopropyl | H | CF3 |
| 6-1787 | 4-chloropyridin-3-yl | H | H | F | H | H | H | I | H | heptafluoroisopropyl | H | CF3 |
| 6-1788 | 4-bromopyridin-3-yl | H | H | F | H | H | H | I | H | heptafluoroisopropyl | H | CF3 |
| 6-1789 | 4-iodopyridin-3-yl | H | H | F | H | H | H | I | H | heptafluoroisopropyl | H | CF3 |
| 6-1790 | 4-(trifluoromethyl)pyridin-3-yl | H | H | F | H | H | H | I | H | heptafluoroisopropyl | H | CF3 |
| 6-1791 | 4-nitropyridin-3-yl | H | H | F | H | H | H | I | H | heptafluoroisopropyl | H | CF3 |
| 6-1792 | 4-cyanopyridin-3-yl | H | H | F | H | H | H | I | H | heptafluoroisopropyl | H | CF3 |
| 6-1793 | 2,6-dichloropyridin-3-yl | H | H | F | H | H | H | I | H | heptafluoroisopropyl | H | CF3 |
| 6-1794 | pyridin-3-yl N-oxide | H | H | F | H | H | H | I | H | heptafluoroisopropyl | H | CF3 |
| 6-1795 | pyridin-4-yl | H | H | F | H | H | H | I | H | heptafluoroisopropyl | H | CF3 |
| 6-1796 | 2-chloropyridin-4-yl | H | H | F | H | H | H | I | H | heptafluoroisopropyl | H | CF3 |
| 6-1797 | 3-bromopyridin-4-yl | H | H | F | H | H | H | I | H | heptafluoroisopropyl | H | CF3 |
| 6-1798 | 3,5-dichloropyridin-4-yl | H | H | F | H | H | H | I | H | heptafluoroisopropyl | H | CF3 |

TABLE 6-continued

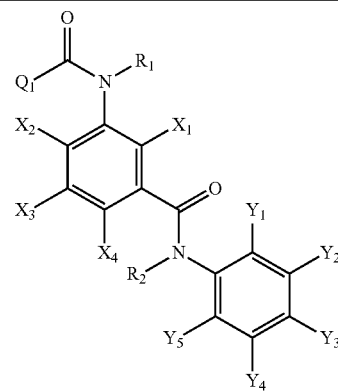

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-1799 | 3-(trifluoromethyl)pyridin-4-yl | H | H | F | H | H | H | I | H | heptafluoroisopropyl | H | CF3 |
| 6-1800 | 2,6-dicyanopyridin-4-yl | H | H | F | H | H | H | I | H | heptafluoroisopropyl | H | CF3 |
| 6-1801 | pyridin-4-yl N-oxide | H | H | F | H | H | H | I | H | heptafluoroisopropyl | H | CF3 |
| 6-1802 | pyridin-2-yl | H | H | F | H | H | H | I | H | heptafluoroisopropyl | H | CF3 |
| 6-1803 | 3-chloropyridin-2-yl | H | H | F | H | H | H | I | H | heptafluoroisopropyl | H | CF3 |
| 6-1804 | 4-bromopyridin-2-yl | H | H | F | H | H | H | I | H | heptafluoroisopropyl | H | CF3 |
| 6-1805 | 5-iodopyridin-2-yl | H | H | F | H | H | H | I | H | heptafluoroisopropyl | H | CF3 |
| 6-1806 | 6-chloropyridin-2-yl | H | H | F | H | H | H | I | H | heptafluoroisopropyl | H | CF3 |
| 6-1807 | 4-cyanopyridin-2-yl | H | H | F | H | H | H | I | H | heptafluoroisopropyl | H | CF3 |
| 6-1808 | phenyl | H | H | F | H | H | H | I | H | nonafluoro-2-butyl | H | CF3 |
| 6-1809 | 2-fluorophenyl | H | H | F | H | H | H | I | H | nonafluoro-2-butyl | H | CF3 |
| 6-1810 | 3-fluorophenyl | H | H | F | H | H | H | I | H | nonafluoro-2-butyl | H | CF3 |
| 6-1811 | 4-fluorophenyl | H | H | F | H | H | H | I | H | nonafluoro-2-butyl | H | CF3 |
| 6-1812 | 2-chlorophenyl | H | H | F | H | H | H | I | H | nonafluoro-2-butyl | H | CF3 |
| 6-1813 | 3-chlorophenyl | H | H | F | H | H | H | I | H | nonafluoro-2-butyl | H | CF3 |
| 6-1814 | 4-chlorophenyl | H | H | F | H | H | H | I | H | nonafluoro-2-butyl | H | CF3 |
| 6-1815 | 2-bromophenyl | H | H | F | H | H | H | I | H | nonafluoro-2-butyl | H | CF3 |
| 6-1816 | 3-bromophenyl | H | H | F | H | H | H | I | H | nonafluoro-2-butyl | H | CF3 |
| 6-1817 | 4-bromophenyl | H | H | F | H | H | H | I | H | nonafluoro-2-butyl | H | CF3 |
| 6-1818 | 2-iodophenyl | H | H | F | H | H | H | I | H | nonafluoro-2-butyl | H | CF3 |
| 6-1819 | 3-iodophenyl | H | H | F | H | H | H | I | H | nonafluoro-2-butyl | H | CF3 |
| 6-1820 | 4-iodophenyl | H | H | F | H | H | H | I | H | nonafluoro-2-butyl | H | CF3 |
| 6-1821 | (2-trifluoromethyl)phenyl | H | H | F | H | H | H | I | H | nonafluoro-2-butyl | H | CF3 |
| 6-1822 | (3-trifluoromethyl)phenyl | H | H | F | H | H | H | I | H | nonafluoro-2-butyl | H | CF3 |
| 6-1823 | (4-trifluoromethyl)phenyl | H | H | F | H | H | H | I | H | nonafluoro-2-butyl | H | CF3 |
| 6-1824 | 2-nitrophenyl | H | H | F | H | H | H | I | H | nonafluoro-2-butyl | H | CF3 |
| 6-1825 | 3-nitrophenyl | H | H | F | H | H | H | I | H | nonafluoro-2-butyl | H | CF3 |
| 6-1826 | 4-nitrophenyl | H | H | F | H | H | H | I | H | nonafluoro-2-butyl | H | CF3 |
| 6-1827 | 2-cyanophenyl | H | H | F | H | H | H | I | H | nonafluoro-2-butyl | H | CF3 |
| 6-1828 | 3-cyanophenyl | H | H | F | H | H | H | I | H | noriafluoro-2-butyl | H | CF3 |
| 6-1829 | 4-cyanophenyl | H | H | F | H | H | H | I | H | nonafluoro-2-butyl | H | CF3 |
| 6-1830 | 2,6-difluorophenyl | H | H | F | H | H | H | I | H | nonafluoro-2-butyl | H | CF3 |
| 6-1831 | 3,4-dichlorophenyl | H | H | F | H | H | H | I | H | nonafluoro-2-butyl | H | CF3 |
| 6-1832 | 2,4-dichlorophenyl | H | H | F | H | H | H | I | H | nonafluoro-2-butyl | H | CF3 |
| 6-1833 | 2-chloro-4-fluorophenyl | H | H | F | H | H | H | I | H | nonafluoro-2-butyl | H | CF3 |
| 6-1834 | 2-chloro-4,5-difluorophenyl | H | H | F | H | H | H | I | H | nonafluoro-2-butyl | H | CF3 |
| 6-1835 | 4-bromo-2-chlorophenyl | H | H | F | H | H | H | I | H | nonafluoro-2-butyl | H | CF3 |
| 6-1836 | 2-bromo-4-chlorophenyl | H | H | F | H | H | H | I | H | nonafluoro-2-butyl | H | CF3 |
| 6-1837 | 2-bromo-4-fluorophenyl | H | H | F | H | H | H | I | H | nonafluoro-2-butyl | H | CF3 |
| 6-1838 | 2-chloro-4-nitrophenyl | H | H | F | H | H | H | I | H | nonafluoro-2-butyl | H | CF3 |
| 6-1839 | 3,5-dicyanophenyl | H | H | F | H | H | H | I | H | nonafluoro-2-butyl | H | CF3 |
| 6-1840 | 4-cyano-2-fluorophenyl | H | H | F | H | H | H | I | H | nonafluoro-2-butyl | H | CF3 |
| 6-1841 | 2-chloro-4-cyanophenyl | H | H | F | H | H | H | I | H | nonafluoro-2-butyl | H | CF3 |
| 6-1842 | pyridin-3-yl | H | H | F | H | H | H | I | H | nonafluoro-2-butyl | H | CF3 |
| 6-1843 | 2-fluoropyridin-3-yl | H | H | F | H | H | H | I | H | nonafluoro-2-butyl | H | CF3 |
| 6-1844 | 2-chloropyridin-3-yl | H | H | F | H | H | H | I | H | nonafluoro-2-butyl | H | CF3 |
| 6-1845 | 2-bromopyridin-3-yl | H | H | F | H | H | H | I | H | nonafluoro-2-butyl | H | CF3 |
| 6-1846 | 2-iodopyridin-3-yl | H | H | F | H | H | H | I | H | nonafluoro-2-butyl | H | CF3 |
| 6-1847 | 2-(trifluoromethyl)pyridin-3-yl | H | H | F | H | H | H | I | H | nonafluoro-2-butyl | H | CF3 |
| 6-1848 | 2-nitropyridin-3-yl | H | H | F | H | H | H | I | H | nonafluoro-2-butyl | H | CF3 |
| 6-1849 | 2-cyanopyridin-3-yl | H | H | F | H | H | H | I | H | nonafluoro-2-butyl | H | CF3 |
| 6-1850 | 6-fluoropyridin-3-yl | H | H | F | H | H | H | I | H | nonafluoro-2-butyl | H | CF3 |
| 6-1851 | 6-chloropyridin-3-yl | H | H | F | H | H | H | I | H | nonafluoro-2-butyl | H | CF3 |
| 6-1852 | 6-bromopyridin-3-yl | H | H | F | H | H | H | I | H | nonafluoro-2-butyl | H | CF3 |
| 6-1853 | 6-iodopyridin-3-yl | H | H | F | H | H | H | I | H | nonafluoro-2-butyl | H | CF3 |
| 6-1854 | 6-(trifluoromethyl)pyridin-3-yl | H | H | F | H | H | H | I | H | nonafluoro-2-butyl | H | CF3 |
| 6-1855 | 6-nitropyridin-3-yl | H | H | F | H | H | H | I | H | nonafluoro-2-butyl | H | CF3 |
| 6-1856 | 6-cyanopyridin-3-yl | H | H | F | H | H | H | I | H | nonafluoro-2-butyl | H | CF3 |

TABLE 6-continued

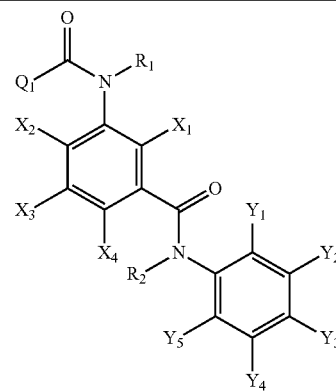

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-1857 | 5-fluoropyridin-3-yl | H | H | F | H | H | H | I | H | nonafluoro-2-butyl | H | CF3 |
| 6-1858 | 5-chloropyridin-3-yl | H | H | F | H | H | H | I | H | nonafluoro-2-butyl | H | CF3 |
| 6-1859 | 5-bromopyridin-3-yl | H | H | F | H | H | H | I | H | nonafluoro-2-butyl | H | CF3 |
| 6-1860 | 5-iodopyridin-3-yl | H | H | F | H | H | H | I | H | nonafluoro-2-butyl | H | CF3 |
| 6-1861 | 5-(trifluoromethyl)pyridin-3-yl | H | H | F | H | H | H | I | H | nonafluoro-2-butyl | H | CF3 |
| 6-1862 | 5-nitropyridin-3-yl | H | H | F | H | H | H | I | H | nonafluoro-2-butyl | H | CF3 |
| 6-1863 | 5-cyanopyridin-3-yl | H | H | F | H | H | H | I | H | nonafluoro-2-butyl | H | CF3 |
| 6-1864 | 4-fluoropyridin-3-yl | H | H | F | H | H | H | I | H | nonafluoro-2-butyl | H | CF3 |
| 6-1865 | 4-chloropyridin-3-yl | H | H | F | H | H | H | I | H | nonafluoro-2-butyl | H | CF3 |
| 6-1866 | 4-bromopyridin-3-yl | H | H | F | H | H | H | I | H | nonafluoro-2-butyl | H | CF3 |
| 6-1867 | 4-iodopyridin-3-yl | H | H | F | H | H | H | I | H | nonafluoro-2-butyl | H | CF3 |
| 6-1868 | 4-(trifluoromethyl)pyridin-3-yl | H | H | F | H | H | H | I | H | nonafluoro-2-butyl | H | CF3 |
| 6-1869 | 4-nitropyridin-3-yl | H | H | F | H | H | H | I | H | nonafluoro-2-butyl | H | CF3 |
| 6-1870 | 4-cyanopyridin-3-yl | H | H | F | H | H | H | I | H | nonafluoro-2-butyl | H | CF3 |
| 6-1871 | 2,6-dichloropyridin-3-yl | H | H | F | H | H | H | I | H | nonafluoro-2-butyl | H | CF3 |
| 6-1872 | pyridin-3-yl N-oxide | H | H | F | H | H | H | I | H | nonafluoro-2-butyl | H | CF3 |
| 6-1873 | pyridin-4-yl | H | H | F | H | H | H | I | H | nonafluoro-2-butyl | H | CF3 |
| 6-1874 | 2-chloropyridin-4-yl | H | H | F | H | H | H | I | H | nonafluoro-2-butyl | H | CF3 |
| 6-1875 | 3-bromopyridin-4-yl | H | H | F | H | H | H | I | H | nonafluoro-2-butyl | H | CF3 |
| 6-1876 | 3,5-dichloropyridin-4-yl | H | H | F | H | H | H | I | H | nonafluoro-2-butyl | H | CF3 |
| 6-1877 | 3-(trifluoromethyl)pyridin-4-yl | H | H | F | H | H | H | I | H | nonafluoro-2-butyl | H | CF3 |
| 6-1878 | 2,6-dicyanopyridin-4-yl | H | H | F | H | H | H | I | H | nonafluoro-2-butyl | H | CF3 |
| 6-1879 | pyridin-4-yl N-oxide | H | H | F | H | H | H | I | H | nonafluoro-2-butyl | H | CF3 |
| 6-1880 | pyridin-2-yl | H | H | F | H | H | H | I | H | nonafluoro-2-butyl | H | CF3 |
| 6-1881 | 3-chloropyridin-2-yl | H | H | F | H | H | H | I | H | nonafluoro-2-butyl | H | CF3 |
| 6-1882 | 4-bromopyridin-2-yl | H | H | F | H | H | H | I | H | nonafluoro-2-butyl | H | CF3 |
| 6-1883 | 5-iodopyridin-2-yl | H | H | F | H | H | H | I | H | nonafluoro-2-butyl | H | CF3 |
| 6-1884 | 6-chloropyridin-2-yl | H | H | F | H | H | H | I | H | nonafluoro-2-butyl | H | CF3 |
| 6-1885 | 4-cyanopyridin-2-yl | H | H | F | H | H | H | I | H | nonafluoro-2-butyl | H | CF3 |
| 6-1886 | phenyl | H | H | F | H | H | H | OCF3 | H | heptafluoroisopropyl | H | OCF3 |
| 6-1901 | 3-cyanophenyl | H | H | F | H | H | H | OCF3 | H | heptafluoroisopropyl | H | OCF3 |
| 6-1902 | 4-cyanophenyl | H | H | F | H | H | H | OCF3 | H | heptafluoroisopropyl | H | OCF3 |
| 6-1917 | 2-chloropyridin-3-yl | H | H | F | H | H | H | OCF3 | H | heptafluoroisopropyl | H | OCF3 |
| 6-1942 | phenyl | H | H | F | H | H | H | OCF3 | H | nonafluoro-2-butyl | H | OCF3 |
| 6-1957 | 3-cyanophenyl | H | H | F | H | H | H | OCF3 | H | nonafluoro-2-butyl | H | OCF3 |
| 6-1958 | 4-cyanophenyl | H | H | F | H | H | H | OCF3 | H | nonafluoro-2-butyl | H | OCF3 |
| 6-1973 | 2-chloropyridin-3-yl | H | H | F | H | H | H | OCF3 | H | nonafluoro-2-butyl | H | OCF3 |
| 6-1998 | phenyl | H | H | F | H | H | H | CF3 | H | heptafluoroisopropyl | H | OCF3 |
| 6-2013 | 3-cyanophenyl | H | H | F | H | H | H | CF3 | H | heptafluoroisopropyl | H | OCF3 |
| 6-2014 | 4-cyanophenyl | H | H | F | H | H | H | CF3 | H | heptafluoroisopropyl | H | OCF3 |
| 6-2029 | 2-chloropyridin-3-yl | H | H | F | H | H | H | CF3 | H | heptafluoroisopropyl | H | OCF3 |
| 6-2054 | phenyl | H | H | F | H | H | H | CF3 | H | nonafluoro-2-butyl | H | OCF3 |
| 6-2069 | 3-cyanophenyl | H | H | F | H | H | H | CF3 | H | nonafluoro-2-butyl | H | OCF3 |
| 6-2070 | 4-cyanophenyl | H | H | F | H | H | H | CF3 | H | nonafluoro-2-butyl | H | OCF3 |
| 6-2085 | 2-chloropyridin-3-yl | H | H | F | H | H | H | CF3 | H | nonafluoro-2-butyl | H | OCF3 |
| 6-2110 | phenyl | H | H | F | H | H | H | CF3 | H | heptafluoroisopropyl | H | CF3 |
| 6-2130 | 3-cyanophenyl | H | H | F | H | H | H | CF3 | H | heptafluoroisopropyl | H | CF3 |
| 6-2131 | 4-cyanophenyl | H | H | F | H | H | H | CF3 | H | heptafluoroisopropyl | H | CF3 |
| 6-2146 | 2-chloropyridin-3-yl | H | H | F | H | H | H | CF3 | H | heptafluoroisopropyl | H | CF3 |
| 6-2178 | phenyl | H | H | F | H | H | H | CF3 | H | nonafluoro-2-butyl | H | CF3 |
| 6-2198 | 3-cyanophenyl | H | H | F | H | H | H | CF3 | H | nonafluoro-2-butyl | H | CF3 |
| 6-2199 | 4-cyanophenyl | H | H | F | H | H | H | CF3 | H | nonafluoro-2-butyl | H | CF3 |
| 6-2214 | 2-chloropyridin-3-yl | H | H | F | H | H | H | CF3 | H | nonafluoro-2-butyl | H | CF3 |
| 6-2246 | phenyl | H | H | H | F | H | H | F | H | heptafluoroisopropyl | H | F |
| 6-2247 | 3-cyanophenyl | H | H | H | F | H | H | F | H | heptafluoroisopropyl | H | F |
| 6-2248 | 4-cyanophenyl | H | H | H | F | H | H | F | H | heptafluoroisopropyl | H | F |
| 6-2249 | 2-chloropyridin-3-yl | H | H | H | F | H | H | F | H | heptafluoroisopropyl | H | F |
| 6-2250 | phenyl | H | H | H | F | H | H | F | H | nonafluoro-2-butyl | H | F |

TABLE 6-continued

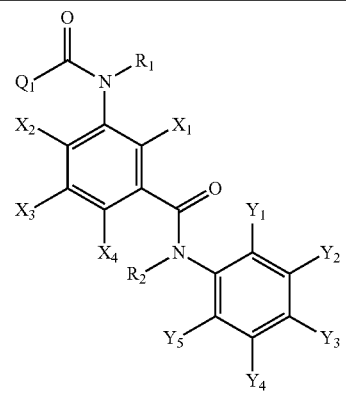

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-2251 | 3-cyanophenyl | H | H | H | F | H | H | F | H | nonafluoro-2-butyl | H | F |
| 6-2252 | 4-cyanophenyl | H | H | H | F | H | H | F | H | nonafluoro-2-butyl | H | F |
| 6-2253 | 2-chloropyridin-3-yl | H | H | H | F | H | H | F | H | nonafluoro-2-butyl | H | F |
| 6-2254 | phenyl | H | H | H | F | H | H | Cl | H | heptafluoroisopropyl | H | Cl |
| 6-2274 | 3-cyanophenyl | H | H | H | F | H | H | Cl | H | heptafluoroisopropyl | H | Cl |
| 6-2275 | 4-cyanophenyl | H | H | H | F | H | H | Cl | H | heptafluoroisopropyl | H | Cl |
| 6-2290 | 2-chloropyridin-3-yl | H | H | H | F | H | H | Cl | H | heptafluoroisopropyl | H | Cl |
| 6-2332 | phenyl | H | H | H | F | H | H | Cl | H | nonafluoro-2-butyl | H | Cl |
| 6-2352 | 3-cyanophenyl | H | H | H | F | H | H | Cl | H | nonafluoro-2-butyl | H | Cl |
| 6-2353 | 4-cyanophenyl | H | H | H | F | H | H | Cl | H | nonafluoro-2-butyl | H | Cl |
| 6-2368 | 2-chloropyridin-3-yl | H | H | H | F | H | H | Cl | H | nonafluoro-2-butyl | H | Cl |
| 6-2410 | phenyl | H | H | H | F | H | H | Br | H | heptafluoroisopropyl | H | Br |
| 6-2430 | 3-cyanophenyl | H | H | H | F | H | H | Br | H | heptafluoroisopropyl | H | Br |
| 6-2431 | 4-cyanophenyl | H | H | H | F | H | H | Br | H | heptafluoroisopropyl | H | Br |
| 6-2446 | 2-chloropyridin-3-yl | H | H | H | F | H | H | Br | H | heptafluoroisopropyl | H | Br |
| 6-2488 | phenyl | H | H | H | F | H | H | Br | H | nonafluoro-2-butyl | H | Br |
| 6-2508 | 3-cyanophenyl | H | H | H | F | H | H | Br | H | nonafluoro-2-butyl | H | Br |
| 6-2509 | 4-cyanophenyl | H | H | H | F | H | H | Br | H | nonafluoro-2-butyl | H | Br |
| 6-2524 | 2-chloropyridin-3-yl | H | H | H | F | H | H | Br | H | nonafluoro-2-butyl | H | Br |
| 6-2566 | phenyl | H | H | H | F | H | H | I | H | heptafluoroisopropyl | H | I |
| 6-2586 | 3-cyanophenyl | H | H | H | F | H | H | I | H | heptafluoroisopropyl | H | I |
| 6-2587 | 4-cyanophenyl | H | H | H | F | H | H | I | H | heptafluoroisopropyl | H | I |
| 6-2602 | 2-chloropyridin-3-yl | H | H | H | F | H | H | I | H | heptafluoroisopropyl | H | I |
| 6-2644 | phenyl | H | H | H | F | H | H | I | H | nonafluoro-2-butyl | H | I |
| 6-2664 | 3-cyanophenyl | H | H | H | F | H | H | I | H | nonafluoro-2-butyl | H | I |
| 6-2665 | 4-cyanophenyl | H | H | H | F | H | H | I | H | nonafluoro-2-butyl | H | I |
| 6-2680 | 2-chloropyridin-3-yl | H | H | H | F | H | H | I | H | nonafluoro-2-butyl | H | I |
| 6-2722 | phenyl | H | H | H | F | H | H | Cl | H | heptafluoroisopropyl | H | OCF3 |
| 6-2742 | 3-cyanophenyl | H | H | H | F | H | H | Cl | H | heptafluoroisopropyl | H | OCF3 |
| 6-2743 | 4-cyanophenyl | H | H | H | F | H | H | Cl | H | heptafluoroisopropyl | H | OCF3 |
| 6-2758 | 2-chloropyridin-3-yl | H | H | H | F | H | H | Cl | H | heptafluoroisopropyl | H | OCF3 |
| 6-2800 | phenyl | H | H | H | F | H | H | Cl | H | nonafluoro-2-butyl | H | OCF3 |
| 6-2820 | 3-cyanophenyl | H | H | H | F | H | H | Cl | H | nonafluoro-2-butyl | H | OCF3 |
| 6-2821 | 4-cyanophenyl | H | H | H | F | H | H | Cl | H | nonafluoro-2-butyl | H | OCF3 |
| 6-2836 | 2-chloropyridin-3-yl | H | H | H | F | H | H | Cl | H | nonafluoro-2-butyl | H | OCF3 |
| 6-2878 | phenyl | H | H | H | F | H | H | Br | H | heptafluoroisopropyl | H | OCF3 |
| 6-2898 | 3-cyanophenyl | H | H | H | F | H | H | Br | H | heptafluoroisopropyl | H | OCF3 |
| 6-2899 | 4-cyanophenyl | H | H | H | F | H | H | Br | H | heptafluoroisopropyl | H | OCF3 |
| 6-2914 | 2-chloropyridin-3-yl | H | H | H | F | H | H | Br | H | heptafluoroisopropyl | H | OCF3 |
| 6-2956 | phenyl | H | H | H | F | H | H | Br | H | nonafluoro-2-butyl | H | OCF3 |
| 6-2976 | 3-cyanophenyl | H | H | H | F | H | H | Br | H | nonafluoro-2-butyl | H | OCF3 |
| 6-2977 | 4-cyanophenyl | H | H | H | F | H | H | Br | H | nonafluoro-2-butyl | H | OCF3 |
| 6-2992 | 2-chloropyridin-3-yl | H | H | H | F | H | H | Br | H | nonafluoro-2-butyl | H | OCF3 |
| 6-3034 | phenyl | H | H | H | F | H | H | I | H | heptafluoroisopropyl | H | OCF3 |
| 6-3054 | 3-cyanophenyl | H | H | H | F | H | H | I | H | heptafluoroisopropyl | H | OCF3 |
| 6-3055 | 4-cyanophenyl | H | H | H | F | H | H | I | H | heptafluoroisopropyl | H | OCF3 |
| 6-3070 | 2-chloropyridin-3-yl | H | H | H | F | H | H | I | H | heptafluoroisopropyl | H | OCF3 |
| 6-3112 | phenyl | H | H | H | F | H | H | I | H | nonafluoro-2-butyl | H | OCF3 |
| 6-3132 | 3-cyanophenyl | H | H | H | F | H | H | I | H | nonafluoro-2-butyl | H | OCF3 |
| 6-3133 | 4-cyanophenyl | H | H | H | F | H | H | I | H | nonafluoro-2-butyl | H | OCF3 |
| 6-3148 | 2-chloropyridin-3-yl | H | H | H | F | H | H | I | H | nonafluoro-2-butyl | H | OCF3 |
| 6-3190 | phenyl | H | H | H | F | H | H | F | H | heptafluoroisopropyl | H | CF3 |
| 6-3191 | phenyl | H | H | H | F | H | H | Cl | H | heptafluoroisopropyl | H | CF3 |
| 6-3211 | 3-cyanophenyl | H | H | H | F | H | H | Cl | H | heptafluoroisopropyl | H | CF3 |
| 6-3212 | 4-cyanophenyl | H | H | H | F | H | H | Cl | H | heptafluoroisopropyl | H | CF3 |
| 6-3227 | 2-chloropyridin-3-yl | H | H | H | F | H | H | Cl | H | heptafluoroisopropyl | H | CF3 |
| 6-3269 | phenyl | H | H | H | F | H | H | F | H | nonafluoro-2-butyl | H | CF3 |
| 6-3270 | phenyl | H | H | H | F | H | H | Cl | H | nonafluoro-2-butyl | H | CF3 |

TABLE 6-continued

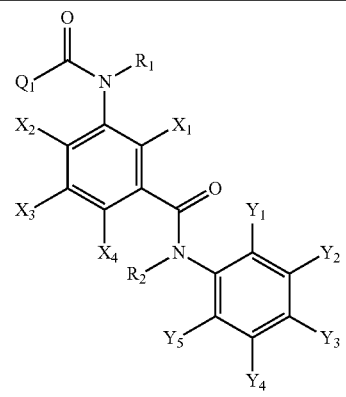

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-3290 | 3-cyanophenyl | H | H | H | F | H | H | Cl | H | nonafluoro-2-butyl | H | CF3 |
| 6-3291 | 4-cyanophenyl | H | H | H | F | H | H | Cl | H | nonafluoro-2-butyl | H | CF3 |
| 6-3306 | 2-chloropyridin-3-yl | H | H | H | F | H | H | Cl | H | nonafluoro-2-butyl | H | CF3 |
| 6-3348 | phenyl | H | H | H | F | H | H | Br | H | heptafluoroisopropyl | H | CF3 |
| 6-3368 | 3-cyanophenyl | H | H | H | F | H | H | Br | H | heptafluoroisopropyl | H | CF3 |
| 6-3369 | 4-cyanophenyl | H | H | H | F | H | H | Br | H | heptafluoroisopropyl | H | CF3 |
| 6-3384 | 2-chloropyridin-3-yl | H | H | H | F | H | H | Br | H | heptafluoroisopropyl | H | CF3 |
| 6-3426 | phenyl | H | H | H | F | H | H | Br | H | nonafluoro-2-butyl | H | CF3 |
| 6-3446 | 3-cyanophenyl | H | H | H | F | H | H | Br | H | nonafluoro-2-butyl | H | CF3 |
| 6-3447 | 4-cyanophenyl | H | H | H | F | H | H | Br | H | nonafluoro-2-butyl | H | CF3 |
| 6-3462 | 2-chloropyridin-3-yl | H | H | H | F | H | H | Br | H | nonafluoro-2-butyl | H | CF3 |
| 6-3504 | phenyl | H | H | H | F | H | H | I | H | heptafluoroisopropyl | H | CF3 |
| 6-3524 | 3-cyanophenyl | H | H | H | F | H | H | I | H | heptafluoroisopropyl | H | CF3 |
| 6-3525 | 4-cyanophenyl | H | H | H | F | H | H | I | H | heptafluoroisopropyl | H | CF3 |
| 6-3540 | 2-chloropyridin-3-yl | H | H | H | F | H | H | I | H | heptafluoroisopropyl | H | CF3 |
| 6-3582 | phenyl | H | H | H | F | H | H | I | H | nonafluoro-2-butyl | H | CF3 |
| 6-3602 | 3-cyanophenyl | H | H | H | F | H | H | I | H | nonafluoro-2-butyl | H | CF3 |
| 6-3603 | 4-cyanophenyl | H | H | H | F | H | H | I | H | nonafluoro-2-butyl | H | CF3 |
| 6-3618 | 2-chloropyridin-3-yl | H | H | H | F | H | H | I | H | nonafluoro-2-butyl | H | CF3 |
| 6-3660 | phenyl | H | H | H | F | H | H | OCF3 | H | heptafluoroisopropyl | H | OCF3 |
| 6-3675 | 3-cyanophenyl | H | H | H | F | H | H | OCF3 | H | heptafluoroisopropyl | H | OCF3 |
| 6-3676 | 4-cyanophenyl | H | H | H | F | H | H | OCF3 | H | heptafluoroisopropyl | H | OCF3 |
| 6-3691 | 2-chloropyridin-3-yl | H | H | H | F | H | H | OCF3 | H | heptafluoroisopropyl | H | OCF3 |
| 6-3716 | phenyl | H | H | H | F | H | H | OCF3 | H | nonafluoro-2-butyl | H | OCF3 |
| 6-3731 | 3-cyanophenyl | H | H | H | F | H | H | OCF3 | H | nonafluoro-2-butyl | H | OCF3 |
| 6-3732 | 4-cyanophenyl | H | H | H | F | H | H | OCF3 | H | nonafluoro-2-butyl | H | OCF3 |
| 6-3747 | 2-chloropyridin-3-yl | H | H | H | F | H | H | OCF3 | H | nonafluoro-2-butyl | H | OCF3 |
| 6-3772 | phenyl | H | H | H | F | H | H | CF3 | H | heptafluoroisopropyl | H | OCF3 |
| 6-3787 | 3-cyanophenyl | H | H | H | F | H | H | CF3 | H | heptafluoroisopropyl | H | OCF3 |
| 6-3788 | 4-cyanophenyl | H | H | H | F | H | H | CF3 | H | heptafluoroisopropyl | H | OCF3 |
| 6-3803 | 2-chloropyridin-3-yl | H | H | H | F | H | H | CF3 | H | heptafluoroisopropyl | H | OCF3 |
| 6-3828 | phenyl | H | H | H | F | H | H | CF3 | H | nonafluoro-2-butyl | H | OCF3 |
| 6-3843 | 3-cyanophenyl | H | H | H | F | H | H | CF3 | H | nonafluoro-2-butyl | H | OCF3 |
| 6-3844 | 4-cyanophenyl | H | H | H | F | H | H | CF3 | H | nonafluoro-2-butyl | H | OCF3 |
| 6-3859 | 2-chloropyridin-3-yl | H | H | H | F | H | H | CF3 | H | nonafluoro-2-butyl | H | OCF3 |
| 6-3884 | phenyl | H | H | H | F | H | H | CF3 | H | heptafluoroisopropyl | H | CF3 |
| 6-3904 | 3-cyanophenyl | H | H | H | F | H | H | CF3 | H | heptafluoroisopropyl | H | CF3 |
| 6-3905 | 4-cyanophenyl | H | H | H | F | H | H | CF3 | H | heptafluoroisopropyl | H | CF3 |
| 6-3920 | 2-chloropyridin-3-yl | H | H | H | F | H | H | CF3 | H | heptafluoroisopropyl | H | CF3 |
| 6-3952 | phenyl | H | H | H | F | H | H | CF3 | H | nonafluoro-2-butyl | H | CF3 |
| 6-3972 | 3-cyanophenyl | H | H | H | F | H | H | CF3 | H | nonafluoro-2-butyl | H | CF3 |
| 6-3973 | 4-cyanophenyl | H | H | H | F | H | H | CF3 | H | nonafluoro-2-butyl | H | CF3 |
| 6-3988 | 2-chloropyridin-3-yl | H | H | H | F | H | H | CF3 | H | nonafluoro-2-butyl | H | CF3 |
| 6-4020 | phenyl | H | H | F | F | H | H | F | H | heptafluoroisopropyl | H | F |
| 6-4021 | 3-cyanophenyl | H | H | F | F | H | H | F | H | heptafluoroisopropyl | H | F |
| 6-4022 | 4-cyanophenyl | H | H | F | F | H | H | F | H | heptafluoroisopropyl | H | F |
| 6-4023 | 2-chloropyridin-3-yl | H | H | F | F | H | H | F | H | heptafluoroisopropyl | H | F |
| 6-4024 | phenyl | H | H | F | F | H | H | F | H | nonafluoro-2-butyl | H | F |
| 6-4025 | 3-cyanophenyl | H | H | F | F | H | H | F | H | nonafluoro-2-butyl | H | F |
| 6-4026 | 4-cyanophenyl | H | H | F | F | H | H | F | H | nonafluoro-2-butyl | H | F |
| 6-4027 | 2-chloropyridin-3-yl | H | H | F | F | H | H | F | H | nonafluoro-2-butyl | H | F |
| 6-4028 | phenyl | H | H | F | F | H | H | Cl | H | heptafluoroisopropyl | H | Cl |
| 6-4048 | 3-cyanophenyl | H | H | F | F | H | H | Cl | H | heptafluoroisopropyl | H | Cl |
| 6-4049 | 4-cyanophenyl | H | H | F | F | H | H | Cl | H | heptafluoroisopropyl | H | Cl |
| 6-4064 | 2-chloropyridin-3-yl | H | H | F | F | H | H | Cl | H | heptafluoroisopropyl | H | Cl |
| 6-4106 | phenyl | H | H | F | F | H | H | Cl | H | nonafluoro-2-butyl | H | Cl |
| 6-4126 | 3-cyanophenyl | H | H | F | F | H | H | Cl | H | nonafluoro-2-butyl | H | Cl |
| 6-4127 | 4-cyanophenyl | H | F | F | F | H | H | Cl | H | nonafluoro-2-butyl | H | Cl |

TABLE 6-continued

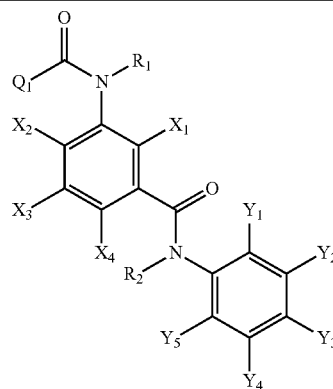

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-4142 | 2-chloropyridin-3-yl | H | H | F | F | H | H | Cl | H | nonafluoro-2-butyl | H | Cl |
| 6-4184 | phenyl | H | H | F | F | H | H | Br | H | heptafluoroisopropyl | H | Br |
| 6-4204 | 3-cyanophenyl | H | H | F | F | H | H | Br | H | heptafluoroisopropyl | H | Br |
| 6-4205 | 4-cyanophenyl | H | H | F | F | H | H | Br | H | heptafluoroisopropyl | H | Br |
| 6-4220 | 2-chloropyridin-3-yl | H | H | F | F | H | H | Br | H | heptafluoroisopropyl | H | Br |
| 6-4262 | phenyl | H | H | F | F | H | H | Br | H | nonafluoro-2-butyl | H | Br |
| 6-4282 | 3-cyanophenyl | H | H | F | F | H | H | Br | H | nonafluoro-2-butyl | H | Br |
| 6-4283 | 4-cyanophenyl | H | H | F | F | H | H | Br | H | nonafluoro-2-butyl | H | Br |
| 6-4298 | 2-chloropyrid6-3-yl | H | H | F | F | H | H | Br | H | nonafluoro-2-butyl | H | Br |
| 6-4340 | phenyl | H | H | F | F | H | H | I | H | heptafluoroisopropyl | H | I |
| 6-4360 | 3-cyanophenyl | H | H | F | F | H | H | I | H | heptafluoroisopropyl | H | I |
| 6-4361 | 4-cyanophenyl | H | H | F | F | H | H | I | H | heptafluoroisopropyl | H | I |
| 6-4376 | 2-chloropyridin-3-yl | H | H | F | F | H | H | I | H | heptafluoroisopropyl | H | I |
| 6-4418 | phenyl | H | H | F | F | H | H | I | H | nonafluoro-2-butyl | H | I |
| 6-4438 | 3-cyanophenyl | H | H | F | F | H | H | I | H | nonafluoro-2-butyl | H | I |
| 6-4439 | 4-cyanophenyl | H | H | F | F | H | H | I | H | nonafluoro-2-butyl | H | I |
| 6-4454 | 2-chloropyridin-3-yl | H | H | F | F | H | H | I | H | nonafluoro-2-butyl | H | I |
| 6-4496 | phenyl | H | H | F | F | H | H | Cl | H | heptafluoroisopropyl | H | OCF3 |
| 6-4516 | 3-cyanophenyl | H | H | F | F | H | H | Cl | H | heptafluoroisopropyl | H | OCF3 |
| 6-4517 | 4-cyanophenyl | H | H | F | F | H | H | Cl | H | heptafluoroisopropyl | H | OCF3 |
| 6-4532 | 2-chloropyridin-3-yl | H | H | F | F | H | H | Cl | H | heptafluoroisopropyl | H | OCF3 |
| 6-4574 | phenyl | H | H | F | F | H | H | Cl | H | nonafluoro-2-butyl | H | OCF3 |
| 6-4594 | 3-cyanophenyl | H | H | F | F | H | H | Cl | H | nonafluoro-2-butyl | H | OCF3 |
| 6-4595 | 4-cyanophenyl | H | H | F | F | H | H | Cl | H | nonafluoro-2-butyl | H | OCF3 |
| 6-4610 | 2-chloropyridin-3-yl | H | H | F | F | H | H | Cl | H | nonafluoro-2-butyl | H | OCF3 |
| 6-4652 | phenyl | H | H | F | F | H | H | Br | H | heptafluoroisopropyl | H | OCF3 |
| 6-4672 | 3-cyanophenyl | H | H | F | F | H | H | Br | H | heptafluoroisopropyl | H | OCF3 |
| 6-4673 | 4-cyanophenyl | H | H | F | F | H | H | Br | H | heptafluoroisopropyl | H | OCF3 |
| 6-4688 | 2-chloropyridin-3-yl | H | H | F | F | H | H | Br | H | heptafluoroisopropyl | H | OCF3 |
| 6-4730 | phenyl | H | H | F | F | H | H | Br | H | nonafluoro-2-butyl | H | OCF3 |
| 6-4750 | 3-cyanophenyl | H | H | F | F | H | H | Br | H | nonafluoro-2-butyl | H | OCF3 |
| 6-4751 | 4-cyanophenyl | H | H | F | F | H | H | Br | H | nonafluoro-2-butyl | H | OCF3 |
| 6-4766 | 2-chloropyridin-3-yl | H | H | F | F | H | H | Br | H | nonafluoro-2-butyl | H | OCF3 |
| 6-4808 | phenyl | H | H | F | F | H | H | I | H | heptafluoroisopropyl | H | OCF3 |
| 6-4828 | 3-cyanophenyl | H | H | F | F | H | H | I | H | heptafluoroisopropyl | H | OCF3 |
| 6-4829 | 4-cyanophenyl | H | H | F | F | H | H | I | H | heptafluoroisopropyl | H | OCF3 |
| 6-4844 | 2-chloropyridin-3-yl | H | H | F | F | H | H | I | H | heptafluoroisopropyl | H | OCF3 |
| 6-4886 | phenyl | H | H | F | F | H | H | I | H | nonafluoro-2-butyl | H | OCF3 |
| 6-4906 | 3-cyanophenyl | H | H | F | F | H | H | I | H | nonafluoro-2-butyl | H | OCF3 |
| 6-4907 | 4-cyanophenyl | H | H | F | F | H | H | I | H | nonafluoro-2-butyl | H | OCF3 |
| 6-4922 | 2-chloropyridin-3-yl | H | H | F | F | H | H | I | H | nonafluoro-2-butyl | H | OCF3 |
| 6-4964 | phenyl | H | H | F | F | H | H | F | H | heptafluoroisopropyl | H | CF3 |
| 6-4965 | phenyl | H | H | F | F | H | H | Cl | H | heptafluoroisopropyl | H | CF3 |
| 6-4985 | 3-cyanophenyl | H | H | F | F | H | H | Cl | H | heptafluoroisopropyl | H | CF3 |
| 6-4986 | 4-cyanophenyl | H | H | F | F | H | H | Cl | H | heptafluoroisopropyl | H | CF3 |
| 6-5001 | 2-chloropyridin-3-yl | H | H | F | F | H | H | Cl | H | heptafluoroisopropyl | H | CF3 |
| 6-5043 | phenyl | H | H | F | F | H | H | F | H | nonafluoro-2-butyl | H | CF3 |
| 6-5044 | phenyl | H | H | F | F | H | H | Cl | H | nonafluoro-2-butyl | H | CF3 |
| 6-5064 | 3-cyanophenyl | H | H | F | F | H | H | Cl | H | nonafluoro-2-butyl | H | CF3 |
| 6-5065 | 4-cyanophenyl | H | H | F | F | H | H | Cl | H | nonafluoro-2-butyl | H | CF3 |
| 6-5080 | 2-chloropyridin-3-yl | H | H | F | F | H | H | Cl | H | nonafluoro-2-butyl | H | CF3 |
| 6-5122 | phenyl | H | H | F | F | H | H | Br | H | heptafluoroisopropyl | H | CF3 |
| 6-5142 | 3-cyanophenyl | H | H | F | F | H | H | Br | H | heptafluoroisopropyl | H | CF3 |
| 6-5143 | 4-cyanophenyl | H | H | F | F | H | H | Br | H | heptafluoroisopropyl | H | CF3 |
| 6-5158 | 2-chloropyridin-3-yl | H | H | F | F | H | H | Br | H | heptafluoroisopropyl | H | CF3 |
| 6-5200 | phenyl | H | H | F | F | H | H | Br | H | nonafluoro-2-butyl | H | CF3 |
| 6-5220 | 3-cyanophenyl | H | H | F | F | H | H | Br | H | nonafluoro-2-butyl | H | CF3 |
| 6-5221 | 4-cyanophenyl | H | H | F | F | H | H | Br | H | nonafluoro-2-butyl | H | CF3 |

TABLE 6-continued

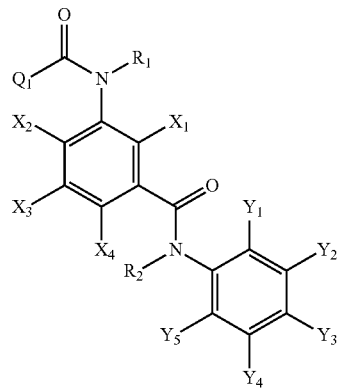

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-5236 | 2-chloropyridin-3-yl | H | H | F | F | H | H | Br | H | nonafluoro-2-butyl | H | CF3 |
| 6-5278 | phenyl | H | H | F | F | H | H | I | H | heptafluoroisopropyl | H | CF3 |
| 6-5298 | 3-cyanophenyl | H | H | F | F | H | H | I | H | heptafluoroisopropyl | H | CF3 |
| 6-5299 | 4-cyanophenyl | H | H | F | F | H | H | I | H | heptafluoroisopropyl | H | CF3 |
| 6-5314 | 2-chloropyridin-3-yl | H | H | F | F | H | H | I | H | heptafluoroisopropyl | H | CF3 |
| 6-5356 | phenyl | H | H | F | F | H | H | I | H | nonafluoro-2-butyl | H | CF3 |
| 6-5376 | 3-cyanophenyl | H | H | F | F | H | H | I | H | nonafluoro-2-butyl | H | CF3 |
| 6-5377 | 4-cyanophenyl | H | H | F | F | H | H | I | H | nonafluoro-2-butyl | H | CF3 |
| 6-5392 | 2-chloropyridin-3-yl | H | H | F | F | H | H | I | H | nonafluoro-2-butyl | H | CF3 |
| 6-5434 | phenyl | H | H | F | F | H | H | OCF3 | H | heptafluoroisopropyl | H | OCF3 |
| 6-5449 | 3-cyanophenyl | H | H | F | F | H | H | OCF3 | H | heptafluoroisopropyl | H | OCF3 |
| 6-5450 | 4-cyanophenyl | H | H | F | F | H | H | OCF3 | H | heptafluoroisopropyl | H | OCF3 |
| 6-5465 | 2-chloropyridin-3-yl | H | H | F | F | H | H | OCF3 | H | heptafluoroisopropyl | H | OCF3 |
| 6-5490 | phenyl | H | H | F | F | H | H | OCF3 | H | nonafluoro-2-butyl | H | OCF3 |
| 6-5505 | 3-cyanophenyl | H | H | F | F | H | H | OCF3 | H | nonafluoro-2-butyl | H | OCF3 |
| 6-5506 | 4-cyanophenyl | H | H | F | F | H | H | OCF3 | H | nonafluoro-2-butyl | H | OCF3 |
| 6-5521 | 2-chloropyridin-3-yl | H | H | F | F | H | H | OCF3 | H | nonafluoro-2-butyl | H | OCF3 |
| 6-5546 | phenyl | H | H | F | F | H | H | CF3 | H | heptafluoroisopropyl | H | OCF3 |
| 6-5561 | 3-cyanophenyl | H | H | F | F | H | H | CF3 | H | heptafluoroisopropyl | H | OCF3 |
| 6-5562 | 4-cyanophenyl | H | H | F | F | H | H | CF3 | H | heptafluoroisopropyl | H | OCF3 |
| 6-5577 | 2-chloropyridin-3-yl | H | H | F | F | H | H | CF3 | H | heptafluoroisopropyl | H | OCF3 |
| 6-5602 | phenyl | H | H | F | F | H | H | CF3 | H | nonafluoro-2-butyl | H | OCF3 |
| 6-5617 | 3-cyanophenyl | H | H | F | F | H | H | CF3 | H | nonafluoro-2-butyl | H | OCF3 |
| 6-5633 | 2-chloropyridin-3-yl | H | H | F | F | H | H | CF3 | H | nonafluoro-2-butyl | H | OCF3 |
| 6-5658 | phenyl | H | H | F | F | H | H | CF3 | H | heptafluoroisopropyl | H | CF3 |
| 6-5678 | 3-cyanophenyl | H | H | F | F | H | H | CF3 | H | heptafluoroisopropyl | H | CF3 |
| 6-5694 | 2-chloropyridin-3-yl | H | H | F | F | H | H | CF3 | H | heptafluoroisopropyl | H | CF3 |
| 6-5726 | phenyl | H | H | F | F | H | H | CF3 | H | nonafluoro-2-butyl | H | CF3 |
| 6-5746 | 3-cyanophenyl | H | H | F | F | H | H | CF3 | H | nonafluoro-2-butyl | H | CF3 |
| 6-5747 | 4-cyanophenyl | H | H | F | F | H | H | CF3 | H | nonafluoro-2-butyl | H | CF3 |
| 6-5762 | 2-chloropyridin-3-yl | H | H | F | F | H | H | CF3 | H | nonafluoro-2-butyl | H | CF3 |
| 6-5794 | phenyl | H | H | F | F | F | H | Cl | H | pentafluoroethyl | H | Cl |
| 6-5795 | phenyl | H | H | F | F | F | H | Br | H | heptafluoroisopropyl | H | Br |
| 6-5796 | phenyl | H | H | F | F | F | H | Br | H | heptafluoroisopropyl | H | OCF3 |
| 6-5797 | phenyl | H | H | F | F | F | H | I | H | heptafluoroisopropyl | H | CF3 |
| 6-5798 | phenyl | H | H | F | F | F | H | CF3 | H | heptafluoroisopropyl | H | CF3 |
| 6-5799 | phenyl | H | H | F | F | F | H | I | H | nonafluoro-2-butyl | H | I |
| 6-5800 | phenyl | H | H | F | F | F | H | Cl | H | nonafluoro-2-butyl | H | OCF3 |
| 6-5801 | phenyl | H | H | F | F | F | H | Br | H | nonafluoro-2-butyl | H | CF3 |
| 6-5802 | phenyl | H | H | F | F | F | H | CF3 | H | nonafluoro-2-butyl | H | CF3 |
| 6-5803 | phenyl | H | H | H | H | F | H | Cl | H | pentafluoroethyl | H | Cl |
| 6-5804 | phenyl | H | H | H | H | F | H | Br | H | heptafluoroisopropyl | H | Br |
| 6-5805 | phenyl | H | H | H | H | F | H | Br | H | heptafluoroisopropyl | H | OCF3 |
| 6-5806 | phenyl | H | H | H | H | F | H | I | H | heptafluoroisopropyl | H | CF3 |
| 6-5807 | phenyl | H | H | H | H | F | H | CF3 | H | heptafluoroisopropyl | H | CF3 |
| 6-5808 | phenyl | H | H | H | H | F | H | I | H | nonafluoro-2-butyl | H | I |
| 6-5809 | phenyl | H | H | H | H | F | H | Cl | H | nonafluoro-2-butyl | H | OCF3 |
| 6-5810 | phenyl | H | H | H | H | F | H | Br | H | nonafluoro-2-butyl | H | CF3 |
| 6-5811 | phenyl | H | H | H | H | F | H | CF3 | H | nonafluoro-2-butyl | H | CF3 |
| 6-5812 | phenyl | H | H | H | H | H | F | Cl | H | pentafluoroethyl | H | Cl |
| 6-5813 | phenyl | H | H | H | H | H | F | Br | H | heptafluoroisopropyl | H | Br |
| 6-5814 | phenyl | H | H | H | H | H | F | Br | H | heptafluoroisopropyl | H | OCF3 |
| 6-5815 | phenyl | H | H | H | H | H | F | I | H | heptafluoroisopropyl | H | CF3 |
| 6-5816 | phenyl | H | H | H | H | H | F | CF3 | H | heptafluoroisopropyl | H | CF3 |
| 6-5817 | phenyl | H | H | H | H | H | F | I | H | nonafluoro-2-butyl | H | I |
| 6-5818 | phenyl | H | H | H | H | H | F | Cl | H | nonafluoro-2-butyl | H | OCF3 |
| 6-5819 | phenyl | H | H | H | H | H | F | Br | H | nonafluoro-2-butyl | H | CF3 |
| 6-5820 | phenyl | H | H | H | H | H | F | CF3 | H | nonafluoro-2-butyl | H | CF3 |

TABLE 6-continued

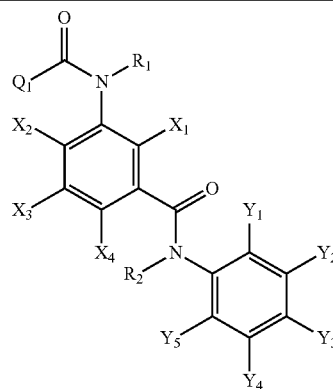

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-5821 | phenyl | H | H | F | H | F | H | Cl | H | pentafluoroethyl | H | Cl |
| 6-5822 | phenyl | H | H | F | H | F | H | Br | H | heptafluoroisopropyl | H | Br |
| 6-5823 | phenyl | H | H | F | H | F | H | Br | H | heptafluoroisopropyl | H | OCF3 |
| 6-5824 | phenyl | H | H | F | H | F | H | I | H | heptafluoroisopropyl | H | CF3 |
| 6-5825 | phenyl | H | H | F | H | F | H | CF3 | H | heptafluoroisopropyl | H | CF3 |
| 6-5826 | phenyl | H | H | F | H | F | H | I | H | nonafluoro-2-butyl | H | I |
| 6-5827 | phenyl | H | H | F | H | F | H | Cl | H | nonafluoro-2-butyl | H | OCF3 |
| 6-5828 | phenyl | H | H | F | H | F | H | Br | H | nonafluoro-2-butyl | H | CF3 |
| 6-5829 | phenyl | H | H | F | H | F | H | CF3 | H | nonafluoro-2-butyl | H | CF3 |
| 6-5830 | phenyl | H | H | F | H | H | F | Cl | H | pentafluoroethyl | H | Cl |
| 6-5831 | phenyl | H | H | F | H | H | F | Br | H | heptafluoroisopropyl | H | Br |
| 6-5832 | phenyl | H | H | F | H | H | F | Br | H | heptafluoroisopropyl | H | OCF3 |
| 6-5833 | phenyl | H | H | F | H | H | F | I | H | heptafluoroisopropyl | H | CF3 |
| 6-5834 | phenyl | H | H | F | H | H | F | CF3 | H | heptafluoroisopropyl | H | CF3 |
| 6-5835 | phenyl | H | H | F | H | H | F | I | H | nonafluoro-2-butyl | H | I |
| 6-5836 | phenyl | H | H | F | H | H | F | Cl | H | nonafluoro-2-butyl | H | OCF3 |
| 6-5837 | phenyl | H | H | F | H | H | F | Br | H | nonafluoro-2-butyl | H | CF3 |
| 6-5838 | phenyl | H | H | F | H | H | F | CF3 | H | nonafluoro-2-butyl | H | CF3 |
| 6-5839 | phenyl | H | H | H | F | F | H | Cl | H | pentafluoroethyl | H | Cl |
| 6-5840 | phenyl | H | H | H | F | F | H | Br | H | heptafluoroisopropyl | H | Br |
| 6-5841 | phenyl | H | H | H | F | F | H | Br | H | heptafluoroisopropyl | H | OCF3 |
| 6-5842 | phenyl | H | H | H | F | F | H | I | H | heptafluoroisopropyl | H | CF3 |
| 6-5843 | phenyl | H | H | H | F | F | H | CF3 | H | heptafluoroisopropyl | H | CF3 |
| 6-5844 | phenyl | H | H | H | F | F | H | I | H | nonafluoro-2-butyl | H | I |
| 6-5845 | phenyl | H | H | H | F | F | H | Cl | H | nonafluoro-2-butyl | H | OCF3 |
| 6-5846 | phenyl | H | H | H | F | F | H | Br | H | nonafluoro-2-butyl | H | CF3 |
| 6-5847 | phenyl | H | H | H | F | F | H | CF3 | H | nonafluoro-2-butyl | H | CF3 |
| 6-5848 | phenyl | H | H | H | F | H | F | Cl | H | pentafluoroethyl | H | Cl |
| 6-5849 | phenyl | H | H | H | F | H | F | Br | H | heptafluoroisopropyl | H | Br |
| 6-5850 | phenyl | H | H | H | F | H | F | Br | H | heptafluoroisopropyl | H | OCF3 |
| 6-5851 | phenyl | H | H | H | F | H | F | I | H | heptafluoroisopropyl | H | CF3 |
| 6-5852 | phenyl | H | H | H | F | H | F | CF3 | H | heptafluoroisopropyl | H | CF3 |
| 6-5853 | phenyl | H | H | H | F | H | F | I | H | nonafluoro-2-butyl | H | I |
| 6-5854 | phenyl | H | H | H | F | H | F | Cl | H | nonafluoro-2-butyl | H | OCF3 |
| 6-5855 | phenyl | H | H | H | F | H | F | Br | H | nonafluoro-2-butyl | H | CF3 |
| 6-5856 | phenyl | H | H | H | F | H | F | CF3 | H | nonafluoro-2-butyl | H | CF3 |
| 6-5857 | phenyl | H | H | H | H | F | F | Cl | H | pentafluoroethyl | H | Cl |
| 6-5858 | phenyl | H | H | H | H | F | F | Br | H | heptafluoroisopropyl | H | Br |
| 6-5859 | phenyl | H | H | H | H | F | F | Br | H | heptafluoroisopropyl | H | OCF3 |
| 6-5860 | phenyl | H | H | H | H | F | F | I | H | heptafluoroisopropyl | H | CF3 |
| 6-5861 | phenyl | H | H | H | H | F | F | CF3 | H | heptafluoroisopropyl | H | CF3 |
| 6-5862 | phenyl | H | H | H | H | F | F | I | H | nonafluoro-2-butyl | H | I |
| 6-5863 | phenyl | H | H | H | H | F | F | Cl | H | nonafluoro-2-butyl | H | OCF3 |
| 6-5864 | phenyl | H | H | H | H | F | F | Br | H | nonafluoro-2-butyl | H | CF3 |
| 6-5865 | phenyl | H | H | H | H | F | F | CF3 | H | nonafluoro-2-butyl | H | CF3 |
| 6-5866 | phenyl | H | H | F | F | H | F | Cl | H | pentafluoroethyl | H | Cl |
| 6-5867 | phenyl | H | H | F | F | H | F | Br | H | heptafluoroisopropyl | H | Br |
| 6-5868 | phenyl | H | H | F | F | H | F | Br | H | heptafluoroisopropyl | H | OCF3 |
| 6-5869 | phenyl | H | H | F | F | H | F | I | H | heptafluoroisopropyl | H | CF3 |
| 6-5870 | phenyl | H | H | F | F | H | F | CF3 | H | heptafluoroisopropyl | H | CF3 |
| 6-5871 | phenyl | H | H | F | F | H | F | I | H | nonafluoro-2-butyl | H | I |
| 6-5872 | phenyl | H | H | F | F | H | F | Cl | H | nonafluoro-2-butyl | H | OCF3 |
| 6-5873 | phenyl | H | H | F | F | H | F | Br | H | nonafluoro-2-butyl | H | CF3 |
| 6-5874 | phenyl | H | H | F | F | H | F | CF3 | H | nonafluoro-2-butyl | H | CF3 |
| 6-5875 | phenyl | H | H | F | H | F | F | Cl | H | pentafluoroethyl | H | Cl |
| 6-5876 | phenyl | H | H | F | H | F | F | Br | H | heptafluoroisopropyl | H | Br |
| 6-5877 | phenyl | H | H | F | H | F | F | Br | H | heptafluoroisopropyl | H | OCF3 |
| 6-5878 | phenyl | H | H | F | H | F | F | I | H | heptafluoroisopropyl | H | CF3 |

TABLE 6-continued

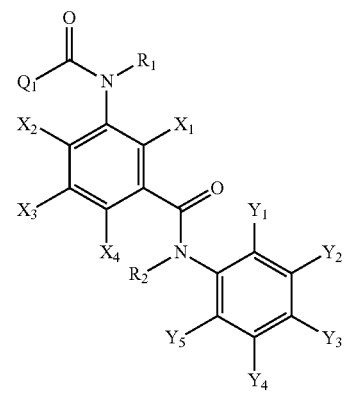

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-5879 | phenyl | H | H | F | H | F | F | CF3 | H | heptafluoroisopropyl | H | CF3 |
| 6-5880 | phenyl | H | H | F | H | F | F | I | H | nonafluoro-2-butyl | H | I |
| 6-5881 | phenyl | H | H | F | H | F | F | Cl | H | nonafluoro-2-butyl | H | OCF3 |
| 6-5882 | phenyl | H | H | F | H | F | F | Br | H | nonafluoro-2-butyl | H | CF3 |
| 6-5883 | phenyl | H | H | F | H | F | F | CF3 | H | nonafluoro-2-butyl | H | CF3 |
| 6-5884 | phenyl | H | H | H | F | F | F | Cl | H | pentafluoroethyl | H | Cl |
| 6-5885 | phenyl | H | H | H | F | F | F | Br | H | heptafluoroisopropyl | H | Br |
| 6-5886 | phenyl | H | H | H | F | F | F | Br | H | heptafluoroisopropyl | H | OCF3 |
| 6-5887 | phenyl | H | H | H | F | F | F | I | H | heptafluoroisopropyl | H | CF3 |
| 6-5888 | phenyl | H | H | H | F | F | F | CF3 | H | heptafluoroisopropyl | H | CF3 |
| 6-5889 | phenyl | H | H | H | F | F | F | I | H | nonafluoro-2-butyl | H | I |
| 6-5890 | phenyl | H | H | H | F | F | F | Cl | H | nonafluoro-2-butyl | H | OCF3 |
| 6-5891 | phenyl | H | H | H | F | F | F | Br | H | nonafluoro-2-butyl | H | CF3 |
| 6-5892 | phenyl | H | H | H | F | F | F | CF3 | H | nonafluoro-2-butyl | H | CF3 |
| 6-5893 | phenyl | H | H | F | F | F | F | Cl | H | pentafluoroethyl | H | Cl |
| 6-5894 | phenyl | H | H | F | F | F | F | Br | H | heptafluoroisopropyl | H | Br |
| 6-5895 | phenyl | H | H | F | F | F | F | Br | H | heptafluoroisopropyl | H | OCF3 |
| 6-5896 | phenyl | H | H | F | F | F | F | I | H | heptafluoroisopropyl | H | CF3 |
| 6-5897 | phenyl | H | H | F | F | F | F | CF3 | H | heptafluoroisopropyl | H | CF3 |
| 6-5898 | phenyl | H | H | F | F | F | F | I | H | nonafluoro-2-butyl | H | I |
| 6-5899 | phenyl | H | H | F | F | F | F | Cl | H | nonafluoro-2-butyl | H | OCF3 |
| 6-5900 | phenyl | H | H | F | F | F | F | Br | H | nonafluoro-2-butyl | H | CF3 |
| 6-5901 | phenyl | H | H | F | F | F | F | CF3 | H | nonafluoro-2-butyl | H | CF3 |
| 6-5902 | phenyl | H | H | F | H | H | H | Br | H | heptafluoroisopropyl | H | Cl |
| 6-5903 | 3-fluorophenyl | H | H | H | H | H | H | I | H | nonafluoro-2-butyl | H | I |
| 6-5904 | 4-fluorophenyl | H | H | H | H | H | H | I | H | nonafluoro-2-butyl | H | I |
| 6-5905 | 3-fluorophenyl | H | H | H | H | H | H | Br | H | nonafluoro-2-butyl | H | Br |
| 6-5906 | 4-fluorophenyl | H | H | H | H | H | H | Br | H | nonafluoro-2-butyl | H | Br |
| 6-5907 | phenyl | H | H | F | H | H | H | Br | H | heptafluoroisopropyl | H | OCF3 |
| 6-5908 | 2-chloropyridin-3-yl | H | H | F | H | H | H | Br | H | heptafluoroisopropyl | H | OCF3 |
| 6-5909 | 4-cyanophenyl | H | H | F | H | H | H | Br | H | heptafluoroisopropyl | H | OCF3 |
| 6-5910 | phenyl | H | H | F | H | H | H | Br | H | heptafluoroisopropyl | H | C2F5 |
| 6-5911 | 4-cyanophenyl | H | H | F | H | H | H | Br | H | heptafluoroisopropyl | H | C2F5 |
| 6-5912 | 2-chloro-4-(methylsulfonyl)phenyl | H | H | H | H | H | H | I | H | heptafluoroisopropyl | H | CF3 |
| 6-5913 | phenyl | H | H | H | H | H | H | Br | H | pentafluoroethyl | H | CF3 |
| 6-5914 | 2-chloropyridin-3-yl | H | H | H | H | H | H | Br | H | pentafluoroethyl | H | CF3 |

TABLE 7

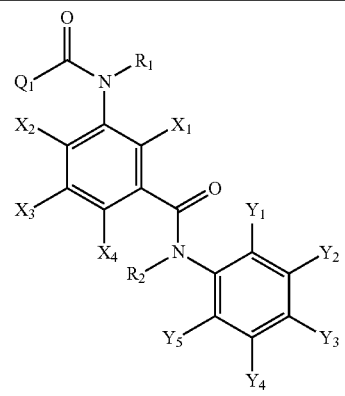

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-1 | phenyl | Me | H | H | H | H | H | F | H | nonafluoro-2-butyl | H | F |
| 7-2 | 3-cyanophenyl | Me | H | H | H | H | H | F | H | nonafluoro-2-butyl | H | F |
| 7-3 | 4-cyanophenyl | Me | H | H | H | H | H | F | H | nonafluoro-2-butyl | H | F |
| 7-4 | 2-chloropyridin-3-yl | Me | H | H | H | H | H | F | H | nonafluoro-2-butyl | H | F |
| 7-5 | phenyl | Me | H | H | H | H | H | Cl | H | nonafluoro-2-butyl | H | Cl |
| 7-12 | 3-cyanophenyl | Me | H | H | H | H | H | Cl | H | nonafluoro-2-butyl | H | Cl |
| 7-13 | 4-cyanophenyl | Me | H | H | H | H | H | Cl | H | nonafluoro-2-butyl | H | Cl |
| 7-24 | 2-chloropyridin-3-yl | Me | H | H | H | H | H | Cl | H | nonafluoro-2-butyl | H | Cl |
| 7-38 | phenyl | Me | H | H | H | H | H | Br | H | nonafluoro-2-butyl | H | Br |
| 7-39 | 2-fluorophenyl | Me | H | H | H | H | H | Br | H | nonafluoro-2-butyl | H | Br |
| 7-45 | 3-cyanophenyl | Me | H | H | H | H | H | Br | H | nonafluoro-2-butyl | H | Br |
| 7-46 | 4-cyanophenyl | Me | H | H | H | H | H | Br | H | nonafluoro-2-butyl | H | Br |
| 7-47 | 2,6-difluorophenyl | Me | H | H | H | H | H | Br | H | nonafluoro-2-butyl | H | Br |
| 7-57 | 2-chloropyridin-3-yl | Me | H | H | H | H | H | Br | H | nonafluoro-2-butyl | H | Br |
| 7-60 | 6-chloropyridin-3-yl | Me | H | H | H | H | H | Br | H | nonafluoro-2-butyl | H | Br |
| 7-71 | phenyl | Me | H | H | H | H | H | I | H | nonafluoro-2-butyl | H | I |
| 7-72 | 2-fluorophenyl | Me | H | H | H | H | H | I | H | nonafluoro-2-butyl | H | I |
| 7-78 | 3-cyanophenyl | Me | H | H | H | H | H | I | H | nonafluoro-2-butyl | H | I |
| 7-79 | 4-cyanophenyl | Me | H | H | H | H | H | I | H | nonafluoro-2-butyl | H | I |
| 7-80 | 2,6-difluorophenyl | Me | H | H | H | H | H | I | H | nonafluoro-2-butyl | H | I |
| 7-90 | 2-chloropyridin-3-yl | Me | H | H | H | H | H | I | H | nonafluoro-2-butyl | H | I |
| 7-93 | 6-chloropyridin-3-yl | Me | H | H | H | H | H | I | H | nonafluoro-2-butyl | H | I |
| 7-104 | phenyl | Me | H | H | H | H | H | F | H | nonafluoro-2-butyl | H | Cl |
| 7-105 | phenyl | Me | H | H | H | H | H | F | H | nonafluoro-2-butyl | H | Br |
| 7-106 | phenyl | Me | H | H | H | H | H | F | H | nonafluoro-2-butyl | H | I |
| 7-107 | phenyl | Me | H | H | H | H | H | Cl | H | nonafluoro-2-butyl | H | Br |
| 7-108 | phenyl | Me | H | H | H | H | H | Cl | H | nonafluoro-2-butyl | H | I |
| 7-109 | phenyl | Me | H | H | H | H | H | Br | H | nonafluoro-2-butyl | H | I |
| 7-110 | phenyl | Me | H | H | H | H | H | F | H | heptafluoroisopropyl | H | CF3 |
| 7-111 | phenyl | Me | H | H | H | H | H | Cl | H | heptafluoroisopropyl | H | CF3 |
| 7-131 | 3-cyanophenyl | Me | H | H | H | H | H | Cl | H | heptafluoroisopropyl | H | CF3 |
| 7-132 | 4-cyanophenyl | Me | H | H | H | H | H | Cl | H | heptafluoroisopropyl | H | CF3 |
| 7-147 | 2-chloropyridin-3-yl | Me | H | H | H | H | H | Cl | H | heptafluoroisopropyl | H | CF3 |
| 7-189 | phenyl | Me | H | H | H | H | H | F | H | nonafluoro-2-butyl | H | CF3 |
| 7-190 | phenyl | Me | H | H | H | H | H | Cl | H | nonafluoro-2-butyl | H | CF3 |
| 7-210 | 3-cyanophenyl | Me | H | H | H | H | H | Cl | H | nonafluoro-2-butyl | H | CF3 |
| 7-211 | 4-cyanophenyl | Me | H | H | H | H | H | Cl | H | nonafluoro-2-butyl | H | CF3 |
| 7-226 | 2-chloropyridin-3-yl | Me | H | H | H | H | H | Cl | H | nonafluoro-2-butyl | H | CF3 |
| 7-268 | phenyl | Me | H | H | H | H | H | Br | H | heptafluoroisopropyl | H | CF3 |
| 7-269 | 2-fluorophenyl | Me | H | H | H | H | H | Br | H | heptafluoroisopropyl | H | CF3 |
| 7-270 | 3-fluorophenyl | Me | H | H | H | H | H | Br | H | heptafluoroisopropyl | H | CF3 |
| 7-271 | 4-fluorophenyl | Me | H | H | H | H | H | Br | H | heptafluoroisopropyl | H | CF3 |
| 7-285 | 3-nitrophenyl | Me | H | H | H | H | H | Br | H | heptafluoroisopropyl | H | CF3 |
| 7-286 | 4-nitrophenyl | Me | H | H | H | H | H | Br | H | heptafluoroisopropyl | H | CF3 |
| 7-288 | 3-cyanophenyl | Me | H | H | H | H | H | Br | H | heptafluoroisopropyl | H | CF3 |
| 7-289 | 4-cyanophenyl | Me | H | H | H | H | H | Br | H | heptafluoroisopropyl | H | CF3 |
| 7-290 | 2,6-difluorophenyl | Me | H | H | H | H | H | Br | H | heptafluoroisopropyl | H | CF3 |
| 7-299 | 3,5-dicyanophenyl | Me | H | H | H | H | H | Br | H | heptafluoroisopropyl | H | CF3 |
| 7-300 | 4-cyano-2-fluorophenyl | Me | H | H | H | H | H | Br | H | heptafluoroisopropyl | H | CF3 |
| 7-301 | 2-chloro-4-cyanophenyl | Me | H | H | H | H | H | Br | H | heptafluoroisopropyl | H | CF3 |
| 7-303 | 2-fluoropyridin-3-yl | Me | H | H | H | H | H | Br | H | heptafluoroisopropyl | H | CF3 |
| 7-304 | 2-chloropyridin-3-yl | Me | H | H | H | H | H | Br | H | heptafluoroisopropyl | H | CF3 |
| 7-305 | 2-bromopyridin-3-yl | Me | H | H | H | H | H | Br | H | heptafluoroisopropyl | H | CF3 |
| 7-311 | 6-chloropyridin-3-yl | Me | H | H | H | H | H | Br | H | heptafluoroisopropyl | H | CF3 |
| 7-316 | 6-cyanopyridin-3-yl | Me | H | H | H | H | H | Br | H | heptafluoroisopropyl | H | CF3 |
| 7-346 | phenyl | Me | H | H | H | H | H | Br | H | nonafluoro-2-butyl | H | CF3 |
| 7-347 | 2-fluorophenyl | Me | H | H | H | H | H | Br | H | nonafluoro-2-butyl | H | CF3 |
| 7-348 | 3-fluorophenyl | Me | H | H | H | H | H | Br | H | nonafluoro-2-butyl | H | CF3 |

TABLE 7-continued

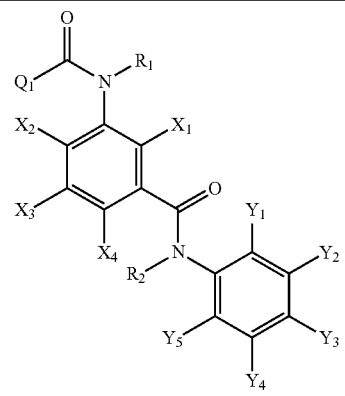

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 7-349 | 4-fluorophenyl | Me | H | H | H | H | H | Br | H | nonafluoro-2-butyl | H | CF3 |
| 7-366 | 3-cyanophenyl | Me | H | H | H | H | H | Br | H | nonafluoro-2-butyl | H | CF3 |
| 7-367 | 4-cyanophenyl | Me | H | H | H | H | H | Br | H | nonafluoro-2-butyl | H | CF3 |
| 7-368 | 2,6-difluorophenyl | Me | H | H | H | H | H | Br | H | nonafluoro-2-butyl | H | CF3 |
| 7-382 | 2-chloropyridin-3-yl | Me | H | H | H | H | H | Br | H | nonafluoro-2-butyl | H | CF3 |
| 7-389 | 6-chloropyridin-3-yl | Me | H | H | H | H | H | Br | H | nonafluoro-2-butyl | H | CF3 |
| 7-424 | phenyl | Me | H | H | H | H | H | I | H | heptafluoroisopropyl | H | CF3 |
| 7-425 | 2-fluorophenyl | Me | H | H | H | H | H | I | H | heptafluoroisopropyl | H | CF3 |
| 7-426 | 3-fluorophenyl | Me | H | H | H | H | H | I | H | heptafluoroisopropyl | H | CF3 |
| 7-427 | 4-fluorophenyl | Me | H | H | H | H | H | I | H | heptafluoroisopropyl | H | CF3 |
| 7-428 | 2-chlorophenyl | Me | H | H | H | H | H | I | H | heptafluoroisopropyl | H | CF3 |
| 7-444 | 3-cyanophenyl | Me | H | H | H | H | H | I | H | heptafluoroisopropyl | H | CF3 |
| 7-445 | 4-cyanophenyl | Me | H | H | H | H | H | I | H | heptafluoroisopropyl | H | CF3 |
| 7-446 | 2,6-difluorophenyl | Me | H | H | H | H | H | I | H | heptafluoroisopropyl | H | CF3 |
| 7-449 | 2-chloro-4-fluorophenyl | Me | H | H | H | H | H | I | H | heptafluoroisopropyl | H | CF3 |
| 7-460 | 2-chloropyridin-3-yl | Me | H | H | H | H | H | I | H | heptafluoroisopropyl | H | CF3 |
| 7-467 | 6-chloropyridin-3-yl | Me | H | H | H | H | H | I | H | heptafluoroisopropyl | H | CF3 |
| 7-502 | phenyl | Me | H | H | H | H | H | I | H | nonafluoro-2-butyl | H | CF3 |
| 7-504 | 3-fluorophenyl | Me | H | H | H | H | H | I | H | nonafluoro-2-butyl | H | CF3 |
| 7-505 | 4-fluorophenyl | Me | H | H | H | H | H | I | H | nonafluoro-2-butyl | H | CF3 |
| 7-522 | 3-cyanophenyl | Me | H | H | H | H | H | I | H | nonafluoro-2-butyl | H | CF3 |
| 7-523 | 4-cyanophenyl | Me | H | H | H | H | H | I | H | nonafluoro-2-butyl | H | CF3 |
| 7-538 | 2-chloropyridin-3-yl | Me | H | H | H | H | H | I | H | nonafluoro-2-butyl | H | CF3 |
| 7-580 | phenyl | Me | H | H | H | H | H | OCF3 | H | heptafluoroisopropyl | H | OCF3 |
| 7-611 | 2-chloropyridin-3-yl | Me | H | H | H | H | H | OCF3 | H | heptafluoroisopropyl | H | OCF3 |
| 7-636 | phenyl | Me | H | H | H | H | H | OCF3 | H | nonafluoro-2-butyl | H | OCF3 |
| 7-667 | 2-chloropyridin-3-yl | Me | H | H | H | H | H | OCF3 | H | nonafluoro-2-butyl | H | OCF3 |
| 7-692 | phenyl | Me | H | H | H | H | H | CF3 | H | heptafluoroisopropyl | H | OCF3 |
| 7-723 | 2-chloropyridin-3-yl | Me | H | H | H | H | H | CF3 | H | heptafluoroisopropyl | H | OCF3 |
| 7-748 | phenyl | Me | H | H | H | H | H | CF3 | H | nonafluoro-2-butyl | H | OCF3 |
| 7-779 | 2-chloropyridin-3-yl | Me | H | H | H | H | H | CF3 | H | nonafluoro-2-butyl | H | OCF3 |
| 7-804 | phenyl | Me | H | H | H | H | H | CF3 | H | heptafluoroisopropyl | H | CF3 |
| 7-824 | 3-cyanophenyl | Me | H | H | H | H | H | CF3 | H | heptafluoroisopropyl | H | CF3 |
| 7-825 | 4-cyanophenyl | Me | H | H | H | H | H | CF3 | H | heptafluoroisopropyl | H | CF3 |
| 7-840 | 2-chloropyridin-3-yl | Me | H | H | H | H | H | CF3 | H | heptafluoroisopropyl | H | CF3 |
| 7-841 | 2-bromopyridin-3-yl | Me | H | H | H | H | H | CF3 | H | heptafluoroisopropyl | H | CF3 |
| 7-872 | phenyl | Me | H | H | H | H | H | CF3 | H | nonafluoro-2-butyl | H | CF3 |
| 7-892 | 3-cyanophenyl | Me | H | H | H | H | H | CF3 | H | nonafluoro-2-butyl | H | CF3 |
| 7-893 | 4-cyanophenyl | Me | H | H | H | H | H | CF3 | H | nonafluoro-2-butyl | H | CF3 |
| 7-908 | 2-chloropyridin-3-yl | Me | H | H | H | H | H | CF3 | H | nonafluoro-2-butyl | H | CF3 |
| 7-940 | phenyl | Me | H | F | H | H | H | F | H | heptafluoroisopropyl | H | F |
| 7-941 | 3-cyanophenyl | Me | H | F | H | H | H | F | H | heptafluoroisopropyl | H | F |
| 7-942 | 4-cyanophenyl | Me | H | F | H | H | H | F | H | heptafluoroisopropyl | H | F |
| 7-943 | 2-chloropyridin-3-yl | Me | H | F | H | H | H | F | H | heptafluoroisopropyl | H | F |
| 7-944 | phenyl | Me | H | F | H | H | H | F | H | nonafluoro-2-butyl | H | F |
| 7-945 | 3-cyanophenyl | Me | H | F | H | H | H | F | H | nonafluoro-2-butyl | H | F |
| 7-946 | 4-cyanophenyl | Me | H | F | H | H | H | F | H | nonafluoro-2-butyl | H | F |
| 7-947 | 2-chloropyridin-3-yl | Me | H | F | H | H | H | F | H | nonafluoro-2-butyl | H | F |
| 7-948 | phenyl | Me | H | F | H | H | H | Cl | H | heptafluoroisopropyl | H | Cl |
| 7-968 | 3-cyanophenyl | Me | H | F | H | H | H | Cl | H | heptafluoroisopropyl | H | Cl |
| 7-969 | 4-cyanophenyl | Me | H | F | H | H | H | Cl | H | heptafluoroisopropyl | H | Cl |
| 7-984 | 2-chloropyridin-3-yl | Me | H | F | H | H | H | Cl | H | heptafluoroisopropyl | H | Cl |
| 7-1026 | phenyl | Me | H | F | H | H | H | Cl | H | nonafluoro-2-butyl | H | Cl |
| 7-1046 | 3-cyanophenyl | Me | H | F | H | H | H | Cl | H | nonafluoro-2-butyl | H | Cl |
| 7-1047 | 4-cyanophenyl | Me | H | F | H | H | H | Cl | H | nonafluoro-2-butyl | H | Cl |
| 7-1062 | 2-chloropyridin-3-yl | Me | H | F | H | H | H | Cl | H | nonafluoro-2-butyl | H | Cl |
| 7-1104 | phenyl | Me | H | F | H | H | H | Br | H | heptafluoroisopropyl | H | Br |
| 7-1105 | 2-fluorophenyl | Me | H | F | H | H | H | Br | H | heptafluoroisopropyl | H | Br |

TABLE 7-continued

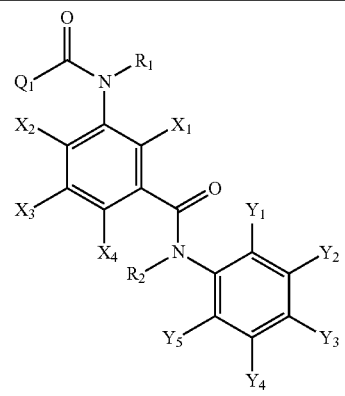

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-1106 | 3-fluorophenyl | Me | H | F | H | H | H | Br | H | heptafluoroisopropyl | H | Br |
| 7-1107 | 4-fluorophenyl | Me | H | F | H | H | H | Br | H | heptafluoroisopropyl | H | Br |
| 7-1124 | 3-cyanophenyl | Me | H | F | H | H | H | Br | H | heptafluoroisopropyl | H | Br |
| 7-1125 | 4-cyanophenyl | Me | H | F | H | H | H | Br | H | heptafluoroisopropyl | H | Br |
| 7-1126 | 2,6-difluorophenyl | Me | H | F | H | H | H | Br | H | heptafluoroisopropyl | H | Br |
| 7-1140 | 2-chloropyridin-3-yl | Me | H | F | H | H | H | Br | H | heptafluoroisopropyl | H | Br |
| 7-1147 | 6-chloropyridin-3-yl | Me | H | F | H | H | H | Br | H | heptafluoroisopropyl | H | Br |
| 7-1182 | phenyl | Me | H | F | H | H | H | Br | H | nonafluoro-2-butyl | H | Br |
| 7-1183 | 2-fluorophenyl | Me | H | F | H | H | H | Br | H | nonafluoro-2-butyl | H | Br |
| 7-1184 | 3-fluorophenyl | Me | H | F | H | H | H | Br | H | nonafluoro-2-butyl | H | Br |
| 7-1185 | 4-fluorophenyl | Me | H | F | H | H | H | Br | H | nonafluoro-2-butyl | H | Br |
| 7-1202 | 3-cyanophenyl | Me | H | F | H | H | H | Br | H | nonafluoro-2-butyl | H | Br |
| 7-1203 | 4-cyanophenyl | Me | H | F | H | H | H | Br | H | nonafluoro-2-butyl | H | Br |
| 7-1204 | 2,6-difluorophenyl | Me | H | F | H | H | H | Br | H | nonafluoro-2-butyl | H | Br |
| 7-1218 | 2-chloropyridin-3-yl | Me | H | F | H | H | H | Br | H | nonafluoro-2-butyl | H | Br |
| 7-1225 | 6-chloropyridin-3-yl | Me | H | F | H | H | H | Br | H | nonafluoro-2-butyl | H | Br |
| 7-1260 | phenyl | Me | H | F | H | H | H | I | H | heptafluoroisopropyl | H | I |
| 7-1261 | 2-fluorophenyl | Me | H | F | H | H | H | I | H | heptafluoroisopropyl | H | I |
| 7-1262 | 3-fluorophenyl | Me | H | F | H | H | H | I | H | heptafluoroisopropyl | H | I |
| 7-1263 | 4-fluorophenyl | Me | H | F | H | H | H | I | H | heptafluoroisopropyl | H | I |
| 7-1280 | 3-cyanophenyl | Me | H | F | H | H | H | I | H | heptafluoroisopropyl | H | I |
| 7-1281 | 4-cyanophenyl | Me | H | F | H | H | H | I | H | heptafluoroisopropyl | H | I |
| 7-1282 | 2,6-difluorophenyl | Me | H | F | H | H | H | I | H | heptafluoroisopropyl | H | I |
| 7-1296 | 2-chloropyridin-3-yl | Me | H | F | H | H | H | I | H | heptafluoroisopropyl | H | I |
| 7-1303 | 6-chloropyridin-3-yl | Me | H | F | H | H | H | I | H | heptafluoroisopropyl | H | I |
| 7-1338 | phenyl | Me | H | F | H | H | H | I | H | nonafluoro-2-butyl | H | I |
| 7-1339 | 2-fluorophenyl | Me | H | F | H | H | H | I | H | nonafluoro-2-butyl | H | I |
| 7-1340 | 3-fluorophenyl | Me | H | F | H | H | H | I | H | nonafluoro-2-butyl | H | I |
| 7-1341 | 4-fluorophenyl | Me | H | F | H | H | H | I | H | nonafluoro-2-butyl | H | I |
| 7-1358 | 3-cyanophenyl | Me | H | F | H | H | H | I | H | nonafluoro-2-butyl | H | I |
| 7-1359 | 4-cyanophenyl | Me | H | F | H | H | H | I | H | nonafluoro-2-butyl | H | I |
| 7-1360 | 2,6-difluorophenyl | Me | H | F | H | H | H | I | H | nonafluoro-2-butyl | H | I |
| 7-1374 | 2-chloropyridin-3-yl | Me | H | F | H | H | H | I | H | nonafluoro-2-butyl | H | I |
| 7-1381 | 6-chloropyridin-3-yl | Me | H | F | H | H | H | I | H | nonafluoro-2-butyl | H | I |
| 7-1416 | phenyl | Me | H | F | H | H | H | F | H | heptafluoroisopropyl | H | CF3 |
| 7-1417 | phenyl | Me | H | F | H | H | H | Cl | H | heptafluoroisopropyl | H | CF3 |
| 7-1428 | 3-iodophenyl | Me | H | F | H | H | H | Cl | H | pentafluoroethyl | H | CF3 |
| 7-1429 | 4-iodophenyl | Me | H | F | H | H | H | Cl | H | pentafluoroethyl | H | CF3 |
| 7-1431 | (3-trifluoromethyl)phenyl | Et | H | F | H | H | H | Cl | H | heptafluoroisopropyl | H | CF3 |
| 7-1436 | 2-cyanophenyl | Me | H | F | H | H | H | Cl | H | pentafluoroethyl | H | C2F5 |
| 7-1437 | 3-cyanophenyl | Me | H | F | H | H | H | Cl | H | heptafluoroisopropyl | H | CF3 |
| 7-1438 | 4-cyanophenyl | Me | H | F | H | H | H | Cl | H | heptafluoroisopropyl | H | CF3 |
| 7-1441 | 24-dichlorophenyl | Me | H | F | H | H | H | Cl | H | heptafluoroisopropyl | H | C2F5 |
| 7-1442 | 2-chloro-4-fluorophenyl | n-Pr | H | F | H | H | H | Cl | H | heptafluoroisopropyl | H | CF3 |
| 7-1445 | 2-bromo-4-chlorophenyl | Me | H | F | H | H | H | Cl | H | heptafluoroisopropyl | H | n-C3F7 |
| 7-1452 | 2-fluoropyridin-3-yl | Me | H | F | H | H | H | Cl | H | pentafluoroethyl | H | CF3 |
| 7-1453 | 2-chloropyridin-3-yl | Me | H | F | H | H | H | Cl | H | heptafluoroisopropyl | H | CF3 |
| 7-1459 | 6-fluoropyridin-3-yl | i-Pr | H | F | H | H | H | Cl | H | heptafluoroisopropyl | H | CF3 |
| 7-1486 | 5-fluoropyridin-3-yl | Me | H | F | H | H | H | Cl | H | heptafluoroisopropyl | H | C2F5 |
| 7-1468 | 5-bromopyridin-3-yl | Me | H | F | H | H | H | Cl | H | heptafluoroisopropyl | H | n-C3F7 |
| 7-1469 | 5-iodopyridin-3-yl | Me | H | F | H | H | H | Cl | H | heptafluoroisopropyl | H | i-C3F7 |
| 7-1471 | 5-nitropyridin-3-yl | Me | H | F | H | H | H | Cl | H | pentafluoroethyl | H | CF3 |
| 7-1473 | 4-fluoropyridin-3-yl | Me | H | F | H | H | H | Cl | H | pentafluoroethyl | H | CF3 |
| 7-1475 | 4-bromopyridin-3-yl | CH2CH=CH2 | H | F | H | H | H | Cl | H | heptafluoroisopropyl | H | n-C3F7 |
| 7-1476 | 4-iodopyridin-3-yl | Me | H | F | H | H | H | Cl | H | heptafluoroisopropyl | H | i-C3F7 |
| 7-1482 | pyridin-4-yl | CN | H | F | H | H | H | Cl | H | heptafluoroisopropyl | H | CF3 |
| 7-1494 | 4-cyanopyridin-2-yl | Me | H | F | H | H | H | Cl | H | pentafluoroethyl | H | CF3 |
| 7-1495 | phenyl | Me | H | F | H | H | H | F | H | nonafluoro-2-butyl | H | CF3 |

TABLE 7-continued

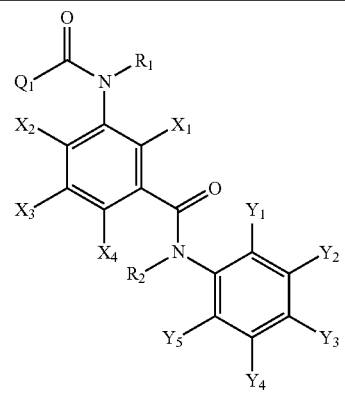

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 7-1496 | phenyl | Me | H | F | H | H | H | Cl | H | nonafluoro-2-butyl | H | CF3 |
| 7-1504 | 3-bromophenyl | CH2C≡CH | H | F | H | H | H | Cl | H | nonafluoro-2-butyl | H | CF3 |
| 7-1509 | (2-trifluoromethyl)phenyl | Me | H | F | H | H | H | Cl | H | nonafluoro-2-butyl | H | C2F5 |
| 7-1511 | (4-trifluoromethyl)phenyl | NH2 | H | F | H | H | H | Cl | H | nonafluoro-2-butyl | H | CF3 |
| 7-1516 | 3-cyanophenyl | Me | H | F | H | H | H | Cl | H | nonafluoro-2-butyl | H | CF3 |
| 7-1517 | 4-cyanophenyl | Me | H | F | H | H | H | Cl | H | nonafluoro-2-butyl | H | CF3 |
| 7-1524 | 2-bromo-4-chlorophenyl | C(O)OMe | H | F | H | H | H | Cl | H | nonafluoro-2-butyl | H | CF3 |
| 7-1526 | 2-chloro-4-nitrophenyl | Me | H | F | H | H | H | Cl | H | nonafluoro-2-butyl | H | i-C3F7 |
| 7-1532 | 2-chloropyridin-3-yl | Me | H | F | H | H | H | Cl | H | nonafluoro-2-butyl | H | CF3 |
| 7-1545 | 5-fluoropyridin-3-yl | C(O)OEt | H | F | H | H | H | Cl | H | nonafluoro-2-butyl | H | C2F5 |
| 7-1547 | 5-bromopyridin-3-yl | Me | H | F | H | H | H | Cl | H | nonafluoro-2-butyl | H | n-C3F7 |
| 7-1548 | 5-iodopyridin-3-yl | Me | H | F | H | H | H | Cl | H | nonafluoro-2-butyl | H | i-C3F7 |
| 7-1552 | 4-fluoropyridin-3-yl | Me | H | F | H | H | H | Cl | H | nonafluoro-2-butyl | H | C2F5 |
| 7-1554 | 4-bromopyridin-3-yl | C(O)C(O)Me | H | F | H | H | H | Cl | H | nonafluoro-2-butyl | H | CF3 |
| 7-1556 | 4-(trifluoromethyl)pyridin-3-yl | Me | H | F | H | H | H | Cl | H | nonafluoro-2-butyl | H | n-C3F7 |
| 7-1557 | 4-nitropyridin-3-yl | C(O)C(O)Et | H | F | H | H | H | Cl | H | nonafluoro-2-butyl | H | i-C3F7 |
| 7-1571 | 5-iodopyridin-2-yl | C(O)Me | H | F | H | H | H | Cl | H | nonafluoro-2-butyl | H | CF3 |
| 7-1573 | 4-cyanopyridin-2-yl | C(O)Et | H | F | H | H | H | Cl | H | nonafluoro-2-butyl | H | C2F5 |
| 7-1574 | phenyl | Me | H | F | H | H | H | Br | H | heptafluoroisopropyl | H | CF3 |
| 7-1575 | 2-fluorophenyl | Me | H | F | H | H | H | Br | H | heptafluoroisopropyl | H | CF3 |
| 7-1576 | 3-fluorophenyl | Me | H | F | H | H | H | Br | H | heptafluoroisopropyl | H | CF3 |
| 7-1577 | 4-fluorophenyl | Me | H | F | H | H | H | Br | H | heptafluoroisopropyl | H | CF3 |
| 7-1578 | 2-chlorophenyl | Me | H | F | H | H | H | Br | H | heptafluoroisopropyl | H | CF3 |
| 7-1579 | 3-chlorophenyl | Me | H | F | H | H | H | Br | H | heptafluoroisopropyl | H | CF3 |
| 7-1580 | 4-chlorophenyl | Me | H | F | H | H | H | Br | H | heptafluoroisopropyl | H | CF3 |
| 7-1581 | 2-bromophenyl | Me | H | F | H | H | H | Br | H | heptafluoroisopropyl | H | CF3 |
| 7-1582 | 3-bromophenyl | Me | H | F | H | H | H | Br | H | heptafluoroisopropyl | H | CF3 |
| 7-1583 | 4-bromophenyl | Me | H | F | H | H | H | Br | H | heptafluoroisopropyl | H | CF3 |
| 7-1584 | 2-iodophenyl | Me | H | F | H | H | H | Br | H | heptafluoroisopropyl | H | CF3 |
| 7-1585 | 3-iodophenyl | Me | H | F | H | H | H | Br | H | heptafluoroisopropyl | H | CF3 |
| 7-1586 | 4-iodophenyl | Me | H | F | H | H | H | Br | H | heptafluoroisopropyl | H | CF3 |
| 7-1587 | (2-trifluoromethyl)phenyl | Me | H | F | H | H | H | Br | H | heptafluoroisopropyl | H | CF3 |
| 7-1588 | (3-trifluoromethyl)phenyl | S(O)2Me | H | F | H | H | H | Br | H | heptafluoroisopropyl | H | CF3 |
| 7-1589 | (4-trifluoromethyl)phenyl | Me | H | F | H | H | H | Br | H | heptafluoroisopropyl | H | CF3 |
| 7-1590 | 2-nitrophenyl | Me | H | F | H | H | H | Br | H | heptafluoroisopropyl | H | CF3 |
| 7-1591 | 3-nitrophenyl | Me | H | F | H | H | H | Br | H | heptafluoroisopropyl | H | CF3 |
| 7-1592 | 4-nitrophenyl | Me | H | F | H | H | H | Br | H | heptafluoroisopropyl | H | CF3 |
| 7-1593 | 2-cyanophenyl | Me | H | F | H | H | H | Br | H | heptafluoroisopropyl | H | CF3 |
| 7-1594 | 3-cyanophenyl | Me | H | F | H | H | H | Br | H | heptafluoroisopropyl | H | CF3 |
| 7-1595 | 4-cyanophenyl | Me | H | F | H | H | H | Br | H | heptafluoroisopropyl | H | CF3 |
| 7-1596 | 2,6-difluorophenyl | Me | H | F | H | H | H | Br | H | heptafluoroisopropyl | H | CF3 |
| 7-1597 | 3,4-dichlorophenyl | Me- | H | F | H | H | H | Br | H | heptafluoroisopropyl | H | CF3 |
| 7-1598 | 2,4-dichlorophenyl | Me | H | F | H | H | H | Br | H | heptafluoroisopropyl | H | CF3 |
| 7-1599 | 2-chloro-4-fluorophenyl | Me | H | F | H | H | H | Br | H | heptafluoroisopropyl | H | CF3 |
| 7-1600 | 2-chloro-4,5-difluorophenyl | Me | H | F | H | H | H | Br | H | heptafluoroisopropyl | H | CF3 |
| 7-1601 | 4-bromo-2-chlorophenyl | Me | H | F | H | H | H | Br | H | heptafluoroisopropyl | H | CF3 |
| 7-1602 | 2-bromo-4-chlorophenyl | Me | H | F | H | H | H | Br | H | heptafluoroisopropyl | H | CF3 |
| 7-1603 | 2-bromo-4-fluorophenyl | Me | H | F | H | H | H | Br | H | heptafluoroisopropyl | H | CF3 |
| 7-1604 | 2-chloro-4-nitrophenyl | S(O)2Et | H | F | H | H | H | Br | H | heptafluoroisopropyl | H | CF3 |
| 7-1605 | 3,5-dicyanophenyl | Me | H | F | H | H | H | Br | H | heptafluoroisopropyl | H | CF3 |
| 7-1606 | 4-cyano-2-fluorophenyl | Me | H | F | H | H | H | Br | H | heptafluoroisopropyl | H | CF3 |
| 7-1607 | 2-chloro-4-cyanophenyl | Me | H | F | H | H | H | Br | H | heptafluoroisopropyl | H | CF3 |
| 7-1608 | pyridin-3-yl | Me | H | F | H | H | H | Br | H | heptafluoroisopropyl | H | CF3 |
| 7-1609 | 2-fluoropyridin-3-yl | Me | H | F | H | H | H | Br | H | heptafluoroisopropyl | H | CF3 |
| 7-1610 | 2-chloropyridin-3-yl | Me | H | F | H | H | H | Br | H | heptafluoroisopropyl | H | CF3 |
| 7-1611 | 2-bromopyridin-3-yl | Me | H | F | H | H | H | Br | H | heptafluoroisopropyl | H | CF3 |
| 7-1612 | 2-iodopyridin-3-yl | Me | H | F | H | H | H | Br | H | heptafluoroisopropyl | H | CF3 |
| 7-1613 | 2-(trifluoromethyl)pyridin-3-yl | Me | H | F | H | H | H | Br | H | heptafluoroisopropyl | H | CF3 |

TABLE 7-continued

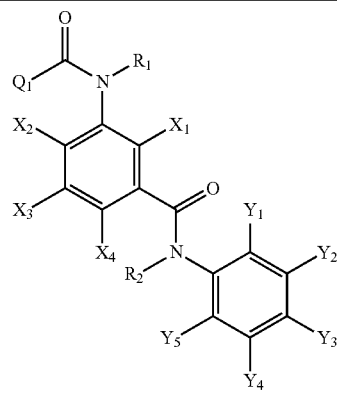

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 7-1614 | 2-nitropyridin-3-yl | Me | H | F | H | H | H | Br | H | heptafluoroisopropyl | H | CF3 |
| 7-1615 | 2-cyanopyridin-3-yl | Me | H | F | H | H | H | Br | H | heptafluoroisopropyl | H | CF3 |
| 7-1616 | 6-fluoropyridin-3-yl | Me | H | F | H | H | H | Br | H | heptafluoroisopropyl | H | CF3 |
| 7-1617 | 6-chloropyridin-3-yl | Me | H | F | H | H | H | Br | H | heptafluoroisopropyl | H | CF3 |
| 7-1618 | 6-bromopyridin-3-yl | Me | H | F | H | H | H | Br | H | heptafluoroisopropyl | H | CF3 |
| 7-1619 | 6-iodopyridin-3-yl | Me | H | F | H | H | H | Br | H | heptafluoroisopropyl | H | CF3 |
| 7-1620 | 6-(trifluoromethyl)pyridin-3-yl | Me | H | F | H | H | H | Br | H | heptafluoroisopropyl | H | CF3 |
| 7-1621 | 6-nitropyridin-3-yl | CH2Ph | H | F | H | H | H | Br | H | heptafluoroisopropyl | H | CF3 |
| 7-1622 | 6-cyanopyridin-3-yl | Me | H | F | H | H | H | Br | H | heptafluoroisopropyl | H | CF3 |
| 7-1623 | 5-fluoropyridin-3-yl | Me | H | F | H | H | H | Br | H | heptafluoroisopropyl | H | CF3 |
| 7-1624 | 5-chloropyridin-3-yl | Me | H | F | H | H | H | Br | H | heptafluoroisopropyl | H | CF3 |
| 7-1625 | 5-bromopyridin-3-yl | Me | H | F | H | H | H | Br | H | heptafluoroisopropyl | H | CF3 |
| 7-1626 | 5-iodopyridin-3-yl | Me | H | F | H | H | H | Br | H | heptafluoroisopropyl | H | CF3 |
| 7-1627 | 5-(trifluoromethyl)pyridin-3-yl | Me | H | F | H | H | H | Br | H | heptafluoroisopropyl | H | CF3 |
| 7-1628 | 5-nitropyridin-3-yl | Me | H | F | H | H | H | Br | H | heptafluoroisopropyl | H | CF3 |
| 7-1629 | 5-cyanopyridin-3-yl | Me | H | F | H | H | H | Br | H | heptafluoroisopropyl | H | CF3 |
| 7-1630 | 4-fluoropyridin-3-yl | CH2(3-Py) | H | F | H | H | H | Br | H | heptafluoroisopropyl | H | CF3 |
| 7-1631 | 4-chloropyridin-3-yl | Me | H | F | H | H | H | Br | H | heptafluoroisopropyl | H | CF3 |
| 7-1632 | 4-bromopyridin-3-yl | Me | H | F | H | H | H | Br | H | heptafluoroisopropyl | H | CF3 |
| 7-1633 | 4-iodopyridin-3-yl | Me | H | F | H | H | H | Br | H | heptafluoroisopropyl | H | CF3 |
| 7-1634 | 4-(trifluoromethyl)pyridin-3-yl | Me | H | F | H | H | H | Br | H | heptafluoroisopropyl | H | CF3 |
| 7-1635 | 4-nitropyridin-3-yl | Me | H | F | H | H | H | Br | H | heptafluoroisopropyl | H | CF3 |
| 7-1636 | 4-cyanopyridin-3-yl | Me | H | F | H | H | H | Br | H | heptafluoroisopropyl | H | CF3 |
| 7-1637 | 2,6-dichloropyridin-3-yl | Me | H | F | H | H | H | Br | H | heptafluoroisopropyl | H | CF3 |
| 7-1638 | pyridin-3-yl N-oxide | Me | H | F | H | H | H | Br | H | heptafluoroisopropyl | H | CF3 |
| 7-1639 | pyridin-4-yl | Me | H | F | H | H | H | Br | H | heptafluoroisopropyl | H | CF3 |
| 7-1640 | 2-chloropyridin-4-yl | Me | H | F | H | H | H | Br | H | heptafluoroisopropyl | H | CF3 |
| 7-1641 | 3-bromopyridin-4--yl | Me | H | F | H | H | H | Br | H | heptafluoroisopropyl | H | CF3 |
| 7-1642 | 3,5-dichloropyridin-4-yl | Me | H | F | H | H | H | Br | H | heptafluoroisopropyl | H | CF3 |
| 7-1643 | 3-(trifluoromethyl)pyridin-4-yl | Me | H | F | H | H | H | Br | H | heptafluoroisopropyl | H | CF3 |
| 7-1644 | 2,6-dicyanopyridin-4-yl | Me | H | F | H | H | H | Br | H | heptafluoroisopropyl | H | CF3 |
| 7-1645 | pyridin-4-yl N-oxide | Me | H | F | H | H | H | Br | H | heptafluoroisopropyl | H | CF3 |
| 7-1646 | pyridin-2-yl | Me | H | F | H | H | H | Br | H | heptafluoroisopropyl | H | CF3 |
| 7-1647 | 3-chloropyridin-2-yl | Me | H | F | H | H | H | Br | H | heptafluoroisopropyl | H | CF3 |
| 7-1648 | 4-bromopyridin-2-yl | Me | H | F | H | H | H | Br | H | heptafluoroisopropyl | H | CF3 |
| 7-1649 | 5-iodopyridin-2-yl | Me | H | F | H | H | H | Br | H | heptafluoroisopropyl | H | CF3 |
| 7-1650 | 6-chloropyridin-2-yl | Me | H | F | H | H | H | Br | H | heptafluoroisopropyl | H | CF3 |
| 7-1651 | 4-cyanopyridin-2-yl | CH2(3-Py—N-oxide) | H | F | H | H | H | Br | H | heptafluoroisopropyl | H | CF3 |
| 7-1652 | phenyl | Me | H | F | H | H | H | Br | H | nonafluoro-2-butyl | H | CF3 |
| 7-1653 | 2-fluorophenyl | Me | H | F | H | H | H | Br | H | nonafluoro-2-butyl | H | CF3 |
| 7-1654 | 3-fluorophenyl | Me | H | F | H | H | H | Br | H | nonafluoro-2-butyl | H | CF3 |
| 7-1655 | 4-fluorophenyl | Me | H | F | H | H | H | Br | H | nonafluoro-2-butyl | H | CF3 |
| 7-1656 | 2-chlorophenyl | Me | H | F | H | H | H | Br | H | nonafluoro-2-butyl | H | CF3 |
| 7-1657 | 3-chlorophenyl | Me | H | F | H | H | H | Br | H | nonafluoro-2-butyl | H | CF3 |
| 7-1658 | 4-chlorophenyl | Me | H | F | H | H | H | Br | H | nonafluoro-2-butyl | H | CF3 |
| 7-1659 | 2-bromophenyl | Me | H | F | H | H | H | Br | H | nonafluoro-2-butyl | H | CF3 |
| 7-1660 | 3-bromophenyl | Me | H | F | H | H | H | Br | H | nonafluoro-2-butyl | H | CF3 |
| 7-1661 | 4-bromophenyl | Me | H | F | H | H | H | Br | H | nonafluoro-2-butyl | H | CF3 |
| 7-1662 | 2-iodophenyl | Me | H | F | H | H | H | Br | H | nonafluoro-2-butyl | H | CF3 |
| 7-1663 | 3-iodophenyl | Me | H | F | H | H | H | Br | H | nonafluoro-2-butyl | H | CF3 |
| 7-1664 | 4-iodophenyl | Me | H | F | H | H | H | Br | H | nonafluoro-2-butyl | H | CF3 |
| 7-1665 | (2-trifluoromethyl)phenyl | Me | H | F | H | H | H | Br | H | nonafluoro-2-butyl | H | CF3 |
| 7-1666 | (3-trifluoromethyl)phenyl | Me | H | F | H | H | H | Br | H | nonafluoro-2-butyl | H | CF3 |
| 7-1667 | (4-trifluoromethyl)phenyl | Me | H | F | H | H | H | Br | H | nonafluoro-2-butyl | H | CF3 |
| 7-1668 | 2-nitrophenyl | Me | H | F | H | H | H | Br | H | nonafluoro-2-butyl | H | CF3 |
| 7-1669 | 3-nitrophenyl | Me | H | F | H | H | H | Br | H | nonafluoro-2-butyl | H | CF3 |
| 7-1670 | 4-nitrophenyl | Me | H | F | H | H | H | Br | H | nonafluoro-2-butyl | H | CF3 |

TABLE 7-continued

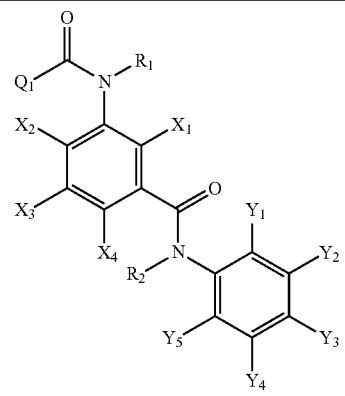

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-1671 | 2-cyanophenyl | Me | H | F | H | H | H | Br | H | nonafluoro-2-butyl | H | CF3 |
| 7-1672 | 3-cyanophenyl | Me | H | F | H | H | H | Br | H | nonafluoro-2-butyl | H | CF3 |
| 7-1673 | 4-cyanophenyl | Me | H | F | H | H | H | Br | H | nonafluoro-2-butyl | H | CF3 |
| 7-1674 | 2,6-difluorophenyl | Me | H | F | H | H | H | Br | H | nonafluoro-2-butyl | H | CF3 |
| 7-1675 | 3,4-dichlorophenyl | Me | H | F | H | H | H | Br | H | nonafluoro-2-butyl | H | CF3 |
| 7-1676 | 2,4-dichlorophenyl | Me | H | F | H | H | H | Br | H | nonafluoro-2-butyl | H | CF3 |
| 7-1677 | 2-chloro-4-fluorophenyl | Me | H | F | H | H | H | Br | H | nonafluoro-2-butyl | H | CF3 |
| 7-1878 | 2-chloro-4,5-difluorophenyl | Me | H | F | H | H | H | Br | H | nonafluoro-2-butyl | H | CF3 |
| 7-1679 | 4-bromo-2-chlorophenyl | Et | H | F | H | H | H | Br | H | nonafluoro-2-butyl | H | CF3 |
| 7-1680 | 2-bromo-4-chlorophenyl | Me | H | F | H | H | H | Br | H | nonafluoro-2-butyl | H | CF3 |
| 7-1681 | 2-bromo-4-fluorophenyl | Me | H | F | H | H | H | Br | H | nonafluoro-2-butyl | H | CF3 |
| 7-1682 | 2-chloro-4-nitrophenyl | Me | H | F | H | H | H | Br | H | nonafluoro-2-butyl | H | CF3 |
| 7-1683 | 3,5-dicyanophenyl | Me | H | F | H | H | H | Br | H | nonafluoro-2-butyl | H | CF3 |
| 7-1684 | 4-cyano-2-fluorophenyl | Me | H | F | H | H | H | Br | H | nonafluoro-2-butyl | H | CF3 |
| 7-1685 | 2-chloro-4-cyanophenyl | Me | H | F | H | H | H | Br | H | nonafluoro-2-butyl | H | CF3 |
| 7-1686 | pyridin-3-yl | Me | H | F | H | H | H | Br | H | nonafluoro-2-butyl | H | CF3 |
| 7-1687 | 2-fluoropyridin-3-yl | Me | H | F | H | H | H | Br | H | nonafluoro-2-butyl | H | CF3 |
| 7-1688 | 2-chloropyridin-3-yl | Me | H | F | H | H | H | Br | H | nonafluoro-2-butyl | H | CF3 |
| 7-1689 | 2-bromopyridin-3-yl | Me | H | F | H | H | H | Br | H | nonafluoro-2-butyl | H | CF3 |
| 7-1690 | 2-iodopyridin-3-yl | Me | H | F | H | H | H | Br | H | nonafluoro-2-butyl | H | CF3 |
| 7-1691 | 2-(trifluoromethyl)pyridin-3-yl | Me | H | F | H | H | H | Br | H | nonafluoro-2-butyl | H | CF3 |
| 7-1692 | 2-nitropyridin-3-yl | Me | H | F | H | H | H | Br | H | nonafluoro-2-butyl | H | CF3 |
| 7-1693 | 2-cyanopyridin-3-yl | Me | H | F | H | H | H | Br | H | nonafluoro-2-butyl | H | CF3 |
| 7-1694 | 6-fluoropyridin-3-yl | Me | H | F | H | H | H | Br | H | nonafluoro-2-butyl | H | CF3 |
| 7-1695 | 6-chloropyridin-3-yl | Me | H | F | H | H | H | Br | H | nonafluoro-2-butyl | H | CF3 |
| 7-1696 | 6-bromopyridin-3-yl | Me | H | F | H | H | H | Br | H | nonafluoro-2-butyl | H | CF3 |
| 7-1697 | 6-iodopyridin-3-yl | Me | H | F | H | H | H | Br | H | nonafluoro-2-butyl | H | CF3 |
| 7-1698 | 6-(trifluoromethyl)pyridin-3-yl | Me | H | F | H | H | H | Br | H | nonafluoro-2-butyl | H | CF3 |
| 7-1699 | 6-nitropyridin-3-yl | Me | H | F | H | H | H | Br | H | nonafluoro-2-butyl | H | CF3 |
| 7-1700 | 6-cyanopyridin-3-yl | Me | H | F | H | H | H | Br | H | nonafluoro-2-butyl | H | CF3 |
| 7-1701 | 5-fluoropyridin-3-yl | Me | H | F | H | H | H | Br | H | nonafluoro-2-butyl | H | CF3 |
| 7-1702 | 5-chloropyridin-3-yl | Me | H | F | H | H | H | Br | H | nonafluoro-2-butyl | H | CF3 |
| 7-1703 | 5-bromopyridin-3-yl | Me | H | F | H | H | H | Br | H | nonafluoro-2-butyl | H | CF3 |
| 7-1704 | 5-iodopyridin-3-yl | Me | H | F | H | H | H | Br | H | nonafluoro-2-butyl | H | CF3 |
| 7-1705 | 5-(trifluoromethyl)pyridin-3-yl | CN | H | F | H | H | H | Br | H | nonafluoro-2-butyl | H | CF3 |
| 7-1706 | 5-nitropyridin-3-yl | Me | H | F | H | H | H | Br | H | nonafluoro-2-butyl | H | CF3 |
| 7-1707 | 5-cyanopyridin-3-yl | Me | H | F | H | H | H | Br | H | nonafluoro-2-butyl | H | CF3 |
| 7-1708 | 4-fluoropyridin-3-yl | Me | H | F | H | H | H | Br | H | nonafluoro-2-butyl | H | CF3 |
| 7-1709 | 4-chloropyridin-3-yl | Me | H | F | H | H | H | Br | H | nonafluoro-2-butyl | H | CF3 |
| 7-1710 | 4-bromopyridin-3-yl | Me | H | F | H | H | H | Br | H | nonafluoro-2-butyl | H | CF3 |
| 7-1711 | 4-iodopyridin-3-yl | Me | H | F | H | H | H | Br | H | nonafluoro-2-butyl | H | CF3 |
| 7-1712 | 4-(trifluoromethyl)pyridin-3-yl | Me | H | F | H | H | H | Br | H | nonafluoro-2-butyl | H | CF3 |
| 7-1713 | 4-nitropyridin-3-yl | Me | H | F | H | H | H | Br | H | nonafluoro-2-butyl | H | CF3 |
| 7-1714 | 4-cyanopyridin-3-yl | Me | H | F | H | H | H | Br | H | nonafluoro-2-butyl | H | CF3 |
| 7-1715 | 2,6-dichloropyridin-3-yl | Me | H | F | H | H | H | Br | H | nonafluoro-2-butyl | H | CF3 |
| 7-1716 | pyridin-3-yl N-oxide | Me | H | F | H | H | H | Br | H | nonafluoro-2-butyl | H | CF3 |
| 7-1717 | pyridin-4-yl | Me | H | F | H | H | H | Br | H | nonafluoro-2-butyl | H | CF3 |
| 7-1718 | 2-chloropyridin-4-yl | Me | H | F | H | H | H | Br | H | nonafluoro-2-butyl | H | CF3 |
| 7-1719 | 3-bromopyridin-4-yl | Me | H | F | H | H | H | Br | H | nonafluoro-2-butyl | H | CF3 |
| 7-1720 | 3,5-dichloropyridin-4-yl | Me | H | F | H | H | H | Br | H | nonafluoro-2-butyl | H | CF3 |
| 7-1721 | 3-(trifluoromethyl)pyridin-4-yl | Me | H | F | H | H | H | Br | H | nonafluoro-2-butyl | H | CF3 |
| 7-1722 | 2,6-dicyanopyridin-4-yl | Me | H | F | H | H | H | Br | H | nonafluoro-2-butyl | H | CF3 |
| 7-1723 | pyridin-4-yl N-oxide | Me | H | F | H | H | H | Br | H | nonafluoro-2-butyl | H | CF3 |
| 7-1724 | pyridin-2-yl | Me | H | F | H | H | H | Br | H | nonafluoro-2-butyl | H | CF3 |
| 7-1725 | 3-chloropyridin-2-yl | Me | H | F | H | H | H | Br | H | nonafluoro-2-butyl | H | CF3 |
| 7-1726 | 4-bromopyridin-2-yl | Me | H | F | H | H | H | Br | H | nonafluoro-2-butyl | H | CF3 |
| 7-1727 | 5-iodopyridin-2-yl | Me | H | F | H | H | H | Br | H | nonafluoro-2-butyl | H | CF3 |
| 7-1728 | 6-chloropyridin-2-yl | Me | H | F | H | H | H | Br | H | nonafluoro-2-butyl | H | CF3 |

TABLE 7-continued

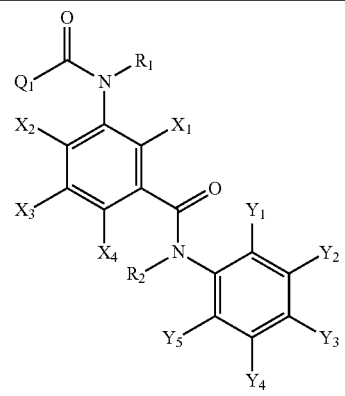

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-1729 | 4-cyanopyridin-2-yl | Me | H | F | H | H | H | Br | H | nonafluoro-2-butyl | H | CF3 |
| 7-1730 | phenyl | Me | H | F | H | H | H | I | H | heptafluoroisopropyl | H | CF3 |
| 7-1731 | 2-fluorophenyl | Me | H | F | H | H | H | I | H | heptafluoroisopropyl | H | CF3 |
| 7-1732 | 3-fluorophenyl | Me | H | F | H | H | H | I | H | heptafluoroisopropyl | H | CF3 |
| 7-1733 | 4-fluorophenyl | Me | H | F | H | H | H | I | H | heptafluoroisopropyl | H | CF3 |
| 7-1734 | 2-chlorophenyl | Me | H | F | H | H | H | I | H | heptafluoroisopropyl | H | CF3 |
| 7-1735 | 3-chlorophenyl | Me | H | F | H | H | H | I | H | heptafluoroisopropyl | H | CF3 |
| 7-1736 | 4-chlorophenyl | Me | H | F | H | H | H | I | H | heptafluoroisopropyl | H | CF3 |
| 7-1737 | 2-bromophenyl | Me | H | F | H | H | H | I | H | heptafluoroisopropyl | H | CF3 |
| 7-1738 | 3-bromophenyl | Me | H | F | H | H | H | I | H | heptafluoroisopropyl | H | CF3 |
| 7-1739 | 4-bromophenyl | Me | H | F | H | H | H | I | H | heptafluoroisopropyl | H | CF3 |
| 7-1740 | 2-iodophenyl | Me | H | F | H | H | H | I | H | heptafluoroisopropyl | H | CF3 |
| 7-1741 | 3-iodophenyl | Me | H | F | H | H | H | I | H | heptafluoroisopropyl | H | CF3 |
| 7-1742 | 4-iodophenyl | Me | H | F | H | H | H | I | H | heptafluoroisopropyl | H | CF3 |
| 7-1743 | (2-trifluoromethyl)phenyl | Me | H | F | H | H | H | I | H | heptafluoroisopropyl | H | CF3 |
| 7-1744 | (3-trifluoromethyl)phenyl | Me | H | F | H | H | H | I | H | heptafluoroisopropyl | H | CF3 |
| 7-1745 | (4-trifluoromethyl)phenyl | Me | H | F | H | H | H | I | H | heptafluoroisopropyl | H | CF3 |
| 7-1746 | 2-nitrophenyl | Me | H | F | H | H | H | I | H | heptafluoroisopropyl | H | CF3 |
| 7-1747 | 3-nitrophenyl | Me | H | F | H | H | H | I | H | heptafluoroisopropyl | H | CF3 |
| 7-1748 | 4-nitrophenyl | Me | H | F | H | H | H | I | H | heptafluoroisopropyl | H | CF3 |
| 7-1749 | 2-cyanophenyl | Me | H | F | H | H | H | I | H | heptafluoroisopropyl | H | CF3 |
| 7-1750 | 3-cyanophenyl | Me | H | F | H | H | H | I | H | heptafluoroisopropyl | H | CF3 |
| 7-1751 | 4-cyanophenyl | Me | H | F | H | H | H | I | H | heptafluoroisopropyl | H | CF3 |
| 7-1752 | 2,6-difluorophenyl | Me | H | F | H | H | H | I | H | heptafluoroisopropyl | H | CF3 |
| 7-1753 | 3,4-dichlorophenyl | Me | H | F | H | H | H | I | H | heptafluoroisopropyl | H | CF3 |
| 7-1754 | 2,4-dichlorophenyl | Me | H | F | H | H | H | I | H | heptafluoroisopropyl | H | CF3 |
| 7-1755 | 2-chloro-4-fluorophenyl | Me | H | F | H | H | H | I | H | heptafluoroisopropyl | H | CF3 |
| 7-1756 | 2-chloro-4,5-difluorophenyl | Me | H | F | H | H | H | I | H | heptafluoroisopropyl | H | CF3 |
| 7-1757 | 4-bromo-2-chlorophenyl | Me | H | F | H | H | H | I | H | heptafluoroisopropyl | H | CF3 |
| 7-1758 | 2-bromo-4-chlorophenyl | Me | H | F | H | H | H | I | H | heptafluoroisopropyl | H | CF3 |
| 7-1759 | 2-bromo-4-fluorophenyl | Me | H | F | H | H | H | I | H | heptafluoroisopropyl | H | CF3 |
| 7-1760 | 2-chloro-4-nitrophenyl | Me | H | F | H | H | H | I | H | heptafluoroisopropyl | H | CF3 |
| 7-1761 | 3,5-dicyanophenyl | Me | H | F | H | H | H | I | H | heptafluoroisopropyl | H | CF3 |
| 7-1762 | 4-cyano-2-fluorophenyl | Me | H | F | H | H | H | I | H | heptafluoroisopropyl | H | CF3 |
| 7-1763 | 2-chloro-4-cyanophenyl | Me | H | F | H | H | H | I | H | heptafluoroisopropyl | H | CF3 |
| 7-1764 | pyridin-3-yl | Me | H | F | H | H | H | I | H | heptafluoroisopropyl | H | CF3 |
| 7-1765 | 2-fluoropyridin-3-yl | Me | H | F | H | H | H | I | H | heptafluoroisopropyl | H | CF3 |
| 7-1766 | 2-chloropyridin-3-yl | Me | H | F | H | H | H | I | H | heptafluoroisopropyl | H | CF3 |
| 7-1767 | 2-bromopyridin-3-yl | Me | H | F | H | H | H | I | H | heptafluoroisopropyl | H | CF3 |
| 7-1768 | 2-iodopyridin-3-yl | Me | H | F | H | H | H | I | H | heptafluoroisopropyl | H | CF3 |
| 7-1769 | 2-(trifluoromethyl)pyridin-3-yl | Me | H | F | H | H | H | I | H | heptafluoroisopropyl | H | CF3 |
| 7-1770 | 2-nitropyridin-3-yl | Me | H | F | H | H | H | I | H | heptafluoroisopropyl | H | CF3 |
| 7-1771 | 2-cyanopyridin-3-yl | Me | H | F | H | H | H | I | H | heptafluoroisopropyl | H | CF3 |
| 7-1772 | 6-fluoropyridin-3-yl | Me | H | F | H | H | H | I | H | heptafluoroisopropyl | H | CF3 |
| 7-1773 | 6-chloropyridin-3-yl | Me | H | F | H | H | H | I | H | heptafluoroisopropyl | H | CF3 |
| 7-1774 | 6-bromopyridin-3-yl | Me | H | F | H | H | H | I | H | heptafluoroisopropyl | H | CF3 |
| 7-1775 | 6-iodopyridin-3-yl | Me | H | F | H | H | H | I | H | heptafluoroisopropyl | H | CF3 |
| 7-1776 | 6-(trifluoromethyl)pyridin-3-yl | Me | H | F | H | H | H | I | H | heptafluoroisopropyl | H | CF3 |
| 7-1777 | 6-nitropyridin-3-yl | Me | H | F | H | H | H | I | H | heptafluoroisopropyl | H | CF3 |
| 7-1778 | 6-cyanopyridin-3-yl | Me | H | F | H | H | H | I | H | heptafluoroisopropyl | H | CF3 |
| 7-1779 | 5-fluoropyridin-3-yl | C(O)Me | H | F | H | H | H | I | H | heptafluoroisopropyl | H | CF3 |
| 7-1780 | 5-chloropyridin-3-yl | Me | H | F | H | H | H | I | H | heptafluoroisopropyl | H | CF3 |
| 7-1781 | 5-bromopyridin-3-yl | Me | H | F | H | H | H | I | H | heptafluoroisopropyl | H | CF3 |
| 7-1782 | 5-iodopyridin-3-yl | Me | H | F | H | H | H | I | H | heptafluoroisopropyl | H | CF3 |
| 7-1783 | 5-(trifluoromethyl)pyridin-3-yl | Me | H | F | H | H | H | I | H | heptafluoroisopropyl | H | CF3 |
| 7-1784 | 5-nitropyridin-3-yl | Me | H | F | H | H | H | I | H | heptafluoroisopropyl | H | CF3 |
| 7-1785 | 5-cyanopyridin-3-yl | Me | H | F | H | H | H | I | H | heptafluoroisopropyl | H | CF3 |
| 7-1786 | 4-fluoropyridin-3-yl | Me | H | F | H | H | H | I | H | heptafluoroisopropyl | H | CF3 |

TABLE 7-continued

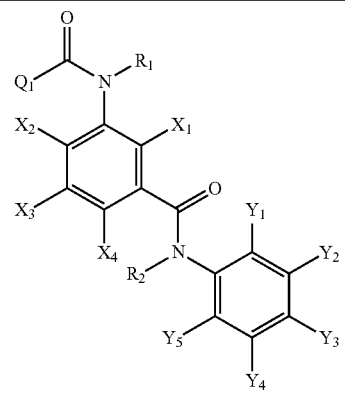

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 7-1787 | 4-chloropyridin-3-yl | Me | H | F | H | H | H | I | H | heptafluoroisopropyl | H | CF3 |
| 7-1788 | 4-bromopyridin-3-yl | Me | H | F | H | H | H | I | H | heptafluoroisopropyl | H | CF3 |
| 7-1789 | 4-iodopyridin-3-yl | Me | H | F | H | H | H | I | H | heptafluoroisopropyl | H | CF3 |
| 7-1790 | 4-(trifluoromethyl)pyridin-3-yl | Me | H | F | H | H | H | I | H | heptafluoroisopropyl | H | CF3 |
| 7-1791 | 4-nitropyridin-3-yl | Me | H | F | H | H | H | I | H | heptafluoroisopropyl | H | CF3 |
| 7-1792 | 4-cyanopyridin-3-yl | Me | H | F | H | H | H | I | H | heptafluoroisopropyl | H | CF3 |
| 7-1793 | 2,6-dichloropyridin-3-yl | Me | H | F | H | H | H | I | H | heptafluoroisopropyl | H | CF3 |
| 7-1794 | pyridin-3-yl N-oxide | Me | H | F | H | H | H | I | H | heptafluoroisopropyl | H | CF3 |
| 7-1795 | pyridin-4-yl | Me | H | F | H | H | H | I | H | heptafluoroisopropyl | H | CF3 |
| 7-1796 | 2-chloropyridin-4-yl | Me | H | F | H | H | H | I | H | heptafluoroisopropyl | H | CF3 |
| 7-1797 | 3-bromopyridin-4-yl | Me | H | F | H | H | H | I | H | heptafluoroisopropyl | H | CF3 |
| 7-1798 | 3,5-dichloropyridin-4-yl | Me | H | F | H | H | H | I | H | heptafluoroisopropyl | H | CF3 |
| 7-1799 | 3-(trifluoromethyl)pyridin-4-yl | Me | H | F | H | H | H | I | H | heptafluoroisopropyl | H | CF3 |
| 7-1800 | 2,6-dicyanopyridin-4-yl | Me | H | F | H | H | H | I | H | heptafluoroisopropyl | H | CF3 |
| 7-1801 | pyridin-4-yl N-oxide | Me | H | F | H | H | H | I | H | heptafluoroisopropyl | H | CF3 |
| 7-1802 | pyridin-2-yl | Me | H | F | H | H | H | I | H | heptafluoroisopropyl | H | CF3 |
| 7-1803 | 3-chloropyridin-2-yl | Me | H | F | H | H | H | I | H | heptafluoroisopropyl | H | CF3 |
| 7-1804 | 4-bromopyridin-2-yl | Me | H | F | H | H | H | I | H | heptafluoroisopropyl | H | CF3 |
| 7-1805 | 5-iodopyridin-2-yl | Me | H | F | H | H | H | I | H | heptafluoroisopropyl | H | CF3 |
| 7-1806 | 6-chloropyridin-2-yl | Me | H | F | H | H | H | I | H | heptafluoroisopropyl | H | CF3 |
| 7-1807 | 4-cyanopyridin-2-yl | Me | H | F | H | H | H | I | H | heptafluoroisopropyl | H | CF3 |
| 7-1808 | phenyl | Me | H | F | H | H | H | I | H | nonafluoro-2-butyl | H | CF3 |
| 7-1809 | 2-fluorophenyl | Me | H | F | H | H | H | I | H | nonafluoro-2-butyl | H | CF3 |
| 7-1810 | 3-fluorophenyl | Me | H | F | H | H | H | I | H | nonafluoro-2-butyl | H | CF3 |
| 7-1811 | 4-fluorophenyl | Me | H | F | H | H | H | I | H | nonafluoro-2-butyl | H | CF3 |
| 7-1812 | 2-chlorophenyl | Me | H | F | H | H | H | I | H | nonafluoro-2-butyl | H | CF3 |
| 7-1813 | 3-chlorophenyl | Me | H | F | H | H | H | I | H | nonafluoro-2-butyl | H | CF3 |
| 7-1814 | 4-chlorophenyl | Me | H | F | H | H | H | I | H | nonafluoro-2-butyl | H | CF3 |
| 7-1815 | 2-bromophenyl | Me | H | F | H | H | H | I | H | nonafluoro-2-butyl | H | CF3 |
| 7-1816 | 3-bromophenyl | Me | H | F | H | H | H | I | H | nonafluoro-2-butyl | H | CF3 |
| 7-1817 | 4-bromophenyl | Me | H | F | H | H | H | I | H | nonafluoro-2-butyl | H | CF3 |
| 7-1818 | 2-iodophenyl | Me | H | F | H | H | H | I | H | nonafluoro-2-butyl | H | CF3 |
| 7-1819 | 3-iodophenyl | Me | H | F | H | H | H | I | H | nonafluoro-2-butyl | H | CF3 |
| 7-1820 | 4-iodophenyl | Me | H | F | H | H | H | I | H | nonafluoro-2-butyl | H | CF3 |
| 7-1821 | (2-trifluoromethyl)phenyl | Me | H | F | H | H | H | I | H | nonafluoro-2-butyl | H | CF3 |
| 7-1822 | (3-trifluoromethyl)phenyl | Me | H | F | H | H | H | I | H | nonafluoro-2-butyl | H | CF3 |
| 7-1823 | (4-trifluoromethyl)phenyl | Me | H | F | H | H | H | I | H | nonafluoro-2-butyl | H | CF3 |
| 7-1824 | 2-nitrophenyl | Me | H | F | H | H | H | I | H | nonafluoro-2-butyl | H | CF3 |
| 7-1825 | 3-nitrophenyl | Me | H | F | H | H | H | I | H | nonafluoro-2-butyl | H | CF3 |
| 7-1826 | 4-nitrophenyl | Me | H | F | H | H | H | I | H | nonafluoro-2-butyl | H | CF3 |
| 7-1827 | 2-cyanophenyl | Me | H | F | H | H | H | I | H | nonafluoro-2-butyl | H | CF3 |
| 7-1828 | 3-cyanophenyl | Me | H | F | H | H | H | I | H | nonafluoro-2-butyl | H | CF3 |
| 7-1829 | 4-cyanophenyl | Me | H | F | H | H | H | I | H | nonafluoro-2-butyl | H | CF3 |
| 7-1830 | 2,6-difluorophenyl | Me | H | F | H | H | H | I | H | nonafluoro-2-butyl | H | CF3 |
| 7-1831 | 3,4-dichlorophenyl | Me | H | F | H | H | H | I | H | nonafluoro-2-butyl | H | CF3 |
| 7-1832 | 2,4-dichlorophenyl | Me | H | F | H | H | H | I | H | nonafluoro-2-butyl | H | CF3 |
| 7-1833 | 2-chloro-4-fluorophenyl | Me | H | F | H | H | H | I | H | nonafluoro-2-butyl | H | CF3 |
| 7-1834 | 2-chloro-4,5-difluorophenyl | Me | H | F | H | H | H | I | H | nonafluoro-2-butyl | H | CF3 |
| 7-1835 | 4-bromo-2-chlorophenyl | Me | H | F | H | H | H | I | H | nonafluoro-2-butyl | H | CF3 |
| 7-1636 | 2-bromo-4-chlorophenyl | Me | H | F | H | H | H | I | H | nonafluoro-2-butyl | H | CF3 |
| 7-1837 | 2-bromo-4-fluorophenyl | Me | H | F | H | H | H | I | H | nonafluoro-2-butyl | H | CF3 |
| 7-1838 | 2-chloro-4-nitrophenyl | Me | H | F | H | H | H | I | H | nonafluoro-2-butyl | H | CF3 |
| 7-1839 | 3,5-dicyanophenyl | Me | H | F | H | H | H | I | H | nonafluoro-2-butyl | H | CF3 |
| 7-1840 | 4-cyano-2-fluorophenyl | Me | H | F | H | H | H | I | H | nonafluoro-2-butyl | H | CF3 |
| 7-1841 | 2-chloro-4-cyanophenyl | Me | H | F | H | H | H | I | H | nonafluoro-2-butyl | H | CF3 |
| 7-1842 | pyridin-3-yl | Me | H | F | H | H | H | I | H | nonafluoro-2-butyl | H | CF3 |
| 7-1843 | 2-fluoropyridin-3-yl | Me | H | F | H | H | H | I | H | nonafluoro-2-butyl | H | CF3 |
| 7-1844 | 2-chloropyridin-3-yl | Me | H | F | H | H | H | I | H | nonafluoro-2-butyl | H | CF3 |

TABLE 7-continued

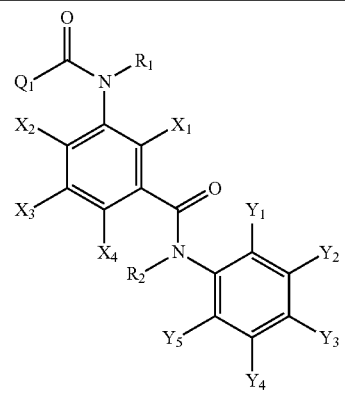

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-1845 | 2-bromopyridin-3-yl | Me | H | F | H | H | H | I | H | nonafluoro-2-butyl | H | CF3 |
| 7-1846 | 2-iodopyridin-3-yl | Me | H | F | H | H | H | I | H | nonafluoro-2-butyl | H | CF3 |
| 7-1847 | 2-(trifluoromethyl)pyridin-3-yl | Me | H | F | H | H | H | I | H | nonafluoro-2-butyl | H | CF3 |
| 7-1848 | 2-nitropyridin-3-yl | Me | H | F | H | H | H | I | H | nonafluoro-2-butyl | H | CF3 |
| 7-1849 | 2-cyanopyridin-3-yl | Me | H | F | H | H | H | I | H | nonafluoro-2-butyl | H | CF3 |
| 7-1850 | 6-fluoropyridin-3-yl | Me | H | F | H | H | H | I | H | nonafluoro-2-butyl | H | CF3 |
| 7-1851 | 6-chloropyridin-3-yl | Me | H | F | H | H | H | I | H | nonafluoro-2-butyl | H | CF3 |
| 7-1852 | 6-bromopyridin-3-yl | Me | H | F | H | H | H | I | H | nonafluoro-2-butyl | H | CF3 |
| 7-1853 | 6-iodopyridin-3-yl | Me | H | F | H | H | H | I | H | nonafluoro-2-butyl | H | CF3 |
| 7-1854 | 6-(trifluoromethyl)pyridin-3-yl | Me | H | F | H | H | H | I | H | nonafluoro-2-butyl | H | CF3 |
| 7-1855 | 6-nitropyridin-3-yl | Me | H | F | H | H | H | I | H | nonafluoro-2-butyl | H | CF3 |
| 7-1856 | 6-cyanopyridin-3-yl | Me | H | F | H | H | H | I | H | nonafluoro-2-butyl | H | CF3 |
| 7-1857 | 5-fluoropyridin-3-yl | Me | H | F | H | H | H | I | H | nonafluoro-2-butyl | H | CF3 |
| 7-1858 | 5-chloropyridin-3-yl | Me | H | F | H | H | H | I | H | nonafluoro-2-butyl | H | CF3 |
| 7-1859 | 5-bromopyridin-3-yl | Me | H | F | H | H | H | I | H | nonafluoro-2-butyl | H | CF3 |
| 7-1860 | 5-iodopyridin-3-yl | Me | H | F | H | H | H | I | H | nonafluoro-2-butyl | H | CF3 |
| 7-1861 | 5-(trifluoromethyl)pyridin-3-yl | Me | H | F | H | H | H | I | H | nonafluoro-2-butyl | H | CF3 |
| 7-1862 | 5-nitropyridin-3-yl | Me | H | F | H | H | H | I | H | nonafluoro-2-butyl | H | CF3 |
| 7-1863 | 5-cyanopyridin-3-yl | Me | H | F | H | H | H | I | H | nonafluoro-2-butyl | H | CF3 |
| 7-1864 | 4-fluoropyridin-3-yl | Me | H | F | H | H | H | I | H | nonafluoro-2-butyl | H | CF3 |
| 7-1865 | 4-chloropyridin-3-yl | Me | H | F | H | H | H | I | H | nonafluoro-2-butyl | H | CF3 |
| 7-1866 | 4-bromopyridin-3-yl | Me | H | F | H | H | H | I | H | nonafluoro-2-butyl | H | CF3 |
| 7-1867 | 4-iodopyridin-3-yl | Me | H | F | H | H | H | I | H | nonafluoro-2-butyl | H | CF3 |
| 7-1868 | 4-(trifluoromethyl)pyridin-3-yl | Me | H | F | H | H | H | I | H | nonafluoro-2-butyl | H | CF3 |
| 7-1869 | 4-nitropyridin-3-yl | Me | H | F | H | H | H | I | H | nonafluoro-2-butyl | H | CF3 |
| 7-1870 | 4-cyanopyridin-3-yl | Me | H | F | H | H | H | I | H | nonafluoro-2-butyl | H | CF3 |
| 7-1871 | 2,6-dichloropyridin-3-yl | Me | H | F | H | H | H | I | H | nonafluoro-2-butyl | H | CF3 |
| 7-1872 | pyridin-3-yl N-oxide | Me | H | F | H | H | H | I | H | nonafluoro-2-butyl | H | CF3 |
| 7-1873 | pyridin-4-yl | Me | H | F | H | H | H | I | H | nonafluoro-2-butyl | H | CF3 |
| 7-1874 | 2-chloropyridin-4-yl | Me | H | F | H | H | H | I | H | nonafluoro-2-butyl | H | CF3 |
| 7-1875 | 3-bromopyridin-4-yl | Me | H | F | H | H | H | I | H | nonafluoro-2-butyl | H | CF3 |
| 7-1876 | 3,5-dichloropyridin-4-yl | Me | H | F | H | H | H | I | H | nonafluoro-2-butyl | H | CF3 |
| 7-1877 | 3-(trifluoromethyl)pyridin-4-yl | Me | H | F | H | H | H | I | H | nonafluoro-2-butyl | H | CF3 |
| 7-1878 | 2,6-dicyanopyridin-4-yl | Me | H | F | H | H | H | I | H | nonafluoro-2-butyl | H | CF3 |
| 7-1879 | pyridin-4-yl N-oxide | Me | H | F | H | H | H | I | H | nonafluoro-2-butyl | H | CF3 |
| 7-1880 | pyridin-2-yl | Me | H | F | H | H | H | I | H | nonafluoro-2-butyl | H | CF3 |
| 7-1881 | 3-chloropyridin-2-yl | Me | H | F | H | H | H | I | H | nonafluoro-2-butyl | H | CF3 |
| 7-1882 | 4-bromopyridin-2-yl | Me | H | F | H | H | H | I | H | nonafluoro-2-butyl | H | CF3 |
| 7-1883 | 5-iodopyridin-2-yl | Me | H | F | H | H | H | I | H | nonafluoro-2-butyl | H | CF3 |
| 7-1884 | 6-chloropyridin-2-yl | Me | H | F | H | H | H | I | H | nonafluoro-2-butyl | H | CF3 |
| 7-1885 | 4-cyanopyridin-2-yl | Me | H | F | H | H | H | I | H | nonafluoro-2-butyl | H | CF3 |
| 7-1886 | phenyl | Me | H | F | H | H | H | OCF3 | H | heptafluoroisopropyl | H | OCF3 |
| 7-1901 | 3-cyanophenyl | Me | H | F | H | H | H | OCF3 | H | heptafluoroisopropyl | H | OCF3 |
| 7-1902 | 4-cyanophenyl | Me | H | F | H | H | H | OCF3 | H | heptafluoroisopropyl | H | OCF3 |
| 7-1917 | 2-chloropyridin-3-yl | Me | H | F | H | H | H | OCF3 | H | heptafluoroisopropyl | H | OCF3 |
| 7-1942 | phenyl | Me | H | F | H | H | H | OCF3 | H | nonafluoro-2-butyl | H | OCF3 |
| 7-1957 | 3-cyanophenyl | Me | H | F | H | H | H | OCF3 | H | nonafluoro-2-butyl | H | OCF3 |
| 7-1958 | 4-cyanophenyl | Me | H | F | H | H | H | OCF3 | H | nonafluoro-2-butyl | H | OCF3 |
| 7-1973 | 2-chloropyridin-3-yl | Me | H | F | H | H | H | OCF3 | H | nonafluoro-2-butyl | H | OCF3 |
| 7-1998 | phenyl | Me | H | F | H | H | H | CF3 | H | heptafluoroisopropyl | H | OCF3 |
| 7-2013 | 3-cyanophenyl | Me | H | F | H | H | H | CF3 | H | heptafluoroisopropyl | H | OCF3 |
| 7-2014 | 4-cyanophenyl | Me | H | F | H | H | H | CF3 | H | heptafluoroisopropyl | H | OCF3 |
| 7-2029 | 2-chloropyridin-3-yl | Me | H | F | H | H | H | CF3 | H | heptafluoroisopropyl | H | OCF3 |
| 7-2054 | phenyl | Me | H | F | H | H | H | CF3 | H | nonafluoro-2-butyl | H | OCF3 |
| 7-2069 | 3-cyanophenyl | Me | H | F | H | H | H | CF3 | H | nonafluoro-2-butyl | H | OCF3 |
| 7-2070 | 4-cyanophenyl | Me | H | F | H | H | H | CF3 | H | nonafluoro-2-butyl | H | OCF3 |
| 7-2085 | 2-chloropyridin-3-yl | Me | H | F | H | H | H | CF3 | H | nonafluoro-2-butyl | H | OCF3 |
| 7-2110 | phenyl | Me | H | F | H | H | H | CF3 | H | heptafluoroisopropyl | H | CF3 |

TABLE 7-continued

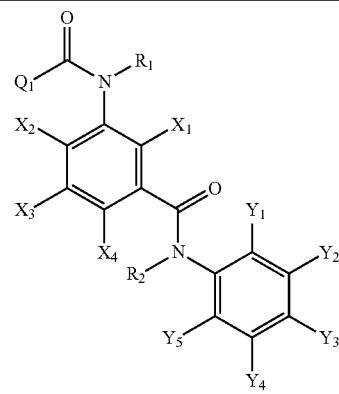

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-2130 | 3-cyanophenyl | Me | H | F | H | H | H | CF3 | H | heptafluoroisopropyl | H | CF3 |
| 7-2131 | 4-cyanophenyl | Me | H | F | H | H | H | CF3 | H | heptafluoroisopropyl | H | CF3 |
| 7-2146 | 2-chloropyridin-3-yl | Me | H | F | H | H | H | CF3 | H | heptafluoroisopropyl | H | CF3 |
| 7-2178 | phenyl | Me | H | F | H | H | H | CF3 | H | nonafluoro-2-butyl | H | CF3 |
| 7-2198 | 3-cyanophenyl | Me | H | F | H | H | H | CF3 | H | nonafluoro-2-butyl | H | CF3 |
| 7-2199 | 4-cyanophenyl | Me | H | F | H | H | H | CF3 | H | nonafluoro-2-butyl | H | CF3 |
| 7-2214 | 2-chloropyridin-3-yl | Me | H | F | H | H | H | CF3 | H | nonafluoro-2-butyl | H | CF3 |
| 7-2246 | phenyl | Me | H | H | F | H | H | F | H | heptafluoroisopropyl | H | F |
| 7-2247 | 3-cyanophenyl | Me | H | H | F | H | H | F | H | heptafluoroisopropyl | H | F |
| 7-2248 | 4-cyanophenyl | Me | H | H | F | H | H | F | H | heptafluoroisopropyl | H | F |
| 7-2249 | 2-chloropyridin-3-yl | Me | H | H | F | H | H | F | H | heptafluoroisopropyl | H | F |
| 7-2250 | phenyl | Me | H | H | F | H | H | F | H | nonafluoro-2-butyl | H | F |
| 7-2251 | 3-cyanophenyl | Me | H | H | F | H | H | F | H | nonafluoro-2-butyl | H | F |
| 7-2252 | 4-cyanophenyl | Me | H | H | F | H | H | F | H | nonafluoro-2-butyl | H | F |
| 7-2253 | 2-chloropyridin-3-yl | Me | H | H | F | H | H | F | H | nonafluoro-2-butyl | H | F |
| 7-2254 | phenyl | Me | H | H | F | H | H | Cl | H | heptafluoroisopropyl | H | Cl |
| 7-2274 | 3-cyanophenyl | Me | H | H | F | H | H | Cl | H | heptafluoroisopropyl | H | Cl |
| 7-2275 | 4-cyanophenyl | Me | H | H | F | H | H | Cl | H | heptafluoroisopropyl | H | Cl |
| 7-2290 | 2-chloropyridin-3-yl | Me | H | H | F | H | H | Cl | H | heptafluoroisopropyl | H | Cl |
| 7-2332 | phenyl | Me | H | H | F | H | H | Cl | H | nonafluoro-2-butyl | H | Cl |
| 7-2352 | 3-cyanophenyl | Me | H | H | F | H | H | Cl | H | nonafluoro-2-butyl | H | Cl |
| 7-2353 | 4-cyanophenyl | Me | H | H | F | H | H | Cl | H | nonafluoro-2-butyl | H | Cl |
| 7-2368 | 2-chloropyridin-3-yl | Me | H | H | F | H | H | Cl | H | nonafluoro-2-butyl | H | Cl |
| 7-2410 | phenyl | Me | H | H | F | H | H | Br | H | heptafluoroisopropyl | H | Br |
| 7-2430 | 3-cyanophenyl | Me | H | H | F | H | H | Br | H | heptafluoroisopropyl | H | Br |
| 7-2431 | 4-cyanophenyl | Me | H | H | F | H | H | Br | H | heptafluoroisopropyl | H | Br |
| 7-2446 | 2-chloropyridin-3-yl | Me | H | H | F | H | H | Br | H | heptafluoroisopropyl | H | Br |
| 7-2488 | phenyl | Me | H | H | F | H | H | Br | H | nonafluoro-2-butyl | H | Br |
| 7-2508 | 3-cyanophenyl | Me | H | H | F | H | H | Br | H | nonafluoro-2-butyl | H | Br |
| 7-2509 | 4-cyanophenyl | Me | H | H | F | H | H | Br | H | nonafluoro-2-butyl | H | Br |
| 7-2524 | 2-chloropyridin-3-yl | Me | H | H | F | H | H | Br | H | nonafluoro-2-butyl | H | Br |
| 7-2566 | phenyl | Me | H | H | F | H | H | I | H | heptafluoroisopropyl | H | I |
| 7-2586 | 3-cyanophenyl | Me | H | H | F | H | H | I | H | heptafluoroisopropyl | H | I |
| 7-2587 | 4-cyanophenyl | Me | H | H | F | H | H | I | H | heptafluoroisopropyl | H | I |
| 7-2602 | 2-chloropyridin-3-yl | Me | H | H | F | H | H | I | H | heptafluoroisopropyl | H | I |
| 7-2644 | phenyl | Me | H | H | F | H | H | I | H | nonafluoro-2-butyl | H | I |
| 7-2664 | 3-cyanophenyl | Me | H | H | F | H | H | I | H | nonafluoro-2-butyl | H | I |
| 7-2665 | 4-cyanophenyl | Me | H | H | F | H | H | I | H | nonafluoro-2-butyl | H | I |
| 7-2680 | 2-chloropyridin-3-yl | Me | H | H | F | H | H | I | H | nonafluoro-2-butyl | H | I |
| 7-2722 | phenyl | Me | H | H | F | H | H | Cl | H | heptafluoroisopropyl | H | OCF3 |
| 7-2742 | 3-cyanophenyl | Me | H | H | F | H | H | Cl | H | heptafluoroisopropyl | H | OCF3 |
| 7-2743 | 4-cyanophenyl | Me | H | H | F | H | H | Cl | H | heptafluoroisopropyl | H | OCF3 |
| 7-2758 | 2-chloropyridin-3-yl | Me | H | H | F | H | H | Cl | H | heptafluoroisopropyl | H | OCF3 |
| 7-2800 | phenyl | Me | H | H | F | H | H | Cl | H | nonafluoro-2-butyl | H | OCF3 |
| 7-2820 | 3-cyanophenyl | Me | H | H | F | H | H | Cl | H | nonafluoro-2-butyl | H | OCF3 |
| 7-2821 | 4-cyanophenyl | Me | H | H | F | H | H | Cl | H | nonafluoro-2-butyl | H | OCF3 |
| 7-2836 | 2-chloropyridin-3-yl | Me | H | H | F | H | H | Cl | H | nonafluoro-2-butyl | H | OCF3 |
| 7-2878 | phenyl | Me | H | H | F | H | H | Br | H | heptafluoroisopropyl | H | OCF3 |
| 7-2898 | 3-cyanophenyl | Me | H | H | F | H | H | Br | H | heptafluoroisopropyl | H | OCF3 |
| 7-2899 | 4-cyanophenyl | Me | H | H | F | H | H | Br | H | heptafluoroisopropyl | H | OCF3 |
| 7-2914 | 2-chloropyridin-3-yl | Me | H | H | F | H | H | Br | H | heptafluoroisopropyl | H | OCF3 |
| 7-2956 | phenyl | Me | H | H | F | H | H | Br | H | nonafluoro-2-butyl | H | OCF3 |
| 7-2976 | 3-cyanophenyl | Me | H | H | F | H | H | Br | H | nonafluoro-2-butyl | H | OCF3 |
| 7-2977 | 4-cyanophenyl | Me | H | H | F | H | H | Br | H | nonafluoro-2-butyl | H | OCF3 |
| 7-2992 | 2-chloropyridin-3-yl | Me | H | H | F | H | H | Br | H | nonafluoro-2-butyl | H | OCF3 |
| 7-3034 | phenyl | Me | H | H | F | H | H | I | H | heptafluoroisopropyl | H | OCF3 |
| 7-3054 | 3-cyanophenyl | Me | H | H | F | H | H | I | H | heptafluoroisopropyl | H | OCF3 |
| 7-3055 | 4-cyanophenyl | Me | H | H | F | H | H | I | H | heptafluoroisopropyl | H | OCF3 |

TABLE 7-continued

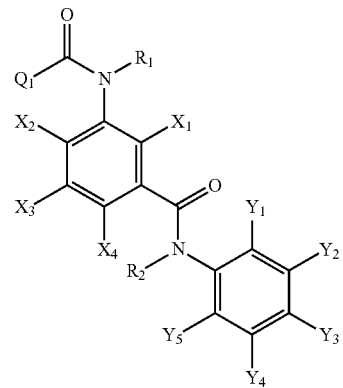

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-3070 | 2-chloropyridin-3-yl | Me | H | H | F | H | H | I | H | heptafluoroisopropyl | H | OCF3 |
| 7-3112 | phenyl | Me | H | H | F | H | H | I | H | nonafluoro-2-butyl | H | OCF3 |
| 7-3132 | 3-cyanophenyl | Me | H | H | F | H | H | I | H | nonafluoro-2-butyl | H | OCF3 |
| 7-3133 | 4-cyanophenyl | Me | H | H | F | H | H | I | H | nonafluoro-2-butyl | H | OCF3 |
| 7-3148 | 2-chloropyridin-3-yl | Me | H | H | F | H | H | I | H | nonafluoro-2-butyl | H | OCF3 |
| 7-3190 | phenyl | Me | H | H | F | H | H | F | H | heptafluoroisopropyl | H | CF3 |
| 7-3191 | phenyl | Me | H | H | F | H | H | Cl | H | heptafluoroisopropyl | H | CF3 |
| 7-3211 | 3-cyanophenyl | Me | H | H | F | H | H | Cl | H | heptafluoroisopropyl | H | CF3 |
| 7-3212 | 4-cyanophenyl | Me | H | H | F | H | H | Cl | H | heptafluoroisopropyl | H | CF3 |
| 7-3227 | 2-chloropyridin-3-yl | Me | H | H | F | H | H | Cl | H | heptafluoroisopropyl | H | CF3 |
| 7-3269 | phenyl | Me | H | H | F | H | H | F | H | nonafluoro-2-butyl | H | CF3 |
| 7-3270 | phenyl | Me | H | H | F | H | H | Cl | H | nonafluoro-2-butyl | H | CF3 |
| 7-3290 | 3-cyanophenyl | Me | H | H | F | H | H | Cl | H | nonafluoro-2-butyl | H | CF3 |
| 7-3291 | 4-cyanophenyl | Me | H | H | F | H | H | Cl | H | nonafluoro-2-butyl | H | CF3 |
| 7-3306 | 2-chloropyridin-3-yl | Me | H | H | F | H | H | Cl | H | nonafluoro-2-butyl | H | CF3 |
| 7-3348 | phenyl | Me | H | H | F | H | H | Br | H | heptafluoroisopropyl | H | CF3 |
| 7-3368 | 3-cyanophenyl | Me | H | H | F | H | H | Br | H | heptafluoroisopropyl | H | CF3 |
| 7-3369 | 4-cyanophenyl | Me | H | H | F | H | H | Br | H | heptafluoroisopropyl | H | CF3 |
| 7-3384 | 2-chloropyridin-3-yl | Me | H | H | F | H | H | Br | H | heptafluoroisopropyl | H | CF3 |
| 7-3426 | phenyl | Me | H | H | F | H | H | Br | H | nonafluoro-2-butyl | H | CF3 |
| 7-3446 | 3-cyanophenyl | Me | H | H | F | H | H | Br | H | nonafluoro-2-butyl | H | CF3 |
| 7-3447 | 4-cyanophenyl | Me | H | H | F | H | H | Br | H | nonafluoro-2-butyl | H | CF3 |
| 7-3462 | 2-chloropyridin-3-yl | Me | H | H | F | H | H | Br | H | nonafluoro-2-butyl | H | CF3 |
| 7-3504 | phenyl | Me | H | H | F | H | H | I | H | heptafluoroisopropyl | H | CF3 |
| 7-3524 | 3-cyanophenyl | Me | H | H | F | H | H | I | H | heptafluoroisopropyl | H | CF3 |
| 7-3525 | 4-cyanophenyl | Me | H | H | F | H | H | I | H | heptafluoroisopropyl | H | CF3 |
| 7-3582 | phenyl | Me | H | H | F | H | H | I | H | nonafluoro-2-butyl | H | CF3 |
| 7-3602 | 3-cyanophenyl | Me | H | H | F | H | H | I | H | nonafluoro-2-butyl | H | CF3 |
| 7-3603 | 4-cyanophenyl | Me | H | H | F | H | H | I | H | nonafluoro-2-butyl | H | CF3 |
| 7-3618 | 2-chloropyridin-3-yl | Me | H | H | F | H | H | I | H | nonafluoro-2-butyl | H | CF3 |
| 7-3660 | phenyl | Me | H | H | F | H | H | OCF3 | H | heptafluoroisopropyl | H | OCF3 |
| 7-3691 | 2-chloropyridin-3-yl | Me | H | H | F | H | H | OCF3 | H | heptafluoroisopropyl | H | OCF3 |
| 7-3716 | phenyl | Me | H | H | F | H | H | OCF3 | H | nonafluoro-2-butyl | H | OCF3 |
| 7-3747 | 2-chloropyridin-3-yl | Me | H | H | F | H | H | OCF3 | H | nonafluoro-2-butyl | H | OCF3 |
| 7-3772 | phenyl | Me | H | H | F | H | H | CF3 | H | heptafluoroisopropyl | H | OCF3 |
| 7-3803 | 2-chloropyridin-3-yl | Me | H | H | F | H | H | CF3 | H | heptafluoroisopropyl | H | OCF3 |
| 7-3828 | phenyl | Me | H | H | F | H | H | CF3 | H | nonafluoro-2-butyl | H | OCF3 |
| 7-3859 | 2-chloropyridin-3-yl | Me | H | H | F | H | H | CF3 | H | nonafluoro-2-butyl | H | OCF3 |
| 7-3884 | phenyl | Me | H | H | F | H | H | CF3 | H | heptafluoroisopropyl | H | CF3 |
| 7-3904 | 3-cyanophenyl | Me | H | H | F | H | H | CF3 | H | heptafluoroisopropyl | H | CF3 |
| 7-3905 | 4-cyanophenyl | Me | H | H | F | H | H | CF3 | H | heptafluoroisopropyl | H | CF3 |
| 7-3920 | 2-chloropyridin-3-yl | Me | H | H | F | H | H | CF3 | H | heptafluoroisopropyl | H | CF3 |
| 7-3952 | phenyl | Me | H | H | F | H | H | CF3 | H | nonafluoro-2-butyl | H | CF3 |
| 7-3972 | 3-cyanophenyl | Me | H | H | F | H | H | CF3 | H | nonafluoro-2-butyl | H | CF3 |
| 7-3973 | 4-cyanophenyl | Me | H | H | F | H | H | CF3 | H | nonafluoro-2-butyl | H | CF3 |
| 7-3988 | 2-chloropyridin-3-yl | Me | H | H | F | H | H | CF3 | H | nonafluoro-2-butyl | H | CF3 |
| 7-4020 | phenyl | Me | H | F | F | H | H | F | H | heptafluoroisopropyl | H | F |
| 7-4021 | 3-cyanophenyl | Me | H | F | F | H | H | F | H | heptafluoroisopropyl | H | F |
| 7-4022 | 4-cyanophenyl | Me | H | F | F | H | H | F | H | heptafluoroisopropyl | H | F |
| 7-4023 | 2-chloropyridin-3-yl | Me | H | F | F | H | H | F | H | heptafluoroisopropyl | H | F |
| 7-4024 | phenyl | Me | H | F | F | H | H | F | H | nonafluoro-2-butyl | H | F |
| 7-4025 | 3-cyanophenyl | Me | H | F | F | H | H | F | H | nonafluoro-2-butyl | H | F |
| 7-4026 | 4-cyanophenyl | Me | H | F | F | H | H | F | H | nonafluoro-2-butyl | H | F |
| 7-4027 | 2-chloropyridin-3-yl | Me | H | F | F | H | H | F | H | nonafluoro-2-butyl | H | F |
| 7-4028 | phenyl | Me | H | F | F | H | H | Cl | H | heptafluoroisopropyl | H | Cl |
| 7-4048 | 3-cyanophenyl | Me | H | F | F | H | H | Cl | H | heptafluoroisopropyl | H | Cl |
| 7-4049 | 4-cyanophenyl | Me | H | F | F | H | H | Cl | H | heptafluoroisopropyl | H | Cl |
| 7-4064 | 2-chloropyridin-3-yl | Me | H | F | F | H | H | Cl | H | heptafluoroisopropyl | H | Cl |

TABLE 7-continued

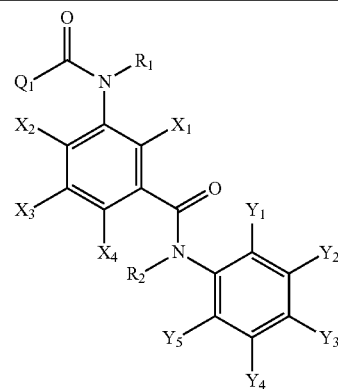

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-4106 | phenyl | Me | H | F | F | H | H | Cl | H | nonafluoro-2-butyl | H | Cl |
| 7-4126 | 3-cyanophenyl | Me | H | F | F | H | H | Cl | H | nonafluoro-2-butyl | H | Cl |
| 7-4127 | 4-cyanophenyl | Me | H | F | F | H | H | Cl | H | nonafluoro-2-butyl | H | Cl |
| 7-4142 | 2-chloropyridin-3-yl | Me | H | F | F | H | H | Cl | H | nonafluoro-2-butyl | H | Cl |
| 7-4184 | phenyl | Me | H | F | F | H | H | Br | H | heptafluoroisopropyl | H | Br |
| 7-4204 | 3-cyanophenyl | Me | H | F | F | H | H | Br | H | heptafluoroisopropyl | H | Br |
| 7-4205 | 4-cyanophenyl | Me | H | F | F | H | H | Br | H | heptafluoroisopropyl | H | Br |
| 7-4220 | 2-chloropyridin-3-yl | Me | H | F | F | H | H | Br | H | heptafluoroisopropyl | H | Br |
| 7-4262 | phenyl | Me | H | F | F | H | H | Br | H | nonafluoro-2-butyl | H | Br |
| 7-4282 | 3-cyanophenyl | Me | H | F | F | H | H | Br | H | nonafluoro-2-butyl | H | Br |
| 7-4283 | 4-cyanophenyl | Me | H | F | F | H | H | Br | H | nonafluoro-2-butyl | H | Br |
| 7-4298 | 2-chloropyridin-3-yl | Me | H | F | F | H | H | Br | H | nonafluoro-2-butyl | H | Br |
| 7-4340 | phenyl | Me | H | F | F | H | H | I | H | heptafluoroisopropyl | H | I |
| 7-4360 | 3-cyanophenyl | Me | H | F | F | H | H | I | H | heptafluoroisopropyl | H | I |
| 7-4361 | 4-cyanophenyl | Me | H | F | F | H | H | I | H | heptafluoroisopropyl | H | I |
| 7-4376 | 2-chloropyridin-3-yl | Me | H | F | F | H | H | I | H | heptafluoroisopropyl | H | I |
| 7-4418 | phenyl | Me | H | F | F | H | H | I | H | nonafluoro-2-butyl | H | I |
| 7-4438 | 3-cyanophenyl | Me | H | F | F | H | H | I | H | nonafluoro-2-butyl | H | I |
| 7-4439 | 4-cyanophenyl | Me | H | F | F | H | H | I | H | nonafluoro-2-butyl | H | I |
| 7-4454 | 2-chloropyridin-3-yl | Me | H | F | F | H | H | I | H | nonafluoro-2-butyl | H | I |
| 7-4496 | phenyl | Me | H | F | F | H | H | Cl | H | heptafluoroisopropyl | H | OCF3 |
| 7-4516 | 3-cyanophenyl | Me | H | F | F | H | H | Cl | H | heptafluoroisopropyl | H | OCF3 |
| 7-4517 | 4-cyanophenyl | Me | H | F | F | H | H | Cl | H | heptafluoroisopropyl | H | OCF3 |
| 7-4532 | 2-chloropyridin-3-yl | Me | H | F | F | H | H | Cl | H | heptafluoroisopropyl | H | OCF3 |
| 7-4574 | phenyl | Me | H | F | F | H | H | Cl | H | nonafluoro-2-butyl | H | OCF3 |
| 7-4594 | 3-cyanophenyl | Me | H | F | F | H | H | Cl | H | nonafluoro-2-butyl | H | OCF3 |
| 7-4595 | 4-cyanophenyl | Me | H | F | F | H | H | Cl | H | nonafluoro-2-butyl | H | OCF3 |
| 7-4610 | 2-chloropyridin-3-yl | Me | H | F | F | H | H | Cl | H | nonafluoro-2-butyl | H | OCF3 |
| 7-4652 | phenyl | Me | H | F | F | H | H | Br | H | heptafluoroisopropyl | H | OCF3 |
| 7-4672 | 3-cyanophenyl | Me | H | F | F | H | H | Br | H | heptafluoroisopropyl | H | OCF3 |
| 7-4673 | 4-cyanophenyl | Me | H | F | F | H | H | Br | H | heptafluoroisopropyl | H | OCF3 |
| 7-4688 | 2-chloropyridin-3-yl | Me | H | F | F | H | H | Br | H | heptafluoroisopropyl | H | OCF3 |
| 7-4730 | phenyl | Me | H | F | F | H | H | Br | H | nonafluoro-2-butyl | H | OCF3 |
| 7-4750 | 3-cyanophenyl | Me | H | F | F | H | H | Br | H | nonafluoro-2-butyl | H | OCF3 |
| 7-4751 | 4-cyanophenyl | Me | H | F | F | H | H | Br | H | nonafluoro-2-butyl | H | OCF3 |
| 7-4766 | 2-chloropyridin-3-yl | Me | H | F | F | H | H | Br | H | nonafluoro-2-butyl | H | OCF3 |
| 7-4808 | phenyl | Me | H | F | F | H | H | I | H | heptafluoroisopropyl | H | OCF3 |
| 7-4828 | 3-cyanophenyl | Me | H | F | F | H | H | I | H | heptafluoroisopropyl | H | OCF3 |
| 7-4829 | 4-cyanophenyl | Me | H | F | F | H | H | I | H | heptafluoroisopropyl | H | OCF3 |
| 7-4844 | 2-chloropyridin-3-yl | Me | H | F | F | H | H | I | H | heptafluoroisopropyl | H | OCF3 |
| 7-4886 | phenyl | Me | H | F | F | H | H | I | H | nonafluoro-2-butyl | H | OCF3 |
| 7-4906 | 3-cyanophenyl | Me | H | F | F | H | H | I | H | nonafluoro-2-butyl | H | OCF3 |
| 7-4907 | 4-cyanophenyl | Me | H | F | F | H | H | I | H | nonafluoro-2-butyl | H | OCF3 |
| 7-4922 | 2-chloropyridin-3-yl | Me | H | F | F | H | H | I | H | nonafluoro-2-butyl | H | OCF3 |
| 7-4964 | phenyl | Me | H | F | F | H | H | F | H | heptafluoroisopropyl | H | CF3 |
| 7-4965 | phenyl | Me | H | F | F | H | H | Cl | H | heptafluoroisopropyl | H | CF3 |
| 7-4985 | 3-cyanophenyl | Me | H | F | F | H | H | Cl | H | heptafluoroisopropyl | H | CF3 |
| 7-4986 | 4-cyanophenyl | Me | H | F | F | H | H | Cl | H | heptafluoroisopropyl | H | CF3 |
| 7-5001 | 2-chloropyridin-3-yl | Me | H | F | F | H | H | Cl | H | heptafluoroisopropyl | H | CF3 |
| 7-5043 | phenyl | Me | H | F | F | H | H | F | H | nonafluoro-2-butyl | H | CF3 |
| 7-5044 | phenyl | Me | H | F | F | H | H | Cl | H | nonafluoro-2-butyl | H | CF3 |
| 7-5064 | 3-cyanophenyl | Me | H | F | F | H | H | Cl | H | nonafluoro-2-butyl | H | CF3 |
| 7-5065 | 4-cyanophenyl | Me | H | F | F | H | H | Cl | H | nonafluoro-2-butyl | H | CF3 |
| 7-5080 | 2-chloropyridin-3-yl | Me | H | F | F | H | H | Cl | H | nonafluoro-2-butyl | H | CF3 |
| 7-5122 | phenyl | Me | H | F | F | H | H | Br | H | heptafluoroisopropyl | H | CF3 |
| 7-5142 | 3-cyanophenyl | Me | H | F | F | H | H | Br | H | heptafluoroisopropyl | H | CF3 |
| 7-5143 | 4-cyanophenyl | Me | H | F | F | H | H | Br | H | heptafluoroisopropyl | H | CF3 |
| 7-5158 | 2-chloropyridin-3-yl | Me | H | F | F | H | H | Br | H | heptafluoroisopropyl | H | CF3 |

TABLE 7-continued

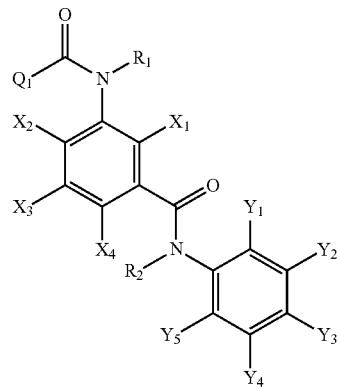

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 7-5200 | phenyl | Me | H | F | F | H | H | Br | H | nonafluoro-2-butyl | H | CF3 |
| 7-5220 | 3-cyanophenyl | Me | H | F | F | H | H | Br | H | nonafluoro-2-butyl | H | CF3 |
| 7-5221 | 4-cyanophenyl | Me | H | F | F | H | H | Br | H | nonafluoro-2-butyl | H | CF3 |
| 7-5236 | 2-chloropyridin-3-yl | Me | H | F | F | H | H | Br | H | nonafluoro-2-butyl | H | CF3 |
| 7-5278 | phenyl | Me | H | F | F | H | H | I | H | heptafluoroisopropyl | H | CF3 |
| 7-5298 | 3-cyanophenyl | Me | H | F | F | H | H | I | H | heptafluoroisopropyl | H | CF3 |
| 7-5299 | 4-cyanophenyl | Me | H | F | F | H | H | I | H | heptafluoroisopropyl | H | CF3 |
| 7-5314 | 2-chloropyridin-3-yl | Me | H | F | F | H | H | I | H | heptafluoroisopropyl | H | CF3 |
| 7-5356 | phenyl | Me | H | F | F | H | H | I | H | nonafluoro-2-butyl | H | CF3 |
| 7-5376 | 3-cyanophenyl | Me | H | F | F | H | H | I | H | nonafluoro-2-butyl | H | CF3 |
| 7-5377 | 4-cyanophenyl | Me | H | F | F | H | H | I | H | nonafluoro-2-butyl | H | CF3 |
| 7-5392 | 2-chloropyridin-3-yl | Me | H | F | F | H | H | I | H | nonafluoro-2-butyl | H | CF3 |
| 7-5434 | phenyl | Me | H | F | F | H | H | OCF3 | H | heptafluoroisopropyl | H | OCF3 |
| 7-5465 | 2-chloropyridin-3-yl | Me | H | F | F | H | H | OCF3 | H | heptafluoroisopropyl | H | OCF3 |
| 7-5490 | phenyl | Me | H | F | F | H | H | OCF3 | H | nonafluoro-2-butyl | H | OCF3 |
| 7-5521 | 2-chloropyridin-3-yl | Me | H | F | F | H | H | OCF3 | H | nonafluoro-2-butyl | H | OCF3 |
| 7-5546 | phenyl | Me | H | F | F | H | H | CF3 | H | heptafluoroisopropyl | H | OCF3 |
| 7-5577 | 2-chloropyridin-3-yl | Me | H | F | F | H | H | CF3 | H | heptafluoroisopropyl | H | OCF3 |
| 7-5602 | phenyl | Me | H | F | F | H | H | CF3 | H | nonafluoro-2-butyl | H | OCF3 |
| 7-5633 | 2-chloropyridin-3-yl | Me | H | F | F | H | H | CF3 | H | nonafluoro-2-butyl | H | OCF3 |
| 7-5658 | phenyl | Me | H | F | F | H | H | CF3 | H | heptafluoroisopropyl | H | CF3 |
| 7-5678 | 3-cyanophenyl | Me | H | F | F | H | H | CF3 | H | heptafluoroisopropyl | H | CF3 |
| 7-5679 | 4-cyanophenyl | Me | H | F | F | H | H | CF3 | H | heptafluoroisopropyl | H | CF3 |
| 7-5694 | 2-chloropyridin-3-yl | Me | H | F | F | H | H | CF3 | H | heptafluoroisopropyl | H | CF3 |
| 7-5726 | phenyl | Me | H | F | F | H | H | CF3 | H | nonafluoro-2-butyl | H | CF3 |
| 7-5746 | 3-cyanophenyl | Me | H | F | F | H | H | CF3 | H | nonafluoro-2-butyl | H | CF3 |
| 7-5747 | 4-cyanophenyl | Me | H | F | F | H | H | CF3 | H | nonafluoro-2-butyl | H | CF3 |
| 7-5762 | 2-chloropyridin-3-yl | Me | H | F | F | H | H | CF3 | H | nonafluoro-2-butyl | H | CF3 |
| 7-5794 | phenyl | Me | H | F | F | F | H | Cl | H | pentafluoroethyl | H | Cl |
| 7-5795 | phenyl | Me | H | F | F | F | H | Br | H | heptafluoroisopropyl | H | Br |
| 7-5796 | phenyl | Me | H | F | F | F | H | Br | H | heptafluoroisopropyl | H | OCF3 |
| 7-5797 | phenyl | Me | H | F | F | F | H | I | H | heptafluoroisopropyl | H | CF3 |
| 7-5798 | phenyl | Me | H | F | F | F | H | CF3 | H | heptafluoroisopropyl | H | CF3 |
| 7-5799 | phenyl | Me | H | F | F | F | H | I | H | nonafluoro-2-butyl | H | I |
| 7-5800 | phenyl | Me | H | F | F | F | H | Cl | H | nonafluoro-2-butyl | H | OCF3 |
| 7-5801 | phenyl | Me | H | F | F | F | H | Br | H | nonafluoro-2-butyl | H | CF3 |
| 7-5802 | phenyl | Me | H | F | F | F | H | CF3 | H | nonafluoro-2-butyl | H | CF3 |
| 7-5803 | phenyl | Me | H | H | H | F | H | Cl | H | pentafluoroethyl | H | Cl |
| 7-5804 | phenyl | Me | H | H | H | F | H | Br | H | heptafluoroisopropyl | H | Br |
| 7-5805 | phenyl | Me | H | H | H | F | H | Br | H | heptafluoroisopropyl | H | OCF3 |
| 7-5806 | phenyl | Me | H | H | H | F | H | I | H | heptafluoroisopropyl | H | CF3 |
| 7-5807 | phenyl | Me | H | H | H | F | H | CF3 | H | heptafluoroisopropyl | H | CF3 |
| 7-5808 | phenyl | Me | H | H | H | F | H | I | H | nonafluoro-2-butyl | H | I |
| 7-5809 | phenyl | Me | H | H | H | F | H | Cl | H | nonafluoro-2-butyl | H | OCF3 |
| 7-5810 | phenyl | Me | H | H | H | F | H | Br | H | nonafluoro-2-butyl | H | CF3 |
| 7-5811 | phenyl | Me | H | H | H | F | H | CF3 | H | nonafluoro-2-butyl | H | CF3 |
| 7-5812 | phenyl | Me | H | H | H | H | F | Cl | H | pentafluoroethyl | H | Cl |
| 7-5813 | phenyl | Me | H | H | H | H | F | Br | H | heptafluoroisopropyl | H | Br |
| 7-5814 | phenyl | Me | H | H | H | H | F | Br | H | heptafluoroisopropyl | H | OCF3 |
| 7-5815 | phenyl | Me | H | H | H | H | F | I | H | heptafluoroisopropyl | H | CF3 |
| 7-5816 | phenyl | Me | H | H | H | H | F | CF3 | H | heptafluoroisopropyl | H | CF3 |
| 7-5817 | phenyl | Me | H | H | H | H | F | I | H | nonafluoro-2-butyl | H | I |
| 7-5818 | phenyl | Me | H | H | H | H | F | Cl | H | nonafluoro-2-butyl | H | OCF3 |
| 7-5819 | phenyl | Me | H | H | H | H | F | Br | H | nonafluoro-2-butyl | H | CF3 |
| 7-5820 | phenyl | Me | H | H | H | H | F | CF3 | H | nonafluoro-2-butyl | H | CF3 |

TABLE 7-continued

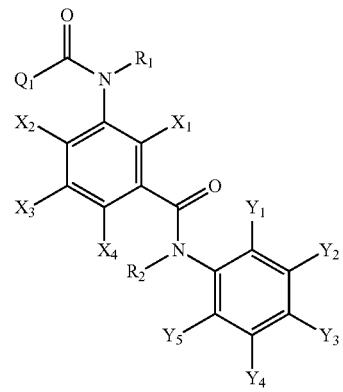

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 7-5821 | phenyl | Me | H | F | H | F | H | Cl | H | pentafluoroethyl | H | Cl |
| 7-5822 | phenyl | Me | H | F | H | F | H | Br | H | heptafluoroisopropyl | H | Br |
| 7-5823 | phenyl | Me | H | F | H | F | H | Br | H | heptafluoroisopropyl | H | OCF3 |
| 7-5824 | phenyl | Me | H | F | H | F | H | I | H | heptafluoroisopropyl | H | CF3 |
| 7-5825 | phenyl | Me | H | F | H | F | H | CF3 | H | heptafluoroisopropyl | H | CF3 |
| 7-5826 | phenyl | Me | H | F | H | F | H | I | H | nonafluoro-2-butyl | H | I |
| 7-5827 | phenyl | Me | H | F | H | F | H | Cl | H | nonafluoro-2-butyl | H | OCF3 |
| 7-5828 | phenyl | Me | H | F | H | F | H | Br | H | nonafluoro-2-butyl | H | CF3 |
| 7-5829 | phenyl | Me | H | F | H | F | H | CF3 | H | nonafluoro-2-butyl | H | CF3 |
| 7-5830 | phenyl | Me | H | F | H | H | F | Cl | H | pentafluoroethyl | H | Cl |
| 7-5831 | phenyl | Me | H | F | H | H | F | Br | H | heptafluoroisopropyl | H | Br |
| 7-5832 | phenyl | Me | H | F | H | H | F | Br | H | heptafluoroisopropyl | H | OCF3 |
| 7-5833 | phenyl | Me | H | F | H | H | F | I | H | heptafluoroisopropyl | H | CF3 |
| 7-5834 | phenyl | Me | H | F | H | H | F | CF3 | H | heptafluoroisopropyl | H | CF3 |
| 7-5835 | phenyl | Me | H | F | H | H | F | I | H | nonafluoro-2-butyl | H | I |
| 7-5836 | phenyl | Me | H | F | H | H | F | Cl | H | nonafluoro-2-butyl | H | OCF3 |
| 7-5837 | phenyl | Me | H | F | H | H | F | Br | H | nonafluoro-2-butyl | H | CF3 |
| 7-5838 | phenyl | Me | H | F | H | H | F | CF3 | H | nonafluoro-2-butyl | H | CF3 |
| 7-5839 | phenyl | Me | H | H | F | F | H | Cl | H | pentafluoroethyl | H | Cl |
| 7-5840 | phenyl | Me | H | H | F | F | H | Br | H | heptafluoroisopropyl | H | Br |
| 7-5841 | phenyl | Me | H | H | F | F | H | Br | H | heptafluoroisopropyl | H | OCF3 |
| 7-5842 | phenyl | Me | H | H | F | F | H | I | H | heptafluoroisopropyl | H | CF3 |
| 7-5843 | phenyl | Me | H | H | F | F | H | CF3 | H | heptafluoroisopropyl | H | CF3 |
| 7-5844 | phenyl | Me | H | H | F | F | H | I | H | nonafluoro-2-butyl | H | I |
| 7-5845 | phenyl | Me | H | H | F | F | H | Cl | H | nonafluoro-2-butyl | H | OCF3 |
| 7-5846 | phenyl | Me | H | H | F | F | H | Br | H | nonafluoro-2-butyl | H | CF3 |
| 7-5847 | phenyl | Me | H | H | F | F | H | CF3 | H | nonafluoro-2-butyl | H | CF3 |
| 7-5848 | phenyl | Me | H | H | F | H | F | Cl | H | pentafluoroethyl | H | Cl |
| 7-5849 | phenyl | Me | H | H | F | H | F | Br | H | heptafluoroisopropyl | H | Br |
| 7-5850 | phenyl | Me | H | H | F | H | F | Br | H | heptafluoroisopropyl | H | OCF3 |
| 7-5851 | phenyl | Me | H | H | F | H | F | I | H | heptafluoroisopropyl | H | CF3 |
| 7-5852 | phenyl | Me | H | H | F | H | F | CF3 | H | heptafluoroisopropyl | H | CF3 |
| 7-5853 | phenyl | Me | H | H | F | H | F | I | H | nonafluoro-2-butyl | H | I |
| 7-5854 | phenyl | Me | H | H | F | H | F | Cl | H | nonafluoro-2-butyl | H | OCF3 |
| 7-5855 | phenyl | Me | H | H | F | H | F | Br | H | nonafluoro-2-butyl | H | CF3 |
| 7-5856 | phenyl | Me | H | H | F | H | F | CF3 | H | nonafluoro-2-butyl | H | CF3 |
| 7-5857 | phenyl | Me | H | H | H | F | F | Cl | H | pentafluoroethyl | H | Cl |
| 7-5858 | phenyl | Me | H | H | H | F | F | Br | H | heptafluoroisopropyl | H | Br |
| 7-5859 | phenyl | Me | H | H | H | F | F | Br | H | heptafluoroisopropyl | H | OCF3 |
| 7-5860 | phenyl | Me | H | H | H | F | F | I | H | heptafluoroisopropyl | H | CF3 |
| 7-5861 | phenyl | Me | H | H | H | F | F | CF3 | H | heptafluoroisopropyl | H | CF3 |
| 7-5862 | phenyl | Me | H | H | H | F | F | I | H | nonafluoro-2-butyl | H | I |
| 7-5863 | phenyl | Me | H | H | H | F | F | Cl | H | nonafluoro-2-butyl | H | OCF3 |
| 7-5864 | phenyl | Me | H | H | H | F | F | Br | H | nonafluoro-2-butyl | H | CF3 |
| 7-5865 | phenyl | Me | H | H | H | F | F | CF3 | H | nonafluoro-2-butyl | H | CF3 |
| 7-5866 | phenyl | Me | H | F | F | H | F | Cl | H | pentafluoroethyl | H | Cl |
| 7-5867 | phenyl | Me | H | F | F | H | F | Br | H | heptafluoroisopropyl | H | Br |
| 7-5868 | phenyl | Me | H | F | F | H | F | Br | H | heptafluoroisopropyl | H | OCF3 |
| 7-5869 | phenyl | Me | H | F | F | H | F | I | H | heptafluoroisopropyl | H | CF3 |
| 7-5870 | phenyl | Me | H | F | F | H | F | CF3 | H | heptafluoroisopropyl | H | CF3 |
| 7-5871 | phenyl | Me | H | F | F | H | F | I | H | nonafluoro-2-butyl | H | I |
| 7-5872 | phenyl | Me | H | F | F | H | F | Cl | H | nonafluoro-2-butyl | H | OCF3 |
| 7-5873 | phenyl | Me | H | F | F | H | F | Br | H | nonafluoro-2-butyl | H | CF3 |
| 7-5874 | phenyl | Me | H | F | F | H | F | CF3 | H | nonafluoro-2-butyl | H | CF3 |

TABLE 7-continued

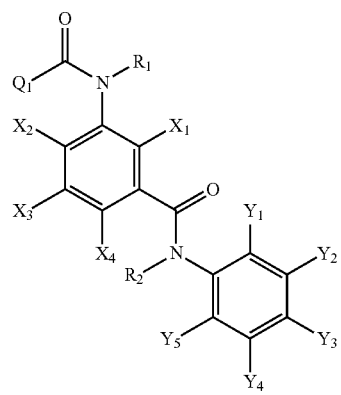

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-5875 | phenyl | Me | H | F | H | F | F | Cl | H | pentafluoroethyl | H | Cl |
| 7-5876 | phenyl | Me | H | F | H | F | F | Br | H | heptafluoroisopropyl | H | Br |
| 7-5877 | phenyl | Me | H | F | H | F | F | Br | H | heptafluoroisopropyl | H | OCF3 |
| 7-5878 | phenyl | Me | H | F | H | F | F | I | H | heptafluoroisopropyl | H | CF3 |
| 7-5879 | phenyl | Me | H | F | H | F | F | CF3 | H | heptafluoroisopropyl | H | CF3 |
| 7-5880 | phenyl | Me | H | F | H | F | F | I | H | nonafluoro-2-butyl | H | I |
| 7-5881 | phenyl | Me | H | F | H | F | F | Cl | H | nonafluoro-2-butyl | H | OCF3 |
| 7-5882 | phenyl | Me | H | F | H | F | F | Br | H | nonafluoro-2-butyl | H | CF3 |
| 7-5883 | phenyl | Me | H | F | H | F | F | CF3 | H | nonafluoro-2-butyl | H | CF3 |
| 7-5884 | phenyl | Me | H | H | F | F | F | Cl | H | pentafluoroethyl | H | Cl |
| 7-5885 | phenyl | Me | H | H | F | F | F | Br | H | heptafluoroisopropyl | H | Br |
| 7-5886 | phenyl | Me | H | H | F | F | F | Br | H | heptafluoroisopropyl | H | OCF3 |
| 7-5887 | phenyl | Me | H | H | F | F | F | I | H | heptafluoroisopropyl | H | CF3 |
| 7-5888 | phenyl | Me | H | H | F | F | F | CF3 | H | heptafluoroisopropyl | H | CF3 |
| 7-5889 | phenyl | Me | H | H | F | F | F | I | H | nonafluoro-2-butyl | H | I |
| 7-5890 | phenyl | Me | H | H | F | F | F | Cl | H | nonafluoro-2-butyl | H | OCF3 |
| 7-5891 | phenyl | Me | H | H | F | F | F | Br | H | nonafluoro-2-butyl | H | CF3 |
| 7-5892 | phenyl | Me | H | H | F | F | F | CF3 | H | nonafluoro-2-butyl | H | CF3 |
| 7-5893 | phenyl | Me | H | F | F | F | F | Cl | H | pentafluoroethyl | H | Cl |
| 7-5894 | phenyl | Me | H | F | F | F | F | Br | H | heptafluoroisopropyl | H | Br |
| 7-5895 | phenyl | Me | H | F | F | F | F | Br | H | heptafluoroisopropyl | H | OCF3 |
| 7-5896 | phenyl | Me | H | F | F | F | F | I | H | heptafluoroisopropyl | H | CF3 |
| 7-5897 | phenyl | Me | H | F | F | F | F | CF3 | H | heptafluoroisopropyl | H | CF3 |
| 7-5898 | phenyl | Me | H | F | F | F | F | I | H | nonafluoro-2-butyl | H | I |
| 7-5899 | phenyl | Me | H | F | F | F | F | Cl | H | nonafluoro-2-butyl | H | OCF3 |
| 7-5900 | phenyl | Me | H | F | F | F | F | Br | H | nonafluoro-2-butyl | H | CF3 |
| 7-5901 | phenyl | Me | H | F | F | F | F | CF3 | H | nonafluoro-2-butyl | H | CF3 |
| 7-5902 | phenyl | Me | H | F | H | H | H | I | H | heptafluoroisopropyl | H | Br |
| 7-5903 | 2-chloropyridine-3-yl | Me | H | F | H | H | H | I | H | heptafluoroisopropyl | H | Br |
| 7-5904 | 3-fluorophenyl | Me | H | H | H | H | H | I | H | nonafluoro-2-butyl | H | I |
| 7-5905 | 4-fluorophenyl | Me | H | H | H | H | H | I | H | nonafluoro-2-butyl | H | I |
| 7-5906 | 3-fluorophenyl | Me | H | H | H | H | H | Br | H | nonafluoro-2-butyl | H | Br |
| 7-5907 | 4-fluorophenyl | Me | H | H | H | H | H | Br | H | nonafluoro-2-butyl | H | Br |
| 7-5908 | 4-(methylsulfonyl)phenyl | Me | H | H | H | H | H | Br | H | heptafluoroisopropyl | H | CF3 |
| 7-5909 | pyrimidine-5-yl | Me | H | H | H | H | H | I | H | heptafluoroisopropyl | H | CF3 |
| 7-5910 | 3-cyano-5-(methoxycarbonyl)phenyl | Me | H | F | H | H | H | Br | H | heptafluoroisopropyl | H | CF3 |
| 7-5911 | phenyl | Me | H | H | H | H | H | Br | H | pentafluoroethyl | H | CF3 |
| 7-5912 | 2-chloropyridine-3-yl | Me | H | H | H | H | H | Br | H | pentafluoroethyl | H | CF3 |

TABLE 8

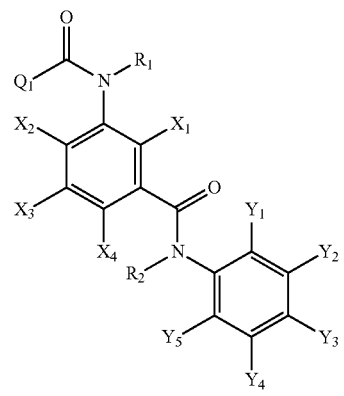

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 8-1 | phenyl | H | Me | H | H | H | H | F | H | nonafluoro-2-butyl | H | F |
| 8-2 | 3-cyanophenyl | H | Me | H | H | H | H | F | H | nonafluoro-2-butyl | H | F |
| 8-3 | 4-cyanophenyl | H | Me | H | H | H | H | F | H | nonafluoro-2-butyl | H | F |
| 8-4 | 2-chloropyridin-3-yl | H | Me | H | H | H | H | F | H | nonafluoro-2-butyl | H | F |
| 8-5 | phenyl | H | Me | H | H | H | H | Cl | H | nonafluoro-2-butyl | H | Cl |
| 8-12 | 3-cyanophenyl | H | Me | H | H | H | H | Cl | H | nonafluoro-2-butyl | H | Cl |
| 8-13 | 4-cyanophenyl | H | Me | H | H | H | H | Cl | H | nonafluoro-2-butyl | H | Cl |
| 8-24 | 2-chloropyridin-3-yl | H | Me | H | H | H | H | Cl | H | nonafluoro-2-butyl | H | Cl |
| 8-38 | phenyl | H | Me | H | H | H | H | Br | H | nonafluoro-2-butyl | H | Br |
| 8-45 | 3-cyanophenyl | H | Me | H | H | H | H | Br | H | nonafluoro-2-butyl | H | Br |
| 8-46 | 4-cyanophenyl | H | Me | H | H | H | H | Br | H | nonafluoro-2-butyl | H | Br |
| 8-57 | 2-chloropyridin-3-yl | H | Me | H | H | H | H | Br | H | nonafluoro-2-butyl | H | Br |
| 8-71 | phenyl | H | Me | H | H | H | H | I | H | nonafluoro-2-butyl | H | I |
| 8-78 | 3-cyanophenyl | H | Me | H | H | H | H | I | H | nonafluoro-2-butyl | H | I |
| 8-79 | 4-cyanophenyl | H | Me | H | H | H | H | I | H | nonafluoro-2-butyl | H | I |
| 8-90 | 2-chloropyridin-3-yl | H | Me | H | H | H | H | I | H | nonafluoro-2-butyl | H | I |
| 8-104 | phenyl | H | Me | H | H | H | H | F | H | nonafluoro-2-butyl | H | Cl |
| 8-105 | phenyl | H | Me | H | H | H | H | F | H | nonafluoro-2-butyl | H | Br |
| 8-106 | phenyl | H | Me | H | H | H | H | F | H | nonafluoro-2-butyl | H | I |
| 8-107 | phenyl | H | Me | H | H | H | H | Cl | H | nonafluoro-2-butyl | H | Br |
| 8-108 | phenyl | H | Me | H | H | H | H | Cl | H | nonafluoro-2-butyl | H | I |
| 8-109 | phenyl | H | Me | H | H | H | H | Br | H | nonafluoro-2-butyl | H | I |
| 8-110 | phenyl | H | Me | H | H | H | H | F | H | heptafluoroisopropyl | H | CF3 |
| 8-111 | phenyl | H | Me | H | H | H | H | Cl | H | heptafluoroisopropyl | H | CF3 |
| 8-131 | 3-cyanophenyl | H | Me | H | H | H | H | Cl | H | heptafluoroisopropyl | H | CF3 |
| 8-132 | 4-cyanophenyl | H | Me | H | H | H | H | Cl | H | heptafluoroisopropyl | H | CF3 |
| 8-147 | 2-chloropyridin-3-yl | H | Me | H | H | H | H | Cl | H | heptafluoroisopropyl | H | CF3 |
| 8-189 | phenyl | H | Me | H | H | H | H | F | H | nonafluoro-2-butyl | H | CF3 |
| 8-190 | phenyl | H | Me | H | H | H | H | Cl | H | nonafluoro-2-butyl | H | CF3 |
| 8-210 | 3-cyanophenyl | H | Me | H | H | H | H | Cl | H | nonafluoro-2-butyl | H | CF3 |
| 8-211 | 4-cyanophenyl | H | Me | H | H | H | H | Cl | H | nonafluoro-2-butyl | H | CF3 |
| 8-226 | 2-chloropyridin-3-yl | H | Me | H | H | H | H | Cl | H | nonafluoro-2-butyl | H | CF3 |
| 8-268 | phenyl | H | Me | H | H | H | H | Br | H | heptafluoroisopropyl | H | CF3 |
| 8-288 | 3-cyanophenyl | H | Me | H | H | H | H | Br | H | heptafluoroisopropyl | H | CF3 |
| 8-289 | 4-cyanophenyl | H | Me | H | H | H | H | Br | H | heptafluoroisopropyl | H | CF3 |
| 8-304 | 2-chloropyridin-3-yl | H | Me | H | H | H | H | Br | H | heptafluoroisopropyl | H | CF3 |
| 8-305 | 2-bromopyridin-3-yl | H | Me | H | H | H | H | Br | H | heptafluoroisopropyl | H | CF3 |
| 8-346 | phenyl | H | Me | H | H | H | H | Br | H | nonafluoro-2-butyl | H | CF3 |
| 8-366 | 3-cyanophenyl | H | Me | H | H | H | H | Br | H | nonafluoro-2-butyl | H | CF3 |
| 8-367 | 4-cyanophenyl | H | Me | H | H | H | H | Br | H | nonafluoro-2-butyl | H | CF3 |
| 8-382 | 2-chloropyridin-3-yl | H | Me | H | H | H | H | Br | H | nonafluoro-2-butyl | H | CF3 |
| 8-424 | phenyl | H | Me | H | H | H | H | I | H | heptafluoroisopropyl | H | CF3 |
| 8-444 | 3-cyanophenyl | H | Me | H | H | H | H | I | H | heptafluoroisopropyl | H | CF3 |
| 8-445 | 4-cyanophenyl | H | Me | H | H | H | H | I | H | heptafluoroisopropyl | H | CF3 |
| 8-460 | 2-chloropyridin-3-yl | H | Me | H | H | H | H | I | H | heptafluoroisopropyl | H | CF3 |
| 8-502 | phenyl | H | Me | H | H | H | H | I | H | nonafluoro-2-butyl | H | CF3 |
| 8-522 | 3-cyanophenyl | H | Me | H | H | H | H | I | H | nonafluoro-2-butyl | H | CF3 |
| 8-523 | 4-cyanophenyl | H | Me | H | H | H | H | I | H | nonafluoro-2-butyl | H | CF3 |
| 8-538 | 2-chloropyridin-3-yl | H | Me | H | H | H | H | I | H | nonafluoro-2-butyl | H | CF3 |
| 8-580 | phenyl | H | Me | H | H | H | H | OCF3 | H | heptafluoroisopropyl | H | OCF3 |
| 8-611 | 2-chloropyridin-3-yl | H | Me | H | H | H | H | OCF3 | H | heptafluoroisopropyl | H | OCF3 |
| 8-636 | phenyl | H | Me | H | H | H | H | OCF3 | H | nonafluoro-2-butyl | H | OCF3 |
| 8-667 | 2-chloropyridin-3-yl | H | Me | H | H | H | H | OCF3 | H | nonafluoro-2-butyl | H | OCF3 |
| 8-692 | phenyl | H | Me | H | H | H | H | CF3 | H | heptafluoroisopropyl | H | OCF3 |
| 8-723 | 2-chloropyridin-3-yl | H | Me | H | H | H | H | CF3 | H | heptafluoroisopropyl | H | OCF3 |
| 8-748 | phenyl | H | Me | H | H | H | H | CF3 | H | nonafluoro-2-butyl | H | OCF3 |
| 8-779 | 2-chloropyridin-3-yl | H | Me | H | H | H | H | CF3 | H | nonafluoro-2-butyl | H | OCF3 |

TABLE 8-continued

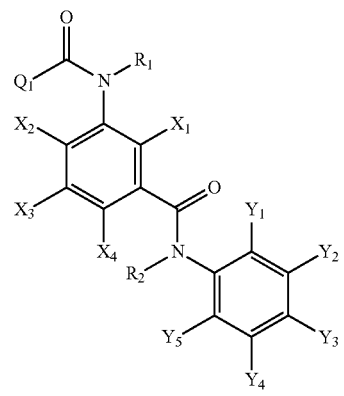

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 8-804 | phenyl | H | Me | H | H | H | H | CF3 | H | heptafluoroisopropyl | H | CF3 |
| 8-824 | 3-cyanophenyl | H | Me | H | H | H | H | CF3 | H | heptafluoroisopropyl | H | CF3 |
| 8-825 | 4-cyanophenyl | H | Me | H | H | H | H | CF3 | H | heptafluoroisopropyl | H | CF3 |
| 8-840 | 2-chloropyridin-3-yl | H | Me | H | H | H | H | CF3 | H | heptafluoroisopropyl | H | CF3 |
| 8-841 | 2-bromopyridin-3-yl | H | Me | H | H | H | H | CF3 | H | heptafluoroisopropyl | H | CF3 |
| 8-872 | phenyl | H | Me | H | H | H | H | CF3 | H | nonafluoro-2-butyl | H | CF3 |
| 8-892 | 3-cyanophenyl | H | Me | H | H | H | H | CF3 | H | nonafluoro-2-butyl | H | CF3 |
| 8-893 | 4-cyanophenyl | H | Me | H | H | H | H | CF3 | H | nonafluoro-2-butyl | H | CF3 |
| 8-908 | 2-chloropyridin-3-yl | H | Me | H | H | H | H | CF3 | H | nonafluoro-2-butyl | H | CF3 |
| 8-940 | phenyl | H | Me | F | H | H | H | F | H | heptafluoroisopropyl | H | F |
| 8-941 | 3-cyanophenyl | H | Me | F | H | H | H | F | H | heptafluoroisopropyl | H | F |
| 8-942 | 4-cyanophenyl | H | Me | F | H | H | H | F | H | heptafluoroisopropyl | H | F |
| 8-943 | 2-chloropyridin-3-yl | H | Me | F | H | H | H | F | H | heptafluorosopropyl | H | F |
| 8-944 | phenyl | H | Me | F | H | H | H | F | H | nonafluoro-2-butyl | H | F |
| 8-945 | 3-cyanophenyl | H | Me | F | H | H | H | F | H | nonafluoro-2-butyl | H | F |
| 8-946 | 4-cyanophenyl | H | Me | F | H | H | H | F | H | nonafluoro-2-butyl | H | F |
| 8-947 | 2-chloropyridin-3-yl | H | Me | F | H | H | H | F | H | nonafluoro-2-butyl | H | F |
| 8-948 | phenyl | H | Me | F | H | H | H | Cl | H | heptafluoroisopropyl | H | Cl |
| 8-952 | 2-chlorophenyl | H | Me | F | H | H | H | F | H | heptafluoroisopropyl | H | Cl |
| 8-956 | 3-bromophenyl | H | Me | F | H | H | H | F | H | heptafluoroisopropyl | H | Br |
| 8-961 | (2-trifluoromethyl)phenyl | H | i-Pr | F | H | H | H | F | H | heptafluoroisopropyl | H | I |
| 8-964 | 2-nitrophenyl | H | Me | F | H | H | H | Cl | H | heptafluoroisopropyl | H | Br |
| 8-968 | 3-cyanophenyl | H | Me | F | H | H | H | Cl | H | heptafluoroisopropyl | H | Cl |
| 8-969 | 4-cyanophenyl | H | Me | F | H | H | H | Cl | H | heptafluoroisopropyl | H | Cl |
| 8-970 | 2,6-difluorophenyl | H | Me | F | H | H | H | Cl | H | heptafluoroisopropyl | H | I |
| 8-982 | pyridin-3-yl | H | Me | F | H | H | H | Br | H | heptafluoroisopropyl | H | I |
| 8-984 | 2-chloropyridin-3-yl | H | Me | F | H | H | H | Cl | H | heptafluoroisopropyl | H | Cl |
| 8-1026 | phenyl | H | Me | F | H | H | H | Cl | H | nonafluoro-2-butyl | H | Cl |
| 8-1046 | 3-cyanophenyl | H | Me | F | H | H | H | Cl | H | nonafluoro-2-butyl | H | Cl |
| 8-1047 | 4-cyanophenyl | H | Me | F | H | H | H | Cl | H | nonafluoro-2-butyl | H | Cl |
| 8-1062 | 2-chloropyridin-3-yl | H | Me | F | H | H | H | Cl | H | nonafluoro-2-butyl | H | Cl |
| 8-1104 | phenyl | H | Me | F | H | H | H | Br | H | heptafluoroisopropyl | H | Br |
| 8-1124 | 3-cyanophenyl | H | Me | F | H | H | H | Br | H | heptafluoroisopropyl | H | Br |
| 8-1125 | 4-cyanophenyl | H | Me | F | H | H | H | Br | H | heptafluoroisopropyl | H | Br |
| 8-1140 | 2-chloropyridin-3-yl | H | Me | F | H | H | H | Br | H | heptafluoroisopropyl | H | Br |
| 8-1182 | phenyl | H | Me | F | H | H | H | Br | H | nonafluoro-2-butyl | H | Br |
| 8-1202 | 3-cyanophenyl | H | Me | F | H | H | H | Br | H | nonafluoro-2-butyl | H | Br |
| 8-1203 | 4-cyanophenyl | H | Me | F | H | H | H | Br | H | nonafluoro-2-butyl | H | Br |
| 8-1218 | 2-chloropyridin-3-yl | H | Me | F | H | H | H | Br | H | nonafluoro-2-butyl | H | Br |
| 8-1260 | phenyl | H | Me | F | H | H | H | I | H | heptafluoroisopropyl | H | I |
| 8-1280 | 3-cyanophenyl | H | Me | F | H | H | H | I | H | heptafluoroisopropyl | H | I |
| 8-1281 | 4-cyanophenyl | H | Me | F | H | H | H | I | H | heptafluoroisopropyl | H | I |
| 8-1296 | 2-chloropyridin-3-yl | H | Me | F | H | H | H | I | H | heptafluoroisopropyl | H | I |
| 8-1338 | phenyl | H | Me | F | H | H | H | I | H | nonafluoro-2-butyl | H | I |
| 8-1358 | 3-cyanophenyl | H | Me | F | H | H | H | I | H | nonafluoro-2-butyl | H | I |
| 8-1359 | 4-cyanophenyl | H | Me | F | H | H | H | I | H | nonafluoro-2-butyl | H | I |
| 8-1374 | 2-chloropyridin-3-yl | H | Me | F | H | H | H | I | H | nonafluoro-2-butyl | H | I |
| 8-1416 | phenyl | H | Me | F | H | H | H | F | H | heptafluoroisopropyl | H | CF3 |
| 8-1417 | phenyl | H | Me | F | H | H | H | Cl | H | heptafluoroisopropyl | H | CF3 |
| 8-1431 | (3-trifluoromethyl)phenyl | H | Et | F | H | H | H | Cl | H | heptafluoroisopropyl | H | CF3 |
| 8-1437 | 3-cyanophenyl | H | Me | F | H | H | H | Cl | H | heptafluoroisopropyl | H | CF3 |
| 8-1438 | 4-cyanophenyl | H | Me | F | H | H | H | Cl | H | heptafluoroisopropyl | H | CF3 |
| 8-1442 | 2-chloro-4-fluorophenyl | H | n-Pr | F | H | H | H | Cl | H | heptafluoroisopropyl | H | CF3 |
| 8-1453 | 2-chloropyridin-3-yl | H | Me | F | H | H | H | Cl | H | heptafluoroisopropyl | H | CF3 |
| 8-1459 | 6-fluoropyridin-3-yl | H | i-Pr | F | H | H | H | Cl | H | heptafluoroisopropyl | H | CF3 |
| 8-1475 | 4-bromopyridin-3-yl | H | CH2CH=CH2 | F | H | H | H | Cl | H | heptafluoroisopropyl | H | n-C3F7 |
| 8-1482 | pyridin-4-yl | H | CN | F | H | H | H | Cl | H | heptafluoroisopropyl | H | CF3 |

TABLE 8-continued

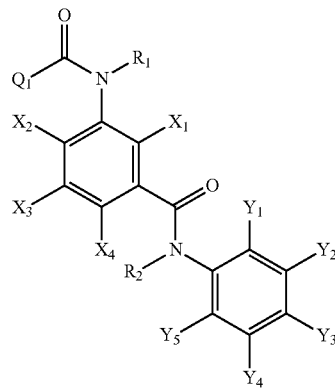

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 8-1495 | phenyl | H | Me | F | H | H | H | F | H | nonafluoro-2-butyl | H | CF3 |
| 8-1496 | phenyl | H | Me | F | H | H | H | Cl | H | nonafluoro-2-butyl | H | CF3 |
| 8-1504 | 3-bromophenyl | H | CH2C≡CH | F | H | H | H | Cl | H | nonafluoro-2-butyl | H | CF3 |
| 8-1511 | (4-trifluoromethyl)phenyl | H | NH2 | F | H | H | H | Cl | H | nonafluoro-2-butyl | H | CF3 |
| 8-1516 | 3-cyanophenyl | H | Me | F | H | H | H | Cl | H | nonafluoro-2-butyl | H | CF3 |
| 8-1517 | 4-cyanophenyl | H | Me | F | H | H | H | Cl | H | nonafluoro-2-butyl | H | CF3 |
| 8-1524 | 2-bromo-4-chlorophenyl | H | C(O)OMe | F | H | H | H | Cl | H | nonafluoro-2-butyl | H | CF3 |
| 8-1532 | 2-chloropyridin-3-yl | H | Me | F | H | H | H | Cl | H | nonafluoro-2-butyl | H | CF3 |
| 8-1545 | 5-fluoropyridin-3-yl | H | C(O)OEt | F | H | H | H | Cl | H | nonafluoro-2-butyl | H | C2F5 |
| 8-1554 | 4-bromopyridin-3-yl | H | C(O)C(O)Me | F | H | H | H | Cl | H | nonafluoro-2-butyl | H | CF3 |
| 8-1557 | 4-nitropyridin-3-yl | H | C(O)C(O)Et | F | H | H | H | Cl | H | nonafluoro-2-butyl | H | i-C3F7 |
| 8-1571 | 5-iodopyridin-2-yl | H | C(O)Me | F | H | H | H | Cl | H | nonafluoro-2-butyl | H | CF3 |
| 8-1573 | 4-cyanopyridin-2-yl | H | C(O)Et | F | H | H | H | Cl | H | nonafluoro-2-butyl | H | C2F5 |
| 8-1574 | phenyl | H | Me | F | H | H | H | Br | H | heptafluoroisopropyl | H | CF3 |
| 8-1588 | (3-trifluoromethyl)phenyl | H | S(O)2Me | F | H | H | H | Br | H | heptafluoroisopropyl | H | CF3 |
| 8-1594 | 3-cyanophenyl | H | Me | F | H | H | H | Br | H | heptafluoroisopropyl | H | CF3 |
| 8-1595 | 4-cyanophenyl | H | Me | F | H | H | H | Br | H | heptafluoroisopropyl | H | CF3 |
| 8-1606 | 4-cyano-2-fluorophenyl | H | S(O)2Et | F | H | H | H | Br | H | heptafluoroisopropyl | H | CF3 |
| 8-1610 | 2-chloropyridin-3-yl | H | Me | F | H | H | H | Br | H | heptafluoroisopropyl | H | CF3 |
| 8-1621 | 6-nitropyridin-3-yl | H | CH2Ph | F | H | H | H | Br | H | heptafluoroisopropyl | H | CF3 |
| 8-1630 | 4-fluoropyridin-3-yl | H | CH2(3-Py) | F | H | H | H | Br | H | heptafluoroisopropyl | H | CF3 |
| 8-1651 | 4-cyanopyridin-2-yl | H | CH2(3-Py—N-oxide) | F | H | H | H | Br | H | heptafluoroisopropyl | H | CF3 |
| 8-1652 | phenyl | H | Me | F | H | H | H | Br | H | nonafluoro-2-butyl | H | CF3 |
| 8-1672 | 3-cyanophenyl | H | Me | F | H | H | H | Br | H | nonafluoro-2-butyl | H | CF3 |
| 8-1673 | 4-cyanophenyl | H | Me | F | H | H | H | Br | H | nonafluoro-2-butyl | H | CF3 |
| 8-1679 | 4-bromo-2-chlorophenyl | H | Et | F | H | H | H | Br | H | nonafluoro-2-butyl | H | CF3 |
| 8-1688 | 2-chloropyridin-3-yl | H | Me | F | H | H | H | Br | H | nonafluoro-2-butyl | H | CF3 |
| 8-1705 | 5-(trifluoromethyl)pyridin-3-yl | H | CN | F | H | H | H | Br | H | nonafluoro-2-butyl | H | CF3 |
| 8-1730 | phenyl | H | Me | F | H | H | H | I | H | heptafluoroisopropyl | H | CF3 |
| 8-1750 | 3-cyanophenyl | H | Me | F | H | H | H | I | H | heptafluoroisopropyl | H | CF3 |
| 8-1751 | 4-cyanophenyl | H | Me | F | H | H | H | I | H | heptafluoroisopropyl | H | CF3 |
| 8-1766 | 2-chloropyridin-3-yl | H | Me | F | H | H | H | I | H | heptafluoroisopropyl | H | CF3 |
| 8-1779 | 5-fluoropyridin-3-yl | H | C(O)Me | F | H | H | H | I | H | heptafluoroisopropyl | H | CF3 |
| 8-1808 | phenyl | H | Me | F | H | H | H | I | H | nonafluoro-2-butyl | H | CF3 |
| 8-1828 | 3-cyanophenyl | H | Me | F | H | H | H | I | H | nonafluoro-2-butyl | H | CF3 |
| 8-1829 | 4-cyanophenyl | H | Me | F | H | H | H | I | H | nonafluoro-2-butyl | H | CF3 |
| 8-1844 | 2-chloropyridin-3-yl | H | Me | F | H | H | H | I | H | nonafluoro-2-butyl | H | CF3 |
| 8-1886 | phenyl | H | Me | F | H | H | H | OCF3 | H | heptafluoroisopropyl | H | OCF3 |
| 8-1901 | 3-cyanophenyl | H | Me | F | H | H | H | OCF3 | H | heptafluoroisopropyl | H | OCF3 |
| 8-1902 | 4-cyanophenyl | H | Me | F | H | H | H | OCF3 | H | heptafluoroisopropyl | H | OCF3 |
| 8-1917 | 2-chloropyridin-3-yl | H | Me | F | H | H | H | OCF3 | H | heptafluoroisopropyl | H | OCF3 |
| 8-1942 | phenyl | H | Me | F | H | H | H | OCF3 | H | nonafluoro-2-butyl | H | OCF3 |
| 8-1957 | 3-cyanophenyl | H | Me | F | H | H | H | OCF3 | H | nonafluoro-2-butyl | H | OCF3 |
| 8-1958 | 4-cyanophenyl | H | Me | F | H | H | H | OCF3 | H | nonafluoro-2-butyl | H | OCF3 |
| 8-1973 | 2-chloropyridin-3-yl | H | Me | F | H | H | H | OCF3 | H | nonafluoro-2-butyl | H | OCF3 |
| 8-1998 | phenyl | H | Me | F | H | H | H | CF3 | H | heptafluoroisopropyl | H | OCF3 |
| 8-2013 | 3-cyanophenyl | H | Me | F | H | H | H | CF3 | H | heptafluoroisopropyl | H | OCF3 |
| 8-2014 | 4-cyanophenyl | H | Me | F | H | H | H | CF3 | H | heptafluoroisopropyl | H | OCF3 |
| 8-2029 | 2-chloropyridin-3-yl | H | Me | F | H | H | H | CF3 | H | heptafluoroisopropyl | H | OCF3 |
| 8-2054 | phenyl | H | Me | F | H | H | H | CF3 | H | nonafluoro-2-butyl | H | OCF3 |
| 8-2069 | 3-cyanophenyl | H | Me | F | H | H | H | CF3 | H | nonafluoro-2-butyl | H | OCF3 |
| 8-2070 | 4-cyanophenyl | H | Me | F | H | H | H | CF3 | H | nonafluoro-2-butyl | H | OCF3 |
| 8-2085 | 2-chloropyridin-3-yl | H | Me | F | H | H | H | CF3 | H | nonafluoro-2-butyl | H | OCF3 |
| 8-2110 | phenyl | H | Me | F | H | H | H | CF3 | H | heptafluoroisopropyl | H | CF3 |
| 8-2130 | 3-cyanophenyl | H | Me | F | H | H | H | CF3 | H | heptafluoroisopropyl | H | CF3 |
| 8-2131 | 4-cyanophenyl | H | Me | F | H | H | H | CF3 | H | heptafluoroisopropyl | H | CF3 |

TABLE 8-continued

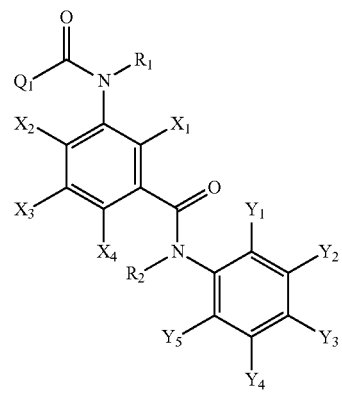

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 8-2146 | 2-chloropyridin-3-yl | H | Me | F | H | H | H | CF3 | H | heptafluoroisopropyl | H | CF3 |
| 8-2178 | phenyl | H | Me | F | H | H | H | CF3 | H | nonafluoro-2-butyl | H | CF3 |
| 8-2198 | 3-cyanophenyl | H | Me | F | H | H | H | CF3 | H | nonafluoro-2-butyl | H | CF3 |
| 8-2199 | 4-cyanophenyl | H | Me | F | H | H | H | CF3 | H | nonafluoro-2-butyl | H | CF3 |
| 8-2214 | 2-chloropyridin-3-yl | H | Me | F | H | H | H | CF3 | H | nonafluoro-2-butyl | H | CF3 |
| 8-2246 | phenyl | H | Me | H | F | H | H | F | H | heptafluoroisopropyl | H | F |
| 8-2247 | 3-cyanophenyl | H | Me | H | F | H | H | F | H | heptafluoroisopropyl | H | F |
| 8-2248 | 4-cyanophenyl | H | Me | H | F | H | H | F | H | heptafluoroisopropyl | H | F |
| 8-2249 | 2-chloropyridin-3-yl | H | Me | H | F | H | H | F | H | heptafluoroisopropyl | H | F |
| 8-2250 | phenyl | H | Me | H | F | H | H | F | H | nonafluoro-2-butyl | H | F |
| 8-2251 | 3-cyanophenyl | H | Me | H | F | H | H | F | H | nonafluoro-2-butyl | H | F |
| 8-2252 | 4-cyanophenyl | H | Me | H | F | H | H | F | H | nonafluoro-2-butyl | H | F |
| 8-2253 | 2-chloropyridin-3-yl | H | Me | H | F | H | H | F | H | nonafluoro-2-butyl | H | F |
| 8-2254 | phenyl | H | Me | H | F | H | H | Cl | H | heptafluoroisopropyl | H | Cl |
| 8-2274 | 3-cyanophenyl | H | Me | H | F | H | H | Cl | H | heptafluoroisopropyl | H | Cl |
| 8-2275 | 4-cyanophenyl | H | Me | H | F | H | H | Cl | H | heptafluoroisopropyl | H | Cl |
| 8-2290 | 2-chloropyridin-3-yl | H | Me | H | F | H | H | Cl | H | heptafluoroisopropyl | H | Cl |
| 8-2332 | phenyl | H | Me | H | F | H | H | Cl | H | nonafluoro-2-butyl | H | Cl |
| 8-2352 | 3-cyanophenyl | H | Me | H | F | H | H | Cl | H | nonafluoro-2-butyl | H | Cl |
| 8-2353 | 4-cyanophenyl | H | Me | H | F | H | H | Cl | H | nonafluoro-2-butyl | H | Cl |
| 8-2368 | 2-chloropyridin-3-yl | H | Me | H | F | H | H | Cl | H | nonafluoro-2-butyl | H | Cl |
| 8-2410 | phenyl | H | Me | H | F | H | H | Br | H | heptafluoroisopropyl | H | Br |
| 8-2430 | 3-cyanophenyl | H | Me | H | F | H | H | Br | H | heptafluoroisopropyl | H | Br |
| 8-2431 | 4-cyanophenyl | H | Me | H | F | H | H | Br | H | heptafluoroisopropyl | H | Br |
| 8-2446 | 2-chloropyridin-3-yl | H | Me | H | F | H | H | Br | H | heptafluoroisopropyl | H | Br |
| 8-2488 | phenyl | H | Me | H | F | H | H | Br | H | nonafluoro-2-butyl | H | Br |
| 8-2508 | 3-cyanophenyl | H | Me | H | F | H | H | Br | H | nonafluoro-2-butyl | H | Br |
| 8-2509 | 4-cyanophenyl | H | Me | H | F | H | H | Br | H | nonafluoro-2-butyl | H | Br |
| 8-2524 | 2-chloropyridin-3-yl | H | Me | H | F | H | H | Br | H | nonafluoro-2-butyl | H | Br |
| 8-2566 | phenyl | H | Me | H | F | H | H | I | H | heptafluoroisopropyl | H | I |
| 8-2586 | 3-cyanophenyl | H | Me | H | F | H | H | I | H | heptafluoroisopropyl | H | I |
| 8-2587 | 4-cyanophenyl | H | Me | H | F | H | H | I | H | heptafluoroisopropyl | H | I |
| 8-2602 | 2-chloropyridin-3-yl | H | Me | H | F | H | H | I | H | heptafluoroisopropyl | H | I |
| 8-2644 | phenyl | H | Me | H | F | H | H | I | H | nonafluoro-2-butyl | H | I |
| 8-2664 | 3-cyanophenyl | H | Me | H | F | H | H | I | H | nonafluoro-2-butyl | H | I |
| 8-2665 | 4-cyanophenyl | H | Me | H | F | H | H | I | H | nonafluoro-2-butyl | H | I |
| 8-2680 | 2-chloropyridin-3-yl | H | Me | H | F | H | H | I | H | nonafluoro-2-butyl | H | I |
| 8-2722 | phenyl | H | Me | H | F | H | H | Cl | H | heptafluoroisopropyl | H | OCF3 |
| 8-2742 | 3-cyanophenyl | H | Me | H | F | H | H | Cl | H | heptafluoroisopropyl | H | OCF3 |
| 8-2743 | 4-cyanophenyl | H | Me | H | F | H | H | Cl | H | heptafluoroisopropyl | H | OCF3 |
| 8-2758 | 2-chloropyridin-3-yl | H | Me | H | F | H | H | Cl | H | heptafluoroisopropyl | H | OCF3 |
| 8-2800 | phenyl | H | Me | H | F | H | H | Cl | H | nonafluoro-2-butyl | H | OCF3 |
| 8-2820 | 3-cyanophenyl | H | Me | H | F | H | H | Cl | H | nonafluoro-2-butyl | H | OCF3 |
| 8-2821 | 4-cyanophenyl | H | Me | H | F | H | H | Cl | H | nonafluoro-2-butyl | H | OCF3 |
| 8-2836 | 2-chloropyridin-3-yl | H | Me | H | F | H | H | Cl | H | nonafluoro-2-butyl | H | OCF3 |
| 8-2878 | phenyl | H | Me | H | F | H | H | Br | H | heptafluoroisopropyl | H | OCF3 |
| 8-2898 | 3-cyanophenyl | H | Me | H | F | H | H | Br | H | heptafluoroisopropyl | H | OCF3 |
| 8-2899 | 4-cyanophenyl | H | Me | H | F | H | H | Br | H | heptafluoroisopropyl | H | OCF3 |
| 8-2914 | 2-chloropyridin-3-yl | H | Me | H | F | H | H | Br | H | heptafluoroisopropyl | H | OCF3 |
| 8-2956 | phenyl | H | Me | H | F | H | H | Br | H | nonafluoro-2-butyl | H | OCF3 |
| 8-2976 | 3-cyanophenyl | H | Me | H | F | H | H | Br | H | nonafluoro-2-butyl | H | OCF3 |
| 8-2977 | 4-cyanophenyl | H | Me | H | F | H | H | Br | H | nonafluoro-2-butyl | H | OCF3 |
| 8-2992 | 2-chloropyridin-3-yl | H | Me | H | F | H | H | Br | H | nonafluoro-2-butyl | H | OCF3 |
| 8-3034 | phenyl | H | Me | H | F | H | H | I | H | heptafluoroisopropyl | H | OCF3 |
| 8-3054 | 3-cyanophenyl | H | Me | H | F | H | H | I | H | heptafluoroisopropyl | H | OCF3 |
| 8-3055 | 4-cyanophenyl | H | Me | H | F | H | H | I | H | heptafluoroisopropyl | H | OCF3 |
| 8-3070 | 2-chloropyridin-3-yl | H | Me | H | F | H | H | I | H | heptafluoroisopropyl | H | OCF3 |

TABLE 8-continued

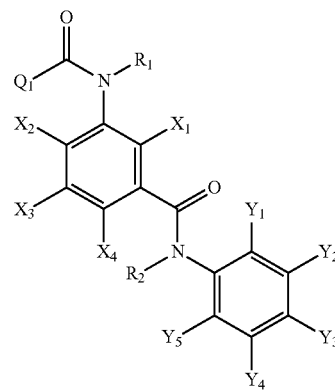

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 8-3112 | phenyl | H | Me | H | F | H | H | I | H | nonafluoro-2-butyl | H | OCF3 |
| 8-3132 | 3-cyanophenyl | H | Me | H | F | H | H | I | H | nonafluoro-2-butyl | H | OCF3 |
| 8-3133 | 4-cyanophenyl | H | Me | H | F | H | H | I | H | nonafluoro-2-butyl | H | OCF3 |
| 8-3148 | 2-chloropyridin-3-yl | H | Me | H | F | H | H | I | H | nonafluoro-2-butyl | H | OCF3 |
| 8-3190 | phenyl | H | Me | H | F | H | H | F | H | heptafluoroisopropyl | H | CF3 |
| 8-3191 | phenyl | H | Me | H | F | H | H | Cl | H | heptafluoroisopropyl | H | CF3 |
| 8-3211 | 3-cyanophenyl | H | Me | H | F | H | H | Cl | H | heptafluoroisopropyl | H | CF3 |
| 8-3212 | 4-cyanophenyl | H | Me | H | F | H | H | Cl | H | heptafluoroisopropyl | H | CF3 |
| 8-3227 | 2-chloropyridin-3-yl | H | Me | H | F | H | H | Cl | H | heptafluoroisopropyl | H | CF3 |
| 8-3269 | phenyl | H | Me | H | F | H | H | F | H | nonafluoro-2-butyl | H | CF3 |
| 8-3270 | phenyl | H | Me | H | F | H | H | Cl | H | nonafluoro-2-butyl | H | CF3 |
| 8-3290 | 3-cyanophenyl | H | Me | H | F | H | H | Cl | H | nonafluoro-2-butyl | H | CF3 |
| 8-3291 | 4-cyanophenyl | H | Me | H | F | H | H | Cl | H | nonafluoro-2-butyl | H | CF3 |
| 8-3306 | 2-chloropyridin-3-yl | H | Me | H | F | H | H | Cl | H | nonafluoro-2-butyl | H | CF3 |
| 8-3348 | phenyl | H | Me | H | F | H | H | Br | H | heptafluoroisopropyl | H | CF3 |
| 8-3368 | 3-cyanophenyl | H | Me | H | F | H | H | Br | H | heptafluoroisopropyl | H | CF3 |
| 8-3369 | 4-cyanophenyl | H | Me | H | F | H | H | Br | H | heptafluoroisopropyl | H | CF3 |
| 8-3384 | 2-chloropyridin-3-yl | H | Me | H | F | H | H | Br | H | heptafluoroisopropyl | H | CF3 |
| 8-3426 | phenyl | H | Me | H | F | H | H | Br | H | nonafluoro-2-butyl | H | CF3 |
| 8-3446 | 3-cyanophenyl | H | Me | H | H | H | H | Br | H | nonafluoro-2-butyl | H | CF3 |
| 8-3447 | 4-cyanophenyl | H | Me | H | F | H | H | Br | H | nonafluoro-2-butyl | H | CF3 |
| 8-3462 | 2-chloropyridin-3-yl | H | Me | H | F | H | H | Br | H | nonafluoro-2-butyl | H | CF3 |
| 8-3504 | phenyl | H | Me | H | F | H | H | I | H | heptafluoroisopropyl | H | CF3 |
| 8-3524 | 3-cyanophenyl | H | Me | H | F | H | H | I | H | heptafluoroisopropyl | H | CF3 |
| 8-3525 | 4-cyanophenyl | H | Me | H | F | H | H | I | H | heptafluoroisopropyl | H | CF3 |
| 8-3540 | 2-chloropyridin-3-yl | H | Me | H | F | H | H | I | H | heptafluoroisopropyl | H | CF3 |
| 8-3582 | phenyl | H | Me | H | F | H | H | I | H | nonafluoro-2-butyl | H | CF3 |
| 8-3602 | 3-cyanophenyl | H | Me | H | F | H | H | I | H | nonafluoro-2-butyl | H | CF3 |
| 8-3603 | 4-cyanophenyl | H | Me | H | F | H | H | I | H | nonafluoro-2-butyl | H | CF3 |
| 8-3618 | 2-chloropyridin-3-yl | H | Me | H | F | H | H | I | H | nonafluoro-2-butyl | H | CF3 |
| 8-3660 | phenyl | H | Me | H | F | H | H | OCF3 | H | heptafluoroisopropyl | H | OCF3 |
| 8-3691 | 2-chloropyridin-3-yl | H | Me | H | F | H | H | OCF3 | H | heptafluoroisopropyl | H | OCF3 |
| 8-3716 | phenyl | H | Me | H | F | H | H | OCF3 | H | nonafluoro-2-butyl | H | OCF3 |
| 8-3747 | 2-chloropyridin-3-yl | H | Me | H | F | H | H | OCF3 | H | nonafluoro-2-butyl | H | OCF3 |
| 8-3772 | phenyl | H | Me | H | F | H | H | CF3 | H | heptafluoroisopropyl | H | OCF3 |
| 8-3803 | 2-chloropyridin-3-yl | H | Me | H | F | H | H | CF3 | H | heptafluoroisopropyl | H | OCF3 |
| 8-3828 | phenyl | H | Me | H | F | H | H | CF3 | H | nonafluoro-2-butyl | H | OCF3 |
| 8-3859 | 2-chloropyridin-3-yl | H | Me | H | F | H | H | CF3 | H | nonafluoro-2-butyl | H | OCF3 |
| 8-3884 | phenyl | H | Me | H | F | H | H | CF3 | H | heptafluoroisopropyl | H | CF3 |
| 8-3904 | 3-cyanophenyl | H | Me | H | F | H | H | CF3 | H | heptafluoroisopropyl | H | CF3 |
| 8-3905 | 4-cyanophenyl | H | Me | H | F | H | H | CF3 | H | heptafluoroisopropyl | H | CF3 |
| 8-3920 | 2-chloropyridin-3-yl | H | Me | H | F | H | H | CF3 | H | heptafluoroisopropyl | H | CF3 |
| 8-3952 | phenyl | H | Me | H | F | H | H | CF3 | H | nonafluoro-2-butyl | H | CF3 |
| 8-3972 | 3-cyanophenyl | H | Me | H | F | H | H | CF3 | H | nonafluoro-2-butyl | H | CF3 |
| 8-3973 | 4-cyanophenyl | H | Me | H | F | H | H | CF3 | H | nonafluoro-2-butyl | H | CF3 |
| 8-3988 | 2-chloropyridin-3-yl | H | Me | H | F | H | H | CF3 | H | nonafluoro-2-butyl | H | CF3 |
| 8-4020 | phenyl | H | Me | F | F | H | H | F | H | heptafluoroisopropyl | H | F |
| 8-4021 | 3-cyanophenyl | H | Me | F | F | H | H | F | H | heptafluoroisopropyl | H | F |
| 8-4022 | 4-cyanophenyl | H | Me | F | F | H | H | F | H | heptafluoroisopropyl | H | F |
| 8-4023 | 2-chloropyridin-3-yl | H | Me | F | F | H | H | F | H | heptafluoroisopropyl | H | F |
| 8-4024 | phenyl | H | Me | F | F | H | H | F | H | nonafluoro-2-butyl | H | F |
| 8-4025 | 3-cyanophenyl | H | Me | F | F | H | H | F | H | nonafluoro-2-butyl | H | F |
| 8-4026 | 4-cyanophenyl | H | Me | F | F | H | H | F | H | nonafluoro-2-butyl | H | F |
| 8-4027 | 2-chloropyridin-3-yl | H | Me | F | F | H | H | F | H | nonafluoro-2-butyl | H | F |
| 8-4028 | phenyl | H | Me | F | F | H | H | Cl | H | heptafluoroisopropyl | H | Cl |
| 8-4048 | 3-cyanophenyl | H | Me | F | F | H | H | Cl | H | heptafluoroisopropyl | H | Cl |
| 8-4049 | 4-cyanophenyl | H | Me | F | F | H | H | Cl | H | heptafluoroisopropyl | H | Cl |

TABLE 8-continued

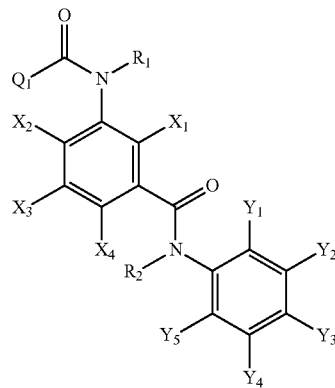

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 8-4064 | 2-chloropyridin-3-yl | H | Me | F | F | H | H | Cl | H | heptafluoroisopropyl | H | Cl |
| 8-4106 | phenyl | H | Me | F | F | H | H | Cl | H | nonafluoro-2-butyl | H | Cl |
| 8-4126 | 3-cyanophenyl | H | Me | F | F | H | H | Cl | H | nonafluoro-2-butyl | H | Cl |
| 8-4127 | 4-cyanophenyl | H | Me | F | F | H | H | Cl | H | nonafluoro-2-butyl | H | Cl |
| 8-4142 | 2-chloropyridin-3-yl | H | Me | F | F | H | H | Cl | H | nonafluoro-2-butyl | H | Cl |
| 8-4184 | phenyl | H | Me | F | F | H | H | Br | H | heptafluoroisopropyl | H | Br |
| 8-4204 | 3-cyanophenyl | H | Me | F | F | H | H | Br | H | heptafluoroisopropyl | H | Br |
| 8-4205 | 4-cyanophenyl | H | Me | F | F | H | H | Br | H | heptafluoroisopropyl | H | Br |
| 8-4220 | 2-chloropyridin-3-yl | H | Me | F | F | H | H | Br | H | heptafluoroisopropyl | H | Br |
| 8-4262 | phenyl | H | Me | F | F | H | H | Br | H | nonafluoro-2-butyl | H | Br |
| 8-4282 | 3-cyanophenyl | H | Me | F | F | H | H | Br | H | nonafluoro-2-butyl | H | Br |
| 8-4283 | 4-cyanophenyl | H | Me | F | F | H | H | Br | H | nonafluoro-2-butyl | H | Br |
| 8-4298 | 2-chloropyridin-3-yl | H | Me | F | F | H | H | Br | H | nonafluoro-2-butyl | H | Br |
| 8-4340 | phenyl | H | Me | F | F | H | H | I | H | heptafluoroisopropyl | H | I |
| 8-4360 | 3-cyanophenyl | H | Me | F | F | H | H | I | H | heptafluoroisopropyl | H | I |
| 8-4361 | 4-cyanophenyl | H | Me | F | F | H | H | I | H | heptafluoroisopropyl | H | I |
| 8-4376 | 2-chloropyridin-3-yl | H | Me | F | F | H | H | I | H | heptafluoroisopropyl | H | I |
| 8-4418 | phenyl | H | Me | F | F | H | H | I | H | nonafluoro-2-butyl | H | I |
| 8-4438 | 3-cyanophenyl | H | Me | F | F | H | H | I | H | nonafluoro-2-butyl | H | I |
| 8-4439 | 4-cyanophenyl | H | Me | F | F | H | H | I | H | nonafluoro-2-butyl | H | I |
| 8-4454 | 2-chloropyridin-3-yl | H | Me | F | F | H | H | I | H | nonafluoro-2-butyl | H | I |
| 8-4496 | phenyl | H | Me | F | F | H | H | Cl | H | heptafluoroisopropyl | H | OCF3 |
| 8-4516 | 3-cyanophenyl | H | Me | F | F | H | H | Cl | H | heptafluoroisopropyl | H | OCF3 |
| 8-4517 | 4-cyanophenyl | H | Me | F | F | H | H | Cl | H | heptafluoroisopropyl | H | OCF3 |
| 8-4532 | 2-chloropyridin-3-yl | H | Me | F | F | H | H | Cl | H | heptafluoroisopropyl | H | OCF3 |
| 8-4574 | phenyl | H | Me | F | F | H | H | Cl | H | nonafluoro-2-butyl | H | OCF3 |
| 8-4594 | 3-cyanophenyl | H | Me | F | F | H | H | Cl | H | nonafluoro-2-butyl | H | OCF3 |
| 8-4595 | 4-cyanophenyl | H | Me | F | F | H | H | Cl | H | nonafluoro-2-butyl | H | OCF3 |
| 8-4610 | 2-chloropyridin-3-yl | H | Me | F | F | H | H | Cl | H | nonafluoro-2-butyl | H | OCF3 |
| 8-4652 | phenyl | H | Me | F | F | H | H | Br | H | heptafluoroisopropyl | H | OCF3 |
| 8-4672 | 3-cyanophenyl | H | Me | F | F | H | H | Br | H | heptafluoroisopropyl | H | OCF3 |
| 8-4673 | 4-cyanophenyl | H | Me | F | F | H | H | Br | H | heptafluoroisopropyl | H | OCF3 |
| 8-4688 | 2-chloropyridin-3-yl | H | Me | F | F | H | H | Br | H | heptafluoroisopropyl | H | OCF3 |
| 8-4730 | phenyl | H | Me | F | F | H | H | Br | H | nonafluoro-2-butyl | H | OCF3 |
| 8-4750 | 3-cyanophenyl | H | Me | F | F | H | H | Br | H | nonafluoro-2-butyl | H | OCF3 |
| 8-4751 | 4-cyanophenyl | H | Me | F | F | H | H | Br | H | nonafluoro-2-butyl | H | OCF3 |
| 8-4808 | phenyl | H | Me | F | F | H | H | I | H | heptafluoroisopropyl | H | OCF3 |
| 8-4828 | 3-cyanophenyl | H | Me | F | F | H | H | I | H | heptafluoroisopropyl | H | OCF3 |
| 8-4829 | 4-cyanophenyl | H | Me | F | F | H | H | I | H | heptafluoroisopropyl | H | OCF3 |
| 8-4844 | 2-chloropyridin-3-yl | H | Me | F | F | H | H | I | H | heptafluoroisopropyl | H | OCF3 |
| 8-4886 | phenyl | H | Me | F | F | H | H | I | H | nonafluoro-2-butyl | H | OCF3 |
| 8-4906 | 3-cyanophenyl | H | Me | F | F | H | H | I | H | nonafluoro-2-butyl | H | OCF3 |
| 8-4907 | 4-cyanophenyl | H | Me | F | F | H | H | I | H | nonafluoro-2-butyl | H | OCF3 |
| 8-4922 | 2-chloropyridin-3-yl | H | Me | F | F | H | H | I | H | nonafluoro-2-butyl | H | OCF3 |
| 8-4964 | phenyl | H | Me | F | F | H | H | F | H | heptafluoroisopropyl | H | CF3 |
| 8-4965 | phenyl | H | Me | F | F | H | H | Cl | H | heptafluoroisopropyl | H | CF3 |
| 8-4985 | 3-cyanophenyl | H | Me | F | F | H | H | Cl | H | heptafluoroisopropyl | H | CF3 |
| 8-4986 | 4-cyanophenyl | H | Me | F | F | H | H | Cl | H | heptafluoroisopropyl | H | CF3 |
| 8-5001 | 2-chloropyridin-3-yl | H | Me | F | F | H | H | Cl | H | heptafluoroisopropyl | H | CF3 |
| 8-5043 | phenyl | H | Me | F | F | H | H | F | H | nonafluoro-2-butyl | H | CF3 |
| 8-5044 | phenyl | H | Me | F | F | H | H | Cl | H | nonafluoro-2-butyl | H | CF3 |
| 8-5064 | 3-cyanophenyl | H | Me | F | F | H | H | Cl | H | nonafluoro-2-butyl | H | CF3 |
| 8-5065 | 4-cyanophenyl | H | Me | F | F | H | H | Cl | H | nonafluoro-2-butyl | H | CF3 |
| 8-5080 | 2-chloropyridin-3-yl | H | Me | F | F | H | H | Cl | H | nonafluoro-2-butyl | H | CF3 |
| 8-5122 | phenyl | H | Me | F | F | H | H | Br | H | heptafluoroisopropyl | H | CF3 |
| 8-5142 | 3-cyanophenyl | H | Me | F | F | H | H | Br | H | heptafluoroisopropyl | H | CF3 |
| 8-5143 | 4-cyanophenyl | H | Me | F | F | H | H | Br | H | heptafluoroisopropyl | H | CF3 |

TABLE 8-continued

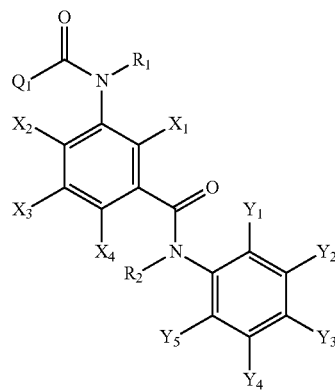

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 8-5158 | 2-chloropyridin-3-yl | H | Me | F | F | H | H | Br | H | heptafluoroisopropyl | H | CF3 |
| 8-5200 | phenyl | H | Me | F | F | H | H | Br | H | nonafluoro-2-butyl | H | CF3 |
| 8-5220 | 3-cyanophenyl | H | Me | F | F | H | H | Br | H | nonafluoro-2-butyl | H | CF3 |
| 8-5221 | 4-cyanophenyl | H | Me | F | F | H | H | Br | H | nonafluoro-2-butyl | H | CF3 |
| 8-5236 | 2-chloropyridin-3-yl | H | Me | F | F | H | H | Br | H | nonafluoro-2-butyl | H | CF3 |
| 8-5278 | phenyl | H | Me | F | F | H | H | I | H | heptafluoroisopropyl | H | CF3 |
| 8-5298 | 3-cyanophenyl | H | Me | F | F | H | H | I | H | heptafluoroisopropyl | H | CF3 |
| 8-5299 | 4-cyanophenyl | H | Me | F | F | H | H | I | H | heptafluoroisopropyl | H | CF3 |
| 8-5314 | 2-chloropyridin-3-yl | H | Me | F | F | H | H | I | H | heptafluoroisopropyl | H | CF3 |
| 8-5356 | phenyl | H | Me | F | F | H | H | I | H | nonafluoro-2-butyl | H | CF3 |
| 8-5376 | 3-cyanophenyl | H | Me | F | F | H | H | I | H | nonafluoro-2-butyl | H | CF3 |
| 8-5377 | 4-cyanophenyl | H | Me | F | F | H | H | I | H | nonafluoro-2-butyl | H | CF3 |
| 8-5392 | 2-chloropyridin-3-yl | H | Me | F | F | H | H | I | H | nonafluoro-2-butyl | H | CF3 |
| 8-5434 | phenyl | H | Me | F | F | H | H | OCF3 | H | heptafluoroisopropyl | H | OCF3 |
| 8-5465 | 2-chloropyridin-3-yl | H | Me | F | F | H | H | OCF3 | H | heptafluoroisopropyl | H | OCF3 |
| 8-5490 | phenyl | H | Me | F | F | H | H | OCF3 | H | nonafluoro-2-butyl | H | OCF3 |
| 8-5521 | 2-chloropyridin-3-yl | H | Me | F | F | H | H | OCF3 | H | nonafluoro-2-butyl | H | OCF3 |
| 8-5546 | phenyl | H | Me | F | F | H | H | CF3 | H | heptafluoroisopropyl | H | OCF3 |
| 8-5577 | 2-chloropyridin-3-yl | H | Me | F | F | H | H | CF3 | H | heptafluoroisopropyl | H | OCF3 |
| 8-5602 | phenyl | H | Me | F | F | H | H | CF3 | H | nonafluoro-2-butyl | H | OCF3 |
| 8-5633 | 2-chloropyridin-3-yl | H | Me | F | F | H | H | CF3 | H | nonafluoro-2-butyl | H | OCF3 |
| 8-5678 | 3-cyanophenyl | H | Me | F | F | H | H | CF3 | H | heptafluoroisopropyl | H | CF3 |
| 8-5679 | 4-cyanophenyl | H | Me | F | F | H | H | CF3 | H | heptafluoroisopropyl | H | CF3 |
| 8-5694 | 2-chloropyridin-3-yl | H | Me | F | F | H | H | CF3 | H | heptafluoroisopropyl | H | CF3 |
| 8-5726 | phenyl | H | Me | F | F | H | H | CF3 | H | nonafluoro-2-butyl | H | CF3 |
| 8-5746 | 3-cyanophenyl | H | Me | F | F | H | H | CF3 | H | nonafluoro-2-butyl | H | CF3 |
| 8-5747 | 4-cyanophenyl | H | Me | F | F | H | H | CF3 | H | nonafluoro-2-butyl | H | CF3 |
| 8-5762 | 2-chloropyridin-3-yl | H | Me | F | F | H | H | CF3 | H | nonafluoro-2-butyl | H | CF3 |
| 8-5794 | phenyl | H | Me | F | F | F | H | Cl | H | pentafluoroethyl | H | Cl |
| 8-5795 | phenyl | H | Me | F | F | F | H | Br | H | heptafluoroisopropyl | H | Br |
| 8-5796 | phenyl | H | Me | F | F | F | H | Br | H | heptafluoroisopropyl | H | OCF3 |
| 8-5797 | phenyl | H | Me | F | F | F | H | I | H | heptafluoroisopropyl | H | CF3 |
| 8-5798 | phenyl | H | Me | F | F | F | H | CF3 | H | heptafluoroisopropyl | H | CF3 |
| 8-5799 | phenyl | H | Me | F | F | F | H | I | H | nonafluoro-2-butyl | H | I |
| 8-5800 | phenyl | H | Me | F | F | F | H | Cl | H | nonafluoro-2-butyl | H | OCF3 |
| 8-5801 | phenyl | H | Me | F | F | F | H | Br | H | nonafluoro-2-butyl | H | CF3 |
| 8-5802 | phenyl | H | Me | F | F | F | H | CF3 | H | nonafluoro-2-butyl | H | CF3 |
| 8-5803 | phenyl | H | Me | H | H | F | H | Cl | H | pentafluoroethyl | H | Cl |
| 8-5804 | phenyl | H | Me | H | H | F | H | Br | H | heptafluoroisopropyl | H | Br |
| 8-5805 | phenyl | H | Me | H | H | F | H | Br | H | heptafluoroisopropyl | H | OCF3 |
| 8-5806 | phenyl | H | Me | H | H | F | H | I | H | heptafluoroisopropyl | H | CF3 |
| 8-5807 | phenyl | H | Me | H | H | F | H | CF3 | H | heptafluoroisopropyl | H | CF3 |
| 8-5808 | phenyl | H | Me | H | H | F | H | I | H | nonafluoro-2-butyl | H | I |
| 8-5809 | phenyl | H | Me | H | H | F | H | Cl | H | nonafluoro-2-butyl | H | OCF3 |
| 8-5810 | phenyl | H | Me | H | H | F | H | Br | H | nonafluoro-2-butyl | H | CF3 |
| 8-5811 | phenyl | H | Me | H | H | F | H | CF3 | H | nonafluoro-2-butyl | H | CF3 |
| 8-5812 | phenyl | H | Me | H | H | H | F | Cl | H | pentafluoroethyl | H | Cl |
| 8-5813 | phenyl | H | Me | H | H | H | F | Br | H | heptafluoroisopropyl | H | Br |
| 8-5814 | phenyl | H | Me | H | H | H | F | Br | H | heptafluoroisopropyl | H | OCF3 |
| 8-5815 | phenyl | H | Me | H | H | H | F | I | H | heptafluoroisopropyl | H | CF3 |
| 8-5816 | phenyl | H | Me | H | H | H | F | CF3 | H | heptafluoroisopropyl | H | CF3 |
| 8-5817 | phenyl | H | Me | H | H | H | F | I | H | nonafluoro-2-butyl | H | I |
| 8-5818 | phenyl | H | Me | H | H | H | F | Cl | H | nonafluoro-2-butyl | H | OCF3 |
| 8-5819 | phenyl | H | Me | H | H | H | F | Br | H | nonafluoro-2-butyl | H | CF3 |
| 8-5820 | phenyl | H | Me | H | H | H | F | CF3 | H | nonafluoro-2-butyl | H | CF3 |
| 8-5821 | phenyl | H | Me | F | H | F | H | Cl | H | pentafluoroethyl | H | Cl |
| 8-5822 | phenyl | H | Me | F | H | F | H | Br | H | heptafluoroisopropyl | H | Br |

TABLE 8-continued

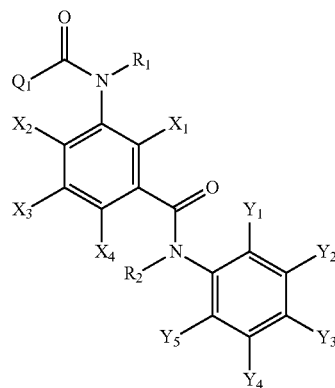

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 8-5823 | phenyl | H | Me | F | H | F | H | Br | H | heptafluoroisopropyl | H | OCF3 |
| 8-5824 | phenyl | H | Me | F | H | F | H | I | H | heptafluoroisopropyl | H | CF3 |
| 8-5825 | phenyl | H | Me | F | H | F | H | CF3 | H | heptafluoroisopropyl | H | CF3 |
| 8-5826 | phenyl | H | Me | F | H | F | H | I | H | nonafluoro-2-butyl | H | I |
| 8-5827 | phenyl | H | Me | F | H | F | H | Cl | H | nonafluoro-2-butyl | H | OCF3 |
| 8-5828 | phenyl | H | Me | F | H | F | H | Br | H | nonafluoro-2-butyl | H | CF3 |
| 8-5829 | phenyl | H | Me | F | H | F | H | CF3 | H | nonafluoro-2-butyl | H | CF3 |
| 8-5830 | phenyl | H | Me | F | H | H | F | Cl | H | pentafluoroethyl | H | Cl |
| 8-5831 | phenyl | H | Me | F | H | H | F | Br | H | heptafluoroisopropyl | H | Br |
| 8-5832 | phenyl | H | Me | F | H | H | F | Br | H | heptafluoroisopropyl | H | OCF3 |
| 8-5833 | phenyl | H | Me | F | H | H | F | I | H | heptafluoroisopropyl | H | CF3 |
| 8-5834 | phenyl | H | Me | F | H | H | F | CF3 | H | heptafluoroisopropyl | H | CF3 |
| 8-5835 | phenyl | H | Me | F | H | H | F | I | H | nonafluoro-2-butyl | H | I |
| 8-5836 | phenyl | H | Me | F | H | H | F | Cl | H | nonafluoro-2-butyl | H | OCF3 |
| 8-5837 | phenyl | H | Me | F | H | H | F | Br | H | nonafluoro-2-butyl | H | CF3 |
| 8-5838 | phenyl | H | Me | F | H | H | F | CF3 | H | nonafluoro-2-butyl | H | CF3 |
| 8-5839 | phenyl | H | Me | H | F | F | H | Cl | H | pentafluoroethyl | H | Cl |
| 8-5840 | phenyl | H | Me | H | F | F | H | Br | H | heptafluoroisopropyl | H | Br |
| 8-5841 | phenyl | H | Me | H | F | F | H | Br | H | heptafluoroisopropyl | H | OCF3 |
| 8-5842 | phenyl | H | Me | H | F | F | H | I | H | heptafluoroisopropyl | H | CF3 |
| 8-5843 | phenyl | H | Me | H | F | F | H | CF3 | H | heptafluoroisopropyl | H | CF3 |
| 8-5844 | phenyl | H | Me | H | F | F | H | I | H | nonafluoro-2-butyl | H | I |
| 8-5845 | phenyl | H | Me | H | F | F | H | Cl | H | nonafluoro-2-butyl | H | OCF3 |
| 8-5846 | phenyl | H | Me | H | F | F | H | Br | H | nonafluoro-2-butyl | H | CF3 |
| 8-5847 | phenyl | H | Me | H | F | F | H | CF3 | H | nonafluoro-2-butyl | H | CF3 |
| 8-5848 | phenyl | H | Me | H | F | H | F | Cl | H | pentafluoroethyl | H | Cl |
| 8-5849 | phenyl | H | Me | H | F | H | F | Br | H | heptafluoroisopropyl | H | Br |
| 8-5850 | phenyl | H | Me | H | F | H | F | Br | H | heptafluoroisopropyl | H | OCF3 |
| 8-5851 | phenyl | H | Me | H | F | H | F | I | H | heptafluoroisopropyl | H | CF3 |
| 8-5852 | phenyl | H | Me | H | F | H | F | CF3 | H | heptafluoroisopropyl | H | CF3 |
| 8-5853 | phenyl | H | Me | H | F | H | F | I | H | nonafluoro-2-butyl | H | I |
| 8-5854 | phenyl | H | Me | H | F | H | F | Cl | H | nonafluoro-2-butyl | H | OCF3 |
| 8-5855 | phenyl | H | Me | H | F | H | F | Br | H | nonafluoro-2-butyl | H | CF3 |
| 8-5856 | phenyl | H | Me | H | F | H | F | CF3 | H | nonafluoro-2-butyl | H | CF3 |
| 8-5857 | phenyl | H | Me | H | H | F | F | Cl | H | pentafluoroethyl | H | Cl |
| 8-5858 | phenyl | H | Me | H | H | F | F | Br | H | heptafluoroisopropyl | H | Br |
| 8-5859 | phenyl | H | Me | H | H | F | F | Br | H | heptafluoroisopropyl | H | OCF3 |
| 8-5860 | phenyl | H | Me | H | H | F | F | I | H | heptafluoroisopropyl | H | CF3 |
| 8-5861 | phenyl | H | Me | H | H | F | F | CF3 | H | heptafluoroisopropyl | H | CF3 |
| 8-5862 | phenyl | H | Me | H | H | F | F | I | H | nonafluoro-2-butyl | H | I |
| 8-5863 | phenyl | H | Me | H | H | F | F | Cl | H | nonafluoro-2-butyl | H | OCF3 |
| 8-5864 | phenyl | H | Me | H | H | F | F | Br | H | nonafluoro-2-butyl | H | CF3 |
| 8-5865 | phenyl | H | Me | H | H | F | F | CF3 | H | nonafluoro-2-butyl | H | CF3 |
| 8-5866 | phenyl | H | Me | F | F | H | F | Cl | H | pentafluoroethyl | H | Cl |
| 8-5867 | phenyl | H | Me | F | F | H | F | Br | H | heptafluoroisopropyl | H | Br |
| 8-5868 | phenyl | H | Me | F | F | H | F | Br | H | heptafluoroisopropyl | H | OCF3 |
| 8-5869 | phenyl | H | Me | F | F | H | F | I | H | heptafluoroisopropyl | H | CF3 |
| 8-5870 | phenyl | H | Me | F | F | H | F | CF3 | H | heptafluoroisopropyl | H | CF3 |
| 8-5871 | phenyl | H | Me | F | F | H | F | I | H | nonafluoro-2-butyl | H | I |
| 8-5872 | phenyl | H | Me | F | F | H | F | Cl | H | nonafluoro-2-butyl | H | OCF3 |
| 8-5873 | phenyl | H | Me | F | F | H | F | Br | H | nonafluoro-2-butyl | H | CF3 |
| 8-5874 | phenyl | H | Me | F | F | H | F | CF3 | H | nonafluoro-2-butyl | H | CF3 |
| 8-5875 | phenyl | H | Me | F | H | F | F | Cl | H | pentafluoroethyl | H | Cl |
| 8-5876 | phenyl | H | Me | F | H | F | F | Br | H | heptafluoroisopropyl | H | Br |
| 8-5877 | phenyl | H | Me | F | H | F | F | Br | H | heptafluoroisopropyl | H | OCF3 |
| 8-5878 | phenyl | H | Me | F | H | F | F | I | H | heptafluoroisopropyl | H | CF3 |
| 8-5879 | phenyl | H | Me | F | H | F | F | CF3 | H | heptafluoroisopropyl | H | CF3 |

TABLE 8-continued

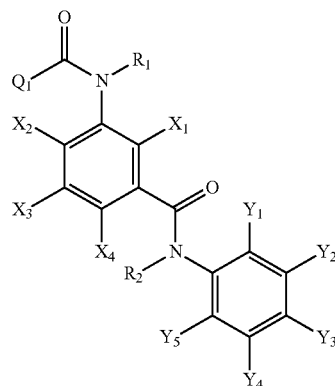

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 8-5880 | phenyl | H | Me | F | H | F | F | I | H | nonafluoro-2-butyl | H | I |
| 8-5881 | phenyl | H | Me | F | H | F | F | Cl | H | nonafluoro-2-butyl | H | OCF3 |
| 8-5882 | phenyl | H | Me | F | H | F | F | Br | H | nonafluoro-2-butyl | H | CF3 |
| 8-5883 | phenyl | H | Me | F | H | F | F | CF3 | H | nonafluoro-2-butyl | H | CF3 |
| 8-5884 | phenyl | H | Me | H | F | F | F | Cl | H | pentafluoroethyl | H | Cl |
| 8-5885 | phenyl | H | Me | H | F | F | F | Br | H | heptafluoroisopropyl | H | Br |
| 8-5886 | phenyl | H | Me | H | F | F | F | Br | H | heptafluoroisopropyl | H | OCF3 |
| 8-5887 | phenyl | H | Me | H | F | F | F | I | H | heptafluoroisopropyl | H | CF3 |
| 8-5888 | phenyl | H | Me | H | F | F | F | CF3 | H | heptafluoroisopropyl | H | CF3 |
| 8-5889 | phenyl | H | Me | H | F | F | F | I | H | nonafluoro-2-butyl | H | I |
| 8-5890 | phenyl | H | Me | H | F | F | F | Cl | H | nonafluoro-2-butyl | H | OCF3 |
| 8-5891 | phenyl | H | Me | H | F | F | F | Br | H | nonafluoro-2-butyl | H | CF3 |
| 8-5892 | phenyl | H | Me | H | F | F | F | CF3 | H | nonafluoro-2-butyl | H | CF3 |
| 8-5893 | phenyl | H | Me | F | F | F | F | Cl | H | pentafluoroethyl | H | Cl |
| 8-5894 | phenyl | H | Me | F | F | F | F | Br | H | heptafluoroisopropyl | H | Br |
| 8-5895 | phenyl | H | Me | F | F | F | F | Br | H | heptafluoroisopropyl | H | OCF3 |
| 8-5896 | phenyl | H | Me | F | F | F | F | I | H | heptafluoroisopropyl | H | CF3 |
| 8-5897 | phenyl | H | Me | F | F | F | F | CF3 | H | heptafluoroisopropyl | H | CF3 |
| 8-5898 | phenyl | H | Me | F | F | F | F | I | H | nonafluoro-2-butyl | H | I |
| 8-5899 | phenyl | H | Me | F | F | F | F | Cl | H | nonafluoro-2-butyl | H | OCF3 |
| 8-5900 | phenyl | H | Me | F | F | F | F | Br | H | nonafluoro-2-butyl | H | CF3 |
| 8-5901 | phenyl | H | Me | F | F | F | F | CF3 | H | nonafluoro-2-butyl | H | CF3 |

TABLE 9

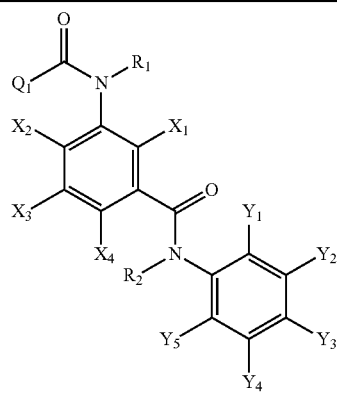

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 9-1 | phenyl | Me | Me | H | H | H | H | F | H | nonafluoro-2-butyl | H | F |
| 9-2 | 3-cyanophenyl | Me | Me | H | H | H | H | F | H | nonafluoro-2-butyl | H | F |
| 9-3 | 4-cyanophenyl | Me | Me | H | H | H | H | F | H | nonafluoro-2-butyl | H | F |
| 9-4 | 2-chloropyridin-3-yl | Me | Me | H | H | H | H | F | H | nonafluoro-2-butyl | H | F |
| 9-5 | phenyl | Me | Me | H | H | H | H | Cl | H | nonafluoro-2-butyl | H | Cl |
| 9-12 | 3-cyanophenyl | Me | Me | H | H | H | H | Cl | H | nonafluoro-2-butyl | H | Cl |
| 9-13 | 4-cyanophenyl | Me | Me | H | H | H | H | Cl | H | nonafluoro-2-butyl | H | Cl |
| 9-24 | 2-chloropyridin-3-yl | Me | Me | H | H | H | H | Cl | H | nonafluoro-2-butyl | H | Cl |

TABLE 9-continued

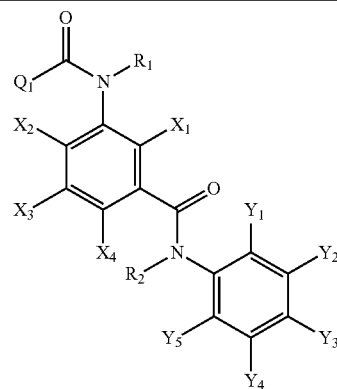

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 9-38 | phenyl | Me | Me | H | H | H | H | Br | H | nonafluoro-2-butyl | H | Br |
| 9-45 | 3-cyanophenyl | Me | Me | H | H | H | H | Br | H | nonafluoro-2-butyl | H | Br |
| 9-46 | 4-cyanophenyl | Me | Me | H | H | H | H | Br | H | nonafluoro-2-butyl | H | Br |
| 9-57 | 2-chloropyridin-3-yl | Me | Me | H | H | H | H | Br | H | nonafluoro-2-butyl | H | Br |
| 9-71 | phenyl | Me | Me | H | H | H | H | I | H | nonafluoro-2-butyl | H | I |
| 9-78 | 3-cyanophenyl | Me | Me | H | H | H | H | I | H | nonafluoro-2-butyl | H | I |
| 9-79 | 4-cyanophenyl | Me | Me | H | H | H | H | I | H | nonafluoro-2-butyl | H | I |
| 9-90 | 2-chloropyridin-3-yl | Me | Me | H | H | H | H | I | H | nonafluoro-2-butyl | H | I |
| 9-109 | phenyl | Me | Me | H | H | H | H | Cl | H | nonafluoro-2-butyl | H | Br |
| 9-112 | phenyl | Me | Me | H | H | H | H | F | H | heptafluoroisopropyl | H | CF3 |
| 9-113 | phenyl | Me | Me | H | H | H | H | Cl | H | heptafluoroisopropyl | H | CF3 |
| 9-133 | 3-cyanophenyl | Me | Me | H | H | H | H | Cl | H | heptafluoroisopropyl | H | CF3 |
| 9-134 | 4-cyanophenyl | Me | Me | H | H | H | H | Cl | H | heptafluoroisopropyl | H | CF3 |
| 9-149 | 2-chloropyridin-3-yl | Me | Me | H | H | H | H | Cl | H | heptafluoroisopropyl | H | CF3 |
| 9-191 | phenyl | Me | Me | H | H | H | H | F | H | nonafluoro-2-butyl | H | CF3 |
| 9-192 | phenyl | Me | Me | H | H | H | H | Cl | H | nonafluoro-2-butyl | H | CF3 |
| 9-212 | 3-cyanophenyl | Me | Me | H | H | H | H | Cl | H | nonafluoro-2-butyl | H | CF3 |
| 9-213 | 4-cyanophenyl | Me | Me | H | H | H | H | Cl | H | nonafluoro-2-butyl | H | CF3 |
| 9-228 | 2-chloropyridin-3-yl | Me | Me | H | H | H | H | Cl | H | nonafluoro-2-butyl | H | CF3 |
| 9-270 | phenyl | Me | Me | H | H | H | H | Br | H | heptafluoroisopropyl | H | CF3 |
| 9-290 | 3-cyanophenyl | Me | Me | H | H | H | H | Br | H | heptafluoroisopropyl | H | CF3 |
| 9-291 | 4-cyanophenyl | Me | Me | H | H | H | H | Br | H | heptafluoroisopropyl | H | CF3 |
| 9-306 | 2-chloropyridin-3-yl | Me | Me | H | H | H | H | Br | H | heptafluoroisopropyl | H | CF3 |
| 9-348 | phenyl | Me | Me | H | H | H | H | Br | H | nonafluoro-2-butyl | H | CF3 |
| 9-368 | 3-cyanophenyl | Me | Me | H | H | H | H | Br | H | nonafluoro-2-butyl | H | CF3 |
| 9-369 | 4-cyanophenyl | Me | Me | H | H | H | H | Br | H | nonafluoro-2-butyl | H | CF3 |
| 9-384 | 2-chloropyridin-3-yl | Me | Me | H | H | H | H | Br | H | nonafluoro-2-butyl | H | CF3 |
| 9-426 | phenyl | Me | Me | H | H | H | H | I | H | heptafluoroisopropyl | H | CF3 |
| 9-446 | 3-cyanophenyl | Me | Me | H | H | H | H | I | H | heptafluoroisopropyl | H | CF3 |
| 9-447 | 4-cyanophenyl | Me | Me | H | H | H | H | I | H | heptafluoroisopropyl | H | CF3 |
| 9-462 | 2-chloropyridin-3-yl | Me | Me | H | H | H | H | I | H | heptafluoroisopropyl | H | CF3 |
| 9-504 | phenyl | Me | Me | H | H | H | H | I | H | nonafluoro-2-butyl | H | CF3 |
| 9-524 | 3-cyanophenyl | Me | Me | H | H | H | H | I | H | nonafluoro-2-butyl | H | CF3 |
| 9-525 | 4-cyanophenyl | Me | Me | H | H | H | H | I | H | nonafluoro-2-butyl | H | CF3 |
| 9-540 | 2-chloropyridin-3-yl | Me | Me | H | H | H | H | I | H | nonafluoro-2-butyl | H | CF3 |
| 9-778 | phenyl | Me | Me | H | H | H | H | OCF3 | H | heptafluoroisopropyl | H | OCF3 |
| 9-809 | 2-chloropyridin-3-yl | Me | Me | H | H | H | H | OCF3 | H | heptafluoroisopropyl | H | OCF3 |
| 9-834 | phenyl | Me | Me | H | H | H | H | OCF3 | H | nonafluoro-2-butyl | H | OCF3 |
| 9-865 | 2-chloropyridin-3-yl | Me | Me | H | H | H | H | OCF3 | H | nonafluoro-2-butyl | H | OCF3 |
| 9-890 | phenyl | Me | Me | H | H | H | H | CF3 | H | heptafluoroisopropyl | H | OCF3 |
| 9-921 | 2-chloropyridin-3-yl | Me | Me | H | H | H | H | CF3 | H | heptafluoroisopropyl | H | OCF3 |
| 9-946 | phenyl | Me | Me | H | H | H | H | CF3 | H | nonafluoro-2-butyl | H | OCF3 |
| 9-977 | 2-chloropyridin-3-yl | Me | Me | H | H | H | H | CF3 | H | nonafluoro-2-butyl | H | OCF3 |
| 9-1002 | phenyl | Me | Me | H | H | H | H | CF3 | H | heptafluoroisopropyl | H | CF3 |
| 9-1022 | 3-cyanophenyl | Me | Me | H | H | H | H | CF3 | H | heptafluoroisopropyl | H | CF3 |
| 9-1023 | 4-cyanophenyl | Me | Me | H | H | H | H | CF3 | H | heptafluoroisopropyl | H | CF3 |
| 9-1038 | 2-chloropyridin-3-yl | Me | Me | H | H | H | H | CF3 | H | heptafluoroisopropyl | H | CF3 |
| 9-1070 | phenyl | Me | Me | H | H | H | H | CF3 | H | nonafluoro-2-butyl | H | CF3 |
| 9-1090 | 3-cyanophenyl | Me | Me | H | H | H | H | CF3 | H | nonafluoro-2-butyl | H | CF3 |
| 9-1091 | 4-cyanophenyl | Me | Me | H | H | H | H | CF3 | H | nonafluoro-2-butyl | H | CF3 |
| 9-1106 | 2-chloropyridin-3-yl | Me | Me | H | H | H | H | CF3 | H | nonafluoro-2-butyl | H | CF3 |
| 9-1334 | phenyl | Me | Me | F | H | H | H | F | H | heptafluoroisopropyl | H | F |
| 9-1335 | 3-cyanophenyl | Me | Me | F | H | H | H | F | H | heptafluoroisopropyl | H | F |
| 9-1336 | 4-cyanophenyl | Me | Me | F | H | H | H | F | H | heptafluoroisopropyl | H | F |
| 9-1337 | 2-chloropyridin-3-yl | Me | Me | F | H | H | H | F | H | heptafluoroisopropyl | H | F |
| 9-1338 | phenyl | Me | Me | F | H | H | H | F | H | nonafluoro-2-butyl | H | F |
| 9-1339 | 3-cyanophenyl | Me | Me | F | H | H | H | F | H | nonafluoro-2-butyl | H | F |
| 9-1340 | 4-cyanophenyl | Me | Me | F | H | H | H | F | H | nonafluoro-2-butyl | H | F |

TABLE 9-continued

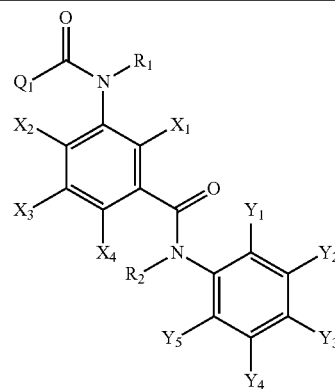

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 9-1341 | 2-chloropyridin-3-yl | Me | Me | F | H | H | H | F | H | nonafluoro-2-butyl | H | F |
| 9-1342 | phenyl | Me | Me | F | H | H | H | Cl | H | heptafluoroisopropyl | H | Cl |
| 9-1362 | 3-cyanophenyl | Me | Me | F | H | H | H | Cl | H | heptafluoroisopropyl | H | Cl |
| 9-1363 | 4-cyanophenyl | Me | Me | F | H | H | H | Cl | H | heptafluoroisopropyl | H | Cl |
| 9-1378 | 2-chloropyridin-3-yl | Me | Me | F | H | H | H | Cl | H | heptafluoroisopropyl | H | Cl |
| 9-1420 | phenyl | Me | Me | F | H | H | H | Cl | H | nonafluoro-2-butyl | H | Cl |
| 9-1440 | 3-cyanophenyl | Me | Me | F | H | H | H | Cl | H | nonafluoro-2-butyl | H | Cl |
| 9-1441 | 4-cyanophenyl | Me | Me | F | H | H | H | Cl | H | nonafluoro-2-butyl | H | Cl |
| 9-1456 | 2-chloropyridin-3-yl | Me | Me | F | H | H | H | Cl | H | nonafluoro-2-butyl | H | Cl |
| 9-1498 | phenyl | Me | Me | F | H | H | H | Br | H | heptafluoroisopropyl | H | Br |
| 9-1518 | 3-cyanophenyl | Me | Me | F | H | H | H | Br | H | heptafluoroisopropyl | H | Br |
| 9-1519 | 4-cyanophenyl | Me | Me | F | H | H | H | Br | H | heptafluoroisopropyl | H | Br |
| 9-1534 | 2-chloropyridin-3-yl | Me | Me | F | H | H | H | Br | H | heptafluoroisopropyl | H | Br |
| 9-1576 | phenyl | Me | Me | F | H | H | H | Br | H | nonafluoro-2-butyl | H | Br |
| 9-1596 | 3-cyanophenyl | Me | Me | F | H | H | H | Br | H | nonafluoro-2-butyl | H | Br |
| 9-1597 | 4-cyanophenyl | Me | Me | F | H | H | H | Br | H | nonafluoro-2-butyl | H | Br |
| 9-1612 | 2-chloropyridin-3-yl | Me | Me | F | H | H | H | Br | H | nonafluoro-2-butyl | H | Br |
| 9-1654 | phenyl | Me | Me | F | H | H | H | I | H | heptafluoroisopropyl | H | I |
| 9-1674 | 3-cyanophenyl | Me | Me | F | H | H | H | I | H | heptafluoroisopropyl | H | I |
| 9-1675 | 4-cyanophenyl | Me | Me | F | H | H | H | I | H | heptafluoroisopropyl | H | I |
| 9-1690 | 2-chloropyridin-3-yl | Me | Me | F | H | H | H | I | H | heptafluoroisopropyl | H | I |
| 9-1732 | phenyl | Me | Me | F | H | H | H | I | H | nonafluoro-2-butyl | H | I |
| 9-1752 | 3-cyanophenyl | Me | Me | F | H | H | H | I | H | nonafluoro-2-butyl | H | I |
| 9-1753 | 4-cyanophenyl | Me | Me | F | H | H | H | I | H | nonafluoro-2-butyl | H | I |
| 9-1768 | 2-chloropyridin-3-yl | Me | Me | F | H | H | H | I | H | nonafluoro-2-butyl | H | I |
| 9-2006 | phenyl | Me | Me | F | H | H | H | F | H | heptafluoroisopropyl | H | CF3 |
| 9-2007 | phenyl | Me | Me | F | H | H | H | Cl | H | heptafluoroisopropyl | H | CF3 |
| 9-2019 | 4-iodophenyl | Me | Et | F | H | H | H | Cl | H | pentafluoroethyl | H | CF3 |
| 9-2021 | (3-trifluoromethyl)phenyl | Et | Me | F | H | H | H | Cl | H | heptafluoroisopropyl | H | C2F5 |
| 9-2027 | 3-cyanophenyl | Me | Me | F | H | H | H | Cl | H | heptafluoroisopropyl | H | CF3 |
| 9-2028 | 4-cyanophenyl | Me | Me | F | H | H | H | Cl | H | heptafluoroisopropyl | H | CF3 |
| 9-2030 | 3,4-dichlorophenyl | Me | n-Pr | F | H | H | H | Cl | H | heptafluoroisopropyl | H | CF3 |
| 9-2032 | 2-chloro-4-fluorophenyl | n-Pr | Me | F | H | H | H | Cl | H | heptafluoroisopropyl | H | CF3 |
| 9-2043 | 2-chloropyridin-3-yl | Me | Me | F | H | H | H | Cl | H | heptafluoroisopropyl | H | CF3 |
| 9-2047 | 2-nitropyridin-3-yl | Me | i-Pr | F | H | H | H | Cl | H | heptafluoroisopropyl | H | CF3 |
| 9-2049 | 6-fluoropyridin-3-yl | i-Pr | Me | F | H | H | H | Cl | H | heptafluoroisopropyl | H | CF3 |
| 9-2063 | 4-fluoropyridin-3-yl | Me | CH2CH=CH2 | F | H | H | H | Cl | H | pentafluoroethyl | H | CF3 |
| 9-2065 | 4-bromopyridin-3-yl | CH2CH=CH2 | Me | F | H | H | H | Cl | H | heptafluoroisopropyl | H | n-C3F7 |
| 9-2070 | 2,6-dichloropyridin-3-yl | Me | CN | F | H | H | H | Cl | H | heptafluoroisopropyl | H | CF3 |
| 9-2072 | pyridin-4-yl | CN | Me | F | H | H | H | Cl | H | heptafluoroisopropyl | H | CF3 |
| 9-2085 | phenyl | Me | Me | F | H | H | H | F | H | nonafluoro-2-butyl | H | CF3 |
| 9-2086 | phenyl | Me | Me | F | H | H | H | Cl | H | nonafluoro-2-butyl | H | CF3 |
| 9-2092 | 4-chlorophenyl | Me | CH2C≡CH | F | H | H | H | Cl | H | nonafluoro-2-butyl | H | CF3 |
| 9-2094 | 3-bromophenyl | CH2C≡CH | Me | F | H | H | H | Cl | H | nonafluoro-2-butyl | H | CF3 |
| 9-2099 | (2-trifluoromethyl)phenyl | Me | NH2 | F | H | H | H | Cl | H | nonafluoro-2-butyl | H | C2F5 |
| 9-2101 | (4-trifluoromethyl)phenyl | NH2 | Me | F | H | H | H | Cl | H | nonafluoro-2-butyl | H | CF3 |
| 9-2106 | 3-cyanophenyl | Me | Me | F | H | H | H | Cl | H | nonafluoro-2-butyl | H | CF3 |
| 9-2107 | 4-cyanophenyl | Me | Me | F | H | H | H | Cl | H | nonafluoro-2-butyl | H | CF3 |
| 9-2112 | 2-chloro-4,5-difluorophenyl | Me | C(O)Me | F | H | H | H | Cl | H | nonafluoro-2-butyl | H | CF3 |
| 9-2114 | 2-bromo-4-chlorophenyl | C(O)OMe | Me | F | H | H | H | Cl | H | nonafluoro-2-butyl | H | CF3 |
| 9-2122 | 2-chloropyridin-3-yl | Me | Me | F | H | H | H | Cl | H | nonafluoro-2-butyl | H | CF3 |
| 9-2133 | 6-nitropyridin-3-yl | Me | C(O)OEt | F | H | H | H | Cl | H | nonafluoro-2-butyl | H | CF3 |
| 9-2135 | 5-fluoropyridin-3-yl | C(O)OEt | Me | F | H | H | H | Cl | H | nonafluoro-2-butyl | H | C2F5 |
| 9-2142 | 4-fluoropyridin-3-yl | Me | C(O)C(O)Me | F | H | H | H | Cl | H | nonafluoro-2-butyl | H | C2F5 |
| 9-2144 | 4-bromopyridin-3-yl | C(O)C(O)Me | Me | F | H | H | H | Cl | H | nonafluoro-2-butyl | H | CF3 |
| 9-2145 | 4-iodopyridin-3-yl | Me | C(O)C(O)Et | F | H | H | H | Cl | H | nonafluoro-2-butyl | H | CF3 |
| 9-2147 | 4-nitropyridin-3-yl | C(O)C(O)Et | Me | F | H | H | H | Cl | H | nonafluoro-2-butyl | H | i-C3F7 |
| 9-2156 | 2,6-dicyanopyridin-4-yl | Me | C(O)Et | F | H | H | H | Cl | H | nonafluoro-2-butyl | H | CF3 |

TABLE 9-continued

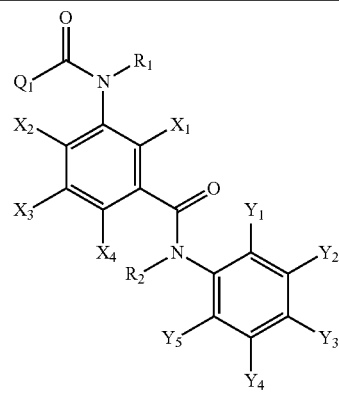

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 9-2159 | 3-chloropyridin-2-yl | Me | C(O)Me | F | H | H | H | Cl | H | nonafluoro-2-butyl | H | CF3 |
| 9-2161 | 5-iodopyridin-2-yl | C(O)Me | Me | F | H | H | H | Cl | H | nonafluoro-2-butyl | H | CF3 |
| 9-2163 | 4-cyanopyridin-2-yl | C(O)Et | Me | F | H | H | H | Cl | H | nonafluoro-2-butyl | H | C2F5 |
| 9-2164 | phenyl | Me | Me | F | H | H | H | Br | H | heptafluoroisopropyl | H | CF3 |
| 9-2176 | 4-iodophenyl | Me | S(O)2Me | F | H | H | H | Br | H | heptafluoroisopropyl | H | CF3 |
| 9-2178 | (3-trifluoromethyl)phenyl | S(O)2Me | Me | F | H | H | H | Br | H | heptafluoroisopropyl | H | CF3 |
| 9-2184 | 3-cyanophenyl | Me | Me | F | H | H | H | Br | H | heptafluoroisopropyl | H | CF3 |
| 9-2188 | 4-cyanophenyl | Me | Me | F | H | H | H | Br | H | heptafluoroisopropyl | H | CF3 |
| 9-2194 | 2-chloro-4-nitrophenyl | Me | S(O)2Et | F | H | H | H | Br | H | heptafluoroisopropyl | H | CF3 |
| 9-2196 | 4-cyano-2-fluorophenyl | S(O)2Et | Me | F | H | H | H | Br | H | heptafluoroisopropyl | H | CF3 |
| 9-2200 | 2-chloropyridin-3-yl | Me | Me | F | H | H | H | Br | H | heptafluoroisopropyl | H | CF3 |
| 9-2209 | 6-iodopyridin-3-yl | Me | CH2Ph | F | H | H | H | Br | H | heptafluoroisopropyl | H | CF3 |
| 9-2211 | 6-nitropyridin-3-yl | CH2Ph | Me | F | H | H | H | Br | H | heptafluoroisopropyl | H | CF3 |
| 9-2218 | 5-nitropyridin-3-yl | Me | CH2(3-Py) | F | H | H | H | Br | H | heptafluoroisopropyl | H | CF3 |
| 9-2220 | 4-fluoropyridin-3-yl | CH2(3-Py) | Me | F | H | H | H | Br | H | heptafluoroisopropyl | H | CF3 |
| 9-2239 | 5-iodopyridin-2-yl | Me | CH2(3-Py—N-oxide) | F | H | H | H | Br | H | heptafluoroisopropyl | H | CF3 |
| 9-2241 | 4-cyanopyridin-2-yl | CH2(3-Py—N-oxide) | Me | F | H | H | H | Br | H | heptafluoroisopropyl | H | CF3 |
| 9-2242 | phenyl | Me | Me | F | H | H | H | Br | H | nonafluoro-2-butyl | H | CF3 |
| 9-2262 | 3-cyanophenyl | Me | Me | F | H | H | H | Br | H | nonafluoro-2-butyl | H | CF3 |
| 9-2263 | 4-cyanophenyl | Me | Me | F | H | H | H | Br | H | nonafluoro-2-butyl | H | CF3 |
| 9-2267 | 2-chloro-4-fluorophenyl | Me | Et | F | H | H | H | Br | H | nonafluoro-2-butyl | H | CF3 |
| 9-2269 | 4-bromo-2-chlorophenyl | Et | Me | F | H | H | H | Br | H | nonafluoro-2-butyl | H | CF3 |
| 9-2278 | 2-chloropyridin-3-yl | Me | Me | F | H | H | H | Br | H | nonafluoro-2-butyl | H | CF3 |
| 9-2293 | 5-bromopyridin-3-yl | Me | CN | F | H | H | H | Br | H | nonafluoro-2-butyl | H | CF3 |
| 9-2295 | 5-(trifluoromethyl)pyridin-3-yl | CN | Me | F | H | H | H | Br | H | nonafluoro-2-butyl | H | CF3 |
| 9-2320 | phenyl | Me | Me | F | H | H | H | I | H | heptafluoroisopropyl | H | CF3 |
| 9-2322 | 3-fluorophenyl | Me | Me | F | H | H | H | I | H | heptafluoroisopropyl | H | CF3 |
| 9-2340 | 3-cyanophenyl | Me | Me | F | H | H | H | I | H | heptafluoroisopropyl | H | CF3 |
| 9-2341 | 4-cyanophenyl | Me | Me | F | H | H | H | 1 | H | heptafluoroisopropyl | H | CF3 |
| 9-2356 | 2-chloropyridin-3-yl | Me | Me | F | H | H | H | I | H | heptafluoroisopropyl | H | CF3 |
| 9-2367 | 6-nitropyridin-3-yl | Me | C(O)Me | F | H | H | H | I | H | heptafluoroisopropyl | H | CF3 |
| 9-2369 | 5-fluoropyridin-3-yl | C(O)Me | Me | F | H | H | H | I | H | heptafluoroisopropyl | H | CF3 |
| 9-2396 | phenyl | Me | Me | F | H | H | H | I | H | nonafluoro-2-butyl | H | CF3 |
| 9-2418 | 3-cyanophenyl | Me | Me | F | H | H | H | I | H | nonafluoro-2-butyl | H | CF3 |
| 9-2419 | 4-cyanophenyl | Me | Me | F | H | H | H | I | H | nonafluoro-2-butyl | H | CF3 |
| 9-2434 | 2-chloropyridin-3-yl | Me | Me | F | H | H | H | I | H | nonafluoro-2-butyl | H | CF3 |
| 9-2476 | phenyl | Et | Et | F | H | H | H | I | H | nonafluoro-2-butyl | H | CF3 |
| 9-2477 | phenyl | Et | n-Pr | F | H | H | H | I | H | nonafluoro-2-butyl | H | CF3 |
| 9-2478 | phenyl | Et | i-Pr | F | H | H | H | I | H | nonafluoro-2-butyl | H | CF3 |
| 9-2479 | phenyl | Et | CH2CH=CH2 | F | H | H | H | I | H | nonafluoro-2-butyl | H | CF3 |
| 9-2480 | phenyl | Et | CN | F | H | H | H | I | H | nonafluoro-2-butyl | H | CF3 |
| 9-2481 | phenyl | Et | CH2C≡CH | F | H | H | H | I | H | nonafluoro-2-butyl | H | CF3 |
| 9-2482 | phenyl | Et | NH2 | F | H | H | H | I | H | nonafluoro-2-butyl | H | CF3 |
| 9-2483 | phenyl | Et | C(O)OMe | F | H | H | H | I | H | nonafluoro-2-butyl | H | CF3 |
| 9-2484 | phenyl | Et | C(O)C(O)OMe | F | H | H | H | I | H | nonafluoro-2-butyl | H | CF3 |
| 9-2485 | phenyl | Et | C(O)Me | F | H | H | H | I | H | nonafluoro-2-butyl | H | CF3 |
| 9-2466 | phenyl | Et | S(O)2Me | F | H | H | H | I | H | nonafluoro-2-butyl | H | CF3 |
| 9-2487 | phenyl | Et | CH2Ph | F | H | H | H | I | H | nonafluoro-2-butyl | H | CF3 |
| 9-2488 | phenyl | Et | CH2(3-Py) | F | H | H | H | I | H | nonafluoro-2-butyl | H | CF3 |
| 9-2489 | phenyl | Et | CH2(3-Py—N-oxide) | F | H | H | H | I | H | nonafluoro-2-butyl | H | CF3 |
| 9-2490 | phenyl | n-Pr | Et | F | H | H | H | I | H | nonafluoro-2-butyl | H | CF3 |
| 9-2491 | phenyl | n-Pr | n-Pr | F | H | H | H | I | H | nonafluoro-2-butyl | H | CF3 |
| 9-2492 | phenyl | n-Pr | i-Pr | F | H | H | H | I | H | nonafluoro-2-butyl | H | CF3 |
| 9-2493 | phenyl | n-Pr | CH2CH=CH2 | F | H | H | H | I | H | nonafluoro-2-butyl | H | CF3 |
| 9-2494 | phenyl | n-Pr | CN | F | H | H | H | I | H | nonafluoro-2-butyl | H | CF3 |

TABLE 9-continued

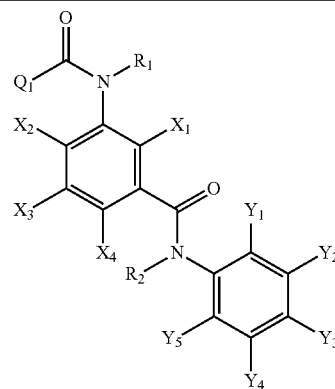

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 9-2495 | phenyl | n-Pr | CH2C≡CH | F | H | H | H | I | H | nonafluoro-2-butyl | H | CF3 |
| 9-2496 | phenyl | n-Pr | NH2 | F | H | H | H | I | H | nonafluoro-2-butyl | H | CF3 |
| 9-2497 | phenyl | n-Pr | C(O)OMe | F | H | H | H | I | H | nonafluoro-2-butyl | H | CF3 |
| 9-2498 | phenyl | n-Pr | C(O)C(O)OMe | F | H | H | H | I | H | nonafluoro-2-butyl | H | CF3 |
| 9-2499 | phenyl | n-Pr | C(O)Me | F | H | H | H | I | H | nonafluoro-2-butyl | H | CF3 |
| 9-2500 | phenyl | n-Pr | S(O)2Me | F | H | H | H | I | H | nonafluoro-2-butyl | H | CF3 |
| 9-2501 | phenyl | n-Pr | CH2Ph | F | H | H | H | I | H | nonafluoro-2-butyl | H | CF3 |
| 9-2502 | phenyl | n-Pr | CH2(3-Py) | F | H | H | H | I | H | nonafluoro-2-butyl | H | CF3 |
| 9-2503 | phenyl | n-Pr | CH2(3-Py—N-oxide) | F | H | H | H | I | H | nonafluoro-2-butyl | H | CF3 |
| 9-2504 | phenyl | i-Pr | Et | F | H | H | H | I | H | nonafluoro-2-butyl | H | CF3 |
| 9-2505 | phenyl | i-Pr | n-Pr | F | H | H | H | I | H | nonafluoro-2-butyl | H | CF3 |
| 9-2506 | phenyl | i-Pr | i-Pr | F | H | H | H | I | H | nonafluoro-2-butyl | H | CF3 |
| 9-2507 | phenyl | i-Pr | CH2CH=CH2 | F | H | H | H | I | H | nonafluoro-2-butyl | H | CF3 |
| 9-2508 | phenyl | i-Pr | CN | F | H | H | H | I | H | nonafluoro-2-butyl | H | CF3 |
| 9-2509 | phenyl | i-Pr | CH2C≡CH | F | H | H | H | I | H | nonafluoro-2-butyl | H | CF3 |
| 9-2510 | phenyl | i-Pr | NH2 | F | H | H | H | I | H | nonafluoro-2-butyl | H | CF3 |
| 9-2511 | phenyl | i-Pr | C(O)OMe | F | H | H | H | I | H | nonafluoro-2-butyl | H | CF3 |
| 9-2512 | phenyl | i-Pr | C(O)C(O)OMe | F | H | H | H | I | H | nonafluoro-2-butyl | H | CF3 |
| 9-2513 | phenyl | i-Pr | C(O)Me | F | H | H | H | I | H | nonafluoro-2-butyl | H | CF3 |
| 9-2514 | phenyl | i-Pr | S(O)2Me | F | H | H | H | I | H | nonafluoro-2-butyl | H | CF3 |
| 9-2515 | phenyl | i-Pr | CH2Ph | F | H | H | H | I | H | nonafluoro-2-butyl | H | CF3 |
| 9-2516 | phenyl | i-Pr | CH2(3-Py) | F | H | H | H | I | H | nonafluoro-2-butyl | H | CF3 |
| 9-2517 | phenyl | i-Pr | CH2(3-Py—N-oxide) | F | H | H | H | I | H | nonafluoro-2-butyl | H | CF3 |
| 9-2518 | phenyl | CH2CH=CH2 | Et | F | H | H | H | I | H | nonafluoro-2-butyl | H | CF3 |
| 9-2519 | phenyl | CH2CH=CH2 | n-Pr | F | H | H | H | I | H | nonafluoro-2-butyl | H | CF3 |
| 9-2520 | phenyl | CH2CH=CH2 | i-Pr | F | H | H | H | I | H | nonafluoro-2-butyl | H | CF3 |
| 9-2521 | phenyl | CH2CH=CH2 | CH2CH=CH2 | F | H | H | H | I | H | nonafluoro-2-butyl | H | CF3 |
| 9-2522 | phenyl | CH2CH=CH2 | CN | F | H | H | H | I | H | nonafluoro-2-butyl | H | CF3 |
| 9-2523 | phenyl | CH2CH=CH2 | CH2C≡CH | F | H | H | H | I | H | nonafluoro-2-butyl | H | CF3 |
| 9-2524 | phenyl | CH2CH=CH2 | NH2 | F | H | H | H | I | H | nonafluoro-2-butyl | H | CF3 |
| 9-2525 | phenyl | CH2CH=CH2 | C(O)OMe | F | H | H | H | I | H | nonafluoro-2-butyl | H | CF3 |
| 9-2526 | phenyl | CH2CH=CH2 | C(O)C(O)OMe | F | H | H | H | I | H | nonafluoro-2-butyl | H | CF3 |
| 9-2527 | phenyl | CH2CH=CH2 | C(O)Me | F | H | H | H | I | H | nonafluoro-2-butyl | H | CF3 |
| 9-2528 | phenyl | CH2CH=CH2 | S(O)2Me | F | H | H | H | I | H | nonafluoro-2-butyl | H | CF3 |
| 9-2529 | phenyl | CH2CH=CH2 | CH2Ph | F | H | H | H | I | H | nonafluoro-2-butyl | H | CF3 |
| 9-2530 | phenyl | CH2CH=CH2 | CH2(3-Py) | F | H | H | H | I | H | nonafluoro-2-butyl | H | CF3 |
| 9-2531 | phenyl | CH2CH=CH2 | CH2(3-Py—N-oxide) | F | H | H | H | I | H | nonafluoro-2-butyl | H | CF3 |
| 9-2532 | phenyl | CN | Et | F | H | H | H | I | H | nonafluoro-2-butyl | H | CF3 |
| 9-2533 | phenyl | CN | n-Pr | F | H | H | H | I | H | nonafluoro-2-butyl | H | CF3 |
| 9-2534 | phenyl | CN | i-Pr | F | H | H | H | I | H | nonafluoro-2-butyl | H | CF3 |
| 9-2535 | phenyl | CN | CH2CH=CH2 | F | H | H | H | I | H | nonafluoro-2-butyl | H | CF3 |
| 9-2536 | phenyl | CN | CN | F | H | H | H | I | H | nonafluoro-2-butyl | H | CF3 |
| 9-2537 | phenyl | CN | CH2C≡CH | F | H | H | H | I | H | nonafluoro-2-butyl | H | CF3 |
| 9-2538 | phenyl | CN | NH2 | F | H | H | H | I | H | nonafluoro-2-butyl | H | CF3 |
| 9-2539 | phenyl | CN | C(O)OMe | F | H | H | H | I | H | nonafluoro-2-butyl | H | CF3 |
| 9-2540 | phenyl | CH | C(O)C(O)OMe | F | H | H | H | I | H | nonafluoro-2-butyl | H | CF3 |
| 9-2541 | phenyl | CN | C(O)Me | F | H | H | H | I | H | nonafluoro-2-butyl | H | CF3 |
| 9-2542 | phenyl | CN | S(O)2Me | F | H | H | H | I | H | nonafluoro-2-butyl | H | CF3 |
| 9-2543 | phenyl | CN | CH2Ph | F | H | H | H | I | H | nonafluoro-2-butyl | H | CF3 |
| 9-2544 | phenyl | CN | CH2(3-Py) | F | H | H | H | I | H | nonafluoro-2-butyl | H | CF3 |
| 9-2545 | phenyl | CN | CH2(3-Py—N-oxide) | F | H | H | H | I | H | nonafluoro-2-butyl | H | CF3 |
| 9-2546 | phenyl | CH2C≡CH | Et | F | H | H | H | I | H | nonafluoro-2-butyl | H | CF3 |
| 9-2547 | phenyl | CH2C≡CH | n-Pr | F | H | H | H | I | H | nonafluoro-2-butyl | H | CF3 |
| 9-2548 | phenyl | CH2C≡CH | i-Pr | F | H | H | H | I | H | nonafluoro-2-butyl | H | CF3 |

TABLE 9-continued

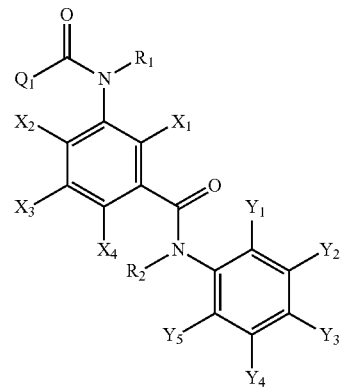

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 9-2549 | phenyl | CH2C≡CH | CH2CH=CH2 | F | H | H | H | I | H | nonafluoro-2-butyl | H | CF3 |
| 9-2550 | phenyl | CH2C≡CH | CN | F | H | H | H | I | H | nonafluoro-2-butyl | H | CF3 |
| 9-2551 | phenyl | CH2C≡CH | CH2C≡CH | F | H | H | H | I | H | nonafluoro-2-butyl | H | CF3 |
| 9-2552 | phenyl | CH2C≡CH | NH2 | F | H | H | H | I | H | nonafluoro-2-butyl | H | CF3 |
| 9-2553 | phenyl | CH2C≡CH | C(O)OMe | F | H | H | H | I | H | nonafluoro-2-butyl | H | CF3 |
| 9-2554 | phenyl | CH2C≡CH | C(O)C(O)OMe | F | H | H | H | I | H | nonafluoro-2-butyl | H | CF3 |
| 9-2555 | phenyl | CH2C≡CH | C(O)Me | F | H | H | H | I | H | nonafluoro-2-butyl | H | CF3 |
| 9-2556 | phenyl | CH2C≡CH | S(O)2Me | F | H | H | H | I | H | nonafluoro-2-butyl | H | CF3 |
| 9-2557 | phenyl | CH2C≡CH | CH2Ph | F | H | H | H | I | H | nonafluoro-2-butyl | H | CF3 |
| 9-2558 | phenyl | CH2C≡CH | CH2(3-Py) | F | H | H | H | I | H | nonafluoro-2-butyl | H | CF3 |
| 9-2559 | phenyl | CH2C≡CH | CH2(3-Py—N-oxide) | F | H | H | H | I | H | nonafluoro-2-butyl | H | CF3 |
| 9-2560 | phenyl | NH2 | Et | F | H | H | H | I | H | nonafluoro-2-butyl | H | CF3 |
| 9-2561 | phenyl | NH2 | n-Pr | F | H | H | H | I | H | nonafluoro-2-butyl | H | CF3 |
| 9-2562 | phenyl | NH2 | i-Pr | F | H | H | H | I | H | nonafluoro-2-butyl | H | CF3 |
| 9-2563 | phenyl | NH2 | CH2CH=CH2 | F | H | H | H | I | H | nonafluoro-2-butyl | H | CF3 |
| 9-2564 | phenyl | NH2 | CN | F | H | H | H | I | H | nonafluoro-2-butyl | H | CF3 |
| 9-2565 | phenyl | NH2 | CH2C≡CH | F | H | H | H | I | H | nonafluoro-2-butyl | H | CF3 |
| 9-2566 | phenyl | NH2 | NH2 | F | H | H | H | I | H | nonafluoro-2-butyl | H | CF3 |
| 9-2567 | phenyl | NH2 | C(O)OMe | F | H | H | H | I | H | nonafluoro-2-butyl | H | CF3 |
| 9-2568 | phenyl | NH2 | C(O)C(O)OMe | F | H | H | H | I | H | nonafluoro-2-butyl | H | CF3 |
| 9-2569 | phenyl | NH2 | C(O)Me | F | H | H | H | I | H | nonafluoro-2-butyl | H | CF3 |
| 9-2570 | phenyl | NH2 | S(O)2Me | F | H | H | H | I | H | nonafluoro-2-butyl | H | CF3 |
| 9-2571 | phenyl | NH2 | CH2Ph | F | H | H | H | I | H | nonafluoro-2-butyl | H | CF3 |
| 9-2572 | phenyl | NH2 | CH2(3-Py) | F | H | H | H | I | H | nonafluoro-2-butyl | H | CF3 |
| 9-2573 | phenyl | NH2 | CH2(3-Py—N-oxide) | F | H | H | H | I | H | nonafluoro-2-butyl | H | CF3 |
| 9-2574 | phenyl | C(O)OMe | Et | F | H | H | H | I | H | nonafluoro-2-butyl | H | CF3 |
| 9-2575 | phenyl | C(O)OMe | n-Pr | F | H | H | H | I | H | nonafluoro-2-butyl | H | CF3 |
| 9-2576 | phenyl | C(O)OMe | i-Pr | F | H | H | H | I | H | nonafluoro-2-butyl | H | CF3 |
| 9-2577 | phenyl | C(O)OMe | CH2CH=CH2 | F | H | H | H | I | H | nonafluoro-2-butyl | H | CF3 |
| 9-2578 | phenyl | C(O)OMe | CN | F | H | H | H | I | H | nonafluoro-2-butyl | H | CF3 |
| 9-2579 | phenyl | C(O)OMe | CH2C≡CH | F | H | H | H | I | H | nonafluoro-2-butyl | H | CF3 |
| 9-2580 | phenyl | C(O)OMe | NH2 | H | H | H | H | I | H | nonafluoro-2-butyl | H | CF3 |
| 9-2581 | phenyl | C(O)OMe | C(O)OMe | F | H | H | H | I | H | nonafluoro-2-butyl | H | CF3 |
| 9-2582 | phenyl | C(O)OMe | C(O)C(O)OMe | F | H | H | H | I | H | nonafluoro-2-butyl | H | CF3 |
| 9-2583 | phenyl | C(O)OMe | C(O)Me | F | H | H | H | I | H | nonafluoro-2-butyl | H | CF3 |
| 9-2584 | phenyl | C(O)OMe | S(O)2Me | F | H | H | H | I | H | nonafluoro-2-butyl | H | CF3 |
| 9-2585 | phenyl | C(O)OMe | CH2Ph | F | H | H | H | I | H | nonafluoro-2-butyl | H | CF3 |
| 9-2586 | phenyl | C(O)OMe | CH2(3-Py) | F | H | H | H | I | H | nonafluoro-2-butyl | H | CF3 |
| 9-2587 | phenyl | C(O)OMe | CH2(3-Py—N-oxide) | F | H | H | H | I | H | nonafluoro-2-butyl | H | CF3 |
| 9-2588 | phenyl | C(O)C(O)OMe | Et | F | H | H | H | I | H | nonafluoro-2-butyl | H | CF3 |
| 9-2589 | phenyl | C(O)C(O)OMe | n-Pr | F | H | H | H | I | H | nonafluoro-2-butyl | H | CF3 |
| 9-2590 | phenyl | C(O)C(O)OMe | i-Pr | H | H | H | H | I | H | nonafluoro-2-butyl | H | CF3 |
| 9-2591 | phenyl | C(O)C(O)OMe | CH2CH=CH2 | F | H | H | H | I | H | nonafluoro-2-butyl | H | CF3 |
| 9-2592 | phenyl | C(O)C(O)OMe | CN | F | H | H | H | I | H | nonafluoro-2-butyl | H | CF3 |
| 9-2593 | phenyl | C(O)C(O)OMe | CH2C≡CH | F | H | H | H | I | H | nonafluoro-2-butyl | H | CF3 |
| 9-2594 | phenyl | C(O)C(O)OMe | NH2 | F | H | H | H | I | H | nonafluoro-2-butyl | H | CF3 |
| 9-2595 | phenyl | C(O)C(O)OMe | C(O)OMe | F | H | H | H | I | H | nonafluoro-2-butyl | H | CF3 |
| 9-2596 | phenyl | C(O)C(O)OMe | C(O)C(O)OMe | F | H | H | H | I | H | nonafluoro-2-butyl | H | CF3 |
| 9-2597 | phenyl | C(O)C(O)OMe | C(O)Me | F | H | H | H | I | H | nonafluoro-2-butyl | H | CF3 |
| 9-2598 | phenyl | C(O)C(O)OMe | S(O)2Me | F | H | H | H | I | H | nonafluoro-2-butyl | H | CF3 |
| 9-2599 | phenyl | C(O)C(O)OMe | CH2Ph | F | H | H | H | I | H | nonafluoro-2-butyl | H | CF3 |
| 9-2600 | phenyl | C(O)C(O)OMe | CH2(3-Py) | F | H | H | H | I | H | nonafluoro-2-butyl | H | CF3 |
| 9-2601 | phenyl | C(O)C(O)OMe | CH2(3-Py—N-oxide) | F | H | H | H | I | H | nonafluoro-2-butyl | H | CF3 |
| 9-2602 | phenyl | C(O)Me | Et | F | H | H | H | I | H | nonafluoro-2-butyl | H | CF3 |

TABLE 9-continued

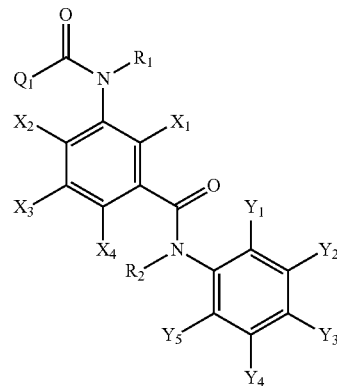

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 9-2603 | phenyl | C(O)Me | n-Pr | F | H | H | H | I | H | nonafluoro-2-butyl | H | CF3 |
| 9-2604 | phenyl | C(O)Me | i-Pr | F | H | H | H | I | H | nonafluoro-2-butyl | H | CF3 |
| 9-2605 | phenyl | C(O)Me | CH2CH=CH2 | F | H | H | H | I | H | nonafluoro-2-butyl | H | CF3 |
| 9-2606 | phenyl | C(O)Me | CN | F | H | H | H | I | H | nonafluoro-2-butyl | H | CF3 |
| 9-2607 | phenyl | C(O)Me | CH2C≡CH | F | H | H | H | I | H | nonafluoro-2-butyl | H | CF3 |
| 9-2608 | phenyl | C(O)Me | NH2 | F | H | H | H | I | H | nonafluoro-2-butyl | H | CF3 |
| 9-2609 | phenyl | C(O)Me | C(O)OMe | F | H | H | H | I | H | nonafluoro-2-butyl | H | CF3 |
| 9-2610 | phenyl | C(O)Me | C(O)C(O)OMe | F | H | H | H | I | H | nonafluoro-2-butyl | H | CF3 |
| 9-2611 | phenyl | C(O)Me | C(O)Me | F | H | H | H | Br | H | heptafluoroisopropyl | H | CF3 |
| 9-2612 | phenyl | C(O)Me | S(O)2Me | F | H | H | H | I | H | nonafluoro-2-butyl | H | CF3 |
| 9-2613 | phenyl | C(O)Me | CH2Ph | F | H | H | H | I | H | nonafluoro-2-butyl | H | CF3 |
| 9-2614 | phenyl | C(O)Me | CH2(3-Py) | F | H | H | H | I | H | nonafluoro-2-butyl | H | CF3 |
| 9-2615 | phenyl | C(O)Me | CH2(3-Py—N-oxide) | F | H | H | H | I | H | nonafluoro-2-butyl | H | CF3 |
| 9-2616 | phenyl | S(O)2Me | Et | F | H | H | H | I | H | nonafluoro-2-butyl | H | CF3 |
| 9-2617 | phenyl | S(O)2Me | n-Pr | F | H | H | H | I | H | nonafluoro-2-butyl | H | CF3 |
| 9-2618 | phenyl | S(O)2Me | i-Pr | F | H | H | H | I | H | nonafluoro-2-butyl | H | CF3 |
| 9-2619 | phenyl | S(O)2Me | CH2CH=CH2 | F | H | H | H | I | H | nonafluoro-2-butyl | H | CF3 |
| 9-2620 | phenyl | S(O)2Me | CN | F | H | H | H | I | H | nonafluoro-2-butyl | H | CF3 |
| 9-2621 | phenyl | S(O)2Me | CH2C≡CH | F | H | H | H | I | H | nonafluoro-2-butyl | H | CF3 |
| 9-2622 | phenyl | S(O)2Me | NH2 | F | H | H | H | I | H | nonafluoro-2-butyl | H | CF3 |
| 9-2623 | phenyl | S(O)2Me | C(O)OMe | F | H | H | H | I | H | nonafluoro-2-butyl | H | CF3 |
| 9-2624 | phenyl | S(O)2Me | C(O)C(O)OMe | F | H | H | H | I | H | nonafluoro-2-butyl | H | CF3 |
| 9-2625 | phenyl | S(O)2Me | C(O)Me | F | H | H | H | I | H | nonafluoro-2-butyl | H | CF3 |
| 9-2626 | phenyl | S(O)2Me | S(O)2Me | F | H | H | H | I | H | nonafluoro-2-butyl | H | CF3 |
| 9-2627 | phenyl | S(O)2Me | CH2Ph | F | H | H | H | I | H | nonafluoro-2-butyl | H | CF3 |
| 9-2628 | phenyl | S(O)2Me | CH2(3-Py) | F | H | H | H | I | H | nonafluoro-2-butyl | H | CF3 |
| 9-2629 | phenyl | S(O)2Me | CH2(3-Py—N-oxide) | F | H | H | H | I | H | nonafluoro-2-butyl | H | CF3 |
| 9-2630 | phenyl | CH2Ph | Et | F | H | H | H | I | H | nonafluoro-2-butyl | H | CF3 |
| 9-2631 | phenyl | CH2Ph | n-Pr | F | H | H | H | I | H | nonafluoro-2-butyl | H | CF3 |
| 9-2632 | phenyl | CH2Ph | i-Pr | F | H | H | H | I | H | nonafluoro-2-butyl | H | CF3 |
| 9-2633 | phenyl | CH2Ph | CH2CH=CH2 | F | H | H | H | I | H | nonafluoro-2-butyl | H | CF3 |
| 9-2634 | phenyl | CH2Ph | CN | F | H | H | H | I | H | nonafluoro-2-butyl | H | CF3 |
| 9-2635 | phenyl | CH2Ph | CH2C≡CH | F | H | H | H | I | H | nonafluoro-2-butyl | H | CF3 |
| 9-2636 | phenyl | CH2Ph | NH2 | F | H | H | H | I | H | nonafluoro-2-butyl | H | CF3 |
| 9-2637 | phenyl | CH2Ph | C(O)OMe | F | H | H | H | I | H | nonafluoro-2-butyl | H | CF3 |
| 9-2638 | phenyl | CH2Ph | C(O)C(O)OMe | F | H | H | H | I | H | nonafluoro-2-butyl | H | CF3 |
| 9-2639 | phenyl | CH2Ph | C(O)Me | F | H | H | H | I | H | nonafluoro-2-butyl | H | CF3 |
| 9-2640 | phenyl | CH2Ph | S(O)2Me | F | H | H | H | I | H | nonafluoro-2-butyl | H | CF3 |
| 9-2641 | phenyl | CH2Ph | CH2Ph | F | H | H | H | I | H | nonafluoro-2-butyl | H | CF3 |
| 9-2642 | phenyl | CH2Ph | CH2(3-Py) | F | H | H | H | I | H | nonafluoro-2-butyl | H | CF3 |
| 9-2643 | phenyl | CH2Ph | CH2(3-Py—N-oxide) | F | H | H | H | I | H | nonafluoro-2-butyl | H | CF3 |
| 9-2644 | phenyl | CH2(3-Py) | Et | F | H | H | H | I | H | nonafluoro-2-butyl | H | CF3 |
| 9-2645 | phenyl | CH2(3-Py) | n-Pr | F | H | H | H | I | H | nonafluoro-2-butyl | H | CF3 |
| 9-2646 | phenyl | CH2(3-Py) | i-Pr | F | H | H | H | I | H | nonafluoro-2-butyl | H | CF3 |
| 9-2647 | phenyl | CH2(3-Py) | CH2CH=CH2 | F | H | H | H | I | H | nonafluoro-2-butyl | H | CF3 |
| 9-2648 | phenyl | CH2(3-Py) | CN | F | H | H | H | I | H | nonafluoro-2-butyl | H | CF3 |
| 9-2649 | phenyl | CH2(3-Py) | CH2C≡CH | F | H | H | H | I | H | nonafluoro-2-butyl | H | CF3 |
| 9-2650 | phenyl | CH2(3-Py) | NH2 | F | H | H | H | I | H | nonafluoro-2-butyl | H | CF3 |
| 9-2651 | phenyl | CH2(3-Py) | C(O)OMe | F | H | H | H | I | H | nonafluoro-2-butyl | H | CF3 |
| 9-2652 | phenyl | CH2(3-Py) | C(O)C(O)OMe | F | H | H | H | I | H | nonafluoro-2-butyl | H | CF3 |
| 9-2653 | phenyl | CH2(3-Py) | C(O)Me | F | H | H | H | I | H | nonafluoro-2-butyl | H | CF3 |
| 9-2654 | phenyl | CH2(3-Py) | S(O)2Me | F | H | H | H | I | H | nonafluoro-2-butyl | H | CF3 |
| 9-2655 | phenyl | CH2(3-Py) | CH2Ph | F | H | H | H | I | H | nonafluoro-2-butyl | H | CF3 |
| 9-2656 | phenyl | CH2(3-Py) | CH2(3-Py) | F | H | H | H | I | H | nonafluoro-2-butyl | H | CF3 |

TABLE 9-continued

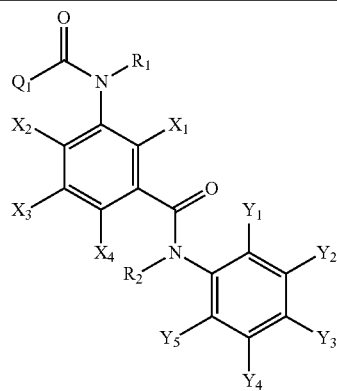

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 9-2657 | phenyl | CH2(3-Py) | CH2(3-Py—N-oxide) | F | H | H | H | I | H | nonafluoro-2-butyl | H | CF3 |
| 9-2658 | phenyl | CH2(3-Py—N-oxide) | Et | F | H | H | H | I | H | nonafluoro-2-butyl | H | CF3 |
| 9-2659 | phenyl | CH2(3-Py—N-oxide) | n-Pr | F | H | H | H | I | H | nonafluoro-2-butyl | H | CF3 |
| 9-2660 | phenyl | CH2(3-Py—N-oxide) | i-Pr | F | H | H | H | I | H | nonafluoro-2-butyl | H | CF3 |
| 9-2661 | phenyl | CH2(3-Py—N-oxide) | CH2CH=CH2 | F | H | H | H | I | H | nonafluoro-2-butyl | H | CF3 |
| 9-2662 | phenyl | CH2(3-Py—N-oxide) | CN | F | H | H | H | I | H | nonafluoro-2-butyl | H | CF3 |
| 9-2663 | phenyl | CH2(3-Py—N-oxide) | CH2C≡CH | F | H | H | H | I | H | nonafluoro-2-butyl | H | CF3 |
| 9-2664 | phenyl | CH2(3-Py—N-oxide) | NH2 | F | H | H | H | I | H | nonafluoro-2-butyl | H | CF3 |
| 9-2665 | phenyl | CH2(3-Py—N-oxide) | C(O)OMe | F | H | H | H | I | H | nonafluoro-2-butyl | H | CF3 |
| 9-2666 | phenyl | CH2(3-Py—N-oxide) | C(O)C(O)OMe | F | H | H | H | I | H | nonafluoro-2-butyl | H | CF3 |
| 9-2667 | phenyl | CH2(3-Py—N-oxide) | C(O)Me | F | H | H | H | I | H | nonafluoro-2-butyl | H | CF3 |
| 9-2668 | phenyl | CH2(3-Py—N-oxide) | S(O)2Me | F | H | H | H | I | H | nonafluoro-2-butyl | H | CF3 |
| 9-2669 | phenyl | CH2(3-Py—N-oxide) | CH2Ph | F | H | H | H | I | H | nonafluoro-2-butyl | H | CF3 |
| 9-2670 | phenyl | CH2(3-Py—N-oxide) | CH2(3-Py) | F | H | H | H | I | H | nonafluoro-2-butyl | H | CF3 |
| 9-2671 | phenyl | CH2(3-Py—N-oxide) | CH2(3-Py—N-oxide) | F | H | H | H | I | H | nonafluoro-2-butyl | H | CF3 |
| 9-2672 | phenyl | Me | Me | F | H | H | H | OCF3 | H | heptafluoroisopropyl | H | OCF3 |
| 9-2687 | 3-cyanophenyl | Me | Me | F | H | H | H | OCF3 | H | heptafluoroisopropyl | H | OCF3 |
| 9-2688 | 4-cyanophenyl | Me | Me | F | H | H | H | OCF3 | H | heptafluoroisopropyl | H | OCF3 |
| 9-2703 | 2-chloropyridin-3-yl | Me | Me | F | H | H | H | OCF3 | H | heptafluoroisopropyl | H | OCF3 |
| 9-2728 | phenyl | Me | Me | F | H | H | H | OCF3 | H | nonafluoro-2-butyl | H | OCF3 |
| 9-2743 | 3-cyanophenyl | Me | Me | F | H | H | H | OCF3 | H | nonafluoro-2-butyl | H | OCF3 |
| 9-2744 | 4-cyanophenyl | Me | Me | F | H | H | H | OCF3 | H | nonafluoro-2-butyl | H | OCF3 |
| 9-2759 | 2-chloropyridin-3-yl | Me | Me | F | H | H | H | OCF3 | H | nonafluoro-2-butyl | H | OCF3 |
| 9-2784 | phenyl | Me | Me | F | H | H | H | CF3 | H | heptafluoroisopropyl | H | OCF3 |
| 9-2799 | 3-cyanophenyl | Me | Me | F | H | H | H | CF3 | H | heptafluoroisopropyl | H | OCF3 |
| 9-2800 | 4-cyanophenyl | Me | Me | F | H | H | H | CF3 | H | heptafluoroisopropyl | H | OCF3 |
| 9-2815 | 2-chloropyridin-3-yl | Me | Me | F | H | H | H | CF3 | H | heptafluoroisopropyl | H | OCF3 |
| 9-2840 | phenyl | Me | Me | F | H | H | H | CF3 | H | nonafluoro-2-butyl | H | OCF3 |
| 9-2855 | 3-cyanophenyl | Me | Me | F | H | H | H | CF3 | H | nonafluoro-2-butyl | H | OCF3 |
| 9-2856 | 4-cyanophenyl | Me | Me | F | H | H | H | CF3 | H | nonafluoro-2-butyl | H | OCF3 |
| 9-2871 | 2-chloropyridin-3-yl | Me | Me | F | H | H | H | CF3 | H | nonafluoro-2-butyl | H | OCF3 |
| 9-2896 | phenyl | Me | Me | F | H | H | H | CF3 | H | heptafluoroisopropyl | H | CF3 |
| 9-2916 | 3-cyanophenyl | Me | Me | F | H | H | H | CF3 | H | heptafluoroisopropyl | H | CF3 |
| 9-2917 | 4-cyanophenyl | Me | Me | F | H | H | H | CF3 | H | heptafluoroisopropyl | H | CF3 |
| 9-2932 | 2-chloropyridin-3-yl | Me | Me | F | H | H | H | CF3 | H | heptafluoroisopropyl | H | CF3 |
| 9-2964 | phenyl | Me | Me | F | H | H | H | CF3 | H | nonafluoro-2-butyl | H | CF3 |
| 9-2984 | 3-cyanophenyl | Me | Me | F | H | H | H | CF3 | H | nonafluoro-2-butyl | H | CF3 |
| 9-2985 | 4-cyanophenyl | Me | Me | F | H | H | H | CF3 | H | nonafluoro-2-butyl | H | CF3 |
| 9-3000 | 2-chloropyridin-3-yl | Me | Me | F | H | H | H | CF3 | H | nonafluoro-2-butyl | H | CF3 |
| 9-3228 | phenyl | Me | Me | H | F | H | H | F | H | heptafluoroisopropyl | H | F |
| 9-3229 | 3-cyanophenyl | Me | Me | H | F | H | H | F | H | heptafluoroisopropyl | H | F |
| 9-3230 | 4-cyanophenyl | Me | Me | H | F | H | H | F | H | heptafluoroisopropyl | H | F |
| 9-3231 | 2-chloropyridin-3-yl | Me | Me | H | F | H | H | F | H | heptafluoroisopropyl | H | F |

TABLE 9-continued

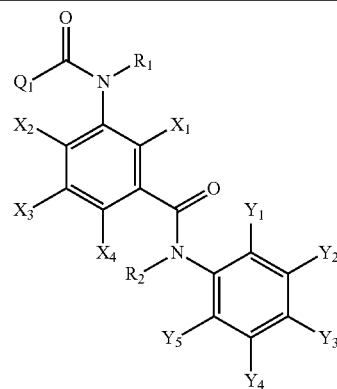

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 9-3232 | phenyl | Me | Me | H | F | H | H | F | H | nonafluoro-2-butyl | H | F |
| -9-3233 | 3-cyanophenyl | Me | Me | H | F | H | H | F | H | nonafluoro-2-butyl | H | F |
| 9-3234 | 4-cyanophenyl | Me | Me | H | F | H | H | F | H | nonafluoro-2-butyl | H | F |
| 9-3235 | 2-chloropyridin-3-yl | Me | Me | H | F | H | H | F | H | nonafluoro-2-butyl | H | F |
| 9-3236 | phenyl | Me | Me | H | F | H | H | Cl | H | heptafluoroisopropyl | H | Cl |
| 9-3256 | 3-cyanophenyl | Me | Me | H | F | H | H | Cl | H | heptafluoroisopropyl | H | Cl |
| 9-3257 | 4-cyanophenyl | Me | Me | H | F | H | H | Cl | H | heptafluoroisopropyl | H | Cl |
| 9-3272 | 2-chloropyridin-3-yl | Me | Me | H | F | H | H | Cl | H | heptafluoroisopropyl | H | Cl |
| 9-3314 | phenyl | Me | Me | H | F | H | H | Cl | H | nonafluoro-2-butyl | H | Cl |
| 9-3334 | 3-cyanophenyl | Me | Me | H | F | H | H | Cl | H | nonafluoro-2-butyl | H | Cl |
| 9-3335 | 4-cyanophenyl | Me | Me | H | F | H | H | Cl | H | nonafluoro-2-butyl | H | Cl |
| 9-3350 | 2-chloropyridin-3-yl | Me | Me | H | F | H | H | Cl | H | nonafluoro-2-butyl | H | Cl |
| 9-3392 | phenyl | Me | Me | H | F | H | H | Br | H | heptafluoroisopropyl | H | Br |
| 9-3412 | 3-cyanophenyl | Me | Me | H | F | H | H | Br | H | heptafluoroisopropyl | H | Br |
| 9-3413 | 4-cyanophenyl | Me | Me | H | F | H | H | Br | H | heptafluoroisopropyl | H | Br |
| 9-3428 | 2-chloropyridin-3-yl | Me | Me | H | F | H | H | Br | H | heptafluoroisopropyl | H | Br |
| 9-3470 | phenyl | Me | Me | H | F | H | H | Br | H | nonafluoro-2-butyl | H | Br |
| 9-3490 | 3-cyanophenyl | Me | Me | H | F | H | H | Br | H | nonafluoro-2-butyl | H | Br |
| 9-3491 | 4-cyanophenyl | Me | Me | H | F | H | H | Br | H | nonafluoro-2-butyl | H | Br |
| 9-3506 | 2-chloropyridin-3-yl | Me | Me | H | F | H | H | Br | H | nonafluoro-2-butyl | H | Br |
| 9-3548 | phenyl | Me | Me | H | F | H | H | I | H | heptafluoroisopropyl | H | I |
| 9-3568 | 3-cyanophenyl | Me | Me | H | F | H | H | I | H | heptafluoroisopropyl | H | I |
| 9-3569 | 4-cyanophenyl | Me | Me | H | F | H | H | I | H | heptafluoroisopropyl | H | I |
| 9-3584 | 2-chloropyridin-3-yl | Me | Me | H | F | H | H | I | H | heptafluoroisopropyl | H | I |
| 9-3626 | phenyl | Me | Me | H | F | H | H | I | H | nonafluoro-2-butyl | H | I |
| 9-3646 | 3-cyanophenyl | Me | Me | H | F | H | H | I | H | nonafluoro-2-butyl | H | I |
| 9-3647 | 4-cyanophenyl | Me | Me | H | F | H | H | I | H | nonafluoro-2-butyl | H | I |
| 9-3662 | 2-chloropyridin-3-yl | Me | Me | H | F | H | H | I | H | nonafluoro-2-butyl | H | I |
| 9-3900 | phenyl | Me | Me | H | F | H | H | Cl | H | heptafluoroisopropyl | H | OCF3 |
| 9-3920 | 3-cyanophenyl | Me | Me | H | F | H | H | Cl | H | heptafluoroisopropyl | H | OCF3 |
| 9-3921 | 4-cyanophenyl | Me | Me | H | F | H | H | Cl | H | heptafluoroisopropyl | H | OCF3 |
| 9-3936 | 2-chloropyridin-3-yl | Me | Me | H | F | H | H | Cl | H | heptafluoroisopropyl | H | OCF3 |
| 9-3978 | phenyl | Me | Me | H | F | H | H | Cl | H | nonafluoro-2-butyl | H | OCF3 |
| 9-3998 | 3-cyanophenyl | Me | Me | H | F | H | H | Cl | H | nonafluoro-2-butyl | H | OCF3 |
| 9-3999 | 4-cyanophenyl | Me | Me | H | F | H | H | Cl | H | nonafluoro-2-butyl | H | OCF3 |
| 9-4014 | 2-chloropyridin-3-yl | Me | Me | H | F | H | H | Cl | H | nonafluoro-2-butyl | H | OCF3 |
| 9-4056 | phenyl | Me | Me | H | F | H | H | Br | H | heptafluoroisopropyl | H | OCF3 |
| 9-4076 | 3-cyanophenyl | Me | Me | H | F | H | H | Br | H | heptafluoroisopropyl | H | OCF3 |
| 9-4077 | 4-cyanophenyl | Me | Me | H | F | H | H | Br | H | heptafluoroisopropyl | H | OCF3 |
| 9-4092 | 2-chloropyridin-3-yl | Me | Me | H | F | H | H | Br | H | heptafluoroisopropyl | H | OCF3 |
| 9-4134 | phenyl | Me | Me | H | F | H | H | Br | H | nonafluoro-2-butyl | H | OCF3 |
| 9-4154 | 3-cyanophenyl | Me | Me | H | F | H | H | Br | H | nonafluoro-2-butyl | H | OCF3 |
| 9-4155 | 4-cyanophenyl | Me | Me | H | F | H | H | Br | H | nonafluoro-2-butyl | H | OCF3 |
| 9-4170 | 2-chloropyridin-3-yl | Me | Me | H | F | H | H | Br | H | nonafluoro-2-butyl | H | OCF3 |
| 9-4212 | phenyl | Me | Me | H | F | H | H | I | H | heptafluoroisopropyl | H | OCF3 |
| 9-4232 | 3-cyanophenyl | Me | Me | H | F | H | H | I | H | heptafluoroisopropyl | H | OCF3 |
| 9-4233 | 4-cyanophenyl | Me | Me | H | F | H | H | I | H | heptafluoroisopropyl | H | OCF3 |
| 9-4248 | 2-chloropyridin-3-yl | Me | Me | H | F | H | H | I | H | heptafluoroisopropyl | H | OCF3 |
| 9-4290 | phenyl | Me | Me | H | F | H | H | I | H | nonafluoro-2-butyl | H | OCF3 |
| 9-4310 | 3-cyanophenyl | Me | Me | H | F | H | H | I | H | nonafluoro-2-butyl | H | OCF3 |
| 9-4311 | 4-cyanophenyl | Me | Me | H | F | H | H | I | H | nonafluoro-2-butyl | H | OCF3 |
| 9-4326 | 2-chloropyridin-3-yl | Me | Me | H | F | H | H | I | H | nonafluoro-2-butyl | H | OCF3 |
| 9-4564 | phenyl | Me | Me | H | F | H | H | F | H | heptafluoroisopropyl | H | CF3 |
| 9-4565 | 3-cyanophenyl | Me | Me | H | F | H | H | Cl | H | heptafluoroisopropyl | H | CF3 |
| 9-4585 | 3-cyanophenyl | Me | Me | H | F | H | H | Cl | H | heptafluoroisopropyl | H | CF3 |
| 9-4586 | 4-cyanophenyl | Me | Me | H | F | H | H | Cl | H | heptafluoroisopropyl | H | CF3 |
| 9-4601 | 2-chloropyridin-3-yl | Me | Me | H | F | H | H | Cl | H | heptafluoroisopropyl | H | CF3 |
| 9-4643 | phenyl | Me | Me | H | F | H | H | F | H | nonafluoro-2-butyl | H | CF3 |

TABLE 9-continued

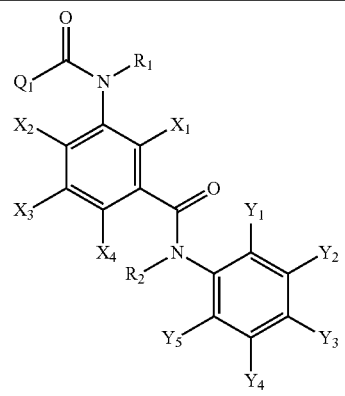

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 9-4644 | phenyl | Me | Me | H | F | H | H | Cl | H | nonafluoro-2-butyl | H | CF3 |
| 9-4664 | 3-cyanophenyl | Me | Me | H | F | H | H | Cl | H | nonafluoro-2-butyl | H | CF3 |
| 9-4665 | 4-cyanophenyl | Me | Me | H | F | H | H | Cl | H | nonafluoro-2-butyl | H | CF3 |
| 9-4680 | 2-chloropyridin-3-yl | Me | Me | H | F | H | H | Cl | H | nonafluoro-2-butyl | H | CF3 |
| 9-4722 | phenyl | Me | Me | H | F | H | H | Br | H | heptafluoroisopropyl | H | CF3 |
| 9-4742 | 3-cyanophenyl | Me | Me | H | F | H | H | Br | H | heptafluoroisopropyl | H | CF3 |
| 9-4743 | 4-cyanophenyl | Me | Me | H | F | H | H | Br | H | heptafluoroisopropyl | H | CF3 |
| 9-4758 | 2-chloropyridin-3-yl | Me | Me | H | F | H | H | Br | H | heptafluoroisopropyl | H | CF3 |
| 9-4800 | phenyl | Me | Me | H | F | H | H | Br | H | nonafluoro-2-butyl | H | CF3 |
| 9-4820 | 3-cyanophenyl | Me | Me | H | F | H | H | Br | H | nonafluoro-2-butyl | H | CF3 |
| 9-4821 | 4-cyanophenyl | Me | Me | H | F | H | H | Br | H | nonafluoro-2-butyl | H | CF3 |
| 9-4836 | 2-chloropyridin-3-yl | Me | Me | H | F | H | H | Br | H | nonafluoro-2-butyl | H | CF3 |
| 9-4878 | phenyl | Me | Me | H | F | H | H | I | H | heptafluoroisopropyl | H | CF3 |
| 9-4898 | 3-cyanophenyl | Me | Me | H | F | H | H | I | H | heptafluoroisopropyl | H | CF3 |
| 9-4899 | 4-cyanophenyl | Me | Me | H | F | H | H | I | H | heptafluoroisopropyl | H | CF3 |
| 9-4914 | 2-chloropyridin-3-yl | Me | Me | H | F | H | H | I | H | heptafluoroisopropyl | H | CF3 |
| 9-4956 | phenyl | Me | Me | H | F | H | H | I | H | nonafluoro-2-butyl | H | CF3 |
| 9-4976 | 3-cyanophenyl | Me | Me | H | F | H | H | I | H | nonafluoro-2-butyl | H | CF3 |
| 9-4977 | 4-cyanophenyl | Me | Me | H | F | H | H | I | H | nonafluoro-2-butyl | H | CF3 |
| 9-4992 | 2-chloropyridin-3-yl | Me | Me | H | F | H | H | I | H | nonafluoro-2-butyl | H | CF3 |
| 9-5230 | phenyl | Me | Me | H | F | H | H | OCF3 | H | heptafluoroisopropyl | H | OCF3 |
| 9-5261 | 2-chloropyridin-3-yl | Me | Me | H | F | H | H | OCF3 | H | heptafluoroisopropyl | H | OCF3 |
| 9-5286 | phenyl | Me | Me | H | F | H | H | OCF3 | H | nonafluoro-2-butyl | H | OCF3 |
| 9-5317 | 2-chloropyridin-3-yl | Me | Me | H | F | H | H | OCF3 | H | nonafluoro-2-butyl | H | OCF3 |
| 9-5342 | phenyl | Me | Me | H | F | H | H | CF3 | H | heptafluoroisopropyl | H | OCF3 |
| 9-5373 | 2-chloropyridin-3-yl | Me | Me | H | F | H | H | CF3 | H | heptafluoroisopropyl | H | OCF3 |
| 9-5398 | phenyl | Me | Me | H | F | H | H | CF3 | H | nonafluoro-2-butyl | H | OCF3 |
| 9-5429 | 2-chloropyridin-3-yl | Me | Me | H | F | H | H | CF3 | H | nonafluoro-2-butyl | H | OCF3 |
| 9-5454 | phenyl | Me | Me | H | F | H | H | CF3 | H | heptafluoroisopropyl | H | CF3 |
| 9-5474 | 3-cyanophenyl | Me | Me | H | F | H | H | CF3 | H | heptafluoroisopropyl | H | CF3 |
| 9-5475 | 4-cyanophenyl | Me | Me | H | F | H | H | CF3 | H | heptafluoroisopropyl | H | CF3 |
| 9-5490 | 2-chloropyridin-3-yl | Me | Me | H | F | H | H | CF3 | H | heptafluoroisopropyl | H | CF3 |
| 9-5522 | phenyl | Me | Me | H | F | H | H | CF3 | H | nonafluoro-2-butyl | H | CF3 |
| 9-5542 | 3-cyanophenyl | Me | Me | H | F | H | H | CF3 | H | nonafluoro-2-butyl | H | CF3 |
| 9-5543 | 4-cyanophenyl | Me | Me | H | F | H | H | CF3 | H | nonafluoro-2-butyl | H | CF3 |
| 9-5568 | 2-chloropyridin-3-yl | Me | Me | H | F | H | H | CF3 | H | nonafluoro-2-butyl | H | CF3 |
| 9-5786 | phenyl | Me | Me | F | F | H | H | F | H | heptafluoroisopropyl | H | F |
| 9-5787 | 3-cyanophenyl | Me | Me | F | F | H | H | F | H | heptafluoroisopropyl | H | F |
| 9-5788 | 4-cyanophenyl | Me | Me | F | F | H | H | F | H | heptafluoroisopropyl | H | F |
| 9-5789 | 2-chloropyridin-3-yl | Me | Me | F | F | H | H | F | H | heptafluoroisopropyl | H | F |
| 9-5790 | phenyl | Me | Me | F | F | H | H | F | H | nonafluoro-2-butyl | H | F |
| 9-5791 | 3-cyanophenyl | Me | Me | F | F | H | H | F | H | nonafluoro-2-butyl | H | F |
| 9-5792 | 4-cyanophenyl | Me | Me | F | F | H | H | F | H | nonafluoro-2-butyl | H | F |
| 9-5793 | 2-chloropyridin-3-yl | Me | Me | F | F | H | H | F | H | nonafluoro-2-butyl | H | F |
| 9-5794 | phenyl | Me | Me | F | F | H | H | Cl | H | heptafluoroisopropyl | H | Cl |
| 9-5814 | 3-cyanophenyl | Me | Me | F | F | H | H | Cl | H | heptafluoroisopropyl | H | Cl |
| 9-5815 | 4-cyanophenyl | Me | Me | F | F | H | H | Cl | H | heptafluoroisopropyl | H | Cl |
| 9-5830 | 2-chloropyridin-3-yl | Me | Me | F | F | H | H | Cl | H | heptafluoroisopropyl | H | Cl |
| 9-5872 | phenyl | Me | Me | F | F | H | H | Cl | H | nonafluoro-2-butyl | H | Cl |
| 9-5892 | 3-cyanophenyl | Me | Me | F | F | H | H | Cl | H | nonafluoro-2-butyl | H | Cl |
| 9-5893 | 4-cyanophenyl | Me | Me | F | F | H | H | Cl | H | nonafluoro-2-butyl | H | Cl |
| 9-5908 | 2-chloropyridin-3-yl | Me | Me | F | F | H | H | Cl | H | nonafluoro-2-butyl | H | Cl |
| 9-5950 | phenyl | Me | Me | F | F | H | H | Br | H | heptafluoroisopropyl | H | Br |
| 9-5970 | 3-cyanophenyl | Me | Me | F | F | H | H | Br | H | heptafluoroisopropyl | H | Br |
| 9-5971 | 4-cyanophenyl | Me | Me | F | F | H | H | Br | H | heptafluoroisopropyl | H | Br |
| 9-5986 | 2-chloropyridin-3-yl | Me | Me | F | F | H | H | Br | H | heptafluoroisopropyl | H | Br |
| 9-6028 | phenyl | Me | Me | F | F | H | H | Br | H | nonafluoro-2-butyl | H | Br |
| 9-6048 | 3-cyanophenyl | Me | Me | F | F | H | H | Br | H | nonafluoro-2-butyl | H | Br |

TABLE 9-continued

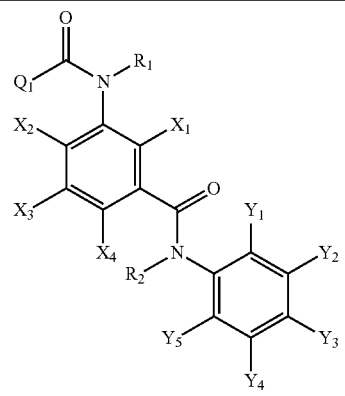

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 9-6049 | 4-cyanophenyl | Me | Me | F | F | H | H | Br | H | nonafluoro-2-butyl | H | Br |
| 9-6064 | 2-chloropyridin-3-yl | Me | Me | F | F | H | H | Br | H | nonafluoro-2-butyl | H | Br |
| 9-6106 | phenyl | Me | Me | F | F | H | H | I | H | heptafluoroisopropyl | H | I |
| 9-6126 | 3-cyanophenyl | Me | Me | F | F | H | H | I | H | heptafluoroisopropyl | H | I |
| 9-6127 | 4-cyanophenyl | Me | Me | F | F | H | H | I | H | heptafluoroisopropyl | H | I |
| 9-6142 | 2-chloropyridin-3-yl | Me | Me | F | F | H | H | I | H | heptafluoroisopropyl | H | I |
| 9-6184 | phenyl | Me | Me | F | F | H | H | I | H | nonafluoro-2-butyl | H | I |
| 9-6204 | 3-cyanophenyl | Me | Me | F | F | H | H | I | H | nonafluoro-2-butyl | H | I |
| 9-6205 | 4-cyanophenyl | Me | Me | F | F | H | H | I | H | nonafluoro-2-butyl | H | I |
| 9-6220 | 2-chloropyridin-3-yl | Me | Me | F | F | H | H | I | H | nonafluoro-2-butyl | H | I |
| 9-6458 | phenyl | Me | Me | F | F | H | H | Cl | H | heptafluoroisopropyl | H | OCF3 |
| 9-6478 | 3-cyanophenyl | Me | Me | F | F | H | H | Cl | H | heptafluoroisopropyl | H | OCF3 |
| 9-6479 | 4-cyanophenyl | Me | Me | F | F | H | H | Cl | H | heptafluoroisopropyl | H | OCF3 |
| 9-6494 | 2-chloropyridin-3-yl | Me | Me | F | F | H | H | Cl | H | heptafluoroisopropyl | H | OCF3 |
| 9-6536 | phenyl | Me | Me | F | F | H | H | Cl | H | nonafluoro-2-butyl | H | OCF3 |
| 9-6556 | 3-cyanophenyl | Me | Me | F | F | H | H | Cl | H | nonafluoro-2-butyl | H | OCF3 |
| 9-6557 | 4-cyanophenyl | Me | Me | F | F | H | H | Cl | H | nonafluoro-2-butyl | H | OCF3 |
| 9-6572 | 2-chloropyridin-3-yl | Me | Me | F | F | H | H | Cl | H | nonafluoro-2-butyl | H | OCF3 |
| 9-6614 | phenyl | Me | Me | F | F | H | H | Br | H | heptafluoroisopropyl | H | OCF3 |
| 9-6634 | 3-cyanophenyl | Me | Me | F | F | H | H | Br | H | heptafluoroisopropyl | H | OCF3 |
| 9-6635 | 4-cyanophenyl | Me | Me | F | F | H | H | Br | H | heptafluoroisopropyl | H | OCF3 |
| 9-6650 | 2-chloropyridin-3-yl | Me | Me | F | F | H | H | Br | H | heptafluoroisopropyl | H | OCF3 |
| 9-6692 | phenyl | Me | Me | F | F | H | H | Br | H | nonafluoro-2-butyl | H | OCF3 |
| 9-6712 | 3-cyanophenyl | Me | Me | F | F | H | H | Br | H | nonafluoro-2-butyl | H | OCF3 |
| 9-6713 | 4-cyanophenyl | Me | Me | F | F | H | H | Br | H | nonafluoro-2-butyl | H | OCF3 |
| 9-6728 | 2-chloropyridin-3-yl | Me | Me | F | F | H | H | Br | H | nonafluoro-2-butyl | H | OCF3 |
| 9-6770 | phenyl | Me | Me | F | F | H | H | I | H | heptafluoroisopropyl | H | OCF3 |
| 9-6790 | 3-cyanophenyl | Me | Me | F | F | H | H | I | H | heptafluoroisopropyl | H | OCF3 |
| 9-6791 | 4-cyanophenyl | Me | Me | F | F | H | H | I | H | heptafluoroisopropyl | H | OCF3 |
| 9-6806 | 2-chloropyridin-3-yl | Me | Me | F | F | H | H | I | H | heptafluoroisopropyl | H | OCF3 |
| 9-6848 | phenyl | Me | Me | F | F | H | H | I | H | nonafluoro-2-butyl | H | OCF3 |
| 9-6868 | 3-cyanophenyl | Me | Me | F | F | H | H | I | H | nonafluoro-2-butyl | H | OCF3 |
| 9-6869 | 4-cyanophenyl | Me | Me | F | F | H | H | I | H | nonafluoro-2-butyl | H | OCF3 |
| 9-6884 | 2-chloropyridin-3-yl | Me | Me | F | F | H | H | I | H | nonafluoro-2-butyl | H | OCF3 |
| 9-7122 | phenyl | Me | Me | F | F | H | H | I | H | heptafluoroisopropyl | H | CF3 |
| 9-7123 | phenyl | Me | Me | F | F | H | H | Cl | H | heptafluoroisopropyl | H | CF3 |
| 9-7143 | 3-cyanophenyl | Me | Me | F | F | H | H | Cl | H | heptafluoroisopropyl | H | CF3 |
| 9-7144 | 4-cyanophenyl | Me | Me | F | F | H | H | Cl | H | heptafluoroisopropyl | H | CF3 |
| 9-7159 | 2-chloropyridin-3-yl | Me | Me | F | F | H | H | Cl | H | heptafluoroisopropyl | H | CF3 |
| 9-7201 | phenyl | Me | Me | F | F | H | H | F | H | nonafluoro-2-butyl | H | CF3 |
| 9-7202 | phenyl | Me | Me | F | F | H | H | Cl | H | nonafluoro-2-butyl | H | CF3 |
| 9-7222 | 3-cyanophenyl | Me | Me | F | F | H | H | Cl | H | nonafluoro-2-butyl | H | CF3 |
| 9-7223 | 4-cyanophenyl | Me | Me | F | F | H | H | Cl | H | nonafluoro-2-butyl | H | CF3 |
| 9-7238 | 2-chloropyridin-3-yl | Me | Me | F | F | H | H | Cl | H | nonafluoro-2-butyl | H | CF3 |
| 9-7280 | phenyl | Me | Me | F | F | H | H | Br | H | heptafluoroisopropyl | H | CF3 |
| 9-7300 | 3-cyanophenyl | Me | Me | F | F | H | H | Br | H | heptafluoroisopropyl | H | CF3 |
| 9-7301 | 4-cyanophenyl | Me | Me | F | F | H | H | Br | H | heptafluoroisopropyl | H | CF3 |
| 9-7316 | 2-chloropyridin-3-yl | Me | Me | F | F | H | H | Br | H | heptafluoroisopropyl | H | CF3 |
| 9-7358 | phenyl | Me | Me | F | F | H | H | Br | H | nonafluoro-2-butyl | H | CF3 |
| 9-7378 | 3-cyanophenyl | Me | Me | F | F | H | H | Br | H | nonafluoro-2-butyl | H | CF3 |
| 9-7379 | 4-cyanophenyl | Me | Me | F | F | H | H | Br | H | nonafluoro-2-butyl | H | CF3 |
| 9-7394 | 2-chloropyridin-3-yl | Me | Me | F | F | H | H | Br | H | nonafluoro-2-butyl | H | CF3 |
| 9-7436 | phenyl | Me | Me | F | F | H | H | I | H | heptafluoroisopropyl | H | CF3 |
| 9-7456 | 3-cyanophenyl | Me | Me | F | F | H | H | I | H | heptafluoroisopropyl | H | CF3 |
| 9-7457 | 4-cyanophenyl | Me | Me | F | F | H | H | I | H | heptafluoroisopropyl | H | CF3 |
| 9-7472 | 2-chloropyridin-3-yl | Me | Me | F | F | H | H | I | H | heptafluoroisopropyl | H | CF3 |
| 9-7514 | phenyl | Me | Me | F | F | H | H | I | H | nonafluoro-2-butyl | H | CF3 |
| 9-7534 | 3-cyanophenyl | Me | Me | F | F | H | H | I | H | nonafluoro-2-butyl | H | CF3 |

TABLE 9-continued

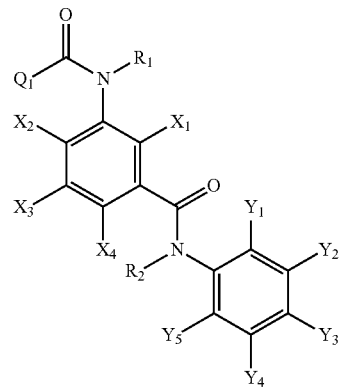

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 9-7535 | 4-cyanophenyl | Me | Me | F | F | H | H | I | H | nonafluoro-2-butyl | H | CF3 |
| 9-7550 | 2-chloropyridin-3-yl | Me | Me | F | F | H | H | I | H | nonafluoro-2-butyl | H | CF3 |
| 9-7788 | phenyl | Me | Me | F | F | H | H | OCF3 | H | heptafluoroisopropyl | H | OCF3 |
| 9-7819 | 2-chloropyridin-3-yl | Me | Me | F | F | H | H | OCF3 | H | heptafluoroisopropyl | H | OCF3 |
| 9-7844 | phenyl | Me | Me | F | F | H | H | OCF3 | H | nonafluoro-2-butyl | H | OCF3 |
| 9-7875 | 2-chloropyridin-3-yl | Me | Me | F | F | H | H | OCF3 | H | nonafluoro-2-butyl | H | OCF3 |
| 9-7900 | phenyl | Me | Me | F | F | H | H | CF3 | H | heptafluoroisopropyl | H | OCF3 |
| 9-7931 | 2-chloropyridin-3-yl | Me | Me | F | F | H | H | CF3 | H | heptafluoroisopropyl | H | OCF3 |
| 9-7956 | phenyl | Me | Me | F | F | H | H | CF3 | H | nonafluoro-2-butyl | H | OCF3 |
| 9-7987 | 2-chloropyridin-3-yl | Me | Me | F | F | H | H | CF3 | H | nonafluoro-2-butyl | H | OCF3 |
| 9-8012 | phenyl | Me | Me | F | F | H | H | CF3 | H | heptafluoroisopropyl | H | CF3 |
| 9-8032 | 3-cyanophenyl | Me | Me | F | F | H | H | CF3 | H | heptafluoroisopropyl | H | CF3 |
| 9-8033 | 4-cyanophenyl | Me | Me | F | F | H | H | CF3 | H | heptafluoroisopropyl | H | CF3 |
| 9-8048 | 2-chloropyridin-3-yl | Me | Me | F | F | H | H | CF3 | H | heptafluoroisopropyl | H | CF3 |
| 9-8080 | phenyl | Me | Me | F | F | H | H | CF3 | H | nonafluoro-2-butyl | H | CF3 |
| 9-8100 | 3-cyanophenyl | Me | Me | F | F | H | H | CF3 | H | nonafluoro-2-butyl | H | CF3 |
| 9-8101 | 4-cyanophenyl | Me | Me | F | F | H | H | CF3 | H | nonafluoro-2-butyl | H | CF3 |
| 9-8116 | 2-chloropyridin-3-yl | Me | Me | F | F | H | H | CF3 | H | nonafluoro-2-butyl | H | CF3 |
| 9-8344 | phenyl | Me | Me | F | F | F | H | Cl | H | pentafluoroethyl | H | Cl |
| 9-8345 | phenyl | Me | Me | F | F | F | H | Br | H | heptafluoroisopropyl | H | Br |
| 9-8346 | phenyl | Me | Me | F | F | F | H | Br | H | heptafluoroisopropyl | H | OCF3 |
| 9-8347 | phenyl | Me | Me | F | F | F | H | I | H | heptafluoroisopropyl | H | CF3 |
| 9-8348 | phenyl | Me | Me | F | F | F | H | CF3 | H | heptafluoroisopropyl | H | CF3 |
| 9-8349 | phenyl | Me | Me | F | F | F | H | I | H | nonafluoro-2-butyl | H | I |
| 9-8350 | phenyl | Me | Me | F | F | F | H | Cl | H | nonafluoro-2-butyl | H | OCF3 |
| 9-8351 | phenyl | Me | Me | F | F | F | H | Br | H | nonafluoro-2-butyl | H | CF3 |
| 9-8352 | phenyl | Me | Me | F | F | F | H | CF3 | H | nonafluoro-2-butyl | H | CF3 |
| 9-8353 | phenyl | Me | Me | H | H | F | H | Cl | H | pentafluoroethyl | H | Cl |
| 9-8354 | phenyl | Me | Me | H | H | F | H | Br | H | heptafluoroisopropyl | H | Br |
| 9-8355 | phenyl | Me | Me | H | H | F | H | Br | H | heptafluoroisopropyl | H | OCF3 |
| 9-8356 | phenyl | Me | Me | H | H | F | H | I | H | heptafluoroisopropyl | H | CF3 |
| 9-8357 | phenyl | Me | Me | H | H | F | H | CF3 | H | heptafluoroisopropyl | H | CF3 |
| 9-8358 | phenyl | Me | Me | H | H | F | H | I | H | nonafluoro-2-butyl | H | I |
| 9-8359 | phenyl | Me | Me | H | H | F | H | Cl | H | nonafluoro-2-butyl | H | OCF3 |
| 9-8360 | phenyl | Me | Me | H | H | F | H | Br | H | nonafluoro-2-butyl | H | CF3 |
| 9-8361 | phenyl | Me | Me | H | H | F | H | CF3 | H | nonsfluoro-2-butyl | H | CF3 |
| 9-8362 | phenyl | Me | Me | H | H | H | F | Cl | H | pentafluoroethyl | H | Cl |
| 9-8363 | phenyl | Me | Me | H | H | H | F | Br | H | heptafluoroisopropyl | H | Br |
| 9-8364 | phenyl | Me | Me | H | H | H | F | Br | H | heptafluoroisopropyl | H | OCF3 |
| 9-8365 | phenyl | Me | Me | H | H | H | F | I | H | heptafluoroisopropyl | H | CF3 |
| 9-8366 | phenyl | Me | Me | H | H | H | F | CF3 | H | heptafluoroisopropyl | H | CF3 |
| 9-8367 | phenyl | Me | Me | H | H | H | F | I | H | nonafluoro-2-butyl | H | I |
| 9-8368 | phenyl | Me | Me | H | H | H | F | Cl | H | nonafluoro-2-butyl | H | OCF3 |
| 9-8369 | phenyl | Me | Me | H | H | H | F | Br | H | nonafluoro-2-butyl | H | CF3 |
| 9-8370 | phenyl | Me | Me | H | H | H | F | CF3 | H | nonafluoro-2-butyl | H | CF3 |
| 9-8371 | phenyl | Me | Me | F | H | F | H | Cl | H | pentafluoroethyl | H | Cl |
| 9-8372 | phenyl | Me | Me | F | H | F | H | Br | H | heptafluoroisopropyl | H | Br |
| 9-8373 | phenyl | Me | Me | F | H | F | H | Br | H | heptafluoroisopropyl | H | OCF3 |
| 9-8374 | phenyl | Me | Me | F | H | F | H | I | H | heptafluoroisopropyl | H | CF3 |
| 9-8375 | phenyl | Me | Me | F | H | F | H | CF3 | H | heptafluoroisopropyl | H | CF3 |
| 9-8376 | phenyl | Me | Me | F | H | F | H | I | H | nonafluoro-2-butyl | H | I |
| 9-8377 | phenyl | Me | Me | F | H | F | H | Cl | H | nonafluoro-2-butyl | H | OCF3 |
| 9-8378 | phenyl | Me | Me | F | H | F | H | Br | H | nonafluoro-2-butyl | H | CF3 |
| 9-8379 | phenyl | Me | Me | F | H | F | H | CF3 | H | nonafluoro-2-butyl | H | CF3 |
| 9-8380 | phenyl | Me | Me | F | H | H | F | Cl | H | pentafluoroethyl | H | Cl |
| 9-8381 | phenyl | Me | Me | F | H | H | F | Br | H | heptafluoroisopropyl | H | Br |
| 9-8382 | phenyl | Me | Me | F | H | H | F | Br | H | heptafluoroisopropyl | H | OCF3 |
| 9-8383 | phenyl | Me | Me | F | H | H | F | I | H | heptafluoroisopropyl | H | CF3 |

TABLE 9-continued

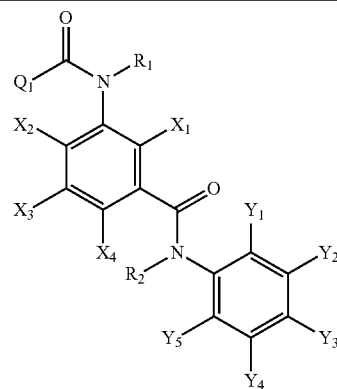

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 9-8384 | phenyl | Me | Me | F | H | H | F | CF3 | H | heptafluoroisopropyl | H | CF3 |
| 9-8385 | phenyl | Me | Me | F | H | H | F | I | H | nonafluoro-2-butyl | H | I |
| 9-8386 | phenyl | Me | Me | F | H | H | F | Cl | H | nonafluoro-2-butyl | H | OCF3 |
| 9-8387 | phenyl | Me | Me | F | H | H | F | Br | H | nonafluoro-2-butyl | H | CF3 |
| 9-8388 | phenyl | Me | Me | F | H | H | F | CF3 | H | nonafluoro-2-butyl | H | CF3 |
| 9-8389 | phenyl | Me | Me | H | F | F | H | Cl | H | pentafluoroethyl | H | Cl |
| 9-8390 | phenyl | Me | Me | H | F | F | H | Br | H | heptafluoroisopropyl | H | Br |
| 9-8391 | phenyl | Me | Me | H | F | F | H | Br | H | heptafluoroisopropyl | H | OCF3 |
| 9-8392 | phenyl | Me | Me | H | F | F | H | I | H | heptafluoroisopropyl | H | CF3 |
| 9-8393 | phenyl | Me | Me | H | F | F | H | CF3 | H | heptafluoroisopropyl | H | CF3 |
| 9-8394 | phenyl | Me | Me | H | F | F | H | I | H | nonafluoro-2-butyl | H | I |
| 9-8395 | phenyl | Me | Me | H | F | F | H | Cl | H | nonafluoro-2-butyl | H | OCF3 |
| 9-8396 | phenyl | Me | Me | H | F | F | H | Br | H | nonafluoro-2-butyl | H | CF3 |
| 9-8397 | phenyl | Me | Me | H | F | F | H | CF3 | H | nonafluoro-2-butyl | H | CF3 |
| 9-8398 | phenyl | Me | Me | H | F | H | F | Cl | H | pentafluoroethyl | H | Cl |
| 9-8399 | phenyl | Me | Me | H | F | H | F | Br | H | heptafluoroisopropyl | H | Br |
| 9-8400 | phenyl | Me | Me | H | F | H | F | Br | H | heptafluoroisopropyl | H | OCF3 |
| 9-8401 | phenyl | Me | Me | H | F | H | F | I | H | heptafluoroisopropyl | H | CF3 |
| 9-8402 | phenyl | Me | Me | H | F | H | F | CF3 | H | heptafluoroisopropyl | H | CF3 |
| 9-8403 | phenyl | Me | Me | H | F | H | F | I | H | nonafluoro-2-butyl | H | I |
| 9-8404 | phenyl | Me | Me | H | F | H | F | Cl | H | nonafluoro-2-butyl | H | OCF3 |
| 9-8405 | phenyl | Me | Me | H | F | H | F | Br | H | nonafluoro-2-butyl | H | CF3 |
| 9-8406 | phenyl | Me | Me | H | F | H | F | CF3 | H | nonafluoro-2-butyl | H | CF3 |
| 9-8407 | phenyl | Me | Me | H | H | F | F | Cl | H | pentafluoroethyl | H | Cl |
| 9-8408 | phenyl | Me | Me | H | H | F | F | Br | H | heptafluoroisopropyl | H | Br |
| 9-8409 | phenyl | Me | Me | H | H | F | F | Br | H | heptafluoroisopropyl | H | OCF3 |
| 9-8410 | phenyl | Me | Me | H | H | F | F | I | H | heptafluoroisopropyl | H | CF3 |
| 9-8411 | phenyl | Me | Me | H | H | F | F | CF3 | H | heptafluoroisopropyl | H | CF3 |
| 9-8412 | phenyl | Me | Me | H | H | F | F | I | H | nonafluoro-2-butyl | H | I |
| 9-8413 | phenyl | Me | Me | H | H | F | F | Cl | H | nonafluoro-2-butyl | H | OCF3 |
| 9-8414 | phenyl | Me | Me | H | H | F | F | Br | H | nonafluoro-2-butyl | H | CF3 |
| 9-8415 | phenyl | Me | Me | H | H | F | F | CF3 | H | nonafluoro-2-butyl | H | CF3 |
| 9-8416 | phenyl | Me | Me | F | F | H | F | Cl | H | pentafluoroethyl | H | Cl |
| 9-8417 | phenyl | Me | Me | F | F | H | F | Br | H | heptafluoroisopropyl | H | Br |
| 9-8418 | phenyl | Me | Me | F | F | H | F | Br | H | heptafluoroisopropyl | H | OCF3 |
| 9-8419 | phenyl | Me | Me | F | F | H | F | I | H | heptafluoroisopropyl | H | CF3 |
| 9-8420 | phenyl | Me | Me | F | F | H | F | CF3 | H | heptafluoroisopropyl | H | CF3 |
| 9-8421 | phenyl | Me | Me | F | F | H | F | I | H | nonafluoro-2-butyl | H | I |
| 9-8422 | phenyl | Me | Me | F | F | H | F | Cl | H | nonafluoro-2-butyl | H | OCF3 |
| 9-8423 | phenyl | Me | Me | F | F | H | F | Br | H | nonafluoro-2-butyl | H | CF3 |
| 9-8424 | phenyl | Me | Me | F | F | H | F | CF3 | H | nonafluoro-2-butyl | H | CF3 |
| 9-8425 | phenyl | Me | Me | F | H | F | F | Cl | H | pentafluoroethyl | H | Cl |
| 9-8426 | phenyl | Me | Me | F | H | F | F | Br | H | heptafluoroisopropyl | H | Br |
| 9-8427 | phenyl | Me | Me | F | H | F | F | Br | H | heptafluoroisopropyl | H | OCF3 |
| 9-8428 | phenyl | Me | Me | F | H | F | F | I | H | heptafluoroisopropyl | H | CF3 |
| 9-8429 | phenyl | Me | Me | F | H | F | F | CF3 | H | heptafluoroisopropyl | H | CF3 |
| 9-8430 | phenyl | Me | Me | F | H | F | F | I | H | nonafluoro-2-butyl | H | I |
| 9-8431 | phenyl | Me | Me | F | H | F | F | Cl | H | nonafluoro-2-butyl | H | OCF3 |
| 9-8432 | phenyl | Me | Me | F | H | F | F | Br | H | nonafluoro-2-butyl | H | CF3 |
| 9-8433 | phenyl | Me | Me | F | H | F | F | CF3 | H | nonafluoro-2-butyl | H | CF3 |
| 9-8434 | phenyl | Me | Me | H | F | F | F | Cl | H | pentafluoroethyl | H | Cl |
| 9-8435 | phenyl | Me | Me | H | F | F | F | Br | H | heptafluoroisopropyl | H | Br |
| 9-8436 | phenyl | Me | Me | H | F | F | F | Br | H | heptafluoroisopropyl | H | OCF3 |
| 9-8437 | phenyl | Me | Me | H | F | F | F | I | H | heptafluoroisopropyl | H | CF3 |
| 9-8438 | phenyl | Me | Me | H | F | F | F | CF3 | H | heptafluoroisopropyl | H | CF3 |
| 9-8439 | phenyl | Me | Me | H | F | F | F | I | H | nonafluoro-2-butyl | H | I |
| 9-8440 | phenyl | Me | Me | H | F | F | F | Cl | H | nonafluoro-2-butyl | H | OCF3 |
| 9-8441 | phenyl | Me | Me | H | F | F | F | Br | H | nonafluoro-2-butyl | H | CF3 |

TABLE 9-continued

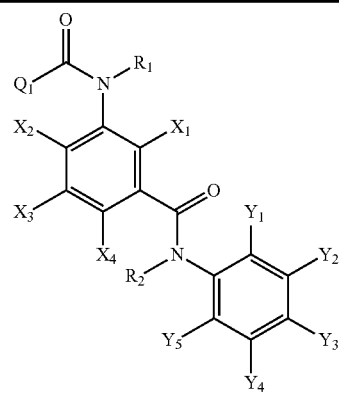

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 9-8442 | phenyl | Me | Me | H | F | F | F | CF3 | H | nonafluoro-2-butyl | H | CF3 |
| 9-8443 | phenyl | Me | Me | F | F | F | F | Cl | H | pentafluoroethyl | H | Cl |
| 9-8444 | phenyl | Me | Me | F | F | F | F | Br | H | heptafluoroisopropyl | H | Br |
| 9-8445 | phenyl | Me | Me | F | F | F | F | Br | H | heptafluoroisopropyl | H | OCF3 |
| 9-8446 | phenyl | Me | Me | F | F | F | F | I | H | heptafluoroisopropyl | H | CF3 |
| 9-8447 | phenyl | Me | Me | F | F | F | F | CF3 | H | heptafluoroisopropyl | H | CF3 |
| 9-8448 | phenyl | Me | Me | F | F | F | F | I | H | nonafluoro-2-butyl | H | I |
| 9-8449 | phenyl | Me | Me | F | F | F | F | Cl | H | nonafluoro-2-butyl | H | OCF3 |
| 9-8450 | phenyl | Me | Me | F | F | F | F | Br | H | nonafluoro-2-butyl | H | CF3 |
| 9-8451 | phenyl | Me | Me | F | F | F | F | CF3 | H | nonafluoro-2-butyl | H | CF3 |

TABLE 10

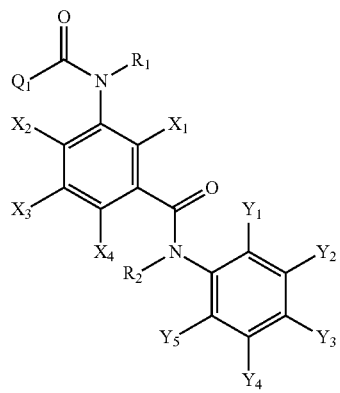

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 10-9 | 3-bromophenyl | H | Et | H | H | H | H | Cl | F | nonafluoro-2-butyl | F | Cl |
| 10-39 | 2-iodopyridin-3-yl | H | H | H | H | H | H | Cl | Me | nonafluoro-2-butyl | Me | I |
| 10-148 | 2-chlorophenyl | H | H | H | H | H | H | F | Br | heptafluoroisopropyl | H | CF3 |
| 10-153 | 4-bromophenyl | H | H | H | H | H | H | Cl | F | heptafluoroisopropyl | Cl | CF3 |
| 10-167 | 3,4-dichlorophenyl | H | H | H | H | H | H | Cl | I | nonafluoro-2-butyl | I | CF3 |
| 10-168 | 2,4-dichlorophenyl | H | H | H | H | H | H | Cl | Me | nonafluoro-2-butyl | H | CF3 |
| 10-169 | 2-chloro-4-fluorophenyl | H | H | H | H | H | H | Cl | H | nonafluoro-2-butyl | Me | CF3 |
| 10-170 | 2-chloro-4,5-difluorophenyl | i-Pr | H | H | H | H | H | Cl | Et | nonafluoro-2-butyl | H | CF3 |
| 10-171 | 4-bromo-2-chlorophenyl | H | H | H | H | H | H | Cl | H | nonafluoro-2-butyl | Et | CF3 |
| 10-182 | 2-iodopyridin-3-yl | H | H | H | H | H | H | Cl | Me | nonafluoro-2-butyl | Me | n-C3F7 |
| 10-183 | 2-(trifluoromethyl)pyridin-3-yl | H | H | H | H | H | H | Cl | Me | nonafluoro-2-butyl | Me | i-C3F7 |
| 10-189 | 6-iodopyridin-3-yl | H | H | H | H | H | H | Cl | Et | nonafluoro-2-butyl | Me | n-C3F7 |
| 10-190 | 6-(trifluoromethyl)pyridin-3-yl | H | H | H | H | H | H | Cl | Et | nonafluoro-2-butyl | Et | i-C3F7 |
| 10-196 | 5-bromopyridin-3-yl | H | H | H | H | H | H | Br | n-Pr | heptafluoroisopropyl | Me | CF3 |
| 10-197 | 5-iodopyridin-3-yl | H | H | H | H | H | H | Br | n-Pr | heptafluoroisopropyl | Et | CF3 |
| 10-203 | 4-bromopyridin-3-yl | Me | n-Pr | H | H | H | H | Br | i-Pr | heptafluoroisopropyl | Me | CF3 |
| 10-204 | 4-iodopyridin-3-yl | H | H | H | H | H | H | Br | i-Pr | heptafluoroisopropyl | Et | CF3 |
| 10-210 | pyridin-4-yl | H | H | H | H | H | H | Br | n-Bu | heptafluoroisopropyl | Me | CF3 |
| 10-211 | 2-chloropyridin-4-yl | H | H | H | H | H | H | Br | n-Bu | heptafluoroisopropyl | Et | CF3 |
| 10-217 | pyridin-2-yl | H | H | H | H | H | H | Br | i-Bu | nonafluoro-2-butyl | Me | CF3 |

TABLE 10-continued

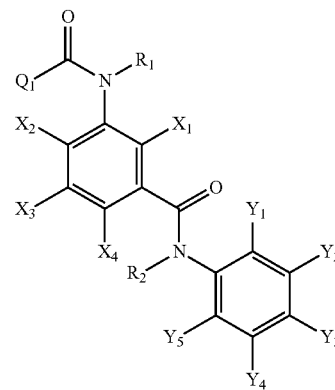

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 10-218 | 3-chloropyridin-2-yl | H | H | H | H | H | H | Br | i-Bu | nonafluoro-2-butyl | Et | CF3 |
| 10-224 | 2-fluorophenyl | H | H | H | H | H | H | Br | s-Bu | nonafluoro-2-butyl | Me | CF3 |
| 10-225 | 3-fluorophenyl | H | H | H | H | H | H | Br | s-Bu | nonafluoro-2-butyl | Et | CF3 |
| 10-231 | 3-bromophenyl | H | H | H | H | H | H | Br | F | nonafluoro-2-butyl | Me | CF3 |
| 10-232 | 4-bromophenyl | H | H | H | H | H | H | Br | F | nonafluoro-2-butyl | Et | CF3 |
| 10-238 | (4-trifluoromethyl)phenyl | Et | i-Pr | H | H | H | H | Br | Cl | nonafluoro-2-butyl | Me | CF3 |
| 10-239 | 2-nitrophenyl | H | H | H | H | H | H | Br | Cl | nonafluoro-2-butyl | Et | CF3 |
| 10-245 | 4-cyanophenyl | H | H | H | H | H | H | I | Br | heptafluoroisopropyl | Me | CF3 |
| 10-246 | 2,6-difluorophenyl | H | H | H | H | H | H | I | Br | heptafluoroisopropyl | Et | CF3 |
| 10-252 | 2-bromo-4-chlorophenyl | n-Pr | Me | H | H | H | H | I | I | heptafluoroisopropyl | Me | CF3 |
| 10-253 | 2-bromo-4-fluorophenyl | H | H | H | H | H | H | I | I | heptafluoroisopropyl | Et | CF3 |
| 10-259 | 2-fluoropyridin-3-yl | H | H | H | H | H | H | I | Me | heptafluoroisopropyl | F | C2F5 |
| 10-260 | 2-chloropyridin-3-yl | H | H | H | H | H | H | I | Me | nonafluoro-2-butyl | Cl | CF3 |
| 10-263 | 2-(trifluoromethyl)pyridin-3-yl | H | H | H | H | H | H | I | Et | nonafluora-2-butyl | F | CF3 |
| 10-264 | 2-nitropyridin-3-yl | H | H | H | H | H | H | I | Et | nonafluoro-2-butyl | Cl | CF3 |
| 10-267 | 6-chloropyridin-3-yl | H | H | H | H | H | H | I | n-Pr | nonafluoro-2-butyl | F | CF3 |
| 10-268 | 6-bromopyridin-3-yl | H | H | H | H | H | H | I | n-Pr | nonafluoro-2-butyl | Cl | CF3 |
| 10-271 | 6-nitropyridin-3-yl | H | H | H | H | H | H | I | i-Pr | nonafluoro-2-butyl | F | i-C3F7 |
| 10-272 | 6-cyanopyridin-3-yl | H | H | H | H | H | H | I | i-Pr | nonafluoro-2-butyl | Cl | CF3 |
| 10-275 | 5-bromopyridin-3-yl | H | H | H | H | H | H | I | n-Bu | nonafluoro-2-butyl | F | CF3 |
| 10-276 | 5-iodopyridin-3-yl | H | H | H | H | H | H | I | n-Bu | nonafluoro-2-butyl | Cl | CF3 |
| 10-279 | 5-cyanopyridin-3-yl | H | H | H | H | H | H | I | i-Bu | nonafluoro-2-butyl | F | CF3 |
| 10-280 | 4-fluoropyridin-3-yl | H | H | H | H | H | H | I | i-Bu | nonafluoro-2-butyl | Cl | CF3 |
| 10-283 | 4-iodopyridin-3-yl | i-Pr | n-Pr | H | H | H | H | I | s-Bu | nonafluoro-2-butyl | F | CF3 |
| 10-284 | 4-(trifluoromethyl)pyridin-3-yl | H | H | H | H | H | H | I | s-Bu | nonafluoro-2-butyl | Cl | CF3 |
| 10-295 | 3-bromophenyl | H | Et | H | H | H | H | OCF3 | F | heptafluoroisopropyl | F | OCF3 |
| 10-325 | 2-iodopyridin-3-yl | H | H | H | H | H | H | OCF3 | Me | nonafluoro-2-butyl | Me | OCF3 |
| 10-438 | 3-bromophenyl | H | Et | H | H | H | H | OCF3 | F | heptafluoroisopropyl | F | CF3 |
| 10-468 | 2-iodopyridin-3-yl | H | H | H | H | H | H | OCF3 | Me | nonafluoro-2-butyl | Me | CF3 |
| 10-581 | 3-bromophenyl | H | Et | H | H | H | H | CF3 | F | heptafluoroisopropyl | F | CF3 |
| 10-611 | 2-iodopyridin-3-yl | H | H | H | H | H | H | CF3 | Me | nonafluoro-2-butyl | Me | CF3 |
| 10-724 | 3-bromophenyl | H | Et | F | H | H | H | Cl | F | heptafluoroisopropyl | F | Cl |
| 10-754 | 2-iodopyridin-3-yl | H | H | F | H | H | H | Cl | Me | heptafluoroisopropyl | Me | I |
| 10-859 | phenyl | H | H | F | H | H | H | Cl | F | heptafluoroisopropyl | H | CF3 |
| 10-860 | 2-fluorophenyl | Me | H | F | H | H | H | Cl | H | heptafluoroisopropyl | F | CF3 |
| 10-861 | 3-fluorophenyl | H | Me | F | H | H | H | Cl | Cl | heptafluoroisopropyl | H | CF3 |
| 10-862 | 4-fluorophenyl | Me | Me | F | H | H | H | Cl | H | heptafluoroisopropyl | Cl | CF3 |
| 10-863 | 2-chlorophenyl | H | H | F | H | H | H | F | Br | heptafluoroisopropyl | H | CF3 |
| 10-864 | 3-chlorophenyl | H | H | F | H | H | H | Cl | H | heptafluoroisopropyl | Br | CF3 |
| 10-865 | 4-chlorophenyl | Et | H | F | H | H | H | Cl | I | heptafluoroisopropyl | H | C2F5 |
| 10-866 | 2-bromophenyl | H | H | F | H | H | H | Cl | H | heptafluoroisopropyl | I | CF3 |
| 10-867 | 3-bromophenyl | H | Et | F | H | H | H | Cl | F | heptafluoroisopropyl | F | CF3 |
| 10-868 | 4-bromophenyl | H | H | F | H | H | H | Cl | F | heptafluoroisopropyl | Cl | CF3 |
| 10-869 | 2-iodophenyl | H | H | F | H | H | H | Cl | F | heptafluoroisopropyl | Br | CF3 |
| 10-870 | 3-iodophenyl | Et | Et | F | H | H | H | Cl | F | pentafluoroethyl | I | C2F5 |
| 70-871 | 4-iodophenyl | H | H | F | H | H | H | Cl | Cl | pentafluoroethyl | F | CF3 |
| 10-872 | (2-trifluoromethyl)phenyl | H | H | F | H | H | H | Cl | Cl | heptafluoroisopropyl | Cl | CF3 |
| 10-873 | (3-trifluoromethyl)phenyl | n-Pr | H | F | H | H | H | Cl | Cl | heptafluoroisopropyl | Br | CF3 |
| 10-874 | (4-trifluoromethyl)phenyl | H | H | F | H | H | H | Cl | Cl | heptafluoroisopropyl | I | n-C3F7 |
| 10-875 | 2-nitrophenyl | H | n-Pr | F | H | H | H | Cl | Br | heptafluoroisopropyl | F | CF3 |
| 10-876 | 3-nitrophenyl | H | H | F | H | H | H | Cl | Br | heptafluoroisopropyl | Cl | CF3 |
| 10-877 | 4-nitrophenyl | H | H | F | H | H | H | Cl | Br | heptafluoroisopropyl | Br | CF3 |
| 10-878 | 2-cyanophenyl | n-Pr | n-Pr | F | H | H | H | Cl | Br | pentafluoroethyl | I | CF3 |
| 10-879 | 3-cyanophenyl | H | H | F | H | H | H | F | I | nonafluoro-2-butyl | F | CF3 |
| 10-880 | 4-cyanophenyl | H | H | F | H | H | H | Cl | I | nonafluoro-2-butyl | Cl | CF3 |
| 10-881 | 2,6-difluorophenyl | H | H | F | H | H | H | Cl | I | nonafluoro-2-butyl | Br | CF3 |
| 10-882 | 3,4-dichlorophenyl | H | H | F | H | H | H | Cl | I | nonafluoro-2-butyl | I | CF3 |

TABLE 10-continued

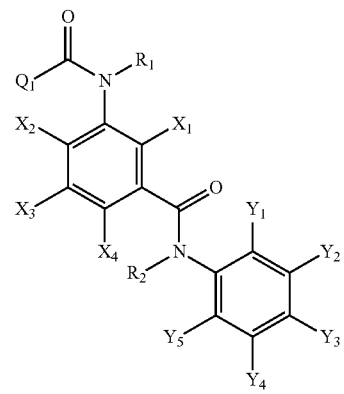

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 10-883 | 2,4-dichlorophenyl | H | H | F | H | H | H | Cl | Me | nonafluoro-2-butyl | H | CF3 |
| 10-884 | 2-chloro-4-fluorophenyl | H | H | F | H | H | H | Cl | H | nonafluoro-2-butyl | Me | CF3 |
| 10-885 | 2-chloro-4,5-difluorophenyl | i-Pr | H | F | H | H | H | Cl | Et | nonafluoro-2-butyl | H | CF3 |
| 10-886 | 4-bromo-2-chlorophenyl | H | H | F | H | H | H | Cl | H | nonafluoro-2-butyl | Et | CF3 |
| 10-887 | 2-bromo-4-chlorophenyl | H | H | F | H | H | H | Cl | n-Pr | nonafluoro-2-butyl | H | CF3 |
| 10-888 | 2-bromo-4-fluorophenyl | H | i-Pr | F | H | H | H | Cl | H | nonafluoro-2-butyl | n-Pr | CF3 |
| 10-889 | 2-chloro-4-nitrophenyl | i-Pr | i-Pr | F | H | H | H | Cl | i-Pr | nonafluoro-2-butyl | H | CF3 |
| 10-890 | 3,5-dicyanophenyl | H | H | F | H | H | H | Cl | H | nonafluoro-2-butyl | i-Pr | CF3 |
| 10-891 | 4-cyano-2-fluorophenyl | H | H | F | H | H | H | Cl | n-Bu | nonafluoro-2-butyl | H | CF3 |
| 10-892 | 2-chloro-4-cyanophenyl | H | H | F | H | H | H | Cl | H | nonafluoro-2-butyl | n-Bu | CF3 |
| 10-893 | pyridin-3-yl | H | H | F | H | H | H | Cl | i-Bu | nonafluoro-2-butyl | H | CF3 |
| 10-894 | 2-fluoropyridin-3-yl | H | H | F | H | H | H | Cl | H | nonafluoro-2-butyl | i-Bu | CF3 |
| 10-895 | 2-chloropyridin-3-yl | H | H | F | H | H | H | Cl | s-Bu | nonafluoro-2-butyl | H | C2F5 |
| 10-896 | 2-bromopyridin-3-yl | H | H | F | H | H | H | Cl | H | nonafluoro-2-butyl | s-Bu | CF3 |
| 10-897 | 2-iodopyridin-3-yl | H | H | F | H | H | H | Cl | Me | nonafluoro-2-butyl | Me | n-C3F7 |
| 10-898 | 2-(trifluoromethyl)pyridin-3-yl | H | H | F | H | H | H | Cl | Me | nonafluoro-2-butyl | Et | i-C3F7 |
| 10-899 | 2-nitropyridin-3-yl | C(O)Me | H | F | H | H | H | Cl | Me | nonafluoro-2-butyl | n-Pr | CF3 |
| 10-900 | 2-cyanopyridin-3-yl | H | H | F | H | H | H | Cl | Me | nonafluora-2-butyl | i-Pr | CF3 |
| 10-901 | 6-fluoropyridin-3-yl | H | H | F | H | H | H | Cl | Me | nonafluoro-2-butyl | n-Bu | CF3 |
| 10-902 | 6-chloropyridin-3-yl | H | H | F | H | H | H | Cl | Me | nonafluoro-2-butyl | i-Bu | CF3 |
| 10-903 | 6-bromopyridin-3-yl | H | C(O)Me | F | H | H | H | Cl | Me | nonafluoro-2-butyl | s-Bu | CF3 |
| 10-904 | 6-iodopyridin-3-yl | H | H | F | H | H | H | Cl | Et | nonafluoro-2-butyl | Me | n-C3F7 |
| 10-905 | 6-(trifluoromethyl)pyridin-3-yl | H | H | F | H | H | H | Cl | Et | nonafluoro-2-butyl | Et | i-C3F7 |
| 10-906 | 6-nitropyridin-3-yl | C(O)Me | C(O)Me | F | H | H | H | Cl | Et | nonafluoro-2-butyl | n-Pr | CF3 |
| 10-907 | 6-cyanopyridin-3-yl | H | H | F | H | H | H | Cl | Et | nonafluoro-2-butyl | i-Pr | CF3 |
| 10-908 | phenyl | H | H | F | H | H | H | Br | Et | heptafluoroisopropyl | n-Bu | CF3 |
| 10-909 | 5-fluoropyridin-3-yl | H | H | F | H | H | H | Br | Et | heptafluoroisopropyl | i-Bu | CF3 |
| 10-910 | 5-chloropyridin-3-yl | H | H | F | H | H | H | Br | Et | heptafluoroisopropyl | s-Bu | CF3 |
| 10-911 | 5-bromopyridin-3-yl | H | H | F | H | H | H | Br | n-Pr | heptafluoroisopropyl | Me | CF3 |
| 10-912 | 5-iodopyridin-3-yl | H | H | F | H | H | H | Br | n-Pr | heptafluoroisopropyl | Et | CF3 |
| 10-913 | 5-(trifluoromethyl)pyridin-3-yl | Me | Et | F | H | H | H | Br | n-Pr | pentafluoroethyl | n-Pr | CF3 |
| 10-914 | 5-nitropyridin-3-yl | H | H | F | H | H | H | Br | n-Pr | heptafluoroisopropyl | i-Pr | CF3 |
| 10-915 | 5-cyanopyridin-3-yl | H | H | F | H | H | H | Br | n-Pr | pentafluoroethyl | n-Bu | CF3 |
| 10-916 | 4-fluoropyridin-3-yl | H | H | F | H | H | H | Br | n-Pr | heptafluoroisopropyl | i-Bu | CF3 |
| 10-917 | 4-chloropyridin-3-yl | H | H | F | H | H | H | Br | n-Pr | heptafluoroisopropyl | s-Bu | CF3 |
| 10-918 | 4-bromopyridin-3-yl | Me | n-Pr | F | H | H | H | Br | i-Pr | heptafluoroisopropyl | Me | CF3 |
| 10-919 | 4-iodopyridin-3-yl | H | H | F | H | H | H | Br | i-Pr | heptafluoroisopropyl | Et | CF3 |
| 10-920 | 4-(trifluoromethyl)pyridin-3-yl | H | H | F | H | H | H | Br | i-Pr | heptafluoroisopropyl | n-Pr | CF3 |
| 10-921 | 4-nitropyridin-3-yl | H | H | F | H | H | H | Br | i-Pr | heptafluoroisopropyl | i-Pr | CF3 |
| 10-922 | 4-cyanopyridin-3-yl | H | H | F | H | H | H | Br | i-Pr | heptafluoroisopropyl | n-Bu | CF3 |
| 10-923 | 2,6-dichloropyridin-3-yl | H | H | F | H | H | H | Br | i-Pr | heptafluoroisopropyl | i-Bu | CF3 |
| 10-924 | pyridin-3-yl N-oxide | Me | i-Pr | F | H | H | H | Br | i-Pr | heptafluoroisopropyl | s-Bu | CF3 |
| 10-925 | pyridin-4-yl | H | H | F | H | H | H | Br | n-Bu | heptafluoroisopropyl | Me | CF3 |
| 10-926 | 2-chloropyridin-4-yl | H | H | F | H | H | H | Br | n-Bu | heptafluoroisopropyl | Et | CF3 |
| 10-927 | 3-bromopyridin-4-yl | H | H | F | H | H | H | Br | n-Bu | heptafluoroisopropyl | n-Pr | CF3 |
| 10-928 | 3,5-dichloropyridin-4-yl | H | H | F | H | H | H | Br | n-Bu | nonafluoro-2-butyl | i-Pr | CF3 |
| 10-929 | 3-(trifluoromethyl)pyridin-4-yl | H | H | F | H | H | H | Br | n-Bu | nonafluoro-2-butyl | n-Bu | CF3 |
| 10-930 | 2,6-dicyanopyridin-4-yl | H | H | F | H | H | H | Br | n-Bu | nonafluoro-2-butyl | i-Bu | CF3 |
| 10-931 | pyridin-4-yl N-oxide | Me | C(O)Me | F | H | H | H | Br | n-Bu | nonafluoro-2-butyl | s-Bu | CF3 |
| 10-932 | pyridin-2-yl | H | H | F | H | H | H | Br | i-Bu | nonafluoro-2-butyl | Me | CF3 |
| 10-933 | 3-chloropyridin-2-yl | H | H | F | H | H | H | Br | i-Bu | nonafluoro-2-butyl | Et | CF3 |
| 10-934 | 4-bromopyridin-2-yl | H | H | F | H | H | H | Br | i-Bu | nonafluoro-2-butyl | n-Pr | CF3 |
| 10-935 | 5-iodopyridin-2-yl | H | H | F | H | H | H | Br | i-Bu | nonafluoro-2-butyl | i-Pr | CF3 |
| 10-936 | 6-chloropyridin-2-yl | H | H | F | H | H | H | Br | i-Bu | nonafluoro-2-butyl | n-Bu | CF3 |
| 10-937 | 4-cyanopyridin-2-yl | H | H | F | H | H | H | Br | i-Bu | nonafluoro-2-butyl | i-Bu | CF3 |
| 10-938 | phenyl | H | H | F | H | H | H | Br | i-Bu | nonafluoro-2-butyl | s-Bu | C2F5 |
| 10-939 | 2-fluorophenyl | H | H | F | H | H | H | Br | s-Bu | nonafluoro-2-butyl | Me | CF3 |

TABLE 10-continued

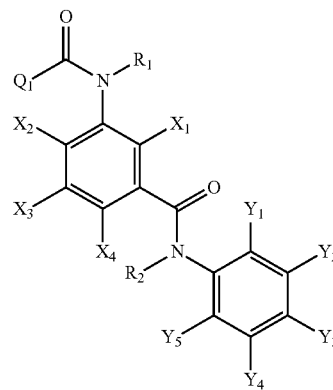

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 10-940 | 3-fluorophenyl | H | H | F | H | H | H | Br | s-Bu | nonafluoro-2-butyl | Et | CF3 |
| 10-941 | 4-fluorophenyl | H | H | F | H | H | H | Br | s-Bu | nonafluoro-2-butyl | n-Pr | CF3 |
| 10-942 | 2-chlorophenyl | H | H | F | H | H | H | Br | s-Bu | nonafluoro-2-butyl | i-Pr | CF3 |
| 10-943 | 3-chlorophenyl | H | H | F | H | H | H | Br | s-Bu | nonafluoro-2-butyl | n-Bu | CF3 |
| 10-944 | 4-chlorophenyl | H | H | F | H | H | H | Br | s-Bu | nonafluoro-2-butyl | i-Bu | CF3 |
| 10-945 | 2-bromophenyl | Et | Me | F | H | H | H | Br | s-Bu | nonafluoro-2-butyl | s-Bu | CF3 |
| 10-946 | 3-bromophenyl | H | H | F | H | H | H | Br | F | nonafluoro-2-butyl | Me | CF3 |
| 10-947 | 4-bromophenyl | H | H | F | H | H | H | Br | F | nonafluoro-2-butyl | Et | CF3 |
| 10-948 | 2-iodophenyl | H | H | F | H | H | H | Br | F | nonafluoro-2-butyl | n-Pr | CF3 |
| 10-949 | 3-iodophenyl | H | H | F | H | H | H | Br | F | nonafluoro-2-butyl | i-Pr | CF3 |
| 10-950 | 4-iodophenyl | H | H | F | H | H | H | Br | F | nonafluoro-2-butyl | n-Bu | CF3 |
| 10-951 | (2-trifluoromethyl)phenyl | H | H | F | H | H | H | Br | F | nonafluoro-2-butyl | i-Bu | CF3 |
| 10-952 | (3-trifluoromethyl)phenyl | Et | n-Pr | F | H | H | H | Br | F | nonafluoro-2-butyl | s-Bu | CF3 |
| 10-953 | (4-trifluoromethyl)phenyl | Et | i-Pr | F | H | H | H | Br | Cl | nonafluoro-2-butyl | Me | CF3 |
| 10-954 | 2-nitrophenyl | H | H | F | H | H | H | Br | Cl | nonafluoro-2-butyl | Et | CF3 |
| 10-955 | phenyl | H | H | F | H | H | H | I | Cl | pentafluoroethyl | n-Pr | i-C3F7 |
| 10-956 | 3-nitrophenyl | H | H | F | H | H | H | I | Cl | heptafluoroisopropyl | i-Pr | CF3 |
| 10-957 | 4-nitrophenyl | H | H | F | H | H | H | I | Cl | heptafluoroisopropyl | n-Bu | CF3 |
| 10-958 | 2-cyanophenyl | Et | C(O)Me | F | H | H | H | I | Cl | heptafluoroisopropyl | i-Bu | CF3 |
| 10-959 | 3-cyanophenyl | H | H | F | H | H | H | I | Cl | heptafluoroisopropyl | s-Bu | CF3 |
| 10-960 | 4-cyanophenyl | H | H | F | H | H | H | I | Br | heptafluoroisopropyl | Me | CF3 |
| 10-961 | 2,6-difluorophenyl | H | H | F | H | H | H | I | Br | heptafluoroisopropyl | Et | CF3 |
| 10-962 | 3,4-dichlorophenyl | H | H | F | H | H | H | I | Br | pentafluoroethyl | n-Pr | CF3 |
| 10-963 | 2,4-dichlorophenyl | H | F | H | H | H | H | I | Br | heptafluoroisopropyl | i-Pr | CF3 |
| 10-964 | 2-chloro-4-fluorophenyl | H | H | F | H | H | H | I | Br | heptafluoroisopropyl | n-Bu | CF3 |
| 10-955 | 2-chloro-4,5-difluorophenyl | H | H | F | H | H | H | I | Br | heptafluoroisopropyl | i-Bu | CF3 |
| 10-966 | 4-bromo-2-chlorophenyl | H | H | F | H | H | H | I | Br | heptafluoroisopropyl | s-Bu | CF3 |
| 10-967 | 2-bromo-4-chlorophenyl | n-Pr | Me | F | H | H | H | I | I | heptafluoroisopropyl | Me | CF3 |
| 10-968 | 2-bromo-4-fluorophenyl | H | H | F | H | H | H | I | I | heptafluoroisopropyl | Et | CF3 |
| 10-969 | 2-chloro-4-nitrophenyl | n-Pr | Et | F | H | H | H | I | I | heptafluoroisopropyl | n-Pr | CF3 |
| 10-970 | 3,5-dicyanophenyl | H | H | F | H | H | H | I | I | heptafluoroisopropyl | i-Pr | CF3 |
| 10-971 | 4-cyano-2-fluorophenyl | H | H | F | H | H | H | I | I | heptafluoroisopropyl | n-Bu | CF3 |
| 10-972 | 2-chloro-4-cyanophenyl | H | H | F | H | H | H | I | I | heptafluoroisopropyl | i-Bu | CF3 |
| 10-973 | pyridin-3-yl | H | H | F | H | H | H | I | I | heptafluoroisopropyl | s-Bu | CF3 |
| 10-974 | 2-fluoropyridin-3-yl | H | H | F | H | H | H | I | Me | heptafluoroisopropyl | F | C2F5 |
| 10-975 | 2-chloropyridin-3-yl | H | H | F | H | H | H | I | Me | nonafluoro-2-butyl | Cl | CF3 |
| 10-976 | 2-bromopyridin-3-yl | H | H | F | H | H | H | I | Me | nonafluoro-2-butyl | Br | n-C3F7 |
| 10-977 | 2-iodopyridin-3-yl | H | H | F | H | H | H | I | Me | nonafluoro-2-butyl | I | i-C3F7 |
| 10-978 | 2-(trifluoromethyl)pyridin-3-yl | H | H | F | H | H | H | I | Et | nonafluoro-2-butyl | F | C2F5 |
| 10-979 | 2-nitropyridin-3-yl | H | H | F | H | H | H | I | Et | nonafluoro-2-butyl | Cl | CF3 |
| 10-980 | 2-cyanopyridin-3-yl | H | H | F | H | H | H | I | Et | nonafluoro-2-butyl | Br | CF3 |
| 10-981 | 6-fluoropyridin-3-yl | n-Pr | i-Pr | F | H | H | H | I | Et | nonafluoro-2-butyl | I | C2F5 |
| 10-982 | 6-chloropyridin-3-yl | H | H | F | H | H | H | I | n-Pr | nonafluoro-2-butyl | F | CF3 |
| 10-983 | 6-bromopyridin-3-yl | H | H | F | H | H | H | I | n-Pr | nonafluoro-2-butyl | Cl | CF3 |
| 10-984 | 6-iodopyridin-3-yl | H | H | F | H | H | H | I | n-Pr | nonafluoro-2-butyl | Br | CF3 |
| 10-985 | 6-(trifluoromethyl)pyridin-3-yl | H | H | F | H | H | H | I | n-Pr | nonafluoro-2-butyl | I | n-C3F7 |
| 10-986 | 6-nitropyridin-3-yl | H | H | F | H | H | H | I | i-Pr | nonafluoro-2-butyl | F | i-C3F7 |
| 10-987 | 6-cyanopyridin-3-yl | H | H | F | H | H | H | I | i-Pr | nonafluoro-2-butyl | Cl | CF3 |
| 10-988 | 5-fluoropyridin-3-yl | n-Pr | C(O)Me | F | H | H | H | I | i-Pr | nonafluoro-2-butyl | Br | CF3 |
| 10-989 | 5-chloropyridin-3-yl | H | H | F | H | H | H | I | i-Pr | nonafluoro-2-butyl | I | CF3 |
| 10-990 | 5-bromopyridin-3-yl | H | H | F | H | H | H | I | n-Bu | nonafluoro-2-butyl | F | CF3 |
| 10-991 | 5-iodopyridin-3-yl | H | H | F | H | H | H | I | n-Bu | nonafluoro-2-butyl | Cl | CF3 |
| 10-992 | 5-(trifluoromethyl)pyridin-3-yl | H | H | F | H | H | H | I | n-Bu | nonafluoro-2-butyl | Br | CF3 |
| 10-993 | 5-nitropyridin-3-yl | i-Pr | Me | F | H | H | H | I | n-Bu | nonafluoro-2-butyl | I | CF3 |
| 10-994 | 5-cyanopyridin-3-yl | H | H | F | H | H | H | I | i-Bu | nonafluoro-2-butyl | F | CF3 |
| 10-995 | 4-fluoropyridin-3-yl | H | H | F | H | H | H | I | i-Bu | nonafluoro-2-butyl | Cl | CF3 |
| 10-996 | 4-chloropyridin-3-yl | H | H | F | H | H | H | I | i-Bu | nonafluoro-2-butyl | Br | CF3 |

TABLE 10-continued

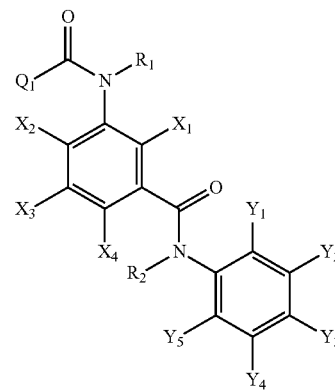

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 10-997 | 4-bromopyridin-3-yl | i-Pr | Et | F | H | H | H | I | i-Bu | nonafluoro-2-butyl | I | CF3 |
| 10-998 | 4-iodopyridin-3-yl | i-Pr | n-Pr | F | H | H | H | I | s-Bu | nonafluoro-2-butyl | F | CF3 |
| 10-999 | 4-(trifluoromethyl)pyridin-3-yl | H | H | F | H | H | H | I | s-Bu | nonafluoro-2-butyl | Cl | CF3 |
| 10-1000 | 4-nitropyridin-3-yl | i-Pr | C(O)Me | F | H | H | H | I | s-Bu | nonafluoro-2-butyl | Br | CF3 |
| 10-1001 | 4-cyanopyridin-3-yl | H | H | F | H | H | H | I | s-Bu | nonafluoro-2-butyl | I | CF3 |
| 10-1010 | 3-bromophenyl | H | Et | F | H | H | H | OCF3 | F | heptafluoroisopropyl | F | OCF3 |
| 10-1040 | 2-iodopyridin-3-yl | H | H | F | H | H | H | OCF3 | Me | nonafluoro-2-butyl | Me | OCF3 |
| 10-1153 | 3-bromophenyl | H | Et | F | H | H | H | OCF3 | F | heptafluoroisopropyl | F | CF3 |
| 10-1183 | 2-iodopyridin-3-yl | H | H | F | H | H | H | OCF3 | Me | nonafluoro-2-butyl | Me | CF3 |
| 10-1296 | 3-bromophenyl | H | Et | F | H | H | H | CF3 | F | heptafluoroisopropyl | F | CF3 |
| 10-1326 | 2-iodopyridin-3-yl | H | H | F | H | H | H | CF3 | Me | nonafluoro-2-butyl | Me | CF3 |
| 10-1439 | 3-bromphenyl | H | Et | H | F | H | H | Cl | F | heptafluoroisopropyl | F | Cl |
| 10-1469 | 2-iodopyridin-3-yl | H | H | H | F | H | H | Cl | Me | nonafluoro-2-butyl | Me | I |
| 10-1582 | 3-bromophenyl | H | Et | H | F | H | H | Cl | F | heptafluoroisopropyl | F | OCF3 |
| 10-1612 | 2-iodopyridin-3-yl | H | H | H | F | H | H | Cl | Me | nonafluoro-2-butyl | Me | OCF3 |
| 10-1726 | 4-bromophenyl | H | H | H | F | H | H | Cl | F | heptafluoroisopropyl | Cl | CF3 |
| 10-1733 | 2-nitrophenyl | H | n-Pr | H | F | H | H | Cl | Br | heptafluoroisopropyl | F | CF3 |
| 10-1741 | 2,4-dichlorophenyl | H | H | H | F | H | H | Cl | Me | nonafluoro-2-butyl | H | CF3 |
| 10-1742 | 2-chloro-4-fluorophenyl | H | H | H | F | H | H | Cl | H | nonafluoro-2-butyl | Me | CF3 |
| 10-1743 | 2-chloro-4,5-difluorophenyl | i-Pr | H | H | F | H | H | Cl | Et | nonafluoro-2-butyl | H | CF3 |
| 10-1744 | 4-bromo-2-chlorophenyl | H | H | H | F | H | H | Cl | H | nonafluoro-2-butyl | Et | CF3 |
| 10-1755 | 2-iodopyridin-3-yl | H | H | H | F | H | H | Cl | Me | nonafluoro-2-butyl | Me | n-C3F7 |
| 10-1756 | 2-(trifluoromethyl)pyridin-3-yl | H | H | H | F | H | H | Cl | Me | nonafluoro-2-butyl | Et | i-C3F7 |
| 10-1762 | 6-iodopyridin-3-yl | H | H | H | F | H | H | Cl | Et | nonafluoro-2-butyl | Me | n-C3F7 |
| 10-1763 | 6-(trifluoromethyl)pyridin-3-yl | H | H | H | F | H | H | Cl | Et | nonafluoro-2-butyl | Et | i-C3F7 |
| 10-1769 | 5-bromopyridin-3-yl | H | H | H | F | H | H | Br | n-Pr | heptafluoroisopropyl | Me | CF3 |
| 10-1770 | 5-iodopyridin-3-yl | H | H | H | F | H | H | Br | n-Pr | heptafluoroisopropyl | Et | CF3 |
| 10-1776 | 4-bromopyridin-3-yl | Me | n-Pr | H | F | H | H | Br | i-Pr | heptafluoroisopropyl | Me | CF3 |
| 10-1777 | 4-iodopyridin-3-yl | H | H | H | F | H | H | Br | i-Pr | heptafluoroisopropyl | Et | CF3 |
| 10-1783 | pyridin-4-yl | H | H | H | F | H | H | Br | n-Bu | heptafluoroisopropyl | Me | CF3 |
| 10-1784 | 2-chloropyridin-4-yl | H | H | H | F | H | H | Br | n-Bu | heptafluoroisopropyl | Et | CF3 |
| 10-1790 | pyrichn-2-yl | H | H | H | F | H | H | Br | i-Bu | nonafluoro-2-butyl | Me | CF3 |
| 10-1791 | 3-chloropyridin-2-yl | H | H | H | F | H | H | Br | i-Bu | nonafluoro-2-butyl | Et | CF3 |
| 10-1797 | 2-fluorophenyl | H | H | H | F | H | H | Br | s-Bu | nonafluoro-2-butyl | Me | CF3 |
| 10-1798 | 3-fluorophenyl | H | H | H | F | H | H | Br | s-Bu | nonafluoro-2-butyl | Et | CF3 |
| 10-1804 | 3-bromophenyl | H | H | H | F | H | H | Br | F | nonafluoro-2-butyl | Me | CF3 |
| 10-1805 | 4-bromophenyl | H | H | H | F | H | H | Br | F | nonafluoro-2-butyl | Et | CF3 |
| 10-1811 | (4-trifluoromethyl)phenyl | Et | i-Pr | H | F | H | H | Br | Cl | nonafluoro-2-butyl | Me | CF3 |
| 10-1812 | 2-nitrophenyl | H | H | H | F | H | H | Br | Cl | nonafluoro-2-butyl | Et | CF3 |
| 10-1818 | 4-cyanophenyl | H | H | H | F | H | H | I | Br | heptafluoroisopropyl | Me | CF3 |
| 10-1819 | 2,6-difluorophenyl | H | H | H | F | H | H | I | Br | heptafluoroisopropyl | Et | CF3 |
| 10-1825 | 2-bromo-4-chlorophenyl | n-Pr | Me | H | F | H | H | I | I | heptafluoroisopropyl | Me | CF3 |
| 10-1826 | 2-bromo-4-fluorophenyl | H | H | H | F | H | H | I | I | heptafluoroisopropyl | Et | CF3 |
| 10-1832 | 2-fluoropyridin-3-yl | H | H | H | F | H | H | I | Me | heptafluoroisopropyl | F | C2F5 |
| 10-1833 | 2-chloropyridin-3-yl | H | H | H | F | H | H | I | Me | nonafluoro-2-butyl | Cl | CF3 |
| 10-7834 | 2-bromopyridin-3-yl | H | H | H | F | H | H | I | Me | nonafluoro-2-butyl | Br | n-C3F7 |
| 10-1837 | 2-nitropyridin-3-yl | H | H | H | F | H | H | I | Et | nonafluoro-2-butyl | Cl | CF3 |
| 10-1838 | 2-cyanopyridin-3-yl | H | H | H | F | H | H | I | Et | nonafluoro-2-butyl | Br | CF3 |
| 10-1841 | 6-bromopyridin-3-yl | H | H | H | F | H | H | I | n-Pr | nonafluoro-2-butyl | Cl | CF3 |
| 10-1842 | 6-iodopyridin-3-yl | H | H | H | F | H | H | I | n-Pr | nonafluoro-2-butyl | Br | CF3 |
| 10-1845 | 6-cyanopyridin-3-yl | H | H | H | F | H | H | I | i-Pr | nonafluoro-2-butyl | Cl | CF3 |
| 10-1846 | 5-fluoropyridin-3-yl | n-Pr | C(O)Me | H | F | H | H | I | i-Pr | nonafluoro-2-butyl | Br | CF3 |
| 10-1849 | 5-iodopyridin-3-yl | H | H | H | F | H | H | I | n-Bu | nonafluoro-2-butyl | Cl | CF3 |
| 10-1850 | 5-(trifluoromethyl)pyridin-3-yl | H | H | H | F | H | H | I | n-Bu | nonafluoro-2-butyl | Br | CF3 |
| 10-1853 | 4-fluoropyridin-3-yl | H | H | H | F | H | H | I | i-Bu | nonafluoro-2-butyl | Cl | CF3 |
| 10-1854 | 4-chloropyridin-3-yl | H | H | H | F | H | H | I | i-Bu | nonafluoro-2-butyl | Br | CF3 |
| 10-1857 | 4-(trifluoromethyl)pyridin-3-yl | H | H | H | F | H | H | I | s-Bu | nonafluoro-2-butyl | Cl | CF3 |

TABLE 10-continued

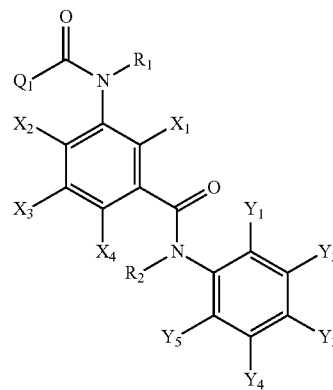

| compound number | Q1 | R1 | R2 | X1 | X2 | X3 | X4 | Y1 | Y2 | Y3 | Y4 | Y5 |
|---|---|---|---|---|---|---|---|---|---|---|---|---|
| 10-1858 | 4-nitropyridin-3-yl | i-Pr | C(O)Me | H | F | H | H | I | s-Bu | nonafluoro-2-butyl | Br | CF3 |
| 10-1898 | 2-iodopyridin-3-yl | H | H | H | F | H | H | OCF3 | Me | nonafluoro-2-butyl | Me | OCF3 |
| 10-2011 | 3-bromophenyl | H | Et | H | F | H | H | OCF3 | F | heptafluoroisopropyl | F | CF3 |
| 10-2041 | 2-iodopyridin-3-yl | H | H | H | F | H | H | OCF3 | Me | nonafluoro-2-butyl | Me | CF3 |
| 10-2154 | 3-bromophenyl | H | Et | H | F | H | H | CF3 | F | heptafluoroisopropyl | F | CF3 |
| 10-2184 | 2-iodopyridin-3-yl | H | H | H | F | H | H | CF3 | Me | nonafluoro-2-butyl | Me | CF3 |
| 10-2297 | 3-bromophenyl | H | Et | F | F | H | H | Cl | F | heptafluoroisopropyl | F | Cl |
| 10-2327 | 2-iodopyridin-3-yl | H | H | F | F | H | H | Cl | Me | nonafluoro-2-butyl | Me | I |
| 10-2440 | 3-bromophenyl | H | Et | F | F | H | H | Cl | F | heptafluoroisopropyl | F | OCF3 |
| 10-2470 | 2-iodopyridin-3-yl | H | H | F | F | H | H | Cl | Me | nonafluoro-2-butyl | Me | OCF3 |
| 10-2584 | 4-bromophenyl | H | H | F | F | H | H | Cl | F | heptafluoroisapropyl | Cl | CF3 |
| 10-2594 | 2-cyanophenyl | n-Pr | n-Pr | F | F | H | H | Cl | Br | pentafluoroethyl | I | CF3 |
| 10-2599 | 2,4-dichlorophenyl | H | H | F | F | H | H | Cl | Me | nonafluoro-2-butyl | H | CF3 |
| 10-2600 | 2-chloro-4-fluorophenyl | H | H | F | F | H | H | Cl | H | nonafluoro-2-butyl | Me | CF3 |
| 10-2613 | 2-iodopyridin-3-yl | H | H | F | F | H | H | Cl | Me | nonafluoro-2-butyl | Me | n-C3F7 |
| 10-2614 | 2-(trifluoromethyl)pyridin-3-yl | H | H | F | F | H | H | Cl | Me | nonafluoro-2-butyl | Et | i-C3F7 |
| 10-2620 | 6-iodopyridin-3-yl | H | H | F | F | H | H | Cl | Et | nonafluoro-2-butyl | Me | n-C3F7 |
| 10-2621 | 6-(trifluoromethyl)pyridin-3-yl | H | H | F | F | H | H | Cl | Et | nonafluoro-2-butyl | Et | i-C3F7 |
| 10-2627 | 5-bromopyridin-3-yl | H | H | F | F | H | H | Br | n-Pr | heptafluoroisopropyl | Me | CF3 |
| 10-2628 | 5-iodopyridin-3-yl | H | H | F | F | H | H | Br | n-Pr | heptafluoroisopropyl | Et | CF3 |
| 10-2634 | 4-bromopyridin-3-yl | Me | n-Pr | F | F | H | H | Br | i-Pr | heptafluoroisopropyl | Me | CF3 |
| 10-2635 | 4-iodopyridin-3-yl | H | H | F | F | H | H | Br | i-Pr | heptafluoroisopropyl | Et | CF3 |
| 10-2641 | pyridin-4-yl | H | H | F | F | H | H | Br | n-Bu | heptafluoroisopropyl | Me | CF3 |
| 10-2642 | 2-chloropyridin-4-yl | H | H | F | F | H | H | Br | n-Bu | heptafluoroisapropyl | Et | CF3 |
| 10-2648 | pyridin-2-yl | H | H | F | F | H | H | Br | i-Bu | nonafluoro-2-butyl | Me | CF3 |
| 10-2649 | 3-chloropyridin-2-yl | H | H | F | F | H | H | Br | i-Bu | nonafluoro-2-butyl | Et | CF3 |
| 10-2655 | 2-fluorophenyl | H | H | F | F | H | H | Br | s-Bu | nonafluoro-2-butyl | Me | CF3 |
| 10-2656 | 3-fluorophenyl | H | H | F | F | H | H | Br | s-Bu | nonafluoro-2-butyl | Et | CF3 |
| 10-2662 | 3-bromophenyl | H | H | F | F | H | H | Br | F | nonafluoro-2-butyl | Me | CF3 |
| 10-2663 | 4-bromophenyl | H | H | F | F | H | H | Br | F | nonafluoro-2-butyl | Et | CF3 |
| 10-2669 | (4-trifluoromethyl)phenyl | Et | i-Pr | F | F | H | H | Br | Cl | nonafluoro-2-butyl | Me | CF3 |
| 10-2670 | 2-nitrophenyl | H | H | F | F | H | H | Br | Cl | nonafluoro-2-butyl | Et | CF3 |
| 10-2676 | 4-cyanophenyl | H | H | F | F | H | H | I | Br | nonafluoro-2-butyl | Me | CF3 |
| 10-2677 | 2,6-difluorophenyl | H | H | F | F | H | H | I | Br | heptafluoroisopropyl | Et | CF3 |
| 10-2683 | 2-bromo-4-chlorophenyl | n-Pr | Me | F | F | H | H | I | I | heptafluoroisopropyl | Me | CF3 |
| 10-2684 | 2-bromo-4-fluorophenyl | H | H | F | F | H | H | I | I | heptafluoroisopropyl | Et | CF3 |
| 10-2690 | 2-fluoropyridin-3-yl | H | H | F | F | H | H | I | Me | heptafluoroisopropyl | F | C2F5 |
| 10-2691 | 2-chloropyridin-3-yl | H | H | F | F | H | H | I | Me | nonafluoro-2-butyl | Cl | CF3 |
| 10-2694 | 2-(trifluoromethyl)pyridin-3-yl | H | H | F | F | H | H | I | Et | nonafluoro-2-butyl | F | CF3 |
| 10-2695 | 2-nitropyridin-3-yl | H | H | F | F | H | H | I | Et | nonafluoro-2-butyl | Cl | CF3 |
| 10-2698 | 6-chloropyridin-3-yl | H | H | F | F | H | H | I | n-Pr | nonafluoro-2-butyl | F | CF3 |
| 10-2699 | 6-bromopyridin-3-yl | H | H | F | F | H | H | I | n-Pr | nonafluoro-2-butyl | Cl | CF3 |
| 10-2702 | 6-nitropyridin-3-yl | H | H | F | F | H | H | I | i-Pr | nonafluoro-2-butyl | F | i-C3F7 |
| 10-2703 | 6-cyanopyridin-3-yl | H | H | F | F | H | H | I | i-Pr | nonafluoro-2-butyl | Cl | CF3 |
| 10-2706 | 5-bromopyridin-3-yl | H | H | F | F | H | H | I | n-Bu | nonafluoro-2-butyl | F | CF3 |
| 10-2707 | 5-iodopyridin-3-yl | H | F | F | F | H | H | I | n-Bu | nonafluoro-2-butyl | Cl | CF3 |
| 10-2710 | 5-cyanopyridin-3-yl | H | H | F | F | H | H | I | i-Bu | nonafluoro-2-butyl | F | CF3 |
| 10-2711 | 4-fluoropyridin-3-yl | H | H | F | F | H | H | I | i-Bu | nonafluoro-2-butyl | Cl | CF3 |
| 10-2714 | 4-iodopyridin-3-yl | i-Pr | n-Pr | F | F | H | H | I | s-Bu | nonafluoro-2-butyl | F | CF3 |
| 10-2715 | 4-(trifluoromethyl)pyridin-3-yl | H | H | F | F | H | H | I | s-Bu | nonafluoro-2-butyl | Cl | CF3 |
| 10-2726 | 3-bromophenyl | H | Et | F | F | H | H | OCF3 | F | heptafluoroisapropyl | F | OCF3 |
| 10-2756 | 2-iodopyridin-3-yl | H | H | F | F | H | H | OCF3 | Me | nonafluoro-2-butyl | Me | OCF3 |
| 10-2869 | 3-bromophenyl | H | Et | F | F | H | H | OCF3 | F | heptafluoroisapropyl | F | CF3 |
| 10-2899 | 2-iodopyridin-3-yl | H | H | F | F | H | H | OCF3 | Me | nonafluoro-2-butyl | Me | CF3 |
| 10-3012 | 3-bromophenyl | H | Et | F | F | H | H | CF3 | F | heptafluoroisopropyl | F | CF3 |
| 10-3042 | 2-iodopyridin-3-yl | H | H | F | F | H | H | CF3 | Me | nonafluoro-2-butyl | Me | CF3 |
| 10-3147 | phenyl | H | H | F | F | F | H | Cl | F | pentafluoroethyl | H | Cl |

TABLE 10-continued

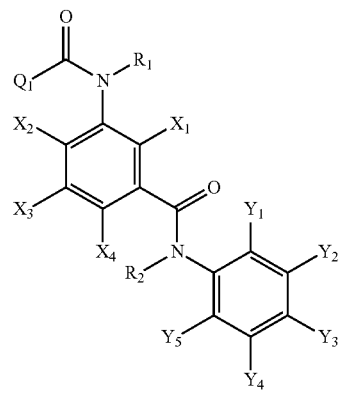

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 10-3168 | phenyl | H | H | H | H | F | H | Cl | I | pentafluoroethyl | Cl | Cl |
| 10-3189 | phenyl | H | H | H | H | H | F | Cl | Me | pentafluoroethyl | n-Bu | Cl |
| 10-3198 | phenyl | H | H | F | H | F | H | Cl | Et | pentafluoroethyl | s-Bu | Cl |
| 10-3218 | phenyl | H | H | F | H | H | F | Cl | n-Bu | pentafluoroethyl | i-Bu | Cl |
| 10-3227 | phenyl | H | H | H | F | F | H | Cl | s-Bu | pentafluoroethyl | Me | Cl |
| 10-3236 | phenyl | H | H | H | F | H | F | Cl | F | pentafluoroethyl | n-Pr | Cl |
| 10-3245 | phenyl | H | H | H | H | F | F | Cl | Cl | pentafluoroethyl | n-Bu | Cl |
| 10-3254 | phenyl | H | H | F | F | H | F | Cl | Br | pentafluoroethyl | s-Bu | Cl |
| 10-3263 | phenyl | H | H | F | H | F | F | Cl | Me | pentafluoroethyl | Cl | Cl |
| 10-3272 | phenyl | H | H | H | F | F | F | Cl | n-Pr | pentafluoroethyl | Br | Cl |
| 10-3281 | phenyl | i-Pr | Me | F | F | F | F | Cl | n-Bu | pentafluoroethyl | I | Cl |

TABLE 11

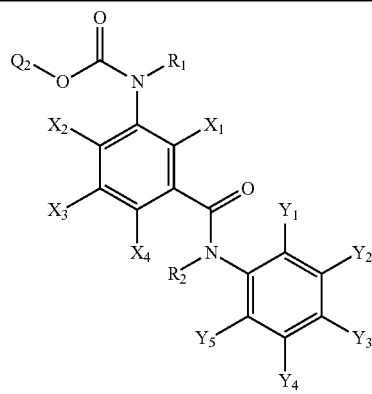

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-1 | 2,2,2-trichloroethyl | H | H | H | H | H | H | F | H | heptafluoroisopropyl | H | OCF3 |
| 11-2 | 2,2,2-trichloroethyl | H | H | H | H | H | H | F | H | nonafluoro-2-butyl | H | OCF3 |
| 11-13 | 2,2,2-trichloroethyl | H | H | H | H | H | H | Cl | H | heptafluoroisopropyl | H | OCF3 |
| 11-42 | 2,2,2-trichloroethyl | H | H | H | H | H | H | Cl | H | nonafluoro-2-butyl | H | OCF3 |
| 11-71 | 2,2,2-trichloroethyl | H | H | H | H | H | H | Br | H | heptafluoroisopropyl | H | OCF3 |
| 11-100 | 2,2,2-trichloroethyl | H | H | H | H | H | H | Br | H | nonafluoro-2-butyl | H | OCF3 |
| 11-129 | 2,2,2-trichloroethyl | H | H | H | H | H | H | I | H | heptafluoroisopropyl | H | OCF3 |
| 11-158 | 2,2,2-trichloroethyl | H | H | H | H | H | H | I | H | nonafluoro-2-butyl | H | OCF3 |
| 11-189 | 2,2,2-trichloroethyl | H | H | H | H | H | H | Cl | H | heptafluoroisopropyl | H | CF3 |
| 11-218 | 2,2,2-trichloroethyl | H | H | H | H | H | H | Cl | H | nonafluoro-2-butyl | H | CF3 |
| 11-247 | 2,2,2-trichloroethyl | H | H | H | H | H | H | Br | H | heptafluoroisopropyl | H | CF3 |
| 11-260 | 4,4,4-trifluoro-n-butyl | H | H | H | H | H | H | Br | H | pentafluoroethyl | H | CF3 |
| 11-276 | 2,2,2-trichloroethyl | H | H | H | H | H | H | Br | H | nonafluoro-2-butyl | H | CF3 |
| 11-289 | 4,4,4-trifluoro-n-butyl | H | H | H | H | H | H | Br | H | nonafluoro-2-butyl | H | CF3 |
| 11-305 | 2,2,2-trichloroethyl | H | H | H | H | H | H | I | H | heptafluoroisopropyl | H | CF3 |
| 11-318 | 4,4,4-trifluoro-n-butyl | H | H | H | H | H | H | I | H | heptafluoroisopropyl | H | C2F5 |
| 11-334 | 2,2,2-trichloroethyl | H | H | H | H | H | H | I | H | nonafluoro-2-butyl | H | CF3 |
| 11-347 | 4,4,4-trifluoro-n-butyl | H | H | H | H | H | H | I | H | nonafluoro-2-butyl | H | CF3 |
| 11-363 | 2,2,2-trichloroethyl | H | H | H | H | H | H | OCF3 | H | heptafluoroisopropyl | H | OCF3 |

TABLE 11-continued

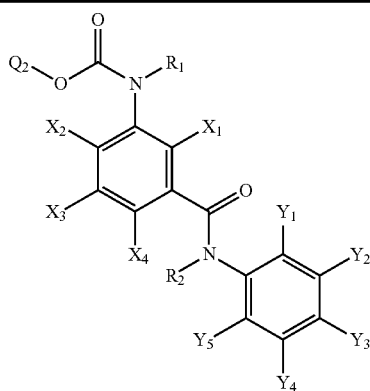

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-392 | 2,2,2-trichloroethyl | H | H | H | H | H | H | OCF3 | H | nonafluoro-2-butyl | H | OCF3 |
| 11-421 | 2,2,2-trichloroethyl | H | H | H | H | H | H | CF3 | H | heptafluoroisopropyl | H | OCF3 |
| 11-450 | 2,2,2-trichloroethyl | H | H | H | H | H | H | CF3 | H | nonafluoro-2-butyl | H | OCF3 |
| 11-479 | 2,2,2-trichloroethyl | H | H | H | H | H | H | CF3 | H | heptafluoroisopropyl | H | CF3 |
| 11-508 | 2,2,2-trichloroethyl | H | H | H | H | H | H | CF3 | H | nonafluoro-2-butyl | H | CF3 |
| 11-527 | 2,2,2-trichloroethyl | H | H | F | H | H | H | F | H | heptafluoroisopropyl | H | F |
| 11-528 | 2,2,2-trichloroethyl | H | H | F | H | H | H | Cl | H | heptafluoroisopropyl | H | Cl |
| 11-529 | 2,2,2-trichloroethyl | H | H | F | H | H | H | Br | H | heptafluoroisopropyl | H | Br |
| 11-530 | 2,2,2-trichloroethyl | H | H | F | H | H | H | I | H | heptafluoroisopropyl | H | I |
| 11-531 | 2,2,2-trichloroethyl | H | H | F | H | H | H | F | H | heptafluoroisopropyl | H | OCF3 |
| 11-532 | 2,2,2-trichloroethyl | H | H | F | H | H | H | F | H | nonafluoro-2-butyl | H | OCF3 |
| 11-543 | 2,2,2-trichloroethyl | H | H | F | H | H | H | Cl | H | heptafluoroisopropyl | H | OCF3 |
| 11-556 | 4,4,4-trifluoro-n-butyl | H | H | F | H | H | H | Cl | H | heptafluoroisopropyl | H | OCF3 |
| 11-572 | 2,2,2-trichloroethyl | H | H | F | H | H | H | Cl | H | nonafluoro-2-butyl | H | OCF3 |
| 11-585 | 4,4,4-trifluoro-n-butyl | H | H | F | H | H | H | Cl | H | pentafluoroethyl | H | OCF3 |
| 11-591 | methyl | H | H | F | H | H | H | Br | H | heptafluoroisopropyl | H | OCF3 |
| 11-592 | ethyl | H | H | F | H | H | H | Br | H | heptafluoroisopropyl | H | OCF3 |
| 11-593 | 2-fluoroethyl | H | H | F | H | H | H | Br | H | heptafluoroisopropyl | H | OCF3 |
| 11-594 | 2-chloroethyl | H | H | F | H | H | H | Br | H | heptafluoroisopropyl | H | OCF3 |
| 11-595 | 2-bromoethyl | H | H | F | H | H | H | Br | H | heptafluoroisopropyl | H | OCF3 |
| 11-596 | 2-iodoethyl | H | H | F | H | H | H | Br | H | heptafluoroisopropyl | H | OC2F5 |
| 11-597 | 2-cyanoethyl | H | H | F | H | H | H | Br | H | heptafluoroisopropyl | H | OCF3 |
| 11-598 | 2,2-difluoroethyl | H | H | F | H | H | H | Br | H | heptafluoroisopropyl | H | OCF3 |
| 11-599 | 2,2-dichloroethyl | H | H | F | H | H | H | Br | H | heptafluoroisopropyl | H | OCF3 |
| 11-600 | 2,2,2-trifluoroethyl | H | H | F | H | H | H | Br | H | heptafluoroisopropyl | H | OCF3 |
| 11-601 | 2,2,2-trichloroethyl | H | H | F | H | H | H | Br | H | heptafluoroisopropyl | H | OCF3 |
| 11-602 | 2,2,2-tribromoethyl | H | H | F | H | H | H | Br | H | heptafluoroisopropyl | H | OCF3 |
| 11-603 | n-propyl | H | H | F | H | H | H | Br | H | heptafluoroisopropyl | H | OCF3 |
| 11-604 | 3-fluoro-n-propyl | H | H | F | H | H | H | Br | H | heptafluoroisopropyl | H | OCF3 |
| 11-605 | 3-chloro-n-propyl | H | H | F | H | H | H | Br | H | heptafluoroisopropyl | H | OCF3 |
| 11-606 | 3-bromo-n-propyl | H | H | F | H | H | H | Br | H | heptafluoroisopropyl | H | OCF3 |
| 11-607 | i-propyl | H | H | F | H | H | H | Br | H | heptafluoroisopropyl | H | OCF3 |
| 11-608 | 1,2-difluoro-2-propyl | H | H | F | H | H | H | Br | H | heptafluoroisopropyl | H | OCF3 |
| 11-609 | 1,3-difluoro-2-propyl | H | H | F | H | H | H | Br | H | heptafluoroisopropyl | H | OCF3 |
| 11-610 | 1,3-dichloro-2-propyl | H | H | F | H | H | H | Br | H | heptafluoroisopropyl | H | OCF3 |
| 11-611 | 1-chloro-3-fluoro-2-propyl | H | H | F | H | H | H | Br | H | heptafluoroisopropyl | H | OCF3 |
| 11-612 | 3,3,3-trifluoro-n-propyl | H | H | F | H | H | H | Br | H | heptafluoroisopropyl | H | OCF3 |
| 11-613 | n-butyl | H | H | F | H | H | H | Br | H | heptafluoroisopropyl | H | OCF3 |
| 11-614 | 4,4,4-trifluoro-n-butyl | H | H | F | H | H | H | Br | H | heptafluoroisopropyl | H | OCF3 |
| 11-615 | i-butyl | H | H | F | H | H | H | Br | H | heptafluoroisopropyl | H | OCF3 |
| 11-616 | s-butyl | H | H | F | H | H | H | Br | H | heptafluoroisopropyl | H | OCF3 |
| 11-617 | vinyl | H | H | F | H | H | H | Br | H | heptafluoroisopropyl | H | OCF3 |
| 11-618 | benzyl | H | H | F | H | H | H | Br | H | heptafluoroisopropyl | H | OCF3 |
| 11-619 | phenyl | H | H | F | H | H | H | Br | H | heptafluoroisopropyl | H | OCF3 |
| 11-620 | methyl | H | H | F | H | H | H | Br | H | nonafluoro-2-butyl | H | OCF3 |
| 11-621 | ethyl | H | H | F | H | H | H | Br | H | nonafluoro-2-butyl | H | OCF3 |
| 11-622 | 2-fluoroethyl | H | H | F | H | H | H | Br | H | nonafluoro-2-butyl | H | OCF3 |
| 11-623 | 2-chloroethyl | H | H | F | H | H | H | Br | H | nonafluoro-2-butyl | H | OCF3 |
| 11-624 | 2-bromoethyl | H | H | F | H | H | H | Br | H | nonafluoro-2-butyl | H | OCF3 |
| 11-625 | 2-iodoethyl | H | H | F | H | H | H | Br | H | nonafluoro-2-butyl | H | OCF3 |
| 11-626 | 2-cyanoethyl | H | H | F | H | H | H | Br | H | nonafluoro-2-butyl | H | OCF3 |
| 11-627 | 2,2-difluoroethyl | H | H | F | H | H | H | Br | H | nonafluoro-2-butyl | H | OCF3 |
| 11-628 | 2,2-dichloroethyl | H | H | F | H | H | H | Br | H | nonafluoro-2-butyl | H | OCF3 |
| 11-629 | 2,2,2-trifluoroethyl | H | H | F | H | H | H | Br | H | nonafluoro-2-butyl | H | OCF3 |
| 11-630 | 2,2,2-trichloroethyl | H | H | F | H | H | H | Br | H | nonafluoro-2-butyl | H | OCF3 |
| 11-631 | 2,2,2-tribromoethyl | H | H | F | H | H | H | Br | H | nonafluoro-2-butyl | H | OCF3 |
| 11-632 | n-propyl | H | H | F | H | H | H | Br | H | nonafluoro-2-butyl | H | OC2F5 |
| 11-633 | 3-fluoro-n-propyl | H | H | F | H | H | H | Br | H | nonafluoro-2-butyl | H | OCF3 |

TABLE 11-continued

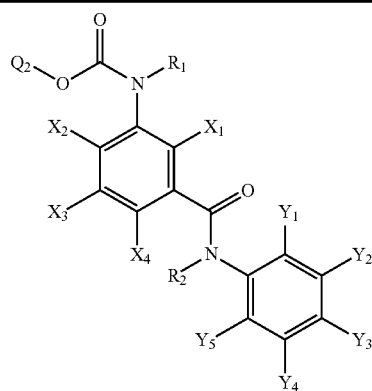

| compound number | $Q_2$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 11-634 | 3-chloro-n-propyl | H | H | F | H | H | H | Br | H | nonafluoro-2-butyl | H | OCF3 |
| 11-635 | 3-bromo-n-propyl | H | H | F | H | H | H | Br | H | nonafluoro-2-butyl | H | OCF3 |
| 11-636 | i-propyl | H | H | F | H | H | H | Br | H | nonafluoro-2-butyl | H | OCF3 |
| 11-637 | 1,2-difluoro-2-propyl | H | H | F | H | H | H | Br | H | nonafluoro-2-butyl | H | OCF3 |
| 11-638 | 1,3-difluoro-2-propyl | H | H | F | H | H | H | Br | H | nonafluoro-2-butyl | H | OCF3 |
| 11-639 | 1,3-dichloro-2-propyl | H | H | F | H | H | H | Br | H | nonafluoro-2-butyl | H | OCF3 |
| 11-640 | 1-chloro-3-fluoro-2-propyl | H | H | F | H | H | H | Br | H | nonafluoro-2-butyl | H | OCF3 |
| 11-641 | 3,3,3-trifluoro-n-propyl | H | H | F | H | H | H | Br | H | nonafluoro-2-butyl | H | OCF3 |
| 11-642 | n-butyl | H | H | F | H | H | H | Br | H | nonafluoro-2-butyl | H | OCF3 |
| 11-643 | 4,4,4-trifluoro-n-butyl | H | H | F | H | H | H | Br | H | nonafluoro-2-butyl | H | OCF3 |
| 11-644 | i-butyl | H | H | F | H | H | H | Br | H | nonafluoro-2-butyl | H | OCF3 |
| 11-645 | s-butyl | H | H | F | H | H | H | Br | H | nonafluoro-2-butyl | H | OCF3 |
| 11-646 | vinyl | H | H | F | H | H | H | Br | H | nonafluoro-2-butyl | H | OCF3 |
| 11-647 | benzyl | H | H | F | H | H | H | Br | H | nonafluoro-2-butyl | H | OCF3 |
| 11-648 | phenyl | H | H | F | H | H | H | Br | H | nonafluoro-2-butyl | H | OCF3 |
| 11-649 | methyl | H | H | F | H | H | H | I | H | heptafluoroisopropyl | H | OCF3 |
| 11-650 | ethyl | H | H | F | H | H | H | I | H | heptafluoroisopropyl | H | OCF3 |
| 11-651 | 2-fluoroethyl | H | H | F | H | H | H | I | H | heptafluoroisopropyl | H | OCF3 |
| 11-652 | 2-chloroethyl | H | H | F | H | H | H | I | H | heptafluoroisopropyl | H | OCF3 |
| 11-653 | 2-bromoethyl | H | H | F | H | H | H | I | H | heptafluoroisopropyl | H | OCF3 |
| 11-654 | 2-iodoethyl | H | H | F | H | H | H | I | H | heptafluoroisopropyl | H | OCF3 |
| 11-655 | 2-cyanoethyl | H | H | F | H | H | H | I | H | heptafluoroisopropyl | H | OCF3 |
| 11-656 | 2,2-difluoroethyl | H | H | F | H | H | H | I | H | heptafluoroisopropyl | H | OCF3 |
| 11-657 | 2,2-dichloroethyl | H | H | F | H | H | H | I | H | heptafluoroisopropyl | H | OCF3 |
| 11-658 | 2,2,2-trifluoroethyl | H | H | F | H | H | H | I | H | heptafluoroisopropyl | H | OCF3 |
| 11-659 | 2,2,2-trichloroethyl | H | H | F | H | H | H | I | H | heptafluoroisopropyl | H | OCF3 |
| 11-660 | 2,2,2-tribromoethyl | H | H | F | H | H | H | I | H | heptafluoroisopropyl | H | OCF3 |
| 11-661 | n-propyl | H | H | F | H | H | H | I | H | heptafluoroisopropyl | H | OCF3 |
| 11-662 | 3-fluoro-n-propyl | H | H | F | H | H | H | I | H | heptafluoroisopropyl | H | OCF3 |
| 11-663 | 3-chloro-n-propyl | H | H | F | H | H | H | I | H | heptafluoroisopropyl | H | OC2F5 |
| 11-664 | 3-bromo-n-propyl | H | H | F | H | H | H | I | H | heptafluoroisopropyl | H | OCF3 |
| 11-665 | i-propyl | H | H | F | H | H | H | I | H | heptafluoroisopropyl | H | OCF3 |
| 11-666 | 1,2-difluoro-2-propyl | H | H | F | H | H | H | I | H | heptafluoroisopropyl | H | OCF3 |
| 11-667 | 1,3-difluoro-2-propyl | H | H | F | H | H | H | I | H | heptafluoroisopropyl | H | OCF3 |
| 11-668 | 1,3-dichloro-2-propyl | H | H | F | H | H | H | I | H | heptafluoroisopropyl | H | OCF3 |
| 11-669 | 1-chloro-3-fluoro-2-propyl | H | H | F | H | H | H | I | H | heptafluoroisopropyl | H | OCF3 |
| 11-670 | 3,3,3-fluoro-n-propyl | H | H | F | H | H | H | I | H | heptafluoroisopropyl | H | OCF3 |
| 11-671 | n-butyl | H | H | F | H | H | H | I | H | heptafluoroisopropyl | H | OCF3 |
| 11-672 | 4,4,4-trifluoro-n-butyl | H | H | F | H | H | H | I | H | heptafluoroisopropyl | H | OCF3 |
| 11-673 | i-butyl | H | H | F | H | H | H | I | H | heptafluoroisopropyl | H | OCF3 |
| 11-674 | s-butyl | H | H | F | H | H | H | I | H | heptafluoroisopropyl | H | OCF3 |
| 11-675 | vinyl | H | H | F | H | H | H | I | H | heptafluoroisopropyl | H | OCF3 |
| 11-676 | benzyl | H | H | F | H | H | H | I | H | heptafluoroisopropyl | H | OCF3 |
| 11-677 | phenyl | H | H | F | H | H | H | I | H | heptafluoroisopropyl | H | OCF3 |
| 11-678 | methyl | H | H | F | H | H | H | I | H | nonafluoro-2-butyl | H | OCF3 |
| 11-679 | ethyl | H | H | F | H | H | H | I | H | nonafluoro-2-butyl | H | OCF3 |
| 11-680 | 2-fluoroethyl | H | H | F | H | H | H | I | H | nonafluoro-2-butyl | H | OCF3 |
| 11-681 | 2-chloroethyl | H | H | F | H | H | H | I | H | nonafluoro-2-butyl | H | OCF3 |
| 11-682 | 2-bromoethyl | H | H | F | H | H | H | I | H | nonafluoro-2-butyl | H | OCF3 |
| 11-683 | 2-iodoethyl | H | H | F | H | H | H | I | H | nonafluoro-2-butyl | H | OCF3 |
| 11-684 | 2-cyanoethyl | H | H | F | H | H | H | I | H | nonafluoro-2-butyl | H | OCF3 |
| 11-685 | 2,2-difluoroethyl | H | H | F | H | H | H | I | H | nonafluoro-2-butyl | H | OCF3 |
| 11-686 | 2,2-dichloroethyl | H | H | F | H | H | H | I | H | nonafluoro-2-butyl | H | OCF3 |
| 11-687 | 2,2,2-trifluoroethyl | H | H | F | H | H | H | I | H | nonafluoro-2-butyl | H | OCF3 |
| 11-688 | 2,2,2-trichloroethyl | H | H | F | H | H | H | I | H | nonafluoro-2-butyl | H | OCF3 |
| 11-689 | 2,2,2-tribromoethyl | H | H | F | H | H | H | I | H | nonafluoro-2-butyl | H | OCF3 |
| 11-690 | n-propyl | H | H | F | H | H | H | I | H | nonafluoro-2-butyl | H | OCF3 |
| 11-691 | 3-fluoro-n-propyl | H | H | F | H | H | H | I | H | nonafluoro-2-butyl | H | OCF3 |

TABLE 11-continued

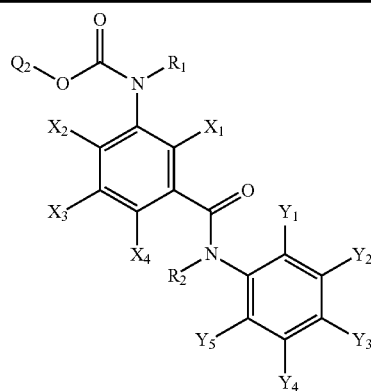

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-692 | 3-chloro-n-propyl | H | H | F | H | H | H | I | H | nonafluoro-2-butyl | H | OCF3 |
| 11-693 | 3-bromo-n-propyl | H | H | F | H | H | H | I | H | nonafluoro-2-butyl | H | OCF3 |
| 11-694 | i-propyl | H | H | F | H | H | H | I | H | nonafluoro-2-butyl | H | OCF3 |
| 11-695 | 1,2-difluoro-2-propyl | H | H | F | H | H | H | I | H | nonafluoro-2-butyl | H | OCF3 |
| 11-696 | 1,3-difluoro-2-propyl | H | H | F | H | H | H | I | H | nonafluoro-2-butyl | H | OCF3 |
| 11-697 | 1,3-dichloro-2-propyl | H | H | F | H | H | H | I | H | nonafluoro-2-butyl | H | OCF3 |
| 11-698 | 1-chloro-3-fluoro-2-propyl | H | H | F | H | H | H | I | H | nonafluoro-2-butyl | H | OCF3 |
| 11-699 | 3,3,3-trifluoro-n-propyl | H | H | F | H | H | H | I | H | nonafluoro-2-butyl | H | OCF3 |
| 11-700 | n-butyl | H | H | F | H | H | H | I | H | nonafluoro-2-butyl | H | OCF3 |
| 11-701 | 4,4,4-trifluoro-n-butyl | H | H | F | H | H | H | I | H | nonafluoro-2-butyl | H | OCF3 |
| 11-702 | i-butyl | H | H | F | H | H | H | I | H | nonafluoro-2-butyl | H | OCF3 |
| 11-703 | s-butyl | H | H | F | H | H | H | I | H | nonafluoro-2-butyl | H | OCF3 |
| 11-704 | vinyl | H | H | F | H | H | H | I | H | nonafluoro-2-butyl | H | OCF3 |
| 11-705 | benzyl | H | H | F | H | H | H | I | H | nonafluoro-2-butyl | H | OC2F5 |
| 11-706 | phenyl | H | H | F | H | H | H | I | H | nonafluoro-2-butyl | H | OCF3 |
| 11-707 | 2,2,2-trichloroethyl | H | H | F | H | H | H | F | H | heptafluoroisopropyl | H | CF3 |
| 11-708 | 2,2,2-trichloroethyl | H | H | F | H | H | H | F | H | nonafluoro-2-butyl | H | CF3 |
| 11-709 | methyl | H | H | F | H | H | H | Cl | H | heptafluoroisopropyl | H | CF3 |
| 11-710 | ethyl | H | H | F | H | H | H | Cl | H | heptafluoroisopropyl | H | CF3 |
| 11-711 | 2-fluoroethyl | H | H | F | H | H | H | Cl | H | heptafluoroisopropyl | H | CF3 |
| 11-712 | 2-chloroethyl | H | H | F | H | H | H | Cl | H | heptafluoroisopropyl | H | CF3 |
| 11-713 | 2-bromoethyl | H | H | F | H | H | H | Cl | H | heptafluoroisopropyl | H | CF3 |
| 11-714 | 2-iodoethyl | H | H | F | H | H | H | Cl | H | heptafluoroisopropyl | H | CF3 |
| 11-715 | 2-cyanoethyl | H | H | F | H | H | H | Cl | H | heptafluoroisopropyl | H | C2F5 |
| 11-716 | 2,2-difluoroethyl | H | H | F | H | H | H | Cl | H | heptafluoroisopropyl | H | CF3 |
| 11-717 | 2,2-dichloroethyl | H | H | F | H | H | H | Cl | H | heptafluoroisopropyl | H | CF3 |
| 11-718 | 2,2,2-trifluoroethyl | H | H | F | H | H | H | Cl | H | heptafluoroisopropyl | H | CF3 |
| 11-719 | 2,2,2-trichloroethyl | H | H | F | H | H | H | Cl | H | heptafluoroisopropyl | H | CF3 |
| 11-720 | 2,2,2-tribromoethyl | H | H | F | H | H | H | Cl | H | heptafluoroisopropyl | H | CF3 |
| 11-721 | n-propyl | H | H | F | H | H | H | Cl | H | pentafluoroethyl | H | CF3 |
| 11-722 | 3-fluoro-n-propyl | H | H | F | H | H | H | Cl | H | heptafluoroisopropyl | H | CF3 |
| 11-723 | 3-chloro-n-propyl | H | H | F | H | H | H | Cl | H | heptafluoroisopropyl | H | CF3 |
| 11-724 | 3-bromo-n-propyl | H | H | F | H | H | H | Cl | H | heptafluoroisopropyl | H | CF3 |
| 11-725 | i-propyl | H | H | F | H | H | H | Cl | H | heptafluoroisopropyl | H | n-C3F7 |
| 11-726 | 1,2-difluoro-2-propyl | H | H | F | H | H | H | Cl | H | heptafluoroisopropyl | H | CF3 |
| 11-727 | 1,3-difluoro-2-propyl | H | H | F | H | H | H | Cl | H | heptafluoroisopropyl | H | CF3 |
| 11-728 | 1,3-dichloro-2-propyl | H | H | F | H | H | H | Cl | H | pentafluoroethyl | H | CF3 |
| 11-729 | 1-chloro-3-fluoro-2-propyl | H | H | F | H | H | H | Cl | H | heptafluoroisopropyl | H | CF3 |
| 11-730 | 3,3,3-trifluoro-n-propyl | H | H | F | H | H | H | Cl | H | heptafluoroisopropyl | H | CF3 |
| 11-731 | n-butyl | H | H | F | H | H | H | Cl | H | heptafluoroisopropyl | H | CF3 |
| 11-732 | 4,4,4-trifluoro-n-butyl | H | H | F | H | H | H | Cl | H | heptafluoroisopropyl | H | CF3 |
| 11-733 | i-butyl | H | H | F | H | H | H | Cl | H | heptafluoroisopropyl | H | CF3 |
| 11-734 | s-butyl | H | H | F | H | H | H | Cl | H | heptafluoroisopropyl | H | CF3 |
| 11-735 | vinyl | H | H | F | H | H | H | Cl | H | heptafluoroisopropyl | H | CF3 |
| 11-736 | benzyl | H | H | F | H | H | H | Cl | H | heptafluoroisopropyl | H | CF3 |
| 11-737 | phenyl | H | H | F | H | H | H | Cl | H | heptafluoroisopropyl | H | CF3 |
| 11-738 | methyl | H | H | F | H | H | H | Cl | H | nonafluoro-2-butyl | H | CF3 |
| 11-739 | ethyl | H | H | F | H | H | H | Cl | H | nonafluoro-2-butyl | H | i-C3F7 |
| 11-740 | 2-fluoroethyl | H | H | F | H | H | H | Cl | H | nonafluoro-2-butyl | H | CF3 |
| 11-741 | 2-chloroethyl | H | H | F | H | H | H | Cl | H | nonafluoro-2-butyl | H | CF3 |
| 11-742 | 2-bromoethyl | H | H | F | H | H | H | Cl | H | nonafluoro-2-butyl | H | CF3 |
| 11-743 | 2-iodoethyl | H | H | F | H | H | H | Cl | H | nonafluoro-2-butyl | H | CF3 |
| 11-744 | 2-cyanoethyl | H | H | F | H | H | H | Cl | H | nonafluoro-2-butyl | H | CF3 |
| 11-745 | 2,2-difluoroethyl | H | H | F | H | H | H | Cl | H | nonafluoro-2-butyl | H | CF3 |
| 11-746 | 2,2-dichloroethyl | H | H | F | H | H | H | Cl | H | nonafluoro-2-butyl | H | CF3 |
| 11-747 | 2,2,2-trifluoroethyl | H | H | F | H | H | H | Cl | H | nonafluoro-2-butyl | H | CF3 |
| 11-748 | 2,2,2-trichloroethyl | H | H | F | H | H | H | Cl | H | nonafluoro-2-butyl | H | CF3 |
| 11-749 | 2,2,2-tribromoethyl | H | H | F | H | H | H | Cl | H | nonafluoro-2-butyl | H | CF3 |

TABLE 11-continued

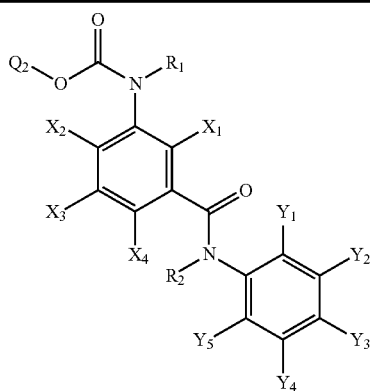

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-750 | n-propyl | H | H | F | H | H | H | Cl | H | nonafluoro-2-butyl | H | CF3 |
| 11-751 | 3-fluoro-n-propyl | H | H | F | H | H | H | Cl | H | nonafluoro-2-butyl | H | CF3 |
| 11-752 | 3-chloro-n-propyl | H | H | F | H | H | H | Cl | H | nonafluoro-2-butyl | H | CF3 |
| 11-753 | 3-bromo-n-propyl | H | H | F | H | H | H | Cl | H | nonafluoro-2-butyl | H | CF3 |
| 11-754 | i-propyl | H | H | F | H | H | H | Cl | H | nonafluoro-2-butyl | H | CF3 |
| 11-755 | 1,2-difluoro-2-propyl | H | H | F | H | H | H | Cl | H | nonafluoro-2-butyl | H | CF3 |
| 11-756 | 1,3-difluoro-2-propyl | H | H | F | H | H | H | Cl | H | nonafluoro-2-butyl | H | CF3 |
| 11-757 | 1,3-dichloro-2-propyl | H | H | F | H | H | H | Cl | H | nonafluoro-2-butyl | H | CF3 |
| 11-758 | 1-chloro-3-fluoro-2-propyl | H | H | F | H | H | H | Cl | H | nonafluoro-2-butyl | H | CF3 |
| 11-759 | 3,3,3-trifluoro-n-propyl | H | H | F | H | H | H | Cl | H | nonafluoro-2-butyl | H | CF3 |
| 11-760 | n-butyl | H | H | F | H | H | H | Cl | H | nonafluoro-2-butyl | H | CF3 |
| 11-761 | 4,4,4-trifluoro-n-butyl | H | H | F | H | H | H | Cl | H | nonafluoro-2-butyl | H | CF3 |
| 11-762 | i-butyl | H | H | F | H | H | H | Cl | H | nonafluoro-2-butyl | H | CF3 |
| 11-763 | s-butyl | H | H | F | H | H | H | Cl | H | nonafluoro-2-butyl | H | CF3 |
| 11-764 | vinyl | H | H | F | H | H | H | Cl | H | nonafluoro-2-butyl | H | CF3 |
| 11-765 | benzyl | H | H | F | H | H | H | Cl | H | nonafluoro-2-butyl | H | CF3 |
| 11-766 | phenyl | H | H | F | H | H | H | Cl | H | nonafluoro-2-butyl | H | CF3 |
| 11-767 | methyl | H | H | F | H | H | H | Br | H | heptafluoroisopropyl | H | CF3 |
| 11-768 | ethyl | H | H | F | H | H | H | Br | H | heptafluoroisopropyl | H | CF3 |
| 11-769 | 2-fluoroethyl | H | H | F | H | H | H | Br | H | heptafluoroisopropyl | H | CF3 |
| 11-770 | 2-chloroethyl | H | H | F | H | H | H | Br | H | heptafluoroisopropyl | H | CF3 |
| 11-771 | 2-bromoethyl | H | H | F | H | H | H | Br | H | heptafluoroisopropyl | H | CF3 |
| 11-772 | 2-iodoethyl | H | H | F | H | H | H | Br | H | heptafluoroisopropyl | H | CF3 |
| 11-773 | 2-cyanoethyl | H | H | F | H | H | H | Br | H | heptafluoroisopropyl | H | C2F5 |
| 11-774 | 2,2-difluoroethyl | H | H | F | H | H | H | Br | H | heptafluoroisopropyl | H | CF3 |
| 11-775 | 2,2-dichloroethyl | H | H | F | H | H | H | Br | H | heptafluoroisopropyl | H | CF3 |
| 11-776 | 2,2,2-trifluoroethyl | H | H | F | H | H | H | Br | H | heptafluoroisopropyl | H | CF3 |
| 11-777 | 2,2,2-trichloroethyl | H | H | F | H | H | H | Br | H | heptafluoroisopropyl | H | CF3 |
| 11-778 | 2,2,2-tribromoethyl | H | H | F | H | H | H | Br | H | heptafluoroisopropyl | H | CF3 |
| 11-779 | n-propyl | H | H | F | H | H | H | Br | H | heptafluoroisopropyl | H | CF3 |
| 11-780 | 3-fluoro-n-propyl | H | H | F | H | H | H | Br | H | heptafluoroisopropyl | H | CF3 |
| 11-781 | 3-chloro-n-propyl | H | H | F | H | H | H | Br | H | heptafluoroisopropyl | H | CF3 |
| 11-782 | 3-bromo-n-propyl | H | H | F | H | H | H | Br | H | heptafluoroisopropyl | H | CF3 |
| 11-783 | i-propyl | H | H | F | H | H | H | Br | H | heptafluoroisopropyl | H | CF3 |
| 11-784 | 1,2-difluoro-2-propyl | H | H | F | H | H | H | Br | H | heptafluoroisopropyl | H | n-C3F7 |
| 11-785 | 1,3-difluoro-2-propyl | H | H | F | H | H | H | Br | H | heptafluoroisopropyl | H | CF3 |
| 11-786 | 1,3-dichloro-2-propyl | H | H | F | H | H | H | Br | H | heptafluoroisopropyl | H | CF3 |
| 11-787 | 1-chloro-3-fluoro-2-propyl | H | H | F | H | H | H | Br | H | heptafluoroisopropyl | H | CF3 |
| 11-788 | 3,3,3-fluoro-n-propyl | H | H | F | H | H | H | Br | H | heptafluoroisopropyl | H | CF3 |
| 11-789 | n-butyl | H | H | F | H | H | H | Br | H | heptafluoroisopropyl | H | CF3 |
| 11-790 | 4,4,4-trifluoro-n-butyl | H | H | F | H | H | H | Br | H | heptafluoroisopropyl | H | CF3 |
| 11-791 | i-butyl | H | H | F | H | H | H | Br | H | heptafluoroisopropyl | H | CF3 |
| 11-792 | s-butyl | H | H | F | H | H | H | Br | H | heptafluoroisopropyl | H | CF3 |
| 11-793 | vinyl | H | H | F | H | H | H | Br | H | heptafluoroisopropyl | H | CF3 |
| 11-794 | benzyl | H | H | F | H | H | H | Br | H | heptafluoroisopropyl | H | CF3 |
| 11-795 | phenyl | H | H | F | H | H | H | Br | H | heptafluoroisopropyl | H | CF3 |
| 11-796 | methyl | H | H | F | H | H | H | Br | H | nonafluoro-2-butyl | H | CF3 |
| 11-797 | ethyl | H | H | F | H | H | H | Br | H | nonafluoro-2-butyl | H | CF3 |
| 11-798 | 2-fluoroethyl | H | H | F | H | H | H | Br | H | nonafluoro-2-butyl | H | CF3 |
| 11-799 | 2-chloroethyl | H | H | F | H | H | H | Br | H | nonafluoro-2-butyl | H | CF3 |
| 11-800 | 2-bromoethyl | H | H | F | H | H | H | Br | H | nonafluoro-2-butyl | H | CF3 |
| 11-801 | 2-iodoethyl | H | H | F | H | H | H | Br | H | nonafluoro-2-butyl | H | CF3 |
| 11-802 | 2-cyanoethyl | H | H | F | H | H | H | Br | H | nonafluoro-2-butyl | H | CF3 |
| 11-803 | 2,2-difluoroethyl | H | H | F | H | H | H | Br | H | nonafluoro-2-butyl | H | CF3 |
| 11-804 | 2,2-dichloroethyl | H | H | F | H | H | H | Br | H | nonafluoro-2-butyl | H | CF3 |
| 11-805 | 2,2,2-trifluoroethyl | H | H | F | H | H | H | Br | H | nonafluoro-2-butyl | H | CF3 |
| 11-806 | 2,2,2-trichloroethyl | H | H | F | H | H | H | Br | H | nonafluoro-2-butyl | H | CF3 |
| 11-807 | 2,2,2-tribromoethyl | H | H | F | H | H | H | Br | H | nonafluoro-2-butyl | H | CF3 |

TABLE 11-continued

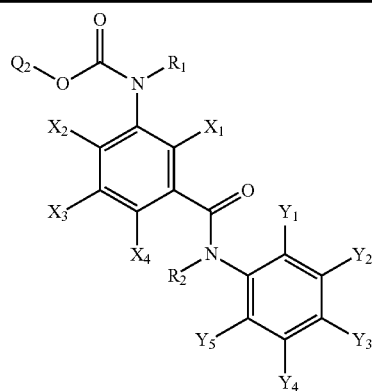

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-808 | n-propyl | H | H | F | H | H | H | Br | H | nonafluoro-2-butyl | H | CF3 |
| 11-809 | 3-fluoro-n-propyl | H | H | F | H | H | H | Br | H | nonafluoro-2-butyl | H | CF3 |
| 11-810 | 3-chloro-n-propyl | H | H | F | H | H | H | Br | H | nonafluoro-2-butyl | H | CF3 |
| 11-811 | 3-bromo-n-propyl | H | H | F | H | H | H | Br | H | nonafluoro-2-butyl | H | CF3 |
| 11-812 | i-propyl | H | H | F | H | H | H | Br | H | nonafluoro-2-butyl | H | CF3 |
| 11-813 | 1,2-difluoro-2-propyl | H | H | F | H | H | H | Br | H | nonafluoro-2-butyl | H | CF3 |
| 11-814 | 1,3-difluoro-2-propyl | H | H | F | H | H | H | Br | H | nonafluoro-2-butyl | H | CF3 |
| 11-815 | 1,3-dichloro-2-propyl | H | H | F | H | H | H | Br | H | nonafluoro-2-butyl | H | CF3 |
| 11-816 | 1-chloro-3-fluoro-2-propyl | H | H | F | H | H | H | Br | H | nonafluoro-2-butyl | H | CF3 |
| 11-817 | 3,3,3-trifluoro-n-propyl | H | H | F | H | H | H | Br | H | nonafluoro-2-butyl | H | CF3 |
| 11-818 | n-butyl | H | H | F | H | H | H | Br | H | nonafluoro-2-butyl | H | CF3 |
| 11-819 | 4,4,4-trifluoro-n-butyl | H | H | F | H | H | H | Br | H | nonafluoro-2-butyl | H | CF3 |
| 11-820 | i-butyl | H | H | F | H | H | H | Br | H | nonafluoro-2-butyl | H | CF3 |
| 11-821 | s-butyl | H | H | F | H | H | H | Br | H | nonafluoro-2-butyl | H | CF3 |
| 11-822 | vinyl | H | H | F | H | H | H | Br | H | nonafluoro-2-butyl | H | CF3 |
| 11-823 | benzyl | H | H | F | H | H | H | Br | H | nonafluoro-2-butyl | H | CF3 |
| 11-824 | phenyl | H | H | F | H | H | H | Br | H | nonafluoro-2-butyl | H | i-C3F7 |
| 11-825 | methyl | H | H | F | H | H | H | I | H | heptafluoroisopropyl | H | CF3 |
| 11-826 | ethyl | H | H | F | H | H | H | I | H | heptafluoroisopropyl | H | CF3 |
| 11-827 | 2-fluoroethyl | H | H | F | H | H | H | I | H | heptafluoroisopropyl | H | CF3 |
| 11-828 | 2-chloroethyl | H | H | F | H | H | H | I | H | heptafluoroisopropyl | H | CF3 |
| 11-829 | 2-bromoethyl | H | H | F | H | H | H | I | H | heptafluoroisopropyl | H | CF3 |
| 11-830 | 2-iodoethyl | H | H | F | H | H | H | I | H | heptafluoroisopropyl | H | CF3 |
| 11-831 | 2-cyanoethyl | H | H | F | H | H | H | I | H | heptafluoroisopropyl | H | CF3 |
| 11-832 | 2,2-difluoroethyl | H | H | F | H | H | H | I | H | heptaflUoroisopropyl | H | CF3 |
| 11-833 | 2,2-dichloroethyl | H | H | F | H | H | H | I | H | heptafluoroisopropyl | H | CF3 |
| 11-834 | 2,2,2-trifluoroethyl | H | H | F | H | H | H | I | H | heptafluoroisopropyl | H | CF3 |
| 11-835 | 2,2,2-trichloroethyl | H | H | F | H | H | H | I | H | heptafluoroisopropyl | H | CF3 |
| 11-836 | 2,2,2-tribromoethyl | H | H | F | H | H | H | I | H | heptafluoroisopropyl | H | CF3 |
| 11-837 | n-propyl | H | H | F | H | H | H | I | H | heptafluoroisopropyl | H | CF3 |
| 11-838 | 3-fluoro-n-propyl | H | H | F | H | H | H | I | H | heptafluoroisopropyl | H | CF3 |
| 11-839 | 3-chloro-n-propyl | H | H | F | H | H | H | I | H | heptafluoroisopropyl | H | CF3 |
| 11-840 | 3-bromo-n-propyl | H | H | F | H | H | H | I | H | heptafluoroisopropyl | H | C2F5 |
| 11-841 | i-propyl | H | H | F | H | H | H | I | H | heptafluoroisopropyl | H | CF3 |
| 11-842 | 1,2-difluoro-2-propyl | H | H | F | H | H | H | I | H | heptafluoroisopropyl | H | CF3 |
| 11-843 | 1,3-difluoro-2-propyl | H | H | F | H | H | H | I | H | heptafluoroisopropyl | H | CF3 |
| 11-844 | 1,3-dichloro-2-propyl | H | H | F | H | H | H | I | H | heptafluoroisopropyl | H | CF3 |
| 11-845 | 1-chloro-3-fluoro-2-propyl | H | H | F | H | H | H | I | H | heptafluoroisopropyl | H | CF3 |
| 11-846 | 3,3,3-trifluoro-n-propyl | H | H | F | H | H | H | I | H | heptafluoroisopropyl | H | CF3 |
| 11-847 | n-butyl | H | H | F | H | H | H | I | H | heptafluoroisopropyl | H | CF3 |
| 11-848 | 4,4,4-trifluoro-n-butyl | H | H | F | H | H | H | I | H | heptafluoroisopropyl | H | CF3 |
| 11-849 | i-butyl | H | H | F | H | H | H | I | H | heptafluoroisopropyl | H | CF3 |
| 11-850 | s-butyl | H | H | F | H | H | H | I | H | heptafluoroisopropyl | H | CF3 |
| 11-851 | vinyl | H | H | F | H | H | H | I | H | heptafluoroisopropyl | H | CF3 |
| 11-852 | benzyl | H | H | F | H | H | H | I | H | heptafluoroisopropyl | H | CF3 |
| 11-853 | phenyl | H | H | F | H | H | H | I | H | heptafluoroisopropyl | H | CF3 |
| 11-854 | methyl | H | H | F | H | H | H | I | H | nonafluoro-2-butyl | H | CF3 |
| 11-855 | ethyl | H | H | F | H | H | H | I | H | nonafluoro-2-butyl | H | CF3 |
| 11-856 | 2-fluoroethyl | H | H | F | H | H | H | I | H | nonafluoro-2-butyl | H | CF3 |
| 11-857 | 2-chloroethyl | H | H | F | H | H | H | I | H | nonafluoro-2-butyl | H | CF3 |
| 11-858 | 2-bromoethyl | H | H | F | H | H | H | I | H | nonafluoro-2-butyl | H | CF3 |
| 11-859 | 2-iodoethyl | H | H | F | H | H | H | I | H | nonafluoro-2-butyl | H | CF3 |
| 11-860 | 2-cyanoethyl | H | H | F | H | H | H | I | H | nonafluoro-2-butyl | H | CF3 |
| 11-861 | 2,2-difluoroethyl | H | H | F | H | H | H | I | H | nonafluoro-2-butyl | H | CF3 |
| 11-862 | 2,2-dichloroethyl | H | H | F | H | H | H | I | H | nonafluoro-2-butyl | H | CF3 |
| 11-863 | 2,2,2-trifluoroethyl | H | H | F | H | H | H | I | H | nonafluoro-2-butyl | H | CF3 |
| 11-864 | 2,2,2-trichloroethyl | H | H | F | H | H | H | I | H | nonafluoro-2-butyl | H | CF3 |
| 11-865 | 2,2,2-tribromoethyl | H | H | F | H | H | H | I | H | nonafluoro-2-butyl | H | CF3 |

TABLE 11-continued

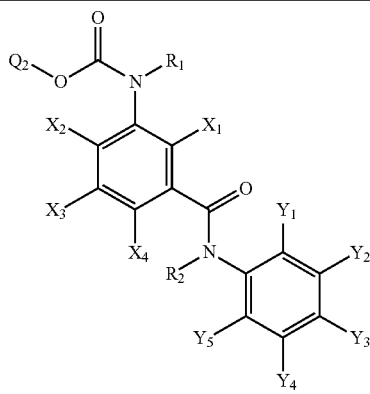

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-866 | n-propyl | H | H | F | H | H | H | I | H | nonafluoro-2-butyl | H | n-C3F7 |
| 11-867 | 3-fluoro-n-propyl | H | H | F | H | H | H | I | H | nonafluoro-2-butyl | H | CF3 |
| 11-868 | 3-chloro-n-propyl | H | H | F | H | H | H | I | H | nonafluoro-2-butyl | H | CF3 |
| 11-869 | 3-bromo-n-propyl | H | H | F | H | H | H | I | H | nonafluoro-2-butyl | H | CF3 |
| 11-870 | i-propyl | H | H | F | H | H | H | I | H | nonafluoro-2-butyl | H | CF3 |
| 11-871 | 1,2-difluoro-2-propyl | H | H | F | H | H | H | I | H | nonafluoro-2-butyl | H | CF3 |
| 11-872 | 1,3-difluoro-2-propyl | H | H | F | H | H | H | I | H | nonafluoro-2-butyl | H | CF3 |
| 11-873 | 1,3-dichloro-2-propyl | H | H | F | H | H | H | I | H | nonafluoro-2-butyl | H | CF3 |
| 11-874 | 1-chloro-3-fluoro-2-propyl | H | H | F | H | H | H | I | H | nonafluoro-2-butyl | H | CF3 |
| 11-875 | 3,3,3-trifluoro-n-propyl | H | H | F | H | H | H | I | H | nonafluoro-2-butyl | H | CF3 |
| 11-876 | n-butyl | H | H | F | H | H | H | I | H | nonafluoro-2-butyl | H | CF3 |
| 11-877 | 4,4,4-trifluoro-n-butyl | H | H | F | H | H | H | I | H | nonafluoro-2-butyl | H | CF3 |
| 11-878 | i-butyl | H | H | F | H | H | H | I | H | nonafluoro-2-butyl | H | CF3 |
| 11-879 | s-butyl | H | H | F | H | H | H | I | H | nonafluoro-2-butyl | H | CF3 |
| 11-880 | vinyl | H | H | F | H | H | H | I | H | nonafluoro-2-butyl | H | i-C3F7 |
| 11-881 | benzyl | H | H | F | H | H | H | I | H | nonafluoro-2-butyl | H | CF3 |
| 11-882 | phenyl | H | H | F | H | H | H | I | H | nonafluoro-2-butyl | H | CF3 |
| 11-893 | 2,2,2-trichloroethyl | H | H | F | H | H | H | OCF3 | H | heptafluoroisopropyl | H | OCF3 |
| 11-922 | 2,2,2-trichloroethyl | H | H | F | H | H | H | OCF3 | H | nonafluoro-2-butyl | H | OCF3 |
| 11-951 | 2,2,2-trichloroethyl | H | H | F | H | H | H | CF3 | H | heptafluoroisopropyl | H | OCF3 |
| 11-980 | 2,2,2-trichloroethyl | H | H | F | H | H | H | CF3 | H | nonafluoro-2-butyl | H | OCF3 |
| 11-999 | methyl | H | H | F | H | H | H | CF3 | H | heptafluoroisopropyl | H | CF3 |
| 11-1000 | ethyl | H | H | F | H | H | H | CF3 | H | heptafluoroisopropyl | H | CF3 |
| 11-1001 | 2-fluoroethyl | H | H | F | H | H | H | CF3 | H | heptafluoroisopropyl | H | CF3 |
| 11-1002 | 2-chloroethyl | H | H | F | H | H | H | CF3 | H | heptafluoroisopropyl | H | CF3 |
| 11-1003 | 2-bromoethyl | H | H | F | H | H | H | CF3 | H | heptafluoroisopropyl | H | CF3 |
| 11-1004 | 2-iodoethyl | H | H | F | H | H | H | CF3 | H | heptafluoroisopropyl | H | CF3 |
| 11-1005 | 2-cyanoethyl | H | H | F | H | H | H | CF3 | H | heptafluoroisopropyl | H | CF3 |
| 11-1006 | 2,2-difluoroethyl | H | H | F | H | H | H | CF3 | H | heptafluoroisopropyl | H | CF3 |
| 11-1007 | 2,2-dichloroethyl | H | H | F | H | H | H | CF3 | H | heptafluoroisopropyl | H | CF3 |
| 11-1008 | 2,2,2-trifluoroethyl | H | H | F | H | H | H | CF3 | H | heptafluoroisopropyl | H | CF3 |
| 11-1009 | 2,2,2-trichloroethyl | H | H | F | H | H | H | CF3 | H | heptafluoroisopropyl | H | CF3 |
| 11-1010 | 2,2,2-tribromoethyl | H | H | F | H | H | H | CF3 | H | heptafluoroisopropyl | H | CF3 |
| 11-1011 | n-propyl | H | H | F | H | H | H | CF3 | H | heptafluoroisopropyl | H | CF3 |
| 11-1012 | 3-fluoro-n-propyl | H | H | F | H | H | H | C2F5 | H | heptafluoroisopropyl | H | CF3 |
| 11-1013 | 3-chloro-n-propyl | H | H | F | H | H | H | CF3 | H | heptafluoroisopropyl | H | CF3 |
| 11-1014 | 3-bromo-n-propyl | H | H | F | H | H | H | CF3 | H | heptafluoroisopropyl | H | CF3 |
| 11-1015 | i-propyl | H | H | F | H | H | H | i-C3F7 | H | heptafluoroisopropyl | H | CF3 |
| 11-1016 | 1,2-difluoro-2-propyl | H | H | F | H | H | H | CF3 | H | heptafluoroisopropyl | H | CF3 |
| 11-1017 | 1,3-difluoro-2-propyl | H | H | F | H | H | H | CF3 | H | pentafluoroethyl | H | CF3 |
| 11-1018 | 1,3-dichloro-2-propyl | H | H | F | H | H | H | CF3 | H | heptafluoroisopropyl | H | CF3 |
| 11-1019 | 1-chloro-3-fluoro-2-propyl | H | H | F | H | H | H | CF3 | H | heptafluoroisopropyl | H | CF3 |
| 11-1020 | 3,3,3-trifluoro-n-propyl | H | H | F | H | H | H | CF3 | H | heptafluoroisopropyl | H | CF3 |
| 11-1021 | n-butyl | H | H | F | H | H | H | C2F5 | H | heptafluoroisopropyl | H | C2F5 |
| 11-1022 | 4,4,4-trifluoro-n-butyl | H | H | F | H | H | H | CF3 | H | heptafluoroisopropyl | H | CF3 |
| 11-1023 | i-butyl | H | H | F | H | H | H | C2F5 | H | heptafluoroisopropyl | H | n-C3F7 |
| 11-1024 | s-butyl | H | H | F | H | H | H | CF3 | H | heptafluoroisopropyl | H | CF3 |
| 11-1025 | vinyl | H | H | F | H | H | H | n-C3F7 | H | heptafluoroisopropyl | H | CF3 |
| 11-1026 | benzyl | H | H | F | H | H | H | CF3 | H | heptafluoroisopropyl | H | CF3 |
| 11-1027 | phenyl | H | H | F | H | H | H | CF3 | H | heptafluoroisopropyl | H | CF3 |
| 11-1030 | 2-fluoroethyl | H | H | F | H | H | H | CF3 | H | nonafluoro-2-butyl | H | CF3 |
| 11-1031 | 2-chloroethyl | H | H | F | H | H | H | CF3 | H | nonafluoro-2-butyl | H | CF3 |
| 11-1032 | 2-bromoethyl | H | H | F | H | H | H | CF3 | H | nonafluoro-2-butyl | H | CF3 |
| 11-1033 | 2-iodoethyl | H | H | F | H | H | H | CF3 | H | nonafluoro-2-butyl | H | CF3 |
| 11-1035 | 2,2-difluoroethyl | H | H | F | H | H | H | CF3 | H | nonafluoro-2-butyl | H | CF3 |
| 11-1036 | 2,2-dichloroethyl | H | H | F | H | H | H | CF3 | H | nonafluoro-2-butyl | H | CF3 |
| 11-1037 | 2,2,2-trifluoroethyl | H | H | F | H | H | H | CF3 | H | nonafluoro-2-butyl | H | CF3 |
| 11-1038 | 2,2,2-trichloroethyl | H | H | F | H | H | H | CF3 | H | nonafluoro-2-butyl | H | CF3 |

TABLE 11-continued

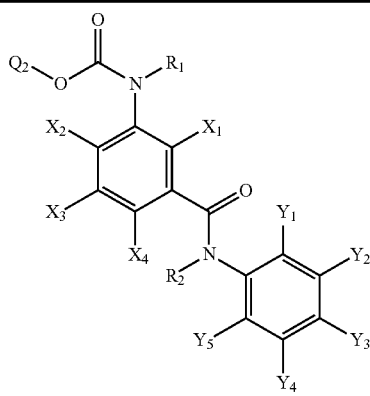

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-1039 | 2,2,2-tribromoethyl | H | H | F | H | H | H | CF3 | H | nonafluoro-2-butyl | H | CF3 |
| 11-1041 | 3-fluoro-n-propyl | H | H | F | H | H | H | CF3 | H | nonafluoro-2-butyl | H | CF3 |
| 11-1042 | 3-chloro-n-propyl | H | H | F | H | H | H | CF3 | H | nonafluoro-2-butyl | H | CF3 |
| 11-1043 | 3-bromo-n-propyl | H | H | F | H | H | H | CF3 | H | nonafluoro-2-butyl | H | CF3 |
| 11-1045 | 1,2-difluoro-2-propyl | H | H | F | H | H | H | CF3 | H | nonafluoro-2-butyl | H | CF3 |
| 11-1046 | 1,3-difluoro-2-propyl | H | H | F | H | H | H | CF3 | H | nonafluoro-2-butyl | H | CF3 |
| 11-1047 | 1,3-dichloro-2-propyl | H | H | F | H | H | H | CF3 | H | nonafluoro-2-butyl | H | CF3 |
| 11-1048 | 1-chloro-3-fluoro-2-propyl | H | H | F | H | H | H | CF3 | H | nonafluoro-2-butyl | H | CF3 |
| 11-1049 | 3,3,3-trifluoro-n-propyl | H | H | F | H | H | H | n-C3F7 | H | nonafluoro-2-butyl | H | i-C3F7 |
| 11-1051 | 4,4,4-trifluoro-n-butyl | H | H | F | H | H | H | CF3 | H | nonafluoro-2-butyl | H | CF3 |
| 11-1057 | 2,2,2-trichloroethyl | H | H | H | F | H | H | F | H | heptafluoroisopropyl | H | F |
| 11-1058 | 2,2,2-trichloroethyl | H | H | H | F | H | H | F | H | nonafluoro-2-butyl | H | F |
| 11-1069 | 2,2,2-trichloroethyl | H | H | H | F | H | H | Cl | H | heptafluoroisopropyl | H | Cl |
| 11-1098 | 2,2,2-trichloroethyl | H | H | H | F | H | H | Cl | H | nonafluoro-2-butyl | H | Cl |
| 11-1127 | 2,2,2-trichloroethyl | H | H | H | F | H | H | Br | H | heptafluoroisopropyl | H | Br |
| 11-1156 | 2,2,2-trichloroethyl | H | H | H | F | H | H | Br | H | nonafluoro-2-butyl | H | Br |
| 11-1185 | 2,2,2-trichloroethyl | H | H | H | F | H | H | I | H | heptafluoroisopropyl | H | I |
| 11-1214 | 2,2,2-trichloroethyl | H | H | H | F | H | H | I | H | nonafluoro-2-butyl | H | I |
| 11-1233 | 2,2,2-trichloroethyl | H | H | H | F | H | H | F | H | heptafluoroisopropyl | H | Cl |
| 11-1234 | 2,2,2-trichloroethyl | H | H | H | F | H | H | F | H | heptafluoroisopropyl | H | Br |
| 11-1235 | 2,2,2-trichloroethyl | H | H | H | F | H | H | F | H | heptafluoroisopropyl | H | I |
| 11-1236 | 2,2,2-trichloroethyl | H | H | H | F | H | H | Cl | H | heptafluoroisopropyl | H | Br |
| 11-1237 | 2,2,2-trichloroethyl | H | H | H | F | H | H | Cl | H | heptafluoroisopropyl | H | I |
| 11-1238 | 2,2,2-trichloroethyl | H | H | H | F | H | H | Br | H | heptafluoroisopropyl | H | I |
| 11-1239 | 2,2,2-trichloroethyl | H | H | H | F | H | H | F | H | nonafluoro-2-butyl | H | Cl |
| 11-1240 | 2,2,2-trichloroethyl | H | H | H | F | H | H | F | H | nonafluoro-2-butyl | H | Br |
| 11-1241 | 2,2,2-trichloroethyl | H | H | H | F | H | H | F | H | nonafluoro-2-butyl | H | I |
| 11-1242 | 2,2,2-trichloroethyl | H | H | H | F | H | H | Cl | H | nonafluoro-2-butyl | H | Br |
| 11-1243 | 2,2,2-trichloroethyl | H | H | H | F | H | H | Cl | H | nonafluoro-2-butyl | H | I |
| 11-1244 | 2,2,2-trichloroethyl | H | H | H | F | H | H | Br | H | nonafluoro-2-butyl | H | I |
| 11-1245 | 2,2,2-trichloroethyl | H | H | H | F | H | H | F | H | heptafluoroisopropyl | H | OCF3 |
| 11-1246 | 2,2,2-trichloroethyl | H | H | H | F | H | H | F | H | nonafluoro-2-butyl | H | OCF3 |
| 11-1257 | 2,2,2-trichloroethyl | H | H | H | F | H | H | Cl | H | heptafluoroisopropyl | H | OCF3 |
| 11-1286 | 2,2,2-trichloroethyl | H | H | H | F | H | H | Cl | H | nonafluoro-2-butyl | H | OCF3 |
| 11-1315 | 2,2,2-trichloroethyl | H | H | H | F | H | H | Br | H | heptafluoroisopropyl | H | OCF3 |
| 11-1344 | 2,2,2-trichloroethyl | H | H | H | F | H | H | Br | H | nonafluoro-2-butyl | H | OCF3 |
| 11-1373 | 2,2,2-trichloroethyl | H | H | H | F | H | H | I | H | heptafluoroisopropyl | H | OCF3 |
| 11-1402 | 2,2,2-trichloroethyl | H | H | H | F | H | H | I | H | nonafluoro-2-butyl | H | OCF3 |
| 11-1421 | 2,2,2-trichloroethyl | H | H | H | F | H | H | F | H | heptafluoroisopropyl | H | CF3 |
| 11-1422 | 2,2,2-trichloroethyl | H | H | H | F | H | H | F | H | nonafluoro-2-butyl | H | CF3 |
| 11-1433 | 2,2,2-trichloroethyl | H | H | H | F | H | H | Cl | H | heptafluoroisopropyl | H | CF3 |
| 11-1461 | 2,2,2-trifluoroethyl | H | H | H | F | H | H | Cl | H | nonafluoro-2-butyl | H | CF3 |
| 11-1491 | 2,2,2-trichloroethyl | H | H | H | F | H | H | Br | H | heptafluoroisopropyl | H | CF3 |
| 11-1504 | 4,4,4-trifluoro-n-butyl | H | H | H | F | H | H | Br | H | heptafluoroisopropyl | H | CF3 |
| 11-1520 | 2,2,2-trichloroethyl | H | H | H | F | H | H | Br | H | nonafluoro-2-butyl | H | CF3 |
| 11-1533 | 4,4,4-trifluoro-n-butyl | H | H | H | F | H | H | Br | H | nonafluoro-2-butyl | H | CF3 |
| 11-1548 | 2,2,2-trifluoroethyl | H | H | H | F | H | H | I | H | heptafluoroisopropyl | H | CF3 |
| 11-1562 | 4,4,4-trifluoro-n-butyl | H | H | H | F | H | H | I | H | heptafluoroisopropyl | H | CF3 |
| 11-1578 | 2,2,2-trichloroethyl | H | H | H | F | H | H | I | H | nonafluoro-2-butyl | H | CF3 |
| 11-1591 | 4,4,4-trifluoro-n-butyl | H | H | H | F | H | H | I | H | nonafluoro-2-butyl | H | CF3 |
| 11-1607 | 2,2,2-trichloroethyl | H | H | H | F | H | H | OCF3 | H | heptafluoroisopropyl | H | OCF3 |
| 11-1636 | 2,2,2-trichloroethyl | H | H | H | F | H | H | OCF3 | H | nonafluoro-2-butyl | H | OCF3 |
| 11-1665 | 2,2,2-trichloroethyl | H | H | H | F | H | H | CF3 | H | heptafluoroisopropyl | H | OCF3 |
| 11-1694 | 2,2,2-trichloroethyl | H | H | H | F | H | H | CF3 | H | nonafluoro-2-butyl | H | OCF3 |
| 11-1723 | 2,2,2-trichloroethyl | H | H | H | F | H | H | CF3 | H | heptafluoroisopropyl | H | CF3 |
| 11-1752 | 2,2,2-trichloroethyl | H | H | H | F | H | H | CF3 | H | nonafluoro-2-butyl | H | CF3 |
| 11-1771 | 2,2,2-trichloroethyl | H | H | F | F | H | H | F | H | heptafluoroisopropyl | H | F |
| 11-1772 | 2,2,2-trichloroethyl | H | H | F | F | H | H | F | H | nonafluoro-2-butyl | H | F |

TABLE 11-continued

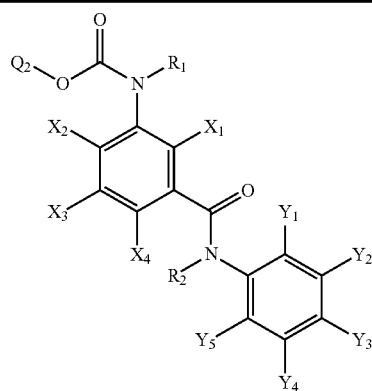

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-1783 | 2,2,2-trichloroethyl | H | H | F | F | H | H | Cl | H | heptafluoroisopropyl | H | Cl |
| 11-1812 | 2,2,2-trichloroethyl | H | H | F | F | H | H | Cl | H | nonafluoro-2-butyl | H | Cl |
| 11-1841 | 2,2,2-trichloroethyl | H | H | F | F | H | H | Br | H | heptafluoroisopropyl | H | Br |
| 11-1870 | 2,2,2-trichloroethyl | H | H | F | F | H | H | Br | H | nonafluoro-2-butyl | H | Br |
| 11-1899 | 2,2,2-trichloroethyl | H | H | F | F | H | H | I | H | heptafluoroisopropyl | H | I |
| 11-1928 | 2,2,2-trichloroethyl | H | H | F | F | H | H | I | H | nonafluoro-2-butyl | H | I |
| 11-1947 | 2,2,2-trichloroethyl | H | H | F | F | H | H | F | H | heptafluoroisopropyl | H | Cl |
| 11-1948 | 2,2,2-trichloroethyl | H | H | F | F | H | H | F | H | heptafluoroisopropyl | H | Br |
| 11-1949 | 2,2,2-trichloroethyl | H | H | F | F | H | H | F | H | heptafluoroisopropyl | H | I |
| 11-1950 | 2,2,2-trichloroethyl | H | H | F | F | H | H | Cl | H | heptafluoroisopropyl | H | Br |
| 11-1951 | 2,2,2-trichloroethyl | H | H | F | F | H | H | Cl | H | heptafluoroisopropyl | H | I |
| 11-1952 | 2,2,2-trichloroethyl | H | H | F | F | H | H | Br | H | heptafluoroisopropyl | H | I |
| 11-1953 | 2,2,2-trichloroethyl | H | H | F | F | H | H | F | H | nonafluoro-2-butyl | H | Cl |
| 11-1954 | 2,2,2-trichloroethyl | H | H | F | F | H | H | F | H | nonafluoro-2-butyl | H | Br |
| 11-1955 | 2,2,2-trichloroethyl | H | H | F | F | H | H | F | H | nonafluoro-2-butyl | H | I |
| 11-1956 | 2,2,2-trichloroethyl | H | H | F | F | H | H | Cl | H | nonafluoro-2-butyl | H | Br |
| 11-1957 | 2,2,2-trichloroethyl | H | H | F | F | H | H | Cl | H | nonafluoro-2-butyl | H | I |
| 11-1958 | 2,2,2-trichloroethyl | H | H | F | F | H | H | Br | H | nonafluoro-2-butyl | H | I |
| 11-1959 | 2,2,2-trichloroethyl | H | H | F | F | H | H | F | H | heptafluoroisopropyl | H | OCF3 |
| 11-1960 | 2,2,2-trichloroethyl | H | H | F | F | H | H | F | H | nonafluoro-2-butyl | H | OCF3 |
| 11-1971 | 2,2,2-trichloroethyl | H | H | F | F | H | H | Cl | H | heptafluoroisopropyl | H | OCF3 |
| 11-2000 | 2,2,2-trichloroethyl | H | H | F | F | H | H | Cl | H | nonafluoro-2-butyl | H | OCF3 |
| 11-2029 | 2,2,2-trichloroethyl | H | H | F | F | H | H | Br | H | heptafluoroisopropyl | H | OCF3 |
| 11-2058 | 2,2,2-trichloroethyl | H | H | F | F | H | H | Br | H | nonafluoro-2-butyl | H | OCF3 |
| 11-2087 | 2,2,2-trichloroethyl | H | H | F | F | H | H | I | H | heptafluoroisopropyl | H | OCF3 |
| 11-2116 | 2,2,2-trichloroethyl | H | H | F | F | H | H | I | H | nonafluoro-2-butyl | H | OCF3 |
| 11-2135 | 2,2,2-trichloroethyl | H | H | F | F | H | H | F | H | heptafluoroisopropyl | H | CF3 |
| 11-2136 | 2,2,2-trichloroethyl | H | H | F | F | H | H | F | H | nonafluoro-2-butyl | H | CF3 |
| 11-2147 | 2,2,2-trichloroethyl | H | H | F | F | H | H | Cl | H | heptafluoroisopropyl | H | CF3 |
| 11-2176 | 2,2,2-trichloroethyl | H | H | F | F | H | H | Cl | H | nonafluoro-2-butyl | H | CF3 |
| 11-2205 | 2,2,2-trichloroethyl | H | H | F | F | H | H | Br | H | heptafluoroisopropyl | H | CF3 |
| 11-2218 | 4,4,4-trifluoro-n-butyl | H | H | F | F | H | H | Br | H | heptafluoroisopropyl | H | CF3 |
| 11-2234 | 2,2,2-trichloroethyl | H | H | F | F | H | H | Br | H | nonafluoro-2-butyl | H | CF3 |
| 11-2247 | 4,4,4-trifluoro-n-butyl | H | H | F | F | H | H | Br | H | nonafluoro-2-butyl | H | CF3 |
| 11-2263 | 2,2,2-trichloroethyl | H | H | F | F | H | H | I | H | heptafluoroisopropyl | H | CF3 |
| 11-2276 | 4,4,4-trifluoro-n-butyl | H | H | F | F | H | H | I | H | heptafluoroisopropyl | H | CF3 |
| 11-2292 | 2,2,2-trichloroethyl | H | H | F | F | H | H | I | H | nonafluoro-2-butyl | H | CF3 |
| 11-2305 | 4,4,4-trifluoro-n-butyl | H | H | F | F | H | H | I | H | nonafluoro-2-butyl | H | CF3 |
| 11-2321 | 2,2,2-trichloroethyl | H | H | F | F | H | H | OCF3 | H | heptafluoroisopropyl | H | OCF3 |
| 11-2350 | 2,2,2-trichloroethyl | H | H | F | F | H | H | OCF3 | H | nonafluoro-2-butyl | H | OCF3 |
| 11-2379 | 2,2,2-trichloroethyl | H | H | F | F | H | H | CF3 | H | heptafluoroisopropyl | H | OCF3 |
| 11-2408 | 2,2,2-trichloroethyl | H | H | F | F | H | H | CF3 | H | nonafluoro-2-butyl | H | OCF3 |
| 11-2437 | 2,2,2-trichloroethyl | H | H | F | F | H | H | CF3 | H | heptafluoroisopropyl | H | CF3 |
| 11-2466 | 2,2,2-trichloroethyl | H | H | F | F | H | H | CF3 | H | nonafluoro-2-butyl | H | CF3 |
| 11-2485 | 2,2,2-trichloroethyl | H | H | F | F | F | H | Cl | H | pentafluoroethyl | H | Cl |
| 11-2486 | 2,2,2-trichloroethyl | H | H | F | F | F | H | Br | H | heptafluoroisopropyl | H | Br |
| 11-2487 | 2,2,2-trichloroethyl | H | H | F | F | F | H | Br | H | heptafluoroisopropyl | H | OCF3 |
| 11-2488 | 2,2,2-trichloroethyl | H | H | F | F | F | H | I | H | heptafluoroisopropyl | H | CF3 |
| 11-2489 | 2,2,2-trichloroethyl | H | H | F | F | F | H | CF3 | H | heptafluoroisopropyl | H | CF3 |
| 11-2490 | 2,2,2-trichloroethyl | H | H | F | F | F | H | I | H | nonafluoro-2-butyl | H | I |
| 11-2491 | 2,2,2-trichloroethyl | H | H | F | F | F | H | Cl | H | nonafluoro-2-butyl | H | OCF3 |
| 11-2492 | 2,2,2-trichloroethyl | H | H | F | F | F | H | Br | H | nonafluoro-2-butyl | H | CF3 |
| 11-2493 | 2,2,2-trichloroethyl | H | H | F | F | F | H | CF3 | H | nonafluoro-2-butyl | H | CF3 |
| 11-2494 | 2,2,2-trichloroethyl | H | H | H | H | F | H | Cl | H | pentafluoroethyl | H | Cl |
| 11-2495 | 2,2,2-trichloroethyl | H | H | H | H | F | H | Br | H | heptafluoroisopropyl | H | Br |
| 11-2496 | 2,2,2-trichloroethyl | H | H | H | H | F | H | Br | H | heptafluoroisopropyl | H | OCF3 |
| 11-2497 | 2,2,2-trichloroethyl | H | H | H | H | F | H | I | H | heptafluoroisopropyl | H | CF3 |
| 11-2498 | 2,2,2-trichloroethyl | H | H | H | H | F | H | CF3 | H | heptafluoroisopropyl | H | CF3 |

TABLE 11-continued

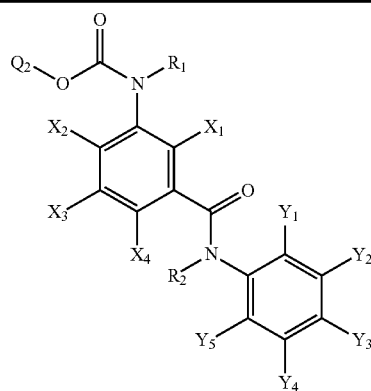

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-2499 | 2,2,2-trichloroethyl | H | H | H | H | F | H | I | H | nonafluoro-2-butyl | H | I |
| 11-2500 | 2,2,2-trichloroethyl | H | H | H | H | F | H | Cl | H | nonafluoro-2-butyl | H | OCF3 |
| 11-2501 | 2,2,2-trichloroethyl | H | H | H | H | F | H | Br | H | nonafluoro-2-butyl | H | CF3 |
| 11-2502 | 2,2,2-trichloroethyl | H | H | H | H | F | H | CF3 | H | nonafluoro-2-butyl | H | CF3 |
| 11-2503 | 2,2,2-trichloroethyl | H | H | H | H | H | F | Cl | H | pentafluoroethyl | H | Cl |
| 11-2504 | 2,2,2-trichloroethyl | H | H | H | H | H | F | Br | H | heptafluoroisopropyl | H | Br |
| 11-2505 | 2,2,2-trichloroethyl | H | H | H | H | H | F | Br | H | heptafluoroisopropyl | H | OCF3 |
| 11-2506 | 2,2,2-trichloroethyl | H | H | H | H | H | F | I | H | heptafluoroisopropyl | H | CF3 |
| 11-2507 | 2,2,2-trichloroethyl | H | H | H | H | H | F | CF3 | H | heptafluoroisopropyl | H | CF3 |
| 11-2508 | 2,2,2-trichloroethyl | H | H | H | H | H | F | I | H | nonafluoro-2-butyl | H | I |
| 11-2509 | 2,2,2-trichloroethyl | H | H | H | H | H | F | Cl | H | nonafluoro-2-butyl | H | OCF3 |
| 11-2510 | 2,2,2-trichloroethyl | H | H | H | H | H | F | Br | H | nonafluoro-2-butyl | H | CF3 |
| 11-2511 | 2,2,2-trichloroethyl | H | H | H | H | H | F | CF3 | H | nonafluoro-2-butyl | H | CF3 |
| 11-2512 | 2,2,2-trichloroethyl | H | H | F | H | F | H | Cl | H | pentafluoroethyl | H | Cl |
| 11-2513 | 2,2,2-trichloroethyl | H | H | F | H | F | H | Br | H | heptafluoroisopropyl | H | Br |
| 11-2514 | 2,2,2-trichloroethyl | H | H | F | H | F | H | Br | H | heptafluoroisopropyl | H | OCF3 |
| 11-2515 | 2,2,2-trichloroethyl | H | H | F | H | F | H | I | H | heptafluoroisopropyl | H | CF3 |
| 11-2516 | 2,2,2-trichloroethyl | H | H | F | H | F | H | CF3 | H | heptafluoroisopropyl | H | CF3 |
| 11-2517 | 2,2,2-trichloroethyl | H | H | F | H | F | H | I | H | nonafluoro-2-butyl | H | I |
| 11-2518 | 2,2,2-trichloroethyl | H | H | F | H | F | H | Cl | H | nonafluoro-2-butyl | H | OCF3 |
| 11-2519 | 2,2,2-trichloroethyl | H | H | F | H | F | H | Br | H | nonafluoro-2-butyl | H | CF3 |
| 11-2520 | 2,2,2-trichloroethyl | H | H | F | H | F | H | CF3 | H | nonafluoro-2-butyl | H | CF3 |
| 11-2521 | 2,2,2-trichloroethyl | H | H | F | H | H | F | Cl | H | pentafluoroethyl | H | Cl |
| 11-2522 | 2,2,2-trichloroethyl | H | H | F | H | H | F | Br | H | heptafluoroisopropyl | H | Br |
| 11-2523 | 2,2,2-trichloroethyl | H | H | F | H | H | F | Br | H | heptafluoroisopropyl | H | OCF3 |
| 11-2524 | 2,2,2-trichloroethyl | H | H | F | H | H | F | I | H | heptafluoroisopropyl | H | CF3 |
| 11-2525 | 2,2,2-trichloroethyl | H | H | F | H | H | F | CF3 | H | heptafluoroisopropyl | H | CF3 |
| 11-2526 | 2,2,2-trichloroethyl | H | H | F | H | H | F | I | H | nonafluoro-2-butyl | H | I |
| 11-2527 | 2,2,2-trichloroethyl | H | H | F | H | H | F | Cl | H | nonafluoro-2-butyl | H | OCF3 |
| 11-2528 | 2,2,2-trichloroethyl | H | H | F | H | H | F | Br | H | nonafluoro-2-butyl | H | CF3 |
| 11-2529 | 2,2,2-trichloroethyl | H | H | F | H | H | F | CF3 | H | nonafluoro-2-butyl | H | CF3 |
| 11-2530 | 2,2,2-trichloroethyl | H | H | H | F | F | H | Cl | H | pentafluoroethyl | H | Cl |
| 11-2531 | 2,2,2-trichloroethyl | H | H | H | F | F | H | Br | H | heptafluoroisopropyl | H | Br |
| 11-2532 | 2,2,2-trichloroethyl | H | H | H | F | F | H | Br | H | heptafluoroisopropyl | H | OCF3 |
| 11-2533 | 2,2,2-trichloroethyl | H | H | H | F | F | H | I | H | heptafluoroisopropyl | H | CF3 |
| 11-2534 | 2,2,2-trichloroethyl | H | H | H | F | F | H | CF3 | H | heptafluoroisopropyl | H | CF3 |
| 11-2535 | 2,2,2-trichloroethyl | H | H | H | F | F | H | I | H | nonafluoro-2-butyl | H | I |
| 11-2536 | 2,2,2-trichloroethyl | H | H | H | F | F | H | Cl | H | nonafluoro-2-butyl | H | OCF3 |
| 11-2537 | 2,2,2-trichloroethyl | H | H | H | F | F | H | Br | H | nonafluoro-2-butyl | H | CF3 |
| 11-2538 | 2,2,2-trichloroethyl | H | H | H | F | F | H | CF3 | H | nonafluoro-2-butyl | H | CF3 |
| 11-2539 | 2,2,2-trichloroethyl | H | H | H | F | H | F | Cl | H | pentafluoroethyl | H | Cl |
| 11-2540 | 2,2,2-trichloroethyl | H | H | H | F | H | F | Br | H | heptafluoroisopropyl | H | Br |
| 11-2541 | 2,2,2-trichloroethyl | H | H | H | F | H | F | Br | H | heptafluoroisopropyl | H | OCF3 |
| 11-2542 | 2,2,2-trichloroethyl | H | H | H | F | H | F | I | H | heptafluoroisopropyl | H | CF3 |
| 11-2543 | 2,2,2-trichloroethyl | H | H | H | F | H | F | CF3 | H | heptafluoroisopropyl | H | CF3 |
| 11-2544 | 2,2,2-trichloroethyl | H | H | H | F | H | F | I | H | nonafluoro-2-butyl | H | I |
| 11-2545 | 2,2,2-trichloroethyl | H | H | H | F | H | F | Cl | H | nonafluoro-2-butyl | H | OCF3 |
| 11-2546 | 2,2,2-trichloroethyl | H | H | H | F | H | F | Br | H | nonafluoro-2-butyl | H | CF3 |
| 11-2547 | 2,2,2-trichloroethyl | H | H | H | F | H | F | CF3 | H | nonafluoro-2-butyl | H | CF3 |
| 11-2548 | 2,2,2-trichloroethyl | H | H | H | H | F | F | Cl | H | pentafluoroethyl | H | Cl |
| 11-2549 | 2,2,2-trichloroethyl | H | H | H | H | F | F | Br | H | heptafluoroisopropyl | H | Br |
| 11-2550 | 2,2,2-trichloroethyl | H | H | H | H | F | F | Br | H | heptafluoroisopropyl | H | OCF3 |
| 11-2551 | 2,2,2-trichloroethyl | H | H | H | H | F | F | I | H | heptafluoroisopropyl | H | CF3 |
| 11-2552 | 2,2,2-trichloroethyl | H | H | H | H | F | F | CF3 | H | heptafluoroisopropyl | H | CF3 |
| 11-2553 | 2,2,2-trichloroethyl | H | H | H | H | F | F | I | H | nonafluoro-2-butyl | H | I |
| 11-2554 | 2,2,2-trichloroethyl | H | H | H | H | F | F | Cl | H | nonafluoro-2-butyl | H | OCF3 |
| 11-2555 | 2,2,2-trichloroethyl | H | H | H | H | F | F | Br | H | nonafluoro-2-butyl | H | CF3 |
| 11-2556 | 2,2,2-trichloroethyl | H | H | H | H | F | F | CF3 | H | nonafluoro-2-butyl | H | CF3 |

TABLE 11-continued

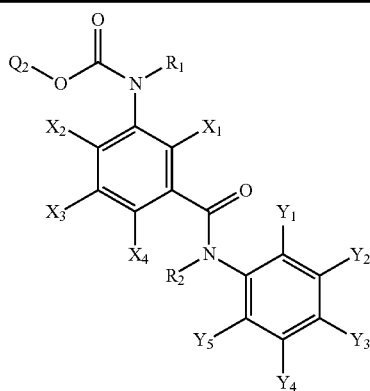

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-2557 | 2,2,2-trichloroethyl | H | H | F | F | H | F | Cl | H | pentafluoroethyl | H | Cl |
| 11-2558 | 2,2,2-trichloroethyl | H | H | F | F | H | F | Br | H | heptafluoroisopropyl | H | Br |
| 11-2559 | 2,2,2-trichloroethyl | H | H | F | F | H | F | Br | H | heptafluoroisopropyl | H | OCF3 |
| 11-2560 | 2,2,2-trichloroethyl | H | H | F | F | H | F | I | H | heptafluoroisopropyl | H | CF3 |
| 11-2561 | 2,2,2-trichloroethyl | H | H | F | F | H | F | CF3 | H | heptafluoroisopropyl | H | CF3 |
| 11-2562 | 2,2,2-trichloroethyl | H | H | F | F | H | F | I | H | nonafluoro-2-butyl | H | I |
| 11-2563 | 2,2,2-trichloroethyl | H | H | F | F | H | F | Cl | H | nonafluoro-2-butyl | H | OCF3 |
| 11-2564 | 2,2,2-trichloroethyl | H | H | F | F | H | F | Br | H | nonafluoro-2-butyl | H | CF3 |
| 11-2565 | 2,2,2-trichloroethyl | H | H | F | F | H | F | CF3 | H | nonafluoro-2-butyl | H | CF3 |
| 11-2566 | 2,2,2-trichloroethyl | H | H | F | H | F | F | Cl | H | pentafluoroethyl | H | Cl |
| 11-2567 | 2,2,2-trichloroethyl | H | H | F | H | F | F | Br | H | heptafluoroisopropyl | H | Br |
| 11-2568 | 2,2,2-trichloroethyl | H | H | F | H | F | F | Br | H | heptafluoroisopropyl | H | OCF3 |
| 11-2569 | 2,2,2-trichloroethyl | H | H | F | H | F | F | I | H | heptafluoroisopropyl | H | CF3 |
| 11-2570 | 2,2,2-trichloroethyl | H | H | F | H | F | F | CF3 | H | heptafluoroisopropyl | H | CF3 |
| 11-2571 | 2,2,2-trichloroethyl | H | H | F | H | F | F | I | H | nonafluoro-2-butyl | H | I |
| 11-2572 | 2,2,2-trichloroethyl | H | H | F | H | F | F | Cl | H | nonafluoro-2-butyl | H | OCF3 |
| 11-2573 | 2,2,2-trichloroethyl | H | H | F | H | F | F | Br | H | nonafluoro-2-butyl | H | CF3 |
| 11-2574 | 2,2,2-trichloroethyl | H | H | F | H | F | F | CF3 | H | nonafluoro-2-butyl | H | CF3 |
| 11-2575 | 2,2,2-trichloroethyl | H | H | H | F | F | F | Cl | H | pentafluoroethyl | H | Cl |
| 11-2576 | 2,2,2-trichloroethyl | H | H | H | F | F | F | Br | H | heptafluoroisopropyl | H | Br |
| 11-2577 | 2,2,2-trichloroethyl | H | H | H | F | F | F | Br | H | heptafluoroisopropyl | H | OCF3 |
| 11-2578 | 2,2,2-trichloroethyl | H | H | H | F | F | F | I | H | heptafluoroisopropyl | H | CF3 |
| 11-2579 | 2,2,2-trichloroethyl | H | H | H | F | F | F | CF3 | H | heptafluoroisopropyl | H | CF3 |
| 11-2580 | 2,2,2-trichloroethyl | H | H | H | F | F | F | I | H | nonafluoro-2-butyl | H | I |
| 11-2581 | 2,2,2-trichloroethyl | H | H | H | F | F | F | Cl | H | nonafluoro-2-butyl | H | OCF3 |
| 11-2582 | 2,2,2-trichloroethyl | H | H | H | F | F | F | Br | H | nonafluoro-2-butyl | H | CF3 |
| 11-2583 | 2,2,2-trichloroethyl | H | H | H | F | F | F | CF3 | H | nonafluoro-2-butyl | H | CF3 |
| 11-2584 | 2,2,2-trichloroethyl | H | H | F | F | F | F | Cl | H | pentafluoroethyl | H | Cl |
| 11-2585 | 2,2,2-trichloroethyl | H | H | F | F | F | F | Br | H | heptafluoroisopropyl | H | Br |
| 11-2586 | 2,2,2-trichloroethyl | H | H | F | F | F | F | Br | H | heptafluoroisopropyl | H | OCF3 |
| 11-2587 | 2,2,2-trichloroethyl | H | H | F | F | F | F | I | H | heptafluoroisopropyl | H | CF3 |
| 11-2588 | 2,2,2-trichloroethyl | H | H | F | F | F | F | CF3 | H | heptafluoroisopropyl | H | CF3 |
| 11-2589 | 2,2,2-trichloroethyl | H | H | F | F | F | F | I | H | nonafluoro-2-butyl | H | I |
| 11-2590 | 2,2,2-trichloroethyl | H | H | F | F | F | F | Cl | H | nonafluoro-2-butyl | H | OCF3 |
| 11-2591 | 2,2,2-trichloroethyl | H | H | F | F | F | F | Br | H | nonafluoro-2-butyl | H | CF3 |
| 11-2592 | 2,2,2-trichloroethyl | H | H | F | F | F | F | CF3 | H | nonafluoro-2-butyl | H | CF3 |
| 11-2593 | 2,2,2-trichloroethyl | H | H | H | CN | H | H | F | H | heptafluoroisopropyl | H | OCF3 |
| 11-2594 | 2,2,2-trichloroethyl | H | H | H | CN | H | H | F | H | nonafluoro-2-butyl | H | OCF3 |
| 11-2605 | 2,2,2-trichloroethyl | H | H | H | CN | H | H | Cl | H | heptafluoroisopropyl | H | OCF3 |
| 11-2634 | 2,2,2-trichloroethyl | H | H | H | CN | H | H | Cl | H | nonafluoro-2-butyl | H | OCF3 |
| 11-2663 | 2,2,2-trichloroethyl | H | H | H | CN | H | H | Br | H | heptafluoroisopropyl | H | OCF3 |
| 11-2692 | 2,2,2-trichloroethyl | H | H | H | CN | H | H | Br | H | nonafluoro-2-butyl | H | OCF3 |
| 11-2721 | 2,2,2-trichloroethyl | H | H | H | CN | H | H | I | H | heptafluoroisopropyl | H | OCF3 |
| 11-2750 | 2,2,2-trichloroethyl | H | H | H | CN | H | H | I | H | nonafluoro-2-butyl | H | OCF3 |
| 11-2769 | 2,2,2-trichloroethyl | H | H | H | CN | H | H | F | H | heptafluoroisopropyl | H | CF3 |
| 11-2770 | 2,2,2-trichloroethyl | H | H | H | CN | H | H | F | H | nonafluoro-2-butyl | H | CF3 |
| 11-2781 | 2,2,2-trichloroethyl | H | H | H | CN | H | H | Cl | H | heptafluoroisopropyl | H | CF3 |
| 11-2810 | 2,2,2-trichloroethyl | H | H | H | CN | H | H | Cl | H | nonafluoro-2-butyl | H | CF3 |
| 11-2839 | 2,2,2-trichloroethyl | H | H | H | CN | H | H | Br | H | heptafluoroisopropyl | H | CF3 |
| 11-2852 | 4,4,4-trifluoro-n-butyl | H | H | H | CN | H | H | Br | H | heptafluoroisopropyl | H | CF3 |
| 11-2868 | 2,2,2-trichloroethyl | H | H | H | CN | H | H | Br | H | nonafluoro-2-butyl | H | CF3 |
| 11-2881 | 4,4,4-trifluoro-n-butyl | H | H | H | CN | H | H | Br | H | nonafluoro-2-butyl | H | CF3 |
| 11-2897 | 2,2,2-trichloroethyl | H | H | H | CN | H | H | I | H | heptafluoroisopropyl | H | CF3 |
| 11-2910 | 4,4,4-trifluoro-n-butyl | H | H | H | CN | H | H | I | H | heptafluoroisopropyl | H | CF3 |
| 11-2926 | 2,2,2-trichloroethyl | H | H | H | CN | H | H | I | H | nonafluoro-2-butyl | H | CF3 |
| 11-2939 | 4,4,4-trifluoro-n-butyl | H | H | H | CN | H | H | I | H | nonafluoro-2-butyl | H | CF3 |
| 11-2955 | 2,2,2-trichloroethyl | H | H | H | CN | H | H | OCF3 | H | heptafluoroisopropyl | H | OCF3 |
| 11-2984 | 2,2,2-trichloroethyl | H | H | H | CN | H | H | OCF3 | H | nonafluoro-2-butyl | H | OCF3 |

TABLE 11-continued

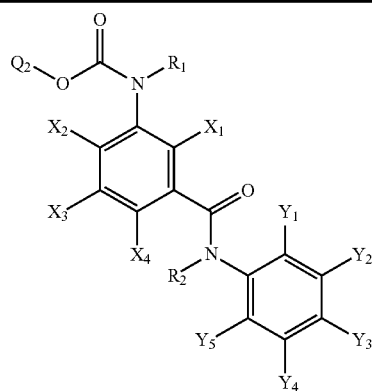

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-3013 | 2,2,2-trichloroethyl | H | H | H | CN | H | H | CF3 | H | heptafluoroisopropyl | H | OCF3 |
| 11-3042 | 2,2,2-trichloroethyl | H | H | H | CN | H | H | CF3 | H | nonafluoro-2-butyl | H | OCF3 |
| 11-3071 | 2,2,2-trichloroethyl | H | H | H | CN | H | H | CF3 | H | heptafluoroisopropyl | H | CF3 |
| 11-3100 | 2,2,2-trichloroethyl | H | H | H | CN | H | H | CF3 | H | nonafluoro-2-butyl | H | CF3 |
| 11-3119 | 2,2,2-trichloroethyl | H | H | F | CN | H | H | F | H | heptafluoroisopropyl | H | F |
| 11-3120 | 2,2,2-trichloroethyl | H | H | F | CN | H | H | F | H | nonafluoro-2-butyl | H | F |
| 11-3131 | 2,2,2-trichloroethyl | H | H | F | CN | H | H | Cl | H | heptafluoroisopropyl | H | Cl |
| 11-3160 | 2,2,2-trichloroethyl | H | H | F | CN | H | H | Cl | H | nonafluoro-2-butyl | H | Cl |
| 11-3189 | 2,2,2-trichloroethyl | H | H | F | CN | H | H | Br | H | heptafluoroisopropyl | H | Br |
| 11-3218 | 2,2,2-trichloroethyl | H | H | F | CN | H | H | Br | H | nonafluoro-2-butyl | H | Br |
| 11-3247 | 2,2,2-trichloroethyl | H | H | F | CN | H | H | I | H | heptafluoroisopropyl | H | I |
| 11-3276 | 2,2,2-trichloroethyl | H | H | F | CN | H | H | I | H | nonafluoro-2-butyl | H | I |
| 11-3295 | 2,2,2-trichloroethyl | H | H | F | CN | H | H | F | H | heptafluoroisopropyl | H | Cl |
| 11-3296 | 2,2,2-trichloroethyl | H | H | F | CN | H | H | F | H | heptafluoroisopropyl | H | Br |
| 11-3297 | 2,2,2-trichloroethyl | H | H | F | CN | H | H | F | H | heptafluoroisopropyl | H | I |
| 11-3298 | 2,2,2-trichloroethyl | H | H | F | CN | H | H | Cl | H | heptafluoroisopropyl | H | Br |
| 11-3299 | 2,2,2-trichloroethyl | H | H | F | CN | H | H | Cl | H | heptafluoroisopropyl | H | I |
| 11-3300 | 2,2,2-trichloroethyl | H | H | F | CN | H | H | Br | H | heptafluoroisopropyl | H | I |
| 11-3301 | 2,2,2-trichloroethyl | H | H | F | CN | H | H | F | H | nonafluoro-2-butyl | H | Cl |
| 11-3302 | 2,2,2-trichloroethyl | H | H | F | CN | H | H | F | H | nonafluoro-2-butyl | H | Br |
| 11-3303 | 2,2,2-trichloroethyl | H | H | F | CN | H | H | F | H | nonafluoro-2-butyl | H | I |
| 11-3304 | 2,2,2-trichloroethyl | H | H | F | CN | H | H | Cl | H | nonafluoro-2-butyl | H | Br |
| 11-3305 | 2,2,2-trichloroethyl | H | H | F | CN | H | H | Cl | H | nonafluoro-2-butyl | H | I |
| 11-3306 | 2,2,2-trichloroethyl | H | H | F | CN | H | H | Br | H | nonafluoro-2-butyl | H | I |
| 11-3307 | 2,2,2-trichloroethyl | H | H | F | CN | H | H | F | H | heptafluoroisopropyl | H | OCF3 |
| 11-3308 | 2,2,2-trichloroethyl | H | H | F | CN | H | H | F | H | nonafluoro-2-butyl | H | OCF3 |
| 11-3319 | 2,2,2-trichloroethyl | H | H | F | CN | H | H | Cl | H | heptafluoroisopropyl | H | OCF3 |
| 11-3348 | 2,2,2-trichloroethyl | H | H | F | CN | H | H | Cl | H | nonafluoro-2-butyl | H | OCF3 |
| 11-3377 | 2,2,2-trichloroethyl | H | H | F | CN | H | H | Br | H | heptafluoroisopropyl | H | OCF3 |
| 11-3406 | 2,2,2-trichloroethyl | H | H | F | CN | H | H | Br | H | nonafluoro-2-butyl | H | OCF3 |
| 11-3435 | 2,2,2-trichloroethyl | H | H | F | CN | H | H | I | H | heptafluoroisopropyl | H | OCF3 |
| 11-3464 | 2,2,2-trichloroethyl | H | H | F | CN | H | H | I | H | nonafluoro-2-butyl | H | OCF3 |
| 11-3483 | 2,2,2-trichloroethyl | H | H | F | CN | H | H | F | H | heptafluoroisopropyl | H | CF3 |
| 11-3484 | 2,2,2-trichloroethyl | H | H | F | CN | H | H | F | H | nonafluoro-2-butyl | H | CF3 |
| 11-3495 | 2,2,2-trichloroethyl | H | H | F | CN | H | H | Cl | H | heptafluoroisopropyl | H | CF3 |
| 11-3524 | 2,2,2-trichloroethyl | H | H | F | CN | H | H | Cl | H | nonafluoro-2-butyl | H | CF3 |
| 11-3553 | 2,2,2-trichloroethyl | H | H | F | CN | H | H | Br | H | heptafluoroisopropyl | H | CF3 |
| 11-3566 | 4,4,4-trifluoro-n-butyl | H | H | F | CN | H | H | Br | H | heptafluoroisopropyl | H | CF3 |
| 11-3582 | 2,2,2-trichloroethyl | H | H | F | CN | H | H | Br | H | nonafluoro-2-butyl | H | CF3 |
| 11-3595 | 4,4,4-trifluoro-n-butyl | H | H | F | CN | H | H | Br | H | nonafluoro-2-butyl | H | CF3 |
| 11-3611 | 2,2,2-trichloroethyl | H | H | F | CN | H | H | I | H | heptafluoroisopropyl | H | CF3 |
| 11-3624 | 4,4,4-trifluoro-n-butyl | H | H | F | CN | H | H | I | H | heptafluoroisopropyl | H | CF3 |
| 11-3640 | 2,2,2-trichloroethyl | H | H | F | CN | H | H | I | H | nonafluoro-2-butyl | H | CF3 |
| 11-3653 | 4,4,4-trifluoro-n-butyl | H | H | F | CN | H | H | I | H | nonafluoro-2-butyl | H | CF3 |
| 11-3669 | 2,2,2-trichloroethyl | H | H | F | CN | H | H | OCF3 | H | heptafluoroisopropyl | H | OCF3 |
| 11-3698 | 2,2,2-trichloroethyl | H | H | F | CN | H | H | OCF3 | H | nonafluoro-2-butyl | H | OCF3 |
| 11-3727 | 2,2,2-trichloroethyl | H | H | F | CN | H | H | CF3 | H | heptafluoroisopropyl | H | OCF3 |
| 11-3756 | 2,2,2-trichloroethyl | H | H | F | CN | H | H | CF3 | H | nonafluoro-2-butyl | H | OCF3 |
| 11-3785 | 2,2,2-trichloroethyl | H | H | F | CN | H | H | CF3 | H | heptafluoroisopropyl | H | CF3 |
| 11-3814 | 2,2,2-trichloroethyl | H | H | F | CN | H | H | CF3 | H | nonafluoro-2-butyl | H | CF3 |
| 11-3833 | 2,2,2-trichloroethyl | H | H | F | CN | F | H | F | H | heptafluoroisopropyl | H | F |
| 11-3834 | 2,2,2-trichloroethyl | H | H | F | CN | F | H | F | H | nonafluoro-2-butyl | H | F |
| 11-3845 | 2,2,2-trichloroethyl | H | H | F | CN | F | H | Cl | H | heptafluoroisopropyl | H | Cl |
| 11-3874 | 2,2,2-trichloroethyl | H | H | F | CN | F | H | Cl | H | nonafluoro-2-butyl | H | Cl |
| 11-3903 | 2,2,2-trichloroethyl | H | H | F | CN | F | H | Br | H | heptafluoroisopropyl | H | Br |

TABLE 11-continued

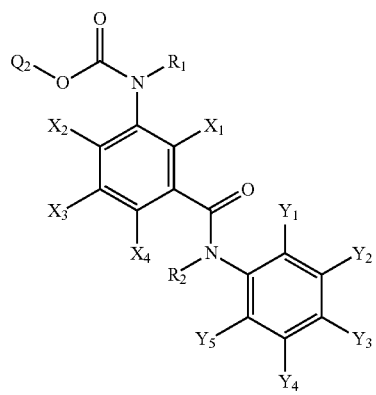

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 11-3932 | 2,2,2-trichloroethyl | H | H | F | CN | F | H | Br | H | nonafluoro-2-butyl | H | Br |
| 11-3961 | 2,2,2-trichloroethyl | H | H | F | CN | F | H | I | H | heptafluoroisopropyl | H | I |
| 11-3990 | 2,2,2-trichloroethyl | H | H | F | CN | F | H | I | H | nonafluoro-2-butyl | H | I |
| 11-4009 | 2,2,2-trichloroethyl | H | H | F | CN | F | H | F | H | heptafluoroisopropyl | H | Cl |
| 11-4010 | 2,2,2-trichloroethyl | H | H | F | CN | F | H | F | H | heptafluoroisopropyl | H | Br |
| 11-4011 | 2,2,2-trichloroethyl | H | H | F | CN | F | H | F | H | heptafluoroisopropyl | H | I |
| 11-4012 | 2,2,2-trichloroethyl | H | H | F | CN | F | H | Cl | H | heptafluoroisopropyl | H | Br |
| 11-4013 | 2,2,2-trichloroethyl | H | H | F | CN | F | H | Cl | H | heptafluoroisopropyl | H | I |
| 11-4014 | 2,2,2-trichloroethyl | H | H | F | CN | F | H | Br | H | heptafluoroisopropyl | H | I |
| 11-4015 | 2,2,2-trichloroethyl | H | H | F | CN | F | H | F | H | nonafluoro-2-butyl | H | Cl |
| 11-4016 | 2,2,2-trichloroethyl | H | H | F | CN | F | H | F | H | nonafluoro-2-butyl | H | Br |
| 11-4017 | 2,2,2-trichloroethyl | H | H | F | CN | F | H | F | H | nonafluoro-2-butyl | H | I |
| 11-4018 | 2,2,2-trichloroethyl | H | H | F | CN | F | H | Cl | H | nonafluoro-2-butyl | H | Br |
| 11-4019 | 2,2,2-trichloroethyl | H | H | F | CN | F | H | Cl | H | nonafluoro-2-butyl | H | I |
| 11-4020 | 2,2,2-trichloroethyl | H | H | F | CN | F | H | Br | H | nonafluoro-2-butyl | H | I |
| 11-4021 | 2,2,2-trichloroethyl | H | H | F | CN | F | H | F | H | heptafluoroisopropyl | H | OCF3 |
| 11-4022 | 2,2,2-trichloroethyl | H | H | F | CN | F | H | F | H | nonafluoro-2-butyl | H | OCF3 |
| 11-4033 | 2,2,2-trichloroethyl | H | H | F | CN | F | H | Cl | H | heptafluoroisopropyl | H | OCF3 |
| 11-4062 | 2,2,2-trichloroethyl | H | H | F | CN | F | H | Cl | H | nonafluoro-2-butyl | H | OCF3 |
| 11-4091 | 2,2,2-trichloroethyl | H | H | F | CN | F | H | Br | H | heptafluoroisopropyl | H | OCF3 |
| 11-4120 | 2,2,2-trichloroethyl | H | H | F | CN | F | H | Br | H | nonafluoro-2-butyl | H | OCF3 |
| 11-4149 | 2,2,2-trichloroethyl | H | H | F | CN | F | H | I | H | heptafluoroisopropyl | H | OCF3 |
| 11-4178 | 2,2,2-trichloroethyl | H | H | F | CN | F | H | I | H | nonafluoro-2-butyl | H | OCF3 |
| 11-4209 | 2,2,2-trichloroethyl | H | H | F | CN | F | H | Cl | H | heptafluoroisopropyl | H | CF3 |
| 11-4238 | 2,2,2-trichloroethyl | H | H | F | CN | F | H | Cl | H | nonafluoro-2-butyl | H | CF3 |
| 11-4267 | 2,2,2-trichloroethyl | H | H | F | CN | F | H | Br | H | heptafluoroisopropyl | H | CF3 |
| 11-4280 | 4,4,4-trifluoro-n-butyl | H | H | F | CN | F | H | Br | H | heptafluoroisopropyl | H | CF3 |
| 11-4296 | 2,2,2-trichloroethyl | H | H | F | CN | F | H | Br | H | nonafluoro-2-butyl | H | CF3 |
| 11-4309 | 4,4,4-trifluoro-n-butyl | H | H | F | CN | F | H | Br | H | nonafluoro-2-butyl | H | CF3 |
| 11-4325 | 2,2,2-trichloroethyl | H | H | F | CN | F | H | I | H | heptafluoroisopropyl | H | CF3 |
| 11-4338 | 4,4,4-trifluoro-n-butyl | H | H | F | CN | F | H | I | H | heptafluoroisopropyl | H | CF3 |
| 11-4354 | 2,2,2-trichloroethyl | H | H | F | CN | F | H | I | H | nonafluoro-2-butyl | H | CF3 |
| 11-4367 | 4,4,4-trifluoro-n-butyl | H | H | F | CN | F | H | I | H | nonafluoro-2-butyl | H | CF3 |
| 11-4383 | 2,2,2-trichloroethyl | H | H | F | CN | F | H | OCF3 | H | heptafluoroisopropyl | H | OCF3 |
| 11-4412 | 2,2,2-trichloroethyl | H | H | F | CN | F | H | OCF3 | H | nonafluoro-2-butyl | H | OCF3 |
| 11-4441 | 2,2,2-trichloroethyl | H | H | F | CN | F | H | CF3 | H | heptafluoroisopropyl | H | OCF3 |
| 11-4470 | 2,2,2-trichloroethyl | H | H | F | CN | F | H | CF3 | H | nonafluoro-2-butyl | H | OCF3 |
| 11-4499 | 2,2,2-trichloroethyl | H | H | F | CN | F | H | CF3 | H | heptafluoroisopropyl | H | CF3 |
| 11-4528 | 2,2,2-trichloroethyl | H | H | F | CN | F | H | CF3 | H | nonafluoro-2-butyl | H | CF3 |

TABLE 12

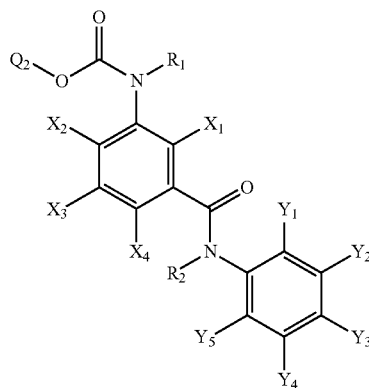

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 12-1 | 2,2,2-trichloroethyl | Me | H | H | H | H | H | F | H | heptafluoroisopropyl | H | OCF3 |
| 12-2 | 2,2,2-trichloroethyl | Me | H | H | H | H | H | F | H | nonafluoro-2-butyl | H | OCF3 |
| 12-13 | 2,2,2-trichloroethyl | Me | H | H | H | H | H | Cl | H | heptafluoroisopropyl | H | OCF3 |
| 12-42 | 2,2,2-trichloroethyl | Me | H | H | H | H | H | Cl | H | nonafluoro-2-butyl | H | OCF3 |
| 12-71 | 2,2,2-trichloroethyl | Me | H | H | H | H | H | Br | H | heptafluoroisopropyl | H | OCF3 |
| 12-100 | 2,2,2-trichloroethyl | Me | H | H | H | H | H | Br | H | nonafluoro-2-butyl | H | OCF3 |
| 12-129 | 2,2,2-trichloroethyl | Me | H | H | H | H | H | I | H | heptafluoroisopropyl | H | OCF3 |
| 12-158 | 2,2,2-trichloroethyl | Me | H | H | H | H | H | I | H | nonafluoro-2-butyl | H | OCF3 |
| 12-177 | 2,2,2-trichloroethyl | Me | H | H | H | H | H | F | H | heptafluoroisopropyl | H | CF3 |
| 12-178 | 2,2,2-trichloroethyl | Me | H | H | H | H | H | F | H | nonafluoro-2-butyl | H | CF3 |
| 12-189 | 2,2,2-trichloroethyl | Me | H | H | H | H | H | Cl | H | heptafluoroisopropyl | H | CF3 |
| 12-218 | 2,2,2-trichloroethyl | Me | H | H | H | H | H | Cl | H | nonafluoro-2-butyl | H | CF3 |
| 12-247 | 2,2,2-trichloroethyl | Me | H | H | H | H | H | Br | H | heptafluoroisopropyl | H | CF3 |
| 12-276 | 2,2,2-trichloroethyl | Me | H | H | H | H | H | Br | H | nonafluoro-2-butyl | H | CF3 |
| 12-305 | 2,2,2-trichloroethyl | Me | H | H | H | H | H | I | H | heptafluoroisopropyl | H | CF3 |
| 12-334 | 2,2,2-trichloroethyl | Me | H | H | H | H | H | I | H | nonafluoro-2-butyl | H | CF3 |
| 12-363 | 2,2,2-trichloroethyl | Me | H | H | H | H | H | OCF3 | H | heptafluoroisopropyl | H | OCF3 |
| 12-392 | 2,2,2-trichloroethyl | Me | H | H | H | H | H | OCF3 | H | nonafluoro-2-butyl | H | OCF3 |
| 12-421 | 2,2,2-trichloroethyl | Me | H | H | H | H | H | CF3 | H | heptafluoroisopropyl | H | OCF3 |
| 12-450 | 2,2,2-trichloroethyl | Me | H | H | H | H | H | CF3 | H | nonafluoro-2-butyl | H | OCF3 |
| 12-479 | 2,2,2-trichloroethyl | Me | H | H | H | H | H | CF3 | H | heptafluoroisopropyl | H | CF3 |
| 12-508 | 2,2,2-trichloroethyl | Me | H | H | H | H | H | CF3 | H | nonafluoro-2-butyl | H | CF3 |
| 12-527 | 2,2,2-trichloroethyl | Me | H | F | H | H | H | F | H | heptafluoroisopropyl | H | F |
| 12-528 | 2,2,2-trichloroethyl | Me | H | F | H | H | H | Cl | H | heptafluoroisopropyl | H | Cl |
| 12-529 | 2,2,2-trichloroethyl | Me | H | F | H | H | H | Br | H | heptafluoroisopropyl | H | Br |
| 12-530 | 2,2,2-trichloroethyl | Me | H | F | H | H | H | I | H | heptafluoroisopropyl | H | I |
| 12-531 | 2,2,2-trichloroethyl | Me | H | F | H | H | H | F | H | heptafluoroisopropyl | H | OCF3 |
| 12-532 | 2,2,2-trichloroethyl | Me | H | F | H | H | H | F | H | nonafluoro-2-butyl | H | OCF3 |
| 12-543 | 2,2,2-trichloroethyl | Me | H | F | H | H | H | Cl | H | heptafluoroisopropyl | H | OCF3 |
| 12-572 | 2,2,2-trichloroethyl | Me | H | F | H | H | H | Cl | H | nonafluoro-2-butyl | H | OCF3 |
| 12-601 | 2,2,2-trichloroethyl | Me | H | F | H | H | H | Br | H | heptafluoroisopropyl | H | OCF3 |
| 12-630 | 2,2,2-trichloroethyl | Me | H | F | H | H | H | Br | H | nonafluoro-2-butyl | H | OCF3 |
| 12-659 | 2,2,2-trichloroethyl | Me | H | F | H | H | H | I | H | heptafluoroisopropyl | H | OCF3 |
| 12-688 | 2,2,2-trichloroethyl | Me | H | F | H | H | H | I | H | nonafluoro-2-butyl | H | OCF3 |
| 12-707 | 2,2,2-trichloroethyl | Me | H | F | H | H | H | F | H | heptafluoroisopropyl | H | CF3 |
| 12-708 | 2,2,2-trichloroethyl | Me | H | F | H | H | H | F | H | nonafluoro-2-butyl | H | CF3 |
| 12-715 | 2-cyanoethyl | Et | H | F | H | H | H | Cl | H | heptafluoroisopropyl | H | C2F5 |
| 12-719 | 2,2,2-trichloroethyl | Me | H | F | H | H | H | Cl | H | heptafluoroisopropyl | H | CF3 |
| 12-721 | n-propyl | Me | H | F | H | H | H | Cl | H | pentafluoroethyl | H | CF3 |
| 12-725 | i-propyl | n-Pr | H | F | H | H | H | Cl | H | heptafluoroisopropyl | H | n-C3F7 |
| 12-728 | 1,3-dichloro-2-propyl | Me | H | F | H | H | H | Cl | H | pentafluoroethyl | H | CF3 |
| 12-729 | 1-chloro-3-fluoro-2-propyl | i-Pr | H | F | H | H | H | Cl | H | heptafluoroisopropyl | H | CF3 |
| 12-733 | i-butyl | CH2CH═CH2 | H | F | H | H | H | Cl | H | heptafluoroisopropyl | H | CF3 |
| 12-739 | ethyl | Me | H | F | H | H | H | Cl | H | nonafluoro-2-butyl | H | i-C3F7 |
| 12-744 | 2-cyanoethyl | CN | H | F | H | H | H | Cl | H | nonafluoro-2-butyl | H | CF3 |
| 12-748 | 2,2,2-trichloroethyl | Me | H | F | H | H | H | Cl | H | nonafluoro-2-butyl | H | CF3 |
| 12-750 | n-propyl | CH2C≡CH | H | F | H | H | H | Cl | H | nonafluoro-2-butyl | H | CF3 |
| 12-762 | i-butyl | NH2 | H | F | H | H | H | Cl | H | nonafluoro-2-butyl | H | CF3 |
| 12-767 | methyl | Me | H | F | H | H | H | Br | H | heptafluoroisopropyl | H | CF3 |
| 12-768 | ethyl | Me | H | F | H | H | H | Br | H | heptafluoroisopropyl | H | CF3 |
| 12-769 | 2-fluoroethyl | Me | H | F | H | H | H | Br | H | heptafluoroisopropyl | H | CF3 |
| 12-770 | 2-chloroethyl | Me | H | F | H | H | H | Br | H | heptafluoroisopropyl | H | CF3 |
| 12-771 | 2-bromoethyl | Me | H | F | H | H | H | Br | H | heptafluoroisopropyl | H | CF3 |
| 12-772 | 2-iodoethyl | Me | H | F | H | H | H | Br | H | heptafluoroisopropyl | H | CF3 |
| 12-773 | 2-cyanoethyl | Me | H | F | H | H | H | Br | H | heptafluoroisopropyl | H | C2F5 |
| 12-774 | 2,2-difluoroethyl | Me | H | F | H | H | H | Br | H | heptafluoroisopropyl | H | CF3 |
| 12-775 | 2,2-dichloroethyl | Me | H | F | H | H | H | Br | H | heptafluoroisopropyl | H | CF3 |

TABLE 12-continued

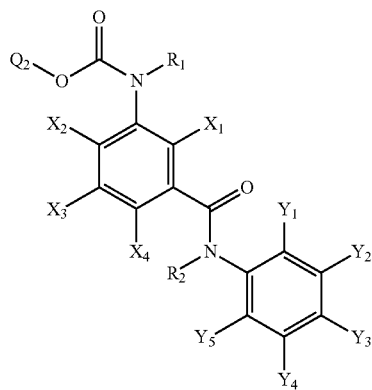

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 12-776 | 2,2,2-trifluoroethyl | Me | H | F | H | H | H | Br | H | heptafluoroisopropyl | H | CF3 |
| 12-777 | 2,2,2-trichloroethyl | Me | H | F | H | H | H | Br | H | heptafluoroisopropyl | H | CF3 |
| 12-778 | 2,2,2-tribromoethyl | Me | H | F | H | H | H | Br | H | heptafluoroisopropyl | H | CF3 |
| 12-779 | n-propyl | C(O)OMe | H | F | H | H | H | Br | H | heptafluoroisopropyl | H | CF3 |
| 12-780 | 3-fluoro-n-propyl | Me | H | F | H | H | H | Br | H | heptafluoroisopropyl | H | CF3 |
| 12-781 | 3-chloro-n-propyl | Me | H | F | H | H | H | Br | H | heptafluoroisopropyl | H | CF3 |
| 12-782 | 3-bromo-n-propyl | Me | H | F | H | H | H | Br | H | heptafluoroisopropyl | H | CF3 |
| 12-783 | i-propyl | Me | H | F | H | H | H | Br | H | heptafluoroisopropyl | H | CF3 |
| 12-784 | 1,2-difluoro-2-propyl | Me | H | F | H | H | H | Br | H | heptafluoroisopropyl | H | n-C3F7 |
| 12-785 | 1,3-difluoro-2-propyl | Me | H | F | H | H | H | Br | H | heptafluoroisopropyl | H | CF3 |
| 12-786 | 1,3-dichloro-2-propyl | Me | H | F | H | H | H | Br | H | heptafluoroisopropyl | H | CF3 |
| 12-787 | 1-chloro-3-fluoro-2-propyl | Me | H | F | H | H | H | Br | H | heptafluoroisopropyl | H | CF3 |
| 12-788 | 3,3,3-trifluoro-n-propyl | Me | H | F | H | H | H | Br | H | heptafluoroisopropyl | H | CF3 |
| 12-789 | n-butyl | Me | H | F | H | H | H | Br | H | heptafluoroisopropyl | H | CF3 |
| 12-790 | 4,4,4-trifluoro-n-butyl | Me | H | F | H | H | H | Br | H | heptafluoroisopropyl | H | CF3 |
| 12-791 | i-butyl | Me | H | F | H | H | H | Br | H | heptafluoroisopropyl | H | CF3 |
| 12-792 | s-butyl | Me | H | F | H | H | H | Br | H | heptafluoroisopropyl | H | CF3 |
| 12-793 | vinyl | C(O)C(O)OMe | H | F | H | H | H | Br | H | heptafluoroisopropyl | H | CF3 |
| 12-794 | benzyl | Me | H | F | H | H | H | Br | H | heptafluoroisopropyl | H | CF3 |
| 12-795 | phenyl | Me | H | F | H | H | H | Br | H | heptafluoroisopropyl | H | CF3 |
| 12-796 | methyl | Me | H | F | H | H | H | Br | H | nonafluoro-2-butyl | H | CF3 |
| 12-797 | ethyl | Me | H | F | H | H | H | Br | H | nonafluoro-2-butyl | H | CF3 |
| 12-798 | 2-fluoroethyl | Me | H | F | H | H | H | Br | H | nonafluoro-2-butyl | H | CF3 |
| 12-799 | 2-chloroethyl | Me | H | F | H | H | H | Br | H | nonafluoro-2-butyl | H | CF3 |
| 12-800 | 2-bromoethyl | Me | H | F | H | H | H | Br | H | nonafluoro-2-butyl | H | CF3 |
| 12-801 | 2-iodoethyl | Me | H | F | H | H | H | Br | H | nonafluoro-2-butyl | H | CF3 |
| 12-802 | 2-cyanoethyl | Me | H | F | H | H | H | Br | H | nonafluoro-2-butyl | H | CF3 |
| 12-803 | 2,2-difluoroethyl | Me | H | F | H | H | H | Br | H | nonafluoro-2-butyl | H | CF3 |
| 12-804 | 2,2-dichloroethyl | Me | H | F | H | H | H | Br | H | nonafluoro-2-butyl | H | CF3 |
| 12-805 | 2,2,2-trifluoroethyl | Me | H | F | H | H | H | Br | H | nonafluoro-2-butyl | H | CF3 |
| 12-806 | 2,2,2-trichloroethyl | Me | H | F | H | H | H | Br | H | nonafluoro-2-butyl | H | CF3 |
| 12-807 | 2,2,2-tribromoethyl | Me | H | F | H | H | H | Br | H | nonafluoro-2-butyl | H | CF3 |
| 12-808 | n-propyl | C(O)OEt | H | F | H | H | H | Br | H | nonafluoro-2-butyl | H | CF3 |
| 12-809 | 3-fluoro-n-propyl | Me | H | F | H | H | H | Br | H | nonafluoro-2-butyl | H | CF3 |
| 12-810 | 3-chloro-n-propyl | Me | H | F | H | H | H | Br | H | nonafluoro-2-butyl | H | CF3 |
| 12-811 | 3-bromo-n-propyl | Me | H | F | H | H | H | Br | H | nonafluoro-2-butyl | H | CF3 |
| 12-812 | i-propyl | C(O)Me | H | F | H | H | H | Br | H | nonafluoro-2-butyl | H | CF3 |
| 12-813 | 1,2-difluoro-2-propyl | Me | H | F | H | H | H | Br | H | nonafluoro-2-butyl | H | CF3 |
| 12-814 | 1,3-difluoro-2-propyl | Me | H | F | H | H | H | Br | H | nonafluoro-2-butyl | H | CF3 |
| 12-815 | 1,3-dichloro-2-propyl | Me | H | F | H | H | H | Br | H | nonafluoro-2-butyl | H | CF3 |
| 12-816 | 1-chloro-3-fluoro-2-propyl | Me | H | F | H | H | H | Br | H | nonafluoro-2-butyl | H | CF3 |
| 12-817 | 3,3,3-trifluoro-n-propyl | Me | H | F | H | H | H | Br | H | nonafluoro-2-butyl | H | CF3 |
| 12-818 | n-butyl | Me | H | F | H | H | H | Br | H | nonafluoro-2-butyl | H | CF3 |
| 12-819 | 4,4,4-trifluoro-n-butyl | Me | H | F | H | H | H | Br | H | nonafluoro-2-butyl | H | CF3 |
| 12-820 | i-butyl | Me | H | F | H | H | H | Br | H | nonafluoro-2-butyl | H | CF3 |
| 12-821 | s-butyl | Me | H | F | H | H | H | Br | H | nonafluoro-2-butyl | H | CF3 |
| 12-822 | vinyl | Me | H | F | H | H | H | Br | H | nonafluoro-2-butyl | H | CF3 |
| 12-823 | benzyl | Me | H | F | H | H | H | Br | H | nonafluoro-2-butyl | H | CF3 |
| 12-824 | phenyl | C(O)C(O)OEt | H | F | H | H | H | Br | H | nonafluoro-2-butyl | H | i-C3F7 |
| 12-825 | methyl | Me | H | F | H | H | H | I | H | heptafluoroisopropyl | H | CF3 |
| 12-826 | ethyl | Me | H | F | H | H | H | I | H | heptafluoroisopropyl | H | CF3 |
| 12-827 | 2-fluoroethyl | Me | H | F | H | H | H | I | H | heptafluoroisopropyl | H | CF3 |
| 12-828 | 2-chloroethyl | Me | H | F | H | H | H | I | H | heptafluoroisopropyl | H | CF3 |
| 12-829 | 2-bromoethyl | Me | H | F | H | H | H | I | H | heptafluoroisopropyl | H | CF3 |
| 12-830 | 2-iodoethyl | Me | H | F | H | H | H | I | H | heptafluoroisopropyl | H | CF3 |
| 12-831 | 2-cyanoethyl | Me | H | F | H | H | H | I | H | heptafluoroisopropyl | H | CF3 |
| 12-832 | 2,2-difluoroethyl | Me | H | F | H | H | H | I | H | heptafluoroisopropyl | H | CF3 |

TABLE 12-continued

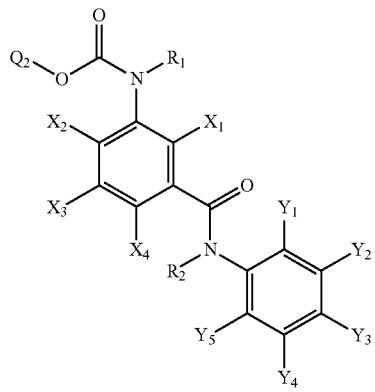

| compound number | $Q_2$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 12-833 | 2,2-dichloroethyl | Me | H | F | H | H | H | I | H | heptafluoroisopropyl | H | CF3 |
| 12-834 | 2,2,2-trifluoroethyl | Me | H | F | H | H | H | I | H | heptafluoroisopropyl | H | CF3 |
| 12-835 | 2,2,2-trichloroethyl | Me | H | F | H | H | H | I | H | heptafluoroisopropyl | H | CF3 |
| 12-836 | 2,2,2-tribromoethyl | Me | H | F | H | H | H | I | H | heptafluoroisopropyl | H | CF3 |
| 12-837 | n-propyl | Me | H | F | H | H | H | I | H | heptafluoroisopropyl | H | CF3 |
| 12-838 | 3-fluoro-n-propyl | Me | H | F | H | H | H | I | H | heptafluoroisopropyl | H | CF3 |
| 12-839 | 3-chloro-n-propyl | Me | H | F | H | H | H | I | H | heptafluoroisopropyl | H | CF3 |
| 12-840 | 3-bromo-n-propyl | C(O)Et | H | F | H | H | H | I | H | heptafluoroisopropyl | H | C2F5 |
| 12-841 | i-propyl | Me | H | F | H | H | H | I | H | heptafluoroisopropyl | H | CF3 |
| 12-842 | 1,2-difluoro-2-propyl | Me | H | F | H | H | H | I | H | heptafluoroisopropyl | H | CF3 |
| 12-843 | 1,3-difluoro-2-propyl | Me | H | F | H | H | H | I | H | heptafluoroisopropyl | H | CF3 |
| 12-844 | 1,3-dichloro-2-propyl | Me | H | F | H | H | H | I | H | heptafluoroisopropyl | H | CF3 |
| 12-845 | 1-chloro-3-fluoro-2-propyl | Me | H | F | H | H | H | I | H | heptafluoroisopropyl | H | CF3 |
| 12-846 | 3,3,3-trifluoro-n-propyl | Me | H | F | H | H | H | I | H | heptafluoroisopropyl | H | CF3 |
| 12-847 | n-butyl | Me | H | F | H | H | H | I | H | heptafluoroisopropyl | H | CF3 |
| 12-848 | 4,4,4-trifluoro-n-butyl | Me | H | F | H | H | H | I | H | heptafluoroisopropyl | H | CF3 |
| 12-849 | i-butyl | Me | H | F | H | H | H | I | H | heptafluoroisopropyl | H | CF3 |
| 12-850 | s-butyl | Me | H | F | H | H | H | I | H | heptafluoroisopropyl | H | CF3 |
| 12-851 | vinyl | Me | H | F | H | H | H | I | H | heptafluoroisopropyl | H | CF3 |
| 12-852 | benzyl | S(O)2Me | H | F | H | H | H | I | H | heptafluoroisopropyl | H | CF3 |
| 12-853 | phenyl | Me | H | F | H | H | H | I | H | heptafluoroisopropyl | H | CF3 |
| 12-854 | methyl | Me | H | F | H | H | H | I | H | nonafluoro-2-butyl | H | CF3 |
| 12-855 | ethyl | Me | H | F | H | H | H | I | H | nonafluoro-2-butyl | H | CF3 |
| 12-856 | 2-fluoroethyl | Me | H | F | H | H | H | I | H | nonafluoro-2-butyl | H | CF3 |
| 12-857 | 2-chloroethyl | Me | H | F | H | H | H | I | H | nonafluoro-2-butyl | H | CF3 |
| 12-858 | 2-bromoethyl | Me | H | F | H | H | H | I | H | nonafluoro-2-butyl | H | CF3 |
| 12-859 | 2-iodoethyl | Me | H | F | H | H | H | I | H | nonafluoro-2-butyl | H | CF3 |
| 12-860 | 2-cyanoethyl | S(O)2Et | H | F | H | H | H | I | H | nonafluoro-2-butyl | H | CF3 |
| 12-861 | 2,2-difluoroethyl | Me | H | F | H | H | H | I | H | nonafluoro-2-butyl | H | CF3 |
| 12-862 | 2,2-dichloroethyl | Me | H | F | H | H | H | I | H | nonafluoro-2-butyl | H | CF3 |
| 12-863 | 2,2,2-trifluoroethyl | Me | H | F | H | H | H | I | H | nonafluoro-2-butyl | H | CF3 |
| 12-864 | 2,2,2-trichloroethyl | Me | H | F | H | H | H | I | H | nonafluoro-2-butyl | H | CF3 |
| 12-865 | 2,2,2-tribromoethyl | Me | H | F | H | H | H | I | H | nonafluoro-2-butyl | H | CF3 |
| 12-866 | n-propyl | CH2Ph | H | F | H | H | H | I | H | nonafluoro-2-butyl | H | n-C3F7 |
| 12-867 | 3-fluoro-n-propyl | Me | H | F | H | H | H | I | H | nonafluoro-2-butyl | H | CF3 |
| 12-868 | 3-chloro-n-propyl | Me | H | F | H | H | H | I | H | nonafluoro-2-butyl | H | CF3 |
| 12-869 | 3-bromo-n-propyl | Me | H | F | H | H | H | I | H | nonafluoro-2-butyl | H | CF3 |
| 12-870 | i-propyl | CH2(3-Py) | H | F | H | H | H | I | H | nonafluoro-2-butyl | H | CF3 |
| 12-871 | 1,2-difluoro-2-propyl | Me | H | F | H | H | H | I | H | nonafluoro-2-butyl | H | CF3 |
| 12-872 | 1,3-difluoro-2-propyl | Me | H | F | H | H | H | I | H | nonafluoro-2-butyl | H | CF3 |
| 12-873 | 1,3-dichloro-2-propyl | Me | H | F | H | H | H | I | H | nonafluoro-2-butyl | H | CF3 |
| 12-874 | 1-chloro-3-fluoro-2-propyl | Me | H | F | H | H | H | I | H | nonafluoro-2-butyl | H | CF3 |
| 12-875 | 3,3,3-trifluoro-n-propyl | Me | H | F | H | H | H | I | H | nonafluoro-2-butyl | H | CF3 |
| 12-876 | n-butyl | Me | H | F | H | H | H | I | H | nonafluoro-2-butyl | H | CF3 |
| 12-877 | 4,4,4-trifluoro-n-butyl | Me | H | F | H | H | H | I | H | nonafluoro-2-butyl | H | CF3 |
| 12-878 | i-butyl | Me | H | F | H | H | H | I | H | nonafluoro-2-butyl | H | CF3 |
| 12-879 | s-butyl | CH2(3-Py—N-oxide) | H | F | H | H | H | I | H | nonafluoro-2-butyl | H | CF3 |
| 12-880 | vinyl | Me | H | F | H | H | H | I | H | nonafluoro-2-butyl | H | i-C3F7 |
| 12-881 | benzyl | Me | H | F | H | H | H | I | H | nonafluoro-2-butyl | H | CF3 |
| 12-882 | phenyl | Me | H | F | H | H | H | I | H | nonafluoro-2-butyl | H | CF3 |
| 12-893 | 2,2,2-trichloroethyl | Me | H | F | H | H | H | OCF3 | H | heptafluoroisopropyl | H | OCF3 |
| 12-922 | 2,2,2-trichloroethyl | Me | H | F | H | H | H | OCF3 | H | nonafluoro-2-butyl | H | OCF3 |
| 12-951 | 2,2,2-trichloroethyl | Me | H | F | H | H | H | CF3 | H | heptafluoroisopropyl | H | OCF3 |
| 12-980 | 2,2,2-trichloroethyl | Me | H | F | H | H | H | CF3 | H | nonafluoro-2-butyl | H | OCF3 |
| 12-1009 | 2,2,2-trichloroethyl | Me | H | F | H | H | H | CF3 | H | heptafluoroisopropyl | H | CF3 |
| 12-1038 | 2,2,2-trichloroethyl | Me | H | F | H | H | H | CF3 | H | nonafluoro-2-butyl | H | CF3 |

TABLE 12-continued

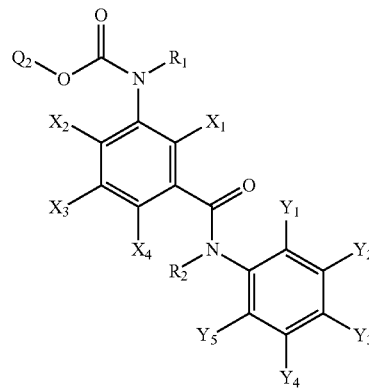

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 12-1057 | 2,2,2-trichloroethyl | Me | H | H | F | H | H | F | H | heptafluoroisopropyl | H | F |
| 12-1058 | 2,2,2-trichloroethyl | Me | H | H | F | H | H | F | H | nonafluoro-2-butyl | H | F |
| 12-1069 | 2,2,2-trichloroethyl | Me | H | H | F | H | H | Cl | H | heptafluoroisopropyl | H | Cl |
| 12-1098 | 2,2,2-trichloroethyl | Me | H | H | F | H | H | Cl | H | nonafluoro-2-butyl | H | Cl |
| 12-1127 | 2,2,2-trichloroethyl | Me | H | H | F | H | H | Br | H | heptafluoroisopropyl | H | Br |
| 12-1156 | 2,2,2-trichloroethyl | Me | H | H | F | H | H | Br | H | nonafluoro-2-butyl | H | Br |
| 12-1185 | 2,2,2-trichloroethyl | Me | H | H | F | H | H | I | H | heptafluoroisopropyl | H | I |
| 12-1214 | 2,2,2-trichloroethyl | Me | H | H | F | H | H | I | H | nonafluoro-2-butyl | H | I |
| 12-1236 | 2,2,2-trichloroethyl | Me | H | H | F | H | H | Cl | H | heptafluoroisopropyl | H | Br |
| 12-1245 | 2,2,2-trichloroethyl | Me | H | H | F | H | H | F | H | heptafluoroisopropyl | H | OCF3 |
| 12-1246 | 2,2,2-trichloroethyl | Me | H | H | F | H | H | F | H | nonafluoro-2-butyl | H | OCF3 |
| 12-1257 | 2,2,2-trichloroethyl | Me | H | H | F | H | H | Cl | H | heptafluoroisopropyl | H | OCF3 |
| 12-1286 | 2,2,2-trichloroethyl | Me | H | H | F | H | H | Cl | H | nonafluoro-2-butyl | H | OCF3 |
| 12-1315 | 2,2,2-trichloroethyl | Me | H | H | F | H | H | Br | H | heptafluoroisopropyl | H | OCF3 |
| 12-1344 | 2,2,2-trichloroethyl | Me | H | H | F | H | H | Br | H | nonafluoro-2-butyl | H | OCF3 |
| 12-1373 | 2,2,2-trichloroethyl | Me | H | H | F | H | H | I | H | heptafluoroisopropyl | H | OCF3 |
| 12-1402 | 2,2,2-trichloroethyl | Me | H | H | F | H | H | I | H | nonafluoro-2-butyl | H | OCF3 |
| 12-1421 | 2,2,2-trichloroethyl | Me | H | H | F | H | H | F | H | heptafluoroisopropyl | H | CF3 |
| 12-1422 | 2,2,2-trichloroethyl | Me | H | H | F | H | H | F | H | nonafluoro-2-butyl | H | CF3 |
| 12-1433 | 2,2,2-trichloroethyl | Me | H | H | F | H | H | Cl | H | heptafluoroisopropyl | H | CF3 |
| 12-1462 | 2,2,2-trichloroethyl | Me | H | H | F | H | H | Cl | H | nonafluoro-2-butyl | H | CF3 |
| 12-1491 | 2,2,2-trichloroethyl | Me | H | H | F | H | H | Br | H | heptafluoroisopropyl | H | CF3 |
| 12-1520 | 2,2,2-trichloroethyl | Me | H | H | F | H | H | Br | H | nonafluoro-2-butyl | H | CF3 |
| 12-1549 | 2,2,2-trichloroethyl | Me | H | H | F | H | H | I | H | heptafluoroisopropyl | H | CF3 |
| 12-1578 | 2,2,2-trichloroethyl | Me | H | H | F | H | H | I | H | nonafluoro-2-butyl | H | CF3 |
| 12-1607 | 2,2,2-trichloroethyl | Me | H | H | F | H | H | OCF3 | H | heptafluoroisopropyl | H | OCF3 |
| 12-1636 | 2,2,2-trichloroethyl | Me | H | H | F | H | H | OCF3 | H | nonafluoro-2-butyl | H | OCF3 |
| 12-1665 | 2,2,2-trichloroethyl | Me | H | H | F | H | H | CF3 | H | heptafluoroisopropyl | H | OCF3 |
| 12-1694 | 2,2,2-trichloroethyl | Me | H | H | F | H | H | CF3 | H | nonafluoro-2-butyl | H | OCF3 |
| 12-1723 | 2,2,2-trichloroethyl | Me | H | H | F | H | H | CF3 | H | heptafluoroisopropyl | H | CF3 |
| 12-1752 | 2,2,2-trichloroethyl | Me | H | H | F | H | H | CF3 | H | nonafluoro-2-butyl | H | CF3 |
| 12-1771 | 2,2,2-trichloroethyl | Me | H | F | F | H | H | F | H | heptafluoroisopropyl | H | F |
| 12-1772 | 2,2,2-trichloroethyl | Me | H | F | F | H | H | F | H | nonafluoro-2-butyl | H | F |
| 12-1783 | 2,2,2-trichloroethyl | Me | H | F | F | H | H | Cl | H | heptafluoroisopropyl | H | Cl |
| 12-1812 | 2,2,2-trichloroethyl | Me | H | F | F | H | H | Cl | H | nonafluoro-2-butyl | H | Cl |
| 12-1841 | 2,2,2-trichloroethyl | Me | H | F | F | H | H | Br | H | heptafluoroisopropyl | H | Br |
| 12-1870 | 2,2,2-trichloroethyl | Me | H | F | F | H | H | Br | H | nonafluoro-2-butyl | H | Br |
| 12-1899 | 2,2,2-trichloroethyl | Me | H | F | F | H | H | I | H | heptafluoroisopropyl | H | I |
| 12-1928 | 2,2,2-trichloroethyl | Me | H | F | F | H | H | I | H | nonafluoro-2-butyl | H | I |
| 12-1956 | 2,2,2-trichloroethyl | Me | H | F | F | H | H | Cl | H | nonafluoro-2-butyl | H | Br |
| 12-1959 | 2,2,2-trichloroethyl | Me | H | F | F | H | H | F | H | heptafluoroisopropyl | H | OCF3 |
| 12-1960 | 2,2,2-trichloroethyl | Me | H | F | F | H | H | F | H | nonafluoro-2-butyl | H | OCF3 |
| 12-1971 | 2,2,2-trichloroethyl | Me | H | F | F | H | H | Cl | H | heptafluoroisopropyl | H | OCF3 |
| 12-2000 | 2,2,2-trichloroethyl | Me | H | F | F | H | H | Cl | H | nonafluoro-2-butyl | H | OCF3 |
| 12-2029 | 2,2,2-trichloroethyl | Me | H | F | F | H | H | Br | H | heptafluoroisopropyl | H | OCF3 |
| 12-2058 | 2,2,2-trichloroethyl | Me | H | F | F | H | H | Br | H | nonafluoro-2-butyl | H | OCF3 |
| 12-2087 | 2,2,2-trichloroethyl | Me | H | F | F | H | H | I | H | heptafluoroisopropyl | H | OCF3 |
| 12-2116 | 2,2,2-trichloroethyl | Me | H | F | F | H | H | I | H | nonafluoro-2-butyl | H | OCF3 |
| 12-2135 | 2,2,2-trichloroethyl | Me | H | F | F | H | H | F | H | heptafluoroisopropyl | H | CF3 |
| 12-2136 | 2,2,2-trichloroethyl | Me | H | F | F | H | H | F | H | nonafluoro-2-butyl | H | CF3 |
| 12-2147 | 2,2,2-trichloroethyl | Me | H | F | F | H | H | Cl | H | heptafluoroisopropyl | H | CF3 |
| 12-2176 | 2,2,2-trichloroethyl | Me | H | F | F | H | H | Cl | H | nonafluoro-2-butyl | H | CF3 |
| 12-2205 | 2,2,2-trichloroethyl | Me | H | F | F | H | H | Br | H | heptafluoroisopropyl | H | CF3 |
| 12-2234 | 2,2,2-trichloroethyl | Me | H | F | F | H | H | Br | H | nonafluoro-2-butyl | H | CF3 |
| 12-2263 | 2,2,2-trichloroethyl | Me | H | F | F | H | H | I | H | heptafluoroisopropyl | H | CF3 |
| 12-2292 | 2,2,2-trichloroethyl | Me | H | F | F | H | H | I | H | nonafluoro-2-butyl | H | CF3 |
| 12-2321 | 2,2,2-trichloroethyl | Me | H | F | F | H | H | OCF3 | H | heptafluoroisopropyl | H | OCF3 |

TABLE 12-continued

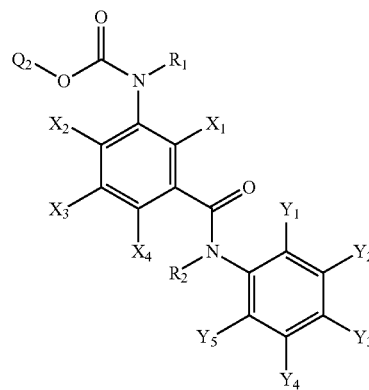

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 12-2350 | 2,2,2-trichloroethyl | Me | H | F | F | H | H | OCF3 | H | nonafluoro-2-butyl | H | OCF3 |
| 12-2379 | 2,2,2-trichloroethyl | Me | H | F | F | H | H | CF3 | H | heptafluoroisopropyl | H | OCF3 |
| 12-2408 | 2,2,2-trichloroethyl | Me | H | F | F | H | H | CF3 | H | nonafluoro-2-butyl | H | OCF3 |
| 12-2437 | 2,2,2-trichloroethyl | Me | H | F | F | H | H | CF3 | H | heptafluoroisopropyl | H | CF3 |
| 12-2466 | 2,2,2-trichloroethyl | Me | H | F | F | H | H | CF3 | H | nonafluoro-2-butyl | H | CF3 |
| 12-2485 | 2,2,2-trichloroethyl | Me | H | F | F | F | H | Cl | H | pentafluoroethyl | H | Cl |
| 12-2486 | 2,2,2-trichloroethyl | Me | H | F | F | F | H | Br | H | heptafluoroisopropyl | H | Br |
| 12-2487 | 2,2,2-trichloroethyl | Me | H | F | F | F | H | Br | H | heptafluoroisopropyl | H | OCF3 |
| 12-2488 | 2,2,2-trichloroethyl | Me | H | F | F | F | H | I | H | heptafluoroisopropyl | H | CF3 |
| 12-2489 | 2,2,2-trichloroethyl | Me | H | F | F | F | H | CF3 | H | heptafluoroisopropyl | H | CF3 |
| 12-2490 | 2,2,2-trichloroethyl | Me | H | F | F | F | H | I | H | nonafluoro-2-butyl | H | I |
| 12-2491 | 2,2,2-trichloroethyl | Me | H | F | F | F | H | Cl | H | nonafluoro-2-butyl | H | OCF3 |
| 12-2492 | 2,2,2-trichloroethyl | Me | H | F | F | F | H | Br | H | nonafluoro-2-butyl | H | CF3 |
| 12-2493 | 2,2,2-trichloroethyl | Me | H | F | F | F | H | CF3 | H | nonafluoro-2-butyl | H | CF3 |
| 12-2494 | 2,2,2-trichloroethyl | Me | H | H | H | F | H | Cl | H | pentafluoroethyl | H | Cl |
| 12-2495 | 2,2,2-trichloroethyl | Me | H | H | H | F | H | Br | H | heptafluoroisopropyl | H | Br |
| 12-2496 | 2,2,2-trichloroethyl | Me | H | H | H | F | H | Br | H | heptafluoroisopropyl | H | OCF3 |
| 12-2497 | 2,2,2-trichloroethyl | Me | H | H | H | F | H | I | H | heptafluoroisopropyl | H | CF3 |
| 12-2498 | 2,2,2-trichloroethyl | Me | H | H | H | F | H | CF3 | H | heptafluoroisopropyl | H | CF3 |
| 12-2499 | 2,2,2-trichloroethyl | Me | H | H | H | F | H | I | H | nonafluoro-2-butyl | H | I |
| 12-2500 | 2,2,2-trichloroethyl | Me | H | H | H | F | H | Cl | H | nonafluoro-2-butyl | H | OCF3 |
| 12-2501 | 2,2,2-trichloroethyl | Me | H | H | H | F | H | Br | H | nonafluoro-2-butyl | H | CF3 |
| 12-2502 | 2,2,2-trichloroethyl | Me | H | H | H | F | H | CF3 | H | nonafluoro-2-butyl | H | CF3 |
| 12-2503 | 2,2,2-trichloroethyl | Me | H | H | H | H | F | Cl | H | pentafluoroethyl | H | Cl |
| 12-2504 | 2,2,2-trichloroethyl | Me | H | H | H | H | F | Br | H | heptafluoroisopropyl | H | Br |
| 12-2505 | 2,2,2-trichloroethyl | Me | H | H | H | H | F | Br | H | heptafluoroisopropyl | H | OCF3 |
| 12-2506 | 2,2,2-trichloroethyl | Me | H | H | H | H | F | I | H | heptafluoroisopropyl | H | CF3 |
| 12-2507 | 2,2,2-trichloroethyl | Me | H | H | H | H | F | CF3 | H | heptafluoroisopropyl | H | CF3 |
| 12-2508 | 2,2,2-trichloroethyl | Me | H | H | H | H | F | I | H | nonafluoro-2-butyl | H | I |
| 12-2509 | 2,2,2-trichloroethyl | Me | H | H | H | H | F | Cl | H | nonafluoro-2-butyl | H | OCF3 |
| 12-2510 | 2,2,2-trichloroethyl | Me | H | H | H | H | F | Br | H | nonafluoro-2-butyl | H | CF3 |
| 12-2511 | 2,2,2-trichloroethyl | Me | H | H | H | H | F | CF3 | H | nonafluoro-2-butyl | H | CF3 |
| 12-2512 | 2,2,2-trichloroethyl | Me | H | F | H | F | H | Cl | H | pentafluoroethyl | H | Cl |
| 12-2513 | 2,2,2-trichloroethyl | Me | H | F | H | F | H | Br | H | heptafluoroisopropyl | H | Br |
| 12-2514 | 2,2,2-trichloroethyl | Me | H | F | H | F | H | Br | H | heptafluoroisopropyl | H | OCF3 |
| 12-2515 | 2,2,2-trichloroethyl | Me | H | F | H | F | H | I | H | heptafluoroisopropyl | H | CF3 |
| 12-2516 | 2,2,2-trichloroethyl | Me | H | F | H | F | H | CF3 | H | heptafluoroisopropyl | H | CF3 |
| 12-2517 | 2,2,2-trichloroethyl | Me | H | F | H | F | H | I | H | nonafluoro-2-butyl | H | I |
| 12-2518 | 2,2,2-trichloroethyl | Me | H | F | H | F | H | Cl | H | nonafluoro-2-butyl | H | OCF3 |
| 12-2519 | 2,2,2-trichloroethyl | Me | H | F | H | F | H | Br | H | nonafluoro-2-butyl | H | CF3 |
| 12-2520 | 2,2,2-trichloroethyl | Me | H | F | H | F | H | CF3 | H | nonafluoro-2-butyl | H | CF3 |
| 12-2521 | 2,2,2-trichloroethyl | Me | H | F | H | H | F | Cl | H | pentafluoroethyl | H | Cl |
| 12-2522 | 2,2,2-trichloroethyl | Me | H | F | H | H | F | Br | H | heptafluoroisopropyl | H | Br |
| 12-2523 | 2,2,2-trichloroethyl | Me | H | F | H | H | F | Br | H | heptafluoroisopropyl | H | OCF3 |
| 12-2524 | 2,2,2-trichloroethyl | Me | H | F | H | H | F | I | H | heptafluoroisopropyl | H | CF3 |
| 12-2525 | 2,2,2-trichloroethyl | Me | H | F | H | H | F | CF3 | H | heptafluoroisopropyl | H | CF3 |
| 12-2526 | 2,2,2-trichloroethyl | Me | H | F | H | H | F | I | H | nonafluoro-2-butyl | H | I |
| 12-2527 | 2,2,2-trichloroethyl | Me | H | F | H | H | F | Cl | H | nonafluoro-2-butyl | H | OCF3 |
| 12-2528 | 2,2,2-trichloroethyl | Me | H | F | H | H | F | Br | H | nonafluoro-2-butyl | H | CF3 |
| 12-2529 | 2,2,2-trichloroethyl | Me | H | F | H | H | F | CF3 | H | nonafluoro-2-butyl | H | CF3 |
| 12-2530 | 2,2,2-trichloroethyl | Me | H | H | F | F | H | Cl | H | pentafluoroethyl | H | Cl |
| 12-2531 | 2,2,2-trichloroethyl | Me | H | H | F | F | H | Br | H | heptafluoroisopropyl | H | Br |
| 12-2532 | 2,2,2-trichloroethyl | Me | H | H | F | F | H | Br | H | heptafluoroisopropyl | H | OCF3 |
| 12-2533 | 2,2,2-trichloroethyl | Me | H | H | F | F | H | I | H | heptafluoroisopropyl | H | CF3 |
| 12-2534 | 2,2,2-trichloroethyl | Me | H | H | F | F | H | CF3 | H | heptafluoroisopropyl | H | CF3 |
| 12-2535 | 2,2,2-trichloroethyl | Me | H | H | F | F | H | I | H | nonafluoro-2-butyl | H | I |
| 12-2536 | 2,2,2-trichloroethyl | Me | H | H | F | F | H | Cl | H | nonafluoro-2-butyl | H | OCF3 |

TABLE 12-continued

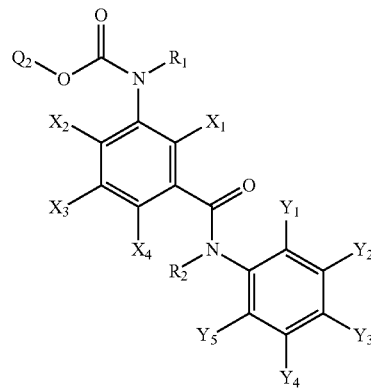

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 12-2537 | 2,2,2-trichloroethyl | Me | H | H | F | F | H | Br | H | nonafluoro-2-butyl | H | CF3 |
| 12-2538 | 2,2,2-trichloroethyl | Me | H | H | F | F | H | CF3 | H | nonafluoro-2-butyl | H | CF3 |
| 12-2539 | 2,2,2-trichloroethyl | Me | H | H | F | H | F | Cl | H | pentafluoroethyl | H | Cl |
| 12-2540 | 2,2,2-trichloroethyl | Me | H | H | F | H | F | Br | H | heptafluoroisopropyl | H | Br |
| 12-2541 | 2,2,2-trichloroethyl | Me | H | H | F | H | F | Br | H | heptafluoroisopropyl | H | OCF3 |
| 12-2542 | 2,2,2-trichloroethyl | Me | H | H | F | H | F | I | H | heptafluoroisopropyl | H | CF3 |
| 12-2543 | 2,2,2-trichloroethyl | Me | H | H | F | H | F | CF3 | H | heptafluoroisopropyl | H | CF3 |
| 12-2544 | 2,2,2-trichloroethyl | Me | H | H | F | H | F | I | H | nonafluoro-2-butyl | H | I |
| 12-2545 | 2,2,2-trichloroethyl | Me | H | H | F | H | F | Cl | H | nonafluoro-2-butyl | H | OCF3 |
| 12-2546 | 2,2,2-trichloroethyl | Me | H | H | F | H | F | Br | H | nonafluoro-2-butyl | H | CF3 |
| 12-2547 | 2,2,2-trichloroethyl | Me | H | H | F | H | F | CF3 | H | nonafluoro-2-butyl | H | CF3 |
| 12-2548 | 2,2,2-trichloroethyl | Me | H | H | H | F | F | Cl | H | pentafluoroethyl | H | Cl |
| 12-2549 | 2,2,2-trichloroethyl | Me | H | H | H | F | F | Br | H | heptafluoroisopropyl | H | Br |
| 12-2550 | 2,2,2-trichloroethyl | Me | H | H | H | F | F | Br | H | heptafluoroisopropyl | H | OCF3 |
| 12-2551 | 2,2,2-trichloroethyl | Me | H | H | H | F | F | I | H | heptafluoroisopropyl | H | CF3 |
| 12-2552 | 2,2,2-trichloroethyl | Me | H | H | H | F | F | CF3 | H | heptafluoroisopropyl | H | CF3 |
| 12-2553 | 2,2,2-trichloroethyl | Me | H | H | H | F | F | I | H | nonafluoro-2-butyl | H | I |
| 12-2554 | 2,2,2-trichloroethyl | Me | H | H | H | F | F | Cl | H | nonafluoro-2-butyl | H | OCF3 |
| 12-2555 | 2,2,2-trichloroethyl | Me | H | H | H | F | F | Br | H | nonafluoro-2-butyl | H | CF3 |
| 12-2556 | 2,2,2-trichloroethyl | Me | H | H | H | F | F | CF3 | H | nonafluoro-2-butyl | H | CF3 |
| 12-2557 | 2,2,2-trichloroethyl | Me | H | F | F | H | F | Cl | H | pentafluoroethyl | H | Cl |
| 12-2558 | 2,2,2-trichloroethyl | Me | H | F | F | H | F | Br | H | heptafluoroisopropyl | H | Br |
| 12-2559 | 2,2,2-trichloroethyl | Me | H | F | F | H | F | Br | H | heptafluoroisopropyl | H | OCF3 |
| 12-2560 | 2,2,2-trichloroethyl | Me | H | F | F | H | F | I | H | heptafluoroisopropyl | H | CF3 |
| 12-2561 | 2,2,2-trichloroethyl | Me | H | F | F | H | F | CF3 | H | heptafluoroisopropyl | H | CF3 |
| 12-2562 | 2,2,2-trichloroethyl | Me | H | F | F | H | F | I | H | nonafluoro-2-butyl | H | I |
| 12-2563 | 2,2,2-trichloroethyl | Me | H | F | F | H | F | Cl | H | nonafluoro-2-butyl | H | OCF3 |
| 12-2564 | 2,2,2-trichloroethyl | Me | H | F | F | H | F | Br | H | nonafluoro-2-butyl | H | CF3 |
| 12-2565 | 2,2,2-trichloroethyl | Me | H | F | F | H | F | CF3 | H | nonafluoro-2-butyl | H | CF3 |
| 12-2566 | 2,2,2-trichloroethyl | Me | H | F | H | F | F | Cl | H | pentafluoroethyl | H | Cl |
| 12-2567 | 2,2,2-trichloroethyl | Me | H | F | H | F | F | Br | H | heptafluoroisopropyl | H | Br |
| 12-2568 | 2,2,2-trichloroethyl | Me | H | F | H | F | F | Br | H | heptafluoroisopropyl | H | OCF3 |
| 12-2569 | 2,2,2-trichloroethyl | Me | H | F | H | F | F | I | H | heptafluoroisopropyl | H | CF3 |
| 12-2570 | 2,2,2-trichloroethyl | Me | H | F | H | F | F | CF3 | H | heptafluoroisopropyl | H | CF3 |
| 12-2571 | 2,2,2-trichloroethyl | Me | H | F | H | F | F | I | H | nonafluoro-2-butyl | H | I |
| 12-2572 | 2,2,2-trichloroethyl | Me | H | F | H | F | F | Cl | H | nonafluoro-2-butyl | H | OCF3 |
| 12-2573 | 2,2,2-trichloroethyl | Me | H | F | H | F | F | Br | H | nonafluoro-2-butyl | H | CF3 |
| 12-2574 | 2,2,2-trichloroethyl | Me | H | F | H | F | F | CF3 | H | nonafluoro-2-butyl | H | CF3 |
| 12-2575 | 2,2,2-trichloroethyl | Me | H | H | F | F | F | Cl | H | pentafluoroethyl | H | Cl |
| 12-2576 | 2,2,2-trichloroethyl | Me | H | H | F | F | F | Br | H | heptafluoroisopropyl | H | Br |
| 12-2577 | 2,2,2-trichloroethyl | Me | H | H | F | F | F | Br | H | heptafluoroisopropyl | H | OCF3 |
| 12-2578 | 2,2,2-trichloroethyl | Me | H | H | F | F | F | I | H | heptafluoroisopropyl | H | CF3 |
| 12-2579 | 2,2,2-trichloroethyl | Me | H | H | F | F | F | CF3 | H | heptafluoroisopropyl | H | CF3 |
| 12-2580 | 2,2,2-trichloroethyl | Me | H | H | F | F | F | I | H | nonafluoro-2-butyl | H | I |
| 12-2581 | 2,2,2-trichloroethyl | Me | H | H | F | F | F | Cl | H | nonafluoro-2-butyl | H | OCF3 |
| 12-2582 | 2,2,2-trichloroethyl | Me | H | H | F | F | F | Br | H | nonafluoro-2-butyl | H | CF3 |
| 12-2583 | 2,2,2-trichloroethyl | Me | H | H | F | F | F | CF3 | H | nonafluoro-2-butyl | H | CF3 |
| 12-2584 | 2,2,2-trichloroethyl | Me | H | F | F | F | F | Cl | H | pentafluoroethyl | H | Cl |
| 12-2585 | 2,2,2-trichloroethyl | Me | H | F | F | F | F | Br | H | heptafluoroisopropyl | H | Br |
| 12-2586 | 2,2,2-trichloroethyl | Me | H | F | F | F | F | Br | H | heptafluoroisopropyl | H | OCF3 |
| 12-2587 | 2,2,2-trichloroethyl | Me | H | F | F | F | F | I | H | heptafluoroisopropyl | H | CF3 |
| 12-2588 | 2,2,2-trichloroethyl | Me | H | F | F | F | F | CF3 | H | heptafluoroisopropyl | H | CF3 |
| 12-2589 | 2,2,2-trichloroethyl | Me | H | F | F | F | F | I | H | nonafluoro-2-butyl | H | I |
| 12-2590 | 2,2,2-trichloroethyl | Me | H | F | F | F | F | Cl | H | nonafluoro-2-butyl | H | OCF3 |
| 12-2591 | 2,2,2-trichloroethyl | Me | H | F | F | F | F | Br | H | nonafluoro-2-butyl | H | CF3 |
| 12-2592 | 2,2,2-trichloroethyl | Me | H | F | F | F | F | CF3 | H | nonafluoro-2-butyl | H | CF3 |
| 12-2593 | 2,2,2-trichloroethyl | Me | H | H | CN | H | H | F | H | heptafluoroisopropyl | H | OCF3 |

TABLE 12-continued

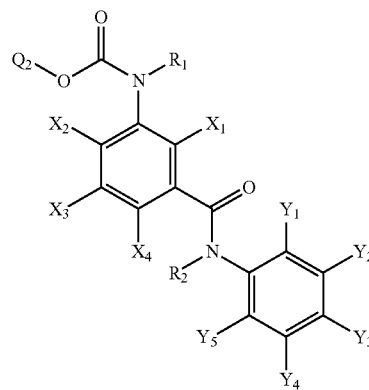

| compound number | $Q_2$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 12-2594 | 2,2,2-trichloroethyl | Me | H | H | CN | H | H | F | H | nonafluoro-2-butyl | H | OCF3 |
| 12-2605 | 2,2,2-trichloroethyl | Me | H | H | CN | H | H | Cl | H | heptafluoroisopropyl | H | OCF3 |
| 12-2634 | 2,2,2-trichloroethyl | Me | H | H | CN | H | H | Cl | H | nonafluoro-2-butyl | H | OCF3 |
| 12-2663 | 2,2,2-trichloroethyl | Me | H | H | CN | H | H | Br | H | heptafluoroisopropyl | H | OCF3 |
| 12-2692 | 2,2,2-trichloroethyl | Me | H | H | CN | H | H | Br | H | nonafluoro-2-butyl | H | OCF3 |
| 12-2721 | 2,2,2-trichloroethyl | Me | H | H | CN | H | H | I | H | heptafluoroisopropyl | H | OCF3 |
| 12-2750 | 2,2,2-trichloroethyl | Me | H | H | CN | H | H | I | H | nonafluoro-2-butyl | H | OCF3 |
| 12-2769 | 2,2,2-trichloroethyl | Me | H | H | CN | H | H | F | H | heptafluoroisopropyl | H | CF3 |
| 12-2770 | 2,2,2-trichloroethyl | Me | H | H | CN | H | H | F | H | nonafluoro-2-butyl | H | CF3 |
| 12-2781 | 2,2,2-trichloroethyl | Me | H | H | CN | H | H | Cl | H | heptafluoroisopropyl | H | CF3 |
| 12-2810 | 2,2,2-trichloroethyl | Me | H | H | CN | H | H | Cl | H | nonafluoro-2-butyl | H | CF3 |
| 12-2839 | 2,2,2-trichloroethyl | Me | H | H | CN | H | H | Br | H | heptafluoroisopropyl | H | CF3 |
| 12-2868 | 2,2,2-trichloroethyl | Me | H | H | CN | H | H | Br | H | nonafluoro-2-butyl | H | CF3 |
| 12-2897 | 2,2,2-trichloroethyl | Me | H | H | CN | H | H | I | H | heptafluoroisopropyl | H | CF3 |
| 12-2926 | 2,2,2-trichloroethyl | Me | H | H | CN | H | H | I | H | nonafluoro-2-butyl | H | CF3 |
| 12-2955 | 2,2,2-trichloroethyl | Me | H | H | CN | H | H | OCF3 | H | heptafluoroisopropyl | H | OCF3 |
| 12-2984 | 2,2,2-trichloroethyl | Me | H | H | CN | H | H | OCF3 | H | nonafluoro-2-butyl | H | OCF3 |
| 12-3013 | 2,2,2-trichloroethyl | Me | H | H | CN | H | H | CF3 | H | heptafluoroisopropyl | H | OCF3 |
| 12-3042 | 2,2,2-trichloroethyl | Me | H | H | CN | H | H | CF3 | H | nonafluoro-2-butyl | H | OCF3 |
| 12-3071 | 2,2,2-trichloroethyl | Me | H | H | CN | H | H | CF3 | H | heptafluoroisopropyl | H | CF3 |
| 12-3100 | 2,2,2-trichloroethyl | Me | H | H | CN | H | H | CF3 | H | nonafluoro-2-butyl | H | CF3 |
| 12-3119 | 2,2,2-trichloroethyl | Me | H | F | CN | H | H | F | H | heptafluoroisopropyl | H | F |
| 12-3120 | 2,2,2-trichloroethyl | Me | H | F | CN | H | H | F | H | nonafluoro-2-butyl | H | F |
| 12-3131 | 2,2,2-trichloroethyl | Me | H | F | CN | H | H | Cl | H | heptafluoroisopropyl | H | Cl |
| 12-3160 | 2,2,2-trichloroethyl | Me | H | F | CN | H | H | Cl | H | nonafluoro-2-butyl | H | Cl |
| 12-3189 | 2,2,2-trichloroethyl | Me | H | F | CN | H | H | Br | H | heptafluoroisopropyl | H | Br |
| 12-3218 | 2,2,2-trichloroethyl | Me | H | F | CN | H | H | Br | H | nonafluoro-2-butyl | H | Br |
| 12-3247 | 2,2,2-trichloroethyl | Me | H | F | CN | H | H | I | H | heptafluoroisopropyl | H | I |
| 12-3276 | 2,2,2-trichloroethyl | Me | H | F | CN | H | H | I | H | nonafluoro-2-butyl | H | I |
| 12-3298 | 2,2,2-trichloroethyl | Me | H | F | CN | H | H | Cl | H | heptafluoroisopropyl | H | Br |
| 12-3307 | 2,2,2-trichloroethyl | Me | H | F | CN | H | H | F | H | heptafluoroisopropyl | H | OCF3 |
| 12-3308 | 2,2,2-trichloroethyl | Me | H | F | CN | H | H | F | H | nonafluoro-2-butyl | H | OCF3 |
| 12-3319 | 2,2,2-trichloroethyl | Me | H | F | CN | H | H | Cl | H | heptafluoroisopropyl | H | OCF3 |
| 12-3348 | 2,2,2-trichloroethyl | Me | H | F | CN | H | H | Cl | H | nonafluoro-2-butyl | H | OCF3 |
| 12-3377 | 2,2,2-trichloroethyl | Me | H | F | CN | H | H | Br | H | heptafluoroisopropyl | H | OCF3 |
| 12-3406 | 2,2,2-trichloroethyl | Me | H | F | CN | H | H | Br | H | nonafluoro-2-butyl | H | OCF3 |
| 12-3435 | 2,2,2-trichloroethyl | Me | H | F | CN | H | H | I | H | heptafluoroisopropyl | H | OCF3 |
| 12-3464 | 2,2,2-trichloroethyl | Me | H | F | CN | H | H | I | H | nonafluoro-2-butyl | H | OCF3 |
| 12-3483 | 2,2,2-trichloroethyl | Me | H | F | CN | H | H | F | H | heptafluoroisopropyl | H | CF3 |
| 12-3484 | 2,2,2-trichloroethyl | Me | H | F | CN | H | H | F | H | nonafluoro-2-butyl | H | CF3 |
| 12-3495 | 2,2,2-trichloroethyl | Me | H | F | CN | H | H | Cl | H | heptafluoroisopropyl | H | CF3 |
| 12-3524 | 2,2,2-trichloroethyl | Me | H | F | CN | H | H | Cl | H | nonafluoro-2-butyl | H | CF3 |
| 12-3553 | 2,2,2-trichloroethyl | Me | H | F | CN | H | H | Br | H | heptafluoroisopropyl | H | CF3 |
| 12-3582 | 2,2,2-trichloroethyl | Me | H | F | CN | H | H | Br | H | nonafluoro-2-butyl | H | CF3 |
| 12-3611 | 2,2,2-trichloroethyl | Me | H | F | CN | H | H | I | H | heptafluoroisopropyl | H | CF3 |
| 12-3640 | 2,2,2-trichloroethyl | Me | H | F | CN | H | H | I | H | nonafluoro-2-butyl | H | CF3 |
| 12-3669 | 2,2,2-trichloroethyl | Me | H | F | CN | H | H | OCF3 | H | heptafluoroisopropyl | H | OCF3 |
| 12-3698 | 2,2,2-trichloroethyl | Me | H | F | CN | H | H | OCF3 | H | nonafluoro-2-butyl | H | OCF3 |
| 12-3727 | 2,2,2-trichloroethyl | Me | H | F | CN | H | H | CF3 | H | heptafluoroisopropyl | H | OCF3 |
| 12-3756 | 2,2,2-trichloroethyl | Me | H | F | CN | H | H | CF3 | H | nonafluoro-2-butyl | H | OCF3 |
| 12-3785 | 2,2,2-trichloroethyl | Me | H | F | CN | H | H | CF3 | H | heptafluoroisopropyl | H | CF3 |
| 12-3814 | 2,2,2-trichloroethyl | Me | H | F | CN | H | H | CF3 | H | nonafluoro-2-butyl | H | CF3 |
| 12-3833 | 2,2,2-trichloroethyl | Me | H | F | CN | F | H | F | H | heptafluoroisopropyl | H | F |
| 12-3834 | 2,2,2-trichloroethyl | Me | H | F | CN | F | H | F | H | nonafluoro-2-butyl | H | F |
| 12-3845 | 2,2,2-trichloroethyl | Me | H | F | CN | F | H | Cl | H | heptafluoroisopropyl | H | Cl |
| 12-3874 | 2,2,2-trichloroethyl | Me | H | F | CN | F | H | Cl | H | nonafluoro-2-butyl | H | Cl |
| 12-3903 | 2,2,2-trichloroethyl | Me | H | F | CN | F | H | Br | H | heptafluoroisopropyl | H | Br |

TABLE 12-continued

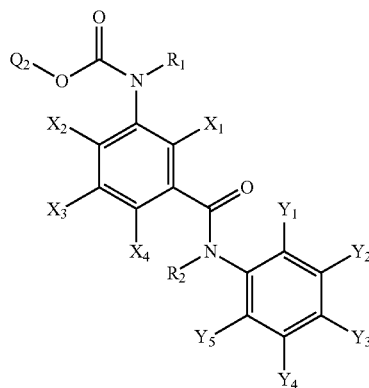

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 12-3932 | 2,2,2-trichloroethyl | Me | H | F | CN | F | H | Br | H | nonafluoro-2-butyl | H | Br |
| 12-3961 | 2,2,2-trichloroethyl | Me | H | F | CN | F | H | I | H | heptafluoroisopropyl | H | I |
| 12-3990 | 2,2,2-trichloroethyl | Me | H | F | CN | F | H | I | H | nonafluoro-2-butyl | H | I |
| 12-4018 | 2,2,2-trichloroethyl | Me | H | F | CN | F | H | Cl | H | nonafluoro-2-butyl | H | Br |
| 12-4021 | 2,2,2-trichloroethyl | Me | H | F | CN | F | H | F | H | heptafluoroisopropyl | H | OCF3 |
| 12-4022 | 2,2,2-trichloroethyl | Me | H | F | CN | F | H | F | H | nonafluoro-2-butyl | H | OCF3 |
| 12-4033 | 2,2,2-trichloroethyl | Me | H | F | CN | F | H | Cl | H | heptafluoroisopropyl | H | OCF3 |
| 12-4062 | 2,2,2-trichloroethyl | Me | H | F | CN | F | H | Cl | H | nonafluoro-2-butyl | H | OCF3 |
| 12-4091 | 2,2,2-trichloroethyl | Me | H | F | CN | F | H | Br | H | heptafluoroisopropyl | H | OCF3 |
| 12-4120 | 2,2,2-trichloroethyl | Me | H | F | CN | F | H | Br | H | nonafluoro-2-butyl | H | OCF3 |
| 12-4149 | 2,2,2-trichloroethyl | Me | H | F | CN | F | H | I | H | heptafluoroisopropyl | H | OCF3 |
| 12-4178 | 2,2,2-trichloroethyl | Me | H | F | CN | F | H | I | H | nonafluoro-2-butyl | H | OCF3 |
| 12-4197 | 2,2,2-trichloroethyl | Me | H | F | CN | F | H | F | H | heptafluoroisopropyl | H | CF3 |
| 12-4198 | 2,2,2-trichloroethyl | Me | H | F | CN | F | H | F | H | nonafluoro-2-butyl | H | CF3 |
| 12-4209 | 2,2,2-trichloroethyl | Me | H | F | CN | F | H | Cl | H | heptafluoroisopropyl | H | CF3 |
| 12-4238 | 2,2,2-trichloroethyl | Me | H | F | CN | F | H | Cl | H | nonafluoro-2-butyl | H | CF3 |
| 12-4267 | 2,2,2-trichloroethyl | Me | H | F | CN | F | H | Br | H | heptafluoroisopropyl | H | CF3 |
| 12-4296 | 2,2,2-trichloroethyl | Me | H | F | CN | F | H | Br | H | nonafluoro-2-butyl | H | CF3 |
| 12-4325 | 2,2,2-trichloroethyl | Me | H | F | CN | F | H | I | H | heptafluoroisopropyl | H | CF3 |
| 12-4354 | 2,2,2-trichloroethyl | Me | H | F | CN | F | H | I | H | nonafluoro-2-butyl | H | CF3 |
| 12-4383 | 2,2,2-trichloroethyl | Me | H | F | CN | F | H | OCF3 | H | heptafluoroisopropyl | H | OCF3 |
| 12-4412 | 2,2,2-trichloroethyl | Me | H | F | CN | F | H | OCF3 | H | nonafluoro-2-butyl | H | OCF3 |
| 12-4441 | 2,2,2-trichloroethyl | Me | H | F | CN | F | H | CF3 | H | heptafluoroisopropyl | H | OCF3 |
| 12-4470 | 2,2,2-trichloroethyl | Me | H | F | CN | F | H | CF3 | H | nonafluoro-2-butyl | H | OCF3 |
| 12-4499 | 2,2,2-trichloroethyl | Me | H | F | CN | F | H | CF3 | H | heptafluoroisopropyl | H | CF3 |
| 12-4528 | 2,2,2-trichloroethyl | Me | H | F | CN | F | H | CF3 | H | nonafluoro-2-butyl | H | CF3 |

TABLE 13

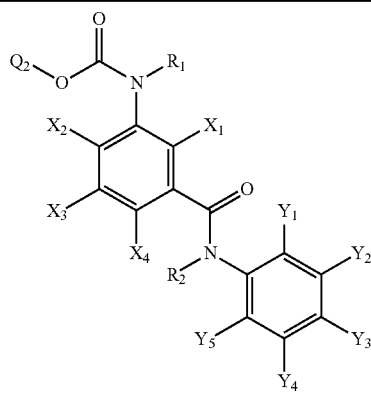

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 13-1 | 2,2,2-trichloroethyl | H | Me | H | H | H | H | F | H | heptafluoroisopropyl | H | OCF3 |
| 13-2 | 2,2,2-trichloroethyl | H | Me | H | H | H | H | F | H | nonafluoro-2-butyl | H | OCF3 |
| 13-13 | 2,2,2-trichloroethyl | H | Me | H | H | H | H | Cl | H | heptafluoroisopropyl | H | OCF3 |
| 13-42 | 2,2,2-trichloroethyl | H | Me | H | H | H | H | Cl | H | nonafluoro-2-butyl | H | OCF3 |

TABLE 13-continued

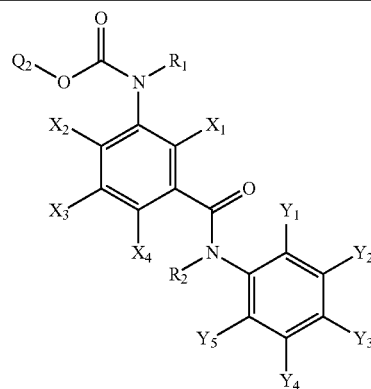

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 13-71 | 2,2,2-trichloroethyl | H | Me | H | H | H | H | Br | H | heptafluoroisopropyl | H | OCF3 |
| 13-100 | 2,2,2-trichloroethyl | H | Me | H | H | H | H | Br | H | nonafluoro-2-butyl | H | OCF3 |
| 13-129 | 2,2,2-trichloroethyl | H | Me | H | H | H | H | I | H | heptafluoroisopropyl | H | OCF3 |
| 13-158 | 2,2,2-trichloroethyl | H | Me | H | H | H | H | I | H | nonafluoro-2-butyl | H | OCF3 |
| 13-177 | 2,2,2-trichloroethyl | H | Me | H | H | H | H | F | H | heptafluoroisopropyl | H | CF3 |
| 13-178 | 2,2,2-trichloroethyl | H | Me | H | H | H | H | F | H | nonafluoro-2-butyl | H | CF3 |
| 13-189 | 2,2,2-trichloroethyl | H | Me | H | H | H | H | Cl | H | heptafluoroisopropyl | H | CF3 |
| 13-218 | 2,2,2-trichloroethyl | H | Me | H | H | H | H | Cl | H | nonafluoro-2-butyl | H | CF3 |
| 13-247 | 2,2,2-trichloroethyl | H | Me | H | H | H | H | Br | H | heptafluoroisopropyl | H | CF3 |
| 13-276 | 2,2,2-trichloroethyl | H | Me | H | H | H | H | Br | H | nonafluoro-2-butyl | H | CF3 |
| 13-305 | 2,2,2-trichloroethyl | H | Me | H | H | H | H | I | H | heptafluoroisopropyl | H | CF3 |
| 13-334 | 2,2,2-trichloroethyl | H | Me | H | H | H | H | I | H | nonafluoro-2-butyl | H | CF3 |
| 13-363 | 2,2,2-trichloroethyl | H | Me | H | H | H | H | OCF3 | H | heptafluoroisopropyl | H | OCF3 |
| 13-392 | 2,2,2-trichloroethyl | h | Me | H | H | H | H | OCF3 | H | nonafluoro-2-butyl | H | OCF3 |
| 13-421 | 2,2,2-trichloroethyl | H | Me | H | H | H | H | CF3 | H | heptafluoroisopropyl | H | OCF3 |
| 13-450 | 2,2,2-trichloroethyl | H | Me | H | H | H | H | CF3 | H | nonafluoro-2-butyl | H | OCF3 |
| 13-479 | 2,2,2-trichloroethyl | H | Me | H | H | H | H | CF3 | H | heptafluoroisopropyl | H | CF3 |
| 13-508 | 2,2,2-trichloroethyl | H | Me | H | H | H | H | CF3 | H | nonafluoro-2-butyl | H | CF3 |
| 13-527 | 2,2,2-trichloroethyl | H | Me | F | H | H | H | F | H | heptafluoroisopropyl | H | F |
| 13-528 | 2,2,2-trichloroethyl | H | Me | F | H | H | H | Cl | H | heptafluoroisopropyl | H | Cl |
| 13-529 | 2,2,2-trichloroethyl | H | Me | F | H | H | H | Br | H | heptafluoroisopropyl | H | Br |
| 13-530 | 2,2,2-trichloroethyl | H | Me | F | H | H | H | I | H | heptafluoroisopropyl | H | I |
| 13-531 | 2,2,2-trichloroethyl | H | Me | F | H | H | H | F | H | heptafluoroisopropyl | H | OCF3 |
| 13-532 | 2,2,2-trichloroethyl | H | Me | F | H | H | H | F | H | nonafluoro-2-butyl | H | OCF3 |
| 13-543 | 2,2,2-trichloroethyl | H | Me | F | H | H | H | Cl | H | heptafluoroisopropyl | H | OCF3 |
| 13-572 | 2,2,2-trichloroethyl | H | Me | F | H | H | H | Cl | H | nonafluoro-2-butyl | H | OCF3 |
| 13-601 | 2,2,2-trichloroethyl | H | Me | F | H | H | H | Br | H | heptafluoroisopropyl | H | OCF3 |
| 13-630 | 2,2,2-trichloroethyl | H | Me | F | H | H | H | Br | H | nonafluoro-2-butyl | H | OCF3 |
| 13-659 | 2,2,2-trichloroethyl | H | Me | F | H | H | H | I | H | heptafluoroisopropyl | H | OCF3 |
| 13-688 | 2,2,2-trichloroethyl | H | Me | F | H | H | H | I | H | nonafluoro-2-butyl | H | OCF3 |
| 13-707 | 2,2,2-trichloroethyl | H | Me | F | H | H | H | F | H | heptafluoroisopropyl | H | CF3 |
| 13-708 | 2,2,2-trichloroethyl | H | Me | F | H | H | H | F | H | nonafluoro-2-butyl | H | CF3 |
| 13-715 | 2-cyanoethyl | H | Et | F | H | H | H | Cl | H | heptafluoroisopropyl | H | C2F5 |
| 13-719 | 2,2,2-trichloroethyl | H | Me | F | H | H | H | Cl | H | heptafluoroisopropyl | H | CF3 |
| 13-721 | n-propyl | H | Me | F | H | H | H | Cl | H | pentafluoroethyl | H | CF3 |
| 13-725 | i-propyl | H | n-Pr | F | H | H | H | Cl | H | heptafluoroisopropyl | H | n-C3F7 |
| 13-728 | 1,3-dichloro-2-propyl | H | Me | F | H | H | H | Cl | H | pentafluoroethyl | H | CF3 |
| 13-729 | 1-chloro-3-fluoro-2-propyl | H | i-Pr | F | H | H | H | Cl | H | heptafluoroisopropyl | H | CF3 |
| 13-733 | i-butyl | H | CH2CH═CH2 | F | H | H | H | Cl | H | heptafluoroisopropyl | H | CF3 |
| 13-739 | ethyl | H | Me | F | H | H | H | Cl | H | nonafluoro-2-butyl | H | i-C3F7 |
| 13-744 | 2-cyanoethyl | H | CN | F | H | H | H | Cl | H | nonafluoro-2-butyl | H | CF3 |
| 13-748 | 2,2,2-trichloroethyl | H | Me | F | H | H | H | Cl | H | nonafluoro-2-butyl | H | CF3 |
| 13-750 | n-propyl | H | CH2C≡CH | F | H | H | H | Cl | H | nonafluoro-2-butyl | H | CF3 |
| 13-762 | i-butyl | H | NH2 | F | H | H | H | Cl | H | nonafluoro-2-butyl | H | CF3 |
| 13-773 | 2-cyanoethyl | H | Me | F | H | H | H | Br | H | heptafluoroisopropyl | H | C2F5 |
| 13-777 | 2,2,2-trichloroethyl | H | Me | F | H | H | H | Br | H | heptafluoroisopropyl | H | CF3 |
| 13-779 | n-propyl | H | C(O)OMe | F | H | H | H | Br | H | heptafluoroisopropyl | H | CF3 |
| 13-784 | 1,2-difluoro-2-propyl | H | Me | F | H | H | H | Br | H | heptafluoroisopropyl | H | n-C3F7 |
| 13-790 | 4,4,4-trifluoro-n-butyl | H | Me | F | H | H | H | Br | H | heptafluoroisopropyl | H | CF3 |
| 13-793 | vinyl | H | C(O)C(O)OMe | F | H | H | H | Br | H | heptafluoroisopropyl | H | CF3 |
| 13-806 | 2,2,2-trichloroethyl | H | Me | F | H | H | H | Br | H | nonafluoro-2-butyl | H | CF3 |
| 13-808 | n-propyl | H | C(O)OEt | F | H | H | H | Br | H | nonafluoro-2-butyl | H | CF3 |
| 13-812 | i-propyl | H | C(O)Me | F | H | H | H | Br | H | nonafluoro-2-butyl | H | CF3 |
| 13-819 | 4,4,4-trifluoro-n-butyl | H | Me | F | H | H | H | Br | H | nonafluoro-2-butyl | H | CF3 |
| 13-824 | phenyl | H | C(O)C(O)OEt | F | H | H | H | Br | H | nonafluoro-2-butyl | H | i-C3F7 |
| 13-835 | 2,2,2-trichloroethyl | H | Me | F | H | H | H | I | H | heptafluoroisopropyl | H | CF3 |
| 13-840 | 3-bromo-n-propyl | H | C(O)Et | F | H | H | H | I | H | heptafluoroisopropyl | H | C2F5 |
| 13-848 | 4,4,4-trifluoro-n-butyl | H | Me | F | H | H | H | I | H | heptafluoroisopropyl | H | CF3 |

TABLE 13-continued

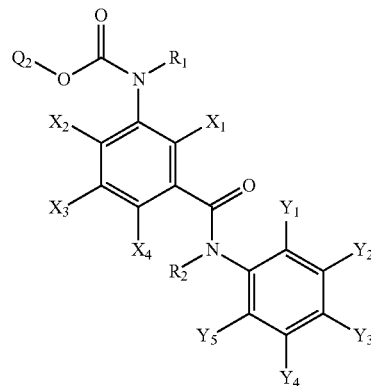

| compound number | $Q_2$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 13-852 | benzyl | H | S(O)2Me | F | H | H | H | I | H | heptafluoroisopropyl | H | CF3 |
| 13-860 | 2-cyanoethyl | H | S(O)2Et | F | H | H | H | I | H | nonafluoro-2-butyl | H | CF3 |
| 13-864 | 2,2,2-trichloroethyl | H | Me | F | H | H | H | I | H | nonafluoro-2-butyl | H | CF3 |
| 13-866 | n-propyl | H | CH2Ph | F | H | H | H | I | H | nonafluoro-2-butyl | H | n-C3F7 |
| 13-870 | i-propyl | H | CH2(3-Py) | F | H | H | H | I | H | nonafluoro-2-butyl | H | CF3 |
| 13-877 | 4,4,4-trifluoro-n-butyl | H | Me | F | H | H | H | I | H | nonafluoro-2-butyl | H | CF3 |
| 13-879 | s-butyl | H | CH2(3-Py—N-oxide) | F | H | H | H | I | H | nonafluoro-2-butyl | H | CF3 |
| 13-880 | vinyl | H | Me | F | H | H | H | I | H | nonafluoro-2-butyl | H | i-C3F7 |
| 13-893 | 2,2,2-trichloroethyl | H | Me | F | H | H | H | OCF3 | H | heptafluoroisopropyl | H | OCF3 |
| 13-922 | 2,2,2-trichloroethyl | H | Me | F | H | H | H | OCF3 | H | nonafluoro-2-butyl | H | OCF3 |
| 13-951 | 2,2,2-trichloroethyl | H | Me | F | H | H | H | CF3 | H | heptafluoroisopropyl | H | OCF3 |
| 13-980 | 2,2,2-trichloroethyl | H | Me | F | H | H | H | CF3 | H | nonafluoro-2-butyl | H | OCF3 |
| 13-1009 | 2,2,2-trichloroethyl | H | Me | F | H | H | H | CF3 | H | heptafluoroisopropyl | H | CF3 |
| 13-1038 | 2,2,2-trichloroethyl | H | Me | F | H | H | H | CF3 | H | nonafluoro-2-butyl | H | CF3 |
| 13-1057 | 2,2,2-trichloroethyl | H | Me | H | F | H | H | F | H | heptafluoroisopropyl | H | F |
| 13-1058 | 2,2,2-trichloroethyl | H | Me | H | F | H | H | F | H | nonafluoro-2-butyl | H | F |
| 13-1069 | 2,2,2-trichloroethyl | H | Me | H | F | H | H | Cl | H | heptafluoroisopropyl | H | Cl |
| 13-1098 | 2,2,2-trichloroethyl | H | Me | H | F | H | H | Cl | H | nonafluoro-2-butyl | H | Cl |
| 13-1127 | 2,2,2-trichloroethyl | H | Me | H | F | H | H | Br | H | heptafluoroisopropyl | H | Br |
| 13-1156 | 2,2,2-trichloroethyl | H | Me | H | F | H | H | Br | H | nonafluoro-2-butyl | H | Br |
| 13-1185 | 2,2,2-trichloroethyl | H | Me | H | F | H | H | I | H | heptafluoroisopropyl | H | I |
| 13-1214 | 2,2,2-trichloroethyl | H | Me | H | F | H | H | I | H | nonafluoro-2-butyl | H | I |
| 13-1236 | 2,2,2-trichloroethyl | H | Me | H | F | H | H | Cl | H | heptafluoroisopropyl | H | Br |
| 13-1245 | 2,2,2-trichloroethyl | H | Me | H | F | H | H | F | H | heptafluoroisopropyl | H | OCF3 |
| 13-1246 | 2,2,2-trichloroethyl | H | Me | H | F | H | H | F | H | nonafluoro-2-butyl | H | OCF3 |
| 13-1257 | 2,2,2-trichloroethyl | H | Me | H | F | H | H | Cl | H | heptafluoroisopropyl | H | OCF3 |
| 13-1286 | 2,2,2-trichloroethyl | H | Me | H | F | H | H | Cl | H | nonafluoro-2-butyl | H | OCF3 |
| 13-1315 | 2,2,2-trichloroethyl | H | Me | H | F | H | H | Br | H | heptafluoroisopropyl | H | OCF3 |
| 13-1344 | 2,2,2-trichloroethyl | H | Me | H | F | H | H | Br | H | nonafluoro-2-butyl | H | OCF3 |
| 13-1373 | 2,2,2-trichloroethyl | H | Me | H | F | H | H | I | H | heptafluoroisopropyl | H | OCF3 |
| 13-1402 | 2,2,2-trichloroethyl | H | Me | H | F | H | H | I | H | nonafluoro-2-butyl | H | OCF3 |
| 13-1421 | 2,2,2-trichloroethyl | H | Me | H | F | H | H | F | H | heptafluoroisopropyl | H | CF3 |
| 13-1422 | 2,2,2-trichloroethyl | H | Me | H | F | H | H | F | H | nonafluoro-2-butyl | H | CF3 |
| 13-1433 | 2,2,2-trichloroethyl | H | Me | H | F | H | H | Cl | H | heptafluoroisopropyl | H | CF3 |
| 13-1462 | 2,2,2-trichloroethyl | H | Me | H | F | H | H | Cl | H | nonafluoro-2-butyl | H | CF3 |
| 13-1491 | 2,2,2-trichloroethyl | H | Me | H | F | H | H | Br | H | heptafluoroisopropyl | H | CF3 |
| 13-1520 | 2,2,2-trichloroethyl | H | Me | H | F | H | H | Br | H | nonafluoro-2-butyl | H | CF3 |
| 13-1549 | 2,2,2-trichloroethyl | H | Me | H | F | H | H | I | H | heptafluoroisopropyl | H | CF3 |
| 13-1578 | 2,2,2-trichloroethyl | H | Me | H | F | H | H | I | H | nonafluoro-2-butyl | H | CF3 |
| 13-1607 | 2,2,2-trichloroethyl | H | Me | H | F | H | H | OCF3 | H | heptafluoroisopropyl | H | OCF3 |
| 13-1636 | 2,2,2-trichloroethyl | H | Me | H | F | H | H | OCF3 | H | nonafluoro-2-butyl | H | OCF3 |
| 13-1665 | 2,2,2-trichloroethyl | H | Me | H | F | H | H | CF3 | H | heptafluoroisopropyl | H | OCF3 |
| 13-1694 | 2,2,2-trichloroethyl | H | Me | H | F | H | H | CF3 | H | nonafluoro-2-butyl | H | OCF3 |
| 13-1723 | 2,2,2-trichloroethyl | H | Me | H | F | H | H | CF3 | H | heptafluoroisopropyl | H | CF3 |
| 13-1752 | 2,2,2-trichloroethyl | H | Me | H | F | H | H | CF3 | H | nonafluoro-2-butyl | H | CF3 |
| 13-1771 | 2,2,2-trichloroethyl | H | Me | F | F | H | H | F | H | heptafluoroisopropyl | H | F |
| 13-1772 | 2,2,2-trichloroethyl | H | Me | F | F | H | H | F | H | nonafluoro-2-butyl | H | F |
| 13-1783 | 2,2,2-trichloroethyl | H | Me | F | F | H | H | Cl | H | heptafluoroisopropyl | H | Cl |
| 13-1812 | 2,2,2-trichloroethyl | H | Me | F | F | H | H | Cl | H | nonafluoro-2-butyl | H | Cl |
| 13-1841 | 2,2,2-trichloroethyl | H | Me | F | F | H | H | Br | H | heptafluoroisopropyl | H | Br |
| 13-1870 | 2,2,2-trichloroethyl | H | Me | F | F | H | H | Br | H | nonafluoro-2-butyl | H | Br |
| 13-1899 | 2,2,2-trichloroethyl | H | Me | F | F | H | H | I | H | heptafluoroisopropyl | H | I |
| 13-1928 | 2,2,2-trichloroethyl | H | Me | F | F | H | H | I | H | nonafluoro-2-butyl | H | I |
| 13-1956 | 2,2,2-trichloroethyl | H | Me | F | F | H | H | Cl | H | nonafluoro-2-butyl | H | Br |
| 13-1959 | 2,2,2-trichloroethyl | H | Me | F | F | H | H | F | H | heptafluoroisopropyl | H | OCF3 |
| 13-1960 | 2,2,2-trichloroethyl | H | Me | F | F | H | H | F | H | nonafluoro-2-butyl | H | OCF3 |
| 13-1971 | 2,2,2-trichloroethyl | H | Me | F | F | H | H | Cl | H | heptafluoroisopropyl | H | OCF3 |

TABLE 13-continued

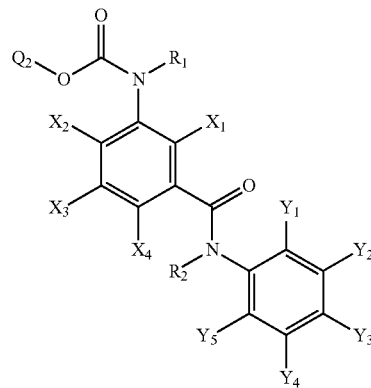

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 13-2000 | 2,2,2-trichloroethyl | H | Me | F | F | H | H | Cl | H | nonafluoro-2-butyl | H | OCF3 |
| 13-2029 | 2,2,2-trichloroethyl | H | Me | F | F | H | H | Br | H | heptafluoroisopropyl | H | OCF3 |
| 13-2058 | 2,2,2-trichloroethyl | H | Me | F | F | H | H | Br | H | nonafluoro-2-butyl | H | OCF3 |
| 13-2087 | 2,2,2-trichloroethyl | H | Me | F | F | H | H | I | H | heptafluoroisopropyl | H | OCF3 |
| 13-2116 | 2,2,2-trichloroethyl | H | Me | F | F | H | H | I | H | nonafluoro-2-butyl | H | OCF3 |
| 13-2135 | 2,2,2-trichloroethyl | H | Me | F | F | H | H | F | H | heptafluoroisopropyl | H | CF3 |
| 13-2136 | 2,2,2-trichloroethyl | H | Me | F | F | H | H | F | H | nonafluoro-2-butyl | H | CF3 |
| 13-2147 | 2,2,2-trichloroethyl | H | Me | F | F | H | H | Cl | H | heptafluoroisopropyl | H | CF3 |
| 13-2176 | 2,2,2-trichloroethyl | H | Me | F | F | H | H | Cl | H | nonafluoro-2-butyl | H | CF3 |
| 13-2205 | 2,2,2-trichloroethyl | H | Me | F | F | H | H | Br | H | heptafluoroisopropyl | H | CF3 |
| 13-2234 | 2,2,2-trichloroethyl | H | Me | F | F | H | H | Br | H | nonafluoro-2-butyl | H | CF3 |
| 13-2263 | 2,2,2-trichloroethyl | H | Me | F | F | H | H | I | H | heptafluoroisopropyl | H | CF3 |
| 13-2292 | 2,2,2-trichloroethyl | H | Me | F | F | H | H | I | H | nonafluoro-2-butyl | H | CF3 |
| 13-2321 | 2,2,2-trichloroethyl | H | Me | F | F | H | H | OCF3 | H | heptafluoroisopropyl | H | OCF3 |
| 13-2350 | 2,2,2-trichloroethyl | H | Me | F | F | H | H | OCF3 | H | nonafluoro-2-butyl | H | OCF3 |
| 13-2379 | 2,2,2-trichloroethyl | H | Me | F | F | H | H | CF3 | H | heptafluoroisopropyl | H | OCF3 |
| 13-2408 | 2,2,2-trichloroethyl | H | Me | F | F | H | H | CF3 | H | nonafluoro-2-butyl | H | OCF3 |
| 13-2437 | 2,2,2-trichloroethyl | H | Me | F | F | H | H | CF3 | H | heptafluoroisopropyl | H | CF3 |
| 13-2439 | n-propyl | H | S(O)2Me | F | F | H | H | CF3 | H | heptafluoroisopropyl | H | CF3 |
| 13-2466 | 2,2,2-trichloroethyl | H | Me | F | F | H | H | CF3 | H | nonafluoro-2-butyl | H | CF3 |
| 13-2485 | 2,2,2-trichloroethyl | H | Me | F | F | F | H | Cl | H | pentafluoroethyl | H | Cl |
| 13-2486 | 2,2,2-trichloroethyl | H | Me | F | F | F | H | Br | H | heptafluoroisopropyl | H | Br |
| 13-2487 | 2,2,2-trichloroethyl | H | Me | F | F | F | H | Br | H | heptafluoroisopropyl | H | OCF3 |
| 13-2488 | 2,2,2-trichloroethyl | H | Me | F | F | F | H | I | H | heptafluoroisopropyl | H | CF3 |
| 13-2489 | 2,2,2-trichloroethyl | H | Me | F | F | F | H | CF3 | H | heptafluoroisopropyl | H | CF3 |
| 13-2490 | 2,2,2-trichloroethyl | H | Me | F | F | F | H | I | H | nonafluoro-2-butyl | H | I |
| 13-2491 | 2,2,2-trichloroethyl | H | Me | F | F | F | H | Cl | H | nonafluoro-2-butyl | H | OCF3 |
| 13-2492 | 2,2,2-trichloroethyl | H | Me | F | F | F | H | Br | H | nonafluoro-2-butyl | H | CF3 |
| 13-2493 | 2,2,2-trichloroethyl | H | Me | F | F | F | H | CF3 | H | nonafluoro-2-butyl | H | CF3 |
| 13-2494 | 2,2,2-trichloroethyl | H | Me | H | H | F | H | Cl | H | pentafluoroethyl | H | Cl |
| 13-2495 | 2,2,2-trichloroethyl | H | Me | H | H | F | H | Br | H | heptafluoroisopropyl | H | Br |
| 13-2496 | 2,2,2-trichloroethyl | H | Me | H | H | F | H | Br | H | heptafluoroisopropyl | H | OCF3 |
| 13-2497 | 2,2,2-trichloroethyl | H | Me | H | H | F | H | I | H | heptafluoroisopropyl | H | CF3 |
| 13-2498 | 2,2,2-trichloroethyl | H | Me | H | H | F | H | CF3 | H | heptafluoroisopropyl | H | CF3 |
| 13-2499 | 2,2,2-trichloroethyl | H | Me | H | H | F | H | I | H | nonafluoro-2-butyl | H | I |
| 13-2500 | 2,2,2-trichloroethyl | H | Me | H | H | F | H | Cl | H | nonafluoro-2-butyl | H | OCF3 |
| 13-2501 | 2,2,2-trichloroethyl | H | Me | H | H | F | H | Br | H | nonafluoro-2-butyl | H | CF3 |
| 13-2502 | 2,2,2-trichloroethyl | H | Me | H | H | F | H | CF3 | H | nonafluoro-2-butyl | H | CF3 |
| 13-2503 | 2,2,2-trichloroethyl | H | Me | H | H | H | F | Cl | H | pentafluoroethyl | H | Cl |
| 13-2504 | 2,2,2-trichloroethyl | H | Me | H | H | H | F | Br | H | heptafluoroisopropyl | H | Br |
| 13-2505 | 2,2,2-trichloroethyl | H | Me | H | H | H | F | Br | H | heptafluoroisopropyl | H | OCF3 |
| 13-2506 | 2,2,2-trichloroethyl | H | Me | H | H | H | F | I | H | heptafluoroisopropyl | H | CF3 |
| 13-2507 | 2,2,2-trichloroethyl | H | Me | H | H | H | F | CF3 | H | heptafluoroisopropyl | H | CF3 |
| 13-2508 | 2,2,2-trichloroethyl | H | Me | H | H | H | F | I | H | nonafluoro-2-butyl | H | I |
| 13-2509 | 2,2,2-trichloroethyl | H | Me | H | H | H | F | Cl | H | nonafluoro-2-butyl | H | OCF3 |
| 13-2510 | 2,2,2-trichloroethyl | H | Me | H | H | H | F | Br | H | nonafluoro-2-butyl | H | CF3 |
| 13-2511 | 2,2,2-trichloroethyl | H | Me | H | H | H | F | CF3 | H | nonafluoro-2-butyl | H | CF3 |
| 13-2512 | 2,2,2-trichloroethyl | H | Me | F | H | F | H | Cl | H | pentafluoroethyl | H | Cl |
| 13-2513 | 2,2,2-trichloroethyl | H | Me | F | H | F | H | Br | H | heptafluoroisopropyl | H | Br |
| 13-2514 | 2,2,2-trichloroethyl | H | Me | F | H | F | H | Br | H | heptafluoroisopropyl | H | OCF3 |
| 13-2515 | 2,2,2-trichloroethyl | H | Me | F | H | F | H | I | H | heptafluoroisopropyl | H | CF3 |
| 13-2516 | 2,2,2-trichloroethyl | H | Me | F | H | F | H | CF3 | H | heptafluoroisopropyl | H | CF3 |
| 13-2517 | 2,2,2-trichloroethyl | H | Me | F | H | F | H | I | H | nonafluoro-2-butyl | H | I |
| 13-2518 | 2,2,2-trichloroethyl | H | Me | F | H | F | H | Cl | H | nonafluoro-2-butyl | H | OCF3 |
| 13-2519 | 2,2,2-trichloroethyl | H | Me | F | H | F | H | Br | H | nonafluoro-2-butyl | H | CF3 |
| 13-2520 | 2,2,2-trichloroethyl | H | Me | F | H | F | H | CF3 | H | nonafluoro-2-butyl | H | CF3 |
| 13-2521 | 2,2,2-trichloroethyl | H | Me | F | H | H | F | Cl | H | pentafluoroethyl | H | Cl |
| 13-2522 | 2,2,2-trichloroethyl | H | Me | F | H | H | F | Br | H | heptafluoroisopropyl | H | Br |

TABLE 13-continued

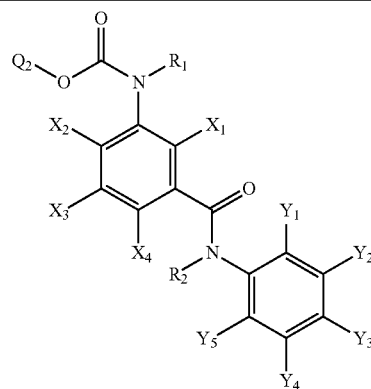

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 13-2523 | 2,2,2-trichloroethyl | H | Me | F | H | H | F | Br | H | heptafluoroisopropyl | H | OCF3 |
| 13-2524 | 2,2,2-trichloroethyl | H | Me | F | H | H | F | I | H | heptafluoroisopropyl | H | CF3 |
| 13-2525 | 2,2,2-trichloroethyl | H | Me | F | H | H | F | CF3 | H | heptafluoroisopropyl | H | CF3 |
| 13-2526 | 2,2,2-trichloroethyl | H | Me | F | H | H | F | I | H | nonafluoro-2-butyl | H | I |
| 13-2527 | 2,2,2-trichloroethyl | H | Me | F | H | H | F | Cl | H | nonafluoro-2-butyl | H | OCF3 |
| 13-2528 | 2,2,2-trichloroethyl | H | Me | F | H | H | F | Br | H | nonafluoro-2-butyl | H | CF3 |
| 13-2529 | 2,2,2-trichloroethyl | H | Me | F | H | H | F | CF3 | H | nonafluoro-2-butyl | H | CF3 |
| 13-2530 | 2,2,2-trichloroethyl | H | Me | H | F | F | H | Cl | H | pentafluoroethyl | H | Cl |
| 13-2531 | 2,2,2-trichloroethyl | H | Me | H | F | F | H | Br | H | heptafluoroisopropyl | H | Br |
| 13-2532 | 2,2,2-trichloroethyl | H | Me | H | F | F | H | Br | H | heptafluoroisopropyl | H | OCF3 |
| 13-2533 | 2,2,2-trichloroethyl | H | Me | H | F | F | H | I | H | heptafluoroisopropyl | H | CF3 |
| 13-2534 | 2,2,2-trichloroethyl | H | Me | H | F | F | H | CF3 | H | heptafluoroisopropyl | H | CF3 |
| 13-2535 | 2,2,2-trichloroethyl | H | Me | H | F | F | H | I | H | nonafluoro-2-butyl | H | I |
| 13-2536 | 2,2,2-trichloroethyl | H | Me | H | F | F | H | Cl | H | nonafluoro-2-butyl | H | OCF3 |
| 13-2537 | 2,2,2-trichloroethyl | H | Me | H | F | F | H | Br | H | nonafluoro-2-butyl | H | CF3 |
| 13-2538 | 2,2,2-trichloroethyl | H | Me | H | F | F | H | CF3 | H | nonafluoro-2-butyl | H | CF3 |
| 13-2539 | 2,2,2-trichloroethyl | H | Me | H | F | H | F | Cl | H | pentafluoroethyl | H | Cl |
| 13-2540 | 2,2,2-trichloroethyl | H | Me | H | F | H | F | Br | H | heptafluoroisopropyl | H | Br |
| 13-2541 | 2,2,2-trichloroethyl | H | Me | H | F | H | F | Br | H | heptafluoroisopropyl | H | OCF3 |
| 13-2542 | 2,2,2-trichloroethyl | H | Me | H | F | H | F | I | H | heptafluoroisopropyl | H | CF3 |
| 13-2543 | 2,2,2-trichloroethyl | H | Me | H | F | H | F | CF3 | H | heptafluoroisopropyl | H | CF3 |
| 13-2544 | 2,2,2-trichloroethyl | H | Me | H | F | H | F | I | H | nonafluoro-2-butyl | H | I |
| 13-2545 | 2,2,2-trichloroethyl | H | Me | H | F | H | F | Cl | H | nonafluoro-2-butyl | H | OCF3 |
| 13-2546 | 2,2,2-trichloroethyl | H | Me | H | F | H | F | Br | H | nonafluoro-2-butyl | H | CF3 |
| 13-2547 | 2,2,2-trichloroethyl | H | Me | H | F | H | F | CF3 | H | nonafluoro-2-butyl | H | CF3 |
| 13-2548 | 2,2,2-trichloroethyl | H | Me | H | H | F | F | Cl | H | pentafluoroethyl | H | Cl |
| 13-2549 | 2,2,2-trichloroethyl | H | Me | H | H | F | F | Br | H | heptafluoroisopropyl | H | Br |
| 13-2550 | 2,2,2-trichloroethyl | H | Me | H | H | F | F | Br | H | heptafluoroisopropyl | H | OCF3 |
| 13-2551 | 2,2,2-trichloroethyl | H | Me | H | H | F | F | I | H | heptafluoroisopropyl | H | CF3 |
| 13-2552 | 2,2,2-trichloroethyl | H | Me | H | H | F | F | CF3 | H | heptafluoroisopropyl | H | CF3 |
| 13-2553 | 2,2,2-trichloroethyl | H | Me | H | H | F | F | I | H | nonafluoro-2-butyl | H | I |
| 13-2554 | 2,2,2-trichloroethyl | H | Me | H | H | F | F | Cl | H | nonafluoro-2-butyl | H | OCF3 |
| 13-2555 | 2,2,2-trichloroethyl | H | Me | H | H | F | F | Br | H | nonafluoro-2-butyl | H | CF3 |
| 13-2556 | 2,2,2-trichloroethyl | H | Me | H | H | F | F | CF3 | H | nonafluoro-2-butyl | H | CF3 |
| 13-2557 | 2,2,2-trichloroethyl | H | Me | F | F | H | F | Cl | H | pentafluoroethyl | H | Cl |
| 13-2558 | 2,2,2-trichloroethyl | H | Me | F | F | H | F | Br | H | heptafluoroisopropyl | H | Br |
| 13-2559 | 2,2,2-trichloroethyl | H | Me | F | F | H | F | Br | H | heptafluoroisopropyl | H | OCF3 |
| 13-2560 | 2,2,2-trichloroethyl | H | Me | F | F | H | F | I | H | heptafluoroisopropyl | H | CF3 |
| 13-2561 | 2,2,2-trichloroethyl | H | Me | F | F | H | F | CF3 | H | heptafluoroisopropyl | H | CF3 |
| 13-2562 | 2,2,2-trichloroethyl | H | Me | F | F | H | F | I | H | nonafluoro-2-butyl | H | I |
| 13-2563 | 2,2,2-trichloroethyl | H | Me | F | F | H | F | Cl | H | nonafluoro-2-butyl | H | OCF3 |
| 13-2564 | 2,2,2-trichloroethyl | H | Me | F | F | H | F | Br | H | nonafluoro-2-butyl | H | CF3 |
| 13-2565 | 2,2,2-trichloroethyl | H | Me | F | F | H | F | CF3 | H | nonafluoro-2-butyl | H | CF3 |
| 13-2566 | 2,2,2-trichloroethyl | H | Me | F | H | F | F | Cl | H | pentafluoroethyl | H | Cl |
| 13-2567 | 2,2,2-trichloroethyl | H | Me | F | H | F | F | Br | H | heptafluoroisopropyl | H | Br |
| 13-2568 | 2,2,2-trichloroethyl | H | Me | F | H | F | F | Br | H | heptafluoroisopropyl | H | OCF3 |
| 13-2569 | 2,2,2-trichloroethyl | H | Me | F | H | F | F | I | H | heptafluoroisopropyl | H | CF3 |
| 13-2570 | 2,2,2-trichloroethyl | H | Me | F | H | F | F | CF3 | H | heptafluoroisopropyl | H | CF3 |
| 13-2571 | 2,2,2-trichloroethyl | H | Me | F | H | F | F | I | H | nonafluoro-2-butyl | H | I |
| 13-2572 | 2,2,2-trichloroethyl | H | Me | F | H | F | F | Cl | H | nonafluoro-2-butyl | H | OCF3 |
| 13-2573 | 2,2,2-trichloroethyl | H | Me | F | H | F | F | Br | H | nonafluoro-2-butyl | H | CF3 |
| 13-2574 | 2,2,2-trichloroethyl | H | Me | F | H | F | F | CF3 | H | nonafluoro-2-butyl | H | CF3 |
| 13-2575 | 2,2,2-trichloroethyl | H | Me | H | F | F | F | Cl | H | pentafluoroethyl | H | Cl |
| 13-2576 | 2,2,2-trichloroethyl | H | Me | H | F | F | F | Br | H | heptafluoroisopropyl | H | Br |
| 13-2577 | 2,2,2-trichloroethyl | H | Me | H | F | F | F | Br | H | heptafluoroisopropyl | H | OCF3 |
| 13-2578 | 2,2,2-trichloroethyl | H | Me | H | F | F | F | I | H | heptafluoroisopropyl | H | CF3 |
| 13-2579 | 2,2,2-trichloroethyl | H | Me | H | F | F | F | CF3 | H | heptafluoroisopropyl | H | CF3 |
| 13-2580 | 2,2,2-trichloroethyl | H | Me | H | F | F | F | I | H | nonafluoro-2-butyl | H | I |

TABLE 13-continued

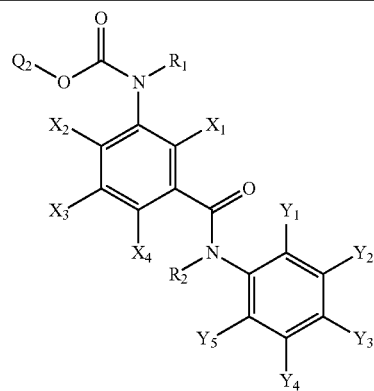

| compound number | $Q_2$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 13-2581 | 2,2,2-trichloroethyl | H | Me | H | F | F | F | Cl | H | nonafluoro-2-butyl | H | OCF3 |
| 13-2582 | 2,2,2-trichloroethyl | H | Me | H | F | F | F | Br | H | nonafluoro-2-butyl | H | CF3 |
| 13-2583 | 2,2,2-trichloroethyl | H | Me | H | F | F | F | CF3 | H | nonafluoro-2-butyl | H | CF3 |
| 13-2584 | 2,2,2-trichloroethyl | H | Me | F | F | F | F | Cl | H | pentafluoroethyl | H | Cl |
| 13-2585 | 2,2,2-trichloroethyl | H | Me | F | F | F | F | Br | H | heptafluoroisopropyl | H | Br |
| 13-2586 | 2,2,2-trichloroethyl | H | Me | F | F | F | F | Br | H | heptafluoroisopropyl | H | OCF3 |
| 13-2587 | 2,2,2-trichloroethyl | H | Me | F | F | F | F | I | H | heptafluoroisopropyl | H | CF3 |
| 13-2588 | 2,2,2-trichloroethyl | H | Me | F | F | F | F | CF3 | H | heptafluoroisopropyl | H | CF3 |
| 13-2589 | 2,2,2-trichloroethyl | H | Me | F | F | F | F | I | H | nonafluoro-2-butyl | H | I |
| 13-2590 | 2,2,2-trichloroethyl | H | Me | F | F | F | F | Cl | H | nonafluoro-2-butyl | H | OCF3 |
| 13-2591 | 2,2,2-trichloroethyl | H | Me | F | F | F | F | Br | H | nonafluoro-2-butyl | H | CF3 |
| 13-2592 | 2,2,2-trichloroethyl | H | Me | F | F | F | F | CF3 | H | nonafluoro-2-butyl | H | CF3 |
| 13-2593 | 2,2,2-trichloroethyl | H | Me | H | CN | H | H | F | H | heptafluoroisopropyl | H | OCF3 |
| 13-2594 | 2,2,2-trichloroethyl | H | Me | H | CN | H | H | F | H | nonafluoro-2-butyl | H | OCF3 |
| 13-2605 | 2,2,2-trichloroethyl | H | Me | H | CN | H | H | Cl | H | heptafluoroisopropyl | H | OCF3 |
| 13-2634 | 2,2,2-trichloroethyl | H | Me | H | CN | H | H | Cl | H | nonafluoro-2-butyl | H | OCF3 |
| 13-2663 | 2,2,2-trichloroethyl | H | Me | H | CN | H | H | Br | H | heptafluoroisopropyl | H | OCF3 |
| 13-2692 | 2,2,2-trichloroethyl | H | Me | H | CN | H | H | Br | H | nonafluoro-2-butyl | H | OCF3 |
| 13-2721 | 2,2,2-trichloroethyl | H | Me | H | CN | H | H | I | H | heptafluoroisopropyl | H | OCF3 |
| 13-2750 | 2,2,2-trichloroethyl | H | Me | H | CN | H | H | I | H | nonafluoro-2-butyl | H | OCF3 |
| 13-2769 | 2,2,2-trichloroethyl | H | Me | H | CN | H | H | F | H | heptafluoroisopropyl | H | CF3 |
| 13-2770 | 2,2,2-trichloroethyl | H | Me | H | CN | H | H | F | H | nonafluoro-2-butyl | H | CF3 |
| 13-2781 | 2,2,2-trichloroethyl | H | Me | H | CN | H | H | Cl | H | heptafluoroisopropyl | H | CF3 |
| 13-2810 | 2,2,2-trichloroethyl | H | Me | H | CN | H | H | Cl | H | nonafluoro-2-butyl | H | CF3 |
| 13-2839 | 2,2,2-trichloroethyl | H | Me | H | CN | H | H | Br | H | heptafluoroisopropyl | H | CF3 |
| 13-2868 | 2,2,2-trichloroethyl | H | Me | H | CN | H | H | Br | H | nonafluoro-2-butyl | H | CF3 |
| 13-2897 | 2,2,2-trichloroethyl | H | Me | H | CN | H | H | I | H | heptafluoroisopropyl | H | CF3 |
| 13-2926 | 2,2,2-trichloroethyl | H | Me | H | CN | H | H | I | H | nonafluoro-2-butyl | H | CF3 |
| 13-2955 | 2,2,2-trichloroethyl | H | Me | H | CN | H | H | OCF3 | H | heptafluoroisopropyl | H | OCF3 |
| 13-2984 | 2,2,2-trichloroethyl | H | Me | H | CN | H | H | OCF3 | H | nonafluoro-2-butyl | H | OCF3 |
| 13-3013 | 2,2,2-trichloroethyl | H | Me | H | CN | H | H | CF3 | H | heptafluoroisopropyl | H | OCF3 |
| 13-3042 | 2,2,2-trichloroethyl | H | Me | H | CN | H | H | CF3 | H | nonafluoro-2-butyl | H | OCF3 |
| 13-3071 | 2,2,2-trichloroethyl | H | Me | H | CN | H | H | CF3 | H | heptafluoroisopropyl | H | CF3 |
| 13-3100 | 2,2,2-trichloroethyl | H | Me | H | CN | H | H | CF3 | H | nonafluoro-2-butyl | H | CF3 |
| 13-3119 | 2,2,2-trichloroethyl | H | Me | F | CN | H | H | F | H | heptafluoroisopropyl | H | F |
| 13-3120 | 2,2,2-trichloroethyl | H | Me | F | CN | H | H | F | H | nonafluoro-2-butyl | H | F |
| 13-3131 | 2,2,2-trichloroethyl | H | Me | F | CN | H | H | Cl | H | heptafluoroisopropyl | H | Cl |
| 13-3160 | 2,2,2-trichloroethyl | H | Me | F | CN | H | H | Cl | H | nonafluoro-2-butyl | H | Cl |
| 13-3189 | 2,2,2-trichloroethyl | H | Me | F | CN | H | H | Br | H | heptafluoroisopropyl | H | Br |
| 13-3218 | 2,2,2-trichloroethyl | H | Me | F | CN | H | H | Br | H | nonafluoro-2-butyl | H | Br |
| 13-3247 | 2,2,2-trichloroethyl | H | Me | F | CN | H | H | I | H | heptafluoroisopropyl | H | I |
| 13-3276 | 2,2,2-trichloroethyl | H | Me | F | CN | H | H | I | H | nonafluoro-2-butyl | H | I |
| 13-3298 | 2,2,2-trichloroethyl | H | Me | F | CN | H | H | Cl | H | heptafluoroisopropyl | H | Br |
| 13-3307 | 2,2,2-trichloroethyl | H | Me | F | CN | H | H | F | H | heptafluoroisopropyl | H | OCF3 |
| 13-3308 | 2,2,2-trichloroethyl | H | Me | F | CN | H | H | F | H | nonafluoro-2-butyl | H | OCF3 |
| 13-3319 | 2,2,2-trichloroethyl | H | Me | F | CN | H | H | Cl | H | heptafluoroisopropyl | H | OCF3 |
| 13-3348 | 2,2,2-trichloroethyl | H | Me | F | CN | H | H | Cl | H | nonafluoro-2-butyl | H | OCF3 |
| 13-3377 | 2,2,2-trichloroethyl | H | Me | F | CN | H | H | Br | H | heptafluoroisopropyl | H | OCF3 |
| 13-3406 | 2,2,2-trichloroethyl | H | Me | F | CN | H | H | Br | H | nonafluoro-2-butyl | H | OCF3 |
| 13-3435 | 2,2,2-trichloroethyl | H | Me | F | CN | H | H | I | H | heptafluoroisopropyl | H | OCF3 |
| 13-3464 | 2,2,2-trichloroethyl | H | Me | F | CN | H | H | I | H | nonafluoro-2-butyl | H | OCF3 |
| 13-3483 | 2,2,2-trichloroethyl | H | Me | F | CN | H | H | F | H | heptafluoroisopropyl | H | CF3 |
| 13-3484 | 2,2,2-trichloroethyl | H | Me | F | CN | H | H | F | H | nonafluoro-2-butyl | H | CF3 |
| 13-3495 | 2,2,2-trichloroethyl | H | Me | F | CN | H | H | Cl | H | heptafluoroisopropyl | H | CF3 |
| 13-3524 | 2,2,2-trichloroethyl | H | Me | F | CN | H | H | Cl | H | nonafluoro-2-butyl | H | CF3 |
| 13-3553 | 2,2,2-trichloroethyl | H | Me | F | CN | H | H | Br | H | heptafluoroisopropyl | H | CF3 |
| 13-3582 | 2,2,2-trichloroethyl | H | Me | F | CN | H | H | Br | H | nonafluoro-2-butyl | H | CF3 |
| 13-3611 | 2,2,2-trichloroethyl | H | Me | F | CN | H | H | I | H | heptafluoroisopropyl | H | CF3 |

TABLE 13-continued

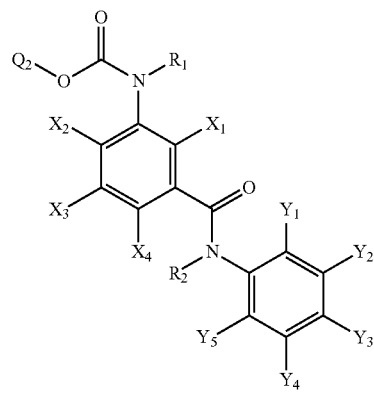

| compound number | $Q_2$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 13-3640 | 2,2,2-trichloroethyl | H | Me | F | CN | H | H | I | H | nonafluoro-2-butyl | H | CF3 |
| 13-3669 | 2,2,2-trichloroethyl | H | Me | F | CN | H | H | OCF3 | H | heptafluoroisopropyl | H | OCF3 |
| 13-3698 | 2,2,2-trichloroethyl | H | Me | F | CN | H | H | OCF3 | H | nonafluoro-2-butyl | H | OCF3 |
| 13-3727 | 2,2,2-trichloroethyl | H | Me | F | CN | H | H | CF3 | H | heptafluoroisopropyl | H | OCF3 |
| 13-3756 | 2,2,2-trichloroethyl | H | Me | F | CN | H | H | CF3 | H | nonafluoro-2-butyl | H | OCF3 |
| 13-3785 | 2,2,2-trichloroethyl | H | Me | F | CN | H | H | CF3 | H | heptafluoroisopropyl | H | CF3 |
| 13-3814 | 2,2,2-trichloroethyl | H | Me | F | CN | H | H | CF3 | H | nonafluoro-2-butyl | H | CF3 |
| 13-3833 | 2,2,2-trichloroethyl | H | Me | F | CN | F | H | F | H | heptafluoroisopropyl | H | F |
| 13-3834 | 2,2,2-trichloroethyl | H | Me | F | CN | F | H | F | H | nonafluoro-2-butyl | H | F |
| 13-3845 | 2,2,2-trichloroethyl | H | Me | F | CN | F | H | Cl | H | heptafluoroisopropyl | H | Cl |
| 13-3874 | 2,2,2-trichloroethyl | H | Me | F | CN | F | H | Cl | H | nonafluoro-2-butyl | H | Cl |
| 13-3903 | 2,2,2-trichloroethyl | H | Me | F | CN | F | H | Br | H | heptafluoroisopropyl | H | Br |
| 13-3932 | 2,2,2-trichloroethyl | H | Me | F | CN | F | H | Br | H | nonafluoro-2-butyl | H | Br |
| 13-3961 | 2,2,2-trichloroethyl | H | Me | F | CN | F | H | I | H | heptafluoroisopropyl | H | I |
| 13-3990 | 2,2,2-trichloroethyl | H | Me | F | CN | F | H | I | H | nonafluoro-2-butyl | H | I |
| 13-4012 | 2,2,2-trichloroethyl | H | Me | F | CN | F | H | Cl | H | heptafluoroisopropyl | H | Br |
| 13-4021 | 2,2,2-trichloroethyl | H | Me | F | CN | F | H | F | H | heptafluoroisopropyl | H | OCF3 |
| 13-4022 | 2,2,2-trichloroethyl | H | Me | F | CN | F | H | F | H | nonafluoro-2-butyl | H | OCF3 |
| 13-4033 | 2,2,2-trichloroethyl | H | Me | F | CN | F | H | Cl | H | heptafluoroisopropyl | H | OCF3 |
| 13-4062 | 2,2,2-trichloroethyl | H | Me | F | CN | F | H | Cl | H | nonafluoro-2-butyl | H | OCF3 |
| 13-4091 | 2,2,2-trichloroethyl | H | Me | F | CN | F | H | Br | H | heptafluoroisopropyl | H | OCF3 |
| 13-4120 | 2,2,2-trichloroethyl | H | Me | F | CN | F | H | Br | H | nonafluoro-2-butyl | H | OCF3 |
| 13-4149 | 2,2,2-trichloroethyl | H | Me | F | CN | F | H | I | H | heptafluoroisopropyl | H | OCF3 |
| 13-4178 | 2,2,2-trichloroethyl | H | Me | F | CN | F | H | I | H | nonafluoro-2-butyl | H | OCF3 |
| 13-4197 | 2,2,2-trichloroethyl | H | Me | F | CN | F | H | F | H | heptafluoroisopropyl | H | CF3 |
| 13-4198 | 2,2,2-trichloroethyl | H | Me | F | CN | F | H | F | H | nonafluoro-2-butyl | H | CF3 |
| 13-4209 | 2,2,2-trichloroethyl | H | Me | F | CN | F | H | Cl | H | heptafluoroisopropyl | H | CF3 |
| 13-4238 | 2,2,2-trichloroethyl | H | Me | F | CN | F | H | Cl | H | nonafluoro-2-butyl | H | CF3 |
| 13-4267 | 2,2,2-trichloroethyl | H | Me | F | CN | F | H | Br | H | heptafluoroisopropyl | H | CF3 |
| 13-4296 | 2,2,2-trichloroethyl | H | Me | F | CN | F | H | Br | H | nonafluoro-2-butyl | H | CF3 |
| 13-4325 | 2,2,2-trichloroethyl | H | Me | F | CN | F | H | I | H | heptafluoroisopropyl | H | CF3 |
| 13-4354 | 2,2,2-trichloroethyl | H | Me | F | CN | F | H | I | H | nonafluoro-2-butyl | H | CF3 |
| 13-4383 | 2,2,2-trichloroethyl | H | Me | F | CN | F | H | OCF3 | H | heptafluoroisopropyl | H | OCF3 |
| 13-4412 | 2,2,2-trichloroethyl | H | Me | F | CN | F | H | OCF3 | H | nonafluoro-2-butyl | H | OCF3 |
| 13-4441 | 2,2,2-trichloroethyl | H | Me | F | CN | F | H | CF3 | H | heptafluoroisopropyl | H | OCF3 |
| 13-4470 | 2,2,2-trichloroethyl | H | Me | F | CN | F | H | CF3 | H | nonafluoro-2-butyl | H | OCF3 |
| 13-4499 | 2,2,2-trichloroethyl | H | Me | F | CN | F | H | CF3 | H | heptafluoroisopropyl | H | CF3 |
| 13-4528 | 2,2,2-trichloroethyl | H | Me | F | CN | F | H | CF3 | H | nonafluoro-2-butyl | H | CF3 |

TABLE 14

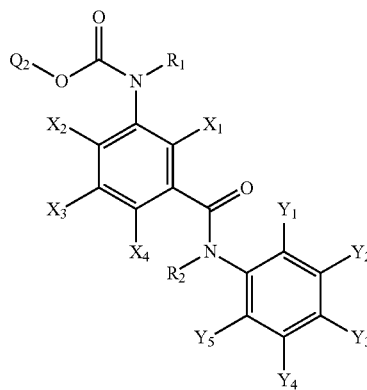

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 14-1 | 2,2,2-trichloroethyl | Me | Me | H | H | H | H | F | H | heptafluoroisopropyl | H | OCF3 |
| 14-2 | 2,2,2-trichloroethyl | Me | Me | H | H | H | H | F | H | nonafluoro-2-butyl | H | OCF3 |
| 14-13 | 2,2,2-trichloroethyl | Me | Me | H | H | H | H | Cl | H | heptafluoroisopropyl | H | OCF3 |
| 14-42 | 2,2,2-trichloroethyl | Me | Me | H | H | H | H | Cl | H | nonafluoro-2-butyl | H | OCF3 |
| 14-71 | 2,2,2-trichloroethyl | Me | Me | H | H | H | H | Br | H | heptafluoroisopropyl | H | OCF3 |
| 14-100 | 2,2,2-trichloroethyl | Me | Me | H | H | H | H | Br | H | nonafluoro-2-butyl | H | OCF3 |
| 14-129 | 2,2,2-trichloroethyl | Me | Me | H | H | H | H | I | H | heptafluoroisopropyl | H | OCF3 |
| 14-158 | 2,2,2-trichloroethyl | Me | Me | H | H | H | H | I | H | nonafluoro-2-butyl | H | OCF3 |
| 14-373 | 2,2,2-trichloroethyl | Me | Me | H | H | H | H | F | H | heptafluoroisopropyl | H | CF3 |
| 14-374 | 2,2,2-trichloroethyl | Me | Me | H | H | H | H | F | H | nonafluoro-2-butyl | H | CF3 |
| 14-385 | 2,2,2-trichloroethyl | Me | Me | H | H | H | H | Cl | H | heptafluoroisopropyl | H | CF3 |
| 14-414 | 2,2,2-trichloroethyl | Me | Me | H | H | H | H | Cl | H | nonafluoro-2-butyl | H | CF3 |
| 14-443 | 2,2,2-trichloroethyl | Me | Me | H | H | H | H | Br | H | heptafluoroisopropyl | H | CF3 |
| 14-472 | 2,2,2-trichloroethyl | Me | Me | H | H | H | H | Br | H | nonafluoro-2-butyl | H | CF3 |
| 14-501 | 2,2,2-trichloroethyl | Me | Me | H | H | H | H | I | H | heptafluoroisopropyl | H | CF3 |
| 14-530 | 2,2,2-trichloroethyl | Me | Me | H | H | H | H | I | H | nonafluoro-2-butyl | H | CF3 |
| 14-755 | 2,2,2-trichloroethyl | Me | Me | H | H | H | H | OCF3 | H | heptafluoroisopropyl | H | OCF3 |
| 14-784 | 2,2,2-trichloroethyl | Me | Me | H | H | H | H | OCF3 | H | nonafluoro-2-butyl | H | OCF3 |
| 14-813 | 2,2,2-trichloroethyl | Me | Me | H | H | H | H | CF3 | H | heptafluoroisopropyl | H | OCF3 |
| 14-842 | 2,2,2-trichloroethyl | Me | Me | H | H | H | H | CF3 | H | nonafluoro-2-butyl | H | OCF3 |
| 14-871 | 2,2,2-trichloroethyl | Me | Me | H | H | H | H | CF3 | H | heptafluoroisopropyl | H | CF3 |
| 14-900 | 2,2,2-trichloroethyl | Me | Me | H | H | H | H | CF3 | H | nonafluoro-2-butyl | H | CF3 |
| 14-1115 | 2,2,2-trichloroethyl | Me | Me | F | H | H | H | F | H | heptafluoroisopropyl | H | F |
| 14-1116 | 2,2,2-trichloroethyl | Me | Me | F | H | H | H | Cl | H | heptafluoroisopropyl | H | Cl |
| 14-1117 | 2,2,2-trichloroethyl | Me | Me | F | H | H | H | Br | H | heptafluoroisopropyl | H | Br |
| 14-1118 | 2,2,2-trichloroethyl | Me | Me | F | H | H | H | I | H | heptafluoroisopropyl | H | I |
| 14-1119 | 2,2,2-trichloroethyl | Me | Me | F | H | H | H | F | H | heptafluoroisopropyl | H | OCF3 |
| 14-1120 | 2,2,2-trichloroethyl | Me | Me | F | H | H | H | F | H | nonafluoro-2-butyl | H | OCF3 |
| 14-1131 | 2,2,2-trichloroethyl | Me | Me | F | H | H | H | Cl | H | heptafluoroisopropyl | H | OCF3 |
| 14-1160 | 2,2,2-trichloroethyl | Me | Me | F | H | H | H | Cl | H | nonafluoro-2-butyl | H | OCF3 |
| 14-1189 | 2,2,2-trichloroethyl | Me | Me | F | H | H | H | Br | H | heptafluoroisopropyl | H | OCF3 |
| 14-1218 | 2,2,2-trichloroethyl | Me | Me | F | H | H | H | Br | H | nonafluoro-2-butyl | H | OCF3 |
| 14-1247 | 2,2,2-trichloroethyl | Me | Me | F | H | H | H | I | H | heptafluoroisopropyl | H | OCF3 |
| 14-1276 | 2,2,2-trichloroethyl | Me | Me | F | H | H | H | I | H | nonafluoro-2-butyl | H | OCF3 |
| 14-1491 | 2,2,2-trichloroethyl | Me | Me | F | H | H | H | F | H | heptafluoroisopropyl | H | CF3 |
| 14-1492 | 2,2,2-trichloroethyl | Me | Me | F | H | H | H | F | H | nonafluoro-2-butyl | H | CF3 |
| 14-1498 | 2-iodoethyl | Me | Et | F | H | H | H | Cl | H | heptafluoroisopropyl | H | CF3 |
| 14-1499 | 2-cyanoethyl | Et | Me | F | H | H | H | Cl | H | heptafluoroisopropyl | H | C2F5 |
| 14-1503 | 2,2,2-trichloroethyl | Me | Me | F | H | H | H | Cl | H | heptafluoroisopropyl | H | CF3 |
| 14-1505 | n-propyl | Me | n-Pr | F | H | H | H | Cl | H | pentafluoroethyl | H | CF3 |
| 14-1509 | i-propyl | n-Pr | Me | F | H | H | H | Cl | H | heptafluoroisopropyl | H | n-C3F7 |
| 14-1512 | 1,3-dichloro-2-propyl | Me | Me | F | H | H | H | Cl | H | pentafluoroethyl | H | CF3 |
| 14-1513 | 1-chloro-3-fluoro-2-propyl | i-Pr | Me | F | H | H | H | Cl | H | heptafluoroisopropyl | H | CF3 |
| 14-1515 | n-butyl | Me | i-Pr | F | H | H | H | Cl | H | heptafluoroisopropyl | H | CF3 |
| 14-1517 | 1-butyl | CH2CH=CH2 | Me | F | H | H | H | Cl | H | heptafluoroisopropyl | H | CF3 |
| 14-1518 | s-butyl | Me | CH2CH=CH2 | F | H | H | H | Cl | H | heptafluoroisopropyl | H | CF3 |
| 14-1519 | vinyl | Me | CN | F | H | H | H | Cl | H | heptafluoroisopropyl | H | CF3 |
| 14-1523 | ethyl | Me | Me | F | H | H | H | Cl | H | nonafluoro-2-butyl | H | i-C3F7 |
| 14-1528 | 2-cyanoethyl | CN | Me | F | H | H | H | Cl | H | nonafluoro-2-butyl | H | CF3 |
| 14-1532 | 2,2,2-trichloroethyl | Me | Me | F | H | H | H | Cl | H | nonafluoro-2-butyl | H | CF3 |
| 14-1533 | 2,2,2-tribromoethyl | Me | CH2C≡CH | F | H | H | H | Cl | H | nonafluoro-2-butyl | H | CF3 |
| 14-1534 | n-propyl | CH2C≡CH | Me | F | H | H | H | Cl | H | nonafluoro-2-butyl | H | CF3 |
| 14-1544 | n-butyl | Me | NH2 | F | H | H | H | Cl | H | nonafluoro-2-butyl | H | CF3 |
| 14-1546 | i-butyl | NH2 | Me | F | H | H | H | Cl | H | nonafluoro-2-butyl | H | CF3 |
| 14-1557 | 2-cyanoethyl | Me | C(O)OMe | F | H | H | H | Br | H | heptafluoroisopropyl | H | C2F5 |
| 14-1561 | 2,2,2-trichloroethyl | Me | Me | F | H | H | H | Br | H | heptafluoroisopropyl | H | CF3 |
| 14-1563 | n-propyl | C(O)OMe | Me | F | H | H | H | Br | H | heptafluoroisopropyl | H | CF3 |

TABLE 14-continued

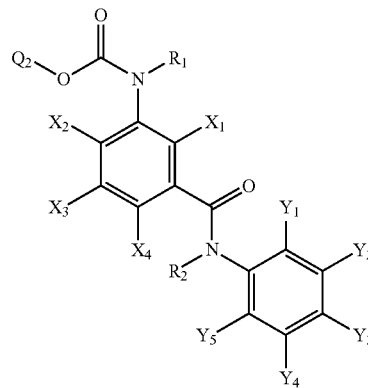

| compound number | Q2 | R1 | R2 | X1 | X2 | X3 | X4 | Y1 | Y2 | Y3 | Y4 | Y5 |
|---|---|---|---|---|---|---|---|---|---|---|---|---|
| 14-1568 | 1,2-difluoro-2-propyl | Me | Me | F | H | H | H | Br | H | heptafluoroisopropyl | H | n-C3F7 |
| 14-1574 | 4,4,4-trifluoro-n-butyl | Me | Me | F | H | H | H | Br | H | heptafluoroisopropyl | H | CF3 |
| 14-1575 | i-butyl | Me | C(O)O(O)OMe | F | H | H | H | Br | H | heptafluoroisopropyl | H | CF3 |
| 14-1577 | vinyl | C(O)C(O)OMe | Me | F | H | H | H | Br | H | heptafluoroisopropyl | H | CF3 |
| 14-1586 | 2-cyanoethyl | Me | C(O)OEt | F | H | H | H | Br | H | nonafluoro-2-butyl | H | CF3 |
| 14-1590 | 2,2,2-trichloroethyl | Me | Me | F | H | H | H | Br | H | nonafluoro-2-butyl | H | CF3 |
| 14-1592 | n-propyl | C(O)OEt | Me | F | H | H | H | Br | H | nonafluoro-2-butyl | H | CF3 |
| 14-1595 | 3-bromo-n-propyl | Me | C(O)Me | F | H | H | H | Br | H | nonafluoro-2-butyl | H | CF3 |
| 14-1596 | i-propyl | C(O)Me | Me | F | H | H | H | Br | H | nonafluoro-2-butyl | H | CF3 |
| 14-1603 | 4,4,4-trifluoro-n-butyl | Me | Me | F | H | H | H | Br | H | nonafluoro-2-butyl | H | CF3 |
| 14-1604 | i-butyl | Me | C(O)C(O)OEt | F | H | H | H | Br | H | nonafluoro-2-butyl | H | CF3 |
| 14-1608 | phenyl | C(O)O(O)OEt | Me | F | H | H | H | Br | H | nonafluoro-2-butyl | H | i-C3F7 |
| 14-1619 | 2,2,2-trichloroethyl | Me | Me | F | H | H | H | I | H | heptafluoroisopropyl | H | CF3 |
| 14-1621 | n-propyl | Me | C(O)Et | F | H | H | H | I | H | heptafluoroisopropyl | H | CF3 |
| 14-1624 | 3-bromo-n-propyl | C(O)Et | Me | F | H | H | H | I | H | heptafluoroisopropyl | H | C2F5 |
| 14-1632 | 4,4,4-trifluoro-n-butyl | Me | Me | F | H | H | H | I | H | heptafluoroisopropyl | H | CF3 |
| 14-1633 | i-butyl | Me | S(O)2Me | F | H | H | H | I | H | heptafluoroisopropyl | H | CF3 |
| 14-1636 | benzyl | S(O)2Me | Me | F | H | H | H | I | H | heptafluoroisopropyl | H | CF3 |
| 14-1643 | 2-iodoethyl | Me | S(O)2Et | F | H | H | H | I | H | nonafluoro-2-butyl | H | CF3 |
| 14-1644 | 2-cyanoethyl | S(O)2Et | Me | F | H | H | H | I | H | nonafluoro-2-butyl | H | CF3 |
| 14-1648 | 2,2,2-trichloroethyl | Me | Me | F | H | H | H | I | H | nonafluoro-2-butyl | H | CF3 |
| 14-1649 | 2,2,2-tribromoethyl | Me | CH2Ph | F | H | H | H | I | H | nonafluoro-2-butyl | H | CF3 |
| 14-1650 | n-propyl | CH2Ph | Me | F | H | H | H | I | H | nonafluoro-2-butyl | H | n-C3F7 |
| 14-1654 | i-proPyl | CH2(3-Py) | Me | H | H | H | H | I | H | nonafluoro-2-butyl | H | CF3 |
| 14-1660 | n-butyl | Me | CH2(3-Py) | F | H | H | H | I | H | nonafluoro-2-butyl | H | CF3 |
| 14-1661 | 4,4,4-trifluoro-n-butyl | Me | Me | F | H | H | H | I | H | nonafluoro-2-butyl | H | CF3 |
| 14-1663 | s-butyl | CH2(3-Py—N-oxide) | Me | F | H | H | H | I | H | nonafluoro-2-butyl | H | CF3 |
| 14-1664 | vinyl | Me | Me | F | H | H | H | I | H | nonafluoro-2-butyl | H | i-C3F7 |
| 14-1666 | phenyl | Me | CH2(3-Py—N-oxide) | F | H | H | H | I | H | nonafluoro-2-butyl | H | CF3 |
| 14-1667 | 2,2,2-trichloroethyl | Et | Et | F | H | H | H | I | H | nonafluoro-2-butyl | H | CF3 |
| 14-1668 | 2,2,2-trichloroethyl | Et | n-Pr | F | H | H | H | I | H | nonafluoro-2-butyl | H | CF3 |
| 14-1669 | 2,2,2-thchloroethyl | Et | i-Pr | F | H | H | H | I | H | nonafluoro-2-butyl | H | CF3 |
| 14-1670 | 2,2,2-trichloroethyl | Et | CH2CH=CH2 | F | H | H | H | I | H | nonafluoro-2-butyl | H | CF3 |
| 14-1671 | 2,2,2-trichloroethyl | Et | CN | F | H | H | H | I | H | nonafluoro-2-butyl | H | CF3 |
| 14-1672 | 2,2,2-trichloroethyl | Et | CH2C≡CH | F | H | H | H | I | H | nonafluoro-2-butyl | H | CF3 |
| 14-1673 | 2,2,2-trichloroethyl | Et | NH2 | F | H | H | H | I | H | nonafluoro-2-butyl | H | CF3 |
| 14-1674 | 2,2,2-trichloroethyl | Et | C(O)OMe | F | H | H | H | I | H | nonafluoro-2-butyl | H | CF3 |
| 14-1675 | 2,2,2-trichloroethyl | Et | C(O)C(O)OMe | F | H | H | H | I | H | nonafluoro-2-butyl | H | CF3 |
| 14-1676 | 2,2,2-trichloroethyl | Et | C(O)Me | F | H | H | H | I | H | nonafluoro-2-butyl | H | CF3 |
| 14-1677 | 2,2,2-trichloroethyl | Et | S(O)2Me | F | H | H | H | I | H | nonafluoro-2-butyl | H | CF3 |
| 14-1678 | 2,2,2-trichloroethyl | Et | CH2Ph | F | H | H | H | I | H | nonafluoro-2-butyl | H | CF3 |
| 14-1679 | 2,2,2-trichloroethyl | Et | CH2(3-Py) | F | H | H | H | I | H | nonafluoro-2-butyl | H | CF3 |
| 14-1680 | 2,2,2-trichloroethyl | Et | CH2(3-Py—N-oxide) | F | H | H | H | I | H | nonafluoro-2-butyl | H | CF3 |
| 14-1681 | 2,2,2-trichloroethyl | n-Pr | Et | F | H | H | H | I | H | nonafluoro-2-butyl | H | CF3 |
| 14-1682 | 2,2,2-trichloroethyl | n-Pr | n-Pr | F | H | H | H | I | H | nonafluoro-2-butyl | H | CF3 |
| 14-1683 | 2,2,2-trichloroethyl | n-Pr | i-Pr | F | H | H | H | I | H | nonafluoro-2-butyl | H | CF3 |
| 14-1684 | 2,2,2-trichloroethyl | n-Pr | CH2CH=CH2 | F | H | H | H | I | H | nonafluoro-2-butyl | H | CF3 |
| 14-1685 | 2,2,2-trichloroethyl | n-Pr | CN | F | H | H | H | I | H | nonafluoro-2-butyl | H | CF3 |
| 14-1686 | 2,2,2-trichloroethyl | n-Pr | CH2C≡CH | F | H | H | H | I | H | nonafluoro-2-butyl | H | CF3 |
| 14-1687 | 2,2,2-trichloroethyl | n-Pr | NH2 | F | H | H | H | I | H | nonafluoro-2-butyl | H | CF3 |
| 14-1688 | 2,2,2-trichloroethyl | n-Pr | C(O)OMe | F | H | H | H | I | H | heptafluoroisopropyl | H | CF3 |
| 14-1689 | 2,2,2-thchloroethyl | n-Pr | C(O)C(O)OMe | F | H | H | H | I | H | nonafluoro-2-butyl | H | CF3 |
| 14-1690 | 2,2,2-trichloroethyl | n-Pr | C(O)Me | F | H | H | H | I | H | nonafluoro-2-butyl | H | CF3 |
| 14-1691 | 2,2,2-trichloroethyl | n-Pr | S(O)2Me | F | H | H | H | I | H | nonafluoro-2-butyl | H | CF3 |

TABLE 14-continued

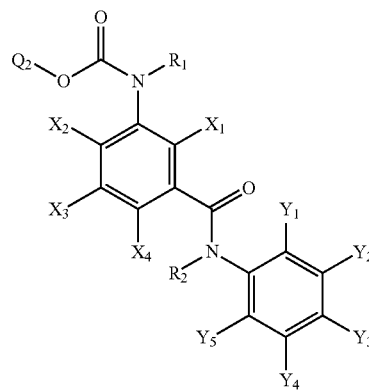

| compound number | Q2 | R1 | R2 | X1 | X2 | X3 | X4 | Y1 | Y2 | Y3 | Y4 | Y5 |
|---|---|---|---|---|---|---|---|---|---|---|---|---|
| 14-1692 | 2,2,2-trichloroethyl | n-Pr | CH2Ph | F | H | H | H | I | H | nonafluoro-2-butyl | H | CF3 |
| 14-1693 | 2,2,2-trichloroethyl | n-Pr | CH2(3-Py) | F | H | H | H | I | H | nonafluoro-2-butyl | H | CF3 |
| 14-1694 | 2,2,2-trichloroethyl | n-Pr | CH2(3-Py—N-oxide) | F | H | H | H | I | H | nonafluoro-2-butyl | H | CF3 |
| 14-1695 | 2,2,2-trichloroethyl | i-Pr | Et | F | H | H | H | I | H | nonafluoro-2-butyl | H | CF3 |
| 14-1696 | 2,2,2-trichloroethyl | i-Pr | n-Pr | F | H | H | H | I | H | nonafluoro-2-butyl | H | CF3 |
| 14-1697 | 2,2,2-trichloroethyl | i-Pr | i-Pr | F | H | H | H | I | H | nonafluoro-2-butyl | H | CF3 |
| 14-1698 | 2,2,2-trichloroethyl | i-Pr | CH2CH=CH2 | F | H | H | H | I | H | nonafluoro-2-butyl | H | CF3 |
| 14-1699 | 2,2,2-trichloroethyl | i-Pr | CN | F | H | H | H | I | H | nonafluoro-2-butyl | H | CF3 |
| 14-1700 | 2,2,2-trichloroethyl | i-Pr | CH2C≡CH | F | H | H | H | I | H | nonafluoro-2-butyl | H | CF3 |
| 14-1701 | 2,2,2-trichloroethyl | i-Pr | NH2 | F | H | H | H | I | H | nonafluoro-2-butyl | H | CF3 |
| 14-1702 | 2,2,2-trichloroethyl | i-Pr | C(O)OMe | F | H | H | H | I | H | nonafluoro-2-butyl | H | CF3 |
| 14-1703 | 2,2,2-trichloroethyl | i-Pr | C(O)C(O)OMe | F | H | H | H | I | H | nonafluoro-2-ibutyl | H | CF3 |
| 14-1704 | 2,2,2-trichloroethyl | i-Pr | C(O)Me | F | H | H | H | I | H | nonafluoro-2-ibutyl | H | CF3 |
| 14-1705 | 2,2,2-trichloroethyl | i-Pr | S(O)2Me | F | H | H | H | I | H | nonafluoro-2-butyl | H | CF3 |
| 14-1706 | 2,2,2-trichloroethyl | i-Pr | CH2Ph | F | H | H | H | I | H | nonafluoro-2-butyl | H | CF3 |
| 14-1707 | 2,2,2-trichloroethyl | i-Pr | CH2(3-Py) | F | H | H | H | I | H | nonafluoro-2-butyl | H | CF3 |
| 14-1708 | 2,2,2-trichloroethyl | i-Pr | CH2(3-Py—N-oxide) | F | H | H | H | I | H | nonafluoro-2-butyl | H | CF3 |
| 14-1709 | 2,2,2-trichloroetbad | CH2CH=CH2 | Et | F | H | H | H | I | H | nonafluoro-2-butyl | H | CF3 |
| 14-1710 | 2,2,2-trichloroethyl | CH2CH=CH2 | n-Pr | F | H | H | H | I | H | nonafluoro-2-butyl | H | CF3 |
| 14-1711 | 2,2,2-trichloroethyl | CH2CH=CH2 | i-Pr | F | H | H | H | I | H | nonafluoro-2-butyl | H | CF3 |
| 14-1712 | 2,2,2-trichloroethyl | CH2CH=CH2 | CH2CH=CH2 | F | H | H | H | I | H | nonafluoro-2-butyl | H | CF3 |
| 14-1713 | 2,2,2-trichloroethyl | CH2CH=CH2 | CN | F | H | H | H | I | H | nonafluoro-2-butyl | H | CF3 |
| 14-1714 | 2,2,2-trichloroethyl | CH2CH=CH2 | CH2C≡CH | F | H | H | H | I | H | nonafluoro-2-butyl | H | CF3 |
| 14-1715 | 2,2,2-trichloroethyl | CH2CH=CH2 | NH2 | F | H | H | H | I | H | nonafluoro-2-butyl | H | CF3 |
| 14-1716 | 2,2,2-trichloroethyl | CH2CH=CH2 | C(O)OMe | F | H | H | H | I | H | nonafluoro-2-butyl | H | CF3 |
| 14-1717 | 2,2,2-trichloroethyl | CH2CH=CH2 | C(O)C(O)OMe | F | H | H | H | I | H | nonafluoro-2-butyl | H | CF3 |
| 14-1718 | 2,2,2-trichloroethyl | CH2CH=CH2 | C(O)Me | F | H | H | H | I | H | nonafluoro-2-butyl | H | CF3 |
| 14-1719 | 2,2,2-trichloroethyl | CH2CH=CH2 | S(O)2Me | F | H | H | H | I | H | nonafluoro-2-butyl | H | CF3 |
| 14-1720 | 2,2,2-trichloroethyl | CH2CH=CH2 | CH2Ph | F | H | H | H | I | H | nonafluoro-2-butyl | H | CF3 |
| 14-1721 | 2,2,2-trichloroethyl | CH2CH=CH2 | CH2(3-Py) | F | H | H | H | I | H | nonafluoro-2-butyl | H | CF3 |
| 14-1722 | 2,2,2-trichloroethyl | CH2CH=CH2 | CH2(3-Py—N-oxide) | F | H | H | H | I | H | nonafluoro-2-butyl | H | CF3 |
| 14-1723 | 2,2,2-trichloroethyl | CN | Et | F | H | H | H | I | H | nonafluoro-2-butyl | H | CF3 |
| 14-1724 | 2,2,2-trichloroethyl | CN | n-Pr | F | H | H | H | I | H | nonafluoro-2-butyl | H | CF3 |
| 14-1725 | 2,2,2-trichloroethyl | CN | i-Pr | F | H | H | H | I | H | nonafluoro-2-butyl | H | CF3 |
| 14-1726 | 2,2,2-trichloroethyl | CN | CH2CH=CH2 | F | H | H | H | I | H | nonafluoro-2-butyl | H | CF3 |
| 14-1727 | 2,2,2-trichloroethyl | CN | CN | F | H | H | H | I | H | nonafluoro-2-butyl | H | CF3 |
| 14-1728 | 2,2,2-trichloroethyl | CN | CH2C≡CH | F | H | H | H | I | H | nonafluoro-2-butyl | H | CF3 |
| 14-1729 | 2,2,2-trichloroethyl | CN | NH2 | F | H | H | H | I | H | nonafluoro-2-butyl | H | CF3 |
| 14-1730 | 2,2,2-trichloroethyl | CN | C(O)OMe | F | H | H | H | I | H | nonafluoro-2-butyl | H | CF3 |
| 14-1731 | 2,2,2-trichloroethyl | CN | C(O)C(O)OMe | F | H | H | H | I | H | nonafluoro-2-butyl | H | CF3 |
| 14-1732 | 2,2,2-trichloroethyl | CN | C(O)Me | F | H | H | H | I | H | nonafluoro-2-butyl | H | CF3 |
| 14-1733 | 2,2,2-trichloroethyl | CN | S(O)2Me | F | H | H | H | I | H | nonafluoro-2-butyl | H | CF3 |
| 14-1734 | 2,2,2-trichloroethyl | CN | CH2Ph | F | H | H | H | I | H | nonafluoro-2-butyl | H | CF3 |
| 14-1735 | 2,2,2-trichloroethyl | CN | CH2(3-Py) | F | H | H | H | I | H | nonafluoro-2-butyl | H | CF3 |
| 14-1736 | 2,2,2-trichloroethyl | CN | CH2(3-Py—N-oxide) | F | H | H | H | I | H | nonafluoro-2-butyl | H | CF3 |
| 14-1737 | 2,2,2-trichloroethyl | CH2C≡CH | Et | F | H | H | H | I | H | nonafluoro-2-butyl | H | CF3 |
| 14-1738 | 2,2,2-trichloroethyl | CH2C≡CH | n-Pr | F | H | H | H | I | H | nonafluoro-2-butyl | H | CF3 |
| 14-1739 | 2,2,2-trichloroethyl | CH2C≡CH | i-Pr | F | H | H | H | I | H | nonafluoro-2-butyl | H | CF3 |
| 14-1740 | 2,2,2-trichloroethyl | CH2C≡CH | CH2CH=CH2 | F | H | H | H | I | H | nonafluoro-2-butyl | H | CF3 |
| 14-1741 | 2,2,2-trichloroethyl | CH2C≡CH | CN | F | H | H | H | I | H | nonafluoro-2-butyl | H | CF3 |
| 14-1742 | 2,2,2-trichloroethyl | CH2C≡CH | CH2C≡CH | F | H | H | H | I | H | nonafluoro-2-butyl | H | CF3 |
| 14-1743 | 2,2,2-trichloroethyl | CH2C≡CH | NH2 | F | H | H | H | I | H | nonafluoro-2-butyl | H | CF3 |
| 14-1744 | 2,2,2-trichloroethyl | CH2C≡CH | C(O)OMe | F | H | H | H | I | H | nonafluoro-2-butyl | H | CF3 |

TABLE 14-continued

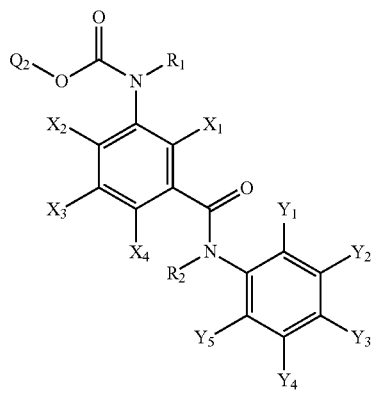

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 14-1745 | 2,2,2-trichloroethyl | CH2C≡CH | C(O)C(O)OMe | F | H | H | H | I | H | nonafluoro-2-butyl | H | CF3 |
| 14-1746 | 2,2,2-trichloroethyl | CH2C≡CH | C(O)Me | F | H | H | H | I | H | nonafluoro-2-butyl | H | CF3 |
| 14-1747 | 2,2,2-trichloroethyl | CH2C≡CH | S(O)2Me | F | H | H | H | I | H | nonafluoro-2-butyl | H | CF3 |
| 14-1748 | 2,2,2-trichloroethyl | CH2C≡CH | CH2Ph | F | H | H | H | I | H | nonafluoro-2-butyl | H | CF3 |
| 14-1749 | 2,2,2-trichloroethyl | CH2C≡CH | CH2(3-Py) | F | H | H | H | I | H | nonafluoro-2-butyl | H | CF3 |
| 14-1750 | 2,2,2-trichloroethyl | CH2C≡CH | CH2(3-Py—N-oxide) | F | H | H | H | I | H | nonafluoro-2-butyl | H | CF3 |
| 14-1751 | 2,2,2-trichloroethyl | NH2 | Et | F | H | H | H | I | H | nonafluoro-2-butyl | H | CF3 |
| 14-1752 | 2,2,2-trichloroethyl | NH2 | n-Pr | F | H | H | H | I | H | nonafluoro-2-butyl | H | CF3 |
| 14-1753 | 2,2,2-trichloroethyl | NH2 | i-Pr | F | H | H | H | I | H | nonafluoro-2-butyl | H | CF3 |
| 14-1754 | 2,2,2-trichloroethyl | NH2 | CH2CH=CH2 | F | H | H | H | I | H | nonafluoro-2-butyl | H | CF3 |
| 14-1755 | 2,2,2-trichloroethyl | NH2 | CN | F | H | H | H | I | H | nonafluoro-2-butyl | H | CF3 |
| 14-1756 | 2,2,2-trichloroethyl | NH2 | CH2C≡CH | F | H | H | H | I | H | nonafluoro-2-butyl | H | CF3 |
| 14-1757 | 2,2,2-trichloroethyl | NH2 | NH2 | F | H | H | H | I | H | nonafluoro-2-butyl | H | CF3 |
| 14-1758 | 2,2,2-trichloreethyl | NH2 | C(O)OMe | F | H | H | H | I | H | nonatluoro-2-butyl | H | CF3 |
| 14-1759 | 2,2,2-trichloroethyl | NH2 | C(O)C(O)OMe | F | H | H | H | I | H | nonafluoro-2-butyl | H | CF3 |
| 14-1760 | 2,2,2-trichloroethyl | NH2 | C(O)Me | F | H | H | H | I | H | nonafluoro-2-butyl | H | CF3 |
| 14-1761 | 2,2,2-trichloroethyl | NH2 | S(O)2Me | F | H | H | H | I | H | nonafluoro-2-butyl | H | CF3 |
| 14-1762 | 2,2,2-trichloroethyl | NH2 | CH2Ph | F | H | H | H | I | H | nonafluoro-2-butyl | H | CF3 |
| 14-1763 | 2,2,2-trichloroethyl | NH2 | CH2(3-Py) | F | H | H | H | I | H | nonafluoro-2-butyl | H | CF3 |
| 14-1764 | 2,2,2-trichloroethyl | NH2 | CH2(3-Py—N-oxide) | F | H | H | H | I | H | nonafluoro-2-butyl | H | CF3 |
| 14-1765 | 2,2,2-trichloroethyl | C(O)OMe | Et | F | H | H | H | I | H | nonafluoro-2-butyl | H | CF3 |
| 14-1766 | 2,2,2-trichloroethyl | C(O)OMe | n-Pr | F | H | H | H | I | H | nonafluoro-2-butyl | H | CF3 |
| 14-1767 | 2,2,2-trichloroethyl | C(O)OMe | F | F | H | H | H | I | H | nonafluoro-2-butyl | H | CF3 |
| 14-1768 | 2,2,2-trichloroethyl | C(O)OMe | CH2CH=CH2 | F | H | H | H | I | H | nonafluoro-2-butyl | H | CF3 |
| 14-1769 | 2,2,2-trichloroethyl | C(O)OMe | CN | F | H | H | H | I | H | nonafluoro-2-butyl | H | CF3 |
| 14-1770 | 2,2,2-trichloroethyl | C(O)OMe | CH2C≡CH | F | H | H | H | I | H | nonafluoro-2-butyl | H | CF3 |
| 14-1771 | 2,2,2-trichloroethyl | C(O)OMe | NH2 | F | H | H | H | I | H | nonafluoro-2-butyl | H | CF3 |
| 14-1772 | 2,2,2-trichloroethyl | C(O)OMe | C(O)OMe | F | H | H | H | I | H | nonafluoro-2-butyl | H | CF3 |
| 14-1773 | 2,2,2-trichloroethyl | C(O)OMe | C(O)C(O)OMe | F | H | H | H | I | H | nonafluoro-2-butyl | H | CF3 |
| 14-1774 | 2,2,2-trichloroethyl | C(O)OMe | C(O)Me | F | H | H | H | I | H | nonafluoro-2-butyl | H | CF3 |
| 14-1775 | 2,2,2-trichloroethyl | C(O)OMe | S(O)2Me | F | H | H | H | I | H | nonafluoro-2-butyl | H | CF3 |
| 14-1776 | 2,2,2-trichloroethyl | C(O)OMe | CH2Ph | F | H | H | H | I | H | nonafluoro-2-butyl | H | CF3 |
| 14-1777 | 2,2,2-trichloroethyl | C(O)OMe | CH2(3-Py) | F | H | H | H | I | H | nonafluoro-2-butyl | H | CF3 |
| 14-1778 | 2,2,2-trichloroethyl | C(O)OMe | CH2(3-Py—N-oxide) | F | H | H | H | I | H | nonafluoro-2-butyl | H | CF3 |
| 14-1779 | 2,2,2-trichloroethyl | C(O)C(O)OMe | Et | F | H | H | H | I | H | nonafluoro-2-butyl | H | CF3 |
| 14-1780 | 2,2,2-trichloroethyl | C(O)C(O)OMe | n-Pr | F | H | H | H | I | H | nonafluoro-2-butyl | H | CF3 |
| 14-1781 | 2,2,2-trichloroethyl | C(O)C(O)OMe | i-Pr | F | H | H | H | I | H | nonafluoro-2-butyl | H | CF3 |
| 14-1782 | 2,2,2-trichloroethyl | C(O)C(O)OMe | CH2CH=CH2 | F | H | H | H | I | H | nonafluoro-2-butyl | H | CF3 |
| 14-1783 | 2,2,2-trichloroethyl | C(O)C(O)OMe | CN | F | H | H | H | I | H | nonafluoro-2-butyl | H | CF3 |
| 14-1784 | 2,2,2-trichloroethyl | C(O)C(O)OMe | CH2C≡CH | F | H | H | H | I | H | nonafluoro-2-butyl | H | CF3 |
| 14-1785 | 2,2,2-trichloroethyl | C(O)C(O)OMe | NH2 | F | H | H | H | I | H | nonafluoro-2-butyl | H | CF3 |
| 14-1786 | 2,2,2-trichloroethyl | C(O)C(O)OMe | C(O)OMe | F | H | H | H | I | H | nonafluoro-2-butyl | H | CF3 |
| 14-1787 | 2,2,2-trichloroethyl | C(O)C(O)OMe | C(O)C(O)OMe | F | H | H | H | I | H | nonafluoro-2-butyl | H | CF3 |
| 14-1788 | 2,2,2-trichloroethyl | C(O)C(O)OMe | C(O)Me | F | H | H | H | I | H | nonafluoro-2-butyl | H | CF3 |
| 14-1789 | 2,2,2-trichloroethyl | C(O)C(O)OMe | S(O)2Me | F | H | H | H | I | H | nonafluoro-2-butyl | H | CF3 |
| 14-1790 | 2,2,2-trichloroethyl | C(O)C(O)OMe | CH2Ph | F | H | H | H | I | H | nonafluoro-2-butyl | H | CF3 |
| 14-1791 | 2,2,2-trichloroethyl | C(O)C(O)OMe | CH2(3-Py) | F | H | H | H | I | H | nonafluoro-2-butyl | H | CF3 |
| 14-1792 | 2,2,2-trichloroethyl | C(O)O(O)OMe | CH2(3-Py—N-oxide) | F | H | H | H | I | H | nonafluoro-2-butyl | H | CF3 |
| 14-1793 | 2,2,2-trichloroethyl | C(O)Me | Et | F | H | H | H | I | H | nonafluoro-2-butyl | H | CF3 |
| 14-1794 | 2,2,2-trichloroethyl | C(O)Me | n-Pr | F | H | H | H | I | H | nonafluoro-2-butyl | H | CF3 |
| 14-1795 | 2,2,2-trichloroethyl | C(O)Me | i-Pr | F | H | H | H | I | H | nonafluoro-2-butyl | H | CF3 |
| 14-1796 | 2,2,2-trichloroethyl | C(O)Me | CH2CH=CH2 | F | H | H | H | I | H | nonafluoro-2-butyl | H | CF3 |
| 14-1797 | 2,2,2-trichloroethyl | C(O)Me | CN | F | H | H | H | I | H | nonafluoro-2-butyl | H | CF3 |

TABLE 14-continued

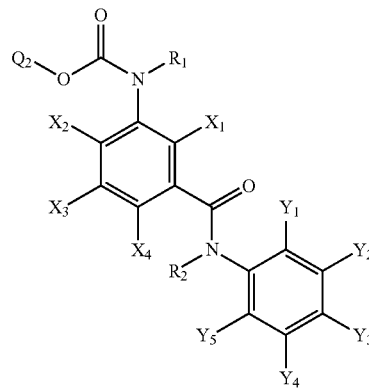

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 14-1798 | 2,2,2-trichloroethyl | C(O)Me | CH2C≡CH | F | H | H | H | I | H | nonafluoro-2-butyl | H | CF3 |
| 14-1799 | 2,2,2-trichloroethyl | C(O)Me | NH2 | F | H | H | H | I | H | nonafluoro-2-butyl | H | CF3 |
| 14-1800 | 2,2,2-trichloroethyl | C(O)Me | C(O)OMe | F | H | H | H | I | H | nonafluoro-2-butyl | H | CF3 |
| 14-1801 | 2,2,2-trichloroethyl | C(O)Me | C(O)C(O)OMe | F | H | H | H | I | H | nonafluoro-2-butyl | H | CF3 |
| 14-1802 | 2,2,2-trichloroethyl | C(O)Me | C(O)Me | F | H | H | H | I | H | nonafluoro-2-butyl | H | CF3 |
| 14-1803 | 2,2,2-trichloroethyl | C(O)Me | S(O)2Me | F | H | H | H | I | H | nonafluoro-2-butyl | H | CF3 |
| 14-1804 | 2,2,2-trichloroethyl | C(O)Me | CH2Ph | F | H | H | H | I | H | nonafluoro-2-butyl | H | CF3 |
| 14-1805 | 2,2,2-trichloroethyl | C(O)Me | CH2(3-Py) | F | H | H | H | I | H | nonafluoro-2-butyl | H | CF3 |
| 14-1806 | 2,2,2-trichloroethyl | C(O)Me | CH2(3-Py—N-oxide) | F | H | H | H | I | H | nonafluoro-2-butyl | H | CF3 |
| 14-1807 | 2,2,2-trichloroethyl | S(O)2Me | Et | F | H | H | H | I | H | nonafluoro-2-butyl | H | CF3 |
| 14-1808 | 2,2,2-trichloroethyl | S(O)2Me | n-Pr | F | H | H | H | I | H | nonafluoro-2-butyl | H | CF3 |
| 14-1809 | 2,2,2-trichloroethyl | S(O)2Me | i-Pr | F | H | H | H | I | H | nonafluoro-2-butyl | H | CF3 |
| 14-1810 | 2,2,2-trichloroethyl | S(O)2Me | CH2CH=CH2 | F | H | H | H | I | H | nonafluoro-2-butyl | H | CF3 |
| 14-1811 | 2,2,2-trichloroethyl | S(O)2Me | CN | F | H | H | H | I | H | nonafluoro-2-butyl | H | CF3 |
| 14-1812 | 2,2,2-trichloroethyl | S(O)2Me | CH2C≡CH | F | H | H | H | I | H | nonafluoro-2-butyl | H | CF3 |
| 14-1813 | 2,2,2-trichloroethyl | S(O)2Me | NH2 | F | H | H | H | I | H | nonafluoro-2-butyl | H | CF3 |
| 14-1814 | 2,2,2-trichloroethyl | S(O)2Me | C(O)OMe | F | H | H | H | I | H | nonafluoro-2-butyl | H | CF3 |
| 14-1815 | 2,2,2-trichloroethyl | S(O)2Me | C(O)C(O)OMe | F | H | H | H | I | H | nonafluoro-2-butyl | H | CF3 |
| 14-1816 | 2,2,2-trichloroethyl | S(O)2Me | C(O)Me | F | H | H | H | I | H | nonafluoro-2-butyl | H | CF3 |
| 14-1817 | 2,2,2-trichloroethyl | S(O)2Me | S(O)2Me | F | H | H | H | I | H | nonafluoro-2-butyl | H | CF3 |
| 14-1818 | 2,2,2-trichloroethyl | S(O)2Me | CH2Ph | F | H | H | H | I | H | nonafluoro-2-butyl | H | CF3 |
| 14-1819 | 2,2,2-trichloroethyl | S(O)2Me | CH2(3-Py) | F | H | H | H | I | H | nonafluoro-2-butyl | H | CF3 |
| 14-1820 | 2,2,2-trichloroethyl | S(O)2Me | CH2(3-Py—N-oxide) | F | H | H | H | I | H | nonafluoro-2-butyl | H | CF3 |
| 14-1821 | 2,2,2-trichloroethyl | CH2Ph | Et | F | H | H | H | I | H | nonafluoro-2-butyl | H | CF3 |
| 14-1822 | 2,2,2-trichloroethyl | CH2Ph | n-Pr | F | H | H | H | I | H | nonafluoro-2-butyl | H | CF3 |
| 14-1823 | 2,2,2-trichloroethyl | CH2Ph | i-Pr | F | H | H | H | I | H | nonafluoro-2-butyl | H | CF3 |
| 14-1824 | 2,2,2-trichloroethyl | CH2Ph | CH2CH=CH2 | F | H | H | H | I | H | nonafluoro-2-butyl | H | CF3 |
| 14-1825 | 2,2,2-trichloroethyl | CH2Ph | CN | F | H | H | H | I | H | nonafluoro-2-butyl | H | CF3 |
| 14-1826 | 2,2,2-trichloroethyl | CH2Ph | CH2C≡CH | F | H | H | H | I | H | nonafluoro-2-butyl | H | CF3 |
| 14-1827 | 2,2,2-trichloroethyl | CH2Ph | NH2 | F | H | H | H | I | H | nonafluoro-2-butyl | H | CF3 |
| 14-1828 | 2,2,2-trichloroethyl | CH2Ph | C(O)OMe | F | H | H | H | I | H | nonafluoro-2-butyl | H | CF3 |
| 14-1829 | 2,2,2-trichloroethyl | CH2Ph | C(O)C(O)OMe | F | H | H | H | I | H | nonafluoro-2-butyl | H | CF3 |
| 14-1830 | 2,2,2-trichloroethyl | CH2Ph | C(O)Me | F | H | H | H | I | H | nonafluoro-2-butyl | H | CF3 |
| 14-1831 | 2,2,2-trichloroethyl | CH2Ph | S(O)2Me | F | H | H | H | I | H | nonafluoro-2-butyl | H | CF3 |
| 14-1832 | 2,2,2-trichloroethyl | CH2Ph | CH2Ph | F | H | H | H | I | H | nonafluoro-2-butyl | H | CF3 |
| 14-1833 | 2,2,2-trichloroethyl | CH2Ph | CH2(3-Py) | F | H | H | H | I | H | nonafluoro-2-butyl | H | CF3 |
| 14-1834 | 2,2,2-trichloroethyl | CH2Ph | CH2(3-Py—N-oxide) | F | H | H | H | I | H | nonafluoro-2-butyl | H | CF3 |
| 14-1835 | 2,2,2-trichloroethyl | CH2(3-Py) | Et | F | H | H | H | I | H | nonafluoro-2-butyl | H | CF3 |
| 14-1836 | 2,2,2-trichloroethyl | CH2(3-Py) | n-Pr | F | H | H | H | I | H | nonafluoro-2-butyl | H | CF3 |
| 14-1837 | 2,2,2-trichloroethyl | CH2(3-Py) | i-Pr | F | H | H | H | I | H | nonafluoro-2-butyl | H | CF3 |
| 14-1838 | 2,2,2-trichloroethyl | CH2(3-Py) | CH2CH=CH2 | F | H | H | H | I | H | nonafluoro-2-butyl | H | CF3 |
| 14-1839 | 2,2,2-trichloroethyl | CH2(3-Py) | CN | F | H | H | H | I | H | nonafluoro-2-butyl | H | CF3 |
| 14-1840 | 2,2,2-trichloroethyl | CH2(3-Py) | CH2C≡CH | F | H | H | H | I | H | nonafluoro-2-butyl | H | CF3 |
| 14-1841 | 2,2,2-trichloroethyl | CH2(3-Py) | NH2 | F | H | H | H | I | H | nonafluoro-2-butyl | H | CF3 |
| 14-1842 | 2,2,2-trichloroethyl | CH2(3-Py) | C(O)OMe | F | H | H | H | I | H | nonafluoro-2-butyl | H | CF3 |
| 14-1843 | 2,2,2-trichloroethyl | CH2(3-Py) | C(O)C(O)OMe | F | H | H | H | I | H | nonafluoro-2-butyl | H | CF3 |
| 14-1844 | 2,2,2-trichloroethyl | CH2(3-Py) | C(O)Me | F | H | H | H | I | H | nonafluoro-2-butyl | H | CF3 |
| 14-1845 | 2,2,2-trichloroethyl | CH2(3-Py) | S(O)2Me | F | H | H | H | I | H | nonafluoro-2-butyl | H | CF3 |
| 14-1846 | 2,2,2-trichloroethyl | CH2(3-Py) | CH2Ph | F | H | H | H | I | H | nonafluoro-2-butyl | H | CF3 |
| 14-1847 | 2,2,2-trichloroethyl | CH2(3-Py) | CH2(3-Py) | F | H | H | H | I | H | nonafluoro-2-butyl | H | CF3 |
| 14-1848 | 2,2,2-trichloroethyl | CH2(3-Py) | CH2(3-Py—N-oxide) | F | H | H | H | I | H | nonafluoro-2-butyl | H | CF3 |
| 14-1849 | 2,2,2-trichloroethyl | CH2(3-Py—N-oxide) | Et | F | H | H | H | I | H | nonafluoro-2-butyl | H | CF3 |

TABLE 14-continued

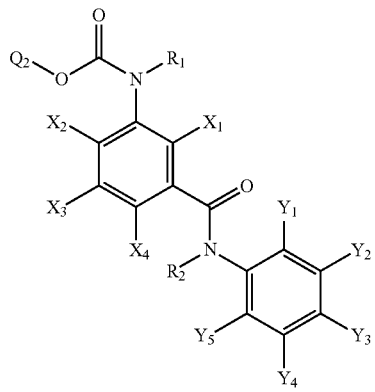

| compound number | Q$_2$ | R$_1$ | R$_2$ | X$_1$ | X$_2$ | X$_3$ | X$_4$ | Y$_1$ | Y$_2$ | Y$_3$ | Y$_4$ | Y$_5$ |
|---|---|---|---|---|---|---|---|---|---|---|---|---|
| 14-1850 | 2,2,2-trichloroethyl | CH2(3Py—N-oxide) | n-Pr | F | H | H | H | I | H | nonafluoro-2-butyl | H | CF3 |
| 14-1851 | 2,2,2-trichloroethyl | CH2(3-Py—N-oxide) | i-Pr | F | H | H | H | I | H | nonafluoro-2-butyl | H | CF3 |
| 14-1852 | 2,2,2-trichloroethyl | CH2(3-Py—N-oxide) | CH2CH=CH2 | F | H | H | H | I | H | nonafluoro-2-butyl | H | CF3 |
| 14-1853 | 2,2,2-trichloroethyl | CH2(3-Py—N-oxide) | CN | F | H | H | H | I | H | nonafluoro-2-butyl | H | CF3 |
| 14-1854 | 2,2,2-trichloroethyl | CH2(3-Py—N-oxide) | CH2C≡CH | F | H | H | H | I | H | nonafluoro-2-butyl | H | CF3 |
| 14-1855 | 2,2,2-trichloroethyl | CH2(3-Py—N-oxide) | NH2 | F | H | H | H | I | H | nonafluoro-2-butyl | H | CF3 |
| 14-1856 | 2,2,2-trichloroethyl | CH2(3-Py—N-oxide) | C(O)OMe | F | H | H | H | I | H | nonafluoro-2-butyl | H | CF3 |
| 14-1857 | 2,2,2-trichloroethyl | CH2(3-Py—N-oxide) | C(O)C(O)OMe | F | H | H | H | I | H | nonafluoro-2-butyl | H | CF3 |
| 14-1858 | 2,2,2-trichloroethyl | CH2(3-Py—N-oxide) | C(O)Me | F | H | H | H | I | H | nonafluoro-2-butyl | H | CF3 |
| 14-1859 | 2,2,2-trichloroethyl | CH2(3-Py—N-oxide) | S(O)2Me | F | H | H | H | I | H | nonafluoro-2-butyl | H | CF3 |
| 14-1860 | 2,2,2-trichloroethyl | CH2(3-Py—N-oxide) | CH2Ph | F | H | H | H | I | H | nonafluoro-2-butyl | H | CF3 |
| 14-1861 | 2,2,2-trichloroethyl | CH2(3-Py—N-oxide) | CH2(3-Py) | F | H | H | H | I | H | nonafluoro-2-butyl | H | CF3 |
| 14-1862 | 2,2,2-trichloroethyl | CH2(3-Py—N-oxide) | CH2(3-Py—N-oxide) | F | H | H | H | I | H | nonafluoro-2-butyl | H | CF3 |
| 14-1873 | 2,2,2-trichloroethyl | Me | Me | F | H | H | H | OCF3 | H | heptafluoroisopropyl | H | OCF3 |
| 14-1902 | 2,2,2-trichloroethyl | Me | Me | F | H | H | H | OCF3 | H | nonafluoro-2-butyl | H | OCF3 |
| 14-1931 | 2,2,2-trichloroethyl | Me | Me | F | H | H | H | CF3 | H | heptafluoroisopropyl | H | OCF3 |
| 14-1960 | 2,2,2-trichloroethyl | Me | Me | F | H | H | H | CF3 | H | nonafluoro-2-butyl | H | OCF3 |
| 14-1989 | 2,2,2-trichloroethyl | Me | Me | F | H | H | H | CF3 | H | heptafluoroisopropyl | H | CF3 |
| 14-2019 | 2,2,2-tribromoethyl | Me | CH2C≡CH | F | H | H | H | CF3 | H | nonafluoro-2-butyl | H | CF3 |
| 14-2233 | 2,2,2-trichloroethyl | Me | Me | H | F | H | H | F | H | heptafluoroisopropyl | H | F |
| 14-2234 | 2,2,2-trichloroethyl | Me | Me | H | F | H | H | F | H | nonafluoro-2-butyl | H | F |
| 14-2245 | 2,2,2-trichloroethyl | Me | Me | H | F | H | H | Cl | H | heptafluoroisopropyl | H | Cl |
| 14-2274 | 2,2,2-trichloroethyl | Me | Me | H | F | H | H | Cl | H | nonafluoro-2-butyl | H | Cl |
| 14-2303 | 2,2,2-trichloroethyl | Me | Me | H | F | H | H | Br | H | heptafluoroisopropyl | H | Br |
| 14-2332 | 2,2,2-trichloroethyl | Me | Me | H | F | H | H | Br | H | nonafluoro-2-butyl | H | Br |
| 14-2361 | 2,2,2-trichloroethyl | Me | Me | H | F | H | H | I | H | heptafluoroisopropyl | H | I |
| 14-2390 | 2,2,2-trichloroethyl | Me | Me | H | F | H | H | I | H | nonafluoro-2-butyl | H | I |
| 13-1236 | 2,2,2-trichloroethyl | Me | Me | H | F | H | H | Cl | H | heptafluoroisopropyl | H | Br |
| 14-2605 | 2,2,2-trichloroethyl | Me | Me | H | F | H | H | F | H | heptafluoroisopropyl | H | OCF3 |
| 14-2606 | 2,2,2-trichloroethyl | Me | Me | H | F | H | H | F | H | nonafluoro-2-butyl | H | OCF3 |
| 14-2617 | 2,2,2-trichloroethyl | Me | Me | H | F | H | H | Cl | H | heptafluoroisopropyl | H | OCF3 |
| 14-2646 | 2,2,2-trichloroethyl | Me | Me | H | F | H | H | Cl | H | nonafluoro-2-butyl | H | OCF3 |
| 14-2675 | 2,2,2-trichloroethyl | Me | Me | H | F | H | H | Br | H | heptafluoroisopropyl | H | OCF3 |
| 14-2704 | 2,2,2-trichloroethyl | Me | Me | H | F | H | H | Br | H | nonafluoro-2-butyl | H | OCF3 |
| 14-2733 | 2,2,2-trichloroethyl | Me | Me | H | F | H | H | I | H | heptafluoroisopropyl | H | OCF3 |
| 14-2762 | 2,2,2-trichloroethyl | Me | Me | H | F | H | H | I | H | nonafluoro-2-butyl | H | OCF3 |
| 14-2977 | 2,2,2-trichloroethyl | Me | Me | H | F | H | H | F | H | heptafluoroisopropyl | H | CF3 |
| 14-2978 | 2,2,2-trichloroethyl | Me | Me | H | F | H | H | F | H | nonafluoro-2-butyl | H | CF3 |
| 14-2989 | 2,2,2-trichloroethyl | Me | Me | H | F | H | H | Cl | H | heptafluoroisopropyl | H | CF3 |
| 14-3018 | 2,2,2-trichloroethyl | Me | Me | H | F | H | H | Cl | H | nonafluoro-2-butyl | H | CF3 |
| 14-3047 | 2,2,2-trichloroethyl | Me | Me | H | F | H | H | Br | H | heptafluoroisopropyl | H | CF3 |
| 14-3076 | 2,2,2-trichloroethyl | Me | Me | H | F | H | H | Br | H | nonafluoro-2-butyl | H | CF3 |
| 14-3105 | 2,2,2-trichloroethyl | Me | Me | H | F | H | H | I | H | heptafluoroisopropyl | H | CF3 |
| 14-3134 | 2,2,2-trichloroethyl | Me | Me | H | F | H | H | I | H | nonafluoro-2-butyl | H | CF3 |

TABLE 14-continued

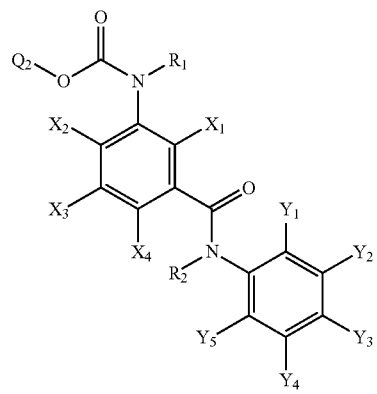

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 14-3359 | 2,2,2-trichloroethyl | Me | Me | H | F | H | H | OCF3 | H | heptafluoroisopropyl | H | OCF3 |
| 14-3388 | 2,2,2-trichloroethyl | Me | Me | H | F | H | H | OCF3 | H | nonafluoro-2-butyl | H | OCF3 |
| 14-3417 | 2,2,2-trichloroethyl | Me | Me | H | F | H | H | CF3 | H | heptafluoroisopropyl | H | OCF3 |
| 14-3446 | 2,2,2-trichloroethyl | Me | Me | H | F | H | H | CF3 | H | nonafluoro-2-butyl | H | OCF3 |
| 14-3475 | 2,2,2-trichloroethyl | Me | Me | H | F | H | H | CF3 | H | heptafluoroisopropyl | H | CF3 |
| 14-3504 | 2,2,2-trichloroethyl | Me | Me | H | F | H | H | CF3 | H | nonafluoro-2-butyl | H | CF3 |
| 14-3719 | 2,2,2-trichloroethyl | Me | Me | F | F | H | H | F | H | heptafluoroisopropyl | H | F |
| 14-3720 | 2,2,2-trichloroethyl | Me | Me | F | F | H | H | F | H | nonafluoro-2-butyl | H | F |
| 14-3731 | 2,2,2-trichloroethyl | Me | Me | F | F | H | H | Cl | H | heptafluoroisopropyl | H | Cl |
| 14-3760 | 2,2,2-trichloroethyl | Me | Me | F | F | H | H | Cl | H | nonafluoro-2-butyl | H | Cl |
| 14-3789 | 2,2,2-trichloroethyl | Me | Me | F | F | H | H | Br | H | heptafluoroisopropyl | H | Br |
| 14-3818 | 2,2,2-trichloroethyl | Me | Me | F | F | H | H | Br | H | nonafluoro-2-butyl | H | Br |
| 14-3847 | 2,2,2-trichloroethyl | Me | Me | F | F | H | H | I | H | heptafluoroisopropyl | H | I |
| 14-3876 | 2,2,2-trichloroethyl | Me | Me | F | F | H | H | I | H | nonafluoro-2-butyl | H | I |
| 13-1950 | 2,2,2-trichloroethyl | Me | Me | F | F | H | H | Cl | H | heptafluoroisopropyl | H | Br |
| 14-4091 | 2,2,2-trichloroethyl | Me | Me | F | F | H | H | F | H | heptafluoroisopropyl | H | OCF3 |
| 14-4092 | 2,2,2-trichloroethyl | Me | Me | F | F | H | H | F | H | nonafluoro-2-butyl | H | OCF3 |
| 14-4103 | 2,2,2-trichloroethyl | Me | Me | F | F | H | H | Cl | H | heptafluoroisopropyl | H | OCF3 |
| 14-4132 | 2,2,2-trichloroethyl | Me | Me | F | F | H | H | Cl | H | nonafluoro-2-butyl | H | OCF3 |
| 14-4161 | 2,2,2-trichloroethyl | Me | Me | F | F | H | H | Br | H | heptafluoroisopropyl | H | OCF3 |
| 14-4190 | 2,2,2-trichloroethyl | Me | Me | F | F | H | H | Br | H | nonafluoro-2-butyl | H | OCF3 |
| 14-4219 | 2,2,2-trichloroethyl | Me | Me | F | F | H | H | I | H | heptafluoroisopropyl | H | OCF3 |
| 14-4248 | 2,2,2-trichloroethyl | Me | Me | F | F | H | H | I | H | nonafluoro-2-butyl | H | OCF3 |
| 14-4463 | 2,2,2-trichloroethyl | Me | Me | F | F | H | H | F | H | heptafluoroisopropyl | H | CF3 |
| 14-4464 | 2,2,2-trichloroethyl | Me | Me | F | F | H | H | F | H | nonafluoro-2-butyl | H | CF3 |
| 14-4475 | 2,2,2-trichloroethyl | Me | Me | F | F | H | H | Cl | H | heptafluoroisopropyl | H | CF3 |
| 14-4504 | 2,2,2-trichloroethyl | Me | Me | F | F | H | H | Cl | H | nonafluoro-2-butyl | H | CF3 |
| 14-4533 | 2,2,2-trichloroethyl | Me | Me | F | F | H | H | Br | H | heptafluoroisopropyl | H | CF3 |
| 14-4562 | 2,2,2-hichloroethyl | Me | Me | F | F | H | H | Br | H | nonafluoro-2-butyl | H | CF3 |
| 14-4591 | 2,2,2-trichloroethyl | Me | Me | F | F | H | H | I | H | heptafluoroisopropyl | H | CF3 |
| 14-4620 | 2,2,2-trichloroethyl | Me | Me | F | F | H | H | I | H | nonafluoro-2-butyl | H | CF3 |
| 14-4845 | 2,2,2-trichloroethyl | Me | Me | F | F | H | H | OCF3 | H | heptafluoroisopropyl | H | OCF3 |
| 14-4874 | 2,2,2-trichloroethyl | Me | Me | F | F | H | H | OCF3 | H | nonafluoro-2-butyl | H | OCF3 |
| 14-4903 | 2,2,2-trichloroethyl | Me | Me | F | F | H | H | CF3 | H | heptafluoroisopropyl | H | OCF3 |
| 14-4932 | 2,2,2-trichloroethyl | Me | Me | F | F | H | H | CF3 | H | nonafluoro-2-butyl | H | OCF3 |
| 14-4961 | 2,2,2-trichloroethyl | Me | Me | F | F | H | H | CF3 | H | heptafluoroisopropyl | H | CF3 |
| 14-4990 | 2,2,2-trichloroethyl | Me | Me | F | F | H | H | CF3 | H | nonafluoro-2-butyl | H | CF3 |
| 14-5205 | 2,2,2-trichloroethyl | Me | Me | F | F | F | H | Cl | H | pentafluoroethyl | H | Cl |
| 14-5206 | 2,2,2-trichloroethyl | Me | Me | F | F | F | H | Br | H | heptafluoroisopropyl | H | Br |
| 14-5207 | 2,2,2-trichloroethyl | Me | Me | F | F | F | H | Br | H | heptafluoroisopropyl | H | OCF3 |
| 14-5208 | 2,2,2-trichloroethyl | Me | Me | F | F | F | H | I | H | heptafluoroisopropyl | H | CF3 |
| 14-5209 | 2,2,2-trichloroethyl | Me | Me | F | F | F | H | CF3 | H | heptafluoroisopropyl | H | CF3 |
| 14-5210 | 2,2,2-trichloroethyl | Me | Me | F | F | F | H | I | H | nonafluoro-2-butyl | H | I |
| 14-5211 | 2,2,2-trichloroethyl | Me | Me | F | F | F | H | Cl | H | nonafluoro-2-butyl | H | OCF3 |
| 14-5212 | 2,2,2-trichloroethyl | Me | Me | F | F | F | H | Br | H | nonafluoro-2-butyl | H | CF3 |
| 14-5213 | 2,2,2-trichloroethyl | Me | Me | F | F | F | H | CF3 | H | nonafluoro-2-butyl | H | CF3 |
| 14-5214 | 2,2,2-trichloroethyl | Me | Me | H | H | F | H | Cl | H | pentafluoroethyl | H | Cl |
| 14-5215 | 2,2,2-trichloroethyl | Me | Me | H | H | F | H | Br | H | heptafluoroisopropyl | H | Br |
| 14-5216 | 2,2,2-trichloroethyl | Me | Me | H | H | F | H | Br | H | heptafluoroisopropyl | H | OCF3 |
| 14-5217 | 2,2,2-trichloroethyl | Me | Me | H | H | F | H | I | H | heptafluoroisopropyl | H | CF3 |
| 14-5218 | 2,2,2-trichloroethyl | Me | Me | H | H | F | H | CF3 | H | heptafluoroisopropyl | H | CF3 |
| 14-5219 | 2,2,2-trichloroethyl | Me | Me | H | H | F | H | I | H | nonafluoro-2-butyl | H | I |
| 14-5220 | 2,2,2-trichloroethyl | Me | Me | H | H | F | H | Cl | H | nonafluoro-2-butyl | H | OCF3 |
| 14-5221 | 2,2,2-trichloroethyl | Me | Me | H | H | F | H | Br | H | nonafluoro-2-butyl | H | CF3 |
| 14-5222 | 2,2,2-trichloroethyl | Me | Me | H | H | F | H | CF3 | H | nonafluoro-2-butyl | H | CF3 |
| 14-5223 | 2,2,2-trichloroethyl | Me | Me | H | H | H | F | Cl | H | pentafluoroethyl | H | Cl |
| 14-5224 | 2,2,2-trichloroethyl | Me | Me | H | H | H | F | Br | H | heptafluoroisopropyl | H | Br |

TABLE 14-continued

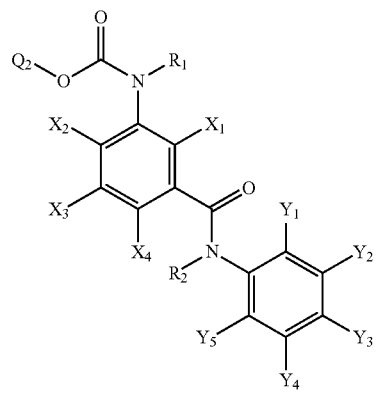

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 14-5225 | 2,2,2-trichloroethyl | Me | Me | H | H | H | F | Br | H | heptafluoroisopropyl | H | OCF3 |
| 14-5226 | 2,2,2-trichloroethyl | Me | Me | H | H | H | F | I | H | heptafluoroisopropyl | H | CF3 |
| 14-5227 | 2,2,2-trichloroethyl | Me | Me | H | H | H | F | CF3 | H | heptafluoroisopropyl | H | CF3 |
| 14-5228 | 2,2,2-trichloroethyl | Me | Me | H | H | H | F | I | H | nonafluoro-2-butyl | H | I |
| 14-5229 | 2,2,2-trichloroethyl | Me | Me | H | H | H | F | Cl | H | nonafluoro-2-butyl | H | OCF3 |
| 14-5230 | 2,2,2-trichloroethyl | Me | Me | H | H | H | F | Br | H | nonafluoro-2-butyl | H | CF3 |
| 14-5231 | 2,2,2-trichloroethyl | Me | Me | H | H | H | F | CF3 | H | nonafluoro-2-butyl | H | CF3 |
| 14-5232 | 2,2,2-trichloroethyl | Me | Me | F | H | F | H | Cl | H | pentafluoroethyl | H | Cl |
| 14-5233 | 2,2,2-trichloroethyl | Me | Me | F | H | F | H | Br | H | heptafluoroisopropyl | H | Br |
| 14-5234 | 2,2,2-trichloroethyl | Me | Me | F | H | F | H | Br | H | heptafluoroisopropyl | H | OCF3 |
| 14-5235 | 2,2,2-trichloroethyl | Me | Me | F | H | F | H | I | H | heptafluoroisopropyl | H | CF3 |
| 14-5236 | 2,2,2-trichloroethyl | Me | Me | F | H | F | H | CF3 | H | heptafluoroisopropyl | H | CF3 |
| 14-5237 | 2,2,2-trichloroethyl | Me | Me | F | H | F | H | I | H | nonafluoro-2-butyl | H | I |
| 14-5238 | 2,2,2-trichloroethyl | Me | Me | F | H | F | H | Cl | H | nonafluoro-2-butyl | H | OCF3 |
| 14-5239 | 2,2,2-trichloroethyl | Me | Me | F | H | F | H | Br | H | nonafluoro-2-butyl | H | CF3 |
| 14-5240 | 2,2,2-trichloroethyl | Me | Me | F | H | F | H | CF3 | H | nonafluoro-2-butyl | H | CF3 |
| 14-5241 | 2,2,2-trichloroethyl | Me | Me | F | H | H | F | Cl | H | pentafluoroethyl | H | Cl |
| 14-5242 | 2,2,2-trichloroethyl | Me | Me | F | H | H | F | Br | H | heptafluoroisopropyl | H | Br |
| 14-5243 | 2,2,2-trichloroethyl | Me | Me | F | H | H | F | Br | H | heptafluoroisopropyl | H | OCF3 |
| 14-5244 | 2,2,2-trichloroethyl | Me | Me | F | H | H | F | I | H | heptafluoroisopropyl | H | CF3 |
| 14-5245 | 2,2,2-trichloroethyl | Me | Me | F | H | H | F | CF3 | H | heptafluoroisopropyl | H | CF3 |
| 14-5246 | 2,2,2-trichloroethyl | Me | Me | F | H | H | F | I | H | nonafluoro-2-butyl | H | I |
| 14-5247 | 2,2,2-trichloroethyl | Me | Me | F | H | H | F | Cl | H | nonafluoro-2-butyl | H | OCF3 |
| 14-5248 | 2,2,2-trichloroethyl | Me | Me | F | H | H | F | Br | H | nonafluoro-2-butyl | H | CF3 |
| 14-5249 | 2,2,2-trichloroethyl | Me | Me | F | H | H | F | CF3 | H | nonafluoro-2-butyl | H | CF3 |
| 14-5250 | 2,2,2-trichloroethyl | Me | Me | H | F | F | H | Cl | H | pentafluoroethyl | H | Cl |
| 14-5251 | 2,2,2-trichloroethyl | Me | Me | H | F | F | H | Br | H | heptafluoroisopropyl | H | Br |
| 14-5252 | 2,2,2-trichloroethyl | Me | Me | H | F | F | H | Br | H | heptafluoroisopropyl | H | OCF3 |
| 14-5253 | 2,2,2-trichloroethyl | Me | Me | H | F | F | H | I | H | heptafluoroisopropyl | H | CF3 |
| 14-5254 | 2,2,2-trichloroethyl | Me | Me | H | F | F | H | CF3 | H | heptafluoroisopropyl | H | CF3 |
| 14-5255 | 2,2,2-trichloroethyl | Me | Me | H | F | F | H | I | H | nonafluoro-2-butyl | H | I |
| 14-5256 | 2,2,2-trichloroethyl | Me | Me | H | F | F | H | Cl | H | nonafluoro-2-butyl | H | OCF3 |
| 14-5257 | 2,2,2-trichloroethyl | Me | Me | H | F | F | H | Br | H | nonafluoro-2-butyl | H | CF3 |
| 14-5258 | 2,2,2-trichloroethyl | Me | Me | H | F | F | H | CF3 | H | nonafluoro-2-butyl | H | CF3 |
| 14-5259 | 2,2,2-trichloroethyl | Me | Me | H | F | H | F | Cl | H | pentafluoroethyl | H | Cl |
| 14-5260 | 2,2,2-trichloroethyl | Me | Me | H | F | H | F | Br | H | heptafluoroisopropyl | H | Br |
| 14-5261 | 2,2,2-trichloroethyl | Me | Me | H | F | H | F | Br | H | heptafluoroisopropyl | H | OCF3 |
| 14-5262 | 2,2,2-trichloroethyl | Me | Me | H | F | H | F | I | H | heptafluoroisopropyl | H | CF3 |
| 14-5263 | 2,2,2-trichloroethyl | Me | Me | H | F | H | F | CF3 | H | heptafluoroisopropyl | H | CF3 |
| 14-5264 | 2,2,2-trichloroethyl | Me | Me | H | F | H | F | I | H | nonafluoro-2-butyl | H | I |
| 14-5265 | 2,2,2-trichloroethyl | Me | Me | H | F | H | F | Cl | H | nonafluoro-2-butyl | H | OCF3 |
| 14-5266 | 2,2,2-trichloroethyl | Me | Me | H | F | H | F | Br | H | nonafluoro-2-butyl | H | CF3 |
| 14-5267 | 2,2,2-trichloroethyl | Me | Me | H | F | H | F | CF3 | H | nonafluoro-2-butyl | H | CF3 |
| 14-5268 | 2,2,2-trichloroethyl | Me | Me | H | H | F | F | Cl | H | pentafluoroethyl | H | Cl |
| 14-5269 | 2,2,2-trichloroethyl | Me | Me | H | H | F | F | Br | H | heptafluoroisopropyl | H | Br |
| 14-5270 | 2,2,2-trichloroethyl | Me | Me | H | H | F | F | Br | H | heptafluoroisopropyl | H | OCF3 |
| 14-5271 | 2,2,2-trichloroethyl | Me | Me | H | H | F | F | I | H | heptafluoroisopropyl | H | CF3 |
| 14-5272 | 2,2,2-trichloroethyl | Me | Me | H | H | F | F | CF3 | H | heptafluoroisopropyl | H | CF3 |
| 14-5273 | 2,2,2-trichloroethyl | Me | Me | H | H | F | F | I | H | nonafluoro-2-butyl | H | I |
| 14-5274 | 2,2,2-trichloroethyl | Me | Me | H | H | F | F | Cl | H | nonafluoro-2-butyl | H | OCF3 |
| 14-5275 | 2,2,2-trichloroethyl | Me | Me | H | H | F | F | Br | H | nonafluoro-2-butyl | H | CF3 |
| 14-5276 | 2,2,2-trichloroethyl | Me | Me | H | H | F | F | CF3 | H | nonafluoro-2-butyl | H | CF3 |
| 14-5277 | 2,2,2-trichloroethyl | Me | Me | F | F | H | F | Cl | H | pentafluoroethyl | H | Cl |
| 14-5278 | 2,2,2-trichloroethyl | Me | Me | F | F | H | F | Br | H | heptafluoroisopropyl | H | Br |
| 14-5279 | 2,2,2-trichloroethyl | Me | Me | F | F | H | F | Br | H | heptafluoroisopropyl | H | OCF3 |
| 14-5280 | 2,2,2-trichloroethyl | Me | Me | F | F | H | F | I | H | heptafluoroisopropyl | H | CF3 |
| 14-5281 | 2,2,2-trichloroethyl | Me | Me | F | F | H | F | CF3 | H | heptafluoroisopropyl | H | CF3 |

TABLE 14-continued

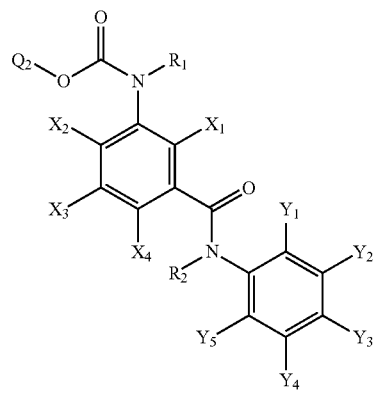

| compound number | Q$_2$ | R$_1$ | R$_2$ | X$_1$ | X$_2$ | X$_3$ | X$_4$ | Y$_1$ | Y$_2$ | Y$_3$ | Y$_4$ | Y$_5$ |
|---|---|---|---|---|---|---|---|---|---|---|---|---|
| 14-5282 | 2,2,2-trichloroethyl | Me | Me | F | F | H | F | I | H | nonafluoro-2-butyl | H | I |
| 14-5283 | 2,2,2-trichloroethyl | Me | Me | F | F | H | F | Cl | H | nonafluoro-2-butyl | H | OCF3 |
| 14-5284 | 2,2,2-trichloroethyl | Me | Me | F | F | H | F | Br | H | nonafluoro-2-butyl | H | CF3 |
| 14-5285 | 2,2,2-trichloroethyl | Me | Me | F | F | H | F | CF3 | H | nonafluoro-2-butyl | H | CF3 |
| 14-5286 | 2,2,2-trichloroethyl | Me | Me | F | H | F | F | Cl | H | pentafluoroethyl | H | Cl |
| 14-5287 | 2,2,2-trichloroethyl | Me | Me | F | H | F | F | Br | H | heptafluoroisopropyl | H | Br |
| 14-5288 | 2,2,2-trichloroethyl | Me | Me | F | H | F | F | Br | H | heptafluoroisopropyl | H | OCF3 |
| 14-5289 | 2,2,2-trichloroethyl | Me | Me | F | H | F | F | I | H | heptafluoroisopropyl | H | CF3 |
| 14-5290 | 2,2,2-trichloroethyl | Me | Me | F | H | F | F | CF3 | H | heptafluoroisopropyl | H | CF3 |
| 14-5291 | 2,2,2-trichloroethyl | Me | Me | F | H | F | F | I | H | nonafluoro-2-butyl | H | I |
| 14-5292 | 2,2,2-trichloroethyl | Me | Me | F | H | F | F | Cl | H | nonafluoro-2-butyl | H | OCF3 |
| 14-5293 | 2,2,2-trichloroethyl | Me | Me | F | H | F | F | Br | H | nonafluoro-2-butyl | H | CF3 |
| 14-5294 | 2,2,2-trichloroethyl | Me | Me | F | H | F | F | CF3 | H | nonafluoro-2-butyl | H | CF3 |
| 14-5295 | 2,2,2-trichloroethyl | Me | Me | H | F | F | F | Cl | H | pentafluoroethyl | H | Cl |
| 14-5296 | 2,2,2-trichloroethyl | Me | Me | H | F | F | F | Br | H | heptafluoroisopropyl | H | Br |
| 14-5297 | 2,2,2-trichloroethyl | Me | Me | H | F | F | F | Br | H | heptafluoroisopropyl | H | OCF3 |
| 14-5298 | 2,2,2-trichloroethyl | Me | Me | H | F | F | F | I | H | heptafluoroisopropyl | H | CF3 |
| 14-5299 | 2,2,2-trichloroethyl | Me | Me | H | F | F | F | CF3 | H | heptafluoroisopropyl | H | CF3 |
| 14-5300 | 2,2,2-trichloroethyl | Me | Me | H | F | F | F | I | H | nonafluoro-2-butyl | H | I |
| 14-5301 | 2,2,2-trichloroethyl | Me | Me | H | F | F | F | Cl | H | nonafluoro-2-butyl | H | OCF3 |
| 14-5302 | 2,2,2-trichloroethyl | Me | Me | H | F | F | F | Br | H | nonafluoro-2-butyl | H | CF3 |
| 14-5303 | 2,2,2-trichloroethyl | Me | Me | H | F | F | F | CF3 | H | nonafluoro-2-butyl | H | CF3 |
| 14-5304 | 2,2,2-trichloroethyl | Me | Me | F | F | F | F | Cl | H | pentafluoroethyl | H | Cl |
| 14-5305 | 2,2,2-trichloroethyl | Me | Me | F | F | F | F | Br | H | heptafluoroisopropyl | H | Br |
| 14-5306 | 2,2,2-trichloroethyl | Me | Me | F | F | F | F | Br | H | heptafluoroisopropyl | H | OCF3 |
| 14-5307 | 2,2,2-trichloroethyl | Me | Me | F | F | F | F | I | H | heptafluoroisopropyl | H | CF3 |
| 14-5308 | 2,2,2-trichloroethyl | Me | Me | F | F | F | F | CF3 | H | heptafluoroisopropyl | H | CF3 |
| 14-5309 | 2,2,2-trichloroethyl | Me | Me | F | F | F | F | I | H | nonafluoro-2-butyl | H | I |
| 14-5310 | 2,2,2-trichloroethyl | Me | Me | F | F | F | F | Cl | H | nonafluoro-2-butyl | H | OCF3 |
| 14-5311 | 2,2,2-trichloroethyl | Me | Me | F | F | F | F | Br | H | nonafluoro-2-butyl | H | CF3 |
| 14-5312 | 2,2,2-trichloroethyl | Me | Me | F | F | F | F | CF3 | H | nonafluoro-2-butyl | H | CF3 |
| 14-5313 | 2,2,2-trichloroethyl | Me | Me | H | CN | H | H | F | H | heptafluoroisopropyl | H | OCF3 |
| 14-5314 | 2,2,2-trichloroethyl | Me | Me | H | CN | H | H | F | H | nonafluoro-2-butyl | H | OCF3 |
| 14-5325 | 2,2,2-trichloroethyl | Me | Me | H | CN | H | H | Cl | H | heptafluoroisopropyl | H | OCF3 |
| 14-5354 | 2,2,2-trichloroethyl | Me | Me | H | CN | H | H | Cl | H | nonafluoro-2-butyl | H | OCF3 |
| 14-5383 | 2,2,2-trichloroethyl | Me | Me | H | CN | H | H | Br | H | heptafluoroisopropyl | H | OCF3 |
| 14-5412 | 2,2,2-trichloroethyl | Me | Me | H | CN | H | H | Br | H | nonafluoro-2-butyl | H | OCF3 |
| 14-5441 | 2,2,2-trichloroethyl | Me | Me | H | CN | H | H | I | H | heptafluoroisopropyl | H | OCF3 |
| 14-5470 | 2,2,2-trichloroethyl | Me | Me | H | CN | H | H | I | H | nonafluoro-2-butyl | H | OCF3 |
| 14-5685 | 2,2,2-trichloroethyl | Me | Me | H | CN | H | H | F | H | heptafluoroisopropyl | H | CF3 |
| 14-5686 | 2,2,2-trichloroethyl | Me | Me | H | CN | H | H | F | H | nonafluoro-2-butyl | H | CF3 |
| 14-5697 | 2,2,2-trichloroethyl | Me | Me | H | CN | H | H | Cl | H | heptafluoroisopropyl | H | CF3 |
| 14-5726 | 2,2,2-trichloroethyl | Me | Me | H | CN | H | H | Cl | H | nonafluoro-2-butyl | H | CF3 |
| 14-5755 | 2,2,2-trichloroethyl | Me | Me | H | CN | H | H | Br | H | heptafluoroisopropyl | H | CF3 |
| 14-5784 | 2,2,2-trichloroethyl | Me | Me | H | CN | H | H | Br | H | nonafluoro-2-butyl | H | CF3 |
| 14-5813 | 2,2,2-trichloroethyl | Me | Me | H | CN | H | H | I | H | heptafluoroisopropyl | H | CF3 |
| 14-5842 | 2,2,2-trichloroethyl | Me | Me | H | CN | H | H | I | H | nonafluoro-2-butyl | H | CF3 |
| 14-6067 | 2,2,2-trichloroethyl | Me | Me | H | CN | H | H | OCF3 | H | heptafluoroisopropyl | H | OCF3 |
| 14-6096 | 2,2,2-trichloroethyl | Me | Me | H | CN | H | H | OCF3 | H | nonafluoro-2-butyl | H | OCF3 |
| 14-6125 | 2,2,2-trichloroethyl | Me | Me | H | CN | H | H | CF3 | H | heptafluoroisopropyl | H | OCF3 |
| 14-6154 | 2,2,2-trichloroethyl | Me | Me | H | CN | H | H | CF3 | H | nonafluoro-2-butyl | H | OCF3 |
| 14-6183 | 2,2,2-trichloroethyl | Me | Me | H | CN | H | H | CF3 | H | heptafluoroisopropyl | H | CF3 |
| 14-6212 | 2,2,2-trichloroethyl | Me | Me | H | CN | H | H | CF3 | H | nonafluoro-2-butyl | H | CF3 |
| 14-6427 | 2,2,2-trichloroethyl | Me | Me | F | CN | H | H | F | H | heptafluoroisopropyl | H | F |
| 14-6428 | 2,2,2-trichloroethyl | Me | Me | F | CN | H | H | F | H | nonafluoro-2-butyl | H | F |
| 14-6439 | 2,2,2-trichloroethyl | Me | Me | F | CN | H | H | Cl | H | heptafluoroisopropyl | H | Cl |
| 14-6468 | 2,2,2-trichloroethyl | Me | Me | F | CN | H | H | Cl | H | nonafluoro-2-butyl | H | Cl |

TABLE 14-continued

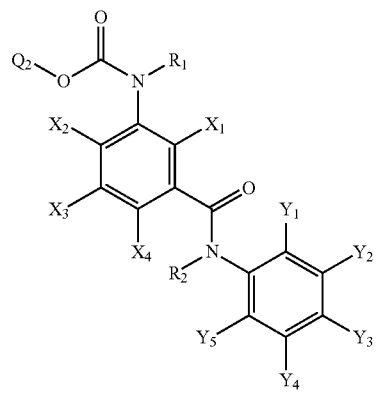

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 14-6497 | 2,2,2-trichloroethyl | Me | Me | F | CN | H | H | Br | H | heptafluoroisopropyl | H | Br |
| 14-6526 | 2,2,2-trichloroethyl | Me | Me | F | CN | H | H | Br | H | nonafluoro-2-butyl | H | Br |
| 14-6555 | 2,2,2-trichloroethyl | Me | Me | F | CN | H | H | I | H | heptafluoroisopropyl | H | I |
| 14-6584 | 2,2,2-trichloroethyl | Me | Me | F | CN | H | H | I | H | nonafluoro-2-butyl | H | I |
| 13-3306 | 2,2,2-trichloroethyl | Me | Me | F | CN | H | H | Br | H | nonafluoro-2-butyl | H | I |
| 14-6799 | 2,2,2-trichloroethyl | Me | Me | F | CN | H | H | F | H | heptafluoroisopropyl | H | OCF3 |
| 14-6800 | 2,2,2-trichloroethyl | Me | Me | F | CN | H | H | F | H | nonafluoro-2-butyl | H | OCF3 |
| 14-6811 | 2,2,2-trichloroethyl | Me | Me | F | CN | H | H | Cl | H | heptafluoroisopropyl | H | OCF3 |
| 14-6840 | 2,2,2-trichloroethyl | Me | Me | F | CN | H | H | Cl | H | nonafluoro-2-butyl | H | OCF3 |
| 14-6869 | 2,2,2-trichloroethyl | Me | Me | F | CN | H | H | Br | H | heptafluoroisopropyl | H | OCF3 |
| 14-6898 | 2,2,2-trichloroethyl | Me | Me | F | CN | H | H | Br | H | nonafluoro-2-butyl | H | OCF3 |
| 14-6927 | 2,2,2-trichloroethyl | Me | Me | F | CN | H | H | I | H | heptafluoroisopropyl | H | OCF3 |
| 14-6956 | 2,2,2-trichloroethyl | Me | Me | F | CN | H | H | I | H | nonafluoro-2-butyl | H | OCF3 |
| 14-7171 | 2,2,2-trichloroethyl | Me | Me | F | CN | H | H | F | H | heptafluoroisopropyl | H | CF3 |
| 14-7172 | 2,2,2-trichloroethyl | Me | Me | F | CN | H | H | F | H | nonafluoro-2-butyl | H | CF3 |
| 14-7183 | 2,2,2-trichloroethyl | Me | Me | F | CN | H | H | Cl | H | heptafluoroisopropyl | H | CF3 |
| 14-7212 | 2,2,2-trichloroethyl | Me | Me | F | CN | H | H | Cl | H | nonafluoro-2-butyl | H | CF3 |
| 14-7241 | 2,2,2-trichloroethyl | Me | Me | F | CN | H | H | Br | H | heptafluoroisopropyl | H | CF3 |
| 14-7270 | 2,2,2-trichloroethyl | Me | Me | F | CN | H | H | Br | H | nonafluoro-2-butyl | H | CF3 |
| 14-7299 | 2,2,2-trichloroethyl | Me | Me | F | CN | H | H | I | H | heptafluoroisopropyl | H | CF3 |
| 14-7328 | 2,2,2-trichloroethyl | Me | Me | F | CN | H | H | I | H | nonafluoro-2-butyl | H | CF3 |
| 14-7553 | 2,2,2-trichloroethyl | Me | Me | F | CN | H | H | OCF3 | H | heptafluoroisopropyl | H | OCF3 |
| 14-7582 | 2,2,2-trichloroethyl | Me | Me | F | CN | H | H | OCF3 | H | nonafluoro-2-butyl | H | OCF3 |
| 14-7611 | 2,2,2-trichloroethyl | Me | Me | F | CN | H | H | CF3 | H | heptafluoroisopropyl | H | OCF3 |
| 14-7640 | 2,2,2-trichloroethyl | Me | Me | F | CN | H | H | CF3 | H | nonafluoro-2-butyl | H | OCF3 |
| 14-7669 | 2,2,2-trichloroethyl | Me | Me | F | CN | H | H | CF3 | H | heptafluoroisopropyl | H | CF3 |
| 14-7698 | 2,2,2-trichloroethyl | Me | Me | F | CN | H | H | CF3 | H | nonafluoro-2-butyl | H | CF3 |
| 14-7913 | 2,2,2-trichloroethyl | Me | Me | F | CN | F | H | F | H | heptafluoroisopropyl | H | F |
| 14-7914 | 2,2,2-trichloroethyl | Me | Me | F | CN | F | H | F | H | nonafluoro-2-butyl | H | F |
| 14-7925 | 2,2,2-trichloroethyl | Me | Me | F | CN | F | H | Cl | H | heptafluoroisopropyl | H | Cl |
| 14-7954 | 2,2,2-trichloroethyl | Me | Me | F | CN | F | H | Cl | H | nonafluoro-2-butyl | H | Cl |
| 14-7983 | 2,2,2-trichloroethyl | Me | Me | F | CN | F | H | Br | H | heptafluoroisopropyl | H | Br |
| 14-8012 | 2,2,2-trichloroethyl | Me | Me | F | CN | F | H | Br | H | nonafluoro-2-butyl | H | Br |
| 14-8041 | 2,2,2-trichloroethyl | Me | Me | F | CN | F | H | I | H | heptafluoroisopropyl | H | I |
| 14-8070 | 2,2,2-trichloroethyl | Me | Me | F | CN | F | H | I | H | nonafluoro-2-butyl | H | I |
| 13-4012 | 2,2,2-trichloroethyl | Me | Me | F | CN | F | H | Cl | H | heptafluoroisopropyl | H | Br |
| 14-8285 | 2,2,2-trichloroethyl | Me | Me | F | CN | F | H | F | H | heptafluoroisopropyl | H | OCF3 |
| 14-8286 | 2,2,2-trichloroethyl | Me | Me | F | CN | F | H | F | H | nonafluoro-2-butyl | H | OCF3 |
| 14-8297 | 2,2,2-trichloroethyl | Me | Me | F | CN | F | H | Cl | H | heptafluoroisopropyl | H | OCF3 |
| 14-8326 | 2,2,2-trichloroethyl | Me | Me | F | CN | F | H | Cl | H | nonafluoro-2-butyl | H | OCF3 |
| 14-8355 | 2,2,2-trichloroethyl | Me | Me | F | CN | F | H | Br | H | heptafluoroisopropyl | H | OCF3 |
| 14-8384 | 2,2,2-trichloroethyl | Me | Me | F | CN | F | H | Br | H | nonafluoro-2-butyl | H | OCF3 |
| 14-8413 | 2,2,2-trichloroethyl | Me | Me | F | CN | F | H | I | H | heptafluoroisopropyl | H | OCF3 |
| 14-8442 | 2,2,2-trichloroethyl | Me | Me | F | CN | F | H | I | H | nonafluoro-2-butyl | H | OCF3 |
| 14-8657 | 2,2,2-trichloroethyl | Me | Me | F | CN | F | H | F | H | heptafluoroisopropyl | H | CF3 |
| 14-8658 | 2,2,2-trichloroethyl | Me | Me | F | CN | F | H | F | H | nonafluoro-2-butyl | H | CF3 |
| 14-8669 | 2,2,2-trichloroethyl | Me | Me | F | CN | F | H | Cl | H | heptafluoroisopropyl | H | CF3 |
| 14-8698 | 2,2,2-trichloroethyl | Me | Me | F | CN | F | H | Cl | H | nonafluoro-2-butyl | H | CF3 |
| 14-8727 | 2,2,2-trichloroethyl | Me | Me | F | CN | F | H | Br | H | heptafluoroisopropyl | H | CF3 |
| 14-8756 | 2,2,2-trichloroethyl | Me | Me | F | CN | F | H | Br | H | nonafluoro-2-butyl | H | CF3 |
| 14-8785 | 2,2,2-trichloroethyl | Me | Me | F | CN | F | H | I | H | heptafluoroisopropyl | H | CF3 |
| 14-8814 | 2,2,2-trichloroethyl | Me | Me | F | CN | F | H | I | H | nonafluoro-2-butyl | H | CF3 |
| 14-9039 | 2,2,2-trichloroethyl | Me | Me | F | CN | F | H | OCF3 | H | heptafluoroisopropyl | H | OCF3 |
| 14-9068 | 2,2,2-trichloroethyl | Me | Me | F | CN | F | H | OCF3 | H | nonafluoro-2-butyl | H | OCF3 |
| 14-9097 | 2,2,2-trichloroethyl | Me | Me | F | CN | F | H | CF3 | H | heptafluoroisopropyl | H | OCF3 |

TABLE 14-continued

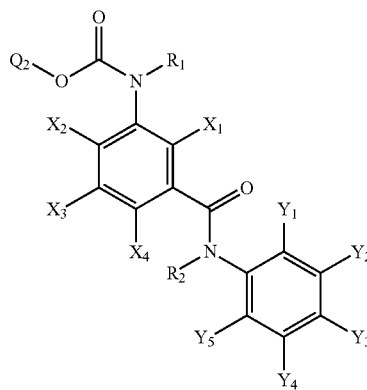

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 14-9126 | 2,2,2-trichloroethyl | Me | Me | F | CN | F | H | CF3 | H | nonafluoro-2-butyl | H | OCF3 |
| 14-9155 | 2,2,2-trichloroethyl | Me | Me | F | CN | F | H | CF3 | H | heptafluoroisopropyl | H | CF3 |
| 14-9184 | 2,2,2-trichloroethyl | Me | Me | F | CN | F | H | CF3 | H | nonafluoro-2-butyl | H | CF3 |

TABLE 15

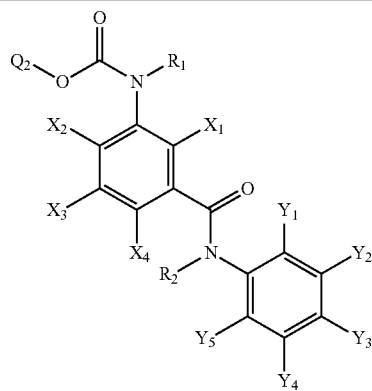

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-9 | 2,2-dichloroethyl | H | Et | H | H | H | H | Cl | F | heptafluoroisopropyl | F | OCF3 |
| 15-39 | 2,2,2-trifluoroethyl | H | H | H | H | H | H | Cl | Me | nonafluoro-2-butyl | Me | OCF3 |
| 15-144 | methyl | H | H | H | H | H | H | Cl | F | heptafluoroisopropyl | H | CF3 |
| 15-147 | 2-chloroethyl | Me | Me | H | H | H | H | Cl | H | heptafluoroisopropyl | Cl | CF3 |
| 15-148 | 2-bromoethyl | H | H | H | H | H | H | F | Br | heptafluoroisopropyl | H | CF3 |
| 15-153 | 2,2,2-trifluoroethyl | H | H | H | H | H | H | Cl | F | heptafluoroisopropyl | Cl | CF3 |
| 15-165 | 3,3,3-trifluoro-n-propyl | H | H | H | H | H | H | Cl | I | nonafluoro-2-butyl | Cl | CF3 |
| 15-168 | i-butyl | H | H | H | H | H | H | Cl | Me | nonafluoro-2-butyl | H | CF3 |
| 15-169 | s-butyl | H | H | H | H | H | H | Cl | H | nonafluoro-2-butyl | Me | CF3 |
| 15-170 | vinyl | i-Pr | H | H | H | H | H | Cl | Et | nonafluoro-2-butyl | H | CF3 |
| 15-171 | benzyl | H | H | H | H | H | H | Cl | H | nonafluoro-2-butyl | Et | CF3 |
| 15-182 | 2,2,2-trifluoroethyl | H | H | H | H | H | H | Cl | Me | nonafluoro-2-butyl | Me | n-C3F7 |
| 15-183 | 2,2,2-trichloroethyl | H | H | H | H | H | H | Cl | Me | nonafluoro-2-butyl | Et | i-C3F7 |
| 15-189 | i-propyl | H | H | H | H | H | H | Cl | Et | nonafluoro-2-butyl | Me | n-C3F7 |
| 15-190 | 1,2-difluoro-2-propyl | H | H | H | H | H | H | Cl | Et | nonafluoro-2-butyl | Et | i-C3F7 |
| 15-196 | 2-chloroethyl | H | H | H | H | H | H | Br | n-Pr | heptafluoroisopropyl | Me | CF3 |
| 15-197 | 2-bromoethyl | H | H | H | H | H | H | Br | n-Pr | heptafluoroisopropyl | Et | CF3 |
| 15-203 | 2,2,2-trichloroethyl | H | H | H | H | H | H | Br | i-Pr | heptafluoroisopropyl | Me | CF3 |
| 15-204 | 2,2,2-tribromoethyl | H | H | H | H | H | H | Br | i-Pr | heptafluoroisopropyl | Et | CF3 |
| 15-210 | 1,2-difluoro-2-propyl | H | H | H | H | H | H | Br | n-Bu | heptafluoroisopropyl | Me | CF3 |
| 15-211 | 1,3-difluoro-2-propyl | H | H | H | H | H | H | Br | n-Bu | heptafluoroisopropyl | Et | CF3 |
| 15-217 | i-butyl | H | H | H | H | H | H | Br | i-Bu | nonafluoro-2-butyl | Me | CF3 |
| 15-218 | s-butyl | H | H | H | H | H | H | Br | i-Bu | nonafluoro-2-butyl | Et | CF3 |
| 15-224 | 2-fluoroethyl | H | H | H | H | H | H | Br | s-Bu | nonafluoro-2-butyl | Me | CF3 |
| 15-225 | 2-chloroethyl | H | H | H | H | H | H | Br | s-Bu | nonafluoro-2-butyl | Et | CF3 |
| 15-231 | 2,2,2-trifluoroethyl | H | H | H | H | H | H | Br | F | nonafluoro-2-butyl | Me | CF3 |
| 15-232 | 2,2,2-trichloroethyl | H | H | H | H | H | H | Br | F | nonafluoro-2-butyl | Et | CF3 |

TABLE 15-continued

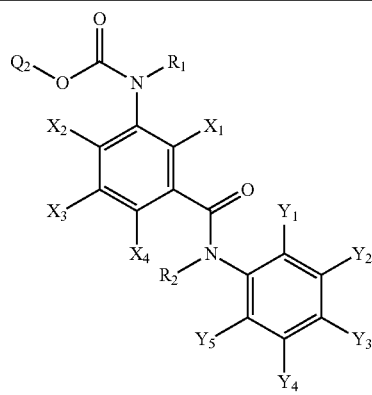

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-238 | i-propyl | Et | i-Pr | H | H | H | H | Br | Cl | nonafluoro-2-butyl | Me | CF3 |
| 15-239 | 1,2-difluoro-2-propyl | H | H | H | H | H | H | Br | Cl | nonafluoro-2-butyl | Et | CF3 |
| 15-245 | 2-iodoethyl | H | H | H | H | H | H | I | Br | heptafluoroisopropyl | Me | CF3 |
| 15-246 | 2-cyanomethyl | H | H | H | H | H | H | I | Br | heptafluoroisopropyl | Et | CF3 |
| 15-252 | n-propyl | n-Pr | Me | H | H | H | H | I | I | heptafluoroisopropyl | Me | CF3 |
| 15-253 | 3-fluoro-n-propyl | H | H | H | H | H | H | I | I | heptafluoroisopropyl | Et | CF3 |
| 15-259 | 1,3-dichloro-2-propyl | H | H | H | H | H | H | I | Me | heptafluoroisopropyl | F | C2F5 |
| 15-260 | 1-chloro-3-fluoro-2-propyl | H | H | H | H | H | H | I | Me | nonafluoro-2-butyl | Cl | CF3 |
| 15-263 | 4,4,4-trifluoro-n-butyl | H | H | H | H | H | H | I | Et | nonafluoro-2-butyl | F | CF3 |
| 15-264 | i-butyl | H | H | H | H | H | H | I | Et | nonafluoro-2-butyl | Cl | CF3 |
| 15-267 | benzyl | H | H | H | H | H | H | I | n-Pr | nonafluoro-2-butyl | F | CF3 |
| 15-268 | phenyl | H | H | H | H | H | H | I | n-Pr | nonafluoro-2-butyl | Cl | CF3 |
| 15-271 | 2-fluoroethyl | H | H | H | H | H | H | I | i-Pr | nonafluoro-2-butyl | F | i-C3F7 |
| 15-272 | 2-chloroethyl | H | H | H | H | H | H | I | i-Pr | nonafluoro-2-butyl | Cl | CF3 |
| 15-275 | 2-cyanoethyl | H | H | H | H | H | H | I | n-Bu | nonafluoro-2-butyl | F | CF3 |
| 15-276 | 2,2-difluoroethyl | H | H | H | H | H | H | I | n-Bu | nonafluoro-2-butyl | Cl | CF3 |
| 15-279 | 2,2,2-trichloroethyl | H | H | H | H | H | H | I | i-Bu | nonafluoro-2-butyl | F | CF3 |
| 15-280 | 2,2,2-tribromoethyl | H | H | H | H | H | H | I | i-Bu | nonafluoro-2-butyl | Cl | CF3 |
| 15-283 | 3-chloro-n-propyl | i-Pr | n-Pr | H | H | H | H | I | s-Bu | nonafluoro-2-butyl | F | CF3 |
| 15-284 | 3-bromo-n-propyl | H | H | H | H | H | H | I | s-Bu | nonafluoro-2-butyl | Cl | CF3 |
| 15-295 | 2,2-dichloroethyl | H | Et | H | H | H | H | OCF3 | F | heptafluoroisopropyl | F | OCF3 |
| 15-325 | 2,2,2-trifluoroethyl | H | H | H | H | H | H | OCF3 | Me | nonafluoro-2-butyl | Me | OCF3 |
| 15-438 | 2,2-dichloroethyl | H | Et | H | H | H | H | OCF3 | F | heptafluoroisopropyl | F | CF3 |
| 15-468 | 2,2,2-trifluoroethyl | H | H | H | H | H | H | OCF3 | Me | nonafluoro-2-butyl | Me | CF3 |
| 15-581 | 2,2-dichloroethyl | H | Et | H | H | H | H | CF3 | F | heptafluoroisopropyl | F | CF3 |
| 15-611 | 2,2,2-trifluoroethyl | H | H | H | H | H | H | CF3 | Me | nonafluoro-2-butyl | Me | CF3 |
| 15-734 | 2,2-dichloroethyl | H | Et | F | H | H | H | Cl | F | heptafluoroisopropyl | F | OCF3 |
| 15-764 | 2,2,2-trifluoroethyl | H | H | F | H | H | H | Cl | Me | nonafluoro-2-butyl | Me | OCF3 |
| 15-869 | methyl | H | H | F | H | H | H | Cl | F | heptafluoroisopropyl | H | CF3 |
| 15-870 | ethyl | Me | H | F | H | H | H | Cl | H | heptafluoroisopropyl | F | CF3 |
| 15-871 | 2-fluoroethyl | H | Me | F | H | H | H | Cl | Cl | heptafluoroisopropyl | H | CF3 |
| 15-872 | 2-chloroethyl | Me | Me | F | H | H | H | Cl | H | heptafluoroisopropyl | Cl | CF3 |
| 15-873 | 2-bromoethyl | H | H | F | H | H | H | F | Br | heptafluoroisopropyl | H | CF3 |
| 15-874 | 2-iodoethyl | H | H | F | H | H | H | Cl | H | heptafluoroisopropyl | Br | CF3 |
| 15-875 | 2-cyanoethyl | Et | H | F | H | H | H | Cl | I | heptafluoroisopropyl | H | C2F5 |
| 15-876 | 2,2-difluoroethyl | H | H | F | H | H | H | Cl | H | heptafluoroisopropyl | I | CF3 |
| 15-877 | 2,2-dichloroethyl | H | Et | F | H | H | H | Cl | F | heptafluoroisopropyl | F | CF3 |
| 15-878 | 2,2,2-trifluoroethyl | H | H | F | H | H | H | Cl | F | heptafluoroisopropyl | Cl | CF3 |
| 15-879 | 2,2,2-trichloroethyl | H | H | F | H | H | H | Cl | F | heptafluoroisopropyl | Br | CF3 |
| 15-880 | 2,2,2-tribromoethyl | Et | Et | F | H | H | H | Cl | F | pentafluoroethyl | I | C2F5 |
| 15-881 | n-propyl | H | H | F | H | H | H | Cl | Cl | pentafluoroethyl | F | CF3 |
| 15-882 | 3-fluoro-n-propyl | H | H | F | H | H | H | Cl | Cl | heptafluoroisopropyl | Cl | CF3 |
| 15-883 | 3-chloro-n-propyl | n-Pr | H | F | H | H | H | Cl | Cl | heptafluoroisopropyl | Br | CF3 |
| 15-884 | 3-bromo-n-propyl | H | H | F | H | H | H | Cl | Cl | heptafluoroisopropyl | I | n-C3F7 |
| 15-885 | i-propyl | H | n-Pr | F | H | H | H | Cl | Br | heptafluoroisopropyl | F | CF3 |
| 15-886 | 1,2-difluoro-2-propyl | H | H | F | H | H | H | Cl | Br | heptafluoroisopropyl | Cl | CF3 |
| 15-887 | 1,3-difluoro-2-propyl | H | H | F | H | H | H | Cl | Br | heptafluoroisopropyl | Br | CF3 |
| 15-888 | 1,3-dichloro-2-propyl | n-Pr | n-Pr | F | H | H | H | Cl | Br | pentafluoroethyl | I | CF3 |
| 15-889 | 1-chloro-3-fluoro-2-propyl | H | H | F | H | H | H | F | I | nonafluoro-2-butyl | F | CF3 |
| 15-890 | 3,3,3-trifluoro-n-propyl | H | H | F | H | H | H | Cl | I | nonafluoro-2-butyl | Cl | CF3 |
| 15-891 | n-butyl | H | H | F | H | H | H | Cl | I | nonafluoro-2-butyl | Br | CF3 |
| 15-892 | 4,4,4-trifluoro-n-butyl | H | H | F | H | H | H | Cl | I | nonafluoro-2-butyl | I | CF3 |
| 15-893 | i-butyl | H | H | F | H | H | H | Cl | Me | nonafluoro-2-butyl | H | CF3 |
| 15-894 | s-butyl | H | H | F | H | H | H | Cl | H | nonafluoro-2-butyl | Me | CF3 |
| 15-895 | vinyl | i-Pr | H | F | H | H | H | Cl | Et | nonafluoro-2-butyl | H | CF3 |
| 15-896 | benzyl | H | H | F | H | H | H | Cl | H | nonafluoro-2-butyl | Et | CF3 |
| 15-897 | phenyl | H | H | F | H | H | H | Cl | n-Pr | nonafluoro-2-butyl | H | CF3 |
| 15-898 | methyl | H | i-Pr | F | H | H | H | Cl | H | nonafluoro-2-butyl | n-Pr | CF3 |

TABLE 15-continued

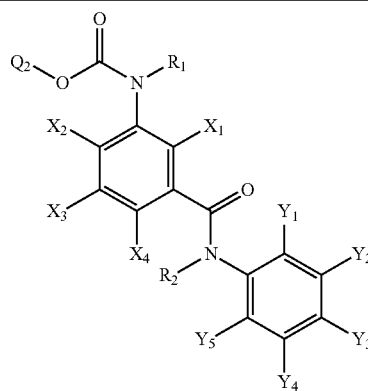

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-899 | ethyl | i-Pr | i-Pr | F | H | H | H | Cl | i-Pr | nonafluoro-2-butyl | H | CF3 |
| 15-900 | 2-fluoroethyl | H | H | F | H | H | H | Cl | H | nonafluoro-2-butyl | i-Pr | CF3 |
| 15-901 | 2-chloroethyl | H | H | F | H | H | H | Cl | n-Bu | nonafluoro-2-butyl | H | CF3 |
| 15-902 | 2-bromoethyl | H | H | F | H | H | H | Cl | H | nonafluoro-2-butyl | n-Bu | CF3 |
| 15-903 | 2-iodoethyl | H | H | F | H | H | H | Cl | i-Bu | nonafluoro-2-butyl | H | CF3 |
| 15-904 | 2-cyanoethyl | H | H | F | H | H | H | Cl | H | nonafluoro-2-butyl | i-Bu | CF3 |
| 15-905 | 2,2-difluoroethyl | H | H | F | H | H | H | Cl | s-Bu | nonafluoro-2-butyl | H | C2F5 |
| 15-906 | 2,2-dichloroethyl | H | H | F | H | H | H | Cl | H | nonafluoro-2-butyl | s-Bu | CF3 |
| 15-907 | 2,2,2-trifluoroethyl | H | H | F | H | H | H | Cl | Me | nonafluoro-2-butyl | Me | n-C3F7 |
| 15-908 | 2,2,2-trichloroethyl | H | H | F | H | H | H | Cl | Me | nonafluoro-2-butyl | Et | i-C3F7 |
| 15-909 | 2,2,2-tribromoethyl | C(O)Me | H | F | H | H | H | Cl | Me | nonafluoro-2-butyl | n-Pr | CF3 |
| 15-910 | n-propyl | H | H | F | H | H | H | Cl | Me | nonafluoro-2-butyl | i-Pr | CF3 |
| 15-911 | 3-fluoro-n-propyl | H | H | F | H | H | H | Cl | Me | nonafluoro-2-butyl | n-Bu | CF3 |
| 15-912 | 3-chloro-n-propyl | H | H | F | H | H | H | Cl | Me | nonafluoro-2-butyl | i-Bu | CF3 |
| 15-913 | 3-bromo-n-propyl | H | C(O)Me | F | H | H | H | Cl | Me | nonafluoro-2-butyl | s-Bu | CF3 |
| 15-914 | i-propyl | H | H | F | H | H | H | Cl | Et | nonafluoro-2-butyl | Me | n-C3F7 |
| 15-915 | 1,2-difluoro-2-propyl | H | H | F | H | H | H | Cl | Et | nonafluoro-2-butyl | Et | i-C3F7 |
| 15-916 | 1,3-difluoro-2-propyl | C(O)Me | C(O)Me | F | H | H | H | Cl | Et | nonafluoro-2-butyl | n-Pr | CF3 |
| 15-917 | 1,3-dichloro-2-propyl | H | H | F | H | H | H | Cl | Et | nonafluoro-2-butyl | i-Pr | CF3 |
| 15-918 | methyl | H | H | F | H | H | H | Br | Et | heptafluoroisopropyl | n-Bu | CF3 |
| 15-919 | ethyl | H | H | F | H | H | H | Br | Et | heptafluoroisopropyl | i-Bu | CF3 |
| 15-920 | 2-fluoroethyl | H | H | F | H | H | H | Br | Et | heptafluoroisopropyl | s-Bu | CF3 |
| 15-921 | 2-chloroethyl | H | H | F | H | H | H | Br | n-Pr | heptafluoroisopropyl | Me | CF3 |
| 15-922 | 2-bromoethyl | H | H | F | H | H | H | Br | n-Pr | heptafluoroisopropyl | Et | CF3 |
| 15-923 | 2-iodoethyl | Me | Et | F | H | H | H | Br | n-Pr | pentafluoroethyl | n-Pr | CF3 |
| 15-924 | 2-cyanoethyl | H | H | F | H | H | H | Br | n-Pr | heptafluoroisopropyl | i-Pr | CF3 |
| 15-925 | 2,2-difluoroethyl | H | H | F | H | H | H | Br | n-Pr | pentafluoroethyl | n-Bu | CF3 |
| 15-926 | 2,2-dichloroethyl | H | H | F | H | H | H | Br | n-Pr | heptafluoroisopropyl | i-Bu | CF3 |
| 15-927 | 2,2,2-trifluoroethyl | H | H | F | H | H | H | Br | n-Pr | heptafluoroisopropyl | s-Bu | CF3 |
| 15-928 | 2,2,2-trichloroethyl | H | H | F | H | H | H | Br | i-Pr | heptafluoroisopropyl | Me | CF3 |
| 15-929 | 2,2,2-tribromoethyl | H | H | F | H | H | H | Br | i-Pr | heptafluoroisopropyl | Et | CF3 |
| 15-930 | n-propyl | Me | n-Pr | F | H | H | H | Br | i-Pr | heptafluoroisopropyl | n-Pr | CF3 |
| 15-931 | 3-fluoro-n-propyl | H | H | F | H | H | H | Br | i-Pr | heptafluoroisopropyl | i-Pr | CF3 |
| 15-932 | 3-chloro-n-propyl | H | H | F | H | H | H | Br | i-Pr | heptafluoroisopropyl | n-Bu | CF3 |
| 15-933 | 3-bromo-n-propyl | H | H | F | H | H | H | Br | i-Pr | heptafluoroisopropyl | i-Bu | CF3 |
| 15-934 | i-propyl | Me | i-Pr | F | H | H | H | Br | i-Pr | heptafluoroisopropyl | s-Bu | CF3 |
| 15-935 | 1,2-difluoro-2-propyl | H | H | F | H | H | H | Br | n-Bu | heptafluoroisopropyl | Me | CF3 |
| 15-936 | 1,3-difluoro-2-propyl | H | H | F | H | H | H | Br | n-Bu | heptafluoroisopropyl | Et | CF3 |
| 15-937 | 1,3-dichloro-2-propyl | H | H | F | H | H | H | Br | n-Bu | heptafluoroisopropyl | n-Pr | CF3 |
| 15-938 | 1-chloro-3-fluoro-2-propyl | H | H | F | H | H | H | Br | n-Bu | nonafluoro-2-butyl | i-Pr | CF3 |
| 15-939 | 3,3,3-trifluoro-n-propyl | H | H | F | H | H | H | Br | n-Bu | nonafluoro-2-butyl | n-Bu | CF3 |
| 15-940 | n-butyl | H | H | F | H | H | H | Br | n-Bu | nonafluoro-2-butyl | i-Bu | CF3 |
| 15-941 | 4,4,4-trifluoro-n-butyl | Me | C(O)Me | F | H | H | H | Br | n-Bu | nonafluoro-2-butyl | s-Bu | CF3 |
| 15-942 | i-butyl | H | H | F | H | H | H | Br | i-Bu | nonafluoro-2-butyl | Me | CF3 |
| 15-943 | s-butyl | H | H | F | H | H | H | Br | i-Bu | nonafluoro-2-butyl | Et | CF3 |
| 15-944 | vinyl | H | H | F | H | H | H | Br | i-Bu | nonafluoro-2-butyl | n-Pr | CF3 |
| 15-945 | benzyl | H | H | F | H | H | H | Br | i-Bu | nonafluoro-2-butyl | i-Pr | CF3 |
| 15-946 | phenyl | H | H | F | H | H | H | Br | i-Bu | nonafluoro-2-butyl | n-Bu | CF3 |
| 15-947 | methyl | H | H | F | H | H | H | Br | i-Bu | nonafluoro-2-butyl | i-Bu | CF3 |
| 15-948 | ethyl | H | H | F | H | H | H | Br | i-Bu | nonafluoro-2-butyl | s-Bu | C2F5 |
| 15-949 | 2-fluoroethyl | H | H | F | H | H | H | Br | s-Bu | nonafluoro-2-butyl | Me | CF3 |
| 15-950 | 2-chloroethyl | H | H | F | H | H | H | Br | s-Bu | nonafluoro-2-butyl | Et | CF3 |
| 15-951 | 2-bromoethyl | H | H | F | H | H | H | Br | s-Bu | nonafluoro-2-butyl | n-Pr | CF3 |
| 15-952 | 2-iodoethyl | H | H | F | H | H | H | Br | s-Bu | nonafluoro-2-butyl | i-Pr | CF3 |
| 15-953 | 2-cyanoethyl | H | H | F | H | H | H | Br | s-Bu | nonafluoro-2-butyl | n-Bu | CF3 |
| 15-954 | 2,2-difluoroethyl | H | H | F | H | H | H | Br | s-Bu | nonafluoro-2-butyl | i-Bu | CF3 |
| 15-955 | 2,2-dichloroethyl | Et | Me | F | H | H | H | Br | s-Bu | nonafluoro-2-butyl | s-Bu | CF3 |
| 15-956 | 2,2,2-trifluoroethyl | H | H | F | H | H | H | Br | F | nonafluoro-2-butyl | Me | CF3 |

TABLE 15-continued

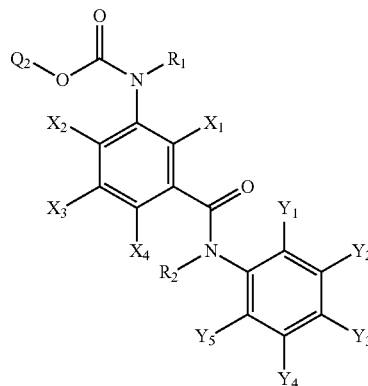

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-957 | 2,2,2-trichloroethyl | H | H | F | H | H | H | Br | F | nonafluoro-2-butyl | Et | CF3 |
| 15-958 | 2,2,2-tribromoethyl | H | H | F | H | H | H | Br | F | nonafluoro-2-butyl | n-Pr | CF3 |
| 15-959 | n-propyl | H | H | F | H | H | H | Br | F | nonafluoro-2-butyl | i-Pr | CF3 |
| 15-960 | 3-fluoro-n-propyl | H | H | F | H | H | H | Br | F | nonafluoro-2-butyl | n-Bu | CF3 |
| 15-961 | 3-chloro-n-propyl | H | H | F | H | H | H | Br | F | nonafluoro-2-butyl | i-Bu | CF3 |
| 15-962 | 3-bromo-n-propyl | Et | n-Pr | F | H | H | H | Br | F | nonafluoro-2-butyl | s-Bu | CF3 |
| 15-963 | i-propyl | Et | i-Pr | F | H | H | H | Br | Cl | nonafluoro-2-butyl | Me | CF3 |
| 15-964 | 1,2-difluoro-2-propyl | H | H | F | H | H | H | Br | Cl | nonafluoro-2-butyl | Et | CF3 |
| 15-965 | methyl | H | H | F | H | H | H | I | Cl | pentafluoroethyl | n-Pr | i-C3F7 |
| 15-966 | ethyl | H | H | F | H | H | H | I | Cl | heptafluoroisopropyl | i-Pr | CF3 |
| 15-967 | 2-fluoroethyl | H | H | F | H | H | H | I | Cl | heptafluoroisopropyl | n-Bu | CF3 |
| 15-968 | 2-chloroethyl | Et | C(O)Me | F | H | H | H | I | Cl | heptafluoroisopropyl | i-Bu | CF3 |
| 15-969 | 2-bromoethyl | H | H | F | H | H | H | I | Cl | heptafluoroisopropyl | s-Bu | CF3 |
| 15-970 | 2-iodoethyl | H | H | F | H | H | H | I | Br | heptafluoroisopropyl | Me | CF3 |
| 15-971 | 2-cyanoethyl | H | H | F | H | H | H | I | Br | heptafluoroisopropyl | Et | CF3 |
| 15-972 | 2,2-difluoroethyl | H | H | F | H | H | H | I | Br | pentafluoroethyl | n-Pr | CF3 |
| 15-973 | 2,2-dichloroethyl | H | H | F | H | H | H | I | Br | heptafluoroisopropyl | i-Pr | CF3 |
| 15-974 | 2,2,2-trifluoroethyl | H | H | F | H | H | H | I | Br | heptafluoroisopropyl | n-Bu | CF3 |
| 15-975 | 2,2,2-trichloroethyl | H | H | F | H | H | H | I | Br | heptafluoroisopropyl | i-Bu | CF3 |
| 15-976 | 2,2,2-tribromoethyl | H | H | F | H | H | H | I | Br | heptafluoroisopropyl | s-Bu | CF3 |
| 15-977 | n-propyl | n-Pr | Me | F | H | H | H | I | I | heptafluoroisopropyl | Me | CF3 |
| 15-978 | 3-fluoro-n-propyl | H | H | F | H | H | H | I | I | heptafluoroisopropyl | Et | CF3 |
| 15-979 | 3-chloro-n-propyl | n-Pr | Et | F | H | H | H | I | I | heptafluoroisopropyl | n-Pr | CF3 |
| 15-980 | 3-bromo-n-propyl | H | H | F | H | H | H | I | I | heptafluoroisopropyl | i-Pr | CF3 |
| 15-981 | i-propyl | H | H | F | H | H | H | I | I | heptafluoroisopropyl | n-Bu | CF3 |
| 15-982 | 1,2-difluoro-2-propyl | H | H | F | H | H | H | I | I | heptafluoroisopropyl | i-Bu | CF3 |
| 15-983 | 1,3-difluoro-2-propyl | H | H | F | H | H | H | I | I | heptafluoroisopropyl | s-Bu | CF3 |
| 15-984 | 1,3-dichloro-2-propyl | H | H | F | H | H | H | I | Me | heptafluoroisopropyl | F | C2F5 |
| 15-985 | 1-chloro-3-fluoro-2-propyl | H | H | F | H | H | H | I | Me | nonafluoro-2-butyl | Cl | CF3 |
| 15-986 | 3,3,3-trifluoro-n-propyl | H | H | F | H | H | H | I | Me | nonafluoro-2-butyl | Br | n-C3F7 |
| 15-987 | n-butyl | H | H | F | H | H | H | I | Me | nonafluoro-2-butyl | I | i-C3F7 |
| 15-988 | 4,4,4-trifluoro-n-butyl | H | H | F | H | H | H | I | Et | nonafluoro-2-butyl | F | CF3 |
| 15-989 | i-butyl | H | H | F | H | H | H | I | Et | nonafluoro-2-butyl | Cl | CF3 |
| 15-990 | s-butyl | H | H | F | H | H | H | I | Et | nonafluoro-2-butyl | Br | CF3 |
| 15-991 | vinyl | n-Pr | i-Pr | F | H | H | H | I | Et | nonafluoro-2-butyl | I | C2F5 |
| 15-992 | benzyl | H | H | F | H | H | H | I | n-Pr | nonafluoro-2-butyl | F | CF3 |
| 15-993 | phenyl | H | H | F | H | H | H | I | n-Pr | nonafluoro-2-butyl | Cl | CF3 |
| 15-994 | methyl | H | H | F | H | H | H | I | n-Pr | nonafluoro-2-butyl | Br | CF3 |
| 15-995 | ethyl | H | H | F | H | H | H | I | n-Pr | nonafluoro-2-butyl | I | n-C3F7 |
| 15-996 | 2-fluoroethyl | H | H | F | H | H | H | I | i-Pr | nonafluoro-2-butyl | F | i-C3F7 |
| 15-997 | 2-chloroethyl | H | H | F | H | H | H | I | i-Pr | nonafluoro-2-butyl | Cl | CF3 |
| 15-998 | 2-bromoethyl | n-Pr | C(O)Me | F | H | H | H | I | i-Pr | nonafluoro-2-butyl | Br | CF3 |
| 15-999 | 2-iodoethyl | H | H | F | H | H | H | I | i-Pr | nonafluoro-2-butyl | I | CF3 |
| 15-1000 | 2-cyanoethyl | H | H | F | H | H | H | I | n-Bu | nonafluoro-2-butyl | F | CF3 |
| 15-1001 | 2,2-difluoroethyl | H | H | F | H | H | H | I | n-Bu | nonafluoro-2-butyl | Cl | CF3 |
| 15-1002 | 2,2-dichloroethyl | H | H | F | H | H | H | I | n-Bu | nonafluoro-2-butyl | Br | CF3 |
| 15-1003 | 2,2,2-trifluoroethyl | i-Pr | Me | F | H | H | H | I | n-Bu | nonafluoro-2-butyl | I | CF3 |
| 15-1004 | 2,2,2-trichloroethyl | H | H | F | H | H | H | I | i-Bu | nonafluoro-2-butyl | F | CF3 |
| 15-1005 | 2,2,2-tribromoethyl | H | H | F | H | H | H | I | i-Bu | nonafluoro-2-butyl | Cl | CF3 |
| 15-1006 | n-propyl | H | H | F | H | H | H | I | i-Bu | nonafluoro-2-butyl | Br | CF3 |
| 15-1007 | 3-fluoro-n-propyl | i-Pr | Et | F | H | H | H | I | i-Bu | nonafluoro-2-butyl | I | CF3 |
| 15-1008 | 3-chloro-n-propyl | i-Pr | n-Pr | F | H | H | H | I | s-Bu | nonafluoro-2-butyl | F | CF3 |
| 15-1009 | 3-bromo-n-propyl | H | H | F | H | H | H | I | s-Bu | nonafluoro-2-butyl | Cl | CF3 |
| 15-1010 | i-propyl | i-Pr | C(O)Me | F | H | H | H | I | s-Bu | nonafluoro-2-butyl | Br | CF3 |
| 15-1011 | 1,2-difluoro-2-propyl | H | H | F | H | H | H | I | s-Bu | nonafluoro-2-butyl | I | CF3 |
| 15-1020 | 2,2-dichloroethyl | H | Et | F | H | H | H | OCF3 | F | heptafluoroisopropyl | F | OCF3 |
| 15-1050 | 2,2,2-trifluoroethyl | H | H | F | H | H | H | OCF3 | Me | nonafluoro-2-butyl | Me | OCF3 |
| 15-1163 | 2,2-dichloroethyl | H | Et | F | H | H | H | OCF3 | F | heptafluoroisopropyl | F | CF3 |

TABLE 15-continued

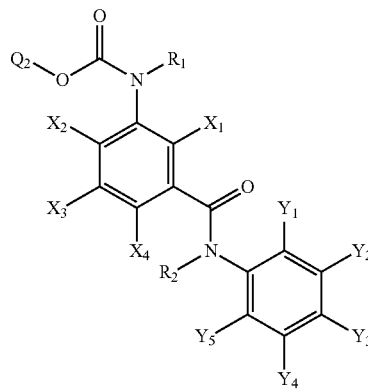

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-1193 | 2,2,2-trifluoroethyl | H | H | F | H | H | H | OCF3 | Me | nonafluoro-2-butyl | Me | CF3 |
| 15-1306 | 2,2-dichloroethyl | H | Et | F | H | H | H | CF3 | F | heptafluoroisopropyl | F | CF3 |
| 15-1336 | 2,2,2-trifluoroethyl | H | H | F | H | H | H | CF3 | Me | nonafluoro-2-butyl | Me | CF3 |
| 15-1449 | 2,2-dichloroethyl | H | Et | H | F | H | H | Cl | F | heptafluoroisopropyl | F | Cl |
| 15-1479 | 2,2,2-trifluoroethyl | H | H | H | F | H | H | Cl | Me | nonafluoro-2-butyl | Me | I |
| 15-1592 | 2,2-dichloroethyl | H | Et | H | F | H | H | Cl | F | heptafluoroisopropyl | F | OCF3 |
| 15-1622 | 2,2,2-trifluoroethyl | H | H | H | F | H | H | Cl | Me | nonafluoro-2-butyl | Me | OCF3 |
| 15-1737 | 2,2,2-trichloroethyl | H | H | H | F | H | H | Cl | F | heptafluoroisopropyl | Br | CF3 |
| 15-1749 | n-butyl | H | H | H | F | H | H | Cl | I | nonafluoro-2-butyl | Br | CF3 |
| 15-1766 | 2,2,2-trichloroethyl | If | H | H | F | H | H | Cl | Me | nonafluoro-2-butyl | Et | i-C3F7 |
| 15-1772 | i-propyl | H | H | H | F | H | H | Cl | Et | nonafluoro-2-butyl | Me | n-C3F7 |
| 15-1773 | 1,2-difluoro-2-propyl | H | H | H | F | H | H | Cl | Et | nonafluoro-2-butyl | Et | i-C3F7 |
| 15-1779 | 2-chloroethyl | H | H | H | F | H | H | Br | n-Pr | heptafluoroisopropyl | Me | CF3 |
| 15-1780 | 2-bromoethyl | H | H | H | F | H | H | Br | n-Pr | heptafluoroisopropyl | Et | CF3 |
| 15-1786 | 2,2,2-trichloroethyl | H | H | H | F | H | H | Br | i-Pr | heptafluoroisopropyl | Me | CF3 |
| 15-1787 | 2,2,2-tribromoethyl | H | H | H | F | H | H | Br | i-Pr | heptafluoroisopropyl | Et | CF3 |
| 15-1793 | 1,2-difluoro-2-propyl | H | H | H | F | H | H | Br | n-Bu | heptafluoroisopropyl | Me | CF3 |
| 15-1794 | 1,3-difluoro-2-propyl | H | H | H | F | H | H | Br | n-Bu | heptafluoroisopropyl | Et | CF3 |
| 15-1800 | i-butyl | H | H | H | F | H | H | Br | i-Bu | nonafluoro-2-butyl | Me | CF3 |
| 15-1801 | s-butyl | H | H | H | F | H | H | Br | i-Bu | nonafluoro-2-butyl | Et | CF3 |
| 15-1807 | 2-fluoroethyl | H | H | H | F | H | H | Br | s-Bu | nonafluoro-2-butyl | Me | CF3 |
| 15-1808 | 2-chloroethyl | H | H | H | F | H | H | Br | s-Bu | nonafluoro-2-butyl | Et | CF3 |
| 15-1814 | 2,2,2-trifluoroethyl | H | H | H | F | H | H | Br | F | nonafluoro-2-butyl | Me | CF3 |
| 15-1815 | 2,2,2-trichloroethyl | H | H | H | F | H | H | Br | F | nonafluoro-2-butyl | Et | CF3 |
| 15-1821 | i-propyl | Et | i-Pr | H | F | H | H | Br | Cl | nonafluoro-2-butyl | Me | CF3 |
| 15-1822 | 1,2-difluoro-2-propyl | H | H | H | F | H | H | Br | Cl | nonafluoro-2-butyl | Et | CF3 |
| 15-1828 | 2-iodoethyl | H | H | H | F | H | H | I | Br | heptafluoroisopropyl | Me | CF3 |
| 15-1829 | 2-cyanoethyl | H | H | H | F | H | H | I | Br | heptafluoroisopropyl | Et | CF3 |
| 15-1835 | n-propyl | n-Pr | Me | H | F | H | H | I | I | heptafluoroisopropyl | Me | CF3 |
| 15-1836 | 3-fluoro-n-propyl | H | H | H | F | H | H | I | I | heptafluoroisopropyl | Et | CF3 |
| 15-1842 | 1,3-dichloro-2-propyl | H | H | H | F | H | H | I | Me | heptafluoroisopropyl | F | C2F5 |
| 15-1843 | 1-chloro-3-fluoro-2-propyl | H | H | H | F | H | H | I | Me | nonafluoro-2-butyl | Cl | CF3 |
| 15-1846 | 4,4,4-trifluoro-n-butyl | H | H | H | F | H | H | I | Et | nonafluoro-2-butyl | F | CF3 |
| 15-1847 | i-butyl | H | H | H | F | H | H | I | Et | nonafluoro-2-butyl | Cl | CF3 |
| 15-1850 | benzyl | H | H | H | F | H | H | I | n-Pr | nonafluoro-2-butyl | F | CF3 |
| 15-1851 | phenyl | H | H | H | F | H | H | I | n-Pr | nonafluoro-2-butyl | Cl | CF3 |
| 15-1854 | 2-fluoroethyl | H | H | H | F | H | H | I | i-Pr | nonafluoro-2-butyl | F | i-C3F7 |
| 15-1855 | 2-chloroethyl | H | H | H | F | H | H | I | i-Pr | nonafluoro-2-butyl | Cl | CF3 |
| 15-1858 | 2-cyanoethyl | H | H | H | F | H | H | I | n-Bu | nonafluoro-2-butyl | F | CF3 |
| 15-1859 | 2,2-difluoroethyl | H | H | H | F | H | H | I | n-Bu | nonafluoro-2-butyl | Cl | CF3 |
| 15-1862 | 2,2,2-trichloroethyl | H | H | H | F | H | H | I | i-Bu | nonafluoro-2-butyl | F | CF3 |
| 15-1863 | 2,2,2-tribromoethyl | H | H | H | F | H | H | I | i-Bu | nonafluoro-2-butyl | Cl | CF3 |
| 15-1866 | 3-chloro-n-propyl | i-Pr | n-Pr | H | F | H | H | I | s-Bu | nonafluoro-2-butyl | F | CF3 |
| 15-1867 | 3-bromo-n-propyl | H | H | H | F | H | H | I | s-Bu | nonafluoro-2-butyl | Cl | CF3 |
| 15-1878 | 2,2-dichloroethyl | H | Et | H | F | H | H | OCF3 | F | heptafluoroisopropyl | F | OCF3 |
| 15-1908 | 2,2,2-trifluoroethyl | H | H | H | F | H | H | OCF3 | Me | nonafluoro-2-butyl | Me | OCF3 |
| 15-2021 | 2,2-dichloroethyl | H | Et | H | F | H | H | OCF3 | F | heptafluoroisopropyl | F | CF3 |
| 15-2051 | 2,2,2-trifluoroethyl | H | H | H | F | H | H | OCF3 | Me | nonafluoro-2-butyl | Me | CF3 |
| 15-2164 | 2,2-dichloroethyl | H | Et | H | F | H | H | CF3 | F | heptafluoroisopropyl | F | CF3 |
| 15-2194 | 222-trifluoroethyl | H | H | H | F | H | H | CF3 | Me | nonafluoro-2-butyl | Me | CF3 |
| 15-2307 | 2,2-dichloroethyl | H | Et | F | F | H | H | Cl | F | heptafluoroisopropyl | F | Cl |
| 15-2337 | 2,2,2-trifluoroethyl | H | H | F | F | H | H | Cl | Me | nonafluoro-2-butyl | Me | I |
| 15-2450 | 2,2-dichloroethyl | H | Et | F | F | H | H | Cl | F | heptafluoroisopropyl | F | OCF3 |
| 15-2480 | 2,2,2-trifluoroethyl | H | H | F | F | H | H | Cl | Me | nonafluoro-2-butyl | Me | OCF3 |
| 15-2585 | methyl | H | H | F | F | H | H | Cl | F | heptafluoroisopropyl | H | CF3 |
| 15-2591 | 2-cyanoethyl | Et | H | F | F | H | H | Cl | I | heptafluoroisopropyl | H | C2F5 |
| 15-2594 | 2,2,2-trifluoroethyl | H | H | F | F | H | H | Cl | F | heptafluoroisopropyl | Cl | CF3 |
| 15-2602 | 1,2-difluoro-2-propyl | H | H | F | F | H | H | Cl | Br | heptafluoroisopropyl | Cl | CF3 |

TABLE 15-continued

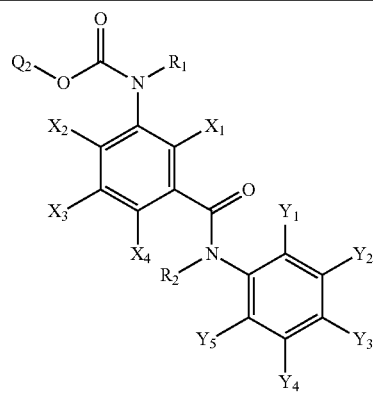

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-2609 | i-butyl | H | H | F | F | H | H | Cl | Me | nonafluoro-2-butyl | H | CF3 |
| 15-2610 | s-butyl | H | H | F | F | H | H | Cl | H | nonafluoro-2-butyl | Me | CF3 |
| 15-2611 | vinyl | i-Pr | H | F | F | H | H | Cl | Et | nonafluoro-2-butyl | H | CF3 |
| 15-2612 | benzyl | H | H | F | F | H | H | Cl | H | nonafluoro-2-butyl | Et | CF3 |
| 15-2623 | 2,2,2-trifluoroethyl | H | H | F | F | H | H | Cl | Me | nonafluoro-2-butyl | Me | n-C3F7 |
| 15-2624 | 2,2,2-trichloroethyl | H | H | F | F | H | H | Cl | Me | nonafluoro-2-butyl | Et | i-C3F7 |
| 15-2630 | i-propyl | H | H | F | F | H | H | Cl | Et | nonafluoro-2-butyl | Me | n-C3F7 |
| 15-2631 | 1,2-difluoro-2-propyl | H | H | F | F | H | H | Cl | Et | nonafluoro-2-butyl | Et | i-C3F7 |
| 15-2637 | 2-chloroethyl | H | H | F | F | H | H | Br | n-Pr | heptafluoroisopropyl | Me | CF3 |
| 15-2638 | 2-bromoethyl | H | H | F | F | H | H | Br | n-Pr | heptafluoroisopropyl | Et | CF3 |
| 15-2644 | 2,2,2-trichloroethyl | H | H | F | F | H | H | Br | i-Pr | heptafluoroisopropyl | Me | CF3 |
| 15-2645 | 2,2,2-tribromoethyl | H | H | F | F | H | H | Br | i-Pr | heptafluoroisopropyl | Et | CF3 |
| 15-2651 | 1,2-difluoro-2-propyl | H | H | F | F | H | H | Br | n-Bu | heptafluoroisopropyl | Me | CF3 |
| 15-2652 | 1,3-difluoro-2-propyl | H | H | F | F | H | H | Br | n-Bu | heptafluoroisopropyl | Et | CF3 |
| 15-2658 | i-butyl | H | H | F | F | H | H | Br | i-Bu | nonafluoro-2-butyl | Me | CF3 |
| 15-2659 | s-butyl | H | H | F | F | H | H | Br | i-Bu | nonafluoro-2-butyl | Et | CF3 |
| 15-2665 | 2-fluoroethyl | H | H | F | F | H | H | Br | s-Bu | nonafluoro-2-butyl | Me | CF3 |
| 15-2666 | 2-chloroethyl | H | H | F | F | H | H | Br | s-Bu | nonafluoro-2-butyl | Et | CF3 |
| 15-2672 | 2,2,2-trifluoroethyl | H | H | F | F | H | H | Br | F | nonafluoro-2-butyl | Me | CF3 |
| 15-2673 | 2,2,2-trichloroethyl | H | H | F | F | H | H | Br | F | nonafluoro-2-butyl | Et | CF3 |
| 15-2679 | i-propyl | Et | i-Pr | F | F | H | H | Br | Cl | nonafluoro-2-butyl | Me | CF3 |
| 15-2680 | 1,2-difluoro-2-propyl | H | H | F | F | H | H | Br | Cl | nonafluoro-2-butyl | Et | CF3 |
| 15-2686 | 2-iodoethyl | H | H | F | F | H | H | I | Br | heptafluoroisopropyl | Me | CF3 |
| 15-2687 | 2-cyanoethyl | H | H | F | F | H | H | I | Br | heptafluoroisopropyl | Et | CF3 |
| 15-2693 | n-propyl | n-Pr | Me | F | F | H | H | I | I | heptafluoroisopropyl | Me | CF3 |
| 15-2694 | 3-fluoro-n-propyl | H | H | F | F | H | H | I | I | heptafluoroisopropyl | Et | CF3 |
| 15-2700 | 1,3-dichloro-2-propyl | H | H | F | F | H | H | I | Me | heptafluoroisopropyl | F | C2F5 |
| 15-2701 | 1-chloro-3-fluoro-2-propyl | H | H | F | F | H | H | I | Me | nonafluoro-2-butyl | Cl | CF3 |
| 15-2704 | 4,4,4-trifluoro-n-butyl | H | H | F | F | H | H | I | Et | nonafluoro-2-butyl | F | CF3 |
| 15-2705 | i-butyl | H | H | F | F | H | H | I | Et | nonafluoro-2-butyl | Cl | CF3 |
| 15-2708 | benzyl | H | H | F | F | H | H | I | n-Pr | nonafluoro-2-butyl | F | CF3 |
| 15-2709 | phenyl | H | H | F | F | H | H | I | n-Pr | nonafluoro-2-butyl | Cl | CF3 |
| 15-2712 | 2-fluoroethyl | H | H | F | F | H | H | I | i-Pr | nonafluoro-2-butyl | F | i-C3F7 |
| 15-2713 | 2-chloroethyl | H | H | F | F | H | H | I | i-Pr | nonafluoro-2-butyl | Cl | CF3 |
| 15-2716 | 2-cyanoethyl | H | H | F | F | H | H | I | n-Bu | nonafluoro-2-butyl | F | CF3 |
| 15-2717 | 2,2-difluoroethyl | H | H | F | F | H | H | I | n-Bu | nonafluoro-2-butyl | Cl | CF3 |
| 15-2720 | 2,2,2-trichloroethyl | H | H | F | F | H | H | I | i-Bu | nonafluoro-2-butyl | F | CF3 |
| 15-2721 | 2,2,2-tribromoethyl | H | H | F | F | H | H | I | i-Bu | nonafluoro-2-butyl | Cl | CF3 |
| 15-2724 | 3-chloro-n-propyl | i-Pr | n-Pr | F | F | H | H | I | s-Bu | nonafluoro-2-butyl | F | CF3 |
| 15-2725 | 3-bromo-n-propyl | H | H | F | F | H | H | I | s-Bu | nonafluoro-2-butyl | Cl | CF3 |
| 15-2736 | 2,2-dichloroethyl | H | Et | F | F | H | H | OCF3 | F | heptafluoroisopropyl | F | OCF3 |
| 15-2766 | 2,2,2-trifluoroethyl | H | H | F | F | H | H | OCF3 | Me | nonafluoro-2-butyl | Me | OCF3 |
| 15-2879 | 2,2-dichloroethyl | H | Et | F | F | H | H | OCF3 | F | heptafluoroisopropyl | F | CF3 |
| 15-2909 | 2,2,2-trifluoroethyl | H | H | F | F | H | H | OCF3 | Me | nonafluoro-2-butyl | Me | CF3 |
| 15-3022 | 2,2-dichloroethyl | H | Et | F | F | H | H | CF3 | F | heptafluoroisopropyl | F | CF3 |
| 15-3052 | 2,2,2-trifluoroethyl | H | H | F | F | H | H | CF3 | Me | nonafluoro-2-butyl | Me | CF3 |
| 15-3157 | 2,2,2-trichloroethyl | H | H | F | F | F | H | Cl | F | pentafluoroethyl | H | Cl |
| 15-3158 | 2,2,2-trichloroethyl | Me | H | F | F | F | H | Cl | H | heptafluoroisopropyl | F | Cl |
| 15-3159 | 2,2,2-trichloroethyl | H | Me | F | F | F | H | Br | Cl | heptafluoroisopropyl | H | Br |
| 15-3160 | 2,2,2-trichloroethyl | Me | Me | F | F | F | H | I | H | heptafluoroisopropyl | Cl | I |
| 15-3161 | 2,2,2-trichloroethyl | H | H | F | F | F | H | Cl | Br | heptafluoroisopropyl | H | OCF3 |
| 15-3162 | 2,2,2-trichloroethyl | H | H | F | F | F | H | Br | H | heptafluoroisopropyl | Br | OCF3 |
| 15-3163 | 2,2,2-trichloroethyl | Et | H | F | F | F | H | I | I | heptafluoroisopropyl | H | OCF3 |
| 15-3164 | 2,2,2-trichloroethyl | H | H | F | F | F | H | Cl | H | heptafluoroisopropyl | I | CF3 |
| 15-3165 | 2,2,2-trichloroethyl | H | Et | F | F | F | H | Br | F | heptafluoroisopropyl | F | CF3 |
| 15-3166 | 2,2,2-trichloroethyl | H | H | F | F | F | H | I | F | heptafluoroisopropyl | Cl | CF3 |
| 15-3167 | 2,2,2-trichloroethyl | H | H | F | F | F | H | CF3 | F | heptafluoroisopropyl | Br | CF3 |
| 15-3168 | 2,2,2-trichloroethyl | Et | Et | F | F | F | H | Cl | F | nonafluoro-2-butyl | I | Cl |

TABLE 15-continued

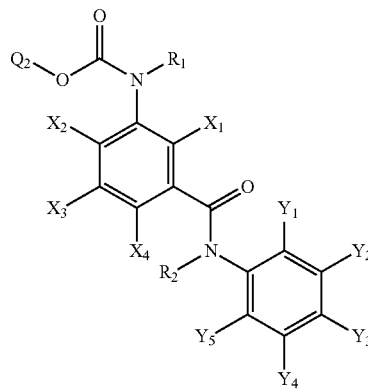

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-3169 | 2,2,2-trichloroethyl | H | H | F | F | F | H | Br | Cl | nonafluoro-2-butyl | F | Br |
| 15-3170 | 2,2,2-trichloroethyl | H | H | F | F | F | H | I | Cl | nonafluoro-2-butyl | Cl | I |
| 15-3171 | 2,2,2-trichloroethyl | n-Pr | H | F | F | F | H | Cl | Cl | nonafluoro-2-butyl | Br | OCF3 |
| 15-3172 | 2,2,2-trichloroethyl | H | H | F | F | F | H | Br | Cl | nonafluoro-2-butyl | I | OCF3 |
| 15-3173 | 2,2,2-trichloroethyl | H | n-Pr | F | F | F | H | I | Br | nonafluoro-2-butyl | F | OCF3 |
| 15-3174 | 2,2,2-trichloroethyl | H | H | F | F | F | H | Cl | Br | nonafluoro-2-butyl | Cl | CF3 |
| 15-3175 | 2,2,2-trichloroethyl | H | H | F | F | F | H | Br | Br | nonafluoro-2-butyl | Br | CF3 |
| 15-3176 | 2,2,2-trichloroethyl | n-Pr | n-Pr | F | F | F | H | I | Br | nonafluoro-2-butyl | I | CF3 |
| 15-3177 | 2,2,2-trichloroethyl | H | H | F | F | F | H | CF3 | I | nonafluoro-2-butyl | F | CF3 |
| 15-3178 | 2,2,2-trichloroethyl | H | H | H | H | F | H | Cl | I | pentafluoroethyl | Cl | Cl |
| 15-3179 | 2,2,2-trichloroethyl | H | H | H | H | F | H | Cl | I | heptafluoroisopropyl | Br | Cl |
| 15-3180 | 2,2,2-trichloroethyl | H | H | H | H | F | H | Br | I | heptafluoroisopropyl | I | Br |
| 15-3181 | 2,2,2-trichloroethyl | H | H | H | H | F | H | I | Me | heptafluoroisopropyl | H | I |
| 15-3182 | 2,2,2-trichloroethyl | H | H | H | H | F | H | Cl | H | heptafluoroisopropyl | Me | OCF3 |
| 15-3183 | 2,2,2-trichloroethyl | i-Pr | H | H | H | F | H | Br | Et | heptafluoroisopropyl | H | OCF3 |
| 15-3184 | 2,2,2-trichloroethyl | H | H | H | H | F | H | I | H | heptafluoroisopropyl | Et | OCF3 |
| 15-3185 | 2,2,2-trichloroethyl | H | H | H | H | F | H | Cl | n-Pr | heptafluoroisopropyl | H | CF3 |
| 15-3186 | 2,2,2-trichloroethyl | H | i-Pr | H | H | F | H | Br | H | heptafluoroisopropyl | n-Pr | CF3 |
| 15-3187 | 2,2,2-trichloroethyl | i-Pr | i-Pr | H | H | F | H | I | i-Pr | heptafluoroisopropyl | H | CF3 |
| 15-3188 | 2,2,2-trichloroethyl | H | H | H | H | F | H | CF3 | H | heptafluoroisopropyl | i-Pr | CF3 |
| 15-3189 | 2,2,2-trichloroethyl | H | H | H | H | F | H | Cl | n-Bu | nonafluoro-2-butyl | H | Cl |
| 15-3190 | 2,2,2-trichloroethyl | H | H | H | H | F | H | Br | H | nonafluoro-2-butyl | n-Bu | Br |
| 15-3191 | 2,2,2-trichloroethyl | H | H | H | H | F | H | I | i-Bu | nonafluoro-2-butyl | H | I |
| 15-3192 | 2,2,2-trichloroethyl | H | H | H | H | F | H | Cl | H | nonafluoro-2-butyl | i-Bu | OCF3 |
| 15-3193 | 2,2,2-trichloroethyl | H | H | H | H | F | H | Br | s-Bu | nonafluoro-2-butyl | H | OCF3 |
| 15-3194 | 2,2,2-trichloroethyl | H | H | H | H | F | H | I | H | nonafluoro-2-butyl | s-Bu | OCF3 |
| 15-3195 | 2,2,2-trichloroethyl | H | H | H | H | F | H | Cl | Me | nonafluoro-2-butyl | Me | CF3 |
| 15-3196 | 2,2,2-trichloroethyl | H | H | H | H | F | H | Br | Me | nonafluoro-2-butyl | Et | CF3 |
| 15-3197 | 2,2,2-trichloroethyl | C(O)Me | H | H | H | F | H | I | Me | nonafluoro-2-butyl | n-Pr | CF3 |
| 15-3198 | 2,2,2-trichloroethyl | H | H | H | H | F | H | CF3 | Me | nonafluoro-2-butyl | i-Pr | CF3 |
| 15-3199 | 2,2,2-trichloroethyl | H | H | H | H | H | F | Cl | Me | pentafluoroethyl | n-Bu | Cl |
| 15-3200 | 2,2,2-trichloroethyl | H | H | H | H | H | F | Br | Me | heptafluoroisopropyl | i-Bu | Br |
| 15-3201 | 2,2,2-trichloroethyl | H | C(O)Me | H | H | H | F | Br | Me | heptafluoroisopropyl | s-Bu | OCF3 |
| 15-3202 | 2,2,2-trichloroethyl | H | H | H | H | H | F | I | Et | heptafluoroisopropyl | Me | CF3 |
| 15-3203 | 2,2,2-trichloroethyl | H | H | H | H | H | F | CF3 | Et | heptafluoroisopropyl | Et | CF3 |
| 15-3204 | 2,2,2-trichloroethyl | C(O)Me | C(O)Me | H | H | H | F | I | Et | nonafluoro-2-butyl | n-Pr | I |
| 15-3205 | 2,2,2-trichloroethyl | H | H | H | H | H | F | Cl | Et | nonafluoro-2-butyl | i-Pr | OCF3 |
| 15-3206 | 2,2,2-trichloroethyl | H | H | H | H | H | F | Br | Et | nonafluoro-2-butyl | n-Bu | CF3 |
| 15-3207 | 2,2,2-trichloroethyl | H | H | H | H | H | F | CF3 | Et | nonafluoro-2-butyl | i-Bu | CF3 |
| 15-3208 | 2,2,2-trichloroethyl | H | H | F | H | F | H | Cl | Et | pentafluoroethyl | s-Bu | Cl |
| 15-3209 | 2,2,2-trichloroethyl | H | H | F | H | F | H | Cl | n-Pr | heptafluoroisopropyl | Me | Cl |
| 15-3210 | 2,2,2-trichloroethyl | H | H | F | H | F | H | Br | n-Pr | heptafluoroisopropyl | Et | Br |
| 15-3211 | 2,2,2-trichloroethyl | Me | Et | F | H | F | H | I | n-Pr | heptafluoroisopropyl | n-Pr | I |
| 15-3212 | 2,2,2-trichloroethyl | H | H | F | H | F | H | Cl | n-Pr | heptafluoroisopropyl | i-Pr | OCF3 |
| 15-3213 | 2,2,2-trichloroethyl | H | H | F | H | F | H | Br | n-Pr | heptafluoroisopropyl | n-Bu | OCF3 |
| 15-3214 | 2,2,2-trichloroethyl | H | H | F | H | F | H | I | n-Pr | heptafluoroisopropyl | i-Bu | OCF3 |
| 15-3215 | 2,2,2-trichloroethyl | H | H | F | H | F | H | Cl | n-Pr | heptafluoroisopropyl | s-Bu | CF3 |
| 15-3216 | 2,2,2-trichloroethyl | Me | n-Pr | F | H | F | H | Br | i-Pr | heptafluoroisopropyl | Me | CF3 |
| 15-3217 | 2,2,2-trichloroethyl | H | H | F | H | F | H | I | i-Pr | heptafluoroisopropyl | Et | CF3 |
| 15-3218 | 2,2,2-trichloroethyl | H | H | F | H | F | H | CF3 | i-Pr | heptafluoroisopropyl | n-Pr | CF3 |
| 15-3219 | 2,2,2-trichloroethyl | H | H | F | H | F | H | Cl | i-Pr | nonafluoro-2-butyl | i-Pr | Cl |
| 15-3220 | 2,2,2-trichloroethyl | H | H | F | H | F | H | Br | i-Pr | nonafluoro-2-butyl | n-Bu | Br |
| 15-3221 | 2,2,2-trichloroethyl | H | H | F | H | F | H | I | i-Pr | nonafluoro-2-butyl | i-Bu | I |
| 15-3222 | 2,2,2-trichloroethyl | Me | i-Pr | F | H | F | H | Cl | i-Pr | nonafluoro-2-butyl | s-Bu | OCF3 |
| 15-3223 | 2,2,2-trichloroethyl | H | H | F | H | F | H | Br | n-Bu | nonafluoro-2-butyl | Me | OCF3 |
| 15-3224 | 2,2,2-trichloroethyl | H | H | F | H | F | H | I | n-Bu | nonafluoro-2-butyl | Et | OCF3 |
| 15-3225 | 2,2,2-trichloroethyl | H | H | F | H | F | H | Br | n-Bu | nonafluoro-2-butyl | n-Pr | CF3 |
| 15-3226 | 2,2,2-trichloroethyl | H | H | F | H | F | H | I | n-Bu | nonafluoro-2-butyl | i-Pr | CF3 |

TABLE 15-continued

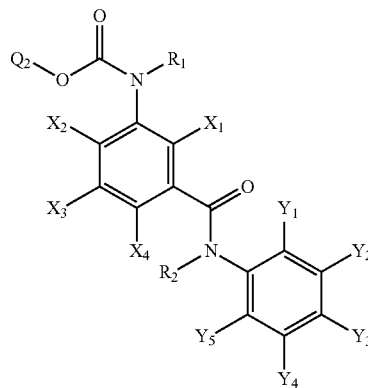

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-3227 | 2,2,2-trichloroethyl | H | H | F | H | F | H | CF3 | n-Bu | nonafluoro-2-butyl | n-Bu | CF3 |
| 15-3228 | 2,2,2-trichloroethyl | H | H | F | H | H | F | Cl | n-Bu | pentafluoroethyl | i-Bu | Cl |
| 15-3229 | 2,2,2-trichloroethyl | Me | C(O)Me | F | H | H | F | Br | n-Bu | heptafluoroisopropyl | s-Bu | Br |
| 15-3230 | 2,2,2-trichloroethyl | H | H | F | H | H | F | Br | i-Bu | heptafluoroisopropyl | Me | OCF3 |
| 15-3231 | 2,2,2-trichloroethyl | H | H | F | H | H | F | I | i-Bu | heptafluoroisopropyl | Et | CF3 |
| 15-3232 | 2,2,2-trichloroethyl | H | H | F | H | H | F | CF3 | i-Bu | heptafluoroisopropyl | n-Pr | CF3 |
| 15-3233 | 2,2,2-trichloroethyl | H | H | F | H | H | F | I | i-Bu | nonafluoro-2-butyl | i-Pr | I |
| 15-3234 | 2,2,2-trichloroethyl | H | H | F | H | H | F | Cl | i-Bu | nonafluoro-2-butyl | n-Bu | OCF3 |
| 15-3235 | 2,2,2-trichloroethyl | H | H | F | H | H | F | Br | i-Bu | nonafluoro-2-butyl | i-Bu | CF3 |
| 15-3236 | 2,2,2-trichloroethyl | H | H | F | H | H | F | CF3 | i-Bu | nonafluoro-2-butyl | s-Bu | CF3 |
| 15-3237 | 2,2,2-trichloroethyl | H | H | H | F | F | H | Cl | s-Bu | pentafluoroethyl | Me | Cl |
| 15-3238 | 2,2,2-trichloroethyl | H | H | H | F | F | H | Br | s-Bu | heptafluoroisopropyl | Et | Br |
| 15-3239 | 2,2,2-trichloroethyl | H | H | H | F | F | H | Br | s-Bu | heptafluoroisopropyl | n-Pr | OCF3 |
| 15-3240 | 2,2,2-trichloroethyl | H | H | H | F | F | H | I | s-Bu | heptafluoroisopropyl | i-Pr | CF3 |
| 15-3241 | 2,2,2-trichloroethyl | H | H | H | F | F | H | CF3 | s-Bu | heptafluoroisopropyl | n-Bu | CF3 |
| 15-3242 | 2,2,2-trichloroethyl | H | H | H | F | F | H | I | s-Bu | nonafluoro-2-butyl | i-Bu | I |
| 15-3243 | 2,2,2-trichloroethyl | Et | Me | H | F | F | H | Cl | s-Bu | nonafluoro-2-butyl | s-Bu | OCF3 |
| 15-3244 | 2,2,2-trichloroethyl | H | H | H | F | F | H | Br | F | nonafluoro-2-butyl | Me | CF3 |
| 15-3245 | 2,2,2-trichloroethyl | H | H | H | F | F | H | CF3 | F | nonafluoro-2-butyl | Et | CF3 |
| 15-3246 | 2,2,2-trichloroethyl | H | H | H | F | H | F | Cl | F | pentafluoroethyl | n-Pr | Cl |
| 15-3247 | 2,2,2-trichloroethyl | H | H | H | F | H | F | Br | F | heptafluoroisopropyl | i-Pr | Br |
| 15-3248 | 2,2,2-trichloroethyl | H | H | H | F | H | F | Br | F | heptafluoroisopropyl | n-Bu | OCF3 |
| 15-3249 | 2,2,2-trichloroethyl | H | H | H | F | H | F | I | F | heptafluoroisopropyl | i-Bu | CF3 |
| 15-3250 | 2,2,2-trichloroethyl | Et | n-Pr | H | F | H | F | CF3 | F | heptafluoroisopropyl | s-Bu | CF3 |
| 15-3251 | 2,2,2-trichloroethyl | Et | i-Pr | H | F | H | F | I | Cl | nonafluoro-2-butyl | Me | I |
| 15-3252 | 2,2,2-trichloroethyl | H | H | H | F | H | F | Cl | Cl | nonafluoro-2-butyl | Et | OCF3 |
| 15-3253 | 2,2,2-trichloroethyl | H | H | H | F | H | F | Br | Cl | nonafluoro-2-butyl | n-Pr | CF3 |
| 15-3254 | 2,2,2-trichloroethyl | H | H | H | F | H | F | CF3 | Cl | nonafluoro-2-butyl | i-Pr | CF3 |
| 15-3255 | 2,2,2-trichloroethyl | H | H | H | H | F | F | Cl | Cl | pentafluoroethyl | n-Bu | Cl |
| 15-3256 | 2,2,2-trichloroethyl | Et | C(O)Me | H | H | F | F | Br | Cl | heptafluoroisopropyl | i-Bu | Br |
| 15-3257 | 2,2,2-trichloroethyl | H | H | H | H | F | F | Br | Cl | heptafluoroisopropyl | s-Bu | OCF3 |
| 15-3258 | 2,2,2-trichloroethyl | H | H | H | H | F | F | I | Br | heptafluoroisopropyl | Me | CF3 |
| 15-3259 | 2,2,2-trichloroethyl | H | H | H | H | F | F | CF3 | Br | heptafluoroisopropyl | Et | CF3 |
| 15-3260 | 2,2,2-trichloroethyl | H | H | H | H | F | F | I | Br | nonafluoro-2-butyl | n-Pr | I |
| 15-3261 | 2,2,2-trichloroethyl | H | H | H | H | F | F | Cl | Br | nonafluoro-2-butyl | i-Pr | OCF3 |
| 15-3262 | 2,2,2-trichloroethyl | H | H | H | H | F | F | Br | Br | nonafluoro-2-butyl | n-Bu | CF3 |
| 15-3263 | 2,2,2-trichloroethyl | H | H | H | H | F | F | CF3 | Br | nonafluoro-2-butyl | i-Bu | CF3 |
| 15-3264 | 2,2,2-trichloroethyl | H | H | F | F | H | F | Cl | Br | pentafluoroethyl | s-Bu | Cl |
| 15-3265 | 2,2,2-trichloroethyl | n-Pr | Me | F | F | H | F | Br | I | heptafluoroisopropyl | Me | Br |
| 15-3266 | 2,2,2-trichloroethyl | H | H | F | F | H | F | Br | I | heptafluoroisopropyl | Et | OCF3 |
| 15-3267 | 2,2,2-trichloroethyl | n-Pr | Et | F | F | H | F | I | I | heptafluoroisopropyl | n-Pr | CF3 |
| 15-3268 | 2,2,2-trichloroethyl | H | H | F | F | H | F | CF3 | I | heptafluoroisopropyl | i-Pr | CF3 |
| 15-3269 | 2,2,2-trichloroethyl | H | H | F | F | H | F | I | I | nonafluoro-2-butyl | n-Bu | I |
| 15-3270 | 2,2,2-trichloroethyl | H | H | F | F | H | F | Cl | I | nonafluoro-2-butyl | i-Bu | OCF3 |
| 15-3271 | 2,2,2-trichloroethyl | H | H | F | F | H | F | Br | I | nonafluoro-2-butyl | s-Bu | CF3 |
| 15-3272 | 2,2,2-trichloroethyl | H | H | F | F | H | F | CF3 | Me | nonafluoro-2-butyl | F | CF3 |
| 15-3273 | 2,2,2-trichloroethyl | H | H | F | H | F | F | Cl | Me | pentafluoroethyl | Cl | Cl |
| 15-3274 | 2,2,2-trichloroethyl | H | H | F | H | F | F | Br | Me | heptafluoroisopropyl | Br | Br |
| 15-3275 | 2,2,2-trichloroethyl | H | H | F | H | F | F | Br | Me | heptafluoroisopropyl | I | OCF3 |
| 15-3276 | 2,2,2-trichloroethyl | H | H | F | H | F | F | I | Et | heptafluoroisopropyl | F | CF3 |
| 15-3277 | 2,2,2-trichloroethyl | H | H | F | H | F | F | CF3 | Et | heptafluoroisopropyl | Cl | CF3 |
| 15-3278 | 2,2,2-trichloroethyl | H | H | F | H | F | F | I | Et | nonafluoro-2-butyl | Br | I |
| 15-3279 | 2,2,2-trichloroethyl | n-Pr | i-Pr | F | H | F | F | Cl | Et | nonafluoro-2-butyl | I | OCF3 |
| 15-3280 | 2,2,2-trichloroethyl | H | H | F | H | F | F | Br | n-Pr | nonafluoro-2-butyl | F | CF3 |
| 15-3281 | 2,2,2-trichloroethyl | H | H | F | H | F | F | CF3 | n-Pr | nonafluoro-2-butyl | Cl | CF3 |
| 15-3282 | 2,2,2-trichloroethyl | H | H | H | F | F | F | Cl | n-Pr | pentafluoroethyl | Br | Cl |
| 15-3283 | 2,2,2-trichloroethyl | H | H | H | F | F | F | Br | n-Pr | heptafluoroisopropyl | I | Br |
| 15-3284 | 2,2,2-trichloroethyl | H | H | H | F | F | F | Br | i-Pr | heptafluoroisopropyl | F | OCF3 |

TABLE 15-continued

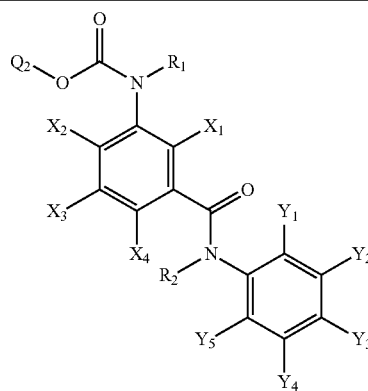

| compound number | Q₂ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 15-3285 | 2,2,2-trichloroethyl | H | H | H | F | F | F | I | i-Pr | heptafluoroisopropyl | Cl | CF3 |
| 15-3286 | 2,2,2-trichloroethyl | n-Pr | C(O)Me | H | F | F | F | CF3 | i-Pr | heptafluoroisopropyl | Br | CF3 |
| 15-3287 | 2,2,2-trichloroethyl | H | H | H | F | F | F | I | i-Pr | nonafluoro-2-butyl | I | I |
| 15-3288 | 2,2,2-trichloroethyl | H | H | H | F | F | F | Cl | n-Bu | nonafluoro-2-butyl | F | OCF3 |
| 15-3289 | 2,2,2-trichloroethyl | H | H | H | F | F | F | Br | n-Bu | nonafluoro-2-butyl | Cl | CF3 |
| 15-3290 | 2,2,2-trichloroethyl | H | H | H | F | F | F | CF3 | n-Bu | nonafluoro-2-butyl | Br | CF3 |
| 15-3291 | 2,2,2-trichloroethyl | i-Pr | Me | F | F | F | F | Cl | n-Bu | pentafluoroethyl | I | Cl |
| 15-3292 | 2,2,2-trichloroethyl | H | H | F | F | F | F | Br | i-Bu | heptafluoroisopropyl | F | Br |
| 15-3293 | 2,2,2-trichloroethyl | H | H | F | F | F | F | Br | i-Bu | heptafluoroisopropyl | Cl | OCF3 |
| 15-3294 | 2,2,2-trichloroethyl | H | H | F | F | F | F | I | i-Bu | heptafluoroisopropyl | Br | CF3 |
| 15-3295 | 2,2,2-trichloroethyl | i-Pr | Et | F | F | F | F | CF3 | i-Bu | heptafluoroisopropyl | I | CF3 |
| 15-3296 | 2,2,2-trichloroethyl | i-Pr | n-Pr | F | F | F | F | I | s-Bu | nonafluoro-2-butyl | F | I |
| 15-3297 | 2,2,2-trichloroethyl | H | H | F | F | F | F | Cl | s-Bu | nonafluoro-2-butyl | Cl | OCF3 |
| 15-3298 | 2,2,2-trichloroethyl | i-Pr | C(O)Me | F | F | F | F | Br | s-Bu | nonafluoro-2-butyl | Br | CF3 |
| 15-3299 | 2,2,2-trichloroethyl | H | H | F | F | F | F | CF3 | s-Bu | nonafluoro-2-butyl | I | CF3 |
| 15-3308 | 2,2-dichloroethyl | H | Et | H | CN | H | H | Cl | F | heptafluoroisopropyl | F | OCF3 |
| 15-3338 | 2,2,2-trifluoroethyl | H | H | H | CN | H | H | Cl | Me | nonafluoro-2-butyl | Me | OCF3 |
| 15-3447 | 2-bromoethyl | H | H | H | CN | H | H | F | Br | heptafluoroisopropyl | H | CF3 |
| 15-3457 | 3-chloro-n-propyl | n-Pr | H | H | CN | H | H | Cl | Cl | heptafluoroisopropyl | Br | CF3 |
| 15-3464 | 3,3,3-trifluoro-n-propyl | H | H | H | CN | H | H | Cl | I | nonafluoro-2-butyl | Cl | CF3 |
| 15-3467 | i-butyl | H | H | H | CN | H | H | Cl | Me | nonafluoro-2-butyl | H | CF3 |
| 15-3468 | s-butyl | H | H | H | CN | H | H | Cl | H | nonafluoro-2-butyl | Me | CF3 |
| 15-3469 | vinyl | i-Pr | H | H | CN | H | H | Cl | Et | nonafluoro-2-butyl | H | CF3 |
| 15-3470 | benzyl | H | H | H | CN | H | H | Cl | H | nonafluoro-2-butyl | Et | CF3 |
| 15-3481 | 2,2,2-trifluoroethyl | H | H | H | CN | H | H | Cl | Me | nonafluoro-2-butyl | Me | n-C3F7 |
| 15-3482 | 2,2,2-trichloroethyl | H | H | H | CN | H | H | Cl | Me | nonafluoro-2-butyl | Et | i-C3F7 |
| 15-3488 | i-propyl | H | H | H | CN | H | H | Cl | Et | nonafluoro-2-butyl | Me | n-C3F7 |
| 15-3489 | 1,2-difluoro-2-propyl | H | H | H | CN | H | H | Cl | Et | nonafluoro-2-butyl | Et | i-C3F7 |
| 15-3495 | 2-chloroethyl | H | H | H | CN | H | H | Br | n-Pr | heptafluoroisopropyl | Me | CF3 |
| 15-3496 | 2-bromoethyl | H | H | H | CN | H | H | Br | n-Pr | heptafluoroisopropyl | Et | CF3 |
| 15-3502 | 2,2,2-trichloroethyl | H | H | H | CN | H | H | Br | i-Pr | heptafluoroisopropyl | Me | CF3 |
| 15-3503 | 2,2,2-tribromoethyl | H | H | H | CN | H | H | Br | i-Pr | heptafluoroisopropyl | Et | CF3 |
| 15-3509 | 1,2-difluoro-2-propyl | H | H | H | CN | H | H | Br | n-Bu | heptafluoroisopropyl | Me | CF3 |
| 15-3510 | 1,3-difluoro-2-propyl | H | H | H | CN | H | H | Br | n-Bu | heptafluoroisopropyl | Et | CF3 |
| 15-3516 | i-butyl | H | H | H | CN | H | H | Br | i-Bu | nonafluoro-2-butyl | Me | CF3 |
| 15-3517 | s-butyl | H | H | H | CN | H | H | Br | i-Bu | nonafluoro-2-butyl | Et | CF3 |
| 15-3523 | 2-fluoroethyl | H | H | H | CN | H | H | Br | s-Bu | nonafluoro-2-butyl | Me | CF3 |
| 15-3524 | 2-chloroethyl | H | H | H | CN | H | H | Br | s-Bu | nonafluoro-2-butyl | Et | CF3 |
| 15-3530 | 2,2,2-trifluoroethyl | H | H | H | CN | H | H | Br | F | nonafluoro-2-butyl | Me | CF3 |
| 15-3531 | 2,2,2-trichloroethyl | H | H | H | CN | H | H | Br | F | nonafluoro-2-butyl | Et | CF3 |
| 15-3537 | i-propyl | Et | i-Pr | H | CN | H | H | Br | Cl | nonafluoro-2-butyl | Me | CF3 |
| 15-3538 | 1,2-difluoro-2-propyl | H | H | H | CN | H | H | Br | Cl | nanafluoro-2-butyl | Et | CF3 |
| 15-3544 | 2-iodoethyl | H | H | H | CN | H | H | I | Br | heptafluoroisopropyl | Me | CF3 |
| 15-3545 | 2-cyanoethyl | H | H | H | CN | H | H | I | Br | heptafluoroisopropyl | Et | CF3 |
| 15-3551 | n-propyl | n-Pr | Me | H | CN | H | H | I | I | heptafluoroisopropyl | Me | CF3 |
| 15-3552 | 3-fluoro-n-propyl | H | H | H | CN | H | H | I | I | heptafluoroisopropyl | Et | CF3 |
| 15-3558 | 1,3-dichloro-2-propyl | H | H | H | CN | H | H | I | Me | heptafluoroisopropyl | F | C2F5 |
| 15-3559 | 1-chloro-3-fluoro-2-propyl | H | H | H | CN | H | H | I | Me | nonafluoro-2-butyl | Cl | CF3 |
| 15-3562 | 4,4,4-trifluoro-n-butyl | H | H | H | CN | H | H | I | Et | nonafluoro-2-butyl | F | CF3 |
| 15-3563 | i-butyl | H | H | H | CN | H | H | I | Et | nonafluoro-2-butyl | Cl | CF3 |
| 15-3566 | benzyl | H | H | H | CN | H | H | I | n-Pr | nonafluoro-2-butyl | F | CF3 |
| 15-3567 | phenyl | H | H | H | CN | H | H | I | n-Pr | nonafluoro-2-butyl | Cl | CF3 |
| 15-3570 | 2-fluoroethyl | H | H | H | CN | H | H | I | i-Pr | nonafluoro-2-butyl | F | i-C3F7 |
| 15-3571 | 2-chloroethyl | H | H | H | CN | H | H | I | i-Pr | nonafluoro-2-butyl | Cl | CF3 |
| 15-3574 | 2-cyanoethyl | H | H | H | CN | H | H | I | n-Bu | nonafluoro-2-butyl | F | CF3 |
| 15-3575 | 2,2-difluoroethyl | H | H | H | CN | H | H | I | n-Bu | nonafluoro-2-butyl | Cl | CF3 |
| 15-3578 | 2,2,2-trichloroethyl | H | H | H | CN | H | H | I | i-Bu | nonafluoro-2-butyl | F | CF3 |
| 15-3579 | 2,2,2-tribromoethyl | H | H | H | CN | H | H | I | i-Bu | nonafluoro-2-butyl | Cl | CF3 |

TABLE 15-continued

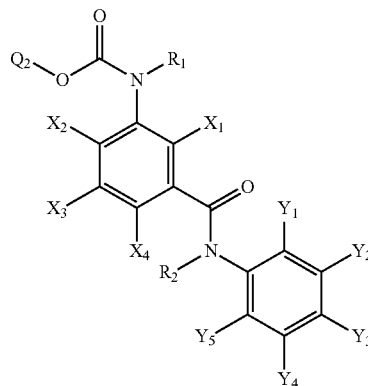

| compound number | $Q_2$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 15-3582 | 3-chloro-n-propyl | i-Pr | n-Pr | H | CN | H | H | I | s-Bu | nonafluoro-2-butyl | F | CF3 |
| 15-3583 | 3-bromo-n-propyl | H | H | H | CN | H | H | I | s-Bu | nonafluoro-2-butyl | Cl | CF3 |
| 15-3594 | 2,2-dichloroethyl | H | Et | H | CN | H | H | OCF3 | F | heptafluoroisopropyl | F | OCF3 |
| 15-3624 | 2,2,2-trifluoroethyl | H | H | H | CN | H | H | OCF3 | Me | nonafluoro-2-butyl | Me | OCF3 |
| 15-3737 | 2,2-dichloroethyl | H | Et | H | CN | H | H | OCF3 | F | heptafluoroisopropyl | F | CF3 |
| 15-3767 | 2,2,2-trifluoroethyl | H | H | H | CN | H | H | OCF3 | Me | nonafluoro-2-butyl | Me | CF3 |
| 15-3880 | 2,2-dichloroethyl | H | Et | H | CN | H | H | CF3 | F | heptafluoroisopropyl | F | CF3 |
| 15-3910 | 2,2,2-trifluoroethyl | H | H | H | CN | H | H | CF3 | Me | nonafluoro-2-butyl | Me | CF3 |
| 15-4023 | 2,2-dichloroethyl | H | Et | F | CN | H | H | Cl | F | heptafluoroisopropyl | F | Cl |
| 15-4053 | 2,2,2-trifluoroethyl | H | H | F | CN | H | H | Cl | Me | nonafluoro-2-butyl | Me | I |
| 15-4166 | 2,2-dichloroethyl | H | Et | F | CN | H | H | Cl | F | heptafluoroisopropyl | F | OCF3 |
| 15-4196 | 2,2,2-trifluoroethyl | H | H | F | CN | H | H | Cl | Me | nonafluoro-2-butyl | Me | OCF3 |
| 15-4304 | 2-chloroethyl | Me | Me | F | CN | H | H | Cl | H | heptafluoroisopropyl | Cl | CF3 |
| 15-4311 | 2,2,2-trichloroethyl | H | H | F | CN | H | H | Cl | F | heptafluoroisopropyl | Br | CF3 |
| 15-4318 | 1,2-difluoro-2-propyl | H | H | F | CN | H | H | Cl | Br | heptafluoroisopropyl | Cl | CF3 |
| 15-4325 | i-butyl | H | H | F | CN | H | H | Cl | Me | nonafluoro-2-butyl | H | CF3 |
| 15-4326 | s-butyl | H | H | F | CN | H | H | Cl | H | nonafluoro-2-butyl | Me | CF3 |
| 15-4327 | vinyl | i-Pr | H | F | CN | H | H | Cl | Et | nonafluoro-2-butyl | H | CF3 |
| 15-4328 | benzyl | H | H | F | CN | H | H | Cl | H | nonafluoro-2-butyl | Et | CF3 |
| 15-4339 | 2,2,2-trifluoroethyl | H | H | F | CN | H | H | Cl | Me | nonafluoro-2-butyl | Me | n-C3F7 |
| 15-4340 | 2,2,2-trichloroethyl | H | H | F | CN | H | H | Cl | Me | nonafluoro-2-butyl | Et | i-C3F7 |
| 15-4346 | i-propyl | H | H | F | CN | H | H | Cl | Et | nonafluoro-2-butyl | Me | n-C3F7 |
| 15-4347 | 1,2-difluoro-2-propyl | H | H | F | CN | H | H | Cl | Et | nonafluoro-2-butyl | Et | i-C3F7 |
| 15-4353 | 2-chloroethyl | H | H | F | CN | H | H | Br | n-Pr | heptafluoroisopropyl | Me | CF3 |
| 15-4354 | 2-bromoethyl | H | H | F | CN | H | H | Br | n-Pr | heptafluoroisopropyl | Et | CF3 |
| 15-4360 | 2,2,2-trichloroethyl | H | H | F | CN | H | H | Br | i-Pr | heptafluoroisopropyl | Me | CF3 |
| 15-4361 | 2,2,2-tribromoethyl | H | H | F | CN | H | H | Br | i-Pr | heptafluoroisopropyl | Et | CF3 |
| 15-4367 | 1,2-difluoro-2-propyl | H | H | F | CN | H | H | Br | n-Bu | heptafluoroisopropyl | Me | CF3 |
| 15-4368 | 1,3-difluoro-2-propyl | H | H | F | CN | H | H | Br | n-Bu | heptafluoroisopropyl | Et | CF3 |
| 15-4374 | i-butyl | H | H | F | CN | H | H | Br | i-Bu | nonafluoro-2-butyl | Me | CF3 |
| 15-4375 | s-butyl | H | H | F | CN | H | H | Br | i-Bu | nonafluoro-2-butyl | Et | CF3 |
| 15-4381 | 2-fluoroethyl | H | H | F | CN | H | H | Br | s-Bu | nonafluoro-2-butyl | Me | CF3 |
| 15-4382 | 2-chloroethyl | H | H | F | CN | H | H | Br | s-Bu | nonafluoro-2-butyl | Et | CF3 |
| 15-4388 | 2,2,2-trifluoroethyl | H | H | F | CN | H | H | Br | F | nonafluoro-2-butyl | Me | CF3 |
| 15-4389 | 2,2,2-trichloroethyl | H | H | F | CN | H | H | Br | F | nonafluoro-2-butyl | Et | CF3 |
| 15-4395 | i-propyl | Et | i-Pr | F | CN | H | H | Br | Cl | nonafluoro-2-butyl | Me | CF3 |
| 15-4396 | 1,2-difluoro-2-propyl | H | H | F | CN | H | H | Br | Cl | nonafluoro-2-butyl | Et | CF3 |
| 15-4402 | 2-iodoethyl | H | H | F | CN | H | H | I | Br | heptafluoroisopropyl | Me | CF3 |
| 15-4403 | 2-cyanoethyl | H | H | F | CN | H | H | I | Br | heptafluoroisopropyl | Et | CF3 |
| 15-4409 | n-propyl | n-Pr | Me | F | CN | H | H | I | I | heptafluoroisopropyl | Me | CF3 |
| 15-4410 | 3-fluoro-n-propyl | H | H | F | CN | H | H | I | I | heptafluoroisopropyl | Et | CF3 |
| 15-4416 | 1,3-dichloro-2-propyl | H | H | F | CN | H | H | I | Me | heptafluoroisopropyl | F | C2F5 |
| 15-4417 | 1-chloro-3-fluoro-2-propyl | H | H | F | CN | H | H | I | Me | nonafluoro-2-butyl | Cl | CF3 |
| 15-4420 | 4,4,4-trifluoro-n-butyl | H | H | F | CN | H | H | I | Et | nonafluoro-2-butyl | F | CF3 |
| 15-4421 | i-butyl | H | H | F | CN | H | H | I | Et | nonafluoro-2-butyl | Cl | CF3 |
| 15-4424 | benzyl | H | H | F | CN | H | H | I | n-Pr | nonafluoro-2-butyl | F | CF3 |
| 15-4425 | phenyl | H | H | F | CN | H | H | I | n-Pr | nonafluoro-2-butyl | Cl | CF3 |
| 15-4428 | 2-fluoroethyl | H | H | F | CN | H | H | I | i-Pr | nonafluoro-2-butyl | F | i-C3F7 |
| 15-4429 | 2-chloroethyl | H | H | F | CN | H | H | I | i-Pr | nonafluoro-2-butyl | Cl | CF3 |
| 15-4432 | 2-cyanoethyl | H | H | F | CN | H | I | I | n-Bu | nonafluoro-2-butyl | F | CF3 |
| 15-4433 | 2,2-difluoroethyl | H | H | F | CN | H | H | I | n-Bu | nonafluoro-2-butyl | Cl | CF3 |
| 15-4436 | 2,2,2-trichloroethyl | H | H | F | CN | H | H | I | i-Bu | nonafluoro-2-butyl | F | CF3 |
| 15-4437 | 2,2,2-tribromoethyl | H | H | F | CN | H | H | I | i-Bu | nonafluoro-2-butyl | Cl | CF3 |
| 15-4440 | 3-chloro-n-propyl | i-Pr | n-Pr | F | CN | H | H | I | s-Bu | nonafluoro-2-butyl | F | CF3 |
| 15-4441 | 3-bromo-n-propyl | H | H | F | CN | H | H | I | s-Bu | nonafluoro-2-butyl | Cl | CF3 |
| 15-4452 | 2,2-dichloroethyl | H | Et | F | CN | H | H | OCF3 | F | heptafluoroisopropyl | F | OCF3 |
| 15-4482 | 2,2,2-trifluoroethyl | H | H | F | CN | H | H | OCF3 | Me | nonafluoro-2-butyl | Me | OCF3 |
| 15-4595 | 2,2-dichloroethyl | H | Et | F | CN | H | H | OCF3 | F | heptafluoroisopropyl | F | CF3 |

TABLE 15-continued

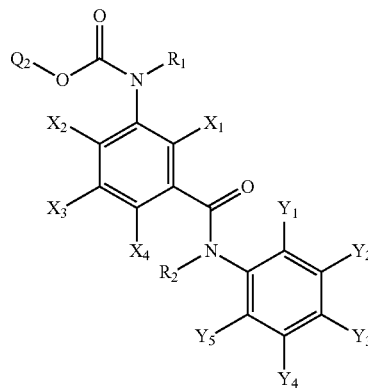

| compound number | $Q_2$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 15-4625 | 2,2,2-trifluoroethyl | H | H | F | CN | H | H | OCF3 | Me | nonafluoro-2-butyl | Me | CF3 |
| 15-4738 | 2,2-dichloroethyl | H | Et | F | CN | H | H | CF3 | F | heptafluoroisopropyl | F | CF3 |
| 15-4768 | 2,2,2-trifluoroethyl | H | H | F | CN | H | H | CF3 | Me | nonafluoro-2-butyl | Me | CF3 |
| 15-4881 | 2,2-dichloroethyl | H | Et | F | CN | F | H | Cl | F | heptafluoroisopropyl | F | Cl |
| 15-4911 | 2,2,2-trifluoroethyl | H | H | F | CN | F | H | Cl | Me | nonafluoro-2-butyl | Me | I |
| 15-5024 | 2,2-dichloroethyl | H | Et | F | CN | F | H | Cl | F | heptafluoroisopropyl | F | OCF3 |
| 15-5054 | 2,2,2-trifluoroethyl | H | H | F | CN | F | H | Cl | Me | nonafluoro-2-butyl | Me | OCF3 |
| 15-5163 | 2-bromoethyl | H | H | F | CN | F | H | F | Br | heptafluoroisopropyl | H | CF3 |
| 15-5168 | 2,2,2-trifluoroethyl | H | H | F | CN | F | H | Cl | F | heptafluoroisopropyl | Cl | CF3 |
| 15-5180 | 3,3,3-trifluoro-n-propyl | H | H | F | CN | F | H | Cl | I | nonafluoro-2-butyl | Cl | CF3 |
| 15-5183 | s-butyl | H | H | F | CN | F | H | Cl | Me | nonafluoro-2-butyl | H | CF3 |
| 15-5184 | s-butyl | H | H | F | CN | F | H | Cl | H | nonafluoro-2-butyl | Me | CF3 |
| 15-5185 | vinyl | i-Pr | H | F | CN | F | H | Cl | Et | nonafluoro-2-butyl | H | CF3 |
| 15-5186 | benzyl | H | H | F | CN | F | H | Cl | H | nonafluoro-2-butyl | Et | CF3 |
| 15-5197 | 2,2,2-trifluoroethyl | H | H | F | CN | F | H | Cl | Me | nonafluoro-2-butyl | Me | n-C3F7 |
| 15-5198 | 2,2,2-trichloroethyl | H | H | F | CN | F | H | Cl | Me | nonafluoro-2-butyl | Et | i-C3F7 |
| 15-5204 | i-propyl | H | H | F | CN | F | H | Cl | Et | nonafluoro-2-butyl | Me | n-C3F7 |
| 15-5205 | 1,2-difluoro-2-propyl | H | H | F | CN | F | H | Cl | Et | nonafluoro-2-butyl | Et | i-C3F7 |
| 15-5211 | 2-chloroethyl | H | H | F | CN | F | H | Br | n-Pr | heptafluoroisopropyl | Me | CF3 |
| 15-5212 | 2-bromoethyl | H | H | F | CN | F | H | Br | n-Pr | heptafluoroisopropyl | Et | CF3 |
| 15-5218 | 2,2,2-trichloroethyl | H | H | F | CN | F | H | Br | i-Pr | heptafluoroisopropyl | Me | CF3 |
| 15-5219 | 2,2,2-tribromoethyl | H | H | F | CN | F | H | Br | i-Pr | heptafluoroisopropyl | Et | CF3 |
| 15-5225 | 1,2-difluoro-2-propyl | H | H | F | CN | F | H | Br | n-Bu | heptafluoroisopropyl | Me | CF3 |
| 15-5226 | 1,3-difluoro-2-propyl | H | H | F | CN | F | H | Br | n-Bu | heptafluoroisopropyl | Et | CF3 |
| 15-5232 | i-butyl | H | H | F | CN | F | H | Br | i-Bu | nonafluoro-2-butyl | Me | CF3 |
| 15-5233 | s-butyl | H | H | F | CN | F | H | Br | i-Bu | nonafluoro-2-butyl | Et | CF3 |
| 15-5239 | 2-fluoroethyl | H | H | F | CN | F | H | Br | s-Bu | nonafluoro-2-butyl | Me | CF3 |
| 15-5240 | 2-chloroethyl | H | H | F | CN | F | H | Br | s-Bu | nonafluoro-2-butyl | Et | CF3 |
| 15-5246 | 2,2,2-trifluoroethyl | H | H | F | CN | F | H | Br | F | nonafluoro-2-butyl | Me | CF3 |
| 15-5247 | 2,2,2-trichloroethyl | H | H | F | CN | F | H | Br | F | nonafluoro-2-butyl | Et | CF3 |
| 15-5253 | i-propyl | Et | i-Pr | F | CN | F | H | Br | Cl | nonafluoro-2-butyl | Me | CF3 |
| 15-5254 | 1,2-difluoro-2-propyl | H | H | F | CN | F | H | Br | Cl | nonafluoro-2-butyl | Et | CF3 |
| 15-5260 | 2-iodoethyl | H | H | F | CN | F | H | I | Br | heptafluoroisopropyl | Me | CF3 |
| 15-5261 | 2-cyanoethyl | H | H | F | CN | F | H | I | Br | heptafluoroisopropyl | Et | CF3 |
| 15-5267 | n-propyl | n-Pr | Me | F | CN | F | H | I | I | heptafluoroisopropyl | Me | CF3 |
| 15-5268 | 3-fluoro-n-propyl | H | H | F | CN | F | H | I | I | heptafluoroisopropyl | Et | CF3 |
| 15-5274 | 1,3-dichloro-2-propyl | H | H | F | CN | F | H | I | Me | nonafluoro-2-butyl | F | C2F5 |
| 15-5275 | 1-chloro-3-fluoro-2-propyl | H | H | F | CN | F | H | I | Me | nonafluoro-2-butyl | Cl | CF3 |
| 15-5278 | 4,4,4-trifluoro-n-butyl | H | H | F | CN | F | H | I | Et | nonafluoro-2-butyl | F | CF3 |
| 15-5279 | i-butyl | H | H | F | CN | F | H | I | Et | nonafluoro-2-butyl | Cl | CF3 |
| 15-5282 | benzyl | H | H | F | CN | F | H | I | n-Pr | nonafluoro-2-butyl | F | CF3 |
| 15-5283 | phenyl | H | H | F | CN | F | H | I | n-Pr | nonafluoro-2-butyl | Cl | CF3 |
| 15-5286 | 2-fluoroethyl | H | H | F | CN | F | H | I | i-Pr | nonafluoro-2-butyl | F | i-C3F7 |
| 15-5287 | 2-chloroethyl | H | H | F | CN | F | H | I | i-Pr | nonafluoro-2-butyl | Cl | CF3 |
| 15-5290 | 2-cyanoethyl | H | H | F | CN | F | H | I | n-Bu | nonafluoro-2-butyl | F | CF3 |
| 15-5291 | 2,2-difluoroethyl | H | H | F | CN | F | H | I | n-Bu | nonafluoro-2-butyl | Cl | CF3 |
| 15-5294 | 2,2,2-trichloroethyl | H | H | F | CN | F | H | I | i-Bu | nonafluoro-2-butyl | F | CF3 |
| 15-5295 | 2,2,2-tribromoethyl | H | H | F | CN | F | H | I | i-Bu | nonafluoro-2-butyl | Cl | CF3 |
| 15-5298 | 3-chloro-n-propyl | i-Pr | n-Pr | F | CN | F | H | I | s-Bu | nonafluoro-2-butyl | F | CF3 |
| 15-5299 | 3-bromo-n-propyl | H | H | F | CN | F | H | I | s-Bu | nonafluoro-2-butyl | Cl | CF3 |
| 15-5310 | 2,2-dichloroethyl | H | Et | F | CN | F | H | OCF3 | F | heptafluoroisopropyl | F | OCF3 |
| 15-5340 | 2,2,2-trifluoroethyl | H | H | F | CN | F | H | OCF3 | Me | nonafluoro-2-butyl | Me | OCF3 |
| 15-5453 | 2,2-dichloroethyl | H | Et | F | CN | F | H | OCF3 | F | heptafluoroisopropyl | F | CF3 |
| 15-5483 | 2,2,2-trifluoroethyl | H | H | F | CN | F | H | OCF3 | Me | nonafluoro-2-butyl | Me | CF3 |
| 15-5596 | 2,2-dichloroethyl | H | Et | F | CN | F | H | CF3 | F | heptafluoroisopropyl | F | CF3 |
| 15-5626 | 2,2,2-trifluoroethyl | H | H | F | CN | F | H | CF3 | Me | nonafluoro-2-butyl | Me | CF3 |

TABLE 16

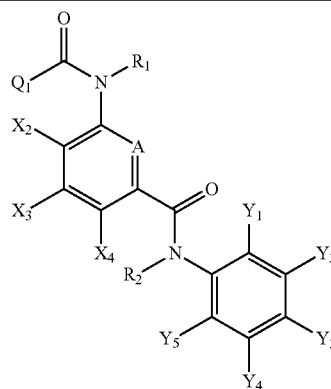

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1 | phenyl | H | H | N | H | H | H | F | H | heptafluoroisopropyl | H | F |
| 16-2 | 3-cyanophenyl | H | H | N | H | H | H | F | H | heptafluoroisopropyl | H | F |
| 16-3 | 4-cyanophenyl | H | H | N | H | H | H | F | H | heptafluoroisopropyl | H | F |
| 16-4 | 2-chloropyridin-3-yl | H | H | N | H | H | H | F | H | heptafluoroisopropyl | H | F |
| 16-5 | phenyl | H | H | N | H | H | H | F | H | nonafluoro-2-butyl | H | F |
| 16-6 | 3-cyanophenyl | H | H | N | H | H | H | F | H | nonafluoro-2-butyl | H | F |
| 16-7 | 4-cyanophenyl | H | H | N | H | H | H | F | H | nonafluoro-2-butyl | H | F |
| 16-8 | 2-chloropyridin-3-yl | H | H | N | H | H | H | F | H | nonafluoro-2-butyl | H | F |
| 16-9 | phenyl | H | H | N | H | H | H | Cl | H | heptafluoroisopropyl | H | Cl |
| 16-13 | 2-chlorophenyl | H | H | N | H | H | H | F | H | heptafluoroisopropyl | H | Cl |
| 16-17 | 3-bromophenyl | H | H | N | H | H | H | F | H | heptafluoroisopropyl | H | Br |
| 16-20 | 3-iodophenyl | H | H | N | H | H | H | Cl | H | pentafluoroethyl | H | Cl |
| 16-22 | (2-trifluoromethyl)phenyl | H | H | N | H | H | H | F | H | heptafluoroisopropyl | H | I |
| 16-25 | 2-nitrophenyl | H | H | N | H | H | H | Cl | H | heptafluoroisopropyl | H | Br |
| 16-28 | 2-cyanophenyl | H | H | N | H | H | H | Cl | H | pentafluoroethyl | H | Cl |
| 16-29 | 3-cyanophenyl | H | H | N | H | H | H | Cl | H | heptafluoroisopropyl | H | Cl |
| 16-30 | 4-cyanophenyl | H | H | N | H | H | H | Cl | H | heptafluoroisopropyl | H | Cl |
| 16-31 | 2,6-difluorophenyl | H | H | N | H | H | H | Cl | H | heptafluoroisopropyl | H | I |
| 16-43 | pyridin-3-yl | H | H | N | H | H | H | Br | H | heptafluoroisopropyl | H | I |
| 16-44 | 2-fluoropyridin-3-yl | H | H | N | H | H | H | Cl | H | pentafluoroethyl | H | Cl |
| 16-45 | 2-chloropyridin-3-yl | H | H | N | H | H | H | Cl | H | heptafluoroisopropyl | H | Cl |
| 16-63 | 5-nitropyridin-3-yl | H | H | N | H | H | H | Cl | H | pentafluoroethyl | H | Cl |
| 16-64 | 5-cyanopyridin-3-yl | H | H | N | H | H | H | Cl | H | heptafluoroisopropyl | H | Cl |
| 16-66 | 4-chloropyridin-3-yl | H | H | N | H | H | H | Cl | H | heptafluoroisopropyl | H | Cl |
| 16-86 | 4-cyanopyridin-2-yl | H | H | N | H | H | H | Cl | H | pentafluoroethyl | H | Cl |
| 16-87 | phenyl | H | H | N | H | H | H | Cl | H | nonafluoro-2-butyl | H | Cl |
| 16-107 | 3-cyanophenyl | H | H | N | H | H | H | Cl | H | nonafluoro-2-butyl | H | Cl |
| 16-108 | 4-cyanophenyl | H | H | N | H | H | H | Cl | H | nonafluoro-2-butyl | H | Cl |
| 16-123 | 2-chloropyridin-3-yl | H | H | N | H | H | H | Cl | H | nonafluoro-2-butyl | H | Cl |
| 16-165 | phenyl | H | H | N | H | H | H | Br | H | heptafluoroisopropyl | H | Br |
| 16-166 | 2-fluorophenyl | H | H | N | H | H | H | Br | H | heptafluoroisopropyl | H | Br |
| 16-177 | 4-iodophenyl | H | H | N | H | H | H | Br | H | pentafluoroethyl | H | Br |
| 16-185 | 3-cyanophenyl | H | H | N | H | H | H | Br | H | heptafluoroisopropyl | H | Br |
| 16-186 | 4-cyanophenyl | H | H | N | H | H | H | Br | H | heptafluoroisopropyl | H | Br |
| 16-200 | 2-fluoropyridin-3-yl | H | H | N | H | H | H | Br | H | pentafluoroethyl | H | Br |
| 16-201 | 2-chloropyridin-3-yl | H | H | N | H | H | H | Br | H | heptafluoroisopropyl | H | Br |
| 16-219 | 5-nitropyridin-3-yl | H | H | N | H | H | H | Br | H | pentafluoroethyl | H | Br |
| 16-220 | 5-cyanopyridin-3-yl | H | H | N | H | H | H | Br | H | heptafluoroisopropyl | H | Br |
| 16-221 | 4-fluoropyridin-3-yl | H | H | N | H | H | H | Br | H | pentafluoroethyl | H | Br |
| 16-242 | 4-cyanopyridin-2-yl | H | H | N | H | H | H | Br | H | pentafluoroethyl | H | Br |
| 16-243 | phenyl | H | H | N | H | H | H | Br | H | nonafluoro-2-butyl | H | Br |
| 16-244 | 2-fluorophenyl | H | H | N | H | H | H | Br | H | nonafluoro-2-butyl | H | Br |
| 16-263 | 3-cyanophenyl | H | H | N | H | H | H | Br | H | nonafluoro-2-butyl | H | Br |
| 16-264 | 4-cyanophenyl | H | H | N | H | H | H | Br | H | nonafluoro-2-butyl | H | Br |
| 16-279 | 2-chloropyridin-3-yl | H | H | N | H | H | H | Br | H | nonafluoro-2-butyl | H | Br |
| 16-321 | phenyl | H | H | N | H | H | H | I | H | heptafluoroisopropyl | H | I |
| 16-328 | 2-bromophenyl | H | H | N | H | H | H | I | H | pentafluoroethyl | H | I |
| 16-341 | 3-cyanophenyl | H | H | N | H | H | H | I | H | heptafluoroisopropyl | H | I |
| 16-342 | 4-cyanophenyl | H | H | N | H | H | H | I | H | heptafluoroisopropyl | H | I |
| 16-356 | 2-fluoropyridin-3-yl | H | H | N | H | H | H | I | H | pentafluoroethyl | H | I |
| 16-357 | 2-chloropyridin-3-yl | H | H | N | H | H | H | I | H | heptafluoroisopropyl | H | I |
| 16-375 | 5-nitropyridin-3-yl | H | H | N | H | H | H | I | H | pentafluoroethyl | H | I |
| 16-399 | phenyl | H | H | N | H | H | H | I | H | nonafluoro-2-butyl | H | I |
| 16-400 | 2-fluorophenyl | H | H | N | H | H | H | I | H | nonafluoro-2-butyl | H | I |
| 16-419 | 3-cyanophenyl | H | H | N | H | H | H | I | H | nonafluoro-2-butyl | H | I |
| 16-420 | 4-cyanophenyl | H | H | N | H | H | H | I | H | nonafluoro-2-butyl | H | I |
| 16-435 | 2-chloropyridin-3-yl | H | H | N | H | H | H | I | H | nonafluoro-2-butyl | H | I |
| 16-477 | phenyl | H | H | N | H | H | H | Cl | H | heptafluoroisopropyl | H | OCF3 |

TABLE 16-continued

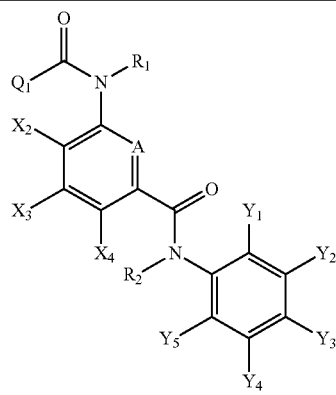

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-478 | 2-fluorophenyl | H | H | N | H | H | H | Cl | H | pentafluoroethyl | H | OCF3 |
| 16-492 | (4-trifluoromethyl)phenyl | H | H | N | H | H | H | Cl | H | heptafluoroisopropyl | H | OC2F5 |
| 16-493 | 2-nitrophenyl | H | H | N | H | H | H | F | H | heptafluoroisopropyl | H | OCF3 |
| 16-496 | 2-cyanophenyl | H | H | N | H | H | H | Cl | H | pentafluoroethyl | H | OC2F5 |
| 16-497 | 3-cyanophenyl | H | H | N | H | H | H | Cl | H | heptafluoroisopropyl | H | OCF3 |
| 16-498 | 4-cyanophenyl | H | H | N | H | H | H | Cl | H | heptafluoroisopropyl | H | OCF3 |
| 16-504 | 4-bromo-2-chlorophenyl | H | H | N | H | H | H | Cl | H | heptafluoroisopropyl | H | OC2F5 |
| 16-512 | 2-fluoropyridin-3-yl | H | H | N | H | H | H | Cl | H | pentafluoroethyl | H | OCF3 |
| 16-513 | 2-chloropyridin-3-yl | H | H | N | H | H | H | Cl | H | heptafluoroisopropyl | H | OCF3 |
| 16-555 | phenyl | H | H | N | H | H | H | Cl | H | nonafluoro-2-butyl | H | OCF3 |
| 16-565 | 2-iodophenyl | H | H | N | H | H | H | Cl | H | nonafluoro-2-butyl | H | OCF3 |
| 16-571 | 2-nitrophenyl | H | H | N | H | H | H | F | H | nonafluoro-2-butyl | H | OCF3 |
| 16-572 | 3-nitrophenyl | H | H | N | H | H | H | Cl | H | nonafluoro-2-butyl | H | OCF3 |
| 16-573 | 4-nitrophenyl | H | H | N | H | H | H | Cl | H | nonafluoro-2-butyl | H | OCF3 |
| 16-581 | 2-chloro-4,5-difluorophenyl | H | H | N | H | H | H | Cl | H | nonafluoro-2-butyl | H | OC2F5 |
| 16-591 | 2-chloropyridin-3-yl | H | H | N | H | H | H | Cl | H | nonafluoro-2-butyl | H | OCF3 |
| 16-597 | 6-fluoropyridin-3-yl | H | H | N | H | H | H | Cl | H | nonafluoro-2-butyl | H | OC2F5 |
| 16-633 | phenyl | H | H | N | H | H | H | Br | H | heptafluoroisopropyl | H | OCF3 |
| 16-646 | (2-trifluoromethyl)phenyl | H | H | N | H | H | H | Br | H | heptafluoroisopropyl | H | OCF3 |
| 16-653 | 3-cyanophenyl | H | H | N | H | H | H | Br | H | heptafluoroisopropyl | H | OCF3 |
| 16-654 | 4-cyanophenyl | H | H | N | H | H | H | Br | H | heptafluoroisopropyl | H | OCF3 |
| 16-669 | 2-chloropyridin-3-yl | H | H | N | H | H | H | Br | H | heptafluoroisopropyl | H | OCF3 |
| 16-676 | 6-chloropyridin-3-yl | H | H | N | H | H | H | Br | H | heptafluoroisopropyl | H | OCF3 |
| 16-711 | phenyl | H | H | N | H | H | H | Br | H | nonafluro-2-butyl | H | OCF3 |
| 16-731 | 3-cyanophenyl | H | H | N | H | H | H | Br | H | nonafluoro-2-butyl | H | OCF3 |
| 16-732 | 4-cyanophenyl | H | H | N | H | H | H | Br | H | nonafluoro-2-butyl | H | OCF3 |
| 16-745 | pyridin-3-yl | H | H | N | H | H | H | Br | H | nonafluoro-2-butyl | H | OCF3 |
| 16-747 | 2-chloropyridin-3-yl | H | H | N | H | H | H | Br | H | nonafluoro-2-butyl | H | OCF3 |
| 16-789 | phenyl | H | H | N | H | H | H | I | H | heptafluoroisopropyl | H | OCF3 |
| 16-794 | 3-chlorophenyl | H | H | N | H | H | H | I | H | heptafluoroisopropyl | H | OCF3 |
| 16-809 | 3-cyanophenyl | H | H | N | H | H | H | I | H | heptafluoroisopropyl | H | OCF3 |
| 16-810 | 4-cyanophenyl | H | H | N | H | H | H | I | H | heptafluoroisopropyl | H | OCF3 |
| 16-825 | 2-chloropyridin-3-yl | H | H | N | H | H | H | I | H | heptafluoroisopropyl | H | OCF3 |
| 16-867 | phenyl | H | H | N | H | H | H | I | H | nonafluoro-2-butyl | H | OCF3 |
| 16-887 | 3-cyanophenyl | H | H | N | H | H | H | I | H | nonafluoro-2-butyl | H | OCF3 |
| 16-888 | 4-cyanophenyl | H | H | N | H | H | H | I | H | nonafluoro-2-butyl | H | OCF3 |
| 16-903 | 2-chloropyridin-3-yl | H | H | N | H | H | H | I | H | nonafluoro-2-butyl | H | OCF3 |
| 16-945 | phenyl | H | H | N | H | H | H | F | H | heptafluoroisopropyl | H | CF3 |
| 16-946 | phenyl | H | H | N | H | H | H | Cl | H | heptafluoroisopropyl | H | CF3 |
| 16-947 | 2-fluorophenyl | H | H | N | H | H | H | Cl | H | heptafluoroisopropyl | H | CF3 |
| 16-958 | 4-iodophenyl | H | H | N | H | H | H | Cl | H | pentafluoroethyl | H | CF3 |
| 16-965 | 2-cyanophenyl | H | H | N | H | H | H | Cl | H | pentafluoroethyl | H | C2F5 |
| 16-966 | 3-cyanophenyl | H | H | N | H | H | H | Cl | H | heptafluoroisopropyl | H | CF3 |
| 16-967 | 4-cyanophenyl | H | H | N | H | H | H | Cl | H | heptafluoroisopropyl | H | CF3 |
| 16-970 | 2,4-dichlorophenyl | H | H | N | H | H | H | Cl | H | heptafluoroisopropyl | H | C2F5 |
| 16-974 | 2-bromo-4-chlorophenyl | H | H | N | H | H | H | Cl | H | heptafluoroisopropyl | H | n-C3F7 |
| 16-981 | 2-fluoropyridin-3-yl | H | H | N | H | H | H | Cl | H | pentafluoroethyl | H | CF3 |
| 16-982 | 2-chloropyridin-3-yl | H | H | N | H | H | H | Cl | H | heptafluoroisopropyl | H | CF3 |
| 16-995 | 5-fluoropyridin-3-yl | H | H | N | H | H | H | Cl | H | heptafluoroisopropyl | H | C2F5 |
| 16-997 | 5-bromopyridin-3-yl | H | H | N | H | H | H | Cl | H | heptafluoroisopropyl | H | n-C3F7 |
| 16-998 | 5-iodopyridin-3-yl | H | H | N | H | H | H | Cl | H | heptafluoroisopropyl | H | i-C3F7 |
| 16-1000 | 5-nitropyridin-3-yl | H | H | N | H | H | H | Cl | H | pentafluoroethyl | H | CF3 |
| 16-1002 | 4-fluoropyridin-3-yl | H | H | N | H | H | H | Cl | H | pentafluoroethyl | H | CF3 |
| 16-1004 | 4-bromopyridin-3-yl | H | H | N | H | H | H | Cl | H | heptafluoroisopropyl | H | n-C3F7 |
| 16-1023 | 4-cyanopyridin-2-yl | H | H | N | H | H | H | Cl | H | pentafluoroethyl | H | CF3 |
| 16-1024 | phenyl | H | H | N | H | H | H | F | H | nonafluoro-2-butyl | H | CF3 |
| 16-1025 | phenyl | H | H | N | H | H | H | Cl | H | nonafluoro-2-butyl | H | CF3 |
| 16-1038 | (2-trifluoromethyl)phenyl | H | H | N | H | H | H | Cl | H | nonafluoro-2-butyl | H | C2F5 |

TABLE 16-continued

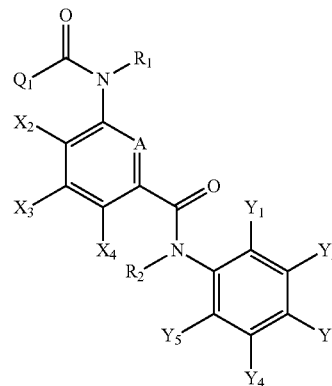

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1045 | 3-cyanophenyl | H | H | N | H | H | H | Cl | H | nonafluoro-2-butyl | H | CF3 |
| 16-1046 | 4-cyanophenyl | H | H | N | H | H | H | Cl | H | nonafluoro-2-butyl | H | CF3 |
| 16-1055 | 2-chloro-4-nitrophenyl | H | H | N | H | H | H | Cl | H | nonafluoro-2-butyl | H | i-C3F7 |
| 16-1061 | 2-chloropyridin-3-yl | H | H | N | H | H | H | Cl | H | nonafluoro-2-butyl | H | CF3 |
| 16-1074 | 5-fluoropyridin-3-yl | H | H | N | H | H | H | Cl | H | nonafluoro-2-butyl | H | C2F5 |
| 16-1076 | 5-bromopyridin-3-yl | H | H | N | H | H | H | Cl | H | nonafluoro-2-butyl | H | n-C3F7 |
| 16-1077 | 5-iodopyridin-3-yl | H | H | N | H | H | H | Cl | H | nonafluoro-2-butyl | H | i-C3F7 |
| 16-1081 | 4-fluoropyridin-3-yl | H | H | N | H | H | H | Cl | H | nonafluoro-2-butyl | H | C2F5 |
| 16-1085 | 4-(trifluoromethyl)pyridin-3-yl | H | H | N | H | H | H | Cl | H | nonafluoro-2-butyl | H | n-C3F7 |
| 16-1086 | 4-nitropyridin-3-yl | H | H | N | H | H | H | Cl | H | nonafluoro-2-butyl | H | i-C3F7 |
| 16-1102 | 4-cyanopyridin-2-yl | H | H | N | H | H | H | Cl | H | nonafluoro-2-butyl | H | C2F5 |
| 16-1103 | phenyl | H | H | N | H | H | H | Br | H | heptafluoroisopropyl | H | CF3 |
| 16-1104 | 2-fluorophenyl | H | H | N | H | H | H | Br | H | heptafluoroisopropyl | H | CF3 |
| 16-1105 | 3-fluorophenyl | H | H | N | H | H | H | Br | H | heptafluoroisopropyl | H | CF3 |
| 16-1106 | 4-fluorophenyl | H | H | N | H | H | H | Br | H | heptafluoroisopropyl | H | CF3 |
| 16-1107 | 2-chlorophenyl | H | H | N | H | H | H | Br | H | heptafluoroisopropyl | H | CF3 |
| 16-1108 | 3-chlorophenyl | H | H | N | H | H | H | Br | H | heptafluoroisopropyl | H | CF3 |
| 16-1109 | 4-chlorophenyl | H | H | N | H | H | H | Br | H | heptafluoroisopropyl | H | CF3 |
| 16-1110 | 2-bromophenyl | H | H | N | H | H | H | Br | H | heptafluoroisopropyl | H | CF3 |
| 16-1111 | 3-bromophenyl | H | H | N | H | H | H | Br | H | heptafluoroisopropyl | H | CF3 |
| 16-1112 | 4-bromophenyl | H | H | N | H | H | H | Br | H | heptafluoroisopropyl | H | CF3 |
| 16-1113 | 2-iodophenyl | H | H | N | H | H | H | Br | H | heptafluoroisopropyl | H | CF3 |
| 16-1114 | 3-iodophenyl | H | H | N | H | H | H | Br | H | heptafluoroisopropyl | H | CF3 |
| 16-1115 | 4-iodophenyl | H | H | N | H | H | H | Br | H | heptafluoroisopropyl | H | CF3 |
| 16-1116 | (2-trifluoromethyl)phenyl | H | H | N | H | H | H | Br | H | heptafluoroisopropyl | H | CF3 |
| 16-1117 | (3-trifluoromethyl)phenyl | H | H | N | H | H | H | Br | H | heptafluoroisopropyl | H | CF3 |
| 16-1118 | (4-trifluoromethyl)phenyl | H | H | N | H | H | H | Br | H | heptafluoroisopropyl | H | CF3 |
| 16-1119 | 2-nitrophenyl | H | H | N | H | H | H | Br | H | heptafluoroisopropyl | H | CF3 |
| 16-1120 | 3-nitrophenyl | H | H | N | H | H | H | Br | H | heptafluoroisopropyl | H | CF3 |
| 16-1121 | 4-nitrophenyl | H | H | N | H | H | H | Br | H | heptafluoroisopropyl | H | CF3 |
| 16-1122 | 2-cyanophenyl | H | H | N | H | H | H | Br | H | heptafluoroisopropyl | H | CF3 |
| 16-1123 | 3-cyanophenyl | H | H | N | H | H | H | Br | H | heptafluoroisopropyl | H | CF3 |
| 16-1124 | 4-cyanophenyl | H | H | N | H | H | H | Br | H | heptafluoroisopropyl | H | CF3 |
| 16-1125 | 2,6-difluorophenyl | H | H | N | H | H | H | Br | H | heptafluoroisopropyl | H | CF3 |
| 16-1126 | 3,4-dichlorophenyl | H | H | N | H | H | H | Br | H | heptafluoroisopropyl | H | CF3 |
| 16-1127 | 2,4-dichlorophenyl | H | H | N | H | H | H | Br | H | heptafluoroisopropyl | H | CF3 |
| 16-1128 | 2-chloro-4-fluorophenyl | H | H | N | H | H | H | Br | H | heptafluoroisopropyl | H | CF3 |
| 16-1129 | 2-chloro-4,5-difluorophenyl | H | H | N | H | H | H | Br | H | heptafluoroisopropyl | H | CF3 |
| 16-1130 | 4-bromo-2-chlorophenyl | H | H | N | H | H | H | Br | H | heptafluoroisopropyl | H | CF3 |
| 16-1131 | 2-bromo-4-chlorophenyl | H | H | N | H | H | H | Br | H | heptafluoroisopropyl | H | CF3 |
| 16-1132 | 2-bromo-4-fluorophenyl | H | H | N | H | H | H | Br | H | heptafluoroisopropyl | H | CF3 |
| 16-1133 | 2-chloro-4-nitrophenyl | H | H | N | H | H | H | Br | H | heptafluoroisopropyl | H | CF3 |
| 16-1134 | 3,5-dicyanophenyl | H | H | N | H | H | H | Br | H | heptafluoroisopropyl | H | CF3 |
| 16-1135 | 4-cyano-2-fluorophenyl | H | H | N | H | H | H | Br | H | heptafluoroisopropyl | H | CF3 |
| 16-1136 | 2-chloro-4-cyanophenyl | H | H | N | H | H | H | Br | H | heptafluoroisopropyl | H | CF3 |
| 16-1137 | pyridin-3-yl | H | H | N | H | H | H | Br | H | heptafluoroisopropyl | H | CF3 |
| 16-1138 | 2-fluoropyridin-3-yl | H | H | N | H | H | H | Br | H | heptafluoroisopropyl | H | CF3 |
| 16-1139 | 2-chloropyridin-3-yl | H | H | N | H | H | H | Br | H | heptafluoroisopropyl | H | CF3 |
| 16-1140 | 2-bromopyridin-3-yl | H | H | N | H | H | H | Br | H | heptafluoroisopropyl | H | CF3 |
| 16-1141 | 2-iodopyridin-3-yl | H | H | N | H | H | H | Br | H | heptafluoroisopropyl | H | CF3 |
| 16-1142 | 2-(trifluoromethyl)pyridin-3-yl | H | H | N | H | H | H | Br | H | heptafluoroisopropyl | H | CF3 |
| 16-1143 | 2-nitropyridin-3-yl | H | H | N | H | H | H | Br | H | heptafluoroisopropyl | H | CF3 |
| 16-1144 | 2-cyanopyridin-3-yl | H | H | N | H | H | H | Br | H | heptafluoroisopropyl | H | CF3 |
| 16-1145 | 6-fluoropyridin-3-yl | H | H | N | H | H | H | Br | H | heptafluoroisopropyl | H | CF3 |
| 16-1146 | 6-chloropyridin-3-yl | H | H | N | H | H | H | Br | H | heptafluoroisopropyl | H | CF3 |
| 16-1147 | 6-bromopyridin-3-yl | H | H | N | H | H | H | Br | H | heptafluoroisopropyl | H | CF3 |
| 16-1148 | 6-iodopyridin-3-yl | H | H | N | H | H | H | Br | H | heptafluoroisopropyl | H | CF3 |
| 16-1149 | 6-(trifluoromethyl)pyridin-3-yl | H | H | N | H | H | H | Br | H | heptafluoroisopropyl | H | CF3 |

TABLE 16-continued

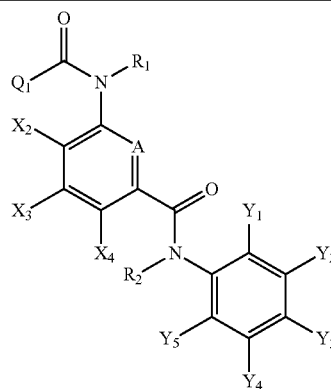

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1150 | 6-nitropyridin-3-yl | H | H | N | H | H | H | Br | H | heptafluoroisopropyl | H | CF3 |
| 16-1151 | 6-cyanopyridin-3-yl | H | H | N | H | H | H | Br | H | heptafluoroisopropyl | H | CF3 |
| 16-1152 | 5-fluoropyridin-3-yl | H | H | N | H | H | H | Br | H | heptafluoroisopropyl | H | CF3 |
| 16-1153 | 5-chloropyridin-3-yl | H | H | N | H | H | H | Br | H | heptafluoroisopropyl | H | CF3 |
| 16-1154 | 5-bromopyridin-3-yl | H | H | N | H | H | H | Br | H | heptafluoroisopropyl | H | CF3 |
| 16-1155 | 5-iodopyridin-3-yl | H | H | N | H | H | H | Br | H | heptafluoroisopropyl | H | CF3 |
| 16-1156 | 5-(trifluoromethyl)pyridin-3-yl | H | H | N | H | H | H | Br | H | heptafluoroisopropyl | H | CF3 |
| 16-1157 | 5-nitropyridin-3-yl | H | H | N | H | H | H | Br | H | heptafluoroisopropyl | H | CF3 |
| 16-1158 | 5-cyanopyridin-3-yl | H | H | N | H | H | H | Br | H | heptafluoroisopropyl | H | CF3 |
| 16-1159 | 4-fluoropyridin-3-yl | H | H | N | H | H | H | Br | H | heptafluoroisopropyl | H | CF3 |
| 16-1160 | 4-chloropyridin-3-yl | H | H | N | H | H | H | Br | H | heptafluoroisopropyl | H | CF3 |
| 16-1161 | 4-bromopyridin-3-yl | H | H | N | H | H | H | Br | H | heptafluoroisopropyl | H | CF3 |
| 16-1162 | 4-iodopyridin-3-yl | H | H | N | H | H | H | Br | H | heptafluoroisopropyl | H | CF3 |
| 16-1163 | 4-(trifluoromethyl)pyridin-3-yl | H | H | N | H | H | H | Br | H | heptafluoroisopropyl | H | CF3 |
| 16-1164 | 4-nitropyridin-3-yl | H | H | N | H | H | H | Br | H | heptafluoroisopropyl | H | CF3 |
| 16-1165 | 4-cyanopyridin-3-yl | H | H | N | H | H | H | Br | H | heptafluoroisopropyl | H | CF3 |
| 16-1166 | 2,6-dichloropyridin-3-yl | H | H | N | H | H | H | Br | H | heptafluoroisopropyl | H | CF3 |
| 16-1167 | pyridin-3-yl N-oxide | H | H | N | H | H | H | Br | H | heptafluoroisopropyl | H | CF3 |
| 16-1168 | pyridin-4-yl | H | H | N | H | H | H | Br | H | heptafluoroisopropyl | H | CF3 |
| 16-1169 | 2-chloropyridin-4-yl | H | H | N | H | H | H | Br | H | heptafluoroisopropyl | H | CF3 |
| 16-1170 | 3-bromopyridin-4-yl | H | H | N | H | H | H | Br | H | heptafluoroisopropyl | H | CF3 |
| 16-1171 | 3,5-dichloropyridin-4-yl | H | H | N | H | H | H | Br | H | heptafluoroisopropyl | H | CF3 |
| 16-1172 | 3-(trifluoromethyl)pyridin-4-yl | H | H | N | H | H | H | Br | H | heptafluoroisopropyl | H | CF3 |
| 16-1173 | 2,6-dicyanopyridin-4-yl | H | H | N | H | H | H | Br | H | heptafluoroisopropyl | H | CF3 |
| 16-1174 | pyridin-4-yl N-oxide | H | H | N | H | H | H | Br | H | heptafluoroisopropyl | H | CF3 |
| 16-1175 | pyridin-2-yl | H | H | N | H | H | H | Br | H | heptafluoroisopropyl | H | CF3 |
| 16-1176 | 3-chloropyridin-2-yl | H | H | N | H | H | H | Br | H | heptafluoroisopropyl | H | CF3 |
| 16-1177 | 4-bromopyridin-2-yl | H | H | N | H | H | H | Br | H | heptafluoroisopropyl | H | CF3 |
| 16-1178 | 5-iodopyridin-2-yl | H | H | N | H | H | H | Br | H | heptafluoroisopropyl | H | CF3 |
| 16-1179 | 6-chloropyridin-2-yl | H | H | N | H | H | H | Br | H | heptafluoroisopropyl | H | CF3 |
| 16-1180 | 4-cyanopyridin-2-yl | H | H | N | H | H | H | Br | H | heptafluoroisopropyl | H | CF3 |
| 16-1181 | phenyl | H | H | N | H | H | H | Br | H | nonafluoro-2-butyl | H | CF3 |
| 16-1182 | 2-fluorophenyl | H | H | N | H | H | H | Br | H | nonafluoro-2-butyl | H | CF3 |
| 16-1183 | 3-fluorophenyl | H | H | N | H | H | H | Br | H | nonafluoro-2-butyl | H | CF3 |
| 16-1184 | 4-fluorophenyl | H | H | N | H | H | H | Br | H | nonafluoro-2-butyl | H | CF3 |
| 16-1185 | 2-chlorophenyl | H | H | N | H | H | H | B | H | nonafluoro-2-butyl | H | CF3 |
| 16-1186 | 3-chlorophenyl | H | H | N | H | H | H | Br | H | nonafluoro-2-butyl | H | CF3 |
| 16-1187 | 4-chlorophenyl | H | H | N | H | H | H | Br | H | nonafluoro-2-butyl | H | CF3 |
| 16-1188 | 2-bromophenyl | H | H | N | H | H | H | Br | H | nonafluoro-2-butyl | H | CF3 |
| 16-1189 | 3-bromophenyl | H | H | N | H | H | H | Br | H | nonafluoro-2-butyl | H | CF3 |
| 16-1190 | 4-bromophenyl | H | H | N | H | H | H | Br | H | nonafluoro-2-butyl | H | CF3 |
| 16-1191 | 2-iodophenyl | H | H | N | H | H | H | Br | H | nonafluoro-2-butyl | H | CF3 |
| 16-1192 | 3-iodophenyl | H | H | N | H | H | H | Br | H | nonafluoro-2-butyl | H | CF3 |
| 16-1193 | 4-iodophenyl | H | H | N | H | H | H | Br | H | nonafluoro-2-butyl | H | CF3 |
| 16-1194 | (2-trifluoromethyl)phenyl | H | N | H | H | H | H | Br | H | nonafluoro-2-butyl | H | CF3 |
| 16-1195 | (3-trifluoromethyl)phenyl | H | H | N | H | H | H | Br | H | nonafluoro-2-butyl | H | CF3 |
| 16-1196 | (4-trifluoromethyl)phenyl | H | H | N | H | H | H | Br | H | nonafluoro-2-butyl | H | CF3 |
| 16-1197 | 2-nitrophenyl | H | H | N | H | H | H | Br | H | nonafluoro-2-butyl | H | CF3 |
| 16-1198 | 3-nitrophenyl | H | H | N | H | H | H | Br | H | nonafluoro-2-butyl | H | CF3 |
| 16-1199 | 4-nitrophenyl | H | H | N | H | H | H | Br | H | nonafluoro-2-butyl | H | CF3 |
| 16-1200 | 2-cyanophenyl | H | H | N | H | H | H | Br | H | nonafluoro-2-butyl | H | CF3 |
| 16-1201 | 3-cyanophenyl | H | H | N | H | H | H | Br | H | nonafluoro-2-butyl | H | CF3 |
| 16-1202 | 4-cyanophenyl | H | H | N | H | H | H | Br | H | nonafluoro-2-butyl | H | CF3 |
| 16-1203 | 2,6-difluorophenyl | H | H | N | H | H | H | Br | H | nonafluoro-2-butyl | H | CF3 |
| 16-1204 | 3,4-dichlorophenyl | H | H | N | H | H | H | Br | H | nonafluoro-2-butyl | H | CF3 |
| 16-1205 | 2,4-dichlorophenyl | H | H | N | H | H | H | Br | H | nonafluoro-2-butyl | H | CF3 |
| 16-1206 | 2-chloro-4-fluorophenyl | H | H | N | H | H | H | Br | H | nonafluoro-2-butyl | H | CF3 |
| 16-1207 | 2-chloro-4,5-difluorophenyl | H | H | N | H | H | H | Br | H | nonafluoro-2-butyl | H | CF3 |

TABLE 16-continued

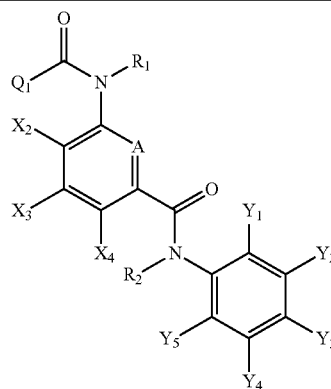

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1208 | 4-bromo-2-chlorophenyl | H | H | N | H | H | H | Br | H | nonafluoro-2-butyl | H | CF3 |
| 16-1209 | 2-bromo-4-chlorophenyl | H | H | N | H | H | H | Br | H | nonafluoro-2-butyl | H | CF3 |
| 16-1210 | 2-bromo-4-fluorophenyl | H | H | N | H | H | H | Br | H | nonafluoro-2-butyl | H | CF3 |
| 16-1211 | 2-chloro-4-nitrophenyl | H | H | N | H | H | H | Br | H | nonafluoro-2-butyl | H | CF3 |
| 16-1212 | 3,5-dicyanophenyl | H | H | N | H | H | H | Br | H | nonafluoro-2-butyl | H | CF3 |
| 16-1213 | 4-cyano-2-fluorophenyl | H | H | N | H | H | H | Br | H | nonafluoro-2-butyl | H | CF3 |
| 16-1214 | 2-chloro-4-cyanophenyl | H | H | N | H | H | H | Br | H | nonafluoro-2-butyl | H | CF3 |
| 16-1215 | pyridin-3-yl | H | H | N | H | H | H | Br | H | nonafluoro-2-butyl | H | CF3 |
| 16-1216 | 2-fluoropyridin-3-yl | H | H | N | H | H | H | Br | H | nonafluoro-2-butyl | H | CF3 |
| 16-1217 | 2-chloropyridin-3-yl | H | H | N | H | H | H | Br | H | nonafluoro-2-butyl | H | CF3 |
| 16-1218 | 2-bromopyridin-3-yl | H | H | N | H | H | H | Br | H | nonafluoro-2-butyl | H | CF3 |
| 16-1219 | 2-iodopyridin-3-yl | H | H | N | H | H | H | Br | H | nonafluoro-2-butyl | H | CF3 |
| 16-1220 | 2-(trifluoromethyl)pyridin-3-yl | H | H | N | H | H | H | Br | H | nonafluoro-2-butyl | H | CF3 |
| 16-1221 | 2-nitropyridin-3-yl | H | H | N | H | H | H | Br | H | nonafluoro-2-butyl | H | CF3 |
| 16-1222 | 2-cyanopyridin-3-yl | H | li | N | H | H | H | Br | H | nonafluoro-2-butyl | H | CF3 |
| 16-1223 | 6-fluoropyridin-3-yl | H | H | N | H | H | H | Br | H | nonafluoro-2-butyl | H | CF3 |
| 16-1224 | 6-chloropyridin-3-yl | H | H | N | H | H | H | Br | H | nonafluoro-2-butyl | H | CF3 |
| 16-1225 | 6-bromopyridin-3-yl | H | H | N | H | H | H | Br | H | nonafluoro-2-butyl | H | CF3 |
| 16-1226 | 6-iodopyridin-3-yl | H | H | N | H | H | H | Br | H | nonafluoro-2-butyl | H | CF3 |
| 16-1227 | 6-(trifluoromethyl)pyridin-3-yl | H | H | N | H | H | H | Br | H | nonafluoro-2-butyl | H | CF3 |
| 16-1228 | 6-nitropyridin-3-yl | H | H | N | H | H | H | Br | H | nonafluoro-2-butyl | H | CF3 |
| 16-1229 | 6-cyanopyridin-3-yl | H | H | N | H | H | H | Br | H | nonafluoro-2-butyl | H | CF3 |
| 16-1230 | 5-fluoropyridin-3-yl | H | H | N | H | H | H | Br | H | nonafluoro-2-butyl | H | CF3 |
| 16-1231 | 5-chloropyridin-3-yl | H | H | N | H | H | H | Br | H | nonafluoro-2-butyl | H | CF3 |
| 16-1232 | 5-bromopyridin-3-yl | H | H | N | H | H | H | Br | H | nonafluoro-2-butyl | H | CF3 |
| 16-1233 | 5-iodopyridin-3-yl | H | H | N | H | H | H | Br | H | nonafluoro-2-butyl | H | CF3 |
| 16-1234 | 5-(trifluoromethyl)pyridin-3-yl | H | H | N | H | H | H | Br | H | nonafluoro-2-butyl | H | CF3 |
| 16-1235 | 5-nitropyridin-3-yl | H | H | N | H | H | H | Br | H | nonafluoro-2-butyl | H | CF3 |
| 16-1236 | 5-cyanopyridin-3-yl | H | H | N | H | H | H | Br | H | nonafluoro-2-butyl | H | CF3 |
| 16-1237 | 4-fluoropyridin-3-yl | H | H | N | H | H | H | Br | H | nonafluoro-2-butyl | H | CF3 |
| 16-1238 | 4-chloropyridin-3-yl | H | H | N | H | H | H | Br | H | nonafluoro-2-butyl | H | CF3 |
| 16-1239 | 4-bromopyridin-3-yl | H | H | N | H | H | H | Br | H | nonafluoro-2-butyl | H | CF3 |
| 16-1240 | 4-iodopyridin-3-yl | H | H | N | H | H | H | Br | H | nonafluoro-2-butyl | H | CF3 |
| 16-1241 | 4-(trifluoromethyl)pyridin-3-yl | H | H | N | H | H | H | Br | H | nonafluoro-2-butyl | H | CF3 |
| 16-1242 | 4-nitropyridin-3-yl | H | H | N | H | H | H | Br | H | nonafluoro-2-butyl | H | CF3 |
| 16-1243 | 4-cyanopyridin-3-yl | H | H | N | H | H | H | Br | H | nonafluoro-2-butyl | H | CF3 |
| 16-1244 | 2,6-dichloropyridin-3-yl | H | H | N | H | H | H | Br | H | nonafluoro-2-butyl | H | CF3 |
| 16-1245 | pyridin-3-yl N-oxide | H | H | N | H | H | H | Br | H | nonafluoro-2-butyl | H | CF3 |
| 16-1246 | pyridin-4-yl | H | H | N | H | H | H | Br | H | nonafluoro-2-butyl | H | CF3 |
| 16-1247 | 2-chloropyridin-4-yl | H | H | N | H | H | H | Br | H | nonafluoro-2-butyl | H | CF3 |
| 16-1248 | 3-bromopyridin-4-yl | H | H | N | H | H | H | Br | H | nonafluoro-2-butyl | H | CF3 |
| 16-1249 | 3,5-dichloropyridin-4-yl | H | H | N | H | H | H | Br | H | nonafluoro-2-butyl | H | CF3 |
| 16-1250 | 3-(trifluoromethyl)pyridin-4-yl | H | H | N | H | H | H | Br | H | nonafluoro-2-butyl | H | CF3 |
| 16-1251 | 2,6-dicyanopyridin-4-yl | H | H | N | H | H | H | Br | H | nonafluoro-2-butyl | H | CF3 |
| 16-1252 | pyridin-4-yl N-oxide | H | H | N | H | H | H | Br | H | nonafluoro-2-butyl | H | CF3 |
| 16-1253 | pyridin-2-yl | H | H | N | H | H | H | Br | H | nonafluoro-2-butyl | H | CF3 |
| 16-1254 | 3-chloropyridin-2-yl | H | H | N | H | H | H | Br | H | nonafluoro-2-butyl | H | CF3 |
| 16-1255 | 4-bromopyridin-2-yl | H | H | N | H | H | H | Br | H | nonafluoro-2-butyl | H | CF3 |
| 16-1256 | 5-iodopyridin-2-yl | H | H | N | H | H | H | Br | H | nonafluoro-2-butyl | H | CF3 |
| 16-1257 | 6-chloropyridin-2-yl | H | H | N | H | H | H | Br | H | nonafluoro-2-butyl | H | CF3 |
| 16-1258 | 4-cyanopyridin-2-yl | H | H | N | H | H | H | Br | H | nonafluoro-2-butyl | H | CF3 |
| 16-1259 | phenyl | H | H | N | H | H | H | I | H | heptafluoroisopropyl | H | CF3 |
| 16-1260 | 2-fluorophenyl | H | H | N | H | H | H | I | H | heptafluoroisopropyl | H | CF3 |
| 16-1261 | 3-fluorophenyl | H | H | N | H | H | H | I | H | heptafluoroisopropyl | H | CF3 |
| 16-1262 | 4-fluorophenyl | H | H | N | H | H | H | I | H | heptafluoroisopropyl | H | CF3 |
| 16-1263 | 2-chlorophenyl | H | H | N | H | H | H | I | H | heptafluoroisopropyl | H | CF3 |
| 16-1264 | 3-chlorophenyl | H | H | N | H | H | H | I | H | heptafluoroisopropyl | H | CF3 |
| 16-1265 | 4-chlorophenyl | H | H | N | H | H | H | I | H | heptafluoroisopropyl | H | CF3 |

TABLE 16-continued

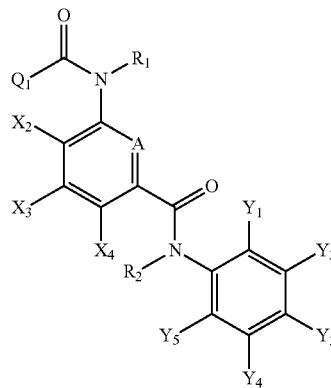

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1266 | 2-bromophenyl | H | H | N | H | H | H | I | H | heptafluoroisopropyl | H | CF3 |
| 16-1267 | 3-bromophenyl | H | H | N | H | H | H | I | H | heptafluoroisopropyl | H | CF3 |
| 16-1268 | 4-bromophenyl | H | H | N | H | H | H | I | H | heptafluoroisopropyl | H | CF3 |
| 16-1269 | 2-iodophenyl | H | H | N | H | H | H | I | H | heptafluoroisopropyl | H | CF3 |
| 16-1270 | 3-iodophenyl | H | H | N | H | H | H | I | H | heptafluoroisopropyl | H | CF3 |
| 16-1271 | 4-iodophenyl | H | H | N | H | H | H | I | H | heptafluoroisopropyl | H | CF3 |
| 16-1272 | (2-trifluoromethyl)phenyl | H | H | N | H | H | H | I | H | heptafluoroisopropyl | H | CF3 |
| 16-1273 | (3-trifluoromethyl)phenyl | H | H | N | H | H | H | I | H | heptafluoroisopropyl | H | CF3 |
| 16-1274 | (4-trifluoromethyl)phenyl | H | H | N | H | H | H | I | H | heptafluoroisopropyl | H | CF3 |
| 16-1275 | 2-nitrophenyl | H | H | N | H | H | H | I | H | heptafluoroisopropyl | H | CF3 |
| 16-1276 | 3-nitrophenyl | H | H | N | H | H | H | I | H | heptafluoroisopropyl | H | CF3 |
| 16-1277 | 4-nitrophenyl | H | H | N | H | H | H | I | H | heptafluoroisopropyl | H | CF3 |
| 16-1278 | 2-cyanophenyl | H | H | N | H | H | H | I | H | heptafluoroisopropyl | H | CF3 |
| 16-1279 | 3-cyanophenyl | H | H | N | H | H | H | I | H | heptafluoroisopropyl | H | CF3 |
| 16-1280 | 4-cyanophenyl | H | H | N | H | H | H | I | H | heptafluoroisopropyl | H | CF3 |
| 16-1281 | 2,6-difluorophenyl | H | H | N | H | H | H | I | H | heptafluoroisopropyl | H | CF3 |
| 16-1282 | 3,4-dichlorophenyl | H | H | N | H | H | H | I | H | heptafluoroisopropyl | H | CF3 |
| 16-1283 | 2,4-dichlorophenyl | H | H | N | H | H | H | I | H | heptafluoroisopropyl | H | CF3 |
| 16-1284 | 2-chloro-4-fluorophenyl | H | H | N | H | H | H | I | H | heptafluoroisopropyl | H | CF3 |
| 16-1285 | 2-chloro-4,5-difluorophenyl | H | H | N | H | H | H | I | H | heptafluoroisopropyl | H | CF3 |
| 16-1286 | 4-bromo-2-chlorophenyl | H | H | N | H | H | H | I | H | heptafluoroisopropyl | H | CF3 |
| 16-1287 | 2-bromo-4-chlorophenyl | H | H | N | H | H | H | I | H | heptafluoroisopropyl | H | CF3 |
| 16-1288 | 2-bromo-4-fluorophenyl | H | H | N | H | H | H | I | H | heptafluoroisopropyl | H | CF3 |
| 16-1289 | 2-chloro-4-nitrophenyl | H | H | N | H | H | H | I | H | heptafluoroisopropyl | H | CF3 |
| 16-1290 | 3,5-dicyanophenyl | H | H | N | H | H | H | I | H | heptafluoroisopropyl | H | CF3 |
| 16-1291 | 4-cyano-2-fluorophenyl | H | H | N | H | H | H | I | H | heptafluoroisopropyl | H | CF3 |
| 16-1292 | 2-chloro-4-cyanophenyl | H | H | N | H | H | H | I | H | heptafluoroisopropyl | H | CF3 |
| 16-1293 | pyridin-3-yl | H | H | N | H | H | H | I | H | heptafluoroisopropyl | H | CF3 |
| 16-1294 | 2-fluoropyridin-3-yl | H | H | N | H | H | H | I | H | heptafluoroisopropyl | H | CF3 |
| 16-1295 | 2-chloropyridin-3-yl | H | H | N | H | H | H | I | H | heptafluoroisopropyl | H | CF3 |
| 16-1296 | 2-bromopyridin-3-yl | H | H | N | H | H | H | I | H | heptafluoroisopropyl | H | CF3 |
| 16-1297 | 2-iodopyridin-3-yl | H | H | N | H | H | H | I | H | heptafluoroisopropyl | H | CF3 |
| 16-1298 | 2-(trifluoromethyl)pyridin-3-yl | H | H | N | H | H | H | I | H | heptafluoroisopropyl | H | CF3 |
| 16-1299 | 2-nitropyridin-3-yl | H | H | N | H | H | H | I | H | heptafluoroisopropyl | H | CF3 |
| 16-1300 | 2-cyanopyridin-3-yl | H | H | N | H | H | H | I | H | heptafluoroisopropyl | H | CF3 |
| 16-1301 | 6-fluoropyridin-3-yl | H | H | N | H | H | H | I | H | heptafluoroisopropyl | H | CF3 |
| 16-1302 | 6-chloropyridin-3-yl | H | H | N | H | H | H | I | H | heptafluoroisopropyl | H | CF3 |
| 16-1303 | 6-bromopyridin-3-yl | H | H | N | H | H | H | I | H | heptafluoroisopropyl | H | CF3 |
| 16-1304 | 6-iodopyridin-3-yl | H | H | N | H | H | H | I | H | heptafluoroisopropyl | H | CF3 |
| 16-1305 | 6-(trifluoromethyl)pyridin-3-yl | H | H | N | H | H | H | I | H | heptafluoroisopropyl | H | CF3 |
| 16-1306 | 6-nitropyridin-3-yl | H | H | N | H | H | H | I | H | heptafluoroisopropyl | H | CF3 |
| 16-1307 | 6-cyanopyridin-3-yl | H | H | N | H | H | H | I | H | heptafluoroisopropyl | H | CF3 |
| 16-1308 | 5-fluoropyridin-3-yl | H | H | N | H | H | H | I | H | heptafluoroisopropyl | H | CF3 |
| 16-1309 | 5-chloropyridin-3-yl | H | H | N | H | H | H | I | H | heptafluoroisopropyl | H | CF3 |
| 16-1310 | 5-bromopyridin-3-yl | H | H | N | H | H | H | I | H | heptafluoroisopropyl | H | CF3 |
| 16-1311 | 5-iodopyridin-3-yl | H | H | N | H | H | H | I | H | heptafluoroisopropyl | H | CF3 |
| 16-1312 | 5-(trifluoromethyl)pyridin-3-yl | H | H | N | H | H | H | I | H | heptafluoroisopropyl | H | CF3 |
| 16-1313 | 5-nitropyridin-3-yl | H | H | N | H | H | H | I | H | heptafluoroisopropyl | H | CF3 |
| 16-1314 | 5-cyanopyridin-3-yl | H | H | N | H | H | H | I | H | heptafluoroisopropyl | H | CF3 |
| 16-1315 | 4-fluoropyridin-3-yl | H | H | N | H | H | H | I | H | heptafluoroisopropyl | H | CF3 |
| 16-1316 | 4-chloropyridin-3-yl | H | H | N | H | H | H | I | H | heptafluoroisopropyl | H | CF3 |
| 16-1317 | 4-bromopyridin-3-yl | H | H | N | H | H | H | I | H | heptafluoroisopropyl | H | CF3 |
| 16-1318 | 4-iodopyridin-3-yl | H | H | N | H | H | H | I | H | heptafluoroisopropyl | H | CF3 |
| 16-1319 | 4-(trifluoromethyl)pyridin-3-yl | H | H | N | H | H | H | I | H | heptafluoroisopropyl | H | CF3 |
| 16-1320 | 4-nitropyridin-3-yl | H | H | N | H | H | H | I | H | heptafluoroisopropyl | H | CF3 |
| 16-1321 | 4-cyanopyridin-3-yl | H | H | N | H | H | H | I | H | heptafluoroisopropyl | H | CF3 |
| 16-1322 | 2,6-dichloropyridin-3-yl | H | H | N | H | H | H | I | H | heptafluoroisopropyl | H | CF3 |
| 16-1323 | pyridin-3-yl N-oxide | H | H | N | H | H | H | I | H | heptafluoroisopropyl | H | CF3 |

TABLE 16-continued

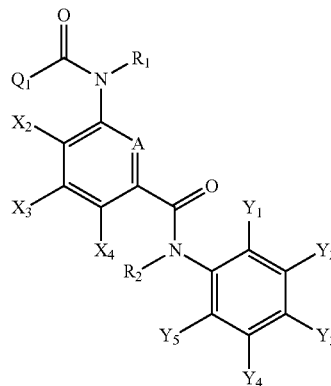

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1324 | pyridin-4-yl | H | H | N | H | H | H | I | H | heptafluoroisopropyl | H | CF3 |
| 16-1325 | 2-chloropyridin-4-yl | H | H | N | H | H | H | I | H | heptafluoroisopropyl | H | CF3 |
| 16-1326 | 3-bromopyridin-4-yl | H | H | N | H | H | H | I | H | heptafluoroisopropyl | H | CF3 |
| 16-1327 | 3,5-dichloropyridin-4-yl | H | H | N | H | H | H | I | H | heptafluoroisopropyl | H | CF3 |
| 16-1328 | 3-(trifluoromethyl)pyridin-4-yl | H | H | N | H | H | H | I | H | heptafluoroisopropyl | H | CF3 |
| 16-1329 | 2,6-dicyanopyridin-4-yl | H | H | N | H | H | H | I | H | heptafluoroisopropyl | H | CF3 |
| 16-1330 | pyridin-4-yl N-oxide | H | H | N | H | H | H | I | H | heptafluoroisopropyl | H | CF3 |
| 16-1331 | pyridin-2-yl | H | H | N | H | H | H | I | H | heptafluoroisopropyl | H | CF3 |
| 16-1332 | 3-chloropyridin-2-yl | H | H | N | H | H | H | I | H | heptafluoroisopropyl | H | CF3 |
| 16-1333 | 4-bromopyridin-2-yl | H | H | N | H | H | H | I | H | heptafluoroisopropyl | H | CF3 |
| 16-1334 | 5-iodopyridin-2-yl | H | H | N | H | H | H | I | H | heptafluoroisopropyl | H | CF3 |
| 16-1335 | 6-chloropyridin-2-yl | H | H | N | H | H | H | I | H | heptafluoroisopropyl | H | CF3 |
| 16-1336 | 4-cyanopyridin-2-yl | H | H | N | H | H | H | I | H | heptafluoroisopropyl | H | CF3 |
| 16-1337 | phenyl | H | H | N | H | H | H | I | H | nonafluoro-2-butyl | H | CF3 |
| 16-1338 | 2-fluorophenyl | H | H | N | H | H | H | I | H | nonafluoro-2-butyl | H | CF3 |
| 16-1339 | 3-fluorophenyl | H | H | N | H | H | H | I | H | nonafluoro-2-butyl | H | CF3 |
| 16-1340 | 4-fluorophenyl | H | H | N | H | H | H | I | H | nonafluoro-2-butyl | H | CF3 |
| 16-1341 | 2-chlorophenyl | H | H | N | H | H | H | I | H | nonafluoro-2-butyl | H | CF3 |
| 16-1342 | 3-chlorophenyl | H | H | N | H | H | H | I | H | nonafluoro-2-butyl | H | CF3 |
| 16-1343 | 4-chlorophenyl | H | H | N | H | H | H | I | H | nonafluoro-2-butyl | H | CF3 |
| 16-1344 | 2-bromophenyl | H | H | N | H | H | H | I | H | nonafluoro-2-butyl | H | CF3 |
| 16-1345 | 3-bromophenyl | H | H | N | H | H | H | I | H | nonafluoro-2-butyl | H | CF3 |
| 16-1346 | 4-bromophenyl | H | H | N | H | H | H | I | H | nonafluoro-2-butyl | H | CF3 |
| 16-1347 | 2-iodophenyl | H | H | N | H | H | H | I | H | nonafluoro-2-butyl | H | CF3 |
| 16-1348 | 3-iodophenyl | H | H | N | H | H | H | I | H | nonafluoro-2-butyl | H | CF3 |
| 16-1349 | 4-iodophenyl | H | H | N | H | H | H | I | H | nonafluoro-2-butyl | H | CF3 |
| 16-1350 | (2-trifluoromethyl)phenyl | H | H | N | H | H | H | I | H | nonafluoro-2-butyl | H | CF3 |
| 16-1351 | (3-trifluoromethyl)phenyl | H | H | N | H | H | H | I | H | nonafluoro-2-butyl | H | CF3 |
| 16-1352 | (4-trifluoromethyl)phenyl | H | H | N | H | H | H | I | H | nonafluoro-2-butyl | H | CF3 |
| 16-1353 | 2-nitrophenyl | H | H | N | H | H | H | I | H | nonafluoro-2-butyl | H | CF3 |
| 16-1354 | 3-nitrophenyl | H | H | N | H | H | H | I | H | nonafluoro-2-butyl | H | CF3 |
| 16-1355 | 4-nitrophenyl | H | H | N | H | H | H | I | H | nonafluoro-2-butyl | H | CF3 |
| 16-1356 | 2-cyanophenyl | H | H | N | H | H | H | I | H | nonafluoro-2-butyl | H | CF3 |
| 16-1357 | 3-cyanophenyl | H | H | N | H | H | H | I | H | nonafluoro-2-butyl | H | CF3 |
| 16-1358 | 4-cyanophenyl | H | H | N | H | H | H | I | H | nonafluoro-2-butyl | H | CF3 |
| 16-1359 | 2,6-difluorophenyl | H | H | N | H | H | H | I | H | nonafluoro-2-butyl | H | CF3 |
| 16-1360 | 3,4-dichlorophenyl | H | H | N | H | H | H | I | H | nonafluoro-2-butyl | H | CF3 |
| 16-1361 | 2,4-dichlorophenyl | H | H | N | H | H | H | I | H | nonafluoro-2-butyl | H | CF3 |
| 16-1362 | 2-chloro-4-fluorophenyl | H | H | N | H | H | H | I | H | nonafluoro-2-butyl | H | CF3 |
| 16-1363 | 2-chloro-4,5-difluorophenyl | H | H | N | H | H | H | I | H | nonafluoro-2-butyl | H | CF3 |
| 16-1364 | 4-bromo-2-chlorophenyl | H | H | N | H | H | H | I | H | nonafluoro-2-butyl | H | CF3 |
| 16-1365 | 2-bromo-4-chlorophenyl | H | H | N | H | H | H | I | H | nonafluoro-2-butyl | H | CF3 |
| 16-1366 | 2-bromo-4-fluorophenyl | H | H | N | H | H | H | I | H | nonafluoro-2-butyl | H | CF3 |
| 16-1367 | 2-chloro-4-nitrophenyl | H | H | N | H | H | H | I | H | nonafluoro-2-butyl | H | CF3 |
| 16-1368 | 3,5-dicyanophenyl | H | H | N | H | H | H | I | H | nonafluoro-2-butyl | H | CF3 |
| 16-1369 | 4-cyano-2-fluorophenyl | H | H | N | H | H | H | I | H | nonafluoro-2-butyl | H | CF3 |
| 16-1370 | 2-chloro-4-cyanophenyl | H | H | N | H | H | H | I | H | nonafluoro-2-butyl | H | CF3 |
| 16-1371 | pyridin-3-yl | H | H | N | H | H | H | I | H | nonafluoro-2-butyl | H | CF3 |
| 16-1372 | 2-fluoropyridin-3-yl | H | H | N | H | H | H | I | H | nonafluoro-2-butyl | H | CF3 |
| 16-1373 | 2-chloropyridin-3-yl | H | H | N | H | H | H | I | H | nonafluoro-2-butyl | H | CF3 |
| 16-1374 | 2-bromopyridin-3-yl | H | H | N | H | H | H | I | H | nonafluoro-2-butyl | H | CF3 |
| 16-1375 | 2-iodopyridin-3-yl | H | H | N | H | H | H | I | H | nonafluoro-2-butyl | H | CF3 |
| 16-1376 | 2-(trifluoromethyl)pyridin-3-yl | H | H | N | H | H | H | I | H | nonafluoro-2-butyl | H | CF3 |
| 16-1377 | 2-nitropyridin-3-yl | H | H | N | H | H | H | I | H | nonafluoro-2-butyl | H | CF3 |
| 16-1378 | 2-cyanopyridin-3-yl | H | H | N | H | H | H | I | H | nonafluoro-2-butyl | H | CF3 |
| 16-1379 | 6-fluoropyridin-3-yl | H | H | N | H | H | H | I | H | nonafluoro-2-butyl | H | CF3 |
| 16-1380 | 6-chloropyridin-3-yl | H | H | N | H | H | H | I | H | nonafluoro-2-butyl | H | CF3 |
| 16-1381 | 6-bromopyridin-3-yl | H | H | N | H | H | H | I | H | nonafluoro-2-butyl | H | CF3 |

TABLE 16-continued

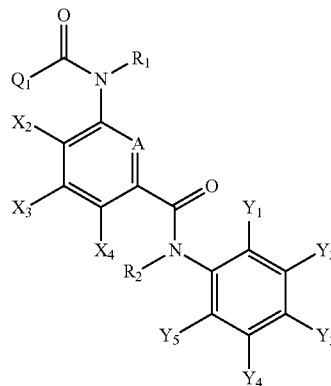

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1382 | 6-iodopyridin-3-yl | H | H | N | H | H | H | I | H | nonafluoro-2-butyl | H | CF3 |
| 16-1383 | 6-(trifluoromethyl)pyridin-3-yl | H | H | N | H | H | H | I | H | nonafluoro-2-butyl | H | CF3 |
| 16-1384 | 6-nitropyridin-3-yl | H | H | N | H | H | H | I | H | nonafluoro-2-butyl | H | CF3 |
| 16-1385 | 6-cyanopyridin-3-yl | H | H | N | H | H | H | I | H | nonafluoro-2-butyl | H | CF3 |
| 16-1386 | 5-fluoropyridin-3-yl | H | H | N | H | H | H | I | H | nonafluoro-2-butyl | H | CF3 |
| 16-1387 | 5-chloropyridin-3-yl | H | H | N | H | H | H | I | H | nonafluoro-2-butyl | H | CF3 |
| 16-1388 | 5-bromopyridin-3-yl | H | H | N | H | H | H | I | H | nonafluoro-2-butyl | H | CF3 |
| 16-1389 | 5-iodopyridin-3-yl | H | H | N | H | H | H | I | H | nonafluoro-2-butyl | H | CF3 |
| 16-1390 | 5-(trifluoromethyl)pyridin-3-yl | H | H | N | H | H | H | I | H | nonafluoro-2-butyl | H | CF3 |
| 16-1391 | 5-nitropyridin-3-yl | H | H | N | H | H | H | I | H | nonafluoro-2-butyl | H | CF3 |
| 16-1392 | 5-cyanopyridin-3-yl | H | H | N | H | H | H | I | H | nonafluoro-2-butyl | H | CF3 |
| 16-1393 | 4-fluoropyridin-3-yl | H | H | N | H | H | H | I | H | nonafluoro-2-butyl | H | CF3 |
| 16-1394 | 4-chloropyridin-3-yl | H | H | N | H | H | H | I | H | nonafluoro-2-butyl | H | CF3 |
| 16-1395 | 4-bromopyridin-3-yl | H | H | N | H | H | H | I | H | nonafluoro-2-butyl | H | CF3 |
| 16-1396 | 4-iodopyridin-3-yl | H | H | N | H | H | H | I | H | nonafluoro-2-butyl | H | CF3 |
| 16-1397 | 4-(trifluoromethyl)pyridin-3-yl | H | H | N | H | H | H | I | H | nonafluoro-2-butyl | H | CF3 |
| 16-1398 | 4-nitropyridin-3-yl | H | H | N | H | H | H | I | H | nonafluoro-2-butyl | H | CF3 |
| 16-1399 | 4-cyanopyridin-3-yl | H | H | N | H | H | H | I | H | nonafluoro-2-butyl | H | CF3 |
| 16-1400 | 2,6-dichloropyridin-3-yl | H | H | N | H | H | H | I | H | nonafluoro-2-butyl | H | CF3 |
| 16-1401 | pyridin-3-yl N-oxide | H | H | N | H | H | H | I | H | nonafluoro-2-butyl | H | CF3 |
| 16-1402 | pyridin-4-yl | H | H | N | H | H | H | I | H | nonafluoro-2-butyl | H | CF3 |
| 16-1403 | 2-chloropyridin-4-yl | H | H | N | H | H | H | I | H | nonafluoro-2-butyl | H | CF3 |
| 16-1404 | 3-bromopyridin-4-yl | H | H | N | H | H | H | I | H | nonafluoro-2-butyl | H | CF3 |
| 16-1405 | 3,5-dichloropyridin-4-yl | H | H | N | H | H | H | I | H | nonafluoro-2-butyl | H | CF3 |
| 16-1406 | 3-(trifluoromethyl)pyridin-4-yl | H | H | N | H | H | H | I | H | nonafluoro-2-butyl | H | CF3 |
| 16-1407 | 2,6-dicyanopyridin-4-yl | H | H | N | H | H | H | I | H | nonafluoro-2-butyl | H | CF3 |
| 16-1408 | pyridin-4-yl N-oxide | H | H | N | H | H | H | I | H | nonafluoro-2-butyl | H | CF3 |
| 16-1409 | pyridin-2-yl | H | H | N | H | H | H | I | H | nonafluoro-2-butyl | H | CF3 |
| 16-1410 | 3-chloropyridin-2-yl | H | H | N | H | H | H | I | H | nonafluoro-2-butyl | H | CF3 |
| 16-1411 | 4-bromopyridin-2-yl | H | H | N | H | H | H | I | H | nonafluoro-2-butyl | H | CF3 |
| 16-1412 | 5-iodopyridin-2-yl | H | H | N | H | H | H | I | H | nonafluoro-2-butyl | H | CF3 |
| 16-1413 | 6-chloropyridin-2-yl | H | H | N | H | H | H | I | H | nonafluoro-2-butyl | H | CF3 |
| 16-1414 | 4-cyanopyridin-2-yl | H | H | N | H | H | H | I | H | nonafluoro-2-butyl | H | CF3 |
| 16-1415 | phenyl | H | H | N | H | H | H | OCF3 | H | heptafluoroisopropyl | H | OCF3 |
| 16-1422 | 2-bromophenyl | H | H | N | H | H | H | OCF3 | H | heptafluoroisopropyl | H | OC2F5 |
| 16-1427 | 4-iodophenyl | H | H | N | H | H | H | OCF3 | H | pentafluoroethyl | H | OCF3 |
| 16-1430 | 3-cyanophenyl | H | H | N | H | H | H | OCF3 | H | heptafluoroisopropyl | H | OCF3 |
| 16-1431 | 4-cyanophenyl | H | H | N | H | H | H | OCF3 | H | heptafluoroisopropyl | H | OCF3 |
| 16-1436 | 2-chloro-4,5-difluorophenyl | H | H | N | H | H | H | OC2F5 | H | heptafluoroisopropyl | H | OC2F5 |
| 16-1439 | 2-bromo-4-fluorophenyl | H | H | N | H | H | H | OC2F5 | H | heptafluoroisopropyl | H | OCF3 |
| 16-1445 | 2-fluoropyridin-3-yl | H | H | N | H | H | H | OCF3 | H | pentafluoroethyl | H | OCF3 |
| 16-1446 | 2-chloropyridin-3-yl | H | H | N | H | H | H | OCF3 | H | heptafluoroisopropyl | H | OCF3 |
| 16-1471 | phenyl | H | H | N | H | H | H | OCF3 | H | nonafluoro-2-butyl | H | OCF3 |
| 16-1478 | 2-bromophenyl | H | H | N | H | H | H | OC2F5 | H | nonafluoro-2-butyl | H | OCF3 |
| 16-1484 | (2-trifluoromethyl)phenyl | H | H | N | H | H | H | OCF3 | H | nonafluoro-2-butyl | H | OC2F5 |
| 16-1486 | 3-cyanophenyl | H | H | N | H | H | H | OCF3 | H | nonafluoro-2-butyl | H | OCF3 |
| 16-1487 | 4-cyanophenyl | H | H | N | H | H | H | OCF3 | H | nonafluoro-2-butyl | H | OCF3 |
| 16-1493 | 4-bromo-2-chlorophenyl | H | H | N | H | H | H | OC2F5 | H | nonafluoro-2-butyl | H | OC2F5 |
| 16-1502 | 2-chloropyridin-3-yl | H | H | N | H | H | H | OCF3 | H | nonafluoro-2-butyl | H | OCF3 |
| 16-1527 | phenyl | H | H | N | H | H | H | CF3 | H | heptafluoroisopropyl | H | OCF3 |
| 16-1534 | 2-bromophenyl | H | H | N | H | H | H | CF3 | H | heptafluoroisopropyl | H | OC2F5 |
| 16-1539 | 4-iodophenyl | H | H | N | H | H | H | CF3 | H | pentafluoroethyl | H | OCF3 |
| 16-1540 | (2-trifluoromethyl)phenyl | H | H | N | H | H | H | C2F5 | H | heptafluoroisopropyl | H | OC2F5 |
| 16-1542 | 3-cyanophenyl | H | H | N | H | H | H | CF3 | H | heptafluoroisopropyl | H | OCF3 |
| 16-1543 | 4-cyanophenyl | H | H | N | H | H | H | CF3 | H | heptafluoroisopropyl | H | OCF3 |
| 16-1550 | 2-bromo-4-chlorophenyl | H | H | N | H | H | H | n-C3F7 | H | heptafluoroisopropyl | H | OCF3 |
| 16-1554 | 4-cyano-2-fluorophenyl | H | H | N | H | H | H | i-C3F7 | H | heptafluoroisopropyl | H | OCF3 |
| 16-1558 | 2-chloropyridin-3-yl | H | H | N | H | H | H | CF3 | H | heptafluoroisopropyl | H | OCF3 |

TABLE 16-continued

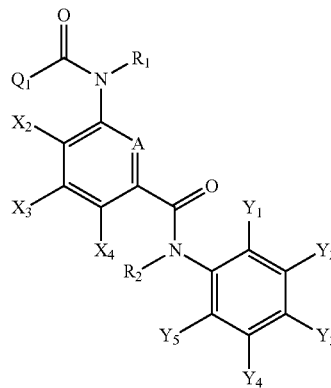

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1564 | 6-chloropyridin-3-yl | H | H | N | H | H | H | n-C3F7 | H | heptafluoroisopropyl | H | OC2F5 |
| 16-1567 | 5-cyanopyridin-3-yl | H | H | N | H | H | H | i-C3F7 | H | heptafluoroisopropyl | H | OC2F5 |
| 16-1568 | 4-chloropyridin-3-yl | H | H | N | H | H | H | CF3 | H | heptafluoroisopropyl | H | OCF3 |
| 16-1583 | phenyl | H | H | N | H | H | H | CF3 | H | nonafluoro-2-butyl | H | OCF3 |
| 16-1594 | 3-iodophenyl | H | H | N | H | H | H | CF3 | H | nonafluoro-2-butyl | H | OC2F5 |
| 16-1597 | 3-nitrophenyl | H | H | N | H | H | H | C2F5 | H | nonafluoro-2-butyl | H | OCF3 |
| 16-1598 | 3-cyanophenyl | H | H | N | H | H | H | CF3 | H | nonafluoro-2-butyl | H | OCF3 |
| 16-1599 | 4-cyanophenyl | H | H | N | H | H | H | CF3 | H | nonafluoro-2-butyl | H | OCF3 |
| 16-1605 | 4-bromo-2-chlorophenyl | H | H | N | H | H | H | i-C3F7 | H | nonafluoro-2-butyl | H | OCF3 |
| 16-1608 | 2-chloro-4-nitrophenyl | H | H | N | H | H | H | n-C3F7 | H | nonafluoro-2-butyl | H | OCF3 |
| 16-1614 | 2-chloropyridin-3-yl | H | H | N | H | H | H | CF3 | H | nonafluoro-2-butyl | H | OCF3 |
| 16-1615 | 2-bromopyridin-3-yl | H | H | N | H | H | H | CF3 | H | nonafluoro-2-butyl | H | OCF3 |
| 16-1616 | 2-iodopyridin-3-yl | H | H | N | H | H | H | CF3 | H | nonafluoro-2-butyl | H | OCF3 |
| 16-1617 | 2-(trifluoromethyl)pyridin-3-yl | H | H | N | H | H | H | CF3 | H | nonafluoro-2-butyl | H | OCF3 |
| 16-1618 | 2-nitropyridin-3-yl | H | H | N | H | H | H | CF3 | H | nonafluoro-2-butyl | H | OCF3 |
| 16-1619 | 2-cyanopyridin-3-yl | H | H | N | H | H | H | CF3 | H | nonafluoro-2-butyl | H | OCF3 |
| 16-1620 | 6-chloropyridin-3-yl | H | H | N | H | H | H | C2F5 | H | nonafluoro-2-butyl | H | OC2F5 |
| 16-1625 | 4-cyanopyridin-3-yl | H | H | N | H | H | H | n-C3F7 | H | nonafluoro-2-butyl | H | OC2F5 |
| 16-1636 | 5-iodopyridin-2-yl | H | H | N | H | H | H | i-C3F7 | H | nonafluoro-2-butyl | H | OC2F5 |
| 16-1639 | phenyl | H | H | N | H | H | H | CF3 | H | heptafluoroisopropyl | H | CF3 |
| 16-1640 | 2-fluorophenyl | H | H | N | H | H | H | CF3 | H | heptafluoroisopropyl | H | CF3 |
| 16-1651 | 4-iodophenyl | H | H | N | H | H | H | CF3 | H | pentafluoroethyl | H | CF3 |
| 16-1653 | (3-trifluoromethyl)phenyl | H | H | N | H | H | H | C2F5 | H | heptafluoroisopropyl | H | CF3 |
| 16-1658 | 2-cyanophenyl | H | H | N | H | H | H | CF3 | H | pentafluoroethyl | H | CF3 |
| 16-1659 | 3-cyanophenyl | H | H | N | H | H | H | CF3 | H | heptafluoroisopropyl | H | CF3 |
| 16-1660 | 4-cyanophenyl | H | H | N | H | H | H | CF3 | H | heptafluoroisopropyl | H | CF3 |
| 16-1666 | 4-bromo-2-chlorophenyl | H | H | N | H | H | H | n-C3F7 | H | heptafluoroisopropyl | H | CF3 |
| 16-1671 | 4-cyano-2-fluorophenyl | H | H | N | H | H | H | i-C3F7 | H | heptafluoroisopropyl | H | CF3 |
| 16-1675 | 2-chloropyridin-3-yl | H | H | N | H | H | H | CF3 | H | heptafluoroisopropyl | H | CF3 |
| 16-1676 | 2-bromopyridin-3-yl | H | H | N | H | H | H | C2F5 | H | heptafluoroisopropyl | H | C2F5 |
| 16-1677 | 2-iodopyridin-3-yl | H | H | N | H | H | H | CF3 | H | heptafluoroisopropyl | H | CF3 |
| 16-1678 | 2-(trifluoromethyl)pyridin-3-yl | H | H | N | H | H | H | CF3 | H | heptafluoroisopropyl | H | CF3 |
| 16-1679 | 2-nitropyridin-3-yl | H | H | N | H | H | H | CF3 | H | heptafluoroisopropyl | H | CF3 |
| 16-1680 | 2-cyanopyridin-3-yl | H | H | N | H | H | H | CF3 | H | heptafluoroisopropyl | H | CF3 |
| 16-1681 | 6-fluoropyridin-3-yl | H | H | N | H | H | H | CF3 | H | heptafluoroisopropyl | H | CF3 |
| 16-1682 | 6-chloropyridin-3-yl | H | H | N | H | H | H | C2F5 | H | heptafluoroisopropyl | H | n-C3F7 |
| 16-1691 | 4-cyanopyridin-3-yl | H | H | N | H | H | H | C2F5 | H | heptafluoroisopropyl | H | i-C3F7 |
| 16-1707 | phenyl | H | H | N | H | H | H | CF3 | H | nonafluoro-2-butyl | H | CF3 |
| 16-1708 | 2-fluorophenyl | H | H | N | H | H | H | CF3 | H | nonafluoro-2-butyl | H | CF3 |
| 16-1719 | 4-iodophenyl | H | H | N | H | H | H | C2F5 | H | nonafluoro-2-butyl | H | CF3 |
| 16-1727 | 3-cyanophenyl | H | H | N | H | H | H | CF3 | H | nonafluoro-2-butyl | H | CF3 |
| 16-1728 | 4-cyanophenyl | H | H | N | H | H | H | CF3 | H | nonafluoro-2-butyl | H | CF3 |
| 16-1734 | 4-bromo-2-chlorophenyl | H | H | N | H | H | H | n-C3F7 | H | nonafluoro-2-butyl | H | CF3 |
| 16-1739 | 4-cyano-2-fluorophenyl | H | H | N | H | H | H | i-C3F7 | H | nonafluoro-2-butyl | H | CF3 |
| 16-1743 | 2-chloropyridin-3-yl | H | H | N | H | H | H | CF3 | H | nonafluoro-2-butyl | H | CF3 |
| 16-1744 | 2-bromopyridin-3-yl | H | H | N | H | H | H | C2F5 | H | nonafluoro-2-butyl | H | C2F5 |
| 16-1755 | 6-cyanopyridin-3-yl | H | H | N | H | H | H | C2F5 | H | nonafluoro-2-butyl | H | n-C3F7 |
| 16-1759 | 4-cyanopyridin-3-yl | H | H | N | H | H | H | C2F5 | H | nonafluoro-2-butyl | H | i-C3F7 |
| 16-1775 | phenyl | H | H | N-oxide | H | H | H | F | H | heptafluoroisopropyl | H | F |
| 16-1776 | 3-cyanophenyl | H | H | N-oxide | H | H | H | F | H | heptafluoroisopropyl | H | F |
| 16-1777 | 4-cyanophenyl | H | H | N-oxide | H | H | H | F | H | heptafluoroisopropyl | H | F |
| 16-1778 | 2-chloropyridin-3-yl | H | H | N-oxide | H | H | H | F | H | heptafluoroisopropyl | H | F |
| 16-1779 | phenyl | H | H | N-oxide | H | H | H | F | H | nonafluoro-2-butyl | H | F |
| 16-1780 | 3-cyanophenyl | H | H | N-oxide | H | H | H | F | H | nonafluoro-2-butyl | H | F |
| 16-1781 | 4-cyanophenyl | H | H | N-oxide | H | H | H | F | H | nonafluoro-2-butyl | H | F |
| 16-1782 | 2-chloropyridin-3-yl | H | H | N-oxide | H | H | H | F | H | nonafluoro-2-butyl | H | F |
| 16-1783 | phenyl | H | H | N-oxide | H | H | H | Cl | H | heptafluoroisopropyl | H | Cl |
| 16-1787 | 2-chlorophenyl | H | H | N-oxide | H | H | H | F | H | heptafluoroisopropyl | H | Cl |

TABLE 16-continued

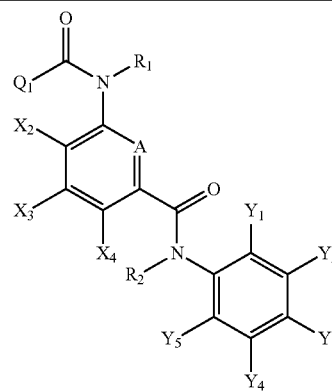

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-1791 | 3-bromophenyl | H | H | N-oxide | H | H | H | F | H | heptafluoroisopropyl | H | Br |
| 16-1795 | 4-iodophenyl | H | H | N-oxide | H | H | H | Cl | H | pentafluoroethyl | H | Cl |
| 16-1796 | (2-trifluoromethyl)phenyl | H | H | N-oxide | H | H | H | F | H | heptafluoroisopropyl | H | I |
| 16-1799 | 2-nitrophenyl | H | H | N-oxide | H | H | H | Cl | H | heptafluoroisopropyl | H | Br |
| 16-1803 | 3-cyanophenyl | H | H | N-oxide | H | H | H | Cl | H | heptafluoroisopropyl | H | Cl |
| 16-1804 | 4-cyanophenyl | H | H | N-oxide | H | H | H | Cl | H | heptafluoroisopropyl | H | Cl |
| 16-1805 | 2,6-difluorophenyl | H | H | N-oxide | H | H | H | Cl | H | heptafluoroisopropyl | H | I |
| 16-1817 | pyridin-3-yl | H | H | N-oxide | H | H | H | Br | H | heptafluoroisopropyl | H | I |
| 16-1818 | 2-fluoropyridin-3-yl | H | H | N-oxide | H | H | H | Cl | H | pentafluoroethyl | H | Cl |
| 16-1819 | 2-chloropyridin-3-yl | H | H | N-oxide | H | H | H | Cl | H | heptafluoroisopropyl | H | Cl |
| 16-1861 | phenyl | H | H | N-oxide | H | H | H | Cl | H | nonafluoro-2-butyl | H | Cl |
| 16-1881 | 3-cyanophenyl | H | H | N-oxide | H | H | H | Cl | H | nonafluoro-2-butyl | H | Cl |
| 16-1882 | 4-cyanophenyl | H | H | N-oxide | H | H | H | Cl | H | nonafluoro-2-butyl | H | Cl |
| 16-1897 | 2-chloropyridin-3-yl | H | H | N-oxide | H | H | H | Cl | H | nonafluoro-2-butyl | H | Cl |
| 16-1939 | phenyl | H | H | N-oxide | H | H | H | Br | H | heptafluoroisopropyl | H | Br |
| 16-1951 | 4-iodophenyl | H | H | N-oxide | H | H | H | Br | H | pentafluoroethyl | H | Br |
| 16-1959 | 3-cyanophenyl | H | H | N-oxide | H | H | H | Br | H | heptafluoroisopropyl | H | Br |
| 16-1960 | 4-cyanophenyl | H | H | N-oxide | H | H | H | Br | H | heptafluoroisopropyl | H | Br |
| 16-1973 | pyridin-3-yl | H | H | N-oxide | H | H | H | Br | H | heptafluoroisopropyl | H | Br |
| 16-1975 | 2-chloropyridin-3-yl | H | H | N-oxide | H | H | H | Br | H | heptafluoroisopropyl | H | Br |
| 16-1982 | 6-chloropyridin-3-yl | H | H | N-oxide | H | H | H | Br | H | heptafluoroisopropyl | H | Br |
| 16-2017 | phenyl | H | H | N-oxide | H | H | H | Br | H | nonafluoro-2-butyl | H | Br |
| 16-2037 | 3-cyanophenyl | H | H | N-oxide | H | H | H | Br | H | nonafluoro-2-butyl | H | Br |
| 16-2038 | 4-cyanophenyl | H | H | N-oxide | H | H | H | Br | H | nonafluoro-2-butyl | H | Br |
| 16-2053 | 2-chloropyridin-3-yl | H | H | N-oxide | H | H | H | Br | H | nonafluoro-2-butyl | H | Br |
| 16-2095 | phenyl | H | H | N-oxide | H | H | H | I | H | heptafluoroisopropyl | H | I |
| 16-2107 | 4-iodophenyl | H | H | N-oxide | H | H | H | I | H | pentafluoroethyl | H | I |
| 16-2115 | 3-cyanophenyl | H | H | N-oxide | H | H | H | I | H | heptafluoroisopropyl | H | I |
| 16-2116 | 4-cyanophenyl | H | H | N-oxide | H | H | H | I | H | heptafluoroisopropyl | H | I |
| 16-2131 | 2-chloropyrdin-3-yl | H | H | N-oxide | H | H | H | I | H | heptafluoroisopropyl | H | I |
| 16-2160 | pyridin-4-yl | H | H | N-oxide | H | H | H | I | H | heptafluoroisopropyl | H | I |
| 16-2173 | phenyl | H | H | N-oxide | H | H | H | I | H | nonafluoro-2-butyl | H | I |
| 16-2193 | 3-cyanophenyl | H | H | N-oxide | H | H | H | I | H | nonafluoro-2-butyl | H | I |
| 16-2194 | 4-cyanophenyl | H | H | N-oxide | H | H | H | I | H | nonafluoro-2-butyl | H | I |
| 16-2209 | 2-chloropyridin-3-yl | H | H | N-oxide | H | H | H | I | H | nonafluoro-2-butyl | H | I |
| 16-2251 | phenyl | H | H | N-oxide | H | H | H | Cl | H | heptafluoroisopropyl | H | OCF3 |
| 16-2263 | 4-iodophenyl | H | H | N-oxide | H | H | H | Cl | H | pentafluoroethyl | H | OCF3 |
| 16-2266 | (4-trifluoromethyl)phenyl | H | H | N-oxide | H | H | H | Cl | H | heptafluoroisopropyl | H | OC2F5 |
| 16-2267 | 2-nitrophenyl | H | H | N-oxide | H | H | H | F | H | heptafluoroisopropyl | H | OCF3 |
| 16-2270 | 2-cyanophenyl | H | H | N-oxide | H | H | H | Cl | H | pentafluoroethyl | H | OC2F5 |
| 16-2271 | 3-cyanophenyl | H | H | N-oxide | H | H | H | Cl | H | heptafluoroisopropyl | H | OCF3 |
| 16-2272 | 4-cyanophenyl | H | H | N-oxide | H | H | H | Cl | H | heptafluoroisopropyl | H | OCF3 |
| 16-2287 | 2-chloropyridin-3-yl | H | H | N-oxide | H | H | H | Cl | H | heptafluoroisopropyl | H | OCF3 |
| 16-2329 | phenyl | H | H | N-oxide | H | H | H | Cl | H | nonafluoro-2-butyl | H | OCF3 |
| 16-2345 | 2-nitrophenyl | H | H | N-oxide | H | H | H | F | H | nonafluoro-2-butyl | H | OCF3 |
| 16-2349 | 3-cyanophenyl | H | H | N-oxide | H | H | H | Cl | H | nonafluoro-2-butyl | H | OCF3 |
| 16-2350 | 4-cyanophenyl | H | H | N-oxide | H | H | H | Cl | H | nonafluoro-2-butyl | H | OCF3 |
| 16-2365 | 2-chloropyridin-3-yl | H | H | N-oxide | H | H | H | Cl | H | nonafluoro-2-butyl | H | OCF3 |
| 16-2407 | phenyl | H | H | N-oxide | H | H | H | Br | H | heptafluoroisopropyl | H | OCF3 |
| 16-2427 | 3-cyanophenyl | H | H | N-oxide | H | H | H | Br | H | heptafluoroisopropyl | H | OCF3 |
| 16-2428 | 4-cyanophenyl | H | H | N-oxide | H | H | H | Br | H | heptafluoroisopropyl | H | OCF3 |
| 16-2444 | 2-bromopyridin-3-yl | H | H | N-oxide | H | H | H | Br | H | heptafluoroisopropyl | H | OCF3 |
| 16-2485 | phenyl | H | H | N-oxide | H | H | H | Br | H | nonafluoro-2-butyl | H | OCF3 |
| 16-2505 | 3-cyanophenyl | H | H | N-oxide | H | H | H | Br | H | nonafluoro-2-butyl | H | OCF3 |
| 16-2506 | 4-cyanophenyl | H | H | N-oxide | H | H | H | Br | H | nonafluoro-2-butyl | H | OCF3 |
| 16-2521 | 2-chloropyridin-3-yl | H | H | N-oxide | H | H | H | Br | H | nonafluoro-2-butyl | H | OCF3 |
| 16-2563 | phenyl | H | H | N-oxide | H | H | H | I | H | heptafluoroisopropyl | H | OCF3 |
| 16-2583 | 3-cyanophenyl | H | H | N-oxide | H | H | H | I | H | heptafluoroisopropyl | H | OCF3 |

TABLE 16-continued

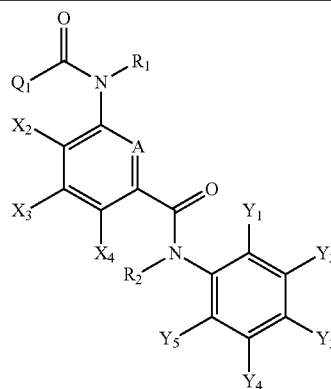

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-2584 | 4-cyanophenyl | H | H | N-oxide | H | H | H | I | H | heptafluoroisopropyl | H | OCF3 |
| 16-2599 | 2-chloropyridin-3-yl | H | H | N-oxide | H | H | H | I | H | heptafluoroisopropyl | H | OCF3 |
| 16-2641 | phenyl | H | H | N-oxide | H | H | H | I | H | nonafluoro-2-butyl | H | OCF3 |
| 16-2661 | 3-cyanophenyl | H | H | N-oxide | H | H | H | I | H | nonafluoro-2-butyl | H | OCF3 |
| 16-2662 | 4-cyanophenyl | H | H | N-oxide | H | H | H | I | H | nonafluoro-2-butyl | H | OCF3 |
| 16-2677 | 2-chloropyridin-3-yl | H | H | N-oxide | H | H | H | I | H | nonafluoro-2-butyl | H | OCF3 |
| 16-2719 | phenyl | H | H | N-oxide | H | H | H | F | H | heptafluoroisopropyl | H | CF3 |
| 16-2720 | phenyl | H | H | N-oxide | H | H | H | Cl | H | heptafluoroisopropyl | H | CF3 |
| 16-2721 | 2-fluorophenyl | H | H | N-oxide | H | H | H | Cl | H | heptafluoroisopropyl | H | CF3 |
| 16-2732 | 4-iodophenyl | H | H | N-oxide | H | H | H | Cl | H | pentafluoroethyl | H | CF3 |
| 16-2739 | 2-cyanophenyl | H | H | N-oxide | H | H | H | Cl | H | pentafluoroethyl | H | C2F5 |
| 16-2740 | 3-cyanophenyl | H | H | N-oxide | H | H | H | Cl | H | heptafluoroisopropyl | H | CF3 |
| 16-2741 | 4-cyanophenyl | H | H | N-oxide | H | H | H | Cl | H | heptafluoroisopropyl | H | CF3 |
| 16-2744 | 2,4-dichlorophenyl | H | H | N-oxide | H | H | H | Cl | H | heptafluoroisopropyl | H | C2F5 |
| 16-2745 | 2-chloro-4-fluorophenyl | H | H | N-oxide | H | H | H | Cl | H | heptafluoroisopropyl | H | CF3 |
| 16-2748 | 2-bromo-4-chlorophenyl | H | H | N-oxide | H | H | H | Cl | H | heptafluoroisopropyl | H | n-C3F7 |
| 16-2756 | 2-chloropyridin-3-yl | H | H | N-oxide | H | H | H | Cl | H | heptafluoroisopropyl | H | CF3 |
| 16-2769 | 5-fluoropyridin-3-yl | H | H | N-oxide | H | H | H | Cl | H | heptafluoroisopropyl | H | C2F5 |
| 16-2771 | 5-bromopyridin-3-yl | H | H | N-oxide | H | H | H | Cl | H | heptafluoroisopropyl | H | n-C3F7 |
| 16-2772 | 5-iodopyridin-3-yl | H | H | N-oxide | H | H | H | Cl | H | heptafluoroisopropyl | H | i-C3F7 |
| 16-2774 | 5-nitropyridin-3-yl | H | H | N-oxide | H | H | H | Cl | H | pentafluoroethyl | H | CF3 |
| 16-2776 | 4-fluoropyridin-3-yl | H | H | N-oxide | H | H | H | Cl | H | pentafluoroethyl | H | CF3 |
| 16-2778 | 4-bromopyridin-3-yl | H | H | N-oxide | H | H | H | Cl | H | heptafluoroisopropyl | H | n-C3F7 |
| 16-2779 | 4-iodopyridin-3-yl | H | H | N-oxide | H | H | H | Cl | H | heptafluoroisopropyl | H | i-C3F7 |
| 16-2796 | 6-chloropyridin-2-yl | H | H | N-oxide | H | H | H | Cl | H | pentafluoroethyl | H | CF3 |
| 16-2798 | phenyl | H | H | N-oxide | H | H | H | F | H | nonafluoro-2-butyl | H | CF3 |
| 16-2799 | phenyl | H | H | N-oxide | H | H | H | Cl | H | nonafluoro-2-butyl | H | CF3 |
| 16-2811 | 4-iodophenyl | H | H | N-oxide | H | H | H | Cl | H | nonafluoro-2-butyl | H | CF3 |
| 16-2812 | (2-trifluoromethyl)phenyl | H | H | N-oxide | H | H | H | Cl | H | nonafluoro-2-butyl | H | C2F5 |
| 16-2819 | 3-cyanophenyl | H | H | N-oxide | H | H | H | Cl | H | nonafluoro-2-butyl | H | CF3 |
| 16-2820 | 4-cyanophenyl | H | H | N-oxide | H | H | H | Cl | H | nonafluoro-2-butyl | H | CF3 |
| 16-2829 | 2-chloro-4-nitrophenyl | H | H | N-oxide | H | H | H | Cl | H | nonafluoro-2-butyl | H | i-C3F7 |
| 16-2835 | 2-chloropyridin-3-yl | H | H | N-oxide | H | H | H | Cl | H | nonafluoro-2-butyl | H | CF3 |
| 16-2848 | 5-fluoropyridin-3-yl | H | H | N-oxide | H | H | H | Cl | H | nonafluoro-2-butyl | H | C2F5 |
| 16-2850 | 5-bromopyridin-3-yl | H | H | N-oxide | H | H | H | Cl | H | nonafluoro-2-butyl | H | n-C3F7 |
| 16-2851 | 5-iodopyridin-3-yl | H | H | N-oxide | H | H | H | Cl | H | nonafluoro-2-butyl | H | i-C3F7 |
| 16-2855 | 4-fluoropyridin-3-yl | H | H | N-oxide | H | H | H | Cl | H | nonafluoro-2-butyl | H | C2F5 |
| 16-2859 | 4-(trifluoromethyl)pyridin-3-yl | H | H | N-oxide | H | H | H | Cl | H | nonafluoro-2-butyl | H | n-C3F7 |
| 16-2860 | 4-nitropyridin-3-yl | H | H | N-oxide | H | H | H | Cl | H | nonafluoro-2-butyl | H | i-C3F7 |
| 16-2877 | phenyl | H | H | N-oxide | H | H | H | Br | H | heptafluoroisopropyl | H | CF3 |
| 16-2878 | 2-fluorophenyl | H | H | N-oxide | H | H | H | Br | H | heptafluoroisopropyl | H | CF3 |
| 16-2897 | 3-cyanophenyl | H | H | N-oxide | H | H | H | Br | H | heptafluoroisopropyl | H | CF3 |
| 16-2898 | 4-cyanophenyl | H | H | N-oxide | H | H | H | Br | H | heptafluoroisopropyl | H | CF3 |
| 16-2913 | 2-chloropyridin-3-yl | H | H | N-oxide | H | H | H | Br | H | heptafluoroisopropyl | H | CF3 |
| 16-2920 | 6-chloropyridin-3-yl | H | H | N-oxide | H | H | H | Br | H | heptafluoroisopropyl | H | CF3 |
| 16-2942 | pyridin-4-yl | H | H | N-oxide | H | H | H | Br | H | heptafluoroisopropyl | H | CF3 |
| 16-2955 | phenyl | H | H | N-oxide | H | H | H | Br | H | nonafluoro-2-butyl | H | CF3 |
| 16-2963 | 3-bromophenyl | H | H | N-oxide | H | H | H | Br | H | nonafluoro-2-butyl | H | CF3 |
| 16-2969 | (3-trifluoromethyl)phenyl | H | H | N-oxide | H | H | H | Br | H | nonafluoro-2-butyl | H | CF3 |
| 16-2975 | 3-cyanophenyl | H | H | N-oxide | H | H | H | Br | H | nonafluoro-2-butyl | H | CF3 |
| 16-2976 | 4-cyanophenyl | H | H | N-oxide | H | H | H | Br | H | nonafluoro-2-butyl | H | CF3 |
| 16-2991 | 2-chloropyridin-3-yl | H | H | N-oxide | H | H | H | Br | H | nonafluoro-2-butyl | H | CF3 |
| 16-2998 | 6-chloropyridin-3-yl | H | H | N-oxide | H | H | H | Br | H | nonafluoro-2-butyl | H | CF3 |
| 16-3005 | 5-chloropyridin-3-yl | H | H | N-oxide | H | H | H | Br | H | nonafluoro-2-butyl | H | CF3 |
| 16-3020 | pyridin-4-yl | H | H | N-oxide | H | H | H | Br | H | nonafluoro-2-butyl | H | CF3 |
| 16-3033 | phenyl | H | H | N-oxide | H | H | H | I | H | heptafluoroisopropyl | H | CF3 |
| 16-3034 | 2-fluorophenyl | H | H | N-oxide | H | H | H | I | H | heptafluoroisopropyl | H | CF3 |
| 16-3035 | 3-fluorophenyl | H | H | N-oxide | H | H | H | I | H | heptafluoroisopropyl | H | CF3 |

TABLE 16-continued

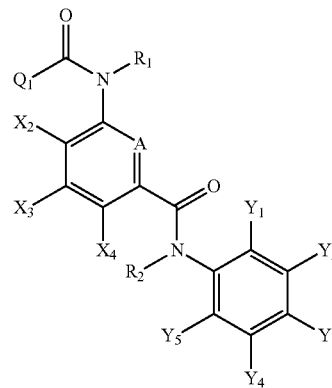

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-3036 | 4-fluorophenyl | H | H | N-oxide | H | H | H | I | H | heptafluoroisopropyl | H | CF3 |
| 16-3037 | 2-chlorophenyl | H | H | N-oxide | H | H | H | I | H | heptafluoroisopropyl | H | CF3 |
| 16-3038 | 3-chlorophenyl | H | H | N-oxide | H | H | H | I | H | heptafluoroisopropyl | H | CF3 |
| 16-3039 | 4-chlorophenyl | H | H | N-oxide | H | H | H | I | H | heptafluoroisopropyl | H | CF3 |
| 16-3040 | 2-bromophenyl | H | H | N-oxide | H | H | H | I | H | heptafluoroisopropyl | H | CF3 |
| 16-3041 | 3-bromophenyl | H | H | N-oxide | H | H | H | I | H | heptafluoroisopropyl | H | CF3 |
| 16-3042 | 4-bromophenyl | H | H | N-oxide | H | H | H | I | H | heptafluoroisopropyl | H | CF3 |
| 16-3043 | 2-iodophenyl | H | H | N-oxide | H | H | H | I | H | heptafluoroisopropyl | H | CF3 |
| 16-3044 | 3-iodophenyl | H | H | N-oxide | H | H | H | I | H | heptafluoroisopropyl | H | CF3 |
| 16-3045 | 4-iodophenyl | H | H | N-oxide | H | H | H | I | H | heptafluoroisopropyl | H | CF3 |
| 16-3046 | (2-trifluoromethyl)phenyl | H | H | N-oxide | H | H | H | I | H | heptafluoroisopropyl | H | CF3 |
| 16-3047 | (3-trifluoromethyl)phenyl | H | H | N-oxide | H | H | H | I | H | heptafluoroisopropyl | H | CF3 |
| 16-3048 | (4-trifluoromethyl)phenyl | H | H | N-oxide | H | H | H | I | H | heptafluoroisopropyl | H | CF3 |
| 16-3049 | 2-nitrophenyl | H | H | N-oxide | H | H | H | I | H | heptafluoroisopropyl | H | CF3 |
| 16-3050 | 3-nitrophenyl | H | H | N-oxide | H | H | H | I | H | heptafluoroisopropyl | H | CF3 |
| 16-3051 | 4-nitrophenyl | H | H | N-oxide | H | H | H | I | H | heptafluoroisopropyl | H | CF3 |
| 16-3052 | 2-cyanophenyl | H | H | N-oxide | H | H | H | I | H | heptafluoroisopropyl | H | CF3 |
| 16-3053 | 3-cyanophenyl | H | H | N-oxide | H | H | H | I | H | heptafluoroisopropyl | H | CF3 |
| 16-3054 | 4-cyanophenyl | H | H | N-oxide | H | H | H | I | H | heptafluoroisopropyl | H | CF3 |
| 16-3055 | 2,6-difluorophenyl | H | H | N-oxide | H | H | H | I | H | heptafluoroisopropyl | H | CF3 |
| 16-3056 | 3,4-dichlorophenyl | H | H | N-oxide | H | H | H | I | H | heptafluoroisopropyl | H | CF3 |
| 16-3057 | 2,4-dichlorophenyl | H | H | N-oxide | H | H | H | I | H | heptafluoroisopropyl | H | CF3 |
| 16-3058 | 2-chloro-4-fluorophenyl | H | H | N-oxide | H | H | H | I | H | heptafluoroisopropyl | H | CF3 |
| 16-3059 | 2-chloro-4,5-difluorophenyl | H | H | N-oxide | H | H | H | I | H | heptafluoroisopropyl | H | CF3 |
| 16-3060 | 4-bromo-2-chlorophenyl | H | H | N-oxide | H | H | H | I | H | heptafluoroisopropyl | H | CF3 |
| 16-3061 | 2-bromo-4-chlorophenyl | H | H | N-oxide | H | H | H | I | H | heptafluoroisopropyl | H | CF3 |
| 16-3062 | 2-bromo-4-fluorophenyl | H | H | N-oxide | H | H | H | I | H | heptafluoroisopropyl | H | CF3 |
| 16-3063 | 2-chloro-4-nitrophenyl | H | H | N-oxide | H | H | H | I | H | heptafluoroisopropyl | H | CF3 |
| 16-3064 | 3,5-dicyanophenyl | H | H | N-oxide | H | H | H | I | H | heptafluoroisopropyl | H | CF3 |
| 16-3065 | 4-cyano-2-fluorophenyl | H | H | N-oxide | H | H | H | I | H | heptafluoroisopropyl | H | CF3 |
| 16-3066 | 2-chloro-4-cyanophenyl | H | H | N-oxide | H | H | H | I | H | heptafluoroisopropyl | H | CF3 |
| 16-3067 | pyridin-3-yl | H | H | N-oxide | H | H | H | I | H | heptafluoroisopropyl | H | CF3 |
| 16-3068 | 2-fluoropyridin-3-yl | H | H | N-oxide | H | H | H | I | H | heptafluoroisopropyl | H | CF3 |
| 16-3069 | 2-chloropyridin-3-yl | H | H | N-oxide | H | H | H | I | H | heptafluoroisopropyl | H | CF3 |
| 16-3070 | 2-bromopyridin-3-yl | H | H | N-oxide | H | H | H | I | H | heptafluoroisopropyl | H | CF3 |
| 16-3071 | 2-iodopyridin-3-yl | H | H | N-oxide | H | H | H | I | H | heptafluoroisopropyl | H | CF3 |
| 16-3072 | 2-(trifluoromethyl)pyridin-3-yl | H | H | N-oxide | H | H | H | I | H | heptafluoroisopropyl | H | CF3 |
| 16-3073 | 2-nitropyridin-3-yl | H | H | N-oxide | H | H | H | I | H | heptafluoroisopropyl | H | CF3 |
| 16-3074 | 2-cyanopyridin-3-yl | H | H | N-oxide | H | H | H | I | H | heptafluoroisopropyl | H | CF3 |
| 16-3075 | 6-fluoropyridin-3-yl | H | H | N-oxide | H | H | H | I | H | heptafluoroisopropyl | H | CF3 |
| 16-3076 | 6-chloropyridin-3-yl | H | H | N-oxide | H | H | H | I | H | heptafluoroisopropyl | H | CF3 |
| 16-3077 | 6-bromopyridin-3-yl | H | H | N-oxide | H | H | H | I | H | heptafluoroisopropyl | H | CF3 |
| 16-3078 | 6-iodopyridin-3-yl | H | H | N-oxide | H | H | H | I | H | heptafluoroisopropyl | H | CF3 |
| 16-3079 | 6-(trifluoromethyl)pyridin-3-yl | H | H | N-oxide | H | H | H | I | H | heptafluoroisopropyl | H | CF3 |
| 16-3080 | 6-nitropyridin-3-yl | H | H | N-oxide | H | H | H | I | H | heptafluoroisopropyl | H | CF3 |
| 16-3081 | 6-cyanopyridin-3-yl | H | H | N-oxide | H | H | H | I | H | heptafluoroisopropyl | H | CF3 |
| 16-3082 | 5-fluoropyridin-3-yl | H | H | N-oxide | H | H | H | I | H | heptafluoroisopropyl | H | CF3 |
| 16-3083 | 5-chloropyridin-3-yl | H | H | N-oxide | H | H | H | I | H | heptafluoroisopropyl | H | CF3 |
| 16-3084 | 5-bromopyridin-3-yl | H | H | N-oxide | H | H | H | I | H | heptafluoroisopropyl | H | CF3 |
| 16-3085 | 5-iodopyridin-3-yl | H | H | N-oxide | H | H | H | I | H | heptafluoroisopropyl | H | CF3 |
| 16-3086 | 5-(trifluoromethyl)pyridin-3-yl | H | H | N-oxide | H | H | H | I | H | heptafluoroisopropyl | H | CF3 |
| 16-3087 | 5-nitropyridin-3-yl | H | H | N-oxide | H | H | H | I | H | heptafluoroisopropyl | H | CF3 |
| 16-3088 | 5-cyanopyridin-3-yl | H | H | N-oxide | H | H | H | I | H | heptafluoroisopropyl | H | CF3 |
| 16-3089 | 4-fluoropyridin-3-yl | H | H | N-oxide | H | H | H | I | H | heptafluoroisopropyl | H | CF3 |
| 16-3090 | 4-chloropyridin-3-yl | H | H | N-oxide | H | H | H | I | H | heptafluoroisopropyl | H | CF3 |
| 16-3091 | 4-bromopyridin-3-yl | H | H | N-oxide | H | H | H | I | H | heptafluoroisopropyl | H | CF3 |
| 16-3092 | 4-iodopyridin-3-yl | H | H | N-oxide | H | H | H | I | H | heptafluoroisopropyl | H | CF3 |
| 16-3093 | 4-(trifluoromethyl)pyridin-3-yl | H | H | N-oxide | H | H | H | I | H | heptafluoroisopropyl | H | CF3 |

TABLE 16-continued

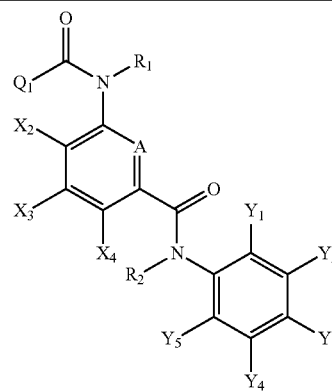

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 16-3094 | 4-nitropyridin-3-yl | H | H | N-oxide | H | H | H | I | H | heptafluoroisopropyl | H | CF3 |
| 16-3095 | 4-cyanopyridin-3-yl | H | H | N-oxide | H | H | H | I | H | heptafluoroisopropyl | H | CF3 |
| 16-3096 | 2,6-dichloropyridin-3-yl | H | H | N-oxide | H | H | H | I | H | heptafluoroisopropyl | H | CF3 |
| 16-3097 | pyridin-3-yl N-oxide | H | H | N-oxide | H | H | H | I | H | heptafluoroisopropyl | H | CF3 |
| 16-3098 | pyridin-4-yl | H | H | N-oxide | H | H | H | I | H | heptafluoroisopropyl | H | CF3 |
| 16-3099 | 2-chloropyridin-4-yl | H | H | N-oxide | H | H | H | I | H | heptafluoroisopropyl | H | CF3 |
| 16-3100 | 3-bromopyridin-4-yl | H | H | N-oxide | H | H | H | I | H | heptafluoroisopropyl | H | CF3 |
| 16-3101 | 3,5-dichloropyridin-4-yl | H | H | N-oxide | H | H | H | I | H | heptafluoroisopropyl | H | CF3 |
| 16-3102 | 3-(trifluoromethyl)pyridin-4-yl | H | H | N-oxide | H | H | H | I | H | heptafluoroisopropyl | H | CF3 |
| 16-3103 | 2,6-dicyanopyridin-4-yl | H | H | N-oxide | H | H | H | I | H | heptafluoroisopropyl | H | CF3 |
| 16-3104 | pyridin-4-yl N-oxide | H | H | N-oxide | H | H | H | I | H | heptafluoroisopropyl | H | CF3 |
| 16-3105 | pyridin-2-yl | H | H | N-oxide | H | H | H | I | H | heptafluoroisopropyl | H | CF3 |
| 16-3106 | 3-chloropyridin-2-yl | H | H | N-oxide | H | H | H | I | H | heptafluoroisopropyl | H | CF3 |
| 16-3107 | 4-bromopyridin-2-yl | H | H | N-oxide | H | H | H | I | H | heptafluoroisopropyl | H | CF3 |
| 16-3108 | 5-iodopyridin-2-yl | H | H | N-oxide | H | H | H | I | H | heptafluoroisopropyl | H | CF3 |
| 16-3109 | 6-chloropyridin-2-yl | H | H | N-oxide | H | H | H | I | H | heptafluoroisopropyl | H | CF3 |
| 16-3110 | 4-cyanopyridin-2-yl | H | H | N-oxide | H | H | H | I | H | heptafluoroisopropyl | H | CF3 |
| 16-3111 | phenyl | H | H | N-oxide | H | H | H | I | H | nonafluoro-2-butyl | H | CF3 |
| 16-3112 | 2-fluorophenyl | H | H | N-oxide | H | H | H | I | H | nonafluoro-2-butyl | H | CF3 |
| 16-3113 | 3-fluorophenyl | H | H | N-oxide | H | H | H | I | H | nonafluoro-2-butyl | H | CF3 |
| 16-3114 | 4-fluorophenyl | H | H | N-oxide | H | H | H | I | H | nonafluoro-2-butyl | H | CF3 |
| 16-3115 | 2-chlorophenyl | H | H | N-oxide | H | H | H | I | H | nonafluoro-2-butyl | H | CF3 |
| 16-3116 | 3-chlorophenyl | H | H | N-oxide | H | H | H | I | H | nonafluoro-2-butyl | H | CF3 |
| 16-3117 | 4-chlorophenyl | H | H | N-oxide | H | H | H | I | H | nonafluoro-2-butyl | H | CF3 |
| 16-3118 | 2-bromophenyl | H | H | N-oxide | H | H | H | I | H | nonafluoro-2-butyl | H | CF3 |
| 16-3119 | 3-bromophenyl | H | H | N-oxide | H | H | H | I | H | nonafluoro-2-butyl | H | CF3 |
| 16-3120 | 4-bromophenyl | H | H | N-oxide | H | H | H | I | H | nonafluoro-2-butyl | H | CF3 |
| 16-3121 | 2-iodophenyl | H | H | N-oxide | H | H | H | I | H | nonafluoro-2-butyl | H | CF3 |
| 16-3122 | 3-iodophenyl | H | H | N-oxide | H | H | H | I | H | nonafluoro-2-butyl | H | CF3 |
| 16-3123 | 4-iodophenyl | H | H | N-oxide | H | H | H | I | H | nonafluoro-2-butyl | H | CF3 |
| 16-3124 | (2-trifluoromethyl)phenyl | H | H | N-oxide | H | H | H | I | H | nonafluoro-2-butyl | H | CF3 |
| 16-3125 | (3-trifluoromethyl)phenyl | H | H | N-oxide | H | H | H | I | H | nonafluoro-2-butyl | H | CF3 |
| 16-3126 | (4-trifluoromethyl)phenyl | H | H | N-oxide | H | H | H | I | H | nonafluoro-2-butyl | H | CF3 |
| 16-3127 | 2-nitrophenyl | H | H | N-oxide | H | H | H | I | H | nonafluoro-2-butyl | H | CF3 |
| 16-3128 | 3-nitrophenyl | H | H | N-oxide | H | H | H | I | H | nonafluoro-2-butyl | H | CF3 |
| 16-3129 | 4-nitrophenyl | H | H | N-oxide | H | H | H | I | H | nonafluoro-2-butyl | H | CF3 |
| 16-3130 | 2-cyanophenyl | H | H | N-oxide | H | H | H | I | H | nonafluoro-2-butyl | H | CF3 |
| 16-3131 | 3-cyanophenyl | H | H | N-oxide | H | H | H | I | H | nonafluoro-2-butyl | H | CF3 |
| 16-3132 | 4-cyanophenyl | H | H | N-oxide | H | H | H | I | H | nonafluoro-2-butyl | H | CF3 |
| 16-3133 | 2,6-difluorophenyl | H | H | N-oxide | H | H | H | I | H | nonafluoro-2-butyl | H | CF3 |
| 16-3134 | 3,4-dichlorophenyl | H | H | N-oxide | H | H | H | I | H | nonafluoro-2-butyl | H | CF3 |
| 16-3135 | 2,4-dichlorophenyl | H | H | N-oxide | H | H | H | I | H | nonafluoro-2-butyl | H | CF3 |
| 16-3136 | 2-chloro-4-fluorophenyl | H | H | N-oxide | H | H | H | I | H | nonafluoro-2-butyl | H | CF3 |
| 16-3137 | 2-chloro-4,5-difluorophenyl | H | H | N-oxide | H | H | H | I | H | nonafluoro-2-butyl | H | CF3 |
| 16-3138 | 4-bromo-2-chlorophenyl | H | H | N-oxide | H | H | H | I | H | nonafluoro-2-butyl | H | CF3 |
| 16-3139 | 2-bromo-4-chlorophenyl | H | H | N-oxide | H | H | H | I | H | nonafluoro-2-butyl | H | CF3 |
| 16-3140 | 2-bromo-4-fluorophenyl | H | H | N-oxide | H | H | H | I | H | nonafluoro-2-butyl | H | CF3 |
| 16-3141 | 2-chloro-4-nitrophenyl | H | H | N-oxide | H | H | H | I | H | nonafluoro-2-butyl | H | CF3 |
| 16-3142 | 3,5-dicyanophenyl | H | H | N-oxide | H | H | H | I | H | nonafluoro-2-butyl | H | CF3 |
| 16-3143 | 4-cyano-2-fluorophenyl | H | H | N-oxide | H | H | H | I | H | nonafluoro-2-butyl | H | CF3 |
| 16-3144 | 2-chloro-4-cyanophenyl | H | H | N-oxide | H | H | H | I | H | nonafluoro-2-butyl | H | CF3 |
| 16-3145 | pyridin-3-yl | H | H | N-oxide | H | H | H | I | H | nonafluoro-2-butyl | H | CF3 |
| 16-3146 | 2-fluoropyridin-3-yl | H | H | N-oxide | H | H | H | I | H | nonafluoro-2-butyl | H | CF3 |
| 16-3147 | 2-chloropyridin-3-yl | H | H | N-oxide | H | H | H | I | H | nonafluoro-2-butyl | H | CF3 |
| 16-3148 | 2-bromopyridin-3-yl | H | H | N-oxide | H | H | H | I | H | nonafluoro-2-butyl | H | CF3 |
| 16-3149 | 2-iodopyridin-3-yl | H | H | N-oxide | H | H | H | I | H | nonafluoro-2-butyl | H | CF3 |
| 16-3150 | 2-(trifluoromethyl)pyridin-3-yl | H | H | N-oxide | H | H | H | I | H | nonafluoro-2-butyl | H | CF3 |
| 16-3151 | 2-nitropyridin-3-yl | H | H | N-oxide | H | H | H | I | H | nonafluoro-2-butyl | H | CF3 |

TABLE 16-continued

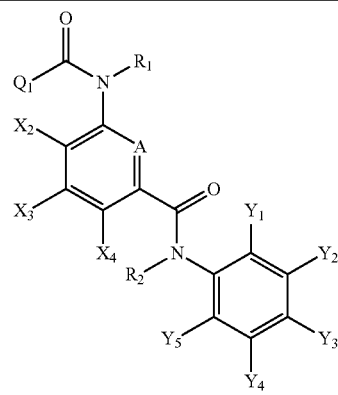

| compound number | Q1 | R1 | R2 | A | X2 | X3 | X4 | Y1 | Y2 | Y3 | Y4 | Y5 |
|---|---|---|---|---|---|---|---|---|---|---|---|---|
| 16-3152 | 2-cyanopyridin-3-yl | H | H | N-oxide | H | H | H | I | H | nonafluoro-2-butyl | H | CF3 |
| 16-3153 | 6-fluoropyridin-3-yl | H | H | N-oxide | H | H | H | I | H | nonafluoro-2-butyl | H | CF3 |
| 16-3154 | 6-chloropyridin-3-yl | H | H | N-oxide | H | H | H | I | H | nonafluoro-2-butyl | H | CF3 |
| 16-3155 | 6-bromopyridin-3-yl | H | H | N-oxide | H | H | H | I | H | nonafluoro-2-butyl | H | CF3 |
| 16-3156 | 6-iodopyridin-3-yl | H | H | N-oxide | H | H | H | I | H | nonafluoro-2-butyl | H | CF3 |
| 16-3157 | 6-(trifluoromethyl)pyridin-3-yl | H | H | N-oxide | H | H | H | I | H | nonafluoro-2-butyl | H | CF3 |
| 16-3158 | 6-nitropyridin-3-yl | H | H | N-oxide | H | H | H | I | H | nonafluoro-2-butyl | H | CF3 |
| 16-3159 | 6-cyanopyridin-3-yl | H | H | N-oxide | H | H | H | I | H | nonafluoro-2-butyl | H | CF3 |
| 16-3160 | 5-fluoropyridin-3-yl | H | H | N-oxide | H | H | H | I | H | nonafluoro-2-butyl | H | CF3 |
| 16-3161 | 5-chloropyridin-3-yl | H | H | N-oxide | H | H | H | I | H | nonafluoro-2-butyl | H | CF3 |
| 16-3162 | 5-bromopyridin-3-yl | H | H | N-oxide | H | H | H | I | H | nonafluoro-2-butyl | H | CF3 |
| 16-3163 | 5-iodopyridin-3-yl | H | H | N-oxide | H | H | H | I | H | nonafluoro-2-butyl | H | CF3 |
| 16-3164 | 5-(trifluoromethyl)pyridin-3-yl | H | H | N-oxide | H | H | H | I | H | nonafluoro-2-butyl | H | CF3 |
| 16-3165 | 5-nitropyridin-3-yl | H | H | N-oxide | H | H | H | I | H | nonafluoro-2-butyl | H | CF3 |
| 16-3166 | 5-cyanopyridin-3-yl | H | H | N-oxide | H | H | H | I | H | nonafluoro-2-butyl | H | CF3 |
| 16-3167 | 4-fluoropyridin-3-yl | H | H | N-oxide | H | H | H | I | H | nonafluoro-2-butyl | H | CF3 |
| 16-3168 | 4-chloropyridin-3-yl | H | H | N-oxide | H | H | H | I | H | nonafluoro-2-butyl | H | CF3 |
| 16-3169 | 4-bromopyridin-3-yl | H | H | N-oxide | H | H | H | I | H | nonafluoro-2-butyl | H | CF3 |
| 16-3170 | 4-iodopyridin-3-yl | H | H | N-oxide | H | H | H | I | H | nonafluoro-2-butyl | H | CF3 |
| 16-3171 | 4-(trifluoromethyl)pyridin-3-yl | H | H | N-oxide | H | H | H | I | H | nonafluoro-2-butyl | H | CF3 |
| 16-3172 | 4-nitropyridin-3-yl | H | H | N-oxide | H | H | H | I | H | nonafluoro-2-butyl | H | CF3 |
| 16-3173 | 4-cyanopyridin-3-yl | H | H | N-oxide | H | H | H | I | H | nonafluoro-2-butyl | H | CF3 |
| 16-3174 | 2,6-dichloropyridin-3-yl | H | H | N-oxide | H | H | H | I | H | nonafluoro-2-butyl | H | CF3 |
| 16-3175 | pyridin-3-yl N-oxide | H | H | N-oxide | H | H | H | I | H | nonafluoro-2-butyl | H | CF3 |
| 16-3176 | pyridin-4-yl | H | H | N-oxide | H | H | H | I | H | nonafluoro-2-butyl | H | CF3 |
| 16-3177 | 2-chloropyridin-4-yl | H | H | N-oxide | H | H | H | I | H | nonafluoro-2-butyl | H | CF3 |
| 16-3178 | 3-bromopyridin-4-yl | H | H | N-oxide | H | H | H | I | H | nonafluoro-2-butyl | H | CF3 |
| 16-3179 | 3,5-dichloropyridin-4-yl | H | H | N-oxide | H | H | H | I | H | nonafluoro-2-butyl | H | CF3 |
| 16-3180 | 3-(trifluoromethyl)pyridin-4-yl | H | H | N-oxide | H | H | H | I | H | nonafluoro-2-butyl | H | CF3 |
| 16-3181 | 2,6-dicyanopyridin-4-yl | H | H | N-oxide | H | H | H | I | H | nonafluoro-2-butyl | H | CF3 |
| 16-3182 | pyridin-4-yl N-oxide | H | H | N-oxide | H | H | H | I | H | nonafluoro-2-butyl | H | CF3 |
| 16-3183 | pyridin-2-yl | H | H | N-oxide | H | H | H | I | H | nonafluoro-2-butyl | H | CF3 |
| 16-3184 | 3-chloropyridin-2-yl | H | H | N-oxide | H | H | H | I | H | nonafluoro-2-butyl | H | CF3 |
| 16-3185 | 4-bromopyridin-2-yl | H | H | N-oxide | H | H | H | I | H | nonafluoro-2-butyl | H | CF3 |
| 16-3186 | 5-iodopyridin-2-yl | H | H | N-oxide | H | H | H | I | H | nonafluoro-2-butyl | H | CF3 |
| 16-3187 | 6-chloropyridin-2-yl | H | H | N-oxide | H | H | H | I | H | nonafluoro-2-butyl | H | CF3 |
| 16-3188 | 4-cyanopyridin-2-yl | H | H | N-oxide | H | H | H | I | H | nonafluoro-2-butyl | H | CF3 |
| 16-3189 | phenyl | H | H | N-oxide | H | H | H | OCF3 | H | heptafluoroisopropyl | H | OCF3 |
| 16-3196 | 2-bromophenyl | H | H | N-oxide | H | H | H | OCF3 | H | heptafluoroisopropyl | H | OC2F5 |
| 16-3201 | 4-iodophenyl | H | H | N-oxide | H | H | H | OCF3 | H | pentafluoroethyl | H | OCF3 |
| 16-3204 | 3-cyanophenyl | H | H | N-oxide | H | H | H | OCF3 | H | heptafluoroisopropyl | H | OCF3 |
| 16-3205 | 4-cyanophenyl | H | H | N-oxide | H | H | H | OCF3 | H | heptafluoroisopropyl | H | OCF3 |
| 16-3213 | 2-bromo-4-fluorophenyl | H | H | N-oxide | H | H | H | OC2F5 | H | heptafluoroisopropyl | H | OCF3 |
| 16-3220 | 2-chloropyridin-3-yl | H | H | N-oxide | H | H | H | OCF3 | H | heptafluoroisopropyl | H | OCF3 |
| 16-3229 | 5-cyanopyridin-3-yl | H | H | N-oxide | H | H | H | OC2F5 | H | heptafluoroisopropyl | H | OC2F5 |
| 16-3231 | 4-cyanopyridin-3-yl | H | H | N-oxide | H | H | H | OCF3 | H | heptafluoroisopropyl | H | OC2F5 |
| 16-3245 | phenyl | H | H | N-oxide | H | H | H | OCF3 | H | nonafluoro-2-butyl | H | OCF3 |
| 16-3252 | 2-bromophenyl | H | H | N-oxide | H | H | H | OC2F5 | H | nonafluoro-2-butyl | H | OCF3 |
| 16-3258 | (2-trifluoromethyl)phenyl | H | H | N-oxide | H | H | H | OCF3 | H | nonafluoro-2-butyl | H | OC2F5 |
| 16-3260 | 3-cyanophenyl | H | H | N-oxide | H | H | H | OCF3 | H | nonafluoro-2-butyl | H | OCF3 |
| 16-3261 | 4-cyanophenyl | H | H | N-oxide | H | H | H | OCF3 | H | nonafluoro-2-butyl | H | OCF3 |
| 16-3276 | 2-chloropyridin-3-yl | H | H | N-oxide | H | H | H | OCF3 | H | nonafluoro-2-butyl | H | OCF3 |
| 16-3283 | 6-cyanopyridin-3-yl | H | H | N-oxide | H | H | H | OC2F5 | H | nonafluoro-2-butyl | H | OCF3 |
| 16-3284 | 5-chloropyridin-3-yl | H | H | N-oxide | H | H | H | OCF3 | H | nonafluoro-2-butyl | H | OC2F5 |
| 16-3301 | phenyl | H | H | N-oxide | H | H | H | CF3 | H | heptafluoroisopropyl | H | OCF3 |
| 16-3308 | 2-bromophenyl | H | H | N-oxide | H | H | H | CF3 | H | heptafluoroisopropyl | H | OC2F5 |
| 16-3313 | 4-iodophenyl | H | H | N-oxide | H | H | H | CF3 | H | pentafluoroethyl | H | OCF3 |
| 16-3314 | (2-trifluoromethyl)phenyl | H | H | N-oxide | H | H | H | C2F5 | H | heptafluoroisopropyl | H | OC2F5 |

TABLE 16-continued

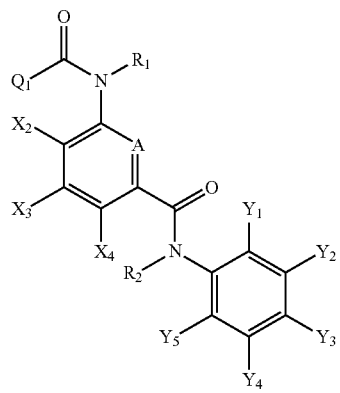

| compound number | $Q_1$ | $R_1$ | $R_2$ | A | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 16-3315 | 3-nitrophenyl | H | H | N-oxide | H | H | H | C2F5 | H | heptafluoroisopropyl | H | OCF3 |
| 16-3316 | 3-cyanophenyl | H | H | N-oxide | H | H | H | CF3 | H | heptafluoroisopropyl | H | OCF3 |
| 16-3317 | 4-cyanophenyl | H | H | N-oxide | H | H | H | CF3 | H | heptafluoroisopropyl | H | OCF3 |
| 16-3324 | 2-bromo-4-chlorophenyl | H | H | N-oxide | H | H | H | n-C3F7 | H | heptafluoroisopropyl | H | OCF3 |
| 16-3328 | 4-cyano-2-fluorophenyl | H | H | N-oxide | H | H | H | i-C3F7 | H | heptafluoroisopropyl | H | OCF3 |
| 16-3332 | 2-chloropyridin-3-yl | H | H | N-oxide | H | H | H | CF3 | H | heptafluoroisopropyl | H | OCF3 |
| 16-3338 | 6-chloropyridin-3-yl | H | H | N-oxide | H | H | H | n-C3F7 | H | heptafluoroisopropyl | H | OC2F5 |
| 16-3341 | 5-cyanopyridin-3-yl | H | H | N-oxide | H | H | H | i-C3F7 | H | heptafluoroisopropyl | H | OC2F5 |
| 16-3357 | phenyl | H | H | N-oxide | H | H | H | CF3 | H | nonafluoro-2-butyl | H | OCF3 |
| 16-3368 | 3-iodophenyl | H | H | N-oxide | 14 | H | H | CF3 | H | nonafluoro-2-butyl | H | OC2F5 |
| 16-3371 | 3-nitrophenyl | H | H | N-oxide | H | H | H | C2F5 | H | nonafluoro-2-butyl | H | OCF3 |
| 16-3372 | 3-cyanophenyl | H | H | N-oxide | H | H | H | CF3 | H | nonafluoro-2-butyl | H | OCF3 |
| 16-3373 | 4-cyanophenyl | H | H | N-oxide | H | H | H | CF3 | H | nonafluoro-2-butyl | H | OCF3 |
| 16-3379 | 4-bromo-2-chlorophenyl | H | H | N-oxide | H | H | H | i-C3F7 | H | nonafluoro-2-butyl | H | OCF3 |
| 16-3382 | 2-chloro-4-nitrophenyl | H | H | N-oxide | H | H | H | n-C3F7 | H | nonafluoro-2-butyl | H | OCF3 |
| 16-3388 | 2-chloropyridin-3-yl | H | H | N-oxide | H | H | H | CF3 | H | nonafluoro-2-butyl | H | OCF3 |
| 16-3397 | 5-cyanopyridin-3-yl | H | H | N-oxide | H | H | H | C2F5 | H | nonafluoro-2-butyl | H | OC2F5 |
| 16-3399 | 4-cyanopyridin-3-yl | H | H | N-oxide | H | H | H | n-C3F7 | H | nonafluoro-2-butyl | H | OC2F5 |
| 16-3410 | 5-iodopyridin-2-yl | H | H | N-oxide | H | H | H | i-C3F7 | H | nonafluoro-2-butyl | H | OC2F5 |
| 16-3413 | phenyl | H | H | N-oxide | H | H | H | CF3 | H | heptafluoroisopropyl | H | CF3 |
| 16-3425 | 4-iodophenyl | H | H | N-oxide | H | H | H | CF3 | H | pentafluoroethyl | H | CF3 |
| 16-3427 | (3-trifluoromethyl)phenyl | H | H | N-oxide | H | H | H | C2F5 | H | heptafluoroisopropyl | H | CF3 |
| 16-3433 | 3-cyanophenyl | H | H | N-oxide | H | H | H | CF3 | H | heptafluoroisopropyl | H | CF3 |
| 16-3434 | 4-cyanophenyl | H | H | N-oxide | H | H | H | CF3 | H | heptafluoroisopropyl | H | CF3 |
| 16-3440 | 4-bromo-2-chlorophenyl | H | H | N-oxide | H | H | H | n-C3F7 | H | heptafluoroisopropyl | H | CF3 |
| 16-3445 | 4-cyano-2-fluorophenyl | H | H | N-oxide | H | H | H | i-C3F7 | H | heptafluoroisopropyl | H | CF3 |
| 16-3447 | pyridin-3-yl | H | H | N-oxide | H | H | H | CF3 | H | heptafluoroisopropyl | H | CF3 |
| 16-3449 | 2-chloropyridin-3-yl | H | H | N-oxide | H | H | H | CF3 | H | heptafluoroisopropyl | H | CF3 |
| 16-3450 | 2-bromopyridin-3-yl | H | H | N-oxide | H | H | H | C2F5 | H | heptafluoroisopropyl | H | C2F5 |
| 16-3461 | 6-cyanopyridin-3-yl | H | H | N-oxide | H | H | H | C2F5 | H | heptafluoroisopropyl | H | n-C3F7 |
| 16-3465 | 4-cyanopyridin-3-yl | H | H | N-oxide | H | H | H | C2F5 | H | heptafluoroisopropyl | H | i-C3F7 |
| 16-3481 | phenyl | H | H | N-oxide | H | H | H | CF3 | H | nonafluoro-2-butyl | H | CF3 |
| 16-3493 | 4-iodophenyl | H | H | N-oxide | H | H | H | C2F5 | H | nonafluoro-2-butyl | H | CF3 |
| 16-3501 | 3-cyanophenyl | H | H | N-oxide | H | H | H | CF3 | H | nonafluoro-2-butyl | H | CF3 |
| 16-3502 | 4-cyanophenyl | H | H | N-oxide | H | H | H | CF3 | H | nonafluoro-2-butyl | H | CF3 |
| 16-3508 | 4-bromo-2-chlorophenyl | H | H | N-oxide | H | H | H | n-C3F7 | H | nonafluoro-2-butyl | H | CF3 |
| 16-3513 | 4-cyano-2-fluorophenyl | H | H | N-oxide | H | H | H | i-C3F7 | H | nonafluoro-2-butyl | H | CF3 |
| 16-3517 | 2-chloropyridin-3-yl | H | H | N-oxide | H | H | H | CF3 | H | nonafluoro-2-butyl | H | CF3 |
| 16-3518 | 2-bromopyridin-3-yl | H | H | N-oxide | H | H | H | C2F5 | H | nonafluoro-2-butyl | H | C2F5 |
| 16-3529 | 6-cyanopyridin-3-yl | H | H | N-oxide | H | H | H | C2F5 | H | nonafluoro-2-butyl | H | n-C3F7 |
| 16-3536 | pyridin-4-yl | H | H | N-oxide | H | H | H | C2F5 | H | nonafluoro-2-butyl | H | i-C3F7 |

TABLE 17

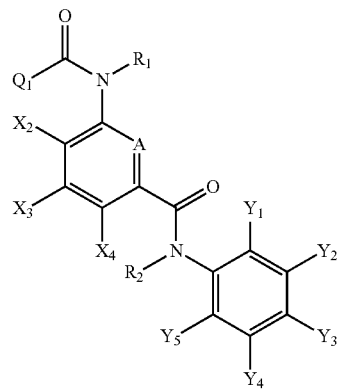

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 17-1 | phenyl | Me | H | N | H | H | H | F | H | heptafluoroisopropyl | H | F |
| 17-2 | 3-cyanophenyl | Me | H | N | H | H | H | F | H | heptafluoroisopropyl | H | F |
| 17-3 | 4-cyanophenyl | Me | H | N | H | H | H | F | H | heptafluoroisopropyl | H | F |
| 17-4 | 2-chloropyridin-3-yl | Me | H | N | H | H | H | F | H | heptafluoroisopropyl | H | F |
| 17-5 | phenyl | Me | H | N | H | H | H | F | H | nonafluoro-2-butyl | H | F |
| 17-6 | 3-cyanophenyl | Me | H | N | H | H | H | F | H | nonafluoro-2-butyl | H | F |
| 17-7 | 4-cyanophenyl | Me | H | N | H | H | H | F | H | nonafluoro-2-butyl | H | F |
| 17-8 | 2-chloropyridin-3-yl | Me | H | N | H | H | H | F | H | nonafluoro-2-butyl | H | F |
| 17-9 | phenyl | Me | H | N | H | H | H | Cl | H | heptafluoroisopropyl | H | Cl |
| 17-29 | 3-cyanophenyl | Me | H | N | H | H | H | Cl | H | heptafluoroisopropyl | H | Cl |
| 17-30 | 4-cyanophenyl | Me | H | N | H | H | H | Cl | H | heptafluoroisopropyl | H | Cl |
| 17-45 | 2-chloropyridin-3-yl | Me | H | N | H | H | H | Cl | H | heptafluoroisopropyl | H | Cl |
| 17-87 | phenyl | Me | H | N | H | H | H | Cl | H | nonafluoro-2-butyl | H | Cl |
| 17-107 | 3-cyanophenyl | Me | H | N | H | H | H | Cl | H | nonafluoro-2-butyl | H | Cl |
| 17-108 | 4-cyanophenyl | Me | H | N | H | H | H | Cl | H | nonafluoro-2-butyl | H | Cl |
| 17-123 | 2-chloropyridin-3-yl | Me | H | N | H | H | H | Cl | H | nonafluoro-2-butyl | H | Cl |
| 17-165 | phenyl | Me | H | N | H | H | H | Br | H | heptafluoroisopropyl | H | Br |
| 17-185 | 3-cyanophenyl | Me | H | N | H | H | H | Br | H | heptafluoroisopropyl | H | Br |
| 17-186 | 4-cyanophenyl | Me | H | N | H | H | H | Br | H | heptafluoroisopropyl | H | Br |
| 17-201 | 2-chloropyridin-3-yl | Me | H | N | H | H | H | Br | H | heptafluoroisopropyl | H | Br |
| 17-243 | phenyl | Me | H | N | H | H | H | Br | H | nonafluoro-2-butyl | H | Br |
| 17-263 | 3-cyanophenyl | Me | H | N | H | H | H | Br | H | nonafluoro-2-butyl | H | Br |
| 17-264 | 4-cyanophenyl | Me | H | N | H | H | H | Br | H | nonafluoro-2-butyl | H | Br |
| 17-279 | 2-chloropyridin-3-yl | Me | H | N | H | H | H | Br | H | nonafluoro-2-butyl | H | Br |
| 17-321 | phenyl | Me | H | N | H | H | H | I | H | heptafluoroisopropyl | H | I |
| 17-341 | 3-cyanophenyl | Me | H | N | H | H | H | I | H | heptafluoroisopropyl | H | I |
| 17-342 | 4-cyanophenyl | Me | H | N | H | H | H | I | H | heptafluoroisopropyl | H | I |
| 17-357 | 2-chloropyridin-3-yl | Me | H | N | H | H | H | I | H | heptafluoroisopropyl | H | I |
| 17-399 | phenyl | Me | H | N | H | H | H | I | H | nonafluoro-2-butyl | H | I |
| 17-400 | 2-fluorophenyl | Me | H | N | H | H | H | I | H | nonafluoro-2-butyl | H | I |
| 17-419 | 3-cyanophenyl | Me | H | N | H | H | H | I | H | nonafluoro-2-butyl | H | I |
| 17-420 | 4-cyanophenyl | Me | H | N | H | H | H | I | H | nonafluoro-2-butyl | H | I |
| 17-435 | 2-chloropyridin-3-yl | Me | H | N | H | H | H | I | H | nonafluoro-2-butyl | H | I |
| 17-477 | phenyl | Me | H | N | H | H | H | Cl | H | heptafluoroisopropyl | H | OCF3 |
| 17-497 | 3-cyanophenyl | Me | H | N | H | H | H | Cl | H | heptafluoroisopropyl | H | OCF3 |
| 17-498 | 4-cyanophenyl | Me | H | N | H | H | H | Cl | H | heptafluoroisopropyl | H | OCF3 |
| 17-513 | 2-chloropyridin-3-yl | Me | H | N | H | H | H | Cl | H | heptafluoroisopropyl | H | OCF3 |
| 17-555 | phenyl | Me | H | N | H | H | H | Cl | H | nonafluoro-2-butyl | H | OCF3 |
| 17-575 | 3-cyanophenyl | Me | H | N | H | H | H | Cl | H | nonafluoro-2-butyl | H | OCF3 |
| 17-576 | 4-cyanophenyl | Me | H | N | H | H | H | Cl | H | nonafluoro-2-butyl | H | OCF3 |
| 17-591 | 2-chloropyridin-3-yl | Me | H | N | H | H | H | Cl | H | nonafluoro-2-butyl | H | OCF3 |
| 17-633 | phenyl | Me | H | N | H | H | H | Br | H | heptafluoroisopropyl | H | OCF3 |
| 17-653 | 3-cyanophenyl | Me | H | N | H | H | H | Br | H | heptafluoroisopropyl | H | OCF3 |
| 17-654 | 4-cyanophenyl | Me | H | N | H | H | H | Br | H | heptafluoroisopropyl | H | OCF3 |
| 17-669 | 2-chloropyridin-3-yl | Me | H | N | H | H | H | Br | H | heptafluoroisopropyl | H | OCF3 |
| 17-711 | phenyl | Me | H | N | H | H | H | Br | H | nonafluoro-2-butyl | H | OCF3 |
| 17-731 | 3-cyanophenyl | Me | H | N | H | H | H | Br | H | nonafluoro-2-butyl | H | OCF3 |
| 17-732 | 4-cyanophenyl | Me | H | N | H | H | H | Br | H | nonafluoro-2-butyl | H | OCF3 |
| 17-747 | 2-chloropyridin-3-yl | Me | H | N | H | H | H | Br | H | nonafluoro-2-butyl | H | OCF3 |
| 17-789 | phenyl | Me | H | N | H | H | H | I | H | heptafluoroisopropyl | H | OCF3 |
| 17-809 | 3-cyanophenyl | Me | H | N | H | H | H | I | H | heptafluoroisopropyl | H | OCF3 |
| 17-810 | 4-cyanophenyl | Me | H | N | H | H | H | I | H | heptafluoroisopropyl | H | OCF3 |
| 17-825 | 2-chloropyridin-3-yl | Me | H | N | H | H | H | I | H | heptafluoroisopropyl | H | OCF3 |
| 17-867 | phenyl | Me | H | N | H | H | H | I | H | nonafluoro-2-butyl | H | OCF3 |
| 17-887 | 3-cyanophenyl | Me | H | N | H | H | H | I | H | nonafluoro-2-butyl | H | OCF3 |
| 17-888 | 4-cyanophenyl | Me | H | N | H | H | H | I | H | nonafluoro-2-butyl | H | OCF3 |
| 17-903 | 2-chloropyridin-3-yl | Me | H | N | H | H | H | I | H | nonafluoro-2-butyl | H | OCF3 |
| 17-945 | phenyl | Me | H | N | H | H | H | F | H | heptafluoroisopropyl | H | CF3 |

TABLE 17-continued

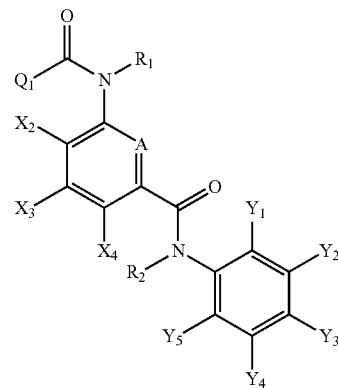

| compound number | $Q_1$ | $R_1$ | $R_2$ | A | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 17-946 | phenyl | Me | H | N | H | H | H | Cl | H | heptafluoroisopropyl | H | CF3 |
| 17-957 | 3-iodophenyl | Me | H | N | H | H | H | Cl | H | pentafluoroethyl | H | CF3 |
| 17-958 | 4-iodophenyl | Me | H | N | H | H | H | Cl | H | pentafluoroethyl | H | CF3 |
| 17-965 | 2-cyanophenyl | Me | H | N | H | H | H | Cl | H | pentafluoroethyl | H | C2F5 |
| 17-966 | 3-cyanophenyl | Me | H | N | H | H | H | Cl | H | heptafluoroisopropyl | H | CF3 |
| 17-967 | 4-cyanophenyl | Me | H | N | H | H | H | Cl | H | heptafluoroisopropyl | H | CF3 |
| 17-970 | 2,4-dichlorophenyl | Me | H | N | H | H | H | Cl | H | heptafluoroisopropyl | H | C2F5 |
| 17-971 | 2-chloro-4-fluorophenyl | n-Pr | H | N | H | H | H | Cl | H | heptafluoroisopropyl | H | CF3 |
| 17-974 | 2-bromo-4-chlorophenyl | Me | H | N | H | H | H | Cl | H | heptafluoroisopropyl | H | n-C3F7 |
| 17-981 | 2-fluoropyridin-3-yl | Me | H | N | H | H | H | Cl | H | pentafluoroethyl | H | CF3 |
| 17-982 | 2-chloropyridin-3-yl | Me | H | N | H | H | H | Cl | H | heptafluoroisopropyl | H | CF3 |
| 17-988 | 6-fluoropyridin-3-yl | i-Pr | H | N | H | H | H | Cl | H | heptafluoroisopropyl | H | CF3 |
| 17-995 | 5-fluoropyridin-3-yl | Me | H | N | H | H | H | Cl | H | heptafluoroisopropyl | H | C2F5 |
| 17-997 | 5-bromopyridin-3-yl | Me | H | N | H | H | H | Cl | H | heptafluoroisopropyl | H | n-C3F7 |
| 17-998 | 5-iodopyridin-3-yl | Me | H | N | H | H | H | Cl | H | heptafluoroisopropyl | H | i-C3F7 |
| 17-1000 | 5-nitropyridin-3-yl | Me | N | H | H | H | H | Cl | H | pentafluoroethyl | H | CF3 |
| 17-1002 | 4-fluoropyridin-3-yl | Me | H | N | H | H | H | Cl | H | pentafluoroethyl | H | CF3 |
| 17-1004 | 4-bromopyridin-3-yl | CH2CH=CH2 | H | N | H | H | H | Cl | H | heptafluoroisopropyl | H | n-C3F7 |
| 17-1005 | 4-iodopyridin-3-yl | Me | H | N | H | H | H | Cl | H | heptafluoroisopropyl | H | i-C3F7 |
| 17-1011 | pyridin-4-yl | CN | H | N | H | H | H | Cl | H | heptafluoroisopropyl | H | CF3 |
| 17-1023 | 4-cyanopyridin-2-yl | Me | H | N | H | H | H | Cl | H | pentafluoroethyl | H | CF3 |
| 17-1024 | phenyl | Me | H | N | H | H | H | F | H | nonafluoro-2-butyl | H | CF3 |
| 17-1025 | phenyl | Me | H | N | H | H | H | Cl | H | nonafluoro-2-butyl | H | CF3 |
| 17-1033 | 3-bromophenyl | CH2C≡CH | H | N | H | H | H | Cl | H | nonafluoro-2-butyl | H | CF3 |
| 17-1038 | (2-trifluoromethyl)phenyl | Me | H | N | H | H | H | Cl | H | nonafluoro-2-butyl | H | C2F5 |
| 17-1040 | (4-trifluoromethyl)phenyl | NH2 | H | N | H | H | H | Cl | H | nonafluoro-2-butyl | H | CF3 |
| 17-1045 | 3-cyanophenyl | Me | H | N | H | H | H | Cl | H | nonafluoro-2-butyl | H | CF3 |
| 17-1046 | 4-cyanophenyl | Me | H | N | H | H | H | Cl | H | nonafluoro-2-butyl | H | CF3 |
| 17-1053 | 2-bromo-4-chlorophenyl | C(O)OMe | H | N | H | H | H | Cl | H | nonafluoro-2-butyl | H | CF3 |
| 17-1055 | 2-chloro-4-nitrophenyl | Me | H | N | H | H | H | Cl | H | nonafluoro-2-butyl | H | i-C3F7 |
| 17-1061 | 2-chloropyridin-3-yl | Me | H | N | H | H | H | Cl | H | nonafluoro-2-butyl | H | CF3 |
| 17-1074 | 5-fluoropyridin-3-yl | C(O)OEt | H | N | H | H | H | Cl | H | nonafluoro-2-butyl | H | C2F5 |
| 17-1076 | 5-bromopyridin-3-yl | Me | H | N | H | H | H | Cl | H | nonafluoro-2-butyl | H | n-C3F7 |
| 17-1077 | 5-iodopyridin-3-yl | Me | H | N | H | H | H | Cl | H | nonafluoro-2-butyl | H | i-C3F7 |
| 17-1081 | 4-fluoropyridin-3-yl | Me | N | H | H | H | H | Cl | H | nonafluoro-2-butyl | H | C2F5 |
| 17-1083 | 4-bromopyridin-3-yl | C(O)C(O)Me | H | N | H | H | H | Cl | H | nonafluoro-2-butyl | H | CF3 |
| 17-1085 | 4-(trifluoromethyl)pyridin-3-yl | Me | H | N | H | H | H | Cl | H | nonafluoro-2-butyl | H | n-C3F7 |
| 17-1086 | 4-nitropyridin-3-yl | C(O)C(O)Et | H | N | H | H | H | Cl | H | nonafluoro-2-butyl | H | i-C3F7 |
| 17-1100 | 5-iodopyridin-2-yl | C(O)Me | H | N | H | H | H | Cl | H | nonafluoro-2-butyl | H | CF3 |
| 17-1102 | 4-cyanopyridin-2-yl | C(O)Et | H | N | H | H | H | Cl | H | nonafluoro-2-butyl | H | C2F5 |
| 17-1103 | phenyl | Me | H | N | H | H | H | Br | H | heptafluoroisopropyl | H | CF3 |
| 17-1104 | 2-fluorophenyl | Me | H | N | H | H | H | Br | H | heptafluoroisopropyl | H | CF3 |
| 17-1117 | (3-trifluoromethyl)phenyl | S(O)2Me | H | N | H | H | H | Br | H | heptafluoroisopropyl | H | CF3 |
| 17-1135 | 4-cyano-2-fluorophenyl | S(O)2Et | H | N | H | H | H | Br | H | heptafluoroisopropyl | H | CF3 |
| 17-1139 | 2-chloropyridin-3-yl | Me | H | N | H | H | H | Br | H | heptafluoroisopropyl | H | CF3 |
| 17-1150 | 6-nitropyridin-3-yl | CH2Ph | H | N | H | H | H | Br | H | heptafluoroisopropyl | H | CF3 |
| 17-1159 | 4-fluoropyridin-3-yl | CH2(3-Py) | H | N | H | H | H | Br | H | heptafluoroisopropyl | H | CF3 |
| 17-1180 | 4-cyanopyridin-2-yl | CH2(3-Py—N-oxide) | H | N | H | H | H | Br | H | heptafluoroisopropyl | H | CF3 |
| 17-1181 | phenyl | Me | H | N | H | H | H | Br | H | nonafluoro-2-butyl | H | CF3 |
| 17-1182 | 2-fluorophenyl | Me | H | N | H | H | H | Br | H | nonafluoro-2-butyl | H | CF3 |
| 17-1201 | 3-cyanophenyl | Me | H | N | H | H | H | Br | H | nonafluoro-2-butyl | H | CF3 |
| 17-1202 | 4-cyanophenyl | Me | H | N | H | H | H | Br | H | nonafluoro-2-butyl | H | CF3 |
| 17-1208 | 4-bromo-2-chlorophenyl | Et | H | N | H | H | H | Br | H | nonafluoro-2-butyl | H | CF3 |
| 17-1217 | 2-chloropyridin-3-yl | Me | H | N | H | H | H | Br | H | nonafluoro-2-butyl | H | CF3 |
| 17-1234 | 5-(trifluoromethyl)pyridin-3-yl | CN | H | N | H | H | H | Br | H | nonafluoro-2-butyl | H | CF3 |
| 17-1259 | phenyl | Me | H | N | H | H | H | I | H | heptafluoroisopropyl | H | CF3 |
| 17-1260 | 2-fluorophenyl | Me | H | N | H | H | H | I | H | heptafluoroisopropyl | H | CF3 |

TABLE 17-continued

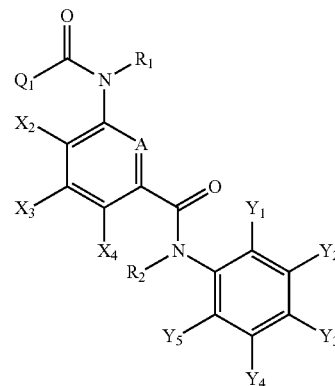

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 17-1279 | 3-cyanophenyl | Me | H | N | H | H | H | I | H | heptafluoroisopropyl | H | CF3 |
| 17-1280 | 4-cyanophenyl | Me | H | N | H | H | H | I | H | heptafluoroisopropyl | H | CF3 |
| 17-1295 | 2-chloropyridin-3-yl | Me | H | N | H | H | H | I | H | heptafluoroisopropyl | H | CF3 |
| 17-1308 | 5-fluoropyridin-3-yl | C(O)Me | H | N | H | H | H | I | H | heptafluoroisopropyl | H | CF3 |
| 17-1337 | phenyl | Me | H | N | H | H | H | I | H | nonafluoro-2-butyl | H | CF3 |
| 17-1338 | 2-fluorophenyl | Me | H | N | H | H | H | I | H | nonafluoro-2-butyl | H | CF3 |
| 17-1357 | 3-cyanophenyl | Me | H | N | H | H | H | I | H | nonafluoro-2-butyl | H | CF3 |
| 17-1358 | 4-cyanophenyl | Me | H | N | H | H | H | I | H | nonafluoro-2-butyl | H | CF3 |
| 17-1373 | 2-chloropyridin-3-yl | Me | H | N | H | H | H | I | H | nonafluoro-2-butyl | H | CF3 |
| 17-1415 | phenyl | Me | H | N | H | H | H | OCF3 | H | heptafluoroisopropyl | H | OCF3 |
| 17-1446 | 2-chloropyridin-3-yl | Me | H | N | H | H | H | OCF3 | H | heptafluoroisopropyl | H | OCF3 |
| 17-1471 | phenyl | Me | H | N | H | H | H | OCF3 | H | nonafluoro-2-butyl | H | OCF3 |
| 17-1502 | 2-chloropyridin-3-yl | Me | H | N | H | H | H | OCF3 | H | nonafluoro-2-butyl | H | OCF3 |
| 17-1527 | phenyl | Me | H | N | H | H | H | CF3 | H | heptafluoroisopropyl | H | OCF3 |
| 17-1558 | 2-chloropyridin-3-yl | Me | H | N | H | H | H | CF3 | H | heptafluoroisopropyl | H | OCF3 |
| 17-1583 | phenyl | Me | H | N | H | H | H | CF3 | H | nonafluoro-2-butyl | H | OCF3 |
| 17-1614 | 2-chloropyridin-3-yl | Me | H | N | H | H | H | CF3 | H | nonafluoro-2-butyl | H | OCF3 |
| 17-1639 | phenyl | Me | H | N | H | H | H | CF3 | H | heptafluoroisopropyl | H | CF3 |
| 17-1659 | 3-cyanophenyl | Me | H | N | H | H | H | CF3 | H | heptafluoroisopropyl | H | CF3 |
| 17-1660 | 4-cyanophenyl | Me | H | N | H | H | H | CF3 | H | heptafluoroisopropyl | H | CF3 |
| 17-1675 | 2-chloropyridin-3-yl | Me | H | N | H | H | H | CF3 | H | heptafluoroisopropyl | H | CF3 |
| 17-1707 | phenyl | Me | H | N | H | H | H | CF3 | H | nonafluoro-2-butyl | H | CF3 |
| 17-1727 | 3-cyanophenyl | Me | H | N | H | H | H | CF3 | H | nonafluoro-2-butyl | H | CF3 |
| 17-1728 | 4-cyanophenyl | Me | H | N | H | H | H | CF3 | H | nonfluoro-2-butyl | H | CF3 |
| 17-1743 | 2-chloropyridin-3-yl | Me | H | N | H | H | H | CF3 | H | nonafluoro-2-butyl | H | CF3 |
| 17-1775 | phenyl | Me | H | N-oxide | H | H | H | F | H | heptafluoroisopropyl | H | F |
| 17-1776 | 3-cyanophenyl | Me | H | N-oxide | H | H | H | F | H | heptafluoroisopropyl | H | F |
| 17-1777 | 4-cyanophenyl | Me | H | N-oxide | H | H | H | F | H | heptafluoroisopropyl | H | F |
| 17-1778 | 2-chloropyridin-3-yl | Me | H | N-oxide | H | H | H | F | H | heptafluoroisopropyl | H | F |
| 17-1779 | phenyl | Me | H | N-oxide | H | H | H | F | H | nonafluoro-2-butyl | H | F |
| 17-1780 | 3-cyanophenyl | Me | H | N-oxide | H | H | H | F | H | nonafluoro-2-butyl | H | F |
| 17-1781 | 4-cyanophenyl | Me | H | N-oxide | H | H | H | F | H | nonafluoro-2-butyl | H | F |
| 17-1782 | 2-chloropyridin-3-yl | Me | H | N-oxide | H | H | H | F | H | nonafluoro-2-butyl | H | F |
| 17-1783 | phenyl | Me | H | N-oxide | H | H | H | Cl | H | heptafluoroisopropyl | H | Cl |
| 17-1803 | 3-cyanophenyl | Me | H | N-oxide | H | H | H | Cl | H | heptafluoroisopropyl | H | Cl |
| 17-1804 | 4-cyanophenyl | Me | H | N-oxide | H | H | H | Cl | H | heptafluoroisopropyl | H | Cl |
| 17-1819 | 2-chloropyridin-3-yl | Me | H | N-oxide | H | H | H | Cl | H | heptafluoroisopropyl | H | Cl |
| 17-1861 | phenyl | Me | H | N-oxide | H | H | H | Cl | H | nonafluoro-2-butyl | H | Cl |
| 17-1881 | 3-cyanophenyl | Me | H | N-oxide | H | H | H | Cl | H | nonafluoro-2-butyl | H | Cl |
| 17-1882 | 4-cyanophenyl | Me | H | N-oxide | H | H | H | Cl | H | nonafluoro-2-butyl | H | Cl |
| 17-1897 | 2-chloropyridin-3-yl | Me | H | N-oxide | H | H | H | Cl | H | nonafluoro-2-butyl | H | Cl |
| 17-1939 | phenyl | Me | H | N-oxide | H | H | H | Br | H | heptafluoroisopropyl | H | Br |
| 17-1959 | 3-cyanophenyl | Me | H | N-oxide | H | H | H | Br | H | heptafluoroisopropyl | H | Br |
| 17-1960 | 4-cyanophenyl | Me | H | N-oxide | H | H | H | Br | H | heptafluoroisopropyl | H | Br |
| 17-1975 | 2-chloropyridin-3-yl | Me | H | N-oxide | H | H | H | Br | H | heptafluoroisopropyl | H | Br |
| 17-2017 | phenyl | Me | H | N-oxide | H | H | H | Br | H | nonafluoro-2-butyl | H | Br |
| 17-2037 | 3-cyanophenyl | Me | H | N-oxide | H | H | H | Br | H | nonafluoro-2-butyl | H | Br |
| 17-2038 | 4-cyanophenyl | Me | H | N-oxide | H | H | H | Br | H | nonafluoro-2-butyl | H | Br |
| 17-2053 | 2-chloropyridin-3-yl | Me | H | N-oxide | H | H | H | Br | H | nonafluoro-2-butyl | H | Br |
| 17-2095 | phenyl | Me | H | N-oxide | H | H | H | I | H | heptafluoroisopropyl | H | I |
| 17-2114 | 2-cyanophenyl | Me | H | N-oxide | H | H | H | I | H | pentafluoroethyl | H | I |
| 17-2115 | 3-cyanophenyl | Me | H | N-oxide | H | H | H | I | H | heptafluoroisopropyl | H | I |
| 17-2131 | 2-chloropyridin-3-yl | Me | H | N-oxide | H | H | H | I | H | heptafluoroisopropyl | H | I |
| 17-2173 | phenyl | Me | H | N-oxide | H | H | H | I | H | nonafluoro-2-butyl | H | I |
| 17-2193 | 3-cyanophenyl | Me | H | N-oxide | H | H | H | I | H | nonafluoro-2-butyl | H | I |
| 17-2194 | 4-cyanophenyl | Me | H | N-oxide | H | H | H | I | H | nonafluoro-2-butyl | H | I |
| 17-2209 | 2-chloropyridin-3-yl | Me | H | N-oxide | H | H | H | I | H | nonafluoro-2-butyl | H | I |
| 17-2251 | phenyl | Me | H | N-oxide | H | H | H | Cl | H | heptafluoroisopropyl | H | OCF3 |

TABLE 17-continued

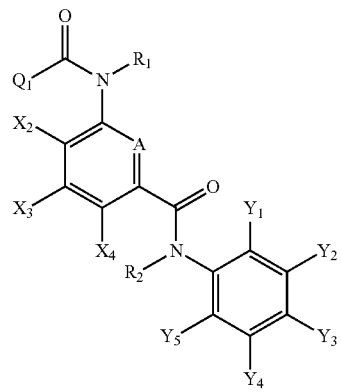

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 17-2271 | 3-cyanophenyl | Me | H | N-oxide | H | H | H | Cl | H | heptafluoroisopropyl | H | OCF3 |
| 17-2272 | 4-cyanophenyl | Me | H | N-oxide | H | H | H | Cl | H | heptafluoroisopropyl | H | OCF3 |
| 17-2287 | 2-chloropyridin-3-yl | Me | H | N-oxide | H | H | H | Cl | H | heptafluoroisopropyl | H | OCF3 |
| 17-2329 | phenyl | Me | H | N-oxide | H | H | H | Cl | H | nonafluoro-2-butyl | H | OCF3 |
| 17-2349 | 3-cyanophenyl | Me | H | N-oxide | H | H | H | Cl | H | nonafluoro-2-butyl | H | OCF3 |
| 17-2350 | 4-cyanophenyl | Me | H | N-oxide | H | H | H | Cl | H | nonafluoro-2-butyl | H | OCF3 |
| 17-2365 | 2-chloropyridin-3-yl | Me | H | N-oxide | H | H | H | Cl | H | nonafluoro-2-butyl | H | OCF3 |
| 17-2407 | phenyl | Me | H | N-oxide | H | H | H | Br | H | heptafluoroisopropyl | H | OCF3 |
| 17-2427 | 3-cyanophenyl | Me | H | N-oxide | H | H | H | Br | H | heptafluoroisopropyl | H | OCF3 |
| 17-2428 | 4-cyanophenyl | Me | H | N-oxide | H | H | H | Br | H | heptafluoroisopropyl | H | OCF3 |
| 17-2443 | 2-chloropyridin-3-yl | Me | H | N-oxide | H | H | H | Br | H | heptafluoroisopropyl | H | OCF3 |
| 17-2485 | phenyl | Me | H | N-oxide | H | H | H | Br | H | nonafluoro-2-butyl | H | OCF3 |
| 17-2505 | 3-cyanophenyl | Me | H | N-oxide | H | H | H | Br | H | nonafluoro-2-butyl | H | OCF3 |
| 17-2506 | 4-cyanophenyl | Me | H | N-oxide | H | H | H | Br | H | nonafluoro-2-butyl | H | OCF3 |
| 17-2563 | phenyl | Me | H | N-oxide | H | H | H | I | H | heptafluoroisopropyl | H | OCF3 |
| 17-2583 | 3-cyanophenyl | Me | H | N-oxide | H | H | H | I | H | heptafluoroisopropyl | H | OCF3 |
| 17-2584 | 4-cyanophenyl | Me | H | N-oxide | H | H | H | I | H | heptafluoroisopropyl | H | OCF3 |
| 17-2599 | 2-chloropyridin-3-yl | Me | H | N-oxide | H | H | H | I | H | heptafluoroisopropyl | H | OCF3 |
| 17-2641 | phenyl | Me | H | N-oxide | H | H | H | I | H | nonafluoro-2-butyl | H | OCF3 |
| 17-2661 | 3-cyanophenyl | Me | H | N-oxide | H | H | H | I | H | nonafluoro-2-butyl | H | OCF3 |
| 17-2662 | 4-cyanophenyl | Me | H | N-oxide | H | H | H | I | H | nonafluoro-2-butyl | H | OCF3 |
| 17-2677 | 2-chloropyridin-3-yl | Me | H | N-oxide | H | H | H | I | H | nonafluoro-2-butyl | H | OCF3 |
| 17-2719 | phenyl | Me | H | N-oxide | H | H | H | F | H | heptafluoroisopropyl | H | CF3 |
| 17-2720 | phenyl | Me | H | N-oxide | H | H | H | Cl | H | heptafluoroisopropyl | H | CF3 |
| 17-2740 | 3-cyanophenyl | Me | H | N-oxide | H | H | H | Cl | H | heptafluoroisopropyl | H | CF3 |
| 17-2741 | 4-cyanophenyl | Me | H | N-oxide | H | H | H | Cl | H | heptafluoroisopropyl | H | CF3 |
| 17-2756 | 2-chloropyridin-3-yl | Me | H | N-oxide | H | H | H | Cl | H | heptafluoroisopropyl | H | CF3 |
| 17-2798 | phenyl | Me | H | N-oxide | H | H | H | F | H | nonafluoro-2-butyl | H | CF3 |
| 17-2799 | phenyl | Me | H | N-oxide | H | H | H | Cl | H | nonafluoro-2-butyl | H | CF3 |
| 17-2819 | 3-cyanophenyl | Me | H | N-oxide | H | H | H | Cl | H | nonafluoro-2-butyl | H | CF3 |
| 17-2820 | 4-cyanophenyl | Me | H | N-oxide | H | H | H | Cl | H | nonafluoro-2-butyl | H | CF3 |
| 17-2835 | 2-chloropyridin-3-yl | Me | H | N-oxide | H | H | H | Cl | H | nonafluoro-2-butyl | H | CF3 |
| 17-2877 | phenyl | Me | H | N-oxide | H | H | H | Br | H | heptafluoroisopropyl | H | CF3 |
| 17-2897 | 3-cyanophenyl | Me | H | N-oxide | H | H | H | Br | H | heptafluoroisopropyl | H | CF3 |
| 17-2898 | 4-cyanophenyl | Me | H | N-oxide | H | H | H | Br | H | heptafluoroisopropyl | H | CF3 |
| 17-2913 | 2-chloropyridin-3-yl | Me | H | N-oxide | H | H | H | Br | H | heptafluoroisopropyl | H | CF3 |
| 17-2914 | 2-bromopyridin-3-yl | Me | H | N-oxide | H | H | H | Br | H | heptafluoroisopropyl | H | CF3 |
| 17-2955 | phenyl | Me | H | N-oxide | H | H | H | Br | H | nonafluoro-2-butyl | H | CF3 |
| 17-2975 | 3-cyanophenyl | Me | H | N-oxide | H | H | H | Br | H | nonafluoro-2-butyl | H | CF3 |
| 17-2976 | 4-cyanophenyl | Me | H | N-oxide | H | H | H | Br | H | nonafluoro-2-butyl | H | CF3 |
| 17-2991 | 2-chloropyridin-3-yl | Me | H | N-oxide | H | H | H | Br | H | nonafluoro-2-butyl | H | CF3 |
| 17-3033 | phenyl | Me | H | N-oxide | H | H | H | I | H | heptafluoroisopropyl | H | CF3 |
| 17-3053 | 3-cyanophenyl | Me | H | N-oxide | H | H | H | I | H | heptafluoroisopropyl | H | CF3 |
| 17-3054 | 4-cyanophenyl | Me | H | N-oxide | H | H | H | I | H | heptafluoroisopropyl | H | CF3 |
| 17-3069 | 2-chloropyridin-3-yl | Me | H | N-oxide | H | H | H | I | H | heptafluoroisopropyl | H | CF3 |
| 17-3111 | phenyl | Me | H | N-oxide | H | H | H | I | H | nonafluoro-2-butyl | H | CF3 |
| 17-3131 | 3-cyanophenyl | Me | H | N-oxide | H | H | H | I | H | nonafluoro-2-butyl | H | CF3 |
| 17-3132 | 4-cyanophenyl | Me | H | N-oxide | H | H | H | I | H | nonafluoro-2-butyl | H | CF3 |
| 17-3147 | 2-chloropyridin-3-yl | Me | H | N-oxide | H | H | H | I | H | nonafluoro-2-butyl | H | CF3 |
| 17-3189 | phenyl | Me | H | N-oxide | H | H | H | OCF3 | H | heptafluoroisopropyl | H | OCF3 |
| 17-3220 | 2-chloropyridin-3-yl | Me | H | N-oxide | H | H | H | OCF3 | H | heptafluoroisopropyl | H | OCF3 |
| 17-3245 | phenyl | Me | H | N-oxide | H | H | H | OCF3 | H | nonafluoro-2-butyl | H | OCF3 |
| 17-3276 | 2-chloropyridin-3-yl | Me | H | N-oxide | H | H | H | OCF3 | H | nonafluoro-2-butyl | H | OCF3 |
| 17-3301 | phenyl | Me | H | N-oxide | H | H | H | CF3 | H | heptafluoroisopropyl | H | OCF3 |
| 17-3332 | 2-chloropyridin-3-yl | Me | H | N-oxide | H | H | H | CF3 | H | heptafluoroisopropyl | H | OCF3 |
| 17-3357 | phenyl | Me | H | N-oxide | H | H | H | CF3 | H | nonafluoro-2-butyl | H | OCF3 |
| 17-3388 | 2-chloropyridin-3-yl | Me | H | N-oxide | H | H | H | CF3 | H | nonafluoro-2-butyl | H | OCF3 |
| 17-3413 | phenyl | Me | H | N-oxide | H | H | H | CF3 | H | heptafluoroisopropyl | H | CF3 |

TABLE 17-continued

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 17-3433 | 3-cyanophenyl | Me | H | N-oxide | H | H | H | CF3 | H | heptafluoroisopropyl | H | CF3 |
| 17-3434 | 4-cyanophenyl | Me | H | N-oxide | H | H | H | CF3 | H | heptafluoroisopropyl | H | CF3 |
| 17-3449 | 2-chloropyridin-3-yl | Me | H | N-oxide | H | H | H | CF3 | H | heptafluoroisopropyl | H | CF3 |
| 17-3481 | phenyl | Me | H | N-oxide | H | H | H | CF3 | H | nonafluoro-2-butyl | H | CF3 |
| 17-3501 | 3-cyanophenyl | Me | H | N-oxide | H | H | H | CF3 | H | nonafluoro-2-butyl | H | CF3 |
| 17-3502 | 4-cyanophenyl | Me | H | N-oxide | H | H | H | CF3 | H | nonafluoro-2-butyl | H | CF3 |
| 17-3517 | 2-chloropyridin-3-yl | Me | H | N-oxide | H | H | H | CF3 | H | nonafluoro-2-butyl | H | CF3 |

TABLE 18

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 18-1 | phenyl | H | Me | N | H | H | H | F | H | heptafluoroisopropyl | H | F |
| 18-2 | 3-cyanophenyl | H | Me | N | H | H | H | F | H | heptafluoroisopropyl | H | F |
| 18-3 | 4-cyanophenyl | H | Me | N | H | H | H | F | H | heptafluoroisopropyl | H | F |
| 18-4 | 2-chloropyridin-3-yl | H | Me | N | H | H | H | F | H | heptafluoroisopropyl | H | F |
| 18-5 | phenyl | H | Me | N | H | H | H | F | H | nonafluoro-2-butyl | H | F |
| 18-6 | 3-cyanophenyl | H | Me | N | H | H | H | F | H | nonafluoro-2-butyl | H | F |
| 18-7 | 4-cyanophenyl | H | Me | N | H | H | H | F | H | nonafluoro-2-butyl | H | F |
| 18-8 | 2-chloropyridin-3-yl | H | Me | N | H | H | H | F | H | nonafluoro-2-butyl | H | F |
| 18-9 | phenyl | H | Me | N | H | H | H | Cl | H | heptafluoroisopropyl | H | Cl |
| 18-29 | 3-cyanophenyl | H | Me | N | H | H | H | Cl | H | heptafluoroisopropyl | H | Cl |
| 18-30 | 4-cyanophenyl | H | Me | N | H | H | H | Cl | H | heptafluoroisopropyl | H | Cl |
| 18-45 | 2-chloropyridin-3-yl | H | Me | N | H | H | H | Cl | H | heptafluoroisopropyl | H | Cl |
| 18-87 | phenyl | H | Me | N | H | H | H | Cl | H | nonafluoro-2-butyl | H | Cl |
| 18-107 | 3-cyanophenyl | H | Me | N | H | H | H | Cl | H | nonafluoro-2-butyl | H | Cl |
| 18-108 | 4-cyanophenyl | H | Me | N | H | H | H | Cl | H | nonafluoro-2-butyl | H | Cl |
| 18-123 | 2-chloropyridin-3-yl | H | Me | N | H | H | H | Cl | H | nonafluoro-2-butyl | H | Cl |
| 18-165 | phenyl | H | Me | N | H | H | H | Br | H | heptafluoroisopropyl | H | Br |
| 18-176 | 3-iodophenyl | H | Me | N | H | H | H | Br | H | pentafluoroethyl | H | Br |
| 18-177 | 4-iodophenyl | H | Me | N | H | H | H | Br | H | pentafluoroethyl | H | Br |
| 18-185 | 3-cyanophenyl | H | Me | N | H | H | H | Br | H | heptafluoroisopropyl | H | Br |
| 18-186 | 4-cyanophenyl | H | Me | N | H | H | H | Br | H | heptafluoroisopropyl | H | Br |
| 18-201 | 2-chloropyridin-3-yl | H | Me | N | H | H | H | Br | H | heptafluoroisopropyl | H | Br |
| 18-243 | phenyl | H | Me | N | H | H | H | Br | H | nonafluoro-2-butyl | H | Br |

TABLE 18-continued

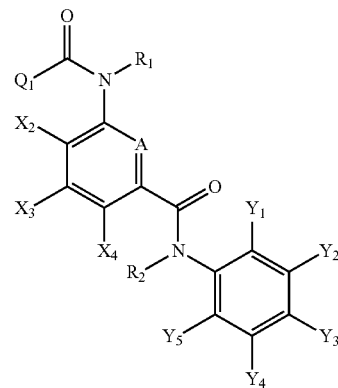

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 18-263 | 3-cyanophenyl | H | Me | N | H | H | H | Br | H | nonafluoro-2-butyl | H | Br |
| 18-264 | 4-cyanophenyl | H | Me | N | H | H | H | Br | H | nonafluoro-2-butyl | H | Br |
| 18-279 | 2-chloropyridin-3-yl | H | Me | N | H | H | H | Br | H | nonafluoro-2-butyl | H | Br |
| 18-321 | phenyl | H | Me | N | H | H | H | I | H | heptafluoroisopropyl | H | I |
| 18-341 | 3-cyanophenyl | H | Me | N | H | H | H | I | H | heptafluoroisopropyl | H | I |
| 18-342 | 4-cyanophenyl | H | Me | N | H | H | H | I | H | heptafluoroisopropyl | H | I |
| 18-357 | 2-chloropyridin-3-yl | H | Me | N | H | H | H | I | H | heptafluoroisopropyl | H | I |
| 18-399 | phenyl | H | Me | N | H | H | H | I | H | nonafluoro-2-butyl | H | I |
| 18-419 | 3-cyanophenyl | H | Me | N | H | H | H | I | H | nonafluoro-2-butyl | H | I |
| 18-420 | 4-cyanophenyl | H | Me | N | H | H | H | I | H | nonafluoro-2-butyl | H | I |
| 18-435 | 2-chloropyridin-3-yl | H | Me | N | H | H | H | I | H | nonafluoro-2-butyl | H | I |
| 18-477 | phenyl | H | Me | N | H | H | H | Cl | H | heptafluoroisopropyl | H | OCF3 |
| 18-497 | 3-cyanophenyl | H | Me | N | H | H | H | Cl | H | heptafluoroisopropyl | H | OCF3 |
| 18-498 | 4-cyanophenyl | H | Me | N | H | H | H | Cl | H | heptafluoroisopropyl | H | OCF3 |
| 18-513 | 2-chloropyridin-3-yl | H | Me | N | H | H | H | Cl | H | heptafluoroisopropyl | H | OCF3 |
| 18-555 | phenyl | H | Me | N | H | H | H | Cl | H | nonafluoro-2-butyl | H | OCF3 |
| 18-575 | 3-cyanophenyl | H | Me | N | H | H | H | Cl | H | nonafluoro-2-butyl | H | OCF3 |
| 18-576 | 4-cyanophenyl | H | Me | N | H | H | H | Cl | H | nonafluoro-2-butyl | H | OCF3 |
| 18-591 | 2-chloropyridin-3-yl | H | Me | N | H | H | H | Cl | H | nonafluoro-2-butyl | H | OCF3 |
| 18-633 | phenyl | H | Me | N | H | H | H | Br | H | heptafluoroisopropyl | H | OCF3 |
| 18-653 | 3-cyanophenyl | H | Me | N | H | H | H | Br | H | heptafluoroisopropyl | H | OCF3 |
| 18-654 | 4-cyanophenyl | H | Me | N | H | H | H | Br | H | heptafluoroisopropyl | H | OCF3 |
| 18-669 | 2-chloropyridin-3-yl | H | Me | N | H | H | H | Br | H | heptafluoroisopropyl | H | OCF3 |
| 18-711 | phenyl | H | Me | N | H | H | H | Br | H | nonafluoro-2-butyl | H | OCF3 |
| 18-731 | 3-cyanophenyl | H | Me | N | H | H | H | Br | H | nonafluoro-2-butyl | H | OCF3 |
| 18-732 | 4-cyanophenyl | H | Me | N | H | H | H | Br | H | nonafluoro-2-butyl | H | OCF3 |
| 18-747 | 2-chloropyridin-3-yl | H | Me | N | H | H | H | Br | H | nonafluoro-2-butyl | H | OCF3 |
| 18-789 | phenyl | H | Me | N | H | H | H | I | H | heptafluoroisopropyl | H | OCF3 |
| 18-809 | 3-cyanophenyl | H | Me | N | H | H | H | I | H | heptafluoroisopropyl | H | OCF3 |
| 18-810 | 4-cyanophenyl | H | Me | N | H | H | H | I | H | heptafluoroisopropyl | H | OCF3 |
| 18-825 | 2-chloropyridin-3-yl | H | Me | N | H | H | H | I | H | heptafluoroisopropyl | H | OCF3 |
| 18-867 | phenyl | H | Me | N | H | H | H | I | H | nonafluoro-2-butyl | H | OCF3 |
| 18-887 | 3-cyanophenyl | H | Me | N | H | H | H | I | H | nonafluoro-2-butyl | H | OCF3 |
| 18-888 | 4-cyanophenyl | H | Me | N | H | H | H | I | H | nonafluoro-2-butyl | H | OCF3 |
| 18-903 | 2-chloropyridin-3-yl | H | Me | N | H | H | H | I | H | nonafluoro-2-butyl | H | OCF3 |
| 18-945 | phenyl | H | Me | N | H | H | H | F | H | heptafluoroisopropyl | H | CF3 |
| 18-946 | phenyl | H | Me | N | H | H | H | Cl | H | heptafluoroisopropyl | H | CF3 |
| 18-957 | 3-iodophenyl | H | Me | N | H | H | H | Cl | H | pentafluoroethyl | H | CF3 |
| 18-958 | 4-iodophenyl | H | Me | N | H | H | H | Cl | H | pentafluoroethyl | H | CF3 |
| 18-960 | (3-trifluoromethyl)phenyl | H | Et | N | H | H | H | Cl | H | heptafluoroisopropyl | H | CF3 |
| 18-965 | 2-cyanophenyl | H | Me | N | H | H | H | Cl | H | pentafluoroethyl | H | C2F5 |
| 18-966 | 3-cyanophenyl | H | Me | N | H | H | H | Cl | H | heptafluoroisopropyl | H | CF3 |
| 18-967 | 4-cyanophenyl | H | Me | N | H | H | H | Cl | H | heptafluoroisopropyl | H | CF3 |
| 18-970 | 2,4-dichlorophenyl | H | Me | N | H | H | H | Cl | H | heptafluoroisopropyl | H | C2F5 |
| 18-971 | 2-chloro-4-fluorophenyl | H | n-Pr | N | H | H | H | Cl | H | heptafluoroisopropyl | H | CF3 |
| 18-974 | 2-bromo-4-chlorophenyl | H | Me | N | H | H | H | Cl | H | heptafluoroisopropyl | H | n-C3F7 |
| 18-981 | 2-fluoropyridin-3-yl | H | Me | N | H | H | H | Cl | H | pentafluoroethyl | H | CF3 |
| 18-982 | 2-chloropyridin-3-yl | H | Me | N | H | H | H | Cl | H | heptafluoroisopropyl | H | CF3 |
| 18-988 | 6-fluoropyridin-3-yl | H | i-Pr | N | H | H | H | Cl | H | heptafluoroisopropyl | H | CF3 |
| 18-995 | 5-fluoropyridin-3-yl | H | Me | N | H | H | H | Cl | H | heptafluoroisopropyl | H | C2F5 |
| 18-997 | 5-bromopyridin-3-yl | H | Me | N | H | H | H | Cl | H | heptafluoroisopropyl | H | n-C3F7 |
| 18-998 | 5-iodopyridin-3-yl | H | Me | N | H | H | H | Cl | H | heptafluoroisopropyl | H | i-C3F7 |
| 18-1000 | 5-nitropyridin-3-yl | H | Me | N | H | H | H | Cl | H | pentafluoroethyl | H | CF3 |
| 18-1002 | 4-fluoropyridin-3-yl | H | Me | N | H | H | H | Cl | H | pentafluoroethyl | H | CF3 |
| 18-1004 | 4-bromopyridin-3-yl | H | CH2CH=CH2 | N | H | H | H | Cl | H | heptafluoroisopropyl | H | n-C3F7 |
| 18-1005 | 4-iodopyridin-3-yl | H | Me | N | H | H | H | Cl | H | heptafluoroisopropyl | H | i-C3F7 |
| 18-1011 | pyridin-4-yl | H | CN | N | H | H | H | Cl | H | heptafluoroisopropyl | H | CF3 |
| 18-1023 | 4-cyanopyridin-2-yl | H | Me | N | H | H | H | Cl | H | pentafluoroethyl | H | CF3 |

TABLE 18-continued

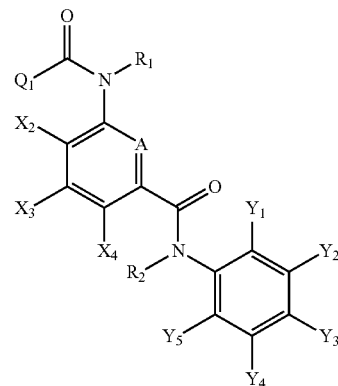

| compound number | Q1 | R1 | R2 | A | X2 | X3 | X4 | Y1 | Y2 | Y3 | Y4 | Y5 |
|---|---|---|---|---|---|---|---|---|---|---|---|---|
| 18-1024 | phenyl | H | Me | N | H | H | H | F | H | nonafluoro-2-butyl | H | CF3 |
| 18-1025 | phenyl | H | Me | N | H | H | H | Cl | H | nonafluoro-2-butyl | H | CF3 |
| 18-1033 | 3-bromophenyl | H | CH2C≡CH | N | H | H | H | Cl | H | nonafluoro-2-butyl | H | CF3 |
| 18-1038 | (2-trifluoromethyl)phenyl | H | Me | N | H | H | H | Cl | H | nonafluoro-2-butyl | H | C2F5 |
| 18-1040 | (4-trifluoromethyl)phenyl | H | NH2 | N | H | H | H | Cl | H | nonafluoro-2-butyl | H | CF3 |
| 18-1045 | 3-cyanophenyl | H | Me | N | H | H | H | Cl | H | nonafluoro-2-butyl | H | CF3 |
| 18-1046 | 4-cyanophenyl | H | Me | N | H | H | H | Cl | H | nonafluoro-2-butyl | H | CF3 |
| 18-1053 | 2-bromo-4-chlorophenyl | H | C(O)OMe | N | H | H | H | Cl | H | nonafluoro-2-butyl | H | CF3 |
| 18-1055 | 2-chloro-4-nitrophenyl | H | Me | N | H | H | H | Cl | H | nonafluoro-2-butyl | H | i-C3F7 |
| 18-1061 | 2-chloropyridin-3-yl | H | Me | N | H | H | H | Cl | H | nonafluoro-2-butyl | H | CF3 |
| 18-1074 | 5-fluoropyridin-3-yl | H | C(O)OEt | N | H | H | H | Cl | H | nonafluoro-2-butyl | H | C2F5 |
| 18-1076 | 5-bromopyridin-3-yl | H | Me | N | H | H | H | Cl | H | nonafluoro-2-butyl | H | n-C3F7 |
| 18-1077 | 5-iodopyridin-3-yl | H | Me | N | H | H | H | Cl | H | nonafluoro-2-butyl | H | i-C3F7 |
| 18-1081 | 4-fluoropyridin-3-yl | H | Me | N | H | H | H | Cl | H | nonafluoro-2-butyl | H | C2F5 |
| 18-1083 | 4-bromopyridin-3-yl | H | C(O)C(O)Me | N | H | H | H | Cl | H | nonafluoro-2-butyl | H | CF3 |
| 18-1085 | 4-(trifluoromethyl)pyridin-3-yl | H | Me | N | H | H | H | Cl | H | nonafluoro-2-butyl | H | n-C3F7 |
| 18-1086 | 4-nitropyridin-3-yl | H | C(O)C(O)Et | N | H | H | H | Cl | H | nonafluoro-2-butyl | H | i-C3F7 |
| 18-1100 | 5-iodopyridin-2-yl | H | C(O)Me | N | H | H | H | Cl | H | nonafluoro-2-butyl | H | CF3 |
| 18-1102 | 4-cyanopyridin-2-yl | H | C(O)Et | N | H | H | H | Cl | H | nonafluoro-2-butyl | H | C2F5 |
| 18-1103 | phenyl | H | Me | N | H | H | H | Br | H | heptafluoroisopropyl | H | CF3 |
| 18-1104 | 2-fluorophenyl | H | Me | N | H | H | H | Br | H | heptafluoroisopropyl | H | CF3 |
| 18-1117 | (3-trifluoromethyl)phenyl | H | S(O)2Me | N | H | H | H | Br | H | heptafluoroisopropyl | H | CF3 |
| 18-1123 | 3-cyanophenyl | H | Me | N | H | H | H | Br | H | heptafluoroisopropyl | H | CF3 |
| 18-1124 | 4-cyanophenyl | H | Me | N | H | H | H | Br | H | heptafluoroisopropyl | H | CF3 |
| 18-1135 | 4-cyano-2-fluorophenyl | H | S(O)2Et | N | H | H | H | Br | H | heptafluoroisopropyl | H | CF3 |
| 18-1139 | 2-chloropyridin-3-yl | H | Me | N | H | H | H | Br | H | heptafluoroisopropyl | H | CF3 |
| 18-1150 | 6-nitropyridin-3-yl | H | CH2Ph | N | H | H | H | Br | H | heptafluoroisopropyl | H | CF3 |
| 18-1159 | 4-fluoropyridin-3-yl | H | CH2(3-Py) | N | H | H | H | Br | H | heptafluoroisopropyl | H | CF3 |
| 18-1180 | 4-cyanopyridin-2-yl | H | CH2(3-Py-N-oxide) | N | H | H | H | Br | H | heptafluoroisopropyl | H | CF3 |
| 18-1181 | phenyl | H | Me | N | H | H | H | Br | H | nonafluoro-2-butyl | H | CF3 |
| 18-1182 | 2-fluorophenyl | H | Me | N | H | H | H | Br | H | nonafluoro-2-butyl | H | CF3 |
| 18-1201 | 3-cyanophenyl | H | Me | N | H | H | H | Br | H | nonafluoro-2-butyl | H | CF3 |
| 18-1202 | 4-cyanophenyl | H | Me | N | H | H | H | Br | H | nonafluoro-2-butyl | H | CF3 |
| 18-1208 | 4-bromo-2-chlorophenyl | H | Et | N | H | H | H | Br | H | nonafluoro-2-butyl | H | CF3 |
| 18-1217 | 2-chloropyridin-3-yl | H | Me | N | H | H | H | Br | H | nonafluoro-2-butyl | H | CF3 |
| 18-1234 | 5-(trifluoromethyl)pyridin-3-yl | H | CN | N | H | H | H | Br | H | nonafluoro-2-butyl | H | CF3 |
| 18-1259 | phenyl | H | Me | N | H | H | H | I | H | heptafluoroisopropyl | H | CF3 |
| 18-1260 | 2-fluorophenyl | H | Me | N | H | H | H | I | H | heptafluoroisopropyl | H | CF3 |
| 18-1279 | 3-cyanophenyl | H | Me | N | H | H | H | I | H | heptafluoroisopropyl | H | CF3 |
| 18-1280 | 4-cyanophenyl | H | Me | N | H | H | H | I | H | heptafluoroisopropyl | H | CF3 |
| 18-1295 | 2-chloropyridin-3-yl | H | Me | N | H | H | H | I | H | heptafluoroisopropyl | H | CF3 |
| 18-1308 | 5-fluoropyridin-3-yl | H | C(O)Me | N | H | H | H | I | H | heptafluoroisopropyl | H | CF3 |
| 18-1337 | phenyl | H | Me | N | H | H | H | I | H | nonafluoro-2-butyl | H | CF3 |
| 18-1338 | 2-fluorophenyl | H | Me | N | H | H | H | I | H | nonafluoro-2-butyl | H | CF3 |
| 18-1357 | 3-cyanophenyl | H | Me | N | H | H | H | I | H | nonafluoro-2-butyl | H | CF3 |
| 18-1358 | 4-cyanophenyl | H | Me | N | H | H | H | I | H | nonafluoro-2-butyl | H | CF3 |
| 18-1373 | 2-chloropyridin-3-yl | H | Me | N | H | H | H | I | H | nonafluoro-2-butyl | H | CF3 |
| 18-1415 | phenyl | H | Me | N | H | H | H | OCF3 | H | heptafluoroisopropyl | H | OCF3 |
| 18-1446 | 2-chloropyridin-3-yl | H | Me | N | H | H | H | OCF3 | H | heptafluoroisopropyl | H | OCF3 |
| 18-1471 | phenyl | H | Me | N | H | H | H | OCF3 | H | nonafluoro-2-butyl | H | OCF3 |
| 18-1502 | 2-chloropyridin-3-yl | H | Me | N | H | H | H | OCF3 | H | nonafluoro-2-butyl | H | OCF3 |
| 18-1527 | phenyl | H | Me | N | H | H | H | CF3 | H | heptafluoroisopropyl | H | OCF3 |
| 18-1558 | 2-chloropyridin-3-yl | H | Me | N | H | H | H | CF3 | H | heptafluoroisopropyl | H | OCF3 |
| 18-1583 | phenyl | H | Me | N | H | H | H | CF3 | H | nonafluoro-2-butyl | H | OCF3 |
| 18-1614 | 2-chloropyridin-3-yl | H | Me | N | H | H | H | CF3 | H | nonafluoro-2-butyl | H | OCF3 |
| 18-1639 | phenyl | H | Me | N | H | H | H | CF3 | H | heptafluoroisopropyl | H | CF3 |
| 16-1659 | 3-cyanophenyl | H | Me | N | H | H | H | CF3 | H | heptafluoroisopropyl | H | CF3 |

TABLE 18-continued

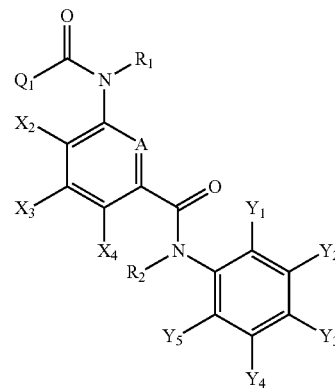

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 18-1660 | 4-cyanophenyl | H | Me | N | H | H | H | CF3 | H | heptafluoroisopropyl | H | CF3 |
| 18-1675 | 2-chloropyridin-3-yl | H | Me | N | H | H | H | CF3 | H | heptafluoroisopropyl | H | CF3 |
| 18-1707 | phenyl | H | Me | N | H | H | H | CF3 | H | nonafluoro-2-butyl | H | CF3 |
| 18-1727 | 3-cyanophenyl | H | Me | N | H | H | H | CF3 | H | nonafluoro-2-butyl | H | CF3 |
| 18-1728 | 4-cyanophenyl | H | Me | N | H | H | H | CF3 | H | nonafluoro-2-butyl | H | CF3 |
| 18-1743 | 2-chloropyridin-3-yl | H | Me | N | H | H | H | CF3 | H | nonafluoro-2-butyl | H | CF3 |
| 18-1775 | phenyl | H | Me | N-oxide | H | H | H | F | H | heptafluoroisopropyl | H | F |
| 18-1776 | 3-cyanophenyl | H | Me | N-oxide | H | H | H | F | H | heptafluoroisopropyl | H | F |
| 18-1777 | 4-cyanophenyl | H | Me | N-oxide | H | H | H | F | H | heptafluoroisopropyl | H | F |
| 18-1778 | 2-chloropyridin-3-yl | H | Me | N-oxide | H | H | H | F | H | heptafluoroisopropyl | H | F |
| 18-1779 | phenyl | H | Me | N-oxide | H | H | H | F | H | nonafluoro-2-butyl | H | F |
| 18-1780 | 3-cyanophenyl | H | Me | N-oxide | H | H | H | F | H | nonafluoro-2-butyl | H | F |
| 18-1781 | 4-cyanophenyl | H | Me | N-oxide | H | H | H | F | H | nonafluoro-2-butyl | H | F |
| 18-1782 | 2-chloropyridin-3-yl | H | Me | N-oxide | H | H | H | F | H | nonafluoro-2-butyl | H | F |
| 18-1783 | phenyl | H | Me | N-oxide | H | H | H | Cl | H | heptafluoroisopropyl | H | Cl |
| 18-1803 | 3-cyanophenyl | H | Me | N-oxide | H | H | H | Cl | H | heptafluoroisopropyl | H | Cl |
| 18-1804 | 4-cyanophenyl | H | Me | N-oxide | H | H | H | Cl | H | heptafluoroisopropyl | H | Cl |
| 18-1819 | 2-chloropyridin-3-yl | H | Me | N-oxide | H | H | H | Cl | H | heptafluoroisopropyl | H | Cl |
| 18-1861 | phenyl | H | Me | N-oxide | H | H | H | Cl | H | nonafluoro-2-butyl | H | Cl |
| 18-1881 | 3-cyanophenyl | H | Me | N-oxide | H | H | H | Cl | H | nonafluoro-2-butyl | H | Cl |
| 18-1882 | 4-cyanophenyl | H | Me | N-oxide | H | H | H | Cl | H | nonafluoro-2-butyl | H | Cl |
| 18-1897 | 2-chloropyridin-3-yl | H | Me | N-oxide | H | H | H | Cl | H | nonafluoro-2-butyl | H | Cl |
| 18-1939 | phenyl | H | Me | N-oxide | H | H | H | Br | H | heptafluoroisopropyl | H | Br |
| 18-1959 | 3-cyanophenyl | H | Me | N-oxide | H | H | H | Br | H | heptafluoroisopropyl | H | Br |
| 18-1960 | 4-cyanophenyl | H | Me | N-oxide | H | H | H | Br | H | heptafluoroisopropyl | H | Br |
| 18-1975 | 2-chloropyridin-3-yl | H | Me | N-oxide | H | H | H | Br | H | heptafluoroisopropyl | H | Br |
| 18-2017 | phenyl | H | Me | N-oxide | H | H | H | Br | H | nonafluoro-2-butyl | H | Br |
| 18-2037 | 3-cyanophenyl | H | Me | N-oxide | H | H | H | Br | H | nonafluoro-2-butyl | H | Br |
| 18-2038 | 4-cyanophenyl | H | Me | N-oxide | H | H | H | Br | H | nonafluoro-2-butyl | H | Br |
| 18-2053 | 2-chloropyridin-3-yl | H | Me | N-oxide | H | H | H | Br | H | nonafluoro-2-butyl | H | Br |
| 18-2095 | phenyl | H | Me | N-oxide | H | H | H | I | H | heptafluoroisopropyl | H | I |
| 18-2115 | 3-cyanophenyl | H | Me | N-oxide | H | H | H | I | H | heptafluoroisopropyl | H | I |
| 18-2116 | 4-cyanophenyl | H | Me | N-oxide | H | H | H | I | H | heptafluoroisopropyl | H | I |
| 18-2131 | 2-chloropyridin-3-yl | H | Me | N-oxide | H | H | H | I | H | heptafluoroisopropyl | H | I |
| 18-2173 | phenyl | H | Me | N-oxide | H | H | H | I | H | nonafluoro-2-butyl | H | I |
| 18-2193 | 3-cyanophenyl | H | Me | N-oxide | H | H | H | I | H | nonafluoro-2-butyl | H | I |
| 18-2194 | 4-cyanophenyl | H | Me | N-oxide | H | H | H | I | H | nonafluoro-2-butyl | H | I |
| 18-2209 | 2-chloropyridin-3-yl | H | Me | N-oxide | H | H | H | I | H | nonafluoro-2-butyl | H | I |
| 18-2251 | phenyl | H | Me | N-oxide | H | H | H | Cl | H | heptafluoroisopropyl | H | OCF3 |
| 18-2271 | 3-cyanophenyl | H | Me | N-oxide | H | H | H | Cl | H | heptafluoroisopropyl | H | OCF3 |
| 18-2272 | 4-cyanophenyl | H | Me | N-oxide | H | H | H | Cl | H | heptafluoroisopropyl | H | OCF3 |
| 18-2287 | 2-chloropyridin-3-yl | H | Me | N-oxide | H | H | H | Cl | H | heptafluoroisopropyl | H | OCF3 |
| 18-2291 | 2-nitropyridin-3-yl | H | Me | N-oxide | H | H | H | Cl | H | heptafluoroisopropyl | H | OC2F5 |
| 18-2329 | phenyl | H | Me | N-oxide | H | H | H | Cl | H | nonafluoro-2-butyl | H | OCF3 |
| 18-2349 | 3-cyanophenyl | H | Me | N-oxide | H | H | H | Cl | H | nonafluoro-2-butyl | H | OCF3 |
| 18-2350 | 4-cyanophenyl | H | Me | N-oxide | H | H | H | Cl | H | nonafluoro-2-butyl | H | OCF3 |
| 18-2365 | 2-chloropyridin-3-yl | H | Me | N-oxide | H | H | H | Cl | H | nonafluoro-2-butyl | H | OCF3 |
| 18-2407 | phenyl | H | Me | N-oxide | H | H | H | Br | H | heptafluoroisopropyl | H | OCF3 |
| 18-2427 | 3-cyanophenyl | H | Me | N-oxide | H | H | H | Br | H | heptafluoroisopropyl | H | OCF3 |
| 18-2428 | 4-cyanophenyl | H | Me | N-oxide | H | H | H | Br | H | heptafluoroisopropyl | H | OCF3 |
| 18-2443 | 2-chloropyridin-3-yl | H | Me | N-oxide | H | H | H | Br | H | heptafluoroisopropyl | H | OCF3 |
| 18-2485 | phenyl | H | Me | N-oxide | H | H | H | Br | H | nonafluoro-2-butyl | H | OCF3 |
| 18-2505 | 3-cyanophenyl | H | Me | N-oxide | H | H | H | Br | H | nonafluoro-2-butyl | H | OCF3 |
| 18-2506 | 4-cyanophenyl | H | Me | N-oxide | H | H | H | Br | H | nonafluoro-2-butyl | H | OCF3 |
| 18-2521 | 2-chloropyridin-3-yl | H | Me | N-oxide | H | H | H | Br | H | nonafluoro-2-butyl | H | OCF3 |
| 18-2563 | phenyl | H | Me | N-oxide | H | H | H | I | H | heptafluoroisopropyl | H | OCF3 |
| 18-2583 | 3-cyanophenyl | H | Me | N-oxide | H | H | H | I | H | heptafluoroisopropyl | H | OCF3 |
| 18-2584 | 4-cyanophenyl | H | Me | N-oxide | H | H | H | I | H | heptafluoroisopropyl | H | OCF3 |

TABLE 18-continued

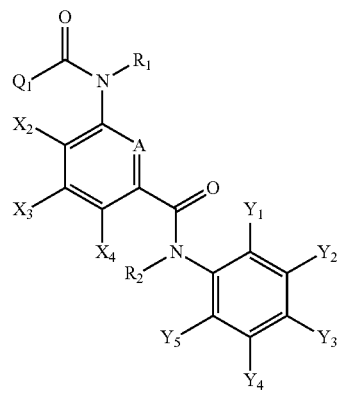

| compound number | $Q_1$ | $R_1$ | $R_2$ | A | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 18-2599 | 2-chloropyridin-3-yl | H | Me | N-oxide | H | H | H | I | H | heptafluoroisopropyl | H | OCF3 |
| 18-2641 | phenyl | H | Me | N-oxide | H | H | H | I | H | nonafluoro-2-butyl | H | OCF3 |
| 18-2661 | 3-cyanophenyl | H | Me | N-oxide | H | H | H | I | H | nonafluoro-2-butyl | H | OCF3 |
| 18-2662 | 4-cyanophenyl | H | Me | N-oxide | H | H | H | I | H | nonafluoro-2-butyl | H | OCF3 |
| 18-2677 | 2-chloropyridin-3-yl | H | Me | N-oxide | H | H | H | I | H | nonafluoro-2-butyl | H | OCF3 |
| 18-2719 | phenyl | H | Me | N-oxide | H | H | H | F | H | heptafluoroisopropyl | H | CF3 |
| 18-2720 | phenyl | H | Me | N-oxide | H | H | H | Cl | H | heptafluoroisopropyl | H | CF3 |
| 18-2740 | 3-cyanophenyl | H | Me | N-oxide | H | H | H | Cl | H | heptafluoroisopropyl | H | CF3 |
| 18-2741 | 4-cyanophenyl | H | Me | N-oxide | H | H | H | Cl | H | heptafluoroisopropyl | H | CF3 |
| 18-2756 | 2-chloropyridin-3-yl | H | Me | N-oxide | H | H | H | Cl | H | heptafluoroisopropyl | H | CF3 |
| 18-2798 | phenyl | H | Me | N-oxide | H | H | H | F | H | nonafluoro-2-butyl | H | CF3 |
| 18-2799 | phenyl | H | Me | N-oxide | H | H | H | Cl | H | nonafluoro-2-butyl | H | CF3 |
| 18-2819 | 3-cyanophenyl | H | Me | N-oxide | H | H | H | Cl | H | nonafluoro-2-butyl | H | CF3 |
| 18-2820 | 4-cyanophenyl | H | Me | N-oxide | H | H | H | Cl | H | nonafluoro-2-butyl | H | CF3 |
| 18-2835 | 2-chloropyridin-3-yl | H | Me | N-oxide | H | H | H | Cl | H | nonafluoro-2-butyl | H | CF3 |
| 18-2877 | phenyl | H | Me | N-oxide | H | H | H | Br | H | heptafluoroisopropyl | H | CF3 |
| 18-2897 | 3-cyanophenyl | H | Me | N-oxide | H | H | H | Br | H | heptafluoroisopropyl | H | CF3 |
| 18-2898 | 4-cyanophenyl | H | Me | N-oxide | H | H | H | Br | H | heptafluoroisopropyl | H | CF3 |
| 18-2913 | 2-chloropyridin-3-yl | H | Me | N-oxide | H | H | H | Br | H | heptafluoroisopropyl | H | CF3 |
| 18-2955 | phenyl | H | Me | N-oxide | H | H | H | Br | H | nonafluoro-2-butyl | H | CF3 |
| 18-2975 | 3-cyanophenyl | H | Me | N-oxide | H | H | H | Br | H | nonafluoro-2-butyl | H | CF3 |
| 18-2976 | 4-cyanophenyl | H | Me | N-oxide | H | H | H | Br | H | nonafluoro-2-butyl | H | CF3 |
| 18-2991 | 2-chloropyridin-3-yl | H | Me | N-oxide | H | H | H | Br | H | nonafluoro-2-butyl | H | CF3 |
| 18-3033 | phenyl | H | Me | N-oxide | H | H | H | I | H | heptafluoroisopropyl | H | CF3 |
| 18-3053 | 3-cyanophenyl | H | Me | N-oxide | H | H | H | I | H | heptafluoroisopropyl | H | CF3 |
| 18-3054 | 4-cyanophenyl | H | Me | N-oxide | H | H | H | I | H | heptafluoroisopropyl | H | CF3 |
| 18-3069 | 2-chloropyridin-3-yl | H | Me | N-oxide | H | H | H | I | H | heptafluoroisopropyl | H | CF3 |
| 18-3111 | phenyl | H | Me | N-oxide | H | H | H | I | H | nonafluoro-2-butyl | H | CF3 |
| 18-3131 | 3-cyanophenyl | H | Me | N-oxide | H | H | H | I | H | nonafluoro-2-butyl | H | CF3 |
| 18-3132 | 4-cyanophenyl | H | Me | N-oxide | H | H | H | I | H | nonafluoro-2-butyl | H | CF3 |
| 18-3147 | 2-chloropyridin-3-yl | H | Me | N-oxide | H | H | H | I | H | nonafluoro-2-butyl | H | CF3 |
| 18-3189 | phenyl | H | Me | N-oxide | H | H | H | OCF3 | H | heptafluoroisopropyl | H | OCF3 |
| 18-3220 | 2-chloropyridin-3-yl | H | Me | N-oxide | H | H | H | OCF3 | H | heptafluoroisopropyl | H | OCF3 |
| 18-3245 | phenyl | H | Me | N-oxide | H | H | H | OCF3 | H | nonafluoro-2-butyl | H | OCF3 |
| 18-3276 | 2-chloropyridin-3-yl | H | Me | N-oxide | H | H | H | OCF3 | H | nonafluoro-2-butyl | H | OCF3 |
| 18-3301 | phenyl | H | Me | N-oxide | H | H | H | CF3 | H | heptafluoroisopropyl | H | OCF3 |
| 18-3332 | 2-chloropyridin-3-yl | H | Me | N-oxide | H | H | H | CF3 | H | heptafluoroisopropyl | H | OCF3 |
| 18-3357 | phenyl | H | Me | N-oxide | H | H | H | CF3 | H | nonafluoro-2-butyl | H | OCF3 |
| 18-3388 | 2-chloropyridin-3-yl | H | Me | N-oxide | H | H | H | CF3 | H | nonafluoro-2-butyl | H | OCF3 |
| 18-3413 | phenyl | H | Me | N-oxide | H | H | H | CF3 | H | heptafluoroisopropyl | H | CF3 |
| 18-3433 | 3-cyanophenyl | H | Me | N-oxide | H | H | H | CF3 | H | heptafluoroisopropyl | H | CF3 |
| 18-3434 | 4-cyanophenyl | H | Me | N-oxide | H | H | H | CF3 | H | heptafluoroisopropyl | H | CF3 |
| 18-3449 | 2-chloropyridin-3-yl | H | Me | N-oxide | H | H | H | CF3 | H | heptafluoroisopropyl | H | CF3 |
| 18-3481 | phenyl | H | Me | N-oxide | H | H | H | CF3 | H | nonafluoro-2-butyl | H | CF3 |
| 18-3501 | 3-cyanophenyl | H | Me | N-oxide | H | H | H | CF3 | H | nonafluoro-2-butyl | H | CF3 |
| 18-3502 | 4-cyanophenyl | H | Me | N-oxide | H | H | H | CF3 | H | nonafluoro-2-butyl | H | CF3 |
| 18-3517 | 2-chloropyridin-3-yl | H | Me | N-oxide | H | H | H | CF3 | H | nonafluoro-2-butyl | H | CF3 |

TABLE 19

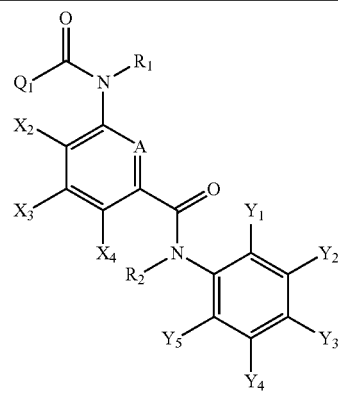

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 19-1 | phenyl | Me | Me | N | H | H | H | F | H | heptafluoroisopropyl | H | F |
| 19-2 | 3-cyanophenyl | Me | Me | N | H | H | H | F | H | heptafluoroisopropyl | H | F |
| 19-3 | 4-cyanophenyl | Me | Me | N | H | H | H | F | H | heptafluoroisopropyl | H | F |
| 19-4 | 2-chloropyridin-3-yl | Me | Me | N | H | H | H | F | H | heptafluoroisopropyl | H | F |
| 19-5 | phenyl | Me | Me | N | H | H | H | F | H | nonafluoro-2-butyl | H | F |
| 19-6 | 3-cyanophenyl | Me | Me | N | H | H | H | F | H | nonafluoro-2-butyl | H | F |
| 19-7 | 4-cyanophenyl | Me | Me | N | H | H | H | F | H | nonafluoro-2-butyl | H | F |
| 19-8 | 2-chloropyridin-3-yl | Me | Me | N | H | H | H | F | H | nonafluoro-2-butyl | H | F |
| 19-9 | phenyl | Me | Me | N | H | H | H | Cl | H | heptafluoroisopropyl | H | Cl |
| 19-11 | 3-fluorophenyl | Et | Me | N | H | H | H | Cl | H | heptafluoroisopropyl | H | Cl |
| 19-12 | 4-fluorophenyl | Me | Et | N | H | H | H | Cl | H | heptafluoroisopropyl | H | Cl |
| 19-29 | 3-cyanophenyl | Me | Me | N | H | H | H | Cl | H | heptafluoroisopropyl | H | Cl |
| 19-30 | 4-cyanophenyl | Me | Me | N | H | H | H | Cl | H | heptafluoroisopropyl | H | Cl |
| 19-45 | 2-chloropyridin-3-yl | Me | Me | N | H | H | H | Cl | H | heptafluoroisopropyl | H | Cl |
| 19-87 | phenyl | Me | Me | N | H | H | H | Cl | H | nonafluoro-2-butyl | H | Cl |
| 19-107 | 3-cyanophenyl | Me | Me | N | H | H | H | Cl | H | nonafluoro-2-butyl | H | Cl |
| 19-108 | 4-cyanophenyl | Me | Me | N | H | H | H | Cl | H | nonafluoro-2-butyl | H | Cl |
| 19-123 | 2-chloropyridin-3-yl | Me | Me | N | H | H | H | Cl | H | nonafluoro-2-butyl | H | Cl |
| 19-165 | phenyl | Me | Me | N | H | H | H | Br | H | heptafluoroisopropyl | H | Br |
| 19-185 | 3-cyanophenyl | Me | Me | N | H | H | H | Br | H | heptafluoroisopropyl | H | Br |
| 19-186 | 4-cyanophenyl | Me | Me | N | H | H | H | Br | H | heptafluoroisopropyl | H | Br |
| 19-201 | 2-chloropyridin-3-yl | Me | Me | N | H | H | H | Br | H | heptafluoroisopropyl | H | Br |
| 19-243 | phenyl | Me | Me | N | H | H | H | Br | H | nonafluoro-2-butyl | H | Br |
| 19-263 | 3-cyanophenyl | Me | Me | N | H | H | H | Br | H | nonafluoro-2-butyl | H | Br |
| 19-264 | 4-cyanophenyl | Me | Me | N | H | H | H | Br | H | nonafluoro-2-butyl | H | Br |
| 19-279 | 2-chloropyridin-3-yl | Me | Me | N | H | H | H | Br | H | nonafluoro-2-butyl | H | Br |
| 19-321 | phenyl | Me | Me | N | H | H | H | I | H | heptafluoroisopropyl | H | I |
| 19-341 | 3-cyanophenyl | Me | Me | N | H | H | H | I | H | heptafluoroisopropyl | H | I |
| 19-342 | 4-cyanophenyl | Me | Me | N | H | H | H | I | H | heptafluoroisopropyl | H | I |
| 19-357 | 2-chloropyridin-3-yl | Me | Me | N | H | H | H | I | H | heptafluoroisopropyl | H | I |
| 19-399 | phenyl | Me | Me | N | H | H | H | I | H | nonafluoro-2-butyl | H | I |
| 19-419 | 3-cyanophenyl | Me | Me | N | H | H | N | I | H | nonafluoro-2-butyl | H | I |
| 19-420 | 4-cyanophenyl | Me | Me | N | H | H | H | I | H | nonafluoro-2-butyl | H | I |
| 19-435 | 2-chloropyridin-3-yl | Me | Me | N | H | H | H | I | H | nonafluoro-2-butyl | H | I |
| 19-673 | phenyl | Me | Me | N | H | H | H | Cl | H | heptafluoroisopropyl | H | OCF3 |
| 19-693 | 3-cyanophenyl | Me | Me | N | H | H | H | Cl | H | heptafluoroisopropyl | H | OCF3 |
| 19-694 | 4-cyanophenyl | Me | Me | N | H | H | H | Cl | H | heptafluoroisopropyl | H | OCF3 |
| 19-709 | 2-chloropyridin-3-yl | Me | Me | N | H | H | H | Cl | H | heptafluoroisopropyl | H | OCF3 |
| 19-751 | phenyl | Me | Me | N | H | H | H | Cl | H | nonafluoro-2-butyl | H | OCF3 |
| 19-771 | 3-cyanophenyl | Me | Me | N | H | H | H | Cl | H | nonafluoro-2-butyl | H | OCF3 |
| 19-772 | 4-cyanophenyl | Me | Me | N | H | H | H | Cl | H | nonafluoro-2-butyl | H | OCF3 |
| 19-787 | 2-chloropyridin-3-yl | Me | Me | N | H | H | H | Cl | H | nonafluoro-2-butyl | H | OCF3 |
| 19-829 | phenyl | Me | Me | N | H | H | H | Br | H | heptafluoroisopropyl | H | OCF3 |
| 19-849 | 3-cyanophenyl | Me | Me | N | H | H | H | Br | H | heptafluoroisopropyl | H | OCF3 |
| 19-850 | 4-cyanophenyl | Me | Me | N | H | H | H | Br | H | heptafluoroisopropyl | H | OCF3 |
| 19-865 | 2-chloropyridin-3-yl | Me | Me | N | H | H | H | Br | H | heptafluoroisopropyl | H | OCF3 |
| 19-907 | phenyl | Me | Me | N | H | H | H | Br | H | nonafluoro-2-butyl | H | OCF3 |
| 19-927 | 3-cyanophenyl | Me | Me | N | H | H | H | Br | H | nonafluoro-2-butyl | H | OCF3 |
| 19-928 | 4-cyanophenyl | Me | Me | N | H | H | H | Br | H | nonafluoro-2-butyl | H | OCF3 |
| 19-943 | 2-chloropyridin-3-yl | Me | Me | N | H | H | H | Br | H | nonafluoro-2-butyl | H | OCF3 |
| 19-985 | phenyl | Me | Me | N | H | H | H | I | H | heptafluoroisopropyl | H | OCF3 |
| 19-1005 | 3-cyanophenyl | Me | Me | N | H | H | H | I | H | heptafluoroisopropyl | H | OCF3 |
| 19-1006 | 4-cyanophenyl | Me | Me | N | H | H | H | I | H | heptafluoroisopropyl | H | OCF3 |
| 19-1021 | 2-chloropyridin-3-yl | Me | Me | N | H | H | H | I | H | heptafluoroisopropyl | H | OCF3 |
| 19-1063 | phenyl | Me | Me | N | H | H | H | I | H | nonafluoro-2-butyl | H | OCF3 |
| 19-1083 | 3-cyanophenyl | Me | Me | N | H | H | H | I | H | nonafluoro-2-butyl | H | OCF3 |
| 19-1084 | 4-cyanophenyl | Me | Me | N | H | H | H | I | H | nonafluoro-2-butyl | H | OCF3 |
| 19-1099 | 2-chloropyridin-3-yl | Me | Me | N | H | H | H | I | H | nonafluoro-2-butyl | H | OCF3 |

TABLE 19-continued

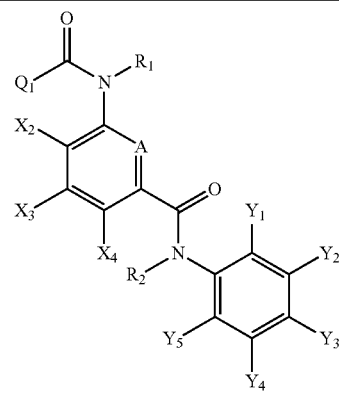

| compound number | Q1 | R1 | R2 | A | X2 | X3 | X4 | Y1 | Y2 | Y3 | Y4 | Y5 |
|---|---|---|---|---|---|---|---|---|---|---|---|---|
| 19-1337 | phenyl | Me | Me | N | H | H | H | F | H | heptafluoroisopropyl | H | CF3 |
| 19-1338 | phenyl | Me | Me | N | H | H | H | Cl | H | heptafluoroisopropyl | H | CF3 |
| 19-1349 | 3-iodophenyl | Me | Me | N | H | H | H | Cl | H | pentafluoroethyl | H | CF3 |
| 19-1350 | 4-iodophenyl | Me | Me | N | H | H | H | Cl | H | pentafluoroethyl | H | CF3 |
| 19-1352 | (3-trifluoromethyl)phenyl | Et | Me | N | H | H | H | Cl | H | heptafluoroisopropyl | H | CF3 |
| 19-1353 | (4-trifluoromethyl)phenyl | Me | Et | N | H | H | H | Cl | H | heptafluoroisopropyl | H | CF3 |
| 19-1357 | 2-cyanophenyl | Me | Me | N | H | H | H | Cl | H | pentafluoroethyl | H | C2F5 |
| 19-1358 | 3-cyanophenyl | Me | Me | N | H | H | H | Cl | H | heptafluoroisopropyl | H | CF3 |
| 19-1359 | 4-cyanophenyl | Me | Me | N | H | H | H | Cl | H | heptafluoroisopropyl | H | CF3 |
| 19-1362 | 2,4-dichlorophenyl | Me | Me | N | H | H | H | Cl | H | heptafluoroisopropyl | H | C2F5 |
| 19-1363 | 2-chloro-4-fluorophenyl | n-Pr | Me | N | H | H | H | Cl | H | heptafluoroisopropyl | H | CF3 |
| 19-1365 | 4-bromo-2-chlorophenyl | Me | n-Pr | N | H | H | H | Cl | H | heptafluoroisopropyl | H | CF3 |
| 19-1366 | 2-bromo-4-chlorophenyl | Me | Me | N | H | H | H | Cl | H | heptafluoroisopropyl | H | n-C3F7 |
| 19-1373 | 2-fluoropyridin-3-yl | Me | Me | N | H | H | H | Cl | H | pentafluoroethyl | H | CF3 |
| 19-1374 | 2-chloropyridin-3-yl | Me | Me | N | H | H | H | Cl | H | heptafluoroisopropyl | H | CF3 |
| 19-1378 | 2-nitropyridin-3-yl | Me | i-Pr | N | H | H | H | Cl | H | heptafluoroisopropyl | H | CF3 |
| 19-1380 | 6-fluoropyridin-3-yl | i-Pr | Me | N | H | H | H | Cl | H | heptafluoroisopropyl | H | CF3 |
| 19-1387 | 5-fluoropyridin-3-yl | Me | Me | N | H | H | H | Cl | H | heptafluoroisopropyl | H | C2F5 |
| 19-1389 | 5-bromopyridin-3-yl | Me | Me | N | H | H | H | Cl | H | heptafluoroisopropyl | H | n-C3F7 |
| 19-1390 | 5-iodopyridin-3-yl | Me | Me | N | H | H | H | Cl | H | heptafluoroisopropyl | H | i-C3F7 |
| 19-1392 | 5-nitropyridin-3-yl | Me | Me | N | H | H | H | Cl | H | pentafluoroethyl | H | CF3 |
| 19-1393 | 5-cyanopyridin-3-yl | Me | CH2CH=CH2 | N | H | H | H | Cl | H | heptafluoroisopropyl | H | CF3 |
| 19-1394 | 4-fluoropyridin-3-yl | Me | Me | N | H | H | H | Cl | H | pentafluoroethyl | H | CF3 |
| 19-1396 | 4-bromopyridin-3-yl | CH2CH=CH2 | Me | N | H | H | H | Cl | H | heptafluoroisopropyl | H | n-C3F7 |
| 19-1397 | 4-iodopyridin-3-yl | Me | Me | N | H | H | H | Cl | H | heptafluoroisopropyl | H | i-C3F7 |
| 19-1400 | 4-cyanopyridin-3-yl | Me | CN | N | H | H | H | Cl | H | heptafluoroisopropyl | H | CF3 |
| 19-1403 | pyridin-4-yl | CN | Me | N | H | H | H | Cl | H | heptafluoroisopropyl | H | CF3 |
| 19-1415 | 4-cyanopyridin-2-yl | Me | Me | N | H | H | H | Cl | H | pentafluoroethyl | H | CF3 |
| 19-1416 | phenyl | Me | Me | N | H | H | H | F | H | nonafluoro-2-butyl | H | CF3 |
| 19-1417 | phenyl | Me | Me | N | H | H | H | Cl | H | nonafluoro-2-butyl | H | CF3 |
| 19-1425 | 3-bromophenyl | CH2C≡CH | Me | N | H | H | H | Cl | H | nonafluoro-2-butyl | H | CF3 |
| 19-1429 | 4-iodophenyl | Me | CH2C≡CH | N | H | H | H | Cl | H | nonafluoro-2-butyl | H | CF3 |
| 19-1430 | (2-trifluoromethyl)phenyl | Me | Me | N | H | H | H | Cl | H | nonafluoro-2-butyl | H | C2F5 |
| 19-1432 | (4-trifluoromethyl)phenyl | NH2 | Me | N | H | H | H | Cl | H | nonafluoro-2-butyl | H | CF3 |
| 19-1436 | 2-cyanophenyl | Me | NH2 | N | H | H | H | Cl | H | nonafluoro-2-butyl | H | CF3 |
| 19-1437 | 3-cyanophenyl | Me | Me | N | H | H | H | Cl | H | nonafluoro-2-butyl | H | CF3 |
| 19-1438 | 4-cyanophenyl | Me | Me | N | H | H | H | Cl | H | nonafluoro-2-butyl | H | CF3 |
| 19-1442 | 2-chloro-4-fluorophenyl | Me | C(O)OMe | N | H | H | H | Cl | H | nonafluoro-2-butyl | H | CF3 |
| 19-1445 | 2-bromo-4-chlorophenyl | C(O)OMe | Me | N | H | H | H | Cl | H | nonafluoro-2-butyl | H | CF3 |
| 19-1447 | 2-chloro-4-nitrophenyl | Me | Me | N | H | H | H | Cl | H | nonafluoro-2-butyl | H | i-C3F7 |
| 19-1453 | 2-chloropyridin-3-yl | Me | Me | N | H | H | H | Cl | H | nonafluoro-2-butyl | H | CF3 |
| 19-1464 | 6-nitropyridin-3-yl | Me | C(O)OEt | N | H | H | H | Cl | H | nonafluoro-2-butyl | H | CF3 |
| 19-1466 | 5-fluoropyridin-3-yl | C(O)OEt | Me | N | H | H | H | Cl | H | nonafluoro-2-butyl | H | C2F5 |
| 19-1468 | 5-bromopyridin-3-yl | Me | Me | N | H | H | H | Cl | H | nonafluoro-2-butyl | H | n-C3F7 |
| 19-1469 | 5-iodopyridin-3-yl | Me | Me | N | H | H | H | Cl | H | nonafluoro-2-butyl | H | i-C3F7 |
| 19-1472 | 5-cyanopyridin-3-yl | Me | C(O)C(O)Me | N | H | H | H | Cl | H | nonafluoro-2-butyl | H | CF3 |
| 19-1473 | 4-fluoropyridin-3-yl | Me | Me | N | H | H | H | Cl | H | nonafluoro-2-butyl | H | C2F5 |
| 19-1475 | 4-bromopyridin-3-yl | C(O)C(O)Me | Me | N | H | H | H | Cl | H | nonafluoro-2-butyl | H | CF3 |
| 19-1477 | 4-(trifluoromethyl)pyridin-3-yl | Me | Me | N | H | H | H | Cl | H | nonafluoro-2-butyl | H | n-C3F7 |
| 19-1478 | 4-nitropyridin-3-yl | C(O)C(O)Et | Me | N | H | H | H | Cl | H | nonafluoro-2-butyl | H | i-C3F7 |
| 19-1479 | 4-cyanopyridin-3-yl | Me | C(O)C(O)Et | N | H | H | H | Cl | H | nonafluoro-2-butyl | H | CF3 |
| 19-1484 | 3-bromopyridin-4-yl | C(O)Et | Me | N | H | H | H | Cl | H | nonafluoro-2-butyl | H | CF3 |
| 19-1491 | 4-bromopyridin-2-yl | Me | C(O)Me | N | H | H | H | Cl | H | nonafluoro-2-butyl | H | CF3 |
| 19-1492 | 5-iodopyridin-2-yl | C(O)Me | Me | N | H | H | H | Cl | H | nonafluoro-2-butyl | H | CF3 |
| 19-1494 | 4-cyanopyridin-2-yl | C(O)Et | Me | N | H | H | H | Cl | H | nonafluoro-2-butyl | H | C2F5 |
| 19-1495 | phenyl | Me | Me | N | H | H | H | Br | H | heptafluoroisopropyl | H | CF3 |
| 19-1496 | 2-fluorophenyl | Me | Me | N | H | H | H | Br | H | heptafluoroisopropyl | H | CF3 |
| 19-1509 | (3-trifluoromethyl)phenyl | S(O)2Me | Me | N | H | H | H | Br | H | heptafluoroisopropyl | H | CF3 |

TABLE 19-continued

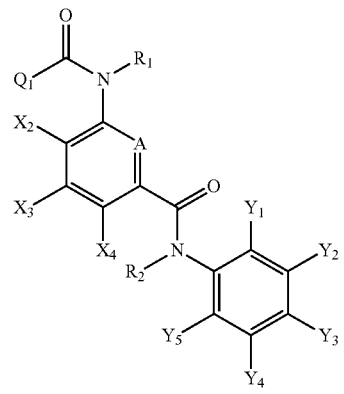

| compound number | $Q_1$ | $R_1$ | $R_2$ | A | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 19-1514 | 2-cyanophenyl | Me | S(O)2Me | N | H | H | H | Br | H | heptafluoroisopropyl | H | CF3 |
| 19-1515 | 3-cyanophenyl | Me | Me | N | H | H | H | Br | H | heptafluoroisopropyl | H | CF3 |
| 19-1516 | 4-cyanophenyl | Me | Me | N | H | H | H | Br | H | heptafluoroisopropyl | H | CF3 |
| 19-1523 | 2-bromo-4-chlorophenyl | Me | S(O)2Et | N | H | H | H | Br | H | heptafluoroisopropyl | H | CF3 |
| 19-1527 | 4-cyano-2-fluorophenyl | S(O)2Et | Me | N | H | H | H | Br | H | heptafluoroisopropyl | H | CF3 |
| 19-1531 | 2-chloropyridin-3-yl | Me | Me | N | H | H | H | Br | H | heptafluoroisopropyl | H | CF3 |
| 19-1542 | 6-nitropyridin-3-yl | CH2Ph | Me | N | H | H | H | Br | H | heptafluoroisopropyl | H | CF3 |
| 19-1546 | 5-bromopyridin-3-yl | Me | CH2Ph | N | H | H | H | Br | H | heptafluoroisopropyl | H | CF3 |
| 19-1551 | 4-fluoropyridin-3-yl | CH2(3-Py) | Me | N | H | H | H | Br | H | heptafluoroisopropyl | H | CF3 |
| 19-1556 | 4-nitropyridin-3-yl | Me | CH2(3-Py) | N | H | H | H | Br | H | heptafluoroisopropyl | H | CF3 |
| 19-1570 | 5-iodopyridin-2-yl | Me | CH2(3-Py-N-oxide) | N | H | H | H | Br | H | heptafluoroisopropyl | H | CF3 |
| 19-1572 | 4-cyanopyridin-2-yl | CH2(3-Py-N-oxide) | Me | N | H | H | H | Br | H | heptafluoroisopropyl | H | CF3 |
| 19-1573 | phenyl | Me | Me | N | H | H | H | Br | H | nonafluoro-2-butyl | H | CF3 |
| 19-1574 | 2-fluorophenyl | Me | Me | N | H | H | H | Br | H | nonafluoro-2-butyl | H | CF3 |
| 19-1593 | 3-cyanophenyl | Me | Me | N | H | H | H | Br | H | nonafluoro-2-butyl | H | CF3 |
| 19-1594 | 4-cyanophenyl | Me | Me | N | H | H | H | Br | H | nonafluoro-2-butyl | H | CF3 |
| 19-1600 | 4-bromo-2-chlorophenyl | Et | Me | N | H | H | H | Br | H | nonafluoro-2-butyl | H | CF3 |
| 19-1603 | 2-chloro-4-nitrophenyl | Me | Et | N | H | H | H | Br | H | nonafluoro-2-butyl | H | CF3 |
| 19-1609 | 2-chloropyridin-3-yl | Me | Me | N | H | H | H | Br | H | nonafluoro-2-butyl | H | CF3 |
| 19-1626 | 5-(trifluoromethyl)pyridin-3-yl | CN | Me | N | H | H | H | Br | H | nonafluoro-2-butyl | H | CF3 |
| 19-1627 | 5-nitropyridin-3-yl | Me | CN | N | H | H | H | Br | H | nonafluoro-2-butyl | H | CF3 |
| 19-1651 | phenyl | Me | Me | N | H | H | H | I | H | heptafluoroisopropyl | H | CF3 |
| 19-1652 | 2-fluorophenyl | Me | Me | N | H | H | H | I | H | heptafluoroisopropyl | H | CF3 |
| 19-1671 | 3-cyanophenyl | Me | Me | N | H | H | H | I | H | heptafluoroisopropyl | H | CF3 |
| 19-1672 | 4-cyanophenyl | Me | Me | N | H | H | H | I | H | heptafluoroisopropyl | H | CF3 |
| 19-1687 | 2-chloropyridin-3-yl | Me | Me | N | H | H | H | I | H | heptafluoroisopropyl | H | CF3 |
| 19-1700 | 5-fluoropyridin-3-yl | C(O)Me | Me | N | H | H | H | I | H | heptafluoroisopropyl | H | CF3 |
| 19-1705 | 5-nitropyridin-3-yl | Me | C(O)Me | N | H | H | H | I | H | heptafluoroisopropyl | H | CF3 |
| 19-1729 | phenyl | Me | Me | N | H | H | H | I | H | nonafluoro-2-butyl | H | CF3 |
| 19-1730 | 2-fluorophenyl | Me | Me | N | H | H | H | I | H | nonafluoro-2-butyl | H | CF3 |
| 19-1749 | 3-cyanophenyl | Me | Me | N | H | H | H | I | H | nonafluoro-2-butyl | H | CF3 |
| 19-1750 | 4-cyanophenyl | Me | Me | N | H | H | H | I | H | nonafluoro-2-butyl | H | CF3 |
| 19-1765 | 2-chloropyridin-3-yl | Me | Me | N | H | H | H | I | H | nonafluoro-2-butyl | H | CF3 |
| 19-2003 | phenyl | Me | Me | N | H | H | H | OCF3 | H | heptafluoroisopropyl | H | OCF3 |
| 19-2034 | 2-chloropyridin-3-yl | Me | Me | N | H | H | H | OCF3 | H | heptafluoroisopropyl | H | OCF3 |
| 19-2059 | phenyl | Me | Me | N | H | H | H | OCF3 | H | nonafluoro-2-butyl | H | OCF3 |
| 19-2090 | 2-chloropyridin-3-yl | Me | Me | N | H | H | H | OCF3 | H | nonafluoro-2-butyl | H | OCF3 |
| 19-2115 | phenyl | Me | Me | N | H | H | H | CF3 | H | heptafluoroisopropyl | H | OCF3 |
| 19-2146 | 2-chloropyridin-3-yl | Me | Me | N | H | H | H | CF3 | H | heptafluoroisopropyl | H | OCF3 |
| 19-2171 | phenol | Me | Me | N | H | H | H | CF3 | H | nonafluoro-2-butyl | H | OCF3 |
| 19-2202 | 2-chloropyridin-3-yl | Me | Me | N | H | H | H | CF3 | H | nonafluoro-2-butyl | H | OCF3 |
| 19-2227 | phenyl | Me | Me | N | H | H | H | CF3 | H | heptafluoroisopropyl | H | CF3 |
| 19-2247 | 3-cyanophenyl | Me | Me | N | H | H | H | CF3 | H | heptafluoroisopropyl | H | CF3 |
| 19-2248 | 4-cyanophenyl | Me | Me | N | H | H | H | CF3 | H | heptafluoroisopropyl | H | CF3 |
| 19-2263 | 2-chloropyridin-3-yl | Me | Me | N | H | H | H | CF3 | H | heptafluoroisopropyl | H | CF3 |
| 19-2295 | phenyl | Me | Me | N | H | H | H | CF3 | H | nonafluoro-2-butyl | H | CF3 |
| 19-2315 | 3-cyanophenyl | Me | Me | N | H | H | H | CF3 | H | nonafluoro-2-butyl | H | CF3 |
| 19-2316 | 4-cyanophenyl | Me | Me | N | H | H | H | CF3 | H | nonafluoro-2-butyl | H | CF3 |
| 19-2331 | 2-chloropyridin-3-yl | Me | Me | N | H | H | H | CF3 | H | nonafluoro-2-butyl | H | CF3 |
| 19-2559 | phenyl | Me | Me | N-oxide | H | H | H | F | H | heptafluoroisopropyl | H | F |
| 19-2560 | 3-cyanophenyl | Me | Me | N-oxide | H | H | H | F | H | heptafluoroisopropyl | H | F |
| 19-2561 | 4-cyanophenyl | Me | Me | N-oxide | H | H | H | F | H | heptafluoroisopropyl | H | F |
| 19-2562 | 2-chloropyridin-3-yl | Me | Me | N-oxide | H | H | H | F | H | heptafluoroisopropyl | H | F |

TABLE 19-continued

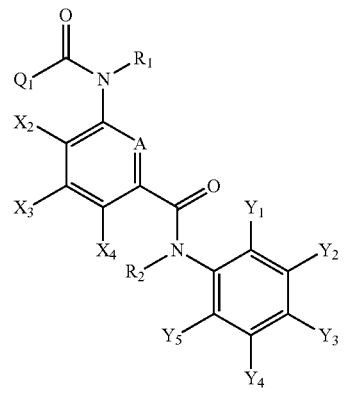

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 19-2563 | phenol | Me | Me | N-oxide | H | H | H | F | H | nonafluoro-2-butyl | H | F |
| 19-2564 | 3-cyanophenyl | Me | Me | N-oxide | H | H | H | F | H | nonafluoro-2-butyl | H | F |
| 19-2565 | 4-cyanophenyl | Me | Me | N-oxide | H | H | H | F | H | nonafluoro-2-butyl | H | F |
| 19-2566 | 2-chloropyridin-3-yl | Me | Me | N-oxide | H | H | H | F | H | nonafluoro-2-butyl | H | F |
| 19-2567 | phenyl | Me | Me | N-oxide | H | H | H | Cl | H | heptafluoroisopropyl | H | Cl |
| 19-2587 | 3-cyanophenyl | Me | Me | N-oxide | H | H | H | Cl | H | heptafluoroisopropyl | H | Cl |
| 19-2588 | 4-cyanophenyl | Me | Me | N-oxide | H | H | H | Cl | H | heptafluoroisopropyl | H | Cl |
| 19-2603 | 2-chloropyridin-3-yl | Me | Me | N-oxide | H | H | H | Cl | H | heptafluoroisopropyl | H | Cl |
| 19-2645 | phenyl | Me | Me | N-oxide | H | H | H | Cl | H | nonafluoro-2-butyl | H | Cl |
| 19-2665 | 3-cyanophenyl | Me | Me | N-oxide | H | H | H | Cl | H | nonafluoro-2-butyl | H | Cl |
| 19-2666 | 4-cyanophenyl | Me | Me | N-oxide | H | H | H | Cl | H | nonafluoro-2-butyl | H | Cl |
| 19-2681 | 2-chloropyridin-3-yl | Me | Me | N-oxide | H | H | H | Cl | H | nonafluoro-2-butyl | H | Cl |
| 19-2723 | phenyl | Me | Me | N-oxide | H | H | H | Br | H | heptafluoroisopropyl | H | Br |
| 19-2743 | 3-cyanophenyl | Me | Me | N-oxide | H | H | H | Br | H | heptafluoroisopropyl | H | Br |
| 19-2744 | 4-cyanophenyl | Me | Me | N-oxide | H | H | H | Br | H | heptafluoroisopropyl | H | Br |
| 19-2759 | 2-chloropyridin-3-yl | Me | Me | N-oxide | H | H | H | Br | H | heptafluoroisopropyl | H | Br |
| 19-2801 | phenyl | Me | Me | N-oxide | H | H | H | Br | H | nonafluoro-2-butyl | H | Br |
| 19-2821 | 3-cyanophenyl | Me | Me | N-oxide | H | H | H | Br | H | nonafluoro-2-butyl | H | Br |
| 19-2822 | 4-cyanophenyl | Me | Me | N-oxide | H | H | H | Br | H | nonafluoro-2-butyl | H | Br |
| 19-2837 | 2-chloropyridin-3-yl | Me | Me | N-oxide | H | H | H | Br | H | nonafluoro-2-butyl | H | Br |
| 19-2879 | phenyl | Me | Me | N-oxide | H | H | H | I | H | heptafluoroisopropyl | H | I |
| 19-2899 | 3-cyanophenyl | Me | Me | N-oxide | H | H | H | I | H | heptafluoroisopropyl | H | I |
| 19-2900 | 4-cyanophenyl | Me | Me | N-oxide | H | H | H | I | H | heptafluoroisopropyl | H | I |
| 19-2915 | 2-chloropyridin-3-yl | Me | Me | N-oxide | H | H | H | I | H | heptafluoroisopropyl | H | I |
| 19-2957 | phenyl | Me | Me | N-oxide | H | H | H | I | H | nonafluoro-2-butyl | H | I |
| 19-2977 | 3-cyanophenyl | Me | Me | N-oxide | H | H | H | I | H | nonafluoro-2-butyl | H | I |
| 19-2978 | 4-cyanophenyl | Me | Me | N-oxide | H | H | H | I | H | nonafluoro-2-butyl | H | I |
| 19-2993 | 2-chloropyridin-3-yl | Me | Me | N-oxide | H | H | H | I | H | nonafluoro-2-butyl | H | I |
| 19-3231 | phenyl | Me | Me | N-oxide | H | H | H | Cl | H | heptafluoroisopropyl | H | OCF3 |
| 19-3251 | 3-cyanophenyl | Me | Me | N-oxide | H | H | H | Cl | H | heptafluoroisopropyl | H | OCF3 |
| 19-3252 | 4-cyanophenyl | Me | Me | N-oxide | H | H | H | Cl | H | heptafluoroisopropyl | H | OCF3 |
| 19-3267 | 2-chloropyridin-3-yl | Me | Me | N-oxide | H | H | H | Cl | H | heptafluoroisopropyl | H | OCF3 |
| 19-3309 | phenyl | Me | Me | N-oxide | H | H | H | Cl | H | nonafluoro-2-butyl | H | OCF3 |
| 19-3329 | 3-cyanophenyl | Me | Me | N-oxide | H | H | H | Cl | H | nonafluoro-2-butyl | H | OCF3 |
| 19-3330 | 4-cyanophenyl | Me | Me | N-oxide | H | H | H | Cl | H | nonafluoro-2-butyl | H | OCF3 |
| 19-3345 | 2-chloropyridin-3-yl | Me | Me | N-oxide | H | H | H | Cl | H | nonafluoro-2-butyl | H | OCF3 |
| 19-3387 | phenyl | Me | Me | N-oxide | H | H | H | Br | H | heptafluoroisopropyl | H | OCF3 |
| 19-3407 | 3-cyanophenyl | Me | Me | N-oxide | H | H | H | Br | H | heptafluoroisopropyl | H | OCF3 |
| 19-3408 | 4-cyanophenyl | Me | Me | N-oxide | H | H | H | Br | H | heptafluoroisopropyl | H | OCF3 |
| 19-3423 | 2-chloropyridin-3-yl | Me | Me | N-oxide | H | H | H | Br | H | heptafluoroisopropyl | H | OCF3 |
| 19-3465 | phenyl | Me | Me | N-oxide | H | H | H | Br | H | nonafluoro-2-butyl | H | OCF3 |
| 19-3485 | 3-cyanophenyl | Me | Me | N-oxide | H | H | H | Br | H | nonafluoro-2-butyl | H | OCF3 |
| 19-3486 | 4-cyanophenyl | Me | Me | N-oxide | H | H | H | Br | H | nonafluoro-2-butyl | H | OCF3 |
| 19-3501 | 2-chloropyridin-3-yl | Me | Me | N-oxide | H | H | H | Br | H | nonafluoro-2-butyl | H | OCF3 |
| 19-3543 | phenyl | Me | Me | N-oxide | H | H | H | I | H | heptafluoroisopropyl | H | OCF3 |
| 19-3563 | 3-cyanophenyl | Me | Me | N-oxide | H | H | H | I | H | heptafluoroisopropyl | H | OCF3 |
| 19-3564 | 4-cyanophenyl | Me | Me | N-oxide | H | H | H | I | H | heptafluoroisopropyl | H | OCF3 |
| 19-3579 | 2-chloropyridin-3-yl | Me | Me | N-oxide | H | H | H | I | H | heptafluoroisopropyl | H | OCF3 |
| 19-3621 | phenyl | Me | Me | N-oxide | H | H | H | I | H | nonafluoro-2-butyl | H | OCF3 |
| 19-3641 | 3-cyanophenyl | Me | Me | N-oxide | H | H | H | I | H | nonafluoro-2-butyl | H | OCF3 |
| 19-3642 | 4-cyanophenyl | Me | Me | N-oxide | H | H | H | I | H | nonafluoro-2-butyl | H | OCF3 |
| 19-3657 | 2-chloropyridin-3-yl | Me | Me | N-oxide | H | H | H | I | H | nonafluoro-2-butyl | H | OCF3 |
| 19-3895 | phenyl | Me | Me | N-oxide | H | H | H | F | H | heptafluoroisopropyl | H | CF3 |
| 19-3896 | phenyl | Me | Me | N-oxide | H | H | H | Cl | H | heptafluoroisopropyl | H | CF3 |
| 19-3916 | 3-cyanophenyl | Me | Me | N-oxide | H | H | H | Cl | H | heptafluoroisopropyl | H | CF3 |

TABLE 19-continued

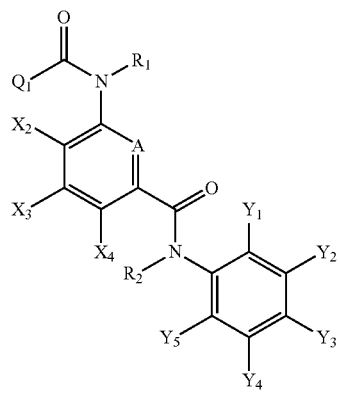

| compound number | $Q_1$ | $R_1$ | $R_2$ | A | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 19-3917 | 4-cyanophenyl | Me | Me | N-oxide | H | H | H | Cl | H | heptafluoroisopropyl | H | CF3 |
| 19-3932 | 2-chloropyridin-3-yl | Me | Me | N-oxide | H | H | H | Cl | H | heptafluoroisopropyl | H | CF3 |
| 19-3974 | phenyl | Me | Me | N-oxide | H | H | H | F | H | nonafluoro-2-butyl | H | CF3 |
| 19-3975 | phenyl | Me | Me | N-oxide | H | H | H | Cl | H | nonafluoro-2-butyl | H | CF3 |
| 19-3995 | 3-cyanophenyl | Me | Me | N-oxide | H | H | H | Cl | H | nonafluoro-2-butyl | H | CF3 |
| 19-3996 | 4-cyanophenyl | Me | Me | N-oxide | H | H | H | Cl | H | nonafluoro-2-butyl | H | CF3 |
| 19-4011 | 2-chloropyridin-3-yl | Me | Me | N-oxide | H | H | H | Cl | H | nonafluoro-2-butyl | H | CF3 |
| 19-4053 | phenyl | Me | Me | N-oxide | H | H | H | Br | H | heptafluoroisopropyl | H | CF3 |
| 19-4073 | 3-cyanophenyl | Me | Me | N-oxide | H | H | H | Br | H | heptafluoroisopropyl | H | CF3 |
| 19-4074 | 4-cyanophenyl | Me | Me | N-oxide | H | H | H | Br | H | heptafluoroisopropyl | H | CF3 |
| 19-4089 | 2-chloropyridin-3-yl | Me | Me | N-oxide | H | H | H | Br | H | heptafluoroisopropyl | H | CF3 |
| 19-4131 | phenyl | Me | Me | N-oxide | H | H | H | Br | H | nonafluoro-2-butyl | H | CF3 |
| 19-4151 | 3-cyanophenol | Me | Me | N-oxide | H | H | H | Br | H | nonafluoro-2-butyl | H | CF3 |
| 19-4152 | 4-cyanophenyl | Me | Me | N-oxide | H | H | H | Br | H | nonafluoro-2-butyl | H | CF3 |
| 19-4167 | 2-chloropyridin-3-yl | Me | Me | N-oxide | H | H | H | Br | H | nonafluoro-2-butyl | H | CF3 |
| 19-4209 | phenol | Me | Me | N-oxide | H | H | H | I | H | heptafluoroisopropyl | H | CF3 |
| 19-4229 | 3-cyanophenyl | Me | Me | N-oxide | H | H | H | I | H | heptafluoroisopropyl | H | CF3 |
| 19-4230 | 4-cyanophenyl | Me | Me | N-oxide | H | H | H | I | H | heptafluoroisopropyl | H | CF3 |
| 19-4245 | 2-chloropyridin-3-yl | Me | Me | N-oxide | H | H | H | I | H | heptafluoroisopropyl | H | CF3 |
| 19-4287 | phenyl | Me | Me | N-oxide | H | H | H | I | H | nonafluoro-2-butyl | H | CF3 |
| 19-4307 | 3-cyanophenyl | Me | Me | N-oxide | H | H | H | I | H | nonafluoro-2-butyl | H | CF3 |
| 19-4308 | 4-cyanophenyl | Me | Me | N-oxide | H | H | H | I | H | nonafluoro-2-butyl | H | CF3 |
| 19-4323 | 2-chloropyridin-3-yl | Me | Me | N-oxide | H | H | H | I | H | nonafluoro-2-butyl | H | CF3 |
| 19-4561 | phenyl | Me | Me | N-oxide | H | H | H | OCF3 | H | heptafluoroisopropyl | H | OCF3 |
| 19-4592 | 2-chloropyridin-3-yl | Me | Me | N-oxide | H | H | H | OCF3 | H | heptafluoroisopropyl | H | OCF3 |
| 19-4617 | phenyl | Me | Me | N-oxide | H | H | H | OCF3 | H | nonafluoro-2-butyl | H | OCF3 |
| 19-4648 | 2-chloropyridin-3-yl | Me | Me | N-oxide | H | H | H | OCF3 | H | nonafluoro-2-butyl | H | OCF3 |
| 19-4673 | phenyl | Me | Me | N-oxide | H | H | H | CF3 | H | heptafluoroisopropyl | H | OCF3 |
| 19-4704 | 2-chloropyridin-3-yl | Me | Me | N-oxide | H | H | H | CF3 | H | heptafluoroisopropyl | H | OCF3 |
| 19-4729 | phenyl | Me | Me | N-oxide | H | H | H | CF3 | H | nonafluoro-2-butyl | H | OCF3 |
| 19-4760 | 2-chloropyridin-3-yl | Me | Me | N-oxide | H | H | H | CF3 | H | nonafluoro-2-butyl | H | OCF3 |
| 19-4785 | phenyl | Me | Me | N-oxide | H | H | H | CF3 | H | heptafluoroisopropyl | H | CF3 |
| 19-4805 | 3-cyanophenyl | Me | Me | N-oxide | H | H | H | CF3 | H | heptafluoroisopropyl | H | CF3 |
| 19-4806 | 4-cyanophenyl | Me | Me | N-oxide | H | H | H | CF3 | H | heptafluoroisopropyl | H | CF3 |
| 19-4821 | 2-chloropyridin-3-yl | Me | Me | N-oxide | H | H | H | CF3 | H | heptafluoroisopropyl | H | CF3 |
| 19-4853 | phenyl | Me | Me | N-oxide | H | H | H | CF3 | H | nonafluoro-2-butyl | H | CF3 |
| 19-4873 | 3-cyanophenyl | Me | Me | N-oxide | H | H | H | CF3 | H | nonafluoro-2-butyl | H | CF3 |
| 19-4874 | 4-cyanophenyl | Me | Me | N-oxide | H | H | H | CF3 | H | nonafluoro-2-butyl | H | CF3 |
| 19-4889 | 2-chloropyridin-3-yl | Me | Me | N-oxide | H | H | H | CF3 | H | nonafluoro-2-butyl | H | CF3 |

TABLE 20

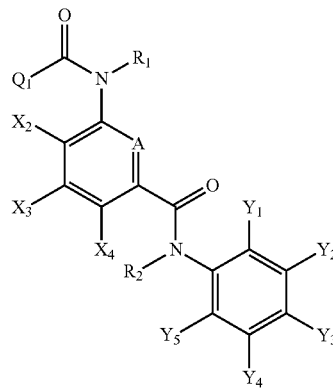

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 20-9 | 3-bromophenyl | H | Et | N | H | H | H | Cl | F | heptafluoroisopropyl | F | Cl |
| 20-39 | 2-iodopyridin-3-yl | H | H | N | H | H | H | Cl | Me | nonafluoro-2-butyl | Me | I |
| 20-152 | 3-bromophenyl | H | Et | N | H | H | H | Cl | F | heptafluoroisopropyl | F | OCF3 |
| 20-182 | 2-iodopyridin-3-yl | H | H | N | H | H | H | Cl | Me | nonafluoro-2-butyl | Me | OCF3 |
| 20-287 | phenyl | H | H | N | H | H | H | Cl | F | heptafluoroisopropyl | H | CF3 |
| 20-288 | 2-fluorophenyl | Me | H | N | H | H | H | Cl | H | heptafluoroisopropyl | F | CF3 |
| 20-289 | 3-fluorophenyl | H | Me | N | H | H | H | Cl | Cl | heptafluoroisopropyl | H | CF3 |
| 20-290 | 4-fluorophenyl | Me | Me | N | H | H | H | Cl | H | heptafluoroisopropyl | Cl | CF3 |
| 20-291 | 2-chlorophenyl | H | H | N | H | H | H | F | Br | heptafluoroisopropyl | H | CF3 |
| 20-292 | 3-chlorophenyl | H | H | N | H | H | H | Cl | H | heptafluoroisopropyl | Br | CF3 |
| 20-293 | 4-chlorophenyl | Et | H | N | H | H | H | Cl | I | heptafluoroisopropyl | H | C2F5 |
| 20-294 | 2-bromophenyl | H | H | N | H | H | H | Cl | H | heptafluoroisopropyl | I | CF3 |
| 20-295 | 3-bromophenyl | H | Et | N | H | H | H | Cl | F | heptafluoroisopropyl | F | CF3 |
| 20-296 | 4-bromophenyl | H | H | N | H | H | H | Cl | F | heptafluoroisopropyl | Cl | CF3 |
| 20-297 | 2-iodophenyl | H | H | N | H | H | H | Cl | F | heptafluoroisopropyl | Br | CF3 |
| 20-298 | 3-iodophenyl | Et | Et | N | H | H | H | Cl | F | pentafluoroethyl | I | C2F5 |
| 20-299 | 4-iodophenyl | H | H | N | H | H | H | Cl | Cl | pentafluoroethyl | F | CF3 |
| 20-300 | (2-trifluoromethyl)phenyl | H | H | N | H | H | H | Cl | Cl | heptafluoroisopropyl | Cl | CF3 |
| 20-301 | (3-trifluoromethyl)phenyl | n-Pr | H | N | H | H | H | Cl | Cl | heptafluoroisopropyl | Br | CF3 |
| 20-302 | (4-trifluoromethyl)phenyl | H | H | N | H | H | H | Cl | Cl | heptafluoroisopropyl | I | n-C3F7 |
| 20-303 | 2-nitrophonyl | H | n-Pr | N | H | H | H | Cl | Br | heptafluoroisopropyl | F | CF3 |
| 20-304 | 3-nitrophenyl | H | H | N | H | H | H | Cl | Br | heptafluoroisopropyl | Cl | CF3 |
| 20-305 | 4-nitrophenyl | H | H | N | H | H | H | Cl | Br | heptafluoroisopropyl | Br | CF3 |
| 20-306 | 2-cyanophenyl | n-Pr | n-Pr | N | H | H | H | Cl | Br | pentafluoroethyl | I | CF3 |
| 20-307 | 3-cyanophenyl | H | H | N | H | H | H | F | I | nonafluoro-2-butyl | F | CF3 |
| 20-308 | 4-cyanophenyl | H | H | N | H | H | H | Cl | I | nonafluoro-2-butyl | Cl | CF3 |
| 20-309 | 2,6-difluorophenyl | H | H | N | H | H | H | Cl | I | nonafluoro-2-butyl | Br | CF3 |
| 20-310 | 3,4-dichlorophenyl | H | H | N | H | H | H | Cl | I | nonafluoro-2-butyl | I | CF3 |
| 20-311 | 2,4-dichlorophenyl | H | H | N | H | H | H | Cl | Me | nonafluoro-2-butyl | H | CF3 |
| 20-312 | 2-chloro-4-fluorophenyl | H | H | N | H | H | H | Cl | H | nonafluoro-2-butyl | Me | CF3 |
| 20-313 | 2-chloro-4,5-difluorophenyl | i-Pr | H | N | H | H | H | Cl | Et | nonafluoro-2-butyl | H | CF3 |
| 20-314 | 4-bromo-2-chlorophenyl | H | H | N | H | H | H | Cl | H | nonafluoro-2-butyl | Et | CF3 |
| 20-315 | 2-bromo-4-chlorophenyl | H | H | N | H | H | H | Cl | n-Pr | nonafluoro-2-butyl | H | CF3 |
| 20-316 | 2-bromo-4-fluorophenyl | H | i-Pr | N | H | H | H | Cl | H | nonafluoro-2-butyl | n-Pr | CF3 |
| 20-317 | 2-chloro-4-nitrophenyl | i-Pr | i-Pr | N | H | H | H | Cl | i-Pr | nonafluoro-2-butyl | H | CF3 |
| 20-318 | 3,5-dicyanophenyl | H | H | N | H | H | H | Cl | H | nonafluoro-2-butyl | i-Pr | CF3 |
| 20-319 | 4-cyano-2-fluorophenyl | H | H | N | H | H | H | Cl | n-Bu | nonafluoro-2-butyl | H | CF3 |
| 20-320 | 2-chloro-4-cyanophenyl | H | H | N | H | H | H | Cl | H | nonafluoro-2-butyl | n-Bu | CF3 |
| 20-321 | pyridin-3-yl | H | H | N | H | H | H | Cl | i-Bu | nonafluoro-2-butyl | H | CF3 |
| 20-322 | 2-fluoropyridin-3-yl | H | H | N | H | H | H | Cl | H | nonafluoro-2-butyl | i-Bu | CF3 |
| 20-323 | 2-chloropyridin-3-yl | H | H | N | H | H | H | Cl | s-Bu | nonafluoro-2-butyl | H | C2F5 |
| 20-324 | 2-bromopyridin-3-yl | H | H | N | H | H | H | Cl | H | nonafluoro-2-butyl | s-Bu | CF3 |
| 20-325 | 2-iodopyridin-3-yl | H | H | N | H | H | H | Cl | Me | nonafluoro-2-butyl | Me | n-C3F7 |
| 20-326 | 2-(trifluoromethyl)pyridin-3-yl | H | H | N | H | H | H | Cl | Me | nonafluoro-2-butyl | Et | i-C3F7 |
| 20-327 | 2-nitropyridin-3-yl | C(O)Me | H | N | H | H | H | Cl | Me | nonafluoro-2-butyl | n-Pr | CF3 |
| 20-328 | 2-cyanopyridin-3-yl | H | H | N | H | H | H | Cl | Me | nonafluoro-2-butyl | i-Pr | CF3 |
| 20-329 | 6-fluoropyridin-3-yl | H | H | N | H | H | H | Cl | Me | nonafluoro-2-butyl | n-Bu | CF3 |
| 20-330 | 6-chloropyridin-3-yl | H | H | N | H | H | H | Cl | Me | nonafluoro-2-butyl | i-Bu | CF3 |
| 20-331 | 6-bromopyridin-3-yl | H | C(O)Me | N | H | H | H | Cl | Me | nonafluoro-2-butyl | s-Bu | CF3 |
| 20-332 | 6-iodopyridin-3-yl | H | H | N | H | H | H | Cl | Et | nonafluoro-2-butyl | Me | n-C3F7 |
| 20-333 | 6-(trifluoromethyl)pyridin-3-yl | H | H | N | H | H | H | Cl | Et | nonafluoro-2-butyl | Et | i-C3F7 |
| 20-334 | 6-nitropyridin-3-yl | C(O)Me | C(O)Me | N | H | H | H | Cl | Et | nonafluoro-2-butyl | n-Pr | CF3 |
| 20-335 | 6-cyanopyridin-3-yl | H | H | N | H | H | H | Cl | Et | nonafluoro-2-butyl | i-Pr | CF3 |
| 20-336 | phenyl | H | H | N | H | H | H | Br | Et | heptafluoroisopropyl | n-Bu | CF3 |
| 20-337 | 5-fluoropyridin-3-yl | H | H | N | H | H | H | Br | Et | heptafluoroisopropyl | i-Bu | CF3 |
| 20-338 | 5-chloropyridin-3-yl | H | H | N | H | H | H | Br | Et | heptafluoroisopropyl | s-Bu | CF3 |
| 20-339 | 5-bromopyridin-3-yl | H | H | N | H | H | H | Br | n-Pr | heptafluoroisopropyl | Me | CF3 |

TABLE 20-continued

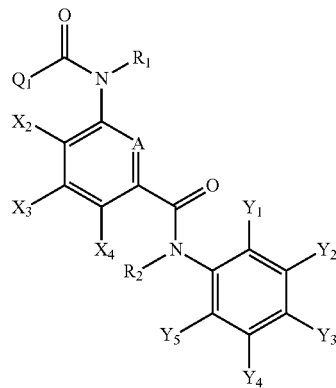

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 20-340 | 5-iodopyridin-3-yl | H | H | N | H | H | H | Br | n-Pr | heptafluoroisopropyl | Et | CF3 |
| 20-341 | 5-(trifluoromethyl)pyridin-3-yl | Me | Et | N | H | H | H | Br | n-Pr | pentafluoroethyl | n-Pr | CF3 |
| 20-342 | 5-nitropyridin-3-yl | H | H | N | H | H | H | Br | n-Pr | heptafluoroisopropyl | i-Pr | CF3 |
| 20-343 | 5-cyanopyridin-3-yl | H | H | N | H | H | H | Br | n-Pr | pentafluoroethyl | n-Bu | CF3 |
| 20-344 | 4-fluoropyridin-3-yl | H | H | N | H | H | H | Br | n-Pr | heptafluoroisopropyl | i-Bu | CF3 |
| 20-345 | 4-chloropyridin-3-yl | H | H | N | H | H | H | Br | n-Pr | heptafluoroisopropyl | s-Bu | CF3 |
| 20-346 | 4-bromopyridin-3-yl | Me | n-Pr | N | H | H | H | Br | i-Pr | heptafluoroisopropyl | Me | CF3 |
| 20-347 | 4-iodopyridin-3-yl | H | H | N | H | H | H | Br | i-Pr | heptafluoroisopropyl | Et | CF3 |
| 20-348 | 4-(trifluoromethyl)pyridin-3-yl | H | H | N | H | H | H | Br | i-Pr | heptafluoroisopropyl | n-Pr | CF3 |
| 20-349 | 4-nitropyridin-3-yl | H | H | N | H | H | H | Br | i-Pr | heptafluoroisopropyl | i-Pr | CF3 |
| 20-350 | 4-cyanopyridin-3-yl | H | H | N | H | H | H | Br | i-Pr | heptafluoroisopropyl | n-Bu | CF3 |
| 20-351 | 2,6-dichloropyridin-3-yl | H | H | N | H | H | H | Br | i-Pr | heptafluoroisopropyl | i-Bu | CF3 |
| 20-352 | pyridin-3-yl N-oxide | Me | i-Pr | N | H | H | H | Br | i-Pr | heptafluoroisopropyl | s-Bu | CF3 |
| 20-353 | pyridin-4-yl | H | H | N | H | H | H | Br | n-Bu | heptafluoroisopropyl | Me | CF3 |
| 20-354 | 2-chloropyridin-4-yl | H | H | N | H | H | H | Br | n-Bu | heptafluoroisopropyl | Et | CF3 |
| 20-355 | 3-bromopyridin-4-yl | H | H | N | H | H | H | Br | n-Bu | heptafluoroisopropyl | n-Pr | CF3 |
| 20-356 | 3,5-dichloropyridin-4-yl | H | H | N | H | H | H | Br | n-Bu | nonafluoro-2-butyl | i-Pr | CF3 |
| 20-357 | 3-(trifluoromethyl)pyridin-4-yl | H | H | N | H | H | H | Br | n-Bu | nonafluoro-2-butyl | n-Bu | CF3 |
| 20-358 | 2,6-dicyanopyridin-4-yl | H | H | N | H | H | H | Br | n-Bu | nonafluoro-2-butyl | i-Bu | CF3 |
| 20-359 | pyridin-4-yl N-oxide | Me | C(O)Me | N | H | H | H | Br | n-Bu | nonafluoro-2-butyl | s-Bu | CF3 |
| 20-360 | pyridin-2-yl | H | H | N | H | H | H | Br | i-Bu | nonafluoro-2-butyl | Me | CF3 |
| 20-361 | 3-chloropyridin-2-yl | H | H | N | H | H | H | Br | i-Bu | nonafluoro-2-butyl | Et | CF3 |
| 20-362 | 4-bromopyridin-2-yl | H | H | N | H | H | H | Br | i-Bu | nonafluoro-2-butyl | n-Pr | CF3 |
| 20-363 | 5-iodopyridin-2-yl | H | H | N | H | H | H | Br | i-Bu | nonafluoro-2-butyl | i-Pr | CF3 |
| 20-364 | 6-chloropyridin-2-yl | H | H | N | H | H | H | Br | i-Bu | nonafluoro-2-butyl | n-Bu | CF3 |
| 20-365 | 4-cyanopyridin-2-yl | H | H | N | H | H | H | Br | i-Bu | nonafluoro-2-butyl | i-Bu | CF3 |
| 20-366 | phenyl | H | H | N | H | H | H | Br | i-Bu | nonafluoro-2-butyl | s-Bu | C2F5 |
| 20-367 | 2-fluorophenyl | H | H | N | H | H | H | Br | s-Bu | nonafluoro-2-butyl | Me | CF3 |
| 20-368 | 3-fluorophenyl | H | H | N | H | H | H | Br | s-Bu | nonafluoro-2-butyl | Et | CF3 |
| 20-369 | 4-fluorophenyl | H | H | N | H | H | H | Br | s-Bu | nonafluoro-2-butyl | n-Pr | CF3 |
| 20-370 | 2-chlorophenyl | H | H | N | H | H | H | Br | s-Bu | nonafluoro-2-butyl | i-Pr | CF3 |
| 20-371 | 3-chlorophenyl | H | H | N | H | H | H | Br | s-Bu | nonafluoro-2-butyl | n-Bu | CF3 |
| 20-372 | 4-chlorophenyl | H | H | N | H | H | H | Br | s-Bu | nonafluoro-2-butyl | i-Bu | CF3 |
| 20-373 | 2-bromophenyl | Et | Me | N | H | H | H | Br | s-Bu | nonafluoro-2-butyl | s-Bu | CF3 |
| 20-374 | 3-bromophenyl | H | H | N | H | H | H | Br | F | nonafluoro-2-butyl | Me | CF3 |
| 20-375 | 4-bromophenyl | H | H | N | H | H | H | Br | F | nonafluoro-2-butyl | Et | CF3 |
| 20-376 | 2-iodophenyl | H | H | N | H | H | H | Br | F | nonafluoro-2-butyl | n-Pr | CF3 |
| 20-377 | 3-iodophenyl | H | H | N | H | H | H | Br | F | nonafluoro-2-butyl | i-Pr | CF3 |
| 20-378 | 4-iodophenyl | H | H | N | H | H | H | Br | F | nonafluoro-2-butyl | n-Bu | CF3 |
| 20-379 | (2-trifluoromethyl)phenyl | H | H | N | H | H | H | Br | F | nonafluoro-2-butyl | i-Bu | CF3 |
| 20-380 | (3-trifluoromethyl)phenyl | Et | n-Pr | N | H | H | H | Br | F | nonafluoro-2-butyl | s-Bu | CF3 |
| 20-381 | (4-trifluoromethyl)phenyl | Et | i-Pr | N | H | H | H | Br | Cl | nonafluoro-2-butyl | Me | CF3 |
| 20-382 | 2-nitrophenyl | H | H | N | H | H | H | Br | Cl | nonafluoro-2-butyl | Et | CF3 |
| 20-383 | phenyl | H | H | N | H | H | H | I | Cl | pentafluoroethyl | n-Pr | i-C3F7 |
| 20-384 | 3-nitrophenyl | H | H | N | H | H | H | I | Cl | heptafluoroisopropyl | i-Pr | CF3 |
| 20-385 | 4-nitrophenyl | H | H | N | H | H | H | I | Cl | heptafluoroisopropyl | n-Bu | CF3 |
| 20-386 | 2-cyanophonyl | Et | C(O)Me | N | H | H | H | I | Cl | heptafluoroisopropyl | i-Bu | CF3 |
| 20-387 | 3-cyanophenyl | H | H | N | H | H | H | I | Cl | heptafluoroisopropyl | s-Bu | CF3 |
| 20-388 | 4-cyanophenyl | H | H | N | H | H | H | I | Br | heptafluoroisopropyl | Me | CF3 |
| 20-389 | 2,6-difluorophenyl | H | H | N | H | H | H | I | Br | heptafluoroisopropyl | Et | CF3 |
| 20-390 | 3,4-dichlorophenyl | H | H | N | H | H | H | I | Br | pentafluoroethyl | n-Pr | CF3 |
| 20-391 | 2,4-dichlorophenyl | H | H | N | H | H | H | I | Br | heptafluoroisopropyl | i-Pr | CF3 |
| 20-392 | 2-chloro-4-fluorophenyl | H | H | N | H | H | H | I | Br | heptafluoroisopropyl | n-Bu | CF3 |
| 20-393 | 2-chloro-4,5-difluorophenyl | H | H | N | H | H | H | I | Br | heptafluoroisopropyl | i-Bu | CF3 |
| 20-394 | 4-bromo-2-chlorophenyl | H | H | N | H | H | H | I | Br | heptafluoroisopropyl | s-Bu | CF3 |
| 20-395 | 2-bromo-4-chlorophenyl | n-Pr | Me | N | H | H | H | I | I | heptafluoroisopropyl | Me | CF3 |
| 20-396 | 2-bromo-4-fluorophenyl | H | H | N | H | H | H | I | I | heptafluoroisopropyl | Et | CF3 |

TABLE 20-continued

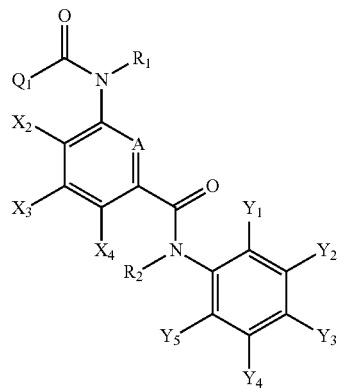

| compound number | Q₁ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 20-397 | 2-chloro-4-nitrophenyl | n-Pr | Et | N | H | H | H | I | I | heptafluoroisopropyl | n-Pr | CF3 |
| 20-398 | 3,5-dicyanophenyl | H | H | N | H | H | H | I | I | heptafluoroisopropyl | i-Pr | CF3 |
| 20-399 | 4-cyano-2-fluorophenyl | H | H | N | H | H | H | I | I | heptafluoroisopropyl | n-Bu | CF3 |
| 20-400 | 2-chloro-4-cyanophenyl | H | H | N | H | H | H | I | I | heptafluoroisopropyl | i-Bu | CF3 |
| 20-401 | pyridin-3-yl | H | H | N | H | H | H | I | I | heptafluoroisopropyl | s-Bu | CF3 |
| 20-402 | 2-fluoropyridin-3-yl | H | H | N | H | H | H | I | Me | heptafluoroisopropyl | F | C2F5 |
| 20-403 | 2-chloropyridin-3-yl | H | H | N | H | H | H | I | Me | nonafluoro-2-butyl | Cl | CF3 |
| 20-404 | 2-bromopyridin-3-yl | H | H | N | H | H | H | I | Me | nonafluoro-2-butyl | Br | n-C3F7 |
| 20-405 | 2-iodopyridin-3-yl | H | H | N | H | H | H | I | Me | nonafluoro-2-butyl | I | i-C3F7 |
| 20-406 | 2-(trifluoromethyl)pyridin-3-yl | H | H | N | H | H | H | I | Et | nonafluoro-2-butyl | F | CF3 |
| 20-407 | 2-nitropyridin-3-yl | H | H | N | H | H | H | I | Et | nonafluoro-2-butyl | Cl | CF3 |
| 20-408 | 2-cyanopyridin-3-yl | H | H | N | H | H | H | I | Et | nonafluoro-2-butyl | Br | CF3 |
| 20-409 | 6-fluoropyridin-3-yl | n-Pr | i-Pr | N | H | H | H | I | Et | nonafluoro-2-butyl | I | C2F5 |
| 20-410 | 6-chloropyridin-3-yl | H | H | N | H | H | H | I | n-Pr | nonafluoro-2-butyl | F | CF3 |
| 20-411 | 6-bromopyridin-3-yl | H | H | N | H | H | H | I | n-Pr | nonafluoro-2-butyl | Cl | CF3 |
| 20-412 | 6-iodopyridin-3-yl | H | H | N | H | H | H | I | n-Pr | nonafluoro-2-butyl | Br | CF3 |
| 20-413 | 6-(trifluoromethyl)pyridin-3-yl | H | H | N | H | H | H | I | n-Pr | nonafluoro-2-butyl | I | n-C3F7 |
| 20-414 | 6-nitropyridin-3-yl | H | H | N | H | H | H | I | i-Pr | nonafluoro-2-butyl | F | i-C3F7 |
| 20-415 | 6-cyanopyridin-3-yl | H | H | N | H | H | H | I | i-Pr | nonafluoro-2-butyl | Cl | CF3 |
| 20-416 | 5-fluoropyridin-3-yl | n-Pr | C(O)Me | N | H | H | H | I | i-Pr | nonafluoro-2-butyl | Br | CF3 |
| 20-417 | 5-chloropyridin-3-yl | H | H | N | H | H | H | I | i-Pr | nonafluoro-2-butyl | I | CF3 |
| 20-418 | 5-bromopyridin-3-yl | H | H | N | H | H | H | I | n-Bu | nonafluoro-2-butyl | F | CF3 |
| 20-419 | 5-iodopyridin-3-yl | H | H | N | H | H | H | I | n-Bu | nonafluoro-2-butyl | Cl | CF3 |
| 20-420 | 5-(trifluoromethyl)pyridin-3-yl | H | H | N | H | H | H | I | n-Bu | nonafluoro-2-butyl | Br | CF3 |
| 20-421 | 5-nitropyridin-3-yl | i-Pr | Me | N | H | H | H | I | n-Bu | nonafluoro-2-butyl | I | CF3 |
| 20-422 | 5-cyanopyridin-3-yl | H | H | N | H | H | H | I | i-Bu | nonafluoro-2-butyl | F | CF3 |
| 20-423 | 4-fluoropyridin-3-yl | H | H | N | H | H | H | I | i-Bu | nonafluoro-2-butyl | Cl | CF3 |
| 20-424 | 4-chloropyridin-3-yl | H | H | N | H | H | H | I | i-Bu | nonafluoro-2-butyl | Br | CF3 |
| 20-425 | 4-bromopyridin-3-yl | i-Pr | Et | N | H | H | H | I | i-Bu | nonafluoro-2-butyl | I | CF3 |
| 20-426 | 4-iodopyridin-3-yl | i-Pr | n-Pr | N | H | H | H | I | s-Bu | nonafluoro-2-butyl | F | CF3 |
| 20-427 | 4-(trifluoromethyl)pyridin-3-yl | H | H | N | H | H | H | I | s-Bu | nonafluoro-2-butyl | Cl | CF3 |
| 20-428 | 4-nitropyridin-3-yl | i-Pr | C(O)Me | N | H | H | H | I | s-Bu | nonafluoro-2-butyl | Br | CF3 |
| 20-429 | 4-cyanopyridin-3-yl | H | H | N | H | H | H | I | s-Bu | nonafluoro-2-butyl | I | CF3 |
| 20-438 | 3-bromophenyl | H | Et | N | H | H | H | OCF3 | F | heptafluoroisopropyl | F | OCF3 |
| 20-468 | 2-iodopyridin-3-yl | H | H | N | H | H | H | OCF3 | Me | nonafluoro-2-butyl | Me | OCF3 |
| 20-581 | 3-bromophenyl | H | Et | N | H | H | H | OCF3 | F | heptafluoroisopropyl | F | CF3 |
| 20-611 | 2-iodopyridin-3-yl | H | H | N | H | H | H | OCF3 | Me | nonafluoro-2-butyl | Me | CF3 |
| 20-724 | 3-bromophenyl | H | Et | N | H | H | H | CF3 | F | heptafluoroisopropyl | F | CF3 |
| 20-754 | 2-iodopyridin-3-yl | H | H | N | H | H | H | CF3 | Me | nonafluoro-2-butyl | Me | CF3 |
| 20-887 | 3-bromophenyl | H | Et | N-oxide | H | H | H | Cl | F | heptafluoroisopropyl | F | Cl |
| 20-897 | 2-iodopyridin-3-yl | H | H | N-oxide | H | H | H | Cl | Me | nonafluoro-2-butyl | Me | I |
| 20-1010 | 3-bromophenyl | H | Et | N-oxide | H | H | H | Cl | F | heptafluoroisopropyl | F | OCF3 |
| 20-1040 | 2-iodopyridin-3-yl | H | H | N-oxide | H | H | H | Cl | Me | nonafluoro-2-butyl | Me | OCF3 |
| 20-1154 | 4-bromophenyl | H | H | N-oxide | H | H | H | Cl | F | heptafluoroisopropyl | Cl | CF3 |
| 20-1169 | 2,4-dichlorophenyl | H | H | N-oxide | H | H | H | Cl | Me | nonafluoro-2-butyl | H | CF3 |
| 20-1233 | 4-bromophenyl | H | H | N-oxide | H | H | H | Br | F | nonafluoro-2-butyl | Et | CF3 |
| 20-1261 | 2-chloropyridin-3-yl | H | H | N-oxide | H | H | H | I | Me | nonafluoro-2-butyl | Cl | CF3 |
| 20-1296 | 3-bromophenyl | H | Et | N-oxide | H | H | H | OCF3 | F | heptafluoroisopropyl | F | OCF3 |
| 20-1326 | 2-iodopyridin-3-yl | H | H | N-oxide | H | H | H | OCF3 | Me | nonafluoro-2-butyl | Me | OCF3 |
| 20-1439 | 3-bromophenyl | H | Et | N-oxide | H | H | H | OCF3 | F | heptafluoroisopropyl | F | CF3 |
| 20-1469 | 2-iodopyridin-3-yl | H | H | N-oxide | H | H | H | OCF3 | Me | nonafluoro-2-butyl | Me | CF3 |
| 20-1582 | 3-bromophenyl | H | Et | N-oxide | H | H | H | CF3 | F | heptafluoroisopropyl | F | CF3 |
| 20-1612 | 2-iodopyridin-3-yl | H | H | N-oxide | H | H | H | CF3 | Me | nonafluoro-2-butyl | Me | CF3 |

TABLE 21

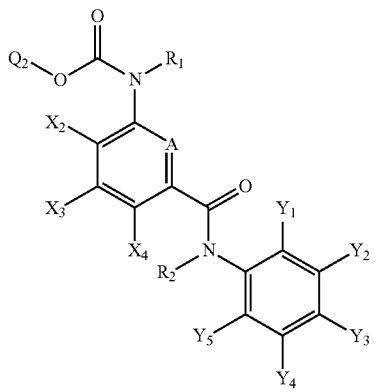

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 21-1 | 2,2,2-trichloroethyl | H | H | N | H | H | H | F | H | heptafluoroisopropyl | H | F |
| 21-2 | 2,2,2-trichloroethyl | H | H | N | H | H | H | F | H | nonafluoro-2-butyl | H | F |
| 21-13 | 2,2,2-trichloroethyl | H | H | N | H | H | H | Cl | H | heptafluoroisopropyl | H | Cl |
| 21-14 | 2,2,2-tribromoethyl | H | H | N | H | H | H | Cl | H | pentafluoroethyl | H | Cl |
| 21-22 | 1,3-dichloro-2-propyl | H | H | N | H | H | H | Cl | H | pentafluoroethyl | H | Cl |
| 21-26 | 4,4,4-trifluoro-n-butyl | H | H | N | H | H | H | Cl | H | heptafluoroisopropyl | H | Cl |
| 21-42 | 2,2,2-trichloroethyl | H | H | N | H | H | H | Cl | H | nonafluoro-2-butyl | H | Cl |
| 21-55 | 4,4,4-trifluoro-n-butyl | H | H | N | H | H | H | Cl | H | nonafluoro-2-butyl | H | Cl |
| 21-71 | 2,2,2-trichloroethyl | H | H | N | H | H | H | Br | H | heptafluoroisopropyl | H | Br |
| 21-74 | 3-fluoro-n-propyl | H | H | N | H | H | H | Br | H | pentafluoroethyl | H | Br |
| 21-80 | 1,3-dichloro-2-propyl | H | H | N | H | H | H | Br | H | pentafluoroethyl | H | Br |
| 21-84 | 4,4,4-trifluoro-n-butyl | H | H | N | H | H | H | Br | H | heptafluoroisopropyl | H | Br |
| 21-100 | 2,2,2-trichloroethyl | H | H | N | H | H | H | Br | H | nonafluoro-2-butyl | H | Br |
| 21-113 | 4,4,4-trifluoro-n-butyl | H | H | N | H | H | H | Br | H | nonafluoro-2-butyl | H | Br |
| 21-129 | 2,2,2-trichloroethyl | H | H | N | H | H | H | I | H | heptafluoroisopropyl | H | I |
| 21-131 | n-propyl | H | H | N | H | H | H | I | H | pentafluoroethyl | H | I |
| 21-138 | 1,3-dichloro-2-propyl | H | H | N | H | H | H | I | H | pentafluoroethyl | H | I |
| 21-142 | 4,4,4-trifluoro-n-butyl | H | H | N | H | H | H | I | H | heptafluoroisopropyl | H | I |
| 21-158 | 2,2,2-trichloroethyl | H | H | N | H | H | H | I | H | nonafluoro-2-butyl | H | I |
| 21-171 | 4,4,4-trifluoro-n-butyl | H | H | N | H | H | H | I | H | nonafluoro-2-butyl | H | I |
| 21-177 | 2,2,2-trichloroethyl | H | H | N | H | H | H | F | H | heptafluoroisopropyl | H | Cl |
| 21-178 | 2,2,2-trichloroethyl | H | H | N | H | H | H | F | H | heptafluoroisopropyl | H | Br |
| 21-179 | 2,2,2-trichloroethyl | H | H | N | H | H | H | F | H | heptafluoroisopropyl | H | I |
| 21-180 | 2,2,2-trichloroethyl | H | H | N | H | H | H | Cl | H | heptafluoroisopropyl | H | Br |
| 21-181 | 2,2,2-trichloroethyl | H | H | N | H | H | H | Cl | H | heptafluoroisopropyl | H | I |
| 21-182 | 2,2,2-trichloroethyl | H | H | N | H | H | H | Br | H | heptafluoroisopropyl | H | I |
| 21-183 | 2,2,2-trichloroethyl | H | H | N | H | H | H | F | H | nonafluoro-2-butyl | H | Cl |
| 21-184 | 2,2,2-trichloroethyl | H | H | N | H | H | H | F | H | nonafluoro-2-butyl | H | Br |
| 21-185 | 2,2,2-trichloroethyl | H | H | N | H | H | H | F | H | nonafluoro-2-butyl | H | I |
| 21-186 | 2,2,2-trichloroethyl | H | H | N | H | H | H | Cl | H | nonafluoro-2-butyl | H | Br |
| 21-187 | 2,2,2-trichloroethyl | H | H | N | H | H | H | Cl | H | nonafluoro-2-butyl | H | I |
| 21-188 | 2,2,2-trichloroethyl | H | H | N | H | H | H | Br | H | nonafluoro-2-butyl | H | I |
| 21-189 | 2,2,2-trichloroethyl | H | H | N | H | H | H | F | H | heptafluoroisopropyl | H | OCF3 |
| 21-190 | 2,2,2-trichloroethyl | H | H | N | H | H | H | F | H | nonafluoro-2-butyl | H | OCF3 |
| 21-201 | 2,2,2-trichloroethyl | H | H | N | H | H | H | Cl | H | heptafluoroisopropyl | H | OCF3 |
| 21-202 | 2,2,2-tribromoethyl | H | H | N | H | H | H | Cl | H | pentafluoroethyl | H | OCF3 |
| 21-206 | 3-bromo-n-propyl | H | H | N | H | H | H | Cl | H | heptafluoroisopropyl | H | OC2F5 |
| 21-210 | 1,3-dichloro-2-propyl | H | H | N | H | H | H | Cl | H | pentafluoroethyl | H | OC2F5 |
| 21-214 | 4,4,4-trifluoro-n-butyl | H | H | N | H | H | H | Cl | H | heptafluoroisopropyl | H | OCF3 |
| 21-226 | 2-cyanoethyl | H | H | N | H | H | H | Cl | H | nonafluoro-2-butyl | H | OC2F5 |
| 21-230 | 2,2,2-trichloroethyl | H | H | N | H | H | H | Cl | H | nonafluoro-2-butyl | H | OCF3 |
| 21-243 | 4,4,4-trifluoro-n-butyl | H | H | N | H | H | H | Cl | H | nonafluoro-2-butyl | H | OCF3 |
| 21-245 | s-butyl | H | H | N | H | H | H | Cl | H | nonafluoro-2-butyl | H | OC2F5 |
| 21-254 | 2-iodoethyl | H | H | N | H | H | H | Br | H | heptafluoroisopropyl | H | OC2F5 |
| 21-259 | 2,2,2-trichloroethyl | H | H | N | H | H | H | Br | H | heptafluoroisopropyl | H | OCF3 |
| 21-260 | 2,2,2-bromoethyl | H | H | N | H | H | H | Br | H | heptafluoroisopropyl | H | OCF3 |
| 21-272 | 4,4,4-trifluoro-n-butyl | H | H | N | H | H | H | Br | H | heptafluoroisopropyl | H | OCF3 |
| 21-288 | 2,2,2-trichloroethyl | H | H | N | H | H | H | Br | H | nonafluoro-2-butyl | H | OCF3 |
| 21-289 | 2,2,2-tribromoethyl | H | H | N | H | H | H | Br | H | nonafluoro-2-butyl | H | OC2F5 |
| 21-301 | 4,4,4-trifluoro-n-butyl | H | H | N | H | H | H | Br | H | nonafluoro-2-butyl | H | OCF3 |
| 21-317 | 2,2,2-trichloroethyl | H | H | N | H | H | H | I | H | heptafluoroisopropyl | H | OCF3 |
| 21-321 | 3-chloro-n-propyl | H | H | N | H | H | H | I | H | heptafluoroisopropyl | H | OC2F5 |
| 21-330 | 4,4,4-trifluoro-n-butyl | H | H | N | H | H | H | I | H | heptafluoroisopropyl | H | OCF3 |
| 21-346 | 2,2,2-trichloroethyl | H | H | N | H | H | H | I | H | nonafluoro-2-butyl | H | OCF3 |
| 21-359 | 4,4,4-trifluoro-n-butyl | H | H | N | H | H | H | I | H | nonafluoro-2-butyl | H | OCF3 |
| 21-363 | benzyl | H | H | N | H | H | H | I | H | nonafluoro-2-butyl | H | OC2F5 |
| 21-365 | 2,2,2-trichloroethyl | H | H | N | H | H | H | F | H | heptafluoroisopropyl | H | CF3 |
| 21-366 | 2,2,2-trichloroethyl | H | H | N | H | H | H | F | H | nonafluoro-2-butyl | H | CF3 |

TABLE 21-continued

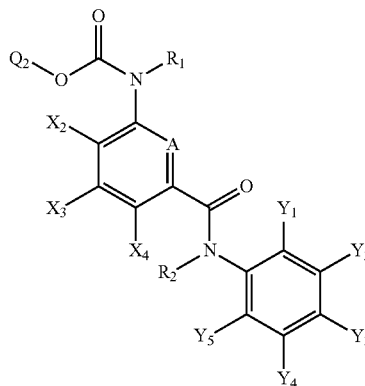

| compound number | Q2 | R1 | R2 | A | X2 | X3 | X4 | Y1 | Y2 | Y3 | Y4 | Y5 |
|---|---|---|---|---|---|---|---|---|---|---|---|---|
| 21-373 | 2-cyanoethyl | H | H | N | H | H | H | Cl | H | heptafluoroisopropyl | H | C2F5 |
| 21-377 | 2,2,2-trichloroethyl | H | H | N | H | H | H | Cl | H | heptafluoroisopropyl | H | CF3 |
| 21-378 | 2,2,2-tribromoethyl | H | H | N | H | H | H | Cl | H | pentafluoroethyl | H | CF3 |
| 21-383 | i-propyl | H | H | N | H | H | H | Cl | H | heptafluoroisopropyl | H | n-C3F7 |
| 21-390 | 4,4,4-trifluoro-n-butyl | H | H | N | H | H | H | Cl | H | heptafluoroisopropyl | H | CF3 |
| 21-397 | ethyl | H | H | N | H | H | H | Cl | H | nonafluoro-2-butyl | H | i-C3F7 |
| 21-406 | 2,2,2-trichloroethyl | H | H | N | H | H | H | Cl | H | nonafluoro-2-butyl | H | CF3 |
| 21-419 | 4,4,4-trifluoro-n-butyl | H | H | N | H | H | H | Cl | H | nonafluoro-2-butyl | H | CF3 |
| 21-425 | methyl | H | H | N | H | H | H | Br | H | heptafluoroisopropyl | H | CF3 |
| 21-426 | ethyl | H | H | N | H | H | H | Br | H | heptafluoroisopropyl | H | CF3 |
| 21-427 | 2-fluoroethyl | H | H | N | H | H | H | Br | H | heptafluoroisopropyl | H | CF3 |
| 21-428 | 2-chloroethyl | H | H | N | H | H | H | Br | H | heptafluoroisopropyl | H | CF3 |
| 21-429 | 2-bromoethyl | H | H | N | H | H | H | Br | H | heptafluoroisopropyl | H | CF3 |
| 21-430 | 2-iodoethyl | H | H | N | H | H | H | Br | H | heptafluoroisopropyl | H | CF3 |
| 21-431 | 2-cyanoethyl | H | H | N | H | H | H | Br | H | heptafluoroisopropyl | H | C2F5 |
| 21-432 | 2,2-difluoroethyl | H | H | N | H | H | H | Br | H | heptafluoroisopropyl | H | CF3 |
| 21-433 | 2,2-dichloroethyl | H | H | N | H | H | H | Br | H | heptafluoroisopropyl | H | CF3 |
| 21-434 | 2,2,2-trifluoroethyl | H | H | N | H | H | H | Br | H | heptafluoroisopropyl | H | CF3 |
| 21-435 | 2,2,2-trichloroethyl | H | H | N | H | H | H | Br | H | heptafluoroisopropyl | H | CF3 |
| 21-436 | 2,2,2-tribromoethyl | H | H | N | H | H | H | Br | H | heptafluoroisopropyl | H | CF3 |
| 21-437 | n-propyl | H | H | N | H | H | H | Br | H | heptafluoroisopropyl | H | CF3 |
| 21-438 | 3-fluoro-n-propyl | H | H | N | H | H | H | Br | H | heptafluoroisopropyl | H | CF3 |
| 21-439 | 3-chloro-n-propyl | H | H | N | H | H | H | Br | H | heptafluoroisopropyl | H | CF3 |
| 21-440 | 3-bromo-n-propyl | H | H | N | H | H | H | Br | H | heptafluoroisopropyl | H | CF3 |
| 21-441 | i-propyl | H | H | N | H | H | H | Br | H | heptafluoroisopropyl | H | CF3 |
| 21-442 | 1,2-difluoro-2-propyl | H | H | N | H | H | H | Br | H | heptafluoroisopropyl | H | n-C3F7 |
| 21-443 | 1,3-difluoro-2-propyl | H | H | N | H | H | H | Br | H | heptafluoroisopropyl | H | CF3 |
| 21-444 | 1,3-dichloro-2-propyl | H | H | N | H | H | H | Br | H | heptafluoroisopropyl | H | CF3 |
| 21-445 | 1-chloro-3-fluoro-2-propyl | H | H | N | H | H | H | Br | H | heptafluoroisopropyl | H | CF3 |
| 21-446 | 3,3,3-trifluoro-n-propyl | H | H | N | H | H | H | Br | H | heptafluoroisopropyl | H | CF3 |
| 21-447 | n-butyl | H | H | N | H | H | H | Br | H | heptafluoroisopropyl | H | CF3 |
| 21-448 | 4,4,4-trifluoro-n-butyl | H | H | N | H | H | H | Br | H | heptafluoroisopropyl | H | CF3 |
| 21-449 | i-butyl | H | H | N | H | H | H | Br | H | heptafluoroisopropyl | H | CF3 |
| 21-450 | s-butyl | H | H | N | H | H | H | Br | H | heptafluoroisopropyl | H | CF3 |
| 21-451 | vinyl | H | H | N | H | H | H | Br | H | heptafluoroisopropyl | H | CF3 |
| 21-452 | benzyl | H | H | N | H | H | H | Br | H | heptafluoroisopropyl | H | CF3 |
| 21-453 | phenyl | H | H | N | H | H | H | Br | H | heptafluoroisopropyl | H | CF3 |
| 21-454 | methyl | H | H | N | H | H | H | Br | H | nonafluoro-2-butyl | H | CF3 |
| 21-455 | ethyl | H | H | N | H | H | H | Br | H | nonafluoro-2-butyl | H | CF3 |
| 21-456 | 2-fluoroethyl | H | H | N | H | H | H | Br | H | nonafluoro-2-butyl | H | CF3 |
| 21-457 | 2-chloroethyl | H | H | N | H | H | H | Br | H | nonafluoro-2-butyl | H | CF3 |
| 21-458 | 2-bromoethyl | H | H | N | H | H | H | Br | H | nonafluoro-2-butyl | H | CF3 |
| 21-459 | 2-iodoethyl | H | H | N | H | H | H | Br | H | nonafluoro-2-butyl | H | CF3 |
| 21-460 | 2-cyanoethyl | H | H | N | H | H | H | Br | H | nonafluoro-2-butyl | H | CF3 |
| 21-461 | 2,2-difluoroethyl | H | H | N | H | H | H | Br | H | nonafluoro-2-butyl | H | CF3 |
| 21-462 | 2,2-dichloroethyl | H | H | N | H | H | H | Br | H | nonafluoro-2-butyl | H | CF3 |
| 21-463 | 2,2,2-trifluoroethyl | H | H | N | H | H | H | Br | H | nonafluoro-2-butyl | H | CF3 |
| 21-464 | 2,2,2-trichloroethyl | H | H | N | H | H | H | Br | H | nonafluoro-2-butyl | H | CF3 |
| 21-465 | 2,2,2-tribromoethyl | H | H | N | H | H | H | Br | H | nonafluoro-2-butyl | H | CF3 |
| 21-466 | n-propyl | H | H | N | H | H | H | Br | H | nonafluoro-2-butyl | H | CF3 |
| 21-467 | 3-fluoro-n-propyl | H | H | N | H | H | H | Br | H | nonafluoro-2-butyl | H | CF3 |
| 21-468 | 3-chloro-n-propyl | H | H | N | H | H | H | Br | H | nonafluoro-2-butyl | H | CF3 |
| 21-469 | 3-bromo-n-propyl | H | H | N | H | H | H | Br | H | nonafluoro-2-butyl | H | CF3 |
| 21-470 | i-propyl | H | H | N | H | H | H | Br | H | nonafluoro-2-butyl | H | CF3 |
| 21-471 | 1,2-difluoro-2-propyl | H | H | N | H | H | H | Br | H | nonafluoro-2-butyl | H | CF3 |
| 21-472 | 1,3-difluoro-2-propyl | H | H | N | H | H | H | Br | H | nonafluoro-2-butyl | H | CF3 |
| 21-473 | 1,3-dichloro-2-propyl | H | H | N | H | H | H | Br | H | nonafluoro-2-butyl | H | CF3 |
| 21-474 | 1-chloro-3-fluoro-2-propyl | H | H | N | H | H | H | Br | H | nonafluoro-2-butyl | H | CF3 |

TABLE 21-continued

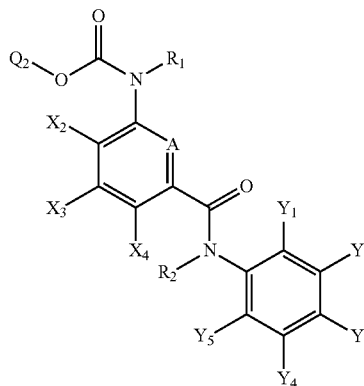

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 21-475 | 3,3,3-trifluoro-n-propyl | H | H | N | H | H | H | Br | H | nonafluoro-2-butyl | H | CF3 |
| 21-476 | n-butyl | H | H | N | H | H | H | Br | H | nonafluoro-2-butyl | H | CF3 |
| 21-477 | 4,4,4-trifluoro-n-butyl | H | H | N | H | H | H | Br | H | nonafluoro-2-butyl | H | CF3 |
| 21-478 | i-butyl | H | H | N | H | H | H | Br | H | nonafluoro-2-butyl | H | CF3 |
| 21-479 | s-butyl | H | H | N | H | H | H | Br | H | nonafluoro-2-butyl | H | CF3 |
| 21-480 | vinyl | H | H | N | H | H | H | Br | H | nonafluoro-2-butyl | H | CF3 |
| 21-481 | benzyl | H | H | N | H | H | H | Br | H | nonafluoro-2-butyl | H | CF3 |
| 21-482 | phenyl | H | H | N | H | H | H | Br | H | nonafluoro-2-butyl | H | i-C3F7 |
| 21-483 | methyl | H | H | N | H | H | H | I | H | heptafluoroisopropyl | H | CF3 |
| 21-484 | ethyl | H | H | N | H | H | H | I | H | heptafluoroisopropyl | H | CF3 |
| 21-485 | 2-fluoroethyl | H | H | N | H | H | H | I | H | heptafluoroisopropyl | H | CF3 |
| 21-486 | 2-chloroethyl | H | H | N | H | H | H | I | H | heptafluoroisopropyl | H | CF3 |
| 21-487 | 2-bromoethyl | H | H | N | H | H | H | I | H | heptafluoroisopropyl | H | CF3 |
| 21-488 | 2-iodoethyl | H | H | N | H | H | H | I | H | heptafluoroisopropyl | H | CF3 |
| 21-489 | 2-cyanoethyl | H | H | N | H | H | H | I | H | heptafluoroisopropyl | H | CF3 |
| 21-490 | 2,2-difluoroethyl | H | H | N | H | H | H | I | H | heptafluoroisopropyl | H | CF3 |
| 21-491 | 2,2-dichloroethyl | H | H | N | H | H | H | I | H | heptafluoroisopropyl | H | CF3 |
| 21-492 | 2,2,2-trifluoroethyl | H | H | N | H | H | H | I | H | heptafluoroisopropyl | H | CF3 |
| 21-493 | 2,2,2-trichloroethyl | H | H | N | H | H | H | I | H | heptafluoroisopropyl | H | CF3 |
| 21-494 | 2,2,2-tribromoethyl | H | H | N | H | H | H | I | H | heptafluoroisopropyl | H | CF3 |
| 21-495 | n-propyl | H | H | N | H | H | H | I | H | heptafluoroisopropyl | H | CF3 |
| 21-496 | 3-fluoro-n-propyl | H | H | N | H | H | H | I | H | heptafluoroisopropyl | H | CF3 |
| 21-497 | 3-chloro-n-propyl | H | H | N | H | H | H | I | H | heptafluoroisopropyl | H | CF3 |
| 21-498 | 3-bromo-n-propyl | H | H | N | H | H | H | I | H | heptafluoroisopropyl | H | C2F5 |
| 21-499 | i-propyl | H | H | N | H | H | H | I | H | heptafluoroisopropyl | H | CF3 |
| 21-500 | 1,2-difluoro-2-propyl | H | H | N | H | H | H | I | H | heptafluoroisopropyl | H | CF3 |
| 21-501 | 1,3-difluoro-2-propyl | H | H | N | H | H | H | I | H | heptafluoroisopropyl | H | CF3 |
| 21-502 | 1,3-dichloro-2-propyl | H | H | N | H | H | H | I | H | heptafluoroisopropyl | H | CF3 |
| 21-503 | 1-chloro-3-fluoro-2-propyl | H | H | N | H | H | H | I | H | heptafluoroisopropyl | H | CF3 |
| 21-504 | 3,3,3-trifluoro-n-propyl | H | H | N | H | H | H | I | H | heptafluoroisopropyl | H | CF3 |
| 21-505 | n-butyl | H | H | N | H | H | H | I | H | heptafluoroisopropyl | H | CF3 |
| 21-506 | 4,4,4-trifluoro-n-butyl | H | H | N | H | H | H | I | H | heptafluoroisopropyl | H | CF3 |
| 21-507 | i-butyl | H | H | N | H | H | H | I | H | heptafluoroisopropyl | H | CF3 |
| 21-508 | s-butyl | H | H | N | H | H | H | I | H | heptafluoroisopropyl | H | CF3 |
| 21-509 | vinyl | H | H | N | H | H | H | I | H | heptafluoroisopropyl | H | CF3 |
| 21-510 | benzyl | H | H | N | H | H | H | I | H | heptafluoroisopropyl | H | CF3 |
| 21-511 | phenyl | H | H | N | H | H | H | I | H | heptafluoroisopropyl | H | CF3 |
| 21-512 | methyl | H | H | N | H | H | H | I | H | nonafluoro-2-butyl | H | CF3 |
| 21-513 | ethyl | H | H | N | H | H | H | I | H | nonafluoro-2-butyl | H | CF3 |
| 21-514 | 2-fluoroethyl | H | H | N | H | H | H | I | H | nonafluoro-2-butyl | H | CF3 |
| 21-515 | 2-chloroethyl | H | H | N | H | H | H | I | H | nonafluoro-2-butyl | H | CF3 |
| 21-516 | 2-bromoethyl | H | H | N | H | H | H | I | H | nonafluoro-2-butyl | H | CF3 |
| 21-517 | 2-iodoethyl | H | H | N | H | H | H | I | H | nonafluoro-2-butyl | H | CF3 |
| 21-518 | 2-cyanoethyl | H | H | N | H | H | H | I | H | nonafluoro-2-butyl | H | CF3 |
| 21-519 | 2,2-difluoroethyl | H | H | N | H | H | H | I | H | nonafluoro-2-butyl | H | CF3 |
| 21-520 | 2,2-dichloroethyl | H | H | N | H | H | H | I | H | nonafluoro-2-butyl | H | CF3 |
| 21-521 | 2,2,2-trifluoroethyl | H | H | N | H | H | H | I | H | nonafluoro-2-butyl | H | CF3 |
| 21-522 | 2,2,2-trichloroethyl | H | H | N | H | H | H | I | H | nonafluoro-2-butyl | H | CF3 |
| 21-523 | 2,2,2-tribromoethyl | H | H | N | H | H | H | I | H | nonafluoro-2-butyl | H | CF3 |
| 21-524 | n-propyl | H | H | N | H | H | H | I | H | nonafluoro-2-butyl | H | n-C3F7 |
| 21-525 | 3-fluoro-n-propyl | H | H | N | H | H | H | I | H | nonafluoro-2-butyl | H | CF3 |
| 21-526 | 3-chloro-n-propyl | H | H | N | H | H | H | I | H | nonafluoro-2-butyl | H | CF3 |
| 21-527 | 3-bromo-n-propyl | H | H | N | H | H | H | I | H | nonafluoro-2-butyl | H | CF3 |
| 21-528 | i-propyl | H | H | N | H | H | H | I | H | nonafluoro-2-butyl | H | CF3 |
| 21-529 | 1,2-difluoro-2-propyl | H | H | N | H | H | H | I | H | nonafluoro-2-butyl | H | CF3 |
| 21-530 | 1,3-difluoro-2-propyl | H | H | N | H | H | H | I | H | nonafluoro-2-butyl | H | CF3 |
| 21-531 | 1,3-dichloro-2-propyl | H | H | N | H | H | H | I | H | nonafluoro-2-butyl | H | CF3 |
| 21-532 | 1-chloro-3-fluoro-2-propyl | H | H | N | H | H | H | I | H | nonafluoro-2-butyl | H | CF3 |

TABLE 21-continued

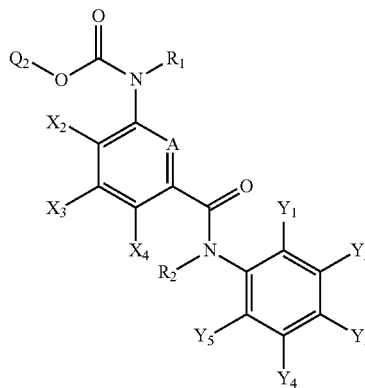

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 21-533 | 3,3,3-trifluoro-n-propyl | H | H | N | H | H | H | I | H | nonafluoro-2-butyl | H | CF3 |
| 21-534 | n-butyl | H | H | N | H | H | H | I | H | nonafluoro-2-butyl | H | CF3 |
| 21-535 | 4,4,4-trifluoro-n-butyl | H | H | N | H | H | H | I | H | nonafluoro-2-butyl | H | CF3 |
| 21-536 | i-butyl | H | H | N | H | H | H | I | H | nonafluoro-2-butyl | H | CF3 |
| 21-537 | s-butyl | H | H | N | H | H | H | I | H | nonafluoro-2-butyl | H | CF3 |
| 21-538 | vinyl | H | H | N | H | H | H | I | H | nonafluoro-2-butyl | H | i-C3F7 |
| 21-539 | benzyl | H | H | N | H | H | H | I | H | nonafluoro-2-butyl | H | CF3 |
| 21-540 | phenyl | H | H | N | H | H | H | I | H | nonafluoro-2-butyl | H | CF3 |
| 21-547 | 2-cyanoethyl | H | H | N | H | H | H | OCF3 | H | heptafluoroisopropyl | H | OC2F5 |
| 21-551 | 2,2,2-trichloroethyl | H | H | N | H | H | H | OCF3 | H | heptafluoroisopropyl | H | OCF3 |
| 21-552 | 2,2,2-tribromoethyl | H | H | N | H | H | H | OCF3 | H | pentafluoroethyl | H | OCF3 |
| 21-561 | 1-chloro-3-fluoro-2-propyl | H | H | N | H | H | H | OC2F5 | H | heptafluoroisopropyl | H | OC2F5 |
| 21-564 | 4,4,4-trifluoro-n-butyl | H | H | N | H | H | H | OCF3 | H | heptafluoroisopropyl | H | OCF3 |
| 21-566 | s-butyl | H | H | N | H | H | H | OC2F5 | H | heptafluoroisopropyl | H | OCF3 |
| 21-576 | 2-cyanoethyl | H | H | N | H | H | H | OC2F5 | H | nonafluoro-2-butyl | H | OCF3 |
| 21-580 | 2,2,2-trichloroethyl | H | H | N | H | H | H | OCF3 | H | nonafluoro-2-butyl | H | OCF3 |
| 21-581 | 2,2,2-tribromoethyl | H | H | N | H | H | H | OCF3 | H | nonafluoro-2-butyl | H | OC2F5 |
| 21-592 | n-butyl | H | H | N | H | H | H | OC2F5 | H | nonafluoro-2-butyl | H | OC2F5 |
| 21-593 | 4,4,4-trifluoro-n-butyl | H | H | N | H | H | H | OCF3 | H | nonafluoro-2-butyl | H | OCF3 |
| 21-605 | 2-cyanoethyl | H | H | N | H | H | H | CF3 | H | heptafluoroisopropyl | H | OC2F5 |
| 21-609 | 2,2,2-trichloroethyl | H | H | N | H | H | H | CF3 | H | heptafluoroisopropyl | H | OCF3 |
| 21-610 | 2,2,2-tribromoethyl | H | H | N | H | F1 | H | C2F5 | H | heptafluoroisopropyl | H | OC2F5 |
| 21-621 | n-butyl | H | H | N | H | H | H | n-C3F7 | H | heptafluoroisopropyl | H | OCF3 |
| 21-622 | 4,4,4-trifluoro-n-butyl | H | H | N | H | H | H | CF3 | H | heptafluoroisopropyl | H | OCF3 |
| 21-625 | vinyl | H | H | N | H | H | H | i-C3F7 | H | heptafluoroisopropyl | H | OCF3 |
| 21-633 | 2-iodoethyl | H | H | N | H | H | H | C2F5 | H | nonafluoro-2-butyl | H | OCF3 |
| 21-638 | 2,2,2-trichloroethyl | H | H | N | H | H | H | CF3 | H | nonafluoro-2-butyl | H | OCF3 |
| 21-640 | n-propyl | H | H | N | H | H | H | n-C3F7 | H | nonafluoro-2-butyl | H | OCF3 |
| 21-644 | i-propyl | H | H | N | H | H | H | CF3 | H | nonafluoro-2-butyl | H | OC2F5 |
| 21-651 | 4,4,4-trifluoro-n-butyl | H | H | N | H | H | H | CF3 | H | nonafluoro-2-butyl | H | OCF3 |
| 21-652 | i-butyl | H | H | N | H | H | H | i-C3F7 | H | nonafluoro-2-butyl | H | OCF3 |
| 21-655 | benzyl | H | H | N | H | H | H | n-C3F7 | H | nonafluoro-2-butyl | H | OC2F5 |
| 21-656 | phenyl | H | H | N | H | H | H | i-C3F7 | H | nonafluoro-2-butyl | H | OC2F5 |
| 21-667 | 2,2,2-trichloroethyl | H | H | N | H | H | H | CF3 | H | heptafluoroisopropyl | H | CF3 |
| 21-670 | 3-fluoro-n-propyl | H | H | N | H | H | H | C2F5 | H | heptafluoroisopropyl | H | CF3 |
| 21-673 | i-propyl | H | H | N | H | H | H | i-C3F7 | H | heptafluoroisopropyl | H | CF3 |
| 21-675 | 1,3-difluoro-2-propyl | H | H | N | H | H | H | CF3 | H | pentafluoroethyl | H | CF3 |
| 21-679 | n-butyl | H | H | N | H | H | H | C2F5 | H | heptafluoroisopropyl | H | C2F5 |
| 21-680 | 4,4,4-trifluoro-n-butyl | H | H | N | H | H | H | CF3 | H | heptafluoroisopropyl | H | CF3 |
| 21-681 | i-butyl | H | H | N | H | H | H | C2F5 | H | heptafluoroisopropyl | H | n-C3F7 |
| 21-683 | vinyl | H | H | N | H | H | H | n-C3F7 | H | heptafluoroisopropyl | H | CF3 |
| 21-696 | 2,2,2-trichloroethyl | H | H | H | H | H | H | CF3 | H | nonafluoro-2-butyl | H | CF3 |
| 21-708 | n-butyl | H | H | N | H | H | H | C2F5 | H | nonafluoro-2-butyl | H | i-C3F7 |
| 21-709 | 4,4,4-trifluoro-n-butyl | H | H | N | H | H | H | CF3 | H | nonafluoro-2-butyl | H | CF3 |
| 21-712 | vinyl | H | H | N | H | H | H | n-C3F7 | H | nonafluoro-2-butyl | H | i-C3F7 |
| 21-715 | 2,2,2-trichloroethyl | H | H | N-oxide | H | H | H | F | H | heptafluoroisopropyl | H | F |
| 21-716 | 2,2,2-trichloroethyl | H | H | N-oxide | H | H | H | F | H | nonafluoro-2-butyl | H | F |
| 21-727 | 2,2,2-trichloroethyl | H | H | N-oxide | H | H | H | Cl | H | heptafluoroisopropyl | H | Cl |
| 21-756 | 2,2,2-trichloroethyl | H | H | N-oxide | H | H | H | Cl | H | nonafluoro-2-butyl | H | Cl |
| 21-785 | 2,2,2-trichloroethyl | H | H | N-oxide | H | H | H | Br | H | heptafluoroisopropyl | H | Br |
| 21-814 | 2,2,2-trichloroethyl | H | H | N-oxide | H | H | H | Br | H | nonafluoro-2-butyl | H | Br |
| 21-843 | 2,2,2-trichloroethyl | H | H | N-oxide | H | H | H | I | H | heptafluoroisopropyl | H | I |
| 21-872 | 2,2,2-trichloroethyl | H | H | N-oxide | H | H | H | I | H | nonafluoro-2-butyl | H | I |
| 21-894 | 2,2,2-trichloroethyl | H | H | N-oxide | H | H | H | Cl | H | heptafluoroisopropyl | H | Br |
| 21-903 | 2,2,2-trichloroethyl | H | H | N-oxide | H | H | H | F | H | heptafluoroisopropyl | H | OCF3 |
| 21-904 | 2,2,2-trichloroethyl | H | H | N-oxide | H | H | H | F | H | nonafluoro-2-butyl | H | OCF3 |
| 21-915 | 2,2,2-trichloroethyl | H | H | N-oxide | H | H | H | Cl | H | heptafluoroisopropyl | H | OCF3 |
| 21-944 | 2,2,2-trichloroethyl | H | H | N-oxide | H | H | H | Cl | H | nonafluoro-2-butyl | H | OCF3 |

TABLE 21-continued

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 21-973 | 2,2,2-trichloroethyl | H | H | N-oxide | H | H | H | Br | H | heptafluoroisopropyl | H | OCF3 |
| 21-1002 | 2,2,2-trichloroethyl | H | H | N-oxide | H | H | H | Br | H | nonafluoro-2-butyl | H | OCF3 |
| 21-1031 | 2,2,2-trichloroethyl | H | H | N-oxide | H | H | H | I | H | heptafluoroisopropyl | H | OCF3 |
| 21-1060 | 2,2,2-trichloroethyl | H | H | N-oxide | H | H | H | I | H | nonafluoro-2-butyl | H | OCF3 |
| 21-1079 | 2,2,2-trichloroethyl | H | H | N-oxide | H | H | H | F | H | heptafluoroisopropyl | H | CF3 |
| 21-1080 | 2,2,2-trichloroethyl | H | H | N-oxide | H | H | H | F | H | nonafluoro-2-butyl | H | CF3 |
| 21-1091 | 2,2,2-trichloroethyl | H | H | N-oxide | H | H | H | Cl | H | heptafluoroisopropyl | H | CF3 |
| 21-1120 | 2,2,2-trichloroethyl | H | H | N-oxide | H | H | H | Cl | H | nonafluoro-2-butyl | H | CF3 |
| 21-1149 | 2,2,2-trichloroethyl | H | H | N-oxide | H | H | H | Br | H | heptafluoroisopropyl | H | CF3 |
| 21-1178 | 2,2,2-trichloroethyl | H | H | N-oxide | H | H | H | Br | H | nonafluoro-2-butyl | H | CF3 |
| 21-1207 | 2,2,2-trichloroethyl | H | H | N-oxide | H | H | H | I | H | heptafluoroisopropyl | H | CF3 |
| 21-1236 | 2,2,2-trichloroethyl | H | H | N-oxide | H | H | H | I | H | nonafluoro-2-butyl | H | CF3 |
| 21-1265 | 2,2,2-trichloroethyl | H | H | N-oxide | H | H | H | OCF3 | H | heptafluoroisopropyl | H | OCF3 |
| 21-1294 | 2,2,2-trichloroethyl | H | H | N-oxide | H | H | H | OCF3 | H | nonafluoro-2-butyl | H | OCF3 |
| 21-1323 | 2,2,2-trichloroethyl | H | H | N-oxide | H | H | H | CF3 | H | heptafluoroisopropyl | H | OCF3 |
| 21-1352 | 2,2,2-trichloroethyl | H | H | N-oxide | H | H | H | CF3 | H | nonafluoro-2-butyl | H | OCF3 |
| 21-1381 | 2,2,2-trichloroethyl | H | H | N-oxide | H | H | H | CF3 | H | heptafluoroisopropyl | H | CF3 |
| 21-1410 | 2,2,2-trichloroethyl | H | H | N-oxide | H | H | H | CF3 | H | nonafluoro-2-butyl | H | CF3 |

TABLE 22

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 22-1 | 2,2,2-trichloroethyl | Me | H | N | H | H | H | F | H | heptafluoroisopropyl | H | F |
| 22-2 | 2,2,2-trichloroethyl | Me | H | N | H | H | H | F | H | nonafluoro-2-butyl | H | F |
| 22-13 | 2,2,2-trichloroethyl | Me | H | N | H | H | H | Cl | H | heptafluoroisopropyl | H | Cl |
| 22-42 | 2,2,2-trichloroethyl | Me | H | N | H | H | H | Cl | H | nonafluoro-2-butyl | H | Cl |
| 22-71 | 2,2,2-trichloroethyl | Me | H | N | H | H | H | Br | H | heptafluoroisopropyl | H | Br |
| 22-100 | 2,2,2-trichloroethyl | Me | H | N | H | H | H | Br | H | nonafluoro-2-butyl | H | Br |
| 22-129 | 2,2,2-trichloroethyl | Me | H | N | H | H | H | I | H | heptafluoroisopropyl | H | I |
| 22-158 | 2,2,2-trichloroethyl | Me | H | N | H | H | H | I | H | nonafluoro-2-butyl | H | I |
| 22-186 | 2,2,2-trichloroethyl | Me | H | N | H | H | H | Cl | H | nonafluoro-2-butyl | H | Br |
| 22-189 | 2,2,2-trichloroethyl | Me | H | N | H | H | H | F | H | heptafluoroisopropyl | H | OCF3 |
| 22-190 | 2,2,2-trichloroethyl | Me | H | N | H | H | H | F | H | nonafluoro-2-butyl | H | OCF3 |
| 22-201 | 2,2,2-trichloroethyl | Me | H | N | H | H | H | Cl | H | heptafluoroisopropyl | H | OCF3 |

TABLE 22-continued

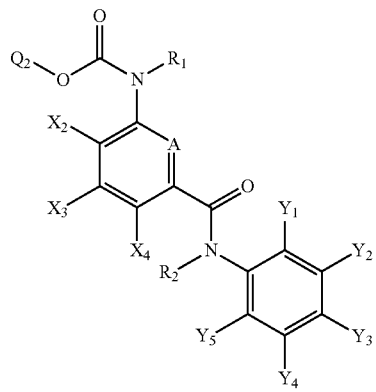

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 22-230 | 2,2,2-trichloroethyl | Me | H | N | H | H | H | Cl | H | nonafluoro-2-butyl | H | OCF3 |
| 22-259 | 2,2,2-trichloroethyl | Me | H | N | H | H | H | Br | H | heptafluoroisopropyl | H | OCF3 |
| 22-288 | 2,2,2-trichloroethyl | Me | H | N | H | H | H | Br | H | nonafluoro-2-butyl | H | OCF3 |
| 22-317 | 2,2,2-trichloroethyl | Me | H | N | H | H | H | I | H | heptafluoroisopropyl | H | OCF3 |
| 22-346 | 2,2,2-trichloroethyl | Me | H | N | H | H | H | I | H | nonafluoro-2-butyl | H | OCF3 |
| 22-365 | 2,2,2-trichloroethyl | Me | H | N | H | H | H | F | H | heptafluoroisopropyl | H | CF3 |
| 22-366 | 2,2,2-trichloroethyl | Me | H | N | H | H | H | F | H | nonafluoro-2-butyl | H | CF3 |
| 22-373 | 2-cyanoethyl | Et | H | N | H | H | H | Cl | H | heptafluoroisopropyl | H | C2F5 |
| 22-377 | 2,2,2-trichloroethyl | Me | H | N | H | H | H | Cl | H | heptafluoroisopropyl | H | CF3 |
| 22-379 | n-propyl | Me | H | N | H | H | H | Cl | H | pentafluoroethyl | H | CF3 |
| 22-383 | i-propyl | n-Pr | H | N | H | H | H | Cl | H | heptafluoroisopropyl | H | n-C3F7 |
| 22-386 | 1,3-dichloro-2-propyl | Me | H | N | H | H | H | Cl | H | pentafluoroethyl | H | CF3 |
| 22-387 | 1-chloro-3-fluoro-2-propyl | i-Pr | H | N | H | H | H | Cl | H | heptafluoroisopropyl | H | CF3 |
| 22-390 | 4,4,4-trifluoro-n-butyl | Me | H | N | H | H | H | Cl | H | heptafluoroisopropyl | H | CF3 |
| 22-391 | i-butyl | CH2CH=CH2 | H | N | H | H | H | Cl | H | heptafluoroisopropyl | H | CF3 |
| 22-397 | ethyl | Me | H | N | H | H | H | Cl | H | nonafluoro-2-butyl | H | i-C3F7 |
| 22-402 | 2-cyanoethyl | CN | H | N | H | H | H | Cl | H | nonafluoro-2-butyl | H | CF3 |
| 22-406 | 2,2,2-trichloroethyl | Me | H | N | H | H | H | Cl | H | nonafluoro-2-butyl | H | CF3 |
| 22-408 | n-propyl | CH2C≡CH | H | N | H | H | H | Cl | H | nonafluoro-2-butyl | H | CF3 |
| 22-419 | 4,4,4-trifluoro-n-butyl | Me | H | N | H | H | H | Cl | H | nonafluoro-2-butyl | H | CF3 |
| 22-420 | i-butyl | NH2 | H | N | H | H | H | Cl | H | nonafluoro-2-butyl | H | CF3 |
| 22-431 | 2-cyanoethyl | Me | H | N | H | H | H | Br | H | heptafluoroisopropyl | H | C2F5 |
| 22-435 | 2,2,2-trichloroethyl | Me | H | N | H | H | H | Br | H | heptafluoroisopropyl | H | CF3 |
| 22-438 | 3-fluoro-n-propyl | C(O)OMe | H | N | H | H | H | Br | H | heptafluoroisopropyl | H | CF3 |
| 22-442 | 1,2-difluoro-2-propyl | Me | H | N | H | H | H | Br | H | heptafluoroisopropyl | H | n-C3F7 |
| 22-448 | 4,4,4-trifluoro-n-butyl | Me | H | N | H | H | H | Br | H | heptafluoroisopropyl | H | CF3 |
| 22-451 | vinyl | C(O)C(O)OMe | H | N | H | H | H | Br | H | heptafluoroisopropyl | H | CF3 |
| 22-464 | 2,2,2-trichloroethyl | Me | H | N | H | H | H | Br | H | nonafluoro-2-butyl | H | CF3 |
| 22-466 | n-propyl | C(O)OEt | H | N | H | H | H | Br | H | nonafluoro-2-butyl | H | CF3 |
| 22-470 | i-propyl | C(O)Me | H | N | H | H | H | Br | H | nonafluoro-2-butyl | H | CF3 |
| 22-477 | 4,4,4-trifluoro-n-butyl | Me | H | N | H | H | H | Br | H | nonafluoro-2-butyl | H | CF3 |
| 22-482 | phenyl | C(O)C(O)OEt | H | N | H | H | H | Br | H | nonafluoro-2-butyl | H | i-C3F7 |
| 22-493 | 2,2,2-trichloroethyl | Me | H | N | H | H | H | I | H | heptafluoroisopropyl | H | CF3 |
| 22-498 | 3-bromo-n-propyl | C(O)Et | H | N | H | H | H | I | H | heptafluoroisopropyl | H | C2F5 |
| 22-506 | 4,4,4-trifluoro-n-butyl | Me | H | N | H | H | H | I | H | heptafluoroisopropyl | H | CF3 |
| 22-510 | benzyl | S(O)2Me | H | N | H | H | H | I | H | heptafluoroisopropyl | H | CF3 |
| 22-518 | 2-cyanoethyl | S(O)2Et | H | H | H | H | H | I | H | nonafluoro-2-butyl | H | CF3 |
| 22-522 | 2,2,2-trichloroethyl | Me | H | N | H | H | H | I | H | nonafluoro-2-butyl | H | CF3 |
| 22-523 | 2,2,2-tribromoethyl | Me | H | N | H | H | H | I | H | nonafluoro-2-butyl | H | CF3 |
| 22-524 | n-propyl | CH2Ph | H | N | H | H | H | I | H | nonafluoro-2-butyl | H | n-C3F7 |
| 22-528 | i-propyl | CH2(3-Py) | H | N | H | H | H | I | H | nonafluoro-2-butyl | H | CF3 |
| 22-535 | 4,4,4-trifluoro-n-butyl | Me | H | N | H | H | H | I | H | nonafluoro-2-butyl | H | CF3 |
| 22-537 | s-butyl | CH2(3-Py-N-oxide) | H | N | H | H | H | I | H | nonafluoro-2-butyl | H | CF3 |
| 22-538 | vinyl | Me | H | N | H | H | H | I | H | nonafluoro-2-butyl | H | i-C3F7 |
| 22-539 | benzyl | Me | H | N | H | H | H | I | H | nonafluoro-2-butyl | H | CF3 |
| 22-540 | phenyl | Me | H | N | H | H | H | I | H | nonafluoro-2-butyl | H | CF3 |
| 22-551 | 2,2,2-trichloroethyl | Me | H | N | H | H | H | OCF3 | H | heptafluoroisopropyl | H | OCF3 |
| 22-580 | 2,2,2-trichloroethyl | Me | H | N | H | H | H | OCF3 | H | nonafluoro-2-butyl | H | OCF3 |
| 22-609 | 2,2,2-trichloroethyl | Me | H | N | H | H | H | CF3 | H | heptafluoroisopropyl | H | OCF3 |
| 22-638 | 2,2,2-trichloroethyl | Me | H | N | H | H | H | CF3 | H | nonafluoro-2-butyl | H | OCF3 |
| 22-667 | 2,2,2-trichloroethyl | Me | H | N | H | H | H | CF3 | H | heptafluoroisopropyl | H | CF3 |
| 22-696 | 2,2,2-trichloroethyl | Me | H | N | H | H | H | CF3 | H | nonafluoro-2-butyl | H | CF3 |
| 22-715 | 2,2,2-trichloroethyl | Me | H | N-oxide | H | H | H | F | H | heptafluoroisopropyl | H | F |
| 22-716 | 2,2,2-trichloroethyl | Me | H | N-oxide | H | H | H | F | H | nonafluoro-2-butyl | H | F |
| 22-727 | 2,2,2-trichloroethyl | Me | H | N-oxide | H | H | H | Cl | H | heptafluoroisopropyl | H | Cl |
| 22-756 | 2,2,2-trichloroethyl | Me | H | N-oxide | H | H | H | Cl | H | nonafluoro-2-butyl | H | Cl |
| 22-785 | 2,2,2-trichloroethyl | Me | H | N-oxide | H | H | H | Br | H | heptafluoroisopropyl | H | Br |

TABLE 22-continued

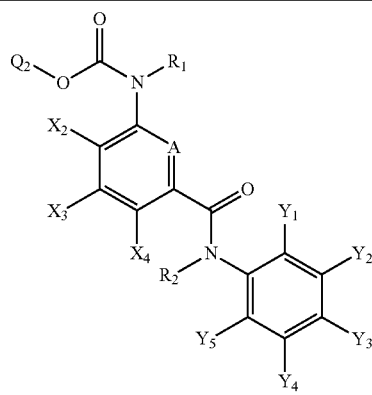

| compound number | $Q_2$ | $R_1$ | $R_2$ | A | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 22-814 | 2,2,2-trichloroethyl | Me | H | N-oxide | H | H | H | Br | H | nonafluoro-2-butyl | H | Br |
| 22-843 | 2,2,2-trichloroethyl | Me | H | N-oxide | H | H | H | I | H | heptafluoroisopropyl | H | I |
| 22-872 | 2,2,2-trichloroethyl | Me | H | N-oxide | H | H | H | I | H | nonafluoro-2-butyl | H | I |
| 22-894 | 2,2,2-trichloroethyl | Me | H | N-oxide | H | H | H | Cl | H | heptafluoroisopropyl | H | Br |
| 22-903 | 2,2,2-trichloroethyl | Me | H | N-oxide | H | H | H | F | H | heptafluoroisopropyl | H | OCF3 |
| 22-904 | 2,2,2-trichloroethyl | Me | H | N-oxide | H | H | H | F | H | nonafluoro-2-butyl | H | OCF3 |
| 22-915 | 2,2,2-trichloroethyl | Me | H | N-oxide | H | H | H | Cl | H | heptafluoroisopropyl | H | OCF3 |
| 22-944 | 2,2,2-trichloroethyl | Me | H | N-oxide | H | H | H | Cl | H | nonafluoro-2-butyl | H | OCF3 |
| 22-973 | 2,2,2-trichloroethyl | Me | H | N-oxide | H | H | H | Br | H | heptafluoroisopropyl | H | OCF3 |
| 22-1002 | 2,2,2-trichloroethyl | Me | H | N-oxide | H | H | H | Br | H | nonafluoro-2-butyl | H | OCF3 |
| 22-1031 | 2,2,2-trichloroethyl | Me | H | N-oxide | H | H | H | I | H | heptafluoroisopropyl | H | OCF3 |
| 22-1060 | 2,2,2-trichloroethyl | Me | H | N-oxide | H | H | H | I | H | nonafluoro-2-butyl | H | OCF3 |
| 22-1079 | 2,2,2-trichloroethyl | Me | H | N-oxide | H | H | H | F | H | heptafluoroisopropyl | H | CF3 |
| 22-1080 | 2,2,2-trichloroethyl | Me | H | N-oxide | H | H | H | F | H | nonafluoro-2-butyl | H | CF3 |
| 22-1091 | 2,2,2-trichloroethyl | Me | H | N-oxide | H | H | H | Cl | H | heptafluoroisopropyl | H | CF3 |
| 22-1120 | 2,2,2-trichloroethyl | Me | H | N-oxide | H | H | H | Cl | H | nonafluoro-2-butyl | H | CF3 |
| 22-1149 | 2,2,2-trichloroethyl | Me | H | N-oxide | H | H | H | Br | H | heptafluoroisopropyl | H | CF3 |
| 22-1178 | 2,2,2-trichloroethyl | Me | H | N-oxide | H | H | H | Br | H | nonafluoro-2-butyl | H | CF3 |
| 22-1207 | 2,2,2-trichloroethyl | Me | H | N-oxide | H | H | H | I | H | heptafluoroisopropyl | H | CF3 |
| 22-1236 | 2,2,2-trichloroethyl | Me | H | N-oxide | H | H | H | I | H | nonafluoro-2-butyl | H | CF3 |
| 22-1265 | 2,2,2-trichloroethyl | Me | H | N-oxide | H | H | H | OCF3 | H | heptafluoroisopropyl | H | OCF3 |
| 22-1294 | 2,2,2-trichloroethyl | Me | H | N-oxide | H | H | H | OCF3 | H | nonafluoro-2-butyl | H | OCF3 |
| 22-1323 | 2,2,2-trichloroethyl | Me | H | N-oxide | H | H | H | CF3 | H | heptafluoroisopropyl | H | OCF3 |
| 22-1352 | 2,2,2-trichloroethyl | Me | H | N-oxide | H | H | H | CF3 | H | nonafluoro-2-butyl | H | OCF3 |
| 22-1381 | 2,2,2-trichloroethyl | Me | H | N-oxide | H | H | H | CF3 | H | heptafluoroisopropyl | H | CF3 |
| 22-1410 | 2,2,2-trichloroethyl | Me | H | N-oxide | H | H | H | CF3 | H | nonafluoro-2-butyl | H | CF3 |

TABLE 23

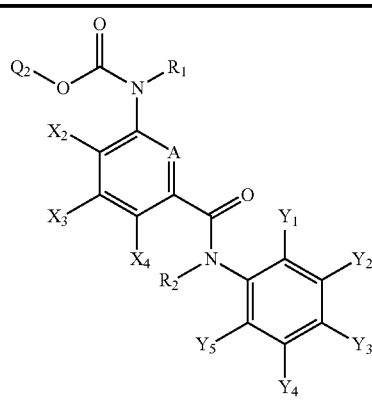

| compound number | $Q_2$ | $R_1$ | $R_2$ | A | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 23-1 | 2,2,2-trichloroethyl | H | Me | N | H | H | H | F | H | heptafluoroisopropyl | H | F |
| 23-2 | 2,2,2-trichloroethyl | H | Me | N | H | H | H | F | H | nonafluoro-2-butyl | H | F |
| 23-13 | 2,2,2-trichloroethyl | H | Me | N | H | H | H | Cl | H | heptafluoroisopropyl | H | Cl |
| 23-42 | 2,2,2-trichloroethyl | H | Me | N | H | H | H | Cl | H | nonafluoro-2-butyl | H | Cl |

TABLE 23-continued

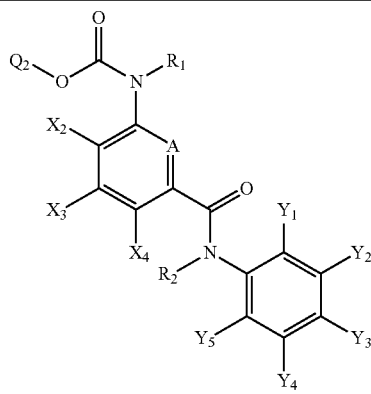

| compound number | $Q_2$ | $R_1$ | $R_2$ | A | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 23-100 | 2,2,2-trichloroethyl | H | Me | N | H | H | H | Br | H | nonafluoro-2-butyl | H | Br |
| 23-129 | 2,2,2-trichloroethyl | H | Me | N | H | H | H | I | H | heptafluoroisopropyl | H | I |
| 23-158 | 2,2,2-trichloroethyl | H | Me | N | H | H | H | I | H | nonafluoro-2-butyl | H | I |
| 23-186 | 2,2,2-trichloroethyl | H | Me | N | H | H | H | Cl | H | nonafluoro-2-butyl | H | Br |
| 23-189 | 2,2,2-trichloroethyl | H | Me | N | H | H | H | F | H | heptafluoroisopropyl | H | OCF3 |
| 23-190 | 2,2,2-trichloroethyl | H | Me | N | H | H | H | F | H | nonafluoro-2-butyl | H | OCF3 |
| 23-201 | 2,2,2-trichloroethyl | H | Me | N | H | H | H | Cl | H | heptafluoroisopropyl | H | OCF3 |
| 23-230 | 2,2,2-trichloroethyl | H | Me | N | H | H | H | Cl | H | nonafluoro-2-butyl | H | OCF3 |
| 23-259 | 2,2,2-trichloroethyl | H | Me | N | H | H | H | Br | H | heptafluoroisopropyl | H | OCF3 |
| 23-288 | 2,2,2-trichloroethyl | H | Me | N | H | H | H | Br | H | nonafluoro-2-butyl | H | OCF3 |
| 23-317 | 2,2,2-trichloroethyl | H | Me | N | H | H | H | I | H | heptafluoroisopropyl | H | OCF3 |
| 23-346 | 2,2,2-trichloroethyl | H | Me | N | H | H | H | I | H | nonafluoro-2-butyl | H | OCF3 |
| 23-365 | 2,2,2-trichloroethyl | H | Me | N | H | H | H | F | H | heptafluoroisopropyl | H | CF3 |
| 23-366 | 2,2,2-trichloroethyl | H | Me | N | H | H | H | F | H | nonafluoro-2-butyl | H | CF3 |
| 23-373 | 2-cyanoethyl | H | Et | N | H | H | H | Cl | H | heptafluoroisopropyl | H | C2F5 |
| 23-377 | 2,2,2-trichloroethyl | H | Me | N | H | H | H | Cl | H | heptafluoroisopropyl | H | CF3 |
| 23-379 | n-propyl | H | Me | N | H | H | H | Cl | H | pentafluoroethyl | H | CF3 |
| 23-383 | i-propyl | H | n-Pr | N | H | H | H | Cl | H | heptafluoroisopropyl | H | n-C3F7 |
| 23-386 | 1,3-dichloro-2-propyl | H | Me | N | H | H | H | Cl | H | pentafluoroethyl | H | CF3 |
| 23-387 | 1-chloro-3-fluoro-2-propyl | H | i-Pr | N | H | H | H | Cl | H | heptafluoroisopropyl | H | CF3 |
| 23-391 | i-butyl | H | CH2CH=CH2 | N | H | H | H | Cl | H | heptafluoroisopropyl | H | CF3 |
| 23-397 | ethyl | H | Me | N | H | H | H | Cl | H | nonafluoro-2-butyl | H | i-C3F7 |
| 23-402 | 2-cyanoethyl | H | CN | N | H | H | H | Cl | H | nonafluoro-2-butyl | H | CF3 |
| 23-406 | 2,2,2-trichloroethyl | H | Me | N | H | H | H | Cl | H | nonafluoro-2-butyl | H | CF3 |
| 23-408 | n-propyl | H | CH2C≡CH | N | H | H | H | Cl | H | nonafluoro-2-butyl | H | CF3 |
| 23-420 | i-butyl | H | NH2 | N | H | H | H | Cl | H | nonafluoro-2-butyl | H | CF3 |
| 23-431 | 2-cyanoethyl | H | Me | N | H | H | H | Br | H | heptafluoroisopropyl | H | C2F5 |
| 23-435 | 2,2,2-trichloroethyl | H | Me | N | H | H | H | Br | H | heptafluoroisopropyl | H | CF3 |
| 23-437 | n-propyl | H | C(O)OMe | N | H | H | H | Br | H | heptafluoroisopropyl | H | CF3 |
| 23-442 | 1,2-difluoro-2-propyl | H | Me | N | H | H | H | Br | H | heptafluoroisopropyl | H | n-C3F7 |
| 23-448 | 4,4,4-trifluoro-n-butyl | H | Me | N | H | H | H | Br | H | heptafluoroisopropyl | H | CF3 |
| 23-451 | vinyl | H | C(O)C(O)OMe | N | H | H | H | Br | H | heptafluoroisopropyl | H | CF3 |
| 23-464 | 2,2,2-trichloroethyl | H | Me | N | H | H | H | Br | H | nonafluoro-2-butyl | H | CF3 |
| 23-466 | n-propyl | H | C(O)OEt | N | H | H | H | Br | H | nonafluoro-2-butyl | H | CF3 |
| 23-470 | i-propyl | H | C(O)Me | N | H | H | H | Br | H | nonafluoro-2-butyl | H | CF3 |
| 23-477 | 4,4,4-trifluoro-n-butyl | H | Me | N | H | H | H | Br | H | nonafluoro-2-butyl | H | CF3 |
| 23-482 | phenyl | H | C(O)C(O)OEt | N | H | H | H | Br | H | nonafluoro-2-butyl | H | i-C3F7 |
| 23-493 | 2,2,2-trichloroethyl | H | Me | N | H | H | H | I | H | heptafluoroisopropyl | H | CF3 |
| 23-498 | 3-bromo-n-propyl | H | C(O)Et | N | H | H | H | I | H | heptafluoroisopropyl | H | C2F5 |
| 23-506 | 4,4,4-trifluoro-n-butyl | H | Me | N | H | H | H | I | H | heptafluoroisopropyl | H | CF3 |
| 23-510 | benzyl | H | S(O)2Me | N | H | H | H | I | H | heptafluoroisopropyl | H | CF3 |
| 23-518 | 2-cyanoethyl | H | S(O)2Et | N | H | H | H | I | H | nonafluoro-2-butyl | H | CF3 |
| 23-522 | 2,2,2-trichloroethyl | H | Me | N | H | H | H | I | H | nonafluoro-2-butyl | H | CF3 |
| 23-524 | n-propyl | H | CH2Ph | N | H | H | H | I | H | nonafluoro-2-butyl | H | n-C3F7 |
| 23-528 | i-propyl | H | CH2(3-Py) | N | H | H | H | I | H | nonafluoro-2-butyl | H | CF3 |
| 23-535 | 4,4,4-trifluoro-n-butyl | H | Me | N | H | H | H | I | H | nonafluoro-2-butyl | H | CF3 |
| 23-537 | s-butyl | H | CH2(3-Py-N-oxide) | N | H | H | H | I | H | nonafluoro-2-butyl | H | CF3 |
| 23-538 | vinyl | H | Me | N | H | H | H | I | H | nonafluoro-2-butyl | H | i-C3F7 |
| 23-551 | 2,2,2-trichloroethyl | H | Me | N | H | H | H | OCF3 | H | heptafluoroisopropyl | H | OCF3 |
| 23-580 | 2,2,2-trichloroethyl | H | Me | N | H | H | H | OCF3 | H | nonafluoro-2-butyl | H | OCF3 |
| 23-609 | 2,2,2-trichloroethyl | H | Me | N | H | H | H | CF3 | H | heptafluoroisopropyl | H | OCF3 |
| 23-638 | 2,2,2-trichloroethyl | H | Me | N | H | H | H | CF3 | H | nonafluoro-2-butyl | H | OCF3 |
| 23-667 | 2,2,2-trichloroethyl | H | Me | N | H | H | H | CF3 | H | heptafluoroisopropyl | H | CF3 |
| 23-696 | 2,2,2-trichloroethyl | H | Me | N | H | H | H | CF3 | H | nonafluoro-2-butyl | H | CF3 |
| 23-715 | 2,2,2-trichloroethyl | H | Me | N-oxide | H | H | H | F | H | heptafluoroisopropyl | H | F |
| 23-716 | 2,2,2-trichloroethyl | H | Me | N-oxide | H | H | H | F | H | nonafluoro-2-butyl | H | F |
| 23-727 | 2,2,2-trichloroethyl | H | Me | N-oxide | H | H | H | Cl | H | heptafluoroisopropyl | H | Cl |

TABLE 23-continued

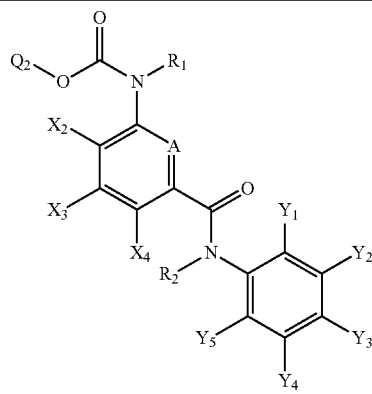

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 23-756 | 2,2,2-trichloroethyl | H | Me | N-oxide | H | H | H | Cl | H | nonafluoro-2-butyl | H | Cl |
| 23-785 | 2,2,2-trichloroethyl | H | Me | N-oxide | H | H | H | Br | H | heptafluoroisopropyl | H | Br |
| 23-814 | 2,2,2-trichloroethyl | H | Me | N-oxide | H | H | H | Br | H | nonafluoro-2-butyl | H | Br |
| 23-843 | 2,2,2-trichloroethyl | H | Me | N-oxide | H | H | H | I | H | heptafluoroisopropyl | H | I |
| 23-872 | 2,2,2-trichloroethyl | H | Me | N-oxide | H | H | H | I | H | nonafluoro-2-butyl | H | I |
| 23-895 | 2,2,2-trichloroethyl | H | Me | N-oxide | H | H | H | Cl | H | heptafluoroisopropyl | H | I |
| 23-903 | 2,2,2-trichloroethyl | H | Me | N-oxide | H | H | H | F | H | heptafluoroisopropyl | H | OCF3 |
| 23-904 | 2,2,2-trichloroethyl | H | Me | N-oxide | H | H | H | F | H | nonafluoro-2-butyl | H | OCF3 |
| 23-915 | 2,2,2-trichloroethyl | H | Me | N-oxide | H | H | H | Cl | H | heptafluoroisopropyl | H | OCF3 |
| 23-944 | 2,2,2-trichloroethyl | H | Me | N-oxide | H | H | H | Cl | H | nonafluoro-2-butyl | H | OCF3 |
| 23-973 | 2,2,2-trichloroethyl | H | Me | N-oxide | H | H | H | Br | H | heptafluoroisopropyl | H | OCF3 |
| 23-1002 | 2,2,2-trichloroethyl | H | Me | N-oxide | H | H | H | Br | H | nonafluoro-2-butyl | H | OCF3 |
| 23-1031 | 2,2,2-trichloroethyl | H | Me | N-oxide | H | H | H | I | H | heptafluoroisopropyl | H | OCF3 |
| 23-1060 | 2,2,2-trichloroethyl | H | Me | N-oxide | H | H | H | I | H | nonafluoro-2-butyl | H | OCF3 |
| 23-1079 | 2,2,2-trichloroethyl | H | Me | N-oxide | H | H | H | F | H | heptafluoroisopropyl | H | CF3 |
| 23-1080 | 2,2,2-trichloroethyl | H | Me | N-oxide | H | H | H | F | H | nonafluoro-2-butyl | H | CF3 |
| 23-1091 | 2,2,2-trichloroethyl | H | Me | N-oxide | H | H | H | Cl | H | heptafluoroisopropyl | H | CF3 |
| 23-1120 | 2,2,2-trichloroethyl | H | Me | N-oxide | H | H | H | Cl | H | nonafluoro-2-butyl | H | CF3 |
| 23-1149 | 2,2,2-trichloroethyl | H | Me | N-oxide | H | H | H | Br | H | heptafluoroisopropyl | H | CF3 |
| 23-1178 | 2,2,2-trichloroethyl | H | Me | N-oxide | H | H | H | Br | H | nonafluoro-2-butyl | H | CF3 |
| 23-1207 | 2,2,2-trichloroethyl | H | Me | N-oxide | H | H | H | I | H | heptafluoroisopropyl | H | CF3 |
| 23-1236 | 2,2,2-trichloroethyl | H | Me | N-oxide | H | H | H | I | H | nonafluoro-2-butyl | H | CF3 |
| 23-1265 | 2,2,2-trichloroethyl | H | Me | N-oxide | H | H | H | OCF3 | H | heptafluoroisopropyl | H | OCF3 |
| 23-1294 | 2,2,2-trichloroethyl | H | Me | N-oxide | H | H | H | OCF3 | H | nonafluoro-2-butyl | H | OCF3 |
| 23-1323 | 2,2,2-trichloroethyl | H | Me | N-oxide | H | H | H | CF3 | H | heptafluoroisopropyl | H | OCF3 |
| 23-1352 | 2,2,2-trichloroethyl | H | Me | N-oxide | H | H | H | CF3 | H | nonafluoro-2-butyl | H | OCF3 |
| 23-1381 | 2,2,2-trichloroethyl | H | Me | N-oxide | H | H | H | CF3 | H | heptafluoroisopropyl | H | CF3 |
| 23-1410 | 2,2,2-trichloroethyl | H | Me | N-oxide | H | H | H | CF3 | H | nonafluoro-2-butyl | H | CF3 |

TABLE 24

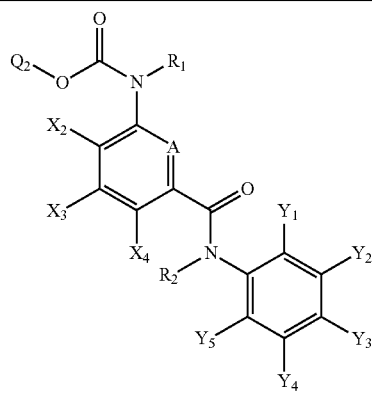

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 24-1 | 2,2,2-trichloroethyl | Me | Me | N | H | H | H | F | H | heptafluoroisopropyl | H | F |
| 24-2 | 2,2,2-trichloroethyl | Me | Me | N | H | H | H | F | H | nonafluoro-2-butyl | H | F |

TABLE 24-continued

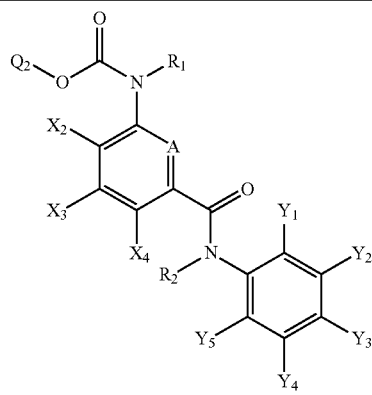

| compound number | Q2 | R1 | R2 | A | X2 | X3 | X4 | Y1 | Y2 | Y3 | Y4 | Y5 |
|---|---|---|---|---|---|---|---|---|---|---|---|---|
| 24-13 | 2,2,2-trichloroethyl | Me | Me | N | H | H | H | Cl | H | heptafluoroisopropyl | H | Cl |
| 24-42 | 2,2,2-trichloroethyl | Me | Me | N | H | H | H | Cl | H | nonafluoro-2-butyl | H | Cl |
| 24-71 | 2,2,2-trichloroethyl | Me | Me | N | H | H | H | Br | H | heptafluoroisopropyl | H | Br |
| 24-100 | 2,2,2-trichloroethyl | Me | Me | N | H | H | H | Br | H | nonafluoro-2-butyl | H | Br |
| 24-129 | 2,2,2-trichloroethyl | Me | Me | N | H | H | H | I | H | heptafluoroisopropyl | H | I |
| 24-158 | 2,2,2-trichloroethyl | Me | Me | N | H | H | H | I | H | nonafluoro-2-butyl | H | I |
| 24-376 | 2,2,2-trichloroethyl | Me | Me | N | H | H | H | Cl | H | heptafluoroisopropyl | H | Br |
| 24-385 | 2,2,2-trichloroethyl | Me | Me | N | H | H | H | F | H | heptafluoroisopropyl | H | OCF3 |
| 24-386 | 2,2,2-trichloroethyl | Me | Me | N | H | H | H | F | H | nonafluoro-2-butyl | H | OCF3 |
| 24-397 | 2,2,2-trichloroethyl | Me | Me | N | H | H | H | Cl | H | heptafluoroisopropyl | H | OCF3 |
| 24-426 | 2,2,2-trichloroethyl | Me | Me | N | H | H | H | Cl | H | nonafluoro-2-butyl | H | OCF3 |
| 24-455 | 2,2,2-trichloroethyl | Me | Me | N | H | H | H | Br | H | heptafluoroisopropyl | H | OCF3 |
| 24-484 | 2,2,2-trichloroethyl | Me | Me | N | H | H | H | Br | H | nonafluoro-2-butyl | H | OCF3 |
| 24-513 | 2,2,2-trichloroethyl | Me | Me | N | H | H | H | I | H | heptafluoroisopropyl | H | OCF3 |
| 24-542 | 2,2,2-trichloroethyl | Me | Me | N | H | H | H | I | H | nonafluoro-2-butyl | H | OCF3 |
| 24-757 | 2,2,2-trichloroethyl | Me | Me | N | H | H | H | F | H | heptafluoroisopropyl | H | CF3 |
| 24-758 | 2,2,2-trichloroethyl | Me | Me | N | H | H | H | F | H | nonafluoro-2-butyl | H | CF3 |
| 24-764 | 2-iodoethyl | Me | Et | N | H | H | H | Cl | H | heptafluoroisopropyl | H | CF3 |
| 24-765 | 2-cyanoethyl | Et | Me | N | H | H | H | Cl | H | heptafluoroisopropyl | H | C2F5 |
| 24-769 | 2,2,2-trichloroethyl | Me | Me | N | H | H | H | Cl | H | nonafluoro-2-butyl | H | CF3 |
| 24-771 | n-propyl | Me | n-Pr | N | H | H | H | Cl | H | pentafluoroethyl | H | CF3 |
| 24-775 | i-propyl | n-Pr | Me | N | H | H | H | Cl | H | heptafluoroisopropyl | H | n-C3F7 |
| 24-778 | 1,3-dichloro-2-propyl | Me | Me | N | H | H | H | Cl | H | pentafluoroethyl | H | CF3 |
| 24-779 | 1-chloro-3-fluoro-2-propyl | i-Pr | Me | N | H | H | H | Cl | H | heptafluoroisopropyl | H | CF3 |
| 24-781 | n-butyl | Me | i-Pr | N | H | H | H | Cl | H | heptafluoroisopropyl | H | CF3 |
| 24-783 | i-butyl | CH2CH=CH2 | Me | N | H | H | H | Cl | H | heptafluoroisopropyl | H | CF3 |
| 24-784 | s-butyl | Me | CH2CH=CH2 | N | H | H | H | Cl | H | heptafluoroisopropyl | H | CF3 |
| 24-785 | vinyl | Me | CN | N | H | H | H | Cl | H | heptafluoroisopropyl | H | CF3 |
| 24-789 | ethyl | Me | Me | N | H | H | H | Cl | H | nonafluoro-2-butyl | H | i-C3F7 |
| 24-794 | 2-cyanoethyl | CN | Me | N | H | H | H | Cl | H | nonafluoro-2-butyl | H | CF3 |
| 24-798 | 2,2,2-trichloroethyl | Me | Me | N | H | H | H | Cl | H | nonafluoro-2-butyl | H | CF3 |
| 24-799 | 2,2,2-tribromoethyl | Me | CH2C≡CH | N | H | H | H | Cl | H | nonafluoro-2-butyl | H | CF3 |
| 24-800 | n-propyl | CH2C≡CH | Me | N | H | H | H | Cl | H | nonafluoro-2-butyl | H | CF3 |
| 24-810 | n-butyl | Me | NH2 | N | H | H | H | Cl | H | nonafluoro-2-butyl | H | CF3 |
| 24-812 | i-butyl | NH2 | Me | N | H | H | H | Cl | H | nonafluoro-2-butyl | H | CF3 |
| 24-823 | 2-cyanoethyl | Me | C(O)OMe | N | H | H | H | Br | H | heptafluoroisopropyl | H | C2F5 |
| 24-827 | 2,2,2-trichloroethyl | Me | Me | N | H | H | H | Br | H | heptafluoroisopropyl | H | CF3 |
| 24-829 | n-propyl | C(O)OMe | Me | N | H | H | H | Br | H | heptafluoroisopropyl | H | CF3 |
| 24-834 | 1,2-difluoro-2-propyl | Me | Me | N | H | H | H | Br | H | heptafluoroisopropyl | H | n-C3F7 |
| 24-840 | 4,4,4-trifluoro-n-butyl | Me | Me | N | H | H | H | Br | H | heptafluoroisopropyl | H | CF3 |
| 24-841 | i-butyl | Me | C(O)C(O)OMe | N | H | H | H | Br | H | heptafluoroisopropyl | H | CF3 |
| 24-842 | s-butyl | Me | C(O)Me | N | H | H | H | Br | H | heptafluoroisopropyl | H | CF3 |
| 24-843 | vinyl | C(O)C(O)OMe | Me | N | H | H | H | Br | H | heptafluoroisopropyl | H | CF3 |
| 24-852 | 2-cyanoethyl | Me | C(O)OEt | N | H | H | H | Br | H | nonafluoro-2-butyl | H | CF3 |
| 24-856 | 2,2,2-trichloroethyl | Me | Me | N | H | H | H | Br | H | nonafluoro-2-butyl | H | CF3 |
| 24-858 | n-propyl | C(O)OEt | Me | N | H | H | H | Br | H | nonafluoro-2-butyl | H | CF3 |
| 24-861 | 3-bromo-n-propyl | Me | C(O)Me | N | H | H | H | Br | H | nonafluoro-2-butyl | H | CF3 |
| 24-862 | i-propyl | C(O)Me | Me | N | H | H | H | Br | H | nonafluoro-2-butyl | H | CF3 |
| 24-869 | 4,4,4-trifluoro-n-butyl | Me | Me | N | H | H | H | Br | H | nonafluoro-2-butyl | H | CF3 |
| 24-870 | i-butyl | Me | C(O)C(O)OEt | N | H | H | H | Br | H | nonafluoro-2-butyl | H | CF3 |
| 24-874 | phenyl | C(O)C(O)OEt | Me | N | H | H | H | Br | H | nonafluoro-2-butyl | H | i-C3F7 |
| 24-885 | 2,2,2-trichloroethyl | Me | Me | N | H | H | H | I | H | heptafluoroisopropyl | H | CF3 |
| 24-887 | n-propyl | Me | C(O)Et | N | H | H | H | I | H | heptafluoroisopropyl | H | CF3 |
| 24-890 | 3-bromo-n-propyl | C(O)Et | Me | N | H | H | H | I | H | heptafluoroisopropyl | H | C2F5 |
| 24-898 | 4,4,4-trifluoro-n-butyl | Me | Me | N | H | H | H | I | H | heptafluoroisopropyl | H | CF3 |
| 24-899 | i-butyl | Me | S(O)2Me | N | H | H | H | I | H | heptafluoroisopropyl | H | CF3 |
| 24-902 | benzyl | S(O)2Me | Me | N | H | H | H | I | H | heptafluoroisopropyl | H | CF3 |
| 24-909 | 2-iodoethyl | Me | S(O)2Et | N | H | H | H | I | H | nonafluoro-2-butyl | H | CF3 |

TABLE 24-continued

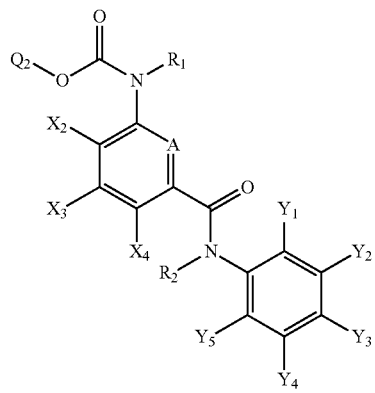

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 24-910 | 2-cyanoethyl | S(O)2Et | Me | N | H | H | H | I | H | nonafluoro-2-butyl | H | CF3 |
| 24-914 | 2,2,2-trichloroethyl | Me | Me | N | H | H | H | I | H | nonafluoro-2-butyl | H | CF3 |
| 24-915 | 2,2,2-tribromoethyl | Me | CH2Ph | N | H | H | H | I | H | nonafluoro-2-butyl | H | CF3 |
| 24-916 | n-propyl | CH2Ph | Me | N | H | H | H | I | H | nonafluoro-2-butyl | H | n-C3F7 |
| 24-920 | i-propyl | CH2(3-Py) | Me | N | H | H | H | I | H | nonafluoro-2-butyl | H | CF3 |
| 24-926 | n-butyl | Me | CH2(3-Py) | N | H | H | H | I | H | nonafluoro-2-butyl | H | CF3 |
| 24-927 | 4,4,4-trifluoro-n-butyl | Me | Me | N | H | H | H | I | H | nonafluoro-2-butyl | H | CF3 |
| 24-929 | s-butyl | CH2(3-Py-N-oxide) | Me | N | H | H | H | I | H | nonafluoro-2-butyl | H | CF3 |
| 24-930 | vinyl | Me | Me | N | H | H | H | I | H | nonafluoro-2-butyl | H | i-C3F7 |
| 24-932 | phenyl | Me | CH2(3-Py-N-oxide) | N | H | H | H | I | H | nonafluoro-2-butyl | H | CF3 |
| 24-1139 | 2,2,2-trichloroethyl | Me | Me | N | H | H | H | OCF3 | H | heptafluoroisopropyl | H | OCF3 |
| 24-1168 | 2,2,2-trichloroethyl | Me | Me | N | H | H | H | OCF3 | H | nonafluoro-2-butyl | H | OCF3 |
| 24-1197 | 2,2,2-trichloroethyl | Me | Me | N | H | H | H | CF3 | H | heptafluoroisopropyl | H | OCF3 |
| 24-1226 | 2,2,2-trichloroethyl | Me | Me | N | H | H | H | CF3 | H | nonafluoro-2-butyl | H | OCF3 |
| 24-1255 | 2,2,2-trichloroethyl | Me | Me | N | H | H | H | CF3 | H | heptafluoroisopropyl | H | CF3 |
| 24-1284 | 2,2,2-trichloroethyl | Me | Me | N | H | H | H | CF3 | H | nonafluoro-2-butyl | H | CF3 |
| 24-1499 | 2,2,2-trichloroethyl | Me | Me | N-oxide | H | H | H | F | H | heptafluoroisopropyl | H | F |
| 24-1500 | 2,2,2-trichloroethyl | Me | Me | N-oxide | H | H | H | F | H | nonafluoro-2-butyl | H | F |
| 24-1511 | 2,2,2-trichloroethyl | Me | Me | N-oxide | H | H | H | Cl | H | heptafluoroisopropyl | H | Cl |
| 24-1540 | 2,2,2-trichloroethyl | Me | Me | N-oxide | H | H | H | Cl | H | nonafluoro-2-butyl | H | Cl |
| 24-1569 | 2,2,2-trichloroethyl | Me | Me | N-oxide | H | H | H | Br | H | heptafluoroisopropyl | H | Br |
| 24-1598 | 2,2,2-trichloroethyl | Me | Me | N-oxide | H | H | H | Br | H | nonafluoro-2-butyl | H | Br |
| 24-1627 | 2,2,2-trichloroethyl | Me | Me | N-oxide | H | H | H | I | H | heptafluoroisopropyl | H | I |
| 24-1656 | 2,2,2-trichloroethyl | Me | Me | N-oxide | H | H | H | I | H | nonafluoro-2-butyl | H | I |
| 24-1875 | 2,2,2-trichloroethyl | Me | Me | N-oxide | H | H | H | Cl | H | heptafluoroisopropyl | H | I |
| 24-1883 | 2,2,2-trichloroethyl | Me | Me | N-oxide | H | H | H | F | H | heptafluoroisopropyl | H | OCF3 |
| 24-1884 | 2,2,2-trichloroethyl | Me | Me | N-oxide | H | H | H | F | H | nonafluoro-2-butyl | H | OCF3 |
| 24-1895 | 2,2,2-trichloroethyl | Me | Me | N-oxide | H | H | H | Cl | H | heptafluoroisopropyl | H | OCF3 |
| 24-1924 | 2,2,2-trichloroethyl | Me | Me | N-oxide | H | H | H | Cl | H | nonafluoro-2-butyl | H | OCF3 |
| 24-1953 | 2,2,2-trichloroethyl | Me | Me | N-oxide | H | H | H | Br | H | heptafluoroisopropyl | H | OCF3 |
| 24-1982 | 2,2,2-trichloroethyl | Me | Me | N-oxide | H | H | H | Br | H | nonafluoro-2-butyl | H | OCF3 |
| 24-2011 | 2,2,2-trichloroethyl | Me | Me | N-oxide | H | H | H | I | H | heptafluoroisopropyl | H | OCF3 |
| 24-2040 | 2,2,2-trichloroethyl | Me | Me | N-oxide | H | H | H | I | H | nonafluoro-2-butyl | H | OCF3 |
| 24-2255 | 2,2,2-trichloroethyl | Me | Me | N-oxide | H | H | H | F | H | heptafluoroisopropyl | H | CF3 |
| 24-2256 | 2,2,2-trichloroethyl | Me | Me | N-oxide | H | H | H | F | H | nonafluoro-2-butyl | H | CF3 |
| 24-2267 | 2,2,2-trichloroethyl | Me | Me | N-oxide | H | H | H | Cl | H | heptafluoroisopropyl | H | CF3 |
| 24-2296 | 2,2,2-trichloroethyl | Me | Me | N-oxide | H | H | H | Cl | H | nonafluoro-2-butyl | H | CF3 |
| 24-2325 | 2,2,2-trichloroethyl | Me | Me | N-oxide | H | H | H | Br | H | heptafluoroisopropyl | H | CF3 |
| 24-2354 | 2,2,2-trichloroethyl | Me | Me | N-oxide | H | H | H | Br | H | nonafluoro-2-butyl | H | CF3 |
| 24-2383 | 2,2,2-trichloroethyl | Me | Me | N-oxide | H | H | H | I | H | heptafluoroisopropyl | H | CF3 |
| 24-2412 | 2,2,2-trichloroethyl | Me | Me | N-oxide | H | H | H | I | H | nonafluoro-2-butyl | H | CF3 |
| 24-2637 | 2,2,2-trichloroethyl | Me | Me | N-oxide | H | H | H | OCF3 | H | heptafluoroisopropyl | H | OCF3 |
| 24-2666 | 2,2,2-trichloroethyl | Me | Me | N-oxide | H | H | H | OCF3 | H | nonafluoro-2-butyl | H | OCF3 |
| 24-2695 | 2,2,2-trichloroethyl | Me | Me | N-oxide | H | H | H | CF3 | H | heptafluoroisopropyl | H | OCF3 |
| 24-2724 | 2,2,2-trichloroethyl | Me | Me | N-oxide | H | H | H | CF3 | H | nonafluoro-2-butyl | H | OCF3 |
| 24-2753 | 2,2,2-trichloroethyl | Me | Me | N-oxide | H | H | H | CF3 | H | heptafluoroisopropyl | H | CF3 |
| 24-2782 | 2,2,2-trichloroethyl | Me | Me | N-oxide | H | H | H | CF3 | H | nonafluoro-2-butyl | H | CF3 |

TABLE 25

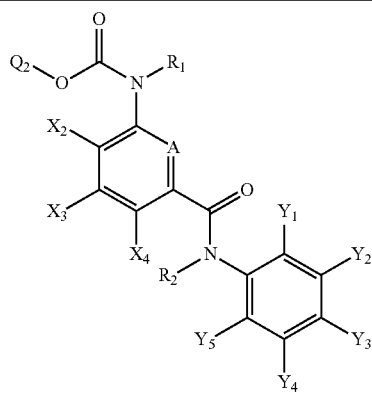

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 25-9 | 2,2-dichloroethyl | H | Et | N | H | H | H | Cl | F | heptafluoroisopropyl | F | Cl |
| 25-39 | 2,2,2-trifluoroethyl | H | H | N | H | H | H | Cl | Me | nonafluoro-2-butyl | Me | I |
| 25-152 | 2,2-dichloroethyl | H | Et | N | H | H | H | Cl | F | heptafluoroisopropyl | F | OCF3 |
| 25-182 | 2,2,2-trifluoroethyl | H | H | N | H | H | H | Cl | Me | nonafluoro-2-butyl | Me | OCF3 |
| 25-287 | methyl | H | H | N | H | H | H | Cl | F | heptafluoroisopropyl | H | CF3 |
| 25-288 | ethyl | Me | H | N | H | H | H | Cl | H | heptafluoroisopropyl | F | CF3 |
| 25-289 | 2-fluoroethyl | H | Me | N | H | H | H | Cl | Cl | heptafluoroisopropyl | H | CF3 |
| 25-290 | 2-chloroethyl | Me | Me | N | H | H | H | Cl | H | heptafluoroisopropyl | Cl | CF3 |
| 25-291 | 2-bromoethyl | H | H | N | H | H | H | F | Br | heptafluoroisopropyl | H | CF3 |
| 25-292 | 2-iodoethyl | H | H | N | H | H | H | Cl | H | heptafluoroisopropyl | Br | CF3 |
| 25-293 | 2-cyanoethyl | Et | H | N | H | H | H | Cl | I | heptafluoroisopropyl | H | C2F5 |
| 25-294 | 2,2-difluoroethyl | If | H | N | H | H | H | Cl | H | heptafluoroisopropyl | I | CF3 |
| 25-295 | 2,2-dichloroethyl | H | Et | N | H | H | H | Cl | F | heptafluoroisopropyl | F | CF3 |
| 25-296 | 2,2,2-trifluoroethyl | H | H | N | H | H | H | Cl | F | heptafluoroisopropyl | Cl | CF3 |
| 25-299 | n-propyl | H | H | N | H | H | H | Cl | Cl | pentafluoroethyl | F | CF3 |
| 25-300 | 3-fluoro-n-propyl | H | H | N | H | H | H | Cl | Cl | heptafluoroisopropyl | Cl | CF3 |
| 25-303 | i-propyl | H | n-Pr | N | H | H | H | Cl | Br | heptafluoroisopropyl | F | CF3 |
| 25-304 | 1,2-difluoro-2-propyl | H | H | N | H | H | H | Cl | Br | heptafluoroisopropyl | Cl | CF3 |
| 25-307 | 1-chloro-3-fluoro-2-propyl | H | H | N | H | H | H | F | I | nonafluoro-2-butyl | F | CF3 |
| 25-308 | 3,3,3-trifluoro-n-propyl | H | H | N | H | H | H | Cl | I | nonafluoro-2-butyl | Cl | CF3 |
| 25-311 | i-butyl | H | H | N | H | H | H | Cl | Me | nonafluoro-2-butyl | H | CF3 |
| 25-312 | s-butyl | H | H | N | H | H | H | Cl | H | nonafluoro-2-butyl | Me | CF3 |
| 25-313 | vinyl | i-Pr | H | N | H | H | H | Cl | Et | nonafluoro-2-butyl | H | CF3 |
| 25-314 | benzyl | H | H | N | H | H | H | Cl | H | nonafluoro-2-butyl | Et | CF3 |
| 25-325 | 2,2,2-trifluoroethyl | H | H | N | H | H | H | Cl | Me | nonafluoro-2-butyl | Me | n-C3F7 |
| 25-326 | 2,2,2-trichloroethyl | H | H | N | H | H | H | Cl | Me | nonafluoro-2-butyl | Et | i-C3F7 |
| 25-332 | i-propyl | H | H | N | H | H | H | Cl | Et | nonafluoro-2-butyl | Me | n-C3F7 |
| 25-333 | 1,2-difluoro-2-propyl | H | H | N | H | H | H | Cl | Et | nonafluoro-2-butyl | Et | i-C3F7 |
| 25-339 | 2-chloroethyl | H | H | N | H | H | H | Br | n-Pr | heptafluoroisopropyl | Me | CF3 |
| 25-340 | 2-bromoethyl | H | H | N | H | H | H | Br | n-Pr | heptafluoroisopropyl | Et | CF3 |
| 25-346 | 2,2,2-trichloroethyl | H | H | N | H | H | H | Br | i-Pr | heptafluoroisopropyl | Me | CF3 |
| 25-347 | 2,2,2-tribromoethyl | H | H | N | H | H | H | Br | i-Pr | heptafluoroisopropyl | Et | CF3 |
| 25-353 | 1,2-difluoro-2-propyl | H | H | N | H | H | H | Br | n-Bu | heptafluoroisopropyl | Me | CF3 |
| 25-354 | 1,3-difluoro-2-propyl | H | H | N | H | H | H | Br | n-Bu | heptafluoroisopropyl | Et | CF3 |
| 25-360 | i-butyl | H | H | N | H | H | H | Br | i-Bu | nonafluoro-2-butyl | Me | CF3 |
| 25-361 | s-butyl | H | H | N | H | H | H | Br | i-Bu | nonafluoro-2-butyl | Et | CF3 |
| 25-367 | 2-fluoroethyl | H | H | N | H | H | H | Br | s-Bu | nonafluoro-2-butyl | Me | CF3 |
| 25-368 | 2-chloroethyl | H | H | N | H | H | H | Br | s-Bu | nonafluoro-2-butyl | Et | CF3 |
| 25-374 | 2,2,2-trifluoroethyl | H | H | N | H | H | H | Br | F | nonafluoro-2-butyl | Me | CF3 |
| 25-375 | 2,2,2-trichloroethyl | H | H | N | H | H | H | Br | F | nonafluoro-2-butyl | Et | CF3 |
| 25-381 | i-propyl | Et | i-Pr | N | H | H | H | Br | Cl | nonafluoro-2-butyl | Me | CF3 |
| 25-382 | 1,2-difluoro-2-propyl | H | H | N | H | H | H | Br | Cl | nonafluoro-2-butyl | Et | CF3 |
| 25-388 | 2-iodoethyl | H | H | N | H | H | H | I | Br | heptafluoroisopropyl | Me | CF3 |
| 25-389 | 2-cyanoethyl | H | H | N | H | H | H | I | Br | heptafluoroisopropyl | Et | CF3 |
| 25-395 | n-propyl | n-Pr | Me | N | H | H | H | I | I | heptafluoroisopropyl | Me | CF3 |
| 25-396 | 3-fluoro-n-propyl | H | H | N | H | H | H | I | I | heptafluoroisopropyl | Et | CF3 |
| 25-402 | 1,3-dichloro-2-propyl | H | H | N | H | H | H | I | Me | heptafluoroisopropyl | F | C2F5 |
| 25-403 | 1-chloro-3-fluoro-2-propyl | H | H | N | H | H | H | I | Me | nonafluoro-2-butyl | Cl | CF3 |
| 25-406 | 4,4,4-trrfluoro-n-butyl | H | H | N | H | H | H | I | Et | nonafluoro-2-butyl | F | CF3 |
| 25-407 | i-butyl | H | H | N | H | H | H | I | Et | nonafluoro-2-butyl | Cl | CF3 |
| 25-410 | benzyl | H | H | N | H | H | H | I | n-Pr | nonafluoro-2-butyl | F | CF3 |
| 25-413 | ethyl | H | H | N | H | H | H | I | n-Pr | nonafluoro-2-butyl | I | n-C3F7 |
| 25-414 | 2-fluoroethyl | H | H | N | H | H | H | I | i-Pr | nonafluoro-2-butyl | F | i-C3F7 |
| 25-415 | 2-chloroethyl | H | H | N | H | H | H | I | i-Pr | nonafluoro-2-butyl | Cl | CF3 |
| 25-418 | 2-cyanoethyl | H | H | N | H | H | H | I | n-Bu | nonafluoro-2-butyl | F | CF3 |
| 25-419 | 2,2-difluoroethyl | H | H | N | H | H | H | I | n-Bu | nonafluoro-2-butyl | Cl | CF3 |
| 25-422 | 2,2,2-trichloroethyl | H | H | N | H | H | H | I | i-Bu | nonafluoro-2-butyl | F | CF3 |

TABLE 25-continued

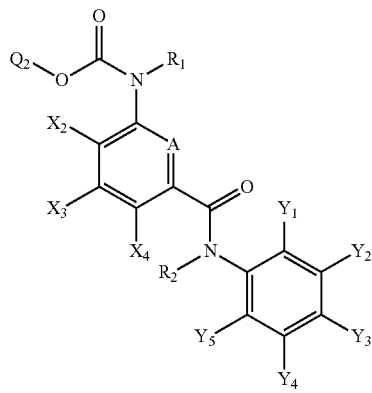

| compound number | Q₂ | R₁ | R₂ | A | X₂ | X₃ | X₄ | Y₁ | Y₂ | Y₃ | Y₄ | Y₅ |
|---|---|---|---|---|---|---|---|---|---|---|---|---|
| 25-423 | 2,2,2-tribromoethyl | H | H | N | H | H | H | I | i-Bu | nonafluoro-2-butyl | Cl | CF3 |
| 25-426 | 3-chloro-n-propyl | i-Pr | n-Pr | N | H | H | H | I | s-Bu | nonafluoro-2-butyl | F | CF3 |
| 25-427 | 3-bromo-n-propyl | H | H | N | H | H | H | I | s-Bu | nonafluoro-2-butyl | Cl | CF3 |
| 25-438 | 2,2-dichloroethyl | H | Et | N | H | H | H | OCF3 | F | heptafluoroisopropyl | F | OCF3 |
| 25-468 | 2,2,2-trifluoroethyl | H | H | N | H | H | H | OCF3 | Me | nonafluoro-2-butyl | Me | OCF3 |
| 25-581 | 2,2-dichloroethyl | H | Et | N | H | H | H | OCF3 | F | heptafluoroisopropyl | F | CF3 |
| 25-611 | 2,2,2-trifluoroethyl | H | H | N | H | H | H | OCF3 | Me | nonafluoro-2-butyl | Me | CF3 |
| 25-724 | 2,2-dichloroethyl | H | Et | N | H | H | H | CF3 | F | heptafluoroisopropyl | F | CF3 |
| 25-754 | 2,2,2-trifluoroethyl | H | H | N | H | H | H | CF3 | Me | nonafluoro-2-butyl | Me | CF3 |
| 25-867 | 2,2-dichloroethyl | H | Et | N-oxide | H | H | H | Cl | F | heptafluoroisopropyl | F | Cl |
| 25-897 | 2,2,2-trifluoroethyl | H | H | N-oxide | H | H | H | Cl | Me | nonafluoro-2-butyl | Me | I |
| 25-1010 | 2,2-dichloroethyl | H | Et | N-oxide | H | H | H | Cl | F | heptafluoroisopropyl | F | OCF3 |
| 25-1040 | 2,2,2-trifluoroethyl | H | H | N-oxide | H | H | H | Cl | Me | nonafluoro-2-butyl | Me | OCF3 |
| 25-1155 | 2,2,2-trichloroethyl | H | H | N-oxide | H | H | H | Cl | F | heptafluoroisopropyl | Br | CF3 |
| 25-1168 | 4,4,4-trifluoro-n-butyl | H | H | N-oxide | H | H | H | Cl | I | nonafluoro-2-butyl | I | CF3 |
| 25-1184 | 2,2,2-trichloroethyl | H | H | N-oxide | H | H | H | Cl | Me | nonafluoro-2-butyl | Et | i-C3F7 |
| 25-1233 | 2,2,2-trichloroethyl | H | H | N-oxide | H | H | H | Br | F | nonafluoro-2-butyl | Et | CF3 |
| 25-1264 | 4,4,4-trifluoro-n-butyl | H | H | N-oxide | H | H | H | I | Et | nonafluoro-2-butyl | F | CF3 |
| 25-1296 | 2,2-dichloroethyl | H | Et | N-oxide | H | H | H | OCF3 | F | heptafluoroisopropyl | F | OCF3 |
| 25-1326 | 2,2,2-trifluoroethyl | H | H | N-oxide | H | H | H | OCF3 | Me | nonafluoro-2-butyl | Me | OCF3 |
| 25-1439 | 2,2-dichloroethyl | H | Et | N-oxide | H | H | H | OCF3 | F | heptafluoroisopropyl | F | CF3 |
| 25-1469 | 2,2,2-trifluoroethyl | H | H | N-oxide | H | H | H | OCF3 | Me | nonafluoro-2-butyl | Me | CF3 |
| 25-1582 | 2,2-dichloroethyl | H | Et | N-oxide | H | H | H | CF3 | F | heptafluoroisopropyl | F | CF3 |
| 25-1612 | 2,2,2-trifluoroethyl | H | H | N-oxide | H | H | H | CF3 | Me | nonafluoro-2-butyl | Me | CF3 |

TABLE 26

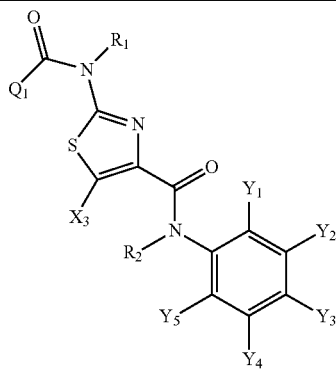

| compound number | Q₁ | R₁ | R₂ | X₃ | Y₁ | Y₂ | Y₃ | Y₄ | Y₅ |
|---|---|---|---|---|---|---|---|---|---|
| 26-1 | phenyl | H | H | H | Cl | H | heptafluoroisopropyl | H | OCF3 |
| 26-4 | 4-fluorophenyl | H | H | Cl | Cl | H | heptafluoroisopropyl | H | OCF3 |
| 26-12 | 3-iodophenyl | H | H | H | Cl | H | pentafluoroethyl | H | OCF3 |
| 26-13 | 4-iodophenyl | H | H | H | Cl | H | pentafluoroethyl | H | OCF3 |
| 26-16 | (4-trifluoromethyl)phenyl | H | H | H | Cl | H | heptafluoroisopropyl | H | OC2F5 |
| 26-17 | 2-nitrophenyl | H | H | H | F | H | heptafluoroisopropyl | H | OCF3 |
| 26-20 | 2-cyanophenyl | H | H | H | Cl | H | pentafluoroethyl | H | OC2F5 |

TABLE 26-continued

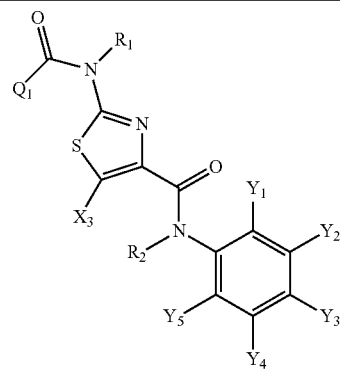

| compound number | Q₁ | R₁ | R₂ | X₃ | Y₁ | Y₂ | Y₃ | Y₄ | Y₅ |
|---|---|---|---|---|---|---|---|---|---|
| 26-21 | 3-cyanophenyl | H | H | H | Cl | H | heptafluoroisopropyl | H | OCF3 |
| 26-22 | 4-cyanophenyl | H | H | H | Cl | H | heptafluoroisopropyl | H | OCF3 |
| 26-28 | 4-bromo-2-chlorophenyl | H | H | H | Cl | H | heptafluoroisopropyl | H | OC2F5 |
| 26-36 | 2-fluoropyridin-3-yl | H | H | H | Cl | H | pentafluoroethyl | H | OCF3 |
| 26-37 | 2-chloropyridin-3-yl | H | H | H | Cl | H | heptafluoroisopropyl | H | OCF3 |
| 26-41 | 2-nitropyridin-3-yl | H | H | H | Cl | H | heptafluoroisopropyl | H | OC2F5 |
| 26-50 | 5-fluoropyridin-3-yl | H | H | H | Cl | H | heptafluoroisopropyl | H | OC2F5 |
| 26-55 | 5-nitropyridin-3-yl | H | H | H | Cl | H | pentafluoroethyl | H | OCF3 |
| 26-59 | 4-bromopyridin-3-yl | H | H | H | Cl | H | heptafluoroisopropyl | H | OC2F5 |
| 26-60 | 4-iodopyridin-3-yl | H | H | H | Cl | H | heptafluoroisopropyl | H | OC2F5 |
| 26-78 | 4-cyanopyridin-2-yl | H | H | H | Cl | H | pentafluoroethyl | H | OCF3 |
| 26-79 | phenyl | H | H | H | Cl | H | nonafluoro-2-butyl | H | OCF3 |
| 26-95 | 2-nitrophenyl | H | H | H | F | H | nonafluoro-2-butyl | H | OCF3 |
| 26-99 | 3-cyanophenyl | H | H | H | Cl | H | nonafluoro-2-butyl | H | OCF3 |
| 26-100 | 4-cyanophenyl | H | H | H | Cl | H | nonafluoro-2-butyl | H | OCF3 |
| 26-105 | 2-chloro-4,5-difluorophenyl | H | H | H | Cl | H | nonafluoro-2-butyl | H | OC2F5 |
| 26-115 | 2-chloropyridin-3-yl | H | H | H | Cl | H | nonafluoro-2-butyl | H | OCF3 |
| 26-121 | 6-fluoropyridin-3-yl | H | H | H | Cl | H | nonafluoro-2-butyl | H | OC2F5 |
| 26-130 | 5-bromopyridin-3-yl | H | H | H | Cl | H | nonafluoro-2-butyl | H | OC2F5 |
| 26-131 | 5-iodopyridin-3-yl | H | H | H | Cl | H | nonafluoro-2-butyl | H | OC2F5 |
| 26-139 | 4-(trifluoromethyl)pyridin-3-yl | H | H | H | Cl | H | nonafluoro-2-butyl | H | OC2F5 |
| 26-140 | 4-nitropyridin-3-yl | H | H | H | Cl | H | nonafluoro-2-butyl | H | OC2F5 |
| 26-157 | phenyl | H | H | H | Br | H | heptafluoroisopropyl | H | OCF3 |
| 26-158 | 2-fluorophenyl | H | H | H | Br | H | heptafluoroisopropyl | H | OCF3 |
| 26-177 | 3-cyanophenyl | H | H | H | Br | H | heptafluoroisopropyl | H | OCF3 |
| 26-178 | 4-cyanophenyl | H | H | H | Br | H | heptafluoroisopropyl | H | OCF3 |
| 26-193 | 2-chloropyridin-3-yl | H | H | H | Br | H | heptafluoroisopropyl | H | OCF3 |
| 26-235 | phenyl | H | H | H | Br | H | nonafluoro-2-butyl | H | OCF3 |
| 26-236 | 2-fluorophenyl | H | H | H | Br | H | nonafluoro-2-butyl | H | OCF3 |
| 26-255 | 3-cyanophenyl | H | H | H | Br | H | nonafluoro-2-butyl | H | OCF3 |
| 26-256 | 4-cyanophenyl | H | H | H | Br | H | nonafluoro-2-butyl | H | OCF3 |
| 26-271 | 2-chloropyridin-3-yl | H | H | H | Br | H | nonafluoro-2-butyl | H | OCF3 |
| 26-313 | phenyl | H | H | H | I | H | heptafluoroisopropyl | H | OCF3 |
| 26-314 | 2-fluorophenyl | H | H | H | I | H | heptafluoroisopropyl | H | OCF3 |
| 26-333 | 3-cyanophenyl | H | H | H | I | H | heptafluoroisopropyl | H | OCF3 |
| 26-334 | 4-cyanophenyl | H | H | H | I | H | heptafluoroisopropyl | H | OCF3 |
| 26-349 | 2-chloropyridin-3-yl | H | H | H | I | H | heptafluoroisopropyl | H | OCF3 |
| 26-391 | phenyl | H | H | H | I | H | nonafluoro-2-butyl | H | OCF3 |
| 26-392 | 2-fluorophenyl | H | H | H | I | H | nonafluoro-2-butyl | H | OCF3 |
| 26-411 | 3-cyanophenyl | H | H | H | I | H | nonafluoro-2-butyl | H | OCF3 |
| 26-412 | 4-cyanophenyl | H | H | H | I | H | nonafluoro-2-butyl | H | OCF3 |
| 26-427 | 2-chloropyridin-3-yl | H | H | H | I | H | nonafluoro-2-butyl | H | OCF3 |
| 26-469 | phenyl | H | H | H | F | H | heptafluoroisopropyl | H | CF3 |
| 26-470 | phenyl | H | H | H | Cl | H | heptafluoroisopropyl | H | CF3 |
| 26-471 | 2-fluorophenyl | H | H | H | Cl | H | heptafluoroisopropyl | H | CF3 |
| 26-481 | 3-iodophenyl | H | H | H | Cl | H | pentafluoroethyl | H | CF3 |
| 26-482 | 4-iodophenyl | H | H | H | Cl | H | pentafluoroethyl | H | CF3 |
| 26-489 | 2-cyanophenyl | H | H | H | Cl | H | pentafluoroethyl | H | C2F5 |
| 26-490 | 3-cyanophenyl | H | H | H | Cl | H | heptafluoroisopropyl | H | CF3 |
| 26-491 | 4-cyanophenyl | H | H | H | Cl | H | heptafluoroisopropyl | H | CF3 |
| 26-494 | 2,4-dichlorophenyl | H | H | H | Cl | H | heptafluoroisopropyl | H | C2F5 |
| 26-498 | 2-bromo-4-chlorophenyl | H | H | H | Cl | H | heptafluoroisopropyl | H | n-C3F7 |
| 26-505 | 2-fluoropyridin-3-yl | H | H | H | Cl | H | pentafluoroethyl | H | CF3 |
| 26-506 | 2-chloropyridin-3-yl | H | H | H | Cl | H | heptafluoroisopropyl | H | CF3 |
| 26-510 | 2-nitropyridin-3-yl | H | H | Cl | Cl | H | heptafluoroisopropyl | H | CF3 |
| 26-519 | 5-fluoropyridin-3-yl | H | H | H | Cl | H | heptafluoroisopropyl | H | C2F5 |
| 26-521 | 5-bromopyridin-3-yl | H | H | H | Cl | H | heptafluoroisopropyl | H | n-C3F7 |
| 26-522 | 5-iodopyridin-3-yl | H | H | H | Cl | H | heptafluoroisopropyl | H | i-C3F7 |
| 26-524 | 5-nitropyridin-3-yl | H | H | H | Cl | H | pentafluoroethyl | H | CF3 |

TABLE 26-continued

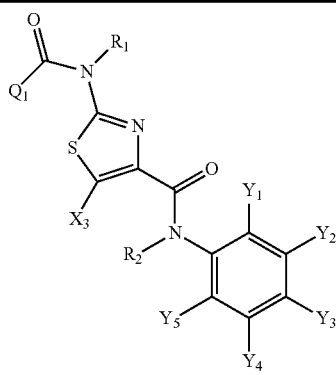

| compound number | Q₁ | R₁ | R₂ | X₃ | Y₁ | Y₂ | Y₃ | Y₄ | Y₅ |
|---|---|---|---|---|---|---|---|---|---|
| 26-526 | 4-fluoropyridin-3-yl | H | H | H | Cl | H | pentafluoroethyl | H | CF3 |
| 26-528 | 4-bromopyridin-3-yl | H | H | H | Cl | H | heptafluoroisopropyl | H | n-C3F7 |
| 26-529 | 4-iodopyridin-3-yl | H | H | H | Cl | H | heptafluoroisopropyl | H | i-C3F7 |
| 26-548 | phenyl | H | H | H | F | H | nonafluoro-2-butyl | H | CF3 |
| 26-549 | phenyl | H | H | H | Cl | H | nonafluoro-2-butyl | H | CF3 |
| 26-550 | 2-fluorophenyl | H | H | H | Cl | H | nonafluoro-2-butyl | H | CF3 |
| 26-562 | (2-trifluoromethyl)phenyl | H | H | H | Cl | H | nonafluoro-2-butyl | H | C2F5 |
| 26-569 | 3-cyanophenyl | H | H | H | Cl | H | nonafluoro-2-butyl | H | CF3 |
| 26-570 | 4-cyanophenyl | H | H | H | Cl | H | nonafluoro-2-butyl | H | CF3 |
| 26-579 | 2-chloro-4-nitrophenyl | H | H | H | Cl | H | nonafluoro-2-butyl | H | i-C3F7 |
| 26-585 | 2-chloropyridin-3-yl | H | H | H | Cl | H | nonafluoro-2-butyl | H | CF3 |
| 26-598 | 5-fluoropyridin-3-yl | H | H | H | Cl | H | nonafluoro-2-butyl | H | C2F5 |
| 26-600 | 5-bromopyridin-3-yl | H | H | H | Cl | H | nonafluoro-2-butyl | H | n-C3F7 |
| 26-601 | 5-iodopyridin-3-yl | H | H | H | Cl | H | nonafluoro-2-butyl | H | i-C3F7 |
| 26-605 | 4-fluoropyridin-3-yl | H | H | H | Cl | H | nonafluoro-2-butyl | H | C2F5 |
| 26-609 | 4-(trifluoromethyl)pyridin-3-yl | H | H | H | Cl | H | nonafluoro-2-butyl | H | n-C3F7 |
| 26-610 | 4-nitropyridin-3-yl | H | H | H | Cl | H | nonafluoro-2-butyl | H | i-C3F7 |
| 26-626 | 4-cyanopyridin-2-yl | H | H | H | Cl | H | nonafluoro-2-butyl | H | C2F5 |
| 26-627 | phenyl | H | H | H | Br | H | heptafluoroisopropyl | H | CF3 |
| 26-628 | 2-fluorophenyl | H | H | H | Br | H | heptafluoroisopropyl | H | CF3 |
| 26-629 | 3-fluorophenyl | H | H | H | Br | H | heptafluoroisopropyl | H | CF3 |
| 26-630 | 4-fluorophenyl | H | H | H | Br | H | heptafluoroisopropyl | H | CF3 |
| 26-631 | 2-chlorophenyl | H | H | H | Br | H | heptafluoroisopropyl | H | CF3 |
| 26-632 | 3-chlorophenyl | H | H | H | Br | H | heptafluoroisopropyl | H | CF3 |
| 26-633 | 4-chlorophenyl | H | H | H | Br | H | heptafluoroisopropyl | H | CF3 |
| 26-634 | 2-bromophenyl | H | H | H | Br | H | heptafluoroisopropyl | H | CF3 |
| 26-635 | 3-bromophenyl | H | H | H | Br | H | heptafluoroisopropyl | H | CF3 |
| 26-636 | 4-bromophenyl | H | H | H | Br | H | heptafluoroisopropyl | H | CF3 |
| 26-637 | 2-iodophenyl | H | H | H | Br | H | heptafluoroisopropyl | H | CF3 |
| 26-638 | 3-iodophenyl | H | H | H | Br | H | heptafluoroisopropyl | H | CF3 |
| 26-639 | 4-iodophenyl | H | H | H | Br | H | heptafluoroisopropyl | H | CF3 |
| 26-640 | (2-trifluoromethyl)phenyl | H | H | H | Br | H | heptafluoroisopropyl | H | CF3 |
| 26-641 | (3-trifluoromethyl)phenyl | H | H | H | Br | H | heptafluoroisopropyl | H | CF3 |
| 26-642 | (4-trifluoromethyl)phenyl | H | H | H | Br | H | heptafluoroisopropyl | H | CF3 |
| 26-643 | 2-nitrophenyl | H | H | H | Br | H | heptafluoroisopropyl | H | CF3 |
| 26-644 | 3-nitrophenyl | H | H | H | Br | H | heptafluoroisopropyl | H | CF3 |
| 26-645 | 4-nitrophenyl | H | H | H | Br | H | heptafluoroisopropyl | H | CF3 |
| 26-646 | 2-cyanophenyl | H | H | H | Br | H | heptafluoroisopropyl | H | CF3 |
| 26-647 | 3-cyanophenyl | H | H | H | Br | H | heptafluoroisopropyl | H | CF3 |
| 26-648 | 4-cyanophenyl | H | H | H | Br | H | heptafluoroisopropyl | H | CF3 |
| 26-649 | 2,6-difluorophenyl | H | H | H | Br | H | heptafluoroisopropyl | H | CF3 |
| 26-650 | 3,4-dichlorophenyl | H | H | H | Br | H | heptafluoroisopropyl | H | CF3 |
| 26-651 | 2,4-dichlorophenyl | H | H | H | Br | H | heptafluoroisopropyl | H | CF3 |
| 26-652 | 2-chloro-4-fluorophenyl | H | H | H | Br | H | heptafluoroisopropyl | H | CF3 |
| 26-653 | 2-chloro-4,5-difluorophenyl | H | H | H | Br | H | heptafluoroisopropyl | H | CF3 |
| 26-654 | 4-bromo-2-chlorophenyl | H | H | H | Br | H | heptafluoroisopropyl | H | CF3 |
| 26-655 | 2-bromo-4-chlorophenyl | H | H | H | Br | H | heptafluoroisopropyl | H | CF3 |
| 26-656 | 2-bromo-4-fluorophenyl | H | H | H | Br | H | heptafluoroisopropyl | H | CF3 |
| 26-657 | 2-chloro-4-nitrophenyl | H | H | H | Br | H | heptafluoroisopropyl | H | CF3 |
| 26-658 | 3,5-dicyanophenyl | H | H | H | Br | H | heptafluoroisopropyl | H | CF3 |
| 26-659 | 4-cyano-2-fluorophenyl | H | H | H | Br | H | heptafluoroisopropyl | H | CF3 |
| 26-660 | 2-chloro-4-cyanophenyl | H | H | H | Br | H | heptafluoroisopropyl | H | CF3 |
| 26-661 | pyridin-3-yl | H | H | H | Br | H | heptafluoroisopropyl | H | CF3 |
| 26-662 | 2-fluoropyridin-3-yl | H | H | H | Br | H | heptafluoroisopropyl | H | CF3 |
| 26-663 | 2-chloropyridin-3-yl | H | H | H | Br | H | heptafluoroisopropyl | H | CF3 |
| 26-664 | 2-bromopyridin-3-yl | H | H | H | Br | H | heptafluoroisopropyl | H | CF3 |
| 26-665 | 2-iodopyridin-3-yl | H | H | H | Br | H | heptafluoroisopropyl | H | CF3 |
| 26-666 | 2-(trifluoromethyl)pyridin-3-yl | H | H | H | Br | H | heptafluoroisopropyl | H | CF3 |
| 26-667 | 2-nitropyridin-3-yl | H | H | H | Br | H | heptafluoroisopropyl | H | CF3 |

TABLE 26-continued

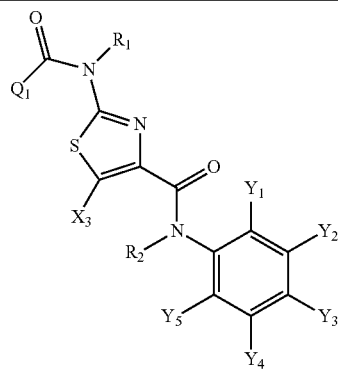

| compound number | Q₁ | R₁ | R₂ | X₃ | Y₁ | Y₂ | Y₃ | Y₄ | Y₅ |
|---|---|---|---|---|---|---|---|---|---|
| 26-668 | 2-cyanopyridin-3-yl | H | H | H | Br | H | heptafluoroisopropyl | H | CF3 |
| 26-669 | 6-fluoropyridin-3-yl | H | H | H | Br | H | heptafluoroisopropyl | H | CF3 |
| 26-670 | 6-chloropyridin-3-yl | H | H | H | Br | H | heptafluoroisopropyl | H | CF3 |
| 26-671 | 6-bromopyridin-3-yl | H | H | H | Br | H | heptafluoroisopropyl | H | CF3 |
| 26-672 | 6-iodopyridin-3-yl | H | H | H | Br | H | heptafluoroisopropyl | H | CF3 |
| 26-673 | 6-(trifluoromethyl)pyridin-3-yl | H | H | H | Br | H | heptafluoroisopropyl | H | CF3 |
| 26-674 | 6-nitropyridin-3-yl | H | H | H | Br | H | heptafluoroisopropyl | H | CF3 |
| 26-675 | 6-cyanopyridin-3-yl | H | H | H | Br | H | heptafluoroisopropyl | H | CF3 |
| 26-676 | 5-fluoropyridin-3-yl | H | H | H | Br | H | heptafluoroisopropyl | H | CF3 |
| 26-677 | 5-chloropyridin-3-yl | H | H | H | Br | H | heptafluoroisopropyl | H | CF3 |
| 26-678 | 5-bromopyridin-3-yl | H | H | H | Br | H | heptafluoroisopropyl | H | CF3 |
| 26-679 | 5-iodopyridin-3-yl | H | H | H | Br | H | heptafluoroisopropyl | H | CF3 |
| 26-680 | 5-(trifluoromethyl)pyridin-3-yl | H | H | H | Br | H | heptafluoroisopropyl | H | CF3 |
| 26-681 | 5-nitropyridin-3-yl | H | H | H | Br | H | heptafluoroisopropyl | H | CF3 |
| 26-682 | 5-cyanopyridin-3-yl | H | H | H | Br | H | heptafluoroisopropyl | H | CF3 |
| 26-683 | 4-fluoropyridin-3-yl | H | H | H | Br | H | heptafluoroisopropyl | H | CF3 |
| 26-684 | 4-chloropyridin-3-yl | H | H | H | Br | H | heptafluoroisopropyl | H | CF3 |
| 26-685 | 4-bromopyridin-3-yl | H | H | H | Br | H | heptafluoroisopropyl | H | CF3 |
| 26-686 | 4-iodopyridin-3-yl | H | H | H | Br | H | heptafluoroisopropyl | H | CF3 |
| 26-687 | 4-(trifluoromethyl)pyridin-3-yl | H | H | H | Br | H | heptafluoroisopropyl | H | CF3 |
| 26-688 | 4-nitropyridin-3-yl | H | H | H | Br | H | heptafluoroisopropyl | H | CF3 |
| 26-689 | 4-cyanopyridin-3-yl | H | H | H | Br | H | heptafluoroisopropyl | H | CF3 |
| 26-690 | 2,6-dichloropyridin-3-yl | H | H | H | Br | H | heptafluoroisopropyl | H | CF3 |
| 26-691 | pyridin-3-yl N-oxide | H | H | H | Br | H | heptafluoroisopropyl | H | CF3 |
| 26-692 | pyridin-4-yl | H | H | H | Br | H | heptafluoroisopropyl | H | CF3 |
| 26-693 | 2-chloropyridin-4-yl | H | H | H | Br | H | heptafluoroisopropyl | H | CF3 |
| 26-694 | 3-bromopyridin-4-yl | H | H | H | Br | H | heptafluoroisopropyl | H | CF3 |
| 26-695 | 3,5-dichloropyridin-4-yl | H | H | H | Br | H | heptafluoroisopropyl | H | CF3 |
| 26-696 | 3-(trifluoromethyl)pyridin-4-yl | H | H | H | Br | H | heptafluoroisopropyl | H | CF3 |
| 26-697 | 2,6-dicyanopyridin-4-yl | H | H | H | Br | H | heptafluoroisopropyl | H | CF3 |
| 26-698 | pyridin-4-yl N-oxide | H | H | H | Br | H | heptafluoroisopropyl | H | CF3 |
| 26-699 | pyridin-2-yl | H | H | H | Br | H | heptafluoroisopropyl | H | CF3 |
| 26-700 | 3-chloropyridin-2-yl | H | H | H | Br | H | heptafluoroisopropyl | H | CF3 |
| 26-701 | 4-bromopyridin-2-yl | H | H | H | Br | H | heptafluoroisopropyl | H | CF3 |
| 26-702 | 5-iodopyridin-2-yl | H | H | H | Br | H | heptafluoroisopropyl | H | CF3 |
| 26-703 | 6-chloropyridin-2-yl | H | H | H | Br | H | heptafluoroisopropyl | H | CF3 |
| 26-704 | 4-cyanopyridin-2-yl | H | H | H | Br | H | heptafluoroisopropyl | H | CF3 |
| 26-705 | phenyl | H | H | H | Br | H | nonafluoro-2-butyl | H | CF3 |
| 26-706 | 2-fluorophenyl | H | H | H | Br | H | nonafluoro-2-butyl | H | CF3 |
| 26-707 | 3-fluorophenyl | H | H | H | Br | H | nonafluoro-2-butyl | H | CF3 |
| 26-708 | 4-fluorophenyl | H | H | H | Br | H | nonafluoro-2-butyl | H | CF3 |
| 26-709 | 2-chlorophenyl | H | H | H | Br | H | nonafluoro-2-butyl | H | CF3 |
| 26-710 | 3-chlorophenyl | H | H | H | Br | H | nonafluoro-2-butyl | H | CF3 |
| 26-711 | 4-chlorophenyl | H | H | H | Br | H | nonafluoro-2-butyl | H | CF3 |
| 26-712 | 2-bromophenyl | H | H | H | Br | H | nonafluoro-2-butyl | H | CF3 |
| 26-713 | 3-bromophenyl | H | H | H | Br | H | nonafluoro-2-butyl | H | CF3 |
| 26-714 | 4-bromophenyl | H | H | H | Br | H | nonafluoro-2-butyl | H | CF3 |
| 26-715 | 2-iodophenyl | H | H | H | Br | H | nonafluoro-2-butyl | H | CF3 |
| 26-716 | 3-iodophenyl | H | H | H | Br | H | nonafluoro-2-butyl | H | CF3 |
| 26-717 | 4-iodophenyl | H | H | H | Br | H | nonafluoro-2-butyl | H | CF3 |
| 26-718 | (2-trifluoromethyl)phenyl | H | H | H | Br | H | nonafluoro-2-butyl | H | CF3 |
| 26-719 | (3-trifluoromethyl)phenyl | H | H | H | Br | H | nonafluoro-2-butyl | H | CF3 |
| 26-720 | (4-trifluoromethyl)phenyl | H | H | H | Br | H | nonafluoro-2-butyl | H | CF3 |
| 26-721 | 2-nitrophenyl | H | H | H | Br | H | nonafluoro-2-butyl | H | CF3 |
| 26-722 | 3-nitrophenyl | H | H | H | Br | H | nonafluoro-2-butyl | H | CF3 |
| 26-723 | 4-nitrophenyl | H | H | H | Br | H | nonafluoro-2-butyl | H | CF3 |
| 26-724 | 2-cyanophenyl | H | H | H | Br | H | nonafluoro-2-butyl | H | CF3 |
| 26-725 | 3-cyanophenyl | H | H | H | Br | H | nonafluoro-2-butyl | H | CF3 |
| 26-726 | 4-cyanophenyl | H | H | H | Br | H | nonafluoro-2-butyl | H | CF3 |

TABLE 26-continued

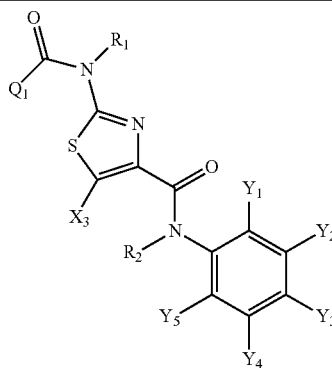

| compound number | $Q_1$ | $R_1$ | $R_2$ | $X_3$ | $Y_1$ | $Y_2$ | $Y_3$ | $Y_4$ | $Y_5$ |
|---|---|---|---|---|---|---|---|---|---|
| 26-727 | 2,6-difluorophenyl | H | H | H | Br | H | nonafluoro-2-butyl | H | CF3 |
| 26-728 | 3,4-dichlorophenyl | H | H | H | Br | H | nonafluoro-2-butyl | H | CF3 |
| 26-729 | 2,4-dichlorophenyl | H | H | H | Br | H | nonafluoro-2-butyl | H | CF3 |
| 26-730 | 2-chloro-4-fluorophenyl | H | H | H | Br | H | nonafluoro-2-butyl | H | CF3 |
| 26-731 | 2-chloro-4,5-difluorophenyl | H | H | H | Br | H | nonafluoro-2-butyl | H | CF3 |
| 26-732 | 4-bromo-2-chlorophenyl | H | H | H | Br | H | nonafluoro-2-butyl | H | CF3 |
| 26-733 | 2-bromo-4-chlorophenyl | H | H | H | Br | H | nonafluoro-2-butyl | H | CF3 |
| 26-734 | 2-bromo-4-fluorophenyl | H | H | H | Br | H | nonafluoro-2-butyl | H | CF3 |
| 26-735 | 2-chloro-4-nitrophenyl | H | H | H | Br | H | nonafluoro-2-butyl | H | CF3 |
| 26-736 | 3,5-dicyanophenyl | H | H | H | Br | H | nonafluoro-2-butyl | H | CF3 |
| 26-737 | 4-cyano-2-fluorophenyl | H | H | H | Br | H | nonafluoro-2-butyl | H | CF3 |
| 26-738 | 2-chloro-4-cyanophenyl | H | H | H | Br | H | nonafluoro-2-butyl | H | CF3 |
| 26-739 | pyridin-3-yl | H | H | H | Br | H | nonafluoro-2-butyl | H | CF3 |
| 26-740 | 2-fluoropyridin-3-yl | H | H | H | Br | H | nonafluoro-2-butyl | H | CF3 |
| 26-741 | 2-chloropyridin-3-yl | H | H | H | Br | H | nonafluoro-2-butyl | H | CF3 |
| 26-742 | 2-bromopyridin-3-yl | H | H | H | Br | H | nonafluoro-2-butyl | H | CF3 |
| 26-743 | 2-iodopyridin-3-yl | H | H | H | Br | H | nonafluoro-2-butyl | H | CF3 |
| 26-744 | 2-(trifluoromethyl)pyridin-3-yl | H | H | H | Br | H | nonafluoro-2-butyl | H | CF3 |
| 26-745 | 2-nitropyridin-3-yl | H | H | H | Br | H | nonafluoro-2-butyl | H | CF3 |
| 26-746 | 2-cyanopyridin-3-yl | H | H | H | Br | H | nonafluoro-2-butyl | H | CF3 |
| 26-747 | 6-fluoropyridin-3-yl | H | H | H | Br | H | nonafluoro-2-butyl | H | CF3 |
| 26-748 | 6-chloropyridin-3-yl | H | H | H | Br | H | nonafluoro-2-butyl | H | CF3 |
| 26-749 | 6-bromopyridin-3-yl | H | H | H | Br | H | nonafluoro-2-butyl | H | CF3 |
| 26-750 | 6-iodopyridin-3-yl | H | H | H | Br | H | nonafluoro-2-butyl | H | CF3 |
| 26-751 | 6-(trifluoromethyl)pyridin-3-yl | H | H | H | Br | H | nonafluoro-2-butyl | H | CF3 |
| 26-752 | 6-nitropyridin-3-yl | H | H | H | Br | H | nonafluoro-2-butyl | H | CF3 |
| 26-753 | 6-cyanopyridin-3-yl | H | H | H | Br | H | nonafluoro-2-butyl | H | CF3 |
| 26-754 | 5-fluoropyridin-3-yl | H | H | H | Br | H | nonafluoro-2-butyl | H | CF3 |
| 26-755 | 5-chloropyridin-3-yl | H | H | H | Br | H | nonafluoro-2-butyl | H | CF3 |
| 26-756 | 5-bromopyridin-3-yl | H | H | H | Br | H | nonafluoro-2-butyl | H | CF3 |
| 26-757 | 5-iodopyridin-3-yl | H | H | H | Br | H | nonafluoro-2-butyl | H | CF3 |
| 26-758 | 5-(trifluoromethyl)pyridin-3-yl | H | H | H | Br | H | nonafluoro-2-butyl | H | CF3 |
| 26-759 | 5-nitropyridin-3-yl | H | H | H | Br | H | nonafluoro-2-butyl | H | CF3 |
| 26-760 | 5-cyanopyridin-3-yl | H | H | H | Br | H | nonafluoro-2-butyl | H | CF3 |
| 26-761 | 4-fluoropyridin-3-yl | H | H | H | Br | H | nonafluoro-2-butyl | H | CF3 |
| 26-762 | 4-chloropyridin-3-yl | H | H | H | Br | H | nonafluoro-2-butyl | H | CF3 |
| 26-763 | 4-bromopyridin-3-yl | H | H | H | Br | H | nonafluoro-2-butyl | H | CF3 |
| 26-764 | 4-iodopyridin-3-yl | H | H | H | Br | H | nonafluoro-2-butyl | H | CF3 |
| 26-765 | 4-(trifluoromethyl)pyridin-3-yl | H | H | H | Br | H | nonafluoro-2-butyl | H | CF3 |
| 26-766 | 4-nitropyridin-3-yl | H | H | H | Br | H | nonafluoro-2-butyl | H | CF3 |
| 26-767 | 4-cyanopyridin-3-yl | H | H | H | Br | H | nonafluoro-2-butyl | H | CF3 |
| 26-768 | 2,6-dichloropyridin-3-yl | H | H | H | Br | H | nonafluoro-2-butyl | H | CF3 |
| 26-769 | pyridin-3-yl N-oxide | H | H | H | Br | H | nonafluoro-2-butyl | H | CF3 |
| 26-770 | pyridin-4-yl | H | H | H | Br | H | nonafluoro-2-butyl | H | CF3 |
| 26-771 | 2-chloropyridin-4-yl | H | H | H | Br | H | nonafluoro-2-butyl | H | CF3 |
| 26-772 | 3-bromopyridin-4-yl | H | H | H | Br | H | nonafluoro-2-butyl | H | CF3 |
| 26-773 | 3,5-dichloropyridin-4-yl | H | H | H | Br | H | nonafluoro-2-butyl | H | CF3 |
| 26-774 | 3-(trifluoromethyl)pyridin-4-yl | H | H | H | Br | H | nonafluoro-2-butyl | H | CF3 |
| 26-775 | 2,6-dicyanopyridin-4-yl | H | H | H | Br | H | nonafluoro-2-butyl | H | CF3 |
| 26-776 | pyridin-4-yl N-oxide | H | H | H | Br | H | nonafluoro-2-butyl | H | CF3 |
| 26-777 | pyridin-2-yl | H | H | H | Br | H | nonafluoro-2-butyl | H | CF3 |
| 26-778 | 3-chloropyridin-2-yl | H | H | H | Br | H | nonafluoro-2-butyl | H | CF3 |
| 26-779 | 4-bromopyridin-2-yl | H | H | H | Br | H | nonafluoro-2-butyl | H | CF3 |
| 26-780 | 5-iodopyridin-2-yl | H | H | H | Br | H | nonafluoro-2-butyl | H | CF3 |
| 26-781 | 6-chloropyridin-2-yl | H | H | H | Br | H | nonafluoro-2-butyl | H | CF3 |
| 26-782 | 4-cyanopyridin-2-yl | H | H | H | Br | H | nonafluoro-2-butyl | H | CF3 |
| 26-783 | phenyl | H | H | H | I | H | heptafluoroisopropyl | H | CF3 |
| 26-784 | 2-fluorophenyl | H | H | H | I | H | heptafluoroisopropyl | H | CF3 |
| 26-785 | 3-fluorophenyl | H | H | H | I | H | heptafluoroisopropyl | H | CF3 |

TABLE 26-continued

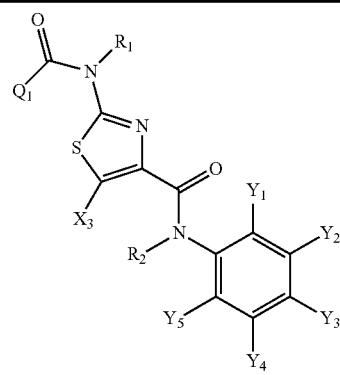

| compound number | Q₁ | R₁ | R₂ | X₃ | Y₁ | Y₂ | Y₃ | Y₄ | Y₅ |
|---|---|---|---|---|---|---|---|---|---|
| 26-786 | 4-fluorophenyl | H | H | H | I | H | heptafluoroisopropyl | H | CF3 |
| 26-787 | 2-chlorophenyl | H | H | H | I | H | heptafluoroisopropyl | H | CF3 |
| 26-788 | 3-chlorophenyl | H | H | H | I | H | heptafluoroisopropyl | H | CF3 |
| 26-789 | 4-chlorophenyl | H | H | H | I | H | heptafluoroisopropyl | H | CF3 |
| 26-790 | 2-bromophenyl | H | H | H | I | H | heptafluoroisopropyl | H | CF3 |
| 26-791 | 3-bromophenyl | H | H | H | I | H | heptafluoroisopropyl | H | CF3 |
| 26-792 | 4-bromophenyl | H | H | H | I | H | heptafluoroisopropyl | H | CF3 |
| 26-793 | 2-iodophenyl | H | H | H | I | H | heptafluoroisopropyl | H | CF3 |
| 26-794 | 3-iodophenyl | H | H | H | I | H | heptafluoroisopropyl | H | CF3 |
| 26-795 | 4-iodophenyl | H | H | H | I | H | heptafluoroisopropyl | H | CF3 |
| 26-796 | (2-trifluoromethyl)phenyl | H | H | H | I | H | heptafluoroisopropyl | H | CF3 |
| 26-797 | (3-trifluoromethyl)phenyl | H | H | H | I | H | heptafluoroisopropyl | H | CF3 |
| 26-798 | (4-trifluoromethyl)phenyl | H | H | H | I | H | heptafluoroisopropyl | H | CF3 |
| 26-799 | 2-nitrophenyl | H | H | H | I | H | heptafluoroisopropyl | H | CF3 |
| 26-800 | 3-nitrophenyl | H | H | H | I | H | heptafluoroisopropyl | H | CF3 |
| 26-801 | 4-nitrophenyl | H | H | H | I | H | heptafluoroisopropyl | H | CF3 |
| 26-802 | 2-cyanophenyl | H | H | H | I | H | heptafluoroisopropyl | H | CF3 |
| 26-803 | 3-cyanophenyl | H | H | H | I | H | heptafluoroisopropyl | H | CF3 |
| 26-804 | 4-cyanophenyl | H | H | H | I | H | heptafluoroisopropyl | H | CF3 |
| 26-805 | 2,6-difluorophenyl | H | H | H | I | H | heptafluoroisopropyl | H | CF3 |
| 26-806 | 3,4-dichlorophenyl | H | H | H | I | H | heptafluoroisopropyl | H | CF3 |
| 26-807 | 2,4-dichlorophenyl | H | H | H | I | H | heptafluoroisopropyl | H | CF3 |
| 26-808 | 2-chloro-4-fluorophenyl | H | H | H | I | H | heptafluoroisopropyl | H | CF3 |
| 26-809 | 2-chloro-4,5-difluorophenyl | H | H | H | I | H | heptafluoroisopropyl | H | CF3 |
| 26-810 | 4-bromo-2-chlorophenyl | H | H | H | I | H | heptafluoroisopropyl | H | CF3 |
| 26-811 | 2-bromo-4-chlorophenyl | H | H | H | I | H | heptafluoroisopropyl | H | CF3 |
| 26-812 | 2-bromo-4-fluorophenyl | H | H | H | I | H | heptafluoroisopropyl | H | CF3 |
| 26-813 | 2-chloro-4-nitrophenyl | H | H | H | I | H | heptafluoroisopropyl | H | CF3 |
| 26-814 | 3,5-dicyanophenyl | H | H | H | I | H | heptafluoroisopropyl | H | CF3 |
| 26-815 | 4-cyano-2-fluorophenyl | H | H | H | I | H | heptafluoroisopropyl | H | CF3 |
| 26-816 | 2-chloro-4-cyanophenyl | H | H | H | I | H | heptafluoroisopropyl | H | CF3 |
| 26-817 | pyridin-3-yl | H | H | H | I | H | heptafluoroisopropyl | H | CF3 |
| 26-818 | 2-fluoropyridin-3-yl | H | H | H | I | H | heptafluoroisopropyl | H | CF3 |
| 26-819 | 2-chloropyridin-3-yl | H | H | H | I | H | heptafluoroisopropyl | H | CF3 |
| 26-820 | 2-bromopyridin-3-yl | H | H | H | I | H | heptafluoroisopropyl | H | CF3 |
| 26-821 | 2-iodopyridin-3-yl | H | H | H | I | H | heptafluoroisopropyl | H | CF3 |
| 26-822 | 2-(trifluoromethyl)pyridin-3-yl | H | H | H | I | H | heptafluoroisopropyl | H | CF3 |
| 26-823 | 2-nitropyridin-3-yl | H | H | H | I | H | heptafluoroisopropyl | H | CF3 |
| 26-824 | 2-cyanopyridin-3-yl | H | H | H | I | H | heptafluoroisopropyl | H | CF3 |
| 26-825 | 6-fluoropyridin-3-yl | H | H | H | I | H | heptafluoroisopropyl | H | CF3 |
| 26-826 | 6-chloropyridin-3-yl | H | H | H | I | H | heptafluoroisopropyl | H | CF3 |
| 26-827 | 6-bromopyridin-3-yl | H | H | H | I | H | heptafluoroisopropyl | H | CF3 |
| 26-828 | 6-iodopyridin-3-yl | H | H | H | I | H | heptafluoroisopropyl | H | CF3 |
| 26-829 | 6-(trifluoromethyl)pyridin-3-yl | H | H | H | I | H | heptafluoroisopropyl | H | CF3 |
| 26-830 | 6-nitropyridin-3-yl | H | H | H | I | H | heptafluoroisopropyl | H | CF3 |
| 26-831 | 6-cyanopyridin-3-yl | H | H | H | I | H | heptafluoroisopropyl | H | CF3 |
| 26-832 | 5-fluoropyridin-3-yl | H | H | H | I | H | heptafluoroisopropyl | H | CF3 |
| 26-833 | 5-chloropyridin-3-yl | H | H | H | I | H | heptafluoroisopropyl | H | CF3 |
| 26-834 | 5-bromopyridin-3-yl | H | H | H | I | H | heptafluoroisopropyl | H | CF3 |
| 26-835 | 5-iodopyridin-3-yl | H | H | H | I | H | heptafluoroisopropyl | H | CF3 |
| 26-836 | 5-(trifluoromethyl)pyridin-3-yl | H | H | H | I | H | heptafluoroisopropyl | H | CF3 |
| 26-837 | 5-nitropyridin-3-yl | H | H | H | I | H | heptafluoroisopropyl | H | CF3 |
| 26-838 | 5-cyanopyridin-3-yl | H | H | H | I | H | heptafluoroisopropyl | H | CF3 |
| 26-839 | 4-fluoropyridin-3-yl | H | H | H | I | H | heptafluoroisopropyl | H | CF3 |
| 26-840 | 4-chloropyridin-3-yl | H | H | H | I | H | heptafluoroisopropyl | H | CF3 |
| 26-841 | 4-bromopyridin-3-yl | H | H | H | I | H | heptafluoroisopropyl | H | CF3 |
| 26-842 | 4-iodopyridin-3-yl | H | H | H | I | H | heptafluoroisopropyl | H | CF3 |
| 26-843 | 4-(trifluoromethyl)pyridin-3-yl | H | H | H | I | H | heptafluoroisopropyl | H | CF3 |
| 26-844 | 4-nitropyridin-3-yl | H | H | H | I | H | heptafluoroisopropyl | H | CF3 |

TABLE 26-continued

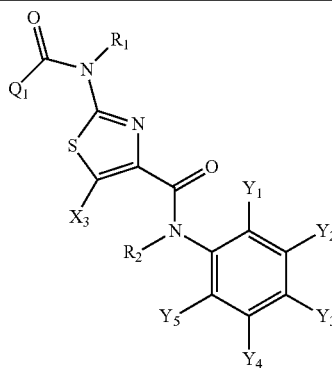

| compound number | Q$_1$ | R$_1$ | R$_2$ | X$_3$ | Y$_1$ | Y$_2$ | Y$_3$ | Y$_4$ | Y$_5$ |
|---|---|---|---|---|---|---|---|---|---|
| 26-845 | 4-cyanopyridin-3-yl | H | H | H | I | H | heptafluoroisopropyl | H | CF3 |
| 26-846 | 2,6-dichloropyridin-3-yl | H | H | H | I | H | heptafluoroisopropyl | H | CF3 |
| 26-847 | pyridin-3-yl N-oxide | H | H | H | I | H | heptafluoroisopropyl | H | CF3 |
| 26-848 | pyridin-4-yl | H | H | H | I | H | heptafluoroisopropyl | H | CF3 |
| 26-849 | 2-chloropyridin-4-yl | H | H | H | I | H | heptafluoroisopropyl | H | CF3 |
| 26-850 | 3-bromopyridin-4-yl | H | H | H | I | H | heptafluoroisopropyl | H | CF3 |
| 26-851 | 3,5-dichloropyridin-4-yl | H | H | H | I | H | heptafluoroisopropyl | H | CF3 |
| 26-852 | 3-(trifluoromethyl)pyridin-4-yl | H | H | H | I | H | heptafluoroisopropyl | H | CF3 |
| 26-853 | 2,6-dicyanopyridin-4-yl | H | H | H | I | H | heptafluoroisopropyl | H | CF3 |
| 26-854 | pyridin-4-yl N-oxide | H | H | H | I | H | heptafluoroisopropyl | H | CF3 |
| 26-855 | pyridin-2-yl | H | H | H | I | H | heptafluoroisopropyl | H | CF3 |
| 26-856 | 3-chloropyridin-2-yl | H | H | H | I | H | heptafluoroisopropyl | H | CF3 |
| 26-857 | 4-bromopyridin-2-yl | H | H | H | I | H | heptafluoroisopropyl | H | CF3 |
| 26-858 | 5-iodopyridin-2-yl | H | H | H | I | H | heptafluoroisopropyl | H | CF3 |
| 26-859 | 6-chloropyridin-2-yl | H | H | H | I | H | heptafluoroisopropyl | H | CF3 |
| 26-860 | 4-cyanopyridin-2-yl | H | H | H | I | H | heptafluoroisopropyl | H | CF3 |
| 26-861 | phenyl | H | H | H | I | H | nonafluoro-2-butyl | H | CF3 |
| 26-862 | 2-fluorophenyl | H | H | H | I | H | nonafluoro-2-butyl | H | CF3 |
| 26-863 | 3-fluorophenyl | H | H | H | I | H | nonafluoro-2-butyl | H | CF3 |
| 26-864 | 4-fluorophenyl | H | H | H | I | H | nonafluoro-2-butyl | H | CF3 |
| 26-865 | 2-chlorophenyl | H | H | H | I | H | nonafluoro-2-butyl | H | CF3 |
| 26-866 | 3-chlorophenyl | H | H | H | I | H | nonafluoro-2-butyl | H | CF3 |
| 26-867 | 4-chlorophenyl | H | H | H | I | H | nonafluoro-2-butyl | H | CF3 |
| 26-868 | 2-bromophenyl | H | H | H | I | H | nonafluoro-2-butyl | H | CF3 |
| 26-869 | 3-bromophenyl | H | H | H | I | H | nonafluoro-2-butyl | H | CF3 |
| 26-870 | 4-bromophenyl | H | H | H | I | H | nonafluoro-2-butyl | H | CF3 |
| 26-871 | 2-iodophenyl | H | H | H | I | H | nonafluoro-2-butyl | H | CF3 |
| 26-872 | 3-iodophenyl | H | H | H | I | H | nonafluoro-2-butyl | H | CF3 |
| 26-873 | 4-iodophenyl | H | H | H | I | H | nonafluoro-2-butyl | H | CF3 |
| 26-874 | (2-trifluoromethyl)phenyl | H | H | H | I | H | nonafluoro-2-butyl | H | CF3 |
| 26-875 | (3-trifluoromethyl)phenyl | H | H | H | I | H | nonafluoro-2-butyl | H | CF3 |
| 26-876 | (4-trifluoromethyl)phenyl | H | H | H | I | H | nonafluoro-2-butyl | H | CF3 |
| 26-877 | 2-nitrophenyl | H | H | H | I | H | nonafluoro-2-butyl | H | CF3 |
| 26-878 | 3-nitrophenyl | H | H | H | I | H | nonafluoro-2-butyl | H | CF3 |
| 26-879 | 4-nitrophenyl | H | H | H | I | H | nonafluoro-2-butyl | H | CF3 |
| 26-880 | 2-cyanophenyl | H | H | H | I | H | nonafluoro-2-butyl | H | CF3 |
| 26-881 | 3-cyanophenyl | H | H | H | I | H | nonafluoro-2-butyl | H | CF3 |
| 26-882 | 4-cyanophenyl | H | H | H | I | H | nonafluoro-2-butyl | H | CF3 |
| 26-883 | 2,6-difluorophenyl | H | H | H | I | H | nonafluoro-2-butyl | H | CF3 |
| 26-884 | 3,4-dichlorophenyl | H | H | H | I | H | nonafluoro-2-butyl | H | CF3 |
| 26-885 | 2,4-dichlorophenyl | H | H | H | I | H | nonafluoro-2-butyl | H | CF3 |
| 26-886 | 2-chloro-4-fluorophenyl | H | H | H | I | H | nonafluoro-2-butyl | H | CF3 |
| 26-887 | 2-chloro-4,5-difluorophenyl | H | H | H | I | H | nonafluoro-2-butyl | H | CF3 |
| 26-888 | 4-bromo-2-chlorophenyl | H | H | H | I | H | nonafluoro-2-butyl | H | CF3 |
| 26-889 | 2-bromo-4-chlorophenyl | H | H | H | I | H | nonafluoro-2-butyl | H | CF3 |
| 26-890 | 2-bromo-4-fluorophenyl | H | H | H | I | H | nonafluoro-2-butyl | H | CF3 |
| 26-891 | 2-chloro-4-nitrophenyl | H | H | H | I | H | nonafluoro-2-butyl | H | CF3 |
| 26-892 | 3,5-dicyanophenyl | H | H | H | I | H | nonafluoro-2-butyl | H | CF3 |
| 26-893 | 4-cyano-2-fluorophenyl | H | H | H | I | H | nonafluoro-2-butyl | H | CF3 |
| 26-894 | 2-chloro-4-cyanophenyl | H | H | H | I | H | nonafluoro-2-butyl | H | CF3 |
| 26-895 | pyridin-3-yl | H | H | H | I | H | nonafluoro-2-butyl | H | CF3 |
| 26-896 | 2-fluoropyridin-3-yl | H | H | H | I | H | nonafluoro-2-butyl | H | CF3 |
| 26-897 | 2-chloropyridin-3-yl | H | H | H | I | H | nonafluoro-2-butyl | H | CF3 |
| 26-898 | 2-bromopyridin-3-yl | H | H | H | I | H | nonafluoro-2-butyl | H | CF3 |
| 26-899 | 2-iodopyridin-3-yl | H | H | H | I | H | nonafluoro-2-butyl | H | CF3 |
| 26-900 | 2-(trifluoromethyl)pyridin-3-yl | H | H | H | I | H | nonafluoro-2-butyl | H | CF3 |
| 26-901 | 2-nitropyridin-3-yl | H | H | H | I | H | nonafluoro-2-butyl | H | CF3 |
| 26-902 | 2-cyanopyridin-3-yl | H | H | H | I | H | nonafluoro-2-butyl | H | CF3 |
| 26-903 | 6-fluoropyridin-3-yl | H | H | H | I | H | nonafluoro-2-butyl | H | CF3 |

TABLE 26-continued

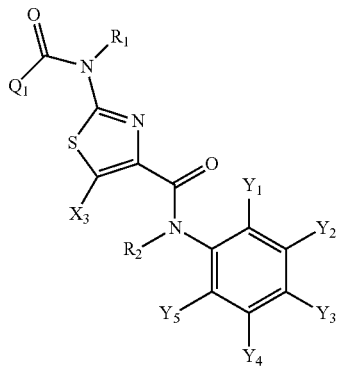

| compound number | Q₁ | R₁ | R₂ | X₃ | Y₁ | Y₂ | Y₃ | Y₄ | Y₅ |
|---|---|---|---|---|---|---|---|---|---|
| 26-904 | 6-chloropyridin-3-yl | H | H | H | I | H | nonafluoro-2-butyl | H | CF3 |
| 26-905 | 6-bromopyridin-3-yl | H | H | H | I | H | nonafluoro-2-butyl | H | CF3 |
| 26-906 | 6-iodopyridin-3-yl | H | H | H | I | H | nonafluoro-2-butyl | H | CF3 |
| 26-907 | 6-(trifluoromethyl)pyridin-3-yl | H | H | H | I | H | nonafluoro-2-butyl | H | CF3 |
| 26-908 | 6-nitropyridin-3-yl | H | H | H | I | H | nonafluoro-2-butyl | H | CF3 |
| 26-909 | 6-cyanopyridin-3-yl | H | H | H | I | H | nonafluoro-2-butyl | H | CF3 |
| 26-910 | 5-fluoropyridin-3-yl | H | H | H | I | H | nonafluoro-2-butyl | H | CF3 |
| 26-911 | 5-chloropyridin-3-yl | H | H | H | I | H | nonafluoro-2-butyl | H | CF3 |
| 26-912 | 5-bromopyridin-3-yl | H | H | H | I | H | nonafluoro-2-butyl | H | CF3 |
| 26-913 | 5-iodopyridin-3-yl | H | H | H | I | H | nonafluoro-2-butyl | H | CF3 |
| 26-914 | 5-(trifluoromethyl)pyridin-3-yl | H | H | H | I | H | nonafluoro-2-butyl | H | CF3 |
| 26-915 | 5-nitropyridin-3-yl | H | H | H | I | H | nonafluoro-2-butyl | H | CF3 |
| 26-916 | 5-cyanopyridin-3-yl | H | H | H | I | H | nonafluoro-2-butyl | H | CF3 |
| 26-917 | 4-fluoropyridin-3-yl | H | H | H | I | H | nonafluoro-2-butyl | H | CF3 |
| 26-918 | 4-chloropyridin-3-yl | H | H | H | I | H | nonafluoro-2-butyl | H | CF3 |
| 26-919 | 4-bromopyridin-3-yl | H | H | H | I | H | nonafluoro-2-butyl | H | CF3 |
| 26-920 | 4-iodopyridin-3-yl | H | H | H | I | H | nonafluoro-2-butyl | H | CF3 |
| 26-921 | 4-(trifluoromethyl)pyridin-3-yl | H | H | H | I | H | nonafluoro-2-butyl | H | CF3 |
| 26-922 | 4-nitropyridin-3-yl | H | H | H | I | H | nonafluoro-2-butyl | H | CF3 |
| 26-923 | 4-cyanopyridin-3-yl | H | H | H | I | H | nonafluoro-2-butyl | H | CF3 |
| 26-924 | 2,6-dichloropyridin-3-yl | H | H | H | I | H | nonafluoro-2-butyl | H | CF3 |
| 26-925 | pyridin-3-yl N-oxide | H | H | H | I | H | nonafluoro-2-butyl | H | CF3 |
| 26-926 | pyridin-4-yl | H | H | H | I | H | nonafluoro-2-butyl | H | CF3 |
| 26-927 | 2-chloropyridin-4-yl | H | H | H | I | H | nonafluoro-2-butyl | H | CF3 |
| 26-928 | 3-bromopyridin-4-yl | H | H | H | I | H | nonafluoro-2-butyl | H | CF3 |
| 26-929 | 3,5-dichloropyridin-4-yl | H | H | H | I | H | nonafluoro-2-butyl | H | CF3 |
| 26-930 | 3-(trifluoromethyl)pyridin-4-yl | H | H | H | I | H | nonafluoro-2-butyl | H | CF3 |
| 26-931 | 2,6-dicyanopyridin-4-yl | H | H | H | I | H | nonafluoro-2-butyl | H | CF3 |
| 26-932 | pyridin-4-yl N-oxide | H | H | H | I | H | nonafluoro-2-butyl | H | CF3 |
| 26-933 | pyridin-2-yl | H | H | H | I | H | nonafluoro-2-butyl | H | CF3 |
| 26-934 | 3-chloropyridin-2-yl | H | H | H | I | H | nonafluoro-2-butyl | H | CF3 |
| 26-935 | 4-bromopyridin-2-yl | H | H | H | I | H | nonafluoro-2-butyl | H | CF3 |
| 26-936 | 5-iodopyridin-2-yl | H | H | H | I | H | nonafluoro-2-butyl | H | CF3 |
| 26-937 | 6-chloropyridin-2-yl | H | H | H | I | H | nonafluoro-2-butyl | H | CF3 |
| 26-938 | 4-cyanopyridin-2-yl | H | H | H | I | H | nonafluoro-2-butyl | H | CF3 |
| 26-939 | phenyl | H | H | H | OCF3 | H | heptafluoroisopropyl | H | OCF3 |
| 26-946 | 2-bromophenyl | H | H | H | OCF3 | H | heptafluoroisopropyl | H | OC2F5 |
| 26-950 | 3-iodophenyl | H | H | H | OCF3 | H | pentafluoroethyl | H | OCF3 |
| 26-951 | 4-iodophenyl | H | H | H | OCF3 | H | pentafluoroethyl | H | OCF3 |
| 26-954 | 3-cyanophenyl | H | H | H | OCF3 | H | heptafluoroisopropyl | H | OCF3 |
| 26-955 | 4-cyanophenyl | H | H | H | OCF3 | H | heptafluoroisopropyl | H | OCF3 |
| 26-960 | 2-chloro-4,5-difluorophenyl | H | H | H | OC2F5 | H | heptafluoroisopropyl | H | OC2F5 |
| 26-963 | 2-bromo-4-fluorophenyl | H | H | H | OC2F5 | H | heptafluoroisopropyl | H | OCF3 |
| 26-964 | 2-chloro-4-nitrophenyl | H | H | Cl | OCF3 | H | heptafluoroisopropyl | H | OCF3 |
| 26-969 | 2-fluoropyridin-3-yl | H | H | H | OCF3 | H | pentafluoroethyl | H | OCF3 |
| 26-970 | 2-chloropyridin-3-yl | H | H | H | OCF3 | H | heptafluoroisopropyl | H | OCF3 |
| 26-979 | 5-cyanopyridin-3-yl | H | H | H | OC2F5 | H | heptafluoroisopropyl | H | OC2F5 |
| 26-981 | 4-cyanopyridin-3-yl | H | H | H | OCF3 | H | heptafluoroisopropyl | H | OC2F5 |
| 26-994 | 4-cyanopyridin-2-yl | H | H | H | OCF3 | H | pentafluoroethyl | H | OCF3 |
| 26-995 | phenyl | H | H | H | OCF3 | H | nonafluoro-2-butyl | H | OCF3 |
| 26-1002 | 2-bromophenyl | H | H | H | OC2F5 | H | nonafluoro-2-butyl | H | OCF3 |
| 26-1008 | (2-trifluoromethyl)phenyl | H | H | H | OCF3 | H | nonafluoro-2-butyl | H | OC2F5 |
| 26-1010 | 3-cyanophenyl | H | H | H | OCF3 | H | nonafluoro-2-butyl | H | OCF3 |
| 26-1011 | 4-cyanophenyl | H | H | H | OCF3 | H | nonafluoro-2-butyl | H | OCF3 |
| 26-1017 | 4-bromo-2-chlorophenyl | H | H | H | OC2F5 | H | nonafluoro-2-butyl | H | OC2F5 |
| 26-1026 | 2-chloropyridin-3-yl | H | H | H | OCF3 | H | nonafluoro-2-butyl | H | OCF3 |
| 26-1033 | 6-cyanopyridin-3-yl | H | H | H | OC2F5 | H | nonafluoro-2-butyl | H | OCF3 |
| 26-1035 | 5-cyanopyridin-3-yl | H | H | H | OCF3 | H | nonafluoro-2-butyl | H | OC2F5 |
| 26-1037 | 4-cyanopyridin-3-yl | H | H | H | OC2F5 | H | nonafluoro-2-butyl | H | OC2F5 |

TABLE 26-continued

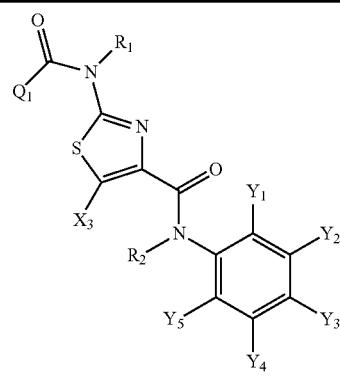

| compound number | Q₁ | R₁ | R₂ | X₃ | Y₁ | Y₂ | Y₃ | Y₄ | Y₅ |
|---|---|---|---|---|---|---|---|---|---|
| 26-1051 | phenyl | H | H | H | CF3 | H | heptafluoroisopropyl | H | OCF3 |
| 26-1058 | 2-bromophenyl | H | H | H | CF3 | H | heptafluoroisopropyl | H | OC2F5 |
| 26-1062 | 3-iodophenyl | H | H | H | CF3 | H | pentafluoroethyl | H | OCF3 |
| 26-1063 | 4-iodophenyl | H | H | H | CF3 | H | pentafluoroethyl | H | OCF3 |
| 26-1064 | (2-trifluoromethyl)phenyl | H | H | H | C2F5 | H | heptafluoroisopropyl | H | OC2F5 |
| 26-1065 | 3-nitrophenyl | H | H | H | C2F5 | H | heptafluoroisopropyl | H | OCF3 |
| 26-1066 | 3-cyanophenyl | H | H | H | CF3 | H | heptafluoroisopropyl | H | OCF3 |
| 26-1067 | 4-cyanophenyl | H | H | H | CF3 | H | heptafluoroisopropyl | H | OCF3 |
| 26-1074 | 2-bromo-4-chlorophenyl | H | H | H | n-C3F7 | H | heptafluoroisopropyl | H | OCF3 |
| 26-1078 | 4-cyano-2-fluorophenyl | H | H | H | i-C3F7 | H | heptafluoroisopropyl | H | OCF3 |
| 26-1081 | 2-fluoropyridin-3-yl | H | H | H | CF3 | H | pentafluoroethyl | H | OCF3 |
| 26-1082 | 2-chloropyridin-3-yl | H | H | H | CF3 | H | heptafluoroisopropyl | H | OCF3 |
| 26-1089 | 6-cyanopyridin-3-yl | H | H | H | n-C3F7 | H | heptafluoroisopropyl | H | OC2F5 |
| 26-1091 | 5-cyanopyridin-3-yl | H | H | H | i-C3F7 | H | heptafluoroisopropyl | H | OC2F5 |
| 26-1106 | 4-cyanopyridin-2-yl | H | H | H | CF3 | H | pentafluoroethyl | H | OCF3 |
| 26-1107 | phenyl | H | H | H | CF3 | H | nonafluoro-2-butyl | H | OCF3 |
| 26-1118 | 3-iodophenyl | H | H | H | CF3 | H | nonafluoro-2-butyl | H | OC2F5 |
| 26-1121 | 3-nitrophenyl | H | H | H | C2F5 | H | nonafluoro-2-butyl | H | OCF3 |
| 26-1122 | 3-cyanophenyl | H | H | H | CF3 | H | nonafluoro-2-butyl | H | OCF3 |
| 26-1123 | 4-cyanophenyl | H | H | H | CF3 | H | nonafluoro-2-butyl | H | OCF3 |
| 26-1129 | 4-bromo-2-chlorophenyl | H | H | H | i-C3F7 | H | nonafluoro-2-butyl | H | OCF3 |
| 26-1132 | 2-chloro-4-nitrophenyl | H | H | H | n-C3F7 | H | nonafluoro-2-butyl | H | OCF3 |
| 26-1138 | 2-chloropyridin-3-yl | H | H | H | CF3 | H | nonafluoro-2-butyl | H | OCF3 |
| 26-1147 | 5-cyanopyridin-3-yl | H | H | H | C2F5 | H | nonafluoro-2-butyl | H | OC2F5 |
| 26-1149 | 4-cyanopyridin-3-yl | H | H | H | n-C3F7 | H | nonafluoro-2-butyl | H | OC2F5 |
| 26-1160 | 5-iodopyridin-2-yl | H | H | H | i-C3F7 | H | nonafluoro-2-butyl | H | OC2F5 |
| 26-1163 | phenyl | H | H | H | CF3 | H | heptafluoroisopropyl | H | CF3 |
| 26-1174 | 3-iodophenyl | H | H | H | CF3 | H | pentafluoroethyl | H | CF3 |
| 26-1175 | 4-iodophenyl | H | H | H | CF3 | H | pentafluoroethyl | H | CF3 |
| 26-1177 | (3-trifluoromethyl)phenyl | H | H | H | C2F5 | H | heptafluoroisopropyl | H | CF3 |
| 26-1183 | 3-cyanophenyl | H | H | H | CF3 | H | heptafluoroisopropyl | H | CF3 |
| 26-1184 | 4-cyanophenyl | H | H | H | CF3 | H | heptafluoroisopropyl | H | CF3 |
| 26-1190 | 4-bromo-2-chlorophenyl | H | H | H | n-C3F7 | H | heptafluoroisopropyl | H | CF3 |
| 26-1195 | 4-cyano-2-fluorophenyl | H | H | H | i-C3F7 | H | heptafluoroisopropyl | H | CF3 |
| 26-1198 | 2-fluoropyridin-3-yl | H | H | H | CF3 | H | pentafluoroethyl | H | CF3 |
| 26-1199 | 2-chloropyridin-3-yl | H | H | H | CF3 | H | heptafluoroisopropyl | H | CF3 |
| 26-1200 | 2-bromopyridin-3-yl | H | H | H | C2F5 | H | heptafluoroisopropyl | H | C2F5 |
| 26-1203 | 2-nitropyridin-3-yl | H | H | Cl | CF3 | H | heptafluoroisopropyl | H | CF3 |
| 26-1211 | 6-cyanopyridin-3-yl | H | H | H | C2F5 | H | heptafluoroisopropyl | H | n-C3F7 |
| 26-1215 | 4-cyanopyridin-3-yl | H | H | H | C2F5 | H | heptafluoroisopropyl | H | i-C3F7 |
| 26-1230 | 4-cyanopyridin-2-yl | H | H | H | CF3 | H | pentafluoroethyl | H | CF3 |
| 26-1231 | phenyl | H | H | H | CF3 | H | nonafluoro-2-butyl | H | CF3 |
| 26-1243 | 4-iodophenyl | H | H | H | C2F5 | H | nonafluoro-2-butyl | H | CF3 |
| 26-1251 | 3-cyanophenyl | H | H | H | CF3 | H | nonafluoro-2-butyl | H | CF3 |
| 26-1252 | 4-cyanophenyl | H | H | H | CF3 | H | nonafluoro-2-butyl | H | CF3 |
| 26-1258 | 4-bromo-2-chlorophenyl | H | H | H | n-C3F7 | H | nonafluoro-2-butyl | H | CF3 |
| 26-1263 | 4-cyano-2-fluorophenyl | H | H | H | i-C3F7 | H | nonafluoro-2-butyl | H | CF3 |
| 26-1267 | 2-chloropyridin-3-yl | H | H | H | CF3 | H | nonafluoro-2-butyl | H | CF3 |
| 26-1268 | 2-bromopyridin-3-yl | H | H | H | C2F5 | H | nonafluoro-2-butyl | H | C2F5 |
| 26-1279 | 6-cyanopyridin-3-yl | H | H | H | C2F5 | H | nonafluoro-2-butyl | H | n-C3F7 |
| 26-1283 | 4-cyanopyridin-3-yl | H | H | H | C2F5 | H | nonafluoro-2-butyl | H | i-C3F7 |

TABLE 27

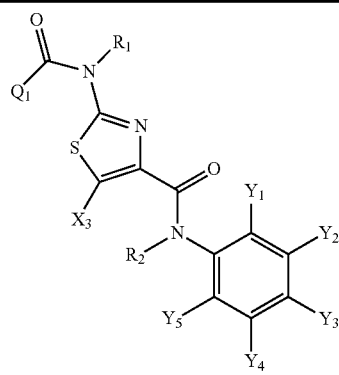

| compound number | Q₁ | R₁ | R₂ | X₃ | Y₁ | Y₂ | Y₃ | Y₄ | Y₅ |
|---|---|---|---|---|---|---|---|---|---|
| 27-1 | phenyl | Me | H | H | Cl | H | heptafluoroisopropyl | H | OCF3 |
| 27-21 | 3-cyanophenyl | Me | H | H | Cl | H | heptafluoroisopropyl | H | OCF3 |
| 27-22 | 4-cyanophenyl | Me | H | H | Cl | H | heptafluoroisopropyl | H | OCF3 |
| 27-37 | 2-chloropyridin-3-yl | Me | H | H | Cl | H | heptafluoroisopropyl | H | OCF3 |
| 27-79 | phenyl | Me | H | H | Cl | H | nonafluoro-2-butyl | H | OCF3 |
| 27-99 | 3-cyanophenyl | Me | H | H | Cl | H | nonafluoro-2-butyl | H | OCF3 |
| 27-100 | 4-cyanophenyl | Me | H | H | Cl | H | nonafluoro-2-butyl | H | OCF3 |
| 27-115 | 2-chloropyridin-3-yl | Me | H | H | Cl | H | nonafluoro-2-butyl | H | OCF3 |
| 27-157 | phenyl | Me | H | H | Br | H | heptafluoroisopropyl | H | OCF3 |
| 27-177 | 3-cyanophenyl | Me | H | H | Br | H | heptafluoroisopropyl | H | OCF3 |
| 27-178 | 4-cyanophenyl | Me | H | H | Br | H | heptafluoroisopropyl | H | OCF3 |
| 27-193 | 2-chloropyridin-3-yl | Me | H | H | Br | H | heptafluoroisopropyl | H | OCF3 |
| 27-235 | phenyl | Me | H | H | Br | H | nonafluoro-2-butyl | H | OCF3 |
| 27-255 | 3-cyanophenyl | Me | H | H | Br | H | nonafluoro-2-butyl | H | OCF3 |
| 27-256 | 4-cyanophenyl | Me | H | H | Br | H | nonafluoro-2-butyl | H | OCF3 |
| 27-271 | 2-chloropyridin-3-yl | Me | H | H | Br | H | nonafluoro-2-butyl | H | OCF3 |
| 27-313 | phenyl | Me | H | H | I | H | heptafluoroisopropyl | H | OCF3 |
| 27-333 | 3-cyanophenyl | Me | H | H | I | H | heptafluoroisopropyl | H | OCF3 |
| 27-334 | 4-cyanophenyl | Me | H | H | I | H | heptafluoroisopropyl | H | OCF3 |
| 27-349 | 2-chloropyridin-3-yl | Me | H | H | I | H | heptafluoroisopropyl | H | OCF3 |
| 27-391 | phenyl | Me | H | H | I | H | nonafluoro-2-butyl | H | OCF3 |
| 27-411 | 3-cyanophenyl | Me | H | H | I | H | nonafluoro-2-butyl | H | OCF3 |
| 27-412 | 4-cyanophenyl | Me | H | H | I | H | nonafluoro-2-butyl | H | OCF3 |
| 27-427 | 2-chloropyridin-3-yl | Me | H | H | I | H | nonafluoro-2-butyl | H | OCF3 |
| 27-469 | phenyl | Me | H | H | F | H | heptafluoroisopropyl | H | CF3 |
| 27-470 | phenyl | Me | H | H | Cl | H | heptafluoroisopropyl | H | CF3 |
| 27-484 | (3-trifluoromethyl)phenyl | Et | H | H | Cl | H | heptafluoroisopropyl | H | CF3 |
| 27-489 | 2-cyanophenyl | Me | H | H | Cl | H | pentafluoroethyl | H | C2F5 |
| 27-490 | 3-cyanophenyl | Me | H | H | Cl | H | heptafluoroisopropyl | H | CF3 |
| 27-491 | 4-cyanophenyl | Me | H | H | Cl | H | heptafluoroisopropyl | H | CF3 |
| 27-494 | 2,4-dichlorophenyl | Me | H | H | Cl | H | heptafluoroisopropyl | H | C2F5 |
| 27-495 | 2-chloro-4-fluorophenyl | n-Pr | H | H | Cl | H | heptafluoroisopropyl | H | CF3 |
| 27-498 | 2-bromo-4-chlorophenyl | Me | H | H | Cl | H | heptafluoroisopropyl | H | n-C3F7 |
| 27-506 | 2-chloropyridin-3-yl | Me | H | H | Cl | H | heptafluoroisopropyl | H | CF3 |
| 27-510 | 2-nitropyridin-3-yl | Me | H | Cl | Cl | H | heptafluoroisopropyl | H | CF3 |
| 27-512 | 6-fluoropyridin-3-yl | i-Pr | H | H | Cl | H | heptafluoroisopropyl | H | CF3 |
| 27-519 | 5-fluoropyridin-3-yl | Me | H | H | Cl | H | heptafluoroisopropyl | H | C2F5 |
| 27-521 | 5-bromopyridin-3-yl | Me | H | H | Cl | H | heptafluoroisopropyl | H | n-C3F7 |
| 27-522 | 5-iodopyridin-3-yl | Me | H | H | Cl | H | heptafluoroisopropyl | H | i-C3F7 |
| 27-528 | 4-bromopyridin-3-yl | CH2CH=CH2 | H | H | Cl | H | heptafluoroisopropyl | H | n-C3F7 |
| 27-529 | 4-iodopyridin-3-yl | Me | H | H | Cl | H | heptafluoroisopropyl | H | i-C3F7 |
| 27-535 | pyridin-4-yl | CN | H | H | Cl | H | heptafluoroisopropyl | H | CF3 |
| 27-548 | phenyl | Me | H | H | F | H | nonafluoro-2-butyl | H | CF3 |
| 27-549 | phenyl | Me | H | H | Cl | H | nonafluoro-2-butyl | H | CF3 |
| 27-557 | 3-bromophenyl | CH2C≡CH | H | H | Cl | H | nonafluoro-2-butyl | H | CF3 |
| 27-562 | (2-trifluoromethyl)phenyl | Me | H | H | Cl | H | nonafluoro-2-butyl | H | C2F5 |
| 27-564 | (4-trifluoromethyl)phenyl | NH2 | H | H | Cl | H | nonafluoro-2-butyl | H | CF3 |
| 27-569 | 3-cyanophenyl | Me | H | H | Cl | H | nonafluoro-2-butyl | H | CF3 |
| 27-570 | 4-cyanophenyl | Me | H | H | Cl | H | nonafluoro-2-butyl | H | CF3 |
| 27-577 | 2-bromo-4-chlorophenyl | C(O)OMe | H | H | Cl | H | nonafluoro-2-butyl | H | CF3 |
| 27-579 | 2-chloro-4-nitrophenyl | Me | H | H | Cl | H | nonafluoro-2-butyl | H | i-C3F7 |
| 27-585 | 2-chloropyridin-3-yl | Me | H | H | Cl | H | nonafluoro-2-butyl | H | CF3 |
| 27-598 | 5-fluoropyridin-3-yl | C(O)OEt | H | H | Cl | H | nonafluoro-2-butyl | H | C2F5 |
| 27-600 | 5-bromopyridin-3-yl | Me | H | H | Cl | H | nonafluoro-2-butyl | H | n-C3F7 |
| 27-601 | 5-iodopyridin-3-yl | Me | H | H | Cl | H | nonafluoro-2-butyl | H | i-C3F7 |
| 27-605 | 4-fluoropyridin-3-yl | Me | H | H | Cl | H | nonafluoro-2-butyl | H | C2F5 |
| 27-607 | 4-bromopyridin-3-yl | C(O)C(O)Me | H | H | Cl | H | nonafluoro-2-butyl | H | CF3 |
| 27-609 | 4-(trifluoromethyl)pyridin-3-yl | Me | H | H | Cl | H | nonafluoro-2-butyl | H | n-C3F7 |
| 27-610 | 4-nitropyridin-3-yl | C(O)C(O)Et | H | H | Cl | H | nonafluoro-2-butyl | H | i-C3F7 |

TABLE 27-continued

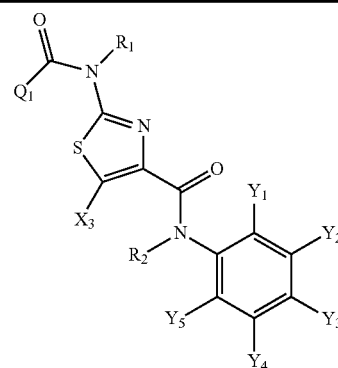

| compound number | Q₁ | R₁ | R₂ | X₃ | Y₁ | Y₂ | Y₃ | Y₄ | Y₅ |
|---|---|---|---|---|---|---|---|---|---|
| 27-624 | 5-iodopyridin-2-yl | C(O)Me | H | H | Cl | H | nonafluoro-2-butyl | H | CF3 |
| 27-626 | 4-cyanopyridin-2-yl | C(O)Et | H | H | Cl | H | nonafluoro-2-butyl | H | C2F5 |
| 27-627 | phenyl | Me | H | H | Br | H | heptafluoroisopropyl | H | CF3 |
| 27-628 | 2-fluorophenyl | Me | H | H | Br | H | heptafluoroisopropyl | H | CF3 |
| 27-629 | 3-fluorophenyl | Me | H | H | Br | H | heptafluoroisopropyl | H | CF3 |
| 27-630 | 4-fluorophenyl | Me | H | H | Br | H | heptafluoroisopropyl | H | CF3 |
| 27-631 | 2-chlorophenyl | Me | H | H | Br | H | heptafluoroisopropyl | H | CF3 |
| 27-632 | 3-chlorophenyl | Me | H | H | Br | H | heptafluoroisopropyl | H | CF3 |
| 27-633 | 4-chlorophenyl | Me | H | H | Br | H | heptafluoroisopropyl | H | CF3 |
| 27-634 | 2-bromophenyl | Me | H | H | Br | H | heptafluoroisopropyl | H | CF3 |
| 27-635 | 3-bromophenyl | Me | H | H | Br | H | heptafluoroisopropyl | H | CF3 |
| 27-636 | 4-bromophenyl | Me | H | H | Br | H | heptafluoroisopropyl | H | CF3 |
| 27-637 | 2-iodophenyl | Me | H | H | Br | H | heptafluoroisopropyl | H | CF3 |
| 27-638 | 3-iodophenyl | Me | H | H | Br | H | heptafluoroisopropyl | H | CF3 |
| 27-639 | 4-iodophenyl | Me | H | H | Br | H | heptafluoroisopropyl | H | CF3 |
| 27-640 | (2-trifluoromethyl)phenyl | Me | H | H | Br | H | heptafluoroisopropyl | H | CF3 |
| 27-641 | (3-trifluoromethyl)phenyl | S(O)2Me | H | H | Br | H | heptafluoroisopropyl | H | CF3 |
| 27-642 | (4-trifluoromethyl)phenyl | Me | H | H | Br | H | heptafluoroisopropyl | H | CF3 |
| 27-643 | 2-nitrophenyl | Me | H | H | Br | H | heptafluoroisopropyl | H | CF3 |
| 27-644 | 3-nitrophenyl | Me | H | H | Br | H | heptafluoroisopropyl | H | CF3 |
| 27-645 | 4-nitrophenyl | Me | H | H | Br | H | heptafluoroisopropyl | H | CF3 |
| 27-646 | 2-cyanophenyl | Me | H | H | Br | H | heptafluoroisopropyl | H | CF3 |
| 27-647 | 3-cyanophenyl | Me | H | H | Br | H | heptafluoroisopropyl | H | CF3 |
| 27-648 | 4-cyanophenyl | Me | H | H | Br | H | heptafluoroisopropyl | H | CF3 |
| 27-649 | 2,6-difluorophenyl | Me | H | H | Br | H | heptafluoroisopropyl | H | CF3 |
| 27-650 | 3,4-dichlorophenyl | Me | H | H | Br | H | heptafluoroisopropyl | H | CF3 |
| 27-651 | 2,4-dichlorophenyl | Me | H | H | Br | H | heptafluoroisopropyl | H | CF3 |
| 27-652 | 2-chloro-4-fluorophenyl | Me | H | H | Br | H | heptafluoroisopropyl | H | CF3 |
| 27-653 | 2-chloro-4,5-difluorophenyl | Me | H | H | Br | H | heptafluoroisopropyl | H | CF3 |
| 27-654 | 4-bromo-2-chlorophenyl | Me | H | H | Br | H | heptafluoroisopropyl | H | CF3 |
| 27-655 | 2-bromo-4-chlorophenyl | Me | H | H | Br | H | heptafluoroisopropyl | H | CF3 |
| 27-656 | 2-bromo-4-fluorophenyl | Me | H | H | Br | H | heptafluoroisopropyl | H | CF3 |
| 27-657 | 2-chloro-4-nitrophenyl | Me | H | H | Br | H | heptafluoroisopropyl | H | CF3 |
| 27-658 | 3,5-dicyanophenyl | Me | H | H | Br | H | heptafluoroisopropyl | H | CF3 |
| 27-659 | 4-cyano-2-fluorophenyl | S(O)2Et | H | H | Br | H | heptafluoroisopropyl | H | CF3 |
| 27-660 | 2-chloro-4-cyanophenyl | Me | H | H | Br | H | heptafluoroisopropyl | H | CF3 |
| 27-661 | pyridin-3-yl | Me | H | H | Br | H | heptafluoroisopropyl | H | CF3 |
| 27-662 | 2-fluoropyridin-3-yl | Me | H | H | Br | H | heptafluoroisopropyl | H | CF3 |
| 27-663 | 2-chloropyridin-3-yl | Me | H | H | Br | H | heptafluoroisopropyl | H | CF3 |
| 27-664 | 2-bromopyridin-3-yl | Me | H | H | Br | H | heptafluoroisopropyl | H | CF3 |
| 27-665 | 2-iodopyridin-3-yl | Me | H | H | Br | H | heptafluoroisopropyl | H | CF3 |
| 27-666 | 2-(trifluoromethyl)pyridin-3-yl | Me | H | H | Br | H | heptafluoroisopropyl | H | CF3 |
| 27-667 | 2-nitropyridin-3-yl | Me | H | H | Br | H | heptafluoroisopropyl | H | CF3 |
| 27-668 | 2-cyanopyridin-3-yl | Me | H | H | Br | H | heptafluoroisopropyl | H | CF3 |
| 27-669 | 6-fluoropyridin-3-yl | Me | H | H | Br | H | heptafluoroisopropyl | H | CF3 |
| 27-670 | 6-chloropyridin-3-yl | Me | H | H | Br | H | heptafluoroisopropyl | H | CF3 |
| 27-671 | 6-bromopyridin-3-yl | Me | H | H | Br | H | heptafluoroisopropyl | H | CF3 |
| 27-672 | 6-iodopyridin-3-yl | Me | H | H | Br | H | heptafluoroisopropyl | H | CF3 |
| 27-673 | 6-(trifluoromethyl)pyridin-3-yl | Me | H | H | Br | H | heptafluoroisopropyl | H | CF3 |
| 27-674 | 6-nitropyridin-3-yl | CH2Ph | H | H | Br | H | heptafluoroisopropyl | H | CF3 |
| 27-675 | 6-cyanopyridin-3-yl | Me | H | H | Br | H | heptafluoroisopropyl | H | CF3 |
| 27-676 | 5-fluoropyridin-3-yl | Me | H | H | Br | H | heptafluoroisopropyl | H | CF3 |
| 27-677 | 5-chloropyridin-3-yl | Me | H | H | Br | H | heptafluoroisopropyl | H | CF3 |
| 27-678 | 5-bromopyridin-3-yl | Me | H | H | Br | H | heptafluoroisopropyl | H | CF3 |
| 27-679 | 5-iodopyridin-3-yl | Me | H | H | Br | H | heptafluoroisopropyl | H | CF3 |
| 27-680 | 5-(trifluoromethyl)pyridin-3-yl | Me | H | H | Br | H | heptafluoroisopropyl | H | CF3 |
| 27-681 | 5-nitropyridin-3-yl | Me | H | H | Br | H | heptafluoroisopropyl | H | CF3 |
| 27-682 | 5-cyanopyridin-3-yl | Me | H | H | Br | H | heptafluoroisopropyl | H | CF3 |
| 27-683 | 4-fluoropyridin-3-yl | CH2(3-Py) | H | H | Br | H | heptafluoroisopropyl | H | CF3 |

TABLE 27-continued

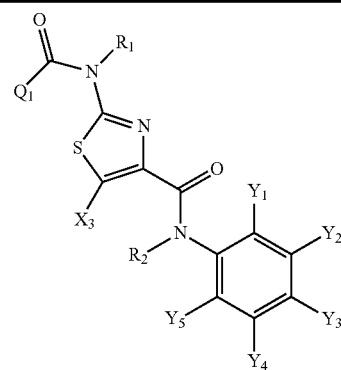

| compound number | Q₁ | R₁ | R₂ | X₃ | Y₁ | Y₂ | Y₃ | Y₄ | Y₅ |
|---|---|---|---|---|---|---|---|---|---|
| 27-684 | 4-chloropyridin-3-yl | Me | H | H | Br | H | heptafluoroisopropyl | H | CF3 |
| 27-685 | 4-bromopyridin-3-yl | Me | H | H | Br | H | heptafluoroisopropyl | H | CF3 |
| 27-686 | 4-iodopyridin-3-yl | Me | H | H | Br | H | heptafluoroisopropyl | H | CF3 |
| 27-687 | 4-(trifluoromethyl)pyridin-3-yl | Me | H | H | Br | H | heptafluoroisopropyl | H | CF3 |
| 27-688 | 4-nitropyridin-3-yl | Me | H | H | Br | H | heptafluoroisopropyl | H | CF3 |
| 27-689 | 4-cyanopyridin-3-yl | Me | H | H | Br | H | heptafluoroisopropyl | H | CF3 |
| 27-690 | 2,6-dichloropyridin-3-yl | Me | H | H | Br | H | heptafluoroisopropyl | H | CF3 |
| 27-691 | pyridin-3-yl N-oxide | Me | H | H | Br | H | heptafluoroisopropyl | H | CF3 |
| 27-692 | pyridin-4-yl | Me | H | H | Br | H | heptafluoroisopropyl | H | CF3 |
| 27-693 | 2-chloropyridin-4-yl | Me | H | H | Br | H | heptafluoroisopropyl | H | CF3 |
| 27-694 | 3-bromopyridin-4-yl | Me | H | H | Br | H | heptafluoroisopropyl | H | CF3 |
| 27-695 | 3,5-dichloropyridin-4-yl | Me | H | H | Br | H | heptafluoroisopropyl | H | CF3 |
| 27-696 | 3-(trifluoromethyl)pyridin-4-yl | Me | H | H | Br | H | heptafluoroisopropyl | H | CF3 |
| 27-697 | 2,6-dicyanopyridin-4-yl | Me | H | H | Br | H | heptafluoroisopropyl | H | CF3 |
| 27-698 | pyridin-4-yl N-oxide | Me | H | H | Br | H | heptafluoroisopropyl | H | CF3 |
| 27-699 | pyridin-2-yl | Me | H | H | Br | H | heptafluoroisopropyl | H | CF3 |
| 27-700 | 3-chloropyridin-2-yl | Me | H | H | Br | H | heptafluoroisopropyl | H | CF3 |
| 27-701 | 4-bromopyridin-2-yl | Me | H | H | Br | H | heptafluoroisopropyl | H | CF3 |
| 27-702 | 5-iodopyridin-2-yl | Me | H | H | Br | H | heptafluoroisopropyl | H | CF3 |
| 27-703 | 6-chloropyridin-2-yl | Me | H | H | Br | H | heptafluoroisopropyl | H | CF3 |
| 27-704 | 4-cyanopyndin-2-yl | CH2(3-Py-N-oxide) | H | H | Br | H | heptafluoroisopropyl | H | CF3 |
| 27-705 | phenyl | Me | H | H | Br | H | nonafluoro-2-butyl | H | CF3 |
| 27-706 | 2-fluorophenyl | Me | H | H | Br | H | nonafluoro-2-butyl | H | CF3 |
| 27-707 | 3-fluorophenyl | Me | H | H | Br | H | nonafluoro-2-butyl | H | CF3 |
| 27-708 | 4-fluorophenyl | Me | H | H | Br | H | nonafluoro-2-butyl | H | CF3 |
| 27-709 | 2-chlorophenyl | Me | H | H | Br | H | nonafluoro-2-butyl | H | CF3 |
| 27-710 | 3-chlorophenyl | Me | H | H | Br | H | nonafluoro-2-butyl | H | CF3 |
| 27-711 | 4-chlorophenyl | Me | H | H | Br | H | nonafluoro-2-butyl | H | CF3 |
| 27-712 | 2-bromophenyl | Me | H | H | Br | H | nonafluoro-2-butyl | H | CF3 |
| 27-713 | 3-bromophenyl | Me | H | H | Br | H | nonafluoro-2-butyl | H | CF3 |
| 27-714 | 4-bromophenyl | Me | H | H | Br | H | nonafluoro-2-butyl | H | CF3 |
| 27-715 | 2-iodophenyl | Me | H | H | Br | H | nonafluoro-2-butyl | H | CF3 |
| 27-716 | 3-iodophenyl | Me | H | H | Br | H | nonafluoro-2-butyl | H | CF3 |
| 27-717 | 4-iodophenyl | Me | H | H | Br | H | nonafluoro-2-butyl | H | CF3 |
| 27-718 | (2-trifluoromethyl)phenyl | Me | H | H | Br | H | nonafluoro-2-butyl | H | CF3 |
| 27-719 | (3-trifluoromethyl)phenyl | Me | H | H | Br | H | nonafluoro-2-butyl | H | CF3 |
| 27-720 | (4-trifluoromethyl)phenyl | Me | H | H | Br | H | nonafluoro-2-butyl | H | CF3 |
| 27-721 | 2-nitrophenyl | Me | H | H | Br | H | nonafluoro-2-butyl | H | CF3 |
| 27-722 | 3-nitrophenyl | Me | H | H | Br | H | nonafluoro-2-butyl | H | CF3 |
| 27-723 | 4-nitrophenyl | Me | H | H | Br | H | nonafluoro-2-butyl | H | CF3 |
| 27-724 | 2-cyanophenyl | Me | H | H | Br | H | nonafluoro-2-butyl | H | CF3 |
| 27-725 | 3-cyanophenyl | Me | H | H | Br | H | nonafluoro-2-butyl | H | CF3 |
| 27-726 | 4-cyanophenyl | Me | H | H | Br | H | nonafluoro-2-butyl | H | CF3 |
| 27-727 | 2,6-difluorophenyl | Me | H | H | Br | H | nonafluoro-2-butyl | H | CF3 |
| 27-728 | 3,4-dichlorophenyl | Me | H | H | Br | H | nonafluoro-2-butyl | H | CF3 |
| 27-729 | 2,4-dichlorophenyl | Me | H | H | Br | H | nonafluoro-2-butyl | H | CF3 |
| 27-730 | 2-chloro-4-fluorophenyl | Me | H | H | Br | H | nonafluoro-2-butyl | H | CF3 |
| 27-731 | 2-chloro-4,5-difluorophenyl | Me | H | H | Br | H | nonafluoro-2-butyl | H | CF3 |
| 27-732 | 4-bromo-2-chlorophenyl | Et | H | H | Br | H | nonafluoro-2-butyl | H | CF3 |
| 27-733 | 2-bromo-4-chlorophenyl | Me | H | H | Br | H | nonafluoro-2-butyl | H | CF3 |
| 27-734 | 2-bromo-4-fluorophenyl | Me | H | H | Br | H | nonafluoro-2-butyl | H | CF3 |
| 27-735 | 2-chloro-4-nitrophenyl | Me | H | H | Br | H | nonafluoro-2-butyl | H | CF3 |
| 27-736 | 3,5-dicyanophenyl | Me | H | H | Br | H | nonafluoro-2-butyl | H | CF3 |
| 27-737 | 4-cyano-2-fluorophenyl | Me | H | H | Br | H | nonafluoro-2-butyl | H | CF3 |
| 27-738 | 2-chloro-4-cyanophenyl | Me | H | H | Br | H | nonafluoro-2-butyl | H | CF3 |
| 27-739 | pyridin-3-yl | Me | H | H | Br | H | nonafluoro-2-butyl | H | CF3 |
| 27-740 | 2-fluoropyridin-3-yl | Me | H | H | Br | H | nonafluoro-2-butyl | H | CF3 |
| 27-741 | 2-chloropyridin-3-yl | Me | H | H | Br | H | nonafluoro-2-butyl | H | CF3 |

TABLE 27-continued

| compound number | Q₁ | R₁ | R₂ | X₃ | Y₁ | Y₂ | Y₃ | Y₄ | Y₅ |
|---|---|---|---|---|---|---|---|---|---|
| 27-742 | 2-bromopyridin-3-yl | Me | H | H | Br | H | nonafluoro-2-butyl | H | CF3 |
| 27-743 | 2-iodopyridin-3-yl | Me | H | H | Br | H | nonafluoro-2-butyl | H | CF3 |
| 27-744 | 2-(trifluoromethyl)pyridin-3-yl | Me | H | H | Br | H | nonafluoro-2-butyl | H | CF3 |
| 27-745 | 2-nitropyridin-3-yl | Me | H | H | Br | H | nonafluoro-2-butyl | H | CF3 |
| 27-746 | 2-cyanopyridin-3-yl | Me | H | H | Br | H | nonafluoro-2-butyl | H | CF3 |
| 27-747 | 6-fluoropyridin-3-yl | Me | H | H | Br | H | nonafluoro-2-butyl | H | CF3 |
| 27-748 | 6-chloropyridin-3-yl | Me | H | H | Br | H | nonafluoro-2-butyl | H | CF3 |
| 27-749 | 6-bromopyridin-3-yl | Me | H | H | Br | H | nonafluoro-2-butyl | H | CF3 |
| 27-750 | 6-iodopyridin-3-yl | Me | H | H | Br | H | nonafluoro-2-butyl | H | CF3 |
| 27-751 | 6-(trifluoromethyl)pyridin-3-yl | Me | H | H | Br | H | nonafluoro-2-butyl | H | CF3 |
| 27-752 | 6-nitropyridin-3-yl | Me | H | H | Br | H | nonafluoro-2-butyl | H | CF3 |
| 27-753 | 6-cyanopyridin-3-yl | Me | H | H | Br | H | nonafluoro-2-butyl | H | CF3 |
| 27-754 | 5-fluoropyridin-3-yl | Me | H | H | Br | H | nonafluoro-2-butyl | H | CF3 |
| 27-755 | 5-chloropyridin-3-yl | Me | H | H | Br | H | nonafluoro-2-butyl | H | CF3 |
| 27-756 | 5-bromopyridin-3-yl | Me | H | H | Br | H | nonafluoro-2-butyl | H | CF3 |
| 27-757 | 5-iodopyridin-3-yl | Me | H | H | Br | H | nonafluoro-2-butyl | H | CF3 |
| 27-758 | 5-(trifluoromethyl)pyridin-3-yl | CN | H | H | Br | H | nonafluoro-2-butyl | H | CF3 |
| 27-759 | 5-nitropyridin-3-yl | Me | H | H | Br | H | nonafluoro-2-butyl | H | CF3 |
| 27-760 | 5-cyanopyridin-3-yl | Me | H | H | Br | H | nonafluoro-2-butyl | H | CF3 |
| 27-761 | 4-fluoropyridin-3-yl | Me | H | H | Br | H | nonafluoro-2-butyl | H | CF3 |
| 27-762 | 4-chloropyridin-3-yl | Me | H | H | Br | H | nonafluoro-2-butyl | H | CF3 |
| 27-763 | 4-bromopyridin-3-yl | Me | H | H | Br | H | nonafluoro-2-butyl | H | CF3 |
| 27-764 | 4-iodopyridin-3-yl | Me | H | H | Br | H | nonafluoro-2-butyl | H | CF3 |
| 27-765 | 4-(trifluoromethyl)pyridin-3-yl | Me | H | H | Br | H | nonafluoro-2-butyl | H | CF3 |
| 27-766 | 4-nitropyridin-3-yl | Me | H | H | Br | H | nonafluoro-2-butyl | H | CF3 |
| 27-767 | 4-cyanopyridin-3-yl | Me | H | H | Br | H | nonafluoro-2-butyl | H | CF3 |
| 27-768 | 2,6-dichloropyridin-3-yl | Me | H | H | Br | H | nonafluoro-2-butyl | H | CF3 |
| 27-769 | pyridin-3-yl N-oxide | Me | H | H | Br | H | nonafluoro-2-butyl | H | CF3 |
| 27-770 | pyridin-4-yl | Me | H | H | Br | H | nonafluoro-2-butyl | H | CF3 |
| 27-771 | 2-chloropyridin-4-yl | Me | H | H | Br | H | nonafluoro-2-butyl | H | CF3 |
| 27-772 | 3-bromopyridin-4-yl | Me | H | H | Br | H | nonafluoro-2-butyl | H | CF3 |
| 27-773 | 3,5-dichloropyridin-4-yl | Me | H | H | Br | H | nonafluoro-2-butyl | H | CF3 |
| 27-774 | 3-(trifluoromethyl)pyridin-4-yl | Me | H | H | Br | H | nonafluoro-2-butyl | H | CF3 |
| 27-775 | 2,6-dicyanopyridin-4-yl | Me | H | H | Br | H | nonafluoro-2-butyl | H | CF3 |
| 27-776 | pyridin-4-yl N-oxide | Me | H | H | Br | H | nonafluoro-2-butyl | H | CF3 |
| 27-777 | pyridin-2-yl | Me | H | H | Br | H | nonafluoro-2-butyl | H | CF3 |
| 27-778 | 3-chloropyridin-2-yl | Me | H | H | Br | H | nonafluoro-2-butyl | H | CF3 |
| 27-779 | 4-bromopyridin-2-yl | Me | H | H | Br | H | nonafluoro-2-butyl | H | CF3 |
| 27-780 | 5-iodopyridin-2-yl | Me | H | H | Br | H | nonafluoro-2-butyl | H | CF3 |
| 27-781 | 6-chloropyridin-2-yl | Me | H | H | Br | H | nonafluoro-2-butyl | H | CF3 |
| 27-782 | 4-cyanopyridin-2-yl | Me | H | H | Br | H | nonafluoro-2-butyl | H | CF3 |
| 27-783 | phenyl | Me | H | H | I | H | heptafluoroisopropyl | H | CF3 |
| 27-784 | 2-fluorophenyl | Me | H | H | I | H | heptafluoroisopropyl | H | CF3 |
| 27-785 | 3-fluorophenyl | Me | H | H | I | H | heptafluoroisopropyl | H | CF3 |
| 27-786 | 4-fluorophenyl | Me | H | H | I | H | heptafluoroisopropyl | H | CF3 |
| 27-787 | 2-chlorophenyl | Me | H | H | I | H | heptafluoroisopropyl | H | CF3 |
| 27-788 | 3-chlorophenyl | Me | H | H | I | H | heptafluoroisopropyl | H | CF3 |
| 27-789 | 4-chlorophenyl | Me | H | H | I | H | heptafluoroisopropyl | H | CF3 |
| 27-790 | 2-bromophenyl | Me | H | H | I | H | heptafluoroisopropyl | H | CF3 |
| 27-791 | 3-bromophenyl | Me | H | H | I | H | heptafluoroisopropyl | H | CF3 |
| 27-792 | 4-bromophenyl | Me | H | H | I | H | heptafluoroisopropyl | H | CF3 |
| 27-793 | 2-iodophenyl | Me | H | H | I | H | heptafluoroisopropyl | H | CF3 |
| 27-794 | 3-iodophenyl | Me | H | H | I | H | heptafluoroisopropyl | H | CF3 |
| 27-795 | 4-iodophenyl | Me | H | H | I | H | heptafluoroisopropyl | H | CF3 |
| 27-796 | (2-trifluoromethyl)phenyl | Me | H | H | I | H | heptafluoroisopropyl | H | CF3 |
| 27-797 | (3-trifluoromethyl)phenyl | Me | H | H | I | H | heptafluoroisopropyl | H | CF3 |
| 27-798 | (4-trifluoromethyl)phenyl | Me | H | H | I | H | heptafluoroisopropyl | H | CF3 |
| 27-799 | 2-nitrophenyl | Me | H | H | I | H | heptafluoroisopropyl | H | CF3 |
| 27-800 | 3-nitrophenyl | Me | H | H | I | H | heptafluoroisopropyl | H | CF3 |

TABLE 27-continued

| compound number | Q₁ | R₁ | R₂ | X₃ | Y₁ | Y₂ | Y₃ | Y₄ | Y₅ |
|---|---|---|---|---|---|---|---|---|---|
| 27-801 | 4-nitrophenyl | Me | H | H | I | H | heptafluoroisopropyl | H | CF3 |
| 27-802 | 2-cyanophenyl | Me | H | H | I | H | heptafluoroisopropyl | H | CF3 |
| 27-803 | 3-cyanophenyl | Me | H | H | I | H | heptafluoroisopropyl | H | CF3 |
| 27-804 | 4-cyanophenyl | Me | H | H | I | H | heptafluoroisopropyl | H | CF3 |
| 27-805 | 2,6-difluorophenyl | Me | H | H | I | H | heptafluoroisopropyl | H | CF3 |
| 27-806 | 3,4-dichlorophenyl | Me | H | H | I | H | heptafluoroisopropyl | H | CF3 |
| 27-807 | 2,4-dichlorophenyl | Me | H | H | I | H | heptafluoroisopropyl | H | CF3 |
| 27-808 | 2-chloro-4-fluorophenyl | Me | H | H | I | H | heptafluoroisopropyl | H | CF3 |
| 27-809 | 2-chloro-4,5-difluorophenyl | Me | H | H | I | H | heptafluoroisopropyl | H | CF3 |
| 27-810 | 4-bromo-2-chlorophenyl | Me | H | H | I | H | heptafluoroisopropyl | H | CF3 |
| 27-811 | 2-bromo-4-chlorophenyl | Me | H | H | I | H | heptafluoroisopropyl | H | CF3 |
| 27-812 | 2-bromo-4-fluorophenyl | Me | H | H | I | H | heptafluoroisopropyl | H | CF3 |
| 27-813 | 2-chloro-4-nitrophenyl | Me | H | H | I | H | heptafluoroisopropyl | H | CF3 |
| 27-814 | 3,5-dicyanophenyl | Me | H | H | I | H | heptafluoroisopropyl | H | CF3 |
| 27-815 | 4-cyano-2-fluorophenyl | Me | H | H | I | H | heptafluoroisopropyl | H | CF3 |
| 27-816 | 2-chloro-4-cyanophenyl | Me | H | H | I | H | heptafluoroisopropyl | H | CF3 |
| 27-817 | pyridin-3-yl | Me | H | H | I | H | heptafluoroisopropyl | H | CF3 |
| 27-818 | 2-fluoropyridin-3-yl | Me | H | H | I | H | heptafluoroisopropyl | H | CF3 |
| 27-819 | 2-chloropyridin-3-yl | Me | H | H | I | H | heptafluoroisopropyl | H | CF3 |
| 27-820 | 2-bromopyridin-3-yl | Me | H | H | I | H | heptafluoroisopropyl | H | CF3 |
| 27-821 | 2-iodopyridin-3-yl | Me | H | H | I | H | heptafluoroisopropyl | H | CF3 |
| 27-822 | 2-(trifluoromethyl)pyridin-3-yl | Me | H | H | I | H | heptafluoroisopropyl | H | CF3 |
| 27-823 | 2-nitropyridin-3-yl | Me | H | H | I | H | heptafluoroisopropyl | H | CF3 |
| 27-824 | 2-cyanopyridin-3-yl | Me | H | H | I | H | heptafluoroisopropyl | H | CF3 |
| 27-825 | 6-fluoropyridin-3-yl | Me | H | H | I | H | heptafluoroisopropyl | H | CF3 |
| 27-826 | 6-chloropyridin-3-yl | Me | H | H | I | H | heptafluoroisopropyl | H | CF3 |
| 27-827 | 6-bromopyridin-3-yl | Me | H | H | I | H | heptafluoroisopropyl | H | CF3 |
| 27-828 | 6-iodopyridin-3-yl | Me | H | H | I | H | heptafluoroisopropyl | H | CF3 |
| 27-829 | 6-(trifluoromethyl)pyridin-3-yl | Me | H | H | I | H | heptafluoroisopropyl | H | CF3 |
| 27-830 | 6-nitropyridin-3-yl | Me | H | H | I | H | heptafluoroisopropyl | H | CF3 |
| 27-831 | 6-cyanopyridin-3-Y1 | Me | H | H | I | H | heptafluoroisopropyl | H | CF3 |
| 27-832 | 5-fluoropyridin-3-yl | C(O)Me | H | H | I | H | heptafluoroisopropyl | H | CF3 |
| 27-833 | 5-chloropyridin-3-yl | Me | H | H | I | H | heptafluoroisopropyl | H | CF3 |
| 27-834 | 5-bromopyridin-3-yl | Me | H | H | I | H | heptafluoroisopropyl | H | CF3 |
| 27-835 | 5-iodopyridin-3-yl | Me | H | H | I | H | heptafluoroisopropyl | H | CF3 |
| 27-836 | 5-(trifluoromethyl)pyridin-3-yl | Me | H | H | I | H | heptafluoroisopropyl | H | CF3 |
| 27-837 | 5-nitropyridin-3-yl | Me | H | H | I | H | heptafluoroisopropyl | H | CF3 |
| 27-838 | 5-cyanopyridin-3-yl | Me | H | H | I | H | heptafluoroisopropyl | H | CF3 |
| 27-839 | 4-fluoropyridin-3-yl | Me | H | H | I | H | heptafluoroisopropyl | H | CF3 |
| 27-840 | 4-chloropyridin-3-yl | Me | H | H | I | H | heptafluoroisopropyl | H | CF3 |
| 27-841 | 4-bromopyridin-3-yl | Me | H | H | I | H | heptafluoroisopropyl | H | CF3 |
| 27-842 | 4-iodopyridin-3-yl | Me | H | H | I | H | heptafluoroisopropyl | H | CF3 |
| 27-843 | 4-(trifluoromethyl)pyridin-3-yl | Me | H | H | I | H | heptafluoroisopropyl | H | CF3 |
| 27-844 | 4-nitropyridin-3-yl | Me | H | H | I | H | heptafluoroisopropyl | H | CF3 |
| 27-845 | 4-cyanopyridin-3-yl | Me | H | H | I | H | heptafluoroisopropyl | H | CF3 |
| 27-846 | 2,6-dichloropyridin-3-yl | Me | H | H | I | H | heptafluoroisopropyl | H | CF3 |
| 27-847 | pyridin-3-yl N-oxide | Me | H | H | I | H | heptafluoroisopropyl | H | CF3 |
| 27-848 | pyridin-4-yl | Me | H | H | I | H | heptafluoroisopropyl | H | CF3 |
| 27-849 | 2-chloropyridin-4-yl | Me | H | H | I | H | heptafluoroisopropyl | H | CF3 |
| 27-850 | 3-bromopyridin-4-yl | Me | H | H | I | H | heptafluoroisopropyl | H | CF3 |
| 27-851 | 3,5-dichloropyridin-4-yl | Me | H | H | I | H | heptafluoroisopropyl | H | CF3 |
| 27-852 | 3-(trifluoromethyl)pyridin-4-yl | Me | H | H | I | H | heptafluoroisopropyl | H | CF3 |
| 27-853 | 2,6-dicyanopyridin-4-yl | Me | H | H | I | H | heptafluoroisopropyl | H | CF3 |
| 27-854 | pyridin-4-yl N-oxide | Me | H | H | I | H | heptafluoroisopropyl | H | CF3 |
| 27-855 | pyridin-2-yl | Me | H | H | I | H | heptafluoroisopropyl | H | CF3 |
| 27-856 | 3-chloropyridin-2-yl | Me | H | H | I | H | heptafluoroisopropyl | H | CF3 |
| 27-857 | 4-bromopyridin-2-yl | Me | H | H | I | H | heptafluoroisopropyl | H | CF3 |
| 27-858 | 5-iodopyridin-2-yl | Me | H | H | I | H | heptafluoroisopropyl | H | CF3 |
| 27-859 | 6-chloropyridin-2-yl | Me | H | H | I | H | heptafluoroisopropyl | H | CF3 |

TABLE 27-continued

| compound number | Q₁ | R₁ | R₂ | X₃ | Y₁ | Y₂ | Y₃ | Y₄ | Y₅ |
|---|---|---|---|---|---|---|---|---|---|
| 27-860 | 4-cyanopyridin-2-yl | Me | H | H | I | H | heptafluoroisopropyl | H | CF3 |
| 27-861 | phenyl | Me | H | H | I | H | nonafluoro-2-butyl | H | CF3 |
| 27-862 | 2-fluorophenyl | Me | H | H | I | H | nonafluoro-2-butyl | H | CF3 |
| 27-863 | 3-fluorophenyl | Me | H | H | I | H | nonafluoro-2-butyl | H | CF3 |
| 27-864 | 4-fluorophenyl | Me | H | H | I | H | nonafluoro-2-butyl | H | CF3 |
| 27-865 | 2-chlorophenyl | Me | H | H | I | H | nonafluoro-2-butyl | H | CF3 |
| 27-866 | 3-chlorophenyl | Me | H | H | I | H | nonafluoro-2-butyl | H | CF3 |
| 27-867 | 4-chlorophenyl | Me | H | H | I | H | nonafluoro-2-butyl | H | CF3 |
| 27-868 | 2-bromophenyl | Me | H | H | I | H | nonafluoro-2-butyl | H | CF3 |
| 27-869 | 3-bromophenyl | Me | H | H | I | H | nonafluoro-2-butyl | H | CF3 |
| 27-870 | 4-bromophenyl | Me | H | H | I | H | nonafluoro-2-butyl | H | CF3 |
| 27-871 | 2-iodophenyl | Me | H | H | I | H | nonafluoro-2-butyl | H | CF3 |
| 27-872 | 3-iodophenyl | Me | H | H | I | H | nonafluoro-2-butyl | H | CF3 |
| 27-873 | 4-iodophenyl | Me | H | H | I | H | nonafluoro-2-butyl | H | CF3 |
| 27-874 | (2-trifluoromethyl)phenyl | Me | H | H | I | H | nonafluoro-2-butyl | H | CF3 |
| 27-875 | (3-trifluoromethyl)phenyl | Me | H | H | I | H | nonafluoro-2-butyl | H | CF3 |
| 27-876 | (4-trifluoromethyl)phenyl | Me | H | H | I | H | nonafluoro-2-butyl | H | CF3 |
| 27-877 | 2-nitrophenyl | Me | H | H | I | H | nonafluoro-2-butyl | H | CF3 |
| 27-878 | 3-nitrophenyl | Me | H | H | I | H | nonafluoro-2-butyl | H | CF3 |
| 27-879 | 4-nitrophenyl | Me | H | H | I | H | nonafluoro-2-butyl | H | CF3 |
| 27-880 | 2-cyanophenyl | Me | H | H | I | H | nonafluoro-2-butyl | H | CF3 |
| 27-881 | 3-cyanophenyl | Me | H | H | I | H | nonafluoro-2-butyl | H | CF3 |
| 27-882 | 4-cyanophenyl | Me | H | H | I | H | nonafluoro-2-butyl | H | CF3 |
| 27-883 | 2,6-difluorophenyl | Me | H | H | I | H | nonafluoro-2-butyl | H | CF3 |
| 27-884 | 3,4-dichlorophenyl | Me | H | H | I | H | nonafluoro-2-butyl | H | CF3 |
| 27-885 | 2,4-dichlorophenyl | Me | H | H | I | H | nonafluoro-2-butyl | H | CF3 |
| 27-886 | 2-chloro-4-fluorophenyl | Me | H | H | I | H | nonafluoro-2-butyl | H | CF3 |
| 27-887 | 2-chloro-4,5-difluorophenyl | Me | H | H | I | H | nonafluoro-2-butyl | H | CF3 |
| 27-888 | 4-bromo-2-chlorophenyl | Me | H | H | I | H | nonafluoro-2-butyl | H | CF3 |
| 27-889 | 2-bromo-4-chlorophenyl | Me | H | H | I | H | nonafluoro-2-butyl | H | CF3 |
| 27-890 | 2-bromo-4-fluorophenyl | Me | H | H | I | H | nonafluoro-2-butyl | H | CF3 |
| 27-891 | 2-chloro-4-nitrophenyl | Me | H | H | I | H | nonafluoro-2-butyl | H | CF3 |
| 27-892 | 3,5-dicyanophenyl | Me | H | H | I | H | nonafluoro-2-butyl | H | CF3 |
| 27-893 | 4-cyano-2-fluorophenyl | Me | H | H | I | H | nonafluoro-2-butyl | H | CF3 |
| 27-894 | 2-chloro-4-cyanophenyl | Me | H | H | I | H | nonafluoro-2-butyl | H | CF3 |
| 27-895 | pyridin-3-yl | Me | H | H | I | H | nonafluoro-2-butyl | H | CF3 |
| 27-896 | 2-fluoropyridin-3-yl | Me | H | H | I | H | nonafluoro-2-butyl | H | CF3 |
| 27-897 | 2-chloropyridin-3-yl | Me | H | H | I | H | nonafluoro-2-butyl | H | CF3 |
| 27-898 | 2-bromopyridin-3-yl | Me | H | H | I | H | nonafluoro-2-butyl | H | CF3 |
| 27-899 | 2-iodopyridin-3-yl | Me | H | H | I | H | nonafluoro-2-butyl | H | CF3 |
| 27-900 | 2-(trifluoromethyl)pyridin-3-yl | Me | H | H | I | H | nonafluoro-2-butyl | H | CF3 |
| 27-901 | 2-nitropyridin-3-yl | Me | H | H | I | H | nonafluoro-2-butyl | H | CF3 |
| 27-902 | 2-cyanopyridin-3-yl | Me | H | H | I | H | nonafluoro-2-butyl | H | CF3 |
| 27-903 | 6-fluoropyridin-3-yl | Me | H | H | I | H | nonafluoro-2-butyl | H | CF3 |
| 27-904 | 6-chloropyridin-3-yl | Me | H | H | I | H | nonafluoro-2-butyl | H | CF3 |
| 27-905 | 6-bromopyridin-3-yl | Me | H | H | I | H | nonafluoro-2-butyl | H | CF3 |
| 27-906 | 6-iodopyridin-3-yl | Me | H | H | I | H | nonafluoro-2-butyl | H | CF3 |
| 27-907 | 6-(trifluoromethyl)pyridin-3-yl | Me | H | H | I | H | nonafluoro-2-butyl | H | CF3 |
| 27-908 | 6-nitropyridin-3-yl | Me | H | H | I | H | nonafluoro-2-butyl | H | CF3 |
| 27-909 | 6-cyanopyridin-3-yl | Me | H | H | I | H | nonafluoro-2-butyl | H | CF3 |
| 27-910 | 5-fluoropyridin-3-yl | Me | H | H | I | H | nonafluoro-2-butyl | H | CF3 |
| 27-911 | 5-chloropyridin-3-yl | Me | H | H | I | H | nonafluoro-2-butyl | H | CF3 |
| 27-912 | 5-bromopyridin-3-yl | Me | H | H | I | H | nonafluoro-2-butyl | H | CF3 |
| 27-913 | 5-iodopyridin-3-yl | Me | H | H | I | H | nonafluoro-2-butyl | H | CF3 |
| 27-914 | 5-(trifluoromethyl)pyridin-3-yl | Me | H | H | I | H | nonafluoro-2-butyl | H | CF3 |
| 27-915 | 5-nitropyridin-3-yl | Me | H | H | I | H | nonafluoro-2-butyl | H | CF3 |

TABLE 27-continued

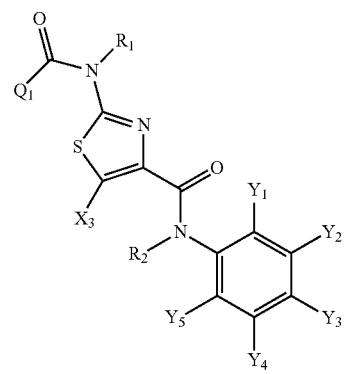

| compound number | $Q_1$ | $R_1$ | $R_2$ | $X_3$ | $Y_1$ | $Y_2$ | $Y_3$ | $Y_4$ | $Y_5$ |
|---|---|---|---|---|---|---|---|---|---|
| 27-916 | 5-cyanopyridin-3-yl | Me | H | H | I | H | nonafluoro-2-butyl | H | CF3 |
| 27-917 | 4-fluoropyridin-3-yl | Me | H | H | I | H | nonafluoro-2-butyl | H | CF3 |
| 27-918 | 4-chloropyridin-3-yl | Me | H | H | I | H | nonafluoro-2-butyl | H | CF3 |
| 27-919 | 4-bromopyridin-3-yl | Me | H | H | I | H | nonafluoro-2-butyl | H | CF3 |
| 27-920 | 4-iodopyridin-3-yl | Me | H | H | I | H | nonafluoro-2-butyl | H | CF3 |
| 27-921 | 4-(trifluoromethyl)pyridin-3-yl | Me | H | H | I | H | nonafluoro-2-butyl | H | CF3 |
| 27-922 | 4-nitropyridin-3-yl | Me | H | H | I | H | nonafluoro-2-butyl | H | CF3 |
| 27-923 | 4-cyanopyridin-3-yl | Me | H | H | I | H | nonafluoro-2-butyl | H | CF3 |
| 27-924 | 2,6-dichloropyridin-3-yl | Me | H | H | I | H | nonafluoro-2-butyl | H | CF3 |
| 27-925 | pyridin-3-yl N-oxide | Me | H | H | I | H | nonafluoro-2-butyl | H | CF3 |
| 27-926 | pyridin-4-yl | Me | H | H | I | H | nonafluoro-2-butyl | H | CF3 |
| 27-927 | 2-chloropyridin-4-yl | Me | H | H | I | H | nonafluoro-2-butyl | H | CF3 |
| 27-928 | 3-bromopyridin-4-yl | Me | H | H | I | H | nonafluoro-2-butyl | H | CF3 |
| 27-929 | 3,5-dichloropyridin-4-yl | Me | H | H | I | H | nonafluoro-2-butyl | H | CF3 |
| 27-930 | 3-(trifluoromethyl)pyridin-4-yl | Me | H | H | I | H | nonafluoro-2-butyl | H | CF3 |
| 27-931 | 2,6-dicyanopyridin-4-yl | Me | H | H | I | H | nonafluoro-2-butyl | H | CF3 |
| 27-932 | pyridin-4-yl N-oxide | Me | H | H | I | H | nonafluoro-2-butyl | H | CF3 |
| 27-933 | pyridin-2-yl | Me | H | H | I | H | nonafluoro-2-butyl | H | CF3 |
| 27-934 | 3-chloropyridin-2-yl | Me | H | H | I | H | nonafluoro-2-butyl | H | CF3 |
| 27-935 | 4-bromopyridin-2-yl | Me | H | H | I | H | nonafluoro-2-butyl | H | CF3 |
| 27-936 | 5-iodopyrdin-2-yl | Me | H | H | I | H | nonafluoro-2-butyl | H | CF3 |
| 27-937 | 6-chloropyridin-2-yl | Me | H | H | I | H | nonafluoro-2-butyl | H | CF3 |
| 27-938 | 4-cyanopyridin-2-yl | Me | H | H | I | H | nonafluoro-2-butyl | H | CF3 |
| 27-939 | phenyl | Me | H | H | OCF3 | H | heptafluoroisopropyl | H | OCF3 |
| 27-970 | 2-chloropyridin-3-yl | Me | H | H | OCF3 | H | heptafluoroisopropyl | H | OCF3 |
| 27-995 | phenyl | Me | H | H | OCF3 | H | nonafluoro-2-butyl | H | OCF3 |
| 27-1026 | 2-chloropyridin-3-yl | Me | H | H | OCF3 | H | nonafluoro-2-butyl | H | OCF3 |
| 27-1051 | phenyl | Me | H | H | CF3 | H | heptafluoroisopropyl | H | OCF3 |
| 27-1082 | 2-chloropyridin-3-yl | Me | H | H | CF3 | H | heptafluoroisopropyl | H | OCF3 |
| 27-1107 | phenyl | Me | H | H | CF3 | H | nonafluoro-2-butyl | H | OCF3 |
| 27-1138 | 2-chloropyridin-3-yl | Me | H | H | CF3 | H | nonafluoro-2-butyl | H | OCF3 |
| 27-1163 | phenyl | Me | H | H | CF3 | H | heptafluoroisopropyl | H | CF3 |
| 27-1183 | 3-cyanophenyl | Me | H | H | CF3 | H | heptafluoroisopropyl | H | CF3 |
| 27-1184 | 4-cyanophenyl | Me | H | H | CF3 | H | heptafluoroisopropyl | H | CF3 |
| 27-1199 | 2-chloropyridin-3-yl | Me | H | H | CF3 | H | heptafluoroisopropyl | H | CF3 |
| 27-1231 | phenyl | Me | H | H | CF3 | H | nonafluoro-2-butyl | H | CF3 |
| 27-1251 | 3-cyanophenyl | Me | H | H | CF3 | H | nonafluoro-2-butyl | H | CF3 |
| 27-1252 | 4-cyanophenyl | Me | H | H | CF3 | H | nonafluoro-2-butyl | H | CF3 |
| 27-1267 | 2-chloropyridin-3-yl | Me | H | H | CF3 | H | nonafluoro-2-butyl | H | CF3 |

TABLE 28

| compound number | Q₁ | R₁ | R₂ | X₃ | Y₁ | Y₂ | Y₃ | Y₄ | Y₅ |
|---|---|---|---|---|---|---|---|---|---|
| 28-1 | phenyl | H | Me | H | Cl | H | heptafluoroisopropyl | H | OCF3 |
| 28-21 | 3-cyanophenyl | H | Me | H | Cl | H | heptafluoroisopropyl | H | OCF3 |
| 28-22 | 4-cyanophenyl | H | Me | H | Cl | H | heptafluoroisopropyl | H | OCF3 |
| 28-37 | 2-chloropyridin-3-yl | H | Me | H | Cl | H | heptafluoroisopropyl | H | OCF3 |
| 28-79 | phenyl | H | Me | H | Cl | H | nonafluoro-2-butyl | H | OCF3 |
| 28-99 | 3-cyanophenyl | H | Me | H | Cl | H | nonafluoro-2-butyl | H | OCF3 |
| 28-100 | 4-cyanophenyl | H | Me | H | Cl | H | nonafluoro-2-butyl | H | OCF3 |
| 28-115 | 2-chloropyridin-3-yl | H | Me | H | Cl | H | nonafluoro-2-butyl | H | OCF3 |
| 28-157 | phenyl | H | Me | H | Br | H | heptafluoroisopropyl | H | OCF3 |
| 28-177 | 3-cyanophenyl | H | Me | H | Br | H | heptafluoroisopropyl | H | OCF3 |
| 28-178 | 4-cyanophenyl | H | Me | H | Br | H | heptafluoroisopropyl | H | OCF3 |
| 28-193 | 2-chloropyridin-3-yl | H | Me | H | Br | H | heptafluoroisopropyl | H | OCF3 |
| 28-235 | phenyl | H | Me | H | Br | H | nonafluoro-2-butyl | H | OCF3 |
| 28-255 | 3-cyanophenyl | H | Me | H | Br | H | nonafluoro-2-butyl | H | OCF3 |
| 28-256 | 4-cyanophenyl | H | Me | H | Br | H | nonafluoro-2-butyl | H | OCF3 |
| 28-271 | 2-chloropyridin-3-yl | H | Me | H | Br | H | nonafluoro-2-butyl | H | OCF3 |
| 28-313 | phenyl | H | Me | H | I | H | heptafluoroisopropyl | H | OCF3 |
| 28-333 | 3-cyanophenyl | H | Me | H | I | H | heptafluoroisopropyl | H | OCF3 |
| 28-334 | 4-cyanophenyl | H | Me | H | I | H | heptafluoroisopropyl | H | OCF3 |
| 28-349 | 2-chloropyridin-3-yl | H | Me | H | I | H | heptafluoroisopropyl | H | OCF3 |
| 28-391 | phenyl | H | Me | H | I | H | nonafluoro-2-butyl | H | OCF3 |
| 28-411 | 3-cyanophenyl | H | Me | H | I | H | nonafluoro-2-butyl | H | OCF3 |
| 28-412 | 4-cyanophenyl | H | Me | H | I | H | nonafluoro-2-butyl | H | OCF3 |
| 28-427 | 2-chloropyridin-3-yl | H | Me | H | I | H | nonafluoro-2-butyl | H | OCF3 |
| 28-469 | phenyl | H | Me | H | F | H | heptafluoroisopropyl | H | CF3 |
| 28-470 | phenyl | H | Me | H | Cl | H | heptafluoroisopropyl | H | CF3 |
| 28-481 | 3-iodophenyl | H | Me | H | Cl | H | pentafluoroethyl | H | CF3 |
| 28-482 | 4-iodophenyl | H | Me | H | Cl | H | pentafluoroethyl | H | CF3 |
| 28-484 | (3-trifluoromethyl)phenyl | H | Et | H | Cl | H | heptafluoroisopropyl | H | CF3 |
| 28-489 | 2-cyanophenyl | H | Me | H | Cl | H | pentafluoroethyl | H | C2F5 |
| 28-490 | 3-cyanophenyl | H | Me | H | Cl | H | heptafluoroisopropyl | H | CF3 |
| 28-491 | 4-cyanophenyl | H | Me | H | Cl | H | heptafluoroisopropyl | H | CF3 |
| 28-494 | 2,4-dichlorophenyl | H | Me | H | Cl | H | heptafluoroisopropyl | H | C2F5 |
| 28-495 | 2-chloro-4-fluorophenyl | H | n-Pr | H | Cl | H | heptafluoroisopropyl | H | CF3 |
| 28-498 | 2-bromo-4-chlorophenyl | H | Me | H | Cl | H | heptafluoroisopropyl | H | n-C3F7 |
| 28-505 | 2-fluoropyridin-3-yl | H | Me | H | Cl | H | pentafluoroethyl | H | CF3 |
| 28-506 | 2-chloropyridin-3-yl | H | Me | H | Cl | H | heptafluoroisopropyl | H | CF3 |
| 28-512 | 6-fluoropyridin-3-yl | H | i-Pr | H | Cl | H | heptafluoroisopropyl | H | CF3 |
| 28-519 | 5-fluoropyridin-3-yl | H | Me | H | Cl | H | heptafluoroisopropyl | H | C2F5 |
| 28-521 | 5-bromopyridin-3-yl | H | Me | H | Cl | H | heptafluoroisopropyl | H | n-C3F7 |
| 28-522 | 5-iodopyridin-3-yl | H | Me | H | Cl | H | heptafluoroisopropyl | H | i-C3F7 |
| 28-524 | 5-nitropyridin-3-yl | H | Me | H | Cl | H | pentafluoroethyl | H | CF3 |
| 28-526 | 4-fluoropyridin-3-yl | H | Me | H | Cl | H | pentafluoroethyl | H | CF3 |
| 28-528 | 4-bromopyridin-3-yl | H | CH2CH=CH2 | H | Cl | H | heptafluoroisopropyl | H | n-C3F7 |
| 28-529 | 4-iodopyridin-3-yl | H | Me | H | Cl | H | heptafluoroisopropyl | H | i-C3F7 |
| 28-531 | 4-nitropyridin-3-yl | H | Me | Cl | Cl | H | heptafluoroisopropyl | H | CF3 |
| 28-535 | pyridin-4-yl | H | CN | H | Cl | H | heptafluoroisopropyl | H | CF3 |
| 28-547 | 4-cyanopyridin-2-yl | H | Me | H | Cl | H | pentafluoroethyl | H | CF3 |
| 28-548 | phenyl | H | Me | H | F | H | nonafluoro-2-butyl | H | CF3 |
| 28-549 | phenyl | H | Me | H | Cl | H | nonafluoro-2-butyl | H | CF3 |
| 28-557 | 3-bromophenyl | H | CH2C≡CH | H | Cl | H | nonafluoro-2-butyl | H | CF3 |
| 28-562 | (2-trifluoromethyl)phenyl | H | Me | H | Cl | H | nonafluoro-2-butyl | H | C2F5 |
| 28-564 | (4-trifluoromethyl)phenyl | H | NH2 | H | Cl | H | nonafluoro-2-butyl | H | CF3 |
| 28-569 | 3-cyanophenyl | H | Me | H | Cl | H | nonafluoro-2-butyl | H | CF3 |
| 28-570 | 4-cyanophenyl | H | Me | H | Cl | H | nonafluoro-2-butyl | H | CF3 |
| 28-577 | 2-bromo-4-chlorophenyl | H | C(O)OMe | H | Cl | H | nonafluoro-2-butyl | H | CF3 |
| 28-579 | 2-chloro-4-nitrophenyl | H | Me | H | Cl | H | nonafluoro-2-butyl | H | i-C3F7 |
| 28-585 | 2-chloropyridin-3-yl | H | Me | H | Cl | H | nonafluoro-2-butyl | H | CF3 |

TABLE 28-continued

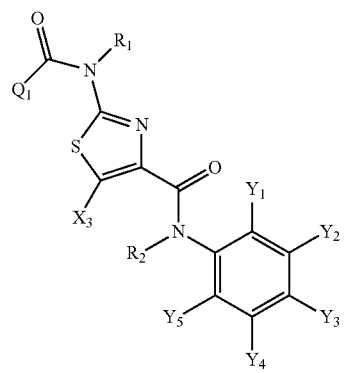

| compound number | $Q_1$ | $R_1$ | $R_2$ | $X_3$ | $Y_1$ | $Y_2$ | $Y_3$ | $Y_4$ | $Y_5$ |
|---|---|---|---|---|---|---|---|---|---|
| 28-598 | 5-fluoropyridin-3-yl | H | C(O)OEt | H | Cl | H | nonafluoro-2-butyl | H | C2F5 |
| 28-600 | 5-bromopyridin-3-yl | H | Me | H | Cl | H | nonafluoro-2-butyl | H | n-C3F7 |
| 28-601 | 5-iodopyridin-3-yl | H | Me | H | Cl | H | nonafluoro-2-butyl | H | i-C3F7 |
| 28-605 | 4-fluoropyridin-3-yl | H | Me | H | Cl | H | nonafluoro-2-butyl | H | C2F5 |
| 28-607 | 4-bromopyridin-3-yl | H | C(O)C(O)Me | H | Cl | H | nonafluoro-2-butyl | H | CF3 |
| 28-609 | 4-(trifluoromethyl)pyridin-3-yl | H | Me | H | Cl | H | nonafluoro-2-butyl | H | n-C3F7 |
| 28-610 | 4-nitropyridin-3-yl | H | C(O)C(O)Et | H | Cl | H | nonafluoro-2-butyl | H | i-C3F7 |
| 28-624 | 5-iodopyridin-2-yl | H | C(O)Me | H | Cl | H | nonafluoro-2-butyl | H | CF3 |
| 28-626 | 4-cyanopyridin-2-yl | H | C(O)Et | H | Cl | H | nonafluoro-2-butyl | H | C2F5 |
| 28-627 | phenyl | H | Me | H | Br | H | heptafluoroisopropyl | H | CF3 |
| 28-628 | 2-fluorophenyl | H | Me | H | Br | H | heptafluoroisopropyl | H | CF3 |
| 28-641 | (3-trifluoromethyl)phenyl | H | S(O)2Me | H | Br | H | heptafluoroisopropyl | H | CF3 |
| 28-647 | 3-cyanophenyl | H | Me | H | Br | H | heptafluoroisopropyl | H | CF3 |
| 28-648 | 4-cyanophenyl | H | Me | H | Br | H | heptafluoroisopropyl | H | CF3 |
| 28-659 | 4-cyano-2-fluorophenyl | H | S(O)2Et | H | Br | H | heptafluoroisopropyl | H | CF3 |
| 28-663 | 2-chloropyridin-3-yl | H | Me | H | Br | H | heptafluoroisopropyl | H | CF3 |
| 28-674 | 6-nitropyridin-3-yl | H | CH2Ph | H | Br | H | heptafluoroisopropyl | H | CF3 |
| 28-683 | 4-fluoropyridin-3-yl | H | CH2(3-Py) | H | Br | H | heptafluoroisopropyl | H | CF3 |
| 28-704 | 4-cyanopyridin-2-yl | H | CH2(3-Py-N-oxide) | H | Br | H | heptafluoroisopropyl | H | CF3 |
| 28-705 | phenyl | H | Me | H | Br | H | nonafluoro-2-butyl | H | CF3 |
| 28-706 | 2-fluorophenyl | H | Me | H | Br | H | nonafluoro-2-butyl | H | CF3 |
| 28-725 | 3-cyanophenyl | H | Me | H | Br | H | nonafluoro-2-butyl | H | CF3 |
| 28-726 | 4-cyanophenyl | H | Me | H | Br | H | nonafluoro-2-butyl | H | CF3 |
| 28-732 | 4-bromo-2-chlorophenyl | H | Et | H | Br | H | nonafluoro-2-butyl | H | CF3 |
| 28-741 | 2-chloropyridin-3-yl | H | Me | H | Br | H | nonafluoro-2-butyl | H | CF3 |
| 28-758 | 5-(trifluoromethyl)pyridin-3-yl | H | CN | H | Br | H | nonafluoro-2-butyl | H | CF3 |
| 28-783 | phenyl | H | Me | H | I | H | heptafluoroisopropyl | H | CF3 |
| 28-784 | 2-fluorophenyl | H | Me | H | I | H | heptafluoroisopropyl | H | CF3 |
| 28-803 | 3-cyanophenyl | H | Me | H | I | H | heptafluoroisopropyl | H | CF3 |
| 28-804 | 4-cyanophenyl | H | Me | H | I | H | heptafluoroisopropyl | H | CF3 |
| 28-819 | 2-chloropyridin-3-yl | H | Me | H | I | H | heptafluoroisopropyl | H | CF3 |
| 28-832 | 5-fluoropyridin-3-yl | H | C(O)Me | H | I | H | heptafluoroisopropyl | H | CF3 |
| 28-861 | phenyl | H | Me | H | I | H | nonafluoro-2-butyl | H | CF3 |
| 28-862 | 2-fluorophenyl | H | Me | H | I | H | nonafluoro-2-butyl | H | CF3 |
| 28-881 | 3-cyanophenyl | H | Me | H | I | H | nonafluoro-2-butyl | H | CF3 |
| 28-882 | 4-cyanophenyl | H | Me | H | I | H | nonafluoro-2-butyl | H | CF3 |
| 28-897 | 2-chloropyridin-3-yl | H | Me | H | I | H | nonafluoro-2-butyl | H | CF3 |
| 28-939 | phenyl | H | Me | H | OCF3 | H | heptafluoroisopropyl | H | OCF3 |
| 28-970 | 2-chloropyridin-3-yl | H | Me | H | OCF3 | H | heptafluoroisopropyl | H | OCF3 |
| 28-995 | phenyl | H | Me | H | OCF3 | H | nonafluoro-2-butyl | H | OCF3 |
| 28-1026 | 2-chloropyridin-3-yl | H | Me | H | OCF3 | H | nonafluoro-2-butyl | H | OCF3 |
| 28-1051 | phenyl | H | Me | H | CF3 | H | heptafluoroisopropyl | H | OCF3 |
| 28-1082 | 2-chloropyridin-3-yl | H | Me | H | CF3 | H | heptafluoroisopropyl | H | OCF3 |
| 28-1107 | phenyl | H | Me | H | CF3 | H | nonafluoro-2-butyl | H | OCF3 |
| 28-1138 | 2-chloropyridin-3-yl | H | Me | H | CF3 | H | nonafluoro-2-butyl | H | OCF3 |
| 28-1163 | phenyl | H | Me | H | CF3 | H | heptafluoroisopropyl | H | CF3 |
| 28-1183 | 3-cyanophenyl | H | Me | H | CF3 | H | heptafluoroisopropyl | H | CF3 |
| 28-1184 | 4-cyanophenyl | H | Me | H | CF3 | H | heptafluoroisopropyl | H | CF3 |
| 28-1199 | 2-chloropyridin-3-yl | H | Me | H | CF3 | H | heptafluoroisopropyl | H | CF3 |
| 28-1231 | phenyl | H | Me | H | CF3 | H | nonafluoro-2-butyl | H | CF3 |
| 28-1251 | 3-cyanophenyl | H | Me | H | CF3 | H | nonafluoro-2-butyl | H | CF3 |
| 28-1252 | 4-cyanophenyl | H | Me | H | CF3 | H | nonafluoro-2-butyl | H | CF3 |
| 28-1267 | 2-chloropyridin-3-yl | H | Me | H | CF3 | H | nonafluoro-2-butyl | H | CF3 |

TABLE 29

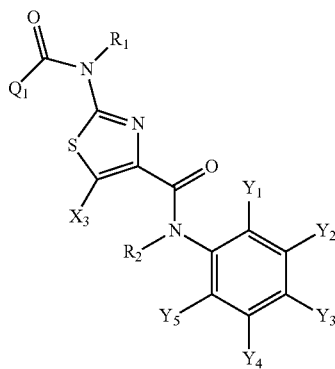

| compound number | Q₁ | R₁ | R₂ | X₃ | Y₁ | Y₂ | Y₃ | Y₄ | Y₅ |
|---|---|---|---|---|---|---|---|---|---|
| 29-1 | phenyl | Me | Me | H | Cl | H | heptafluoroisopropyl | H | OCF3 |
| 29-21 | 3-cyanophenyl | Me | Me | H | Cl | H | heptafluoroisopropyl | H | OCF3 |
| 29-22 | 4-cyanophenyl | Me | Me | H | Cl | H | heptafluoroisopropyl | H | OCF3 |
| 29-37 | 2-chloropyridin-3-yl | Me | Me | H | Cl | H | heptafluoroisopropyl | H | OCF3 |
| 29-79 | phenyl | Me | Me | H | Cl | H | nonafluoro-2-butyl | H | OCF3 |
| 29-99 | 3-cyanophenyl | Me | Me | H | Cl | H | nonafluoro-2-butyl | H | OCF3 |
| 29-100 | 4-cyanophenyl | Me | Me | H | Cl | H | nonafluoro-2-butyl | H | OCF3 |
| 29-115 | 2-chloropyridin-3-yl | Me | Me | H | Cl | H | nonafluoro-2-butyl | H | OCF3 |
| 29-157 | phenyl | Me | Me | H | Br | H | heptafluoroisopropyl | H | OCF3 |
| 29-177 | 3-cyanophenyl | Me | Me | H | Br | H | heptafluoroisopropyl | H | OCF3 |
| 29-178 | 4-cyanophenyl | Me | Me | H | Br | H | heptafluoroisopropyl | H | OCF3 |
| 29-193 | 2-chloropyridin-3-yl | Me | Me | H | Br | H | heptafluoroisopropyl | H | OCF3 |
| 29-235 | phenyl | Me | Me | H | Br | H | nonafluoro-2-butyl | H | OCF3 |
| 29-255 | 3-cyanophenyl | Me | Me | H | Br | H | nonafluoro-2-butyl | H | OCF3 |
| 29-256 | 4-cyanophenyl | Me | Me | H | Br | H | nonafluoro-2-butyl | H | OCF3 |
| 29-271 | 2-chloropyridin-3-yl | Me | Me | H | Br | H | nonafluoro-2-butyl | H | OCF3 |
| 29-313 | phenyl | Me | Me | H | I | H | heptafluoroisopropyl | H | OCF3 |
| 29-333 | 3-cyanophenyl | Me | Me | H | I | H | heptafluoroisopropyl | H | OCF3 |
| 29-334 | 4-cyanophenyl | Me | Me | H | I | H | heptafluoroisopropyl | H | OCF3 |
| 29-349 | 2-chloropyridin-3-yl | Me | Me | H | I | H | heptafluoroisopropyl | H | OCF3 |
| 29-391 | phenyl | Me | Me | H | I | H | nonafluoro-2-butyl | H | OCF3 |
| 29-411 | 3-cyanophenyl | Me | Me | H | I | H | nonafluoro-2-butyl | H | OCF3 |
| 29-412 | 4-cyanophenyl | Me | Me | H | I | H | nonafluoro-2-butyl | H | OCF3 |
| 29-427 | 2-chloropyridin-3-yl | Me | Me | H | I | H | nonafluoro-2-butyl | H | OCF3 |
| 29-665 | phenyl | Me | Me | H | F | H | heptafluoroisopropyl | H | CF3 |
| 29-666 | phenyl | Me | Me | H | Cl | H | heptafluoroisopropyl | H | CF3 |
| 29-677 | 3-iodophenyl | Me | Me | H | Cl | H | pentafluoroethyl | H | CF3 |
| 29-678 | 4-iodophenyl | Me | Et | H | Cl | H | pentafluoroethyl | H | CF3 |
| 29-680 | (3-trifluoromethyl)phenyl | Et | Me | H | Cl | H | heptafluoroisopropyl | H | CF3 |
| 29-682 | 2-nitrophenyl | Me | Me | Cl | Cl | H | heptafluoroisopropyl | H | CF3 |
| 29-685 | 2-cyanophenyl | Me | Me | H | Cl | H | pentafluoroethyl | H | C2F5 |
| 29-686 | 3-cyanophenyl | Me | Me | H | Cl | H | heptafluoroisopropyl | H | CF3 |
| 29-687 | 4-cyanophenyl | Me | Me | H | Cl | H | heptafluoroisopropyl | H | CF3 |
| 29-689 | 3,4-dichlorophenyl | Me | n-Pr | H | Cl | H | heptafluoroisopropyl | H | CF3 |
| 29-690 | 2,4-dichlorophenyl | Me | Me | H | Cl | H | heptafluoroisopropyl | H | C2F5 |
| 29-691 | 2-chloro-4-fluorophenyl | n-Pr | Me | H | Cl | H | heptafluoroisopropyl | H | CF3 |
| 29-694 | 2-bromo-4-chlorophenyl | Me | Me | H | Cl | H | heptafluoroisopropyl | H | n-C3F7 |
| 29-701 | 2-fluoropyridin-3-yl | Me | Me | H | Cl | H | pentafluoroethyl | H | CF3 |
| 29-702 | 2-chloropyridin-3-yl | Me | Me | H | Cl | H | heptafluoroisopropyl | H | CF3 |
| 29-706 | 2-nitropyridin-3-yl | Me | i-Pr | H | Cl | H | heptafluoroisopropyl | H | CF3 |
| 29-708 | 6-fluoropyridin-3-yl | i-Pr | Me | H | Cl | H | heptafluoroisopropyl | H | CF3 |
| 29-715 | 5-fluoropyridin-3-yl | Me | Me | H | Cl | H | heptafluoroisopropyl | H | C2F5 |
| 29-717 | 5-bromopyridin-3-yl | Me | Me | H | Cl | H | heptafluoroisopropyl | H | n-C3F7 |
| 29-718 | 5-iodopyridin-3-yl | Me | Me | H | Cl | H | heptafluoroisopropyl | H | i-C3F7 |
| 29-720 | 5-nitropyridin-3-yl | Me | Me | H | Cl | H | pentafluoroethyl | H | CF3 |
| 29-722 | 4-fluoropyridin-3-yl | Me | CH2CH=CH2 | H | Cl | H | pentafluoroethyl | H | CF3 |
| 29-724 | 4-bromopyridin-3-yl | CH2CH=CH2 | Me | H | Cl | H | heptafluoroisopropyl | H | n-C3F7 |
| 29-725 | 4-iodopyridin-3-yl | Me | Me | H | Cl | H | heptafluoroisopropyl | H | i-C3F7 |
| 29-729 | 2,6-dichloropyridin-3-yl | Me | CN | H | Cl | H | heptafluoroisopropyl | H | CF3 |
| 29-731 | pyridin-4-yl | CN | Me | H | Cl | H | heptafluoroisopropyl | H | CF3 |
| 29-743 | 4-cyanopyridin-2-yl | Me | Me | H | Cl | H | pentafluoroethyl | H | CF3 |
| 29-744 | phenyl | Me | Me | H | F | H | nonafluoro-2-butyl | H | CF3 |
| 29-745 | phenyl | Me | Me | H | Cl | H | nonafluoro-2-butyl | H | CF3 |
| 29-751 | 4-chlorophenyl | Me | CH2C≡CH | H | Cl | H | nonafluoro-2-butyl | H | CF3 |
| 29-753 | 3-bromophenyl | CH2C≡CH | Me | H | Cl | H | nonafluoro-2-butyl | H | CF3 |
| 29-758 | (2-trifluoromethyl)phenyl | Me | NH2 | H | Cl | H | nonafluoro-2-butyl | H | C2F5 |
| 29-760 | (4-trifluoromethyl)phenyl | NH2 | Me | H | Cl | H | nonafluoro-2-butyl | H | CF3 |
| 29-765 | 3-cyanophenyl | Me | Me | H | Cl | H | nonafluoro-2-butyl | H | CF3 |

TABLE 29-continued

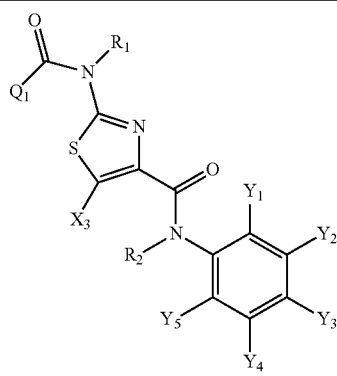

| compound number | Q₁ | R₁ | R₂ | X₃ | Y₁ | Y₂ | Y₃ | Y₄ | Y₅ |
|---|---|---|---|---|---|---|---|---|---|
| 29-766 | 4-cyanophenyl | Me | Me | H | Cl | H | nonafluoro-2-butyl | H | CF3 |
| 29-771 | 2-chloro-4,5-difluorophenyl | Me | C(O)OMe | H | Cl | H | nonafluoro-2-butyl | H | CF3 |
| 29-773 | 2-bromo-4-chlorophenyl | C(O)OMe | Me | H | Cl | H | nonafluoro-2-butyl | H | CF3 |
| 29-775 | 2-chloro-4-nitrophenyl | Me | Me | H | Cl | H | nonafluoro-2-butyl | H | i-C3F7 |
| 29-781 | 2-chloropyridin-3-yl | Me | Me | H | Cl | H | nonafluoro-2-butyl | H | CF3 |
| 29-792 | 6-nitropyridin-3-yl | Me | C(O)OEt | H | Cl | H | nonafluoro-2-butyl | H | CF3 |
| 29-794 | 5-fluoropyridin-3-yl | C(O)OEt | Me | H | Cl | H | nonafluoro-2-butyl | H | C2F5 |
| 29-796 | 5-bromopyridin-3-yl | Me | Me | H | Cl | H | nonafluoro-2-butyl | H | n-C3F7 |
| 29-797 | 5-iodopyridin-3-yl | Me | Me | H | Cl | H | nonafluoro-2-butyl | H | i-C3F7 |
| 29-801 | 4-fluoropyridin-3-yl | Me | C(O)C(O)Me | H | Cl | H | nonafluoro-2-butyl | H | C2F5 |
| 29-803 | 4-bromopyridin-3-yl | C(O)C(O)Me | Me | H | Cl | H | nonafluoro-2-butyl | H | CF3 |
| 29-804 | 4-iodopyridin-3-yl | Me | C(O)C(O)Et | H | Cl | H | nonafluoro-2-butyl | H | CF3 |
| 29-805 | 4-(trifluoromethyl)pyridin-3-yl | Me | Me | H | Cl | H | nonafluoro-2-butyl | H | n-C3F7 |
| 29-806 | 4-nitropyridin-3-yl | C(O)C(O)Et | Me | H | Cl | H | nonafluoro-2-butyl | H | i-C3F7 |
| 29-818 | 3-chloropyridin-2-yl | Me | C(O)Me | H | Cl | H | nonafluoro-2-butyl | H | CF3 |
| 29-820 | 5-iodopyridin-2-yl | C(O)Me | Me | H | Cl | H | nonafluoro-2-butyl | H | CF3 |
| 29-821 | 6-chloropyridin-2-yl | Me | C(O)Et | H | Cl | H | nonafluoro-2-butyl | H | CF3 |
| 29-822 | 4-cyanopyridin-2-yl | C(O)Et | Me | H | Cl | H | nonafluoro-2-butyl | H | C2F5 |
| 29-823 | phenyl | Me | Me | H | Br | H | heptafluoroisopropyl | H | CF3 |
| 29-824 | 2-fluorophenyl | Me | Me | H | Br | H | heptafluoroisopropyl | H | CF3 |
| 29-835 | 4-iodophenyl | Me | S(O)2Me | H | Br | H | heptafluoroisopropyl | H | CF3 |
| 29-837 | (3-trifluoromethyl)phenyl | S(O)2Me | Me | H | Br | H | heptafluoroisopropyl | H | CF3 |
| 29-843 | 3-cyanophenyl | Me | Me | H | Br | H | heptafluoroisopropyl | H | CF3 |
| 29-844 | 4-cyanophenyl | Me | Me | H | Br | H | heptafluoroisopropyl | H | CF3 |
| 29-853 | 2-chloro-4-nitrophenyl | Me | S(O)2Et | H | Br | H | heptafluoroisopropyl | H | CF3 |
| 29-855 | 4-cyano-2-fluorophenyl | S(O)2Et | Me | H | Br | H | heptafluoroisopropyl | H | CF3 |
| 29-859 | 2-chloropyridin-3-yl | Me | Me | H | Br | H | heptafluoroisopropyl | H | CF3 |
| 29-868 | 6-iodopyridin-3-yl | Me | CH2Ph | H | Br | H | heptafluoroisopropyl | H | CF3 |
| 29-870 | 6-nitropyridin-3-yl | CH2Ph | Me | H | Br | H | heptafluoroisopropyl | H | CF3 |
| 29-877 | 5-nitropyridin-3-yl | Me | CH2(3-Py) | H | Br | H | heptafluoroisopropyl | H | CF3 |
| 29-879 | 4-fluoropyridin-3-yl | CH2(3-Py) | Me | H | Br | H | heptafluoroisopropyl | H | CF3 |
| 29-898 | 5-iodopyridin-2-yl | Me | CH2(3-Py-N-oxide) | H | Br | H | heptafluoroisopropyl | H | CF3 |
| 29-900 | 4-cyanopyridin-2-yl | CH2(3-Py-N-oxide) | Me | H | Br | H | heptafluoroisopropyl | H | CF3 |
| 29-901 | phenyl | Me | Me | H | Br | H | nonafluoro-2-butyl | H | CF3 |
| 29-902 | 2-fluorophenyl | Me | Me | H | Br | H | nonafluoro-2-butyl | H | CF3 |
| 29-921 | 3-cyanophenyl | Me | Me | H | Br | H | nonafluoro-2-butyl | H | CF3 |
| 29-922 | 4-cyanophenyl | Me | Me | H | Br | H | nonafluoro-2-butyl | H | CF3 |
| 29-926 | 2-chloro-4-fluorophenyl | Me | Et | H | Br | H | nonafluoro-2-butyl | H | CF3 |
| 29-928 | 4-bromo-2-chlorophenyl | Et | Me | H | Br | H | nonafluoro-2-butyl | H | CF3 |
| 29-937 | 2-chloropyridin-3-yl | Me | Me | H | Br | H | nonafluoro-2-butyl | H | CF3 |
| 29-952 | 5-bromopyridin-3-yl | Me | CN | H | Br | H | nonafluoro-2-butyl | H | CF3 |
| 29-954 | 5-(trifluoromethyl)pyridin-3-yl | CN | Me | H | Br | H | nonafluoro-2-butyl | H | CF3 |
| 29-979 | phenyl | Me | Me | H | I | H | heptafluoroisopropyl | H | CF3 |
| 29-980 | 2-fluorophenyl | Me | Me | H | I | H | heptafluoroisopropyl | H | CF3 |
| 29-999 | 3-cyanophenyl | Me | Me | H | I | H | heptafluoroisopropyl | H | CF3 |
| 29-1000 | 4-cyanophenyl | Me | Me | H | I | H | heptafluoroisopropyl | H | CF3 |
| 29-1015 | 2-chloropyridin-3-yl | Me | Me | H | I | H | heptafluoroisopropyl | H | CF3 |
| 29-1026 | 6-nitropyridin-3-yl | Me | C(O)Me | H | I | H | heptafluoroisopropyl | H | CF3 |
| 29-1028 | 5-fluoropyridin-3-yl | C(O)Me | Me | H | I | H | heptafluoroisopropyl | H | CF3 |
| 29-1057 | phenyl | Me | Me | H | I | H | nonafluoro-2-butyl | H | CF3 |
| 29-1058 | 2-fluorophenyl | Me | Me | H | I | H | nonafluoro-2-butyl | H | CF3 |
| 29-1077 | 3-cyanophenyl | Me | Me | H | I | H | nonafluoro-2-butyl | H | CF3 |
| 29-1078 | 4-cyanophenyl | Me | Me | H | I | H | nonafluoro-2-butyl | H | CF3 |
| 29-1093 | 2-chloropyridin-3-yl | Me | Me | H | I | H | nonafluoro-2-butyl | H | CF3 |
| 29-1331 | phenyl | Me | Me | H | OCF3 | H | heptafluoroisopropyl | H | OCF3 |
| 29-1362 | 2-chloropyridin-3-yl | Me | Me | H | OCF3 | H | heptafluoroisopropyl | H | OCF3 |

TABLE 29-continued

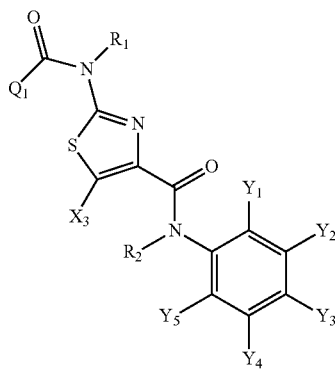

| compound number | Q₁ | R₁ | R₂ | X₃ | Y₁ | Y₂ | Y₃ | Y₄ | Y₅ |
|---|---|---|---|---|---|---|---|---|---|
| 29-1387 | phenyl | Me | Me | H | OCF3 | H | nonafluoro-2-butyl | H | OCF3 |
| 29-1418 | 2-chloropyridin-3-yl | Me | Me | H | OCF3 | H | nonafluoro-2-butyl | H | OCF3 |
| 29-1443 | phenyl | Me | Me | H | CF3 | H | heptafluoroisopropyl | H | OCF3 |
| 29-1474 | 2-chloropyridin-3-yl | Me | Me | H | CF3 | H | heptafluoroisopropyl | H | OCF3 |
| 29-1499 | phenyl | Me | Me | H | CF3 | H | nonafluoro-2-butyl | H | OCF3 |
| 29-1530 | 2-chloropyridin-3-yl | Me | Me | H | CF3 | H | nonafluoro-2-butyl | H | OCF3 |
| 29-1555 | phenyl | Me | Me | H | CF3 | H | heptafluoroisopropyl | H | CF3 |
| 29-1575 | 3-cyanophenyl | Me | Me | H | CF3 | H | heptafluoroisopropyl | H | CF3 |
| 29-1576 | 4-cyanophenyl | Me | Me | H | CF3 | H | heptafluoroisopropyl | H | CF3 |
| 29-1591 | 2-chloropyridin-3-yl | Me | Me | H | CF3 | H | heptafluoroisopropyl | H | CF3 |
| 29-1623 | phenyl | Me | Me | H | CF3 | H | nonafluoro-2-butyl | H | CF3 |
| 29-1643 | 3-cyanophenyl | Me | Me | H | CF3 | H | nonafluoro-2-butyl | H | CF3 |
| 29-1644 | 4-cyanophenyl | Me | Me | H | CF3 | H | nonafluoro-2-butyl | H | CF3 |
| 29-1659 | 2-chloropyridin-3-yl | Me | Me | H | CF3 | H | nonafluoro-2-butyl | H | CF3 |

TABLE 30

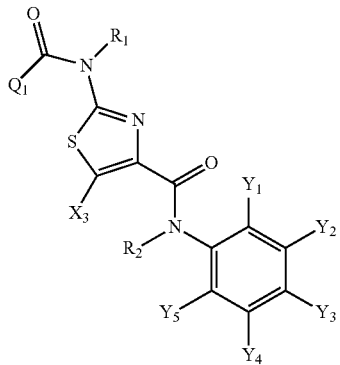

| compound number | Q₁ | R₁ | R₂ | X₃ | Y₁ | Y₂ | Y₃ | Y₄ | Y₅ |
|---|---|---|---|---|---|---|---|---|---|
| 30-9 | 3-bromophenyl | H | Et | H | Cl | F | heptafluoroisopropyl | F | OCF3 |
| 30-39 | 2-iodopyridin-3-yl | H | H | H | Cl | Me | nonafluoro-2-butyl | Me | OCF3 |
| 30-144 | phenyl | H | H | H | Cl | F | heptafluoroisopropyl | H | CF3 |
| 30-154 | 2-iodophenyl | H | H | H | Cl | F | heptafluoroisopropyl | Br | CF3 |
| 30-161 | 3-nitrophenyl | H | H | H | Cl | Br | heptafluoroisopropyl | Cl | CF3 |
| 30-168 | 2,4-dichlorophenyl | H | H | H | Cl | Me | nonafluoro-2-butyl | H | CF3 |
| 30-182 | 2-iodopyridin-3-yl | H | H | H | Cl | Me | nonafluoro-2-butyl | Me | n-C3F7 |
| 30-183 | 2-(trifluoromethyl)pyridin-3-yl | H | H | H | Cl | Me | nonafluoro-2-butyl | Et | i-C3F7 |
| 30-189 | 6-iodopyridin-3-yl | H | H | H | Cl | Et | nonafluoro-2-butyl | Me | n-C3F7 |
| 30-190 | 6-(trifluoromethyl)pyridin-3-yl | H | H | H | Cl | Et | nonafluoro-2-butyl | Et | i-C3F7 |
| 30-196 | 5-bromopyridin-3-yl | H | H | H | Br | n-Pr | heptafluoroisopropyl | Me | CF3 |
| 30-197 | 5-iodopyridin-3-yl | H | H | H | Br | n-Pr | heptafluoroisopropyl | Et | CF3 |
| 30-203 | 4-bromopyridin-3-yl | Me | n-Pr | H | Br | i-Pr | heptafluoroisopropyl | Me | CF3 |
| 30-204 | 4-iodopyridin-3-yl | H | H | H | Br | i-Pr | heptafluoroisopropyl | Et | CF3 |
| 30-210 | pyridin-4-yl | H | H | H | Br | n-Bu | heptafluoroisopropyl | Me | CF3 |
| 30-211 | 2-chloropyridin-4-yl | H | H | H | Br | n-Bu | heptafluoroisopropyl | Et | CF3 |
| 30-217 | pyridin-2-yl | H | H | H | Br | i-Bu | nonafluoro-2-butyl | Me | CF3 |
| 30-218 | 3-chloropyridin-2-yl | H | H | H | Br | i-Bu | nonafluoro-2-butyl | Et | CF3 |

TABLE 30-continued

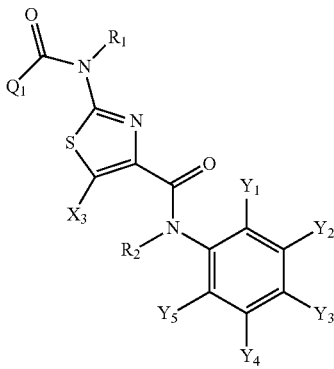

| compound number | Q₁ | R₁ | R₂ | X₃ | Y₁ | Y₂ | Y₃ | Y₄ | Y₅ |
|---|---|---|---|---|---|---|---|---|---|
| 30-224 | 2-fluorophenyl | H | H | H | Br | s-Bu | nonafluoro-2-butyl | Me | CF3 |
| 30-225 | 3-fluorophenyl | H | H | H | Br | s-Bu | nonafluoro-2-butyl | Et | CF3 |
| 30-231 | 3-bromophenyl | H | H | H | Br | F | nonafluoro-2-butyl | Me | CF3 |
| 30-232 | 4-bromophenyl | H | H | H | Br | F | nonafluoro-2-butyl | Et | CF3 |
| 30-238 | (4-trifluoromethyl)phenyl | Et | i-Pr | H | Br | Cl | nonafluoro-2-butyl | Me | CF3 |
| 30-239 | 2-nitrophenyl | H | H | H | Br | Cl | nonafluoro-2-butyl | Et | CF3 |
| 30-245 | 4-cyanophenyl | H | H | H | I | Br | heptafluoroisopropyl | Me | CF3 |
| 30-246 | 2,6-difluorophenyl | H | H | H | I | Br | heptafluoroisopropyl | Et | CF3 |
| 30-252 | 2-bromo-4-chlorophenyl | n-Pr | Me | H | I | I | heptafluoroisopropyl | Me | CF3 |
| 30-253 | 2-bromo-4-fluorophenyl | H | H | H | I | I | heptafluoroisopropyl | Et | CF3 |
| 30-259 | 2-fluoropyridin-3-yl | H | H | H | I | Me | heptafluoroisopropyl | F | C2F5 |
| 30-260 | 2-chloropyridin-3-yl | H | H | H | I | Me | nonafluoro-2-butyl | Cl | CF3 |
| 30-263 | 2-(trifluoromethyl)pyridin-3-yl | H | H | H | I | Et | nonafluoro-2-butyl | F | CF3 |
| 30-264 | 2-nitropyridin-3-yl | H | H | H | I | Et | nonafluoro-2-butyl | Cl | CF3 |
| 30-267 | 6-chloropyridin-3-yl | H | H | H | I | n-Pr | nonafluoro-2-butyl | F | CF3 |
| 30-268 | 6-bromopyridin-3-yl | H | H | H | I | n-Pr | nonafluoro-2-butyl | Cl | CF3 |
| 30-271 | 6-nitropyridin-3-yl | H | H | H | I | i-Pr | nonafluoro-2-butyl | F | i-C3F7 |
| 30-272 | 6-cyanopyridin-3-yl | H | H | H | I | i-Pr | nonafluoro-2-butyl | Cl | CF3 |
| 30-275 | 5-bromopyridin-3-yl | H | H | H | I | n-Bu | nonafluoro-2-butyl | F | CF3 |
| 30-276 | 5-iodopyridin-3-yl | H | H | H | I | n-Bu | nonafluoro-2-butyl | Cl | CF3 |
| 30-279 | 5-cyanopyridin-3-yl | H | H | H | I | i-Bu | nonafluoro-2-butyl | F | CF3 |
| 30-280 | 4-fluoropyridin-3-yl | H | H | H | I | i-Bu | nonafluoro-2-butyl | Cl | CF3 |
| 30-283 | 4-iodopyridin-3-yl | i-Pr | n-Pr | H | I | s-Bu | nonafluoro-2-butyl | F | CF3 |
| 30-284 | 4-(trifluoromethyl)pyridin-3-yl | H | H | H | I | s-Bu | nonafluoro-2-butyl | Cl | CF3 |
| 30-295 | 3-bromophenyl | H | Et | H | OCF3 | F | heptafluoroisopropyl | F | OCF3 |
| 30-325 | 2-iodopyridin-3-yl | H | H | H | OCF3 | Me | nonafluoro-2-butyl | Me | OCF3 |
| 30-438 | 3-bromophenyl | H | Et | H | OCF3 | F | heptafluoroisopropyl | F | CF3 |
| 30-468 | 2-iodopyridin-3-yl | H | H | H | OCF3 | Me | nonafluoro-2-butyl | Me | CF3 |
| 30-581 | 3-bromophenyl | H | Et | H | CF3 | F | heptafluoroisopropyl | F | CF3 |
| 30-611 | 2-iodopyridin-3-yl | H | H | H | CF3 | Me | nonafluoro-2-butyl | Me | CF3 |

TABLE 31

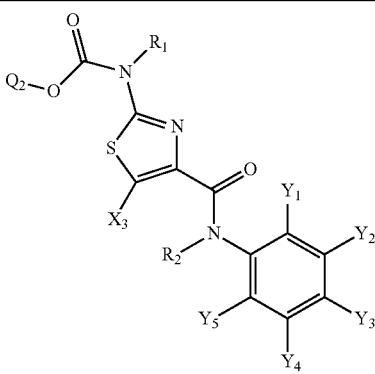

| compound number | Q₂ | R₁ | R₂ | X₃ | Y₁ | Y₂ | Y₃ | Y₄ | Y₅ |
|---|---|---|---|---|---|---|---|---|---|
| 31-1 | 2,2,2-trichloroethyl | H | H | H | F | H | heptafluoroisopropyl | H | OCF3 |
| 31-2 | 2,2,2-trichloroethyl | H | H | H | F | H | nonafluoro-2-butyl | H | OCF3 |

TABLE 31-continued

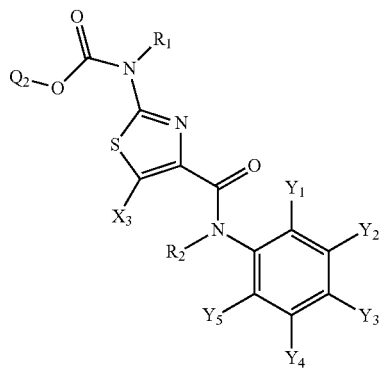

| compound number | Q₂ | R₁ | R₂ | X₃ | Y₁ | Y₂ | Y₃ | Y₄ | Y₅ |
|---|---|---|---|---|---|---|---|---|---|
| 31-9 | 2-chloroethyl | H | H | Cl | Cl | H | heptafluoroisopropyl | H | OCF3 |
| 31-13 | 2,2,2-trichloroethyl | H | H | H | Cl | H | heptafluoroisopropyl | H | OCF3 |
| 31-16 | 3-fluoro-n-propyl | H | H | H | Cl | H | pentafluoroethyl | H | OCF3 |
| 31-18 | 3-bromo-n-propyl | H | H | H | Cl | H | heptafluoroisopropyl | H | OC2F5 |
| 31-22 | 1,3-dichloro-2-propyl | H | H | H | Cl | H | pentafluoroethyl | H | OC2F5 |
| 31-26 | 4,4,4-trifluoro-n-butyl | H | H | H | Cl | H | heptafluoroisopropyl | H | OCF3 |
| 31-36 | 2-bromoethyl | H | H | H | Cl | H | nonafluoro-2-butyl | H | OC2F5 |
| 31-42 | 2,2,2-trichloroethyl | H | H | H | Cl | H | nonafluoro-2-butyl | H | OCF3 |
| 31-55 | 4,4,4-trifluoro-n-butyl | H | H | H | Cl | H | nonafluoro-2-butyl | H | OCF3 |
| 31-57 | s-butyl | H | H | H | Cl | H | nonafluoro-2-butyl | H | OC2F5 |
| 31-66 | 2-iodoethyl | H | H | H | Br | H | heptafluoroisopropyl | H | OC2F5 |
| 31-71 | 2,2,2-trichloroethyl | H | H | H | Br | H | heptafluoroisopropyl | H | OCF3 |
| 31-84 | 4,4,4-trifluoro-n-butyl | H | H | H | Br | H | heptafluoroisopropyl | H | OCF3 |
| 31-100 | 2,2,2-trichloroethyl | H | H | H | Br | H | nonafluoro-2-butyl | H | OCF3 |
| 31-102 | n-propyl | H | H | H | Br | H | nonafluoro-2-butyl | H | OC2F5 |
| 31-113 | 4,4,4-trifluoro-n-butyl | H | H | H | Br | H | nonafluoro-2-butyl | H | OCF3 |
| 31-129 | 2,2,2-trichloroethyl | H | H | H | I | H | heptafluoroisopropyl | H | OCF3 |
| 31-133 | 3-chloro-n-propyl | H | H | H | I | H | heptafluoroisopropyl | H | OC2F5 |
| 31-142 | 4,4,4-trifluoro-n-butyl | H | H | H | I | H | heptafluoroisopropyl | H | OCF3 |
| 31-158 | 2,2,2-trichloroethyl | H | H | H | I | H | nonafluoro-2-butyl | H | OCF3 |
| 31-171 | 4,4,4-trifluoro-n-butyl | H | H | H | I | H | nonafluoro-2-butyl | H | OCF3 |
| 31-175 | benzyl | H | H | H | I | H | nonafluoro-2-butyl | H | OC2F5 |
| 31-177 | 2,2,2-trichloroethyl | H | H | H | F | H | heptafluoroisopropyl | H | CF3 |
| 31-178 | 2,2,2-trichloroethyl | H | H | H | F | H | nonafluoro-2-butyl | H | CF3 |
| 31-179 | methyl | H | H | H | Cl | H | heptafluoroisopropyl | H | CF3 |
| 31-180 | ethyl | H | H | H | Cl | H | heptafluoroisopropyl | H | CF3 |
| 31-181 | 2-fluoroethyl | H | H | H | Cl | H | heptafluoroisopropyl | H | CF3 |
| 31-182 | 2-chloroethyl | H | H | H | Cl | H | heptafluoroisopropyl | H | CF3 |
| 31-183 | 2-bromoethyl | H | H | H | Cl | H | heptafluoroisopropyl | H | CF3 |
| 31-184 | 2-iodoethyl | H | H | H | Cl | H | heptafluoroisopropyl | H | CF3 |
| 31-185 | 2-cyanoethyl | H | H | H | Cl | H | heptafluoroisopropyl | H | C2F5 |
| 31-186 | 2,2-difluoroethyl | H | H | H | Cl | H | heptafluoroisopropyl | H | CF3 |
| 31-187 | 2,2-dichloroethyl | H | H | H | Cl | H | heptafluoroisopropyl | H | CF3 |
| 31-188 | 2,2,2-trifluoroethyl | H | H | H | Cl | H | heptafluoroisopropyl | H | CF3 |
| 31-189 | 2,2,2-trichloroethyl | H | H | H | Cl | H | heptafluoroisopropyl | H | CF3 |
| 31-190 | 2,2,2-tribromoethyl | H | H | H | Cl | H | heptafluoroisopropyl | H | CF3 |
| 31-191 | n-propyl | H | H | H | Cl | H | pentafluoroethyl | H | CF3 |
| 31-192 | 3-fluoro-n-propyl | H | H | H | Cl | H | heptafluoroisopropyl | H | CF3 |
| 31-193 | 3-chloro-n-propyl | H | H | H | Cl | H | heptafluoroisopropyl | H | CF3 |
| 31-194 | 3-bromo-n-propyl | H | H | H | Cl | H | heptafluoroisopropyl | H | CF3 |
| 31-195 | i-propyl | H | H | H | Cl | H | heptafluoroisopropyl | H | n-C3F7 |
| 31-196 | 1,2-difluoro-2-propyl | H | H | H | Cl | H | heptafluoroisopropyl | H | CF3 |
| 31-197 | 1,3-difluoro-2-propyl | H | H | H | Cl | H | heptafluoroisopropyl | H | CF3 |
| 31-198 | 1,3-dichloro-2-propyl | H | H | H | Cl | H | pentafluoroethyl | H | CF3 |
| 31-199 | 1-chloro-3-fluoro-2-propyl | H | H | H | Cl | H | heptafluoroisopropyl | H | CF3 |
| 31-200 | 3,3,3-trifluoro-n-propyl | H | H | H | Cl | H | heptafluoroisopropyl | H | CF3 |
| 31-201 | n-butyl | H | H | H | Cl | H | heptafluoroisopropyl | H | CF3 |
| 31-202 | 4,4,4-trifluoro-n-butyl | H | H | H | Cl | H | heptafluoroisopropyl | H | CF3 |
| 31-203 | i-butyl | H | H | Cl | Cl | H | heptafluoroisopropyl | H | CF3 |
| 31-204 | s-butyl | H | H | H | Cl | H | heptafluoroisopropyl | H | CF3 |
| 31-205 | vinyl | H | H | H | Cl | H | heptafluoroisopropyl | H | CF3 |
| 31-206 | benzyl | H | H | H | Cl | H | heptafluoroisopropyl | H | CF3 |
| 31-207 | phenyl | H | H | H | Cl | H | heptafluoroisopropyl | H | CF3 |
| 31-208 | methyl | H | H | H | Cl | H | nonafluoro-2-butyl | H | CF3 |
| 31-209 | ethyl | H | H | H | Cl | H | nonafluoro-2-butyl | H | i-C3F7 |
| 31-210 | 2-fluoroethyl | H | H | H | Cl | H | nonafluoro-2-butyl | H | CF3 |
| 31-211 | 2-chloroethyl | H | H | H | Cl | H | nonafluoro-2-butyl | H | CF3 |
| 31-212 | 2-bromoethyl | H | H | H | Cl | H | nonafluoro-2-butyl | H | CF3 |
| 31-213 | 2-iodoethyl | H | H | H | Cl | H | nonafluoro-2-butyl | H | CF3 |

TABLE 31-continued

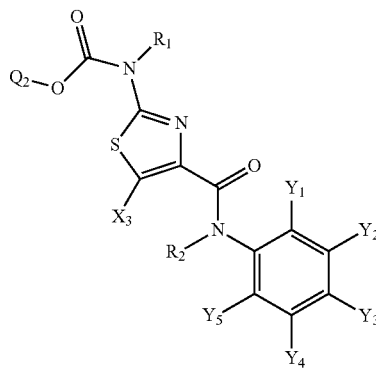

| compound number | Q₂ | R₁ | R₂ | X₃ | Y₁ | Y₂ | Y₃ | Y₄ | Y₅ |
|---|---|---|---|---|---|---|---|---|---|
| 31-214 | 2-cyanoethyl | H | H | H | Cl | H | nonafluoro-2-butyl | H | CF3 |
| 31-215 | 2,2-difluoroethyl | H | H | H | Cl | H | nonafluoro-2-butyl | H | CF3 |
| 31-216 | 2,2-dichloroethyl | H | H | H | Cl | H | nonafluoro-2-butyl | H | CF3 |
| 31-217 | 2,2,2-trifluoroethyl | H | H | H | Cl | H | nonafluoro-2-butyl | H | CF3 |
| 31-218 | 2,2,2-trichloroethyl | H | H | H | Cl | H | nonafluoro-2-butyl | H | CF3 |
| 31-219 | 2,2,2-tribromoethyl | H | H | H | Cl | H | nonafluoro-2-butyl | H | CF3 |
| 31-220 | n-propyl | H | H | H | Cl | H | nonafluoro-2-butyl | H | CF3 |
| 31-221 | 3-fluoro-n-propyl | H | H | H | Cl | H | nonafluoro-2-butyl | H | CF3 |
| 31-222 | 3-chloro-n-propyl | H | H | H | Cl | H | nonafluoro-2-butyl | H | CF3 |
| 31-223 | 3-bromo-n-propyl | H | H | H | Cl | H | nonafluoro-2-butyl | H | CF3 |
| 31-224 | i-propyl | H | H | H | Cl | H | nonafluoro-2-butyl | H | CF3 |
| 31-225 | 1,2-difluoro-2-propyl | H | H | H | Cl | H | nonafluoro-2-butyl | H | CF3 |
| 31-226 | 1,3-difluoro-2-propyl | H | H | H | Cl | H | nonafluoro-2-butyl | H | CF3 |
| 31-227 | 1,3-dichloro-2-propyl | H | H | H | Cl | H | nonafluoro-2-butyl | H | CF3 |
| 31-228 | 1-chloro-3-fluoro-2-propyl | H | H | H | Cl | H | nonafluoro-2-butyl | H | CF3 |
| 31-229 | 3,3,3-trifluoro-n-propyl | H | H | H | Cl | H | nonafluoro-2-butyl | H | CF3 |
| 31-230 | n-butyl | H | H | H | Cl | H | nonafluoro-2-butyl | H | CF3 |
| 31-231 | 4,4,4-trifluoro-n-butyl | H | H | H | Cl | H | nonafluoro-2-butyl | H | CF3 |
| 31-232 | i-butyl | H | H | H | Cl | H | nonafluoro-2-butyl | H | CF3 |
| 31-233 | s-butyl | H | H | H | Cl | H | nonafluoro-2-butyl | H | CF3 |
| 31-234 | vinyl | H | H | H | Cl | H | nonafluoro-2-butyl | H | CF3 |
| 31-235 | benzyl | H | H | H | Cl | H | nonafluoro-2-butyl | H | CF3 |
| 31-236 | phenyl | H | H | H | Cl | H | nonafluoro-2-butyl | H | CF3 |
| 31-237 | methyl | H | H | H | Br | H | heptafluoroisopropyl | H | CF3 |
| 31-238 | ethyl | H | H | H | Br | H | heptafluoroisopropyl | H | CF3 |
| 31-239 | 2-fluoroethyl | H | H | H | Br | H | heptafluoroisopropyl | H | CF3 |
| 31-240 | 2-chloroethyl | H | H | H | Br | H | heptafluoroisopropyl | H | CF3 |
| 31-241 | 2-bromoethyl | H | H | H | Br | H | heptafluoroisopropyl | H | CF3 |
| 31-242 | 2-iodoethyl | H | H | H | Br | H | heptafluoroisopropyl | H | CF3 |
| 31-243 | 2-cyanoethyl | H | H | H | Br | H | heptafluoroisopropyl | H | C2F5 |
| 31-244 | 2,2-difluoroethyl | H | H | H | Br | H | heptafluoroisopropyl | H | CF3 |
| 31-245 | 2,2-dichloroethyl | H | H | H | Br | H | heptafluoroisopropyl | H | CF3 |
| 31-246 | 2,2,2-trifluoroethyl | H | H | H | Br | H | heptafluoroisopropyl | H | CF3 |
| 31-247 | 2,2,2-trichloroethyl | H | H | H | Br | H | heptafluoroisopropyl | H | CF3 |
| 31-248 | 2,2,2-tribromoethyl | H | H | H | Br | H | heptafluoroisopropyl | H | CF3 |
| 31-249 | n-propyl | H | H | H | Br | H | heptafluoroisopropyl | H | CF3 |
| 31-250 | 3-fluoro-n-propyl | H | H | H | Br | H | heptafluoroisopropyl | H | CF3 |
| 31-251 | 3-chloro-n-propyl | H | H | H | Br | H | heptafluoroisopropyl | H | CF3 |
| 31-252 | 3-bromo-n-propyl | H | H | H | Br | H | heptafluoroisopropyl | H | CF3 |
| 31-253 | i-propyl | H | H | H | Br | H | heptafluoroisopropyl | H | CF3 |
| 31-254 | 1,2-difluoro-2-propyl | H | H | H | Br | H | heptafluoroisopropyl | H | n-C3F7 |
| 31-255 | 1,3-difluoro-2-propyl | H | H | H | Br | H | heptafluoroisopropyl | H | CF3 |
| 31-256 | 1,3-dichloro-2-propyl | H | H | H | Br | H | heptafluoroisopropyl | H | CF3 |
| 31-257 | 1-chloro-3-fluoro-2-propyl | H | H | H | Br | H | heptafluoroisopropyl | H | CF3 |
| 31-258 | 3,3,3-trifluoro-n-propyl | H | H | H | Br | H | heptafluoroisopropyl | H | CF3 |
| 31-259 | n-butyl | H | H | H | Br | H | heptafluoroisopropyl | H | CF3 |
| 31-260 | 4,4,4-trifluoro-n-butyl | H | H | H | Br | H | heptafluoroisopropyl | H | CF3 |
| 31-261 | i-butyl | H | H | H | Br | H | heptafluoroisopropyl | H | CF3 |
| 31-262 | s-butyl | H | H | H | Br | H | heptafluoroisopropyl | H | CF3 |
| 31-263 | vinyl | H | H | H | Br | H | heptafluoroisopropyl | H | CF3 |
| 31-264 | benzyl | H | H | H | Br | H | heptafluoroisopropyl | H | CF3 |
| 31-265 | phenyl | H | H | H | Br | H | heptafluoroisopropyl | H | CF3 |
| 31-266 | methyl | H | H | H | Br | H | nonafluoro-2-butyl | H | CF3 |
| 31-267 | ethyl | H | H | H | Br | H | nonafluoro-2-butyl | H | CF3 |
| 31-268 | 2-fluoroethyl | H | H | H | Br | H | nonafluoro-2-butyl | H | CF3 |
| 31-269 | 2-chloroethyl | H | H | H | Br | H | nonafluoro-2-butyl | H | CF3 |
| 31-270 | 2-bromoethyl | H | H | H | Br | H | nonafluoro-2-butyl | H | CF3 |
| 31-271 | 2-iodoethyl | H | H | H | Br | H | nonafluoro-2-butyl | H | CF3 |
| 31-272 | 2-cyanoethyl | H | H | H | Br | H | nonafluoro-2-butyl | H | CF3 |

TABLE 31-continued

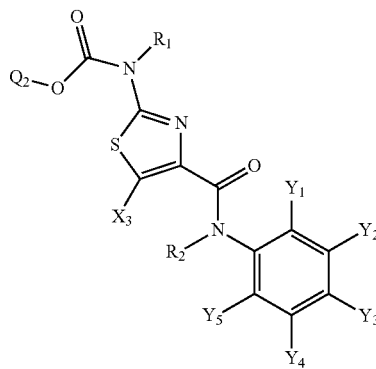

| compound number | Q2 | R1 | R2 | X3 | Y1 | Y2 | Y3 | Y4 | Y5 |
|---|---|---|---|---|---|---|---|---|---|
| 31-273 | 2,2-difluoroethyl | H | H | H | Br | H | nonafluoro-2-butyl | H | CF3 |
| 31-274 | 2,2-dichloroethyl | H | H | H | Br | H | nonafluoro-2-butyl | H | CF3 |
| 31-275 | 2,2,2-trifluoroethyl | H | H | H | Br | H | nonafluoro-2-butyl | H | CF3 |
| 31-276 | 2,2,2-trichloroethyl | H | H | H | Br | H | nonafluoro-2-butyl | H | CF3 |
| 31-277 | 2,2,2-tribromoethyl | H | H | H | Br | H | nonafluoro-2-butyl | H | CF3 |
| 31-278 | n-propyl | H | H | H | Br | H | nonafluoro-2-butyl | H | CF3 |
| 31-279 | 3-fluoro-n-propyl | H | H | H | Br | H | nonafluoro-2-butyl | H | CF3 |
| 31-280 | 3-chloro-n-propyl | H | H | H | Br | H | nonafluoro-2-butyl | H | CF3 |
| 31-281 | 3-bromo-n-propyl | H | H | H | Br | H | nonafluoro-2-butyl | H | CF3 |
| 31-282 | i-propyl | H | H | H | Br | H | nonafluoro-2-butyl | H | CF3 |
| 31-283 | 1,2-difluoro-2-propyl | H | H | H | Br | H | nonafluoro-2-butyl | H | CF3 |
| 31-284 | 1,3-difluoro-2-propyl | H | H | H | Br | H | nonafluoro-2-butyl | H | CF3 |
| 31-285 | 1,3-dichloro-2-propyl | H | H | H | Br | H | nonafluoro-2-butyl | H | CF3 |
| 31-286 | 1-chloro-3-fluoro-2-propyl | H | H | H | Br | H | nonafluoro-2-butyl | H | CF3 |
| 31-287 | 3,3,3-trifluoro-n-propyl | H | H | H | Br | H | nonafluoro-2-butyl | H | CF3 |
| 31-288 | n-butyl | H | H | H | Br | H | nonafluoro-2-butyl | H | CF3 |
| 31-289 | 4,4,4-trifluoro-n-butyl | H | H | H | Br | H | nonafluoro-2-butyl | H | CF3 |
| 31-290 | i-butyl | H | H | H | Br | H | nonafluoro-2-butyl | H | CF3 |
| 31-291 | s-butyl | H | H | H | Br | H | nonafluoro-2-butyl | H | CF3 |
| 31-292 | vinyl | H | H | H | Br | H | nonafluoro-2-butyl | H | CF3 |
| 31-293 | benzyl | H | H | H | Br | H | nonafluoro-2-butyl | H | CF3 |
| 31-294 | phenyl | H | H | H | Br | H | nonafluoro-2-butyl | H | i-C3F7 |
| 31-295 | methyl | H | H | H | I | H | heptafluoroisopropyl | H | CF3 |
| 31-296 | ethyl | H | H | H | I | H | heptafluoroisopropyl | H | CF3 |
| 31-297 | 2-fluoroethyl | H | H | H | I | H | heptafluoroisopropyl | H | CF3 |
| 31-298 | 2-chloroethyl | H | H | H | I | H | heptafluoroisopropyl | H | CF3 |
| 31-299 | 2-bromoethyl | H | H | H | I | H | heptafluoroisopropyl | H | CF3 |
| 31-300 | 2-iodoethyl | H | H | H | I | H | heptafluoroisopropyl | H | CF3 |
| 31-301 | 2-cyanoethyl | H | H | H | I | H | heptafluoroisopropyl | H | CF3 |
| 31-302 | 2,2-difluoroethyl | H | H | H | I | H | heptafluoroisopropyl | H | CF3 |
| 31-303 | 2,2-dichloroethyl | H | H | H | I | H | heptafluoroisopropyl | H | CF3 |
| 31-304 | 2,2,2-trifluoroethyl | H | H | H | I | H | heptafluoroisopropyl | H | CF3 |
| 31-305 | 2,2,2-trichloroethyl | H | H | H | I | H | heptafluoroisopropyl | H | CF3 |
| 31-306 | 2,2,2-tribromoethyl | H | H | H | I | H | heptafluoroisopropyl | H | CF3 |
| 31-307 | n-propyl | H | H | H | I | H | heptafluoroisopropyl | H | CF3 |
| 31-308 | 3-fluoro-n-propyl | H | H | H | I | H | heptafluoroisopropyl | H | CF3 |
| 31-309 | 3-chloro-n-propyl | H | H | H | I | H | heptafluoroisopropyl | H | CF3 |
| 31-310 | 3-bromo-n-propyl | H | H | H | I | H | heptafluoroisopropyl | H | C2F5 |
| 31-311 | i-propyl | H | H | H | I | H | heptafluoroisopropyl | H | CF3 |
| 31-312 | 1,2-difluoro-2-propyl | H | H | H | I | H | heptafluoroisopropyl | H | CF3 |
| 31-313 | 1,3-difluoro-2-propyl | H | H | H | I | H | heptafluoroisopropyl | H | CF3 |
| 31-314 | 1,3-dichloro-2-propyl | H | H | H | I | H | heptafluoroisopropyl | H | CF3 |
| 31-315 | 1-chloro-3-fluoro-2-propyl | H | H | H | I | H | heptafluoroisopropyl | H | CF3 |
| 31-316 | 3,3,3-trifluoro-n-propyl | H | H | H | I | H | heptafluoroisopropyl | H | CF3 |
| 31-317 | n-butyl | H | H | H | I | H | heptafluoroisopropyl | H | CF3 |
| 31-318 | 4,4,4-trifluoro-n-butyl | H | H | H | I | H | heptafluoroisopropyl | H | CF3 |
| 31-319 | i-butyl | H | H | H | I | H | heptafluoroisopropyl | H | CF3 |
| 31-320 | s-butyl | H | H | H | I | H | heptafluoroisopropyl | H | CF3 |
| 31-321 | vinyl | H | H | H | I | H | heptafluoroisopropyl | H | CF3 |
| 31-322 | benzyl | H | H | H | I | H | heptafluoroisopropyl | H | CF3 |
| 31-323 | phenyl | H | H | H | I | H | heptafluoroisopropyl | H | CF3 |
| 31-324 | methyl | H | H | H | I | H | nonafluoro-2-butyl | H | CF3 |
| 31-325 | ethyl | H | H | H | I | H | nonafluoro-2-butyl | H | CF3 |
| 31-326 | 2-fluoroethyl | H | H | H | I | H | nonafluoro-2-butyl | H | CF3 |
| 31-327 | 2-chloroethyl | H | H | H | I | H | nonafluoro-2-butyl | H | CF3 |
| 31-328 | 2-bromoethyl | H | H | H | I | H | nonafluoro-2-butyl | H | CF3 |
| 31-329 | 2-iodoethyl | H | H | H | I | H | nonafluoro-2-butyl | H | CF3 |
| 31-330 | 2-cyanoethyl | H | H | H | I | H | nonafluoro-2-butyl | H | CF3 |
| 31-331 | 2,2-difluoroethyl | H | H | H | I | H | nonafluoro-2-butyl | H | CF3 |

TABLE 31-continued

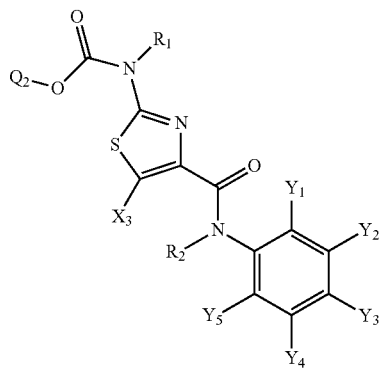

| compound number | Q₂ | R₁ | R₂ | X₃ | Y₁ | Y₂ | Y₃ | Y₄ | Y₅ |
|---|---|---|---|---|---|---|---|---|---|
| 31-332 | 2,2-dichloroethyl | H | H | H | I | H | nonafluoro-2-butyl | H | CF3 |
| 31-333 | 2,2,2-trifluoroethyl | H | H | H | I | H | nonafluoro-2-butyl | H | CF3 |
| 31-334 | 2,2,2-trichloroethyl | H | H | H | I | H | nonafluoro-2-butyl | H | CF3 |
| 31-335 | 2,2,2-tribromoethyl | H | H | H | I | H | nonafluoro-2-butyl | H | CF3 |
| 31-336 | n-propyl | H | H | H | I | H | nonafluoro-2-butyl | H | n-C3F7 |
| 31-337 | 3-fluoro-n-propyl | H | H | H | I | H | nonafluoro-2-butyl | H | CF3 |
| 31-338 | 3-chloro-n-propyl | H | H | H | I | H | nonafluoro-2-butyl | H | CF3 |
| 31-339 | 3-bromo-n-propyl | H | H | H | I | H | nonafluoro-2-butyl | H | CF3 |
| 31-340 | i-propyl | H | H | H | I | H | nonafluoro-2-butyl | H | CF3 |
| 31-341 | 1,2-difluoro-2-propyl | H | H | H | I | H | nonafluoro-2-butyl | H | CF3 |
| 31-342 | 1,3-difluoro-2-propyl | H | H | H | I | H | nonafluoro-2-butyl | H | CF3 |
| 31-343 | 1,3-dichloro-2-propyl | H | H | H | I | H | nonafluoro-2-butyl | H | CF3 |
| 31-344 | 1-chloro-3-fluoro-2-propyl | H | H | H | I | H | nonafluoro-2-butyl | H | CF3 |
| 31-345 | 3,3,3-trifluoro-n-propyl | H | H | H | I | H | nonafluoro-2-butyl | H | CF3 |
| 31-346 | n-butyl | H | H | H | I | H | nonafluoro-2-butyl | H | CF3 |
| 31-347 | 4,4,4-trifluoro-n-butyl | H | H | H | I | H | nonafluoro-2-butyl | H | CF3 |
| 31-348 | i-butyl | H | H | H | I | H | nonafluoro-2-butyl | H | CF3 |
| 31-349 | s-butyl | H | H | H | I | H | nonafluoro-2-butyl | H | CF3 |
| 31-350 | vinyl | H | H | H | I | H | nonafluoro-2-butyl | H | i-C3F7 |
| 31-351 | benzyl | H | H | H | I | H | nonafluoro-2-butyl | H | CF3 |
| 31-352 | phenyl | H | H | H | I | H | nonafluoro-2-butyl | H | CF3 |
| 31-359 | 2-cyanoethyl | H | H | H | OCF3 | H | heptafluoroisopropyl | H | OC2F5 |
| 31-363 | 2,2,2-trichloroethyl | H | H | H | OCF3 | H | heptafluoroisopropyl | H | OCF3 |
| 31-364 | 2,2,2-tribromoethyl | H | H | H | OCF3 | H | pentafluoroethyl | H | OCF3 |
| 31-373 | 1-chloro-3-fluoro-2-propyl | H | H | H | OC2F5 | H | heptafluoroisopropyl | H | OC2F5 |
| 31-376 | 4,4,4-trifluoro-n-butyl | H | H | H | OCF3 | H | heptafluoroisopropyl | H | OCF3 |
| 31-378 | s-butyl | H | H | H | OC2F5 | H | heptafluoroisopropyl | H | OCF3 |
| 31-391 | 2,2,2-trifluoroethyl | H | H | H | OC2F5 | H | nonafluoro-2-butyl | H | OCF3 |
| 31-392 | 2,2,2-trichloroethyl | H | H | H | OCF3 | H | nonafluoro-2-butyl | H | OCF3 |
| 31-394 | n-propyl | H | H | Cl | OCF3 | H | nonafluoro-2-butyl | H | OC2F5 |
| 31-403 | 3,3,3-trifluoro-n-propyl | H | H | H | OC2F5 | H | nonafluoro-2-butyl | H | OC2F5 |
| 31-405 | 4,4,4-trifluoro-n-butyl | H | H | H | OCF3 | H | nonafluoro-2-butyl | H | OCF3 |
| 31-417 | 2-cyanoethyl | H | H | H | CF3 | H | heptafluoroisopropyl | H | OC2F5 |
| 31-421 | 2,2,2-trichloroethyl | H | H | H | CF3 | H | heptafluoroisopropyl | H | OCF3 |
| 31-423 | n-propyl | H | H | H | C2F5 | H | heptafluoroisopropyl | H | OC2F5 |
| 31-427 | i-propyl | H | H | H | CF3 | H | pentafluoroethyl | H | OCF3 |
| 31-432 | 3,3,3-trifluoro-n-propyl | H | H | Cl | n-C3F7 | H | heptafluoroisopropyl | H | OCF3 |
| 31-434 | 4,4,4-trifluoro-n-butyl | H | H | H | CF3 | H | heptafluoroisopropyl | H | OCF3 |
| 31-437 | vinyl | H | H | H | i-C3F7 | H | heptafluoroisopropyl | H | OCF3 |
| 31-445 | 2-iodoethyl | H | H | H | C2F5 | H | nonafluoro-2-butyl | H | OCF3 |
| 31-450 | 2,2,2-trichloroethyl | H | H | H | CF3 | H | nonafluoro-2-butyl | H | OCF3 |
| 31-452 | n-propyl | H | H | H | n-C3F7 | H | nonafluoro-2-butyl | H | OCF3 |
| 31-456 | i-propyl | H | H | H | CF3 | H | nonafluoro-2-butyl | H | OC2F5 |
| 31-463 | 4,4,4-trifluoro-n-butyl | H | H | H | CF3 | H | nonafluoro-2-butyl | H | OCF3 |
| 31-464 | i-butyl | H | H | H | i-C3F7 | H | nonafluoro-2-butyl | H | OCF3 |
| 31-467 | benzyl | H | H | H | n-C3F7 | H | nonafluoro-2-butyl | H | OC2F5 |
| 31-468 | phenyl | H | H | H | i-C3F7 | H | nonafluoro-2-butyl | H | OC2F5 |
| 31-479 | 2,2,2-trichloroethyl | H | H | H | CF3 | H | heptafluoroisopropyl | H | CF3 |
| 31-482 | 3-fluoro-n-propyl | H | H | H | C2F5 | H | heptafluoroisopropyl | H | CF3 |
| 31-485 | i-propyl | H | H | H | i-C3F7 | H | heptafluoroisopropyl | H | CF3 |
| 31-487 | 1,3-difluoro-2-propyl | H | H | H | CF3 | H | pentafluoroethyl | H | CF3 |
| 31-490 | 3,3,3-trifluoro-n-propyl | H | H | H | C2F5 | H | heptafluoroisopropyl | H | C2F5 |
| 31-492 | 4,4,4-trifluoro-n-butyl | H | H | H | CF3 | H | heptafluoroisopropyl | H | CF3 |
| 31-493 | i-butyl | H | H | H | C2F5 | H | heptafluoroisopropyl | H | n-C3F7 |
| 31-495 | vinyl | H | H | H | n-C3F7 | H | heptafluoroisopropyl | H | CF3 |
| 31-508 | 2,2,2-trichloroethyl | H | H | H | CF3 | H | nonafluoro-2-butyl | H | CF3 |
| 31-520 | n-butyl | H | H | H | C2F5 | H | nonafluoro-2-butyl | H | i-C3F7 |

TABLE 31-continued

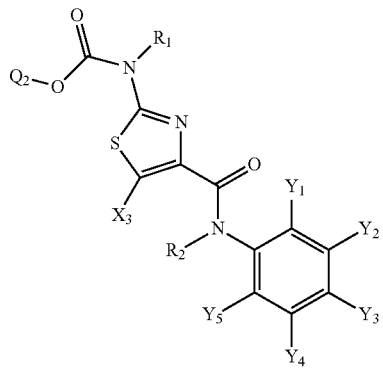

| compound number | Q₂ | R₁ | R₂ | X₃ | Y₁ | Y₂ | Y₃ | Y₄ | Y₅ |
|---|---|---|---|---|---|---|---|---|---|
| 31-521 | 4,4,4-trifluoro-n-butyl | H | H | H | CF3 | H | nonafluoro-2-butyl | H | CF3 |
| 31-522 | i-butyl | H | H | Cl | CF3 | H | nonafluoro-2-butyl | H | CF3 |
| 31-524 | vinyl | H | H | H | n-C3F7 | H | nonafluoro-2-butyl | H | i-C3F7 |

TABLE 32

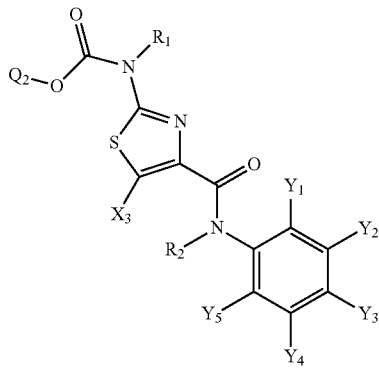

| compound number | Q₂ | R₁ | R₂ | X₃ | Y₁ | Y₂ | Y₃ | Y₄ | Y₅ |
|---|---|---|---|---|---|---|---|---|---|
| 32-1 | 2,2,2-trichloroethyl | Me | H | H | F | H | heptafluoroisopropyl | H | OCF3 |
| 32-2 | 2,2,2-trichloroethyl | Me | H | H | F | H | nonafluoro-2-butyl | H | OCF3 |
| 32-13 | 2,2,2-trichloroethyl | Me | H | H | Cl | H | heptafluoroisopropyl | H | OCF3 |
| 32-42 | 2,2,2-trichloroethyl | Me | H | H | Cl | H | nonafluoro-2-butyl | H | OCF3 |
| 32-71 | 2,2,2-trichloroethyl | Me | H | H | Br | H | heptafluoroisopropyl | H | OCF3 |
| 32-100 | 2,2,2-trichloroethyl | Me | H | H | Br | H | nonafluoro-2-butyl | H | OCF3 |
| 32-129 | 2,2,2-trichloroethyl | Me | H | H | I | H | heptafluoroisopropyl | H | OCF3 |
| 32-158 | 2,2,2-trichloroethyl | Me | H | H | I | H | nonafluoro-2-butyl | H | OCF3 |
| 32-177 | 2,2,2-trichloroethyl | Me | H | H | F | H | heptafluoroisopropyl | H | CF3 |
| 32-178 | 2,2,2-trichloroethyl | Me | H | H | F | H | nonafluoro-2-butyl | H | CF3 |
| 32-185 | 2-cyanoethyl | Et | H | H | Cl | H | heptafluoroisopropyl | H | C2F5 |
| 32-189 | 2,2,2-trichloroethyl | Me | H | H | Cl | H | heptafluoroisopropyl | H | CF3 |
| 32-191 | n-propyl | Me | H | H | Cl | H | pentafluoroethyl | H | CF3 |
| 32-195 | i-propyl | n-Pr | H | H | Cl | H | heptafluoroisopropyl | H | n-C3F7 |
| 32-198 | 1,3-dichloro-2-propyl | Me | H | H | Cl | H | pentafluoroethyl | H | CF3 |
| 32-199 | 1-chloro-3-fluoro-2-propyl | i-Pr | H | H | Cl | H | heptafluoroisopropyl | H | CF3 |
| 32-202 | 4,4,4-trifluoro-n-butyl | Me | H | H | Cl | H | heptafluoroisopropyl | H | CF3 |
| 32-203 | i-butyl | CH2CH=CH2 | H | H | Cl | H | heptafluoroisopropyl | H | CF3 |
| 32-207 | phenyl | Me | H | Cl | Cl | H | heptafluoroisopropyl | H | CF3 |
| 32-209 | ethyl | Me | H | H | Cl | H | nonafluoro-2-butyl | H | i-C3F7 |
| 32-214 | 2-cyanoethyl | CN | H | H | Cl | H | nonafluoro-2-butyl | H | CF3 |
| 32-218 | 2,2,2-trichloroethyl | Me | H | H | Cl | H | nonafluoro-2-butyl | H | CF3 |
| 32-220 | n-propyl | CH2C≡CH | H | H | Cl | H | nonafluoro-2-butyl | H | CF3 |
| 32-231 | 4,4,4-trifluoro-n-butyl | Me | H | H | Cl | H | nonafluoro-2-butyl | H | CF3 |
| 32-232 | i-butyl | NH2 | H | H | Cl | H | nonafluoro-2-butyl | H | CF3 |
| 32-243 | 2-cyanoethyl | Me | H | H | Br | H | heptafluoroisopropyl | H | C2F5 |
| 32-247 | 2,2,2-trichloroethyl | Me | H | H | Br | H | heptafluoroisopropyl | H | CF3 |
| 32-249 | n-propyl | C(O)OMe | H | H | Br | H | heptafluoroisopropyl | H | CF3 |
| 32-254 | 1,2-difluoro-2-propyl | Me | H | H | Br | H | heptafluoroisopropyl | H | n-C3F7 |

TABLE 32-continued

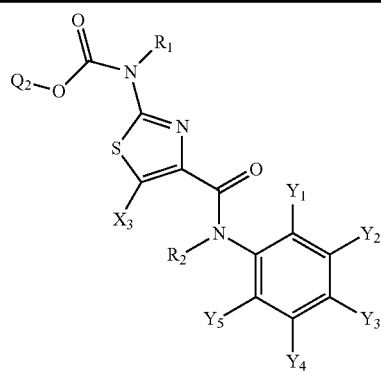

| compound number | Q₂ | R₁ | R₂ | X₃ | Y₁ | Y₂ | Y₃ | Y₄ | Y₅ |
|---|---|---|---|---|---|---|---|---|---|
| 32-260 | 4,4,4-trifluoro-n-butyl | Me | H | H | Br | H | heptafluoroisopropyl | H | CF3 |
| 32-263 | vinyl | C(O)C(O)OMe | H | H | Br | H | heptafluoroisopropyl | H | CF3 |
| 32-276 | 2,2,2-trichloroethyl | Me | H | H | Br | H | nonafluoro-2-butyl | H | CF3 |
| 32-278 | n-propyl | C(O)OEt | H | H | Br | H | nonafluoro-2-butyl | H | CF3 |
| 32-282 | i-propyl | C(O)Me | H | H | Br | H | nonafluoro-2-butyl | H | CF3 |
| 32-289 | 4,4,4-trifluoro-n-butyl | Me | H | H | Br | H | nonafluoro-2-butyl | H | CF3 |
| 32-294 | phenyl | C(O)C(O)OEt | H | H | Br | H | nonafluoro-2-butyl | H | i-C3F7 |
| 32-305 | 2,2,2-trichloroethyl | Me | H | H | I | H | heptafluoroisopropyl | H | CF3 |
| 32-310 | 3-bromo-n-propyl | C(O)Et | H | H | I | H | heptafluoroisopropyl | H | C2F5 |
| 32-318 | 4,4,4-trifluoro-n-butyl | Me | H | H | I | H | heptafluoroisopropyl | H | CF3 |
| 32-322 | benzyl | S(O)2Me | H | H | I | H | heptafluoroisopropyl | H | CF3 |
| 32-330 | 2-cyanoethyl | S(O)2Et | H | H | I | H | nonafluoro-2-butyl | H | CF3 |
| 32-334 | 2,2,2-trichloroethyl | Me | H | H | I | H | nonafluoro-2-butyl | H | CF3 |
| 32-336 | n-propyl | CH2Ph | H | H | I | H | nonafluoro-2-butyl | H | n-C3F7 |
| 32-340 | i-propyl | CH2(3-Py) | H | H | I | H | nonafluoro-2-butyl | H | CF3 |
| 32-347 | 4,4,4-trifluoro-n-butyl | Me | H | H | I | H | nonafluoro-2-butyl | H | CF3 |
| 32-349 | s-butyl | CH2(3-Py-N-oxide) | H | H | I | H | nonafluoro-2-butyl | H | CF3 |
| 32-350 | vinyl | Me | H | H | I | H | nonafluoro-2-butyl | H | i-C3F7 |
| 32-363 | 2,2,2-trichloroethyl | Me | H | H | OCF3 | H | heptafluoroisopropyl | H | OCF3 |
| 32-392 | 2,2,2-trichloroethyl | Me | H | H | OCF3 | H | nonafluoro-2-butyl | H | OCF3 |
| 32-421 | 2,2,2-trichloroethyl | Me | H | H | CF3 | H | heptafluoroisopropyl | H | OCF3 |
| 32-450 | 2,2,2-trichloroethyl | Me | H | H | CF3 | H | nonafluoro-2-butyl | H | OCF3 |
| 32-479 | 2,2,2-trichloroethyl | Me | H | H | CF3 | H | heptafluoroisopropyl | H | CF3 |
| 32-508 | 2,2,2-trichloroethyl | Me | H | H | CF3 | H | nonafluoro-2-butyl | H | CF3 |

TABLE 33

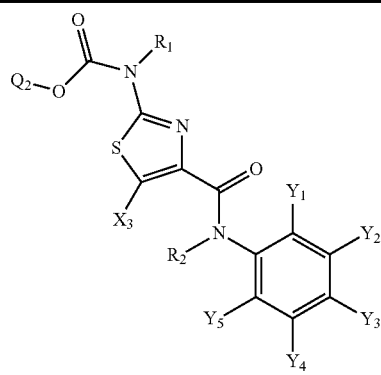

| compound number | Q₂ | R₁ | R₂ | X₃ | Y₁ | Y₂ | Y₃ | Y₄ | Y₅ |
|---|---|---|---|---|---|---|---|---|---|
| 33-1 | 2,2,2-trichloroethyl | H | Me | H | F | H | heptafluoroisopropyl | H | OCF3 |
| 33-2 | 2,2,2-trichloroethyl | H | Me | H | F | H | nonafluoro-2-butyl | H | OCF3 |
| 33-13 | 2,2,2-trichloroethyl | H | Me | H | Cl | H | heptafluoroisopropyl | H | OCF3 |
| 33-42 | 2,2,2-trichloroethyl | H | Me | H | Cl | H | nonafluoro-2-butyl | H | OCF3 |
| 33-71 | 2,2,2-trichloroethyl | H | Me | H | Br | H | heptafluoroisopropyl | H | OCF3 |
| 33-100 | 2,2,2-trichloroethyl | H | Me | H | Br | H | nonafluoro-2-butyl | H | OCF3 |
| 33-129 | 2,2,2-trichloroethyl | H | Me | H | I | H | heptafluoroisopropyl | H | OCF3 |

TABLE 33-continued

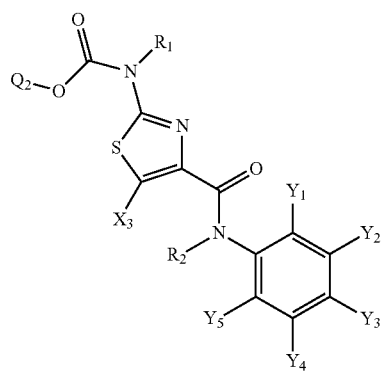

| compound number | Q2 | R1 | R2 | X3 | Y1 | Y2 | Y3 | Y4 | Y5 |
|---|---|---|---|---|---|---|---|---|---|
| 33-158 | 2,2,2-trichloroethyl | H | Me | H | I | H | nonafluoro-2-butyl | H | OCF3 |
| 33-177 | 2,2,2-trichloroethyl | H | Me | H | F | H | heptafluoroisopropyl | H | CF3 |
| 33-178 | 2,2,2-trichloroethyl | H | Me | H | F | H | nonafluoro-2-butyl | H | CF3 |
| 33-185 | 2-cyanoethyl | H | Et | H | Cl | H | heptafluoroisopropyl | H | C2F5 |
| 33-189 | 2,2,2-trichloroethyl | H | Me | H | Cl | H | heptafluoroisopropyl | H | CF3 |
| 33-191 | n-propyl | H | Me | H | Cl | H | pentafluoroethyl | H | CF3 |
| 33-195 | i-propyl | H | n-Pr | H | Cl | H | heptafluoroisopropyl | H | n-C3F7 |
| 33-198 | 1,3-dichloro-2-propyl | H | Me | H | Cl | H | pentafluoroethyl | H | CF3 |
| 33-199 | 1-chloro-3-fluoro-2-propyl | H | i-Pr | H | Cl | H | heptafluoroisopropyl | H | CF3 |
| 33-203 | i-butyl | H | CH2CH=CH2 | H | Cl | H | heptafluoroisopropyl | H | CF3 |
| 33-207 | phenyl | H | Me | Cl | Cl | H | heptafluoroisopropyl | H | CF3 |
| 33-209 | ethyl | H | Me | H | Cl | H | nonafluoro-2-butyl | H | i-C3F7 |
| 33-214 | 2-cyanoethyl | H | CN | H | Cl | H | nonafluoro-2-butyl | H | CF3 |
| 33-218 | 2,2,2-trichloroethyl | H | Me | H | Cl | H | nonafluoro-2-butyl | H | CF3 |
| 33-220 | n-propyl | H | CH2C≡CH | H | Cl | H | nonafluoro-2-butyl | H | CF3 |
| 33-232 | i-butyl | H | NH2 | H | Cl | H | nonafluoro-2-butyl | H | CF3 |
| 33-243 | 2-cyanoethyl | H | Me | H | Br | H | heptafluoroisopropyl | H | C2F5 |
| 33-247 | 2,2,2-trichloroethyl | H | Me | H | Br | H | heptafluoroisopropyl | H | CF3 |
| 33-249 | n-propyl | H | C(O)OMe | H | Br | H | heptafluoroisopropyl | H | CF3 |
| 33-254 | 1,2-difluoro-2-propyl | H | Me | H | Br | H | heptafluoroisopropyl | H | n-C3F7 |
| 33-260 | 4,4,4-trifluoro-n-butyl | H | Me | H | Br | H | heptafluoroisopropyl | H | CF3 |
| 33-263 | vinyl | H | C(O)C(O)OMe | H | Br | H | heptafluoroisopropyl | H | CF3 |
| 33-276 | 2,2,2-trichloroethyl | H | Me | H | Br | H | nonafluoro-2-butyl | H | CF3 |
| 33-278 | n-propyl | H | C(O)OEt | H | Br | H | nonafluoro-2-butyl | H | CF3 |
| 33-282 | i-propyl | H | C(O)Me | H | Br | H | nonafluoro-2-butyl | H | CF3 |
| 33-289 | 4,4,4-trifluoro-n-butyl | H | Me | H | Br | H | nonafluoro-2-butyl | H | CF3 |
| 33-294 | phenyl | H | C(O)C(O)OEt | H | Br | H | nonafluoro-2-butyl | H | i-C3F7 |
| 33-305 | 2,2,2-trichloroethyl | H | Me | H | I | H | heptafluoroisopropyl | H | CF3 |
| 33-310 | 3-bromo-n-propyl | H | C(O)Et | H | I | H | heptafluoroisopropyl | H | C2F5 |
| 33-318 | 4,4,4-trifluoro-n-butyl | H | Me | H | I | H | heptafluoroisopropyl | H | CF3 |
| 33-322 | benzyl | H | S(O)2Me | H | I | H | heptafluoroisopropyl | H | CF3 |
| 33-330 | 2-cyanoethyl | H | S(O)2Et | H | I | H | nonafluoro-2-butyl | H | CF3 |
| 33-334 | 2,2,2-trichloroethyl | H | Me | H | I | H | nonafluoro-2-butyl | H | CF3 |
| 33-336 | n-propyl | H | CH2Ph | H | I | H | nonafluoro-2-butyl | H | n-C3F7 |
| 33-340 | i-propyl | H | CH2(3-Py) | H | I | H | nonafluoro-2-butyl | H | CF3 |
| 33-347 | 4,4,4-trifluoro-n-butyl | H | Me | H | I | H | nonafluoro-2-butyl | H | CF3 |
| 33-349 | s-butyl | H | CH2(3-Py-N-oxide) | H | I | H | nonafluoro-2-butyl | H | CF3 |
| 33-350 | vinyl | H | Me | H | I | H | nonafluoro-2-butyl | H | i-C3F7 |
| 33-363 | 2,2,2-trichloroethyl | H | Me | H | OCF3 | H | heptafluoroisopropyl | H | OCF3 |
| 33-392 | 2,2,2-trichloroethyl | H | Me | H | OCF3 | H | nonafluoro-2-butyl | H | OCF3 |
| 33-421 | 2,2,2-trichloroethyl | H | Me | H | CF3 | H | heptafluoroisopropyl | H | OCF3 |
| 33-450 | 2,2,2-trichloroethyl | H | Me | H | CF3 | H | nonafluoro-2-butyl | H | OCF3 |
| 33-479 | 2,2,2-trichloroethyl | H | Me | H | CF3 | H | heptafluoroisopropyl | H | CF3 |
| 33-508 | 2,2,2-trichloroethyl | H | Me | H | CF3 | H | nonafluoro-2-butyl | H | CF3 |

TABLE 34

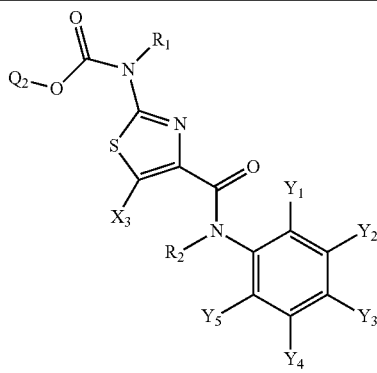

| compound number | Q2 | R1 | R2 | X3 | Y1 | Y2 | Y3 | Y4 | Y5 |
|---|---|---|---|---|---|---|---|---|---|
| 34-1 | 2,2,2-trichloroethyl | Me | Me | H | F | H | heptafluoroisopropyl | H | OCF3 |
| 34-2 | 2,2,2-trichloroethyl | Me | Me | H | F | H | nonafluoro-2-butyl | H | OCF3 |
| 34-13 | 2,2,2-trichloroethyl | Me | Me | H | Cl | H | heptafluoroisopropyl | H | OCF3 |
| 34-42 | 2,2,2-trichloroethyl | Me | Me | H | Cl | H | nonafluoro-2-butyl | H | OCF3 |
| 34-71 | 2,2,2-trichloroethyl | Me | Me | H | Br | H | heptafluoroisopropyl | H | OCF3 |
| 34-100 | 2,2,2-trichloroethyl | Me | Me | H | Br | H | nonafluoro-2-butyl | H | OCF3 |
| 34-129 | 2,2,2-trichloroethyl | Me | Me | H | I | H | heptafluoroisopropyl | H | OCF3 |
| 34-158 | 2,2,2-trichloroethyl | Me | Me | H | I | H | nonafluoro-2-butyl | H | OCF3 |
| 34-373 | 2,2,2-trichloroethyl | Me | Me | H | F | H | heptafluoroisopropyl | H | CF3 |
| 34-374 | 2,2,2-trichloroethyl | Me | Me | H | F | H | nonafluoro-2-butyl | H | CF3 |
| 34-380 | 2-iodoethyl | Me | Et | H | Cl | H | heptafluoroisopropyl | H | CF3 |
| 34-381 | 2-cyanoethyl | Et | Me | H | Cl | H | heptafluoroisopropyl | H | C2F5 |
| 34-385 | 2,2,2-trichloroethyl | Me | Me | H | Cl | H | heptafluoroisopropyl | H | CF3 |
| 34-387 | n-propyl | Me | n-Pr | H | Cl | H | pentafluoroethyl | H | CF3 |
| 34-391 | i-propyl | n-Pr | Me | H | Cl | H | heptafluoroisopropyl | H | n-C3F7 |
| 34-394 | 1,3-dichloro-2-propyl | Me | Me | H | Cl | H | pentafluoroethyl | H | CF3 |
| 34-395 | 1-chloro-3-fluoro-2-propyl | i-Pr | Me | H | Cl | H | heptafluoroisopropyl | H | CF3 |
| 34-397 | n-butyl | Me | i-Pr | H | Cl | H | heptafluoroisopropyl | H | CF3 |
| 34-399 | i-butyl | CH2CH=CH2 | Me | H | Cl | H | heptafluoroisopropyl | H | CF3 |
| 34-400 | s-butyl | Me | CH2CH=CH2 | H | Cl | H | heptafluoroisopropyl | H | CF3 |
| 34-401 | vinyl | Me | CN | H | Cl | H | heptafluoroisopropyl | H | CF3 |
| 34-405 | ethyl | Me | Me | H | Cl | H | nonafluoro-2-butyl | H | i-C3F7 |
| 34-410 | 2-cyanoethyl | CN | Me | H | Cl | H | nonafluoro-2-butyl | H | CF3 |
| 34-414 | 2,2,2-trichloroethyl | Me | Me | H | Cl | H | nonafluoro-2-butyl | H | CF3 |
| 34-415 | 2,2,2-tribromoethyl | Me | CH2C≡CH | H | Cl | H | nonafluoro-2-butyl | H | CF3 |
| 34-416 | n-propyl | CH2C≡CH | Me | H | Cl | H | nonafluoro-2-butyl | H | CF3 |
| 34-420 | i-propyl | Me | Me | Cl | Cl | H | nonafluoro-2-butyl | H | CF3 |
| 34-426 | n-butyl | Me | NH2 | H | Cl | H | nonafluoro-2-butyl | H | CF3 |
| 34-428 | i-butyl | NH2 | Me | H | Cl | H | nonafluoro-2-butyl | H | CF3 |
| 34-439 | 2-cyanoethyl | Me | C(O)OMe | H | Br | H | heptafluoroisopropyl | H | C2F5 |
| 34-443 | 2,2,2-trichloroethyl | Me | Me | H | Br | H | heptafluoroisopropyl | H | CF3 |
| 34-445 | n-propyl | C(O)OMe | Me | H | Br | H | heptafluoroisopropyl | H | CF3 |
| 34-450 | 1,2-difluoro-2-propyl | Me | Me | H | Br | H | heptafluoroisopropyl | H | n-C3F7 |
| 34-456 | 4,4,4-trifluoro-n-butyl | Me | Me | H | Br | H | heptafluoroisopropyl | H | CF3 |
| 34-457 | i-butyl | Me | C(O)C(O)OMe | H | Br | H | heptafluoroisopropyl | H | CF3 |
| 34-459 | vinyl | C(O)C(O)OMe | Me | H | Br | H | heptafluoroisopropyl | H | CF3 |
| 34-468 | 2-cyanoethyl | Me | C(O)OEt | H | Br | H | nonafluoro-2-butyl | H | CF3 |
| 34-472 | 2,2,2-trichloroethyl | Me | Me | H | Br | H | nonafluoro-2-butyl | H | CF3 |
| 34-474 | n-propyl | C(O)OEt | Me | H | Br | H | nonafluoro-2-butyl | H | CF3 |
| 34-477 | 3-bromo-n-propyl | Me | C(O)Me | H | Br | H | nonafluoro-2-butyl | H | CF3 |
| 34-478 | i-propyl | C(O)Me | Me | H | Br | H | nonafluoro-2-butyl | H | CF3 |
| 34-485 | 4,4,4-trifluoro-n-butyl | Me | Me | H | Br | H | nonafluoro-2-butyl | H | CF3 |
| 34-486 | i-butyl | Me | C(O)C(O)OEt | H | Br | H | nonafluoro-2-butyl | H | CF3 |
| 34-490 | phenyl | C(O)C(O)OEt | Me | H | Br | H | nonafluoro-2-butyl | H | i-C3F7 |
| 34-501 | 2,2,2-chloroethyl | Me | Me | H | I | H | heptafluoroisopropyl | H | CF3 |
| 34-503 | n-propyl | Me | C(O)Et | H | I | H | heptafluoroisopropyl | H | CF3 |
| 34-506 | 3-bromo-n-propyl | C(O)Et | Me | H | I | H | heptafluoroisopropyl | H | C2F5 |
| 34-514 | 4,4,4-trifluoro-n-butyl | Me | Me | H | I | H | heptafluoroisopropyl | H | CF3 |
| 34-515 | i-butyl | Me | S(O)2Me | H | I | H | heptafluoroisopropyl | H | CF3 |
| 34-518 | benzyl | S(O)2Me | Me | H | I | H | heptafluoroisopropyl | H | CF3 |
| 34-525 | 2-iodoethyl | Me | S(O)2Et | H | I | H | nonafluoro-2-butyl | H | CF3 |
| 34-526 | 2-cyanoethyl | S(O)2Et | Me | H | I | H | nonafluoro-2-butyl | H | CF3 |
| 34-530 | 2,2,2-trichloroethyl | Me | Me | H | I | H | nonafluoro-2-butyl | H | CF3 |
| 34-531 | 2,2,2-tribromoethyl | Me | CH2Ph | H | I | H | nonafluoro-2-butyl | H | CF3 |
| 34-532 | n-propyl | CH2Ph | Me | H | I | H | nonafluoro-2-butyl | H | n-C3F7 |
| 34-536 | i-propyl | CH2(3-Py) | Me | H | I | H | nonafluoro-2-butyl | H | CF3 |
| 34-542 | n-butyl | Me | CH2(3-Py) | H | I | H | nonafluoro-2-butyl | H | CF3 |
| 34-543 | 4,4,4-trifluoro-n-butyl | Me | Me | H | I | H | nonafluoro-2-butyl | H | CF3 |
| 34-545 | s-butyl | CH2(3-Py-N- | Me | H | I | H | nonafluoro-2-butyl | H | CF3 |

TABLE 34-continued

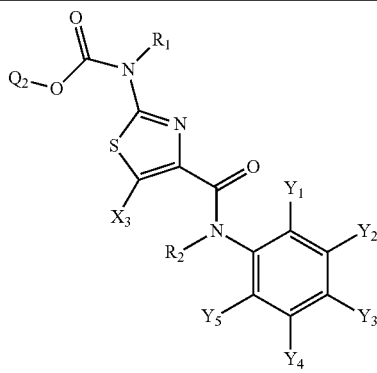

| compound number | Q₂ | R₁ | R₂ | X₃ | Y₁ | Y₂ | Y₃ | Y₄ | Y₅ |
|---|---|---|---|---|---|---|---|---|---|
| 34-546 | vinyl | Me | Me | H | I | H | nonafluoro-2-butyl | H | i-C3F7 |
| 34-548 | phenyl | Me | CH2(3-Py-N-oxide) | H | I | H | nonafluoro-2-butyl | H | CF3 |
| 34-755 | 2,2,2-trichloroethyl | Me | Me | H | OCF3 | H | heptafluoroisopropyl | H | OCF3 |
| 34-784 | 2,2,2-trichloroethyl | Me | Me | H | OCF3 | H | nonafluoro-2-butyl | H | OCF3 |
| 34-813 | 2,2,2-trichloroethyl | Me | Me | H | CF3 | H | heptafluoroisopropyl | H | OCF3 |
| 34-842 | 2,2,2-trichloroethyl | Me | Me | H | CF3 | H | nonafluoro-2-butyl | H | OCF3 |
| 34-871 | 2,2,2-trichloroethyl | Me | Me | H | CF3 | H | heptafluoroisopropyl | H | CF3 |
| 34-900 | 2,2,2-trichloroethyl | Me | Me | H | CF3 | H | nonafluoro-2-butyl | H | CF3 |

TABLE 35

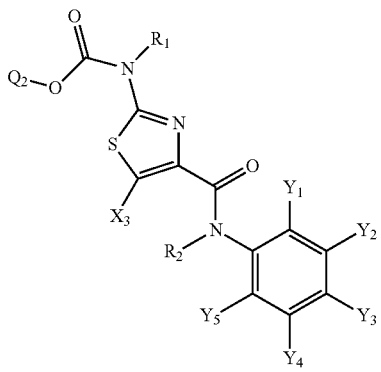

| compound number | Q₂ | R₁ | R₂ | X₃ | Y₁ | Y₂ | Y₃ | Y₄ | Y₅ |
|---|---|---|---|---|---|---|---|---|---|
| 35-9 | 2,2-dichloroethyl | H | Et | H | Cl | F | heptafluoroisopropyl | F | OCF3 |
| 35-39 | 2,2,2-trifluoroethyl | H | H | H | Cl | Me | nonafluoro-2-butyl | Me | OCF3 |
| 35-154 | 2,2,2-trichloroethyl | H | H | H | Cl | F | heptafluoroisopropyl | Br | CF3 |
| 35-183 | 2,2,2-trichloroethyl | H | H | H | Cl | Me | nonafluoro-2-butyl | Et | i-C3F7 |
| 35-189 | i-propyl | H | H | Cl | Cl | Et | nonafluoro-2-butyl | Me | n-C3F7 |
| 35-190 | 1,2-difluoro-2-propyl | H | H | H | Cl | Et | nonafluoro-2-butyl | Et | i-C3F7 |
| 35-196 | 2-chloroethyl | H | H | H | Br | n-Pr | heptafluoroisopropyl | Me | CF3 |
| 35-197 | 2-bromoethyl | H | H | H | Br | n-Pr | heptafluoroisopropyl | Et | CF3 |
| 35-203 | 2,2,2-trichloroethyl | H | H | H | Br | i-Pr | heptafluoroisopropyl | Me | CF3 |
| 35-204 | 2,2,2-tribromoethyl | H | H | H | Br | i-Pr | heptafluoroisopropyl | Et | CF3 |
| 35-210 | 1,2-difluoro-2-propyl | H | H | H | Br | n-Bu | heptafluoroisopropyl | Me | CF3 |
| 35-211 | 1,3-difluoro-2-propyl | H | H | H | Br | n-Bu | heptafluoroisopropyl | Et | CF3 |
| 35-217 | i-butyl | H | H | H | Br | i-Bu | nonafluoro-2-butyl | Me | CF3 |
| 35-218 | s-butyl | H | H | H | Br | i-Bu | nonafluoro-2-butyl | Et | CF3 |
| 35-224 | 2-fluoroethyl | H | H | H | Br | s-Bu | nonafluoro-2-butyl | Me | CF3 |
| 35-225 | 2-chloroethyl | H | H | H | Br | s-Bu | nonafluoro-2-butyl | Et | CF3 |
| 35-231 | 2,2,2-trifluoroethyl | H | H | H | Br | F | nonafluoro-2-butyl | Me | CF3 |
| 35-232 | 2,2,2-trichloroethyl | H | H | H | Br | F | nonafluoro-2-butyl | Et | CF3 |
| 35-238 | i-propyl | Et | i-Pr | H | Br | Cl | nonafluoro-2-butyl | Me | CF3 |
| 35-239 | 1,2-difluoro-2-propyl | H | H | H | Br | Cl | nonafluoro-2-butyl | Et | CF3 |
| 35-245 | 2-iodoethyl | H | H | H | I | Br | heptafluoroisopropyl | Me | CF3 |
| 35-246 | 2-cyanoethyl | H | H | H | I | Br | heptafluoroisopropyl | Et | CF3 |

TABLE 35-continued

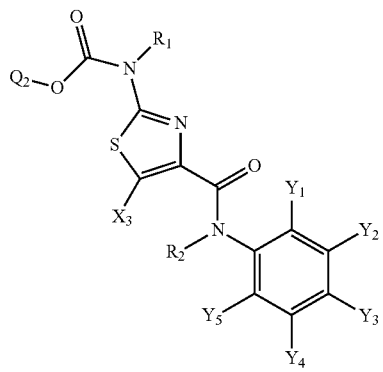

| compound number | $Q_2$ | $R_1$ | $R_2$ | $X_3$ | $Y_1$ | $Y_2$ | $Y_3$ | $Y_4$ | $Y_5$ |
|---|---|---|---|---|---|---|---|---|---|
| 35-252 | n-propyl | n-Pr | Me | H | I | I | heptafluoroisopropyl | Me | CF3 |
| 35-253 | 3-fluoro-n-propyl | H | H | H | I | I | heptafluoroisopropyl | Et | CF3 |
| 35-259 | 1,3-dichloro-2-propyl | H | H | H | I | Me | heptafluoroisopropyl | F | C2F5 |
| 35-260 | 1-chloro-3-fluoro-2-propyl | H | H | H | I | Me | nonafluoro-2-butyl | Cl | CF3 |
| 35-261 | 3,3,3-trifluoro-n-propyl | H | H | H | I | Me | nonafluoro-2-butyl | Br | n-C3F7 |
| 35-262 | n-butyl | H | H | H | I | Me | nonafluoro-2-butyl | I | i-C3F7 |
| 35-263 | 4,4,4-trifluoro-n-butyl | H | H | H | I | Et | nonafluoro-2-butyl | F | CF3 |
| 35-264 | i-butyl | H | H | H | I | Et | nonafluoro-2-butyl | Cl | CF3 |
| 35-265 | s-butyl | H | H | H | I | Et | nonafluoro-2-butyl | Br | CF3 |
| 35-266 | vinyl | n-Pr | i-Pr | H | I | Et | nonafluoro-2-butyl | I | C2F5 |
| 35-267 | benzyl | H | H | H | I | n-Pr | nonafluoro-2-butyl | F | CF3 |
| 35-268 | phenyl | H | H | H | I | n-Pr | nonafluoro-2-butyl | Cl | CF3 |
| 35-271 | 2-fluoroethyl | H | H | H | I | i-Pr | nonafluoro-2-butyl | F | i-C3F7 |
| 35-272 | 2-chloroethyl | H | H | H | I | i-Pr | nonafluoro-2-butyl | Cl | CF3 |
| 35-273 | 2-bromoethyl | n-Pr | C(O)Me | H | I | i-Pr | nonafluoro-2-butyl | Br | CF3 |
| 35-274 | 2-iodoethyl | H | H | H | I | i-Pr | nonafluoro-2-butyl | I | CF3 |
| 35-275 | 2-cyanoethyl | H | H | H | I | n-Bu | nonafluoro-2-butyl | F | CF3 |
| 35-276 | 2,2-difluoroethyl | H | H | H | I | n-Bu | nonafluoro-2-butyl | Cl | CF3 |
| 35-279 | 2,2,2-trichloroethyl | H | H | H | I | i-Bu | nonafluoro-2-butyl | F | CF3 |
| 35-280 | 2,2,2-tribromoethyl | H | H | H | I | i-Bu | nonafluoro-2-butyl | Cl | CF3 |
| 35-283 | 3-chloro-n-propyl | i-Pr | n-Pr | H | I | s-Bu | nonafluoro-2-butyl | F | CF3 |
| 35-284 | 3-bromo-n-propyl | H | H | H | I | s-Bu | nonafluoro-2-butyl | Cl | CF3 |
| 35-301 | 3-chloro-n-propyl | n-Pr | H | H | OCF3 | Cl | heptafluoroisopropyl | Br | OCF3 |
| 35-454 | i-butyl | H | H | H | OCF3 | Me | nonafluoro-2-butyl | H | CF3 |
| 35-582 | 2,2,2-trifluoroethyl | H | H | H | CF3 | F | heptafluoroisopropyl | Cl | CF3 |

TABLE 36

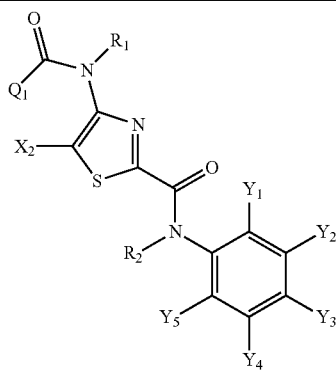

| compound number | $Q_1$ | $R_1$ | $R_2$ | $X_2$ | $Y_1$ | $Y_2$ | $Y_3$ | $Y_4$ | $Y_5$ |
|---|---|---|---|---|---|---|---|---|---|
| 36-1 | phenyl | H | H | H | Cl | H | heptafluoroisopropyl | H | OCF3 |
| 36-2 | phenyl | H | H | H | Br | H | heptafluoroisopropyl | H | CF3 |
| 36-3 | phenyl | H | H | Cl | Br | H | heptafluoroisopropyl | H | CF3 |
| 36-4 | phenyl | H | H | H | CF3 | H | heptafluoroisopropyl | H | CF3 |
| 36-5 | phenyl | H | H | H | I | H | nonafluoro-2-butyl | H | OCF3 |
| 36-6 | phenyl | H | H | H | Cl | H | nonafluoro-2-butyl | H | CF3 |
| 36-7 | phenyl | H | H | H | CF3 | H | nonafluoro-2-butyl | H | CF3 |

TABLE 36-continued

| compound number | $Q_1$ | $R_1$ | $R_2$ | $X_2$ | $Y_1$ | $Y_2$ | $Y_3$ | $Y_4$ | $Y_5$ |
|---|---|---|---|---|---|---|---|---|---|
| 36-8 | phenyl | Me | H | H | Cl | H | heptafluoroisopropyl | H | OCF3 |
| 36-9 | phenyl | Me | H | H | Br | H | heptafluoroisopropyl | H | CF3 |
| 36-10 | phenyl | Me | H | H | CF3 | H | heptafluoroisopropyl | H | CF3 |
| 36-11 | phenyl | Me | H | H | I | H | nonafluoro-2-butyl | H | OCF3 |
| 36-12 | phenyl | Me | H | H | Cl | H | nonafluoro-2-butyl | H | CF3 |
| 36-13 | phenyl | Me | H | H | CF3 | H | nonafluoro-2-butyl | H | CF3 |
| 36-14 | phenyl | H | Me | H | Cl | H | heptafluoroisopropyl | H | OCF3 |
| 36-15 | phenyl | H | Me | H | Br | H | heptafluoroisopropyl | H | CF3 |
| 36-16 | phenyl | H | Me | H | CF3 | H | heptafluoroisopropyl | H | CF3 |
| 36-17 | phenyl | H | Me | H | I | H | nonafluoro-2-butyl | H | OCF3 |
| 36-18 | phenyl | H | Me | H | Cl | H | nonafluoro-2-butyl | H | CF3 |
| 36-19 | phenyl | H | Me | H | CF3 | H | nonafluoro-2-butyl | H | CF3 |
| 36-20 | phenyl | Me | Me | H | Cl | H | heptafluoroisopropyl | H | OCF3 |
| 36-21 | phenyl | Me | Me | H | Br | H | heptafluoroisopropyl | H | CF3 |
| 36-22 | phenyl | Me | Me | H | CF3 | H | heptafluoroisopropyl | H | CF3 |
| 36-23 | phenyl | Me | Me | H | I | H | nonafluoro-2-butyl | H | OCF3 |
| 36-24 | phenyl | Me | Me | H | Cl | H | nonafluoro-2-butyl | H | CF3 |
| 36-25 | phenyl | Me | Me | H | CF3 | H | nonafluoro-2-butyl | H | CF3 |
| 36-26 | phenyl | H | H | H | Cl | F | heptafluoroisopropyl | H | OCF3 |
| 36-27 | phenyl | Me | H | H | Br | H | heptafluoroisopropyl | F | CF3 |
| 36-28 | phenyl | H | Me | H | CF3 | Cl | heptafluoroisopropyl | H | CF3 |
| 36-29 | phenyl | H | H | H | I | H | nonafluoro-2-butyl | Cl | OCF3 |
| 36-30 | phenyl | H | H | H | Cl | Br | nonafluoro-2-butyl | H | CF3 |
| 36-31 | phenyl | H | H | H | Br | H | nonafluoro-2-butyl | I | CF3 |
| 36-32 | phenyl | H | H | H | I | Me | nonafluoro-2-butyl | H | CF3 |
| 36-33 | phenyl | H | H | H | CF3 | H | nonafluoro-2-butyl | Et | CF3 |

TABLE 37

| compound number | $Q_1$ | $R_1$ | $R_2$ | $X_3$ | $Y_1$ | $Y_2$ | $Y_3$ | $Y_4$ | $Y_5$ |
|---|---|---|---|---|---|---|---|---|---|
| 37-1 | phenyl | H | H | H | Br | H | heptafluoroisopropyl | H | OCF3 |
| 37-2 | phenyl | H | H | H | I | H | heptafluoroisopropyl | H | CF3 |
| 37-3 | phenyl | H | H | Cl | I | H | heptafluoroisopropyl | H | CF3 |
| 37-4 | phenyl | H | H | H | CF3 | H | heptafluoroisopropyl | H | CF3 |
| 37-5 | phenyl | H | H | H | Cl | H | nonafluoro-2-butyl | H | OCF3 |
| 37-6 | phenyl | H | H | H | Br | H | nonafluoro-2-butyl | H | CF3 |

TABLE 37-continued

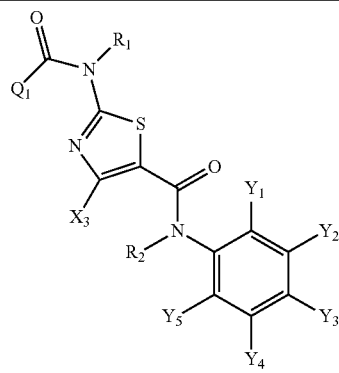

| compound number | Q₁ | R₁ | R₂ | X₃ | Y₁ | Y₂ | Y₃ | Y₄ | Y₅ |
|---|---|---|---|---|---|---|---|---|---|
| 37-7 | phenyl | H | H | H | CF3 | H | nonafluoro-2-butyl | H | CF3 |
| 37-8 | phenyl | Me | H | H | Br | H | heptafluoroisopropyl | H | OCF3 |
| 37-9 | phenyl | Me | H | H | I | H | heptafluoroisopropyl | H | CF3 |
| 37-10 | phenyl | Me | H | H | CF3 | H | heptafluoroisopropyl | H | CF3 |
| 37-11 | phenyl | Me | H | H | Cl | H | nonafluoro-2-butyl | H | OCF3 |
| 37-12 | phenyl | Me | H | H | Br | H | nonafluoro-2-butyl | H | CF3 |
| 37-13 | phenyl | Me | H | H | CF3 | H | nonafluoro-2-butyl | H | CF3 |
| 37-14 | phenyl | H | Me | H | Br | H | heptafluoroisopropyl | H | OCF3 |
| 37-15 | phenyl | H | Me | H | I | H | heptafluoroisopropyl | H | CF3 |
| 37-16 | phenyl | H | Me | H | CF3 | H | heptafluoroisopropyl | H | CF3 |
| 37-17 | phenyl | H | Me | H | Cl | H | nonafluoro-2-butyl | H | OCF3 |
| 37-18 | phenyl | H | Me | H | Br | H | nonafluoro-2-butyl | H | CF3 |
| 37-19 | phenyl | H | Me | H | CF3 | H | nonafluoro-2-butyl | H | CF3 |
| 37-20 | phenyl | Me | Me | H | Br | H | heptafluoroisopropyl | H | OCF3 |
| 37-21 | phenyl | Me | Me | H | I | H | heptafluoroisopropyl | H | CF3 |
| 37-22 | phenyl | Me | Me | H | CF3 | H | heptafluoroisopropyl | H | CF3 |
| 37-23 | phenyl | Me | Me | H | Cl | H | nonafluoro-2-butyl | H | OCF3 |
| 37-24 | phenyl | Me | Me | H | Br | H | nonafluoro-2-butyl | H | CF3 |
| 37-25 | phenyl | Me | Me | H | CF3 | H | nonafluoro-2-butyl | H | CF3 |
| 37-26 | phenyl | Me | H | H | Br | F | heptafluoroisopropyl | H | OCF3 |
| 37-27 | phenyl | H | H | H | I | H | heptafluoroisopropyl | F | CF3 |
| 37-28 | phenyl | H | Me | H | CF3 | Cl | heptafluoroisopropyl | H | CF3 |
| 37-29 | phenyl | H | H | H | Cl | H | nonafluoro-2-butyl | Cl | OCF3 |
| 37-30 | phenyl | H | H | H | Br | Br | nonafluoro-2-butyl | H | CF3 |
| 37-31 | phenyl | H | H | H | I | H | nonafluoro-2-butyl | I | CF3 |
| 37-32 | phenyl | H | H | H | Cl | Me | nonafluoro-2-butyl | H | CF3 |
| 37-33 | phenyl | H | H | H | CF3 | H | nonafluoro-2-butyl | Et | CF3 |

TABLE 38

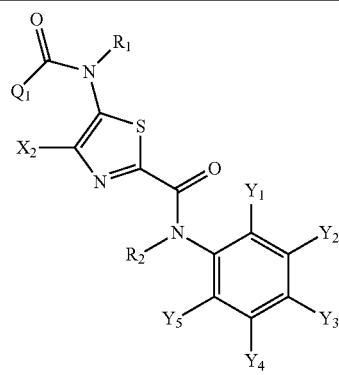

| compound number | Q₁ | R₁ | R₂ | X₂ | Y₁ | Y₂ | Y₃ | Y₄ | Y₅ |
|---|---|---|---|---|---|---|---|---|---|
| 38-1 | phenyl | H | H | H | I | H | heptafluoroisopropyl | H | OCF3 |
| 38-2 | phenyl | H | H | H | Cl | H | heptafluoroisopropyl | H | CF3 |
| 38-3 | phenyl | H | H | Cl | Cl | H | heptafluoroisopropyl | H | CF3 |
| 38-4 | phenyl | H | H | H | CF3 | H | heptafluoroisopropyl | H | CF3 |
| 38-5 | phenyl | H | H | H | Br | H | nonafluoro-2-butyl | H | OCF3 |

TABLE 38-continued

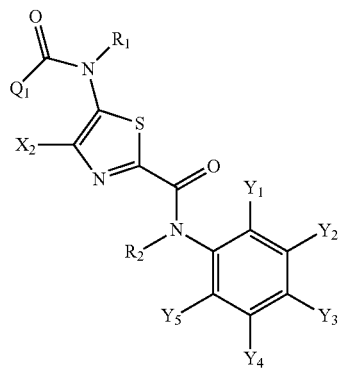

| compound number | $Q_1$ | $R_1$ | $R_2$ | $X_2$ | $Y_1$ | $Y_2$ | $Y_3$ | $Y_4$ | $Y_5$ |
|---|---|---|---|---|---|---|---|---|---|
| 38-6 | phenyl | H | H | H | I | H | nonafluoro-2-butyl | H | CF3 |
| 38-7 | phenyl | H | H | H | CF3 | H | nonafluoro-2-butyl | H | CF3 |
| 38-8 | phenyl | Me | H | H | I | H | heptafluoroisopropyl | H | OCF3 |
| 38-9 | phenyl | Me | H | H | Cl | H | heptafluoroisopropyl | H | CF3 |
| 38-10 | phenyl | Me | H | H | CF3 | H | heptafluoroisopropyl | H | CF3 |
| 38-11 | phenyl | Me | H | H | Br | H | nonafluoro-2-butyl | H | OCF3 |
| 38-12 | phenyl | Me | H | H | I | H | nonafluoro-2-butyl | H | CF3 |
| 38-13 | phenyl | Me | H | H | CF3 | H | nonafluoro-2-butyl | H | CF3 |
| 38-14 | phenyl | H | Me | H | I | H | heptafluoroisopropyl | H | OCF3 |
| 38-15 | phenyl | H | Me | H | Cl | H | heptafluoroisopropyl | H | CF3 |
| 38-16 | phenyl | H | Me | H | CF3 | H | heptafluoroisopropyl | H | CF3 |
| 38-17 | phenyl | H | Me | H | Br | H | nonafluoro-2-butyl | H | OCF3 |
| 38-18 | phenyl | H | Me | H | I | H | nonafluoro-2-butyl | H | CF3 |
| 38-19 | phenyl | H | Me | H | CF3 | H | nonafluoro-2-butyl | H | CF3 |
| 38-20 | phenyl | Me | Me | H | I | H | heptafluoroisopropyl | H | OCF3 |
| 38-21 | phenyl | Me | Me | H | Cl | H | heptafluoroisopropyl | H | CF3 |
| 38-22 | phenyl | Me | Me | H | CF3 | H | heptafluoroisopropyl | H | CF3 |
| 38-23 | phenyl | Me | Me | H | Br | H | nonafluoro-2-butyl | H | OCF3 |
| 38-24 | phenyl | Me | Me | H | I | H | nonafluoro-2-butyl | H | CF3 |
| 38-25 | phenyl | Me | Me | H | CF3 | H | nonafluoro-2-butyl | H | CF3 |
| 38-26 | phenyl | H | H | H | I | F | heptafluoroisopropyl | H | OCF3 |
| 38-27 | phenyl | F | H | H | Cl | H | heptafluoroisopropyl | F | CF3 |
| 38-28 | phenyl | Me | H | H | CF3 | Cl | heptafluoroisopropyl | H | CF3 |
| 38-29 | phenyl | H | H | H | Br | H | nonafluoro-2-butyl | Cl | OCF3 |
| 38-30 | phenyl | H | Me | H | I | Br | nonafluoro-2-butyl | H | CF3 |
| 38-31 | phenyl | H | H | H | Cl | H | nonafluoro-2-butyl | I | CF3 |
| 38-32 | phenyl | H | H | H | Br | Me | nonafluoro-2-butyl | H | CF3 |
| 38-33 | phenyl | H | H | H | CF3 | H | nonafluoro-2-butyl | Et | CF3 |

TABLE 39

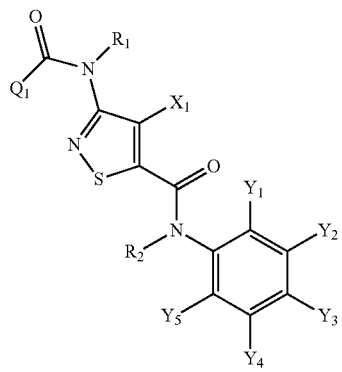

| compound number | $Q_1$ | $R_1$ | $R_2$ | $X_1$ | $Y_1$ | $Y_2$ | $Y_3$ | $Y_4$ | $Y_5$ |
|---|---|---|---|---|---|---|---|---|---|
| 39-1 | phenyl | H | H | H | Cl | H | heptafluoroisopropyl | H | OCF3 |
| 39-2 | phenyl | H | H | H | Br | H | heptafluoroisopropyl | H | CF3 |
| 39-3 | phenyl | H | H | Cl | Br | H | heptafluoroisopropyl | H | CF3 |
| 39-4 | phenyl | H | H | H | CF3 | H | heptafluoroisopropyl | H | CF3 |

TABLE 39-continued

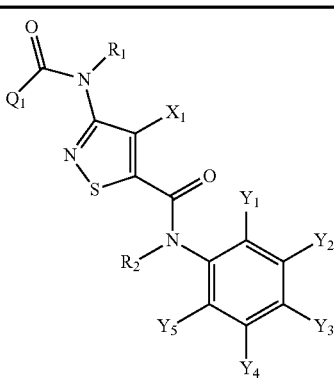

| compound number | $Q_1$ | $R_1$ | $R_2$ | $X_1$ | $Y_1$ | $Y_2$ | $Y_3$ | $Y_4$ | $Y_5$ |
|---|---|---|---|---|---|---|---|---|---|
| 39-5 | phenyl | H | H | H | I | H | nonafluoro-2-butyl | H | OCF3 |
| 39-6 | phenyl | H | H | H | Cl | H | nonafluoro-2-butyl | H | CF3 |
| 39-7 | phenyl | H | H | H | CF3 | H | nonafluoro-2-butyl | H | CF3 |
| 39-8 | phenyl | Me | H | H | Cl | H | heptafluoroisopropyl | H | OCF3 |
| 39-9 | phenyl | Me | H | H | Br | H | heptafluoroisopropyl | H | CF3 |
| 39-10 | phenyl | Me | H | H | CF3 | H | heptafluoroisopropyl | H | CF3 |
| 39-11 | phenyl | Me | H | H | I | H | nonafluoro-2-butyl | H | OCF3 |
| 39-12 | phenyl | Me | H | H | Cl | H | nonafluoro-2-butyl | H | CF3 |
| 39-13 | phenyl | Me | H | H | CF3 | H | nonafluoro-2-butyl | H | CF3 |
| 39-14 | phenyl | H | Me | H | Cl | H | heptafluoroisopropyl | H | OCF3 |
| 39-15 | phenyl | H | Me | H | Br | H | heptafluoroisopropyl | H | CF3 |
| 39-16 | phenyl | H | Me | H | CF3 | H | heptafluoroisopropyl | H | CF3 |
| 39-17 | phenyl | H | Me | H | I | H | nonafluoro-2-butyl | H | OCF3 |
| 39-18 | phenyl | H | Me | H | Cl | H | nonafluoro-2-butyl | H | CF3 |
| 39-19 | phenyl | H | Me | H | CF3 | H | nonafluoro-2-butyl | H | CF3 |
| 39-20 | phenyl | Me | Me | H | Cl | H | heptafluoroisopropyl | H | OCF3 |
| 39-21 | phenyl | Me | Me | H | Br | H | heptafluoroisopropyl | H | CF3 |
| 39-22 | phenyl | Me | Me | H | CF3 | H | heptafluoroisopropyl | H | CF3 |
| 39-23 | phenyl | Me | Me | H | I | H | nonafluoro-2-butyl | H | OCF3 |
| 39-24 | phenyl | Me | Me | H | Cl | H | nonafluoro-2-butyl | H | CF3 |
| 39-25 | phenyl | Me | Me | H | CF3 | H | nonafluoro-2-butyl | H | CF3 |
| 39-26 | phenyl | H | H | H | Cl | F | heptafluoroisopropyl | H | OCF3 |
| 39-27 | phenyl | Me | H | H | Br | H | heptafluoroisopropyl | F | CF3 |
| 39-28 | phenyl | H | Me | H | CF3 | Cl | heptafluoroisopropyl | H | CF3 |
| 39-29 | phenyl | H | H | H | I | H | nonafluoro-2-butyl | Cl | OCF3 |
| 39-30 | phenyl | H | H | H | Cl | Br | nonafluoro-2-butyl | H | CF3 |
| 39-31 | phenyl | H | H | H | Br | H | nonafluoro-2-butyl | I | CF3 |
| 39-32 | phenyl | H | H | H | I | Me | nonafluoro-2-butyl | H | CF3 |
| 39-33 | phenyl | H | H | H | CF3 | H | nonafluoro-2-butyl | Et | CF3 |

TABLE 40

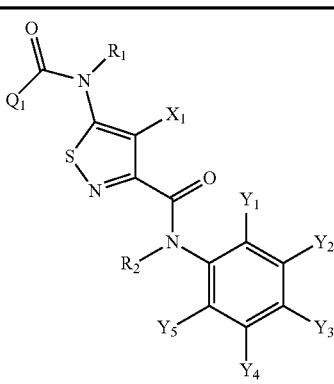

| compound number | $Q_1$ | $R_1$ | $R_2$ | $X_1$ | $Y_1$ | $Y_2$ | $Y_3$ | $Y_4$ | $Y_5$ |
|---|---|---|---|---|---|---|---|---|---|
| 40-1 | phenyl | H | H | H | Br | H | heptafluoroisopropyl | H | OCF3 |
| 40-2 | phenyl | H | H | H | I | H | heptafluoroisopropyl | H | CF3 |
| 40-3 | phenyl | H | H | Cl | I | H | heptafluoroisopropyl | H | CF3 |

TABLE 40-continued

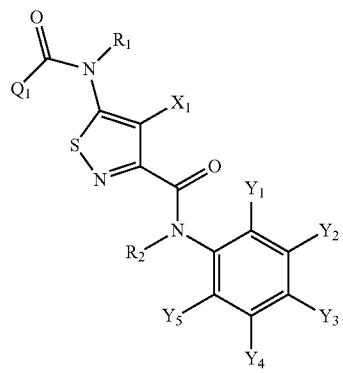

| compound number | $Q_1$ | $R_1$ | $R_2$ | $X_1$ | $Y_1$ | $Y_2$ | $Y_3$ | $Y_4$ | $Y_5$ |
|---|---|---|---|---|---|---|---|---|---|
| 40-4 | phenyl | H | H | H | CF3 | H | heptafluoroisopropyl | H | CF3 |
| 40-5 | phenyl | H | H | H | Cl | H | nonafluoro-2-butyl | H | OCF3 |
| 40-6 | phenyl | H | H | H | Br | H | nonafluoro-2-butyl | H | CF3 |
| 40-7 | phenyl | H | H | H | CF3 | H | nonafluoro-2-butyl | H | CF3 |
| 40-8 | phenyl | Me | H | H | Br | H | heptafluoroisopropyl | H | OCF3 |
| 40-9 | phenyl | Me | H | H | I | H | heptafluoroisopropyl | H | CF3 |
| 40-10 | phenyl | Me | H | H | CF3 | H | heptafluoroisopropyl | H | CF3 |
| 40-11 | phenyl | Me | H | H | Cl | H | nonafluoro-2-butyl | H | OCF3 |
| 40-12 | phenyl | Me | H | H | Br | H | nonafluoro-2-butyl | H | CF3 |
| 40-13 | phenyl | Me | H | H | CF3 | H | nonafluoro-2-butyl | H | CF3 |
| 40-14 | phenyl | H | Me | H | Br | H | heptafluoroisopropyl | H | OCF3 |
| 40-15 | phenyl | H | Me | H | I | H | heptafluoroisopropyl | H | CF3 |
| 40-16 | phenyl | H | Me | H | CF3 | H | heptafluoroisopropyl | H | CF3 |
| 40-17 | phenyl | H | Me | H | Cl | H | nonafluoro-2-butyl | H | OCF3 |
| 40-18 | phenyl | H | Me | H | Br | H | nonafluoro-2-butyl | H | CF3 |
| 40-19 | phenyl | H | Me | H | CF3 | H | nonafluoro-2-butyl | H | CF3 |
| 40-20 | phenyl | Me | Me | H | Br | H | heptafluoroisopropyl | H | OCF3 |
| 40-21 | phenyl | Me | Me | H | I | H | heptafluoroisopropyl | H | CF3 |
| 40-22 | phenyl | Me | Me | H | CF3 | H | heptafluoroisopropyl | H | CF3 |
| 40-23 | phenyl | Me | Me | H | Cl | H | nonafluoro-2-butyl | H | OCF3 |
| 40-24 | phenyl | Me | Me | H | Br | H | nonafluoro-2-butyl | H | CF3 |
| 40-25 | phenyl | Me | Me | H | CF3 | H | nonafluoro-2-butyl | H | CF3 |
| 40-26 | phenyl | H | H | H | Br | F | heptafluoroisopropyl | H | OCF3 |
| 40-27 | phenyl | H | H | H | I | H | heptafluoroisopropyl | F | CF3 |
| 40-28 | phenyl | Me | H | H | CF3 | Cl | heptafluoroisopropyl | H | CF3 |
| 40-29 | phenyl | H | H | H | Cl | H | nonafluoro-2-butyl | Cl | OCF3 |
| 40-30 | phenyl | H | H | H | Br | Br | nonafluoro-2-butyl | H | CF3 |
| 40-31 | phenyl | H | H | H | I | H | nonafluoro-2-butyl | I | CF3 |
| 40-32 | phenyl | H | H | H | Cl | Me | nonafluoro-2-butyl | H | CF3 |
| 40-33 | phenyl | H | Me | H | CF3 | H | nonafluoro-2-butyl | Et | CF3 |

TABLE 41

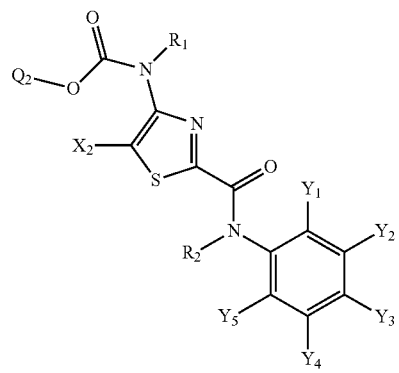

| compound number | $Q_2$ | $R_1$ | $R_2$ | $X_2$ | $Y_1$ | $Y_2$ | $Y_3$ | $Y_4$ | $Y_5$ |
|---|---|---|---|---|---|---|---|---|---|
| 41-1 | 2,2,2-trichloroethyl | H | H | H | Cl | H | heptafluoroisopropyl | H | OCF3 |
| 41-2 | 2,2,2-trichloroethyl | H | H | H | Br | H | heptafluoroisopropyl | H | CF3 |

TABLE 41-continued

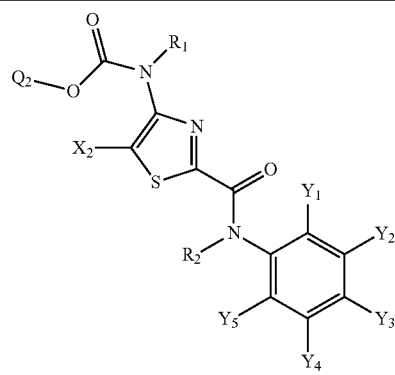

| compound number | $Q_2$ | $R_1$ | $R_2$ | $X_2$ | $Y_1$ | $Y_2$ | $Y_3$ | $Y_4$ | $Y_5$ |
|---|---|---|---|---|---|---|---|---|---|
| 41-3 | 2,2,2-trichloroethyl | H | H | H | CF3 | H | heptafluoroisopropyl | H | CF3 |
| 41-4 | 2,2,2-trichloroethyl | H | H | H | I | H | nonafluoro-2-butyl | H | OCF3 |
| 41-5 | 2,2,2-trichloroethyl | H | H | H | Cl | H | nonafluoro-2-butyl | H | CF3 |
| 41-6 | 2,2,2-trichloroethyl | H | H | H | CF3 | H | nonafluoro-2-butyl | H | CF3 |
| 41-7 | 2,2,2-trichloroethyl | Me | H | H | Br | H | heptafluoroisopropyl | H | OCF3 |
| 41-8 | 2,2,2-trichloroethyl | Me | H | H | I | H | heptafluoroisopropyl | H | CF3 |
| 41-9 | 2,2,2-trichloroethyl | Me | H | H | CF3 | H | heptafluoroisopropyl | H | CF3 |
| 41-10 | 2,2,2-trichloroethyl | Me | H | H | Cl | H | nonafluoro-2-butyl | H | OCF3 |
| 41-11 | 2,2,2-trichloroethyl | Me | H | H | Br | H | nonafluoro-2-butyl | H | CF3 |
| 41-12 | 2,2,2-trichloroethyl | Me | H | H | CF3 | H | nonafluoro-2-butyl | H | CF3 |
| 41-13 | 2,2,2-trichloroethyl | H | Me | H | I | H | heptafluoroisopropyl | H | OCF3 |
| 41-14 | 2,2,2-trichloroethyl | H | Me | H | Cl | H | heptafluoroisopropyl | H | CF3 |
| 41-15 | 2,2,2-trichloroethyl | H | Me | H | CF3 | H | heptafluoroisopropyl | H | CF3 |
| 41-16 | 2,2,2-trichloroethyl | H | Me | H | Br | H | nonafluoro-2-butyl | H | OCF3 |
| 41-17 | 2,2,2-trichloroethyl | H | Me | H | I | H | nonafluoro-2-butyl | H | CF3 |
| 41-18 | 2,2,2-trichloroethyl | H | Me | H | CF3 | H | nonafluoro-2-butyl | H | CF3 |
| 41-19 | 2,2,2-trichloroethyl | Me | Me | H | Cl | H | heptafluoroisopropyl | H | OCF3 |
| 41-20 | 2,2,2-trichloroethyl | Me | Me | H | Br | H | heptafluoroisopropyl | H | CF3 |
| 41-21 | 2,2,2-trichloroethyl | Me | Me | H | CF3 | H | heptafluoroisopropyl | H | CF3 |
| 41-22 | 2,2,2-trichloroethyl | Me | Me | H | I | H | nonafluoro-2-butyl | H | OCF3 |
| 41-23 | 2,2,2-trichloroethyl | Me | Me | H | Cl | H | nonafluoro-2-butyl | H | CF3 |
| 41-24 | 2,2,2-trichloroethyl | Me | Me | H | CF3 | H | nonafluoro-2-butyl | H | CF3 |
| 41-25 | 2,2,2-trichloroethyl | H | H | H | Br | F | heptafluoroisopropyl | H | OCF3 |
| 41-26 | 2,2,2-trichloroethyl | H | H | H | I | H | heptafluoroisopropyl | Cl | CF3 |
| 41-27 | 2,2,2-trichloroethyl | H | H | H | CF3 | Br | heptafluoroisopropyl | H | CF3 |
| 41-28 | 2,2,2-trichloroethyl | H | H | H | I | H | nonafluoro-2-butyl | I | OCF3 |
| 41-29 | 2,2,2-trichloroethyl | H | H | H | Br | Me | nonafluoro-2-butyl | H | CF3 |
| 41-30 | 2,2,2-trichloroethyl | H | H | H | CF3 | H | nonafluoro-2-butyl | Et | CF3 |
| 41-31 | 2,2,2-trichloroethyl | H | H | Cl | Br | H | heptafluoroisopropyl | H | CF3 |

TABLE 42

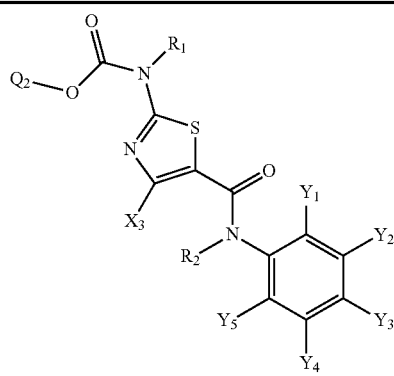

| compound number | $Q_2$ | $R_1$ | $R_2$ | $X_3$ | $Y_1$ | $Y_2$ | $Y_3$ | $Y_4$ | $Y_5$ |
|---|---|---|---|---|---|---|---|---|---|
| 42-1 | 2,2,2-trichloroethyl | H | H | H | Cl | H | heptafluoroisopropyl | H | OCF3 |
| 42-2 | 2,2,2-trichloroethyl | H | H | H | Br | H | heptafluoroisopropyl | H | CF3 |
| 42-3 | 2,2,2-trichloroethyl | H | H | H | CF3 | H | heptafluoroisopropyl | H | CF3 |

TABLE 42-continued

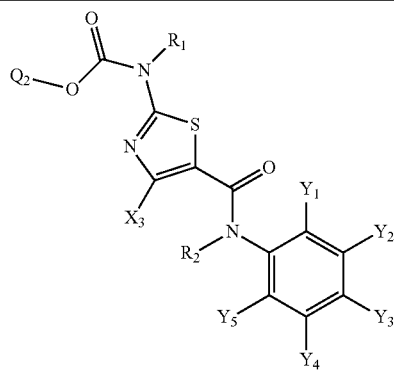

| compound number | Q₂ | R₁ | R₂ | X₃ | Y₁ | Y₂ | Y₃ | Y₄ | Y₅ |
|---|---|---|---|---|---|---|---|---|---|
| 42-4 | 2,2,2-trichloroethyl | H | H | H | I | H | nonafluoro-2-butyl | H | OCF3 |
| 42-5 | 2,2,2-trichloroethyl | H | H | H | Cl | H | nonafluoro-2-butyl | H | CF3 |
| 42-6 | 2,2,2-trichloroethyl | H | H | H | CF3 | H | nonafluoro-2-butyl | H | CF3 |
| 42-7 | 2,2,2-trichloroethyl | Me | H | H | Br | H | heptafluoroisopropyl | H | OCF3 |
| 42-8 | 2,2,2-trichloroethyl | Me | H | H | I | H | heptafluoroisopropyl | H | CF3 |
| 42-9 | 2,2,2-trichloroethyl | Me | H | H | CF3 | H | heptafluoroisopropyl | H | CF3 |
| 42-10 | 2,2,2-trichloroethyl | Me | H | H | Cl | H | nonafluoro-2-butyl | H | OCF3 |
| 42-11 | 2,2,2-trichloroethyl | Me | H | H | Br | H | nonafluoro-2-butyl | H | CF3 |
| 42-12 | 2,2,2-trichloroethyl | Me | H | H | CF3 | H | nonafluoro-2-butyl | H | CF3 |
| 42-13 | 2,2,2-trichloroethyl | H | Me | H | I | H | heptafluoroisopropyl | H | OCF3 |
| 42-14 | 2,2,2-trichloroethyl | H | Me | H | Cl | H | heptafluoroisopropyl | H | CF3 |
| 42-15 | 2,2,2-trichloroethyl | H | Me | H | CF3 | H | heptafluoroisopropyl | H | CF3 |
| 42-16 | 2,2,2-trichloroethyl | H | Me | H | Br | H | nonafluoro-2-butyl | H | OCF3 |
| 42-17 | 2,2,2-trichloroethyl | H | Me | H | I | H | nonafluoro-2-butyl | H | CF3 |
| 42-18 | 2,2,2-trichloroethyl | H | Me | H | CF3 | H | nonafluoro-2-butyl | H | CF3 |
| 42-19 | 2,2,2-trichloroethyl | Me | Me | H | Cl | H | heptafluoroisopropyl | H | OCF3 |
| 42-20 | 2,2,2-trichloroethyl | Me | Me | H | Br | H | heptafluoroisopropyl | H | CF3 |
| 42-21 | 2,2,2-trichloroethyl | Me | Me | H | CF3 | H | heptafluoroisopropyl | H | CF3 |
| 42-22 | 2,2,2-trichloroethyl | Me | Me | H | I | H | nonafluoro-2-butyl | H | OCF3 |
| 42-23 | 2,2,2-trichloroethyl | Me | Me | H | Cl | H | nonafluoro-2-butyl | H | CF3 |
| 42-24 | 2,2,2-trichloroethyl | Me | Me | H | CF3 | H | nonafluoro-2-butyl | H | CF3 |
| 42-25 | 2,2,2-trichloroethyl | H | H | H | Br | F | heptafluoroisopropyl | H | OCF3 |
| 42-26 | 2,2,2-trichloroethyl | H | H | H | I | H | heptafluoroisopropyl | Cl | CF3 |
| 42-27 | 2,2,2-trichloroethyl | H | H | H | CF3 | Br | heptafluoroisopropyl | H | CF3 |
| 42-28 | 2,2,2-trichloroethyl | H | H | H | I | H | nonafluoro-2-butyl | I | OCF3 |
| 42-29 | 2,2,2-trichloroethyl | H | H | H | Br | Me | nonafluoro-2-butyl | H | CF3 |
| 42-30 | 2,2,2-trichloroethyl | H | H | H | CF3 | H | nonafluoro-2-butyl | Et | CF3 |
| 42-31 | 2,2,2-trichloroethyl | H | H | Cl | Br | H | heptafluoroisopropyl | H | CF3 |

TABLE 43

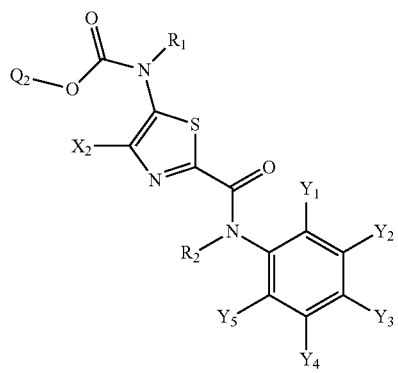

| compound number | Q₂ | R₁ | R₂ | X₂ | Y₁ | Y₂ | Y₃ | Y₄ | Y₅ |
|---|---|---|---|---|---|---|---|---|---|
| 43-1 | 2,2,2-trichloroethyl | H | H | H | Cl | H | heptafluoroisopropyl | H | OCF3 |
| 43-2 | 2,2,2-trichloroethyl | H | H | H | Br | H | heptafluoroisopropyl | H | CF3 |
| 43-3 | 2,2,2-trichloroethyl | H | H | H | CF3 | H | heptafluoroisopropyl | H | CF3 |
| 43-4 | 2,2,2-trichloroethyl | H | H | H | I | H | nonafluoro-2-butyl | H | OCF3 |

TABLE 43-continued

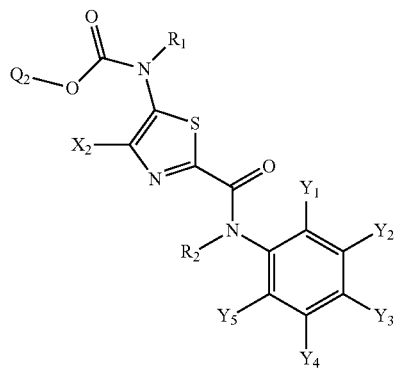

| compound number | Q₂ | R₁ | R₂ | X₂ | Y₁ | Y₂ | Y₃ | Y₄ | Y₅ |
|---|---|---|---|---|---|---|---|---|---|
| 43-5 | 2,2,2-trichloroethyl | H | H | H | Cl | H | nonafluoro-2-butyl | H | CF3 |
| 43-6 | 2,2,2-trichloroethyl | H | H | H | CF3 | H | nonafluoro-2-butyl | H | CF3 |
| 43-7 | 2,2,2-trichloroethyl | Me | H | H | Br | H | heptafluoroisopropyl | H | OCF3 |
| 43-8 | 2,2,2-trichloroethyl | Me | H | H | I | H | heptafluoroisopropyl | H | CF3 |
| 43-9 | 2,2,2-trichloroethyl | Me | H | H | CF3 | H | heptafluoroisopropyl | H | CF3 |
| 43-10 | 2,2,2-trichloroethyl | Me | H | H | Cl | H | nonafluoro-2-butyl | H | OCF3 |
| 43-11 | 2,2,2-trichloroethyl | Me | H | H | Br | H | nonafluoro-2-butyl | H | CF3 |
| 43-12 | 2,2,2-trichloroethyl | Me | H | H | CF3 | H | nonafluoro-2-butyl | H | CF3 |
| 43-13 | 2,2,2-trichloroethyl | H | Me | H | I | H | heptafluoroisopropyl | H | OCF3 |
| 43-14 | 2,2,2-trichloroethyl | H | Me | H | Cl | H | heptafluoroisopropyl | H | CF3 |
| 43-15 | 2,2,2-trichloroethyl | H | Me | H | CF3 | H | heptafluoroisopropyl | H | CF3 |
| 43-16 | 2,2,2-trichloroethyl | H | Me | H | Br | H | nonafluoro-2-butyl | H | OCF3 |
| 43-17 | 2,2,2-trichloroethyl | H | Me | H | I | H | nonafluoro-2-butyl | H | CF3 |
| 43-18 | 2,2,2-trichloroethyl | H | Me | H | CF3 | H | nonafluoro-2-butyl | H | CF3 |
| 43-19 | 2,2,2-trichloroethyl | Me | Me | H | Cl | H | heptafluoroisopropyl | H | OCF3 |
| 43-20 | 2,2,2-trichloroethyl | Me | Me | H | Br | H | heptafluoroisopropyl | H | CF3 |
| 43-21 | 2,2,2-trichloroethyl | Me | Me | H | CF3 | H | heptafluoroisopropyl | H | CF3 |
| 43-22 | 2,2,2-trichloroethyl | Me | Me | H | I | H | nonafluoro-2-butyl | H | OCF3 |
| 43-23 | 2,2,2-trichloroethyl | Me | Me | H | Cl | H | nonafluoro-2-butyl | H | CF3 |
| 43-24 | 2,2,2-trichloroethyl | Me | Me | H | CF3 | H | nonafluoro-2-butyl | H | CF3 |
| 43-25 | 2,2,2-trichloroethyl | H | H | H | Br | F | heptafluoroisopropyl | H | OCF3 |
| 43-26 | 2,2,2-trichloroethyl | H | H | H | I | H | heptafluoroisopropyl | Cl | CF3 |
| 43-27 | 2,2,2-trichloroethyl | H | H | H | CF3 | Br | heptafluoroisopropyl | H | CF3 |
| 43-28 | 2,2,2-trichloroethyl | H | H | H | I | H | nonafluoro-2-butyl | I | OCF3 |
| 43-29 | 2,2,2-trichloroethyl | H | H | H | Br | Me | nonafluoro-2-butyl | H | CF3 |
| 43-30 | 2,2,2-trichloroethyl | H | H | H | CF3 | H | nonafluoro-2-butyl | Et | CF3 |
| 43-31 | 2,2,2-trichloroethyl | H | H | Cl | Br | H | heptafluoroisopropyl | H | CF3 |

TABLE 44

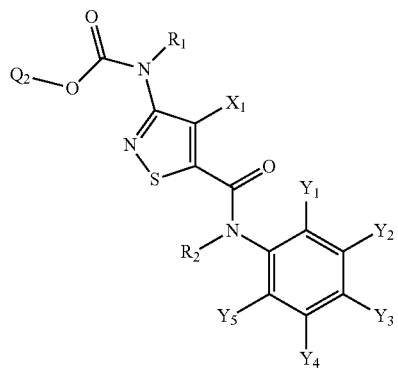

| compound number | Q₂ | R₁ | R₂ | X₁ | Y₁ | Y₂ | Y₃ | Y₄ | Y₅ |
|---|---|---|---|---|---|---|---|---|---|
| 44-1 | 2,2,2-trichloroethyl | H | H | H | Cl | H | heptafluoroisopropyl | H | OCF3 |
| 44-2 | 2,2,2-trichloroethyl | H | H | H | Br | H | heptafluoroisopropyl | H | CF3 |
| 44-3 | 2,2,2-trichloroethyl | H | H | H | CF3 | H | heptafluoroisopropyl | H | CF3 |
| 44-4 | 2,2,2-trichloroethyl | H | H | H | I | H | nonafluoro-2-butyl | H | OCF3 |
| 44-5 | 2,2,2-trichloroethyl | H | H | H | Cl | H | nonafluoro-2-butyl | H | CF3 |

TABLE 44-continued

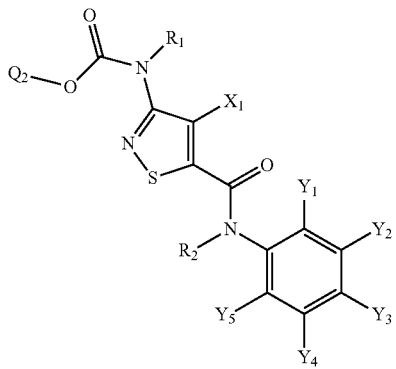

| compound number | Q₂ | R₁ | R₂ | X₁ | Y₁ | Y₂ | Y₃ | Y₄ | Y₅ |
|---|---|---|---|---|---|---|---|---|---|
| 44-6 | 2,2,2-trichloroethyl | H | H | H | CF3 | H | nonafluoro-2-butyl | H | CF3 |
| 44-7 | 2,2,2-trichloroethyl | Me | H | H | Br | H | heptafluoroisopropyl | H | OCF3 |
| 44-8 | 2,2,2-trichloroethyl | Me | H | H | I | H | heptafluoroisopropyl | H | CF3 |
| 44-9 | 2,2,2-trichloroethyl | Me | H | H | CF3 | H | heptafluoroisopropyl | H | CF3 |
| 44-10 | 2,2,2-trichloroethyl | Me | H | H | Cl | H | nonafluoro-2-butyl | H | OCF3 |
| 44-11 | 2,2,2-trichloroethyl | Me | H | H | Br | H | nonafluoro-2-butyl | H | CF3 |
| 44-12 | 2,2,2-trichloroethyl | Me | H | H | CF3 | H | nonafluoro-2-butyl | H | CF3 |
| 44-13 | 2,2,2-trichloroethyl | H | Me | H | I | H | heptafluoroisopropyl | H | OCF3 |
| 44-14 | 2,2,2-trichloroethyl | H | Me | H | Cl | H | heptafluoroisopropyl | H | CF3 |
| 44-15 | 2,2,2-trichloroethyl | H | Me | H | CF3 | H | heptafluoroisopropyl | H | CF3 |
| 44-16 | 2,2,2-trichloroethyl | H | Me | H | Br | H | nonafluoro-2-butyl | H | OCF3 |
| 44-17 | 2,2,2-trichloroethyl | H | Me | H | I | H | nonafluoro-2-butyl | H | CF3 |
| 44-18 | 2,2,2-trichloroethyl | H | Me | H | CF3 | H | nonafluoro-2-butyl | H | CF3 |
| 44-19 | 2,2,2-trichloroethyl | Me | Me | H | Cl | H | heptafluoroisopropyl | H | OCF3 |
| 44-20 | 2,2,2-trichloroethyl | Me | Me | H | Br | H | heptafluoroisopropyl | H | CF3 |
| 44-21 | 2,2,2-trichloroethyl | Me | Me | H | CF3 | H | heptafluoroisopropyl | H | CF3 |
| 44-22 | 2,2,2-trichloroethyl | Me | Me | H | I | H | nonaffuoro-2-butyl | H | OCF3 |
| 44-23 | 2,2,2-trichloroethyl | Me | Me | H | Cl | H | nonafluoro-2-butyl | H | CF3 |
| 44-24 | 2,2,2-trichloroethyl | Me | Me | H | CF3 | H | nonafluoro-2-butyl | H | CF3 |
| 44-25 | 2,2,2-trichloroethyl | H | H | H | Br | F | heptafluoroisopropyl | H | OCF3 |
| 44-26 | 2,2,2-trichloroethyl | H | H | H | I | H | heptafluoroisopropyl | Cl | CF3 |
| 44-27 | 2,2,2-trichloroethyl | H | H | H | CF3 | Br | heptafluoroisopropyl | H | CF3 |
| 44-28 | 2,2,2-trichloroethyl | H | H | H | I | H | nonafluoro-2-butyl | I | OCF3 |
| 44-29 | 2,2,2-trichloroethyl | H | H | H | Br | Me | nonafluoro-2-butyl | H | CF3 |
| 44-30 | 2,2,2-trichloroethyl | H | H | H | CF3 | H | nonafluoro-2-butyl | Et | CF3 |
| 44-31 | 2,2,2-trichloroethyl | H | H | Cl | Br | H | heptafluoroisopropyl | H | CF3 |

TABLE 45

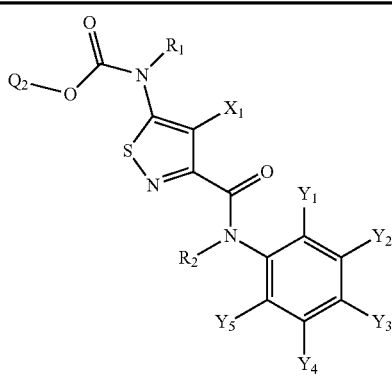

| compound number | Q₂ | R₁ | R₂ | X₁ | Y₁ | Y₂ | Y₃ | Y₄ | Y₅ |
|---|---|---|---|---|---|---|---|---|---|
| 45-1 | 2,2,2-trichloroethyl | H | H | H | Cl | H | heptafluoroisopropyl | H | OCF3 |
| 45-2 | 2,2,2-trichloroethyl | H | H | H | Br | H | heptafluoroisopropyl | H | CF3 |
| 45-3 | 2,2,2-trichloroethyl | H | H | H | CF3 | H | heptafluoroisopropyl | H | CF3 |
| 45-4 | 2,2,2-trichloroethyl | H | H | H | I | H | nonafluoro-2-butyl | H | OCF3 |
| 45-5 | 2,2,2-trichloroethyl | H | H | H | Cl | H | nonafluoro-2-butyl | H | CF3 |
| 45-6 | 2,2,2-trichloroethyl | H | H | H | CF3 | H | nonafluoro-2-butyl | H | CF3 |

TABLE 45-continued

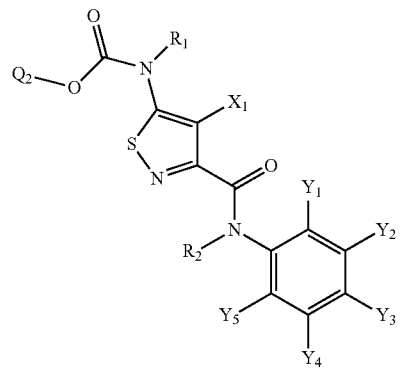

| compound number | Q₂ | R₁ | R₂ | X₁ | Y₁ | Y₂ | Y₃ | Y₄ | Y₅ |
|---|---|---|---|---|---|---|---|---|---|
| 45-7 | 2,2,2-trichloroethyl | Me | H | H | Br | H | heptafluoroisopropyl | H | OCF3 |
| 45-8 | 2,2,2-trichloroethyl | Me | H | H | I | H | heptafluoroisopropyl | H | CF3 |
| 45-9 | 2,2,2-trichloroethyl | Me | H | H | CF3 | H | heptafluoroisopropyl | H | CF3 |
| 45-10 | 2,2,2-trichloroethyl | Me | H | H | Cl | H | nonafluoro-2-butyl | H | OCF3 |
| 45-11 | 2,2,2-trichloroethyl | Me | H | H | Br | H | nonafluoro-2-butyl | H | CF3 |
| 45-12 | 2,2,2-trichloroethyl | Me | H | H | CF3 | H | nonafluoro-2-butyl | H | CF3 |
| 45-13 | 2,2,2-trichloroethyl | H | Me | H | I | H | heptafluoroisopropyl | H | OCF3 |
| 45-14 | 2,2,2-trichloroethyl | H | Me | H | Cl | H | heptafluoroisopropyl | H | CF3 |
| 45-15 | 2,2,2-trichloroethyl | H | Me | H | CF3 | H | heptafluoroisopropyl | H | CF3 |
| 45-16 | 2,2,2-trichloroethyl | H | Me | H | Br | H | nonafluoro-2-butyl | H | OCF3 |
| 45-17 | 2,2,2-trichloroethyl | H | Me | H | I | H | nonafluoro-2-butyl | H | CF3 |
| 45-18 | 2,2,2-trichloroethyl | H | Me | H | CF3 | H | nonafluoro-2-butyl | H | CF3 |
| 45-19 | 2,2,2-trichloroethyl | Me | Me | H | Cl | H | heptafluoroisopropyl | H | OCF3 |
| 45-20 | 2,2,2-trichloroethyl | Me | Me | H | Br | H | heptafluoroisopropyl | H | CF3 |
| 45-21 | 2,2,2-trichloroethyl | Me | Me | H | CF3 | H | heptafluoroisopropyl | H | CF3 |
| 45-22 | 2,2,2-trichloroethyl | Me | Me | H | I | H | nonafluoro-2-butyl | H | OCF3 |
| 45-23 | 2,2,2-trichloroethyl | Me | Me | H | Cl | H | nonafluoro-2-butyl | H | CF3 |
| 45-24 | 2,2,2-trichloroethyl | Me | Me | H | CF3 | H | nonafluoro-2-butyl | H | CF3 |
| 45-25 | 2,2,2-trichloroethyl | H | H | H | Br | F | heptafluoroisopropyl | H | OCF3 |
| 45-26 | 2,2,2-trichloroethyl | H | H | H | I | H | heptafluoroisopropyl | Cl | CF3 |
| 45-27 | 2,2,2-trichloroethyl | H | H | H | CF3 | Br | heptafluoroisopropyl | H | CF3 |
| 45-28 | 2,2,2-trichloroethyl | H | H | H | I | H | nonafluoro-2-butyl | I | OCF3 |
| 45-29 | 2,2,2-trichloroethyl | H | H | H | Br | Me | nonafluoro-2-butyl | H | CF3 |
| 45-30 | 2,2,2-trichloroethyl | H | H | H | CF3 | H | nonafluoro-2-butyl | Et | CF3 |
| 45-31 | 2,2,2-trichloroethyl | H | H | Cl | Br | H | heptafluoroisopropyl | H | CF3 |

TABLE 46

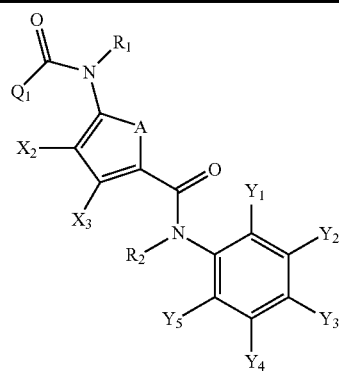

| compound number | Q₁ | R₁ | R₂ | A | X₂ | X₃ | Y₁ | Y₂ | Y₃ | Y₄ | Y₅ |
|---|---|---|---|---|---|---|---|---|---|---|---|
| 46-1 | phenyl | H | H | S | H | H | Cl | H | heptafluoroisopropyl | H | OCF3 |
| 46-2 | phenyl | H | H | S | H | H | Br | H | heptafluoroisopropyl | H | CF3 |
| 46-3 | phenyl | H | H | S | H | H | CF3 | H | heptafluoroisopropyl | H | CF3 |
| 46-4 | phenyl | H | H | S | H | H | I | H | nonafluoro-2-butyl | H | OCF3 |
| 46-5 | phenyl | H | H | S | H | H | Cl | H | nonafluoro-2-butyl | H | CF3 |
| 46-6 | phenyl | H | H | S | H | H | CF3 | H | nonafluoro-2-butyl | H | CF3 |
| 46-7 | phenyl | H | H | O | H | H | Br | H | heptafluoroisopropyl | H | OCF3 |

TABLE 46-continued

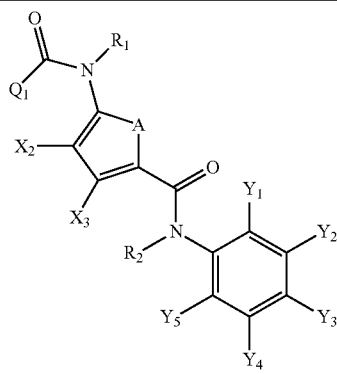

| compound number | Q₁ | R₁ | R₂ | A | X₂ | X₃ | Y₁ | Y₂ | Y₃ | Y₄ | Y₅ |
|---|---|---|---|---|---|---|---|---|---|---|---|
| 46-8 | phenyl | H | H | O | H | H | I | H | heptafluoroisopropyl | H | CF3 |
| 46-9 | phenyl | H | H | O | H | H | CF3 | H | heptafluoroisopropyl | H | CF3 |
| 46-10 | phenyl | H | H | O | H | H | Cl | H | nonafluoro-2-butyl | H | OCF3 |
| 46-11 | phenyl | H | H | O | H | H | Br | H | nonafluoro-2-butyl | H | CF3 |
| 46-12 | phenyl | H | H | O | H | H | CF3 | H | nonafluoro-2-butyl | H | CF3 |
| 46-13 | phenyl | H | H | NH | H | H | I | H | heptafluoroisopropyl | H | OCF3 |
| 46-14 | phenyl | H | H | NH | H | H | Cl | H | heptafluoroisopropyl | H | CF3 |
| 46-15 | phenyl | H | H | NH | H | H | CF3 | H | heptafluoroisopropyl | H | CF3 |
| 46-16 | phenyl | H | H | NH | H | H | Br | H | nonafluoro-2-butyl | H | OCF3 |
| 46-17 | phenyl | H | H | NH | H | H | I | H | nonafluoro-2-butyl | H | CF3 |
| 46-18 | phenyl | H | H | NH | H | H | CF3 | H | nonafluoro-2-butyl | H | CF3 |
| 46-19 | phenyl | Me | H | S | H | H | Cl | H | heptafluoroisopropyl | H | OCF3 |
| 46-20 | phenyl | Me | H | S | H | H | Br | H | heptafluoroisopropyl | H | CF3 |
| 46-21 | phenyl | Me | H | S | H | H | CF3 | H | heptafluoroisopropyl | H | CF3 |
| 46-22 | phenyl | Me | H | S | H | H | I | H | nonafluoro-2-butyl | H | OCF3 |
| 46-23 | phenyl | Me | H | S | H | H | Cl | H | nonafluoro-2-butyl | H | CF3 |
| 46-24 | phenyl | Me | H | S | H | H | CF3 | H | nonafluoro-2-butyl | H | CF3 |
| 46-25 | phenyl | Me | H | O | H | H | Br | H | heptafluoroisopropyl | H | OCF3 |
| 46-26 | phenyl | Me | H | O | H | H | I | H | heptafluoroisopropyl | H | CF3 |
| 46-27 | phenyl | Me | H | O | H | H | CF3 | H | heptafluoroisopropyl | H | CF3 |
| 46-28 | phenyl | Me | H | O | H | H | Cl | H | nonafluoro-2-butyl | H | OCF3 |
| 46-29 | phenyl | Me | H | O | H | H | Br | H | nonafluoro-2-butyl | H | CF3 |
| 46-30 | phenyl | Me | H | O | H | H | CF3 | H | nonafluoro-2-butyl | H | CF3 |
| 46-31 | phenyl | Me | H | NH | H | H | I | H | heptafluoroisopropyl | H | OCF3 |
| 46-32 | phenyl | Me | H | NH | H | H | Cl | H | heptafluoroisopropyl | H | CF3 |
| 46-33 | phenyl | Me | H | NH | H | H | CF3 | H | heptafluoroisopropyl | H | CF3 |
| 46-34 | phenyl | Me | H | NH | H | H | Br | H | nonafluoro-2-butyl | H | OCF3 |
| 46-35 | phenyl | Me | H | NH | H | H | I | H | nonafluoro-2-butyl | H | CF3 |
| 46-36 | phenyl | Me | H | NH | H | H | CF3 | H | nonafluoro-2-butyl | H | CF3 |
| 46-37 | phenyl | H | Me | S | H | H | Cl | H | heptafluoroisopropyl | H | OCF3 |
| 46-38 | phenyl | H | Me | S | H | H | Br | H | heptafluoroisopropyl | H | CF3 |
| 46-39 | phenyl | H | Me | S | H | H | CF3 | H | heptafluoroisopropyl | H | CF3 |
| 46-40 | phenyl | H | Me | S | H | H | I | H | nonafluoro-2-butyl | H | OCF3 |
| 46-41 | phenyl | H | Me | S | H | H | Cl | H | nonafluoro-2-butyl | H | CF3 |
| 46-42 | phenyl | H | Me | S | H | H | CF3 | H | nonafluoro-2-butyl | H | CF3 |
| 46-43 | phenyl | H | Me | O | H | H | Br | H | heptafluoroisopropyl | H | OCF3 |
| 46-44 | phenyl | H | Me | O | H | H | I | H | heptafluoroisopropyl | H | CF3 |
| 46-45 | phenyl | H | Me | O | H | H | CF3 | H | heptafluoroisopropyl | H | CF3 |
| 46-46 | phenyl | H | Me | O | H | H | Cl | H | nonafluoro-2-butyl | H | OCF3 |
| 46-47 | phenyl | H | Me | O | H | H | Br | H | nonafluoro-2-butyl | H | CF3 |
| 46-48 | phenyl | H | Me | O | H | H | CF3 | H | nonafluoro-2-butyl | H | CF3 |
| 46-49 | phenyl | H | Me | NH | H | H | I | H | heptafluoroisopropyl | H | OCF3 |
| 46-50 | phenyl | H | Me | NH | H | H | Cl | H | heptafluoroisopropyl | H | CF3 |
| 46-51 | phenyl | H | Me | NH | H | H | CF3 | H | heptafluoroisopropyl | H | CF3 |
| 46-52 | phenyl | H | Me | NH | H | H | Br | H | nonafluoro-2-butyl | H | OCF3 |
| 46-53 | phenyl | H | Me | NH | H | H | I | H | nonafluoro-2-butyl | H | CF3 |
| 46-54 | phenyl | H | Me | NH | H | H | CF3 | H | nonafluoro-2-butyl | H | CF3 |
| 46-55 | phenyl | Me | Me | S | H | H | Cl | H | heptafluoroisopropyl | H | OCF3 |
| 46-56 | phenyl | Me | Me | S | H | H | Br | H | heptafluoroisopropyl | H | CF3 |
| 46-57 | phenyl | Me | Me | S | H | H | CF3 | H | heptafluoroisopropyl | H | CF3 |
| 46-58 | phenyl | Me | Me | S | H | H | I | H | nonafluoro-2-butyl | H | OCF3 |
| 46-59 | phenyl | Me | Me | S | H | H | Cl | H | nonafluoro-2-butyl | H | CF3 |
| 46-60 | phenyl | Me | Me | S | H | H | CF3 | H | nonafluoro-2-butyl | H | CF3 |
| 46-61 | phenyl | Me | Me | O | H | H | Br | H | heptafluoroisopropyl | H | OCF3 |
| 46-62 | phenyl | Me | Me | O | H | H | I | H | heptafluoroisopropyl | H | CF3 |
| 46-63 | phenyl | Me | Me | O | H | H | CF3 | H | heptafluoroisopropyl | H | CF3 |
| 46-64 | phenyl | Me | Me | O | H | H | Cl | H | nonafluoro-2-butyl | H | OCF3 |
| 46-65 | phenyl | Me | Me | O | H | H | Br | H | nonafluoro-2-butyl | H | CF3 |
| 46-66 | phenyl | Me | Me | O | H | H | CF3 | H | nonafluoro-2-butyl | H | CF3 |

TABLE 46-continued

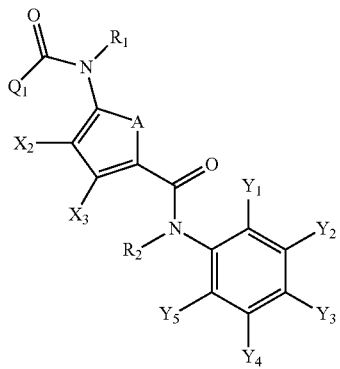

| compound number | Q₁ | R₁ | R₂ | A | X₂ | X₃ | Y₁ | Y₂ | Y₃ | Y₄ | Y₅ |
|---|---|---|---|---|---|---|---|---|---|---|---|
| 46-67 | phenyl | Me | Me | NH | H | H | I | H | heptafluoroisopropyl | H | OCF3 |
| 46-68 | phenyl | Me | Me | NH | H | H | Cl | H | heptafluoroisopropyl | H | CF3 |
| 46-69 | phenyl | Me | Me | NH | H | H | CF3 | H | heptafluoroisopropyl | H | CF3 |
| 46-70 | phenyl | Me | Me | NH | H | H | Br | H | nonafluoro-2-butyl | H | OCF3 |
| 46-71 | phenyl | Me | Me | NH | H | H | I | H | nonafluoro-2-butyl | H | CF3 |
| 46-72 | phenyl | Me | Me | NH | H | H | CF3 | H | nonafluoro-2-butyl | H | CF3 |
| 46-73 | phenyl | Me | H | S | H | H | Cl | F | heptafluoroisopropyl | H | OCF3 |
| 46-74 | phenyl | H | H | S | H | H | Br | H | heptafluoroisopropyl | F | CF3 |
| 46-75 | phenyl | H | H | S | H | H | CF3 | Cl | heptafluoroisopropyl | H | CF3 |
| 46-76 | phenyl | H | H | S | H | H | I | H | nonafluoro-2-butyl | Cl | OCF3 |
| 46-77 | phenyl | H | H | S | H | H | Cl | Br | nonafluoro-2-butyl | H | CF3 |
| 46-78 | phenyl | H | H | S | H | H | CF3 | H | nonafluoro-2-butyl | Br | CF3 |
| 46-79 | phenyl | H | H | O | H | H | Br | I | heptafluoroisopropyl | H | OCF3 |
| 46-80 | phenyl | Me | H | O | H | H | I | H | heptafluoroisopropyl | I | CF3 |
| 46-81 | phenyl | H | H | O | H | H | CF3 | Me | heptafluoroisopropyl | H | CF3 |
| 46-82 | phenyl | H | H | O | H | H | Cl | H | nonafluoro-2-butyl | Me | OCF3 |
| 46-83 | phenyl | H | H | O | H | H | Br | F | nonafluoro-2-butyl | F | CF3 |
| 46-84 | phenyl | H | H | O | H | H | CF3 | Cl | nonafluoro-2-butyl | Cl | CF3 |
| 46-85 | phenyl | H | H | NH | H | H | I | Br | heptafluoroisopropyl | Br | OCF3 |
| 46-86 | phenyl | H | H | NH | H | H | Cl | I | heptafluoroisopropyl | I | CF3 |
| 46-87 | phenyl | Me | H | NH | H | H | CF3 | F | heptafluoroisopropyl | Me | CF3 |
| 46-88 | phenyl | H | H | NH | H | H | Br | Cl | nonafluoro-2-butyl | Me | OCF3 |
| 46-89 | phenyl | H | H | NH | H | H | I | Br | nonafluoro-2-butyl | Me | CF3 |
| 46-90 | phenyl | H | H | NH | H | H | CF3 | I | nonafluoro-2-butyl | Me | CF3 |

TABLE 47

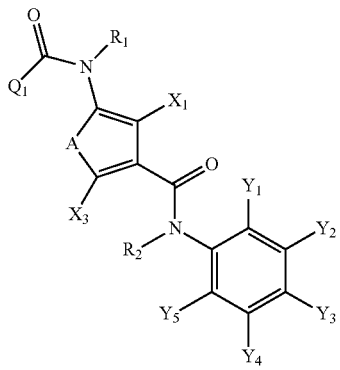

| compound number | Q₁ | R₁ | R₂ | A | X₁ | X₃ | Y₁ | Y₂ | Y₃ | Y₄ | Y₅ |
|---|---|---|---|---|---|---|---|---|---|---|---|
| 47-1 | phenyl | H | H | S | H | H | Cl | H | heptafluoroisopropyl | H | OCF3 |
| 47-2 | phenyl | H | H | S | H | H | Br | H | heptafluoroisopropyl | H | CF3 |
| 47-3 | phenyl | H | H | S | H | H | CF3 | H | heptafluoroisopropyl | H | CF3 |
| 47-4 | phenyl | H | H | S | H | H | I | H | nonafluoro-2-butyl | H | OCF3 |
| 47-5 | phenyl | H | H | S | H | H | Cl | H | nonafluoro-2-butyl | H | CF3 |
| 47-6 | phenyl | H | H | S | H | H | CF3 | H | nonafluoro-2-butyl | H | CF3 |
| 47-7 | phenyl | H | H | O | H | H | Br | H | heptafluoroisopropyl | H | OCF3 |
| 47-8 | phenyl | H | H | O | H | H | I | H | heptafluoroisopropyl | H | CF3 |

TABLE 47-continued

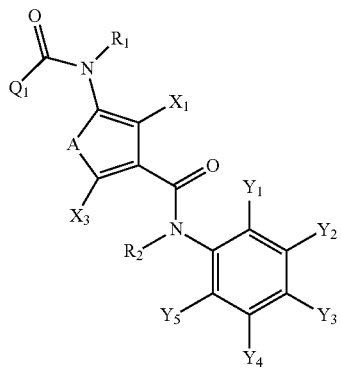

| compound number | $Q_1$ | $R_1$ | $R_2$ | A | $X_1$ | $X_3$ | $Y_1$ | $Y_2$ | $Y_3$ | $Y_4$ | $Y_5$ |
|---|---|---|---|---|---|---|---|---|---|---|---|
| 47-9 | phenyl | H | H | O | H | H | CF3 | H | heptafluoroisopropyl | H | CF3 |
| 47-10 | phenyl | H | H | O | H | H | Cl | H | nonafluoro-2-butyl | H | OCF3 |
| 47-11 | phenyl | H | H | O | H | H | Br | H | nonafluoro-2-butyl | H | CF3 |
| 47-12 | phenyl | H | H | O | H | H | CF3 | H | nonafluoro-2-butyl | H | CF3 |
| 47-13 | phenyl | H | H | NH | H | H | I | H | heptafluoroisopropyl | H | OCF3 |
| 47-14 | phenyl | H | H | NH | H | H | Cl | H | heptafluoroisopropyl | H | CF3 |
| 47-15 | phenyl | H | H | NH | H | H | CF3 | H | heptafluoroisopropyl | H | CF3 |
| 47-16 | phenyl | H | H | NH | H | H | Br | H | nonafluoro-2-butyl | H | OCF3 |
| 47-17 | phenyl | H | H | NH | H | H | I | H | nonafluoro-2-butyl | H | CF3 |
| 47-18 | phenyl | H | H | NH | H | H | CF3 | H | nonafluoro-2-butyl | H | CF3 |
| 47-19 | phenyl | Me | H | S | H | H | Cl | H | heptafluoroisopropyl | H | OCF3 |
| 47-20 | phenyl | Me | H | S | H | H | Br | H | heptafluoroisopropyl | H | CF3 |
| 47-21 | phenyl | Me | H | S | H | H | CF3 | H | heptafluoroisopropyl | H | CF3 |
| 47-22 | phenyl | Me | H | S | H | H | I | H | nonafluoro-2-butyl | H | OCF3 |
| 47-23 | phenyl | Me | H | S | H | H | Cl | H | nonafluoro-2-butyl | H | CF3 |
| 47-24 | phenyl | Me | H | S | H | H | CF3 | H | nonafluoro-2-butyl | H | CF3 |
| 47-25 | phenyl | Me | H | O | H | H | Br | H | heptafluoroisopropyl | H | OCF3 |
| 47-26 | phenyl | Me | H | O | H | H | I | H | heptafluoroisopropyl | H | CF3 |
| 47-27 | phenyl | Me | H | O | H | H | CF3 | H | heptafluoroisopropyl | H | CF3 |
| 47-28 | phenyl | Me | H | O | H | H | Cl | H | nonafluoro-2-butyl | H | OCF3 |
| 47-29 | phenyl | Me | H | O | H | H | Br | H | nonafluoro-2-butyl | H | CF3 |
| 47-30 | phenyl | Me | H | O | H | H | CF3 | H | nonafluoro-2-butyl | H | CF3 |
| 47-31 | phenyl | Me | H | NH | H | H | I | H | heptafluoroisopropyl | H | OCF3 |
| 47-32 | phenyl | Me | H | NH | H | H | Cl | H | heptafluoroisopropyl | H | CF3 |
| 47-33 | phenyl | Me | H | NH | H | H | CF3 | H | heptafluoroisopropyl | H | CF3 |
| 47-34 | phenyl | Me | H | NH | H | H | Br | H | nonafluoro-2-butyl | H | OCF3 |
| 47-35 | phenyl | Me | H | NH | H | H | I | H | nonafluoro-2-butyl | H | CF3 |
| 47-36 | phenyl | Me | H | NH | H | H | CF3 | H | nonafluoro-2-butyl | H | CF3 |
| 47-37 | phenyl | H | Me | S | H | H | Cl | H | heptafluoroisopropyl | H | OCF3 |
| 47-38 | phenyl | H | Me | S | H | H | Br | H | heptafluoroisopropyl | H | CF3 |
| 47-39 | phenyl | H | Me | S | H | H | CF3 | H | heptafluoroisopropyl | H | CF3 |
| 47-40 | phenyl | H | Me | S | H | H | I | H | nonafluoro-2-butyl | H | OCF3 |
| 47-41 | phenyl | H | Me | S | H | H | Cl | H | nonafluoro-2-butyl | H | CF3 |
| 47-42 | phenyl | H | Me | S | H | H | CF3 | H | nonafluoro-2-butyl | H | CF3 |
| 47-43 | phenyl | H | Me | O | H | H | Br | H | heptafluoroisopropyl | H | OCF3 |
| 47-44 | phenyl | H | Me | O | H | H | I | H | heptafluoroisopropyl | H | CF3 |
| 47-45 | phenyl | H | Me | O | H | H | CF3 | H | heptafluoroisopropyl | H | CF3 |
| 47-46 | phenyl | H | Me | O | H | H | Cl | H | nonafluoro-2-butyl | H | OCF3 |
| 47-47 | phenyl | H | Me | O | H | H | Br | H | nonafluoro-2-butyl | H | CF3 |
| 47-48 | phenyl | H | Me | O | H | H | CF3 | H | nonafluoro-2-butyl | H | CF3 |
| 47-49 | phenyl | H | Me | NH | H | H | I | H | heptafluoroisopropyl | H | OCF3 |
| 47-50 | phenyl | H | Me | NH | H | H | Cl | H | heptafluoroisopropyl | H | CF3 |
| 47-51 | phenyl | H | Me | NH | H | H | CF3 | H | heptafluoroisopropyl | H | CF3 |
| 47-52 | phenyl | H | Me | NH | H | H | Br | H | nonafluoro-2-butyl | H | OCF3 |
| 47-53 | phenyl | H | Me | NH | H | H | I | H | nonafluoro-2-butyl | H | CF3 |
| 47-54 | phenyl | H | Me | NH | H | H | CF3 | H | nonafluoro-2-butyl | H | CF3 |
| 47-55 | phenyl | Me | Me | S | H | H | Cl | H | heptafluoroisopropyl | H | OCF3 |
| 47-56 | phenyl | Me | Me | S | H | H | Br | H | heptafluoroisopropyl | H | CF3 |
| 47-57 | phenyl | Me | Me | S | H | H | CF3 | H | heptafluoroisopropyl | H | CF3 |
| 47-58 | phenyl | Me | Me | S | H | H | I | H | nonafluoro-2-butyl | H | OCF3 |
| 47-59 | phenyl | Me | Me | S | H | H | Cl | H | nonafluoro-2-butyl | H | CF3 |
| 47-60 | phenyl | Me | Me | S | H | H | CF3 | H | nonafluoro-2-butyl | H | CF3 |
| 47-61 | phenyl | Me | Me | O | H | H | Br | H | heptafluoroisopropyl | H | OCF3 |
| 47-62 | phenyl | Me | Me | O | H | H | I | H | heptafluoroisopropyl | H | CF3 |
| 47-63 | phenyl | Me | Me | O | H | H | CF3 | H | heptafluoroisopropyl | H | CF3 |
| 47-64 | phenyl | Me | Me | O | H | H | Cl | H | nonafluoro-2-butyl | H | OCF3 |
| 47-65 | phenyl | Me | Me | O | H | H | Br | H | nonafluoro-2-butyl | H | CF3 |
| 47-66 | phenyl | Me | Me | O | H | H | CF3 | H | nonafluoro-2-butyl | H | CF3 |
| 47-67 | phenyl | Me | Me | NH | H | H | I | H | heptafluoroisopropyl | H | OCF3 |

TABLE 47-continued

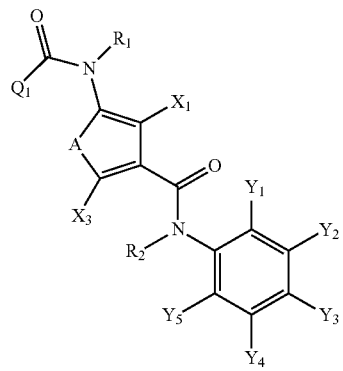

| compound number | $Q_1$ | $R_1$ | $R_2$ | A | $X_1$ | $X_3$ | $Y_1$ | $Y_2$ | $Y_3$ | $Y_4$ | $Y_5$ |
|---|---|---|---|---|---|---|---|---|---|---|---|
| 47-68 | phenyl | Me | Me | NH | H | H | Cl | H | heptafluoroisopropyl | H | CF3 |
| 47-69 | phenyl | Me | Me | NH | H | H | CF3 | H | heptafluoroisopropyl | H | CF3 |
| 47-70 | phenyl | Me | Me | NH | H | H | Br | H | nonafluoro-2-butyl | H | OCF3 |
| 47-71 | phenyl | Me | Me | NH | H | H | I | H | nonafluoro-2-butyl | H | CF3 |
| 47-72 | phenyl | Me | Me | NH | H | H | CF3 | H | nonafluoro-2-butyl | H | CF3 |
| 47-73 | phenyl | Me | H | S | H | H | Cl | F | heptafluoroisopropyl | H | OCF3 |
| 47-74 | phenyl | H | H | S | H | H | Br | H | heptafluoroisopropyl | F | CF3 |
| 47-75 | phenyl | H | H | S | H | H | CF3 | Cl | heptafluoroisopropyl | H | CF3 |
| 47-76 | phenyl | H | H | S | H | H | I | H | nonafluoro-2-butyl | Cl | OCF3 |
| 47-77 | phenyl | H | H | S | H | H | Cl | Br | nonafluoro-2-butyl | H | CF3 |
| 47-78 | phenyl | H | H | S | H | H | CF3 | H | nonafluoro-2-butyl | Br | CF3 |
| 47-79 | phenyl | H | H | O | H | H | Br | I | heptafluoroisopropyl | H | OCF3 |
| 47-80 | phenyl | Me | H | O | H | H | I | H | heptafluoroisopropyl | I | CF3 |
| 47-81 | phenyl | H | H | O | H | H | CF3 | Me | heptafluoroisopropyl | H | CF3 |
| 47-82 | phenyl | H | H | O | H | H | Cl | H | nonafluoro-2-butyl | Me | OCF3 |
| 47-83 | phenyl | H | H | O | H | H | Br | F | nonafluoro-2-butyl | F | CF3 |
| 47-84 | phenyl | H | H | O | H | H | CF3 | Cl | nonafluoro-2-butyl | Cl | CF3 |
| 47-85 | phenyl | H | H | NH | H | H | I | Br | heptafluoroisopropyl | Br | OCF3 |
| 47-86 | phenyl | H | H | NH | H | H | Cl | I | heptafluoroisopropyl | I | CF3 |
| 47-87 | phenyl | Me | H | NH | H | H | CF3 | F | heptafluoroisopropyl | Me | CF3 |
| 47-88 | phenyl | H | H | NH | H | H | Br | Cl | nonafluoro-2-butyl | Me | OCF3 |
| 47-89 | phenyl | H | H | NH | H | H | I | Br | nonafluoro-2-butyl | Me | CF3 |
| 47-90 | phenyl | H | H | NH | H | H | CF3 | I | nonafluoro-2-butyl | Me | CF3 |

TABLE 48

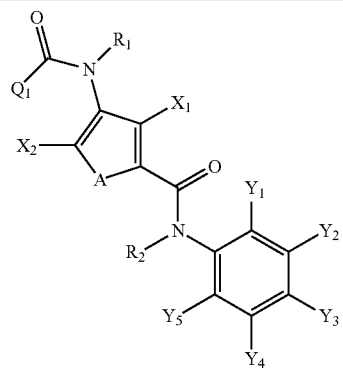

| compound number | $Q_1$ | $R_1$ | $R_2$ | A | $X_1$ | $X_2$ | $Y_1$ | $Y_2$ | $Y_3$ | $Y_4$ | $Y_5$ |
|---|---|---|---|---|---|---|---|---|---|---|---|
| 48-1 | phenyl | H | H | S | H | H | Cl | H | heptafluoroisopropyl | H | OCF3 |
| 48-2 | phenyl | H | H | S | H | H | Br | H | heptafluoroisopropyl | H | CF3 |
| 48-3 | phenyl | H | H | S | H | H | CF3 | H | heptafluoroisopropyl | H | CF3 |
| 48-4 | phenyl | H | H | S | H | H | I | H | nonafluoro-2-butyl | H | OCF3 |
| 48-5 | phenyl | H | H | S | H | H | Cl | H | nonafluoro-2-butyl | H | CF3 |
| 48-6 | phenyl | H | H | S | H | H | CF3 | H | nonafluoro-2-butyl | H | CF3 |
| 48-7 | phenyl | H | H | O | H | H | Br | H | heptafluoroisopropyl | H | OCF3 |
| 48-8 | phenyl | H | H | O | H | H | I | H | heptafluoroisopropyl | H | CF3 |
| 48-9 | phenyl | H | H | O | H | H | CF3 | H | heptafluoroisopropyl | H | CF3 |

TABLE 48-continued

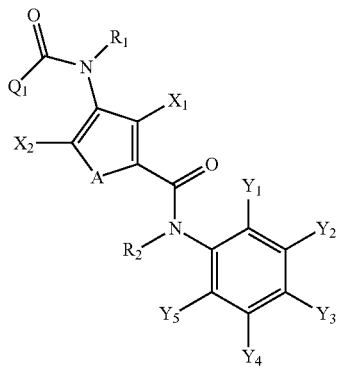

| compound number | $Q_1$ | $R_1$ | $R_2$ | A | $X_1$ | $X_2$ | $Y_1$ | $Y_2$ | $Y_3$ | $Y_4$ | $Y_5$ |
|---|---|---|---|---|---|---|---|---|---|---|---|
| 48-10 | phenyl | H | H | O | H | H | Cl | H | nonafluoro-2-butyl | H | OCF3 |
| 48-11 | phenyl | H | H | O | H | H | Br | H | nonafluoro-2-butyl | H | CF3 |
| 48-12 | phenyl | H | H | O | H | H | CF3 | H | nonafluoro-2-butyl | H | CF3 |
| 48-13 | phenyl | H | H | NH | H | H | I | H | heptafluoroisopropyl | H | OCF3 |
| 48-14 | phenyl | H | H | NH | H | H | Cl | H | heptafluoroisopropyl | H | CF3 |
| 48-15 | phenyl | H | H | NH | H | H | CF3 | H | heptafluoroisopropyl | H | CF3 |
| 48-16 | phenyl | H | H | NH | H | Fl | Br | H | nonafluoro-2-butyl | H | OCF3 |
| 48-17 | phenyl | H | H | NH | H | H | I | H | nonafluoro-2-butyl | H | CF3 |
| 48-18 | phenyl | H | H | NH | H | H | CF3 | H | nonafluoro-2-butyl | H | CF3 |
| 48-19 | phenyl | Me | H | S | H | H | Cl | H | heptafluoroisopropyl | H | OCF3 |
| 48-20 | phenyl | Me | H | S | H | H | Br | H | heptafluoroisopropyl | H | CF3 |
| 48-21 | phenyl | Me | H | S | H | H | CF3 | H | heptafluoroisopropyl | H | CF3 |
| 48-22 | phenyl | Me | H | S | H | H | I | H | nonafluoro-2-butyl | H | OCF3 |
| 48-23 | phenyl | Me | H | S | H | H | Cl | H | nonafluoro-2-butyl | H | CF3 |
| 48-24 | phenyl | Me | H | S | H | H | CF3 | H | nonafluoro-2-butyl | H | CF3 |
| 48-25 | phenyl | Me | H | O | H | H | Br | H | heptafluoroisopropyl | H | OCF3 |
| 48-26 | phenyl | Me | H | O | H | H | I | H | heptafluoroisopropyl | H | CF3 |
| 48-27 | phenyl | Me | H | O | H | H | CF3 | H | heptafluoroisopropyl | H | CF3 |
| 48-28 | phenyl | Me | H | O | H | H | Cl | H | nonafluoro-2-butyl | H | OCF3 |
| 48-29 | phenyl | Me | H | O | H | H | Br | H | nonafluoro-2-butyl | H | CF3 |
| 48-30 | phenyl | Me | H | O | H | H | CF3 | H | nonafluoro-2-butyl | H | CF3 |
| 48-31 | phenyl | Me | H | NH | H | H | I | H | heptafluoroisopropyl | H | OCF3 |
| 48-32 | phenyl | Me | H | NH | H | H | Cl | H | heptafluoroisopropyl | H | CF3 |
| 48-33 | phenyl | Me | H | NH | H | H | CF3 | H | heptafluoroisopropyl | H | CF3 |
| 48-34 | phenyl | Me | H | NH | H | H | Br | H | nonafluoro-2-butyl | H | OCF3 |
| 48-35 | phenyl | Me | H | NH | H | H | I | H | nonafluoro-2-butyl | H | CF3 |
| 48-36 | phenyl | Me | H | NH | H | H | CF3 | H | nonafluoro-2-butyl | H | CF3 |
| 48-37 | phenyl | H | Me | S | H | H | Cl | H | heptafluoroisopropyl | H | OCF3 |
| 48-38 | phenyl | H | Me | S | H | H | Br | H | heptafluoroisopropyl | H | CF3 |
| 48-39 | phenyl | H | Me | S | H | H | CF3 | H | heptafluoroisopropyl | H | CF3 |
| 48-40 | phenyl | H | Me | S | H | H | I | H | nonafluoro-2-butyl | H | OCF3 |
| 48-41 | phenyl | H | Me | S | H | H | Cl | H | nonafluoro-2-butyl | H | CF3 |
| 48-42 | phenyl | H | Me | S | H | H | CF3 | H | nonafluoro-2-butyl | H | CF3 |
| 48-43 | phenyl | H | Me | O | H | H | Br | H | heptafluoroisopropyl | H | OCF3 |
| 48-44 | phenyl | H | Me | O | H | H | I | H | heptafluoroisopropyl | H | CF3 |
| 48-45 | phenyl | H | Me | O | H | H | CF3 | H | heptafluoroisopropyl | H | CF3 |
| 48-46 | phenyl | H | Me | O | H | H | Cl | H | nonafluoro-2-butyl | H | OCF3 |
| 48-47 | phenyl | H | Me | O | H | H | Br | H | nonafluoro-2-butyl | H | CF3 |
| 48-48 | phenyl | H | Me | O | H | H | CF3 | H | nonafluoro-2-butyl | H | CF3 |
| 48-49 | phenyl | H | Me | NH | H | H | I | H | heptafluoroisopropyl | H | OCF3 |
| 48-50 | phenyl | H | Me | NH | H | H | Cl | H | heptafluoroisopropyl | H | CF3 |
| 48-51 | phenyl | H | Me | NH | H | H | CF3 | H | heptafluoroisopropyl | H | CF3 |
| 48-52 | phenyl | H | Me | NH | H | H | Br | H | nonafluoro-2-butyl | H | OCF3 |
| 48-53 | phenyl | H | Me | NH | H | H | I | H | nonafluoro-2-butyl | H | CF3 |
| 48-54 | phenyl | H | Me | NH | H | H | CF3 | H | nonafluoro-2-butyl | H | CF3 |
| 48-55 | phenyl | Me | Me | S | H | H | Cl | H | heptafluoroisopropyl | H | OCF3 |
| 48-56 | phenyl | Me | Me | S | H | H | Br | H | heptafluoroisopropyl | H | CF3 |
| 48-57 | phenyl | Me | Me | S | H | H | CF3 | H | heptafluoroisopropyl | H | CF3 |
| 48-58 | phenyl | Me | Me | S | H | H | I | H | nonafluoro-2-butyl | H | OCF3 |
| 48-59 | phenyl | Me | Me | S | H | H | Cl | H | nonafluoro-2-butyl | H | CF3 |
| 48-60 | phenyl | Me | Me | S | H | H | CF3 | H | nonafluoro-2-butyl | H | CF3 |
| 48-61 | phenyl | Me | Me | O | H | H | Br | H | heptafluoroisopropyl | H | OCF3 |
| 48-62 | phenyl | Me | Me | O | H | H | I | H | heptafluoroisopropyl | H | CF3 |
| 48-63 | phenyl | Me | Me | O | H | H | CF3 | H | heptafluoroisopropyl | H | CF3 |
| 48-64 | phenyl | Me | Me | O | H | H | Cl | H | nonafluoro-2-butyl | H | OCF3 |
| 48-65 | phenyl | Me | Me | O | H | H | Br | H | nonafluoro-2-butyl | H | CF3 |
| 48-66 | phenyl | Me | Me | O | H | H | CF3 | H | nonafluoro-2-butyl | H | CF3 |
| 48-67 | phenyl | Me | Me | NH | H | H | I | H | heptafluoroisopropyl | H | OCF3 |
| 48-68 | phenyl | Me | Me | NH | H | H | Cl | H | heptafluoroisopropyl | H | CF3 |

TABLE 48-continued

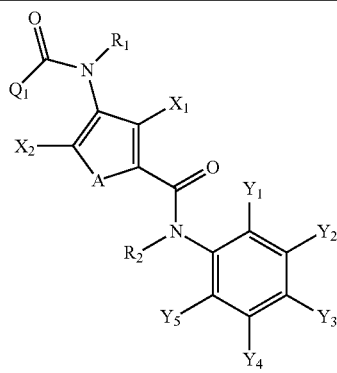

| compound number | Q₁ | R₁ | R₂ | A | X₁ | X₂ | Y₁ | Y₂ | Y₃ | Y₄ | Y₅ |
|---|---|---|---|---|---|---|---|---|---|---|---|
| 48-69 | phenyl | Me | Me | NH | H | H | CF3 | H | heptafluoroisopropyl | H | CF3 |
| 48-70 | phenyl | Me | Me | NH | H | H | Br | H | nonafluoro-2-butyl | H | OCF3 |
| 48-71 | phenyl | Me | Me | NH | H | H | I | H | nonafluoro-2-butyl | H | CF3 |
| 48-72 | phenyl | Me | Me | NH | H | H | CF3 | H | nonafluoro-2-butyl | H | CF3 |
| 48-73 | phenyl | Me | H | S | H | H | Cl | F | heptafluoroisopropyl | H | OCF3 |
| 48-74 | phenyl | H | H | S | H | H | Br | H | heptafluoroisopropyl | F | CF3 |
| 48-75 | phenyl | H | H | S | H | H | CF3 | Cl | heptafluoroisopropyl | H | CF3 |
| 48-76 | phenyl | H | H | S | H | H | I | H | nonafluoro-2-butyl | Cl | OCF3 |
| 48-77 | phenyl | H | H | S | H | H | Cl | Br | nonafluoro-2-butyl | H | CF3 |
| 48-78 | phenyl | H | H | S | H | H | CF3 | H | nonafluoro-2-butyl | Br | CF3 |
| 48-79 | phenyl | H | H | O | H | H | Br | I | heptafluoroisopropyl | H | OCF3 |
| 48-80 | phenyl | Me | H | O | H | H | I | H | heptafluoroisopropyl | I | CF3 |
| 48-81 | phenyl | H | H | O | H | H | CF3 | Me | heptafluoroisopropyl | H | CF3 |
| 48-82 | phenyl | H | H | O | H | H | Cl | H | nonafluoro-2-butyl | Me | OCF3 |
| 48-83 | phenyl | H | H | O | H | H | Br | F | nonafluoro-2-butyl | F | CF3 |
| 48-84 | phenyl | H | H | O | H | H | CF3 | Cl | nonafluoro-2-butyl | Cl | CF3 |
| 48-85 | phenyl | H | H | NH | H | H | I | Br | heptafluoroisopropyl | Br | OCF3 |
| 48-86 | phenyl | H | H | NH | H | H | Cl | I | heptafluoroisopropyl | I | CF3 |
| 48-87 | phenyl | Me | H | NH | H | H | CF3 | F | heptafluoroisopropyl | Me | CF3 |
| 48-88 | phenyl | H | H | NH | H | H | Br | Cl | nonafluoro-2-butyl | Me | OCF3 |
| 48-89 | phenyl | H | H | NH | H | H | I | Br | nonafluoro-2-butyl | Me | CF3 |
| 48-90 | phenyl | H | H | NH | H | H | CF3 | I | nonafluoro-2-butyl | Me | CF3 |

TABLE 49

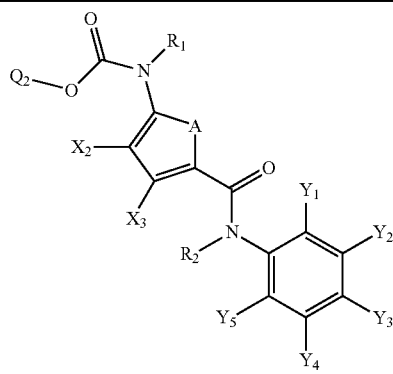

| compound number | Q₂ | R₁ | R₂ | A | X₂ | X₃ | Y₁ | Y₂ | Y₃ | Y₄ | Y₅ |
|---|---|---|---|---|---|---|---|---|---|---|---|
| 49-1 | 2,2,2-trichloroethyl | H | H | S | H | H | Cl | H | heptafluoroisopropyl | H | OCF3 |
| 49-2 | 2,2,2-trichloroethyl | H | H | S | H | H | Br | H | heptafluoroisopropyl | H | CF3 |
| 49-3 | 2,2,2-trichloroethyl | H | H | S | H | H | CF3 | H | heptafluoroisopropyl | H | CF3 |
| 49-4 | 2,2,2-trichloroethyl | H | H | S | H | H | I | H | nonafluoro-2-butyl | H | OCF3 |
| 49-5 | 2,2,2-trichloroethyl | H | H | S | H | H | Cl | H | nonafluoro-2-butyl | H | CF3 |
| 49-6 | 2,2,2-trichloroethyl | H | H | S | H | H | CF3 | H | nonafluoro-2-butyl | H | CF3 |
| 49-7 | 2,2,2-trichloroethyl | H | H | O | H | H | Br | H | heptafluoroisopropyl | H | OCF3 |
| 49-8 | 2,2,2-trichloroethyl | H | H | O | H | H | I | H | heptafluoroisopropyl | H | CF3 |
| 49-9 | 2,2,2-trichloroethyl | H | H | O | H | H | CF3 | H | heptafluoroisopropyl | H | CF3 |
| 49-10 | 2,2,2-trichloroethyl | H | H | O | H | H | Cl | H | nonafluoro-2-butyl | H | OCF3 |

TABLE 49-continued

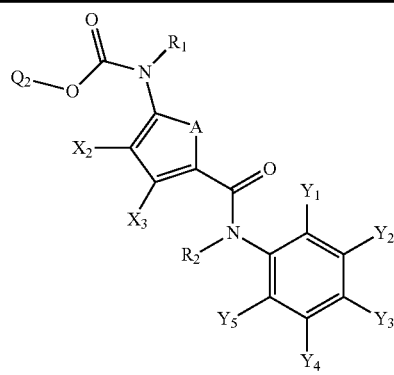

| compound number | Q₂ | R₁ | R₂ | A | X₂ | X₃ | Y₁ | Y₂ | Y₃ | Y₄ | Y₅ |
|---|---|---|---|---|---|---|---|---|---|---|---|
| 49-11 | 2,2,2-trichloroethyl | H | H | O | H | H | Br | H | nonafluoro-2-butyl | H | CF3 |
| 49-12 | 2,2,2-trichloroethyl | H | H | O | H | H | CF3 | H | nonafluoro-2-butyl | H | CF3 |
| 49-13 | 2,2,2-trichloroethyl | H | H | NH | H | H | I | H | heptafluoroisopropyl | H | OCF3 |
| 49-14 | 2,2,2-trichloroethyl | H | H | NH | H | H | Cl | H | heptafluoroisopropyl | H | CF3 |
| 49-15 | 2,2,2-trichloroethyl | H | H | NH | H | H | CF3 | H | heptafluoroisopropyl | H | CF3 |
| 49-16 | 2,2,2-trichloroethyl | H | H | NH | H | H | Br | H | nonafluoro-2-butyl | H | OCF3 |
| 49-17 | 2,2,2-trichloroethyl | H | H | NH | H | H | I | H | nonafluoro-2-butyl | H | CF3 |
| 49-18 | 2,2,2-trichloroethyl | H | H | NH | H | H | CF3 | H | nonafluoro-2-butyl | H | CF3 |
| 49-19 | 2,2,2-trichloroethyl | Me | H | S | H | H | Cl | H | heptafluoroisopropyl | H | OCF3 |
| 49-20 | 2,2,2-trichloroethyl | Me | H | S | H | H | Br | H | heptafluoroisopropyl | H | CF3 |
| 49-21 | 2,2,2-trichloroethyl | Me | H | S | H | H | CF3 | H | heptafluoroisopropyl | H | CF3 |
| 49-22 | 2,2,2-trichloroethyl | Me | H | S | H | H | I | H | nonafluoro-2-butyl | H | OCF3 |
| 49-23 | 2,2,2-trichloroethyl | Me | H | S | H | H | Cl | H | nonafluoro-2-butyl | H | CF3 |
| 49-24 | 2,2,2-trichloroethyl | Me | H | S | H | H | CF3 | H | nonafluoro-2-butyl | H | CF3 |
| 49-25 | 2,2,2-trichloroethyl | Me | H | O | H | H | Br | H | heptafluoroisopropyl | H | OCF3 |
| 49-26 | 2,2,2-trichloroethyl | Me | H | O | H | H | I | H | heptafluoroisopropyl | H | CF3 |
| 49-27 | 2,2,2-trichloroethyl | Me | H | O | H | H | CF3 | H | heptafluoroisopropyl | H | CF3 |
| 49-28 | 2,2,2-trichloroethyl | Me | H | O | H | H | Cl | H | nonafluoro-2-butyl | H | OCF3 |
| 49-29 | 2,2,2-trichloroethyl | Me | H | O | H | H | Br | H | nonafluoro-2-butyl | H | CF3 |
| 49-30 | 2,2,2-trichloroethyl | Me | H | O | H | H | CF3 | H | nonafluoro-2-butyl | H | CF3 |
| 49-31 | 2,2,2-trichloroethyl | Me | H | NH | H | H | I | H | heptafluoroisopropyl | H | OCF3 |
| 49-32 | 2,2,2-trichloroethyl | Me | H | NH | H | H | Cl | H | heptafluoroisopropyl | H | CF3 |
| 49-33 | 2,2,2-trichloroethyl | Me | H | NH | H | H | CF3 | H | heptafluoroisopropyl | H | CF3 |
| 49-34 | 2,2,2-trichloroethyl | Me | H | NH | H | H | Br | H | nonafluoro-2-butyl | H | OCF3 |
| 49-35 | 2,2,2-trichloroethyl | Me | H | NH | H | H | I | H | nonafluoro-2-butyl | H | CF3 |
| 49-36 | 2,2,2-trichloroethyl | Me | H | NH | H | H | CF3 | H | nonafluoro-2-butyl | H | CF3 |
| 49-37 | 2,2,2-trichloroethyl | H | Me | S | H | H | Cl | H | heptafluoroisopropyl | H | OCF3 |
| 49-38 | 2,2,2-trichloroethyl | H | Me | S | H | H | Br | H | heptafluoroisopropyl | H | CF3 |
| 49-39 | 2,2,2-trichloroethyl | H | Me | S | H | H | CF3 | H | heptafluoroisopropyl | H | CF3 |
| 49-40 | 2,2,2-trichloroethyl | H | Me | S | H | H | I | H | nonafluoro-2-butyl | H | OCF3 |
| 49-41 | 2,2,2-trichloroethyl | H | Me | S | H | H | Cl | H | nonafluoro-2-butyl | H | CF3 |
| 49-42 | 2,2,2-trichloroethyl | H | Me | S | H | H | CF3 | H | nonafluoro-2-butyl | H | CF3 |
| 49-43 | 2,2,2-trichloroethyl | H | Me | O | H | H | Br | H | heptafluoroisopropyl | H | OCF3 |
| 49-44 | 2,2,2-trichloroethyl | H | Me | O | H | H | I | H | heptafluoroisopropyl | H | CF3 |
| 49-45 | 2,2,2-trichloroethyl | H | Me | O | H | H | CF3 | H | heptafluoroisopropyl | H | CF3 |
| 49-46 | 2,2,2-trichloroethyl | H | Me | O | H | H | Cl | H | nonafluoro-2-butyl | H | OCF3 |
| 49-47 | 2,2,2-trichloroethyl | H | Me | O | H | H | Br | H | nonafluoro-2-butyl | H | CF3 |
| 49-48 | 2,2,2-trichloroethyl | H | Me | O | H | H | CF3 | H | nonafluoro-2-butyl | H | CF3 |
| 49-49 | 2,2,2-trichloroethyl | H | Me | NH | H | H | I | H | heptafluoroisopropyl | H | OCF3 |
| 49-50 | 2,2,2-trichloroethyl | H | Me | NH | H | H | Cl | H | heptafluoroisopropyl | H | CF3 |
| 49-51 | 2,2,2-trichloroethyl | H | Me | NH | H | H | CF3 | H | heptafluoroisopropyl | H | CF3 |
| 49-52 | 2,2,2-trichloroethyl | H | Me | NH | H | H | Br | H | nonafluoro-2-butyl | H | OCF3 |
| 49-53 | 2,2,2-trichloroethyl | H | Me | NH | H | H | I | H | nonafluoro-2-butyl | H | CF3 |
| 49-54 | 2,2,2-trichloroethyl | H | Me | NH | H | H | CF3 | H | nonafluoro-2-butyl | H | CF3 |
| 49-55 | 2,2,2-trichloroethyl | Me | Me | S | H | H | Cl | H | heptafluoroisopropyl | H | OCF3 |
| 49-56 | 2,2,2-trichloroethyl | Me | Me | S | H | H | Br | H | heptafluoroisopropyl | H | CF3 |
| 49-57 | 2,2,2-trichloroethyl | Me | Me | S | H | H | CF3 | H | heptafluoroisopropyl | H | CF3 |
| 49-58 | 2,2,2-trichloroethyl | Me | Me | S | H | H | I | H | nonafluoro-2-butyl | H | OCF3 |
| 49-59 | 2,2,2-trichloroethyl | Me | Me | S | H | H | Cl | H | nonafluoro-2-butyl | H | CF3 |
| 49-60 | 2,2,2-trichloroethyl | Me | Me | S | H | H | CF3 | H | nonafluoro-2-butyl | H | CF3 |
| 49-61 | 2,2,2-trichloroethyl | Me | Me | O | H | H | Br | H | heptafluoroisopropyl | H | OCF3 |
| 49-62 | 2,2,2-trichloroethyl | Me | Me | O | H | H | I | H | heptafluoroisopropyl | H | CF3 |
| 49-63 | 2,2,2-trichloroethyl | Me | Me | O | H | H | CF3 | H | heptafluoroisopropyl | H | CF3 |
| 49-64 | 2,2,2-trichloroethyl | Me | Me | O | H | H | Cl | H | nonafluoro-2-butyl | H | OCF3 |
| 49-65 | 2,2,2-trichloroethyl | Me | Me | O | H | H | Br | H | nonafluoro-2-butyl | H | CF3 |
| 49-66 | 2,2,2-trichloroethyl | Me | Me | O | H | H | CF3 | H | nonafluoro-2-butyl | H | CF3 |
| 49-67 | 2,2,2-trichloroethyl | Me | Me | NH | H | H | I | H | heptafluoroisopropyl | H | OCF3 |
| 49-68 | 2,2,2-trichloroethyl | Me | Me | NH | H | H | Cl | H | heptafluoroisopropyl | H | CF3 |
| 49-69 | 2,2,2-trichloroethyl | Me | Me | NH | H | H | CF3 | H | heptafluoroisopropyl | H | CF3 |

TABLE 49-continued

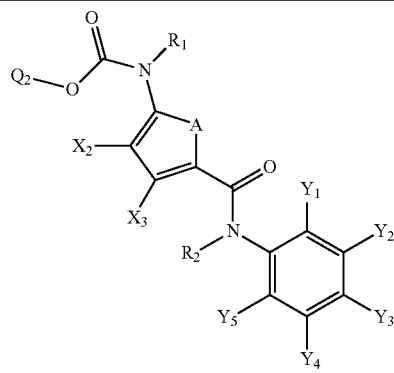

| compound number | Q₂ | R₁ | R₂ | A | X₂ | X₃ | Y₁ | Y₂ | Y₃ | Y₄ | Y₅ |
|---|---|---|---|---|---|---|---|---|---|---|---|
| 49-70 | 2,2,2-trichloroethyl | Me | Me | NH | H | H | Br | H | nonafluoro-2-butyl | H | OCF3 |
| 49-71 | 2,2,2-trichloroethyl | Me | Me | NH | H | H | I | H | nonafluoro-2-butyl | H | CF3 |
| 49-72 | 2,2,2-trichloroethyl | Me | Me | NH | H | H | CF3 | H | nonafluoro-2-butyl | H | CF3 |
| 49-73 | 2,2,2-trichloroethyl | Me | H | S | H | H | Cl | F | heptafluoroisopropyl | H | OCF3 |
| 49-74 | 2,2,2-trichloroethyl | H | H | S | H | H | Br | H | heptafluoroisopropyl | F | CF3 |
| 49-75 | 2,2,2-trichloroethyl | H | H | S | H | H | CF3 | Cl | heptafluoroisopropyl | H | CF3 |
| 49-76 | 2,2,2-trichloroethyl | H | H | S | H | H | I | H | nonafluoro-2-butyl | Cl | OCF3 |
| 49-77 | 2,2,2-trichloroethyl | H | H | S | H | H | Cl | Br | nonafluoro-2-butyl | H | CF3 |
| 49-78 | 2,2,2-trichloroethyl | H | H | S | H | H | CF3 | H | nonafluoro-2-butyl | Br | CF3 |
| 49-79 | 2,2,2-trichloroethyl | H | H | O | H | H | Br | I | heptafluoroisopropyl | H | OCF3 |
| 49-80 | 2,2,2-trichloroethyl | Me | H | O | H | H | I | H | heptafluoroisopropyl | I | CF3 |
| 49-81 | 2,2,2-trichloroethyl | H | H | O | H | H | CF3 | Me | heptafluoroisopropyl | H | CF3 |
| 49-82 | 2,2,2-trichloroethyl | H | H | O | H | H | Cl | H | nonafluoro-2-butyl | Me | OCF3 |
| 49-83 | 2,2,2-trichloroethyl | H | H | O | H | H | Br | F | nonafluoro-2-butyl | F | CF3 |
| 49-84 | 2,2,2-trichloroethyl | H | H | O | H | H | CF3 | Cl | nonafluoro-2-butyl | Cl | CF3 |
| 49-85 | 2,2,2-trichloroethyl | H | H | NH | H | H | I | Br | heptafluoroisopropyl | Br | OCF3 |
| 49-86 | 2,2,2-trichloroethyl | H | H | NH | H | H | Cl | I | heptafluoroisopropyl | I | CF3 |
| 49-87 | 2,2,2-trichloroethyl | Me | H | NH | H | H | CF3 | F | heptafluoroisopropyl | Me | CF3 |
| 49-88 | 2,2,2-trichloroethyl | H | H | NH | H | H | Br | Cl | nonafluoro-2-butyl | Me | OCF3 |
| 49-89 | 2,2,2-trichloroethyl | H | H | NH | H | H | I | Br | nonafluoro-2-butyl | Me | CF3 |
| 49-90 | 2,2,2-trichloroethyl | H | H | NH | H | H | CF3 | I | nonafluoro-2-butyl | Me | CF3 |

TABLE 50

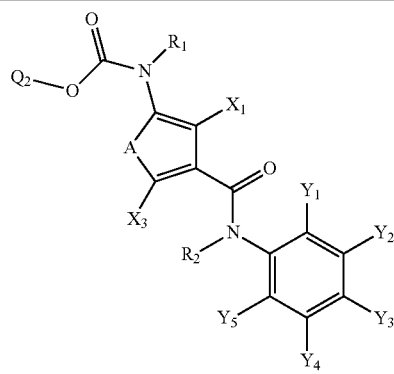

| compound number | Q₂ | R₁ | R₂ | A | X₁ | X₃ | Y₁ | Y₂ | Y₃ | Y₄ | Y₅ |
|---|---|---|---|---|---|---|---|---|---|---|---|
| 50-1 | 2,2,2-trichloroethyl | H | H | S | H | H | Cl | H | heptafluoroisopropyl | H | OCF3 |
| 50-2 | 2,2,2-trichloroethyl | H | H | S | H | H | Br | H | heptafluoroisopropyl | H | CF3 |
| 50-3 | 2,2,2-trichloroethyl | H | H | S | H | H | CF3 | H | heptafluoroisopropyl | H | CF3 |
| 50-4 | 2,2,2-trichloroethyl | H | H | S | H | H | I | H | nonafluoro-2-butyl | H | OCF3 |
| 50-5 | 2,2,2-trichloroethyl | H | H | S | H | H | Cl | H | nonafluoro-2-butyl | H | CF3 |
| 50-6 | 2,2,2-trichloroethyl | H | H | S | H | H | CF3 | H | nonafluoro-2-butyl | H | CF3 |
| 50-7 | 2,2,2-trichloroethyl | H | H | O | H | H | Br | H | heptafluoroisopropyl | H | OCF3 |
| 50-8 | 2,2,2-trichloroethyl | H | H | O | H | H | I | H | heptafluoroisopropyl | H | CF3 |
| 50-9 | 2,2,2-trichloroethyl | H | H | O | H | H | CF3 | H | heptafluoroisopropyl | H | CF3 |
| 50-10 | 2,2,2-trichloroethyl | H | H | O | H | H | Cl | H | nonafluoro-2-butyl | H | OCF3 |
| 50-11 | 2,2,2-trichloroethyl | H | H | O | H | H | Br | H | nonafluoro-2-butyl | H | CF3 |

TABLE 50-continued

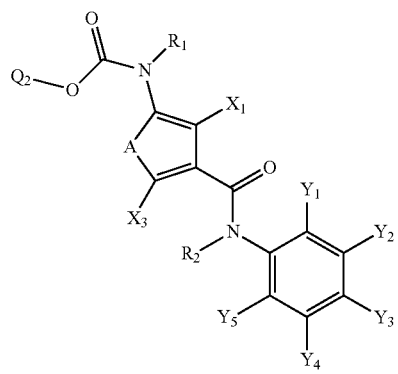

| compound number | $Q_2$ | $R_1$ | $R_2$ | A | $X_1$ | $X_3$ | $Y_1$ | $Y_2$ | $Y_3$ | $Y_4$ | $Y_5$ |
|---|---|---|---|---|---|---|---|---|---|---|---|
| 50-12 | 2,2,2-trichloroethyl | H | H | O | H | H | CF3 | H | nonafluoro-2-butyl | H | CF3 |
| 50-13 | 2,2,2-trichloroethyl | H | H | NH | H | H | I | H | heptafluoroisopropyl | H | OCF3 |
| 50-14 | 2,2,2-trichloroethyl | H | H | NH | H | H | Cl | H | heptafluoroisopropyl | H | CF3 |
| 50-15 | 2,2,2-trichloroethyl | H | H | NH | H | H | CF3 | H | heptafluoroisopropyl | H | CF3 |
| 50-16 | 2,2,2-trichloroethyl | H | H | NH | H | H | Br | H | nonafluoro-2-butyl | H | OCF3 |
| 50-17 | 2,2,2-trichloroethyl | H | H | NH | H | H | I | H | nonafluoro-2-butyl | H | CF3 |
| 50-18 | 2,2,2-trichloroethyl | H | H | NH | H | H | CF3 | H | nonafluoro-2-butyl | H | CF3 |
| 50-19 | 2,2,2-trichloroethyl | Me | H | S | H | H | Cl | H | heptafluoroisopropyl | H | OCF3 |
| 50-20 | 2,2,2-trichloroethyl | Me | H | S | H | H | Br | H | heptafluoroisopropyl | H | CF3 |
| 50-21 | 2,2,2-trichloroethyl | Me | H | S | H | H | CF3 | H | heptafluoroisopropyl | H | CF3 |
| 50-22 | 2,2,2-trichloroethyl | Me | H | S | H | H | I | H | nonafluoro-2-butyl | H | OCF3 |
| 50-23 | 2,2,2-trichloroethyl | Me | H | S | H | H | Cl | H | nonafluoro-2-butyl | H | CF3 |
| 50-24 | 2,2,2-trichloroethyl | Me | H | S | H | H | CF3 | H | nonafluoro-2-butyl | H | CF3 |
| 50-25 | 2,2,2-trichloroethyl | Me | H | O | H | H | Br | H | heptafluoroisopropyl | H | OCF3 |
| 50-26 | 2,2,2-trichloroethyl | Me | H | O | H | H | I | H | heptafluoroisopropyl | H | CF3 |
| 50-27 | 2,2,2-trichloroethyl | Me | H | O | H | H | CF3 | H | heptafluoroisopropyl | H | CF3 |
| 50-28 | 2,2,2-trichloroethyl | Me | H | O | H | H | Cl | H | nonafluoro-2-butyl | H | OCF3 |
| 50-29 | 2,2,2-trichloroethyl | Me | H | O | H | H | Br | H | nonafluoro-2-butyl | H | CF3 |
| 50-30 | 2,2,2-trichloroethyl | Me | H | O | H | H | CF3 | H | nonafluoro-2-butyl | H | CF3 |
| 50-31 | 2,2,2-trichloroethyl | Me | H | NH | H | H | I | H | heptafluoroisopropyl | H | OCF3 |
| 50-32 | 2,2,2-trichloroethyl | Me | H | NH | H | H | Cl | H | heptafluoroisopropyl | H | CF3 |
| 50-33 | 2,2,2-trichloroethyl | Me | H | NH | H | H | CF3 | H | heptafluoroisopropyl | H | CF3 |
| 50-34 | 2,2,2-trichloroethyl | Me | H | NH | H | H | Br | H | nonafluoro-2-butyl | H | OCF3 |
| 50-35 | 2,2,2-trichloroethyl | Me | H | NH | H | H | I | H | nonafluoro-2-butyl | H | CF3 |
| 50-36 | 2,2,2-trichloroethyl | Me | H | NH | H | H | CF3 | H | nonafluoro-2-butyl | H | CF3 |
| 50-37 | 2,2,2-trichloroethyl | H | Me | S | H | H | Cl | H | heptafluoroisopropyl | H | OCF3 |
| 50-38 | 2,2,2-trichloroethyl | H | Me | S | H | H | Br | H | heptafluoroisopropyl | H | CF3 |
| 50-39 | 2,2,2-trichloroethyl | H | Me | S | H | H | CF3 | H | heptafluoroisopropyl | H | CF3 |
| 50-40 | 2,2,2-trichloroethyl | H | Me | S | H | H | I | H | nonafluoro-2-butyl | H | OCF3 |
| 50-41 | 2,2,2-trichloroethyl | H | Me | S | H | H | Cl | H | nonafluoro-2-butyl | H | CF3 |
| 50-42 | 2,2,2-trichloroethyl | H | Me | S | H | H | CF3 | H | nonafluoro-2-butyl | H | CF3 |
| 50-43 | 2,2,2-trichloroethyl | H | Me | O | H | H | Br | H | heptafluoroisopropyl | H | OCF3 |
| 50-44 | 2,2,2-trichloroethyl | H | Me | O | H | H | I | H | heptafluoroisopropyl | H | CF3 |
| 50-45 | 2,2,2-trichloroethyl | H | Me | O | H | H | CF3 | H | heptafluoroisopropyl | H | CF3 |
| 50-46 | 2,2,2-trichloroethyl | H | Me | O | H | H | Cl | H | nonafluoro-2-butyl | H | OCF3 |
| 50-47 | 2,2,2-trichloroethyl | H | Me | O | H | H | Br | H | nonafluoro-2-butyl | H | CF3 |
| 50-48 | 2,2,2-trichloroethyl | H | Me | O | H | H | CF3 | H | nonafluoro-2-butyl | H | CF3 |
| 50-49 | 2,2,2-trichloroethyl | H | Me | NH | H | H | I | H | heptafluoroisopropyl | H | OCF3 |
| 50-50 | 2,2,2-trichloroethyl | H | Me | NH | H | H | Cl | H | heptafluoroisopropyl | H | CF3 |
| 50-51 | 2,2,2-trichloroethyl | H | Me | NH | H | H | CF3 | H | heptafluoroisopropyl | H | CF3 |
| 50-52 | 2,2,2-trichloroethyl | H | Me | NH | H | H | Br | H | nonafluoro-2-butyl | H | OCF3 |
| 50-53 | 2,2,2-trichloroethyl | H | Me | NH | H | H | I | H | nonafluoro-2-butyl | H | CF3 |
| 50-54 | 2,2,2-trichloroethyl | H | Me | NH | H | H | CF3 | H | nonafluoro-2-butyl | H | CF3 |
| 50-55 | 2,2,2-trichloroethyl | Me | Me | S | H | H | Cl | H | heptafluoroisopropyl | H | OCF3 |
| 50-56 | 2,2,2-trichloroethyl | Me | Me | S | H | H | Br | H | heptafluoroisopropyl | H | CF3 |
| 50-57 | 2,2,2-trichloroethyl | Me | Me | S | H | H | CF3 | H | heptafluoroisopropyl | H | CF3 |
| 50-58 | 2,2,2-trichloroethyl | Me | Me | S | H | H | I | H | nonafluoro-2-butyl | H | OCF3 |
| 50-59 | 2,2,2-trichloroethyl | Me | Me | S | H | H | Cl | H | nonafluoro-2-butyl | H | CF3 |
| 50-60 | 2,2,2-trichloroethyl | Me | Me | S | H | H | CF3 | H | nonafluoro-2-butyl | H | CF3 |
| 50-61 | 2,2,2-trichloroethyl | Me | Me | O | H | H | Br | H | heptafluoroisopropyl | H | OCF3 |
| 50-62 | 2,2,2-trichloroethyl | Me | Me | O | H | H | I | H | heptafluoroisopropyl | H | CF3 |

TABLE 50-continued

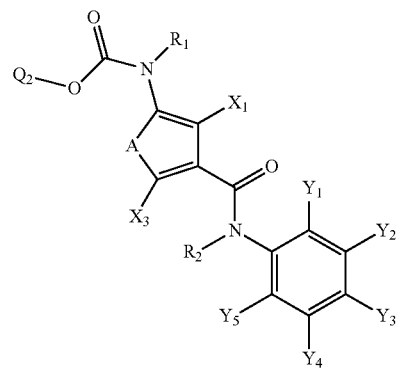

| compound number | Q₂ | R₁ | R₂ | A | X₁ | X₃ | Y₁ | Y₂ | Y₃ | Y₄ | Y₅ |
|---|---|---|---|---|---|---|---|---|---|---|---|
| 50-63 | 2,2,2-trichloroethyl | Me | Me | O | H | H | CF3 | H | heptafluoroisopropyl | H | CF3 |
| 50-64 | 2,2,2-trichloroethyl | Me | Me | O | H | H | Cl | H | nonafluoro-2-butyl | H | OCF3 |
| 50-65 | 2,2,2-trichloroethyl | Me | Me | O | H | H | Br | H | nonafluoro-2-butyl | H | CF3 |
| 50-66 | 2,2,2-trichloroethyl | Me | Me | O | H | H | CF3 | H | nonafluoro-2-butyl | H | CF3 |
| 50-67 | 2,2,2-trichloroethyl | Me | Me | NH | H | H | I | H | heptafluoroisopropyl | H | OCF3 |
| 50-68 | 2,2,2-trichloroethyl | Me | Me | NH | H | H | Cl | H | heptafluoroisopropyl | H | CF3 |
| 50-69 | 2,2,2-trichloroethyl | Me | Me | NH | H | H | CF3 | H | heptafluoroisopropyl | H | CF3 |
| 50-70 | 2,2,2-trichloroethyl | Me | Me | NH | H | H | Br | H | nonafluoro-2-butyl | H | OCF3 |
| 50-71 | 2,2,2-trichloroethyl | Me | Me | NH | H | H | I | H | nonafluoro-2-butyl | H | CF3 |
| 50-72 | 2,2,2-trichloroethyl | Me | Me | NH | H | H | CF3 | H | nonafluoro-2-butyl | H | CF3 |
| 50-73 | 2,2,2-trichloroethyl | Me | H | S | H | H | Cl | F | heptafluoroisopropyl | H | OCF3 |
| 50-74 | 2,2,2-trichloroethyl | H | H | S | H | H | Br | H | heptafluoroisopropyl | F | CF3 |
| 50-75 | 2,2,2-trichloroethyl | H | H | S | H | H | CF3 | Cl | heptafluoroisopropyl | H | CF3 |
| 50-76 | 2,2,2-trichloroethyl | H | H | S | H | H | I | H | nonafluoro-2-butyl | Cl | OCF3 |
| 50-77 | 2,2,2-trichloroethyl | H | H | S | H | H | Cl | Br | nonafluoro-2-butyl | H | CF3 |
| 50-78 | 2,2,2-trichloroethyl | H | H | S | H | H | CF3 | H | nonafluoro-2-butyl | Br | CF3 |
| 50-79 | 2,2,2-trichloroethyl | H | H | O | H | H | Br | I | heptafluoroisopropyl | H | OCF3 |
| 50-80 | 2,2,2-trichloroethyl | Me | H | O | H | H | I | H | heptafluoroisopropyl | I | CF3 |
| 50-81 | 2,2,2-trichloroethyl | H | H | O | H | H | CF3 | Me | heptafluoroisopropyl | H | CF3 |
| 50-82 | 2,2,2-trichloroethyl | H | H | O | H | H | Cl | H | nonafluoro-2-butyl | Me | OCF3 |
| 50-83 | 2,2,2-trichloroethyl | H | H | O | H | H | Br | F | nonafluoro-2-butyl | F | CF3 |
| 50-84 | 2,2,2-trichloroethyl | H | H | O | H | H | CF3 | Cl | nonafluoro-2-butyl | Cl | CF3 |
| 50-85 | 2,2,2-trichloroethyl | H | H | NH | H | H | I | Br | heptafluoroisopropyl | Br | OCF3 |
| 50-86 | 2,2,2-trichloroethyl | H | H | NH | H | H | Cl | I | heptafluoroisopropyl | I | CF3 |
| 50-87 | 2,2,2-trichloroethyl | Me | H | NH | H | H | CF3 | F | heptafluoroisopropyl | Me | CF3 |
| 50-88 | 2,2,2-trichloroethyl | H | H | NH | H | H | Br | Cl | nonafluoro-2-butyl | Me | OCF3 |
| 50-89 | 2,2,2-trichloroethyl | H | H | NH | H | H | I | Br | nonafluoro-2-butyl | Me | CF3 |
| 50-90 | 2,2,2-trichloroethyl | H | H | NH | H | H | CF3 | I | nonafluoro-2-butyl | Me | CF3 |

TABLE 51

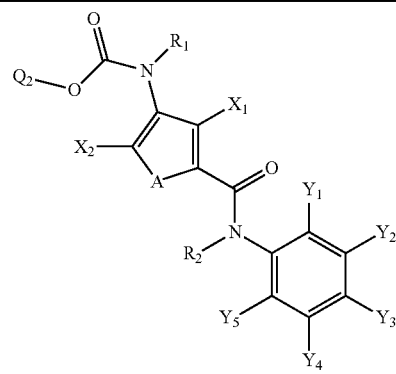

| compound number | Q₂ | R₁ | R₂ | A | X₁ | X₂ | Y₁ | Y₂ | Y₃ | Y₄ | Y₅ |
|---|---|---|---|---|---|---|---|---|---|---|---|
| 51-1 | 2,2,2-trichloroethyl | H | H | S | H | H | Cl | H | heptafluoroisopropyl | H | OCF3 |
| 51-2 | 2,2,2-trichloroethyl | H | H | S | H | H | Br | H | heptafluoroisopropyl | H | CF3 |
| 51-3 | 2,2,2-trichloroethyl | H | H | S | H | H | CF3 | H | heptafluoroisopropyl | H | CF3 |
| 51-4 | 2,2,2-trichloroethyl | H | H | S | H | H | I | H | nonafluoro-2-butyl | H | OCF3 |

TABLE 51-continued

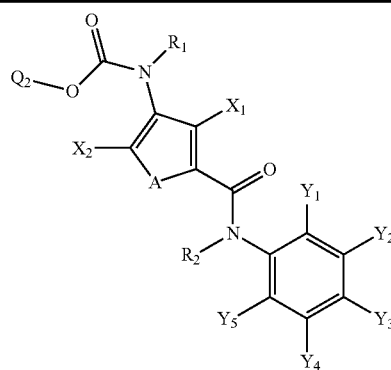

| compound number | Q₂ | R₁ | R₂ | A | X₁ | X₂ | Y₁ | Y₂ | Y₃ | Y₄ | Y₅ |
|---|---|---|---|---|---|---|---|---|---|---|---|
| 51-5 | 2,2,2-trichloroethyl | H | H | S | H | H | Cl | H | nonafluoro-2-butyl | H | CF3 |
| 51-6 | 2,2,2-trichloroethyl | H | H | S | H | H | CF3 | H | nonafluoro-2-butyl | H | CF3 |
| 51-7 | 2,2,2-trichloroethyl | H | H | O | H | H | Br | H | heptafluoroisopropyl | H | OCF3 |
| 51-8 | 2,2,2-trichloroethyl | H | H | O | H | H | I | H | heptafluoroisopropyl | H | CF3 |
| 51-9 | 2,2,2-trichloroethyl | H | H | O | H | H | CF3 | H | heptafluoroisopropyl | H | CF3 |
| 51-10 | 2,2,2-trichloroethyl | H | H | O | H | H | Cl | H | nonafluoro-2-butyl | H | OCF3 |
| 51-11 | 2,2,2-trichloroethyl | H | H | O | H | H | Br | H | nonafluoro-2-butyl | H | CF3 |
| 51-12 | 2,2,2-trichloroethyl | H | H | O | H | H | CF3 | H | nonafluoro-2-butyl | H | CF3 |
| 51-13 | 2,2,2-trichloroethyl | H | H | NH | H | H | I | H | heptafluoroisopropyl | H | OCF3 |
| 51-14 | 2,2,2-trichloroethyl | H | H | NH | H | H | Cl | H | heptafluoroisopropyl | H | CF3 |
| 51-15 | 2,2,2-trichloroethyl | H | H | NH | H | H | CF3 | H | heptafluoroisopropyl | H | CF3 |
| 51-16 | 2,2,2-trichloroethyl | H | H | NH | H | H | Br | H | nonafluoro-2-butyl | H | OCF3 |
| 51-17 | 2,2,2-trichloroethyl | H | H | NH | H | H | I | H | nonafluoro-2-butyl | H | CF3 |
| 51-18 | 2,2,2-trichloroethyl | H | H | NH | H | H | CF3 | H | nonafluoro-2-butyl | H | CF3 |
| 51-19 | 2,2,2-trichloroethyl | Me | H | S | H | H | Cl | H | heptafluoroisopropyl | H | OCF3 |
| 51-20 | 2,2,2-trichloroethyl | Me | H | S | H | H | Br | H | heptafluoroisopropyl | H | CF3 |
| 51-21 | 2,2,2-trichloroethyl | Me | H | S | H | H | CF3 | H | heptafluoroisopropyl | H | CF3 |
| 51-22 | 2,2,2-trichloroethyl | Me | H | S | H | H | I | H | nonafluoro-2-butyl | H | OCF3 |
| 51-23 | 2,2,2-trichloroethyl | Me | H | S | H | H | Cl | H | nonafluoro-2-butyl | H | CF3 |
| 51-24 | 2,2,2-trichloroethyl | Me | H | S | H | H | CF3 | H | nonafluoro-2-butyl | H | CF3 |
| 51-25 | 2,2,2-trichloroethyl | Me | H | O | H | H | Br | H | heptafluoroisopropyl | H | OCF3 |
| 51-26 | 2,2,2-trichloroethyl | Me | H | O | H | H | I | H | heptafluoroisopropyl | H | CF3 |
| 51-27 | 2,2,2-trichloroethyl | Me | H | O | H | H | CF3 | H | heptafluoroisopropyl | H | CF3 |
| 51-28 | 2,2,2-trichloroethyl | Me | H | O | H | H | Cl | H | nonafluoro-2-butyl | H | OCF3 |
| 51-29 | 2,2,2-trichloroethyl | Me | H | O | H | H | Br | H | nonafluoro-2-butyl | H | CF3 |
| 51-30 | 2,2,2-trichloroethyl | Me | H | O | H | H | CF3 | H | nonafluoro-2-butyl | H | CF3 |
| 51-31 | 2,2,2-trichloroethyl | Me | H | NH | H | H | I | H | heptafluoroisopropyl | H | OCF3 |
| 51-32 | 2,2,2-trichloroethyl | Me | H | NH | H | H | Cl | H | heptafluoroisopropyl | H | CF3 |
| 51-33 | 2,2,2-trichloroethyl | Me | H | NH | H | H | CF3 | H | heptafluoroisopropyl | H | CF3 |
| 51-34 | 2,2,2-trichloroethyl | Me | H | NH | H | H | Br | H | nonafluoro-2-butyl | H | OCF3 |
| 51-35 | 2,2,2-trichloroethyl | Me | H | NH | H | H | I | H | nonafluoro-2-butyl | H | CF3 |
| 51-36 | 2,2,2-trichloroethyl | Me | H | NH | H | H | CF3 | H | nonafluoro-2-butyl | H | CF3 |
| 51-37 | 2,2,2-trichloroethyl | H | Me | S | H | H | Cl | H | heptafluoroisopropyl | H | OCF3 |
| 51-38 | 2,2,2-trichloroethyl | H | Me | S | H | H | Br | H | heptafluoroisopropyl | H | CF3 |
| 51-39 | 2,2,2-trichloroethyl | H | Me | S | H | H | CF3 | H | heptafluoroisopropyl | H | CF3 |
| 51-40 | 2,2,2-trichloroethyl | H | Me | S | H | H | I | H | nonafluoro-2-butyl | H | OCF3 |
| 51-41 | 2,2,2-trichloroethyl | H | Me | S | H | H | Cl | H | nonafluoro-2-butyl | H | CF3 |
| 51-42 | 2,2,2-trichloroethyl | H | Me | S | H | H | CF3 | H | nonafluoro-2-butyl | H | CF3 |
| 51-43 | 2,2,2-trichloroethyl | H | Me | O | H | H | Br | H | heptafluoroisopropyl | H | OCF3 |
| 51-44 | 2,2,2-trichloroethyl | H | Me | O | H | H | I | H | heptafluoroisopropyl | H | CF3 |
| 51-45 | 2,2,2-trichloroethyl | H | Me | O | H | H | CF3 | H | heptafluoroisopropyl | H | CF3 |
| 51-46 | 2,2,2-trichloroethyl | H | Me | O | H | H | Cl | H | nonafluoro-2-butyl | H | OCF3 |
| 51-47 | 2,2,2-trichloroethyl | H | Me | O | H | H | Br | H | nonafluoro-2-butyl | H | CF3 |
| 51-48 | 2,2,2-trichloroethyl | H | Me | O | H | H | CF3 | H | nonafluoro-2-butyl | H | CF3 |
| 51-49 | 2,2,2-trichloroethyl | H | Me | NH | H | H | I | H | heptafluoroisopropyl | H | OCF3 |
| 51-50 | 2,2,2-trichloroethyl | H | Me | NH | H | H | Cl | H | heptafluoroisopropyl | H | CF3 |
| 51-51 | 2,2,2-trichloroethyl | H | Me | NH | H | H | CF3 | H | heptafluoroisopropyl | H | CF3 |
| 51-52 | 2,2,2-trichloroethyl | H | Me | NH | H | H | Br | H | nonafluoro-2-butyl | H | OCF3 |
| 51-53 | 2,2,2-trichloroethyl | H | Me | NH | H | H | I | H | nonafluoro-2-butyl | H | CF3 |
| 51-54 | 2,2,2-trichloroethyl | H | Me | NH | H | H | CF3 | H | nonafluoro-2-butyl | H | CF3 |
| 51-55 | 2,2,2-trichloroethyl | Me | Me | S | H | H | Cl | H | heptafluoroisopropyl | H | OCF3 |
| 51-56 | 2,2,2-trichloroethyl | Me | Me | S | H | H | Br | H | heptafluoroisopropyl | H | CF3 |
| 51-57 | 2,2,2-trichloroethyl | Me | Me | S | H | H | CF3 | H | heptafluoroisopropyl | H | CF3 |
| 51-58 | 2,2,2-trichloroethyl | Me | Me | S | H | H | I | H | nonafluoro-2-butyl | H | OCF3 |
| 51-59 | 2,2,2-trichloroethyl | Me | Me | S | H | H | Cl | H | nonafluoro-2-butyl | H | CF3 |
| 51-60 | 2,2,2-trichloroethyl | Me | Me | S | H | H | CF3 | H | nonafluoro-2-butyl | H | CF3 |
| 51-61 | 2,2,2-trichloroethyl | Me | Me | O | H | H | Br | H | heptafluoroisopropyl | H | OCF3 |
| 51-62 | 2,2,2-trichloroethyl | Me | Me | O | H | H | I | H | heptafluoroisopropyl | H | CF3 |
| 51-63 | 2,2,2-trichloroethyl | Me | Me | O | H | H | CF3 | H | heptafluoroisopropyl | H | CF3 |

TABLE 51-continued

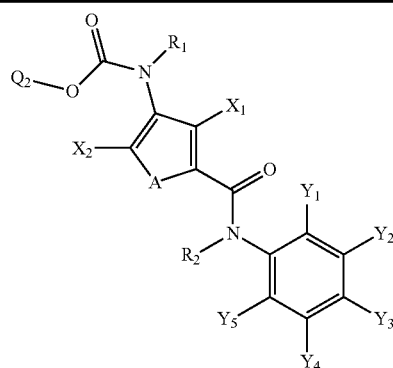

| compound number | Q₂ | R₁ | R₂ | A | X₁ | X₂ | Y₁ | Y₂ | Y₃ | Y₄ | Y₅ |
|---|---|---|---|---|---|---|---|---|---|---|---|
| 51-64 | 2,2,2-trichloroethyl | Me | Me | O | H | H | Cl | H | nonafluoro-2-butyl | H | OCF3 |
| 51-65 | 2,2,2-trichloroethyl | Me | Me | O | H | H | Br | H | nonafluoro-2-butyl | H | CF3 |
| 51-66 | 2,2,2-trichloroethyl | Me | Me | O | H | H | CF3 | H | nonafluoro-2-butyl | H | CF3 |
| 51-67 | 2,2,2-trichloroethyl | Me | Me | NH | H | H | I | H | heptafluoroisopropyl | H | OCF3 |
| 51-68 | 2,2,2-trichloroethyl | Me | Me | NH | H | H | Cl | H | heptafluoroisopropyl | H | CF3 |
| 51-69 | 2,2,2-trichloroethyl | Me | Me | NH | H | H | CF3 | H | heptafluoroisopropyl | H | CF3 |
| 51-70 | 2,2,2-trichloroethyl | Me | Me | NH | H | H | Br | H | nonafluoro-2-butyl | H | OCF3 |
| 51-71 | 2,2,2-trichloroethyl | Me | Me | NH | H | H | I | H | nonafluoro-2-butyl | H | CF3 |
| 51-72 | 2,2,2-trichloroethyl | Me | Me | NH | H | H | CF3 | H | nonafluoro-2-butyl | H | CF3 |
| 51-73 | 2,2,2-trichloroethyl | Me | H | S | H | H | Cl | F | heptafluoroisopropyl | H | OCF3 |
| 51-74 | 2,2,2-trichloroethyl | H | H | S | H | H | Br | H | heptafluoroisopropyl | F | CF3 |
| 51-75 | 2,2,2-trichloroethyl | H | H | S | H | H | CF3 | Cl | heptafluoroisopropyl | H | CF3 |
| 51-76 | 2,2,2-trichloroethyl | H | H | S | H | H | I | H | heptafluoro-2-butyl | Cl | OCF3 |
| 51-77 | 2,2,2-trichloroethyl | H | H | S | H | H | Cl | Br | nonafluoro-2-butyl | H | CF3 |
| 51-78 | 2,2,2-trichloroethyl | H | H | S | H | H | CF3 | H | nonafluoro-2-butyl | Br | CF3 |
| 51-79 | 2,2,2-trichloroethyl | H | H | O | H | H | Br | I | heptafluoroisopropyl | H | OCF3 |
| 51-80 | 2,2,2-trichloroethyl | Me | H | O | H | H | I | H | heptafluoroisopropyl | I | CF3 |
| 51-81 | 2,2,2-trichloroethyl | H | H | O | H | H | CF3 | Me | heptafluoroisopropyl | H | CF3 |
| 51-82 | 2,2,2-trichloroethyl | H | H | O | H | H | Cl | H | nonafluoro-2-butyl | Me | OCF3 |
| 51-83 | 2,2,2-trichloroethyl | H | H | O | H | H | Br | F | nonafluoro-2-butyl | F | CF3 |
| 51-84 | 2,2,2-trichloroethyl | H | H | O | H | H | CF3 | Cl | nonafluoro-2-butyl | Cl | CF3 |
| 51-85 | 2,2,2-trichloroethyl | H | H | NH | H | H | I | Br | heptafluoroisopropyl | Br | OCF3 |
| 51-86 | 2,2,2-trichloroethyl | H | H | NH | H | H | Cl | I | heptafluoroisopropyl | I | CF3 |
| 51-87 | 2,2,2-trichloroethyl | Me | H | NH | H | H | CF3 | F | heptafluoroisopropyl | Me | CF3 |
| 51-88 | 2,2,2-trichloroethyl | H | H | NH | H | H | Br | Cl | nonafluoro-2-butyl | Me | OCF3 |
| 51-89 | 2,2,2-trichloroethyl | H | H | NH | H | H | I | Br | nonafluoro-2-butyl | Me | CF3 |
| 51-90 | 2,2,2-trichloroethyl | H | H | NH | H | H | CF3 | I | nonafluoro-2-butyl | Me | CF3 |

Hereinbelow, Table 52 shows the physical properties of the representative compounds of the amide derivative of the present invention. The ¹H-NMR chemical shift values shown therein are based on tetramethylsilane as an internal standard substance unless specified otherwise.

TABLE 52

| compound number | ¹H-NMR (CDCl₃, ppm) |
|---|---|
| 1-470 | δ 7.55-7.68 (3H, m), 7.80-7.99 (6H, m), 8.58 (1H, s), 8.61 (1H, s), 9.12 (1H, d, J = 1.5 Hz). |
| 1-491 | δ 7.34-7.91 (4H, m), 8.00 (1H, s), 8.08 (2H, dd, J = 1.9, 6.8 Hz), 8.00 (1H, s), 8.49 (1H, s), 8.59 (1H, s), 9.04 (1H, s). |
| 1-506 | δ 7.48 (1H, dd, J = 4.9, 7.81 Hz), 7.83-7.90 (3H, m), 8.00 (1H, s), 8.31 (1H, dd, J = 1.9, 7.8 Hz), 8.34 (1H, s), 8.61 (1H, dd, J = 1.9, 4.9 Hz), 9.09 (1H, s), 9.10 (1H, s). |
| 1-513 | δ 7.54 (1H, d, J = 7.8 Hz), 7.83-7.90 (3H, m), 8.00 (1H, s), 8.21 (1H, dd, J = 2.4, 8.3 Hz), 8.31 (1H, s), 8.51 (1H, s), 9.00 (1H, s), 9.01 (1H, d, J = 7.8 Hz). |
| 1-627 | δ 7.56-7.59 (3H, m), 7.64-7.66 (1H, m), 7.80-7.87 (2H, m), 7.94-7.97 (2H, m), 8.16 (1H, s), 8.46 (1H, s), 8.57 (1H, s), 9.16 (1H, s). |
| 1-1925 | δ 7.52-7.59 (2H, m), 7.65-7.71 (2H, m), 7.93-7.95 (2H, m), 8.00-8.02 (2H, m), 8.12-8.16 (2H, m), 8.52 (1H, d, J = 11.2 Hz). |
| 1-1968 | δ 7.54 (1H, d J = 8.8 Hz), 7.72 (1H, d J = 8.8 Hz), 7.93 (1H, s), 8.09 (1H, s), 8.17-8.18 (2H, m), 8.27 (1H, dd, J = 2.4, 8.8 Hz), 8.38 (1H, d J = 10.8 Hz), 8.98 (1H, d, J = 2.4 Hz). |
| 2-491 | δ 3.81 (3H, broad-s), 7.52-7.84 (8H, m), 7.89 (1H, s), 8.00 (1H, s). |
| 2-513 | δ 3.58 (3H, s), 7.34-7.36 (1H, m), 7.81-8.00 (8H, m). |
| 2-518 | δ 3.59 (3H, s), 7.69 (1H, broad-s), 7.81-8.01 (7H, m), 8.50 (1H, broad-s). |
| 6-38 | δ 7.51-7.62 (4H, m), 7.75-8.00 (8H, m), 8.32 (1H, s). |
| 6-39 | δ 7.22 (1H, dd, J = 8.0, 12.4 Hz), 7.32-7.36 (1H, m), 7.51-7.55 (2H, m), 7.78 (1H, d, J = 7.6 Hz), 7.86-7.90 (3H, m), 8.11 (1H, s), 8.17-8.18 (1H, m), 8.35 (1H, s), 8.62-8.67 (1H, m). |

TABLE 52-continued

| compound number | ¹H-NMR (CDCl₃, ppm) |
|---|---|
| 6-45 | δ 7.57-7.59 (1H, m), 7.65-7.69 (1H, m), 7.77-7.79 (1H, m), 7.89-7.9 (5H, m), 8.14-8.29 (4H, m). |
| 6-46 | δ 7.55-7.59 (1H, m), 7.77-8.07 (10H, m), 8.27 (1H, s). |
| 6-47 | δ 7.01-7.05 (2H, m), 7.44-7.56 (2H, m), 7.78-7.86 (4H, m), 8.03 (1H, s), 8.11 (1H, s), 8.33 (1H, s). |
| 6-57 | δ 7.28-7.32 (1H, m), 7.45-7.67 (4H, m), 7.76-8.02 (5H, m), 8.30 (1H, s). |
| 6-60 | δ 7.50-7.60 (2H, m), 7.78-8.02 (6H, m), 8.19-8.27 (2H, m), 8.91 (1H, s). |
| 6-71 | δ 7.51-7.62 (4H, m), 7.78-7.80 (1H, d, J = 8.0 Hz), 7.90-7.92 (3H, m), 8.06-8.09 (4H, m), 8.34 (1H, s). |
| 6-72 | δ 7.22-7.25 (1H, m), 7.35 (1H, t, J = 8.0 Hz), 7.55-7.60 (2H, m), 7.80 (1H, d, J = 8.0 Hz), 7.92 (1H, d, J = 8.0 Hz), 8.01 (1H, s), 8.10 (2H, s), 8.20 (1H, t, J = 8.0 Hz), 8.37 (1H, s), 8.65 (1H, d, J = 16.8 Hz). |
| 6-78 | δ 7.58 (1H, t, J = 7.8 Hz), 7.68 (1H, t, J = 7.8), 7.80 (1H, d, J = 8.0 Hz), 7.87 (1H, d, 8.0 Hz), 7.95 (1H, d, J = 8.0 Hz), 8.00 (1H, s), 8.09 (2H, s), 8.15 (1H, d, J = 8.0 Hz), 8.23 (1H, s), 8.26 (1H, s), 8.30 (1H, s). |
| 6-79 | δ 7.58 (1H, t, J = 8.2 Hz), 7.79-7.83 (3H, m), 7.97 (2H, s), 8.01 (2H, d, J = 8.0 Hz), 8.09 (2H, s), 8.18 (1H, s), 8.29 (1H, s). |
| 6-80 | δ 7.05 (2H, t, J = 8.2 Hz), 7.48 (1H, t, J = 6.6 Hz), 7.56 (1H, t, J = 7.8 Hz), 7.81 (1H, d, J = 8.0 Hz), 7.89-7.91 (2H, m), 7.98 (1H, s), 8.10 (2H, s), 8.33 (1H, s). |
| 6-90 | δ 7.43-7.46 (1H, m), 7.59 (1H, t, J = 7.2 Hz), 7.82 (1H, d, J = 7.2 Hz), 7.93 (2H, d, J = 9.6 Hz), 8.10 (2H, s), 8.24 (1H, d, J = 6.4 Hz), 8.33 (1H, s), 8.44 (1H, s), 8.56 (1H, s). |
| 6-93 | δ 7.51 (1H, d, J = 8.4 Hz), 7.59 (1H, t, J = 7.6 Hz), 7.81 (1H, d, J = 7.6 Hz), 7.94 (2H, s), 8.10-8.11 (3H, m), 8.20 (1H, d, J = 8.0 Hz), 8.28 (1H, s), 8.91 (1H, s). |
| 6-111 | (DMSO-d₆) δ 7.50-7.60 (4H, m), 7.70-7.73 (1H, m), 7.93-8.00 (3H, m), 8.04-8.08 (1H, m), 8.34-8.36 (2H, m), 10.48 (1H, s), 10.60 (1H, s). |
| 6-147 | (DMSO-d₆) δ 7.55-7.61 (2H, m), 7.74 (1H, d, J = 7.9 Hz), 7.94-7.97 (2H, m), 8.10 (1H, dd, J = 2.0, 7.6 Hz), 8.27 (1H, s), 8.34 (1H, s), 8.54 (1H, dd, J = 2.0, 4.9 Hz), 10.65 (1H, s), 10.89 (1H, s). |
| 6-268 | δ 7.50-7.61 (4H, m), 7.70 (1H, d, J = 7.8 Hz), 7.85-7.92 (4H, m), 7.96-8.01 (2H, m), 8.14 (1H, s), 8.24 (1H, t, J = 2.0 Hz). |
| 6-269 | δ 7.22-7.25 (1H, m), 7.36 (1H, t, J = 8.0 Hz), 7.56-7.57 (2H, m), 7.75 (1H, d, J = 8.0 Hz), 7.90-8.00 (2H, m), 8.07 (1H, s), 8.17-8.20 (2H, m), 8.33 (1H, s), 8.65 (1H, d, J = 16.4 Hz). |
| 6-270 | δ 7.25 (1H, t, J = 8.0 Hz), 7.43-7.53 (2H, m), 7.77-7.81 (4H, m), 7.85 (1H, d, J = 8.0 Hz), 7.91 (1H, s), 8.13 (1H, s), 8.19 (1H, d, J = 8.0 Hz), 8.24 (1H, s). |
| 6-271 | δ 7.09-7.22 (2H, m), 7.55 (1H, t, J = 7.8 Hz), 7.71 (1H, d, J = 8.0 Hz), 7.89-7.93 (4H, m), 8.03 (2H, d, J = 8.0 Hz), 8.14 (1H, s), 8.23 (1H, s). |
| 6-272 | δ 7.40-7.50 (4H, m), 7.56 (1H, t, J = 8.0 Hz), 7.80 (2H, d, J = 8.4 Hz), 7.87 (2H, s), 7.91 (1H, d, J = 7.9 Hz), 8.09 (1H, s), 8.32 (1H, s). |
| 6-288 | δ 7.54-7.55 (1H, m), 7.65-7.66 (1H, m), 7.72 (1H, d, J = 7.8 Hz), 7.85 (1H, d, J = 7.8 Hz), 7.91 (1H, s), 7.95-7.98 (2H, m), 8.13-8.23 (4H, m), 8.36 (1H, s). |
| 6-289 | δ 7.55-7.56 (1H, m), 7.71 (1H, d, J = 7.8 Hz), 7.80 (2H, d, J = 8.3 Hz), 7.91-7.96 (3H, m), 7.99 (2H, d, J = 8.3 Hz), 8.20 (1H, s), 8.21-8.22 (2H, m). |
| 6-290 | δ 7.01-7.05 (2H, m), 7.42-7.44 (1H, m), 7.55 (1H, t, J = 8.0 Hz), 7.75 (1H, d, J = 8.0 Hz), 7.90-7.95 (3H, m), 8.01 (1H, s), 8.14 (1H, s), 8.26 (1H, s). |
| 6-293 | δ 7.14 (1H, t, J = 8.0 Hz), 7.22-7.29 (2H, m), 7.54 (1H, t, J = 7.8 Hz), 7.74 (1H, d, J = 7.8 Hz), 7.84-7.88 (3H, m), 8.11 (1H, s), 8.15 (1H, s), 8.25 (1H, s). |
| 6-300 | δ 7.06-7.59 (2H, m), 7.62 (1H, dd, J = 1.5, 7.8 Hz), 7.81 (1H, d, J = 7.8 Hz), 7.92 (1H, s), 8.08-8.16 (4H, m), 9.35-9.40 (1H, m), 9.51 (1H, broad-s). |
| 6-304 | δ 7.44 (1H, dd, J = 4.9, 7.8 Hz), 7.58 (1H, t, J = 7.8 Hz), 7.75 (1H, d, J = 7.8 Hz), 7.81 (1H, s), 7.92-7.96 (2H, m), 8.15 (1H, s), 8.22-8.26 (2H, m), 8.38 (1H, s), 8.55 (1H, dd, J = 2.0, 4.9 Hz). |
| 6-306 | δ 7.42-7.45 (1H, m), 7.58 (1H, t, J = 7.8 Hz), 7.75 (1H, d, J = 7.8 Hz), 7.88 (1H, broad-s), 7.93-7.95 (2H, m), 8.15 (1H, broad-s), 8.23 (1H, dd, J = 2.0, 7.8 Hz), 8.24 (1H, s), 8.39 (1H, broad-s), 8.55 (1H, dd, J = 2.0, 4.8 Hz). |
| 6-311 | δ 7.45-7.52 (1H, m), 7.74 (1H, d, J = 8.0 Hz), 7.92-7.96 (1H, m), 8.00 (1H, s), 8.14 (1H, s), 8.22-8.23 (3H, m), 8.29 (1H, d, J = 8.0 Hz), 8.91 (1H, s), 9.07 (1H, s). |
| 6-346 | δ 7.50-7.62 (4H, m), 7.71-7.73 (1H, m), 7.89-7.93 (4H, m), 8.02-8.04 (2H, m), 8.13 (1H, s), 8.27 (1H, s). |
| 6-347 | δ 7.19-7.25 (1H, m), 7.33-7.37 (1H, m), 7.52-7.59 (2H, m), 7.73-7.75 (1H, m), 7.89-7.91 (2H, m), 8.09-8.21 (3H, m), 8.31 (1H, s), 8.65 (1H, s). |
| 6-348 | δ 7.30-7.31 (1H, m), 7.48-7.74 (5H, m), 7.91-7.92 (2H, m), 8.02 (1H, s), 8.07 (1H, s), 8.13 (1H, s), 8.25 (1H, s). |
| 6-349 | δ 7.17-7.21 (2H, m), 7.51-7.55 (1H, m), 7.70-7.72 (1H, m), 7.88-7.93 (4H, m), 8.04 (1H, s), 8.11-8.23 (2H, m), 8.23 (1H, s). |
| 6-366 | δ 7.53-7.55 (1H, m), 7.62-7.72 (2H, m), 7.84-7.94 (3H, m), 8.09-8.16 (3H, m), 8.22-8.24 (2H, m), 8.40 (1H, s). |
| 6-367 | δ 7.54-7.58 (1H, m), 7.72-7.74 (1H, m), 7.80-7.83 (2H, m), 7.91-7.94 (2H, m), 8.00-8.07 (2H, m), 8.13 (1H, s), 8.18 (1H, s), 8.23 (1H, s), 8.24 (1H, s). |
| 6-368 | δ 7.01-7.06 (2H, m), 7.44-7.57 (3H, m), 7.74-7.76 (1H, m), 7.86-7.91 (2H, m), 8.07 (1H, s), 8.13-8.14 (1H, m), 8.28 (1H, s). |
| 6-382 | δ 7.43-7.46 (1H, m), 7.56-7.60 (1H, m), 7.76-7.78 (1H, m), 7.90-7.91 (2H, m), 8.02 (1H, s), 8.14 (1H, s), 8.25 (2H, s), 8.43 (1H, s), 8.54-8.56 (1H, m). |
| 6-389 | δ 7.30-7.60 (2H, m), 7.74-7.76 (1H, m), 7.91-7.98 (3H, m), 8.07 (1H, s), 8.14 (1H, s), 8.19-8.23 (2H, m), 8.90 (1H, s). |
| 6-424 | δ 7.51-7.62 (4H, m), 7.73 (1H, d, J = 8.3 Hz), 7.89-7.94 (4H, m), 8.01 (1H, s), 8.10 (1H, s), 8.27 (1H, t, J = 1.5 Hz), 8.35 (1H, s). |
| 6-425 | δ 7.20-7.25 (1H, m), 7.34-7.37 (1H, m), 7.54-7.58 (2H, m), 7.75 (1H, d, J = 7.6 Hz), 7.88-7.95 (2H, m), 8.18-8.22 (2H, m), 8.33-8.34 (2H, m), 8.66 (1H, d, J = 16.4 Hz). |
| 6-426 | δ 7.28-7.30 (1H, m), 7.46-7.66 (5H, m), 7.71-7.94 (2H, m), 8.11-8.24 (3H, m), 8.34 (1H, s). |
| 6-427 | δ 7.18-7.22 (2H, m), 7.52-7.57 (1H, m), 7.73 (1H, d, J = 7.6 Hz), 7.89-8.03 (5H, m), 8.22-8.25 (2H, m), 8.35 (1H, s). |
| 6-428 | δ 7.42-7.50 (4H, m), 7.56 (1H, t, J = 8.0 Hz), 7.75 (1H, d, J = 8.0 Hz), 7.81 (1H, d, J = 7.8 Hz), 7.95-7.96 (2H, m), 8.09 (1H, s), 8.28 (1H, s), 8.36 (1H, s). |
| 6-444 | δ 7.56 (1H, t, J = 7.8 Hz), 7.66 (1H, t, J = 7.8 Hz), 7.73 (1H, t, J = 7.8 Hz), 7.86 (1H, dd, J = 1.5, 7.8 Hz), 7.93-7.96 (2H, m), 8.07 (1H, s), 8.14-8.16 (1H, m), 8.22-8.26 (3H, m), 8.34 (1H, s). |
| 6-445 | δ 7.57 (1H, t, J = 7.8 Hz), 7.74 (1H, d, J = 7.8 Hz), 7.81-7.83 (2H, m), 7.95 (1H, s), 7.97-8.04 (4H, m), 8.12 (1H, broad-s), 8.23 (1H, t, J = 2.0 Hz), 8.35 (1H, broad-s). |

TABLE 52-continued

| compound number | ¹H-NMR (CDCl₃, ppm) |
|---|---|
| 6-446 | δ 7.01-7.05 (2H, m), 7.43-7.57 (2H, m), 7.75-7.77 (1H, m), 7.88-7.94 (3H, m), 8.13 (1H, s), 8.27 (1H, s), 8.35 (1H, s). |
| 6-448 | δ 7.39-7.41 (1H, m), 7.51-7.58 (2H, m), 7.74-7.78 (2H, m), 7.90-7.95 (2H, m), 8.04 (1H, s), 8.15 (1H, s), 8.26 (1H, s), 8.35 (1H, s). |
| 6-449 | δ 7.12-7.36 (3H, m), 7.52-7.58 (1H, m), 7.75-7.95 (4H, m), 8.21-8.35 (3H, m). |
| 6-450 | 6.82-6.86 (1H, m), 7.00-7.01 (1H, m), 7.15 (1H, t, J = 7.8 Hz), 7.56 (1H, t, J = 8.2 Hz), 7.74 (1H, d, J = 8.1 Hz), 7.84 (1H, t, J = 8.8 Hz), 7.90-7.91 (1H, m), 7.95 (1H, s), 8.04 (1H, s), 8.42 (1H, s). |
| 6-451 | δ 7.23-7.69 (8H, m), 7.85 (1H, s), 8.04 (1H, s), 8.42 (1H, s). |
| 6-452 | δ 7.44 (1H, dd, J = 2.0, 8.3 Hz), 7.59 (1H, t, J = 8.3 Hz), 7.66 (1H, d, J = 8.3 Hz), 7.70 (1H, d, J = 2.0 Hz), 7.75 (1H, d, J = 8.3 Hz), 7.86 (2H, broad-s), 7.95 (2H, broad-s), 8.24 (1H, broad-s), 8.37 (1H, broad-s). |
| 6-453 | δ 7.15 (1H, dt, J = 2.4, 8.3 Hz), 7.40 (1H, dd, J = 2.4, 8.3 Hz), 7.60 (1H, t, J = 8.3 Hz), 7.68-7.74 (2H, m), 7.95-8.02 (4H, m), 8.24 (1H, s), 8.35 (1H, s). |
| 6-454 | δ 7.59 (1H, t, J = 7.8 Hz), 7.75 (1H, d, J = 7.8 Hz), 7.93 (1H, s), 7.95-7.99 (3H, m), 8.10 (1H, broad-s), 8.23-8.26 (2H, m), 8.36 (2H, d, J = 1.9 Hz). |
| 6-460 | δ 7.43-7.46 (1H, m), 7.58 (1H, t, J = 7.8 Hz), 7.77 (1H, d, J = 7.8 Hz), 7.91-7.95 (2H, m), 8.01 (1H, s), 8.24 (1H, dd, J = 2.0, 7.8 Hz), 8.28 (1H, s), 8.36 (1H, s), 8.41 (1H, s), 8.54-8.56 (1H, m). |
| 6-461 | δ 7.45 (1H, dd, J = 4.9, 7.3 Hz), 7.59 (1H, t, J = 7.8 Hz), 7.77 (1H, d, J = 7.8 Hz), 7.92-7.99 (3H, m), 8.24-8.29 (2H, m), 8.36-8.39 (2H, m), 8.55 (1H, dd, J = 2.0, 4.9 Hz). |
| 6-467 | δ 7.45-7.60 (2H, m), 7.74 (1H, d, J = 8.0 Hz), 7.95-7.97 (2H, m), 8.03 (1H, s), 8.12 (1H, s), 8.19-8.35 (2H, m), 8.35 (1H, s), 8.90 (1H, s). |
| 6-502 | δ 7.51-7.62 (4H, m), 7.73 (1H, d, J = 7.6 Hz), 7.89-7.95 (4H, m), 8.01 (2H, d, J = 14.4 Hz), 8.27 (1H, s), 8.34 (1H, s). |
| 6-503 | δ 7.20-7.23 (1H, m), 7.34 (1H, t, J = 7.8 Hz), 7.54-7.60 (2H, m), 7.74 (1H, d, J = 7.8 Hz), 7.94 (2H, s), 8.05 (1H, s), 8.19 (1H, t, J = 7.8 Hz), 8.33 (2H, d, J = 12.0 Hz), 8.65 (1H, d, J = 16.0 Hz). |
| 6-504 | δ 7.47-7.69 (5H, m), 7.73 (1H, d, J = 7.8 Hz), 7.93 (2H, s), 8.05 (2H, d, J = 11.0 Hz), 8.25 (1H, s), 8.34 (1H, s). |
| 6-505 | δ 7.20 (2H, t, J = 7.8 Hz), 7.56 (1H, t, J = 8.0 Hz), 7.73 (1H, d, J = 8.2 Hz), 7.91-7.94 (5H, m), 8.02 (1H, s), 8.24 (1H, s), 8.35 (1H, s). |
| 6-522 | δ 7.68-7.75 (2H, m), 7.86 (1H, d, J = 8.2 Hz), 7.93-7.96 (2H, m), 8.08 (1H, s), 8.14 (1H, d, J = 8.0 Hz), 8.24 (2H, d, J = 8.2 Hz), 8.28 (1H, s), 8.33 (1H, s), 8.62 (1H, s). |
| 6-523 | δ 7.57 (1H, t, J = 7.8 Hz), 7.82 (2H, d, J = 8.0 Hz), 7.93-8.02 (6H, m), 8.14 (1H, s), 8.23 (1H, s), 8.34 (1H, s). |
| 6-524 | δ 7.05 (2H, t, J = 8.0 Hz), 7.43-7.50 (1H, m), 7.56 (1H, t, J = 8.0 Hz), 7.75 (1H, d, J = 7.8 Hz), 7.86 (1H, s), 7.92 (2H, d, J = 8.2 Hz), 8.00 (1H, s), 8.27 (1H, s), 8.34 (1H, s). |
| 6-538 | δ 7.45 (1H, t, J = 7.6 Hz), 7.59 (2H, s), 7.70 (1H, d, J = 4.0 Hz), 7.93 (2H, d, J = 7.6 Hz), 7.98 (1H, s), 8.28 (1H, s), 8.34 (2H, d, J = 7.6 Hz), 8.41 (1H, s). |
| 6-545 | δ 7.56-7.60 (1H, m), 7.75 (1H, d, J = 8.0 Hz), 7.92-8.00 (4H, m), 8.09 (1H, s), 8.19-8.23 (2H, m), 8.35 (1H, s), 8.90 (1H, s). |
| 6-804 | δ 7.50-7.62 (4H, m), 7.68-7.70 (1H, m), 7.85-7.91 (3H, m), 8.10 (1H, s), 8.16-8.22 (4H, m). |
| 6-824 | δ 7.55-7.59 (2H, m), 7.66-7.76 (2H, m), 7.86-7.92 (2H, m), 7.99-8.08 (2H, m), 8.13-8.22 (2H, m), 8.39-8.43 (2H, m). |
| 6-825 | δ 7.55-7.59 (2H, m), 7.66-7.70 (2H, m), 7.72-7.73 (2H, m), 7.86-7.92 (2H, m), 7.99-8.22 (3H, m), 8.40-8.42 (1H, m). |
| 6-840 | δ 7.42-7.45 (1H, m), 7.55-7.59 (1H, t, J = 7.8 Hz), 7.71-7.30 (1H, d, J = 7.8 Hz), 7.88-7.91 (1H, m), 8.00 (1H, s), 8.20-8.24 (4H, m), 8.41 (1H, s), 8.54-8.55 (1H, m). |
| 6-1104 | δ 7.40 (1H, t, J = 7.8 Hz), 7.53-7.64 (3H, m), 7.89 (2H, s), 7.90-7.95 (3H, m), 8.11-8.14 (2H, m), 8.69-8.70 (1H, m). |
| 6-1105 | δ 7.22-7.26 (1H, m), 7.35-7.41 (2H, m), 7.58 (1H, d, J = 8.0 Hz), 7.88-7.92 (3H, m), 8.15-8.25 (2H, m), 8.74-8.75 (2H, m). |
| 6-1106 | δ 7.35-7.34 (1H, m), 7.417-7.42 (1H, m), 7.53-7.54 (1H, m), 7.67-7.68 (2H, m), 7.89-7.90 (3H, m), 8.09-8.10 (2H, m), 8.66-8.68 (1H, m). |
| 6-1107 | δ 7.21-7.26 (2H, m), 7.39-7.41 (1H, m), 7.89-7.96 (4H, m), 8.05-8.13 (3H, m), 8.70-8.72 (1H, m). |
| 6-1124 | δ 7.42-7.43 (1H, m), 7.70-7.72 (1H, m), 7.89-7.92 (4H, m), 8.09-8.17 (3H, m), 8.22 (1H, s), 8.62-8.63 (1H, m). |
| 6-1125 | δ 7.42-7.44 (1H, m), 7.84-7.94 (5H, m), 8.02-8.11 (4H, m), 8.63-8.64 (1H, m). |
| 6-1126 | δ 7.05-7.09 (2H, m), 7.38-7.42 (1H, m), 7.49-7.50 (1H, m), 7.88-7.99 (4H, m), 8.09-8.12 (1H, m), 8.71-8.72 (1H, m). |
| 6-1140 | δ 7.40-7.49 (2H, m), 7.89 (2H, s), 7.94-7.96 (1H, m), 8.13 (1H, d, J = 12.7 Hz), 8.32-8.34 (1H, m), 8.57-8.59 (1H, m), 8.67-8.71 (1H, m), 8.75 (1H, broad-s). |
| 6-1147 | δ 7.39-7.44 (1H, m), 7.52-7.55 (1H, m), 7.89 (1H, s), 7.96-7.98 (1H, m), 8.05-8.11 (3H, m), 8.21-8.23 (1H, m), 8.61-8.62 (1H, m), 8.93 (1H, s). |
| 6-1182 | δ 7.37-7.41 (1H, m), 7.53-7.64 (3H, m), 7.87-7.94 (5H, m), 8.11-8.14 (2H, m), 8.67-8.71 (1H, m). |
| 6-1183 | δ 7.35-7.41 (2H, m), 7.58-7.61 (1H, m), 7.86-7.92 (3H, m), 8.17-8.25 (2H, m), 8.61 (1H, s), 8.74 (1H, t, J = 7.8 Hz), 8.90-8.93 (1H, m). |
| 6-1184 | δ 7.33 (1H, t, J = 8.0 Hz), 7.40 (1H, t, J = 7.8 Hz), 7.50-7.56 (1H, m), 7.64-7.69 (2H, m), 7.88 (2H, s), 7.92 (1H, t, J = 7.8 Hz), 8.09-8.12 (2H, m), 8.63 (1H, t, J = 8.2 Hz). |
| 6-1185 | δ 7.22 (2H, t, J = 7.8 Hz), 7.29-7.30 (1H, m), 7.40 (1H, t, J = 8.0 Hz), 7.88 (2H, s), 7.90-7.97 (2H, m), 8.05 (1H, s), 8.10-8.13 (1H, m), 8.64 (1H, t, J = 7.8 Hz). |
| 6-1202 | δ 7.42-7.44 (1H, m), 7.68-7.72 (1H, m), 7.88-7.94 (4H, m), 8.10-8.23 (4H, m), 8.60-8.65 (1H, m). |
| 6-1203 | δ 7.39-7.44 (1H, m), 7.84-7.88 (4H, m), 7.92-7.95 (1H, m), 8.02-8.13 (4H, m), 8.61-8.65 (1H, m). |
| 6-1204 | δ 7.05 (2H, t, J = 8.0 Hz), 7.40 (1H, t, J = 8.0 Hz), 7.48-7.52 (1H, m), 7.87 (2H, s), 7.92 (1H, t, J = 8.0 Hz), 8.01 (1H, s), 8.11-8.14 (1H, m), 8.68 (1H, t, J = 7.4 Hz). |
| 6-1218 | δ 7.40-7.49 (2H, m), 7.95 (2H, s), 7.94 (1H, t, J = 7.8 Hz), 8.12-8.16 (1H, m), 8.34 (1H, d, J = 8.0 Hz), 8.58 (1H, s), 8.70 (1H, t, J = 7.8 Hz), 8.77 (1H, s). |
| 6-1225 | δ 7.42 (1H, t, J = 8.2 Hz), 7.53 (1H, d, J = 8.0 Hz), 7.88 (2H, s), 7.94 (1H, t, J = 7.0 Hz), 8.06 (1H, s), 8.09-8.12 (1H, m), 8.20-8.23 (1H, m), 8.60 (1H, t, J = 8.0 Hz), 8.93 (1H, s). |
| 6-1260 | δ 7.39 (1H, t, J = 7.8 Hz), 7.52-7.57 (4H, m), 7.60-7.63 (2H, m), 7.93-7.94 (4H, m), 8.70 (1H, t, J = 6.3 Hz). |
| 6-1261 | δ 7.22-7.28 (1H, m), 7.35-7.42 (2H, m), 7.59-7.61 (1H, m), 7.94-7.95 (1H, m), 8.12 (2H, s), 8.15-8.25 (2H, m), 8.78 (1H, t, J = 1.5 Hz), 9.00 (1H, d, J = 7.8 Hz). |
| 6-1262 | δ 7.30-7.33 (1H, m), 7.40-7.44 (1H, m), 7.52-7.55 (2H, m), 7.64-7.70 (3H, m), 7.95-7.96 (1H, m), 8.09-8.13 (2H, m), 8.67-8.68 (1H, m). |
| 6-1263 | δ 7.20-7.26 (3H, m), 7.38-7.42 (1H, m), 7.91-7.98 (3H, m), 8.07-8.12 (3H, m), 8.63-8.67 (1H, m). |

TABLE 52-continued

| compound number | ¹H-NMR (CDCl₃, ppm) |
| --- | --- |
| 6-1280 | δ 7.41-7.45 (1H, m), 7.68-7.72 (1H, m), 7.90-7.99 (2H, m), 8.08-8.25 (5H, m), 8.22-8.24 (1H, m), 8.56-8.65 (1H, m). |
| 6-1281 | δ 7.41-7.50 (1H, m), 7.86-7.87 (2H, m), 7.95-7.98 (1H, m), 8.03-8.13 (6H, m), 8.65-8.67 (1H, m). |
| 6-1282 | δ 7.06 (2H, t, J = 8.3 Hz), 7.38-7.42 (1H, m), 7.47-7.52 (1H, m), 7.93-7.97 (1H, m), 8.01 (1H, s), 8.11-8.13 (3H, m), 8.68-8.72 (1H, m). |
| 6-1296 | δ 7.41-7.52 (2H, m), 7.96-8.00 (1H, m), 8.12-8.14 (3H, m), 8.33-8.35 (1H, m), 8.57-8.59 (1H, m), 8.68-8.76 (2H, m). |
| 6-1303 | δ 7.41-7.45 (1H, m), 7.51-7.54 (1H, m), 7.96-7.99 (1H, m), 8.06-8.24 (5H, m), 8.61 (1H, m), 8.94 (1H, m). |
| 6-1338 | δ 7.38-7.42 (1H, m), 7.52-7.64 (3H, m), 7.90-7.94 (3H, m), 8.11-8.15 (4H, m), 8.67-8.71 (1H, m). |
| 6-1339 | δ 7.35-7.42 (2H, m), 7.60 (1H, d, J = 8.0 Hz), 7.94 (1H, t, J = 8.0 Hz), 8.11 (2H, s), 8.17-8.25 (2H, m), 8.62 (1H, s), 8.74 (1H, t, J = 7.4 Hz), 8.92 (1H, d, J = 16.4 Hz). |
| 6-1340 | δ 7.28-7.35 (2H, m), 7.40 (1H, t, J = 8.0 Hz), 7.51-7.56 (1H, m), 7.64-7.70 (2H, m), 7.94 (1H, t, J = 8.0 Hz), 8.10 (2H, s), 8.14 (1H, s), 8.65 (1H, t, J = 8.0 Hz). |
| 6-1341 | δ 7.20-7.25 (2H, m), 7.40 (1H, t, J = 8.0 Hz), 7.92-7.97 (3H, m), 8.09 (1H, d, J = 8.0 Hz), 8.11 (2H, s), 8.14 (1H, s), 8.64 (1H, t, J = 8.0 Hz). |
| 6-1358 | δ 7.41-7.45 (1H, m), 7.68-7.72 (1H, m), 7.89-7.98 (2H, m), 8.10-8.23 (6H, m), 8.60-8.64 (1H, m). |
| 6-1359 | δ 7.41-7.45 (1H, m), 7.83-7.89 (2H, m), 7.94-7.99 (1H, m), 8.03-8.14 (6H, m), 8.62-8.66 (1H, m). |
| 6-1360 | δ 7.05 (1H, t, J = 8.8 Hz), 7.41-7.46 (1H, m), 7.52 (1H, t, J = 7.8 Hz), 7.95 (1H, t, J = 7.8 Hz), 8.03 (1H, s), 8.10 (2H, s), 8.15 (1H, s), 8.61 (1H, t, J = 8.0 Hz). |
| 6-1374 | δ 7.41-7.49 (2H, m), 8.00 (1H, t, J = 8.0 Hz), 8.11 (2H, s), 8.16 (1H, s), 8.34 (1H, d, J = 7.2 Hz), 8.58 (1H, d, J = 2.0 Hz), 8.70 (1H, t, J = 7.8 Hz), 8.78 (1H, s). |
| 6-1381 | δ 7.43 (1H, t, J = 8.0 Hz), 7.53 (1H, d, J = 8.0 Hz), 7.97 (1H, t, J = 7.8 Hz), 8.11-8.12 (3H, m), 8.14 (1H, s), 8.22 (1H, d, J = 8.0 Hz), 8.57 (1H, t, J = 8.0 Hz), 8.94 (1H, s). |
| 6-1574 | δ 7.37-7.41 (1H, m), 7.53-7.64 (3H, m), 7.86-7.94 (4H, m), 8.13-8.22 (3H, m), 8.67-8.72 (1H, m). |
| 6-1575 | δ 7.22-7.27 (1H, m), 7.35-7.41 (2H, m), 7.57-7.60 (1H, m), 7.88-7.93 (2H, m), 8.16 (1H, s), 8.20-8.25 (2H, m), 8.74-8.75 (1H, m), 8.77-9.00 (1H, m). |
| 6-1576 | δ 7.27-7.37 (2H, m), 7.48-7.53 (1H, m), 7.72-7.80 (3H, m), 7.92 (1H, s), 8.15 (1H, s), 8.27-8.31 (1H, m), 9.16 (1H, s), 9.35 (1H, d, J = 7.3 Hz). |
| 6-1577 | δ 7.20-7.23 (3H, m), 7.24-7.26 (1H, m), 7.39-7.40 (3H, m), 7.86-7.97 (1H, m), 8.06 (1H, d, J = 2.4 Hz), 8.16-8.20 (1H, m), 8.62-8.67 (1H, m). |
| 6-1594 | δ 7.41-7.42 (1H, m), 7.70-7.71 (1H, m), 7.93-8.89 (3H, m), 8.12-8.24 (5H, m), 8.60-8.61 (1H, m). |
| 6-1595 | δ 7.41 (1H, t, J = 7.8 Hz), 7.84-7.87 (2H, m), 7.90-7.94 (2H, m), 8.03-8.05 (2H, m), 8.12-8.18 (3H, m), 8.62-8.66 (1H, m). |
| 6-1596 | δ 7.00-7.09 (2H, m), 7.40-7.41 (1H, m), 7.46-7.53 (1H, m), 7.89-7.92 (2H, m), 8.00 (1H, s), 8.16-8.19 (2H, m), 8.71-8.72 (1H, m). |
| 6-1610 | δ 7.42-7.49 (1H, m), 7.93-7.94 (2H, m), 8.15-8.21 (2H, m), 8.31-8.34 (1H, m), 8.57-8.59 (1H, m), 8.63-8.69 (2H, m). |
| 6-1617 | δ 7.31-7.38 (1H, m), 7.49 (1H, d, J = 8.3 Hz), 7.82-7.86 (1H, m), 7.92 (1H, s), 8.15 (1H, s), 8.19-8.23 (1H, m), 8.30 (1H, dd, J = 2.4, 8.3 Hz), 9.04-9.09 (2H, m), 9.53 (1H, s). |
| 6-1652 | δ 7.40 (1H, t, J = 7.8 Hz), 7.53-7.64 (3H, m), 7.86-7.94 (4H, m), 8.13-8.20 (3H, m), 8.71-8.72 (1H, m). |
| 6-1653 | δ 7.22-7.25 (1H, m), 7.35-7.41 (2H, m), 7.57-7.60 (1H, m), 7.88-7.92 (2H, m), 8.15 (1H, s), 8.20-8.29 (2H, m), 8.71-8.75 (1H, m), 8.89-8.93 (1H, m). |
| 6-1654 | δ 7.32-7.34 (1H, m), 7.38-7.42 (1H, m), 7.50-7.56 (1H, m), 7.63-7.70 (2H, m), 7.88-7.91 (2H, m), 8.09-8.20 (3H, m), 8.63-8.68 (1H, m). |
| 6-1655 | δ 7.21-7.30 (2H, m), 7.37-7.41 (1H, m), 7.86-7.97 (4H, m), 8.06-8.21 (3H, m), 8.63-8.67 (1H, m). |
| 6-1672 | δ 7.37-7.41 (1H, m), 7.67-7.71 (1H, m), 7.88-7.91 (3H, m), 8.15-8.18 (2H, m), 8.24-8.28 (3H, m), 8.52-8.56 (1H, m). |
| 6-1673 | δ 7.39-7.44 (1H, m), 7.85-7.93 (4H, m), 8.03-8.05 (2H, m), 8.13-8.18 (3H, m), 8.61-8.65 (1H, m). |
| 6-1674 | δ 7.04-7.09 (2H, m), 7.38-7.42 (1H, m), 7.47-7.52 (1H, m), 7.89-7.93 (2H, m), 8.00 (1H, s), 8.14-8.20 (2H, m), 8.69-8.73 (1H, m). |
| 6-1688 | δ 7.42 (1H, t, J = 7.8 Hz), 7.47 (1H, dd, J = 4.9, 7.8 Hz), 7.92-7.96 (2H, m), 8.14 (1H, s), 8.19 (1H, d, J = 12.7 Hz), 8.33 (1H, dd, J = 2.0, 7.8 Hz), 8.58 (1H, dd, J = 2.0, 4.9 Hz), 8.70-8.71 (1H, m), 8.74 (1H, s). |
| 6-1695 | δ 7.39-7.43 (1H, m), 7.52-7.54 (1H, m), 7.92-7.95 (2H, m), 8.08-8.09 (1H, m), 8.15 (1H, s), 8.17-8.23 (2H, m), 8.57-8.93 (1H, m), 8.94 (1H, s). |
| 6-1730 | δ 7.40 (1H, t, J = 7.8 Hz), 7.53-7.64 (3H, m), 7.87-7.95 (4H, m), 8.14 (1H, s), 8.22 (1H, d, J = 12.7 Hz), 8.37 (1H, s), 8.71-8.72 (1H, m). |
| 6-1731 | δ 7.22-7.25 (1H, m), 7.35-7.37 (2H, m), 7.58-7.60 (1H, m), 7.90 (1H, t, J = 8.6 Hz), 7.96 (1H, s), 8.22 (1H, t, J = 8.8 Hz), 8.29-8.32 (1H, d, J = 12.4 Hz), 8.37 (1H, s), 8.73 (1H, m), 8.94 (1H, s). |
| 6-1732 | δ 7.32-7.33 (1H, m), 7.37 (1H, t, J = 8.0 Hz), 7.52-7.54 (1H, m), 7.64-7.70 (2H, m), 7.90 (1H, t, J = 6.4 Hz), 7.96 (1H, m), 8.10 (1H, s), 8.23 (1H, d, J = 12.0 Hz), 8.37 (1H, s), 8.65 (1H, t, J = 8.0 Hz). |
| 6-1733 | δ 7.19-7.25 (2H, m), 7.35 (1H, t, J = 7.8 Hz), 7.87-7.97 (4H, m), 8.08 (1H, s), 8.25 (1H, d, J = 12.0 Hz), 8.37 (1H, s), 8.65 (1H, t, J = 8.0 Hz). |
| 6-1734 | δ 7.43-7.52 (5H, m), 7.87-7.95 (3H, m), 8.22 (1H, d, J = 10.0 Hz), 8.35 (1H, d, J = 8.2 Hz), 8.74 (1H, t, J = 8.4 Hz). |
| 6-1750 | δ 7.40 (1H, t, J = 8.2 Hz), 7.68 (1H, t, J = 8.0 Hz), 7.88-7.95 (2H, m), 8.12 (1H, s), 8.16 (1H, d, J = 8.0 Hz), 8.23-8.25 (2H, m), 8.30-8.33 (1H, m), 8.36 (1H, s), 8.53 (1H, t, J = 7.4 Hz). |
| 6-1751 | δ 7.44 (1H, t, J = 8.0 Hz), 7.86 (2H, d, J = 8.0 Hz), 7.91-7.96 (2H, m), 8.03 (2H, d, J = 7.6 Hz), 8.13-8.22 (2H, m), 8.37 (1H, s), 8.64 (1H, t, J = 8.6 Hz). |
| 6-1752 | δ 7.04-7.11 (2H, m), 7.38-7.53 (2H, m), 7.90-7.95 (2H, m), 8.01 (1H, s), 8.22 (1H, d, J = 12.8 Hz), 8.37 (1H, s), 8.69-8.73 (1H, m). |
| 6-1754 | δ 7.39-7.44 (2H, m), 7.54 (1H, s), 7.85 (1H, d, J = 8.0 Hz), 7.90-7.95 (2H, m), 8.22 (1H, d, J = 12.0 Hz), 8.68 (1H, s), 8.70 (1H, s), 8.69 (1H, t, J = 7.8 Hz). |
| 6-1755 | δ 7.16-7.19 (1H, m), 7.40 (1H, t, J = 8.0 Hz), 7.92-7.95 (2H, m), 8.07 (2H, t, J = 4.8 Hz), 8.24 (1H, d, J = 12.8 Hz), 8.37 (1H, s), 8.42 (1H, s), 8.70 (1H, t, J = 8.0 Hz). |
| 6-1766 | δ 7.41-7.49 (2H, m), 7.93-7.97 (2H, m), 8.22 (1H, d, J = 13.2 Hz), 8.33 (1H, dd, J = 2.0, 7.3 Hz), 8.37 (1H, s), 8.58 (1H, dd, J = 2.0, 4.9 Hz), 8.70-8.73 (2H, m). |
| 6-1773 | δ 7.40 (1H, t, J = 8.2 Hz), 7.52 (1H, d, J = 8.0 Hz), 7.91-7.96 (2H, m), 8.12-8.28 (3H, m), 8.37 (1H, s), 8.57 (1H, s), 8.94 (1H, s). |

TABLE 52-continued

| compound number | $^1$H-NMR (CDCl$_3$, ppm) |
|---|---|
| 6-1808 | δ 7.38-7.42 (1H, m), 7.53-7.64 (3H, m), 7.87-7.94 (4H, m), 8.14 (1H, s), 8.23-8.26 (1H, m), 8.36 (1H, s), 8.68-8.71 (1H, m). |
| 6-1809 | δ 7.22-7.25 (2H, m), 7.38 (1H, t, J = 8.0 Hz), 7.58-7.61 (1H, m), 7.89-7.94 (2H, m), 8.23 (1H, t, J = 6.3 Hz), 8.29 (1H, d, J = 13.2 Hz), 8.36 (1H, s), 8.74 (1H, t, J = 6.3 Hz), 8.93-8.94 (1H, m). |
| 6-1810 | δ 7.30-7.33 (2H, m), 7.40 (1H, t, J = 7.8 Hz), 7.51-7.56 (1H, m), 7.64-7.70 (2H, m), 7.88-7.94 (1H, m), 8.10 (1H, s), 8.23 (1H, d, J = 12.2 Hz), 8.36 (1H, s), 8.67 (1H, t, J = 7.8 Hz). |
| 6-1811 | δ 7.39 (1H, t, J = 8.3 Hz), 7.86-7.97 (3H, m), 8.08 (2H, s), 8.25 (1H, d, J = 12.2 Hz), 8.36 (2H, s), 8.65 (2H, t, J = 6.3 Hz). |
| 6-1828 | δ 7.30-7.33 (2H, m), 7.41 (1H, t, J = 7.6 Hz), 7.68-7.73 (1H, m), 7.89-7.94 (2H, m), 8.16 (1H, d, J = 7.6 Hz), 8.23-8.27 (1H, m), 8.41 (1H, s), 8.63-8.64 (2H, m). |
| 6-1829 | δ 7.29-7.31 (1H, m), 7.42 (1H, t, J = 8.0 Hz), 7.90-7.94 (2H, m), 8.04 (2H, d, J = 4.4 Hz), 8.15 (1H, s), 8.23 (1H, d, J = 12.0 Hz), 8.36 (1H, s), 8.60-8.66 (2H, m). |
| 6-1830 | δ 7.06 (1H, t, J = 8.3 Hz), 7.41 (1H, t, J = 7.8 Hz), 7.67-7.69 (1H, m), 7.90-7.93 (2H, m), 8.03 (1H, s), 8.25 (1H, d, J = 12.7 Hz), 8.35 (1H, s), 8.61 (1H, s), 8.70 (1H, t, J = 7.8 Hz). |
| 6-1851 | δ 7.42 (1H, t, J = 8.0 Hz), 7.53 (1H, d, J = 7.9 Hz), 7.92-7.94 (2H, m), 8.09 (1H, s), 8.21-8.24 (2H, m), 8.36 (1H, s), 8.59 (1H, t, J = 8.0 Hz), 8.94 (1H, s). |
| 6-2110 | δ 7.36-7.40 (1H, m), 7.53-7.64 (3H, m), 7.84-7.97 (1H, m), 7.92-7.94 (2H, m), 8.04-8.07 (1H, m), 8.08-8.13 (1H, m), 8.20 (2H, s), 8.68-8.72 (1H, m). |
| 6-3348 | δ 7.29-7.34 (1H, m), 7.53-7.65 (3H, m), 7.80-7.84 (1H, m), 7.90-7.92 (3H, m), 8.14 (1H, broad-s), 8.20 (1H, d, J = 2.9 Hz), 8.25 (1H, broad-s), 9.10 (1H, dd, J = 1.9, 7.3 Hz). |
| 6-3384 | δ 7.32-7.36 (1H, m), 7.45-7.48 (1H, m), 7.83-7.87 (1H, m), 7.93 (1H, broad-s), 8.10 (1H, broad-s), 8.15 (1H, broad-s), 8.30 (1H, dd, J = 1.5, 7.3 Hz), 8.57-8.79 (1H, m), 8.78 (1H, broad-s), 9.09 (1H, dd, J = 2.4, 7.3 Hz). |
| 6-5902 | (DMSO-d$_6$) δ 7.39 (1H, t, J = 7.8 Hz), 7.52-7.64 (4H, m), 7.81 (1H, t, J = 6.8 Hz), 7.95 (1H, s), 7.98-8.01 (3H, m), 10.29 (1H, s), 10.68 (1H, s). |
| 6-5903 | δ 7.50-7.67 (5H, m), 7.79 (1H, d, J = 8.0 Hz), 7.92 (1H, d, J = 8.0 Hz), 8.01 (2H, d, J = 8.0 Hz), 8.10 (2H, s), 8.31 (1H, s). |
| 6-5904 | δ 7.19-7.23 (1H, m), 7.28-7.31 (1H, m), 7.58 (1H, t, J = 8.2 Hz), 7.78 (1H, d, J = 8.0 Hz), 7.91-7.94 (3H, m), 8.01 (2H, d, J = 8.0 Hz), 8.30 (2H, s), 8.61 (1H, s). |
| 6-5905 | δ 7.26 (1H, s), 7.43-7.46 (1H, m), 7.56-7.60 (1H, m), 7.80-7.94 (5H, m), 8.22-8.56 (4H, m). |
| 6-5906 | δ 7.18-7.12 (2H, m), 7.53-7.57 (1H, m), 7.76 (1H, d, J = 7.6 Hz), 7.86-8.28 (7H, m), 8.28 (1H, s). |
| 6-5907 | δ 7.39 (1H, t, J = 7.8 Hz), 7.52-7.64 (4H, m), 7.85-7.94 (4H, m), 8.06 (1H, d, J = 12.2 Hz), 8.14 (1H, broad-s), 8.67-8.71 (1H, m). |
| 6-5908 | δ 7.39-7.49 (2H, m), 7.59 (1H, s), 7.88-7.94 (2H, m), 8.07 (1H, d, J = 12.2 Hz), 8.31-8.33 (1H, m), 8.57-8.58 (1H, m), 8.60-8.70 (1H, m), 8.74 (1H, broad-s). |
| 6-5909 | δ 7.42 (1H, t, J = 7.8 Hz), 7.59 (1H, s), 7.85-7.92 (4H, m), 7.99 (1H, broad-s), 8.02-8.05 (2H, m), 8.10 (1H, broad-s), 8.61-8.67 (1H, m). |
| 6-5910 | δ 7.39 (1H, t, J = 8.3 Hz), 7.53-7.64 (3H, m), 7.88-7.94 (4H, m), 8.13 (1H, broad-s), 8.19 (1H, broad-s), 8.24 (1H, d, J = 13.2 Hz), 8.70-8.72 (1H, m). |
| 6-5911 | δ 7.41 (1H, t, J = 8.3 Hz), 7.84-7.87 (3H, m), 7.91-7.95 (1H, m), 8.03-8.05 (2H, m), 8.10 (1H, broad-s), 8.17-8.20 (2H, m), 8.63-8.67 (1H, m). |
| 6-5912 | δ 3.10 (3H, s), 7.59 (1H, t, J = 7.8 Hz), 7.76 (1H, d, J = 7.8 hz), 7.77-8.00 (5H, m), 8.03 (1H, s), 8.19 (1H, s), 8.24 (1H, s), 8.36 (1H, s). |
| 6-5913 | δ 7.51-7.62 (4H, m), 7.72 (1H, dd, J = 1.5, 7.8 Hz), 7.89-8.00 (6H, m), 8.14 (1H, s), 8.27 (1H, t, J = 2.0 Hz). |
| 6-5914 | δ 7.44 (1H, dd, J = 4.9, 7.8 Hz), 7.56-7.60 (1H, m), 7.76 (1H, d, J = 7.8 Hz), 7.92 (3H, broad-s), 8.14 (1H, s), 8.22-8.27 (1H, m), 8.27 (1H, s), 8.41 (1H, s), 8.55 (1H, dd, J = 2.0, 4.4 Hz). |
| 7-38 | δ 3.57 (3H, s), 7.21-7.24 (1H, m), 7.32-7.34 (4H, m), 7.40-7.44 (2H, m), 7.59 (1H, s), 7.71 (1H, d, J = 8.0 Hz), 7.84 (3H, s). |
| 7-39 | δ 3.54 (3H, s), 7.06-7.19 (1H, m), 7.28-7.34 (2H, m), 7.43-7.48 (2H, m), 7.57 (1H, s), 7.69 (1H, s), 7.75 (1H, d, J = 8.0 Hz), 7.90 (1H, d, J = 8.0 Hz), 8.06 (2H, s). |
| 7-45 | δ 3.57 (3H, s), 7.29-7.30 (2H, m), 7.48 (1H, t, J = 8.0 Hz), 7.59 (1H, s), 7.68-7.71 (3H, m), 7.77 (1H, d, J = 7.8 Hz), 7.85 (2H, s), 8.24 (1H, s). |
| 7-46 | δ 3.57 (3H, s), 7.41-7.45 (3H, m), 7.52 (2H, s), 7.55 (1H, d, J = 8.0 Hz), 7.69 (1H, s), 7.74 (1H, d, J = 7.8 Hz), 7.86 (2H, s), 8.62 (1H, s). |
| 7-47 | δ 3.56 (3H, s), 6.97-7.05 (3H, m), 7.17-7.19 (1H, m), 7.43-7.50 (3H, m), 7.73 (1H, s), 7.85 (2H, s). |
| 7-57 | δ 3.57 (3H, s), 7.15 (1H, t, J = 6.0 Hz), 7.41 (2H, s), 7.50 (1H, s), 7.52 (1H, s), 7.60 (1H, d, J = 6.4 Hz), 7.73 (1H, s), 7.85 (2H, s), 8.27 (1H, s). |
| 7-60 | 3.57 (3H, s), 7.30 (1H, d, J = 8.0 Hz), 7.47 (1H, t, J = 8.0 Hz), 7.61 (1H, s), 7.76 (2H, s), 7.78-7.81 (1H, m), 7.85 (2H, s), 8.11 (1H, s), 8.24 (1H, s). |
| 7-71 | δ 3.56 (3H, s), 7.20-7.25 (1H, m), 7.33-7.38 (3H, m), 7.43-7.47 (3H, m), 7.56 (1H, s), 7.74 (1H, d, J = 6.8 Hz), 8.06-8.10 (3H, m). |
| 7-72 | δ 3.55 (3H, s), 7.06-7.10 (1H, m), 7.30-7.36 (2H, m), 7.43-7.48 (2H, m), 7.57 (1H, s), 7.68 (1H, s), 7.78 (1H, d, J = 8.0 Hz), 7.90 (1H, d, J = 8.0 Hz), 8.07 (2H, s). |
| 7-78 | δ 3.57 (3H, s), 7.29-7.64 (2H, m), 7.70 (1H, s), 7.79 (1H, d, J = 8.0 Hz), 7.86 (1H, d, J = 8.0 Hz), 7.95 (1H, t, J = 8.0 Hz), 8.08 (2H, s), 8.33 (1H, d, J = 8.0 Hz), 8.40 (1H, s), 8.71 (1H, s). |
| 7-79 | δ 3.58 (3H, s), 7.42-7.53 (3H, m), 7.60-7.66 (1H, m), 7.77 (1H, d, J = 8.0 Hz), 7.89 (1H, t, J = 8.0 Hz), 8.08 (2H, s), 8.21 (1H, d, J = 8.0 Hz), 8.70 (2H, s). |
| 7-80 | δ 3.56 (3H, s), 7.02 (1H, t, J = 8.0 Hz), 7.42-7.44 (1H, m), 7.55 (1H, t, J = 8.0 Hz), 7.75 (1H, d, J = 8.0 Hz), 7.90-7.95 (3H, m), 8.01 (1H, s), 8.14 (1H, s), 8.26 (1H, s). |
| 7-90 | δ 3.59 (3H, s), 7.59 (1H, s), 7.60 (1H, d, J = 6.0 Hz), 7.80-7.83 (1H, m), 8.08 (2H, s), 8.26-8.30 (2H, m), 8.53 (1H, d, J = 4.0 Hz), 8.69 (2H, s). |
| 7-93 | δ 3.58 (3H, s), 7.34-7.52 (3H, m), 7.63 (1H, d, J = 16.0 Hz), 7.69 (1H, d, J = 8.0 Hz), 7.80 (1H, d, J = 8.0 Hz), 7.85 (1H, t, J = 8.0 Hz), 8.25 (1H, s), 8.29 (1H, d, J = 8.0 Hz), 8.69 (1H, s). |
| 7-132 | δ 3.57 (3H, s), 7.26-7.28 (1H, m), 7.41-7.46 (3H, m), 7.52-7.54 (3H, m), 7.63 (1H, s), 7.68 (1H, d, J = 7.8 Hz), 7.87 (1H, s), 7.98 (1H, s). |
| 7-147 | δ 3.58 (3H, s), 7.14 (1H, dd, J = 4.9, 7.8 Hz), 7.41-7.42 (2H, m), 7.52 (1H, s), 7.59 (1H, dd, J = 1.5, 7.8 Hz), 7.67 (2H, broad-s), 7.87 (1H, s), 7.97 (1H, s), 8.26 (1H, dd, J = 1.5, 4.9 Hz). |
| 7-268 | δ 3.49 (3H, s), 7.12-7.16 (2H, m), 7.21-7.28 (4H, m), 7.35 (1H, t, J = 7.8 Hz), 7.64 (1H, s), 7.70 (1H, dd, J = 1.5, 8.8 Hz), 7.86 (1H, s), 8.07 (1H, d, J = 1.5 Hz), 8.29 (1H, s). |

TABLE 52-continued

| compound number | $^1$H-NMR (CDCl$_3$, ppm) |
|---|---|
| 7-269 | δ 3.54 (3H, s), 6.80-6.81 (1H, m), 7.70-7.08 (1H, m), 7.25-7.26 (1H, m), 7.39-7.41 (4H, m), 7.52-7.53 (1H, m), 7.70-7.71 (1H, m), 7.90 (1H, s), 8.12 (1H, s). |
| 7-270 | δ 3.55 (3H, s), 6.97-6.99 (1H, m), 7.04-7.06 (2H, m), 7.15-7.21 (1H, m), 7.32-7.34 (1H, m), 7.44 (1H, t, J = 7.8 Hz), 7.58-7.59 (2H, m), 7.70 (1H, d, J = 7.8 Hz), 7.90 (1H, s), 8.12 (1H, s). |
| 7-271 | δ 3.55 (3H, s), 6.88-6.92 (2H, m), 7.30-7.34 (3H, m), 7.43 (1H, t, J = 7.8 Hz), 7.57-7.58 (2H, m), 7.67-7.69 (1H, m), 7.90-7.91 (1H, m), 8.13-8.14 (1H, m). |
| 7-285 | δ 3.59 (3H, s), 7.34-7.52 (3H, m), 7.65-7.73 (4H, m), 7.90 (1H, s), 8.13-8.16 (3H, m). |
| 7-286 | δ 3.59 (3H, s), 7.29-7.30 (1H, m), 7.42-7.52 (4H, m), 7.63 (1H, s), 7.69 (1H, d, J = 7.8 Hz), 7.91 (1H, s), 8.08-8.13 (3H, m). |
| 7-288 | δ 3.57 (3H, s), 7.15-7.37 (2H, m), 7.47-7.48 (1H, m), 7.52-7.62 (5H, m), 7.72 (1H, d, J = 7.8 Hz), 7.91 (1H, s), 8.14 (1H, s). |
| 7-289 | δ 3.57 (3H, s), 7.26-7.29 (1H, m), 7.40-7.46 (3H, m), 7.52 (2H, d, J = 8.3 Hz), 7.58-7.61 (2H, m), 7.70 (1H, d, J = 7.8 Hz), 7.92 (1H, s), 8.14 (1H, s). |
| 7-290 | δ 3.55 (3H, s), 6.70-6.74 (2H, m), 7.14-7.19 (1H, m), 7.43-7.44 (2H, m), 7.52 (1H, s), 7.67 (1H, s), 7.74-7.77 (1H, m), 7.91 (1H, s), 8.13 (1H, s). |
| 7-299 | δ 3.58 (3H, s), 7.33 (1H, d, J = 6.8 Hz), 7.52 (1H, t, J = 7.8 Hz), 7.64-7.65 (2H, m), 7.75-7.79 (3H, m), 7.83 (1H, s), 7.92 (1H, s), 8.14 (1H, s). |
| 7-300 | δ 3.56 (3H, broad-s), 7.14 (1H, broad-d, J = 8.3 Hz), 7.33-7.53 (4H, m), 7.59-7.60 (2H, m), 7.71-7.72 (1H, m), 7.92 (1H, s), 8.14 (1H, s). |
| 7-301 | δ 3.57 (3H, s), 7.33-7.59 (4H, m), 7.60 (1H, s), 7.64 (1H, s), 7.68-7.70 (2H, m), 7.92 (1H, s), 8.15 (1H, s). |
| 7-303 | δ 3.56 (3H, s), 7.17-7.12 (1H, m), 7.39-7.45 (2H, m), 7.55 (2H, s), 7.69 (1H, d, J = 7.8 Hz), 7.90 (2H, s), 8.13-8.14 (2H, m). |
| 7-304 | δ 3.54 (3H, s), 7.10 (1H, dd, J = 4.9, 7.8 Hz), 7.35-7.40 (2H, m), 7.56 (1H, dd, J = 1.5, 7.8 Hz), 7.70 (2H, s), 7.88-7.90 (2H, m), 8.12 (1H, s), 8.22 (1H, dd, J = 1.5, 4.9 Hz). |
| 7-305 | δ 3.57 (3H, s), 7.13 (1H, dd, J = 4.9, 7.8 Hz), 7.41-7.42 (2H, m), 7.57-7.62 (2H, m), 7.67-7.69 (2H, m), 7.91 (1H, s), 8.13 (1H, s), 8.24-8.26 (1H, m). |
| 7-311 | δ 3.57 (3H, s), 7.23-7.31 (2H, m), 7.47-7.48 (1H, m), 7.66-7.73 (4H, m), 7.92 (1H, s), 8.14 (1H, s), 8.23 (1H, d, J = 1.9 Hz). |
| 7-316 | δ 3.59 (3H, s), 7.27-7.30 (1H, m), 7.48-7.49 (1H, m), 7.60-7.67 (3H, m), 7.73 (1H, d, J = 7.8 Hz), 7.85 (1H, dd, J = 1.9, 7.8 Hz), 7.92 (1H, s), 8.15 (1H, d, J = 1.5 Hz), 8.52 (1H, s). |
| 7-346 | δ 3.54 (3H, s), 7.18-7.34 (4H, m), 7.40 (1H, t, J = 7.8 Hz), 7.57 (1H, s), 7.67-7.69 (1H, m), 7.88 (1H, s), 8.10 (1H, s). |
| 7-347 | δ 3.53 (3H, s), 6.82 (1H, s), 7.07 (1H, s), 7.23-7.70 (7H, m), 7.89 (1H, s), 8.11 (1H, s). |
| 7-348 | δ 3.53 (3H, s), 6.96-6.99 (1H, m), 7.00-7.06 (2H, m), 7.15-7.19 (1H, m), 7.32-7.34 (1H, m), 7.42-7.46 (1H, m), 7.60 (1H, s), 7.68-7.71 (2H, m), 7.89 (1H, s), 8.11 (1H, s). |
| 7-349 | δ 3.54 (3H, s), 6.88-6.92 (2H, m), 7.29-7.34 (3H, m), 7.41-7.44 (2H, m), 7.59 (1H, s), 7.68-7.70 (1H, m), 7.89 (1H, s), 8.11 (1H, s). |
| 7-366 | δ 3.64 (3H, s), 7.31-7.36 (2H, m), 7.44-7.48 (2H, m), 7.52-7.58 (1H, m), 7.61 (2H, s), 7.71-7.73 (2H, m), 7.89 (1H, s), 8.12 (1H, s). |
| 7-367 | δ 3.56 (3H, s), 7.22-7.31 (3H, m), 7.44-7.48 (1H, m), 7.66-7.77 (4H, m), 7.90 (1H, s), 8.12 (1H, s), 8.22 (1H, s). |
| 7-368 | δ 3.52 (3H, s), 6.67-6.72 (2H, m), 7.00 (1H, s), 7.13-7.17 (1H, m), 7.41-7.42 (2H, m), 7.72-7.89 (3H, m), 8.11 (1H, s). |
| 7-382 | δ 3.58 (3H, s), 7.13-7.16 (1H, m), 7.43-7.61 (4H, m), 7.67 (2H, s), 7.90 (1H, s), 8.13 (1H, s), 8.26-8.27 (1H, m). |
| 7-389 | δ 3.57 (3H, s), 7.29 (1H, s), 7.40-7.46 (3H, m), 7.52-7.54 (2H, m), 7.59-7.62 (1H, m), 7.69-7.70 (1H, m), 7.90 (1H, s), 8.13 (1H, s). |
| 7-424 | δ 3.56 (3H, s), 7.19-7.37 (6H, m), 7.44-7.45 (1H, m), 7.54 (1H, s), 7.60 (1H, broad-s), 7.68 (1H, d, J = 7.8 Hz), 7.92 (1H, s), 8.31 (1H, s). |
| 7-425 | δ 3.54 (3H, broad-s), 6.82 (1H, broad-s), 7.07 (1H, broad-s), 7.23-7.30 (2H, m), 7.31-7.51 (3H, m), 7.52-7.56 (1H, m), 7.71 (1H, broad-s), 7.92 (1H, s), 8.33 (1H, s). |
| 7-426 | δ 3.56 (3H, s), 6.96-7.00 (1H, m), 7.05-7.07 (2H, m), 7.15-7.21 (1H, m), 7.34-7.36 (1H, m), 7.46-7.47 (1H, m), 7.58-7.66 (2H, m), 7.71 (1H, d, J = 7.3 Hz), 7.93 (1H, s), 8.33 (1H, s). |
| 7-427 | δ 3.56 (3H, s), 6.88-6.92 (2H, m), 7.31-7.34 (2H, m), 7.45-7.46 (1H, m), 7.56 (1H, s), 7.62 (1H, s), 7.65 (1H, s), 7.70 (1H, d, J = 7.3 Hz), 7.93 (1H, s), 8.33 (1H, s). |
| 7-428 | δ 3.58 (3H, s), 7.00-7.24 (4H, m), 7.42-7.43 (3H, m), 7.62 (1H, s), 7.66 (1H, s), 7.94 (1H, s), 8.34 (1H, s). |
| 7-444 | δ 3.57 (3H, s), 7.33-7.37 (2H, m), 7.48-7.49 (1H, m), 7.52-7.61 (4H, m), 7.69-7.74 (2H, m), 7.93 (1H, s), 8.34 (1H, s). |
| 7-445 | δ 3.58 (3H, s), 7.30 (1H, d, J = 9.5 Hz), 7.41-7.48 (3H, m), 7.51-7.53 (3H, m), 7.59 (1H, s), 7.70 (1H, d, J = 7.9 Hz), 7.94 (1H, s), 8.34 (1H, s). |
| 7-446 | δ 3.56 (3H, s), 6.69-6.73 (2H, m), 7.14-7.18 (1H, m), 7.44-7.45 (2H, m), 7.61 (1H, s), 7.69 (1H, s), 7.75-7.77 (1H, m), 7.93 (1H, s), 8.34 (1H, s). |
| 7-449 | δ 3.51 (3H, s), 6.82-6.86 (1H, m), 6.94-6.98 (1H, m), 7.14-7.24 (1H, m), 7.28-7.29 (2H, m), 7.41 (1H, s), 7.64 (1H, s), 7.69 (1H, d, J = 5.9 Hz), 7.94 (1H, s), 8.34 (1H, s). |
| 7-460 | δ 3.59 (3H, s), 7.13 (1H, dd, J = 4.8, 7.1 Hz), 7.43-7.44 (2H, m), 7.52 (1H, s), 7.58-7.60 (1H, m), 7.67 (2H, broad-s), 7.94 (1H, s), 8.26 (1H, dd, J = 1.6, 4.8 Hz), 8.34 (1H, s). |
| 7-467 | δ 3.58 (3H, s), 7.23 (1H, d, J = 8.3 Hz), 7.33 (1H, d, J = 7.8 Hz), 7.49-7.50 (1H, m), 7.62 (1H, s), 7.67-7.68 (2H, m), 7.73 (1H, d, J = 7.8 Hz), 7.93 (1H, s), 8.23 (1H, d, J = 2.0 Hz), 8.34 (1H, s). |
| 7-502 | δ 3.57 (3H, s), 7.20-7.26 (3H, m), 7.27-7.37 (3H, m), 7.45 (1H, t, J = 7.6 Hz), 7.56 (1H, s), 7.68 (1H, s), 7.71 (1H, d, J = 8.0 Hz), 7.91 (1H, s), 8.31 (1H, s). |
| 7-504 | 3.56 (3H, s), 6.96-7.01 (1H, m), 7.06 (2H, d, J = 7.2 Hz), 7.18 (1H, t, J = 6.8 Hz), 7.35 (1H, d, J = 8.0 Hz), 7.45 (1H, t, J = 8.0 Hz), 7.56 (2H, s), 7.71 (1H, d, J = 8.0 Hz), 7.91 (1H, s), 8.32 (1H, s). |
| 7-505 | δ 3.57 (3H, s), 6.90 (2H, t, J = 8.8 Hz), 7.31-7.35 (3H, m), 7.45 (1H, t, J = 8.0 Hz), 7.54 (2H, d, J = 13.6 Hz), 7.69 (1H, d, J = 8.0 Hz), 7.91 (1H, s), 8.32 (1H, s). |
| 7-522 | δ 3.57 (3H, s), 7.32-7.37 (2H, m), 7.46 (1H, t, J = 8.0 Hz), 7.55 (1H, t, J = 7.6 Hz), 7.59 (2H, d, J = 8.0 Hz), 7.75 (1H, d, J = 8.0 Hz), 7.88 (1H, s), 7.92 (2H, s), 8.33 (1H, s). |
| 7-523 | δ 3.56 (3H, s), 7.41-7.47 (4H, m), 7.53 (2H, d, J = 8.2 Hz), 7.61 (1H, s), 7.71-7.72 (2H, m), 7.92 (1H, s), 8.33 (1H, s). |
| 7-538 | δ 3.58 (3H, s), 7.14 (1H, t, J = 6.0 Hz), 7.40-7.43 (2H, m), 7.56-7.58 (2H, m), 7.68-7.69 (2H, m), 7.92 (1H, s), 8.26 (1H, s), 8.33 (1H, s). |
| 7-804 | δ 3.55 (3H, s), 7.19-7.52 (9H, m), 7.62 (1H, d, J = 7.8 Hz), 8.16 (2H, s). |

TABLE 52-continued

| compound number | $^1$H-NMR (CDCl$_3$, ppm) |
|---|---|
| 7-824 | δ 3.57 (3H, s), 7.33-7.75 (7H, m), 7.98-7.99 (1H, m), 8.12 (2H, s), 8.18-8.43 (1H, m). |
| 7-825 | δ 3.57 (3H, s), 7.22-7.66 (7H, m), 7.85-7.88 (1H, m), 7.97-7.99 (2H, m), 8.17-8.27 (1H, m). |
| 7-840 | δ 3.57 (3H, s), 7.13-7.26 (1H, m), 7.40-7.44 (2H, m), 7.58-7.71 (3H, m), 8.18-8.23 (4H, m). |
| 7-948 | δ 3.49 (3H, s), 7.23-7.52 (8H, m), 7.66 (2H, s), 8.00 (1H, t, J = 6.8 Hz). |
| 7-969 | δ 3.51 (3H, s), 7.45-7.46 (3H, m), 7.53-7.55 (3H, m), 7.67 (2H, s), 7.92-7.93 (1H, m), 8.05-8.06 (1H, m). |
| 7-984 | δ 3.53 (3H, s), 7.13-7.16 (1H, m), 7.20-7.24 (1H, m), 7.52-7.53 (1H, m), 7.65-7.68 (3H, m), 7.99-8.03 (2H, m), 8.28-8.30 (1H, m). |
| 7-1104 | δ 3.51 (3H, s), 7.22-7.44 (7H, m), 7.86 (2H, s), 8.00-8.03 (2H, m). |
| 7-1105 | δ 3.52 (3H, s), 6.82 (1H, t, J = 8.8 Hz), 7.06-7.08 (1H, m), 7.18-7.24 (2H, m), 7.40-7.44 (2H, m), 7.87 (3H, s), 8.01-8.05 (1H, m). |
| 7-1106 | δ 3.50 (3H, s), 7.00-7.23 (4H, m), 7.29-7.31 (1H, m), 7.45 (1H, s), 7.87 (3H, s), 8.03-8.07 (1H, m). |
| 7-1107 | δ 3.49 (3H, s), 6.91-6.93 (2H, m), 7.28-7.44 (4H, m), 7.86 (2H, s), 8.00-8.10 (2H, m). |
| 7-1124 | δ 3.52 (3H, s), 7.30-7.34 (2H, m), 7.46-7.59 (3H, m), 7.71 (1H, broad-s), 7.87 (2H, s), 7.97-8.09 (2H, m). |
| 7-1125 | δ 3.52 (3H, s), 7.29-7.32 (1H, m), 7.45-7.52 (5H, m), 7.84 (2H, s), 7.95-8.06 (2H, m). |
| 7-1126 | δ 3.49 (3H, s), 6.72-6.76 (2H, m), 7.16-7.23 (2H, m), 7.43-7.50 (1H, m), 7.88 (2H, s), 8.02-8.06 (1H, m), 8.13-8.17 (1H, m). |
| 7-1140 | δ 3.54 (3H, s), 7.13-7.16 (1H, m), 7.21-7.26 (1H, m), 7.43-7.46 (1H, m), 7.52 (1H, broad-s), 7.65-7.69 (1H, m), 7.88 (2H, s), 8.00-8.04 (1H, m), 8.28-8.30 (1H, m). |
| 7-1147 | δ 3.52 (3H, s), 7.22-7.26 (1H, m), 7.34 (1H, t, J = 7.8 Hz), 7.46-7.52 (1H, m), 7.62-7.68 (1H, m), 7.87 (2H, s), 7.91-7.95 (1H, m), 8.07-8.11 (1H, m), 8.34 (1H, broad-s). |
| 7-1182 | δ 3.51 (3H, s), 7.22-7.44 (7H, m), 7.85 (2H, s), 8.00-8.03 (2H, m). |
| 7-1183 | δ 3.51 (3H, s), 6.79-6.83 (1H, m), 7.05 (1H, t, J = 7.8 Hz), 7.17-7.23 (2H, m), 7.40-7.43 (2H, m), 7.85 (2H, s), 7.98-8.00 (2H, m). |
| 7-1184 | δ 3.52 (3H, s), 6.99-7.22 (4H, m), 7.28-7.30 (1H, m), 7.44-7.45 (1H, m), 7.88 (2H, s), 8.02-8.06 (2H, m). |
| 7-1185 | δ 3.49 (3H, s), 6.91-7.00 (2H, m), 7.26-7.44 (4H, m), 7.85 (2H, s), 8.01-8.10 (2H, m). |
| 7-1202 | δ 3.52 (3H, s), 7.26-7.32 (1H, m), 7.45-7.52 (5H, m), 7.86 (2H, s), 7.84-7.95 (1H, m), 8.06-8.08 (1H, m). |
| 7-1203 | δ 3.52 (3H, s), 7.26-7.32 (1H, m), 7.45-7.52 (5H, m), 7.86 (2H, s), 7.84-7.95 (1H, m), 8.06-8.08 (1H, m). |
| 7-1204 | δ 3.51 (3H, s), 7.02 (1H, t, J = 8.8 Hz), 7.39-7.44 (1H, m), 7.50 (1H, t, J = 7.4 Hz), 7.93 (1H, t, J = 7.8 Hz), 8.02 (1H, s), 8.10 (2H, s), 8.13 (1H, s), 8.68 (1H, t, J = 8.0 Hz). |
| 7-1218 | δ 3.52 (3H, s), 7.39-7.47 (1H, m), 7.96 (1H, t, J = 8.0 Hz), 8.11 (2H, s), 8.16 (1H, s), 8.33 (1H, d, J = 7.2 Hz), 8.58-8.59 (1H, m), 8.68 (1H, t, J = 7.8 Hz), 8.78 (1H, s). |
| 7-1225 | δ 3.52 (3H, s), 7.22-7.24 (1H, m), 7.32-7.36 (1H, m), 7.46-7.50 (1H, m), 7.66-7.68 (1H, m), 7.85 (2H, s), 7.93-7.96 (1H, m), 8.07-8.11 (1H, m), 8.34 (1H, broad-s). |
| 7-1260 | δ 4.09 (3H, s), 7.21-7.49 (7H, m), 7.99-8.08 (4H, m). |
| 7-1261 | δ 3.53 (3H, s), 6.79-6.83 (1H, m), 7.03-7.07 (1H, m), 7.19-7.23 (2H, m), 7.42-7.43 (2H, m), 8.01-8.10 (4H, m). |
| 7-1262 | δ 3.51 (3H, s), 6.99-7.00 (1H, m), 7.08-7.14 (2H, m), 7.29-7.33 (2H, m), 7.46-7.47 (1H, m), 8.05-8.12 (4H, m). |
| 7-1263 | δ 3.52 (3H, s), 6.88-6.93 (2H, m), 7.29-7.37 (3H, m), 7.46-7.48 (1H, m), 8.04-8.09 (4H, m). |
| 7-1280 | δ 3.52 (3H, s), 7.31-7.47 (2H, m), 7.49 (1H, s), 7.57 (2H, m), 7.69 (1H, s), 8.07-8.10 (4H, m). |
| 7-1281 | δ 3.53 (3H, s), 7.23-7.52 (6H, m), 7.90-8.09 (4H, m). |
| 7-1282 | δ 3.55 (3H, s), 6.72-6.76 (2H, m), 7.17-7.24 (2H, m), 7.48-7.49 (1H, m), 8.04-8.16 (4H, m). |
| 7-1296 | δ 3.55 (3H, s), 7.12-7.15 (1H, m), 7.46-7.51 (1H, broad-s), 7.67-7.69 (1H, m), 8.03-8.12 (5H, m), 8.27-8.29 (1H, m). |
| 7-1303 | δ 3.54 (3H, s), 7.20-7.23 (1H, m), 7.35-7.39 (1H, m), 7.52-7.53 (1H, m), 7.65 (1H, s), 7.97 (1H, broad-s), 8.09-8.14 (3H, m), 8.34-8.35 (1H, m). |
| 7-1338 | δ 3.52 (3H, s), 7.10-7.35 (6H, m), 7.45-7.52 (1H, m), 8.02-8.07 (4H, m). |
| 7-1339 | δ 3.53 (3H, s), 6.80 (1H, t, J = 8.0 Hz), 7.04 (1H, t, J = 8.0 Hz), 7.29-7.32 (1H, m), 7.43 (1H, t, J = 8.0 Hz), 7.68-7.71 (1H, m), 8.01-8.04 (2H, m), 8.09 (2H, s), 8.63 (1H, s). |
| 7-1340 | δ 3.56 (3H, s), 7.04-7.08 (1H, m), 7.30-7.33 (1H, m), 7.43-7.48 (2H, m), 7.57 (1H, s), 7.64 (1H, s), 7.77 (1H, d, J = 8.0 Hz), 7.90 (1H, d, J = 8.0 Hz), 8.07 (2H, s). |
| 7-1341 | δ 3.52 (3H, s), 6.91-6.92 (2H, m), 7.30 (1H, t, J = 8.0 Hz), 7.36 (1H, s), 7.47 (1H, t, J = 8.0 Hz), 8.00-8.06 (2H, m), 8.08 (2H, s). |
| 7-1358 | δ 3.53 (3H, s), 7.31-7.40 (2H, m), 7.45-7.60 (3H, m), 7.69 (1H, s), 7.99-8.11 (4H, m). |
| 7-1359 | δ 3.53 (3H, s), 7.26-7.34 (1H, m), 7.40-7.60 (5H, m), 7.83-7.95 (1H, m), 8.01-8.06 (3H, m). |
| 7-1360 | δ 3.55 (3H, s), 6.72-6.76 (2H, m), 7.22-7.24 (1H, m), 7.42-7.44 (1H, m), 7.49 (1H, t, J = 8.0 Hz), 8.05 (1H, d, J = 8.0 Hz), 8.10 (2H, s), 8.17 (1H, d, J = 8.0 Hz). |
| 7-1374 | δ 3.55 (3H, s), 7.12-7.15 (1H, m), 7.52-7.53 (2H, m), 7.68 (1H, d, J = 8.0 Hz), 8.02-8.06 (2H, m), 8.11 (2H, s), 8.28 (1H, s). |
| 7-1381 | δ 3.54 (3H, s), 7.19-7.22 (1H, m), 7.37 (1H, t, J = 8.0 Hz), 7.54 (1H, t, J = 6.0 Hz), 7.66 (1H, d, J = 6.8 Hz), 7.93-7.96 (1H, m), 8.09-8.13 (3H, m), 8.35 (1H, s). |
| 7-1417 | δ 3.49 (3H, s), 7.23-7.26 (3H, m), 7.27-7.33 (3H, m), 7.52-7.53 (1H, m), 7.85 (1H, s), 7.96-8.06 (3H, m). |
| 7-1574 | δ 3.50 (3H, s), 6.99-7.33 (6H, m), 7.43-7.45 (1H, m), 7.90 (1H, s), 7.97-8.06 (2H, m), 8.13 (1H, s). |
| 7-1575 | δ 3.52 (3H, s), 6.82-6.83 (1H, m), 7.06-7.07 (1H, m), 7.19-7.26 (2H, m), 7.39-7.46 (2H, m), 7.91 (1H, s), 7.99-8.01 (1H, m), 8.07-8.14 (2H, m). |
| 7-1576 | δ 3.50 (3H, s), 7.01-7.17 (4H, m), 7.27-7.31 (1H, m), 7.46-7.52 (1H, m), 7.91 (1H, s), 8.01-8.05 (2H, m), 8.13 (1H, s). |
| 7-1577 | δ 3.50 (3H, s), 6.90-6.94 (2H, m), 7.26-7.35 (3H, m), 7.45-7.46 (1H, m), 7.90 (1H, s), 8.00-8.07 (2H, m), 8.13 (1H, s). |
| 7-1594 | δ 3.52 (3H, s), 7.29-7.36 (2H, m), 7.50 (2H, broad-s), 7.60 (1H, broad-d, J = 6.8 Hz), 7.70 (1H, broad-s), 7.91 (1H, broad-s), 8.04-8.07 (3H, m), 8.14 (1H, s). |
| 7-1595 | δ 3.51 (3H, s), 7.29-7.31 (2H, m), 7.44-7.52 (4H, m), 7.92 (1H, s), 8.03-8.06 (2H, m), 8.14 (1H, broad-s). |
| 7-1596 | δ 3.54 (3H, s), 6.75 (2H, broad-s), 7.17-7.26 (2H, m), 7.50-7.51 (1H, m), 7.92 (1H, s), 8.01-8.05 (1H, m), 8.14-8.20 (2H, m). |
| 7-1605 | δ 3.53 (3H, s), 7.41 (1H, t, J = 7.8 Hz), 7.53-7.55 (1H, m), 7.82-7.86 (3H, m), 7.91 (1H, s), 7.99-8.01 (1H, m), 8.10-8.14 (2H, m). |
| 7-1606 | δ 2.53 (3H, s), 7.15-7.17 (1H, m), 7.24-7.28 (1H, m), 7.39-7.41 (1H, m), 7.41-7.44 (1H, m), 7.53-7.56 (1H, m), 7.93 (1H, s), 8.04-8.08 (2H, m), 8.15 (1H, s). |
| 7-1608 | δ 3.52 (3H, s), 7.22-7.23 (1H, m), 7.29-7.33 (1H, m), 7.48-7.52 (1H, m), 7.71-7.72 (1H, m), 7.90 (1H, s), 8.00-8.03 (2H, m), 8.13 (1H, s), 8.54-8.55 (2H, m). |

TABLE 52-continued

| compound number | ¹H-NMR (CDCl₃, ppm) |
|---|---|
| 7-1610 | δ 3.54 (3H, s), 7.14-7.17 (2H, m), 7.45-7.70 (2H, m), 7.96 (1H, s), 8.00-8.07 (3H, m), 8.28-8.30 (1H, m). |
| 7-1616 | δ 3.52 (3H, s), 7.27-7.23 (1H, m), 7.35-7.36 (1H, m), 7.49-7.51 (1H, m), 7.68 (1H, d, J = 6.8 Hz), 7.91 (1H, s), 8.09-8.05 (2H, m), 8.13 (1H, s), 8.30 (1H, s). |
| 7-1617 | δ 3.52 (3H, s), 7.23-7.27 (1H, m), 7.33-7.37 (1H, m), 7.47-7.51 (1H, m), 7.67-7.68 (1H, m), 7.91 (1H, s), 8.05-8.09 (1H, m), 8.13 (2H, s), 8.30 (1H, s). |
| 7-1638 | δ 3.50 (3H, s), 7.19-7.27 (2H, m), 7.32-7.33 (1H, m), 7.40-7.42 (1H, m), 7.91 (1H, s), 8.00-8.02 (1H, m), 7.09-8.11 (1H, m), 8.14 (1H, s), 8.18 (1H, s), 8.56 (1H, d, J = 8.8 Hz). |
| 7-1639 | δ 3.52 (3H, broad-s), 7.00-7.29 (3H, m), 7.44 (1H, broad-s), 7.52 (1H, s), 7.91-8.14 (3H, m), 8.51 (2H, broad-s). |
| 7-1645 | δ 3.50 (3H, s), 7.22-7.27 (2H, m), 7.33-7.37 (1H, m), 7.43-7.47 (1H, m), 7.92 (1H, s), 8.02-8.10 (3H, m), 8.15-8.19 (2H, m). |
| 7-1652 | δ 3.50 (3H, s), 7.23-7.26 (2H, m), 7.27-7.32 (4H, m), 7.44-7.45 (1H, m), 7.88 (1H, s), 7.98 (1H, t, J = 6.8 Hz), 8.04-8.08 (1H, m), 8.11 (1H, s). |
| 7-1672 | δ 3.51 (3H, s), 7.29-7.35 (2H, m), 7.49-7.50 (2H, m), 7.60 (1H, d, J = 6.3 Hz), 7.69 (1H, s), 7.89 (1H, s), 8.03-8.06 (2H, m), 8.12 (1H, s). |
| 7-1673 | δ 3.52 (3H, s), 7.29-7.32 (1H, m), 7.44-7.52 (5H, m), 7.89 (1H, s), 8.02-8.06 (2H, m), 8.12 (1H, s). |
| 7-1730 | δ 3.51 (3H, s), 7.21-7.23 (2H, m), 7.27-7.33 (4H, m), 7.44-7.46 (1H, m), 7.92 (1H, s), 8.00 (1H, t, J = 6.3 Hz), 8.08-8.09 (1H, m), 8.33 (1H, s). |
| 7-1731 | δ 3.51 (3H, s), 6.79-6.83 (1H, m), 7.05 (1H, t, J = 7.6 Hz), 7.18-7.46 (4H, m), 7.94-8.00 (2H, m), 8.20 (1H, d, J = 12.4 Hz), 8.34 (1H, s). |
| 7-1732 | δ 3.50 (3H, s), 7.00-7.18 (4H, m), 7.27-7.31 (1H, m), 7.45-7.48 (1H, m), 7.93 (1H, s), 8.01-8.03 (1H, m), 8.12 (1H, broad-s), 8.34 (1H, s). |
| 7-1733 | δ 3.50 (3H, s), 6.91 (2H, s), 6.93-7.35 (3H, m), 7.47 (1H, t, J = 7.0 Hz), 7.93 (1H, s), 8.01-8.10 (1H, m), 8.13 (1H, broad-s), 8.34 (1H, s). |
| 7-1750 | δ 3.52 (3H, s), 7.28-7.71 (6H, m), 7.93 (1H, s), 8.06 (1H, t, J = 8.4 Hz), 8.34 (1H, s), 8.60 (1H, s). |
| 7-1751 | δ 3.52 (3H, s), 7.32 (1H, t, J = 8.3 Hz), 7.44-7.52 (5H, m), 7.93 (1H, s), 8.04-8.07 (2H, m), 8.34 (1H, s). |
| 7-1752 | δ 3.54 (3H, s), 6.74 (2H, m), 7.16-7.24 (2H, m), 7.50 (1H, t, J = 7.4 Hz), 7.94 (1H, s), 8.01-8.05 (1H, m), 8.25 (1H, broad-s), 8.35 (1H, s). |
| 7-1764 | δ 3.53 (3H, s), 7.20-7.21 (1H, m), 7.32 (1H, t, J = 7.8 Hz), 7.50 (1H, t, J = 7.8 Hz), 7.70-7.71 (1H, m), 7.92 (1H, s), 8.01-8.04 (2H, m), 8.33 (1H, s), 8.53-8.54 (2H, m). |
| 7-1766 | δ 3.53 (3H, s), 7.14-7.17 (1H, m), 7.23-7.25 (1H, m), 7.54-7.55 (1H, m), 7.68 (1H, d, J = 8.0 Hz), 7.95 (1H, s), 8.00 (1H, t, J = 7.0 Hz), 8.10-8.20 (1H, m), 8.28 (1H, d, J = 4.8 Hz), 8.36 (1H, s). |
| 7-1773 | δ 3.53 (3H, s), 7.19-7.40 (3H, m), 7.52-7.53 (1H, m), 7.67-7.68 (1H, m), 7.93 (2H, s), 8.07-8.09 (1H, m), 8.32 (1H, d, J = 14.4 Hz), 8.35 (1H, s). |
| 7-1794 | δ 3.51 (3H, s), 7.18-7.23 (2H, m), 7.32 (1H, t, J = 7.8 Hz), 7.43-7.46 (1H, m), 7.92 (1H, s), 7.98-8.01 (1H, m), 8.08-8.09 (1H, m), 8.23-8.24 (1H, m), 8.32 (1H, s), 8.56-8.59 (1H, m). |
| 7-1808 | δ 3.51 (3H, s), 7.23-7.43 (6H, m), 7.44-7.60 (1H, m), 7.91 (1H, s), 7.98-8.01 (1H, m), 8.10 (1H, broad-s), 8.32 (1H, s). |
| 7-1809 | δ 3.52 (3H, s), 6.80 (1H, t, J = 8.8 Hz), 7.06 (1H, t, J = 3.6 Hz), 7.17-7.23 (2H, m), 7.39-7.44 (1H, m), 7.92-7.93 (1H, m), 7.99 (1H, t, J = 5.2 Hz), 8.16 (1H, d, J = 13.2 Hz), 8.33 (1H, s). |
| 7-1810 | δ 3.48 (3H, s), 6.99-7.16 (3H, m), 7.28-7.34 (2H, m), 7.43-7.45 (1H, m), 7.72 (1H, t, J = 8.0 Hz), 7.92 (1H, s), 8.00 (1H, t, J = 8.0 Hz), 8.33 (1H, s). |
| 7-1811 | δ 3.53 (3H, s), 6.90 (2H, t, J = 8.0 Hz), 7.28-7.40 (3H, m), 7.46 (1H, t, J = 7.2 Hz), 7.92 (1H, s), 8.02 (1H, t, J = 8.0 Hz), 8.13 (1H, d, J = 12.4 Hz), 8.33 (1H, s). |
| 7-1828 | δ 3.52 (3H, s), 7.32-7.35 (2H, m), 7.49-7.60 (3H, m), 7.69 (1H, s), 7.92 (1H, s), 8.05-8.08 (2H, m), 8.36 (1H, s). |
| 7-1829 | δ 3.53 (3H, s), 7.30-7.34 (1H, m), 7.45-7.52 (5H, m), 7.92 (1H, s), 8.04-8.07 (2H, m), 8.34 (1H, s). |
| 7-1844 | δ 3.54 (3H, s), 7.15 (1H, t, J = 5.2 Hz), 7.52-7.54 (1H, m), 7.68-7.71 (2H, m), 7.94 (1H, s), 8.00 (1H, t, J = 5.2 Hz), 8.15-8.16 (1H, m), 8.28 (1H, d, J = 4.8 Hz), 8.34 (1H, s). |
| 7-1851 | δ 3.52 (3H, s), 7.65 (1H, d, J = 6.8 Hz), 7.92 (1H, s), 8.05-8.08 (2H, m), 8.11-8.18 (3H, m), 8.26-8.31 (1H, m), 8.33 (1H, s). |
| 7-3348 | δ 3.48 (3H, s), 7.18-7.30 (6H, m), 7.45 (1H, broad-s), 7.52 (1H, broad-s), 7.74-7.76 (1H, m), 7.89 (1H, s), 8.11 (1H, s). |
| 7-3369 | δ 3.49 (3H, s), 7.18-7.22 (1H, m), 7.45-7.53 (5H, m), 7.56 (2H, broad-s), 7.92 (1H, s), 8.14 (1H, s). |
| 7-3384 | δ 3.52 (3H, s), 7.15-7.20 (2H, m), 7.45-7.85 (4H, m), 7.92 (1H, s), 8.12-8.15 (1H, m), 8.27-8.29 (1H, m). |
| 7-5902 | δ 3.51 (3H, s), 7.00-7.52 (7H, m), 7.88 (1H, d, J = 1.5 Hz), 8.01-8.06 (3H, m). |
| 7-5903 | δ 3.55 (3H, s), 7.14 (1H, dd, J = 4.8, 7.8 Hz), 7.24-7.26 (1H, m), 7.40-7.60 (1H, m), 7.66-7.68 (1H, m), 7.91 (1H, s), 8.01-8.05 (2H, m), 8.08 (1H, d, J = 1.5 Hz), 8.28 (1H, dd, J = 2.0, 4.8 Hz). |
| 7-5904 | δ 3.56 (3H, s), 7.05-7.09 (1H, m), 7.30-7.36 (2H, m), 7.43-7.48 (2H, m), 7.56 (1H, s), 7.65 (1H, s), 7.77 (1H, d, J = 8.0 Hz), 7.90 (1H, d, J = 8.0 Hz), 8.07 (2H, s). |
| 7-5905 | δ 3.57 (3H, s), 6.89 (1H, t, J = 8.0 Hz), 7.15 (1H, t, J = 8.0 Hz), 7.32-7.36 (2H, m), 7.47 (1H, t, J = 8.0 Hz), 7.53 (1H, s), 7.61 (1H, s), 7.77 (1H, d, J = 8.0 Hz), 8.09 (2H, s), 8.70 (1H, broad-s). |
| 7-5906 | δ 3.55 (3H, s), 7.00 (1H, t, J = 8.0 Hz), 7.07 (2H, d, J = 7.8 Hz), 7.16-7.22 (1H, m), 7.32 (1H, d, J = 6.8 Hz), 7.44 (1H, t, J = 8.0 Hz), 7.57 (1H, s), 7.65-7.67 (1H, m), 7.74 (1H, d, J = 8.0 Hz), 7.85 (2H, s). |
| 7-5907 | δ 3.57 (3H, s), 6.90 (2H, t, J = 7.8 Hz), 7.29-7.34 (3H, m), 7.44 (1H, t, J = 7.8 Hz), 7.49 (1H, s), 7.62 (1H, s), 7.73 (1H, d, J = 7.8 Hz), 7.85 (2H, s). |
| 7-5908 | δ 2.99 (3H, s), 3.58 (3H, s), 7.27-7.30 (1H, m), 7.43-7.44 (1H, m), 7.51 (2H, d, J = 8.3 Hz), 7.65-7.70 (3H, m), 7.81 (2H, d, J = 8.3 Hz), 7.91 (1H, s), 8.14 (1H, s). |
| 7-5909 | δ 3.60 (3H, s), 7.33 (1H, d, J = 7.9 Hz), 7.50 (1H, t, J = 7.9 Hz), 7.63 (1H, s), 7.70 (1H, s), 7.75 (1H, d, J = 7.9 Hz), 7.94 (1H, s), 8.34 (1H, s), 8.65 (2H, s), 9.10 (1H, s). |
| 7-5910 | δ 3.53 (3H, s), 3.89 (3H, s), 7.32 (1H, t, J = 7.8 Hz), 7.48-7.49 (1H, m), 7.83-7.91 (2H, m), 8.01 (1H, t, J = 7.3 Hz), 8.10-8.14 (3H, m), 8.22-8.23 (1H, m). |
| 7-5911 | δ 3.57 (3H, s), 7.20-7.35 (6H, m), 7.41-7.45 (2H, m), 7.53 (1H, s), 7.67 (1H, d, J = 7.8 Hz), 7.89 (1H, s), 8.11 (1H, s). |
| 7-5912 | δ 3.58 (3H, s), 7.14 (1H, dd, J = 4.9, 7.8 Hz), 7.42-7.43 (2H, m), 7.55 (1H, s), 7.59 (1H, dd, J = 2.0, 7.8 Hz), 7.67-7.68 (2H, m), 7.91 (1H, s), 8.13 (1H, s), 8.26 (1H, dd, J = 2.0, 4.9 Hz). |
| 8-268 | δ 3.28 (2/3*3H, s), 3.39 (1/3*3H, s), 7.13-7.14 (1/3*1H, m), 7.15-7.17 (1/3*1H, m), 7.34 (1/3*1H, s), 7.36 (1/3*1H, s), 7.46-7.57 (12/3*1H, m), 7.74-7.90 (13/3*1H, m), 7.94 (2/3*1H, s), 8.05 (1/3*1H, s), 8.15 (2/3*1H, s), 8.24 (2/3*1H, s). |

TABLE 52-continued

| compound number | ¹H-NMR (CDCl₃, ppm) |
|---|---|
| 8-288 | (CDCl₃ + DMSO-d₆) δ 3.30 (3/4*3H, s), 3.40 (1/4*3H, s), 7.10-7.15 (1/4*1H, m), 7.20-7.25 (1/4*1H, m), 7.35 (1/4*1H, s), 7.37 (1/4*1H, s), 7.50 (3/4*1H, t, J = 7.8 Hz), 7.62-7.66 (6/4*1H, m), 7.82-7.84 (5/4*1H, m), 7.94 (1/4*1H, s), 7.95 (3/4*1H, s), 8.00 (3/4*1H, t, J = 1.5 Hz), 8.08-8.10 (4/4*1H, m), 8.17 (3/4*1H, s), 8.18-8.19 (1/4*1H, m), 8.32-8.36 (4/4*1H, m), 8.48 (3/4*1H, t, J = 1.5 Hz), 10.00 (1/4*1H, s), 10.29 (3/4*1H, s). |
| 8-289 | δ 3.26 (2/3*3H, s), 3.38 (1/3*3H, s), 7.08-7.09 (1/3*1H, m), 7.12-7.14 (1/3*1H, m), 7.32 (2/3*1H, d, J = 7.8 Hz), 7.45-7.49 (3/3*1H, m), 7.72-7.76 (9/*13H, m), 7.83 (1/3*1H, s), 7.85-7.89 (4/3*1H, m), 7.95 (2/3*1H, s), 7.98-8.00 (4/3*1H, m), 8.04 (2/3*1H, d, J = 6.3 Hz), 8.16 (2/3*1H, s), 8.57 (2/3*1H, s). |
| 8-304 | δ 3.29 (3/5*3H, s), 3.38 (2/5*3H, s), 7.14-7.18 (4/5*1H, m), 7.37-7.41 (8/5*1H, m), 7.50-7.52 (5/5*1H, m), 7.72 (2/5*1H, s), 7.83-7.86 (8/5*1H, m), 7.95 (3/5*1H, s), 8.05-8.07 (4/5*1H, m), 8.14-8.17 (6/5*1H, m), 8.30 (2/5*1H, s), 8.51-8.53 (5/5*1H, m), 8.57 (3/5*1H, s). |
| 8-804 | δ 3.31 (3H, s), 7.30-7.33 (1H, m), 7.48-7.52 (3H, m), 7.56-7.60 (1H, m), 7.72-7.74 (1H, m), 7.86-7.91 (3H, m), 8.06 (1H, s), 8.22 (2H, s). |
| 8-824 | (DMSO-d₆) δ 3.32 (12/13*3H, s), 3.43 (1/13*3H, s), 7.01-7.02 (1/13*1H, m), 7.20-7.21 (1/13*1H, m), 7.28 (12/13*1H, d, J = 7.8 Hz), 7.50 (12/13*1H, t, J = 7.8 Hz), 7.60-7.61 (1/13*1H, m), 7.65 (12/13*1H, t, J = 7.8 Hz), 7.83-7.84 (13/13*1H, m), 7.85 (1/13*1H, d, J = 1.5 Hz), 7.94 (12/13*1H, d, J = 1.5 Hz), 8.10-8.12 (12/13*1H, m), 8.14 (1/13*2H, s), 8.21-8.22 (1/13*1H, m), 8.23 (12/13*2H, s), 8.32-8.35 (13/13*1H, m), 8.47-8.48 (13/13*1H, m), 10.05 (1/13*1H, s), 10.37 (12/13*1H, s). |
| 8-840 | δ 3.30 (10/11*3H, s), 3.43 (1/11*3H, s), 7.17-7.18 (1/11*1H, m), 7.19-7.20 (1/11*1H, m), 7.33-7.42 (22/11*1H, m), 7.52 (10/11*1H, t, J = 7.8 Hz), 7.71 (1/11*1H, s), 7.75 (10/11*1H, s), 7.87 (10/11*1H, d, J = 8.3 Hz), 8.12-8.13 (1/11*1H, m), 8.14 (1/11*2H, s), 8.17 (10/11*1H, dd, J = 2.0, 7.8 Hz), 8.23 (10/11*2H, s), 8.47-8.50 (11/11*1H, m), 8.52-8.53 (11/11*1H, m). |
| 9-270 | δ 2.64 (3/4*3H, s), 3.28 (1/4*3H, s), 3.37 (1/4*3H, s), 3.56 (3/4*3H, s), 6.70-6.71 (1/4*1H, m), 6.80-6.81 (1/4*1H, m), 7.02-7.03 (4/4*1H, m), 7.16-7.26 (16/4*1H, m), 7.34-7.36 (10/4*1H, m), 7.39-7.40 (1/4*1H, m), 7.46 (3/4*1H, t, J = 7.8 Hz), 7.80 (1/4*1H, s), 7.91 (3/4*1H, s), 8.01 (1/4*1H, s), 8.11 (3/4*1H, s). |
| 9-290 | δ 2.88 (2/3*3H, s), 3.33 (1/3*3H, s), 3.37 (1/3*3H, s), 3.56 (2/3*3H, s), 6.70-6.71 (1/3*1H, m), 6.95-6.98 (2/3*1H, m), 7.10 (2/3*1H, s), 7.28-7.42 (9/3*1H, m), 7.47-7.60 (6/3*1H, m), 7.62-7.63 (4/3*1H, m), 7.86 (1/3*1H, s), 7.93 (2/3*1H, s), 8.08 (1/3*1H, s), 8.14 (2/3*1H, s). |
| 9-291 | δ 2.82 (2/3*3H, s), 3.30 (1/3*3H, s), 3.37 (1/3*3H, s), 3.56 (2/3*3H, s), 6.75-6.76 (1/3*1H, m), 6.95 (1/3*1H, t, J = 7.8 Hz), 7.00-7.01 (1/3*1H, m), 7.06 (2/3*1H, s), 7.28-7.32 (4/3*1H, m), 7.39-7.54 (15/3*1H, m), 7.83 (1/3*1H, s), 7.93 (2/3*1H, s), 8.04 (1/3*1H, s), 8.14 (2/3*1H, s). |
| 9-306 | δ 2.89 (2/3*3H, s), 3.30 (1/3*3H, s), 3.36 (1/3*3H, s), 3.57 (2/3*3H, s), 6.96-6.97 (1/3*1H, m), 7.04-7.05 (2/3*1H, m), 7.13-7.17 (2/3*1H, m), 7.27-7.41 (10/3*1H, m), 7.60-7.63 (3/3*1H, m), 7.81 (1/3*1H, s), 7.94 (2/3*1H, s), 8.02 (1/3*1H, s), 8.15 (2/3*1H, s), 8.24-8.25 (3/3*1H, m). |
| 9-2164 | δ 2.18-2.19 (3H, m), 3.48 (3H, s), 7.21-7.25 (4H, m), 7.32-7.40 (4H, m), 7.92 (1H, s), 8.13 (1H, s). |
| 9-2322 | δ 2.71-2.72 (3H, m), 3.47 (3H, s), 6.95-6.96 (1H, m), 7.11-7.16 (3H, m), 7.38-7.39 (2H, m), 7.95 (1H, s), 8.02 (1H, s), 8.34 (1H, s). |
| 11-777 | δ 4.88 (2H, s), 7.20-7.21 (1H, m), 7.36 (1H, t, J = 7.8 Hz), 7.84-7.87 (1H, m), 7.92 (1H, s), 8.14-8.17 (2H, m), 8.36 (1H, broad-s). |
| 11-835 | δ 4.88 (2H, s), 7.22-7.23 (1H, m), 7.36 (1H, t, J = 7.8 Hz), 7.85-7.88 (1H, m), 7.95 (1H, s), 8.19 (1H, d, J = 13.1 Hz), 8.36-8.37 (2H, m). |
| 12-777 | δ 3.39 (3H, s), 4.74 (2H, broad-s), 7.37 (1H, t, J = 7.8 Hz), 7.52-7.56 (1H, m), 7.92 (1H, s), 8.11-8.14 (2H, m), 8.25 (1H, d, J = 14.1 Hz). |
| 12-835 | δ 3.40 (3H, s), 4.74 (2H, broad-s), 7.37 (1H, t, J = 7.8 Hz), 7.55-7.58 (1H, m), 7.95 (1H, s), 8.12-8.13 (1H, m), 8.28-8.31 (1H, m), 8.36 (1H, s). |
| 12-864 | δ 3.40 (3H, s), 4.74 (2H, broad-s), 7.37 (1H, t, J = 7.8 Hz), 7.52-7.58 (1H, m), 7.93 (1H, s), 8.12-8.15 (1H, m), 8.28-8.34 (2H, m). |
| 17-1103 | δ 3.65 (3H, s), 7.28-7.41 (6H, m), 7.77 (1H, t, J = 7.8 Hz), 7.91 (1H, s), 8.00-8.02 (1H, m), 8.14 (1H, s), 9.39 (1H, s). |
| 22-435 | δ 3.63 (3H, s), 4.90 (2H, s), 7.92-7.97 (2H, m), 8.08-8.15 (3H, m), 9.72 (1H, s). |
| 27-627 | δ 3.72 (3H, s), 7.51-7.60 (5H, m), 7.90 (1H, s), 8.05 (1H, s), 8.14 (1H, s), 9.11 (1H, s). |
| 27-628 | δ 3.67 (3H, s), 6.99-7.24 (1H, m), 7.29-7.35 (1H, m), 7.52-7.59 (2H, m), 7.90 (1H, s), 8.06 (1H, s), 8.14 (1H, s), 9.08 (1H, s). |
| 27-663 | δ 3.63 (3H, s), 7.44-7.47 (1H, m), 7.80 (1H, dd, J = 2.0, 7.8 Hz), 7.90 (1H, s), 8.10 (1H, s), 8.14 (1H, s), 8.58-8.60 (1H, m), 9.04 (1H, s). |
| 32-247 | δ 3.77-3.78 (3H, m), 4.96 (2H, s), 7.90 (1H, s), 8.00 (1H, s), 8.14 (1H, s), 9.02 (1H, s). |

The pest control agent including the compound of the present invention as an active ingredient can effectively control, at a low concentration thereof, any pests such as insects including various agricultural pests damaging agricultural/horticultural crops, trees, and the like, insanitary pests adversely affecting the living environment of humans such as houses and the like in various manners, stored grain pests damaging grain and the like stored in a warehouse, wood-eating pests damaging wood such as buildings and the like, and mites, crustaceans, molluscs, and nematodes which propagate and cause damage in a manner similar to that in the case of the insects.

Specific examples of the insects, the mites, the crustaceans, molluscs and nematodes which can be controlled using the compound of the present invention include lepidopteran insects such as *Adoxophyes honmai, Adoxophyes orana faciata, Archips breviplicanus, Grapholita inopinata, Archips fuscocupreanus, Grapholita molesta, Choristoneura magnanima, Leguminivora glycinivorella, Olethreutes mori, Caloptilia zachrysa, Argyresthia conjugella, Spulerrina astaurota, Matsumuraeses phaseoli, Pandemis heparana, Bucculatrix pyrivorella, Lyonetia clerkella, Carposina niponensis, Lyonetia prunifoliella malinella, Caloptilia theivora, Phyllonorycter ringoniella, Phyllocnistis citrella, Acrolepiopsis sapporensis, Acrolepiopsis suzukiella, Plutella xylostella, Stathmopoda masinissa, Helcystogramma triannulella, Pectinophora gossypiella, Carposina sasakii, Chilo suppressalis, Cnaphalocrocis medinalis, Ephestia elutella, Conogethes punctiferalis, Diaphania indica, Etiella zinckenella, Glyphodes pyloalis, Scirpophaga incertulas, Hellula* undalis, Ostrinia furnacalis, Ostrinia scapulalis, Parapediasia teterrella, Parnara guttata, Pieris brassicae, Pieris rapae crucivora, Papilio xuthus, Ascotis selenaria, Pseudoplusia includens, Euproctis pseudoconspersa, Lymantria dispar, Orgyia thyellina, Hyphantria cunea, Lemyra imparilis, Adris tyrannus, Aedia leucomelas, Agrotis ipsilon, Agrotis segetum, Autographa nigrisigna, Ctenoplusia agnata, Cydla pomonella, Helicoverpa armigera, Helicoverpa assulta, Helicoverpa zea, Heliothis virescens, Ostrinia nubilalis, Mamestra brassicae, Mythimna separata, Sesamia inferens, Naranga aenescens, Spodoptera eridania, Spodoptera exigua, Spodoptera frugiperda, Spodoptera littoralis, Spodoptera litura, Spodoptera depravata, Trichoplusia ni, Endopiza viteana, Manduca quinquemaculata, Manduca sexta, and the like;

Hemipteran insects such as *Arboridia apicalis, Balclutha saltuella, Epiacanthus stramineus, Empoasca fabae, Empoasca nipponica, Empoasca onukii, Empoasca sakaii, Macrosteles striifrons, Nephotettix cinctinceps, Psuedatomoscelis seriatus, Laodelphax striatella, Nilaparvata lugens, Sogatella furcifera, Diaphorina citri, Psylla pyrisuga, Aleurocanthus spiniferus, Bemisia argentifolii, Bemisia tabaci, Dialeurodes citri, Trialeurodes vaporariorum, Aleurolobus taonabae, Viteus vitifolii, Lipaphis erysimi, Aphis gossypii, Aphis spiraecola, Myzus persicae, Toxoptera aurantii, Drosicha corpulenta, kerya purchasi, Phenacoccus solani, Pulvinaria aurantii, Planococcus citri, Pseudaonidia duplex, Planococcus kuraunhiae, Pseudococcus comstocki, Comstockaspis perniciosa, Ceroplastes ceriferus, Ceroplastes rubens, Aonidiella aurantii, Fiorinia theae, Pseudaonidia paeoniae, Pseudaulacaspis pentagona, Pseudaulacaspis prunicola, Unaspis euonymi, Unaspis yanonensis, Cimex lectularius, Dolycoris baccarum, Eurydema rugosum, Eysarcoris aeneus, Eysarcoris lewisi, Eysarcoris ventralis, Glaucias subpunctatus, Halyomorpha halys, Nezara antennata, Nezara viridula, Piezodorus hybneri, Plautia crossota, Scotinophora lurida, Cletus punctiger, Leptocorisa chinensis, Riptortus clavatus, Rhopalus msculatus, Cavelerius saccharivorus, Togo hemipterus, Dysdercus cingulatus, Stephanitis pyrioides, Halticus insularis, Lygus lineolaris, Stenodema sibiricum, Stenotus rubrovittatus, Trigonotylus caelestialium*, and the like;

Coleopteran insects such as *Anomala cuprea, Anomala rufocuprea, Gametis jucunda, Heptophylla picea, Popillia japonica, Lepinotarsa decemlineata, Epilachna varivestis, Melanotus fortnumi, Melanotus tamsuyensis, Lasioderma serricorne, Lyctusbrunneus, Tomicus piniperda, Rhizopertha dominica, Epuraea domino, Epilachna varivestis, Epilachna vigintioctopunctata, Tenebrio molitor, Tribolium castaneum, Anoplophora malasiaca, Monochamus alternatus, Psacothea hilaris, Xylotrechus pyrrhoderus, Callosobruchus chinensis, Aulacophora femoralis, Oulema oryzae, Chaetocnema concinna, Diabrotica undecimpunctata, Diabrotica virgifera, Diabrotica barberi, Phyllotreta striolata, Psylliodes angusticollis, Rhynchites heros, Cylas formicarius, Anthonomus grandis, Echinocnemus squameus, Euscepes postfasciatus, Hypera postica, Lissohoptrus oryzophilus, Otiorhynchus sulcatus, Sitophilus granarius, Sitophilus zeamais, Sphenophorus venatus vestitus, Paederus fuscipes*, and the like;

Thysanopteran insects such as *Frankliniella intonsa, Thrips flavus, Frankliniella occidentalis, Heliothrips haemorrhoidalis, Scirtothrips dorsalis, Thrips palmi, Thrips tabaci, Ponticulothrips diospyrosi*, and the like;

Dipterous insects such as *Asphondylia yushimai, Sitodiplosis mosellana, Bactrocera cucurbitae, Bactrocera dorsalis, Ceratitis capitata, Hydrellia griseola, Drosophila suzukii, Agromyza oryzae, Chromatomyia horticola, Liriomyza bryoniae, Liriomyza chinensis, Liriomyza sativae, Liriomyza trifolii, Delia platura, Delia antique, Pegomya cunicularia, Rhagoletis pomonella, Mayetiola destructor, Musca domestica, Stomoxys calcitrans, Melophagus ovines, Hypoderma bovis, Hypoderma lineatum, Oestrus ovis, Glossina palpalis, Glossina morsitans, Prosimulium yezoensis, Tabanus trigonus, Telmatoscopus albipunctatus, Leptoconops nipponensis, Culex pipiens pallens, Aedes aegypti, Aedes albopicutus, Anopheles hyracanus sinesis*, and the like;

Hymenopteran insects such as *Apethymus kuri, Athalia rosae, Arge pagana, Neodiprion sertifer, Dryocosmus kuriphilus, Eciton burchelli, Eciton schmitti, Camponotus japonicus, Vespa mandarina, Myrmecia* spp., *Solenopsis* spp., *Monomorium pharaonic*, and the like;

Orthopteran insects such as *Teleogryllus emma, Gryllotalpa orientalis, Locusta migratoria, Oxya yezoensis, Schistocerca gregaria*, and the like;

Collembolan insects such as *Onychiurus folsomi, Onychiurus sibiricus, Bourletiella hortensis*, and the like;

Dictyopteran insects such as *Periplaneta fuliginosa, Periplaneta japonica, Blattella germanica, Periplaneta Americana*, and the like;

Isopterous insects such as *Coptotermes formosanus, Reticulitermes speratus, Odontotermes formosanus*, and the like;

Isopterous insects such as *Ctenocephalidae felis, Ctenocephalides canis, Echidnophaga gallinacea, Pulex irritans, Xenopsylla cheopis*, and the like;

Mallophaga insects such as *Menacanthus stramineus, Bovicola bovis*, and the like;

Anoplura insects such as *Haematopinus eurysternus, Haematopinus suis, Linognathus vituli, Solenopotes capillatus*, and the like;

Tarsonemidae such as *Phytonemus pallidus, Polyphagotarsonemus latus, Tarsonemus bilobatus*, and the like;

Eupodidae such as *Penthaleus erythrocephalus, Penthaleus major*, and the like;

Tetranychidae such as *Oligonychus shinkajii, Panonychus citri, Panonychus mori, Panonychus ulmi, Tetranychus kanzawai, Tetranychus urticae*, and the like;

Eriophydae such as *Acaphylla theavagrans, Aceria tulipae, Aculops lycopersici, Aculops pelekassi, Aculus schlechtendali, Eriophyes chibaensis, Phyllocoptruta oleivora*, and the like;

Acaridae such as *Rhizoglyphus robini, Tyrophagus putrescentiae, Tyrophagus similis*, and the like;

Varroidae such as *Varroa jacobsoni*, and the like;

Ixodidae such as *Boophilus microplus, Rhipicephalus sanguineus, Haemaphysalis longicornis, Haemophysalis flava, Haemophysalis campanulata, Ixodes ovatus, Ixodes persulcatus, Amblyomma* spp., *Dermacentor* spp., and the like;

Cheyletidae such as *Cheyletiella yasguri, Cheyletiella blakei*, and the like;

Demodicidae such as *Demodex canis, Demodex cati*, and the like;

Psoroptidae such as *Psoroptes ovis*, and the like;

Sarcoptidae such as *Sarcoptes scabiei, Notoedres cati, Knemidocoptes* spp., and the like;

Crustacea such as *Armadillidium vulgare*, and the like;

Gastropoda such as *Pomacea canaliculata, Achatina fulica, Meghimatium bilineatum, Limax Valentiana, Acusta despecta sieboldiana, Euhadra peliomphala*, and the like; and Nematoda such as *Prathylenchus coffeae, Prathylenchus penetrans, Prathylenchus vulnus, Globodera rostochiensis, Heterodera glycines, Meloidogyne hapla, Meloidogyne*

*incognita, Aphelenchoides besseyi, Bursaphelenchus xylophilus*, and the like, but the present invention is not limited thereto.

The pest control agent including the compound according to the present invention as an active ingredient has a significant control effect against the above-described harmful crops which damage lowland crops, upland crops, fruit trees, vegetables, and other crops and ornamental flowers, and therefore, the effect as a pest control agent of the present invention can be obtained by treating the paddy field water, plant stems and leaves, or soil of the crops of lowland, upland, fruit trees, vegetables, other crops, ornamental flowers, and the like during the seasons in which the appearance of such pests is expected, or before or at the point when the pest appearance is observed.

The pest control agent including the compound according to the present invention as an active ingredient has a significant control effect against stored grain pests and the like generated during storage of the harvest. That is, the pest control agent having the compound of the present invention as an active ingredient may be subjected to a treatment after the harvest (post harvest) such as spray-spreading, coating, dipping, dressing, fumigation/smoking, pressurized injection, and the like with respect to the harvest or the place for storage of the harvest.

Further, the pest control agent including the compound according to the present invention as an active ingredient can be applied to plant seeds to prevent the damage caused by pests generated in the plants after seeding. That is, the pest control agent having the compound of the present invention as an active ingredient may be subjected to a treatment such as spray-spreading, dipping, dressing, and the like on the plant seeds in an effective amount for controlling the pests as it is, as an adequate dilution with water or the like, or as a suspension to bring the compound of the present invention into contact with the plant seeds.

The plant seeds refer to those used for breeding in agriculture by storing the nutrients for seedling germination, and examples thereof include seeds such as corn, soybeans, red beans, cotton, rice, sugar beet, wheat, barley, sunflower, tomato, cucumber, eggplant, spinach, sting beans, squash, sugarcane, tobacco, pimento, canola, and the like, seed tubers such as taro, potato, sweet potato, konjac, and the like, bulbs such as edible lily, tulips, and the like, and seed balls such as rakkyo and the like.

The pest control agent having the compound of the present invention as an active ingredient has a significant control effect against insanitary pests such as Diptera pests (*Culex pipiens pallens, Culex pipiens, Chironomidae*, houseflies, sandflies, horsefly, and the like) Dictyoptera pests (*Blattella germanica, Periplaneta fuliginosa, Periplaneta americana*, and the like), and other pests.

The pest control agent having the compound of the present invention as an active ingredient has a significant control effect against wood-feeding pests such as termites, *Lyctus-brunneus, Rhizopertha dominica, Anobiidae, Cerambycidae*, and the like, thus, the above-described wood-feeding pests can be controlled by treatment of wood, soil, buildings, and the like with the pest control agent.

Since the compound of the present invention exhibits a control effect against various pests and also exhibits an effect of protecting useful crops and an excellent control effect as a pesticide or a miticide at a low dose, it has an effect of contributing to reduction in an environmental impact. In addition, the compound of the present invention also exerts an excellent control effect when used in combination with other agricultural/horticultural pesticides, miticides, nematocides, fungicides, herbicides, plant growth regulators, biological agricultural chemicals, or the like.

For the use of the compound of the present invention, the compound can be put to practical use as a preparation in any form such as a soluble concentrate, an emulsifiable concentrate, a wettable powder, a water-soluble powder, a water dispersible granule, a water-soluble granule, a suspension concentrate, a concentrated emulsion, a suspoemulsion, a microemulsion, a dustable powder, a granule, a tablet, and an emulsifiable gel, typically by mixing the compound with a suitable solid carrier or liquid carrier, further if desired by adding to the resultant mixture, a surfactant, a penetrant, a spreader, a thickener, an antifreezing agent, a binder, an anti-caking agent, a disintegrant, a defoaming agent, an antiseptic or a stabilizer. In addition, from the labor-saving and safety-enhancing viewpoints, the compound can be put to use by encapsulating the above preparation in any form in a water-soluble packaging material such as a water-soluble capsule and a bag of water-soluble film.

The inert carrier which can be used in the present invention may be solids or liquids, and examples thereof include soybean powders, grain powders, wood powders, bark powders, sawdust powders, tobacco stem powders, walnut shell powders, brans, cellulose powders, residues from plant extraction, synthetic polymers such as pulverized synthetic resins, clays (for example, kaolin, bentonite, acidic white clay), talcs (for examples, talc, pyrophyllite, etc.), silica (for examples, diatomaceous earth, sand, mica, white carbon [hydrous silica powders, synthetic high dispersity silicates called hydrous silicate, there are also products containing calcium silicate as a main component]), activated carbon, sulfur powder, pumice, calcined diatomaceous powders, pulverized bricks, fly ash, sand, inorganic mineral powders such as calcium carbonate, calcium phosphate, and the like, chemical fertilizers such as ammonium sulfate, ammonium phosphate, ammonium nitrate, urea, ammonium chloride, and the like, a compost, and others, which are used alone or as a mixture of two or more kinds thereof.

Materials which can be used as the liquid inert carrier are selected from those having the function as solvent, as well as those capable of dispersing the active ingredient compound with the aid of an adjuvant even if the inert carrier does not have a function as a solvent. Representative examples thereof include the carriers listed below: water, alcohols (for example, methanol, ethanol, isopropanol, butanol, ethylene glycol, and the like), ketones (for example, acetone, methyl ethyl ketone, methyl isobutyl ketone, diisobutylketone, cyclohexanone, and the like), ethers (for example, diethyl ether, dioxane, cellosolve, diisopropyl ether, tetrahydrofuran, and the like), aliphatic hydrocarbons (for example, kerosene, mineral oil, and the like), aromatic hydrocarbons (for example, benzene, toluene, xylene, solvent naphtha, alkyl naphthalene, and the like), halogenated hydrocarbons (for example, dichloromethane, chloroform, tetrachlorocarbon, chlorobenzene, and the like), esters (for example, ethyl acetate, butyl acetate, ethyl propionate, diisobutyl phthalate, dibutyl phthalate, dioctyl phthalate, and the like), amides (for example, dimethyl formamide, diethyl formamide, dimethyl acetamide, and the like), and nitriles (for example, acetonitrile, and the like), which are used alone or as mixtures of two or more kinds thereof.

These solid and liquid carriers may be used alone or in a combination of two or more kinds thereof.

Examples of the surfactant include nonionic surfactants such as polyoxyethylene alkyl ethers, polyoxyethylene alkyl (mono- or di-)phenyl ethers, polyoxyethylene (mono-, di-, or tri-)styryl phenyl ethers, polyoxyethylene-polyoxypropylene block copolymers, polyoxyethylene aliphatic acid (mono- or di-) esters, sorbitan aliphatic acid esters, polyoxyethylene sorbitan aliphatic acid esters, castor oil ethylene-oxide adducts, acetylene glycol, acetylene alcohols, acetylene glycol ethylene-oxide adducts, acetylene alcohol ethylene-oxide adducts, alkylglucosides, and the like; anionic surfactants such as alkyl sulfate ester salts, alkylbenzene sulfonates, lignin sulfonates, alkyl sulfosuccinates, naphthalene sulfonates, alkylnaphthalene sulfonates, salts of naphthalene sulfonate formalin condensate, salts of alkylnaphthalene sulfonate formalin condensate, polyoxyethylenealkylether sulfate or phosphate esters salts, polyoxyethylene (mono- or di-) allylphenyl ether sulfate or phosphate esters, polyoxyethylene (mono-, di-, or tri-) styrylphenyl ether sulfate or phosphate esters, polycarboxylic acid salts (such as polyacrylic acid salts, polymaleic acid salts, maleic acid-olefin copolymers, and the like), polystyrene sulfonates, and the like; cationic surfactants such as alkylamine salts, alkyl quaternary ammonium salts, and the like; amphoteric surfactants such as amino acid-type surfactants, betaine-type surfactants, and the like; silicone-based surfactants; and fluorinated surfactants.

The content of these surfactants is not particularly limited, but it is preferably in the range of usually 0.05 part by weight to 20 parts by weight, with respect to 100 parts by weight of the preparation of the present invention. In addition, these surfactants may be used alone or in combination of two or more kinds thereof.

In order to control various pests, an amount effective for blight control can be applied as it is or as an adequate dilution with water or the like, or as a suspension, to the crops on which appearance of the corresponding pests is expected or to places where such occurrence is not preferable. The amount of use depends on various factors such as, for example, the purpose, the pest to be controlled, the state of plant growth, trends in pest appearance, climate, environmental conditions, Formulation, method of use, place of use, timing of use, and the like, but it is preferable to use the active ingredient in the concentration of 0.0001 ppm to 5000 ppm, and preferably 0.01 ppm to 1000 ppm. The dose that can be used per 10 a is generally in the range of 1 g to 300 g of the active ingredient.

The amount of the active ingredient of the compound of the present invention is usually 0.1% by weight to 20% by weight for powders, 5% by weight to 50% by weight for emulsifiable concentrates, 3% by weight to 90% by weight for wettable powders, 0.1% by weight to 20% by weight for granules, 5% by weight to 90% by weight for flowable Formulations, or 3% by weight to 90% by weight for water dispersible granules. The amount of the carrier in each form is usually 60% by weight to 99.9% by weight for powders, 40% by weight to 95% by weight for emulsifiable concentrates, 10% by weight to 90% by weight for wettable powders, 80% by weight to 99.9% by weight for granules, 10% by weight to 95% by weight for flowable Formulations, or 10% by weight to 90% by weight for water dispersible granules. Further, the amount of the adjuvant is usually 0.1% by weight to 20% by weight for powders, 1% by weight to 20% by weight for emulsifiable concentrates, 0.1% by weight to 20% by weight for wettable powders, 0.1% by weight to 20% by weight for granules, 0.1% by weight to 20% by weight for flowable Formulations, and 0.1% by weight to 20% by weight for water dispersible granules.

When the compound of the present invention is used as an agricultural chemical, it may be used, if required, as a mixture with other herbicides, various pesticides, miticides, nematocides, fungicides, plant growth regulators, synergists, fertilizers, soil conditioners, or the like to be applied during the preparation or the dusting.

All literature, patent applications, and technical specifications cited in the present specification are herein incorporated by reference as if each such individual piece of literature, patent application, and technical specification were specifically and individually indicated to be incorporated herein by reference.

EXAMPLES

Representative Examples of the present invention will be described with reference to the following Examples, but the present invention is not limited thereto. In the present Examples, DMF means N,N-dimethyl formamide, THF means tetrahydrofuran, IPE means isopropyl ether, DMI means 1,3-dimethyl-2-imidazolidinone, and DMSO means dimethylsulfoxide.

Furthermore, "%" is based on mass unless specified otherwise.

Example 1

Preparation of N-(2-bromo-4-(perfluoropropan-2-yl)-6-(trifluoromethyl)phenyl)-2-fluoro-3-(N-methylbenzamide)benzamide (Compound No. 7-1574)

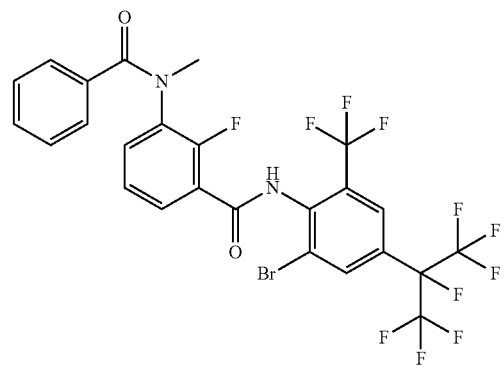 [SMILES: CN(C(=O)c1ccccc1)c1cccc(C(=O)Nc2c(Br)cc(C(F)(C(F)(F)F)C(F)(F)F)cc2C(F)(F)F)c1F]

1-1

Preparation of 4-(perfluoropropan-2-yl)-2-(trifluoromethyl)aniline

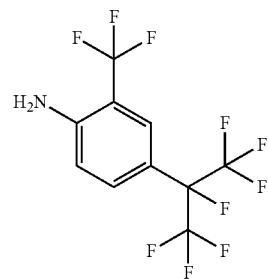 [SMILES: Nc1ccc(C(F)(C(F)(F)F)C(F)(F)F)cc1C(F)(F)F]

100 g (0.608 mol) of 2-(trifluoromethyl)aniline, 131 g (0.639 mol) of 85% sodium hydrosulfite, and 20.9 g (0.0608 mol) of tetrabutylammonium hydrogen sulfate were charged to a mixed solution of 1500 ml of ethyl acetate and 1500 ml of water, and 53.9 g (0.639 mol) of sodium hydrogen carbonate was added thereto. 198 g (0.669 mol) of heptafluoroisopropyl iodide was added dropwise thereto at room temperature, followed by stirring at room temperature for 6 hours. After the liquid separation, the solvent of the organic layer was evaporated under reduced pressure, and 500 ml of ethyl acetate was charged thereto. 160 g (0.608 mol) of a 4 M hydrogen chloride/ethyl acetate solution was added dropwise thereto, followed by stirring at room temperature for 30 minutes, and then stirring at 5° C. for 1 hour. After the filtration, the filtrate was washed with water and a saturated aqueous sodium hydrogen carbonate in this order, and then dried over anhydrous magnesium sulfate, and the solvent was evaporated under reduced pressure. The obtained residue was purified by silica gel column chromatography (eluent solvent; hexane:ethyl acetate=10:1) to prepare 60.0 g (yield 30%) of a target compound.

$^1$H-NMR (CDCl$_3$, ppm) δ 4.49 (2H, broad-s), 6.81 (1H, d, J=8.3 Hz), 7.48 (1H, d, J=8.3 Hz), 7.64 (1H, s).

1-2

Preparation of 2-bromo-4-(perfluoropropan-2-yl)-6-(trifluoromethyl)aniline

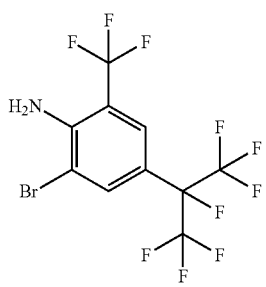 [SMILES: Nc1c(Br)cc(C(F)(C(F)(F)F)C(F)(F)F)cc1C(F)(F)F]

100 g (0.273 mol) of 4-(perfluoropropan-2-yl)-2-(trifluoromethyl)aniline was charged to 500 ml of DMF, and 52.1 g (0.287 mol) of N-bromosuccinimide was charged in separate portions thereto over 30 minutes. After stirring at 60° C. for 2 hours, and then cooling to room temperature, the mixture was discharged to 2000 ml of water. The mixture was extracted with ethyl acetate, then washed with saturated brine, and dried over anhydrous magnesium sulfate. The solvent was evaporated under reduced pressure and the obtained residue was purified by silica gel column chromatography (eluent solvent; hexane:ethyl acetate=20:1) to prepare 89.0 g (yield 80%) of a target compound.

$^1$H-NMR (CDCl$_3$, ppm) δ 5.03 (2H, broad-s), 7.61 (1H, s), 7.79 (1H, s).

1-3

Preparation of N-(2-bromo-4-(perfluoropropan-2-yl)-6-(trifluoromethyl)phenyl)-2-chloro-3-nitrobenzamide

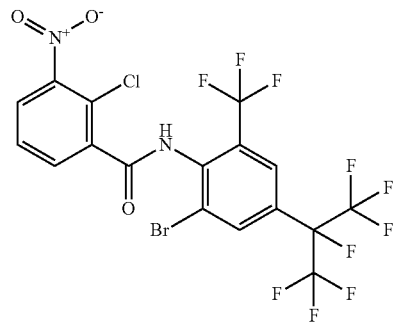

3.60 g (8.82 mmol) of 2-bromo-4-(perfluoropropan-2-yl)-6-(trifluoromethyl)aniline was charged to 20 ml of anhydrous THF, and cooled to −70° C. under a nitrogen atmosphere. 4.85 ml (9.70 mmol) of a 2.0 M lithium diisopropyl amide hexane solution was added dropwise thereto, then 2.34 g (10.7 mmol) of acid chloride which was prepared from 2-chloro-3-nitrobenzoic acid and thionyl chloride was dissolved in 5 ml of anhydrous THF, and was added dropwise thereto, followed by stirring at −70° C. for 30 minutes and then stirring at room temperature for 30 minutes. The mixture was discharged to an aqueous ammonium chloride solution, then extracted with ethyl acetate, and dried over anhydrous magnesium sulfate. The solvent was evaporated under reduced pressure and the obtained residue was purified by silica gel column chromatography (eluent solvent; hexane:ethyl acetate=10:1→8:2→3:1) to prepare 1.76 g (yield: 34%) of a target compound.

$^1$H-NMR (CDCl$_3$, ppm) δ 7.61 (1H, t, J=7.8 Hz), 7.67 (1H, broad-s), 7.93-7.97 (3H, m), 8.18 (1H, broad-s).

1-4

Preparation of N-(2-bromo-4-(perfluoropropan-2-yl)-6-(trifluoromethyl)phenyl)-2-fluoro-3-nitrobenzamide

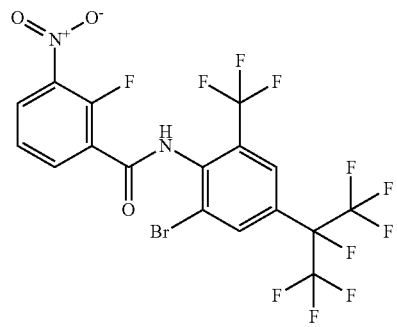 [SMILES: O=C(Nc1c(Br)cc(C(F)(C(F)(F)F)C(F)(F)F)cc1C(F)(F)F)c1cccc([N+](=O)[O-])c1F]

To a solution of N-(2-bromo-4-(perfluoropropan-2-yl)-6-(trifluoromethyl)phenyl)-2-chloro-3-nitrobenzamide 4.89 g (8.27 mmol) in 50 ml of anhydrous DMF was added 2.40 g (41.3 mmol) of potassium fluoride (spray-dried product) under a flow of nitrogen, followed by stirring at 130° C. for 10 hours. Liquid separation was carried out by adding ethyl acetate, hexane, and water to the reaction mixture, and then the organic layer was washed with water and saturated brine, and dried over anhydrous magnesium sulfate. The solvent was evaporated under reduced pressure and the obtained residue was purified by silica gel column chromatography (eluent solvent; hexane:ethyl acetate=10:1) to prepare 0.940 g (yield 20%) of a target compound.

$^1$H-NMR (CDCl$_3$, ppm) δ 7.53 (1H, t, J=7.3 Hz), 7.93 (1H, broad-s), 8.17-8.18 (2H, m), 8.28-8.32 (1H, m), 8.44-8.48 (1H, m).

1-5

Preparation of 3-amino-N-(2-bromo-4-(perfluoropropan-2-yl)-6-(trifluoromethyl)phenyl)-2-fluorobenzamide

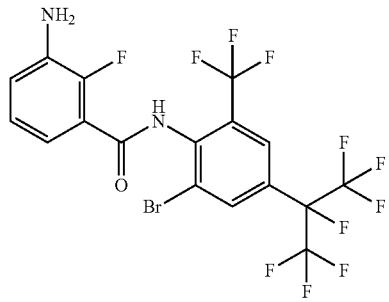

0.940 g (1.63 mmol) of N-(2-bromo-4-(perfluoropropan-2-yl)-6-(trifluoromethyl)phenyl)-2-fluoro-3-nitrobenzamide and 0.960 g (5.05 mmol) of stannous chloride (anhydrous) were added to 10 ml of ethanol, and 1.02 ml (9.78 mmol) of concentrated hydrochloric acid was added thereto, followed by stirring at 60° C. for 4 hours. The reaction mixture was adjusted to pH 10 by the addition of an aqueous sodium hydroxide solution, and the precipitated insolubles were removed by filtration using Celite. The filtrate on Celite was washed with ethyl acetate. The filtrate was extracted with ethyl acetate, and the organic layer was washed with a 20% aqueous sodium hydroxide solution and saturated brine, and then dried over anhydrous magnesium sulfate. The solvent was evaporated under reduced pressure and the obtained residue was purified by silica gel column chromatography (eluent solvent; hexane:ethyl acetate=4:1) to prepare 0.930 g (yield 99%) of a target compound.

$^1$H-NMR (CDCl$_3$, ppm) δ 3.93 (2H, broad-s), 6.99-7.04 (1H, m), 7.11 (1H, t, J=7.8 Hz), 7.47-7.49 (1H, m), 7.91 (1H, s), 8.14 (1H, s), 8.28 (1H, d, J=14.6 Hz).

1-6

Preparation of N-(2-bromo-4-(perfluoropropan-2-yl)-6-(trifluoromethyl)phenyl)-2-fluoro-3-(methylamino)benzamide

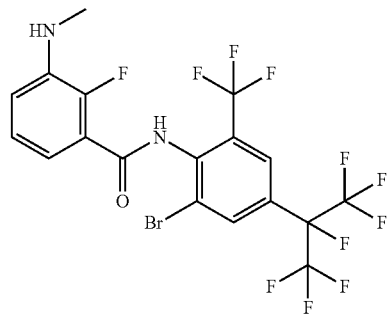 [SMILES: CNc1cccc(C(=O)Nc2c(Br)cc(C(F)(C(F)(F)F)C(F)(F)F)cc2C(F)(F)F)c1F]

0.930 g (1.71 mmol) of 3-amino-N-(2-bromo-4-(perfluoropropan-2-yl)-6-(trifluoromethyl)phenyl)-2-fluorobenzamide was added to 5 ml of concentrated sulfuric acid, and 10 ml of a 37% aqueous formaldehyde solution was charged dropwise thereto at 40° C. The reaction mixture was poured into ice-water, adjusted to pH 10 using an aqueous sodium hydroxide solution, and extracted with the addition of ethyl acetate. The organic layer was washed with a 20% aqueous sodium hydroxide solution and saturated brine, and then dried over anhydrous magnesium sulfate. The solvent was evaporated under reduced pressure and the obtained residue was purified by silica gel column chromatography (eluent solvent; hexane:ethyl acetate=8:1) to prepare 0.690 g (yield 72%) of a target compound.

$^1$H-NMR (CDCl$_3$, ppm) δ 2.94 (3H, s), 4.14 (1H, broad-s), 6.88-6.93 (1H, m), 7.18 (1H, t, J=7.8 Hz), 7.37-7.41 (1H, m), 7.90 (1H, s), 8.13 (1H, s), 8.27 (1H, d, J=14.6 Hz).

[1-7] Preparation of N-(2-bromo-4-(perfluoropropan-2-yl)-6-(trifluoromethyl)phenyl)-2-fluoro-3-(N-methylbenzamide)benzamide (Compound No. 7-1574)

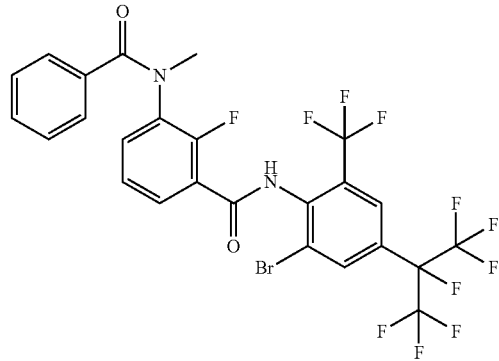 [SMILES: CN(C(=O)c1ccccc1)c1cccc(C(=O)Nc2c(Br)cc(C(F)(C(F)(F)F)C(F)(F)F)cc2C(F)(F)F)c1F]

To a solution of 1.54 g (2.75 mmol) of N-(2-bromo-4-(perfluoropropan-2-yl)-6-(trifluoromethyl)phenyl)-2-fluoro-3-(methylamino)benzamide and 0.330 g (4.13 mmol) of pyridine in 5 ml of THF was added 0.460 g (3.30 mmol) of benzoyl chloride, followed by stirring at 60° C. for 5 hours. To the reaction mixture were added water and ethyl acetate, and the organic layer was washed with 1 M hydrochloric acid, a saturated aqueous sodium hydrogen carbonate solution, and saturated brine, and then dried over anhydrous magnesium sulfate. The solvent was evaporated under reduced pressure and the obtained residue was purified by silica gel column chromatography (eluent solvent; hexane:ethyl acetate=8:1), and the obtained solid was washed with IPE to prepare 1.45 g (yield 80%) of a target compound.

$^1$H-NMR (CDCl$_3$, ppm) δ 3.50 (3H, s), 6.99-7.33 (6H, m), 7.43-7.45 (1H, m), 7.90 (1H, s), 7.97-8.06 (2H, m), 8.13 (1H, s).

Example 2

Preparation of 2-chloro-N-(3-(2,6-dibromo-4-(perfluoropropan-2-yl)phenylcarbamoyl)-2-fluorophenyl)nicotinamide (Compound No. 6-1140)

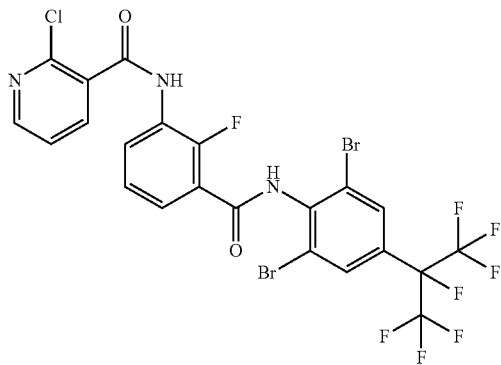 [SMILES: O=C(Nc1cccc(C(=O)Nc2c(Br)cc(C(F)(C(F)(F)F)C(F)(F)F)cc2Br)c1F)c1cccnc1Cl]

2-1

Preparation of 4-(perfluoropropan-2-yl)aniline

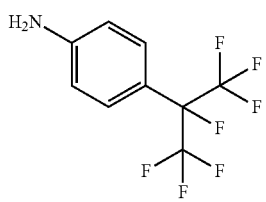 [SMILES: Nc1ccc(C(F)(C(F)(F)F)C(F)(F)F)cc1]

100 g (1.02 mol) of aniline, 230 g (1.12 mol) of 85% sodium hydrosulfite, and 35.1 g (0.100 mol) of tetrabutylammonium hydrogen sulfate were charged to a mixed solution of 1500 ml of t-butyl methyl ether and 1500 ml of water, and 94.7 g (1.12 mol) of sodium hydrogen carbonate was added thereto. 350 g (1.12 mol) of heptafluoroisopropyl iodide was added dropwise thereto at room temperature, followed by stirring at room temperature for 6 hours. After the liquid separation, the organic layer was washed with 1 M hydrochloric acid, water, and a saturated aqueous sodium hydrogen carbonate solution, and then dried over anhydrous sodium sulfate. The solvent was evaporated under reduced pressure, and 500 ml of ethyl acetate was charged thereto. 255 g (1.02 mol) of a 4 M hydrogen chloride/ethyl acetate solution was added dropwise thereto, followed by stirring at room temperature for 30 minutes and at 5° C. for 1 hour. The precipitated solid was separated by filtration, and the solid was charged to 1000 ml of ethyl acetate, adjusted to pH 8 to 9 by the addition of 1000 ml of a saturated aqueous sodium hydrogen carbonate solution at 20° C. or lower, and subjected to liquid separation. The organic layer was dried over anhydrous sodium sulfate, and then the solvent was evaporated under reduced pressure to prepare 188 g (yield 71%) of a target compound.

$^1$H-NMR (CDCl$_3$, ppm) δ 3.92 (2H, broad-s), 6.69-6.74 (2H, m), 7.35 (2H, d, J=9.3 Hz).

2-2

Preparation of 2,6-dibromo-4-(perfluoropropan-2-yl)aniline

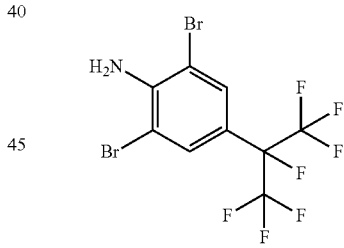

216 g (0.802 mol) of 4-(perfluoropropan-2-yl)aniline was charged to 863 ml of DMF, followed by cooling to 5° C. 285 g (1.60 mol) of N-bromosuccinimide was charged in separate portions thereto over 1 hour. The mixture was stirred at room temperature for 1 hour and then stirred at 37° C. for 2 hours. The mixture was discharged to 2000 ml of water, extracted with 2000 ml of ethyl acetate, and washed with 1000 ml of saturated brine. After dried over anhydrous magnesium sulfate, the solvent was evaporated under reduced pressure. The obtained residue was purified by silica gel column chromatography (eluent solvent; hexane:ethyl acetate=20:1) to prepare 304 g (yield 90%) of a target compound.

$^1$H-NMR (CDCl$_3$, ppm) δ 4.88 (2H, broad-s), 7.59 (2H, s).

2-3

Preparation of 2-chloro-N-(2,6-dibromo-4-(perfluoropropan-2-yl)phenyl)-3-nitrobenzamide

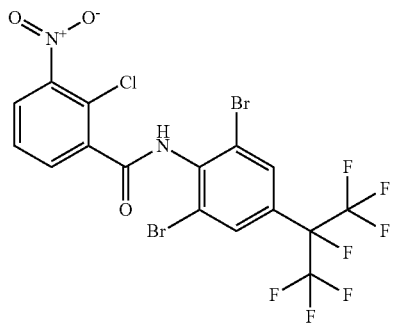

According to the method of 1-3 of Example 1, a target compound was prepared from 2,6-dibromo-4-(perfluoropropan-2-yl)aniline.

¹H-NMR (CDCl₃, ppm) δ 7.58 (1H, t, J=7.8 Hz), 7.66 (1H, broad-s), 7.90 (2H, s), 7.93 (1H, dd, J=1.5, 7.8 Hz), 7.98 (1H, d, J=7.8 Hz).

2-4

Preparation of N-(2,6-dibromo-4-(perfluoropropan-2-yl)phenyl)-2-fluoro-3-nitrobenzamide

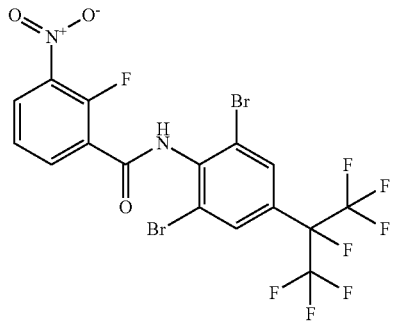

According to the method of 1-4 of Example 1, a target compound was prepared from 2-chloro-N-(2,6-dibromo-4-(perfluoropropan-2-yl)phenyl)-3-nitrobenzamide.

¹H-NMR (CDCl₃, ppm) δ 7.51-7.55 (1H, m); 7.90 (2H, s), 8.16 (1H, d, J=11.7 Hz), 8.27-8.31 (1H, m), 8.48 (1H, t, J=6.3 Hz).

2-5

Preparation of 3-amino-N-(2,6-dibromo-4-(perfluoropropan-2-yl)phenyl)-2-fluorobenzamide

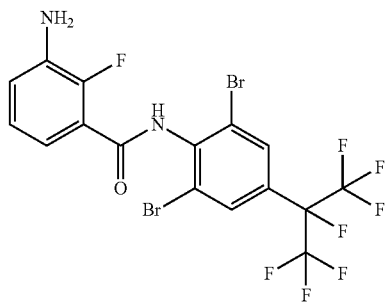 [SMILES: Nc1cccc(C(=O)Nc2c(Br)cc(C(F)(C(F)(F)F)C(F)(F)F)cc2Br)c1F]

According to the method of 1-5 of Example 1, a target compound was prepared from N-(2,6-dibromo-4-(perfluoropropan-2-yl)phenyl)-2-fluoro-3-nitrobenzamide.

¹H-NMR (CDCl₃, ppm) δ 3.93 (2H, broad-s), 6.99-7.04 (1H, m), 7.11 (1H, t, J=7.8 Hz), 7.47-7.49 (1H, m), 7.91 (1H, s), 8.14 (1H, s), 8.28 (1H, d, J=14.6 Hz).

2-6

Preparation of 2-chloro-N-(3-(2,6-dibromo-4-(perfluoropropan-2-yl)phenylcarbamoyl)-2-fluorophenyl)nicotinamide (Compound No. 6-1140)

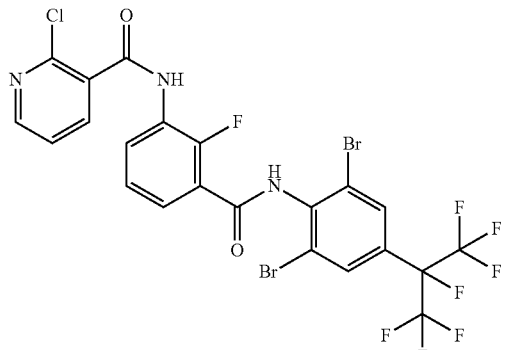

According to the method of 1-7 of Example 1, a target compound was prepared from 3-amino-N-(2,6-dibromo-4-(perfluoropropan-2-yl)phenyl)-2-fluorobenzamide and 2-chloronicotinic acid chloride.

$^1$H-NMR (CDCl$_3$, ppm) δ 7.40-7.49 (2H, m), 7.89 (2H, s), 7.94-7.96 (1H, m), 8.13 (1H, d, J=12.7 Hz), 8.32-8.34 (1H, m), 8.57-8.59 (1H, m), 8.67-8.71 (1H, m), 8.75 (1H, broad-s).

Example 3

Preparation of 3-benzamide-2-fluoro-N-(4-(perfluoropropan-2-yl)-2,6-bis(trifluoromethyl)phenyl)benzamide (Compound No. 6-2110)

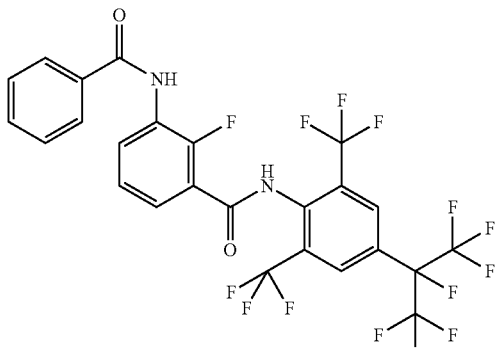

3-1

Preparation of 2,6-diiodo-4-(perfluoropropan-2-yl)aniline

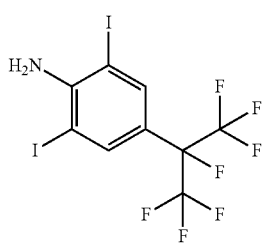 [SMILES: Nc1c(I)cc(C(F)(C(F)(F)F)C(F)(F)F)cc1I]

To a solution of 5.74 g (22.0 mmol) of 4-(perfluoropropan-2-yl)aniline obtained in 2-1 of Example 2 in 50 ml of ethanol was added 2.16 g (22.0 mmol) of concentrated sulfuric acid at 5° C. The reaction mixture was warmed to room temperature, and 10.0 g (44.0 mmol) of N-iodosuccinimide was added thereto, followed by stirring for 3 hours. The reaction mixture was neutralized with a saturated aqueous sodium hydrogen carbonate solution. The precipitated crystals were filtered, washed with water, and then dried to prepare 9.00 g (yield 80%) of a target compound.

$^1$H-NMR (CDCl$_3$, ppm) δ 4.95 (2H, broad-s), 7.79 (2H, s).

3-2

Preparation of 2-chloro-N-(2,6-diiodo-4-(perfluoropropan-2-yl)phenyl)-3-nitrobenzamide

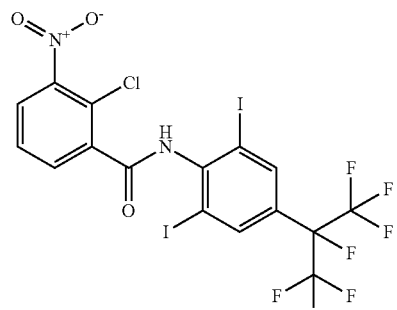

To a solution of 40.0 g (78.0 mmol) of 2,6-diiodo-4-(perfluoropropan-2-yl)aniline in 100 ml of DMI was added 20.6 g (94.0 mmol) of 2-chloro-3-nitrobenzoyl chloride, followed by stirring at 135° C. for 3 hours. After cooling to room temperature, the reaction mixture was poured into 1000 ml of water. After extraction with the addition of 1000 ml of ethyl acetate, the organic layer was washed with water and then dried over anhydrous magnesium sulfate. The solvent was evaporated under reduced pressure and the obtained residue was washed with hexane to prepare 56.2 g (yield 99%) of a target compound.

$^1$H-NMR (CDCl$_3$, ppm) δ 7.58 (1H, t, J=8.3 Hz), 7.70 (1H, d, J=3.4 Hz), 7.93 (1H, dd, J=1.5, 6.3 Hz), 8.08-8.10 (1H, m), 8.13 (2H, s).

3-3

Preparation of N-(2,6-diiodo-4-(perfluoropropan-2-yl)phenyl)-2-fluoro-3-nitrobenzamide

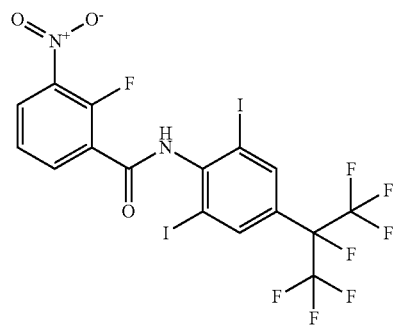 [SMILES: O=C(Nc1c(I)cc(C(F)(C(F)(F)F)C(F)(F)F)cc1I)c1cccc([N+](=O)[O-])c1F]

According to the method of 1-4 of Example 1, a target compound was prepared from 2-chloro-N-(2,6-diiodo-4-(perfluoropropan-2-yl)phenyl)-3-nitrobenzamide.

1H-NMR (CDCl₃, ppm) δ 7.52-7.55 (1H, m), 8.12-8.18 (3H, m), 8.29-8.32 (1H, 8.48-8.51 (1H, m).

3-4

Preparation of 3-amino-N-(2,6-diiodo-4-(perfluoropropan-2-yl)phenyl)-2-fluorobenzamide

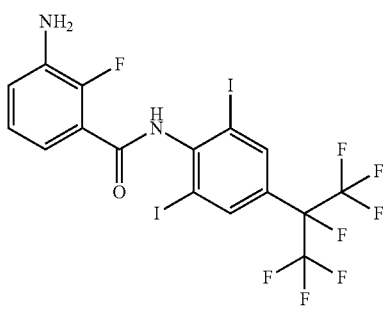 [SMILES: Nc1cccc(C(=O)Nc2c(I)cc(C(F)(C(F)(F)F)C(F)(F)F)cc2I)c1F]

According to the method of 1-5 of Example 1, a target compound was prepared from N-(2,6-diiodo-4-(perfluoropropan-2-yl)phenyl)-2-fluoro-3-nitrobenzamide.

¹H-NMR (CDCl₃, ppm) δ 3.93 (2H, broad-s), 6.99-7.04 (1H, m), 7.08 (1H, t, J=7.8 Hz), 7.39-7.43 (1H, m), 8.10 (2H, s), 8.72 (1H, d, J=11.2 Hz).

3-5

Preparation of 3-benzamide-N-(2,6-diiodo-4-(perfluoropropan-2-yl)phenyl)-2-fluorobenzamide (Compound No. 6-1260)

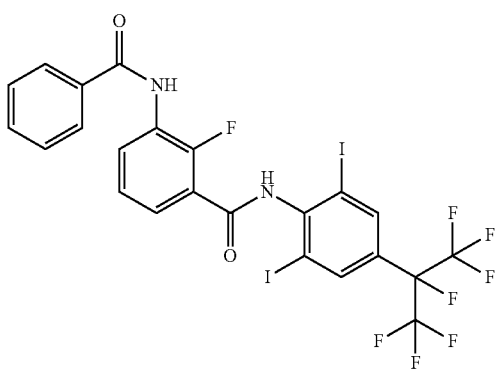 [SMILES: O=C(Nc1cccc(C(=O)Nc2c(I)cc(C(F)(C(F)(F)F)C(F)(F)F)cc2I)c1F)c1ccccc1]

According to the method of 1-7 of Example 1, a target compound was prepared from 3-amino-N-(2,6-diiodo-4-(perfluoropropan-2-yl)phenyl)-2-fluorobenzamide.

¹H-NMR (CDCl₃, ppm) δ 7.39 (1H, t, J=7.8 Hz), 7.52-7.57 (4H, m), 7.60-7.63 (2H, m), 7.93-7.94 (4H, m), 8.70 (1H, t, J=6.3 Hz).

3-6

Preparation of 3-benzamide-2-fluoro-N-(4-(perfluoropropan-2-yl)-2,6-bis(trifluoromethyl)phenyl)benzamide (Compound No. 6-2110)

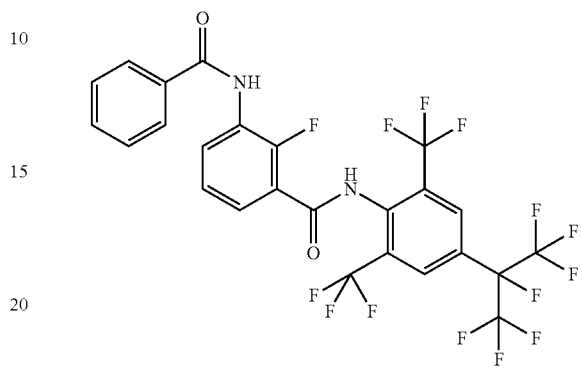

A solution of 1.95 g (2.59 mmol) of 3-benzamide-N-(2,6-diiodo-4-(perfluoropropan-2-yl)phenyl)-2-fluorobenzamide, 0.10 g (0.520 mmol) of copper iodide, and 1.24 g (6.48 mmol) of methyl fluorosulfonyl difluoroacetate in 50 ml of DMF was stirred at 100° C. for 6 hours. The reaction mixture was cooled to room temperature, and then 10 ml of water and 100 ml of ethyl acetate were added thereto, followed by filtration through Celite. The organic layer of the liquid was washed with water and a saturated aqueous sodium hydrogen carbonate solution, and then dried over anhydrous magnesium sulfate. The solvent was evaporated under reduced pressure and the obtained residue was purified by silica gel column chromatography (eluent solvent; hexane:ethyl acetate=1:1). The obtained solid was washed with hexane to prepare 0.840 g (yield 51%) of a target compound.

¹H-NMR (CDCl₃, ppm) δ 7.36-7.40 (1H, m), 7.53-7.64 (3H, m), 7.84-7.97 (1H, m), 7.92-7.94 (2H, m), 8.04-8.07 (1H, m), 8.08-8.13 (1H, m), 8.20 (2H, s), 8.68-8.72 (1H, m).

Example 4

Preparation of N-(2,6-dibromo-4-(perfluorobutan-2-yl)phenyl)-2-fluoro-3-(N methylbenzamide)benzamide (Compound No. 7-1182)

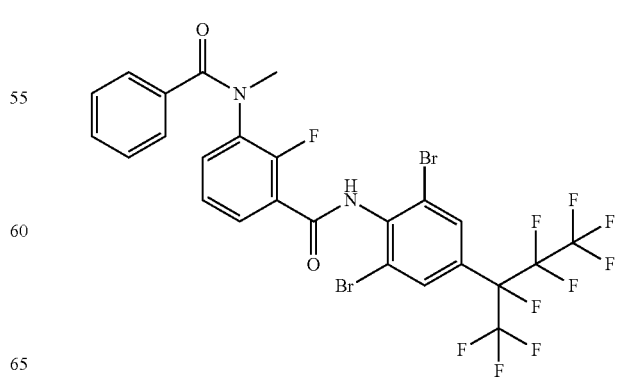

4-1

Preparation of 4-(perfluorobutan-2-yl)aniline

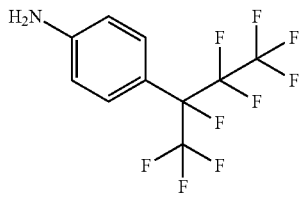 [SMILES: Nc1ccc(C(F)(C(F)(F)F)C(F)(F)C(F)(F)F)cc1]

4.90 g (52.6 mmol) of aniline, 10.1 g (58.0 mmol) of 85% sodium hydrosulfite, and 1.90 g (5.77 mmol) of tetrabutylammonium hydrogen sulfate were charged to a mixed solution of 150 ml of t-butyl methyl ether and 150 ml of water using a light-shielded reaction vessel, and 4.84 g (57.6 mmol) of sodium hydrogen carbonate was added thereto. 20.0 g (57.8 mmol) of nonafluoro-s-butyliodide was added dropwise thereto at room temperature, followed by stirring at room temperature for 5 hours. The organic phase was collected by separation, washed with 2 mol/L of an aqueous hydrochloric acid solution twice, and then washed with saturated brine, an aqueous sodium hydrogen carbonate solution, and saturated brine. The organic layer was dried over anhydrous magnesium sulfate, and then the solvent was evaporated under reduced pressure to prepare 8.32 g (yield 51%) of a target compound.

$^1$H-NMR (CDCl$_3$, ppm) δ 3.92 (2H, broad-s), 6.72 (2H, d, J=8.8 Hz), 7.34 (2H, d, J=8.8 Hz).

4-2

Preparation of 2,6-dibromo-4-(perfluorobutan-2-yl)aniline

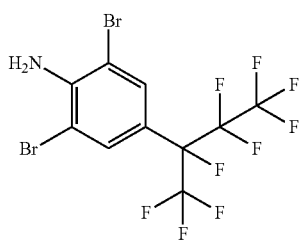 [SMILES: Nc1c(Br)cc(C(F)(C(F)(F)F)C(F)(F)C(F)(F)F)cc1Br]

According to the method of 2-2 of Example 2, a target compound was prepared from 4-(perfluorobutan-2-yl)aniline.

$^1$H-NMR (CDCl$_3$, ppm) δ 4.89 (2H, broad-s), 7.57 (2H, s).

4-3

Preparation of 2-chloro-N-(2,6-dibromo-4-(perfluorobutan-2-yl)phenyl)-3-nitrobenzamide

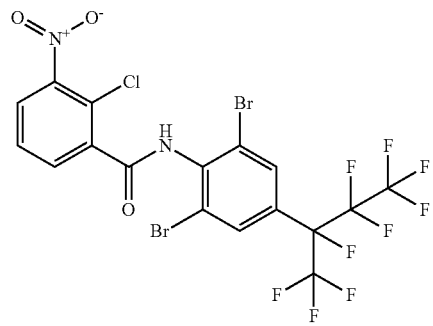 [SMILES: O=C(Nc1c(Br)cc(C(F)(C(F)(F)F)C(F)(F)C(F)(F)F)cc1Br)c1cccc([N+](=O)[O-])c1Cl]

To 27 ml of DMI were added 9.90 g (21.1 mmol) of 2,6-dibromo-4-(perfluorobutan-2-yl)aniline and 4.60 g (20.9 mmol) of 2-chloro-3-nitrobenzoyl chloride, followed by stirring at 140° C. for 4 hours. To the reaction solution were added water and ethyl acetate, and the organic phase was extracted, and washed with 1 mol/L of an aqueous sodium hydroxide solution, saturated brine, and dried over anhydrous magnesium sulfate. Then, the solvent was evaporated under reduced pressure. The obtained residue was purified by silica gel column chromatography (eluent solvent; hexane:ethyl acetate=20:1→10:1→5:1→3:1) to prepare 5.44 g (yield 40%) of a target compound.

$^1$H-NMR (CDCl$_3$, ppm) δ 7.52-7.61 (2H, m), 7.89 (2H, s), 7.94 (1H, dd, J=1.5, 8.3 Hz), 7.99 (1H, d, J=7.8 Hz).

4-4

Preparation of N-(2,6-dibromo-4-(perfluorobutan-2-yl)phenyl)-2-fluoro-3-nitrobenzamide

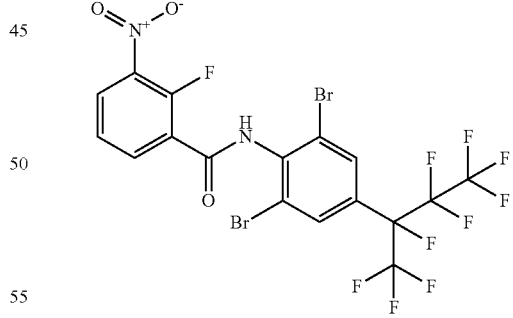

To 108 ml of DMSO were added 5.44 g (8.34 mmol) of 2-chloro-N-(2,6-dibromo-4-(perfluorobutan-2-yl)phenyl)-3-nitrobenzamide and 4.90 g (84.3 mmol) of potassium fluoride (spray-dried product), followed by stirring at 145° C. for 2 hours. The reaction solution was poured into ice-water to precipitate the crystal, and the obtained crystals were filtered and washed with hexane. The obtained crystals were purified by silica gel column chromatography (eluent solvent; hexane: ethyl acetate=5:1) to prepare 2.42 g (yield 46%) of a target compound.

¹H-NMR (CDCl₃, ppm) δ 7.53-7.54 (1H, m), 7.89 (2H, s), 8.17 (1H, d, J=12.2 Hz), 8.29-8.30 (1H, m), 8.48-8.49 (1H, m).

4-5

Preparation of 3-amino-N-(2,6-dibromo-4-(perfluorobutan-2-yl)phenyl)-2-fluorobenzamide

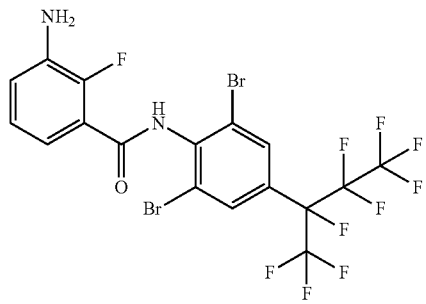 [SMILES: Nc1cccc(C(=O)Nc2c(Br)cc(C(F)(C(F)(F)F)C(F)(F)C(F)(F)F)cc2Br)c1F]

According to the method of 1-5 of Example 1, a target compound was prepared from N-(2,6-dibromo-4-(perfluorobutan-2-yl)phenyl)-2-fluoro-3-nitrobenzamide.

¹H-NMR (CDCl₃, ppm) δ 3.92 (2H, broad-s), 6.99-7.04 (1H, m), 7.11-7.12 (1H, m), 7.48-7.52 (1H, m), 7.86 (2H, s), 8.22 (1H, d, J=14.1 Hz).

4-6

Preparation of N-(2,6-dibromo-4-(perfluorobutan-2-yl)phenyl)-2-fluoro-3-(methylamino)benzamide

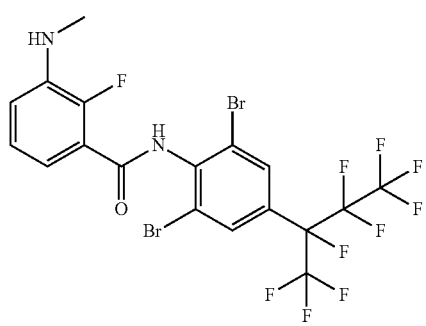 [SMILES: CNc1cccc(C(=O)Nc2c(Br)cc(C(F)(C(F)(F)F)C(F)(F)C(F)(F)F)cc2Br)c1F]

According to the method of 1-6 of Example 1, a target compound was prepared from 3-amino-N-(2,6-dibromo-4-(perfluorobutan-2-yl)phenyl)-2-fluorobenzamide.

¹H-NMR (CDCl₃, ppm) δ 2.95 (3H, s), 4.14 (1H, broad-s), 6.91-6.92 (1H, m), 7.17-7.21 (1H, m), 7.39-7.43 (1H, m), 7.85 (2H, s), 8.21 (1H, d, J=14.1 Hz).

4-7

Preparation of N-(2,6-dibromo-4-(perfluorobutan-2-yl)phenyl)-2-fluoro-3-(N-methylbenzamide)benzamide (Compound No. 7-1182)

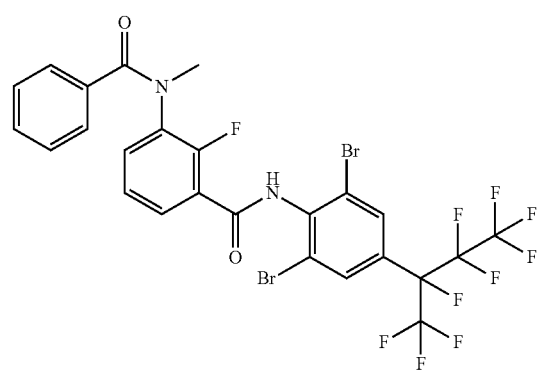 [SMILES: CN(C(=O)c1ccccc1)c1cccc(C(=O)Nc2c(Br)cc(C(F)(C(F)(F)F)C(F)(F)C(F)(F)F)cc2Br)c1F]

According to the method of 1-7 of Example 1, a target compound was prepared from N-(2,6-dibromo-4-(perfluorobutan-2-yl)phenyl)-2-fluoro-3-(methylamino)benzamide.

¹H-NMR (CDCl₃, ppm) δ 3.51 (3H, s), 7.22-7.44 (7H, m), 7.85 (2H, s), 8.00-8.03 (2H, m).

Example 5

Preparation of N-(2-bromo-6-(perfluoroethyl)-4-(perfluoropropan-2-yl)phenyl)-3-(4-cyanobenzamide)-2-fluorobenzamide (Compound No. 6-5911)

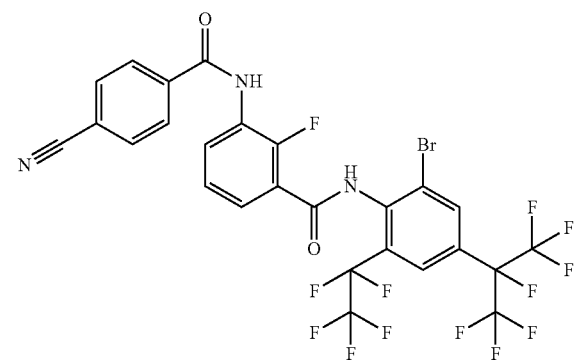 [SMILES: N#Cc1ccc(C(=O)Nc2cccc(C(=O)Nc3c(Br)cc(C(F)(C(F)(F)F)C(F)(F)F)cc3C(F)(F)C(F)(F)F)c2F)cc1]

5-1

Preparation of 2-(perfluoroethyl)-4-(perfluoropropan-2-yl)aniline

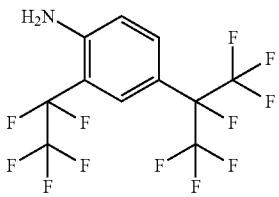

According to the method of 1-1 of Example 1, a target compound was prepared from 4-(perfluoropropan-2-yl)aniline obtained in Example 2-1 and 1,1,2,2,2-pentafluoroethyliodide.

$^1$H-NMR (CDCl$_3$, ppm) δ 4.56 (2H, broad-s), 6.79 (1H, d, J=8.8 Hz), 7.47 (1H, d, J=8.8 Hz), 7.53 (1H, s).

5-2

Preparation of 2-bromo-6-(perfluoroethyl)-4-(perfluoropropan-2-yl)aniline

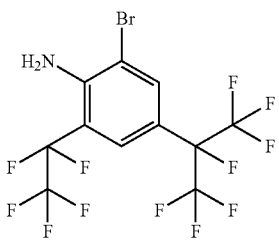 [SMILES: Nc1c(Br)cc(C(F)(C(F)(F)F)C(F)(F)F)cc1C(F)(F)C(F)(F)F]

According to the method of 1-2 of Example 1, a target compound was prepared from 2-(perfluoroethyl)-4-(perfluoropropan-2-yl)aniline.

According to the method of 4-3 of Example 4, a target compound was prepared from 2-bromo-6-(perfluoroethyl)-4-(perfluoropropan-2-yl)aniline.

$^1$H-NMR (CDCl$_3$, ppm) δ 5.14 (2H, broad-s), 7.58 (1H, s), 7.81 (1H, s).

5-3

Preparation of N-(2-bromo-6-(perfluoroethyl)-4-(perfluoropropan-2-yl)phenyl)-2-chloro-3-nitrobenzamide

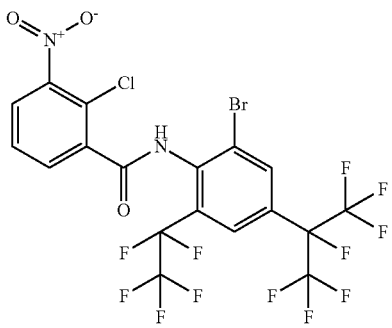 [SMILES: O=C(Nc1c(Br)cc(C(F)(C(F)(F)F)C(F)(F)F)cc1C(F)(F)C(F)(F)F)c1cccc([N+](=O)[O-])c1Cl]

$^1$H-NMR (CDCl$_3$, ppm) δ 7.56-7.61 (1H, m), 7.73 (1H, s), 7.88 (1H, d, J=1.5 Hz), 7.92-7.98 (2H, m), 8.21 (1H, s).

5-4

Preparation of N-(2-bromo-6-(perfluoroethyl)-4-(perfluoropropan-2-yl)phenyl)-2-fluoro-3-nitrobenzamide

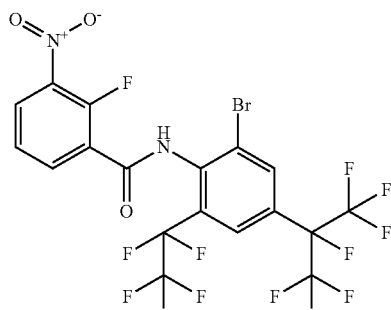

According to the method of 1-4 of Example 1, a target compound was prepared from N-(2-bromo-6-(perfluoroethyl)-4-(perfluoropropan-2-yl)phenyl)-2-chloro-3-nitrobenzamide.

APCI-MS m/z (M+1):626

5-5

Preparation of 3-amino-N-(2-bromo-6-(perfluoroethyl)-4-(perfluoropropan-2-yl)phenyl)-2-fluorobenzamide

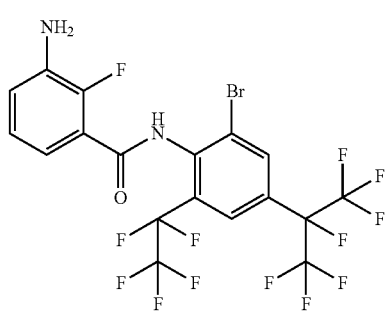 [SMILES: Nc1cccc(C(=O)Nc2c(Br)cc(C(F)(C(F)(F)F)C(F)(F)F)cc2C(F)(F)C(F)(F)F)c1F]

According to the method of 1-5 of Example 1, a target compound was prepared from N-(2-bromo-6-(perfluoroethyl)-4-(perfluoropropan-2-yl)phenyl)-2-fluoro-3-nitrobenzamide.

¹H-NMR (CDCl₃, ppm) δ 3.92 (2H, broad-s), 6.99-7.04 (1H, m), 7.05-7.18 (1H, m), 7.46-7.51 (1H, m), 7.85 (1H, broad-s), 8.17 (1H, broad-s), 8.34 (1H, d, J=15.1 Hz).

5-6

Preparation of N-(2-bromo-6-(perfluoroethyl)-4-(perfluoropropan-2-yl)phenyl)-3-(4-cyanobenzamide)-2-fluorobenzamide (Compound No. 6-5911)

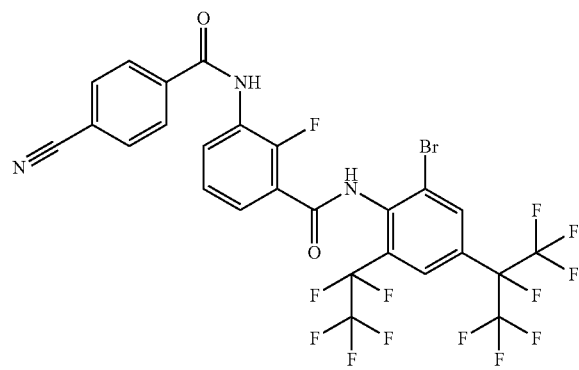 [SMILES: N#Cc1ccc(C(=O)Nc2cccc(C(=O)Nc3c(Br)cc(C(F)(C(F)(F)F)C(F)(F)F)cc3C(F)(F)C(F)(F)F)c2F)cc1]

According to the method of 1-7 of Example 1, a target compound was prepared from 3-amino-N-(2-bromo-6-(perfluoroethyl)-4-(perfluoropropan-2-yl)phenyl)-2-fluorobenzamide and 4-cyanobenzoylchloride.

¹H-NMR (CDCl₃, ppm) δ 7.41 (1H, t, J=8.3 Hz), 7.84-7.87 (3H, m), 7.91-7.95 (1H, m), 8.03-8.05 (2H, m), 8.10 (1H, broad-s), 8.17-8.20 (2H, m), 8.63-8.67 (1H, m).

Example 6

Preparation of N-(2-bromo-4-(perfluoropropan-2-yl)-6-(trifluoromethyl)phenyl)-6-(N-methylbenzamide)picolinamide (Compound No. 17-1103)

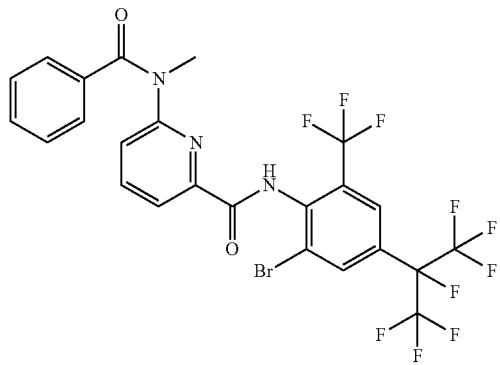 [SMILES: CN(C(=O)c1ccccc1)c1cccc(C(=O)Nc2c(Br)cc(C(F)(C(F)(F)F)C(F)(F)F)cc2C(F)(F)F)n1]

6-1

Preparation of N-(2-bromo-4-(perfluoropropan-2-yl)-6-(trifluoromethyl)phenyl)-6-chloropicoline amide

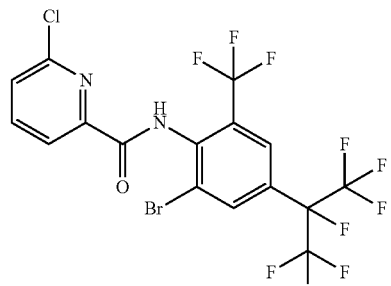

According to the method of 1-3 of Example 1, a target compound was prepared from 2-chloropyridine-6-carboxylic acid chloride prepared from 2-chloropyridine-6-carboxylic acid and thionyl chloride, and 2-bromo-4-(perfluoropropan-2-yl)-6-(trifluoromethyl)aniline obtained in 1-2 of Example 1.

¹H-NMR (CDCl₃, ppm) δ 7.59 (1H, d, J=7.3 Hz), 7.90-7.93 (2H, m), 8.14 (1H, s), 8.20-8.24 (1H, m), 9.60 (1H, s).

6-2

Preparation of N-(2-bromo-4-(perfluoropropan-2-yl)-6-(trifluoromethyl)phenyl)-6-(methylamino)picolinamide

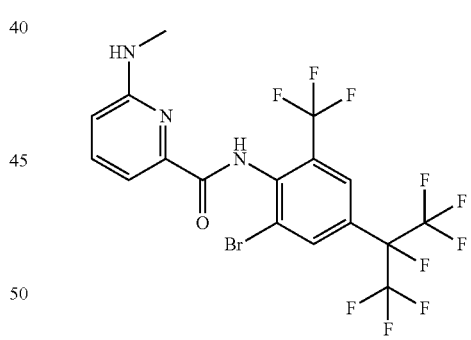

To a solution of 0.100 g (0.180 mmol) of N-(2-bromo-4-(perfluoropropan-2-yl)-6-(trifluoromethyl)phenyl)-6-chloropicoline amide in 5 ml of 1,4-dioxane were added 0.00600 g (0.0360 mmol) of copper sulfate and 0.140 g (1.80 mmol) of a 40% aqueous methylamine solution, followed by stirring at an oil bath temperature 80° C. for 3 hours under an enclosed condition. The reaction liquid was returned to room temperature and opened, and water and ethyl acetate were added thereto. The organic layer was washed with water and saturated brine, and dried over anhydrous magnesium sulfate. The solvent was evaporated under reduced pressure and the obtained residue was purified by silica gel column chromatography (eluent solvent; hexane:ethyl acetate=2:1) to prepare 0.0700 g (yield 69%) of a target compound.

¹H-NMR (CDCl₃, ppm) δ 2.64 (3H, s), 3.79 (1H, broad-s), 7.56-7.60 (1H, m), 7.87-7.93 (2H, m), 8.14-8.15 (1H, m), 8.20-8.23 (1H, m), 9.60 (1H, s).

6-3

Preparation of N-(2-bromo-4-(perfluoropropan-2-yl)-6-(trifluoromethyl)phenyl)-6-(N-methylbenzamide)picolinamide (Compound No. 17-1103)

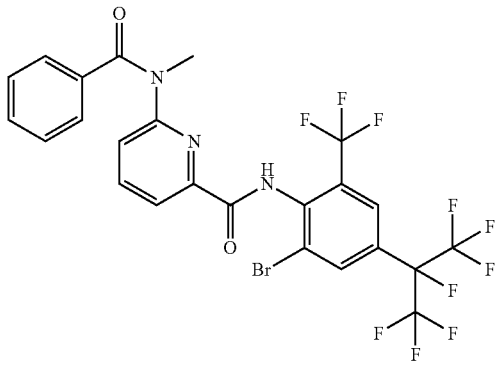 [SMILES: CN(C(=O)c1ccccc1)c1cccc(C(=O)Nc2c(Br)cc(C(F)(C(F)(F)F)C(F)(F)F)cc2C(F)(F)F)n1]

According to the method of 1-7 of Example 1, a target compound was prepared from N-(2-bromo-4-(perfluoropropan-2-yl)-6-(trifluoromethyl)phenyl)-6-(methylamino)picolinamide.

¹H-NMR (CDCl₃, ppm) δ 3.65 (3H, s), 7.28-7.41 (6H, m), 7.77 (1H, t, J=7.8 Hz), 7.91 (1H, s), 8.00-8.02 (1H, m), 8.14 (1H, s), 9.39 (1H, s).

Example 7

Preparation of N-(2-bromo-4-(perfluoropropan-2-yl)-6-(trifluoromethyl)phenyl)-2-(2-fluoro-N-methylbenzamide)thiazole-4-carboxamide (Compound No. 27-628)

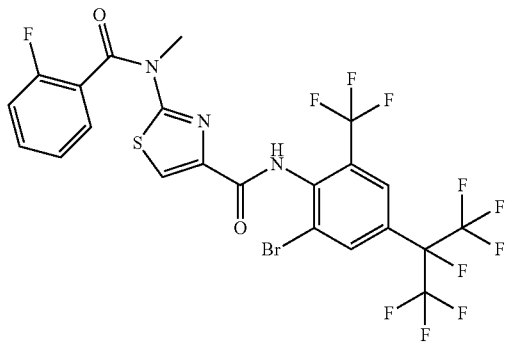 [SMILES: CN(C(=O)c1ccccc1F)c1nc(C(=O)Nc2c(Br)cc(C(F)(C(F)(F)F)C(F)(F)F)cc2C(F)(F)F)cs1]

7-1

Preparation of 2-aminothiazole-4-carboxylic acid

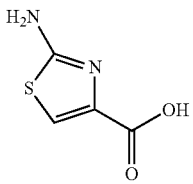

To 40 ml of an aqueous solution of 4.00 g (23.2 mmol) of ethyl 2-aminothiazole-4-carboxylate was added 1.86 g (46.5 mmol) of sodium hydroxide, followed by stirring at room temperature for 5 hours. The reaction liquid was adjusted to pH 1 by the addition of concentrated hydrochloric acid, and the precipitated crystals were collected by filtration to prepare 2.84 g (yield 85%) of a target compound.

¹H-NMR (CDCl₃, ppm) δ 7.18 (2H, broad-s), 7.38 (1H, s).
The proton of the carboxylic acid was not detected.

7-2

Preparation of 2-chlorothiazole-4-carboxylic acid

To a solution of 2.84 g (19.7 mmol) of 2-aminothiazole-4-carboxylic acid in 30 ml of 1,4-dioxane was added 50 ml of concentrated hydrochloric acid, followed by cooling to 0° C., and 10 ml of an aqueous solution of 2.04 g (29.6 mmol) of sodium nitrite was added charged dropwise thereto at 0° C. to 5° C. The reaction liquid was stirred at 0° C. for 2 hours, and then 2.93 g (29.6 mmol) of copper chloride was charged in separate portions thereto. The reaction liquid was returned to room temperature, followed by stirring for 8 hours. To the reaction liquid were added water and ethyl acetate, followed by extraction with ethyl acetate four times. The organic layer was washed with saturated brine, and then dried over anhydrous magnesium sulfate. The solvent was evaporated under reduced pressure to prepare 1.77 g (yield 55%) of a target compound.

¹H-NMR (DMSO-d₆, ppm) δ 8.41 (1H, s).
The proton of the carboxylic acid was not detected.

7-3

Preparation of N-(2-bromo-4-(perfluoropropan-2-yl)-6-(trifluoromethyl)phenyl)-2-chlorothiazole-4-carboxamide

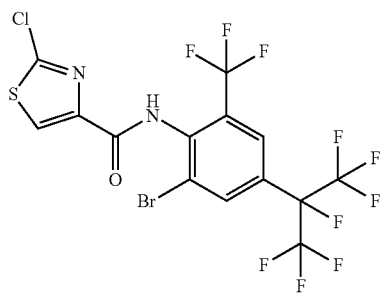 [SMILES: O=C(Nc1c(Br)cc(C(F)(C(F)(F)F)C(F)(F)F)cc1C(F)(F)F)c1csc(Cl)n1]

According to the method of 4-3 of Example 4, a target compound was prepared from 2-chlorothiazole-4-carbonyl-chloride prepared from 2-chlorothiazole-4-carboxylic acid and thionyl chloride, and 2-bromo-4-(perfluoropropan-2-yl)-6-(trifluoromethyl)aniline obtained in 1-2 of Example 1.

$^1$H-NMR (CDCl$_3$, ppm) δ 7.91 (1H, s), 8.13 (1H, s), 8.19 (1H, s), 8.82 (1H, s).

7-4

Preparation of N-(2-bromo-4-(perfluoropropan-2-yl)-6-(trifluoromethyl)phenyl)-2-(methylamino)thiazole-4-carboxamide

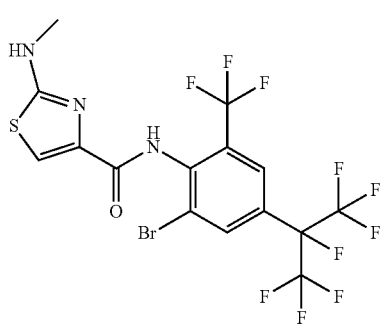 [SMILES: CNc1nc(C(=O)Nc2c(Br)cc(C(F)(C(F)(F)F)C(F)(F)F)cc2C(F)(F)F)cs1]

According to the method of 6-2 of Example 6, a target compound was prepared from N-(2-bromo-4-(perfluoropropan-2-yl)-6-(trifluoromethyl)phenyl)-2-chlorothiazole-4-carboxamide.

$^1$H-NMR (CDCl$_3$, ppm) δ 3.03 (3H, s), 5.11-5.12 (1H, m), 7.50 (1H, s), 7.88 (1H, s), 8.11 (1H, s), 8.99 (1H, s).

7-5

Preparation of N-(2-bromo-4-(perfluoropropan-2-yl)-6-(trifluoromethyl)phenyl)-2-(2-fluoro-N-methylbenzamide)thiazole-4-carboxamide (Compound No. 27-628)

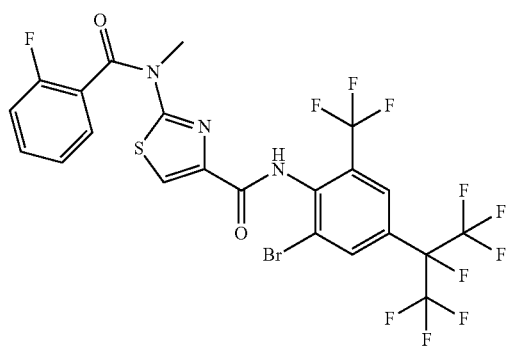 [SMILES: CN(C(=O)c1ccccc1F)c1nc(C(=O)Nc2c(Br)cc(C(F)(C(F)(F)F)C(F)(F)F)cc2C(F)(F)F)cs1]

According to the method of 1-7 of Example 1, a target compound was prepared from N-(2-bromo-4-(perfluoropropan-2-yl)-6-(trifluoromethyl)phenyl)-2-(methylamino)thiazole-4-carboxamide and 2-fluorobenzoyl chloride.

$^1$H-NMR (CDCl$_3$, ppm) δ 3.67 (3H, s), 6.99-7.24 (1H, m), 7.29-7.35 (1H, m), 7.52-7.59 (2H, m), 7.90 (1H, s), 8.06 (1H, s), 8.14 (1H, s), 9.08 (1H, s).

Example 8

Preparation of 2,2,2-trichloroethyl 2-fluoro-3-(2-iodo-4-(perfluorobutan-2-yl)-6-(trifluoromethyl)phenylcarbamoyl)phenyl(methyl)carbamate (Compound No. 12-864)

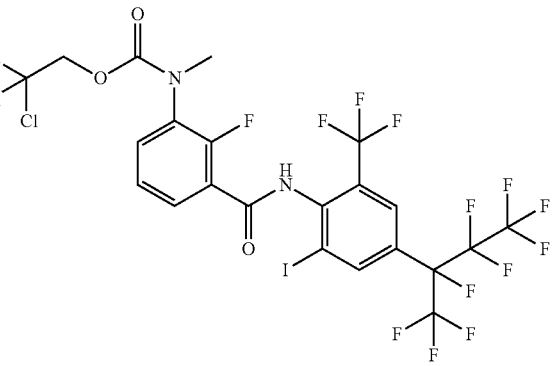

8-1

Preparation of 4-(perfluorobutan-2-yl)-2-(trifluoromethyl)aniline

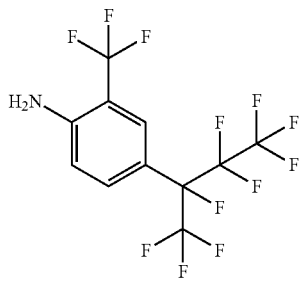 [SMILES: Nc1ccc(C(F)(C(F)(F)F)C(F)(F)C(F)(F)F)cc1C(F)(F)F]

According to the method of 1-1 of Example 1, a target compound was prepared from 2-(trifluoromethyl)aniline and nonafluoro-s-butyliodide under the light-shielding reaction condition.

$^1$H-NMR (CDCl$_3$, ppm) δ 4.49 (2H, broad-s), 6.81 (1H, d, J=8.8 Hz), 7.47 (1H, d, J=8.8 Hz), 7.61 (1H, s).

8-2

Preparation of 2-iodo-4-(perfluorobutan-2-yl)-6-(trifluoromethyl)aniline

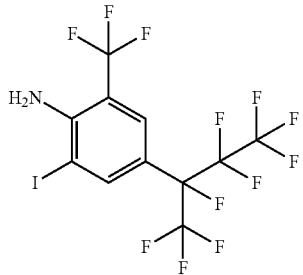 [SMILES: Nc1c(I)cc(C(F)(C(F)(F)F)C(F)(F)C(F)(F)F)cc1C(F)(F)F]

To 100 mL of ethanol was added 17.0 g (44.8 mmol) of 4-(perfluorobutan-2-yl)-2-(trifluoromethyl)aniline, and 5.28 g (53.8 mmol) of concentrated sulfuric acid and 12.6 g (55.8 mmol) of N-iodosuccinimide were added thereto under ice-cooling, followed by stirring at room temperature for 1 hour and 30 minutes and at 40° C. for 4 hours. To the reaction solution was added a 4 M aqueous sodium hydroxide solution to neutralize the reaction solution, and then ethyl acetate was added thereto to extract the organic phase. The organic phase was washed with saturated brine, and dried over anhydrous magnesium sulfate, and then the solvent was evaporated under reduced pressure. The obtained residue was purified by silica gel column chromatography (eluent solvent; hexane: ethyl acetate=10:1) to prepare 14.6 g (yield 65%) of a target compound.

$^1$H-NMR (CDCl$_3$, ppm) δ 5.04 (2H, broad-s), 7.62 (1H, s), 7.97 (1H, s).

8-3

Preparation of 2-chloro-N-(2-iodo-4-(perfluorobutan-2-yl)-6-(trifluoromethyl)phenyl)-3-nitrobenzamide

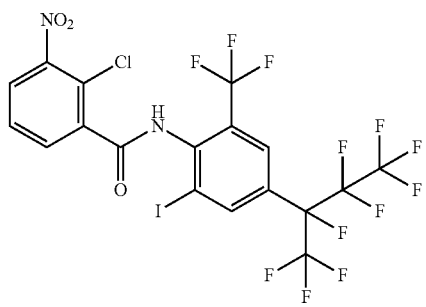 [SMILES: O=C(Nc1c(I)cc(C(F)(C(F)(F)F)C(F)(F)C(F)(F)F)cc1C(F)(F)F)c1cccc([N+](=O)[O-])c1Cl]

According to the method of 4-3 of Example 4, a target compound was prepared from 2-iodo-4-(perfluorobutan-2-yl)-6-(trifluoromethyl)aniline.

$^1$H-NMR (CDCl$_3$, ppm) δ 7.60-7.61 (1H, m), 7.77 (1H, s), 7.89-7.96 (2H, m), 8.03-8.04 (1H, m), 8.38 (1H, s).

8-4

Preparation of 2-fluoro-N-(2-iodo-4-(perfluorobutan-2-yl)-6-(trifluoromethyl)phenyl)-3-nitrobenzamide

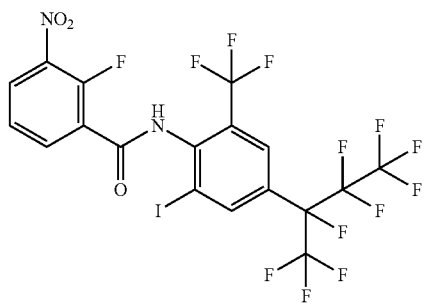

According to the method of 1-4 of Example 1, a target compound was prepared from 2-chloro-N-(2-iodo-4-(perfluorobutan-2-yl)-6-(trifluoromethyl)phenyl)-3-nitrobenzamide.

¹H-NMR (CDCl₃, ppm) δ 7.53-7.54 (1H, m), 7.95 (1H, s), 8.24-8.32 (2H, m), 8.36 (1H, s), 8.44-8.48 (1H, m).

8-5

Preparation of 3-amino-2-fluoro-N-(2-iodo-4-(perfluorobutan-2-yl)-6-(trifluoromethyl)phenyl)benzamide

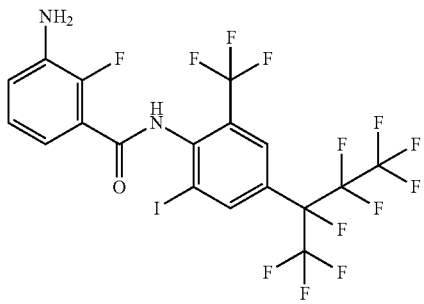 [SMILES: O=C(Nc1c(I)cc(C(F)(C(F)(F)F)C(F)(F)C(F)(F)F)cc1C(F)(F)F)c1cccc([N+](=O)[O-])c1F]

According to the method of 1-5 of Example 1, a target compound was prepared from 2-fluoro-N-(2-iodo-4-(perfluorobutan-2-yl)-6-(trifluoromethyl)phenyl)-3-nitrobenzamide.

¹H-NMR (CDCl₃, ppm) δ 3.93 (2H, broad-s), 7.02-7.03 (1H, m), 7.11-7.13 (1H, m), 7.47-7.51 (1H, m), 7.92 (1H, s), 8.31-8.34 (2H, m).

8-6

Preparation of 2-fluoro-N-(2-iodo-4-(perfluorobutan-2-yl)-6-(trifluoromethyl)phenyl)-3-(methylamino)benzamide

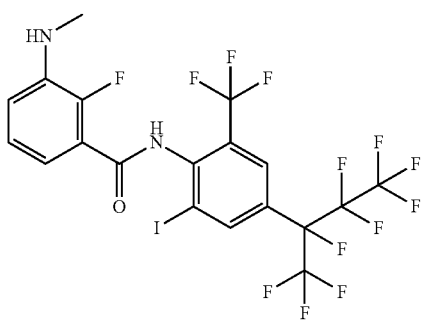 [SMILES: CNc1cccc(C(=O)Nc2c(I)cc(C(F)(C(F)(F)F)C(F)(F)C(F)(F)F)cc2C(F)(F)F)c1F]

According to the method of 1-6 of Example 1, a target compound was prepared from 3-amino-2-fluoro-N-(2-iodo-4-(perfluorobutan-2-yl)-6-(trifluoromethyl)phenyl)benzamide.

¹H-NMR (CDCl₃, ppm) δ 2.95-2.96 (3H, m), 4.15 (1H, broad-s), 6.91-6.93 (1H, m), 7.19-7.20 (1H, m), 7.38-7.42 (1H, m), 7.92 (1H, s), 8.32 (1H, d, J=14.1 Hz), 8.34 (1H, s).

8-7

Preparation of 2,2,2-trichloroethyl 2-fluoro-3-(2-iodo-4-(perfluorobutan-2-yl)-6-(trifluoromethyl)phenylcarbamoyl)phenyl(methyl)carbamate (Compound No. 12-864)

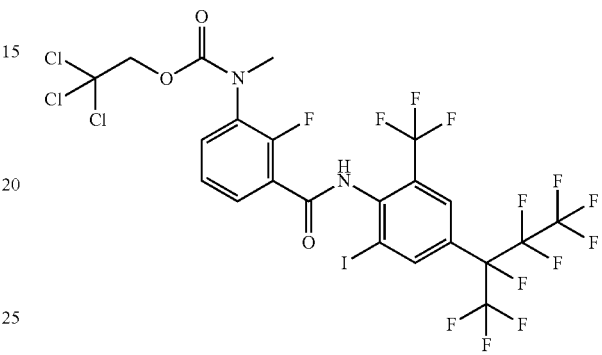

According to the method of 1-7 of Example 1, a target compound was prepared from 2-fluoro-N-(2-iodo-4-(perfluorobutan-2-yl)-6-(trifluoromethyl)phenyl)-3-(methylamino)benzamide and 2,2,2-trichloroethoxycarbonylchloride.

¹H-NMR (CDCl₃, ppm) δ 3.40 (3H, s), 4.74 (2H, broad-s), 7.37 (1H, t, J=7.8 Hz), 7.52-7.58 (1H, m), 7.93 (1H, s), 8.12-8.15 (1H, m), 8.28-8.34 (2H, m).

Example 9

Preparation of N-(2-chloro-4-(perfluoropropan-2-yl)-6-(trifluoromethyl)phenyl)-4-cyano-3-(4-cyano-N-methylbenzamide)benzamide (Compound No. 2-491)

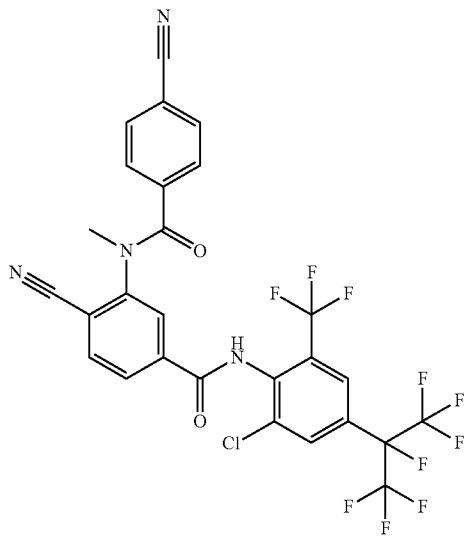 [SMILES: CN(C(=O)c1ccc(C#N)cc1)c1cc(C(=O)Nc2c(Cl)cc(C(F)(C(F)(F)F)C(F)(F)F)cc2C(F)(F)F)ccc1C#N]

9-1

Preparation of 2-chloro-4-(perfluoropropan-2-yl)-6-(trifluoromethyl)aniline

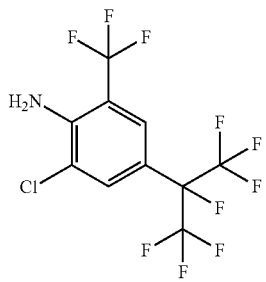 [SMILES: Nc1c(Cl)cc(C(F)(C(F)(F)F)C(F)(F)F)cc1C(F)(F)F]

According to the method of 1-2 of Example 1, a target compound was prepared from 4-(perfluoropropan-2-yl)-2-(trifluoromethyl)aniline obtained in 1-1 of Example 1 and N-chlorosuccinimide.

$^1$H-NMR (CDCl$_3$, ppm) δ 4.97 (2H, broad-s), 7.57 (1H, s), 7.64 (1H, s).

9-2

Preparation of N-(2-chloro-4-(perfluoropropan-2-yl)-6-(trifluoromethyl)phenyl)-4-iodo-3-nitrobenzamide

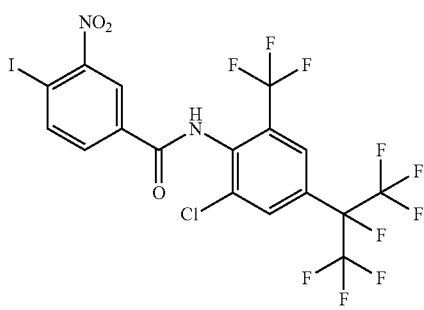

According to the method of 1-3 of Example 1, a target compound was prepared from 4-iodo-3-nitrobenzoyl chloride prepared from 4-iodo-3-nitrobenzoic acid and thionyl chloride, and 2-chloro-4-(perfluoropropan-2-yl)-6-(trifluoromethyl)aniline.

$^1$H-NMR (CDCl$_3$, ppm) δ 7.52-7.81 (2H, m), 7.89 (1H, s), 8.00 (1H, s), 8.25 (1H, d, J=8.3 Hz), 8.38 (1H, d, J=1.9 Hz).

9-3

Preparation of 3-amino-N-(2-chloro-4-(perfluoropropan-2-yl)-6-(trifluoromethyl)phenyl)-4-iodobenzamide

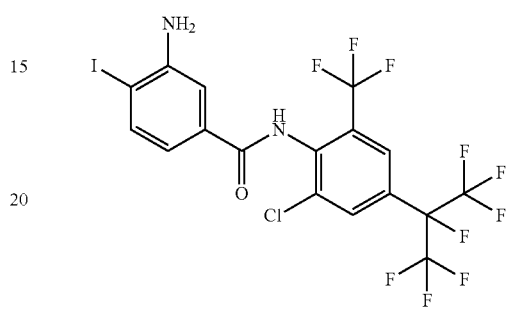

According to the method of 1-5 of Example 1, a target compound was prepared from N-(2-chloro-4-(perfluoropropan-2-yl)-6-(trifluoromethyl)phenyl)-4-iodo-3-nitrobenzamide.

$^1$H-NMR (CDCl$_3$, ppm) δ 4.35 (2H, s), 6.92 (1H, dd, J=1.9, 8.3 Hz), 7.29 (1H, d, J=1.9 Hz), 7.60 (1H, s), 7.79 (1H, d, J=8.3 Hz), 7.86 (1H, s), 7.97 (1H, s).

9-4

Preparation of N-(2-chloro-4-(perfluoropropan-2-yl)-6-(trifluoromethyl)phenyl)-4-iodo-3-(methylamino)benzamide

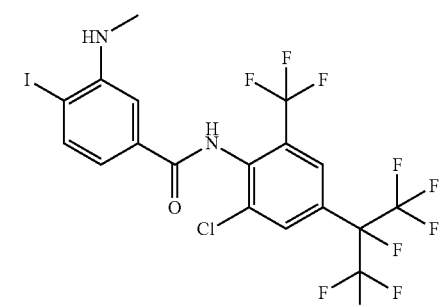

According to the method of 1-6 of Example 1, a target compound was prepared from 3-amino-N-(2-chloro-4-(perfluoropropan-2-yl)-6-(trifluoromethyl)phenyl)-4-iodobenzamide.

$^1$H-NMR (CDCl$_3$, ppm) δ 2.97 (3H, s), 4.46 (1H, broad-s), 6.89 (1H, dd, J=1.9, 8.3 Hz), 7.07 (1H, d, J=1.9 Hz), 7.65 (1H, s), 7.80 (1H, d, J=8.3 Hz), 7.86 (1H, s), 7.97 (1H, s).

9-5

Preparation of N-(2-chloro-4-(perfluoropropan-2-yl)-6-(trifluoromethyl)phenyl)-4-cyano-3-(methylamino)benzamide

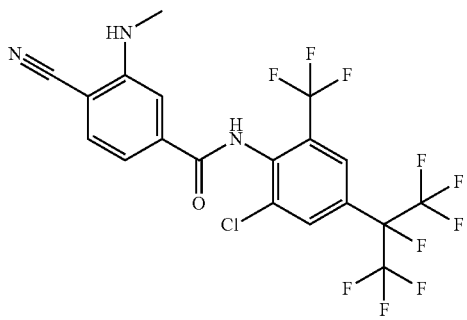 [SMILES: CNc1cc(C(=O)Nc2c(Cl)cc(C(F)(C(F)(F)F)C(F)(F)F)cc2C(F)(F)F)ccc1C#N]

To 10 mL of DMF were added 0.350 g (0.560 mmol) of N-(2-chloro-4-(perfluoropropan-2-yl)-6-(trifluoromethyl)phenyl)-4-iodo-3-(methylamino)benzamide and 0.200 g (2.25 mmol) of copper (I) cyanide, followed by stirring at 140° C. for 1 hour and 30 minutes. A saturated aqueous sodium thiosulfate solution was poured into the reaction solution to quench the reaction, and the organic layer was collected with ethyl acetate and washed with saturated brine. The organic layer was dried over anhydrous magnesium sulfate, and then the solvent was evaporated under reduced pressure. The obtained residue was purified by silica gel column chromatography (eluent solvent; hexane:ethyl acetate=5:1→3:1) to prepare 0.250 g (yield 86%) of a target compound.

$^1$H-NMR (CDCl$_3$, ppm) δ 3.01 (1/2*3H, s), 3.03 (1/2*3H, s), 4.89 (1/2*1H, s), 4.90 (1/2*1H, s), 7.80 (1H, dd, J=1.5, 8.3 Hz), 7.21-7.22 (1H, m), 7.54 (1H, d, J=8.3 Hz), 7.67 (1H, s), 7.88 (1H, s), 7.99 (1H, s).

9-6

Preparation of N-(2-chloro-4-(perfluoropropan-2-yl)-6-(trifluoromethyl)phenyl)-4-cyano-3-(4-cyano-N-methylbenzamide)benzamide (Compound No. 2-491)

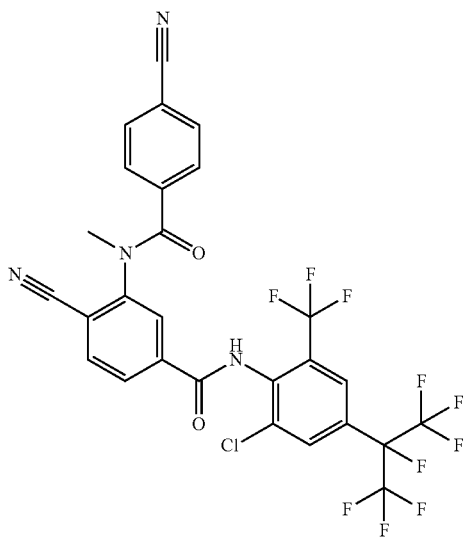 [SMILES: CN(C(=O)c1ccc(C#N)cc1)c1cc(C(=O)Nc2c(Cl)cc(C(F)(C(F)(F)F)C(F)(F)F)cc2C(F)(F)F)ccc1C#N]

According to the method of 1-7 of Example 1, a target compound was prepared from N-(2-chloro-4-(perfluoropropan-2-yl)-6-(trifluoromethyl)phenyl)-4-cyano-3-(methylamino)benzamide and 4-cyanobenzoylchloride.

$^1$H-NMR (CDCl$_3$, ppm) δ 3.81 (3H, broad-s), 7.52-7.84 (8H, m), 7.89 (1H, s), 8.00 (1H, s).

Example 10

Preparation of N-(3-(2-bromo-4-(perfluoropropan-2-yl)-6-(trifluoromethyl)phenylcarbamoyl)-6-cyano-2-fluorophenyl)-6-chloronicotinamide (Compound No. 1-1968)

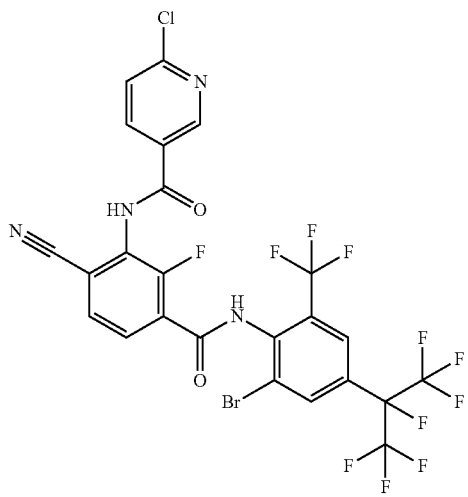 [SMILES: N#Cc1ccc(C(=O)Nc2c(Br)cc(C(F)(C(F)(F)F)C(F)(F)F)cc2C(F)(F)F)c(F)c1NC(=O)c1ccc(Cl)nc1]

10-1

Preparation of N-(2-bromo-4-(perfluoropropan-2-yl)-6-(trifluoromethyl)phenyl)-4-cyano-2,3-difluorobenzamide

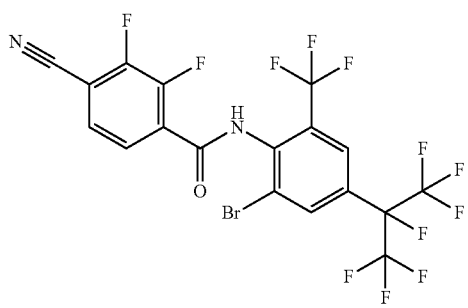 [SMILES: N#Cc1ccc(C(=O)Nc2c(Br)cc(C(F)(C(F)(F)F)C(F)(F)F)cc2C(F)(F)F)c(F)c1F]

To a solution of 0.840 g (4.59 mmol) of 4-cyano-2,3-difluorobenzoic acid in 10 ml of dichloromethane were added one drop of DMF and 0.470 ml (5.51 mmol) of oxalyl chloride, followed by stirring at room temperature for 1 hour. The solvent was evaporated under reduced pressure and the obtained 4-cyano-2,3-difluorobenzoyl chloride was added to a solution of 1.56 g (3.83 mmol) of 2-bromo-4-(perfluoropropan-2-yl)-6-(trifluoromethyl)aniline obtained in 1-2 of Example 1 in 5 ml of DMI, followed by stirring at 130° C. for 5 hours. To the reaction liquid were added water and ethyl acetate, and the organic layer was washed with a saturated aqueous sodium hydrogen carbonate solution and saturated brine, and then dried over anhydrous magnesium sulfate. The solvent was evaporated under reduced pressure and the obtained residue was purified by silica gel column chromatography (eluent solvent; hexane:ethyl acetate=1:0→10:1) to prepare 0.58 g (yield 27%) of a target compound.

¹H-NMR (CDCl₃, ppm) δ 7.52-7.62 (1H, m), 7.92-7.94 (1H, m), 8.02-8.06 (1H, m), 8.13-8.16 (2H, m).

10-2

Preparation of 3-amino-N-(2-bromo-4-(perfluoropropan-2-yl)-6-(trifluoromethyl)phenyl)-4-cyano-2-fluorobenzamide

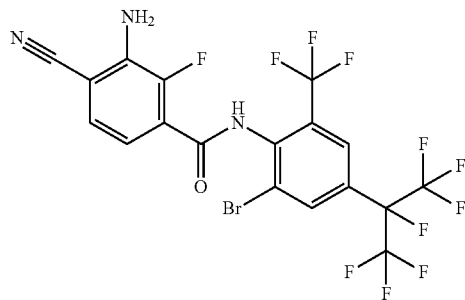 [SMILES: N#Cc1ccc(C(=O)Nc2c(Br)cc(C(F)(C(F)(F)F)C(F)(F)F)cc2C(F)(F)F)c(F)c1N]

To a solution of N-(2-bromo-4-(perfluoropropan-2-yl)-6-(trifluoromethyl)phenyl)-4-cyano-2,3-difluorobenzamide in 5 ml of DMSO was added 49.0 mg of ammonium carbonate, followed by stirring 100° C. for 5 hours. To the reaction liquid were added water and ethyl acetate, and the organic layer was washed with water, and then and dried over anhydrous magnesium sulfate. The solvent was evaporated under reduced pressure and the obtained residue was purified by silica gel column chromatography (eluent solvent; hexane:ethyl acetate=8:1→4:1) to prepare 0.30 g (yield 51%) of a target compound.

¹H-NMR (CDCl₃, ppm) δ 4.71 (2H, broad-s), 7.35-7.39 (1H, m), 7.40-7.44 (1H, m), 7.92 (1H, s), 8.12-8.15 (2H, m).

10-3

Preparation of N-(3-(2-bromo-4-(perfluoropropan-2-yl)-6-(trifluoromethyl)phenylcarbamoyl)-6-cyano-2-fluorophenyl)-6-chloronicotinamide (Compound No. 1-1968)

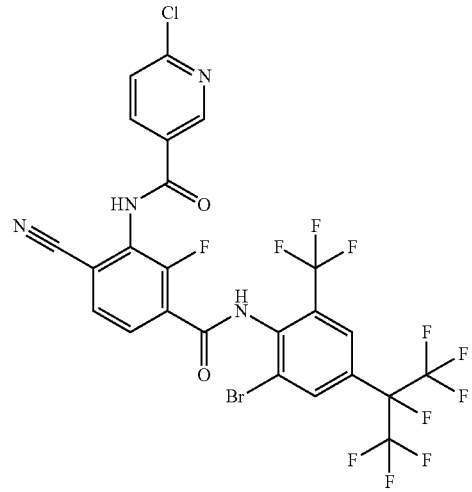 [SMILES: N#Cc1ccc(C(=O)Nc2c(Br)cc(C(F)(C(F)(F)F)C(F)(F)F)cc2C(F)(F)F)c(F)c1NC(=O)c1ccc(Cl)nc1]

To a solution of 0.0500 g (0.0877 mol) of 3-amino-N-(2-bromo-4-(perfluoropropan-2-yl)-6-(trifluoromethyl)phenyl)-4-cyano-2-fluorobenzamide in 0.200 ml of DMI was added 0.0308 g (0.175 mmol) of 6-chloronicotinoylchloride, followed by stirring at 130° C. for 6 hours. To the reaction liquid were added water and ethyl acetate, and the organic layer was washed with 1 M hydrochloric acid, a saturated aqueous sodium hydrogen carbonate solution, and saturated brine, and then dried over anhydrous magnesium sulfate. The solvent was evaporated under reduced pressure and the obtained residue was purified by silica gel column chromatography (eluent solvent; hexane:ethyl acetate=2:1) to prepare 0.0100 g (yield 16%) of a target compound.

¹H-NMR (CDCl₃, ppm) δ 7.54 (1H, d, J=8.8 Hz), 7.72 (1H, d, J=8.8 Hz), 7.93 (1H, s), 8.09 (1H, s), 8.17-8.18 (2H, m), 8.27 (1H, dd, J=2.4 Hz 8.8 Hz), 8.38 (1H, d, J=10.8 Hz), 8.98 (1H, d, J=2.4 Hz).

Example 11

Preparation of 3-(4-cyanobenzamide)-N-(2,6-diiodo-4-(perfluorobutan-2-yl)phenyl)benzamide (Compound No. 6-79)

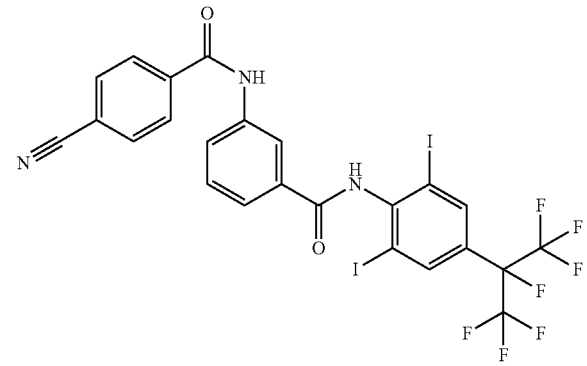 [SMILES: N#Cc1ccc(C(=O)Nc2cccc(C(=O)Nc3c(I)cc(C(F)(C(F)(F)F)C(F)(F)F)cc3I)c2)cc1]

11-1

Preparation of 2,6-diiodo-4-(perfluorobutan-2-yl)aniline

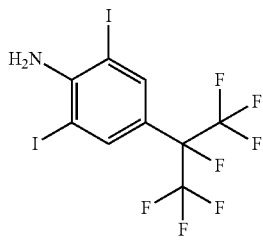 [SMILES: Nc1c(I)cc(C(F)(C(F)(F)F)C(F)(F)F)cc1I]

According to the method of 3-1 of Example 3, a target compound was prepared from 4-(perfluorobutan-2-yl)aniline obtained in 4-1 of Example 4.

$^1$H-NMR (CDCl$_3$, ppm) δ 4.95 (2H, broad-s), 7.78 (2H, s).

11-2

Preparation of N-(2,6-diiodo-4-(perfluorobutan-2-yl)phenyl)-3-nitrobenzamide

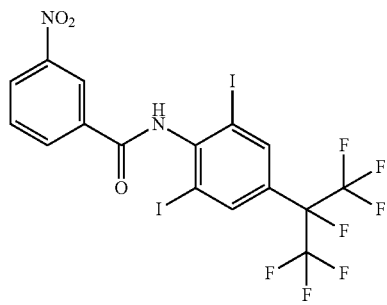 [SMILES: O=C(Nc1c(I)cc(C(F)(C(F)(F)F)C(F)(F)F)cc1I)c1cccc([N+](=O)[O-])c1]

According to the method of 4-3 of Example 4, a target compound was prepared from 2,6-diiodo-4-(perfluorobutan-2-yl)aniline and 3-nitrobenzoyl chloride.

$^1$H-NMR (CDCl$_3$, ppm) δ 7.74 (1H, t, J=8.0 Hz), 8.11 (2H, s), 8.42 (1H, d, J=7.6 Hz), 8.46 (1H, d, J=8.4 Hz), 8.90 (1H, d, J=12.4 Hz), 8.92 (1H, s).

11-3

Preparation of 3-amino-N-(2,6-diiodo-4-(perfluorobutan-2-yl)phenyl)benzamide

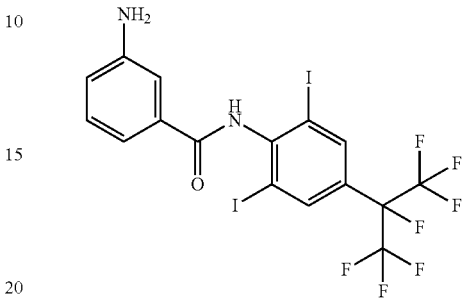

According to the method of 1-5 of Example 1, a target compound was prepared from N-(2,6-diiodo-4-(perfluorobutan-2-yl)phenyl)-3-nitrobenzamide.

$^1$H-NMR (CDCl$_3$, ppm) δ 5.39 (2H, broad-s), 6.89-6.93 (1H, m), 7.29-7.31 (3H, m), 7.68 (1H, s), 8.08 (2H, s).

11-4

Preparation of 3-(4-cyanobenzamide)-N-(2,6-diiodo-4-(perfluorobutan-2-yl)phenyl)benzamide (Compound No. 6-79)

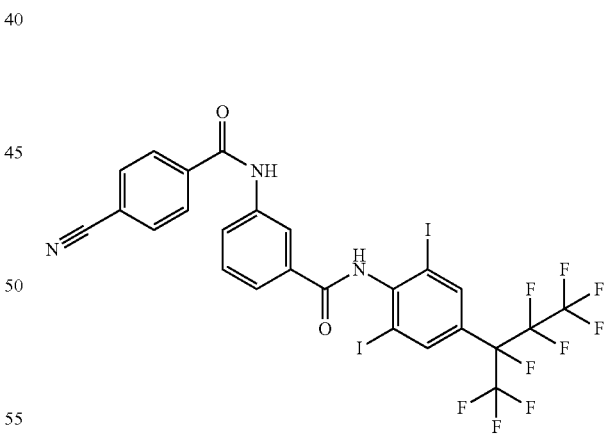

According to the method of 1-7 of Example 1, a target compound was prepared from 3-amino-N-(2,6-diiodo-4-(perfluorobutan-2-yl)phenyl)benzamide and 4-cyanobenzoylchloride.

$^1$H-NMR (CDCl$_3$, ppm) δ 7.58 (1H, t, J=8.2 Hz), 7.79-7.83 (3H, m), 7.97 (2H, s), 8.01 (2H, d, J=8.0 Hz), 8.09 (2H, s), 8.18 (1H, s), 8.29 (1H, s).

Example 12

Preparation of N-(3-(2-bromo-4-(perfluoropropan-2-yl)-6-(trifluoromethoxy)phenylcarbamoyl)-2-fluorophenyl)-2-chloronicotinamide (Compound No. 6-5908)

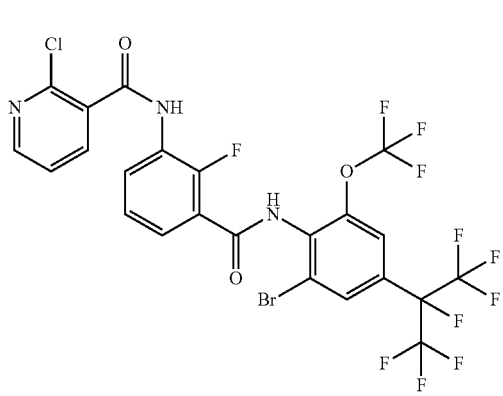 [SMILES: O=C(Nc1cccc(C(=O)Nc2c(Br)cc(C(F)(C(F)(F)F)C(F)(F)F)cc2OC(F)(F)F)c1F)c1cccnc1Cl]

12-1

Preparation of 4-(perfluoropropan-2-yl)-2-(trifluoromethoxy)aniline

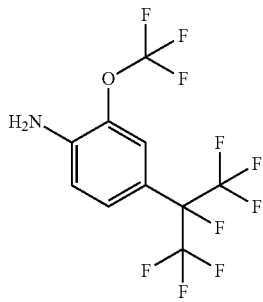 [SMILES: Nc1ccc(C(F)(C(F)(F)F)C(F)(F)F)cc1OC(F)(F)F]

According to the method of 1-1 of Example 1, a target compound was prepared from 2-trifluoromethoxy aniline.
$^1$H-NMR (CDCl$_3$, ppm) δ 4.19 (2H, broad-s), 6.86 (1H, d, J=8.8 Hz), 7.30 (1H, d, J=8.8 Hz), 7.36 (1H, s).

12-2

Preparation of 2-bromo-4-(perfluoropropan-2-yl)-6-(trifluoromethoxy)aniline

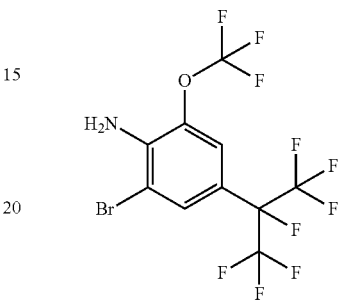

According to the method of 1-2 of Example 1, a target compound was prepared from 4-(perfluoropropan-2-yl)-2-(trifluoromethoxy)aniline.
$^1$H-NMR (CDCl$_3$, ppm) δ 4.65 (2H, broad-s), 7.33 (1H, s), 7.71 (1H, s).

12-3

Preparation of N-(2-bromo-4-(perfluoropropan-2-yl)-6-(trifluoromethoxy)phenyl)-2-chloro-3-nitrobenzamide

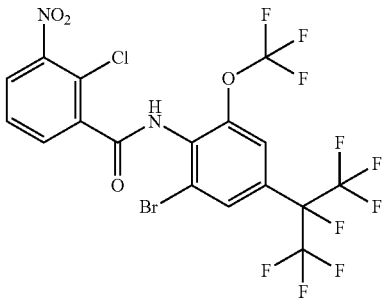 [SMILES: O=C(Nc1c(Br)cc(C(F)(C(F)(F)F)C(F)(F)F)cc1OC(F)(F)F)c1cccc([N+](=O)[O-])c1Cl]

According to the method of 1-3 of Example 1, a target compound was prepared from 2-bromo-4-(perfluoropropan-2-yl)-6-(trifluoromethoxy)aniline.

¹H-NMR (CDCl₃, ppm) δ 7.49-7.61 (3H, m), 7.80-7.96 (3H, m).

12-4

Preparation of N-(2-bromo-4-(perfluoropropan-2-yl)-6-(trifluoromethoxy)phenyl)-2-fluoro-3-nitrobenzamide

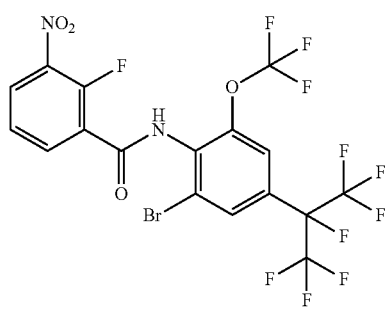

According to the method of 1-4 of Example 1, a target compound was prepared from N-(2-bromo-4-(perfluoropropan-2-yl)-6-(trifluoromethoxy)phenyl)-2-chloro-3-nitrobenzamide.

¹H-NMR (CDCl₃, ppm) δ 7.53 (1H, t, J=7.8 Hz), 7.60 (1H, broad-s), 7.89 (1H, d, J=1.5 Hz), 8.07 (1H, broad-d, J=12.7 Hz), 8.29-8.30 (1H, m), 8.43-8.47 (1H, m).

12-5

Preparation of 3-amino-N-(2-bromo-4-(perfluoropropan-2-yl)-6-(trifluoromethoxy)phenyl)-2-fluorobenzamide

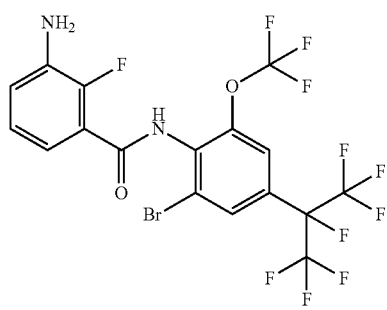 [SMILES: O=C(Nc1c(Br)cc(C(F)(C(F)(F)F)C(F)(F)F)cc1OC(F)(F)F)c1cccc([N+](=O)[O-])c1F]

According to the method of 1-5 of Example 1, a target compound was prepared from N-(2-bromo-4-(perfluoropropan-2-yl)-6-(trifluoromethoxy)phenyl)-2-fluoro-3-nitrobenzamide.

¹H-NMR (CDCl₃, ppm) δ 3.92 (2H, broad-s), 6.99-7.04 (1H, m), 7.11 (1H, t, J=7.8 Hz), 7.45-7.49 (1H, m), 7.57 (1H, broad-s), 7.87 (1H, d, J=2.0 Hz), 8.14 (1H, d, J=14.2 Hz).

12-6

Preparation of N-(3-(2-bromo-4-(perfluoropropan-2-yl)-6-(trifluoromethoxy)phenylcarbamoyl)-2-fluorophenyl)-2-chloronicotinamide (Compound No. 6-5908)

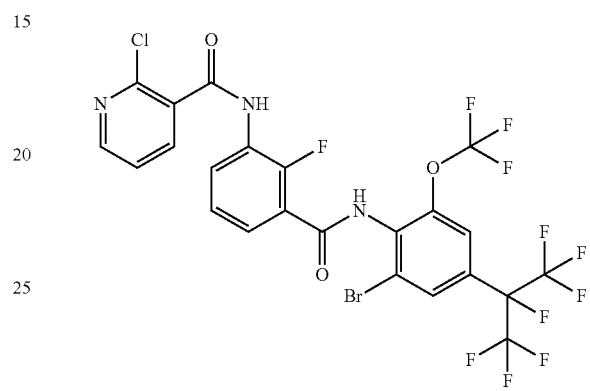

According to the method of 1-7 of Example 1, a target compound was prepared from 3-amino-N-(2-bromo-4-(perfluoropropan-2-yl)-6-(trifluoromethoxy)phenyl)-2-fluorobenzamide and 2-chloronicotinoylchloride.

¹H-NMR (CDCl₃, ppm) δ 7.39-7.49 (2H, m), 7.59 (1H, s), 7.88-7.94 (2H, m), 8.07 (1H, d, J=12.2 Hz), 8.31-8.33 (1H, m), 8.57-8.58 (1H, m), 8.60-8.70 (1H, m), 8.74 (1H, broad-s).

Example 13

Preparation of 3-benzamide-N-(2-bromo-4-(perfluoropropan-2-yl)-6-(trifluoromethyl)phenyl)-4-fluorobenzamide (Compound No. 6-3348)

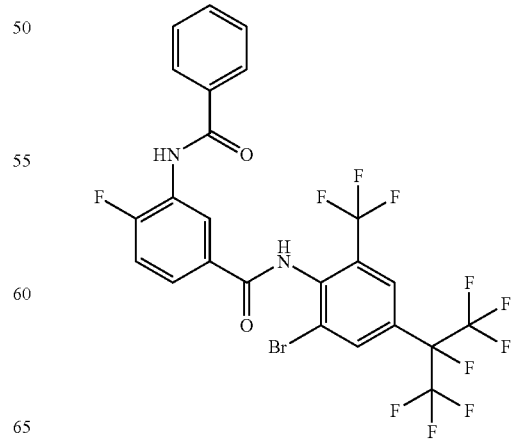

13-1

Preparation of N-(2-bromo-4-(perfluoropropan-2-yl)-6-(trifluoromethyl)phenyl)-4-fluoro-3-nitrobenzamide

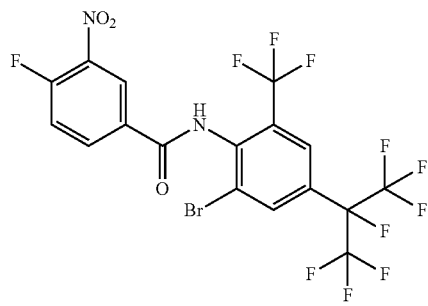

According to the method of 1-3 of Example 1, a target compound was prepared from 4-fluoro-3-nitrobenzoyl chloride prepared from 4-fluoro-3-nitrobenzoic acid and thionyl chloride, and 2-bromo-4-(perfluoropropan-2-yl)-6-(trifluoromethyl)aniline obtained in 1-2 of Example 1.

$^1$H-NMR (CDCl$_3$, ppm) δ 7.47-7.50 (1H, m), 7.92 (2H, d, J=5.9 Hz), 8.16 (1H, s), 8.23-8.28 (1H, m), 8.65-8.67 (1H, m).

13-2

Preparation of 3-amino-N-(2-bromo-4-(perfluoropropan-2-yl)-6-(trifluoromethyl)phenyl)-4-fluorobenzamide

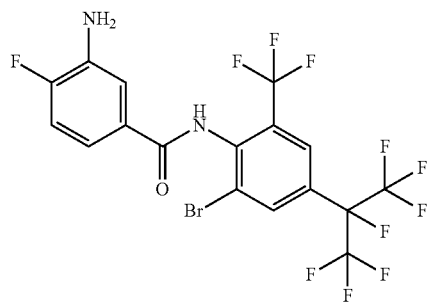

According to the method of 1-5 of Example 1, a target compound was prepared from N-(2-bromo-4-(perfluoropropan-2-yl)-6-(trifluoromethyl)phenyl)-4-fluoro-3-nitrobenzamide.

APCI-MS m/z (M+1):546

13-3

Preparation of 3-benzamide-N-(2-bromo-4-(perfluoropropan-2-yl)-6-(trifluoromethyl)phenyl)-4-fluorobenzamide (Compound No. 6-3348)

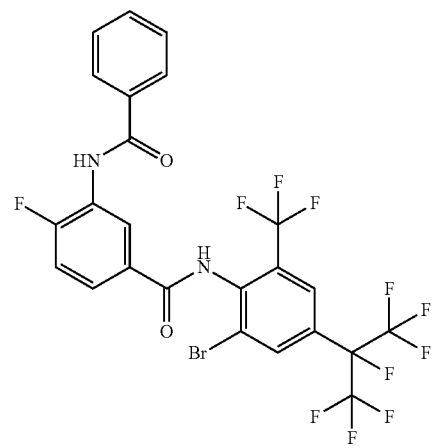 [SMILES: O=C(Nc1cc(C(=O)Nc2c(Br)cc(C(F)(C(F)(F)F)C(F)(F)F)cc2C(F)(F)F)ccc1F)c1ccccc1]

According to the method of 1-7 of Example 1, a target compound was prepared from 3-amino-N-(2-bromo-4-(perfluoropropan-2-yl)-6-(trifluoromethyl)phenyl)-4-fluorobenzamide.

$^1$H-NMR (CDCl$_3$, ppm) δ 7.29-7.34 (1H, m), 7.53-7.65 (3H, m), 7.80-7.84 (1H, m), 7.90-7.92 (3H, m), 8.14 (1H, broad-s), 8.20 (1H, d, J=2.9 Hz), 8.25 (1H, broad-s), 9.10 (1H, dd, J=1.9, 7.3 Hz).

Example 14

Preparation of 2-chloro-N-(3-(2-iodo-4-(perfluoropropan-2-yl)-6-(trifluoromethyl)phenylcarbamoyl)phenyl)nicotinamide (Compound No. 6-460)

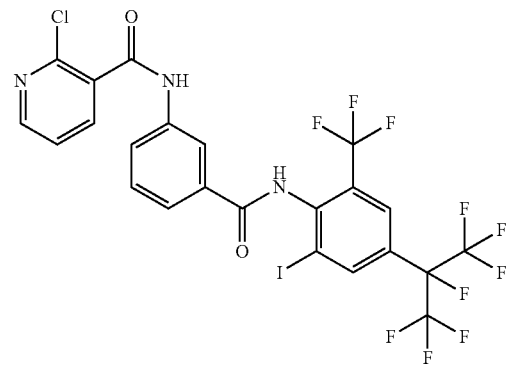 [SMILES: O=C(Nc1c(I)cc(C(F)(C(F)(F)F)C(F)(F)F)cc1C(F)(F)F)c1cccc(NC(=O)c2cccnc2Cl)c1]

14-1

Preparation of 2-iodo-4-(perfluoropropan-2-yl)-6-(trifluoromethyl)aniline

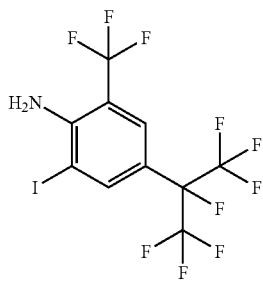 [SMILES: Nc1c(I)cc(C(F)(C(F)(F)F)C(F)(F)F)cc1C(F)(F)F]

According to the method of 8-2 of Example 8, a target compound was prepared from 4-(perfluoropropan-2-yl)-2-(trifluoromethyl)aniline obtained in 1-1 of Example 1 and N-iodosuccinimide.

$^1$H-NMR (CDCl$_3$, ppm) δ 5.04 (2H, broad-s), 7.64 (1H, s), 7.99 (1H, s).

14-2

Preparation of N-(2-iodo-4-(perfluoropropan-2-yl)-6-(trifluoromethyl)phenyl)-3-nitrobenzamide

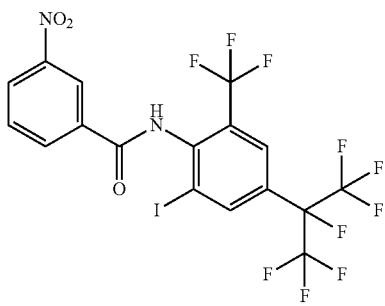

According to the method of 4-3 of Example 4, a target compound was prepared from 2-iodo-4-(perfluoropropan-2-yl)-6-(trifluoromethyl)aniline and 3-nitrobenzoyl chloride.

$^1$H-NMR (CDCl$_3$, ppm) δ 7.76-7.80 (2H, m), 7.97 (1H, s), 8.28-8.30 (1H, m), 8.37 (1H, s), 8.49-8.52 (1H, m), 8.78 (1H, s).

14-3

Preparation of 3-amino-N-(2-iodo-4-(perfluoropropan-2-yl)-6-(trifluoromethyl)phenyl)benzamide

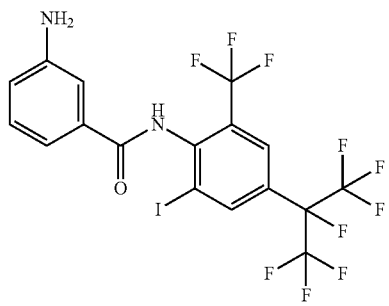 [SMILES: O=C(Nc1c(I)cc(C(F)(C(F)(F)F)C(F)(F)F)cc1C(F)(F)F)c1cccc([N+](=O)[O-])c1]

According to the method of 1-5 of Example 1, a target compound was prepared from N-(2-iodo-4-(perfluoropropan-2-yl)-6-(trifluoromethyl)phenyl)-3-nitrobenzamide.

$^1$H-NMR (CDCl$_3$, ppm) δ 3.89 (2H, broad-s), 6.89-6.92 (1H, m), 7.23-7.32 (3H, m), 7.68 (1H, s), 7.93 (1H, s), 8.34-8.36 (1H, m).

14-4

Preparation of 2-chloro-N-(3-(2-iodo-4-(perfluoropropan-2-yl)-6-(trifluoromethyl)phenylcarbamoyl)phenyl)nicotinamide (Compound No. 6-460)

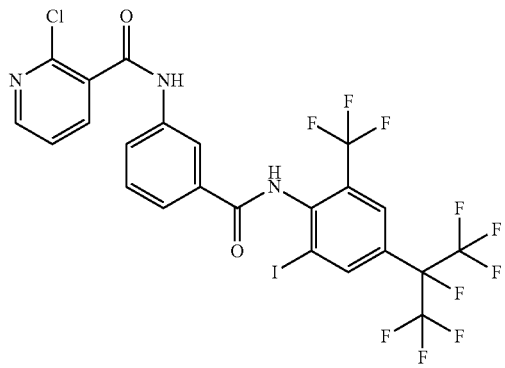 [SMILES: O=C(Nc1c(I)cc(C(F)(C(F)(F)F)C(F)(F)F)cc1C(F)(F)F)c1cccc(NC(=O)c2cccnc2Cl)c1]

According to the method of 1-7 of Example 1, a target compound was prepared from 3-amino-N-(2-iodo-4-(perfluoropropan-2-yl)-6-(trifluoromethyl)phenyl)benzamide and 2-chloronicotinoylchloride.

$^1$H-NMR (CDCl$_3$, ppm) δ 7.43-7.46 (1H, m), 7.58 (1H, t, J=7.8 Hz), 7.77 (1H, d, J=7.8 Hz), 7.91-7.95 (2H, m), 8.01

(1H, s), 8.24 (1H, dd, J=2.0, 7.8 Hz), 8.28 (1H, s), 8.36 (1H, s), 8.41 (1H, s), 8.54-8.56 (1H, m).

Example 15

Preparation of 2-fluoro-3-(4-fluoro-N-methylbenzamide)-N-(2-iodo-4-(perfluoropropan-2-yl)-6-(trifluoromethyl)phenyl)benzamide (Compound No. 7-1733)

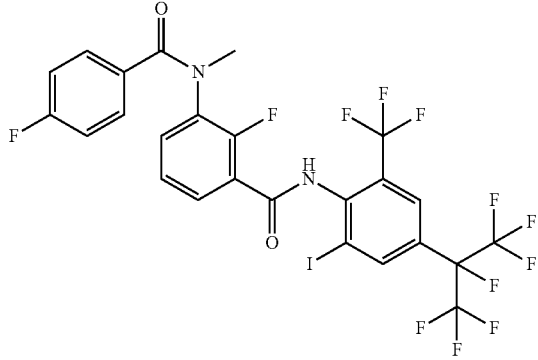 [SMILES: CN(C(=O)c1ccc(F)cc1)c1cccc(C(=O)Nc2c(I)cc(C(F)(C(F)(F)F)C(F)(F)F)cc2C(F)(F)F)c1F]

15-1

Preparation of 2-chloro-N-(2-iodo-4-(perfluoropropan-2-yl)-6-(trifluoromethyl)phenyl)-3-nitrobenzamide

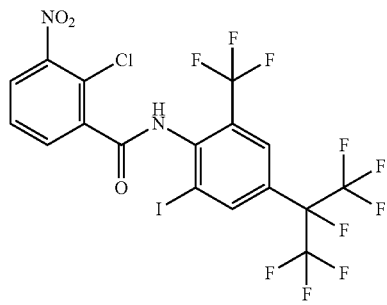 [SMILES: O=C(Nc1c(I)cc(C(F)(C(F)(F)F)C(F)(F)F)cc1C(F)(F)F)c1cccc([N+](=O)[O-])c1F]

According to the method of 4-3 of Example 4, a target compound was prepared from 2-iodo-4-(perfluoropropan-2-yl)-6-(trifluoromethyl)aniline obtained in 14-1 of Example 14 and 2-chloro-3-nitrobenzoyl chloride.

$^{1}$H-NMR (CDCl$_{3}$, ppm) δ 7.60 (1H, t, J=7.8 Hz), 7.76 (1H, s), 7.94 (1H, dd, J=1.5, 7.8 Hz), 7.97 (1H, s), 8.03 (1H, dd, J=1.5, 7.8 Hz), 8.39 (1H, s).

15-2

Preparation of 2-fluoro-N-(2-iodo-4-(perfluoropropan-2-yl)-6-(trifluoromethyl)phenyl)-3-nitrobenzamide

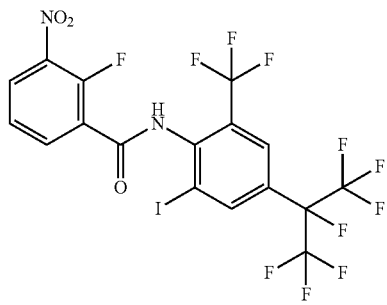

According to the method of 1-4 of Example 1, a target compound was prepared from 2-chloro-N-(2-iodo-4-(perfluoropropan-2-yl)-6-(trifluoromethyl)phenyl)-3-nitrobenzamide.

$^{1}$H-NMR (CDCl$_{3}$, ppm) δ 7.51-7.55 (1H, m), 7.97 (1H, s), 8.23 (1H, d, J=12.2 Hz), 8.28-8.32 (1H, m), 8.37 (1H, s), 8.44-8.48 (1H, m).

15-3

Preparation of 3-amino-2-fluoro-N-(2-iodo-4-(perfluoropropan-2-yl)-6-(trifluoromethyl)phenyl)benzamide

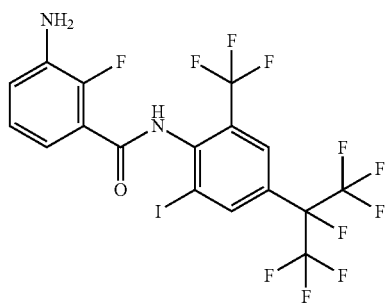 [SMILES: Nc1cccc(C(=O)Nc2c(I)cc(C(F)(C(F)(F)F)C(F)(F)F)cc2C(F)(F)F)c1F]

According to the method of 1-5 of Example 1, a target compound was prepared from 2-fluoro-N-(2-iodo-4-(perfluoropropan-2-yl)-6-(trifluoromethyl)phenyl)-3-nitrobenzamide.

$^1$H-NMR (CDCl$_3$, ppm) δ 3.92 (2H, broad-s), 7.02-7.04 (1H, m), 7.11 (1H, t, J=7.8 Hz), 7.47-7.52 (1H, m), 7.94 (1H, s), 8.30-8.35 (2H, m).

15-4

Preparation of 2-fluoro-N-(2-iodo-4-(perfluoropropan-2-yl)-6-(trifluoromethyl)phenyl)-3-(methylamino)benzamide

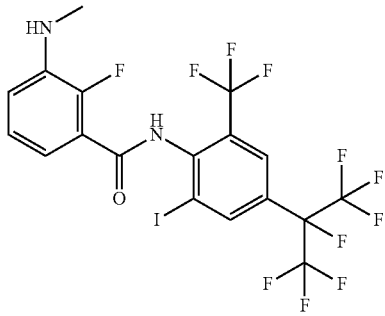 [SMILES: CNc1cccc(C(=O)Nc2c(I)cc(C(F)(C(F)(F)F)C(F)(F)F)cc2C(F)(F)F)c1F]

According to the method of 1-6 of Example 1, a target compound was prepared from 3-amino-2-fluoro-N-(2-iodo-4-(perfluoropropan-2-yl)-6-(trifluoromethyl)phenyl)benzamide.

$^1$H-NMR (CDCl$_3$, ppm) δ 2.95 (3H, s), 4.15 (1H, broad-s), 6.90 (1H, t, J=8.2 Hz), 7.19 (1H, t, J=7.8 Hz), 7.40 (1H, t, J=7.8 Hz), 7.92 (1H, s), 8.30 (1H, s), 8.34 (1H, s).

15-5

Preparation of 2-fluoro-3-(4-fluoro-N-methylbenzamide)-N-(2-iodo-4-(perfluoropropan-2-yl)-6-(trifluoromethyl)phenyl)benzamide (Compound No. 7-1733)

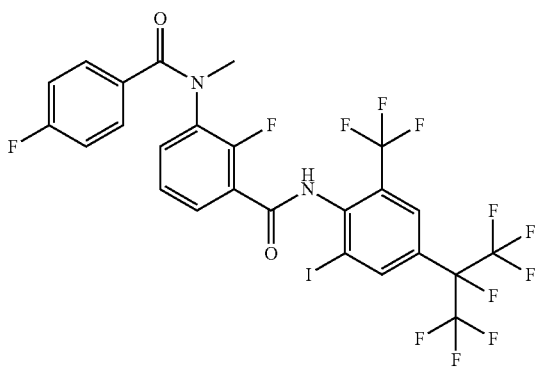 [SMILES: CN(C(=O)c1ccc(F)cc1)c1cccc(C(=O)Nc2c(I)cc(C(F)(C(F)(F)F)C(F)(F)F)cc2C(F)(F)F)c1F]

According to the method of 1-7 of Example 1, a target compound was prepared from 2-fluoro-N-(2-iodo-4-(perfluoropropan-2-yl)-6-(trifluoromethyl)phenyl)-3-(methylamino)benzamide and 4-fluorobenzoyl chloride.

$^1$H-NMR (CDCl$_3$, ppm) δ 3.50 (3H, s), 6.91 (2H, s), 6.93-7.35 (3H, m), 7.46 (1H, t, J=7.0 Hz), 7.93 (1H, s), 8.01-8.10 (1H, m), 8.13 (1H, broad-s), 8.34 (1H, s).

Example 16

Preparation of N-(2-bromo-4-(perfluoropropan-2-yl)-6-(trifluoromethyl)phenyl)-2-fluoro-N-methyl-3-(N-methylbenzamide)benzamide (Compound No. 9-2164)

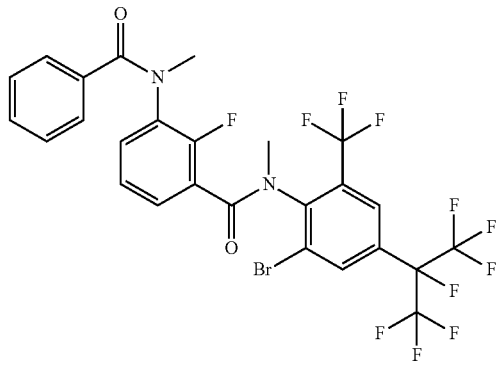

To a solution of 0.100 g (0.150 mmol) of N-(2-bromo-4-(perfluoropropan-2-yl)-6-(trifluoromethyl)phenyl)-2-fluoro-3-(N-methylbenzamide)benzamide obtained in 1-7 of Example 1 in 5 ml of DMF was added 0.00900 g (0.230 mmol) of sodium hydride (60% in oil), followed by stirring at room temperature for 40 minutes. To the reaction liquid was added 0.0300 g (0.180 mmol) of methyl iodide, followed by stirring at the same temperature for 6 hours. To the reaction liquid were added water and ethyl acetate, and the organic layer was washed with water and saturated brine, and dried over anhydrous magnesium sulfate. The solvent was evaporated under reduced pressure and the obtained residue was purified by silica gel column chromatography (eluent solvent; hexane:ethyl acetate=4:1) to prepare 0.106 g of a target compound quantitatively.

$^1$H-NMR (CDCl$_3$, ppm) δ 2.18-2.19 (3H, m), 3.48 (3H, s), 7.21-7.25 (4H, m), 7.32-7.40 (4H, m), 7.92 (1H, s), 8.13 (1H, s).

Example 17

Preparation of N-(2-bromo-4-(perfluoropropan-2-yl)-6-(trifluoromethyl)phenyl)-3-(4-cyanobenzamide)-N-methylbenzamide (Compound No. 8-289)

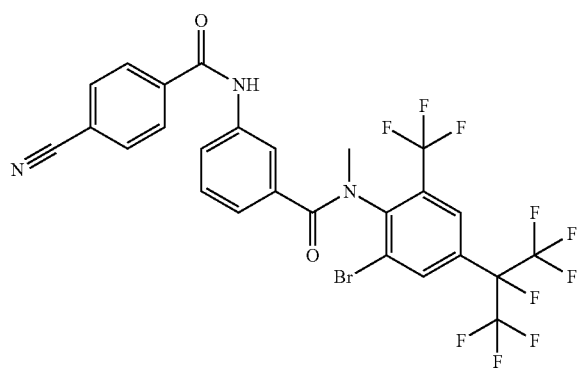 [SMILES: CN(C(=O)c1cccc(NC(=O)c2ccc(C#N)cc2)c1)c1c(Br)cc(C(F)(C(F)(F)F)C(F)(F)F)cc1C(F)(F)F]

17-1

Preparation of N-(2-bromo-4-(perfluoropropan-2-yl)-6-(trifluoromethyl)phenyl)-3-nitrobenzamide

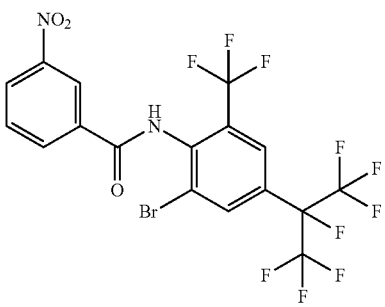 [SMILES: O=C(Nc1c(Br)cc(C(F)(C(F)(F)F)C(F)(F)F)cc1C(F)(F)F)c1cccc([N+](=O)[O-])c1]

According to the method of 4-3 of Example 4, a target compound was prepared from 2-bromo-4-(perfluoropropan-2-yl)-6-(trifluoromethyl)aniline obtained in 1-2 of Example 1 and 3-nitrobenzoyl chloride.

$^1$H-NMR (CDCl$_3$, ppm) δ 7.75-7.79 (2H, m), 7.94 (1H, s), 8.17 (1H, d, J=1.0 Hz), 8.28 (1H, dd, J=1.5, 7.8 Hz), 8.48-8.51 (1H, m), 8.76-8.77 (1H, m).

17-2

Preparation of N-(2-bromo-4-(perfluoropropan-2-yl)-6-(trifluoromethyl)phenyl)-N-methyl-3-nitrobenzamide

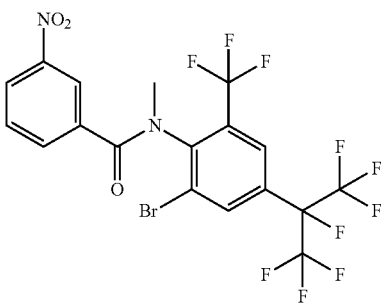 [SMILES: CN(C(=O)c1cccc([N+](=O)[O-])c1)c1c(Br)cc(C(F)(C(F)(F)F)C(F)(F)F)cc1C(F)(F)F]

According to the method of Example 16, a target compound was prepared from N-(2-bromo-4-(perfluoropropan-2-yl)-6-(trifluoromethyl)phenyl)-3-nitrobenzamide.

$^1$H-NMR (CDCl$_3$, ppm) δ 3.28 (1/2*3H, s), 3.44 (1/2*3H, s), 7.41 (1/2*1H, t, J=7.8 Hz), 7.71-7.76 (2/2*1H, m), 7.84 (1/2*1H, s), 7.93-7.95 (1/2*1H, m), 7.98 (1/2*1H, s), 8.07-8.09 (2/2*1H, m), 8.14-8.16 (1/2*1H, m), 8.19 (1/2*1H, s), 8.39-8.41 (1/2*1H, m), 8.45-8.46 (1/2*1H, m).

17-3

Preparation of 3-amino-N-(2-bromo-4-(perfluoropropan-2-yl)-6-(trifluoromethyl)phenyl)-N-methylbenzamide

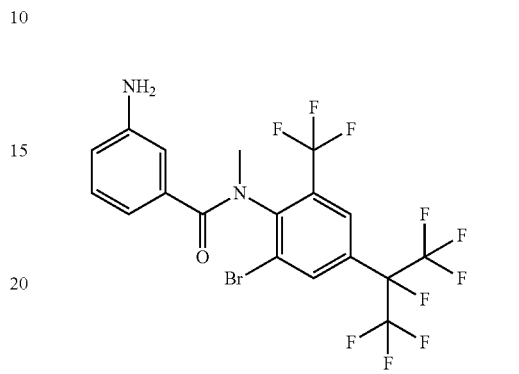

According to the method of 1-5 of Example 1, a target compound was prepared from N-(2-bromo-4-(perfluoropropan-2-yl)-6-(trifluoromethyl)phenyl)-N-methyl-3-nitrobenzamide.

$^1$H-NMR (CDCl$_3$, ppm) δ 3.24 (3/4*3H, s), 3.37 (1/4*3H, s), 3.80 (2H, broad-s), 6.47 (1/4*1H, d, J=7.8 Hz), 6.54-6.57 (1/4*1H, m), 6.78-6.84 (5/4*1H, m), 6.86 (3/4*1H, t, J=2.0 Hz), 6.96 (3/4*1H, d, J=7.8 Hz), 7.23-7.27 (3/4*1H, m), 7.79 (1/4*1H, s), 7.94 (3/4*1H, s), 8.00 (1/4*1H, s), 8.15 (3/4*1H, s).

17-4

Preparation of N-(2-bromo-4-(perfluoropropan-2-yl)-6-(trifluoromethyl)phenyl)-3-(4-cyanobenzamide)-N-methylbenzamide (Compound No. 8-289)

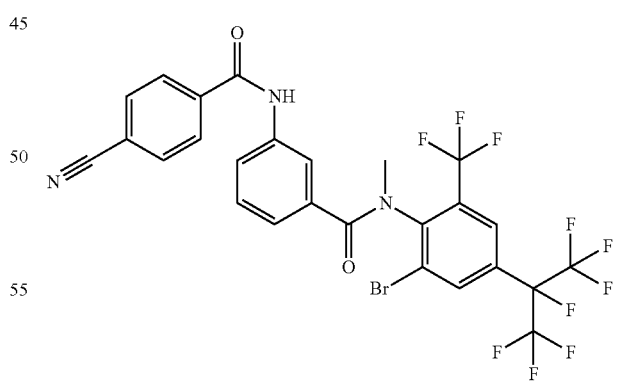

According to the method of 1-7 of Example 1, a target compound was prepared from 3-amino-N-(2-bromo-4-(perfluoropropan-2-yl)-6-(trifluoromethyl)phenyl)-N-methylbenzamide and 4-cyanobenzoylchloride.

$^1$H-NMR (CDCl$_3$, ppm) δ 3.26 (2/3*3H, s), 3.38 (1/3*3H, s), 7.08-7.09 (1/3*1H, 7.12-7.14 (1/3*1H, m), 7.32 (2/3*1H, d, J=7.8 Hz), 7.45-7.49 (3/3*1H, m), 7.72-7.76 (9/3*1H, m), 7.83 (1/3*1H, s), 7.85-7.89 (4/3*1H, m), 7.95 (2/3*1H, s), 7.98-8.00 (4/3*1H, m), 8.04 (2/3*1H, d, J=6.3 Hz), 8.16 (2/3*1H, s), 8.57 (2/3*1H, s).

Example 18

Preparation of 3-benzamide-N-(2-bromo-4-(perfluoroethyl)-6-(trifluoromethyl)phenyl)benzamide (Compound No. 6-5913)

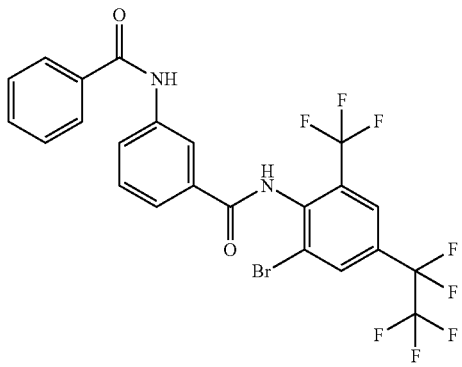 [SMILES: O=C(Nc1cccc(C(=O)Nc2c(Br)cc(C(F)(F)C(F)(F)F)cc2C(F)(F)F)c1)c1ccccc1]

18-1

Preparation of 4-(perfluoroethyl)-2-(trifluoromethyl)aniline

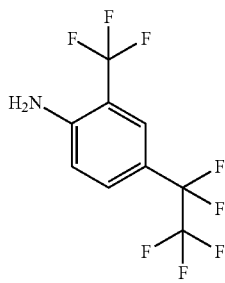 [SMILES: Nc1ccc(C(F)(F)C(F)(F)F)cc1C(F)(F)F]

To 40 ml of an aqueous solution of 7.04 g (40.4 mmol) of 85% sodium hydrosulfite and 3.40 g (40.4 mmol) of sodium hydrogen carbonate were added 13.6 g (33.7 mmol) of 2-(trifluoromethyl)aniline and 40 ml of DMF. To this reaction liquid was added 50 ml of a solution of 11.2 g (45.5 mmol) of 1,1,2,2,2-pentafluoroethyliodide in DMF (DMF was cooled to −30° C., and 1,1,2,2,2-pentafluoroethyl iodide was dissolved therein), and placed in an autoclave, followed by stirring at 110° C. for 9 hours. After being left to stand at room temperature overnight, water and ethyl acetate were added to the reaction liquid, followed by extraction with ethyl acetate. The organic layer was washed with water, a saturated aqueous sodium hydrogen carbonate solution, and saturated brine. The organic layer was dried over anhydrous sodium sulfate, then the solvent was evaporated under reduced pressure, and the obtained residue was purified by silica gel column chromatography (eluent solvent; hexane:ethyl acetate=10:1→5:1) to prepare 1.95 g (yield 21%) of a target compound.

$^1$H-NMR (CDCl$_3$, ppm) δ 4.53 (2H, broad-s), 6.81 (1H, d, J=8.3 Hz), 7.48 (1H, d, J=8.3 Hz), 7.63 (1H, broad-s).

18-2

Preparation of 2-bromo-4-(perfluoroethyl)-6-(trifluoromethyl)aniline

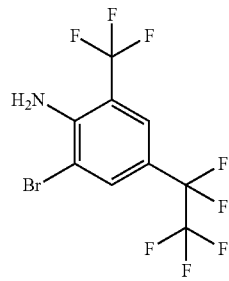 [SMILES: Nc1c(Br)cc(C(F)(F)C(F)(F)F)cc1C(F)(F)F]

According to the method of 1-2 of Example 1, a target compound was prepared from 4-(perfluoroethyl)-2-(trifluoromethyl)aniline.

$^1$H-NMR (CDCl$_3$, ppm) δ 5.08 (2H, broad-s), 7.62 (1H, s), 7.80 (1H, s).

18-3

Preparation of N-(2-bromo-4-(perfluoroethyl)-6-(trifluoromethyl)phenyl)-3-nitrobenzamide

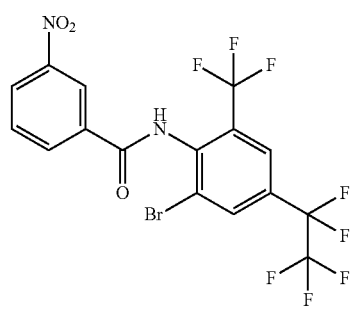 [SMILES: O=C(Nc1c(Br)cc(C(F)(F)C(F)(F)F)cc1C(F)(F)F)c1cccc([N+](=O)[O-])c1]

To a solution of 2.50 g (6.99 mmol) of 2-bromo-4-(perfluoroethyl)-6-(trifluoromethyl)aniline in 20 ml of pyridine was added 2.72 g (14.7 mmol) of 3-nitrobenzoyl chloride, followed by stirring at 100° C. for 12 hours. To the reaction liquid were added water and ethyl acetate, followed by extraction with ethyl acetate. The organic layer was washed with 1 M hydrochloric acid, a saturated aqueous sodium hydrogen carbonate solution, and saturated brine. The organic layer was dried over anhydrous sodium sulfate, and then the solvent was evaporated under reduced pressure. To the obtained residue were added THF and an aqueous sodium hydroxide solution, followed by stirring at room temperature for 8 hours. The reaction liquid was extracted/dried in the same manner as described above, and the solvent was evaporated under reduced pressure. The obtained residue was purified by silica gel column chromatography (eluent solvent; hexane:ethyl acetate=7:1→5:1) to prepare 0.202 g (yield 6%) of a target compound.

$^1$H-NMR (CDCl$_3$, ppm) δ 7.75 (1H, s), 7.78 (1H, t, J=7.8 Hz), 7.94 (1H, s), 8.17 (1H, s), 8.29-8.30 (1H, m), 8.50-8.52 (1H, m), 8.78 (1H, t, J=2.0 Hz).

18-4

Preparation of 3-amino-N-(2-bromo-4-(perfluoroethyl)-6-(trifluoromethyl)phenyl)benzamide

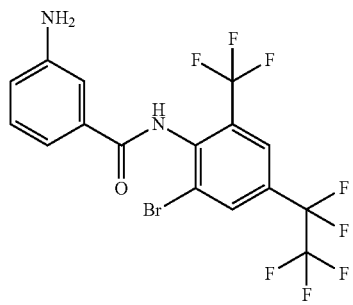

According to the method of 1-5 of Example 1, a target compound was prepared from N-(2-bromo-4-(perfluoroethyl)-6-(trifluoromethyl)phenyl)-3-nitrobenzamide.

$^1$H-NMR (CDCl$_3$, ppm) δ 3.89 (2H, broad-s), 6.90-6.92 (1H, m), 7.23-7.32 (3H, m), 7.64 (1H, s), 7.90 (1H, s), 8.13 (1H, s).

18-5

Preparation of 3-benzamide-N-(2-bromo-4-(perfluoroethyl)-6-(trifluoromethyl)phenyl)benzamide (Compound No. 6-5913)

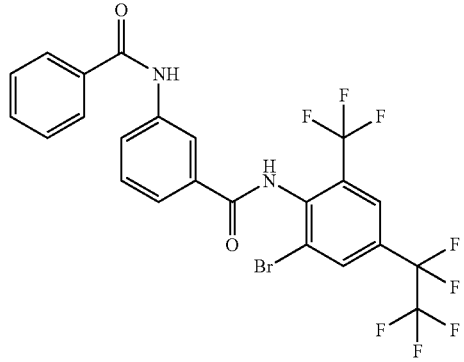 [SMILES: O=C(Nc1cccc(C(=O)Nc2c(Br)cc(C(F)(F)C(F)(F)F)cc2C(F)(F)F)c1)c1ccccc1]

According to the method of 1-7 of Example 1, a target compound was prepared from 3-amino-N-(2-bromo-4-(perfluoroethyl)-6-(trifluoromethyl)phenyl)benzamide.

$^1$H-NMR (CDCl$_3$, ppm) δ 7.51-7.62 (4H, m), 7.72 (1H, dd, J=1.5, 7.8 Hz), 7.89-8.00 (6H, m), 8.14 (1H, s), 8.27 (1H, t, J=2.0 Hz).

Example 19

Preparation of 3-benzamide-N-(2-bromo-4-(perfluoropropan-2-yl)-6-(trifluoromethyl)phenyl)-4-cyanobenzamide (Compound No. 1-627)

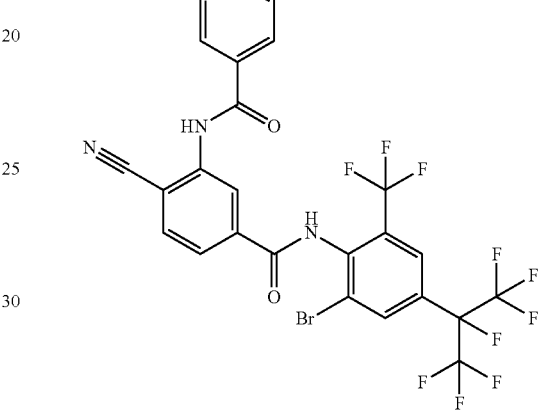

19-1

Preparation of N-(2-bromo-4-(perfluoropropan-2-yl)-6-(trifluoromethyl)phenyl)-4-fluoro-3-nitrobenzamide

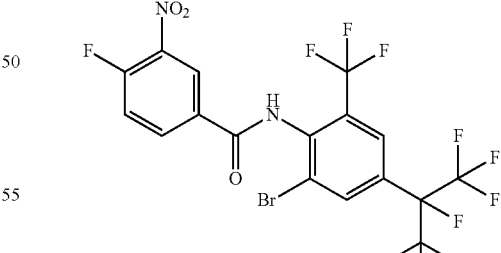

According to the method of 4-3 of Example 4, a target compound was prepared from 4-fluoro-3-nitrobenzoyl chloride prepared from 4-fluoro-3-nitrobenzoic acid and thionyl chloride, and 2-bromo-4-(perfluoropropan-2-yl)-6-(trifluoromethyl)aniline obtained in 1-2 of Example 1.

$^1$H-NMR (CDCl$_3$, ppm) δ 7.47-7.50 (1H, m), 7.92 (2H, d, J=5.9 Hz), 8.16 (1H, s), 8.23-8.28 (1H, m), 8.65-8.67 (1H, m).

19-2

Preparation of N-(2-bromo-4-(perfluoropropan-2-yl)-6-(trifluoromethyl)phenyl)-4-cyano-3-nitrobenzamide

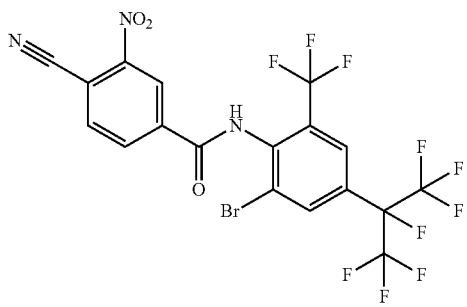

To a solution of 0.500 g (0.870 mmol) of N-(2-bromo-4-(perfluoropropan-2-yl)-6-(trifluoromethyl)phenyl)-4-fluoro-3-nitrobenzamide in 5 ml of DMF was added 0.0639 g (1.31 mmol) of sodium cyanide, followed by stirring at room temperature for 10 hours. To the reaction liquid were added water and ethyl acetate, followed by extraction with ethyl acetate. The organic layer was washed with a 10% aqueous sodium hydroxide solution and saturated brine. The organic layer was dried over anhydrous sodium sulfate, and then the solvent was evaporated under reduced pressure. The obtained residue was purified by silica gel column chromatography to prepare 0.0500 g (yield 10%) of a target compound.

$^1$H-NMR (CDCl$_3$, ppm) δ 7.80 (1H, s), 7.96 (1H, s), 8.12-8.14 (1H, m), 8.18 (1H, s), 8.36 (1H, dd, J=2.0, 8.3 Hz), 8.84 (1H, d, J=1.5 Hz).

19-3

Preparation of 3-amino-N-(2-bromo-4-(perfluoropropan-2-yl)-6-(trifluoromethyl)phenyl)-4-cyanobenzamide

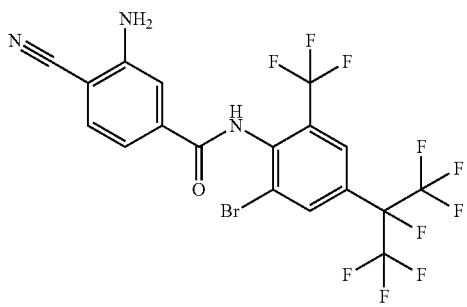 [SMILES: N#Cc1ccc(C(=O)Nc2c(Br)cc(C(F)(C(F)(F)F)C(F)(F)F)cc2C(F)(F)F)cc1N]

According to the method of 1-5 of Example 1, a target compound was prepared from N-(2-bromo-4-(perfluoropropan-2-yl)-6-(trifluoromethyl)phenyl)-4-cyano-3-nitrobenzamide.

$^1$H-NMR (CDCl$_3$, ppm) δ 4.68 (2H, broad-s), 7.18 (1H, dd, J=1.9, 8.3 Hz), 7.29 (1H, s), 7.52-7.55 (1H, m), 7.68 (1H, s), 7.92 (1H, s), 8.14 (1H, d, J=1.5 Hz).

19-4

Preparation of 3-benzamide-N-(2-bromo-4-(perfluoropropan-2-yl)-6-(trifluoromethyl)phenyl)-4-cyanobenzamide (Compound No. 1-627)

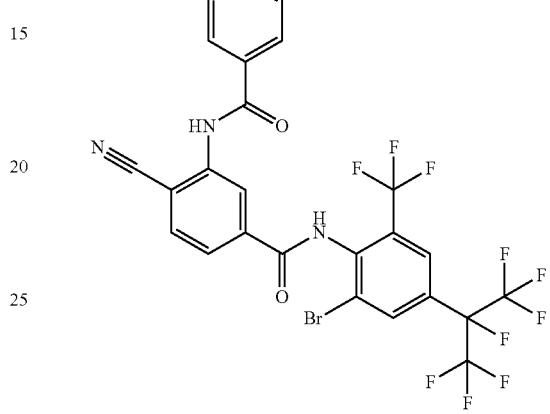

According to the method of 1-7 of Example 1, a target compound was prepared from 3-amino-N-(2-bromo-4-(perfluoropropan-2-yl)-6-(trifluoromethyl)phenyl)-4-cyanobenzamide.

$^1$H-NMR (CDCl$_3$, ppm) δ 7.56-7.59 (3H, m), 7.64-7.66 (1H, m), 7.80-7.87 (2H, m), 7.94-7.97 (2H, m), 8.16 (1H, s), 8.46 (1H, s), 8.57 (1H, s), 9.16 (1H, s).

Next, Preparation Examples in which the compound of the present invention is contained as an active ingredient will be shown, but the present invention is not limited thereto. Further, in Preparation Examples, parts represent parts by weight.

Preparation Example 1

20 parts of the compound represented by Formula (1) of the present invention, 10 parts of polyoxyethylene styrylphenyl ether, and 70 parts of xylene were mixed uniformly to obtain an emulsion.

Preparation Example 2

10 parts of the compound represented by Formula (1) of the present invention, 2 parts of sodium lauryl sulfate, 2 parts of dialkyl sulfosuccinate, 1 part of a β-naphthalene sulfonic acid formalin condensate sodium salt, and 85 parts of diatomaceous earth were stirred and mixed uniformly to obtain a wettable powder.

Preparation Example 3

0.3 parts of the compound represented by Formula (1) of the present invention and 0.3 parts of white carbon were mixed uniformly, and 99.2 parts of clay and 0.2 parts of DRILESS A (manufactured by Sankyo Agro Co., Ltd.) were added thereto, followed by pulverizing and mixing uniformly, thereby obtaining powders.

Preparation Example 4

3 parts of the compound represented by Formula (1) of the present invention, 1.5 parts of a polyoxyethylene/polyoxypropylene condensate, 3 parts of carboxymethyl cellulose, 64.8 parts of clay, and 27.7 parts of talc were pulverized and mixed uniformly, and water was added thereto, followed by kneading, granulating, and drying, thereby obtaining powders.

Preparation Example 5

10 parts of the compound represented by Formula (1) of the present invention, 3 parts of a β-naphthalene sulfonic acid formalin condensate sodium salt, 1 part of tristyrylphenol, 5 parts of propylene glycol, 0.5 parts of a silicon-based defoaming agent, and 33.5 parts of water were sufficiently stirred and mixed, and then 0.3 parts of xanthan gum and 46.7 parts of water were mixed therewith, followed by stirring and mixing again, thereby obtaining a flowable Formulation.

Preparation Example 6

20 parts of the compound represented by Formula (1) of the present invention, 6 parts of a naphthalene sulfonic acid formaldehyde condensate metal salt, 1 part of dialkylsulfosuccinate metal salt, and 73 parts of calcium carbonate were pulverized and mixed uniformly, and water was added thereto, followed by kneading, granulating, and drying, thereby obtaining a granule wettable powder.

For the use of Formulations obtained above, Formulation was diluted to 1-fold to 10000-fold with water or was not diluted, and then directly sprayed.

Next, the usefulness of the compound of the present invention as a pest control agent will be described specifically with reference to the following Test Examples, but the present invention is not limited thereto.

Test Example 1

Pesticidal Test Against *Spodoptera litura*

A piece of a cabbage leaf was immersed for 30 seconds in a chemical solution in which a test compound had been prepared at a predetermined concentration, and air-dried, and then put into a 7 cm polyethylene cup having a filter paper laid on the bottom thereof, and 2-stage larvae of *Spodoptera litura* were released. They were left to stand in a thermostatic chamber at 25° C., and the numbers of the living pests and the dead pests were examined after 6 days. The test was carried out with five larvae per group in two replicates.

Further, the following compound (A) disclosed in the pamphlet of International Publication WO 2005/73165 was used as a comparative compound.

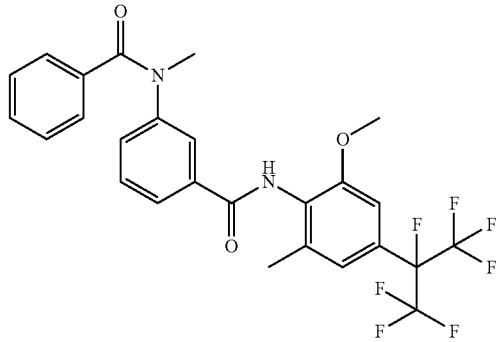

compound (A)

As the results of the above tests, the compounds of Compound Nos. 1-470, 1-491, 1-513, 1-627, 1-1925, 2-491, 6-38, 6-39, 6-45, 6-46, 6-47, 6-57, 6-60, 6-71, 6-72, 6-78, 6-79, 6-80, 6-90, 6-93, 6-111, 6-147, 6-268, 6-269, 6-270, 6-271, 6-272, 6-288, 6-289, 6-290, 6-293, 6-300, 6-304, 6-306, 6-311, 6-346, 6-347, 6-348, 6-349, 6-366, 6-367, 6-368, 6-382, 6-389, 6-424, 6-425, 6-426, 6-427, 6-428, 6-444, 6-445, 6-446, 6-448, 6-449, 6-450, 6-452, 6-453, 6-460, 6-461, 6-467, 6-502, 6-503, 6-504, 6-505, 6-522, 6-523, 6-524, 6-538, 6-545, 6-804, 6-824, 6-825, 6-840, 6-1104, 6-1105, 6-1106, 6-1107, 6-1124, 6-1125, 6-1126, 6-1140, 6-1147, 6-1182, 6-1183, 6-1184, 6-1185, 6-1202, 6-1203, 6-1204, 6-1218, 6-1225, 6-1260, 6-1261, 6-1262, 6-1263, 6-1280, 6-1281, 6-1282, 6-1296, 6-1303, 6-1338, 6-1339, 6-1340, 6-1341, 6-1358, 6-1359, 6-1360, 6-1374, 6-1381, 6-1574, 6-1575, 6-1576, 6-1577, 6-1594, 6-1595, 6-1596, 6-1610, 6-1617, 6-1652, 6-1653, 6-1654, 6-1655, 6-1672, 6-1673, 6-1674, 6-1688, 6-1695, 6-1730, 6-1731, 6-1732, 6-1733, 6-1734, 6-1750, 6-1751, 6-1752, 6-1754, 6-1755, 6-1766, 6-1773, 6-1808, 6-1809, 6-1810, 6-1811, 6-1828, 6-1829, 6-1830, 6-1851, 6-2110, 6-3348, 6-3384, 6-5902, 6-5903, 6-5904, 6-5905, 6-5906, 6-5907, 6-5908, 6-5909, 6-5910, 6-5911, 6-5912, 7-38, 7-39, 7-45, 7-46, 7-47, 7-57, 7-60, 7-71, 7-72, 7-78, 7-79, 7-80, 7-90, 7-93, 7-132, 7-147, 7-268, 7-269, 7-270, 7-271, 7-285, 7-286, 7-288, 7-289, 7-290, 7-299, 7-300, 7-301, 7-303, 7-304, 7-305, 7-311, 7-346, 7-347, 7-348, 7-349, 7-366, 7-367, 7-368, 7-382, 7-389, 7-424, 7-425, 7-426, 7-427, 7-428, 7-444, 7-445, 7-446, 7-449, 7-460, 7-467, 7-502, 7-504, 7-505, 7-522, 7-523, 7-538, 7-804, 7-824, 7-825, 7-840, 7-948, 7-969, 7-984, 7-1104, 7-1105, 7-1106, 7-1107, 7-1124, 7-1125, 7-1126, 7-1140, 7-1147, 7-1182, 7-1183, 7-1184, 7-1185, 7-1202, 7-1203, 7-1204, 7-1218, 7-1225, 7-1260, 7-1261, 7-1262, 7-1263, 7-1280, 7-1281, 7-1282, 7-1296, 7-1303, 7-1338, 7-1339, 7-1340, 7-1341, 7-1358, 7-1359, 7-1360, 7-1374, 7-1381, 7-1417, 7-1574, 7-1575, 7-1576, 7-1577, 7-1594, 7-1595, 7-1596, 7-1605, 7-1606, 7-1608, 7-1610, 7-1616, 7-1617, 7-1638, 7-1639, 7-1645, 7-1652, 7-1672, 7-1673, 7-1730, 7-1731, 7-1732, 7-1733, 7-1750, 7-1751, 7-1752, 7-1764, 7-1766, 7-1773, 7-1794, 7-1808, 7-1809, 7-1810, 7-1811, 7-1828, 7-1829, 7-1844, 7-1851, 7-3348, 7-3369, 7-3384, 7-5902, 7-5903, 7-5904, 7-5905, 7-5906, 7-5907, 7-5910, 8-268, 8-288, 8-289, 8-304, 8-804, 8-824, 8-840, 9-270, 9-290, 9-291, 9-306, 9-2164, 9-2322, 11-777, 11-835, 12-777, 12-835, 12-864, 27-627, and 27-663 each showed a pesticidal rate of 70% or more at a concentration of 1 ppm.

Furthermore, the compounds of Compound Nos. 1-506, 1-1968, 2-513, 2-518, 6-454, 6-5913, 6-5914, 7-316, 7-5911, 7-5912, 7-5908, 7-5909, 17-1103, and 27-628 each showed a pesticidal rate of 70% or more at a concentration of 10 ppm.

Meanwhile, the compound (A) had a pesticidal rate of 50% or less at a concentration of 10 ppm.

Test Example 2

Pesticidal Test Against *Plutella xylostella*

A piece of a cabbage leaf was immersed for 30 seconds in a chemical solution in which a test compound had been prepared at a predetermined concentration, and air-dried, and then put into a 7 cm polyethylene cup having a filter paper laid on the bottom thereof, and 2-stage larvae of *Plutella xylostella* were released. They were left to stand in a thermostatic chamber at 25° C., and the numbers of the living pests and the dead pests were examined after 6 days. The test was carried out with five larvae per group in two replicates.

Further, the above compound (A) was used as a comparative compound.

As the results of the above tests, the compounds of Compound Nos. 1-491, 1-513, 1-627, 1-1925, 1-1968, 2-491, 2-513, 6-38, 6-39, 6-45, 6-46, 6-47, 6-57, 6-71, 6-72, 6-78, 6-79, 6-80, 6-90, 6-111, 6-147, 6-268, 6-270, 6-271, 6-272, 6-288, 6-289, 6-290, 6-293, 6-300, 6-304, 6-305, 6-306, 6-346, 6-347, 6-348, 6-349, 6-366, 6-367, 6-368, 6-382, 6-389, 6-424, 6-425, 6-426, 6-427, 6-428, 6-444, 6-445, 6-446, 6-449, 6-450, 6-453, 6-460, 6-461, 6-467, 6-502, 6-503, 6-504, 6-505, 6-522, 6-523, 6-524, 6-538, 6-545, 6-804, 6-824, 6-825, 6-840, 6-1104, 6-1105, 6-1106, 6-1107, 6-1124, 6-1125, 6-1126, 6-1140, 6-1147, 6-1182, 6-1183, 6-1184, 6-1185, 6-1202, 6-1203, 6-1204, 6-1218, 6-1225, 6-1260, 6-1261, 6-1262, 6-1263, 6-1280, 6-1281, 6-1282, 6-1296, 6-1303, 6-1338, 6-1339, 6-1340, 6-1341, 6-1358, 6-1359, 6-1360, 6-1374, 6-1381, 6-1574, 6-1575, 6-1576, 6-1577, 6-1594, 6-1595, 6-1596, 6-1610, 6-1617, 6-1652, 6-1653, 6-1654, 6-1655, 6-1672, 6-1673, 6-1674, 6-1688, 6-1695, 6-1730, 6-1731, 6-1732, 6-1733, 6-1734, 6-1750, 6-1751, 6-1752, 6-1754, 6-1755, 6-1766, 6-1773, 6-1808, 6-1809, 6-1810, 6-1811, 6-1828, 6-1829, 6-1830, 6-1851, 6-2110, 6-3348, 6-3384, 6-5903, 6-5904, 6-5905, 6-5906, 6-5907, 6-5908, 6-5909, 6-5910, 6-5911, 6-5912, 7-38, 7-39, 7-45, 7-46, 7-47, 7-57, 7-60, 7-71, 7-72, 7-78, 7-79, 7-80, 7-90, 7-93, 7-132, 7-147, 7-268, 7-271, 7-286, 7-288, 7-289, 7-290, 7-299, 7-300, 7-301, 7-303, 7-304, 7-305, 7-311, 7-346, 7-347, 7-348, 7-349, 7-366, 7-367, 7-368, 7-382, 7-389, 7-424, 7-425, 7-426, 7-427, 7-428, 7-444, 7-445, 7-446, 7-449, 7-460, 7-467, 7-502, 7-504, 7-505, 7-522, 7-523, 7-538, 7-824, 7-840, 7-948, 7-969, 7-984, 7-1104, 7-1105, 7-1106, 7-1107, 7-1124, 7-1125, 7-1126, 7-1140, 7-1147, 7-1182, 7-1183, 7-1184, 7-1185, 7-1202, 7-1203, 7-1204, 7-1218, 7-1225, 7-1260, 7-1261, 7-1262, 7-1263, 7-1280, 7-1281, 7-1282, 7-1296, 7-1303, 7-1338, 7-1339, 7-1340, 7-1341, 7-1358, 7-1359, 7-1360, 7-1374, 7-1381, 7-1417, 7-1574, 7-1575, 7-1576, 7-1577, 7-1594, 7-1595, 7-1596, 7-1605, 7-1606, 7-1608, 7-1610, 7-1616, 7-1617, 7-1638, 7-1639, 7-1645, 7-1652, 7-1672, 7-1673, 7-1730, 7-1731, 7-1732, 7-1733, 7-1750, 7-1751, 7-1752, 7-1764, 7-1766, 7-1773, 7-1794, 7-1808, 7-1809, 7-1810, 7-1811, 7-1828, 7-1829, 7-1844, 7-1851, 7-3348, 7-3369, 7-3384, 7-5902, 7-5903, 7-5904, 7-5905, 7-5906, 7-5907, 7-5909, 7-5910, 8-268, 8-288, 8-289, 8-304, 8-824, 9-270, 9-290, 9-291, 9-306, 9-2164, 9-2322, 11-777, 11-835, 12-777, 12-835, and 12-864 each showed a pesticidal rate of 70% or more at a concentration of 1 ppm.

Furthermore, the compounds of Compound Nos. 1-470, 1-506, 2-518, 6-60, 6-93, 6-269, 6-311, 6-448, 6-452, 6-454, 6-5913, 6-5914, 7-269, 7-270, 7-285, 7-316, 7-804, 7-825, 7-5908, 7-5911, 7-5912, 8-804, 8-840, 17-1103, 27-627, 27-628, and 27-663 each showed a pesticidal rate of 70% or more at a concentration of 10 ppm.

Meanwhile, the compound (A) had a pesticidal rate of 50% or less at a concentration of 10 ppm.

Test Example 3

Pesticidal Test Against *Adoxophyes honmai*

A thinly sliced artificial feed was immersed for 30 seconds in a chemical solution in which a test compound had been prepared at a predetermined concentration, and air-dried, and then put into a 7 cm polyethylene cup having a filter paper laid on the bottom thereof, and 2-stage larvae of *Adoxophyes honmai* were released. They were left to stand in a thermostatic chamber at 25° C., and the numbers of the living pests and the dead pests were examined after 6 days. The test was carried out with five larvae per group in two replicates.

Further, the above compound (A) was used as a comparative compound.

As the results of the above tests, the compounds of Compound Nos. 6-72, 6-80, 6-90, 6-347, 6-348, 6-349, 6-366, 6-382, 6-427, 6-446, 6-449, 6-460, 6-503, 6-504, 6-505, 6-522, 6-524, 6-538, 6-1106, 6-1182, 6-1202, 6-1260, 6-1262, 6-1263, 6-1341, 6-1358, 6-1574, 6-1576, 6-1594, 6-1596, 6-1652, 6-1654, 6-1655, 6-1672, 6-1674, 6-1688, 6-1730, 6-1732, 6-1733, 6-1750, 6-1809, 6-1811, 6-1828, 6-1830, 7-348, 7-366, 7-382, 7-502, 7-505, 7-522, 7-538, 7-1106, 7-1202, 7-1262, 7-1280, 7-1303, 7-1338, 7-1358, 7-1574, 7-1576, 7-1594, 7-1605, 7-1652, 7-1730, 7-1732, 7-1733, 7-1750, 7-1764, 7-1808, 7-1809, 7-1810, and 7-1811 each showed a pesticidal rate of 70% or more at a concentration of 1 ppm.

Furthermore, the compounds of Compound Nos. 6-271, 6-367, 6-389, 6-426, 6-523, 6-1104, 6-1577, 6-1695, 6-1851, 6-2110, 7-424, 7-444, 7-523, 7-1104, 7-1124, 7-1260, 7-1263, 7-1577, 7-1616, 7-1731, 7-1773, and 7-1851 each showed a pesticidal rate of 70% or more at a concentration of 10 ppm.

Meanwhile, the compound (A) had a pesticidal rate of 50% or less at a concentration of 10 ppm.

Test Example 4

Pesticidal Test Against *Choristoneura magnanima*

A thinly sliced artificial feed was immersed for 30 seconds in a chemical solution in which a test compound had been prepared at a predetermined concentration, and air-dried, and then put into a 7 cm polyethylene cup having a filter paper laid on the bottom thereof, and 2-stage larvae of *Choristoneura magnanima* were released. They were left to stand in a thermostatic chamber at 25° C., and the numbers of the living pests and the dead pests were examined after 6 days. The test was carried out with five larvae per group in two replicates.

Further, the above compound (A) was used as a comparative compound.

As the results of the above tests, the compounds of Compound Nos. 6-72, 6-80, 6-90, 6-271, 6-349, 6-366, 6-367, 6-426, 6-427, 6-1104, 6-1106, 6-1182, 6-1260, 6-1263, 6-1358, 6-1574, 6-1577, 6-1595, 6-1596, 6-1652, 6-1654, 6-1655, 6-1672, 6-1673, 6-1674, 6-1695, 6-1730, 6-1732, 6-1733, 6-1750, 6-1751, 6-1809, 6-1811, 6-1828, 6-1829, 6-1830, 6-1851, 7-90, 7-348, 7-366, 7-382, 7-389, 7-444, 7-502, 7-504, 7-505, 7-523, 7-1104, 7-1106, 7-1107, 7-1124, 7-1125, 7-1260, 7-1262, 7-1263, 7-1280, 7-1281, 7-1303, 7-1358, 7-1359, 7-1574, 7-1576, 7-1577, 7-1594, 7-1595, 7-1605, 7-1616, 7-1617, 7-1652, 7-1730, 7-1732, 7-1733, 7-1750, 7-1764, 7-1773, 7-1808, 7-1809, 7-1810, 7-1811, 7-1829, and 7-1851 each showed a pesticidal rate of 70% or more at a concentration of 1 ppm.

Furthermore, the compounds of Compound Nos. 6-382, 6-446, 6-460, 6-2110, 7-424, 7-538, and 7-1606 each showed a pesticidal rate of 70% or more at a concentration of 10 ppm.

Meanwhile, the compound (A) had a pesticidal rate of 50% or less at a concentration of 10 ppm.

Test Example 5

Pesticidal Test Against *Helicoverpa armigera*

A cabbage leaf disk was immersed for 30 seconds in a chemical solution in which a test compound had been prepared at a predetermined concentration, and air-dried. The leaf disk was put into a 6-hole plastic cup having a filter paper laid on the bottom thereof, and 2-stage larvae of *Helicoverpa armigera* were released with one insect being released per hole. They were left to stand in a thermostatic chamber at 25° C., and the numbers of the living pests and the dead pests were examined after 3 days. The test was carried out with five larvae per group in two replicates.

Further, the above compound (A) was used as a comparative compound.

As the results of the above tests, the compounds of Compound Nos. 6-72, 6-80, 6-90, 6-271, 6-347, 6-348, 6-349, 6-366, 6-367, 6-382, 6-389, 6-426, 6-427, 6-446, 6-449, 6-460, 6-503, 6-504, 6-505, 6-522, 6-523, 6-524, 6-538, 6-1104, 6-1106, 6-1260, 6-1262, 6-1263, 6-1281, 6-1341, 6-1358, 6-1359, 6-1574, 6-1576, 6-1577, 6-1594, 6-1595, 6-1596, 6-1652, 6-1654, 6-1655, 6-1672, 6-1673, 6-1674, 6-1695, 6-1730, 6-1732, 6-1733, 6-1750, 6-1751, 6-1808, 6-1809, 6-1811, 6-1828, 6-1829, 6-1830, 6-1851, 6-2110, 7-90, 7-348, 7-366, 7-382, 7-389, 7-424, 7-444, 7-502, 7-505, 7-522, 7-523, 7-538, 7-1106, 7-1107, 7-1125, 7-1262, 7-1263, 7-1280, 7-1303, 7-1338, 7-1358, 7-1359, 7-1574, 7-1576, 7-1577, 7-1594, 7-1595, 7-1605, 7-1606, 7-1616, 7-1617, 7-1652, 7-1730, 7-1731, 7-1732, 7-1733, 7-1750, 7-1751, 7-1764, 7-1773, 7-1808, 7-1809, 7-1810, 7-1811, 7-1829, and 7-1851 each showed a pesticidal rate of 70% or more at a concentration of 1 ppm.

Furthermore, the compound of Compound No. 7-1104 showed a pesticidal rate of 70% or more at a concentration of 10 ppm.

Meanwhile, the compound (A) had a pesticidal rate of 50% or less at a concentration of 10 ppm.

Test Example 6

Pesticidal Test Against *Laodelphax striatellus*

2.5 ml of an acetone solution in which a test compound had been prepared at a predetermined concentration was sprayed on rice seedlings, air-dried, and then put into a glass tube having a diameter of 3 cm and a height of 13 cm, having water therein, and 3-stage larvae of *Laodelphax striatellus* were released and the tube was capped. They were left to stand in a thermostatic chamber at 25° C., and the numbers of the living pests and the dead pests were examined after 6 days. The test was carried out with ten larvae per group in two replicates.

As the results of the above tests, the compounds of Compound Nos. 1-491, 1-627, 2-491, 6-39, 6-45, 6-47, 6-57, 6-71, 6-72, 6-79, 6-80, 6-90, 6-147, 6-268, 6-269, 6-270, 6-271, 6-290, 6-304, 6-306, 6-311, 6-346, 6-347, 6-368, 6-382, 6-425, 6-427, 6-444, 6-445, 6-446, 6-460, 6-461, 6-503, 6-1104, 6-1106, 6-1107, 6-1124, 6-1126, 6-1140, 6-1147, 6-1182, 6-1183, 6-1184, 6-1185, 6-1202, 6-1203, 6-1204, 6-1218, 6-1225, 6-1260, 6-1261, 6-1262, 6-1263, 6-1280, 6-1281, 6-1282, 6-1296, 6-1303, 6-1338, 6-1339, 6-1340, 6-1341, 6-1358, 6-1359, 6-1360, 6-1374, 6-1381, 6-1574, 6-1575, 6-1576, 6-1577, 6-1594, 6-1595, 6-1596, 6-1610, 6-1617, 6-1652, 6-1653, 6-1654, 6-1655, 6-1672, 6-1673, 6-1674, 6-1688, 6-1695, 6-1730, 6-1731, 6-1732, 6-1733, 6-1734, 6-1750, 6-1751, 6-1752, 6-1754, 6-1766, 6-1773, 6-1808, 6-1809, 6-1810, 6-1811, 6-1828, 6-1829, 6-1830, 6-1851, 6-2110, 6-3348, 6-3384, 6-5903, 6-5904, 6-5905, 6-5906, 6-5907, 6-5908, 6-5909, 6-5910, 6-5911, 6-5914, 7-47, 7-57, 7-90, 7-268, 7-285, 7-286, 7-288, 7-289, 7-301, 7-303, 7-304, 7-305, 7-311, 7-316, 7-346, 7-348, 7-368, 7-382, 7-389, 7-424, 7-426, 7-427, 7-444, 7-445, 7-446, 7-460, 7-467, 7-538, 7-825, 7-840, 7-948, 7-984, 7-1104, 7-1105, 7-1106, 7-1107, 7-1124, 7-1125, 7-1126, 7-1140, 7-1147, 7-1182, 7-1183, 7-1184, 7-1185, 7-1202, 7-1203, 7-1204, 7-1218, 7-1225, 7-1260, 7-1261, 7-1262, 7-1263, 7-1280, 7-1281, 7-1282, 7-1296, 7-1303, 7-1338, 7-1339, 7-1340, 7-1341, 7-1358, 7-1359, 7-1360, 7-1374, 7-1381, 7-1417, 7-1574, 7-1575, 7-1576, 7-1577, 7-1594, 7-1595, 7-1596, 7-1605, 7-1606, 7-1608, 7-1610, 7-1616, 7-1617, 7-1638, 7-1639, 7-1645, 7-1652, 7-1672, 7-1673, 7-1730, 7-1731, 7-1732, 7-1733, 7-1750, 7-1751, 7-1752, 7-1764, 7-1766, 7-1773, 7-1794, 7-1808, 7-1809, 7-1810, 7-1811, 7-1828, 7-1829, 7-1844, 7-1851, 7-3348, 7-3369, 7-5902, 7-5903, 7-5904, 7-5906, 7-5907, 7-5909, 7-5912, 8-289, 8-304, 8-840, 9-270, 9-290, 9-291, 9-306, 9-2164, 9-2322, 12-835, and 12-864 each showed a pesticidal rate of 70% or more at a concentration of 100 ppm.

Test Example 7

Pesticidal Test Against *Musca domestica*

1 ml of an acetone solution in which a test compound had been prepared at a predetermined concentration was added dropwise to a petri dish having a diameter of 9 cm, and air-dried, and then the female adults of *Musca domestica* were released and the petri dish was capped. They were left to stand in a thermostatic chamber at 25° C., and the numbers of the living pests and the dead pests were examined after 1 day. The test was carried out with five larvae per group in two replicates.

As the results of the above tests, the compounds of Compound Nos. 1-1925, 1-1968, 6-39, 6-47, 6-72, 6-272, 6-293, 6-346, 6-347, 6-348, 6-366, 6-368, 6-382, 6-389, 6-426, 6-427, 6-428, 6-450, 6-452, 6-453, 6-460, 6-503, 6-504, 6-505, 6-522, 6-523, 6-524, 6-538, 6-1105, 6-1107, 6-1124, 6-1125, 6-1126, 6-1147, 6-1184, 6-1204, 6-1218, 6-1260, 6-1281, 6-1338, 6-1341, 6-1358, 6-1359, 6-1360, 6-1374, 6-1575, 6-1576, 6-1577, 6-1594, 6-1596, 6-1617, 6-1652, 6-1672, 6-1673, 6-1695, 6-1730, 6-1731, 6-1732, 6-1733, 6-1734, 6-1750, 6-1751, 6-1752, 6-1773, 6-1808, 6-1809, 6-1810, 6-1811, 6-1828, 6-1829, 6-1830, 6-1851, 6-2110, 6-5905, 7-39, 7-57, 7-90, 7-268, 7-346, 7-348, 7-349, 7-366, 7-367, 7-368, 7-382, 7-389, 7-424, 7-428, 7-444, 7-446, 7-449, 7-504, 7-522, 7-538, 7-1104, 7-1105, 7-1106, 7-1107, 7-1126, 7-1262, 7-1280, 7-1282, 7-1296, 7-1303, 7-1338, 7-1340, 7-1358, 7-1359, 7-1360, 7-1381, 7-1417, 7-1574, 7-1575, 7-1576, 7-1577, 7-1596, 7-1652, 7-1731, 7-1732, 7-1733, 7-1750, 7-1752, 7-1764, 7-1766, 7-1730, 7-1773, 7-1794, 7-1808, 7-1809, 7-1810, 7-1811, 7-1828, 7-1829, 7-1851, 9-2164, 9-2322, 11-777, 11-835, 12-777, 12-835, 12-864, 17-1103, and 27-627 each showed a pesticidal rate of 70% or more at a concentration of 100 ppm.

Test Example 8

Pesticidal Test Against *Blattella germanica*

1 ml of an acetone solution in which a test compound had been prepared at a predetermined concentration was added dropwise to a petri dish having a diameter of 9 cm, and air-dried, and then the female adults of *Blattella germanica* were released and the petri dish was capped. They were left to stand in a thermostatic chamber at 25° C., and the numbers of the living pests and the dead pests were examined after 1 day. The test was carried out with five larvae per group in two replicates.

As the results of the above tests, the compounds of Compound Nos. 1-1925, 6-39, 6-47, 6-346, 6-347, 6-367, 6-368, 6-382, 6-389, 6-426, 6-427, 6-503, 6-538, 6-1105, 6-1106, 6-1107, 6-1124, 6-1125, 6-1126, 6-1147, 6-1184, 6-1204, 6-1218, 6-1280, 6-1296, 6-1338, 6-1358, 6-1359, 6-1575, 6-1576, 6-1577, 6-1594, 6-1595, 6-1596, 6-1610, 6-1617, 6-1730, 6-1731, 6-1732, 6-1733, 6-1750, 6-1751, 6-1752, 6-1773, 6-1811, 6-5905, 7-57, 7-268, 7-305, 7-347, 7-349, 7-367, 7-382, 7-389, 7-424, 7-444, 7-446, 7-502, 7-505, 7-538, 7-1104, 7-1105, 7-1106, 7-1107, 7-1125, 7-1126, 7-1261, 7-1262, 7-1280, 7-1282, 7-1296, 7-1303, 7-1381, 7-1574, 7-1575, 7-1576, 7-1577, 7-1594, 7-1595, 7-1596, 7-1617, 7-1731, 7-1732, 7-1733, 7-1750, 7-1752, 7-1766, 7-1773, and 7-1851 each showed a pesticidal rate of 70% or more at a concentration of 100 ppm.

Test Example 9

Pesticidal Test Against *Culex pipiens molestus*

1 ml of an acetone solution in which a test compound had been prepared at a predetermined concentration was added dropwise to a petri dish having a diameter of 9 cm, and air-dried, and then the female adults of *Culex pipiens molestus* were released and the petri dish was capped. They were left to stand in a thermostatic chamber at 25° C., and the numbers of the living pests and the dead pests were examined after 1 day of treatment. The test was carried out with five larvae per group in two replicates.

As the results of the above tests, the compounds of Compound Nos. Compound No. 7-424, 7-1574, 7-1577, 7-1730, 7-1732, and 7-1733 each showed a pesticidal rate of 70% or more at a concentration of 1000 ppm.

Test Example 10

Pesticidal Test Against *Coptotermes formosanus*

20 μl of an acetone solution in which a test compound had been prepared at a predetermined concentration was added dropwise to the filter paper having a diameter of 2.6 mm included in a polypropylene cup, and air-dried, and then 20 μl of water was added thereto. *Coptotermes formosanus* was released and the cup was capped. They were left to stand in a thermostatic chamber at 28° C., and the numbers of the living pests and the dead pests were examined after 5 days of treatment. The test was carried out with ten larvae per group in two replicates.

As the results of the above tests, the compounds of Compound Nos. Compound No. 6-460, 6-1260, 6-1652, 7-268, 7-424, 7-1104, 7-1574, 7-1577, 7-1730, 7-1732, and 7-1733 each showed a pesticidal rate of 70% or more at a concentration of 30 ppm.

According to the present invention, it becomes possible to provide a novel amide derivative. The amide derivative shows a significant effect for a pest control activity, and has a high industrial availability.

The present invention also provides a composition and method for exterminating animal parasites.

WO2005/21488, WO2005/73165, WO2006/137376, and WO2006/137395 disclose various compounds which are amide derivatives having the ability to control pests, and methods for using them. Further WO2009/080203 discloses amide derivatives which are animal parasiticides, and methods for using them.

In addition, conventional parasiticides for administration to an animal to exterminate animal parasites include formulations of imidacloprid, fipronil, etc.

However, some parasites are impossible or difficult to exterminate with said animal parasiticides.

Thus, an objective of the invention is to provide a composition that has excellent activity for exterminating animal parasites, and a method for exterminating animal parasites.

As the result of earnest research for solving the above problem, the present inventors found that an aromatic carboxamide derivative represented by Formula (A1) of the present invention is a novel compound that is not disclosed in the literature, and a composition containing the present aromatic carboxamide derivative as an active ingredient has exellent activity for exterminating animal parasites, thereby completing the present invention.

A first aspect of the present invention provides a composition for exterminating animal parasites which comprises as an active ingredient at least one amide derivative represented by the following Formula (A1).

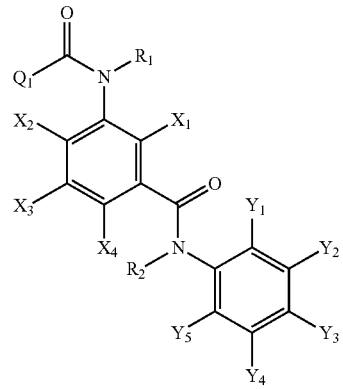

Formula (A1)

In Formula (A1), $Q_1$ represents a phenyl group or a phenyl group substituted with a halogen atom; $X_1$ represents a fluorine atom, and $X_2$, $X_3$, and $X_4$ are each a hydrogen atom; $R_1$ represents a hydrogen atom or a C1-C3 alkyl group; $R_2$ is a hydrogen atom; $Y_1$ and $Y_5$ each independently represent a halogen atom or a C1-C3 haloalkyl group; $Y_2$ and $Y_4$ each represent a hydrogen atom; and $Y_3$ represents a heptafluoroisopropyl group.

In Formula (A1), $Q_1$ represents a phenyl group or a phenyl group substituted with a single fluorine atom; $R_1$ represents a hydrogen atom or a methyl group; and $Y_1$ and $Y_5$ each independently represent a bromine or iodine atom or a trifluoromethyl group preferably.

The amide derivative represented by Formula (A1) is preferably 2-fluoro-3-(N-methylbenzamide)-N-(2-bromo-6-trifluoromethyl-4-(heptafluoropropan-2-yl)phenyl)benzamide, 2-fluoro-3-(4-fluoro-N-methylbenzamide)-N-(2-iodo-6-trifluoromethyl-4-(heptafluoropropan-2-yl)phenyl)benzamide, 2-fluoro-3-(3-fluoro-N-methylbenzamide)-N-(2-iodo-6-trifluoromethyl-4-(heptafluoropropan-2-yl)phenyl)benzamide, 2-fluoro-3-(4-fluorobenzamide)-N-(2-iodo-6-trifluoromethyl-4-(heptafluoropropan-2-yl)phenyl)benzamide, or 2-fluoro-3-(N-methylbenzamide)-N-(2,6-dibromo-4-(heptafluoropropan-2-yl)phenyl)benzamide.

In Formula (A1), $Q_1$ represents preferably a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, or a 4-iodophenyl group.

The amide derivative represented by Formula (A1) is preferably 3-benzamide-N-(2-bromo-6-chloro-4-(heptafluoropropan-2-yl)phenyl)-2-fluorobezamide, 3-benzamide-N-(2,6-diiodo-4-(heptafluoropropan-2-yl)phenyl)-2-fluorobezamide, 3-benzamide-N-(2,6-dibromo-4-(heptafluoropropan-2-yl)phenyl)-2-fluorobezamide, N-(2,6-dibromo-4-(heptafluoropropan-2-yl)phenyl)-2-fluoro-3-(N-methylbenzamide)bezamide, N-(2,6-dichloro-4-(heptafluoropropan-2-yl)phenyl)-2-fluoro-3-(N-methylbenzamide)bezamide, N-(2,6-diiodo-4-(heptafluoropropan-2-yl)phenyl)-2-fluoro-3-(N-methylbenzamide)bezamide, N-(2,6-diiodo-4-(heptafluoropropan-2-yl)phenyl)-2-fluoro-3-(2-fluorobenzamide)bezamide, N-(2,6-diiodo-4-(heptafluoropropan-2-yl)phenyl)-2-fluoro-3-(4-fluorobenzamide)bezamide, 3-(2,6-difluorobenzamide)-N-(2,6-diiodo-4-(heptafluoropropan-2-yl)phenyl)-2-fluorobezamide, N-(2-bromo-6-iodo-4-(heptafluoropropan-2-yl)phenyl)-2-fluoro-3-(N-methylbenzamide)bezamide, N-(2,6-diiodo-4-(heptafluoropropan-2-yl)phenyl)-2-fluoro-3-(3-fluorobenzamide)bezamide, N-(3-(2,6-diiodo-4-(heptafluoropropan-2-yl)phenylcarbamoyl)-2-fluorophenyl)-2-fluoro-N-methylbezamide, N-(2,6-diiodo-4-(heptafluoropropan-2-yl)phenyl)-2-fluoro-3-(3-fluoro-N-methylbenzamide)bezamide, N-(2,6-diiodo-4-(heptafluoropropan-2-yl)phenyl)-2-fluoro-3-(4-fluoro-N-methylbenzamide)bezamide, N-(3-(2,6-diiodo-4-(heptafluoropropan-2-yl)phenylcarbamoyl)-2-fluorophenyl)-2,6-difluoro-N-methylbezamide, N-(2,6-dibromo-4-(heptalluoropropan-2-yl)phenyl)-2-fluoro-3-(2-fluorobenzamide)bezamide, N-(2,6-dibromo-4-(heptafluoropropan-2-yl)phenyl)-2-fluoro-3-(3-fluorobenzamide)bezamide, N-(2,6-dibromo-4-(heptafluoropropan-2-yl)phenyl)-2-fluoro-3-(4-fluorobenzamide)bezamide, N-(2,6-dibromo-4-(heptafluoropropan-2-yl)phenyl)-3-(2,6-difluorobenzamide)-2-fluorobezamide, N-(3-(2,6-dibromo-4-(heptafluoropropan-2-yl)phenylcarbamoyl)-2-fluorophenyl)-2-fluoro-N-methylbezamide, N-(2,6-dibromo-4-(heptafluoropropan-2-yl)phenyl)-2-fluoro-3-(3-fluoro-N-methylbenzamide)bezamide, N-(2,6-dibromo-4-(heptafluoropropan-2-yl)phenyl)-2-fluoro-3-(4-fluoro-N-methylbenzamide)bezamide, N-(3-(2,6-dibromo-4-(heptafluoropropan-2-yl)phenylcarbamoyl)-2-fluorophenyl)-2,6-difluoro-N-methylbezamide, 3-benzamide-N-(2-bromo-4-(heptafluoropropan-2-yl)-6-(trifluoromethyl)phenyl)-2-fluorobezamide, N-(2-bromo-4-(heptafluoropropan-2-yl)-6-(trifluoromethyl)phenyl)-2-fluoro-3-(N-methylbenzamide)bezamide, 3-benzamide-2-fluoro-N-(4-(heptafluoropropan-2-yl)-2,6-bis(trifluoromethyl)phenyl)bezamide, 3-benzamide-2-fluoro-N-(2-iodo-4-(heptafluoropropan-2-yl)-6-(trifluoromethyl)phenyl)bezamide, 3-benzamide-N-(2-bromo-6-(pentafluoroethyl)-4-(heptafluoropropan-2-yl)phenyl)-2-fluorobezamide, 2-fluoro-N-(2-iodo-4-(heptafluoropropan-2-yl)-6-(trifluoromethyl)phenyl)-3-(N-methylbenzamide)bezamide, 2-fluoro-N-(2-fluoro-3-(2-iodo-4-(heptafluoropropan-2-yl)-6-(trifluoromethyl)phenylcarbamoyl)phenyl)-N-methylbezamide, 2-fluoro-3-(3-fluoro-N-methylbenzamide)-N-(2-iodo-4-(heptafluoropropan-2-yl)-6-(trifluoromethyl)phenyl)bezamide, 2-fluoro-3-(4-fluoro-N-methylbenzamide)-N-(2-iodo-4-(heptafluoropropan-2-yl)-6-(trifluoromethyl)phenyl)bezamide, 2,6-difluoro-N-(2-fluoro-3-(2-iodo-4-(heptafluoropropan-2-yl)-6-(trifluoromethyl)phenylcarbamoyl)phenyl)-N-methylbezamide, 2-fluoro-3-(2-fluorobenzamide)-N-(2-iodo-4-(heptafluoropropan-2-yl)-6-(trifluoromethyl)phenyl)bezamide, 2-fluoro-3-(3-fluorobenzamide)-N-(2-iodo-4-(heptafluoropropan-2-yl)-6-(trifluoromethyl)phenyl)bezamide, N-(3-(2-bromo-4-(heptafluoropropan-2-yl)-6-(trifluoromethyl)phenylcarbamoyl)-2-fluorophenyl)-2-fluoro-N-methylbezamide, N-(3-(2-bromo-4-(heptafluoropropan-2-yl)-6-(trifluoromethyl)phenylcarbamoyl)-2-fluorophenyl)-2,6-difluoro-N-methylbezamide, N-(2-bromo-4-(heptafluoropropan-2-yl)-6-(trifluoromethyl)phenyl)-2-fluoro-3-(3-fluoro-N-methylbenzamide)bezamide, N-(2-bromo-4-(heptafluoropropan-2-yl)-6-(trifluoromethyl)phenyl)-2-fluoro-3-(4-fluoro-N-methylbenzamide)bezamide, N-(2-bromo-4-(heptafluoropropan-2-yl)-6-(trifluoromethyl)phenyl)-2-fluoro-3-(2-fluorobenzamide)bezamide, N-(2-bromo-4-(heptafluoropropan-2-yl)-6-(trifluoromethyl)phenyl)-2-fluoro-3-(3-fluorobenzamide)bezamide, N-(2-bromo-4-(heptafluoropropan-2-yl)-6-(trifluoromethyl)phenyl)-2-fluoro-3-(4-fluorobenzamide)bezamide, 2-fluoro-3-(4-fluorobenzamide)-N-(2-iodo-4-(heptafluoropropan-2-yl)-6-(trifluoromethyl)phenyl)bezamide, 3-(2,6-difluorobenzamide)-2-fluoro-N-(2-iodo-4-(heptafluoropropan-2-yl)-6-(trifluoromethyl)phenyl)bezamide, N-(2-bromo-4-(heptafluoropropan-2-yl)-6-(trifluoromethyl)phenyl)-3-(2,6-difluorobenzamide)-2-fluorobezamide, 3-(2,4-dichlorobenzamide)-2-fluoro-N-(2-iodo-4-(heptafluoropropan-2-yl)-6-(trifluoromethyl)phenyl)bezamide, 3-(2-chloro-4-fluorobenzamide)-2-fluoro-N-(2-iodo-4-(heptafluoropropan-2-yl)-6-(trifluoromethyl)phenyl)bezamide, 3-(2-chlorobenzamide)-2-fluoro-N-(2-iodo-4-(heptafluoropropan-2-yl)-6-(trifluoromethyl)phenyl)bezamide, or N-(2-chloro-4-(heptafluoropropan-2-yl)-6-(trifluoromethyl)phenyl)-2-fluoro-3-(N-methylbenzamide)bezamide.

A second aspect of the present invention provides a method for exterminating animal parasites comprising administering to the animal the composition for exterminating animal parasites Wherein, the animal parasite is preferably an ectoparasite and the ectoparasite is more preferably Siphonaptera pests or the ectoparasite is Acarina pests.

According to the present invention, a composition which has excellent activity for exterminating animal parasites and a method for exterminating animal parasites are provided.

A composition for exterminating animal parasites according to the present invention includes at least one amide derivative represented by the following Formula (A1).

By adopting such a constitution, it becomes possible to show excellent activity for exterminating animal parasites in the case of giving the composition to an animal.

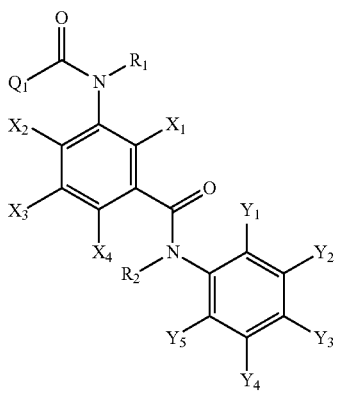

Formula (A1)

In Formula (A1), $Q_1$ represents a phenyl group or a phenyl group substituted with a halogen atom. $X_1$ represents a fluorine atom, and $X_2$, $X_3$, and $X_4$ are each a hydrogen atom. $R_1$ represents a hydrogen atom or a C1-C3 alkyl group, and $R_2$ is a hydrogen atom. $Y_1$ and $Y_5$ each independently represent a halogen atom or a C1-C3 haloalkyl group, $Y_2$ and $Y_4$ each represent a hydrogen atom, and $Y_3$ represents a heptafluoroisopropyl group.

The terms used in the formulae including the Formula (A1) and the like according to the present invention, have the same meanings as described below in the definitions.

The "halogen atom" represents a fluorine atom, a chlorine atom, a bromine atom, or an iodine atom.

The expression "Ca—Cb (wherein a and b represent an integer of 1 or more)", for example, "C1-C3" means the number of carbon atoms of from 1 to 3, the "C2-C6" means the number of carbon atoms of from 2 to 6.

The "C1-C3 alkyl group" in the present invention represents, for example, a linear or branched alkyl group having from 1 to 3 carbon atoms such as methyl, ethyl, n-propyl, i-propyl, and the like.

The "C1-C3 haloalkyl group" represents, for example, a linear or branched alkyl group having from 1 to 3 carbon atoms, that is substituted with one or more halogen atoms which may be the same as or different from each other, such as trifluoromethyl, pentafluoroethyl, heptafluoro-n-propyl, heptafluoro-i-propyl, 2,2-difluoroethyl, 2,2-dichloroethyl, 2,2,2-trifluoroethyl, 2-fluoroethyl, 2-chloroethyl, 2-bromoethyl, 2-iodoethyl, 2,2,2-trichloroethyl, 2,2,2-tribromoethyl, 1,3-difluoro-2-propyl, 1,3-dichloro-2-propyl, 1-chloro-3-fluoro-2-propyl, 1,1,1-trifluoro-2-propyl, 2,3,3,3-trifluoro-n-propyl, 1,1,1,3,3,3-hexafluoro-2-propyl, 1,1,1,3,3,3-hexafluoro-2-chloro-2-propyl, 1,1,1,3,3,3-hexafluoro-2-bromo-2-propyl, 1,1,2,3,3,3-hexafluoro-2-chloro-n-propyl, 1,1,2,3,3,3-hexafluoro-2-bromo-n-propyl, 1,1,2,3,3,3-hexafluoro-1-bromo-2-propyl, 2,2,3,3,3-pentafluoro-n-propyl, 3-fluoro-n-propyl, 3-chloro-n-propyl, 3-bromo-n-propyl, and the like.

The "C1-C6 alkyl group" in the present invention represents, for example, a linear or branched alkyl group having from 1 to 6 carbon atoms such as methyl, ethyl, n-propyl, propyl, n-butyl, s-butyl, t-butyl, n-pentyl, 2-pentyl, neopentyl, 4-methyl-2-pentyl, n-hexyl, 3-methyl-n-pentyl, and the like.

The "C3-C9 cycloalkyl group" represents, for example, a cycloalkyl group having from 3 to 9 carbon atoms, that has a cyclic structure, such as cyclopropyl, cyclobutyl, cyclopentyl, 2-methylcyclopentyl, 3-methylcyclopentyl, cyclohexyl, 2-methylcyclohexyl, 3-methylcyclohexyl, 4-methylcyclohexyl, and the like.

The "C2-C6 alkenyl group" represents, for example, an alkenyl group having from 2 to 6 carbon atoms, that has a double bond in the carbon chain, such as vinyl, allyl, 2-butenyl, 3-butenyl, and the like.

The "C2-C6 alkynyl group" represents, for example, an alkynyl group having from 2 to 6 carbon atoms, that has a triple bond in the carbon chain, such as propargyl, 1-butyn-3-yl, 1-butyn-3-methyl-3-yl, and the like.

The compounds represented by Formula (A1) according to the present invention may include one or plural chiral carbon atoms or chiral centers in their structural Formulae, and thus two or more optical isomers may exist. However, the present invention includes each of the optical isomers and a mixture thereof at any proportions. Further, the compounds represented by Formula (A1) according to the present invention may include two or more kinds of geometrical isomers derived from carbon-carbon double bonds in the structural Formulae. The present invention includes each of the geometrical isomers and a mixture thereof at any proportions.

The representative methods for producing the compound according to the present invention are shown below, and the method for producing the amide derivative according to the present invention is not limited to the preparation methods below.

In Formula shown in the following preparation method, $X_1$, $X_2$, $X_3$, $X_4$, $R_1$, $R_2$, $Q_1$, $Y_1$, $Y_2$, $Y_3$, $Y_4$, and $Y_5$ represent the same definitions as $X_1$, $X_2$, $X_3$, $X_4$, $R_1$, $R_2$, $Q_1$, $Y_1$, $Y_2$, $Y_3$, $Y_4$, and $Y_5$, respectively, in Formula (A1). LG represents a functional group having a leaving ability, such as a halogen atom, a hydroxy group, or the like, Hal represents a chlorine atom or a bromine atom, and Xa and Xb represent chlorine atoms, bromine atoms, or iodine atoms. R3 represents a C1-C6 alkyl group, a C3-C9 cycloalkyl group, a C2-C6 alkenyl group, a C2-C6 alkynyl group.

<Preparation Method 1>

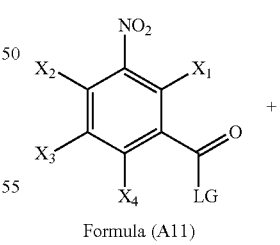

Formula (A11)

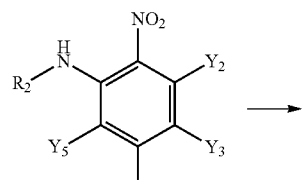

Formula (A12)

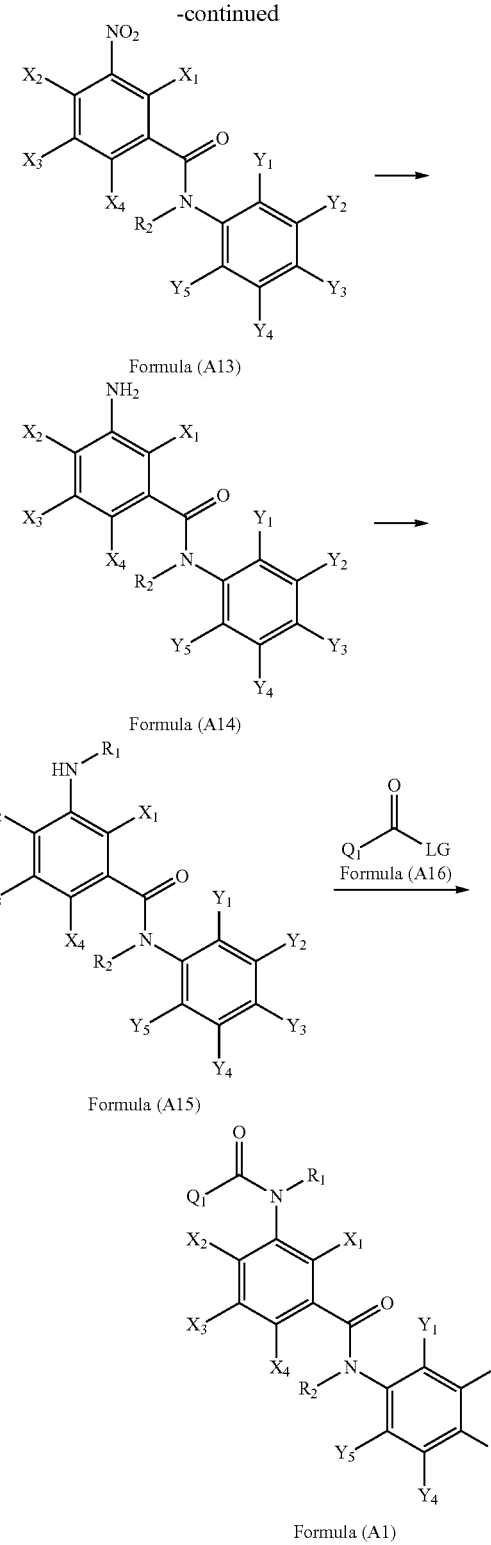

Formula(A11)+Formula(A12)→Formula(A13)    1-(i):

A nitro aromatic carboxamide derivative represented by Formula (A13) can be prepared by reacting a nitro aromatic carboxylic acid derivative having a leaving group represented by Formula (A11) with an aromatic amine derivative represented by Formula (A12) in a suitable solvent or without a solvent. In the present step, a suitable base can be used.

The solvent may be any of those which do not inhibit the present reaction significantly. Examples thereof may include water and aromatic hydrocarbons such as benzene, toluene, xylene, and the like, halogenated hydrocarbons such as dichloromethane, chloroform, carbon tetrachloride, and the like, chained or cyclic ethers such as diethyl ether, dioxane, tetrahydrofuran, 1,2-dimethoxy ethane, and the like, esters such as ethyl acetate, butyl acetate, and the like, alcohols such as methanol, ethanol, and the like, ketones such as acetone, methyl isobutyl ketone, cyclohexanone, and the like, amides such as dimethyl formamide, dimethylacetamide, and the like, nitriles such as acetonitrile and the like, and inert solvents such as 1,3-dimethyl-2-imidazolidinone and the like. These solvents may be used alone or as a mixture of two or more kinds thereof.

Furthermore, examples of the base may include organic bases such as triethylamine, tri-n-butyl amine, pyridine, 4-dimethylamino pyridine, and the like, alkali metal hydroxides such as sodium hydroxide, potassium hydroxide, and the like, carbonates such as sodium hydrogen carbonate, potassium carbonate, and the like, phosphates such as dipotassium monohydrogen phosphate, trisodium phosphate, and the like, alkali metal hydride salts such as sodium hydride and the like, alkali metal alkoxides such as sodium methoxide, sodium ethoxide, and the like, and lithium amides such as lithium diisopropyl amide, and the like.

These bases may be appropriately used in an amount in the range from 0.01-fold molar equivalent to 5-fold molar equivalents with respect to the compound represented by Formula (A11).

The reaction temperature may be appropriately selected from −20° C. to the reflux temperature of the solvent used. Further, the reaction time may be appropriately selected within the range from several minutes to 96 hours.

Among the compounds represented by Formula (A11), the aromatic carbonyl halide derivative can be prepared easily by a general method using a halogenating agent from an aromatic carboxylic acid. Examples of the halogenating agent include thionyl chloride, thionyl bromide, phosphorus oxychloride, oxalyl chloride, phosphorus trichloride, and the like.

Meanwhile, it is possible to prepare the compound represented by Formula (A13) from the nitro aromatic carboxylic acid derivative and the compound represented by Formula (A12) without using a halogenating agent. Examples of the method may include a method described in, for example, Chem. Ber. p. 788 (1970), in which a condensing agent such as N,N'-dicyclohexylcarbodiimide and the like is appropriately used, suitably with the use of an additive such as 1-hydroxybenzotriazole and the like. Other condensing agents that can be used in this case may include 1-ethyl-3-(3-dimethylaminopropyl)carbodiimide, 1,1'-carbonylbis-1H-imidazole, and the like.

Furthermore, examples of other methods for producing the compound represented by Formula (A13) may include a mixed acid anhydride method using chloroformic acid esters, and examples thereof include a method described in J. Am. Chem. Soc., p. 5012 (1967), whereby the compound represented by Formula (A13) can be prepared. Examples of the chloroformic acid esters used in this case may include isobutyl chloroformate, isopropyl chloroformate and the like. In addition to chloroformic acid esters, diethylacetyl chloride, trimethylacetyl chloride and the like may also be included.

Both the method using a condensing agent and the mixed acid anhydride method are not limited by the solvent, the reaction temperature, and the reaction time according to the literature above. An inert solvent may be used which does not inhibit the progress of the appropriate reaction significantly, and the reaction temperature and the reaction time may also be selected appropriately according to the progress of the reaction.

Formula(A13)→Formula(A14)    1-(ii):

An aromatic carboxamide derivative having an amino group represented by Formula (A14) can be derived from the aromatic carboxamide derivative having a nitro group represented by Formula (A13) by means of a reduction reaction. Examples of such reduction include a method using a hydrogenation reaction and a method using a metal compound (for example, stannous chloride (anhydride), iron powder, zinc powder, and the like).

The reaction of the former method can be carried out in a suitable solvent in the presence of a catalyst at normal pressure or a higher pressure under a hydrogen atmosphere. Examples of the catalyst may include palladium catalysts such as palladium-carbon and the like, nickel catalysts such as Raney-nickel and the like, cobalt catalysts, ruthenium catalysts, rhodium catalysts, platinum catalysts, and the like, and examples of the solvent may include water; alcohols such as methanol, ethanol, and the like; aromatic hydrocarbons such as benzene, toluene, and the like; chained or cyclic ethers such as ether, dioxane, tetrahydrofuran, and the like; and esters such as ethyl acetate and the like. The pressure may be appropriately selected within a range of 0.1 MPa to 10 MPa, the reaction temperature may be appropriately selected within a range of −20° C. to the reflux temperature of the solvent used, and the reaction time may be appropriately selected within a range of several minutes to 96 hours, whereby the compound of Formula (14) can be efficiently prepared.

Examples of the latter method include a method using stannous chloride (anhydride) as a metal compound under the conditions described in "Organic Syntheses" Coll. Vol. III, P. 453.

Formula(A14)→Formula(A15)    1-(iii):

(Method A)

A compound represented by Formula (A15) can be prepared by reacting the compound represented by Formula (A14) with an aldehyde or a ketone in a solvent, and reacting them under a hydrogen atmosphere with the addition of a catalyst.

The solvent may be any of those which do not inhibit the progress of the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, ketones such as acetone, methyl isobutyl ketone, cyclohexanone, methyl ethyl ketone, and the like, esters such as ethyl acetate, butyl acetate, and the like, alcohols such as methanol, ethanol, and the like, inert solvents such as 1,3-dimethyl-2-imidazolidinone, sulfolane, dimethylsulfoxide, and the like, water, and the like. These solvents may be used alone or as a mixture of two or more kinds thereof.

Examples of the catalyst may include palladium catalysts such as palladium-carbon, palladium hydroxide-carbon, and the like, nickel catalysts such as Raney-nickel and the like, cobalt catalysts, platinum catalysts, ruthenium catalysts, rhodium catalysts, and the like.

Examples of the aldehydes may include formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, bromoacetaldehyde, and the like.

Examples of the ketones may include acetone, perfluoroacetone, methyl ethyl ketone, and the like.

The reaction pressure may be appropriately selected within the range of 1 atm to 100 atm. The reaction temperature may be appropriately selected within the range from −20° C. to the reflux temperature of the solvent used. Further, the reaction time may be appropriately selected within the range from several minutes to 96 hours.

(Method B)

A compound represented by Formula (A15) can be prepared by reacting the compound represented by Formula (A14) with an aldehyde or a ketone in a solvent, and treating the product with a reducing agent.

The solvent may be any of those which do not inhibit the progress of the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, ketones such as acetone, methyl isobutyl ketone, cyclohexanone, methyl ethyl ketone, and the like, esters such as ethyl acetate, butyl acetate, and the like, alcohols such as methanol, ethanol, and the like, inert solvents such as 1,3-dimethyl-2-imidazolidinone, sulfolane, dimethylsulfoxide, and the like, water, and the like. These solvents may be used alone or as a mixture of two or more kinds thereof.

Examples of the reducing agent may include, for example, borohydrides such as sodium borohydride, sodium cyanoborohydride, sodium triacetate borohydride, and the like.

Examples of the aldehydes may include formaldehyde, acetaldehyde, propionaldehyde, trifluoroacetaldehyde, difluoroacetaldehyde, fluoroacetaldehyde, chloroacetaldehyde, dichloroacetaldehyde, trichloroacetaldehyde, bromoacetaldehyde, and the like.

Examples of the ketones may include acetone, perfluoroacetone, methyl ethyl ketone, and the like.

The reaction temperature may be appropriately selected within the range from −20° C. to the reflux temperature of the solvent used. Further, the reaction time may be appropriately selected within the range from several minutes to 96 hours.

(Method C)

A compound of Formula (A15) can be prepared by reacting the compound represented by Formula (A14) with an aldehyde in a solvent or without a solvent.

The solvent may be any of those which do not inhibit the progress of the reaction significantly, and examples thereof may include aliphatic hydrocarbons such as hexane, cyclohexane, methylcyclohexane, and the like, aromatic hydrocarbons such as benzene, xylene, toluene, and the like, halogenated hydrocarbons such as dichloromethane, chloroform, carbon tetrachloride, 1,2-dichloroethane, and the like, ethers such as diethyl ether, dioxane, tetrahydrofuran, 1,2-dimethoxy ethane, and the like, amides such as dimethyl formamide, dimethylacetamide, and the like, nitriles such as acetonitrile, propionitrile, and the like, ketones such as acetone, methyl isobutyl ketone, cyclohexanone, methyl ethyl ketone, and the like, esters such as ethyl acetate, butyl acetate, and the like, alcohols such as methanol, ethanol, and the like, inert solvents such as 1,3-dimethyl-2-imidazolidinone, sulfolane, dimethylsulfoxide, and the like, inorganic acids such as sulfuric acid, hydrochloric acid, and the like, organic acids such as formic acid, acetic acid, and the like, water, and the like. These solvents may be used alone or as a mixture of two or more kinds thereof.

Examples of the aldehydes may include formaldehyde, acetaldehyde, propionaldehyde, and the like.

The reaction temperature may be appropriately selected within the range from −20° C. to the reflux temperature of the solvent used, and the reaction time may be appropriately selected within the range from several minutes to 96 hours.

Formula(A15)+Formula(A16)→Formula(A1)   1-(iv):

An aromatic carboxamide derivative represented by Formula (A1) can be prepared by reacting the aromatic amine derivative represented by Formula (A15) with the carboxylic acid derivative or the carbonate ester derivative having a leaving group represented by Formula (A16) in a suitable solvent. In the present step, a suitable base or solvent can be used, and as the base or solvent, those exemplified in 1-(i) can be used. Examples of the reaction temperature, the reaction time, and the like may include those exemplified in 1-(i).

In Formula (A16), the carbonyl chloride derivative can be prepared easily from a carboxylic acid derivative by a general method using a halogenating agent. The halogenating agent may include those exemplified in 1-(i).

There may be exemplified a method for producing a compound represented by Formula (A1) from the carboxylic acid derivative (A16) and the compound represented by Formula (A15) without the use of a halogenating agent, and the preparation can be conducted according to the method exemplified in 1-(i).

<Preparation Method 2>

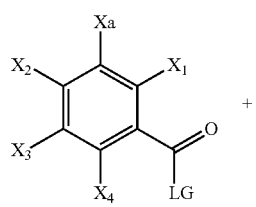

Formula (A17)

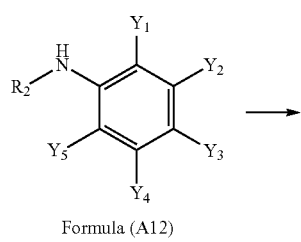

Formula (A12)

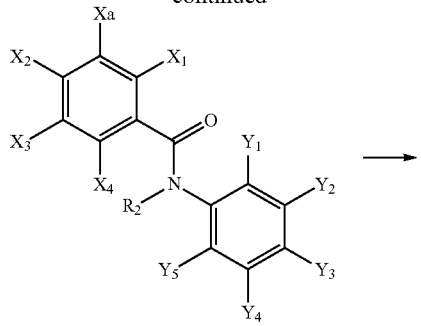

Formula (A18)

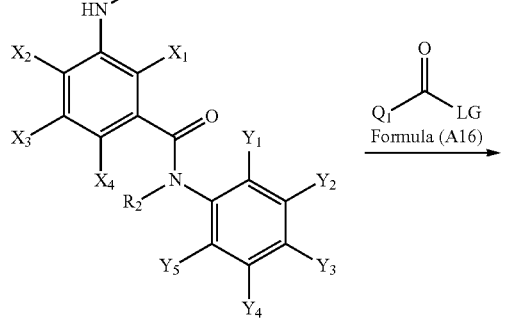

Formula (A15)

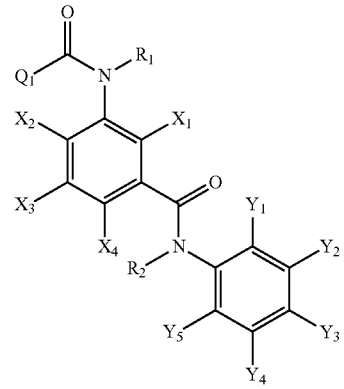

Formula (A1)

Formula(A17)+Formula(A12)→Formula(A18)   2-(i):

A compound represented by Formula (A18) can be prepared by reacting the compound represented by Formula (A17) with a compound represented by Formula (A12) under the condition described in 1-(i).

Formula(A18)→Formula(A15)   2-(ii):

A compound represented by Formula (A15) can be prepared by carrying out an amination reaction using an amination agent such as ammonia and the like according to the conditions described, for example, in J. Org. Chem. p. 280 (1958). However, the conditions such as a reaction solvent and the like are not restricted to those described in the literature, and an inert solvent which does not inhibit the proper progress of the reaction significantly may be used. The reaction temperature and reaction time may be suitably selected as the reaction proceeds. Further, examples of the amination agent include methylamine, ethylamine or the like, in addition to ammonia.

Formula(A15)+Formula(A16)→Formula(A1)  2-(iii):

The compound represented by Formula (A1) can be prepared by reacting the compound represented by Formula (A15) with a compound represented by Formula (A16) according to the conditions described in 1-(i).

<Preparation Method 3>

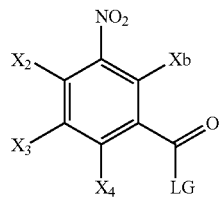

Formula (A19)

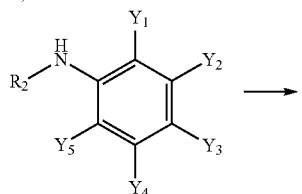

Formula (A12)

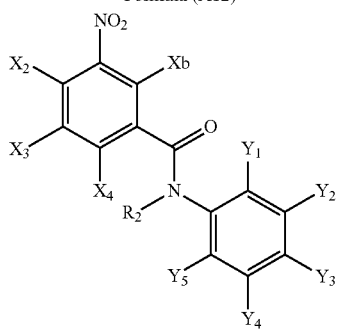

Formula (A20)

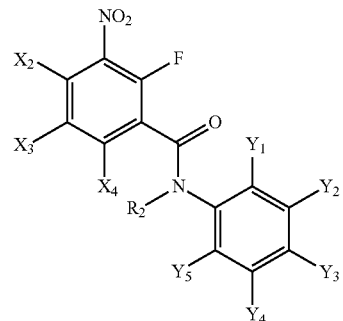

Formula (A21)

Formula(A19)+Formula(A12)→Formula(A20)  3-(i):

A compound represented by Formula (A20) can be prepared by reacting the compound represented by Formula (A19) and the compound represented by Formula (A12) according to the conditions described in 1-(i).

Formula(A20)→Formula(A21)  3-(ii):

A compound represented by Formula (A21) can be prepared by reacting the nitro aromatic carboxamide derivative represented by Formula (A20) with a suitable fluorinating agent in a suitable solvent or without a solvent.

The solvent may be any of those which do not inhibit the progress of the reaction significantly, and examples thereof may include aliphatic hydrocarbons such as hexane, cyclohexane, methylcyclohexane, and the like, aromatic hydrocarbons such as benzene, toluene, xylene, and the like, halogenated hydrocarbons such as dichloromethane, chloroform, carbon tetrachloride, 1,2-dichloroethane, and the like, chained or cyclic ethers such as diethyl ether, dioxane, tetrahydrofuran, 1,2-dimethoxy ethane, and the like, esters such as ethyl acetate, butyl acetate, and the like, ketones such as acetone, methyl isobutyl ketone, cyclohexanone, methyl ethyl ketone, and the like, nitriles such as acetonitrile, propionitrile, and the like, and aprotic polar solvents such as 1,3-dimethyl-2-imidazolidinone, sulfolane, dimethylsulfoxide, N,N-dimethyl formamide, N-methylpyrrolidone, N,N-dimethylacetamide, and the like. These solvents may be used alone or as a mixture of two or more kinds thereof.

Examples of the fluorinating agent may include 1,1,2,2-tetrafluoroethyl diethylamine, 2-chloro-1,1,2-trifluoroethyl diethylamine, trifluorodiphenylphospholane, difluorotriphenylphospholane, fluoroformic acid esters, sulfur tetrafluoride, potassium fluoride, potassium hydrogen fluoride, cesium fluoride, rubidium fluoride, sodium fluoride, lithium fluoride, antimony (III) fluoride, antimony (V) fluoride, zinc fluoride, cobalt fluoride, lead fluoride, copper fluoride, mercury (II) fluoride, silver fluoride, silver fluoroborate, thallium (I) fluoride, molybdenum (VI) fluoride, arsenic (III) fluoride, bromine fluoride, selenium tetrafluoride, tris(dimethylamino)sulfonium difluorotrimethylsilicate, sodium hexafluorosilicate, quaternary ammonium fluorides, (2-chloroethyl)diethylamine, diethylaminosulfur trifluoride, morpholinosulfur trifluoride, silicon tetrafluoride, hydrogen fluoride, hydrofluoric acid, hydrogen fluoride-pyridine complex, hydrogen fluoride-triethylamine complex, hydrogen fluoride salts, bis(2-methoxyethyl)amino sulfurtrifluoride, 2,2-difluoro-1,3-dimethyl-2-imidazolidinone, iodine pentafluoride, tris(diethylamino)phosphonium 2,2,3,3,4,4-hexafluorocyclobutanilide, triethylammonium hexafluorocylcobutanilide, hexafluoropropene, and the like. These fluorinating agents may be used alone or as a mixture of two or more kinds thereof.

The fluorinating agent may be appropriately selected and used as a solvent, in the range of 1-fold molar equivalent to 10-fold molar equivalents with respect to the nitro aromatic carboxamide derivative represented by Formula (A20).

Additives may be used, and examples thereof may include crown ethers such as 18-crown-6 and the like, phase transfer catalysts such as a tetraphenylphosphonium salt and the like, inorganic salts such as calcium fluoride, calcium chloride, and the like, metal oxides such as mercury oxide and the like, ion exchange resins, and the like. These additives may not only be added to the reaction system but also used as a pretreating agent for the fluorinating agent.

The reaction temperature may be appropriately selected within the range from −80° C. to the reflux temperature of the solvent used, and the reaction time may be appropriately selected within the range from several minutes to 96 hours.

<Preparation Method 4>

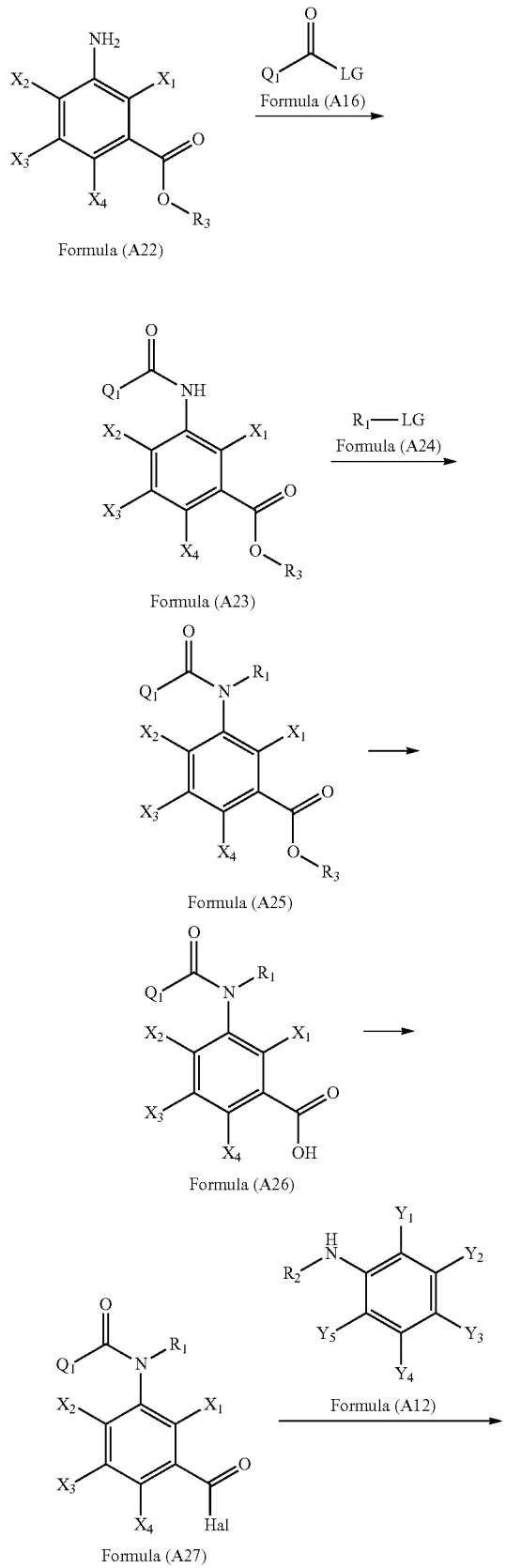

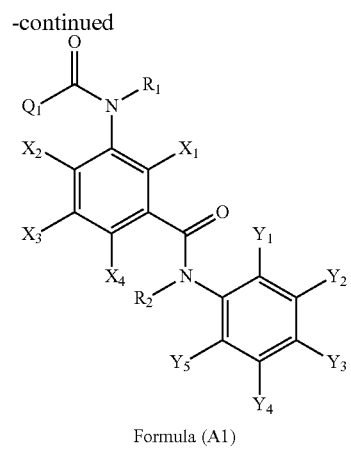

Formula (A1)

Formula(A22)+Formula(A16)→Formula(A23)　　4-(i):

A carboxylic acid having an acylamino group represented by Formula (A23) can be prepared by reacting a compound represented by Formula (A22) as a starting material with a compound represented by Formula (A16) according to the conditions described in 1-(i).

Formula(A23)+Formula(A24)→Formula(A25)　　4-(ii):

The compound represented by Formula (A25) can be prepared by reacting the amide compound represented by Formula (A23) with the compound having a leaving group such as a halogen and the like, represented by Formula (A24) in a solvent or without a solvent. In the present step, a suitable base or solvent can be used, and as the base or solvent, those exemplified in 1-(i) can be used. Examples of the reaction temperature, the reaction time, and the like may include those exemplified in 1-(i).

Formula(A25)→Formula(A26)　　4-(iii):

The compound represented by Formula (A26) can be prepared from the compound represented by Formula (A25) through hydrolysis conducted by a general technique or a method using a Pd catalyst. In the hydrolysis, the compound can be obtained by base hydrolysis using one equivalent to 5-fold molar amount of aqueous or alcoholic lithium hydroxide, sodium hydroxide, or potassium hydroxide in a single solvent of methanol, ethanol, tetrahydrofuran, or dioxane, or a combination thereof. Also in a non-aqueous solvent such as toluene and xylene, hydrolysis can be conducted with the combination of a base such as aqueous sodium hydroxide, potassium hydroxide, or lithium hydroxide and a phase-transfer catalyst such as tetrabutylammonium bromide, benzyltriethylammonium chloride, or crown ether. Alternatively, acid hydrolysis can be conducted with inorganic acid such as hydrochloric acid and sulfuric acid, organic acid such as acetic acid and trifluoroacetic acid, or strongly acidic resin.

The reaction temperature may be appropriately selected in the range from −20° C. to the reflux temperature of the solvent to be used. And the reaction time may be appropriately selected in the range from a few minutes to 96 hours.

The method using Pd can include, for example, the method described in Tetrahedron Letters p. 4371 (1987). The conditions such as the solvent and the reaction temperature are not limited to those described in the reference.

Formula(A26)→Formula(A27)　　4-(iv):

The compound represented by Formula (A27) can be prepared according to the known routine procedure in which the compound represented by Formula (A26) is reacted with thionyl chloride, oxalyl chloride, phosgene, phosphorus oxychloride, phosphorus pentachloride, phosphorous trichloride, thionyl bromide, phosphorus tribromide, diethylaminosulfur trifluoride, or the like.

Formula(*A*27)+Formula(*A*12)→Formula(*A*1)  4-(v):

The compound represented by Formula (A1) can be produced by reacting the compound represented by Formula (A27) with the compound represented by Formula (A12) according to the conditions described in 1-(i).

Formula(*A*26)+Formula(*A*12)→Formula(*A*1)  4-(vi):

The amide derivative represented by Formula (A1) can be produced by reacting the compound represented by Formula (A26) with the compound represented by Formula (A12) according to the conditions of the method in which a condensing agent is used or the mixed anhydride method both described in 1-(i).

<Production Method 5>

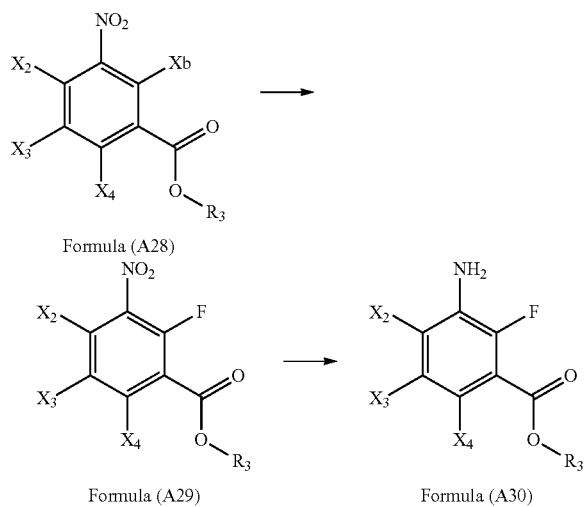

Formula(*A*28)→Formula(*A*29)  5-(i):

The compound represented by Formula (A29) can be produced by fluorinating the compound represented by Formula (A28) according to the conditions described in 3-(ii).

Formula(*A*29)→Formula(*A*30)  5-(ii):

The compound represented by Formula (A30) can be produced by reducing the compound represented by Formula (A29) according to the conditions described in 1-(ii).

In all of the preparation methods as described above, a desired product may be isolated from the reaction system after the reaction is completed according to a general method, but if required, purification can be carried out by operations such as recrystallization, column chromatography, distillation, and the like. In addition, the desired product can be also provided to the subsequent reaction process without being separated from the reaction system.

Hereinbelow, examples of the representative compounds of the amide derivative represented by Formula (A1) as an active ingredient for the composition for exterminating animal parasites according to the present invention will be given in Table A1 and Table A2 below, but the present invention is not limited thereto.

In addition, in the tables, "Me" represents a methyl group, "n-Pr" represents a normal propyl group, "CF3" represents a trifluoromethyl group, "C2F5" represents a pentafluoroethyl group, "n-C3F7" represents a heptafluoronormalpropyl group, "H" represents a hydrogen atom, "F" represents a fluorine atom, "Cl" represents a chlorine atom, "Br" represents a bromine atom, and "I" represents an iodine atom, respectively.

TABLE A1

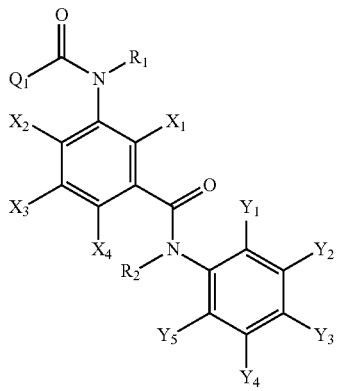

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 6-940 | phenyl | H | H | F | H | H | H | F | H | heptafluoroisopropyl | H | F |
| 6-948 | phenyl | H | H | F | H | H | H | Cl | H | heptafluoroisopropyl | H | Cl |
| 6-952 | 2-chlorophenyl | H | H | F | H | H | H | F | H | heptafluoroisopropyl | H | Cl |
| 6-956 | 3-bromophenyl | H | H | F | H | H | H | F | H | heptafluoroisopropyl | H | Br |

TABLE A1-continued

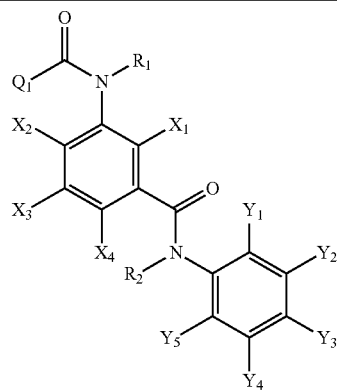

| compound number | Q₁ | R₁ | R₂ | X₁ | X₂ | X₃ | X₄ | Y₁ | Y₂ | Y₃ | Y₄ | Y₅ |
|---|---|---|---|---|---|---|---|---|---|---|---|---|
| 6-970 | 2,6-difluorophenyl | H | H | F | H | H | H | Cl | H | heptafluoroisopropyl | H | I |
| 6-1104 | phenyl | H | H | F | H | H | H | Br | H | heptafluoroisopropyl | H | Br |
| 6-1105 | 2-fluorophenyl | H | H | F | H | H | H | Br | H | heptafluoroisopropyl | H | Br |
| 6-1106 | 3-fluorophenyl | H | H | F | H | H | H | Br | H | heptafluoroisopropyl | H | Br |
| 6-1107 | 4-fluorophenyl | H | H | F | H | H | H | Br | H | heptafluoroisopropyl | H | Br |
| 6-1126 | 2,6-difluorophenyl | H | H | F | H | H | H | Br | H | heptafluoroisopropyl | H | Br |
| 6-1260 | phenyl | H | H | F | H | H | H | I | H | heptafluoroisopropyl | H | I |
| 6-1261 | 2-fluorophenyl | H | H | F | H | H | H | I | H | heptafluoroisopropyl | H | I |
| 6-1262 | 3-fluorophenyl | H | H | F | H | H | H | I | H | heptafluoroisopropyl | H | I |
| 6-1263 | 4-fluorophenyl | H | H | F | H | H | H | I | H | heptafluoroisopropyl | H | I |
| 6-1282 | 2,6-difluorophenyl | H | H | F | H | H | H | I | H | heptafluoroisopropyl | H | I |
| 6-1416 | phenyl | H | H | F | H | H | H | F | H | heptafluoroisopropyl | H | CF3 |
| 6-1417 | phenyl | H | H | F | H | H | H | Cl | H | heptafluoroisopropyl | H | CF3 |
| 6-1418 | 2-fluorophenyl | H | H | F | H | H | H | Cl | H | heptafluoroisopropyl | H | CF3 |
| 6-1422 | 3-chlorophenyl | H | H | F | H | H | H | Cl | H | heptafluoroisopropyl | H | CF3 |
| 6-1426 | 4-bromophenyl | H | H | F | H | H | H | Cl | H | heptafluoroisopropyl | H | CF3 |
| 6-1439 | 2,6-difluorophenyl | H | H | F | H | H | H | Cl | H | heptafluoroisopropyl | H | CF3 |
| 6-1440 | 3,4-dichlorophenyl | H | H | F | H | H | H | Cl | H | heptafluoroisopropyl | H | CF3 |
| 6-1441 | 2,4-dichlorophenyl | H | H | F | H | H | H | Cl | H | heptafluoroisopropyl | H | C2F5 |
| 6-1442 | 2-chloro-4-fluorophenyl | H | H | F | H | H | H | Cl | H | heptafluoroisopropyl | H | CF3 |
| 6-1445 | 2-bromo-4-chlorophenyl | H | H | F | H | H | H | Cl | H | heptafluoroisopropyl | H | n-C3F7 |
| 6-1446 | 2-bromo-4-fluorophenyl | H | H | F | H | H | H | Cl | H | heptafluoroisopropyl | H | CF3 |
| 6-1574 | phenyl | H | H | F | H | H | H | Br | H | heptafluoroisopropyl | H | CF3 |
| 6-1575 | 2-fluorophenyl | H | H | F | H | H | H | Br | H | heptafluoroisopropyl | H | CF3 |
| 6-1576 | 3-fluorophenyl | H | H | F | H | H | H | Br | H | heptafluoroisopropyl | H | CF3 |
| 6-1577 | 4-fluorophenyl | H | H | F | H | H | H | Br | H | heptafluoroisopropyl | H | CF3 |
| 6-1578 | 2-chlorophenyl | H | H | F | H | H | H | Br | H | heptafluoroisopropyl | H | CF3 |
| 6-1579 | 3-chlorophenyl | H | H | F | H | H | H | Br | H | heptafluoroisopropyl | H | CF3 |
| 6-1580 | 4-chlorophenyl | H | H | F | H | H | H | Br | H | heptafluoroisopropyl | H | CF3 |
| 6-1581 | 2-bromophenyl | H | H | F | H | H | H | Br | H | heptafluoroisopropyl | H | CF3 |
| 6-1582 | 3-bromophenyl | H | H | F | H | H | H | Br | H | heptafluoroisopropyl | H | CF3 |
| 6-1583 | 4-bromophenyl | H | H | F | H | H | H | Br | H | heptafluoroisopropyl | H | CF3 |
| 6-1584 | 2-iodophenyl | H | H | F | H | H | H | Br | H | heptafluoroisopropyl | H | CF3 |
| 6-1585 | 3-iodophenyl | H | H | F | H | H | H | Br | H | heptafluoroisopropyl | H | CF3 |
| 6-1586 | 4-iodophenyl | H | H | F | H | H | H | Br | H | heptafluoroisopropyl | H | CF3 |
| 6-1596 | 2,6-difluorophenyl | H | H | F | H | H | H | Br | H | heptafluoroisopropyl | H | CF3 |
| 6-1597 | 3,4-dichlorophenyl | H | H | F | H | H | H | Br | H | heptafluoroisopropyl | H | CF3 |
| 6-1598 | 2,4-dichlorophenyl | H | H | F | H | H | H | Br | H | heptafluoroisopropyl | H | CF3 |
| 6-1599 | 2-chloro-4-fluorophenyl | H | H | F | H | H | H | Br | H | heptafluoroisopropyl | H | CF3 |
| 6-1600 | 2-chloro-4,5-difluorophenyl | H | H | F | H | H | H | Br | H | heptafluoroisopropyl | H | CF3 |
| 6-1601 | 4-bromo-2-chlorophenyl | H | H | F | H | H | H | Br | H | heptafluoroisopropyl | H | CF3 |
| 6-1602 | 2-bromo-4-chlorophenyl | H | H | F | H | H | H | Br | H | heptafluoroisopropyl | H | CF3 |
| 6-1603 | 2-bromo-4-fluorophenyl | H | H | F | H | H | H | Br | H | heptafluoroisopropyl | H | CF3 |
| 6-1730 | phenyl | H | H | F | H | H | H | I | H | heptafluoroisopropyl | H | CF3 |
| 6-1731 | 2-fluorophenyl | H | H | F | H | H | H | I | H | heptafluoroisopropyl | H | CF3 |
| 6-1732 | 3-fluorophenyl | H | H | F | H | H | H | I | H | heptafluoroisopropyl | H | CF3 |
| 6-1733 | 4-fluorophenyl | H | H | F | H | H | H | I | H | heptafluoroisopropyl | H | CF3 |
| 6-1734 | 2-chlorophenyl | H | H | F | H | H | H | I | H | heptafluoroisopropyl | H | CF3 |
| 6-1735 | 3-chlorophenyl | H | H | F | H | H | H | I | H | heptafluoroisopropyl | H | CF3 |
| 6-1736 | 4-chlorophenyl | H | H | F | H | H | H | I | H | heptafluoroisopropyl | H | CF3 |
| 6-1737 | 2-bromophenyl | H | H | F | H | H | H | I | H | heptafluoroisopropyl | H | CF3 |
| 6-1738 | 3-bromophenyl | H | H | F | H | H | H | I | H | heptafluoroisopropyl | H | CF3 |
| 6-1739 | 4-bromophenyl | H | H | F | H | H | H | I | H | heptafluoroisopropyl | H | CF3 |
| 6-1740 | 2-iodophenyl | H | H | F | H | H | H | I | H | heptafluoroisopropyl | H | CF3 |
| 6-1741 | 3-iodophenyl | H | H | F | H | H | H | I | H | heptafluoroisopropyl | H | CF3 |
| 6-1742 | 4-iodophenyl | H | H | F | H | H | H | I | H | heptafluoroisopropyl | H | CF3 |
| 6-1752 | 2,6-difluorophenyl | H | H | F | H | H | H | I | H | heptafluoroisopropyl | H | CF3 |
| 6-1753 | 3,4-dichlorophenyl | H | H | F | H | H | H | I | H | heptafluoroisopropyl | H | CF3 |

TABLE A1-continued

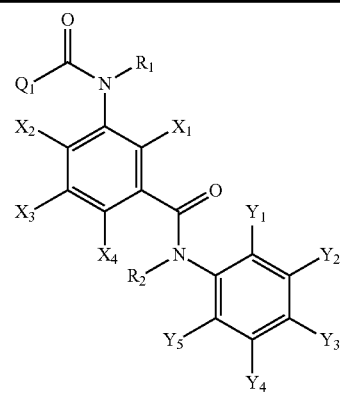

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 6-1754 | 2,4-dichlorophenyl | H | H | F | H | H | H | I | H | heptafluoroisopropyl | H | CF3 |
| 6-1755 | 2-chloro-4-fluorophenyl | H | H | F | H | H | H | I | H | heptafluoroisopropyl | H | CF3 |
| 6-1756 | 2-chloro-4,5-difluorophenyl | H | H | F | H | H | H | I | H | heptafluoroisopropyl | H | CF3 |
| 6-1757 | 4-bromo-2-chlorophenyl | H | H | F | H | H | H | I | H | heptafluoroisopropyl | H | CF3 |
| 6-1758 | 2-bromo-4-chlorophenyl | H | H | F | H | H | H | I | H | heptafluoroisopropyl | H | CF3 |
| 6-1759 | 2-bromo-4-fluorophenyl | H | H | F | H | H | H | I | H | heptafluoroisopropyl | H | CF3 |
| 6-2110 | phenyl | H | H | F | H | H | H | CF3 | H | heptafluoroisopropyl | H | CF3 |
| 6-5902 | phenyl | H | H | F | H | H | H | Br | H | heptafluoroisopropyl | H | Cl |
| 6-5910 | phenyl | H | H | F | H | H | H | Br | H | heptafluoroisopropyl | H | C2F5 |

TABLE A2

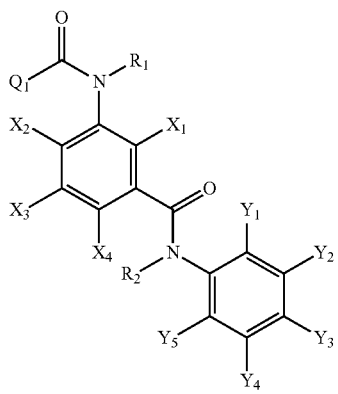

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-940 | phenyl | Me | H | F | H | H | H | F | H | heptafluoroisopropyl | H | F |
| 7-948 | phenyl | Me | H | F | H | H | H | Cl | H | heptafluoroisopropyl | H | Cl |
| 7-1104 | phenyl | Me | H | F | H | H | H | Br | H | heptafluoroisopropyl | H | Br |
| 7-1105 | 2-fluorophenyl | Me | H | F | H | H | H | Br | H | heptafluoroisopropyl | H | Br |
| 7-1106 | 3-fluorophenyl | Me | H | F | H | H | H | Br | H | heptafluoroisopropyl | H | Br |
| 7-1107 | 4-fluorophenyl | Me | H | F | H | H | H | Br | H | heptafluoroisopropyl | H | Br |
| 7-1126 | 2,6-difluorophenyl | Me | H | F | H | H | H | Br | H | heptafluoroisopropyl | H | Br |
| 7-1260 | phenyl | Me | H | F | H | H | H | I | H | heptafluoroisopropyl | H | I |
| 7-1261 | 2-fluorophenyl | Me | H | F | H | H | H | I | H | heptafluoroisopropyl | H | I |
| 7-1262 | 3-fluorophenyl | Me | H | F | H | H | H | I | H | heptafluoroisopropyl | H | I |
| 7-1263 | 4-fluorophenyl | Me | H | F | H | H | H | I | H | heptafluoroisopropyl | H | I |
| 7-1282 | 2,6-difluorophenyl | Me | H | F | H | H | H | I | H | heptafluoroisopropyl | H | I |
| 7-1416 | phenyl | Me | H | F | H | H | H | F | H | heptafluoroisopropyl | H | CF3 |
| 7-1417 | phenyl | Me | H | F | H | H | H | Cl | H | heptafluoroisopropyl | H | CF3 |
| 7-1441 | 2,4-dichlorophenyl | Me | H | F | H | H | H | Cl | H | heptafluoroisopropyl | H | C2F5 |
| 7-1442 | 2-chloro-4-fluorophenyl | n-Pr | H | F | H | H | H | Cl | H | heptafluoroisopropyl | H | CF3 |
| 7-1445 | 2-bromo-4-chlorophenyl | Me | H | F | H | H | H | Cl | H | heptafluoroisopropyl | H | n-C3F7 |
| 7-1574 | phenyl | Me | H | F | H | H | H | Br | H | heptafluoroisopropyl | H | CF3 |
| 7-1575 | 2-fluorophenyl | Me | H | F | H | H | H | Br | H | heptafluoroisopropyl | H | CF3 |
| 7-1576 | 3-fluorophenyl | Me | H | F | H | H | H | Br | H | heptafluoroisopropyl | H | CF3 |
| 7-1577 | 4-fluorophenyl | Me | H | F | H | H | H | Br | H | heptafluoroisopropyl | H | CF3 |

TABLE A2-continued

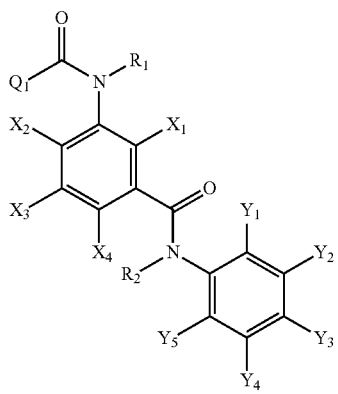

| compound number | $Q_1$ | $R_1$ | $R_2$ | $X_1$ | $X_2$ | $X_3$ | $X_4$ | $Y_1$ | $Y_2$ | $Y_3$ | $Y_4$ | $Y_5$ |
|---|---|---|---|---|---|---|---|---|---|---|---|---|
| 7-1578 | 2-chlorophenyl | Me | H | F | H | H | H | Br | H | heptafluoroisopropyl | H | CF3 |
| 7-1579 | 3-chlorophenyl | Me | H | F | H | H | H | Br | H | heptafluoroisopropyl | H | CF3 |
| 7-1580 | 4-chlorophenyl | Me | H | F | H | H | H | Br | H | heptafluoroisopropyl | H | CF3 |
| 7-1581 | 2-bromophenyl | Me | H | F | H | H | H | Br | H | heptafluoroisopropyl | H | CF3 |
| 7-1582 | 3-bromophenyl | Me | H | F | H | H | H | Br | H | heptafluoroisopropyl | H | CF3 |
| 7-1583 | 4-bromophenyl | Me | H | F | H | H | H | Br | H | heptafluoroisopropyl | H | CF3 |
| 7-1584 | 2-iodophenyl | Me | H | F | H | H | H | Br | H | heptafluoroisopropyl | H | CF3 |
| 7-1585 | 3-iodophenyl | Me | H | F | H | H | H | Br | H | heptafluoroisopropyl | H | CF3 |
| 7-1586 | 4-iodophenyl | Me | H | F | H | H | H | Br | H | heptafluoroisopropyl | H | CF3 |
| 7-1596 | 2,6-difluorophenyl | Me | H | F | H | H | H | Br | H | heptafluoroisopropyl | H | CF3 |
| 7-1597 | 3,4-dichlorophenyl | Me | H | F | H | H | H | Br | H | heptafluoroisopropyl | H | CF3 |
| 7-1598 | 2,4-dichlorophenyl | Me | H | F | H | H | H | Br | H | heptafluoroisopropyl | H | CF3 |
| 7-1599 | 2-chloro-4-fluorophenyl | Me | H | F | H | H | H | Br | H | heptafluoroisopropyl | H | CF3 |
| 7-1600 | 2-chloro-4,5-difluorophenyl | Me | H | F | H | H | H | Br | H | heptafluoroisopropyl | H | CF3 |
| 7-1601 | 4-bromo-2-chlorophenyl | Me | H | F | H | H | H | Br | H | heptafluoroisopropyl | H | CF3 |
| 7-1602 | 2-bromo-4-chlorophenyl | Me | H | F | H | H | H | Br | H | heptafluoroisopropyl | H | CF3 |
| 7-1603 | 2-bromo-4-fluorophenyl | Me | H | F | H | H | H | Br | H | heptafluoroisopropyl | H | CF3 |
| 7-1730 | phenyl | Me | H | F | H | H | H | I | H | heptafluoroisopropyl | H | CF3 |
| 7-1731 | 2-fluorophenyl | Me | H | F | H | H | H | I | H | heptafluoroisopropyl | H | CF3 |
| 7-1732 | 3-fluorophenyl | Me | H | F | H | H | H | I | H | heptafluoroisopropyl | H | CF3 |
| 7-1733 | 4-fluorophenyl | Me | H | F | H | H | H | I | H | heptafluoroisopropyl | H | CF3 |
| 7-1734 | 2-chlorophenyl | Me | H | F | H | H | H | I | H | heptafluoroisopropyl | H | CF3 |
| 7-1735 | 3-chlorophenyl | Me | H | F | H | H | H | I | H | heptafluoroisopropyl | H | CF3 |
| 7-1736 | 4-chlorophenyl | Me | H | F | H | H | H | I | H | heptafluoroisopropyl | H | CF3 |
| 7-1737 | 2-bromophenyl | Me | H | F | H | H | H | I | H | heptafluoroisopropyl | H | CF3 |
| 7-1738 | 3-bromophenyl | Me | H | F | H | H | H | I | H | heptafluoroisopropyl | H | CF3 |
| 7-1739 | 4-bromophenyl | Me | H | F | H | H | H | I | H | heptafluoroisopropyl | H | CF3 |
| 7-1740 | 2-iodophenyl | Me | H | F | H | H | H | I | H | heptafluoroisopropyl | H | CF3 |
| 7-1741 | 3-iodophenyl | Me | H | F | H | H | H | I | H | heptafluoroisopropyl | H | CF3 |
| 7-1742 | 4-iodophenyl | Me | H | F | H | H | H | I | H | heptafluoroisopropyl | H | CF3 |
| 7-1752 | 2,6-difluorophenyl | Me | H | F | H | H | H | I | H | heptafluoroisopropyl | H | CF3 |
| 7-1753 | 3,4-dichlorophenyl | Me | H | F | H | H | H | I | H | heptafluoroisopropyl | H | CF3 |
| 7-1754 | 2,4-dichlorophenyl | Me | H | F | H | H | H | I | H | heptafluoroisopropyl | H | CF3 |
| 7-1755 | 2-chloro-4-fluorophenyl | Me | H | F | H | H | H | I | H | heptafluoroisopropyl | H | CF3 |
| 7-1756 | 2-chloro-4,5-difluorophenyl | Me | H | F | H | H | H | I | H | heptafluoroisopropyl | H | CF3 |
| 7-1757 | 4-bromo-2-chlorophenyl | Me | H | F | H | H | H | I | H | heptafluoroisopropyl | H | CF3 |
| 7-1758 | 2-bromo-4-chlorophenyl | Me | H | F | H | H | H | I | H | heptafluoroisopropyl | H | CF3 |
| 7-1759 | 2-bromo-4-fluorophenyl | Me | H | F | H | H | H | I | H | heptafluoroisopropyl | H | CF3 |
| 7-2110 | phenyl | Me | H | F | H | H | H | CF3 | H | heptafluoroisopropyl | H | CF3 |
| 7-5902 | phenyl | Me | H | F | H | H | H | I | H | heptafluoroisopropyl | H | Br |

Hereinbelow, Table A3 shows the physical properties of the representative compounds of the amide derivative according to the present invention. The $^1$H-NMR chemical shift values shown therein are based on tetramethylsilane as an internal standard substance unless specified otherwise.

TABLE A3

| compound number | $^1$H-NMR (CDCl$_3$, ppm) |
|---|---|
| 6-1104 | δ 7.40 (1H, t, J = 7.8 Hz), 7.53-7.64 (3H, m), 7.89 (2H, s), 7.90-7.95 (3H, m), 8.11-8.14 (2H, m), 8.69-8.70 (1H, m). |

TABLE A3-continued

| compound number | $^1$H-NMR (CDCl$_3$, ppm) |
|---|---|
| 6-1105 | δ 7.22-7.26 (1H, m), 7.35-7.41 (2H, m), 7.58 (1H, d, J = 8.0 Hz), 7.88-7.92 (3H, m), 8.15-8.25 (2H, m), 8.74-8.75 (2H, m). |
| 6-1106 | δ 7.35-7.34 (1H, m), 7.417.42 (1H, m), 7.53-7.54 (1H, m), 7.67-7.68 (2H, m), 7.89-7.90 (3H, m), 8.09-8.10 (2H, m), 8.66-8.68 (1H, m). |
| 6-1107 | δ 7.21-7.26 (2H, m), 7.39-7.41 (1H, m), 7.89-7.96 (4H, m), 8.05-8.13 (3H, m), 8.70-8.72 (1H, m). |
| 6-1126 | δ 7.05-7.09 (2H, m), 7.38-7.42 (1H, m), 7.49-7.50 (1H, m), 7.88-7.99 (4H, m), 8.09-8.12 (1H, m), 8.71-8.72 (1H, m). |
| 6-1260 | δ 7.39 (1H, t, J = 7.8 Hz), 7.52-7.57 (4H, m), 7.60-7.63 (2H, m), 7.93-7.94 (4H, m), 8.70 (1H, t, J = 6.3 Hz). |
| 6-1261 | δ 7.22-7.28 (1H, m), 7.35-7.42 (2H, m), 7.59-7.61 (1H, m), 7.94-7.95 (1H, m), 8.12 (2H, s), 8.15-8.25 (2H, m), 8.78 (1H, t, J = 1.5 Hz), 9.00 (1H, d, J = 7.8 Hz). |
| 6-1262 | δ 7.30-7.33 (1H, m), 7.40-7.44 (1H, m), 7.52-7.55 (2H, m), 7.64-7.70 (3H, m), 7.95-7.96 (1H, m), 8.09-8.13 (2H, m), 8.67-8.68 (1H, m). |
| 6-1263 | δ 7.20-7.26 (3H, m), 7.38-7.42 (1H, m), 7.91-7.98 (3H, m), 8.07-8.12 (3H, m), 8.63-8.67 (1H, m). |
| 6-1282 | δ 7.06 (2H, t, J = 8.3 Hz), 7.38-7.42 (1H, m), 7.47-7.52 (1H, m), 7.93-7.97 (1H, m), 8.01 (1H, s), 8.11-8.13 (3H, m), 8.68-8.72 (1H, m). |
| 6-1574 | δ 7.37-7.41 (1H, m), 7.53-7.64 (3H, m), 7.86-7.94 (4H, m), 8.13-8.22 (3H, m), 8.67-8.72 (1H, m). |
| 6-1575 | δ 7.22-7.27 (1H, m), 7.35-7.41 (2H, m), 7.57-7.60 (1H, m), 7.88-7.93 (2H, m), 8.16 (1H, s), 8.20-8.25 (2H, m), 8.74-8.75 (1H, m), 8.77-9.00 (1H, m). |
| 6-1576 | δ 7.27-7.37 (2H, m), 7.48-7.53 (1H, m), 7.72-7.80 (3H, m), 7.92 (1H, s), 8.15 (1H, s), 8.27-8.31 (1H, m), 9.16 (1H, s), 9.35 (1H, d, J = 7.3 Hz). |
| 6-1577 | δ 7.20-7.23 (3H, m), 7.24-7.26 (1H, m), 7.39-7.40 (3H, m), 7.86-7.97 (1H, m), 8.06 (1H, d, J = 2.4 Hz), 8.16-8.20 (1H, m), 8.62-8.67 (1H, m). |
| 6-1596 | δ 7.00-7.09 (2H, m), 7.40-7.41 (1H, m), 7.46-7.53 (1H, m), 7.89-7.92 (2H, m), 8.00 (1H, s), 8.16-8.19 (2H, m), 8.71-8.72 (1H, m). |
| 6-1730 | δ 7.40 (1H, t, J = 7.8 Hz), 7.53-7.64 (3H, m), 7.87-7.95 (4H, m), 8.14 (1H, s), 8.22 (1H, d, J = 12.7 Hz), 8.37 (1H, s), 8.71-8.72 (1H, m). |
| 6-1731 | δ 7.22-7.25 (1H, m), 7.35-7.37 (2H, m), 7.58-7.60 (1H, m), 7.90 (1H, t, J = 8.6 Hz), 7.96 (1H, s), 8.22 (1H, t, J = 8.8 Hz), 8.29-8.32 (1H, d, J = 12.4 Hz), 8.37 (1H, s), 8.73 (1H, m), 8.94 (1H, s). |
| 6-1732 | δ 7.32-7.33 (1H, m), 7.37 (1H, t, J = 8.0 Hz), 7.52-7.54 (1H, m), 7.64-7.70 (2H, m), 7.90 (1H, t, J = 6.4 Hz), 7.96 (1H, s), 8.10 (1H, s), 8.23 (1H, d, J = 12.0 Hz), 8.37 (1H, s), 8.65 (1H, t, J = 8.0 Hz). |
| 6-1733 | δ 7.19-7.25 (2H, m), 7.35 (1H, t, J = 7.8 Hz), 7.87-7.97 (4H, m), 8.08 (1H, s), 8.25 (1H, d, J = 12.0 Hz), 8.37 (1H, s), 8.65 (1H, t, J = 8.0 Hz). |
| 6-1734 | δ 7.43-7.52 (5H, m), 7.87-7.95 (3H, m), 8.22 (1H, d, J = 10.0 Hz), 8.35 (1H, d, J = 8.2 Hz), 8.74 (1H, t, J = 8.4 Hz). |
| 6-2110 | δ 7.36-7.40 (1H, m), 7.53-7.64 (3H, m), 7.84-7.97 (1H, m), 7.92-7.94 (2H, m), 8.04-8.07 (1H, m), 8.08-8.13 (1H, m), 8.20 (2H, s), 8.68-8.72 (1H, m). |
| 6-5902 | (DMSO-d$_6$) δ 7.39 (1H, t, J = 7.8 Hz), 7.52-7.64 (4H, m), 7.81 (1H, t, J = 6.8 Hz), 7.95 (1H, s), 7.98-8.01 (3H, m), 10.29 (1H, s), 10.68 (1H, s). |
| 6-5910 | δ 7.39 (1H, t, J = 8.3 Hz), 7.53-7.64 (3H, m), 7.88-7.94 (4H, m), 8.13 (1H, broad-s), 8.19 (1H, broad-s), 8.24 (1H, d, J = 13.2 Hz), 8.70-8.72 (1H, m). |
| 7-948 | δ 3.49 (3H, s), 7.23-7.52 (8H, m), 7.66 (2H, s), 8.00 (1H, t, J = 6.8 Hz). |
| 7-1104 | δ 3.51 (3H, s), 7.22-7.44 (7H, m), 7.86 (2H, s), 8.00-8.03 (2H, m). |
| 7-1105 | δ 3.52 (3H, s), 6.82 (1H, t, J = 8.8 Hz), 7.06-7.08 (1H, m), 7.18-7.24 (2H, m), 7.40-7.44 (2H, m), 7.87 (3H, s), 8.01-8.05 (1H, m). |
| 7-1106 | δ 3.50 (3H, s), 7.00-7.23 (4H, m), 7.29-7.31 (1H, m), 7.45 (1H, s), 7.87 (3H, s), 8.03-8.07 (1H, m). |
| 7-1107 | δ 3.49 (3H, s), 6.91-6.93 (2H, m), 7.28-7.44 (4H, m), 7.86 (2H, s), 8.00-8.10 (2H, m). |
| 7-1126 | δ 3.49 (3H, s), 6.72-6.76 (2H, m), 7.16-7.23 (2H, m), 7.43-7.50 (1H, m), 7.88 (2H, s), 8.02-8.06 (1H, m), 8.13-8.17 (1H, m). |
| 7-1260 | δ 4.09 (3H, s), 7.21-7.49 (7H, m), 7.99-8.08 (4H, m). |
| 7-1261 | δ 3.53 (3H, s), 6.79-6.83 (1H, m), 7.03-7.07 (1H, m), 7.19-7.23 (2H, m), 7.42-7.43 (2H, m), 8.01-8.10 (4H, m). |
| 7-1417 | δ 3.49 (3H, s), 7.23-7.26 (3H, m), 7.27-7.33 (3H, m), 7.52-7.53 (1H, m), 7.85 (1H, s), 7.96-8.06 (3H, m). |
| 7-1574 | δ 3.50 (3H, s), 6.99-7.33 (6H, m), 7.43-7.45 (1H, m), 7.90 (1H, s), 7.97-8.06 (2H, m), 8.13 (1H, s). |
| 7-1575 | δ 3.52 (3H, s), 6.82-6.83 (1H, m), 7.06-7.07 (1H, m), 7.19-7.26 (2H, m), 7.39-7.46 (2H, m), 7.91 (1H, s), 7.99-8.01 (1H, m), 8.07-8.14 (2H, m). |
| 7-1576 | δ 3.50 (3H, s), 7.01-7.17 (4H, m), 7.27-7.31 (1H, m), 7.46-7.52 (1H, m), 7.91 (1H, s), 8.01-8.05 (2H, m), 8.13 (1H, s). |
| 7-1577 | δ 3.50 (3H, s), 6.90-6.94 (2H, m), 7.26-7.35 (3H, m), 7.45-7.46 (1H, m), 7.90 (1H, s), 8.00-8.07 (2H, m), 8.13 (1H, s). |
| 7-1596 | δ 3.54 (3H, s), 6.75 (2H, broad-s), 7.17-7.26 (2H, m), 7.50-7.51 (1H, m), 7.92 (1H, s), 8.01-8.05 (1H, m), 8.14-8.20 (2H, m). |
| 7-1730 | δ 3.51 (3H, s), 7.21-7.23 (2H, m), 7.27-7.33 (4H, m), 7.44-7.46 (1H, m), 7.92 (1H, s), 8.00 (1H, t, J = 6.3 Hz), 8.08-8.09 (1H, m), 8.33 (1H, s). |
| 7-1731 | δ 3.51 (3H, s), 6.79-6.83 (1H, m), 7.05 (1H, t, J = 7.6 Hz), 7.18-7.46 (4H, m), 7.94-8.00 (2H, m), 8.20 (1H, d, J = 12.4 Hz), 8.34 (1H, s). |
| 7-1732 | δ 3.50 (3H, s), 7.00-7.18 (4H, m), 7.27-7.31 (1H, m), 7.45-7.48 (1H, m), 7.93 (1H, s), 8.01-8.03 (1H, m), 8.12 (1H, broad-s), 8.34 (1H, s). |
| 7-1733 | δ 3.50 (3H, s), 6.91 (2H, s), 6.93-7.35 (3H, m), 7.47 (1H, t, J = 7.0 Hz), 7.93 (1H, s), 8.01-8.10 (1H, m), 8.13 (1H, broad-s), 8.34 (1H, s). |
| 7-1752 | δ 3.54 (3H, s), 6.74 (2H, s), 7.16-7.24 (2H, m), 7.50 (1H, t, J = 7.4 Hz), 7.94 (1H, s), 8.01-8.05 (1H, m), 8.25 (1H, broad-s), 8.35 (1H, s). |
| 7-5902 | δ 3.51 (3H, s), 7.00-7.52 (7H, m), 7.88 (1H, d, J = 1.5 Hz), 8.01-8.06 (3H, m). |

In particular, for example, animal parasites that can be exterminated by the composition for exterminating animal parasites according to the invention include the followings, although the invention is not limited thereto.

The ectoparasites include Siphonaptera pests such as *Ctenocephalides fells, Ctenocephalides canis, Xenopsylla cheopis, Echidnophaga gallinacea*), and *Pulex irritans;* acarine pests such as *Haemaphyxalislongicornis, Haemaphysalis japonica, Rhipicephalus sanguineus, Boophilus microplus, Dermacentor recticulatus, Dermacentor taiwanensis, Haemaphysalis flava, Ixodes ovatus, Ixodes persulcatus, Amblyomma americanum, Amblyomma maculatum, Dermacentor andersoni, Dermacentor occidentalis, Dermacentor variabilis, Haemaphysalis campanulata, Haemaphysalis megaspinosa, Ixodes nipponensis, Ixodes pacifcus, Ixodes ricinus,* and *Ixodes scapularisand;* dipterous pests such as *Musca hervei, Musca bezzii, Haematobia irritans, Simulium iwatens, Culicoides oxystoma, Tabanus chrysurus, Culex pipiens,* and *Aedes albopictus;*

Phthiraptera pests such as *Haematopinus eurysternus* and *Damalinia ovis;* and the like.

The endoparasites include:

Protozoa such as *Rhizopoda* including *Endamoeba histolytica, Mastigophora* including *Leishmania* and *Trichomonas, Sporozoea* including *Plasmodium* and *Toxoplasma*, and *Ciliophora* including *Balantidium coli;* helminths such as *Nematoda* including *Ascaris lumbricoides* and *Ancylostoma, Acannthocephala* including *Macracanthorhynchus hirudinaceus, Nematomorpha* including *Paragordius tricuspidatus, Trematoda* including *Clonorchis sinensis*, and *Cestoda* including *Taenia saginata;* nematodes such as *Ascaris, Toxocara, Toxascaris, Parascaris, Ascaridia, Heterakis, Oxyuris, Capillaria, Trichinella, Strongylus, Triodontophorus, Trichonema, Stephanurus, Desophagostomum, Chabertia, Syngamus, Ancylostoma, Uncinaria, Necator, Bunostomum, Trichostrongylus, Cooperia, Nematodirus, Haemonchus, Ostertagia, Dictyocaulus, Metastrongylus, Dirofilaria, Parafilaria, Setaria, Onchocerca, Habronema, Arduenna,* and *Acuaria;* cestodes such as *Diphyllobothrium, Anoplocephara, Moniezia, Dipylidium, Taenia, Dithyridium, Raillietina,* and *Echinococcus;* flukes such as *Schistosoma, Paramphistomum,* and *Fasciola;* and the like.

In the invention, said animal parasites are preferably ectoparasites from the viewpoint of parasiticidal activity, and they are preferably at least one of Siphonaptera pests (especially preferably *Ctenocephalides felis*) and Acarina pests (especially preferably *Haemaphyxalislongicornis, Rhipicephalus sanguineus,* and *Boophilus microplus*).

The animals to which the composition for exterminating animal parasites according to the invention can be applied include domestic animals such as human, horses, cows, pigs, sheep, goats, rabbits, camels, buffalos, deer, minks, and chinchillas; fowls such as chickens, ducks, geese, and turkeys; pets such as dogs, cats, small birds, and monkeys; laboratory animals such as rats, mice, golden hamsters, and guinea pigs; and the like, although the invention is not limited thereto.

The composition for exterminating animal parasites according to the invention can be used as a parasiticide by any of the methods normally used, with no particular restriction.

In particular, for example, the composition may be dissolved, suspended, mixed, impregnated, adsorbed, or adhered on suitable solid and/or liquid carriers according to a formulation generally used, and, if required, together with adjuvant in a suitable proportion. And the composition may be prepared into an appropriate form in accordance with the intended use.

The solid or liquid carrier for use in the invention may be those normally used in agents for animals. From the viewpoint of easiness of treatment on the target animals, it is preferable to use a liquid carrier. The liquid carrier includes, for example, alcohol such as methyl alcohol, ethyl alcohol, isopropyl alcohol, tertiary butyl alcohol, and benzyl alcohol; propylene carbonate; N-methyl-2-pyrrolidone; water; and the like. As the adjuvant, surfactant, antioxidant, emulsifier, and the like can be used. The adjuvant can include, for example, surfactant such as polyoxyethylene alkylaryl ether, polyoxyethylene sorbitan monolaurate, alkyl allyl sorbitan monolaurate, alkylbenzenesulfonate, alkylnaphthalene sulfonic acid, ligninsulfonic acid salts, higher alcohol sulfate salts, glycol monoalkyl ethers, and glycols; emulsifier such as sorbitan monooleate, sorbitan monolaurate, caprylic acid monoglyceride, capric acid monoglyceride, isostearic acid monoglyceride, and propylene glycol monocaprylate; and antioxidant such as BHA and BHT.

The composition for exterminating animal parasites according to the invention may be administered orally or parenterally to an animal.

If the composition for exteiminating animal parasites according to the invention is administered orally, the composition may be in the form of capsules, tablets, pills, powders, granules, fine granules, syrups, enteric agents, suspensions, paste, or beverage or feeds mixed with the drug.

If the composition for exterminating animal parasites according to the invention is administered parenterally, the composition may be in the form of injectables, drips, suppositories, emulsions, suspensions, drops, ointments, creams, solutions, lotions, sprays, aerosols, cataplasms, and tapes.

The method for administration includes the spot-on method in which drops are dropped on the skin of the back shoulder region and the like of the target animal to exterminate ectoparasites; local methods such as the pour-on method in which a liquid agent is applied along the back center line of the target animal to allow the applied agent to diffuse on the body surface, resulting in control of ectoparasites; the methods in which the agent is released from a collar containing the agent; the methods in which a liquid agent, ointment, or the like is directly applied to the body surface; the methods in which an aerosol or the like is applied with a spray or the like; the methods in which an injectable is injected intramuscularly, subcutaneously, or the like; and rectal administration with a suppository.

In addition to extermination of endoparasites and exoparasites, the composition for exterminating animal parasites according to the invention also can prophylactically prevent parasitic infections by applying it to the environments which are to be the infection routes. For example, the composition can prevent soil infections from soils of upland fields and parks; percutaneous infections from aqueous systems such as river, lake, wetland, and paddy field; oral infections from excrements of animals such as dogs and cats; and oral infections from raw meats of sea water fish, fresh water fish, Crustaceae, shellfish, domestic animals, and the like; and infections from mosquitoes, horseflies, flies, cockroaches, ticks, fleas, lice, assassin bugs, chiggers, etc.; and the like.

If the composition for exterminating animal parasites according to the invention is used to exterminate parasites in the animals that are mammals or birds, the optimal dosage varies depending on whether it is used for therapeutic purposes or for preventive purposes, and also varies with the type of infected parasites, the type and extent of infection, dosage form, etc. But generally, in case of oral administration, the dosage is in the range from about 0.0001 to 10,000 mg per kilogram of body weight per day. In case of parenteral administration, the dosage is in the range from about 0.0001 to 10,000 mg per kilogram of body weight per day, and the composition is administered in single or in divided doses.

The concentration of the active ingredient in the composition for exterminating animal parasites according to the invention is typically from 0.0001 to 100% by weight, preferably from 0.001 to 99% by weight, and more preferably from 0.005 to 80% by weight. In general, the parasiticides may be provided as a high-concentrated composition to be diluted to the appropriate concentration prior to use.

In addition to the amide derivatives represented by Formula (1) according to the invention, the composition for exterminating animal parasites according to the invention can further contain other insecticidal components that are generally known. The other insecticidal components can include, for example, pyrethroid compounds such as permethrin, d-phenothrin, allethrin, pyrethrum, prallethrin, cyphenothrin, cyfluthrin, fenvalerate, fenpropathrin, transfluthrin, metofluthrin, resmethrin, cypermethrin, alpha-cypermethrin, bifenthrin, deltamethrin, lambda-cyhalothrin, d,d-trans-cyphenothrin, tetramethrin, and ethofenprox; organic phosphorus compounds such as dichlorvos, tetrachlorvinphos, fenthion, chlorpyrifos, chlorpyrifos-methyl, malathion, pirimiphos-methyl, fenitrothion, and diazinon; N-phenylpyrazole compounds such as fipronil; carbamate compounds such as propoxur, carbaryl, metoxadiazone, and fenocarb; neonicotinoid compounds such as imidacloprid, clothianidin, thiamethoxam, acetamiprid, nitenpyram, and dinotefuran; growth inhibitors for insect such as methoprene, pyriproxyfen, lufenuron, fenoxycarb, triflumuron, and chromafenozide; milbemycin oxime; milbemectin; lepimectin; abamectin; ivermectin; selamectin; spinosad; rotenone; and the like.

The disclosure of Japanese Patent Application JP 2010-019747 is incorporated herein in its entirety.

All publications, patent applications, and technical specifications cited herein are incorporated herein by reference to the same extent as if each individual publication, patent application, and technical specification were specifically and individually indicated to be incorporated by reference.

EXAMPLES

Representative Examples of the present invention will be described with reference to the following Examples, but the present invention is not limited thereto. In the present Examples, DMF means N,N-dimethyl formamide, THF means tetrahydrofuran, IPE means isopropyl ether, and DMI means 1,3-dimethyl-2-imidazolidinone.

Furthermore, "%" is based on mass unless specified otherwise.

Example 1

Preparation of N-(2-bromo-4-(heptafluoropropan-2-yl)-6-(trifluoromethyl)phenyl)-2-fluoro-3-(N-methylbenzamide)benzamide (Compound No. 7-1574)

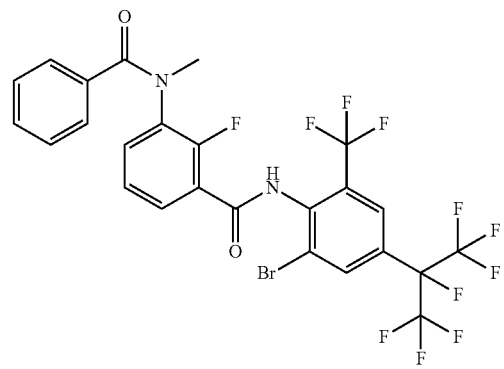 [SMILES: CN(C(=O)c1ccccc1)c1cccc(C(=O)Nc2c(Br)cc(C(F)(C(F)(F)F)C(F)(F)F)cc2C(F)(F)F)c1F]

1-1

Preparation of 4-(heptafluoropropan-2-yl)-2-(trifluoromethyl)aniline

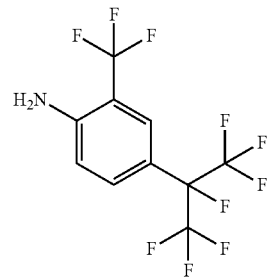 [SMILES: Nc1ccc(C(F)(C(F)(F)F)C(F)(F)F)cc1C(F)(F)F]

100 g (0.608 mol) of 2-(trifluoromethyl)aniline, 131 g (0.639 mol) of 85% sodium hydrosulfite, and 20.9 g (0.0608 mol) of tetrabutylammonium hydrogen sulfate were charged to a mixed solution of 1500 ml of ethyl acetate and 1500 ml of water, and 53.9 g (0.639 mol) of sodium hydrogen carbonate was added thereto. 198 g (0.669 mol) of heptafluoroisopropyl iodide was added dropwise thereto at room temperature, followed by stirring at room temperature for 6 hours. After the liquid separation, the solvent of the organic layer was evaporated under reduced pressure, and 500 ml of ethyl acetate was charged thereto. 160 g (0.608 mol) of a 4 M hydrogen chloride/ethyl acetate solution was added dropwise thereto, followed by stirring at room temperature for 30 minutes, and then stirring at 5° C. for 1 hour. After the filtration, the filtrate was washed with water and a saturated aqueous sodium hydrogen carbonate in this order, and then dried over anhydrous magnesium sulfate, and the solvent was evaporated under reduced pressure. The obtained residue was purified by silica gel column chromatography (eluent solvent; hexane:ethyl acetate=10:1) to prepare 60.0 g (yield 30%) of a target compound.

$^1$H-NMR (CDCl$_3$, ppm) δ 4.49 (2H, broad-s), 6.81 (1H, d, J=8.3 Hz), 7.48 (1H, d, J=8.3 Hz), 7.64 (1H, s).

1-2

Preparation of 2-bromo-4-(heptafluoropropan-2-yl)-6-(trifluoromethyl)aniline

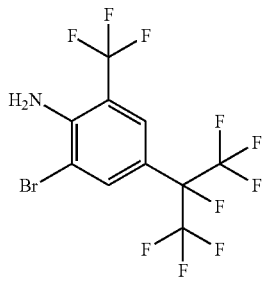 [SMILES: Nc1c(Br)cc(C(F)(C(F)(F)F)C(F)(F)F)cc1C(F)(F)F]

100 g (0.273 mol) of 4-(heptafluoropropan-2-yl)-2-(trifluoromethyl)aniline was charged to 500 ml of DMF, and 52.1 g (0.287 mol) of N-bromosuccinimide was charged in separate portions thereto over 30 minutes. After stirring at 60° C. for 2 hours, and then cooling to room temperature, the mixture was discharged to 2000 ml of water. The mixture was extracted with ethyl acetate, then washed with saturated brine, and dried over anhydrous magnesium sulfate. The solvent was evaporated under reduced pressure and the obtained residue was purified by silica gel column chromatography (eluent solvent; hexane:ethyl acetate=20:1) to prepare 89.0 g (yield 80%) of a target compound.

$^1$H-NMR (CDCl$_3$, ppm) δ 5.03 (2H, broad-s), 7.61 (1H, s), 7.79 (1H, s).

1-3

Preparation of N-(2-bromo-4-(heptafluoropropan-2-yl)-6-(trifluoromethyl)phenyl)-2-chloro-3-nitrobenzamide

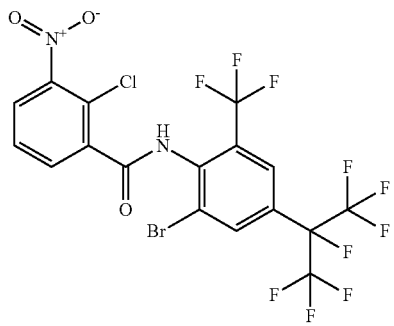

3.60 g (8.82 mmol) of 2-bromo-4-(heptafluoropropan-2-yl)-6-(trifluoromethyl)aniline was charged to 20 ml of anhydrous THF, and cooled to −70° C. under a nitrogen atmosphere. 4.85 ml (9.70 mmol) of a 2.0 M lithium diisopropyl amide hexane solution was added dropwise thereto, then 2.34 g (10.7 mmol) of acid chloride which was prepared from 2-chloro-3-nitrobenzoic acid and thionyl chloride was dissolved in 5 ml of anhydrous THF, and was added dropwise thereto, followed by stirring at −70° C. for 30 minutes and then stirring at room temperature for 30 minutes. The mixture was discharged to an aqueous ammonium chloride solution, then extracted with ethyl acetate, and dried over anhydrous magnesium sulfate. The solvent was evaporated under reduced pressure and the obtained residue was purified by silica gel column chromatography (eluent solvent; hexane:ethyl acetate=10:1→8:2→3:1) to prepare 1.76 g (yield: 34%) of a target compound.

$^1$H-NMR (CDCl$_3$, ppm) δ 7.61 (1H, t, J=7.8 Hz), 7.67 (1H, broad-s), 7.93-7.97 (3H, m), 8.18 (1H, broad-s).

1-4

Preparation of N-(2-bromo-4-(heptafluoropropan-2-yl)-6-(trifluoromethyl)phenyl)-2-fluoro-3-nitrobenzamide

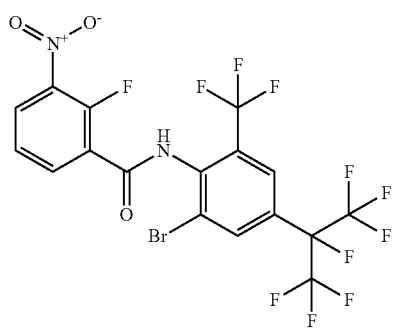 [SMILES: O=C(Nc1c(Br)cc(C(F)(C(F)(F)F)C(F)(F)F)cc1C(F)(F)F)c1cccc([N+](=O)[O-])c1F]

To a solution of N-(2-bromo-4-(heptafluoropropan-2-yl)-6-(trifluoromethyl)phenyl)-2-chloro-3-nitrobenzamide 4.89 g (8.27 mmol) in 50 ml of anhydrous DMF was added 2.40 g (41.3 mmol) of potassium fluoride (spray-dried product) under a flow of nitrogen, followed by stirring at 130° C. for 10 hours. Liquid separation was carried out by adding ethyl acetate, hexane, and water to the reaction mixture, and then the organic layer was washed with water and saturated brine, and dried over anhydrous magnesium sulfate. The solvent was evaporated under reduced pressure and the obtained residue was purified by silica gel column chromatography (eluent solvent; hexane:ethyl acetate=10:1) to prepare 0.940 g (yield 20%) of a target compound.

$^1$H-NMR (CDCl$_3$, ppm) δ 7.53 (1H, t, J=7.3 Hz), 7.93 (1H, broad-s), 8.17-8.18 (2H, m), 8.28-8.32 (1H, m), 8.44-8.48 (1H, m).

1-5

Preparation of 3-amino-N-(2-bromo-4-(heptafluoropropan-2-yl)-6-(trifluoromethyl)phenyl)-2-fluorobenzamide

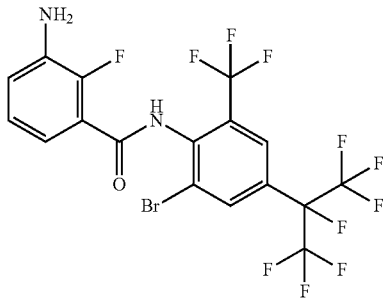 [SMILES: Nc1cccc(C(=O)Nc2c(Br)cc(C(F)(C(F)(F)F)C(F)(F)F)cc2C(F)(F)F)c1F]

0.940 g (1.63 mmol) of N-(2-bromo-4-(heptafluoropropan-2-yl)-6-(trifluoromethyl)phenyl)-2-fluoro-3-nitrobenzamide and 0.960 g (5.05 mmol) of stannous chloride (anhydrous) were added to 10 ml of ethanol, and 1.02 ml (9.78 mmol) of concentrated hydrochloric acid was added thereto, followed by stirring at 60° C. for 4 hours. The reaction mixture was adjusted to pH 10 by the addition of an aqueous sodium hydroxide solution, and the precipitated insolubles were removed by filtration using Celite. The filtrate on Celite was washed with ethyl acetate. The filtrate was extracted with ethyl acetate, and the organic layer was washed with a 20% aqueous sodium hydroxide solution and saturated brine, and then dried over anhydrous magnesium sulfate. The solvent was evaporated under reduced pressure and the obtained residue was purified by silica gel column chromatography (eluent solvent; hexane:ethyl acetate=4:1) to prepare 0.930 g (yield 99%) of a target compound.

$^1$H-NMR (CDCl$_3$, ppm) δ 3.93 (2H, broad-s), 6.99-7.04 (1H, m), 7.11 (1H, t, J=7.8 Hz), 7.47-7.49 (1H, m), 7.91 (1H, s), 8.14 (1H, s), 8.28 (1H, d, J=14.6 Hz).

1-6

Preparation of N-(2-bromo-4-(heptafluoropropan-2-yl)-6-(trifluoromethyl)phenyl)-2-fluoro-3-(methylamino)benzamide

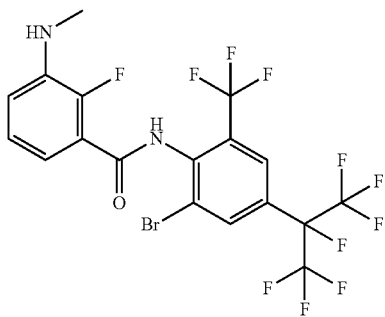 [SMILES: CNc1cccc(C(=O)Nc2c(Br)cc(C(F)(C(F)(F)F)C(F)(F)F)cc2C(F)(F)F)c1F]

0.930 g (1.71 mmol) of 3-amino-N-(2-bromo-4-(heptafluoropropan-2-yl)-6-(trifluoromethyl)phenyl)-2-fluorobenzamide was added to 5 ml of concentrated sulfuric acid, and 10 ml of a 37% aqueous formaldehyde solution was charged dropwise thereto at 40° C. The reaction mixture was poured into ice-water, adjusted to pH 10 using an aqueous sodium hydroxide solution, and extracted with the addition of ethyl acetate. The organic layer was washed with a 20% aqueous sodium hydroxide solution and saturated brine, and then dried over anhydrous magnesium sulfate. The solvent was evaporated under reduced pressure and the obtained residue was purified by silica gel column chromatography (eluent solvent; hexane:ethyl acetate=8:1) to prepare 0.690 g (yield 72%) of a target compound.

$^1$H-NMR (CDCl$_3$, ppm) δ 2.94 (3H, s), 4.14 (1H, broad-s), 6.88-6.93 (1H, m), 7.18 (1H, t, J=7.8 Hz), 7.37-7.41 (1H, m), 7.90 (1H, s), 8.13 (1H, s), 8.27 (1H, d, J=14.6 Hz).

1-7

Preparation of N-(2-bromo-4-(heptafluoropropan-2-yl)-6-(trifluoromethyephenyl)-2-fluoro-3-(N-methylbenzamide)benzamide (Compound No. 7-1574)

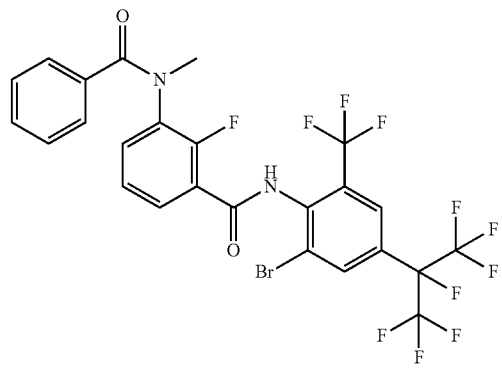 [SMILES: CN(C(=O)c1ccccc1)c1cccc(C(=O)Nc2c(Br)cc(C(F)(C(F)(F)F)C(F)(F)F)cc2C(F)(F)F)c1F]

To a solution of 1.54 g (2.75 mmol) of N-(2-bromo-4-(heptafluoropropan-2-yl)-6-(trifluoromethyl)phenyl)-2-fluoro-3-(methylamino)benzamide and 0.330 g (4.13 mmol) of pyridine in 5 ml of THF was added 0.460 g (3.30 mmol) of benzoyl chloride, followed by stirring at 60° C. for 5 hours. To the reaction mixture were added water and ethyl acetate, and the organic layer was washed with 1 M hydrochloric acid, a saturated aqueous sodium hydrogen carbonate solution, and saturated brine, and then dried over anhydrous magnesium sulfate. The solvent was evaporated under reduced pressure and the obtained residue was purified by silica gel column chromatography (eluent solvent; hexane:ethyl acetate=8:1), and the obtained solid was washed with IPE to prepare 1.45 g (yield 80%) of a target compound.

$^1$H-NMR (CDCl$_3$, ppm) δ 3.50 (3H, s), 6.99-7.33 (6H, m), 7.43-7.45 (1H, m), 7.90 (1H, s), 7.97-8.06 (2H, m), 8.13 (1H, s).

Example 2

Preparation of N-(2,6-dibromo-4-(heptafluoropropan-2-yl)phenyl)-2-fluoro-3-(N-methylbenzamide)benzamide (Compound No. 7-1104)

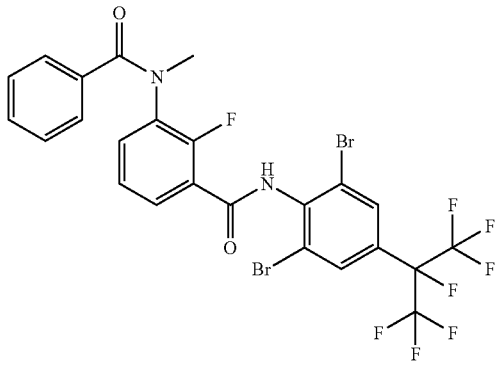 [SMILES: CN(C(=O)c1ccccc1)c1cccc(C(=O)Nc2c(Br)cc(C(F)(C(F)(F)F)C(F)(F)F)cc2Br)c1F]

2-1

Preparation of 4-(heptafluoropropan-2-yl)aniline

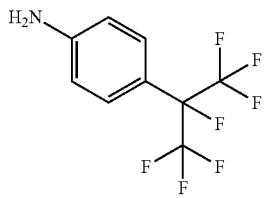 [SMILES: Nc1ccc(C(F)(C(F)(F)F)C(F)(F)F)cc1]

100 g (1.02 mol) of aniline, 230 g (1.12 mol) of 85% sodium hydrosulfite, and 35.1 g (0.100 mol) of tetrabutylammonium hydrogen sulfate were charged to a mixed solution of 1500 ml of t-butyl methyl ether and 1500 ml of water, and 94.7 g (1.12 mol) of sodium hydrogen carbonate was added thereto. 350 g (1.12 mol) of heptafluoroisopropyl iodide was added dropwise thereto at room temperature, followed by stirring at room temperature for 6 hours. After the liquid separation, the organic layer was washed with 1 M hydrochloric acid, water, and a saturated aqueous sodium hydrogen carbonate solution, and then dried over anhydrous sodium sulfate. The solvent was evaporated under reduced pressure, and 500 ml of ethyl acetate was charged thereto. 255 g (1.02 mol) of a 4 M hydrogen chloride/ethyl acetate solution was added dropwise thereto, followed by stirring at room temperature for 30 minutes and at 5° C. for 1 hour. The precipitated solid was separated by filtration, and the solid was charged to 1000 ml of ethyl acetate, adjusted to pH 8 to 9 by the addition of 1000 ml of a saturated aqueous sodium hydrogen carbonate solution at 20° C. or lower, and subjected to liquid separation. The organic layer was dried over anhydrous sodium sulfate, and then the solvent was evaporated under reduced pressure to prepare 188 g (yield 71%) of a target compound.

$^1$H-NMR (CDCl$_3$, ppm) δ 3.92 (2H, broad-s), 6.69-6.74 (2H, m), 7.35 (2H, d, J=9.3 Hz).

2-2

Preparation of 2,6-dibromo-4-(heptafluoropropan-2-yl)aniline

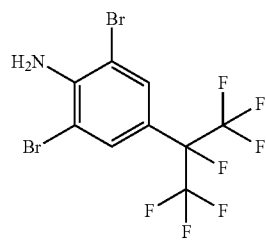 [SMILES: Nc1c(Br)cc(C(F)(C(F)(F)F)C(F)(F)F)cc1Br]

216 g (0.802 mol) of 4-(heptafluoropropan-2-yl)aniline was charged to 863 ml of DMF, followed by cooling to 5° C. 285 g (1.60 mol) of N-bromosuccinimide was charged in separate portions thereto over 1 hour. The mixture was stirred at room temperature for 1 hour and then stirred at 37° C. for 2 hours. The mixture was discharged to 2000 ml of water, extracted with 2000 ml of ethyl acetate, and washed with 1000 ml of saturated brine. After dried over anhydrous magnesium sulfate, the solvent was evaporated under reduced pressure. The obtained residue was purified by silica gel column chromatography (eluent solvent; hexane:ethyl acetate=20:1) to prepare 304 g (yield 90%) of a target compound.

$^1$H-NMR (CDCl$_3$, ppm) δ 4.88 (2H, broad-s), 7.59 (2H, s).

2-3

Preparation of 2-chloro-N-(2,6-dibromo-4-(heptafluoropropan-2-yl)phenyl)-3-nitrobenzamide

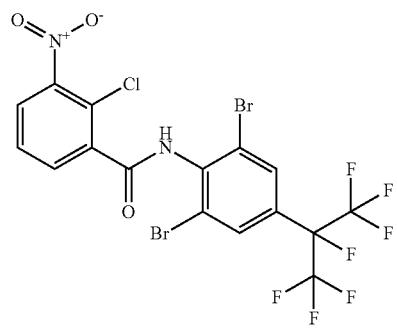 [SMILES: O=C(Nc1c(Br)cc(C(F)(C(F)(F)F)C(F)(F)F)cc1Br)c1cccc([N+](=O)[O-])c1Cl]

According to the method of 1-3 of Example 1, a target compound was prepared from 2,6-dibromo-4-(heptafluoropropan-2-yl)aniline.

¹H-NMR (CDCl₃, ppm) δ 7.58 (1H, t, J=7.8 Hz), 7.66 (1H, broad-s), 7.90 (2H, s), 7.93 (1H, dd, J=1.5, 7.8 Hz), 7.98 (1H, d, J=7.8 Hz).

2-4

Preparation of N-(2,6-dibromo-4-(heptafluoropropan-2-yl)phenyl)-2-fluoro-3-nitrobenzamide

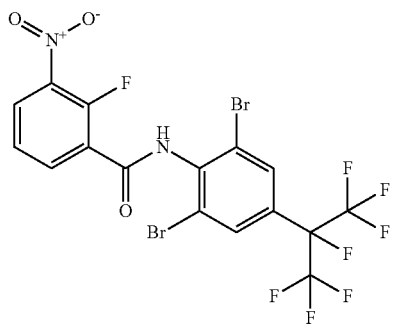 [SMILES: O=C(Nc1c(Br)cc(C(F)(C(F)(F)F)C(F)(F)F)cc1Br)c1cccc([N+](=O)[O-])c1F]

According to the method of 1-4 of Example 1, a target compound was prepared from 2-chloro-N-(2,6-dibromo-4-(heptafluoropropan-2-yl)phenyl)-3-nitrobenzamide.

¹H-NMR (CDCl₃, ppm) δ 7.51-7.55 (1H, m), 7.90 (2H, s), 8.16 (1H, d, J=11.7 Hz), 8.27-8.31 (1H, m), 8.48 (1H, t, J=6.3 Hz).

2-5

Preparation of 3-amino-N-(2,6-dibromo-4-(heptafluoropropan-2-yl)phenyl)-2-fluorobenzamide

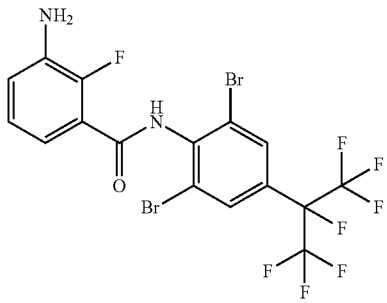 [SMILES: Nc1cccc(C(=O)Nc2c(Br)cc(C(F)(C(F)(F)F)C(F)(F)F)cc2Br)c1F]

According to the method of 1-5 of Example 1, a target compound was prepared from N-(2,6-dibromo-4-(heptafluoropropan-2-yl)phenyl)-2-fluoro-3-nitrobenzamide.

¹H-NMR (CDCl₃, ppm) δ 3.93 (2H, broad-s), 6.99-7.04 (1H, m), 7.11 (1H, t, J=7.8 Hz), 7.47-7.49 (1H, m), 7.91 (1H, s), 8.14 (1H, s), 8.28 (1H, d, J=14.6 Hz).

2-6

Preparation of N-(2,6-dibromo-4-(heptafluoropropan-2-yl)phenyl)-2-fluoro-3-(methylamino)benzamide

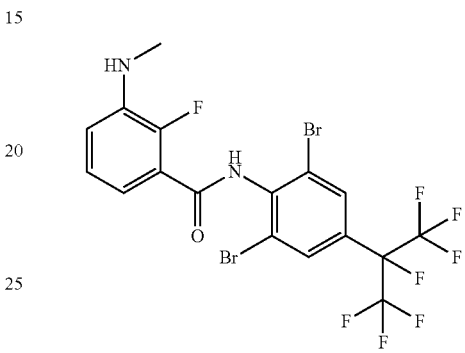

According to the method of 1-6 of Example 1, a target compound was prepared from 3-amino-N-(2,6-dibromo-4-(heptafluoropropan-2-yl)phenyl)-2-fluorobenzamide.

¹H-NMR (CDCl₃, ppm) δ 2.94 (3H, d, J=5.6 HZ), 4.87-4.91 (1H, m), 6.91 (1H, t, J=7.9 Hz), 7.18 (1H, t, J=7.9 Hz), 7.41 (1H, t, J=7.1 Hz), 7.87 (2H, s), 8.20 (1H, d, J=13.5 Hz).

2-7

Preparation of N-(2,6-dibromo-4-(heptafluoropropan-2-yl)phenyl)-2-fluoro-3-(N-methylbenzamide)benzamide (Compound No. 7-1104)

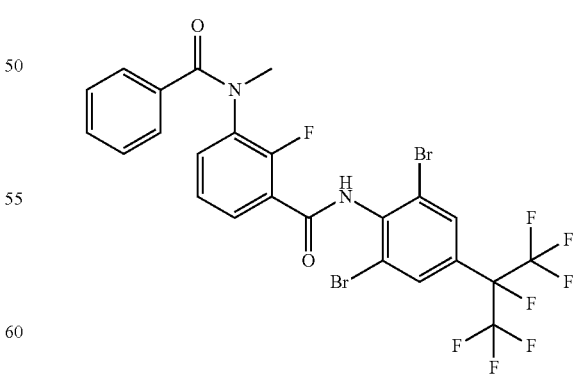

According to the method of 1-7 of Example 1, a target compound was prepared from N-(2,6-dibromo-4-(heptafluoropropan-2-yl)phenyl)-2-fluoro-3-(methylamino)benzamide and benzoyl chloride.

1H-NMR (CDCl₃, ppm) δ 3.51 (3H, s), 7.22-7.44 (7H, m), 7.86 (2H, s), 8.00-8.03 (2H, m).

Example 3

Preparation of 3-benzamide-2-fluoro-N-(4-(heptafluoropropan-2-yl)-2,6-bis(trifluoromethyl)phenyl)benzamide (Compound No. 6-2110)

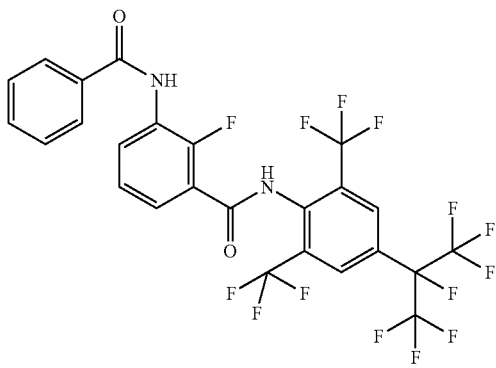 [SMILES: O=C(Nc1cccc(C(=O)Nc2c(C(F)(F)F)cc(C(F)(C(F)(F)F)C(F)(F)F)cc2C(F)(F)F)c1F)c1ccccc1]

3-1

Preparation of 2,6-diiodo-4-(heptafluoropropan-2-yl)aniline

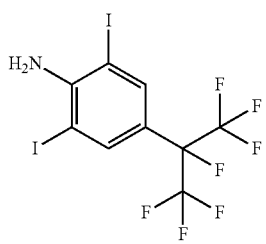 [SMILES: Nc1c(I)cc(C(F)(C(F)(F)F)C(F)(F)F)cc1I]

To a solution of 5.74 g (22.0 mmol) of 4-(heptafluoropropan-2-yl)aniline obtained in 2-1 of Example 2 in 50 ml of ethanol was added 2.16 g (22.0 mmol) of concentrated sulfuric acid at 5° C. The reaction mixture was warmed to room temperature, and 10.0 g (44.0 mmol) of N-iodosuccinimide was added thereto, followed by stirring for 3 hours. The reaction mixture was neutralized with a saturated aqueous sodium hydrogen carbonate solution. The precipitated crystals were filtered, washed with water, and then dried to prepare 9.00 g (yield 80%) of a target compound.

¹H-NMR (CDCl₃, ppm) δ 4.95 (2H, broad-s), 7.79 (2H, s).

3-2

Preparation of 2-chloro-N-(2,6-diiodo-4-(heptafluoropropan-2-yl)phenyl)-3-nitrobenzamide

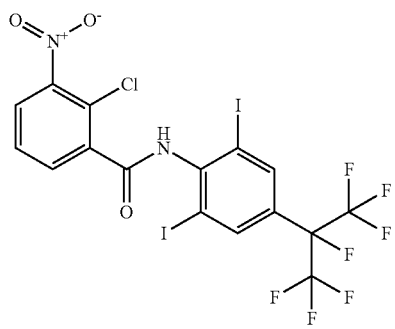

To a solution of 40.0 g (78.0 mmol) of 2,6-diiodo-4-(heptafluoropropan-2-yl)aniline in 100 ml of DMI was added 20.6 g (94.0 mmol) of 2-chloro-3-nitrobenzoyl chloride, followed by stirring at 135° C. for 3 hours. After cooling to room temperature, the reaction mixture was poured into 1000 ml of water. After extraction with the addition of 1000 ml of ethyl acetate, the organic layer was washed with water and then dried over anhydrous magnesium sulfate. The solvent was evaporated under reduced pressure and the obtained residue was washed with hexane to prepare 56.2 g (yield 99%) of a target compound.

1H-NMR (CDCl₃, ppm) δ 7.58 (1H, t, J=8.3 Hz), 7.70 (1H, d, J=3.4 Hz), 7.93 (1H, dd, J=1.5, 6.3 Hz), 8.08-8.10 (1H, m), 8.13 (2H, s).

3-3

Preparation of N-(2,6-diiodo-4-(heptafluoropropan-2-yl)phenyl)-2-fluoro-3-nitrobenzamide

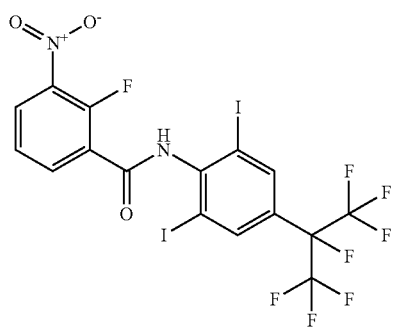 [SMILES: O=C(Nc1c(I)cc(C(F)(C(F)(F)F)C(F)(F)F)cc1I)c1cccc([N+](=O)[O-])c1F]

According to the method of 1-4 of Example 1, a target compound was prepared from 2-chloro-N-(2,6-diiodo-4-(heptafluoropropan-2-yl)phenyl)-3-nitrobenzamide.

$^1$H-NMR (CDCl$_3$, ppm) δ 7.52-7.55 (1H, m), 8.12-8.18 (3H, m), 8.29-8.32 (1H, m), 8.48-8.51 (1H, m).

3-4

Preparation of 3-amino-N-(2,6-diiodo-4-(heptafluoropropan-2-yl)phenyl)-2-fluorobenzamide

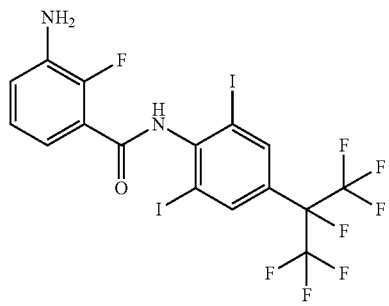 [SMILES: Nc1cccc(C(=O)Nc2c(I)cc(C(F)(C(F)(F)F)C(F)(F)F)cc2I)c1F]

According to the method of 1-5 of Example 1, a target compound was prepared from N-(2,6-diiodo-4-(heptafluoropropan-2-yl)phenyl)-2-fluoro-3-nitrobenzamide.

$^1$H-NMR (CDCl$_3$, ppm) δ 3.93 (2H, broad-s), 6.99-7.04 (1H, m), 7.08 (1H, t, J=7.8 Hz), 7.39-7.43 (1H, m), 8.10 (2H, s), 8.72 (1H, d, J=11.2 Hz).

3-5

Preparation of 3-benzamide-N-(2,6-diiodo-4-(heptafluoropropan-2-yl)phenyl)-2-fluorobenzamide (Compound No. 6-1260)

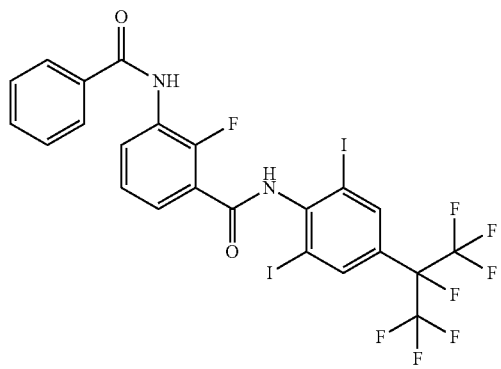 [SMILES: O=C(Nc1cccc(C(=O)Nc2c(I)cc(C(F)(C(F)(F)F)C(F)(F)F)cc2I)c1F)c1ccccc1]

According to the method of 1-7 of Example 1, a target compound was prepared from 3-amino-N-(2,6-diiodo-4-(heptafluoropropan-2-yl)phenyl)-2-fluorobenzamide.

$^1$H-NMR (CDCl$_3$, ppm) δ 7.39 (1H, t, J=7.8 Hz), 7.52-7.57 (4H, m), 7.60-7.63 (2H, m), 7.93-7.94 (4H, m), 8.70 (1H, t, J=6.3 Hz).

3-6

Preparation of 3-benzamide-2-fluoro-N-(4-(heptafluoropropan-2-yl)-2,6-bis(trifluoromethyl)phenyl)benzamide (Compound No. 6-2110)

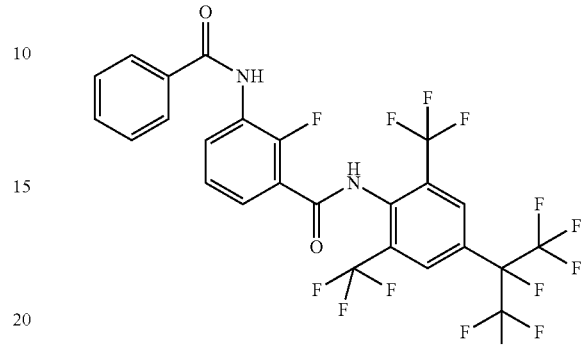

A solution of 1.95 g (2.59 mmol) of 3-benzamide-N-(2,6-diiodo-4-(heptafluoropropan-2-yl)phenyl)-2-fluorobenzamide, 0.10 g (0.520 mmol) of copper iodide, and 1.24 g (6.48 mmol) of methyl fluorosulfonyl difluoroacetate in 50 ml of DMF was stirred at 100° C. for 6 hours. The reaction mixture was cooled to room temperature, and then 10 ml of water and 100 ml of ethyl acetate were added thereto, followed by filtration through Celite. The organic layer of the liquid was washed with water and a saturated aqueous sodium hydrogen carbonate solution, and then dried over anhydrous magnesium sulfate. The solvent was evaporated under reduced pressure and the obtained residue was purified by silica gel column chromatography (eluent solvent; hexane:ethyl acetate=1:1). The obtained solid was washed with hexane to prepare 0.840 g (yield 51%) of a target compound.

$^1$H-NMR (CDCl$_3$, ppm) δ 7.36-7.40 (1H, m), 7.53-7.64 (3H, m), 7.84-7.97 (1H, m), 7.92-7.94 (2H, m), 8.04-8.07 (1H, m), 8.08-8.13 (1H, m), 8.20 (2H, s), 8.68-8.72 (1H, m).

Example 4

Preparation of 2-fluoro-3-(4-fluoro-N-methylbenzamide)-N-(2-iodo-4-(heptafluoropropan-2-yl)-6-(trifluoromethyl)phenyl)benzamide (Compound No. 7-1733)

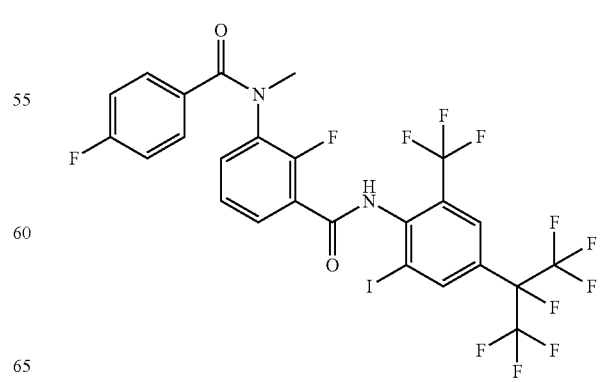

4-1

Preparation of 2-iodo-4-(heptafluoropropan-2-yl)-6-(trifluoromethyl)aniline

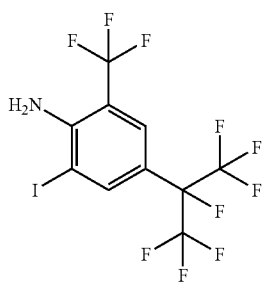 [SMILES: Nc1c(I)cc(C(F)(C(F)(F)F)C(F)(F)F)cc1C(F)(F)F]

To 1200 mL of ethanol was added 200 g (0.600 mol) of 4-(heptafluoropropan-2-yl)-2-(trifluoromethyl)aniline which was obtained in 1-1 of example 1, and 63.2 g (0.630 mol) of concentrated sulfuric acid and 155 g (0.660 mol) of N-iodosuccinimide were added thereto under ice-cooling, followed by stirring at room temperature for 1 hour and 30 minutes and at 40° C. for 4 hours. To the reaction solution was added a 4 M aqueous sodium hydroxide solution to neutralize the reaction solution, and then ethyl acetate was added thereto to extract the organic phase. The organic phase was washed with saturated brine, and dried over anhydrous magnesium sulfate, and then the solvent was evaporated under reduced pressure. The obtained residue was purified by silica gel column chromatography (eluent solvent; hexane:ethyl acetate=10:1) to prepare 216 g (yield 80%) of a target compound.

$^1$H-NMR (CDCl$_3$, ppm) δ 5.04 (2H, broad-s), 7.64 (1H, s), 7.99 (1H, s).

4-2

Preparation of 2-chloro-N-(2-iodo-4-(heptafluoropropan-2-yl)-6-(trifluoromethyl)phenyl)-3-nitrobenzamide

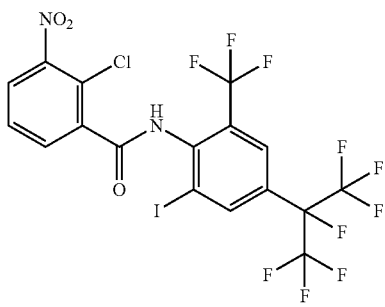

According to the method of 3-2 of Example 3, a target compound was prepared from 2-iodo-4-(heptafluoropropan-2-yl)-6-(trifluoromethyl)aniline and 2-chloro-3-nitrobenzoyl chloride.

$^1$H-NMR (CDCl$_3$, ppm) δ 7.60 (1H, t, J=7.8 Hz), 7.76 (1H, s), 7.94 (1H, dd, J=1.5, 7.8 Hz), 7.97 (1H, s), 8.03 (1H, dd, J=1.5, 7.8 Hz), 8.39 (1H, s).

4-3

Preparation of 2-fluoro-N-(2-iodo-4-(heptafluoropropan-2-yl)-6-(trifluoromethyl)phenyl)-3-nitrobenzamide

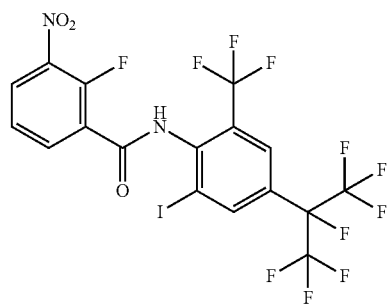

According to the method of 1-4 of Example 1, a target compound was prepared from 2-chloro-N-(2-iodo-4-(heptafluoropropan-2-yl)-6-(trifluoromethyl)phenyl)-3-nitrobenzamide.

$^1$H-NMR (CDCl$_3$, ppm) δ 7.51-7.55 (1H, m), 7.97 (1H, s), 8.23 (1H, d, J=12.2 Hz), 8.28-8.32 (1H, m), 8.37 (1H, s), 8.44-8.48 (1H, m).

4-4

Preparation of 3-amino-2-fluoro-N-(2-iodo-4-(heptafluoropropan-2-yl)-6-(trifluoromethyl)phenyl)benzamide

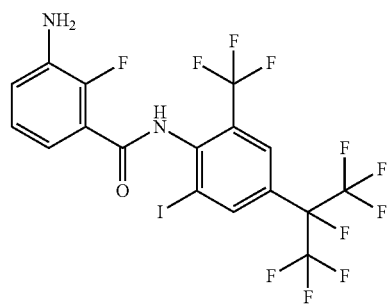

According to the method of 1-5 of Example 1, a target compound was prepared from 2-fluoro-N-(2-iodo-4-(heptafluoropropan-2-yl)-6-(trifluoromethyl)phenyl)-3-nitrobenzamide.

¹H-NMR (CDCl₃, ppm) δ 3.92 (2H, broad-s), 7.02-7.04 (1H, m), 7.11 (1H, t, J=7.8 Hz), 7.47-7.52 (1H, m), 7.94 (1H, s), 8.30-8.35 (2H, m).

4-5

Preparation of 2-fluoro-N-(2-iodo-4-(heptafluoropropan-2-yl)-6-(trifluoromethyl)phenyl)-3-(methylamino)benzamide

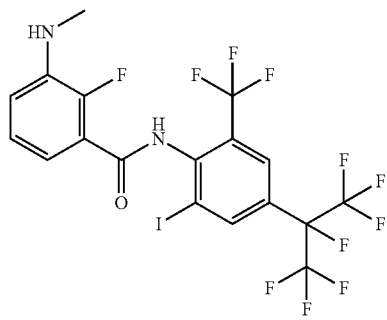 [SMILES: CNc1cccc(C(=O)Nc2c(I)cc(C(F)(C(F)(F)F)C(F)(F)F)cc2C(F)(F)F)c1F]

According to the method of 1-6 of Example 1, a target compound was prepared from 3-amino-2-fluoro-N-(2-iodo-4-(heptafluoropropan-2-yl)-6-(trifluoromethyl)phenyl)benzamide.

¹H-NMR (CDCl₃, ppm) δ 2.95 (3H, s), 4.15 (1H, broad-s), 6.90 (1H, t, J=8.2 Hz), 7.19 (1H, t, J=7.8 Hz), 7.40 (1H, t, J=7.8 Hz), 7.92 (1H, s), 8.30 (1H, s), 8.34 (1H, s).

4-6

Preparation of 2-fluoro-3-(4-fluoro-N-methylbenzamide)-N-(2-iodo-4-(heptafluoropropan-2-yl)-6-(trifluoromethyl)phenyl)benzamide (Compound No. 7-1733)

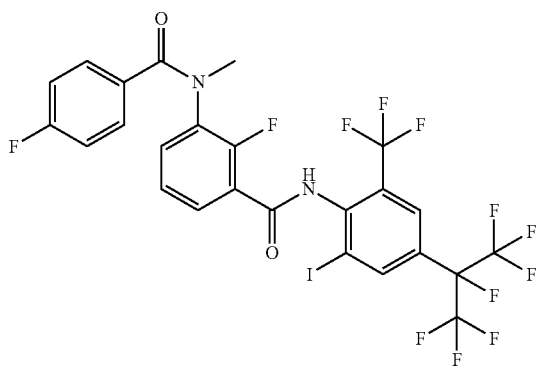 [SMILES: CN(C(=O)c1ccc(F)cc1)c1cccc(C(=O)Nc2c(I)cc(C(F)(C(F)(F)F)C(F)(F)F)cc2C(F)(F)F)c1F]

According to the method of 1-7 of Example 1, a target compound was prepared from 2-fluoro-N-(2-iodo-4-(heptafluoropropan-2-yl)-6-(trifluoromethyl)phenyl)-3-(methylamino)benzamide and 4-fluorobenzoyl chloride.

¹H-NMR (CDCl₃, ppm) δ 3.50 (3H, s), 6.91 (2H, s), 6.93-7.35 (3H, m), 7.46 (1H, t, J=7.0 Hz), 7.93 (1H, s), 8.01-8.10 (1H, m), 8.13 (1H, broad-s), 8.34 (1H, s).

Example 5

Preparation of 2-fluoro-3-(3-fluoro-N-methylbenzamide)-N-(2-iodo-4-(heptafluoropropan-2-yl)-6-(trifluoromethyl)phenyl)benzamide (Compound No. 7-1732)

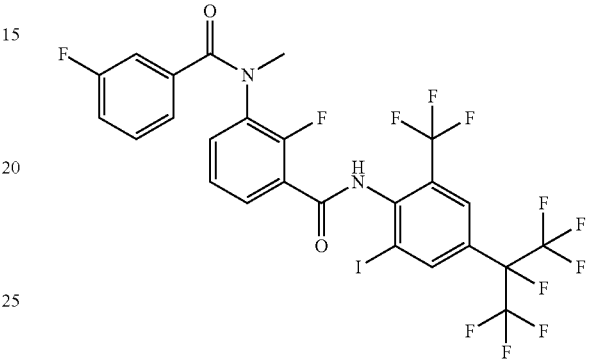

According to the method of 1-7 of Example 1, a target compound was prepared from 2-fluoro-N-(2-iodo-4-(heptafluoropropan-2-yl)-6-(trifluoromethyl)phenyl)-3-(methylamino)benzamide and 3-fluorobenzoyl chloride.

¹H-NMR (CDCl₃, ppm) δ 3.50 (3H, s), 6.91 (2H, s), 7.00-7.18 (4H, m), 7.27-7.31 (1H, m), 7.45-7.48 (1H, m), 7.93 (1H, s), 8.01-8.03 (1H, m), 8.12 (1H, broad-s), 8.34 (1H, s).

Example 6

Preparation of 2-fluoro-3-(4-fluorobenzamide)-N-(2-iodo-4-(heptafluoropropan-2-yl)-6-(trifluoromethyl)phenyl)benzamide (Compound No. 6-1733)

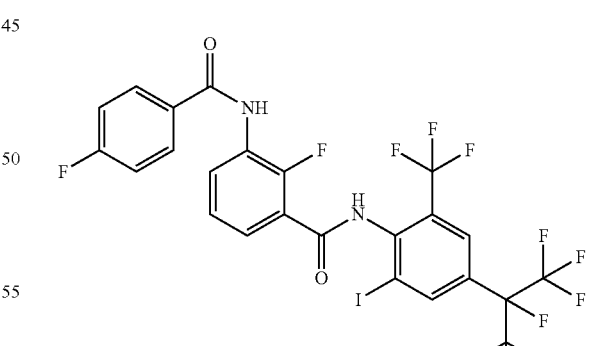

According to the method of 1-7 of Example 1, a target compound was prepared from 3-amino-2-fluoro-N-(2-iodo-4-(heptafluoropropan-2-yl)-6-(trifluoromethyl)phenyl)benzamide and 4-fluorobenzoyl chloride.

¹H-NMR (CDCl₃, ppm) δ 7.19-7.25 (2H, m), 7.35 (1H, t, J=7.8 Hz), 7.87-7.97 (4H, m), 8.08 (1H, s), 8.25 (1H, d, J=12.0 Hz), 8.37 (1H, s), 8.65 (1H, t, J=8.0 Hz).

713

Now, the representative examples of the formulations according to the invention will be shown, although the invention is not limited thereto. "Parts" in Formulation Examples indicates "parts by weight".

Formulation Example 1

Emulsion 10 parts of Compound No. 7-1574 or 7-1733, 6 parts of Sol Pol 355S (surfactant available from Toho Chemical Industry Co.), and 84 parts of Solvesso 150 (available from ExxonMobil Chemical Co.) were homogeneously mixed with stirring to obtain as emulsion the composition for exterminating animal parasites.

Formulation Example 2

Ointment 1 part of Compound No. 7-1574 or 7-1733, 50 parts of white beeswax, and 49 parts of white petrolatum were thoroughly mixed to obtain as ointment the composition for exterminating animal parasites.

Formulation Example 3

Tablets 2 parts of Compound No. 7-1574 or 7-1733, 10 parts of vegetable oil (olive oil), 3 parts of crystalline cellulose, 20 parts of white carbon, and 65 parts of kaolin were thoroughly mixed and then compressed to obtain as tablets the composition for exterminating animal parasites.

Formulation Example 4

Injectable 10 parts of Compound No. 7-1574 or 7-1733, 10 parts of propylene glycol for food additives, 80 parts of vegetable oil (corn oil) were mixed to obtain as injectable the composition for exterminating animal parasites.

Formulation Example 5

Solution 5 parts of Compound No. 7-1574 or 7-1733, 20 parts of surfactant, and 75 parts of ion-exchanged water were thoroughly mixed to obtain as solution the composition for exterminating animal parasites.

Next, the utility of the composition of the invention as a parasiticide will be concretely explained in the following Test Examples, although the invention is not limited thereto.

Test Example 1

Insecticidal Test for *Ctenocephalides Felis*

0.5 ml of a solution of acetone, the active ingredient, prepared to the prescribed concentration was added dropwise to a glass tube with a flat bottom (internal diameter: 2.6 cm, bottom area: 5.3 cm$^2$, height: 12 cm), and the solvent was evaporated at room temperature to form a dry film of the agent on the bottom surface. About 10 adults of *Ctenocephalides Felis* per glass tube were added, and the adults were contact-exposed to the test compound. After 24 hours of the exposure, the conditions of the adults were examined and classified into "alive" and "dead (including a moribund condition)" to determine the death rate (in triplicate). The results are shown in Table A4.

As the comparative compounds, the following Compounds (A), (B), and (C) disclosed in WO2009/080203, and fipronil were used.

compound (A)

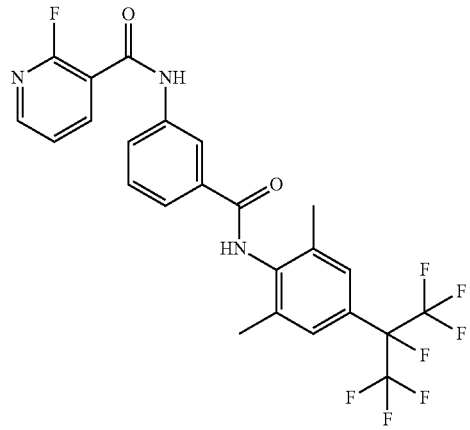

compound (B)

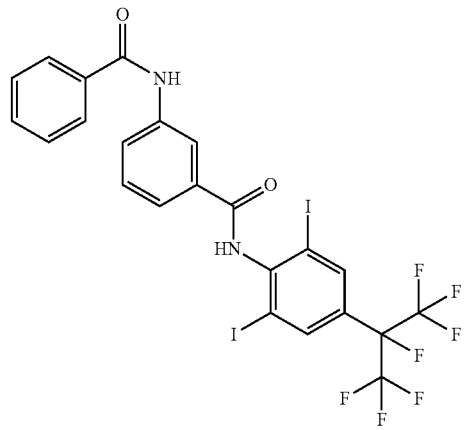

compound (C)

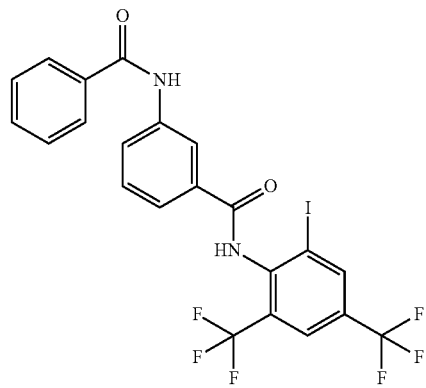

TABLE A4

| active ingredient (compound number) | concentration (µg/ml) | death rate (%) |
|---|---|---|
| 7-1574 | 0.1 | 100.0 |
| 7-1733 | 0.1 | 100.0 |
| 7-1732 | 0.1 | 76.7 |
| 6-1733 | 0.1 | 70.0 |
| 7-1104 | 0.1 | 73.3 |
| compound (A) | 1.0 | 0.0 |
| compound (B) | 1.0 | 3.2 |
| compound (C) | 1.0 | 0.0 |
| fipronil | 0.1 | 92.1 |
| only acetone | — | 4.7 |

The amide derivatives of Compound No. 7-1574 and 7-1104 were found to be effective even in the examination after 12 hours of the exposure. In addition, they showed immediate effect as compared with the fipronil.

Test Example 2

Insecticidal Test for *Haemaphyxalis longicornis*

1 ml of a solution of acetone, the active ingredient, prepared to the prescribed concentration was added dropwise to filter paper inside a petri dish with a diameter of 9 cm, and the acetone was evaporated at room temperature. About 100 larvae of *Haemaphyxalis longicornis* per dish were added to the filter paper. The dish was covered by a polyethylene sheet, sealed with a rubber band, and placed in a dark place at a temperature of 25° C. and a relative humidity of 100% to expose the larvae to the test substance. After 24 hours of the exposure, the conditions of the larvae were examined and classified into "alive" and "dead (including a moribund condition)".

As a result, the amide derivatives according to the invention were found to be effective in killing *Haemaphyxalis longicornis*.

Test Example 3

Insecticidal Test for *Ctenocephalides felis*

0.96 ml of a solution of acetone, the active ingredient, prepared to the prescribed concentration was added dropwise to a glass tube with a flat bottom (internal diameter: 3.6 cm, height: 12 cm), and the solvent was evaporated at room temperature to form a dry film of the agent on the bottom surface. About 10 adults of *Ctenocephalides felis* per glass tube were added, and they were contact-exposed to the test compound. After 24 hours of the exposure, the conditions of the adults were examined and classified into "alive" and "dead (including a moribund condition)" to determine the death rate was determined (in triplicate). The results are shown in Table A5.

As the comparative compounds, the following Compounds (D) and (E) disclosed in WO2009/080203, and fipronil were used.

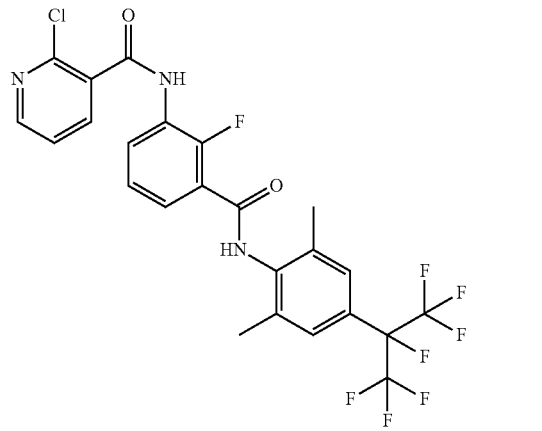

compound (D)

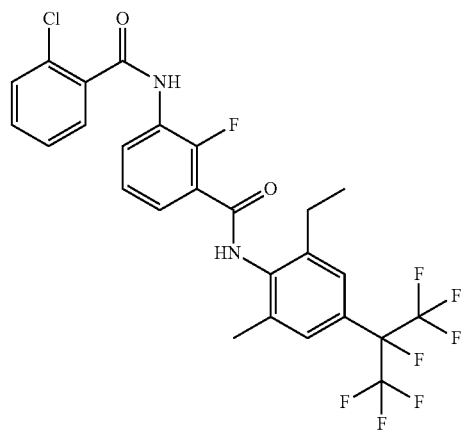

compound (E)

TABLE A5

| active ingredient (compound number) | concentration (µg/ml) | death rate (%) |
|---|---|---|
| 7-1574 | 0.03 | 72.0 |
|  | 0.1 | 98.9 |
| 7-1733 | 0.03 | 21.1 |
|  | 0.1 | 91.6 |
| componud (D) | 0.3 | 22.0 |
|  | 1 | 61.4 |
| compound (E) | 1 | 0.0 |
| fipronil | 0.03 | 70.0 |
|  | 0.1 | 100.0 |
| only acetone | — | 1.4 |

Test Example 4

Insecticidal Test for *Rhipicephalus sanguineus*

0.5 ml of a solution of acetone, the active ingredient, prepared to the prescribed dose was added dropwise into a glass petri dish with a diameter of 10 cm, and the acetone was evaporated at room temperature. About 10 adults of *Rhipicephalus sanguineus* per dish were added, and the dish was covered by another glass petri dish that was treated with the active ingredient in the same manner described above. After 18 hour exposure to the test substance, the adults were transferred into a glass petri dish that was not treated with the active ingredient. After 48 hours of the exposure, the conditions of the adults were examined and classified into "alive" and "dead (including a moribund condition)" to determine the death rate (in single). The results are shown in Table A6.

As the comparative compounds, said Compounds (B), (C), and (D), and the following Compound (F) disclosed in WO2009/080203, and fipronil were used.

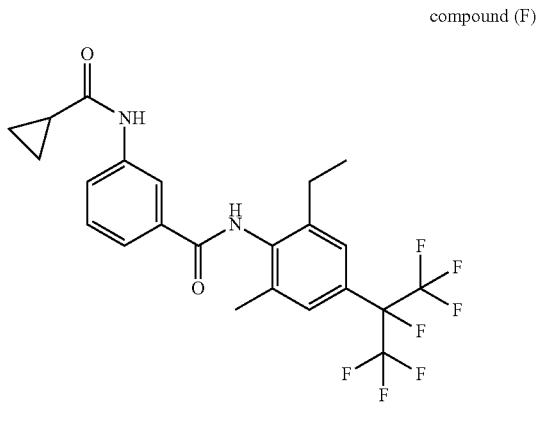 [SMILES: CCc1cc(C(F)(C(F)(F)F)C(F)(F)F)cc(C)c1NC(=O)c1cccc(NC(=O)C2CC2)c1]

compound (F)

TABLE A6

| active ingredient (compound number) | concentration (mg/m²) | death rate (%) |
|---|---|---|
| 7-1574 | 0.0431 | 10.0 |
| | 0.0861 | 100.0 |
| | 0.172 | 100.0 |
| 7-1733 | 0.0431 | 0.0 |
| | 0.0861 | 80.0 |
| | 0.172 | 100.0 |
| compound (B) | 0.673 | 0.0 |
| | 2.69 | 20.0 |
| | 10.8 | 50.0 |
| compound (C) | 0.673 | 0.0 |
| | 2.69 | 11.1 |
| | 10.8 | 10.0 |
| compound (D) | 0.673 | 0.0 |
| | 2.69 | 10.0 |
| | 10.8 | 50.0 |
| compound (F) | 0.673 | 0.0 |
| | 2.69 | 0.0 |
| | 10.8 | 0.0 |
| fipronil | 0.0431 | 0.0 |
| | 0.172 | 45.5 |
| | 0.673 | 100.0 |

As the composition for exterminating animal parasites according to the invention has excellent activity for exterminating animal parasites, the composition has wide industrial applicability.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

All publications, patent applications, and technical standards mentioned in this specification are herein incorporated by reference to the same extent as if each individual publication, patent application, or technical standard was specifically and individually indicated to be incorporated by reference.

What is claimed is:

1. A pest control agent, wherein the pest is an animal parasite, the pest control agent comprising an amide derivative represented by the following Formula (7):

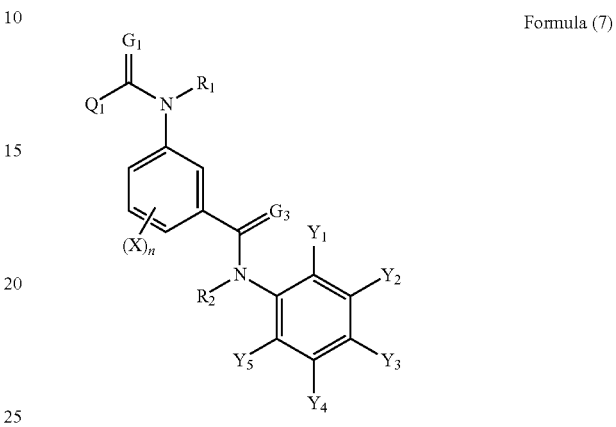

Formula (7)

wherein in Formula (7), n represents 4;
X's each independently represent a hydrogen atom, a halogen atom, or a cyano group;
$Y_3$ represents a C2-C4 perfluoroalkyl group;
$Y_2$ and $Y_4$ each represent a hydrogen atom;
$Y_1$ and $Y_5$ each independently represent a halogen atom or a C1-C3 haloalkyl group, and either $Y_1$ or $Y_5$ represents a C1-C3 haloalkyl group;
$G_1$ and $G_3$ each independently represent an oxygen atom or a sulfur atom;
$Q_1$ represents a hydrogen atom, a C1-C6 alkyl group, a C1-C6 haloalkyl group, a C2-C6 alkenyl group, a C2-C6 haloalkenyl group, a C2-C6 alkenyl group, a C2-C6 haloalkenyl group, a C3-C9 cycloalkyl group, a C3-C9 halocycloalkyl group, a benzyl group, a phenyl group which may have a substituent, a naphthyl group, or a heterocyclic group which may have a substituent;
wherein, in $Q_1$, the substituent of the phenyl group which may have a substituent and the heterocyclic group which may have a substituent represents one or more substituents selected from the group consisting of:
a halogen atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkylcarbonyloxy group, a C2-C7 haloalkylcarbonyloxy group, a C1-C6 alkylsulfonyloxy group, a C1-C6 haloalkylsulfonyloxy group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a C4-C10 cycloalkyloxycarbonyl group, a C4-C10 halocycloalkyloxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkenylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, an amino group, a carbamoyl group, a cyano group, a nitro group, a hydroxy group, a pentafluorosulfanyl group, a phenyl group which may have a substituent, and a heterocyclic group which may have a substituent, and when there are two or more substituents, the substituents may be the same as or different from each other;

wherein, the heterocyclic group in $Q_1$ represents a pyridyl group, a pyridine-N-oxide group, a pyrimidinyl group, a pyrazinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrolyl group, an imidazolyl group, a triazolyl group, a pyrazolyl group, or a tetrazolyl group; and $R_1$ and $R_2$ each independently represent a hydrogen atom, an oxygen atom, a halogen atom, a hydroxy group, a nitro group, a nitroso group, a trimethylsilyl group, a t-butyldimethylsilyl group, a cyano group, an amino group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)R$_7$, wherein R$_7$ represents a C1-C6 alkyl group, a C1-C6 haloalkyl group, a C1-C6 alkoxy group, or a C1-C6 haloalkoxy group.

2. A pest control agent, wherein the pest is an animal parasite, the pest control agent comprising an amide derivative represented by the following Formula (8):

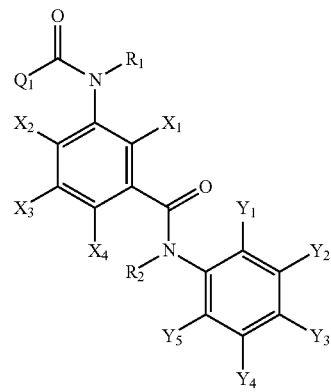

Formula (8)

wherein in Formula (8), $Q_1$ represents a phenyl group or a pyridyl group which may have a substituent selected from the group consisting of a halogen atom, a C1 haloalkyl, group, a nitro group, and a cyano group, and in case where $Q_1$ has the substituents, the number of the substituents is 1 or 2;

$X_1$ and $X_2$ each independently represent a hydrogen atom or a fluorine atom and $X_3$ and $X_4$ each represent a hydrogen atom;

$R_1$ and $R_2$ each independently represent a hydrogen atom or a methyl group;

$Y_1$ and $Y_5$ each independently represent a chlorine atom, a bromine atom, an iodine atom, a trifluoromethoxy group, a trifluoromethyl group, or a pentafluoroethyl group;

$Y_2$ and $Y_4$ each represent a hydrogen atom;

$Y_3$ represents a C3-C4 perfluoroalkyl group;

in a case where $Y_1$ and $Y_5$ represent halogen atoms simultaneously, at least one of $X_1$ or $X_2$ represents a fluorine atom; and in a case where $Y_1$ or $Y_5$ represents a trifluoromethoxy group, $X_2$ represents a fluorine atom.

3. A pest control agent, wherein the pest is an animal parasite, the pest control agent comprising an amide derivative represented by the following Formula (9):

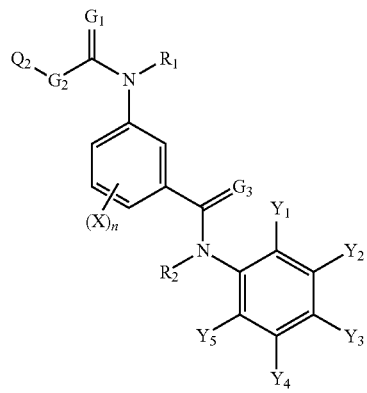

Formula (9)

wherein in Formula (9), n represents 4;

four X's each independently represent a hydrogen atom, a halogen atom, or a cyano group;

$Y_3$ represents a C2-C4 perfluoroalkyl group;

$Y_2$ and $Y_4$ each represent a hydrogen atom;

Y₁ and Y₅ each independently represent a halogen atom or a C1-C3 haloalkyl group, and either Y₁ or Y₅ represents a C1-C3 haloalkyl group;

G₁, G₂, and G₃ each independently represent an oxygen atom or a sulfur atom;

Q₂ represents a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C9 cycloalkyl group, a C3-C9 halocycloalkyl group, a benzyl group, a phenyl group which may have a substituent, a naphthyl group, or a heterocyclic group which may have a substituent;

wherein, in Q₂, the substituent of the phenyl group which may have a substituent and the heterocyclic group which may have a substituent represents one or more substituents selected from the group consisting of:

a halogen atom, a C1-C6 alkyl group, a C1-C6 haloalkyl group, a C3-C9 cycloalkyl group, a C3-C9 halocycloalkyl group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C2-C6 alkenyloxy group, a C2-C6 haloalkenyloxy group, a C2-C6 alkynyloxy group, a C2-C6 haloalkynyloxy group, a C3-C9 cycloalkoxy group, a C3-C9 halocycloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a C2-C7 alkylcarbonyl group, a C2-C7 haloalkylcarbonyl group, a C3-C7 alkenylcarbonyl group, a C3-C7 haloalkenylcarbonyl group, a C3-C7 alkynylcarbonyl group, a C3-C7 haloalkynylcarbonyl group, a C4-C10 cycloalkylcarbonyl group, a C4-C10 halocycloalkylcarbonyl group, a C2-C7 alkylcarbonyloxy group, a C2-C7 haloalkylcarbonyloxy group, a C1-C6 alkylsulfonyloxy group, a C1-C6 haloalkylsulfonyloxy group, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a C4-C10 cycloalkyloxycarbonyl group, a C4-C10 halocycloalkyloxycarbonyl group, a C2-C7 alkylcarbonylamino group, a C2-C7 haloalkylcarbonylamino group, a C2-C7 alkoxycarbonylamino group, a C2-C7 haloalkoxycarbonylamino group, a C1-C6 alkylamino group, a C1-C6 haloalkylamino group, a C2-C6 alkenylamino group, a C2-C6 haloalkenylamino group, a C2-C6 alkynylamino group, a C2-C6 haloalkynylamino group, a C3-C9 cycloalkylamino group, a C3-C9 halocycloalkylamino group, a C2-C7 alkylaminocarbonyl group, a C2-C7 haloalkylaminocarbonyl group, a C3-C7 alkenylaminocarbonyl group, a C3-C7 haloalkenylaminocarbonyl group, a C3-C7 alkynylaminocarbonyl group, a C3-C7 haloalkynylaminocarbonyl group, a C4-C10 cycloalkylaminocarbonyl group, a C4-C10 halocycloalkylaminocarbonyl group, an amino group, a carbamoyl group, a cyano group, a nitro group, a hydroxy group, a pentafluorosulfanyl group, a phenyl group which may have a substituent, and a heterocyclic group which may have a substituent, and when there are two or more substituents, the substituents may be the same as or different from each other;

wherein, the heterocyclic group in Q₂ represents a pyridyl group, a pyridine-N-oxide group, a pyrimidinyl group, a pyrazinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrolyl group, an imidazolyl group, a triazolyl group, a pyrazolyl group, or a tetrazolyl group;

R₁ and R₂ each independently represent a hydrogen atom, an oxygen atom, a halogen atom, a hydroxy group, a nitro group, a nitroso group, a trimethylsilyl group, a t-butyldimethylsilyl group, a cyano group, an amino group, a C1-C6 alkyl group which may have a substituent, a C1-C6 haloalkyl group which may have a substituent, a C2-C7 alkylcarbonyl group, a C2-C7 haloalkylcarbonyl group, a C2-C6 alkenyl group which may have a substituent, a C2-C6 haloalkenyl group which may have a substituent, a C2-C6 alkynyl group which may have a substituent, a C2-C6 haloalkynyl group which may have a substituent, a C2-C7 alkoxycarbonyl group, a C2-C7 haloalkoxycarbonyl group, a C3-C7 alkenyloxycarbonyl group, a C3-C7 haloalkenyloxycarbonyl group, a C3-C7 alkynyloxycarbonyl group, a C3-C7 haloalkynyloxycarbonyl group, a phenoxycarbonyl group, a C2-C7 alkylaminocarbonyl group, a C2-C7 haloalkylaminocarbonyl group, a C2-C7 alkylcarbonyloxy group, a C2-C7 haloalkylcarbonyloxy group, a benzoyl group, a C1-C6 alkoxy group, a C1-C6 haloalkoxy group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a benzenesulfonyl group, a benzylsulfonyl group, a benzyl group, or —C(=O)C(=O)R₇, wherein R₇ represents a C1-C6 alkyl group, a C1-C6 haloalkyl group, a C1-C6 alkoxy group, or a C1-C6 haloalkoxy group.

4. A pest controlling method comprising applying the pest control agent according to claim 1 to the animal parasite.

5. The pest control agent according to claim 1, wherein the amide derivative is represented by the following Formula (A1):

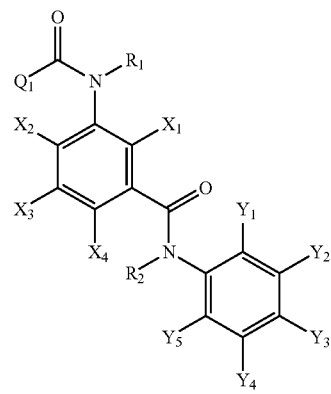

Formula (A1)

wherein, in Formula (A1), Q₁ represents a phenyl group or a phenyl group substituted with a halogen atom; X₁ represents a fluorine atom; X₂, X₃, and X₄ are each a hydrogen atom; R₁ represents a hydrogen atom or a C1-C3 alkyl group; R₂ is a hydrogen atom; Y₁ and Y₅ each independently represent a halogen atom or a C1-C3 haloalkyl group, and either Y₁ or Y₅ represents a C1-C3 haloalkyl group; Y₂ and Y₄ each represent a hydrogen atom; and Y₃ represents a heptafluoroisopropyl group.

6. The pest control agent according to claim 5, wherein in Formula (A1), Q₁ represents a phenyl group or a phenyl group substituted with a single fluorine atom; $R_1$ represents a hydrogen atom or a methyl group; and $Y_1$ and $Y_5$ each independently represent a bromine or iodine atom or a trifluoromethyl group.

7. The pest control agent according to claim 6, wherein the amide derivative represented by Formula (A1) is 2-fluoro-3-(N-methylbenzamide)-N-(2-bromo-6-trifluoromethyl-4-(heptafluoropropan-2-yl) phenyl)benzamide, 2-fluoro-3-(4-fluoro-N-methylbenzamide)-N-(2-iodo-6-trifluoromethyl-4-(heptafluoropropan-2-yl)phenyl) benzamide, 2-fluoro-3-(3-fluoro-N-methylbenzamide)-N-(2-iodo-6-trifluoromethyl-4-(heptafluoropropan-2-yl)phenyl) benzamide, 2-fluoro-3-(4-fluorobenzamide)-N-(2-iodo-6-trifluoromethyl-4-(heptafluoropropan-2-yl) phenyl)benzamide, or 2-fluoro-3-(N-methylbenzamide)-N-(2,6-dibromo-4-(heptafluoropropan-2-yl)phenyl) benzamide.

8. The method according to claim 4, wherein the animal parasite is an ectoparasite.

9. The method according to claim 8, wherein the ectoparasite is Siphonaptera pests.

10. The method according to claim 8, wherein the ectoparasite is Acarina pests.

11. A pest controlling method comprising applying the pest control agent according to claim 3 to the animal parasite.

12. The method according to claim 11, wherein the animal parasite is an ectoparasite.

13. The method according to claim 12, wherein the ectoparasite is Siphonaptera pests.

14. The method according to claim 12, wherein the ectoparasite is Acarina pests.

\* \* \* \* \*

UNITED STATES PATENT AND TRADEMARK OFFICE
CERTIFICATE OF CORRECTION

PATENT NO. : 9,237,745 B2
APPLICATION NO. : 13/845664
DATED : January 19, 2016
INVENTOR(S) : Yumi Kobayashi et al.

It is certified that error appears in the above-identified patent and that said Letters Patent is hereby corrected as shown below:

Claims

Column 718, Line 39, (Claim 1), delete "alkenyl" and insert --alkynyl--.

Column 718, Line 40, (Claim 1), delete "haloalkenyl" and insert --haloalkynyl--.

Column 720, Line 23, (Claim 2), delete "in case" and insert --in a case--.

Signed and Sealed this
Twenty-eighth Day of June, 2016

Michelle K. Lee
*Director of the United States Patent and Trademark Office*